United States Patent
Aga et al.

(10) Patent No.: US 10,131,679 B2
(45) Date of Patent: Nov. 20, 2018

(54) SUBSTITUTED DIHYDROPYRROLOPYRAZOLE COMPOUND

(71) Applicant: UBE INDUSTRIES, LTD., Ube-shi, Yamaguchi (JP)

(72) Inventors: Yasuhiro Aga, Ube (JP); Shigeru Ushiyama, Ube (JP); Noriaki Iwase, Ube (JP); Shigeyuki Kono, Ube (JP); Hidetoshi Sunamoto, Ube (JP); Takashi Matsushita, Ube (JP); Sayaka Ogi, Ube (JP); Masayuki Tanaka, Ube (JP); Masaaki Matoyama, Ube (JP); Satoshi Umezaki, Ube (JP); Yusuke Shiraishi, Ube (JP); Kazuhiro Onuma, Ube (JP); Masahiro Kojima, Ube (JP); Hayato Nishiyama, Ube (JP); Tomio Kimura, Tokyo (JP)

(73) Assignee: UBE INDUSTRIES, LTD., Ube-Shi, Yamaguchi (JP)

( * ) Notice: Subject to any disclaimer, the term of this patent is extended or adjusted under 35 U.S.C. 154(b) by 0 days.

(21) Appl. No.: 15/522,592

(22) PCT Filed: Oct. 30, 2015

(86) PCT No.: PCT/JP2015/080727
§ 371 (c)(1),
(2) Date: Apr. 27, 2017

(87) PCT Pub. No.: WO2016/068287
PCT Pub. Date: May 6, 2016

(65) Prior Publication Data
US 2017/0313727 A1    Nov. 2, 2017

(30) Foreign Application Priority Data
Oct. 31, 2014    (JP) ................................ 2014-223221

(51) Int. Cl.
C07F 7/10        (2006.01)
A61K 31/695      (2006.01)

(52) U.S. Cl.
CPC ...................................... C07F 7/10 (2013.01)

(58) Field of Classification Search
CPC combination set(s) only.
See application file for complete search history.

(56) References Cited

U.S. PATENT DOCUMENTS

| 2002/0123484 A1* | 9/2002 | Das | A61K 31/425 514/80 |
| 2007/0004705 A1* | 1/2007 | Brasca | C07D 487/04 514/218 |
| 2010/0010008 A1* | 1/2010 | Caruso | C07D 487/04 514/254.06 |
| 2010/0249128 A1* | 9/2010 | Botrous | C07D 487/04 514/234.2 |

FOREIGN PATENT DOCUMENTS

| JP | 2001-522800 A | 11/2001 |
| JP | 2006-514026 A | 4/2006 |
| JP | 2010-505905 A | 2/2010 |
| JP | 2010-523643 A | 7/2010 |
| WO | 02/12242 A2 | 2/2002 |
| WO | 2004/056827 A2 | 7/2004 |
| WO | 2004/080457 A1 | 9/2004 |
| WO | 2007/068637 A1 | 6/2007 |
| WO | 2007/072153 A2 | 6/2007 |
| WO | 2007/099171 A2 | 9/2007 |
| WO | 2008/043745 A1 | 4/2008 |

(Continued)

OTHER PUBLICATIONS

Fisher, Robert. "Secrets of a double agent: CDK7 in cell-cycle control and transcription". Journal of Cell Science, vol. 118(22), p. 5171-p. 5180, 2005.

Malumbres, Marcos et al. "Cell cycle, CDKs and cancer: a changing paradigm". Nature, vol. 9, p. 153-p. 166, 2009.

Svejstrup, Jesper. "The RNA polymerase II transcription cycle: cycling through chromatin". Biochim Biophys Acta, vol. 1677, p. 64-p. 73, 2004.

Kwiatkowski, Nicholas et al. "Targeting transcription regulation in cancer with a covalent CDK7 inhibitor". Nature, vol. 511, p. 616-p. 620, 2014.

(Continued)

*Primary Examiner* — Amanda L Aguirre
(74) *Attorney, Agent, or Firm* — Oliff PLC

(57) ABSTRACT

Provided is a compound represented by formula (I) or a pharmacologically acceptable salt thereof:

[Chemical Formula 1]

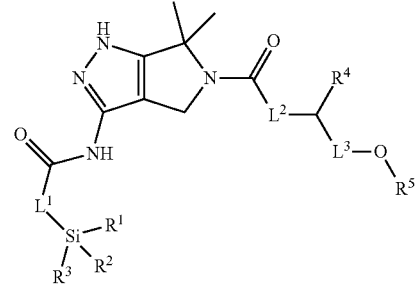

(I)

wherein $L^1$ is an optionally substituted $C_{1-6}$ alkylene group or the like, $L^2$ is a single bond or the like, $L^3$ is a single bond or the like, $R^1$, $R^2$, and $R^3$ are each independently an optionally substituted $C_{1-4}$ alkyl group or the like, $R^4$ is a hydrogen atom or the like, and $R^5$ is a hydrogen atom or the like.

39 Claims, No Drawings

(56) References Cited

FOREIGN PATENT DOCUMENTS

| WO | 2008/125945 A2 | 10/2008 |
|---|---|---|
| WO | 2008/151304 A1 | 12/2008 |
| WO | 2011/044264 A2 | 4/2011 |
| WO | 2013/128028 A1 | 9/2013 |
| WO | 2013/128029 A1 | 9/2013 |
| WO | 2014/063068 A1 | 4/2014 |
| WO | 2015/058126 A1 | 4/2015 |
| WO | 2015/058140 A1 | 4/2015 |
| WO | 2015/058163 A2 | 4/2015 |
| WO | 2015/124941 A1 | 8/2015 |
| WO | 2015/154022 A1 | 10/2015 |
| WO | 2015/154038 A1 | 10/2015 |
| WO | 2015/154039 A2 | 10/2015 |

OTHER PUBLICATIONS

Ali, Simak et al. "The development of a selective cyclin-dependent kinase inhibitor which demonstrates anti-tumor activity". Cancer Res, vol. 69(15), p. 6208-p. 6215, 2009.

Xia, Yong et al. "Selective inhibition of CDK7 ameliorates experimental arthritis; in mice". Clin Exp Med, vol. 15, p. 269-p. 275, 2015.

Fuente, Cynthia et al. "Pharmacological Cyclin-Dependent Kinase Inhibitors as HIV-1 Antiviral; Therapeutics". Current HIV Research, vol. 1, p. 131-p. 152, 2003.

Abdellatif, Maha. "A Ras-Dependent Pathway Regulates RNA Polymerase II; Phosphorylation in Cardiac Myocytes: Implications for; Cardiac Hypertrophy". Molecular and Cellular Biology, vol. 18, p. 6729-p. 6736, 1998.

Miracco, C. et al. "Cyclin D1, B and A expression and cell turnover in psoriatic skin; lesions before and after cyclosporin treatment". British Journal of Dermatology, vol. 143, p. 950-p. 956, 2000.

Yoshida, Hideyuki et al. "CDK inhibitors suppress Th17 and promote iTreg differentiation, and ameliorate experimental autoimmune encephalomyelitis in mice". Biochemical and Biophysical Research Communications, vol. 435, p. 378-p. 384, 2013.

Zhu, Xiongwei et al. "Neuronal CDK7 in hippocampus is related to aging; and Alzheimer disease". Neurobiology of Aging, vol. 21, p. 807-p. 813, 2000.

Guo, Chuangxing et al. "Discovery of Pyrroloaminopyrazoles as Novel PAK Inhibitors". Journal of Medicinal Chemistry, vol. 55, p. 4728-p. 4739, 2012.

Brasca, Maria et al. "Optimization of 6,6-dimethyl pyrrolo[3,4-c]pyrazoles: Identification; of PHA-793887, a potent CDK Inhibitor suitable for intravenous dosing". Bioorganic & Medicinal Chemistry, vol. 18, p. 1844-p. 1853, 2010.

Brasca, Maria et al. "6-Substituted Pyrrolo[3,4-c]pyrazoles: An; Improved Class of CDK2 Inhibitors". ChemMedChem, vol. 2, p. 841-p. 852, 2007.

Krystof, Vladimir et al. "Cyclin-Dependent Kinase Inhibitors as Anticancer Drugs". Current Drug Targets, vol. 11, p. 291-p. 302, 2010.

Farahi, N et al. "Effects of the cyclin-dependent kinase inhibitor R-roscovitine on eosinophil; survival and clearance". Olinical & Experimental Allergy, vol. 41, p. 673-p. 687, 2011.

Leitch, AE et al. "Cyclin-dependent kinases 7 and 9 specifically regulate; neutrophil transcription and their inhibition drives; apoptosis to promote resolution of inflammation". Cell Death and Differentiation, vol. 19, p. 1950-p. 1961, 2012.

Inoshima, Ichiro et al. "Induction of CDK inhibitor p21 gene as a new therapeutic; strategy against pulmonary fibrosis". Am J Physiol Lung Cell Mol Physiol, vol. 286, p. L727-p. L733, 2004.

Jan. 26, 2016 International Search Report issued in Patent Application No. PCT/UP2015/080727.

May 2, 2017 International Preliminary Report on Patentability issued in International Patent Application No. PCT/UP2015/080727.

* cited by examiner

SUBSTITUTED DIHYDROPYRROLOPYRAZOLE COMPOUND

TECHNICAL FIELD

The present invention relates to a substituted dihydropyrrolopyrazole compound or a pharmacologically acceptable salt thereof which has excellent CDK7 inhibitory activity and is useful as a medicament (e.g., a medicament for the treatment or prevention of cancers or inflammatory diseases), or a prodrug thereof.

BACKGROUND ART

CDKs (cyclin-dependent kinases) are cell growth control factors that are involved in entry to DNA synthesis (S phase) of the cell cycle and a mitotic phase (M phase), etc., and many types of CDKs are known. Also, the activation of CDK is controlled in multiple stages through the phosphorylation or dephosphorylation of the threonine residue of active loop (T loop) in its three-dimensional structure. When the particular threonine residue of CDK is phosphorylated, it forms a complex with a particular cyclin and is activated. This complex, which is important for cell cycle control, includes CDK1, CDK2/cyclin A, CDK1/cyclins B1 to B3 and CDK2, CDK4, CDK5, CDK6/cyclin D1 to D3, and CDK2/cyclin E, which are respectively involved in the particular periods of the cell cycle. CDK7 forms a CDK-activating kinase (CAK) together with cyclin H and MAT1 in metazoans and participates in the phosphorylation of CDKs (e.g., CDK1, CDK2, CDK4, and CDK6) necessary for the progression of the cell cycle (see Non Patent Literature 1).

Cell overgrowth by the abnormal activation of CDKs is a common feature in many cancers, and it is known that this is associated with a loss of checkpoint functions involved in the cell cycle control of cancer cells (see Non Patent Literature 2). Also, CDKs are known to have functions other than cell cycle control, and CDK7 is known to promote the binding of RNA polymerase II (RNAPII) to DNA and elongation thereof to positively control the transcription through the phosphorylation of serine in the COOH-terminal domain of the RNAPII (see Non Patent Literature 3).

CDK7 inhibitors exhibit effects in cell growth tests of various cancer cells and cancer-bearing mouse models, and the inhibition is expected to be useful as anticancer agents (see Non Patent Literatures 4 and 5).

Furthermore, it has been reported that in collagen-induced rheumatism mouse models, amelioration of clinical scores or tissue damage, decrease in the levels of inflammation-induced cytokines such as IL-6, IL-1β, and IL-17, and anti-CII-IgG2α, and decrease in the proportion of Th17 cells are attained by inhibiting CDK7 (see Non Patent Literature 6).

The CDK7 inhibitors, which play an important role in the progression of the cell cycle, are further expected to also have effects on the suppression of infection by viruses such as HIV, EBV, and HCV, and cardiomegaly (see Non Patent Literatures 7 and 8). Examples of diseases for which the CDK7 inhibitors seem to be useful, in addition to those described above, include autoimmune diseases typified by psoriasis and multiple sclerosis, neurodegenerative diseases typified by Alzheimer's disease, etc., allergic diseases typified by atopic dermatitis, etc., chronic respiratory diseases typified by chronic obstructive pulmonary disease (COPD), etc., and fibrosis typified by idiopathic pulmonary fibrosis, etc. (see Non Patent Literatures 9 to 11 and Non Patent Literatures 16 to 18).

Although the development of many CDK inhibitors is currently underway, there are not many compounds having an excellent CDK7 inhibitory effect (see Non Patent Literature 15).

CITATION LIST

Patent Literature

Patent Literature 1: WO 2002/012242
Patent Literature 2: WO 2004/056827
Patent Literature 3: WO 2004/080457
Patent Literature 4: WO 2007/068637
Patent Literature 5: WO 2007/072153
Patent Literature 6: WO 2007/099171
Patent Literature 7: WO 2008/043745
Patent Literature 8: WO 2008/125945
Patent Literature 9: WO 2011/044264
Patent Literature 10: WO 2008/151304
Patent Literature 11: WO 2013/128028
Patent Literature 12: WO 2013/128029
Patent Literature 13: WO 2014/063068
Patent Literature 14: WO 2015/058126
Patent Literature 15: WO 2015/058140
Patent Literature 16: WO 2015/058163
Patent Literature 17: WO 2015/124941
Patent Literature 18: WO 2015/154022
Patent Literature 19: WO 2015/154038
Patent Literature 20: WO 2015/154039

Non Patent Literature

Non Patent Literature 1: Journal of Cell Science 2005, 118 (20), 5171-5180
Non Patent Literature 2: Nature Reviews Cancer 2009, 9, 153-166
Non Patent Literature 3: Biochim Biophys Acta 2004, 1677, 64-73
Non Patent Literature 4: Nature 2014, 511, 616-620
Non Patent Literature 5: Cancer Res 2009, 69, 6208-6215
Non Patent Literature 6: Clinical and Experimental Medicine, 2015, 15, 269-275
Non Patent Literature 7: Curr HIV Res 2003, 1 (2), 131-152
Non Patent Literature 8: Mol Cell Biol 1998, 18 (11), 6729-6736
Non Patent Literature 9: Br J Dermatol 2000, 143 (5), 950-956
Non Patent Literature 10: Biochem Biophys Res Commun 2013, 435 (3), 378-384
Non Patent Literature 11: Neurobiol Aging 2000, 6, 807-813
Non Patent Literature 12: Journal of Medicinal Chemistry 2012, 55 (10), 4728-4739
Non Patent Literature 13: Bioorganic & Medicinal Chemistry 2010, 18 (5), 1844-1853
Non Patent Literature 14: Chem Med Chem 2007, 2, 841-852
Non Patent Literature 15: Current Drug Targets, 2010, 11, 291-302
Non Patent Literature 16: Clinical & Experimental Allergy, 2011, 41, 673-687
Non Patent Literature 17: Cell Death and Differentiation, 2012, 19, 1950-1961

Non Patent Literature 18: Am. J. Physiol. Lung Cell Mol, 2004, 286, 727-733

SUMMARY OF INVENTION

Technical Problem

The present inventors have conducted studies on novel substituted dihydropyrrolopyrazole compounds with the aim of developing excellent CDK7 inhibitors and completed the present invention by finding that a novel substituted dihydropyrrolopyrazole compound having a particular structure or a pharmacologically acceptable salt thereof has excellent CDK7 inhibitory activity and is useful as a medicament (e.g., a medicament for the treatment or prevention of cancers or inflammatory diseases), and further finding even a compound that can serve as a prodrug of the compound.

Patent Literatures 1 to 9 and Non Patent Literatures 12 to 14 describe a compound having a 6,6-dimethyl-4,6-dihydropyrrolo[3,4-c]pyrazole skeleton, but do not disclose the compound according to the present invention or the pharmacologically acceptable salt thereof.

As compounds inhibiting CDK7, pyrazolopyrimidine derivatives are disclosed in Patent Literature 10, pyrazolotriazine derivatives are disclosed in Patent Literatures 11 and 12, phenyl derivatives are disclosed in Patent Literature 13 and Non Patent Literature 4, and heterocyclic compounds are disclosed in Patent Literatures 14 to 20; however, a compound having a 4,6-dihydropyrrolo[3,4-c]pyrazole skeleton is not disclosed.

Solution to Problem

The present invention provides a novel substituted dihydropyrrolopyrazole compound or a pharmacologically acceptable salt thereof which has excellent CDK7 inhibitory activity, or a prodrug thereof;
a pharmaceutical composition, preferably a pharmaceutical composition for the treatment or prevention of cancers, inflammatory diseases (e.g., autoimmune diseases), infection by viruses (HIV, EBV, HCV, etc.), neurodegenerative diseases (e.g., Alzheimer's disease), allergic diseases (e.g., atopic dermatitis), chronic respiratory diseases (e.g., chronic obstructive pulmonary disease (COPD)), fibrosis (e.g., idiopathic pulmonary fibrosis), circulatory diseases such as cardiomegaly, or impotence, comprising the substituted dihydropyrrolopyrazole compound or the pharmacologically acceptable salt thereof, or the prodrug thereof as an active ingredient;
use of the substituted dihydropyrrolopyrazole compound or the pharmacologically acceptable salt thereof, or the prodrug thereof for the production of a pharmaceutical composition for the treatment or prevention (preferably, treatment) of diseases (preferably, the diseases described above);
a method for treating or preventing (preferably, treating) diseases (preferably, the diseases described above) by administering a pharmaceutically effective amount of the substituted dihydropyrrolopyrazole compound or the pharmacologically acceptable salt thereof, or the prodrug thereof to a warm-blooded animal (preferably, a human); and a method for producing the substituted dihydropyrrolopyrazole compound or the pharmacologically acceptable salt thereof, or the prodrug thereof, or an intermediate thereof.

Examples of the cancers include urinary bladder cancer, breast cancer, large intestine cancer (e.g., colorectal cancer, for example, colon adenocarcinoma and colon adenoma), gastrointestinal stromal tumor, kidney cancer, epidermal cancer, liver cancer, lung cancer (e.g., adenocarcinoma, small-cell lung cancer, and non-small cell lung cancer), esophageal cancer, gallbladder cancer, ovary cancer, pancreatic cancer (e.g., exocrine pancreatic tumor), gastric cancer, cervical cancer, endometrial cancer, thyroid gland cancer, cancer of the nose, head and neck cancer, prostate cancer, skin cancer (e.g., squamous cell cancer), hematopoietic organ tumors of the lymphatic system (e.g., leukemia, acute lymphatic leukemia, chronic lymphatic leukemia, B cell lymphoma (e.g., diffuse large B cell lymphoma), T cell lymphoma, multiple myeloma, Hodgkin's lymphoma, non-Hodgkin's lymphoma, hairy cell lymphoma, and Burkitt's lymphoma), hematopoietic organ tumors of the myeloid system (e.g., acute or chronic myeloid leukemia, myelodysplastic syndrome, and promyelocytic leukemia), follicular carcinoma of thyroid, mesenchymal tumors (e.g., fibrosarcoma, Ewing's sarcoma, and rhabdomyosarcoma), tumors of the central or peripheral nervous system (e.g., astrocytoma, neuroblastoma, glioma, brain tumor, and schwannoma), melanoma, seminoma, teratoma, osteosarcoma, xeroderma pigmentosum, keratoacanthoma, follicular carcinoma of thyroid, and Kaposi's sarcoma.

Examples of the autoimmune diseases include multiple sclerosis, Guillain-Barre syndrome, myasthenia gravis, chronic atrophic gastritis, autoimmune hepatitis, primary biliary cirrhosis, ulcerative colitis, Crohn's disease, primary sclerosing cholangitis, autoimmune pancreatitis, aortitis syndrome, Goodpasture's syndrome, rapidly progressive glomerulonephritis, megaloblastic anemia, autoimmune hemolytic anemia, autoimmune neutropenia, idiopathic thrombocytopenic purpura, Graves' disease, Hashimoto disease, primary hypothyroidism, idiopathic Addison's disease, type 1 diabetes mellitus, circumscribed scleroderma, epidermolysis bullosa acquisita, vitiligo vulgaris, autoimmune optic neuropathy, autoimmune inner ear disorder, idiopathic azoospermia, rheumatoid arthritis, systemic lupus erythematosus, drug-induced lupus erythematosus, Sjogren's syndrome, polymyositis, psoriasis, dermatomyositis, scleroderma, vasculitis syndrome, mixed connective-tissue disease, and inflammatory bowel disease. In this context, the inflammatory bowel disease (IBD) is a generic name for diseases that cause chronic inflammation or ulcer in the large intestinal or small intestinal mucosa, and examples thereof include Crohn disease and ulcerative colitis.

In one aspect, the present invention provides the following [1] to [24]:
[1] A compound represented by formula (I) or a pharmacologically acceptable salt thereof:

[Chemical Formula 1]

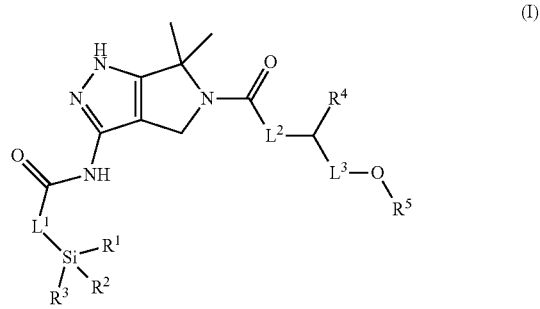

(I)

wherein

L¹ is an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group, L² is a single bond, an oxygen atom, an optionally substituted nitrogen atom, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group, L³ is a single bond, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group, $R^1$, $R^2$, and $R^3$ are each independently an optionally substituted linear or branched $C_{1-4}$ alkyl group, an optionally substituted linear or branched $C_{2-4}$ alkenyl group, an optionally substituted linear or branched $C_{2-4}$ alkynyl group, an optionally substituted $C_{6-10}$ aryl group, or an optionally substituted heterocyclic group, $R^4$ is a hydrogen atom, an optionally substituted linear or branched $C_{1-6}$ alkyl group, an optionally substituted linear or branched $C_{2-6}$ alkenyl group, an optionally substituted linear or branched $C_{2-6}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group, and $R^5$ is a hydrogen atom, an optionally substituted linear or branched $C_{1-16}$ alkyl group, an optionally substituted linear or branched $C_{2-16}$ alkenyl group, an optionally substituted linear or branched $C_{2-16}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group.

[2] The compound or a pharmacologically acceptable salt thereof according to [1], wherein L¹ is an optionally substituted linear or branched $C_{1-6}$ alkylene group or an optionally substituted $C_{3-6}$ cycloalkylene group.

[3] A compound represented by formula (II) or a pharmacologically acceptable salt thereof:

[Chemical Formula 2]

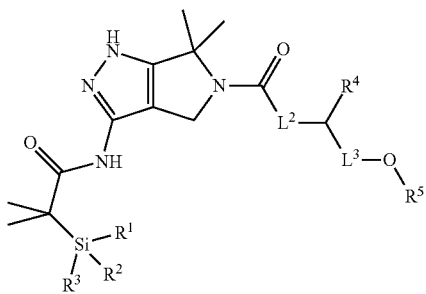

(II)

wherein

L² is a single bond, an oxygen atom, an optionally substituted nitrogen atom, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group, L³ is a single bond, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group, $R^1$, $R^2$, and $R^3$ are each independently an optionally substituted linear or branched $C_{1-4}$ alkyl group, an optionally substituted linear or branched $C_{2-4}$ alkenyl group, an optionally substituted linear or branched $C_{2-4}$ alkynyl group, an optionally substituted $C_{6-10}$ aryl group, or an optionally substituted heterocyclic group, $R^4$ is a hydrogen atom, an optionally substituted linear or branched $C_{1-6}$ alkyl group, an optionally substituted linear or branched $C_{2-6}$ alkenyl group, an optionally substituted linear or branched $C_{2-6}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group, and $R^5$ is a hydrogen atom, an optionally substituted linear or branched $C_{1-16}$ alkyl group, an optionally substituted linear or branched $C_{2-16}$ alkenyl group, an optionally substituted linear or branched $C_{2-16}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group.

[4] The compound or a pharmacologically acceptable salt thereof according to [3], wherein $R^1$, $R^2$, and $R^3$ are each independently an optionally substituted linear or branched $C_{1-4}$ alkyl group.

[5] A compound represented by formula (III) or a pharmacologically acceptable salt thereof:

[Chemical Formula 3]

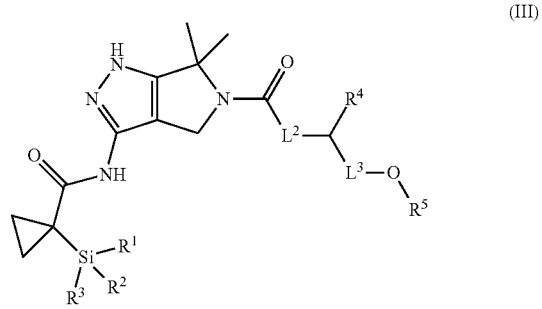

(III)

wherein

L² is a single bond, an oxygen atom, an optionally substituted nitrogen atom, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group, L³ is a single bond, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group, $R^1$, $R^2$, and $R^3$ are each independently an optionally substituted linear or branched $C_{1-4}$ alkyl group, an optionally substituted linear or branched $C_{2-4}$ alkenyl group, an optionally substituted linear or branched $C_{2-4}$ alkynyl group, an optionally substituted $C_{6-10}$ aryl group, or an optionally substituted heterocyclic group, $R^4$ is a hydrogen atom, an optionally substituted linear or branched $C_{1-6}$ alkyl group, an optionally substituted linear or branched $C_{2-6}$ alkenyl group, an optionally substituted linear or branched $C_{2-6}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group, and $R^5$ is a hydrogen atom, an optionally substituted linear or branched $C_{1-16}$ alkyl group, an optionally substituted linear or branched $C_{2-16}$ alkenyl group, an optionally substituted linear or branched $C_{2-16}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group.

[6] The compound or a pharmacologically acceptable salt thereof according to [5], wherein $R^1$, $R^2$, and $R^3$ are each independently an optionally substituted linear or branched $C_{1-4}$ alkyl group.

[7] A compound represented by formula (IV) or a pharmacologically acceptable salt thereof:

[Chemical Formula 4]

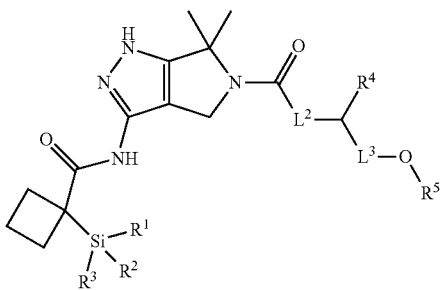

(IV)

wherein $L^2$ is a single bond, an oxygen atom, an optionally substituted nitrogen atom, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group, $L^3$ is a single bond, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group, $R^1$, $R^2$, and $R^3$ are each independently an optionally substituted linear or branched $C_{1-4}$ alkyl group, an optionally substituted linear or branched $C_{2-4}$ alkenyl group, an optionally substituted linear or branched $C_{2-4}$ alkynyl group, an optionally substituted $C_{6-10}$ aryl group, or an optionally substituted heterocyclic group, $R^4$ is a hydrogen atom, an optionally substituted linear or branched $C_{1-6}$ alkyl group, an optionally substituted linear or branched $C_{2-6}$ alkenyl group, an optionally substituted linear or branched $C_{2-6}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group, and $R^5$ is a hydrogen atom, an optionally substituted linear or branched $C_{1-16}$ alkyl group, an optionally substituted linear or branched $C_{2-16}$ alkenyl group, an optionally substituted linear or branched $C_{2-16}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group.

[8] The compound or a pharmacologically acceptable salt thereof according to [7], wherein $R^1$, $R^2$, and $R^3$ are each independently an optionally substituted linear or branched $C_{1-4}$ alkyl group.

[9] A compound represented by formula (V) or (VI) or a pharmacologically acceptable salt thereof:

[Chemical Formula 5]

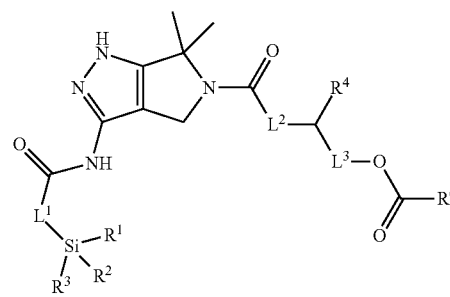

(V)

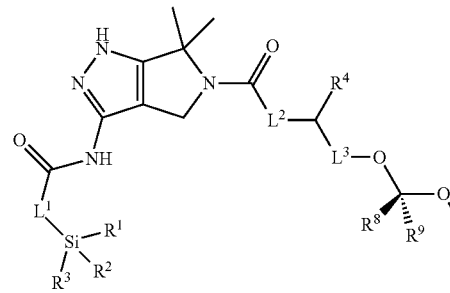

(VI)

wherein $L^1$ is an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group, $L^2$ is a single bond, an oxygen atom, an optionally substituted nitrogen atom, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group, $L^3$ is a single bond, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group, $R^1$, $R^2$, and $R^3$ are each independently an optionally substituted linear or branched $C_{1-4}$ alkyl group, an optionally substituted linear or branched $C_{2-4}$ alkenyl group, an optionally substituted linear or branched $C_{2-4}$ alkynyl group, an optionally substituted $C_{6-10}$ aryl group, or an optionally substituted heterocyclic group, $R^4$ is a hydrogen atom, an optionally substituted linear or branched $C_{1-6}$ alkyl group, an optionally substituted linear or branched $C_{2-6}$ alkenyl group, an optionally substituted linear or branched $C_{2-6}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group, and $R^6$ is a hydrogen atom, an optionally substituted linear or branched $C_{1-16}$ alkyl group, an optionally substituted linear or branched $C_{2-16}$ alkenyl group, an optionally substituted linear or branched $C_{2-16}$ alkynyl group, an optionally substituted $C_{3-6}$ cycloalkyl group, an optionally substituted $C_{3-6}$ cycloalkenyl group, an optionally substituted linear or branched $C_{1-6}$ alkoxy group, an optionally substituted $C_{6-10}$ aryl group, or an optionally substituted heterocyclic group, $R^7$ is an optionally substituted linear or branched $C_{1-16}$ alkyl group, an optionally substituted linear or branched $C_{2-16}$ alkenyl group, an optionally substituted linear or branched $C_{2-16}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group, and $R^8$ and $R^9$ are each independently a hydrogen atom or a $C_{1-4}$ alkyl group.

[10] The compound or a pharmacologically acceptable salt thereof according to [9], wherein $L^1$ is an optionally substituted linear or branched $C_{1-6}$ alkylene group or an optionally substituted $C_{3-6}$ cycloalkylene group, and $R^1$, $R^2$, and $R^3$ are each independently an optionally substituted linear or branched $C_{1-4}$ alkyl group.

[11] A compound selected from a compound group consisting of (S)—N-(2-hydroxy-1-phenylethyl)-6,6-dimethyl-3-[1-(trimethylsilyl)cyclobutanecarboxamido]-4,6-dihydropyrrolo[3,4-c]pyrazole-5(1H)-carboxamide, (S)—N-(2-hydroxy-1-phenylethyl)-6,6-dimethyl-3-[1-(trimethylsilyl)cyclopropanecarboxamido]-4,6-dihydropyrrolo[3,4-c]pyrazole-5(1H)-carboxamide, (S)—N-(2-hydroxy-1-phenylethyl)-6,6-dimethyl-3-[2-methyl-2-(trimethylsilyl)propaneamido]-4,6-dihydropyrrolo[3,4-c]pyrazole-5(1H)-carboxamide, (S)-3-[1-(ethyldimethylsilyl)cyclobutanecarboxamido]-N-(2-hydroxy-1-phenylethyl)-6,6-dimethyl-4,6-dihydropyrrolo[3,4-c]pyrazole-5(1H)-carboxamide, (S)-3-[2-(ethyldimethylsilyl)-2-methylpropaneamido]-N-(2-hydroxy-1-phenylethyl)-6,6-dimethyl-4,6-dihydropyrrolo[3,4-c]pyrazole-5(1H)-carboxamide, (S)—N-(2-hydroxy-1-phenylethyl)-N,6,6-trimethyl-3-[1-(trimethylsilyl)cyclobutanecarboxamido]-4,6-dihydropyrrolo[3,4-c]pyrazole-5(1H)-carboxamide, (S)-2-[(2-methoxypropan-2-yl)oxy]-1-phenylethyl6,6-dimethyl-3-[1-(trimethylsilyl)cyclobutanecarboxamido]-4,6-dihydropyrrolo[3,4-c]pyrazole-5(1H)-carboxylate, (S)-2-hydroxy-1-phenylethyl 6,6-dimethyl-3-[1-(trimethylsilyl)cyclobutanecarboxamido]-4,6-dihydropyrrolo[3,4-c]pyrazole-5(1H)-carboxylate, 2-Methoxy-1-phenylethyl 6,6-dimethyl-3-[1-(trimethylsilyl)cyclopropanecarboxamido]-4,6-dihydropyrrolo[3,4-c]pyrazole-5(1H)-carboxylate, N-[5-(4-hydroxy-3-phenylbutanoyl)-6,6-dimethyl-1,4,5,6-tetrahydropyrrolo[3,4-c]pyrazol-3-yl]-1-(trimethylsilyl)cyclobutanecarboxamide, N-[5-(3-hydroxy-3-phenylpropanoyl)-6,6-dimethyl-1,4,5,6-tetrahydropyrrolo[3,4-c]pyrazol-3-yl]-1-(trimethylsilyl)cyclobutanecarboxamide, (R)—N-(3-hydroxy-1-phenylpropyl)-6,6-dimethyl-3-[1-(trimethylsilyl)cyclobutanecarboxamido]-4,6-dihydropyrrolo[3,4-c]pyrazole-5(1H)-carboxamide, (R)—N-(3-hydroxy-1-phenylpropyl)-6,6-dimethyl-3-[1-(trimethylsilyl)cyclopropanecarboxamido]-4,6-dihydropyrrolo[3,4-c]pyrazole-5(1H)-carboxamide, (R)—N-(4-hydroxy-1-phenylbutyl)-6,6-dimethyl-3-[1-(trimethylsilyl)cyclobutanecarboxamido]-4,6-dihydropyrrolo[3,4-c]pyrazole-5(1H)-carboxamide, (R)—N-(5-hydroxy-1-phenylpentyl)-6,6-dimethyl-3-[1-(trimethylsilyl)cyclobutanecarboxamido]-4,6-dihydropyrrolo[3,4-c]pyrazole-5(1H)-carboxamide, (S)—N-(2-hydroxy-2-methyl-1-phenylpropyl)-6,6-dimethyl-3-[1-(trimethylsilyl)cyclobutanecarboxamido]-4,6-dihydropyrrolo[3,4-c]pyrazole-5(1H)-carboxamide, (S)—N-(2-hydroxy-2-methyl-1-phenylpropyl)-6,6-dimethyl-3-[1-(trimethylsilyl)cyclopropanecarboxamido]-4,6-dihydropyrrolo[3,4-c]pyrazole-5(1H)-carboxamide, N-(3-hydroxy-2,2-dimethyl-1-phenylpropyl)-6,6-dimethyl-3-[1-(trimethylsilyl)cyclobutanecarboxamido]-4,6-dihydropyrrolo[3,4-c]pyrazole-5(1H)-carboxamide, (R)—N-(3-hydroxy-3-methyl-1-phenylbutyl)-6,6-dimethyl-3-[1-(trimethylsilyl)cyclobutanecarboxamido]-4,6-dihydropyrrolo[3,4-c]pyrazole-5(1H)-carboxamide, (S)—N-(2-methoxy-1-phenylethyl)-6,6-dimethyl-3-[1-(trimethylsilyl)cyclobutanecarboxamido]-4,6-dihydropyrrolo[3,4-c]pyrazole-5(1H)-carboxamide, (S)—N-[2-(difluoromethoxy)-1-phenylethyl]-6,6-dimethyl-3-[1-(trimethylsilyl)cyclobutanecarboxamido]-4,6-dihydropyrrolo[3,4-c]pyrazole-5(1H)-carboxamide, (S)—N-(2-ethoxy-1-phenylethyl)-6,6-dimethyl-3-[1-(trimethylsilyl)cyclobutanecarboxamido]-4,6-dihydropyrrolo[3,4-c]pyrazole-5(1H)-carboxamide, (R)—N-(3-methoxy-1-phenylpropyl)-6,6-dimethyl-3-[1-(trimethylsilyl)cyclobutanecarboxamido]-4,6-dihydropyrrolo[3,4-c]pyrazole-5(1H)-carboxamide, Sodium (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylacetate, (R)—N-(2-hydroxy-1-phenylethyl)-6,6-dimethyl-3-[1-(trimethylsilyl)cyclobutanecarboxamido]-4,6-dihydropyrrolo[3,4-c]pyrazole-5(1H)-carboxamide, N-[1-(2-fluorophenyl)-2-hydroxyethyl]-6,6-dimethyl-3-[1-(trimethylsilyl)cyclobutanecarboxamido]-4,6-dihydropyrrolo[3,4-c]pyrazole-5(1H)-carboxamide, (S)—N-[1-(3-fluorophenyl)-2-hydroxyethyl]-6,6-dimethyl-3-[1-(trimethylsilyl)cyclobutanecarboxamido]-4,6-dihydropyrrolo[3,4-c]pyrazole-5(1H)-carboxamide, (S)—N-[1-(4-fluorophenyl)-2-hydroxyethyl]-6,6-dimethyl-3-[1-(trimethylsilyl)cyclobutanecarboxamido]-4,6-dihydropyrrolo[3,4-c]pyrazole-5(1H)-carboxamide, N-[2-hydroxy-1-(pyridin-2-yl)ethyl]-6,6-dimethyl-3-[1-(trimethylsilyl)cyclobutanecarboxamido]-4,6-dihydropyrrolo[3,4-c]pyrazole-5(1H)-carboxamide, N-[2-hydroxy-1-(pyridin-3-yl)ethyl]-6,6-dimethyl-3-[1-(trimethylsilyl)cyclobutanecarboxamido]-4,6-dihydropyrrolo[3,4-c]pyrazole-5(1H)-carboxamide, N-[1-(benzo[d][1,3]dioxol-4-yl)-2-hydroxyethyl]-6,6-dimethyl-3-[1-(trimethylsilyl)cyclobutanecarboxamido]-4,6-dihydropyrrolo[3,4-c]pyrazole-5(1H)-carboxamide, (S)—N-(1-cyclohexyl-2-hydroxyethyl)-6,6-dimethyl-3-[1-(trimethylsilyl) cyclobutanecarboxamido]-4,6-dihydropyrrolo[3,4-c]pyrazole-5(1H)-carboxamide, (S)—N-(1-hydroxy-3-methylbutan-2-yl)-6,6-dimethyl-3-[1-(trimethylsilyl)cyclobutanecarboxamido]-4,6-dihydropyrrolo[3,4-c]pyrazole-5(1H)-carboxamide, (S)—N-(1-hydroxypropan-2-yl)-6,6-dimethyl-3-[1-(trimethylsilyl)cyclobutanecarboxamido]-4,6-dihydropyrrolo[3,4-c]pyrazole-5(1H)-carboxamide, N-(2-hydroxyethyl)-6,6-dimethyl-3-[1-(trimethylsilyl)cyclobutanecarboxamido]-4,6-dihydropyrrolo[3,4-c]pyrazole-5(1H)-carboxamide, N-(2-hydroxy-2-phenylethyl)-6,6-dimethyl-3-[1-(trimethylsilyl)cyclobutanecarboxamido]-4,6-dihydropyrrolo[3,4-c]pyrazole-5(1H)-carboxamide, N-(2-hydroxypropyl)-6,6-dimethyl-3-[1-(trimethylsilyl)cyclobutanecarboxamido]-4,6-dihydropyrrolo[3,4-c]pyrazole-5(1H)-carboxamide, N-[(2S)-1-hydroxy-3-methyl-1-phenylbutan-2-yl]-6,6-dimethyl-3-[1-(trimethylsilyl)cyclobutanecarboxamido]-4,6-dihydropyrrolo[3,4-c]pyrazole-5(1H)-carboxamide, N-(4-hydroxy-1-phenyl-2-butyn-1-yl)-6,6-dimethyl-3-[1-(trimethylsilyl) cyclobutanecarboxamido]-4,6-dihydropyrrolo[3,4-c]pyrazole-5(1H)-carboxamide, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl acetate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl propionate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl butanoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl pentanoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl octanoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl dodecanoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl palmitate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl isobutanoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl pivalate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl 3-methyl butanoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl benzoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl ethyl carbonate, Sodium (S)-4-(2-{6,6-dimethyl-3-[1-(trimethylsilyl)cyclobutanecarboxamido]-1,4,5,6-tetrahydropyrrolo[3,4-c]pyrazole-5-carboxamido}-2-phenylethoxy)-4-oxobutanoate, (S)-(2-{6,6-dimethyl-3-[1-(trimethylsilyl)cyclobutanecarboxamido]-1,4,5,6-tetrahydropyrrolo[3,4-c]pyrazole-5-carboxamido}-2-phenylethoxy) methyl pivalate, (S)-2-acetoxy-1-phenylethyl 6,6-dimethyl-3-[1-(trimethylsilyl)cyclobutanecarboxamido]-4,6-dihydropyrrolo[3,4-c]pyrazole-5(1H)-carboxylate, (S)-benzyl 2-{6,6-dimethyl-3-[1-(trimethylsilyl)cyclobutanecarboxamido]-1,4,5,6-tetrahydropyrrolo[3,4-c]pyrazole-5-carboxamido}-2-phenylacetate, (S)-methyl 2-{6,6-dimethyl-3-[1-(trimethylsilyl)cyclobutanecarboxamido]-1,4,5,6-tetrahydropyrrolo[3,4-c]pyrazole-5-carboxamido}-2-phenylacetate, N-(2,2-difluoro-3-hydroxy-1-phenylpropyl)-6,6-dimethyl-3-[1-(trimethylsilyl)cyclobutanecarboxamido]-4,6-dihydropyrrolo[3,4-c]pyrazole-5(1H)-carboxamide, N-(2-isopropoxy-1-phenylethyl)-6,6-dimethyl-3-[1-(trimethylsilyl)cyclobutanecarboxamido]-4,6-dihydropyrrolo[3,4-c]pyrazole-5(1H)-carboxamide, 6,6-Dimethyl-N-(2-phenoxy-1-phenylethyl)-3-[1-(trimethylsilyl)cyclobutanecarboxamido]-4,6-dihydropyrrolo[3,4-c]pyrazole-5(1H)-carboxamide, (S)—N-[1-(2-chlorophenyl)-2-hydroxyethyl]-6,6-dimethyl-3-[1-(trimethylsilyl)cyclobutanecarboxamido]-4,6-dihydropyrrolo[3,4-c]pyrazole-5(1H)-carboxamide, (S)—N-[2-hydroxy-1-(o-tolyl)ethyl]-6,6-dimethyl-3-[1-(trimethylsilyl)cyclobutanecarboxamido]-4,6-dihydropyrrolo[3,4-c]pyrazole-5(1H)-carboxamide, (S)—N-(1-hydroxy-3-phenylpropan-2-yl)-6,6-dimethyl-3-[1-(trimethylsilyl)cyclobutanecarboxamido]-4,6-dihydropyrrolo[3,4-c]pyrazole-5(1H)-carboxamide, N-(2-hydroxy-3-methylbutyl)-6,6-dimethyl-3-[1-(trimethylsilyl)cyclobutanecarboxamido]-4,6-dihydropyrrolo[3,4-c]pyrazole-5(1H)-carboxamide, (R)—N-(1-hydroxy-3-phenylpropan-2-yl)-6,6-dimethyl-3-[1-(trimethylsilyl)cyclobutanecarboxamido]-4,6-dihydropyrrolo[3,4-c]pyrazole-5(1H)-carboxamide, (R)—N-(2-hydroxy-2-phenylethyl)-6,6-dimethyl-3-[1-(trimethylsilyl)cyclobutanecarboxamido]-4,6-dihydropyrrolo[3,4-c]pyrazole-5(1H)-carboxamide, (S)—N-(2-hydroxy-2-phenylethyl)-6,6-dimethyl-3-[1-(trimethylsilyl)cyclobutanecarboxamido]-4,6-dihydropyrrolo[3,4-c]pyrazole-5(1H)-carboxamide, 2-Hydroxy-2-phenylethyl 6,6-dimethyl-3-[1-(trimethylsilyl)cyclobutanecarboxamido]-4,6-dihydropyrrolo[3,4-c]pyrazole-5(1H)-carboxylate, (R)—N-[6,6-dimethyl-5-(2-phenoxypropanoyl)-1,4,5,6-tetrahydropyrrolo[3,4-c]pyrazol-3-yl]-1-(trimethylsilyl)cyclobutanecarboxamide, (S)—N-[6,6-dimethyl-5-(2-phenoxypropanoyl)-1,4,5,6-tetrahydropyrrolo[3,4-c]pyrazol-3-yl]-1-(trimethylsilyl)cyclobutanecarboxamide, N-[6,6-dimethyl-5-(2-phenoxyacetyl)-1,4,5,6-tetrahydropyrrolo[3,4-c]pyrazol-3-yl]-1-(trimethylsilyl)cyclobutanecarboxamide, (R)—N-[6,6-dimethyl-5-(2-phenoxypropanoyl)-1,4,5,6-tetrahydropyrrolo[3,4-c]pyrazol-3-yl]-1-(trimethylsilyl)cyclopropanecarboxamide, N-{5-[3-(benzyloxy)-2-phenoxypropanoyl]-6,6-dimethyl-1,4,5,6-tetrahydropyrrolo[3,4-c]pyrazol-3-yl}-1-(trimethylsilyl)cyclobutanecarboxamide, N-[5-(3-hydroxy-2-phenoxypropanoyl)-6,6-dimethyl-1,4,5,6-tetrahydropyrrolo[3,4-c]pyrazol-3-yl]-1-(trimethylsilyl)cyclobutanecarboxamide, N-{5-[2-(4-chlorophenoxy)propanoyl]-6,6-dimethyl-1,4,5,6-tetrahydropyrrolo[3,4-c]pyrazol-3-yl}-1-(trimethylsilyl)cyclobutanecarboxamide, N-{5-[2-(2-chlorophenoxy)propanoyl]-6,6-dimethyl-1,4,5,6-tetrahydropyrrolo[3,4-c]pyrazol-3-yl}-1-(trimethylsilyl)cyclobutanecarboxamide, N-{5-[2-(cyclohexyloxy)propanoyl]-6,6-dimethyl-1,4,5,6-tetrahydropyrrolo[3,4-c]pyrazol-3-yl}-1-(trimethylsilyl)cyclobutanecarboxamide, N-{5-[2-(3-chlorophenoxy)propanoyl]-6,6-dimethyl-1,4,5,6-tetrahydropyrrolo[3,4-c]pyrazol-3-yl}-1-(trimethylsilyl)cyclobutanecarboxamide, N-[5-(2-methoxypropanoyl)-6,6-dimethyl-1,4,5,6-tetrahydropyrrolo[3,4-c]pyrazol-3-yl]-1-(trimethylsilyl)cyclobutanecarboxamide, N-[5-(3-methoxy-2-phenoxypropanoyl)-6,6-dimethyl-1,4,5,6-tetrahydropyrrolo[3,4-c]pyrazol-3-yl]-1-(trimethylsilyl)cyclobutanecarboxamide, N-{6,6-dimethyl-5-[2-(pyridin-3-yloxy)propanoyl]-1,4,5,6-tetrahydropyrrolo[3,4-c]pyrazol-3-yl}-1-(trimethylsilyl)cyclobutanecarboxamide, N-{5-[3-(dimethylamino)-2-phenoxypropanoyl]-6,6-dimethyl-1,4,5,6-tetrahydropyrrolo[3,4-c]pyrazol-3-yl}-1-(trimethylsilyl)cyclobutanecarboxamide, N-[6,6-dimethyl-5-(2-phenoxy-2-phenylacetyl)-1,4,5,6-tetrahydropyrrolo[3,4-c]pyrazol-3-yl]-1-(trimethylsilyl)cyclobutanecarboxamide, N-{5-[3-(3,3-difluoropyrrolidin-1-yl)-2-phenoxypropanoyl]-6,6-dimethyl-1,4,5,6-tetrahydropyrrolo[3,4-c]pyrazol-3-yl}-1-(trimethylsilyl)cyclobutanecarboxamide, N-[5-(3-hydroxy-2-phenylpropanoyl)-6,6-dimethyl-1,4,5,6-tetrahydropyrrolo[3,4-c]pyrazol-3-yl]-1-(trimethylsilyl)cyclobutanecarboxamide, (S)—N-[5-(3-hydroxy-2-phenylpropanoyl)-6,6-dimethyl-1,4,5,6-tetrahydropyrrolo[3,4-c]pyrazol-3-yl]-1-(trimethylsilyl)cyclobutanecarboxamide, (R)—N-{5-[3-(benzyloxy)-2-phenylpropanoyl]-6,6-dimethyl-1,4,5,6-tetrahydropyrrolo[3,4-c]pyrazol-3-yl}-1-(trimethylsilyl)cyclobutanecarboxamide, (R)—N-[5-(3-hydroxy-2-phenylpropanoyl)-6,6-dimethyl-1,4,5,6-tetrahydropyrrolo[3,4-c]pyrazol-3-yl]-1-(trimethylsilyl)cyclobutanecarboxamide, (R)—N-[5-(2-methoxy-2-phenylacetyl)-6,6-dimethyl-1,4,5,6-tetrahydropyrrolo[3,4-c]pyrazol-3-yl]-1-(trimethylsilyl)cyclobutanecarboxamide, (S)—N-[5-(2-methoxy-2-phenylacetyl)-6,6-dimethyl-1,4,5,6-tetrahydropyrrolo[3,4-c]pyrazol-3-yl]-1-(trimethylsilyl)cyclobutanecarboxamide, N-[5-(3-methoxy-2-phenylpropanoyl)-6,6-dimethyl-1,4,5,6-tetrahydropyrrolo[3,4-c]pyrazol-3-yl]-1-(trimethylsilyl)cyclobutanecarboxamide, N-[5-(4-methoxy-2-phenylbutanoyl)-6,6-dimethyl-1,4,5,6-tetrahydropyrrolo[3,4-c]pyrazol-3-yl]-1-(trimethylsilyl)cyclobutanecarboxamide, (S)—N-[5-(3-hydroxy-2-phenylpropanoyl)-6,6-dimethyl-1,4,5,6-tetrahydropyrrolo[3,4-c]pyrazol-3-yl]-1-(trimethylsilyl)cyclopropanecarboxamide, (R)—N-[5-(2-methoxy-2-phenylacetyl)-6,6-dimethyl-1,4,5,6-tetrahydropyrrolo[3,4-c]pyrazol-3-yl]-1-(trimethylsilyl)cyclopropanecarboxamide, (R)—N-{5-[2-(difluoromethoxy)-2-phenylacetyl]-6,6-dimethyl-1,4,5,6-tetrahydropyrrolo[3,4-c]pyrazol-3-yl}-1-(trimethylsilyl)cyclobutanecarboxamide, (R)—N-[5-(2-ethoxy-2-phenylacetyl)-6,6-dimethyl-1,4,5,6-tetrahydropyrrolo[3,4-c]pyrazol-3-yl]-1-(trimethylsilyl)cyclobutanecarboxamide, (R)-1-(ethyldimethylsilyl)-N-[5-(2-methoxy-2-phenylacetyl)-6,6-dimethyl-1,4,5,6-tetrahydropyrrolo[3,4-c]pyrazol-3-yl]cyclobutanecarboxamide, (R)—N-[5-(2-cyclopropoxy-2-phenylacetyl)-6,6-dimethyl-1,4,5,6-tetrahydropyrrolo[3,4-c]pyrazol-3-yl]-1-(trimethylsilyl)cyclobutanecarboxamide, (R)—N-[5-(2-isopropoxy-2-phenylacetyl)-6,6-dimethyl-1,4,5,6-tetrahydropyrrolo[3,4-c]pyrazol-3-yl]-1-(trimethylsilyl)cyclobutanecarboxamide, (R)—N-{6,6-dimethyl-5-[2-phenyl-2-(trifluoromethoxy)acetyl]-1,4,5,6-tetrahydropyrrolo[3,4-c]pyrazol-3-yl}-1-(trimethylsilyl)cyclobutanecarboxamide, (R)—N-[6,6-dimethyl-5-(2-phenyl-2-propoxyacetyl)-1,4,5,6-tetrahydropyrrolo[3,4-c]pyrazol-3-yl]-1-(trimethylsilyl)cyclobutanecarboxamide, N-{5-[2-(4-fluorophenyl)-2-methoxyacetyl]-6,6-dimethyl-1,4,5,6-tetrahydropyrrolo[3,4-c]pyrazol-3-yl}-1-(trimethylsilyl)cyclobutanecarboxamide, N-{5-[2-(3-fluorophenyl)-2-methoxyacetyl]-6,6-dimethyl-1,4,5,6-tetrahydropyrrolo[3,4-c]pyrazol-3-yl}-1-(trimethylsilyl)cyclobutanecarboxamide, (R)—N-{5-[2-(2-fluorophenyl)-2-methoxyacetyl]-6,6-dimethyl-1,4,5,6-tetrahydropyrrolo[3,4-c]pyrazol-3-yl}-1-(trimethylsilyl)cyclobutanecarboxamide, N-{5-[2-methoxy-2-(thiophen-2-yl)acetyl]-6,6-dimethyl-1,4,5,6-tetrahydropyrrolo[3,4-c]pyrazol-3-yl}-1-(trimethylsilyl)cyclobutanecarboxamide, (−)-N-{5-[2-methoxy-2-(thiophen-2-yl)acetyl]-6,6-dimethyl-1,4,5,6-tetrahydropyrrolo[3,4-c]pyrazol-3-yl}-1-(trimethylsilyl)cyclobutanecarboxamide, (+)-N-{5-[2-methoxy-2-(thiophen-2-yl)acetyl]-6,6-dimethyl-1,4,5,6-tetrahydropyrrolo[3,4-c]pyrazol-3-yl}-1-(trimethylsilyl)cyclobutanecarboxamide, N-{[1-(hydroxymethyl)cyclobutyl](phenyl)methyl}-6,6-dimethyl-3-[1-(trimethylsilyl)cyclobutanecarboxamido]-4,6-dihydropyrrolo[3,4-c]pyrazole-5(1H)-carboxamide, (R)—N-[2-(1-hydroxycyclopropyl)-1-phenylethyl]-6,6-dimethyl-3-[1-(trimethylsilyl)cyclobutanecarboxamido]-4,6-dihydropyrrolo[3,4-c]pyrazole-5(1H)-carboxamide, (R)—N-(3-ethyl-3-hydroxy-1-phenylpentyl)-6,6-dimethyl-3-[1-(trimethylsilyl)cyclobutanecarboxamido]-4,6-dihydropyrrolo[3,4-c]pyrazole-5(1H)-carboxamide, (R)—N-[1-(4-fluorophenyl)-3-hydroxy-3-methylbutyl]-6,6-dimethyl-3-[1-(trimethylsilyl)cyclobutanecarboxamido]-4,6-dihydropyrrolo[3,4-c]pyrazole-5(1H)-carboxamide, (R)—N-[1-(3-fluorophenyl)-3-hydroxy-3-methylbutyl]-6,6-dimethyl-3-[1-(trimethylsilyl)cyclobutanecarboxamido]-4,6-dihydropyrrolo[3,4-c]pyrazole-5(1H)-carboxamide, (R)—N-[1-(2-fluorophenyl)-3-hydroxy-3-methylbutyl]-6,6-dimethyl-3-[1-(trimethylsilyl)cyclobutanecarboxamido]-4,6-dihydropyrrolo[3,4-c]pyrazole-5(1H)-carboxamide, (R)—N-(5-hydroxy-2,5-dimethylhexan-3-yl)-6,6-dimethyl-3-[1-(trimethylsilyl)cyclobutanecarboxamido]-4,6-dihydropyrrolo[3,4-c]pyrazole-5(1H)-carboxamide, N-[1-(4-fluorophenyl)-3-hydroxy2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide, N-[1-(3-fluorophenyl)-3-hydroxy-2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide, (−)-N-[1-(3-fluorophenyl)-3-hydroxy-2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide, (+)-N-[1-(3-fluorophenyl)-3-hydroxy-2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide, N-[1-(2-fluorophenyl)-3-hydroxy-2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide, N-(1-hydroxy-2,2,4-trimethylpentan-3-yl)-6,6-dimethyl-3-[1-(trimethylsilyl)cyclobutanecarboxamido]-4,6-dihydropyrrolo[3,4-c]pyrazole-5(1H)-carboxamide, (R)—N-(3-hydroxy-3-methyl-1-phenylbutyl)-6,6-dimethyl-3-[1-(trimethylsilyl)cyclopropanecarboxamido]-4,6-dihydropyrrolo[3,4-c]pyrazole-5(1H)-carboxamide, N-(3-hydroxy-2,2-dimethyl-1-phenylpropyl)-6,6-dimethyl-3-[1-(trimethylsilyl)cyclopropanecarboxamido]-4,6-dihydropyrrolo[3,4-c]pyrazole-5(1H)-carboxamide, (−)-N-(3-hydroxy-2,2-dimethyl-1-phenylpropyl)-6,6-dimethyl-3-[1-(trimethylsilyl)cyclobutanecarboxamido]-4,6-dihydropyrrolo[3,4-c]pyrazole-5(1H)-carboxamide, (+)-N-(3-hydroxy-2,2-dimethyl-1-phenylpropyl)-6,6-dimethyl-3-[1-(trimethylsilyl)cyclobutanecarboxamido]-4,6-dihydropyrrolo[3,4-c]pyrazole-5(1H)-carboxamide, (R)—N-[5-(2-butoxy-2-phenylacetyl)-6,6-dimethyl-1,4,5,6-tetrahydropyrrolo[3,4-c]pyrazol-3-yl]-1-(trimethylsilyl)cyclobutanecarboxamide, and N-(3-methoxy-2,2-dimethyl-1-phenylpropyl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof.

[12]
(R)—N-[1-(4-fluorophenyl)-3-hydroxy-3-methylbutyl]-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof.

[13]
(−)-N-(3-hydroxy-2,2-dimethyl-1-phenylpropyl)-6,6-dimethyl-3-[1-(trimethylsilyl)cyclopropane-1-carboxamido]-4,6-dihydropyrrolo[3,4-c]pyrazole-5(1H)-carboxamide or a pharmacologically acceptable salt thereof.

[14]
(R)—N-[5-(2-methoxy-2-phenylacetyl)-6,6-dimethyl-1,4,5,6-tetrahydropyrrolo[3,4-c]pyrazol-3-yl]-1-(trimethylsilyl)cyclobutanecarboxamide or a pharmacologically acceptable salt thereof.

[15]
(R)—N-[6,6-dimethyl-5-(2-phenyl-2-propoxyacetyl)-1,4,5,6-tetrahydropyrrolo[3,4-c]pyrazol-3-yl]-1-(trimethylsilyl)cyclobutanecarboxamide or a pharmacologically acceptable salt thereof.

[16]
(R)—N-{5-[2-(2-fluorophenyl)-2-methoxyacetyl]-6,6-dimethyl-1,4,5,6-tetrahydropyrrolo[3,4-c]pyrazol-3-yl}-1-(trimethylsilyl)cyclobutanecarboxamide or a pharmacologically acceptable salt thereof.

[17]
(R)—N-[5-(2-ethoxy-2-phenylacetyl)-6,6-dimethyl-1,4,5,6-tetrahydropyrrolo[3,4-c]pyrazol-3-yl]-1-(trimethylsilyl)cyclobutanecarboxamide or a pharmacologically acceptable salt thereof.

[18]
(R)—N-[5-(2-cyclopropoxy-2-phenylacetyl)-6,6-dimethyl-1,4,5,6-tetrahydropyrrolo[3,4-c]pyrazol-3-yl]-1-(trimethylsilyl)cyclobutanecarboxamide or a pharmacologically acceptable salt thereof.

[19]
(R)—N-[5-(2-isopropoxy-2-phenylacetyl)-6,6-dimethyl-1,4,5,6-tetrahydropyrrolo[3,4-c]pyrazol-3-yl]-1-(trimethylsilyl)cyclobutanecarboxamide or a pharmacologically acceptable salt thereof.

[20]
(+)-N-{5-[2-methoxy-2-(thiophen-2-yl)acetyl]-6,6-dimethyl-1,4,5,6-tetrahydropyrrolo[3,4-c]pyrazol-3-yl}-1-(trimethylsilyl)cyclobutanecarboxamide or a pharmacologically acceptable salt thereof.

[21]
(−)-N-[1-(3-fluorophenyl)-3-hydroxy-2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof.

[22]
N-{5-[2-(3-fluorophenyl)-2-methoxyacetyl]-6,6-dimethyl-1,4,5,6-tetrahydropyrrolo[3,4-c]pyrazol-3-yl}-1-(trimethylsilyl)cyclobutanecarboxamide or a pharmacologically acceptable salt thereof.

[23]
N-[1-(4-fluorophenyl)-3-hydroxy-2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof.

[24]
(R)—N-[1-(3-fluorophenyl)-3-hydroxy-3-methylbutyl]-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof.

[25]
(R)—N-{6,6-dimethyl-5-[2-phenyl-2-(trifluoromethoxy)acetyl]-1,4,5,6-tetrahydropyrrolo[3,4-c]pyrazol-3-yl}-1-(trimethylsilyl)cyclobutanecarboxamide or a pharmacologically acceptable salt thereof.

[26]
(R)—N-[2-(1-hydroxycyclopropyl)-1-phenylethyl]-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof.

[27]
(R)—N-(3-hydroxy-3-methyl-1-phenylbutyl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof.

[28]
(R)—N-[5-(2-methoxy-2-phenylacetyl)-6,6-dimethyl-1,4,5,6-tetrahydropyrrolo[3,4-c]pyrazol-3-yl]-1-(trimethylsilyl)cyclopropanecarboxamide or a pharmacologically acceptable salt thereof.

[29]
(R)—N-{5-[2-(difluoromethoxy)-2-phenylacetyl]-6,6-dimethyl-1,4,5,6-tetrahydropyrrolo[3,4-c]pyrazol-3-yl}-1-(trimethylsilyl)cyclobutanecarboxamide or a pharmacologically acceptable salt thereof.

[30]
(R)-1-(ethyldimethylsilyl)-N-[5-(2-methoxy-2-phenylacetyl)-6,6-dimethyl-1,4,5,6-tetrahydropyrrolo[3,4-c]pyrazol-3-yl]cyclobutanecarboxamide or a pharmacologically acceptable salt thereof.

[31]
N-{[1-(hydroxymethyl)cyclobutyl](phenyl)methyl}-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof.

[32] A pharmaceutical composition comprising the compound or a pharmacologically acceptable salt thereof according to any of [1] to [31].

[33] The pharmaceutical composition according to [32], wherein the pharmaceutical composition is a CDK7 inhibitor or a prophylactic agent.

[34] The pharmaceutical composition according to [32] or [33], wherein the pharmaceutical composition is for treating or preventing a cancer or an inflammatory disease.

[35] The pharmaceutical composition according to [34], wherein the inflammatory disease is an autoimmune disease.

[36] The pharmaceutical composition according to [35], wherein the autoimmune disease is rheumatoid arthritis or psoriasis.

[37] A method for treating or preventing a cancer or an inflammatory disease, comprising administering the compound or the pharmacologically acceptable salt thereof according to any of [1] to [31] to a subject in need thereof.

[38] The method according to [37], wherein the inflammatory disease is an autoimmune disease.

[39] The method according to [38], wherein the autoimmune disease is rheumatoid arthritis or psoriasis.

[40] Use of the compound or the pharmacologically acceptable salt thereof according to any of [1] to [31] for the production of a pharmaceutical composition which is a CDK7 inhibitor or a prophylactic agent.

[41] Use of the compound or the pharmacologically acceptable salt thereof according to any of [1] to [31] for inhibiting CDK7.

[42] Use of the compound or the pharmacologically acceptable salt thereof according to any of [1] to [31] for treating or preventing a cancer or an inflammatory disease.

[43] Use according to [42], wherein the inflammatory disease is an autoimmune disease.

[44] Use according to [43], wherein the autoimmune disease is rheumatoid arthritis or psoriasis.

[45] The compound or the pharmacologically acceptable salt thereof according to any of [1] to [31] for use as an active ingredient for a pharmaceutical composition.

[46] The compound or the pharmacologically acceptable salt thereof according to [45], wherein the pharmaceutical composition is a pharmaceutical composition for the treatment of a cancer or an inflammatory disease.

[47] The compound or the pharmacologically acceptable salt thereof according to [46], wherein the inflammatory disease is an autoimmune disease.

[48] The compound or the pharmacologically acceptable salt thereof according to [47], wherein the autoimmune disease is rheumatoid arthritis or psoriasis.

Specific examples of the compound represented by formula (I) of the present invention can include compounds as shown in Tables 1 to 164 described below. In Tables 1 to 164 described below, Me represents a methyl group, Et represents an ethyl group, nPr represents a n-propyl group, iPr represents an isopropyl group, cPr represents a cyclopropyl group, nBu represents a n-butyl group, iBu represents an isobutyl group, tBu represents a tert-butyl group, cHex represents a cyclohexyl group, Ph represents a phenyl group, 2-F-Ph represents a 2-fluorophenyl group, 3-F-Ph represents a 3-fluorophenyl group, 4-F-Ph represents a 4-fluorophenyl group, 2-Cl-Ph represents a 2-chlorophenyl group, 3-Cl-Ph represents a 3-chlorophenyl group, 4-Cl-Ph represents a 4-chlorophenyl group, 2-Me-Ph represents a 2-methylphenyl group, 3-Me-Ph represents a 3-methylphenyl group, 4-Me-Ph represents a 4-methylphenyl group, 2-Py represents a 2-pyridyl group, 3-Py represents a 3-pyridyl group, 4-Py represents a 4-pyridyl group, Bn represents a benzyl group, "-" represents a single bond, "(R)—" and "(S)—" each represent the configuration of a carbon atom with "*" in the following formulas (I), (II), (III), (IV), (Va), (Vb), (Vc), (VIa), (VIb), and (VIc), "racemic" represents being a racemate, "(+)" represents being a dextrorotatory optically active form, and "(−)" represents being a levorotatory optically active form. As for each chemical structure described as $L^1$, $L^2$, or $L^3$ in the tables, the atom positioned on the left side of the chemical structure binds to a silicon atom, a carbonyl group, or a carbon atom with "*" in the corresponding formula. In the case of, for example, a compound of compound No. I-21, $CH_2$—$C(Me)_2$ corresponding to $L^1$ means that the methylene carbon atom ($CH_2$) binds to a silicon atom and the quaternary carbon atom (C) binds to a carbonyl group, and C≡$CCH_2$ corresponding to $L^3$ means that the quaternary carbon atom (C) binds to a carbon atom with "*" and the methylene carbon atom ($CH_2$) binds to an oxygen atom adjacent to $R^5$.

TABLE 1

(I)

| Compound No. | $R^1$ | $R^2$ | $R^3$ | $L^1$ | $L^2$ | $R^4$ | $L^3$ | $R^5$ | Configuration |
|---|---|---|---|---|---|---|---|---|---|
| I-1 | Me | Me | Me | $CH_2$ | O | Ph | $CH_2$ | H | racemic |
| I-2 | Me | Me | Me | $CH_2$ | O | Ph | $CH_2$ | H | (S)- |
| I-3 | Me | Me | Me | $CH_2$ | O | Ph | $CH_2$ | Me | racemic |
| I-4 | Me | Me | Me | $CH_2$ | O | Ph | $CH_2$ | Me | (S)- |
| I-5 | Me | Me | Me | $CH_2$ | O | Ph | $(CH_2)_2$ | H | racemic |
| I-6 | Me | Me | Me | $CH_2$ | O | Ph | $(CH_2)_2$ | H | (R)- |
| I-7 | Me | Me | Me | $CH_2$ | O | Ph | $(CH_2)_2$ | Me | racemic |
| I-8 | Me | Me | Me | $CH_2$ | O | Ph | $(CH_2)_2$ | Me | (R)- |
| I-9 | Me | Me | Me | $CH_2$ | O | Ph | C≡$CCH_2$ | H | racemic |
| I-10 | Me | Me | Me | $CH_2$ | O | Ph | C≡$CCH_2$ | H | (S)- |
| I-11 | Me | Me | Me | $CH_2$ | O | Ph | C≡$CCH_2$ | Me | racemic |
| I-12 | Me | Me | Me | $CH_2$ | O | Ph | C≡$CCH_2$ | Me | (S)- |
| I-13 | Me | Me | Me | $CH_2C(Me)_2$ | O | Ph | $CH_2$ | H | racemic |
| I-14 | Me | Me | Me | $CH_2C(Me)_2$ | O | Ph | $CH_2$ | H | (S)- |
| I-15 | Me | Me | Me | $CH_2C(Me)_2$ | O | Ph | $CH_2$ | Me | racemic |
| I-16 | Me | Me | Me | $CH_2C(Me)_2$ | O | Ph | $CH_2$ | Me | (S)- |
| I-17 | Me | Me | Me | $CH_2C(Me)_2$ | O | Ph | $(CH_2)_2$ | H | racemic |
| I-18 | Me | Me | Me | $CH_2C(Me)_2$ | O | Ph | $(CH_2)_2$ | H | (R)- |
| I-19 | Me | Me | Me | $CH_2C(Me)_2$ | O | Ph | $(CH_2)_2$ | Me | racemic |
| I-20 | Me | Me | Me | $CH_2C(Me)_2$ | O | Ph | $(CH_2)_2$ | Me | (R)- |
| I-21 | Me | Me | Me | $CH_2C(Me)_2$ | O | Ph | C≡$CCH_2$ | H | racemic |
| I-22 | Me | Me | Me | $CH_2C(Me)_2$ | O | Ph | C≡$CCH_2$ | H | (S)- |
| I-23 | Me | Me | Me | $CH_2C(Me)_2$ | O | Ph | C≡$CCH_2$ | Me | racemic |
| I-24 | Me | Me | Me | $CH_2C(Me)_2$ | O | Ph | C≡$CCH_2$ | Me | (S)- |
| I-25 | Me | Me | Me | $CH_2CH$=$CH$ | O | Ph | $CH_2$ | H | racemic |
| I-26 | Me | Me | Me | $CH_2CH$=$CH$ | O | Ph | $CH_2$ | H | (S)- |
| I-27 | Me | Me | Me | $CH_2CH$=$CH$ | O | Ph | $CH_2$ | Me | racemic |
| I-28 | Me | Me | Me | $CH_2CH$=$CH$ | O | Ph | $CH_2$ | Me | (S)- |
| I-29 | Me | Me | Me | $CH_2CH$=$CH$ | O | Ph | $(CH_2)_2$ | H | racemic |
| I-30 | Me | Me | Me | $CH_2CH$=$CH$ | O | Ph | $(CH_2)_2$ | H | (R)- |
| I-31 | Me | Me | Me | $CH_2CH$=$CH$ | O | Ph | $(CH_2)_2$ | Me | racemic |
| I-32 | Me | Me | Me | $CH_2CH$=$CH$ | O | Ph | $(CH_2)_2$ | Me | (R)- |
| I-33 | Me | Me | Me | $CH_2CH$=$CH$ | O | Ph | C≡$CCH_2$ | H | racemic |
| I-34 | Me | Me | Me | $CH_2CH$=$CH$ | O | Ph | C≡$CCH_2$ | H | (S)- |
| I-35 | Me | Me | Me | $CH_2CH$=$CH$ | O | Ph | C≡$CCH_2$ | Me | racemic |
| I-36 | Me | Me | Me | $CH_2CH$=$CH$ | O | Ph | C≡$CCH_2$ | Me | (S)- |
| I-37 | Me | Me | Me | $CH_2C$≡$C$ | O | Ph | $CH_2$ | H | racemic |
| I-38 | Me | Me | Me | $CH_2C$≡$C$ | O | Ph | $CH_2$ | H | (S)- |
| I-39 | Me | Me | Me | $CH_2C$≡$C$ | O | Ph | $CH_2$ | Me | racemic |
| I-40 | Me | Me | Me | $CH_2C$≡$C$ | O | Ph | $CH_2$ | Me | (S)- |
| I-41 | Me | Me | Me | $CH_2C$≡$C$ | O | Ph | $(CH_2)_2$ | H | racemic |
| I-42 | Me | Me | Me | $CH_2C$≡$C$ | O | Ph | $(CH_2)_2$ | H | (R)- |
| I-43 | Me | Me | Me | $CH_2C$≡$C$ | O | Ph | $(CH_2)_2$ | Me | racemic |
| I-44 | Me | Me | Me | $CH_2C$≡$C$ | O | Ph | $(CH_2)_2$ | Me | (R)- |
| I-45 | Me | Me | Me | $CH_2C$≡$C$ | O | Ph | C≡$CCH_2$ | H | racemic |
| I-46 | Me | Me | Me | $CH_2C$≡$C$ | O | Ph | C≡$CCH_2$ | H | (S)- |
| I-47 | Me | Me | Me | $CH_2C$≡$C$ | O | Ph | C≡$CCH_2$ | Me | racemic |
| I-48 | Me | Me | Me | $CH_2C$≡$C$ | O | Ph | C≡$CCH_2$ | Me | (S)- |
| I-49 | Me | Me | Me | 1,2-Cyclopropylene | O | Ph | $CH_2$ | H | racemic |
| I-50 | Me | Me | Me | 1,2-Cyclopropylene | O | Ph | $CH_2$ | H | (S)- |

TABLE 2

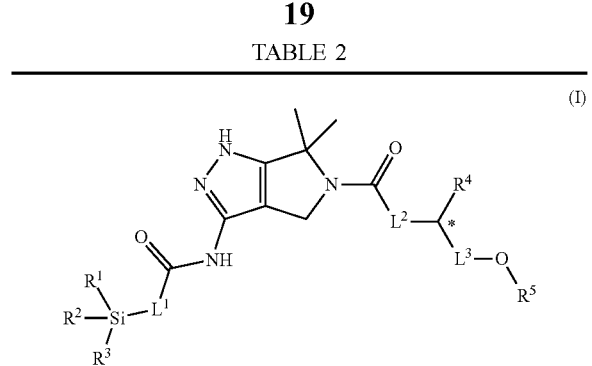

(I)

| Compound No. | R¹ | R² | R³ | L¹ | L² | R⁴ | L³ | R⁵ | Configuration |
|---|---|---|---|---|---|---|---|---|---|
| I-51 | Me | Me | Me | 1,2-Cyclopropylene | O | Ph | $CH_2$ | Me | racemic |
| I-52 | Me | Me | Me | 1,2-Cyclopropylene | O | Ph | $CH_2$ | Me | (S)- |
| I-53 | Me | Me | Me | 1,2-Cyclopropylene | O | Ph | $(CH_2)_2$ | H | racemic |
| I-54 | Me | Me | Me | 1,2-Cyclopropylene | O | Ph | $(CH_2)_2$ | H | (R)- |
| I-55 | Me | Me | Me | 1,2-Cyclopropylene | O | Ph | $(CH_2)_2$ | Me | racemic |
| I-56 | Me | Me | Me | 1,2-Cyclopropylene | O | Ph | $(CH_2)_2$ | Me | (R)- |
| I-57 | Me | Me | Me | 1,2-Cyclopropylene | O | Ph | $C\equiv CCH_2$ | H | racemic |
| I-58 | Me | Me | Me | 1,2-Cyclopropylene | O | Ph | $C\equiv CCH_2$ | H | (S)- |
| I-59 | Me | Me | Me | 1,2-Cyclopropylene | O | Ph | $C\equiv CCH_2$ | Me | racemic |
| I-60 | Me | Me | Me | 1,2-Cyclopropylene | O | Ph | $C\equiv CCH_2$ | Me | (S)- |
| I-61 | Me | Me | Me | 5,5-Spiro[2.3]hexylene | O | Ph | $CH_2$ | H | racemic |
| I-62 | Me | Me | Me | 5,5-Spiro[2.3]hexylene | O | Ph | $CH_2$ | H | (S)- |
| I-63 | Me | Me | Me | 5,5-Spiro[2.3]hexylene | O | Ph | $CH_2$ | Me | racemic |
| I-64 | Me | Me | Me | 5,5-Spiro[2.3]hexylene | O | Ph | $CH_2$ | Me | (S)- |
| I-65 | Me | Me | Me | 5,5-Spiro[2.3]hexylene | O | Ph | $(CH_2)_2$ | H | racemic |
| I-66 | Me | Me | Me | 5,5-Spiro[2.3]hexylene | O | Ph | $(CH_2)_2$ | H | (R)- |
| I-67 | Me | Me | Me | 5,5-Spiro[2.3]hexylene | O | Ph | $(CH_2)_2$ | Me | racemic |
| I-68 | Me | Me | Me | 5,5-Spiro[2.3]hexylene | O | Ph | $(CH_2)_2$ | Me | (R)- |
| I-69 | Me | Me | Me | 5,5-Spiro[2.3]hexylene | O | Ph | $C\equiv CCH_2$ | H | racemic |
| I-70 | Me | Me | Me | 5,5-Spiro[2.3]hexylene | O | Ph | $C\equiv CCH_2$ | H | (S)- |
| I-71 | Me | Me | Me | 5,5-Spiro[2.3]hexylene | O | Ph | $C\equiv CCH_2$ | Me | racemic |
| I-72 | Me | Me | Me | 5,5-Spiro[2.3]hexylene | O | Ph | $C\equiv CCH_2$ | Me | (S)- |
| I-73 | Me | Me | Me | 4,4-Cyclopentenylene | O | Ph | $CH_2$ | H | racemic |
| I-74 | Me | Me | Me | 4,4-Cyclopentenylene | O | Ph | $CH_2$ | H | (S)- |
| I-75 | Me | Me | Me | 4,4-Cyclopentenylene | O | Ph | $CH_2$ | Me | racemic |
| I-76 | Me | Me | Me | 4,4-Cyclopentenylene | O | Ph | $CH_2$ | Me | (S)- |
| I-77 | Me | Me | Me | 4,4-Cyclopentenylene | O | Ph | $(CH_2)_2$ | H | racemic |
| I-78 | Me | Me | Me | 4,4-Cyclopentenylene | O | Ph | $(CH_2)_2$ | H | (R)- |
| I-79 | Me | Me | Me | 4,4-Cyclopentenylene | O | Ph | $(CH_2)_2$ | Me | racemic |
| I-80 | Me | Me | Me | 4,4-Cyclopentenylene | O | Ph | $(CH_2)_2$ | Me | (R)- |
| I-81 | Me | Me | Me | 4,4-Cyclopentenylene | O | Ph | $C\equiv CCH_2$ | H | racemic |
| I-82 | Me | Me | Me | 4,4-Cyclopentenylene | O | Ph | $C\equiv CCH_2$ | H | (S)- |
| I-83 | Me | Me | Me | 4,4-Cyclopentenylene | O | Ph | $C\equiv CCH_2$ | Me | racemic |
| I-84 | Me | Me | Me | 4,4-Cyclopentenylene | O | Ph | $C\equiv CCH_2$ | Me | (S)- |
| I-85 | Me | Me | Me | $CH_2$ | NH | Ph | $CH_2$ | H | racemic |
| I-86 | Me | Me | Me | $CH_2$ | NH | Ph | $CH_2$ | H | (S)- |
| I-87 | Me | Me | Me | $CH_2$ | NH | Ph | $CH_2$ | Me | racemic |
| I-88 | Me | Me | Me | $CH_2$ | NH | Ph | $CH_2$ | Me | (S)- |
| I-89 | Me | Me | Me | $CH_2$ | NH | Ph | $(CH_2)_2$ | H | racemic |
| I-90 | Me | Me | Me | $CH_2$ | NH | Ph | $(CH_2)_2$ | H | (R)- |
| I-91 | Me | Me | Me | $CH_2$ | NH | Ph | $(CH_2)_2$ | Me | racemic |
| I-92 | Me | Me | Me | $CH_2$ | NH | Ph | $(CH_2)_2$ | Me | (R)- |
| I-93 | Me | Me | Me | $CH_2$ | NH | Ph | $C\equiv CCH_2$ | H | racemic |
| I-94 | Me | Me | Me | $CH_2$ | NH | Ph | $C\equiv CCH_2$ | H | (S)- |
| I-95 | Me | Me | Me | $CH_2$ | NH | Ph | $C\equiv CCH_2$ | Me | racemic |
| I-96 | Me | Me | Me | $CH_2$ | NH | Ph | $C\equiv CCH_2$ | Me | (S)- |
| I-97 | Me | Me | Me | $CH_2C(Me)_2$ | NH | Ph | $CH_2$ | H | racemic |
| I-98 | Me | Me | Me | $CH_2C(Me)_2$ | NH | Ph | $CH_2$ | H | (S)- |
| I-99 | Me | Me | Me | $CH_2C(Me)_2$ | NH | Ph | $CH_2$ | Me | racemic |
| I-100 | Me | Me | Me | $CH_2C(Me)_2$ | NH | Ph | $CH_2$ | Me | (S)- |

TABLE 3

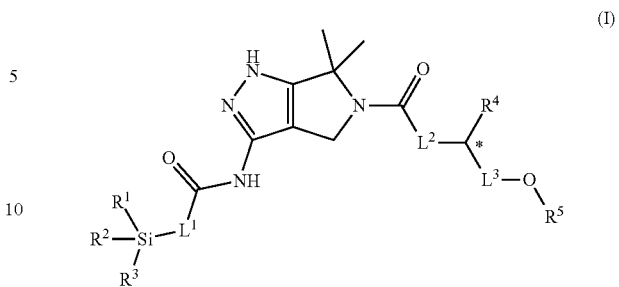

(I)

| Compound No. | R¹ | R² | R³ | L¹ | L² | R⁴ | L³ | R⁵ | Configuration |
|---|---|---|---|---|---|---|---|---|---|
| I-101 | Me | Me | Me | $CH_2C(Me)_2$ | NH | Ph | $(CH_2)_2$ | H | racemic |
| I-102 | Me | Me | Me | $CH_2C(Me)_2$ | NH | Ph | $(CH_2)_2$ | H | (R)- |
| I-103 | Me | Me | Me | $CH_2C(Me)_2$ | NH | Ph | $(CH_2)_2$ | Me | racemic |

TABLE 3-continued (I)

| Compound No. | R¹ | R² | R³ | L¹ | L² | R⁴ | L³ | R⁵ | Configuration |
|---|---|---|---|---|---|---|---|---|---|
| I-104 | Me | Me | Me | CH₂C(Me)₂ | NH | Ph | (CH₂)₂ | Me | (R)- |
| I-105 | Me | Me | Me | CH₂C(Me)₂ | NH | Ph | C=CH₂ | H | racemic |
| I-106 | Me | Me | Me | CH₂C(Me)₂ | NH | Ph | C=CH₂ | H | (S)- |
| I-107 | Me | Me | Me | CH₂C(Me)₂ | NH | Ph | C=CH₂ | Me | racemic |
| I-108 | Me | Me | Me | CH₂C(Me)₂ | NH | Ph | C=CH₂ | Me | (S)- |
| I-109 | Me | Me | Me | CH₂CH=CH | NH | Ph | CH₂ | H | racemic |
| I-110 | Me | Me | Me | CH₂CH=CH | NH | Ph | CH₂ | H | (S)- |
| I-111 | Me | Me | Me | CH₂CH=CH | NH | Ph | CH₂ | Me | racemic |
| I-112 | Me | Me | Me | CH₂CH=CH | NH | Ph | CH₂ | Me | (S)- |
| I-113 | Me | Me | Me | CH₂CH=CH | NH | Ph | (CH₂)₂ | H | racemic |
| I-114 | Me | Me | Me | CH₂CH=CH | NH | Ph | (CH₂)₂ | H | (R)- |
| I-115 | Me | Me | Me | CH₂CH=CH | NH | Ph | (CH₂)₂ | Me | racemic |
| I-116 | Me | Me | Me | CH₂CH=CH | NH | Ph | (CH₂)₂ | Me | (R)- |
| I-117 | Me | Me | Me | CH₂CH=CH | NH | Ph | C=CH₂ | H | racemic |
| I-118 | Me | Me | Me | CH₂CH=CH | NH | Ph | C=CH₂ | H | (S)- |
| I-119 | Me | Me | Me | CH₂CH=CH | NH | Ph | C=CH₂ | Me | racemic |
| I-120 | Me | Me | Me | CH₂CH=CH | NH | Ph | C=CH₂ | Me | (S)- |
| I-121 | Me | Me | Me | CH₂C≡C | NH | Ph | CH₂ | H | racemic |
| I-122 | Me | Me | Me | CH₂C≡C | NH | Ph | CH₂ | H | (S)- |
| I-123 | Me | Me | Me | CH₂C≡C | NH | Ph | CH₂ | Me | racemic |
| I-124 | Me | Me | Me | CH₂C≡C | NH | Ph | CH₂ | Me | (S)- |
| I-125 | Me | Me | Me | CH₂C≡C | NH | Ph | (CH₂)₂ | H | racemic |
| I-126 | Me | Me | Me | CH₂C≡C | NH | Ph | (CH₂)₂ | H | (R)- |
| I-127 | Me | Me | Me | CH₂C≡C | NH | Ph | (CH₂)₂ | Me | racemic |
| I-128 | Me | Me | Me | CH₂C≡C | NH | Ph | (CH₂)₂ | Me | (R)- |
| I-129 | Me | Me | Me | CH₂C≡C | NH | Ph | C=CH₂ | H | racemic |
| I-130 | Me | Me | Me | CH₂C≡C | NH | Ph | C=CH₂ | H | (S)- |
| I-131 | Me | Me | Me | CH₂C≡C | NH | Ph | C=CH₂ | Me | racemic |
| I-132 | Me | Me | Me | CH₂C≡C | NH | Ph | C=CH₂ | Me | (S)- |
| I-133 | Me | Me | Me | 1,2-Cyclopropylene | NH | Ph | CH₂ | H | racemic |
| I-134 | Me | Me | Me | 1,2-Cyclopropylene | NH | Ph | CH₂ | H | (S)- |
| I-135 | Me | Me | Me | 1,2-Cyclopropylene | NH | Ph | CH₂ | Me | racemic |
| I-136 | Me | Me | Me | 1,2-Cyclopropylene | NH | Ph | CH₂ | Me | (S)- |
| I-137 | Me | Me | Me | 1,2-Cyclopropylene | NH | Ph | (CH₂)₂ | H | racemic |
| I-138 | Me | Me | Me | 1,2-Cyclopropylene | NH | Ph | (CH₂)₂ | H | (R)- |
| I-139 | Me | Me | Me | 1,2-Cyclopropylene | NH | Ph | (CH₂)₂ | Me | racemic |
| I-140 | Me | Me | Me | 1,2-Cyclopropylene | NH | Ph | (CH₂)₂ | Me | (R)- |
| I-141 | Me | Me | Me | 1,2-Cyclopropylene | NH | Ph | C=CH₂ | H | racemic |
| I-142 | Me | Me | Me | 1,2-Cyclopropylene | NH | Ph | C=CH₂ | H | (S)- |
| I-143 | Me | Me | Me | 1,2-Cyclopropylene | NH | Ph | C=CH₂ | Me | racemic |
| I-144 | Me | Me | Me | 1,2-Cyclopropylene | NH | Ph | C=CH₂ | Me | (S)- |
| I-145 | Me | Me | Me | 5,5-Spiro[2.3]hexylene | NH | Ph | CH₂ | H | racemic |
| I-146 | Me | Me | Me | 5,5-Spiro[2.3]hexylene | NH | Ph | CH₂ | H | (S)- |
| I-147 | Me | Me | Me | 5,5-Spiro[2.3]hexylene | NH | Ph | CH₂ | Me | racemic |
| I-148 | Me | Me | Me | 5,5-Spiro[2.3]hexylene | NH | Ph | CH₂ | Me | (S)- |
| I-149 | Me | Me | Me | 5,5-Spiro[2.3]hexylene | NH | Ph | (CH₂)₂ | H | racemic |
| I-150 | Me | Me | Me | 5,5-Spiro[2.3]hexylene | NH | Ph | (CH₂)₂ | H | (R)- |

TABLE 4

(I)

| Compound No. | R¹ | R² | R³ | L¹ | L² | R⁴ | L³ | R⁵ | Configuration |
|---|---|---|---|---|---|---|---|---|---|
| I-151 | Me | Me | Me | 5,5-Spiro[2.3]hexylene | NH | Ph | (CH₂)₂ | Me | racemic |
| I-152 | Me | Me | Me | 5,5-Spiro[2.3]hexylene | NH | Ph | (CH₂)₂ | Me | (R)- |
| I-153 | Me | Me | Me | 5,5-Spiro[2.3]hexylene | NH | Ph | C=CH₂ | H | racemic |
| I-154 | Me | Me | Me | 5,5-Spiro[2.3]hexylene | NH | Ph | C=CH₂ | H | (S)- |
| I-155 | Me | Me | Me | 5,5-Spiro[2.3]hexylene | NH | Ph | C=CH₂ | Me | racemic |
| I-156 | Me | Me | Me | 5,5-Spiro[2.3]hexylene | NH | Ph | C=CH₂ | Me | (S)- |
| I-157 | Me | Me | Me | 4,4-Cyclopentenylene | NH | Ph | CH₂ | H | racemic |
| I-158 | Me | Me | Me | 4,4-Cyclopentenylene | NH | Ph | CH₂ | H | (S)- |
| I-159 | Me | Me | Me | 4,4-Cyclopentenylene | NH | Ph | CH₂ | Me | racemic |
| I-160 | Me | Me | Me | 4,4-Cyclopentenylene | NH | Ph | CH₂ | Me | (S)- |
| I-161 | Me | Me | Me | 4,4-Cyclopentenylene | NH | Ph | (CH₂)₂ | H | racemic |
| I-162 | Me | Me | Me | 4,4-Cyclopentenylene | NH | Ph | (CH₂)₂ | H | (R)- |
| I-163 | Me | Me | Me | 4,4-Cyclopentenylene | NH | Ph | (CH₂)₂ | Me | racemic |
| I-164 | Me | Me | Me | 4,4-Cyclopentenylene | NH | Ph | (CH₂)₂ | Me | (R)- |

TABLE 4-continued (I)

| Compound No. | R¹ | R² | R³ | L¹ | L² | R⁴ | L³ | R⁵ | Configuration |
|---|---|---|---|---|---|---|---|---|---|
| I-165 | Me | Me | Me | 4,4-Cyclopentenylene | NH | Ph | C≡CCH$_2$ | H | racemic |
| I-166 | Me | Me | Me | 4,4-Cyclopentenylene | NH | Ph | C≡CCH$_2$ | H | (S)- |
| I-167 | Me | Me | Me | 4,4-Cyclopentenylene | NH | Ph | C≡CCH$_2$ | Me | racemic |
| I-168 | Me | Me | Me | 4,4-Cyclopentenylene | NH | Ph | C≡CCH$_2$ | Me | (S)- |
| I-169 | Me | Me | Me | CH$_2$ | CH$_2$ | Ph | CH$_2$ | H | racemic |
| I-170 | Me | Me | Me | CH$_2$ | CH$_2$ | Ph | CH$_2$ | H | (S)- |
| I-171 | Me | Me | Me | CH$_2$ | CH$_2$ | Ph | — | H | racemic |
| I-172 | Me | Me | Me | CH$_2$ | CH$_2$ | Ph | — | H | (S)- |
| I-173 | Me | Me | Me | CH$_2$ | CH$_2$ | Ph | CH$_2$ | Me | racemic |
| I-174 | Me | Me | Me | CH$_2$ | CH$_2$ | Ph | CH$_2$ | Me | (S)- |
| I-175 | Me | Me | Me | CH$_2$ | CH$_2$ | Ph | C(Me)$_2$ | H | racemic |
| I-176 | Me | Me | Me | CH$_2$ | CH$_2$ | Ph | C(Me)$_2$ | H | (S)- |
| I-177 | Me | Me | Me | CH$_2$ | CH$_2$ | Ph | C(Me)$_2$ | Me | racemic |
| I-178 | Me | Me | Me | CH$_2$ | CH$_2$ | Ph | C(Me)$_2$ | Me | (S)- |
| I-179 | Me | Me | Me | CH$_2$ | CH$_2$ | Ph | (CH$_2$)$_2$ | H | racemic |
| I-180 | Me | Me | Me | CH$_2$ | CH$_2$ | Ph | (CH$_2$)$_2$ | H | (S)- |
| I-181 | Me | Me | Me | CH$_2$ | CH$_2$ | Ph | (CH$_2$)$_2$ | Me | racemic |
| I-182 | Me | Me | Me | CH$_2$ | CH$_2$ | Ph | (CH$_2$)$_2$ | Me | (S)- |
| I-183 | Me | Me | Me | CH$_2$ | CH$_2$ | Ph | C≡CCH$_2$ | H | racemic |
| I-184 | Me | Me | Me | CH$_2$ | CH$_2$ | Ph | C≡CCH$_2$ | H | (S)- |
| I-185 | Me | Me | Me | CH$_2$ | CH$_2$ | Ph | C≡CCH$_2$ | Me | racemic |
| I-186 | Me | Me | Me | CH$_2$ | CH$_2$ | Ph | C≡CCH$_2$ | Me | (S)- |
| I-187 | Me | Me | Me | CH$_2$C(Me)$_2$ | CH$_2$ | Ph | CH$_2$ | H | racemic |
| I-188 | Me | Me | Me | CH$_2$C(Me)$_2$ | CH$_2$ | Ph | CH$_2$ | H | (S)- |
| I-189 | Me | Me | Me | CH$_2$C(Me)$_2$ | CH$_2$ | Ph | — | H | racemic |
| I-190 | Me | Me | Me | CH$_2$C(Me)$_2$ | CH$_2$ | Ph | — | H | (S)- |
| I-191 | Me | Me | Me | CH$_2$C(Me)$_2$ | CH$_2$ | Ph | CH$_2$ | Me | racemic |
| I-192 | Me | Me | Me | CH$_2$C(Me)$_2$ | CH$_2$ | Ph | CH$_2$ | Me | (S)- |
| I-193 | Me | Me | Me | CH$_2$C(Me)$_2$ | CH$_2$ | Ph | C(Me)$_2$ | H | racemic |
| I-194 | Me | Me | Me | CH$_2$C(Me)$_2$ | CH$_2$ | Ph | C(Me)$_2$ | H | (S)- |
| I-195 | Me | Me | Me | CH$_2$C(Me)$_2$ | CH$_2$ | Ph | C(Me)$_2$ | Me | racemic |
| I-196 | Me | Me | Me | CH$_2$C(Me)$_2$ | CH$_2$ | Ph | C(Me)$_2$ | Me | (S)- |
| I-197 | Me | Me | Me | CH$_2$C(Me)$_2$ | CH$_2$ | Ph | (CH$_2$)$_2$ | H | racemic |
| I-198 | Me | Me | Me | CH$_2$C(Me)$_2$ | CH$_2$ | Ph | (CH$_2$)$_2$ | H | (S)- |
| I-199 | Me | Me | Me | CH$_2$C(Me)$_2$ | CH$_2$ | Ph | (CH$_2$)$_2$ | Me | racemic |
| I-200 | Me | Me | Me | CH$_2$C(Me)$_2$ | CH$_2$ | Ph | (CH$_2$)$_2$ | Me | (S)- |

TABLE 5

(I)

| Compound No. | R¹ | R² | R³ | L¹ | L² | R⁴ | L³ | R⁵ | Configuration |
|---|---|---|---|---|---|---|---|---|---|
| I-201 | Me | Me | Me | CH$_2$C(Me)$_2$ | CH$_2$ | Ph | C≡CCH$_2$ | H | racemic |
| I-202 | Me | Me | Me | CH$_2$C(Me)$_2$ | CH$_2$ | Ph | C≡CCH$_2$ | H | (S)- |
| I-203 | Me | Me | Me | CH$_2$C(Me)$_2$ | CH$_2$ | Ph | C≡CCH$_2$ | Me | racemic |
| I-204 | Me | Me | Me | CH$_2$C(Me)$_2$ | CH$_2$ | Ph | C≡CCH$_2$ | Me | (S)- |
| I-205 | Me | Me | Me | CH$_2$CH=CH | CH$_2$ | Ph | CH$_2$ | H | racemic |
| I-206 | Me | Me | Me | CH$_2$CH=CH | CH$_2$ | Ph | CH$_2$ | H | (S)- |
| I-207 | Me | Me | Me | CH$_2$CH=CH | CH$_2$ | Ph | — | H | racemic |
| I-208 | Me | Me | Me | CH$_2$CH=CH | CH$_2$ | Ph | — | H | (S)- |
| I-209 | Me | Me | Me | CH$_2$CH=CH | CH$_2$ | Ph | CH$_2$ | Me | racemic |
| I-210 | Me | Me | Me | CH$_2$CH=CH | CH$_2$ | Ph | CH$_2$ | Me | (S)- |
| I-211 | Me | Me | Me | CH$_2$CH=CH | CH$_2$ | Ph | C(Me)$_2$ | H | racemic |
| I-212 | Me | Me | Me | CH$_2$CH=CH | CH$_2$ | Ph | C(Me)$_2$ | H | (S)- |
| I-213 | Me | Me | Me | CH$_2$CH=CH | CH$_2$ | Ph | C(Me)$_2$ | Me | racemic |
| I-214 | Me | Me | Me | CH$_2$CH=CH | CH$_2$ | Ph | C(Me)$_2$ | Me | (S)- |
| I-215 | Me | Me | Me | CH$_2$CH=CH | CH$_2$ | Ph | (CH$_2$)$_2$ | H | racemic |
| I-216 | Me | Me | Me | CH$_2$CH=CH | CH$_2$ | Ph | (CH$_2$)$_2$ | H | (S)- |
| I-217 | Me | Me | Me | CH$_2$CH=CH | CH$_2$ | Ph | (CH$_2$)$_2$ | Me | racemic |
| I-218 | Me | Me | Me | CH$_2$CH=CH | CH$_2$ | Ph | (CH$_2$)$_2$ | Me | (S)- |
| I-219 | Me | Me | Me | CH$_2$CH=CH | CH$_2$ | Ph | C≡CCH$_2$ | H | racemic |
| I-220 | Me | Me | Me | CH$_2$CH=CH | CH$_2$ | Ph | C≡CCH$_2$ | H | (S)- |
| I-221 | Me | Me | Me | CH$_2$CH=CH | CH$_2$ | Ph | C≡CCH$_2$ | Me | racemic |
| I-222 | Me | Me | Me | CH$_2$CH=CH | CH$_2$ | Ph | C≡CCH$_2$ | Me | (S)- |
| I-223 | Me | Me | Me | CH$_2$C≡C | CH$_2$ | Ph | CH$_2$ | H | racemic |
| I-224 | Me | Me | Me | CH$_2$C≡C | CH$_2$ | Ph | CH$_2$ | H | (S)- |
| I-225 | Me | Me | Me | CH$_2$C≡C | CH$_2$ | Ph | — | H | racemic |
| I-226 | Me | Me | Me | CH$_2$C≡C | CH$_2$ | Ph | — | H | (S)- |
| I-227 | Me | Me | Me | CH$_2$C≡C | CH$_2$ | Ph | CH$_2$ | Me | racemic |
| I-228 | Me | Me | Me | CH$_2$C≡C | CH$_2$ | Ph | CH$_2$ | Me | (S)- |
| I-229 | Me | Me | Me | CH$_2$C≡C | CH$_2$ | Ph | C(Me)$_2$ | H | racemic |
| I-230 | Me | Me | Me | CH$_2$C≡C | CH$_2$ | Ph | C(Me)$_2$ | H | (S)- |
| I-231 | Me | Me | Me | CH$_2$C≡C | CH$_2$ | Ph | C(Me)$_2$ | Me | racemic |
| I-232 | Me | Me | Me | CH$_2$C≡C | CH$_2$ | Ph | C(Me)$_2$ | Me | (S)- |
| I-233 | Me | Me | Me | CH$_2$C≡C | CH$_2$ | Ph | (CH$_2$)$_2$ | H | racemic |
| I-234 | Me | Me | Me | CH$_2$C≡C | CH$_2$ | Ph | (CH$_2$)$_2$ | H | (S)- |
| I-235 | Me | Me | Me | CH$_2$C≡C | CH$_2$ | Ph | (CH$_2$)$_2$ | Me | racemic |
| I-236 | Me | Me | Me | CH$_2$C≡C | CH$_2$ | Ph | (CH$_2$)$_2$ | Me | (S)- |
| I-237 | Me | Me | Me | CH$_2$C≡C | CH$_2$ | Ph | C≡CCH$_2$ | H | racemic |
| I-238 | Me | Me | Me | CH$_2$C≡C | CH$_2$ | Ph | C≡CCH$_2$ | H | (S)- |
| I-239 | Me | Me | Me | CH$_2$C≡C | CH$_2$ | Ph | C≡CCH$_2$ | Me | racemic |
| I-240 | Me | Me | Me | CH$_2$C≡C | CH$_2$ | Ph | C≡CCH$_2$ | Me | (S)- |
| I-241 | Me | Me | Me | 1,2-Cyclopropylene | CH$_2$ | Ph | CH$_2$ | H | racemic |
| I-242 | Me | Me | Me | 1,2-Cyclopropylene | CH$_2$ | Ph | CH$_2$ | H | (S)- |
| I-243 | Me | Me | Me | 1,2-Cyclopropylene | CH$_2$ | Ph | — | H | racemic |
| I-244 | Me | Me | Me | 1,2-Cyclopropylene | CH$_2$ | Ph | — | H | (S)- |
| I-245 | Me | Me | Me | 1,2-Cyclopropylene | CH$_2$ | Ph | CH$_2$ | Me | racemic |
| I-246 | Me | Me | Me | 1,2-Cyclopropylene | CH$_2$ | Ph | CH$_2$ | Me | (S)- |
| I-247 | Me | Me | Me | 1,2-Cyclopropylene | CH$_2$ | Ph | C(Me)$_2$ | H | racemic |
| I-248 | Me | Me | Me | 1,2-Cyclopropylene | CH$_2$ | Ph | C(Me)$_2$ | H | (S)- |
| I-249 | Me | Me | Me | 1,2-Cyclopropylene | CH$_2$ | Ph | C(Me)$_2$ | Me | racemic |
| I-250 | Me | Me | Me | 1,2-Cyclopropylene | CH$_2$ | Ph | C(Me)$_2$ | Me | (S)- |

TABLE 6

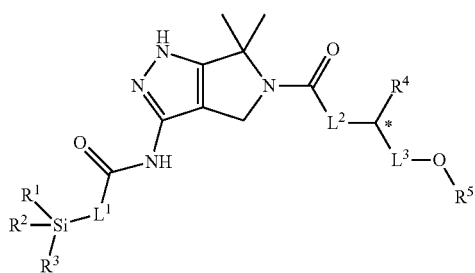

(I)

| Compound No. | R¹ | R² | R³ | L¹ | L² | R⁴ | L³ | R⁵ | Configuration |
|---|---|---|---|---|---|---|---|---|---|
| I-251 | Me | Me | Me | 1,2-Cyclopropylene | $CH_2$ | Ph | $(CH_2)_2$ | H | racemic |
| I-252 | Me | Me | Me | 1,2-Cyclopropylene | $CH_2$ | Ph | $(CH_2)_2$ | H | (S)- |
| I-253 | Me | Me | Me | 1,2-Cyclopropylene | $CH_2$ | Ph | $(CH_2)_2$ | Me | racemic |
| I-254 | Me | Me | Me | 1,2-Cyclopropylene | $CH_2$ | Ph | $(CH_2)_2$ | Me | (S)- |
| I-255 | Me | Me | Me | 1,2-Cyclopropylene | $CH_2$ | Ph | $C\equiv CH_2$ | H | racemic |
| I-256 | Me | Me | Me | 1,2-Cyclopropylene | $CH_2$ | Ph | $C\equiv CH_2$ | H | (S)- |
| I-257 | Me | Me | Me | 1,2-Cyclopropylene | $CH_2$ | Ph | $C\equiv CH_2$ | Me | racemic |
| I-258 | Me | Me | Me | 1,2-Cyclopropylene | $CH_2$ | Ph | $C\equiv CH_2$ | Me | (S)- |
| I-259 | Me | Me | Me | 5,5-Spiro-[2.3]hexylene | $CH_2$ | Ph | $CH_2$ | H | racemic |
| I-260 | Me | Me | Me | 5,5-Spiro-[2.3]hexylene | $CH_2$ | Ph | $CH_2$ | H | (S)- |
| I-261 | Me | Me | Me | 5,5-Spiro-[2.3]hexylene | $CH_2$ | Ph | — | H | racemic |
| I-262 | Me | Me | Me | 5,5-Spiro-[2.3]hexylene | $CH_2$ | Ph | — | H | (S)- |
| I-263 | Me | Me | Me | 5,5-Spiro-[2.3]hexylene | $CH_2$ | Ph | $CH_2$ | Me | racemic |
| I-264 | Me | Me | Me | 5,5-Spiro-[2.3]hexylene | $CH_2$ | Ph | $CH_2$ | Me | (S)- |
| I-265 | Me | Me | Me | 5,5-Spiro-[2.3]hexylene | $CH_2$ | Ph | $C(Me)_2$ | H | racemic |
| I-266 | Me | Me | Me | 5,5-Spiro-[2.3]hexylene | $CH_2$ | Ph | $C(Me)_2$ | H | (S)- |
| I-267 | Me | Me | Me | 5,5-Spiro-[2.3]hexylene | $CH_2$ | Ph | $C(Me)_2$ | Me | racemic |
| I-268 | Me | Me | Me | 5,5-Spiro-[2.3]hexylene | $CH_2$ | Ph | $C(Me)_2$ | Me | (S)- |
| I-269 | Me | Me | Me | 5,5-Spiro-[2.3]hexylene | $CH_2$ | Ph | $(CH_2)_2$ | H | racemic |
| I-270 | Me | Me | Me | 5,5-Spiro-[2.3]hexylene | $CH_2$ | Ph | $(CH_2)_2$ | H | (S)- |
| I-271 | Me | Me | Me | 5,5-Spiro-[2.3]hexylene | $CH_2$ | Ph | $(CH_2)_2$ | Me | racemic |
| I-272 | Me | Me | Me | 5,5-Spiro-[2.3]hexylene | $CH_2$ | Ph | $(CH_2)_2$ | Me | (S)- |
| I-273 | Me | Me | Me | 5,5-Spiro-[2.3]hexylene | $CH_2$ | Ph | $C\equiv CH_2$ | H | racemic |

TABLE 6-continued

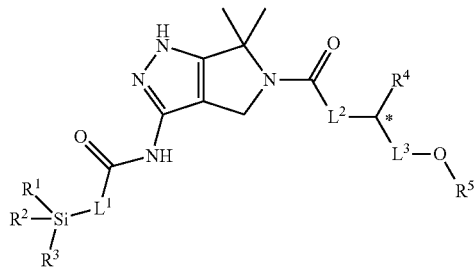

(I)

| Compound No. | R¹ | R² | R³ | L¹ | L² | R⁴ | L³ | R⁵ | Configuration |
|---|---|---|---|---|---|---|---|---|---|
| I-274 | Me | Me | Me | 5,5-Spiro-[2.3]hexylene | $CH_2$ | Ph | $C\equiv CH_2$ | H | (S)- |
| I-275 | Me | Me | Me | 5,5-Spiro-[2.3]hexylene | $CH_2$ | Ph | $C\equiv CH_2$ | Me | racemic |
| I-276 | Me | Me | Me | 5,5-Spiro-[2.3]hexylene | $CH_2$ | Ph | $C\equiv CH_2$ | Me | (S)- |
| I-277 | Me | Me | Me | 4,4-Cyclopentenylene | $CH_2$ | Ph | $CH_2$ | H | racemic |
| I-278 | Me | Me | Me | 4,4-Cyclopentenylene | $CH_2$ | Ph | $CH_2$ | H | (S)- |
| I-279 | Me | Me | Me | 4,4-Cyclopentenylene | $CH_2$ | Ph | — | H | racemic |
| I-280 | Me | Me | Me | 4,4-Cyclopentenylene | $CH_2$ | Ph | — | H | (S)- |
| I-281 | Me | Me | Me | 4,4-Cyclopentenylene | $CH_2$ | Ph | $CH_2$ | Me | racemic |
| I-282 | Me | Me | Me | 4,4-Cyclopentenylene | $CH_2$ | Ph | $CH_2$ | Me | (S)- |
| I-283 | Me | Me | Me | 4,4-Cyclopentenylene | $CH_2$ | Ph | $C(Me)_2$ | H | racemic |
| I-284 | Me | Me | Me | 4,4-Cyclopentenylene | $CH_2$ | Ph | $C(Me)_2$ | H | (S)- |
| I-285 | Me | Me | Me | 4,4-Cyclopentenylene | $CH_2$ | Ph | $C(Me)_2$ | Me | racemic |
| I-286 | Me | Me | Me | 4,4-Cyclopentenylene | $CH_2$ | Ph | $C(Me)_2$ | Me | (S)- |
| I-287 | Me | Me | Me | 4,4-Cyclopentenylene | $CH_2$ | Ph | $(CH_2)_2$ | H | racemic |
| I-288 | Me | Me | Me | 4,4-Cyclopentenylene | $CH_2$ | Ph | $(CH_2)_2$ | H | (S)- |
| I-289 | Me | Me | Me | 4,4-Cyclopentenylene | $CH_2$ | Ph | $(CH_2)_2$ | Me | racemic |
| I-290 | Me | Me | Me | 4,4-Cyclopentenylene | $CH_2$ | Ph | $(CH_2)_2$ | Me | (S)- |
| I-291 | Me | Me | Me | 4,4-Cyclopentenylene | $CH_2$ | Ph | $C\equiv CH_2$ | H | racemic |
| I-292 | Me | Me | Me | 4,4-Cyclopentenylene | $CH_2$ | Ph | $C\equiv CH_2$ | H | (S)- |
| I-293 | Me | Me | Me | 4,4-Cyclopentenylene | $CH_2$ | Ph | $C\equiv CH_2$ | Me | racemic |
| I-294 | Me | Me | Me | 4,4-Cyclopentenylene | $CH_2$ | Ph | $C\equiv CH_2$ | Me | (S)- |

TABLE 7

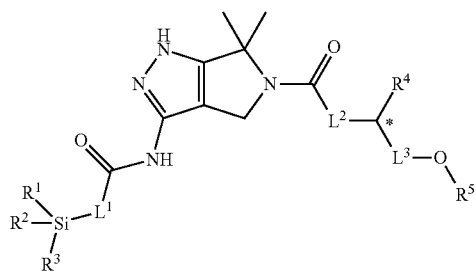

(I)

| Compound No. | R¹ | R² | R³ | L¹ | L² | R⁴ | L³ | R⁵ | Configuration |
|---|---|---|---|---|---|---|---|---|---|
| I-295 | Me | Me | Me | 5,5-Spiro-[2.3]hexylene | NH | Ph | CH₂C(Me)₂ | H | racemic |
| I-296 | Me | Me | Me | 5,5-Spiro-[2.3]hexylene | NH | Ph | CH₂C(Me)₂ | H | (R)- |
| I-297 | Me | Me | Me | 5,5-Spiro-[2.3]hexylene | NH | Ph | CH₂C(Me)₂ | Me | racemic |
| I-298 | Me | Me | Me | 5,5-Spiro-[2.3]hexylene | NH | Ph | CH₂C(Me)₂ | Me | (R)- |
| I-299 | Me | Me | Me | 5,5-Spiro-[2.3]hexylene | NH | Ph | C(Me)₂CH₂ | H | racemic |
| I-300 | Me | Me | Me | 5,5-Spiro-[2.3]hexylene | NH | Ph | C(Me)₂CH₂ | H | (+) |
| I-301 | Me | Me | Me | 5,5-Spiro-[2.3]hexylene | NH | Ph | C(Me)₂CH₂ | H | (−) |
| I-302 | Me | Me | Me | 5,5-Spiro-[2.3]hexylene | NH | Ph | C(Me)₂CH₂ | Me | racemic |
| I-303 | Me | Me | Me | 5,5-Spiro-[2.3]hexylene | NH | Ph | C(Me)₂CH₂ | Me | (+) |
| I-304 | Me | Me | Me | 5,5-Spiro-[2.3]hexylene | NH | Ph | C(Me)₂CH₂ | Me | (−) |
| I-305 | Me | Me | Me | 4,4-Cyclopentenylene | NH | Ph | CH₂C(Me)₂ | H | racemic |
| I-306 | Me | Me | Me | 4,4-Cyclopentenylene | NH | Ph | CH₂C(Me)₂ | H | (R)- |
| I-307 | Me | Me | Me | 4,4-Cyclopentenylene | NH | Ph | CH₂C(Me)₂ | Me | racemic |
| I-308 | Me | Me | Me | 4,4-Cyclopentenylene | NH | Ph | CH₂C(Me)₂ | Me | (R)- |
| I-309 | Me | Me | Me | 4,4-Cyclopentenylene | NH | Ph | C(Me)₂CH₂ | H | racemic |
| I-310 | Me | Me | Me | 4,4-Cyclopentenylene | NH | Ph | C(Me)₂CH₂ | H | (+) |
| I-311 | Me | Me | Me | 4,4-Cyclopentenylene | NH | Ph | C(Me)₂CH₂ | H | (−) |
| I-312 | Me | Me | Me | 4,4-Cyclopentenylene | NH | Ph | C(Me)₂CH₂ | Me | racemic |
| I-313 | Me | Me | Me | 4,4-Cyclopentenylene | NH | Ph | C(Me)₂CH₂ | Me | (+) |
| I-314 | Me | Me | Me | 4,4-Cyclopentenylene | NH | Ph | C(Me)₂CH₂ | Me | (−) |
| I-315 | Me | Me | Me | 1,2-Cyclopropylene | — | Ph | — | H | racemic |
| I-316 | Me | Me | Me | 1,2-Cyclopropylene | — | Ph | — | H | (S)- |
| I-317 | Me | Me | Me | 1,2-Cyclopropylene | — | Ph | — | Me | racemic |
| I-318 | Me | Me | Me | 1,2-Cyclopropylene | — | Ph | — | Me | (S)- |
| I-319 | Me | Me | Me | 5,5-Spiro-[2.3]hexylene | — | Ph | — | H | racemic |
| I-320 | Me | Me | Me | 5,5-Spiro-[2.3]hexylene | — | Ph | — | H | (S)- |
| I-321 | Me | Me | Me | 5,5-Spiro-[2.3]hexylene | — | Ph | — | Me | racemic |
| I-322 | Me | Me | Me | 5,5-Spiro-[2.3]hexylene | — | Ph | — | Me | (S)- |
| I-323 | Me | Me | Me | 4,4-Cyclopentenylene | — | Ph | — | H | racemic |
| I-324 | Me | Me | Me | 4,4-Cyclopentenylene | — | Ph | — | H | (S)- |
| I-325 | Me | Me | Me | 4,4-Cyclopentenylene | — | Ph | — | Me | racemic |
| I-326 | Me | Me | Me | 4,4-Cyclopentenylene | — | Ph | — | Me | (S)- |
| I-327 | Me | Me | Me | 1,2-Cyclopropylene | — | Ph | CH₂ | H | racemic |
| I-328 | Me | Me | Me | 1,2-Cyclopropylene | — | Ph | CH₂ | H | (S)- |
| I-329 | Me | Me | Me | 1,2-Cyclopropylene | — | Ph | CH₂ | Me | racemic |
| I-330 | Me | Me | Me | 1,2-Cyclopropylene | — | Ph | CH₂ | Me | (S)- |
| I-331 | Me | Me | Me | 1,2-Cyclopropylene | — | Ph | (CH₂)₂ | H | racemic |
| I-332 | Me | Me | Me | 1,2-Cyclopropylene | — | Ph | (CH₂)₂ | H | (S)- |
| I-333 | Me | Me | Me | 1,2-Cyclopropylene | — | Ph | (CH₂)₂ | Me | racemic |
| I-334 | Me | Me | Me | 1,2-Cyclopropylene | — | Ph | (CH₂)₂ | Me | (S)- |
| I-335 | Me | Me | Me | 5,5-Spiro-[2.3]hexylene | — | Ph | CH₂ | H | racemic |
| I-336 | Me | Me | Me | 5,5-Spiro-[2.3]hexylene | — | Ph | CH₂ | H | (S)- |
| I-337 | Me | Me | Me | 5,5-Spiro-[2.3]hexylene | — | Ph | CH₂ | Me | racemic |
| I-338 | Me | Me | Me | 5,5-Spiro-[2.3]hexylene | — | Ph | CH₂ | Me | (S)- |
| I-339 | Me | Me | Me | 5,5-Spiro-[2.3]hexylene | — | Ph | (CH₂)₂ | H | racemic |
| I-340 | Me | Me | Me | 5,5-Spiro-[2.3]hexylene | — | Ph | (CH₂)₂ | H | (S)- |
| I-341 | Me | Me | Me | 5,5-Spiro-[2.3]hexylene | — | Ph | (CH₂)₂ | Me | racemic |
| I-342 | Me | Me | Me | 5,5-Spiro-[2.3]hexylene | — | Ph | (CH₂)₂ | Me | (S)- |
| I-343 | Me | Me | Me | 4,4-Cyclopentenylene | — | Ph | CH₂ | H | racemic |
| I-344 | Me | Me | Me | 4,4-Cyclopentenylene | — | Ph | CH₂ | H | (S)- |

TABLE 7-continued (I) [structure shown: pyrazole-pyrrolidinone with silyl amide substituent]

| Compound No. | R¹ | R² | R³ | L¹ | L² | R⁴ | L³ | R⁵ | Configuration |
|---|---|---|---|---|---|---|---|---|---|
| I-345 | Me | Me | Me | 4,4-Cyclopentenylene | — | Ph | CH₂ | Me | racemic |

TABLE 8

(I) [structure shown]

| Compound No. | R¹ | R² | R³ | L¹ | L² | R⁴ | L³ | R⁵ | Configuration |
|---|---|---|---|---|---|---|---|---|---|
| I-346 | Me | Me | Me | 4,4-Cyclopentenylene | — | Ph | CH₂ | Me | (S)- |
| I-347 | Me | Me | Me | 4,4-Cyclopentenylene | — | Ph | (CH₂)₂ | H | racemic |
| I-348 | Me | Me | Me | 4,4-Cyclopentenylene | — | Ph | (CH₂)₂ | H | (S)- |
| I-349 | Me | Me | Me | 4,4-Cyclopentenylene | — | Ph | (CH₂)₂ | Me | racemic |
| I-350 | Me | Me | Me | 4,4-Cyclopentenylene | — | Ph | (CH₂)₂ | Me | (S)- |

TABLE 9

(II) [structure shown]

| Compound No. | R¹ | R² | R³ | L² | R⁴ | L³ | R⁵ | Configuration |
|---|---|---|---|---|---|---|---|---|
| II-1 | Me | Me | Me | O | Ph | CH₂ | H | racemic |
| II-2 | Me | Me | Me | O | Ph | CH₂ | H | (S)- |
| II-3 | Me | Et | Me | O | Ph | CH₂ | H | racemic |
| II-4 | Me | Et | Me | O | Ph | CH₂ | H | (S)- |
| II-5 | Me | Me | Me | O | Ph | CH₂ | Me | racemic |
| II-6 | Me | Me | Me | O | Ph | CH₂ | Me | (S)- |
| II-7 | Me | Et | Me | O | Ph | CH₂ | Me | racemic |
| II-8 | Me | Et | Me | O | Ph | CH₂ | Me | (S)- |
| II-9 | Me | Me | Me | O | Ph | CH₂ | CHF₂ | racemic |
| II-10 | Me | Me | Me | O | Ph | CH₂ | CHF₂ | (S)- |
| II-11 | Me | Et | Me | O | Ph | CH₂ | CHF₂ | racemic |
| II-12 | Me | Et | Me | O | Ph | CH₂ | CHF₂ | (S)- |
| II-13 | Me | Me | Me | O | Ph | CH₂ | Et | racemic |
| II-14 | Me | Me | Me | O | Ph | CH₂ | Et | (S)- |
| II-15 | Me | Et | Me | O | Ph | CH₂ | Et | racemic |
| II-16 | Me | Et | Me | O | Ph | CH₂ | Et | (S)- |
| II-17 | Me | Me | Me | O | Ph | CH₂ | iPr | racemic |
| II-18 | Me | Me | Me | O | Ph | CH₂ | iPr | (S)- |
| II-19 | Me | Et | Me | O | Ph | CH₂ | iPr | racemic |
| II-20 | Me | Et | Me | O | Ph | CH₂ | iPr | (S)- |
| II-21 | Me | Me | Me | O | Ph | CH₂ | cPr | racemic |
| II-22 | Me | Me | Me | O | Ph | CH₂ | cPr | (S)- |
| II-23 | Me | Et | Me | O | Ph | CH₂ | cPr | racemic |
| II-24 | Me | Et | Me | O | Ph | CH₂ | cPr | (S)- |
| II-25 | Me | Me | Me | O | Ph | CH₂ | Ph | racemic |
| II-26 | Me | Me | Me | O | Ph | CH₂ | Ph | (S)- |
| II-27 | Me | Et | Me | O | Ph | CH₂ | Ph | racemic |
| II-28 | Me | Et | Me | O | Ph | CH₂ | Ph | (S)- |
| II-29 | Me | Me | Me | O | Ph | C(Me)₂ | H | racemic |
| II-30 | Me | Me | Me | O | Ph | C(Me)₂ | H | (S)- |
| II-31 | Me | Et | Me | O | Ph | C(Me)₂ | H | racemic |
| II-32 | Me | Et | Me | O | Ph | C(Me)₂ | H | (S)- |
| II-33 | Me | Me | Me | O | Ph | C(Me)₂ | Me | racemic |
| II-34 | Me | Me | Me | O | Ph | C(Me)₂ | Me | (S)- |
| II-35 | Me | Et | Me | O | Ph | C(Me)₂ | Me | racemic |
| II-36 | Me | Et | Me | O | Ph | C(Me)₂ | Me | (S)- |
| II-37 | Me | Me | Me | O | Ph | C(Me)₂ | CHF₂ | racemic |
| II-38 | Me | Me | Me | O | Ph | C(Me)₂ | CHF₂ | (S)- |
| II-39 | Me | Et | Me | O | Ph | C(Me)₂ | CHF₂ | racemic |
| II-40 | Me | Et | Me | O | Ph | C(Me)₂ | CHF₂ | (S)- |
| II-41 | Me | Me | Me | O | Ph | C(Me)₂ | Et | racemic |
| II-42 | Me | Me | Me | O | Ph | C(Me)₂ | Et | (S)- |
| II-43 | Me | Et | Me | O | Ph | C(Me)₂ | Et | racemic |
| II-44 | Me | Et | Me | O | Ph | C(Me)₂ | Et | (S)- |
| II-45 | Me | Me | Me | O | Ph | C(Me)₂ | iPr | racemic |
| II-46 | Me | Me | Me | O | Ph | C(Me)₂ | iPr | (S)- |
| II-47 | Me | Et | Me | O | Ph | C(Me)₂ | iPr | racemic |
| II-48 | Me | Et | Me | O | Ph | C(Me)₂ | iPr | (S)- |
| II-49 | Me | Me | Me | O | Ph | C(Me)₂ | cPr | racemic |
| II-50 | Me | Me | Me | O | Ph | C(Me)₂ | cPr | (S)- |

TABLE 10

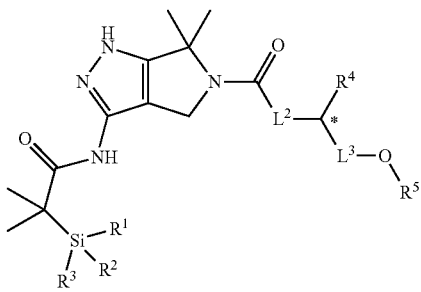

(II)

| Compound No. | R¹ | R² | R³ | L² | R⁴ | L³ | R⁵ | Configuration |
|---|---|---|---|---|---|---|---|---|
| II-51 | Me | Et | Me | O | Ph | C(Me)$_2$ | cPr | racemic |
| II-52 | Me | Et | Me | O | Ph | C(Me)$_2$ | cPr | (S)- |
| II-53 | Me | Me | Me | O | Ph | C(Me)$_2$ | Ph | racemic |
| II-54 | Me | Me | Me | O | Ph | C(Me)$_2$ | Ph | (S)- |
| II-55 | Me | Et | Me | O | Ph | C(Me)$_2$ | Ph | racemic |
| II-56 | Me | Et | Me | O | Ph | C(Me)$_2$ | Ph | (S)- |
| II-57 | Me | Me | Me | O | Ph | (CH$_2$)$_2$ | H | racemic |
| II-58 | Me | Me | Me | O | Ph | (CH$_2$)$_2$ | H | (R)- |
| II-59 | Me | Et | Me | O | Ph | (CH$_2$)$_2$ | H | racemic |
| II-60 | Me | Et | Me | O | Ph | (CH$_2$)$_2$ | H | (R)- |
| II-61 | Me | Me | Me | O | Ph | (CH$_2$)$_2$ | Me | racemic |
| II-62 | Me | Me | Me | O | Ph | (CH$_2$)$_2$ | Me | (R)- |
| II-63 | Me | Et | Me | O | Ph | (CH$_2$)$_2$ | Me | racemic |
| II-64 | Me | Et | Me | O | Ph | (CH$_2$)$_2$ | Me | (R)- |
| II-65 | Me | Me | Me | O | Ph | (CH$_2$)$_2$ | CHF$_2$ | racemic |
| II-66 | Me | Me | Me | O | Ph | (CH$_2$)$_2$ | CHF$_2$ | (R)- |
| II-67 | Me | Et | Me | O | Ph | (CH$_2$)$_2$ | CHF$_2$ | racemic |
| II-68 | Me | Et | Me | O | Ph | (CH$_2$)$_2$ | CHF$_2$ | (R)- |
| II-69 | Me | Me | Me | O | Ph | (CH$_2$)$_2$ | Et | racemic |
| II-70 | Me | Me | Me | O | Ph | (CH$_2$)$_2$ | Et | (R)- |
| II-71 | Me | Et | Me | O | Ph | (CH$_2$)$_2$ | Et | racemic |
| II-72 | Me | Et | Me | O | Ph | (CH$_2$)$_2$ | Et | (R)- |
| II-73 | Me | Me | Me | O | Ph | (CH$_2$)$_2$ | iPr | racemic |
| II-74 | Me | Me | Me | O | Ph | (CH$_2$)$_2$ | iPr | (R)- |
| II-75 | Me | Et | Me | O | Ph | (CH$_2$)$_2$ | iPr | racemic |
| II-76 | Me | Et | Me | O | Ph | (CH$_2$)$_2$ | iPr | (R)- |
| II-77 | Me | Me | Me | O | Ph | (CH$_2$)$_2$ | cPr | racemic |
| II-78 | Me | Me | Me | O | Ph | (CH$_2$)$_2$ | cPr | (R)- |
| II-79 | Me | Et | Me | O | Ph | (CH$_2$)$_2$ | cPr | racemic |
| II-80 | Me | Et | Me | O | Ph | (CH$_2$)$_2$ | cPr | (R)- |
| II-81 | Me | Me | Me | O | Ph | (CH$_2$)$_2$ | Ph | racemic |
| II-82 | Me | Me | Me | O | Ph | (CH$_2$)$_2$ | Ph | (R)- |
| II-83 | Me | Et | Me | O | Ph | (CH$_2$)$_2$ | Ph | racemic |
| II-84 | Me | Et | Me | O | Ph | (CH$_2$)$_2$ | Ph | (R)- |
| II-85 | Me | Me | Me | O | Ph | CH$_2$C(Me)$_2$ | H | racemic |
| II-86 | Me | Me | Me | O | Ph | CH$_2$C(Me)$_2$ | H | (R)- |
| II-87 | Me | Et | Me | O | Ph | CH$_2$C(Me)$_2$ | H | racemic |
| II-88 | Me | Et | Me | O | Ph | CH$_2$C(Me)$_2$ | H | (R)- |
| II-89 | Me | Me | Me | O | Ph | CH$_2$C(Me)$_2$ | Me | racemic |
| II-90 | Me | Me | Me | O | Ph | CH$_2$C(Me)$_2$ | Me | (R)- |
| II-91 | Me | Et | Me | O | Ph | CH$_2$C(Me)$_2$ | Me | racemic |
| II-92 | Me | Et | Me | O | Ph | CH$_2$C(Me)$_2$ | Me | (R)- |
| II-93 | Me | Me | Me | O | Ph | CH$_2$C(Me)$_2$ | CHF$_2$ | racemic |
| II-94 | Me | Me | Me | O | Ph | CH$_2$C(Me)$_2$ | CHF$_2$ | (R)- |
| II-95 | Me | Et | Me | O | Ph | CH$_2$C(Me)$_2$ | CHF$_2$ | racemic |
| II-96 | Me | Et | Me | O | Ph | CH$_2$C(Me)$_2$ | CHF$_2$ | (R)- |
| II-97 | Me | Me | Me | O | Ph | CH$_2$C(Me)$_2$ | Et | racemic |
| II-98 | Me | Me | Me | O | Ph | CH$_2$C(Me)$_2$ | Et | (R)- |
| II-99 | Me | Et | Me | O | Ph | CH$_2$C(Me)$_2$ | Et | racemic |
| II-100 | Me | Et | Me | O | Ph | CH$_2$C(Me)$_2$ | Et | (R)- |

TABLE 11

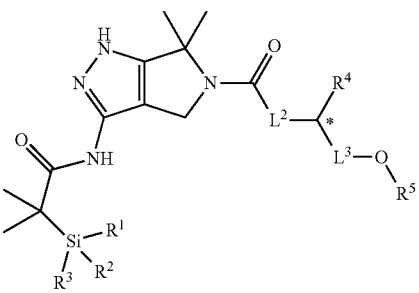

(II)

| Compound No. | R¹ | R² | R³ | L² | R⁴ | L³ | R⁵ | Configuration |
|---|---|---|---|---|---|---|---|---|
| II-101 | Me | Me | Me | O | Ph | CH$_2$C(Me)$_2$ | iPr | racemic |
| II-102 | Me | Me | Me | O | Ph | CH$_2$C(Me)$_2$ | iPr | (R)- |
| II-103 | Me | Et | Me | O | Ph | CH$_2$C(Me)$_2$ | iPr | racemic |
| II-104 | Me | Et | Me | O | Ph | CH$_2$C(Me)$_2$ | iPr | (R)- |
| II-105 | Me | Me | Me | O | Ph | CH$_2$C(Me)$_2$ | cPr | racemic |
| II-106 | Me | Me | Me | O | Ph | CH$_2$C(Me)$_2$ | cPr | (R)- |
| II-107 | Me | Et | Me | O | Ph | CH$_2$C(Me)$_2$ | cPr | racemic |
| II-108 | Me | Et | Me | O | Ph | CH$_2$C(Me)$_2$ | cPr | (R)- |
| II-109 | Me | Me | Me | O | Ph | CH$_2$C(Me)$_2$ | Ph | racemic |
| II-110 | Me | Me | Me | O | Ph | CH$_2$C(Me)$_2$ | Ph | (R)- |
| II-111 | Me | Et | Me | O | Ph | CH$_2$C(Me)$_2$ | Ph | racemic |
| II-112 | Me | Et | Me | O | Ph | CH$_2$C(Me)$_2$ | Ph | (R)- |
| II-113 | Me | Me | Me | NH | Ph | CH$_2$ | H | racemic |
| II-114 | Me | Me | Me | NH | Ph | CH$_2$ | H | (S)- |
| II-115 | Me | Et | Me | NH | Ph | CH$_2$ | H | racemic |
| II-116 | Me | Et | Me | NH | Ph | CH$_2$ | H | (S)- |
| II-117 | Me | Me | Me | N(Me) | Ph | CH$_2$ | H | racemic |
| II-118 | Me | Me | Me | N(Me) | Ph | CH$_2$ | H | (S)- |
| II-119 | Me | Et | Me | N(Me) | Ph | CH$_2$ | H | racemic |
| II-120 | Me | Et | Me | N(Me) | Ph | CH$_2$ | H | (S)- |
| II-121 | Me | Me | Me | NH | Ph | CH$_2$ | Me | racemic |
| II-122 | Me | Me | Me | NH | Ph | CH$_2$ | Me | (S)- |
| II-123 | Me | Et | Me | NH | Ph | CH$_2$ | Me | racemic |
| II-124 | Me | Et | Me | NH | Ph | CH$_2$ | Me | (S)- |
| II-125 | Me | Me | Me | N(Me) | Ph | CH$_2$ | Me | racemic |
| II-126 | Me | Me | Me | N(Me) | Ph | CH$_2$ | Me | (S)- |
| II-127 | Me | Et | Me | N(Me) | Ph | CH$_2$ | Me | racemic |
| II-128 | Me | Et | Me | N(Me) | Ph | CH$_2$ | Me | (S)- |
| II-129 | Me | Me | Me | NH | Ph | CH$_2$ | CHF$_2$ | racemic |
| II-130 | Me | Me | Me | NH | Ph | CH$_2$ | CHF$_2$ | (S)- |
| II-131 | Me | Et | Me | NH | Ph | CH$_2$ | CHF$_2$ | racemic |
| II-132 | Me | Et | Me | NH | Ph | CH$_2$ | CHF$_2$ | (S)- |
| II-133 | Me | Me | Me | N(Me) | Ph | CH$_2$ | CHF$_2$ | racemic |
| II-134 | Me | Me | Me | N(Me) | Ph | CH$_2$ | CHF$_2$ | (S)- |
| II-135 | Me | Et | Me | N(Me) | Ph | CH$_2$ | CHF$_2$ | racemic |
| II-136 | Me | Et | Me | N(Me) | Ph | CH$_2$ | CHF$_2$ | (S)- |
| II-137 | Me | Me | Me | NH | Ph | CH$_2$ | Et | racemic |
| II-138 | Me | Me | Me | NH | Ph | CH$_2$ | Et | (S)- |
| II-139 | Me | Et | Me | NH | Ph | CH$_2$ | Et | racemic |
| II-140 | Me | Et | Me | NH | Ph | CH$_2$ | Et | (S)- |
| II-141 | Me | Me | Me | N(Me) | Ph | CH$_2$ | Et | racemic |
| II-142 | Me | Me | Me | N(Me) | Ph | CH$_2$ | Et | (S)- |
| II-143 | Me | Et | Me | N(Me) | Ph | CH$_2$ | Et | racemic |
| II-144 | Me | Et | Me | N(Me) | Ph | CH$_2$ | Et | (S)- |
| II-145 | Me | Me | Me | NH | Ph | CH$_2$ | iPr | racemic |
| II-146 | Me | Me | Me | NH | Ph | CH$_2$ | iPr | (S)- |
| II-147 | Me | Et | Me | NH | Ph | CH$_2$ | iPr | racemic |
| II-148 | Me | Et | Me | NH | Ph | CH$_2$ | iPr | (S)- |
| II-149 | Me | Me | Me | N(Me) | Ph | CH$_2$ | iPr | racemic |
| II-150 | Me | Me | Me | N(Me) | Ph | CH$_2$ | iPr | (S)- |

TABLE 12

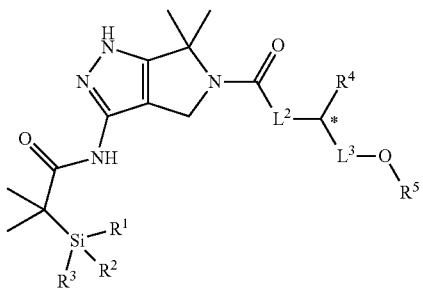

(II)

| Compound No. | R¹ | R² | R³ | L² | R⁴ | L³ | R⁵ | Configuration |
|---|---|---|---|---|---|---|---|---|
| II-151 | Me | Et | Me | N(Me) | Ph | CH$_2$ | iPr | racemic |
| II-152 | Me | Et | Me | N(Me) | Ph | CH$_2$ | iPr | (S)- |
| II-153 | Me | Me | Me | NH | Ph | CH$_2$ | cPr | racemic |
| II-154 | Me | Me | Me | NH | Ph | CH$_2$ | cPr | (S)- |
| II-155 | Me | Et | Me | NH | Ph | CH$_2$ | cPr | racemic |
| II-156 | Me | Et | Me | NH | Ph | CH$_2$ | cPr | (S)- |
| II-157 | Me | Me | Me | N(Me) | Ph | CH$_2$ | cPr | racemic |
| II-158 | Me | Me | Me | N(Me) | Ph | CH$_2$ | cPr | (S)- |
| II-159 | Me | Et | Me | N(Me) | Ph | CH$_2$ | cPr | racemic |
| II-160 | Me | Et | Me | N(Me) | Ph | CH$_2$ | cPr | (S)- |
| II-161 | Me | Me | Me | NH | Ph | CH$_2$ | Ph | racemic |
| II-162 | Me | Me | Me | NH | Ph | CH$_2$ | Ph | (S)- |
| II-163 | Me | Et | Me | NH | Ph | CH$_2$ | Ph | racemic |
| II-164 | Me | Et | Me | NH | Ph | CH$_2$ | Ph | (S)- |
| II-165 | Me | Me | Me | N(Me) | Ph | CH$_2$ | Ph | racemic |
| II-166 | Me | Me | Me | N(Me) | Ph | CH$_2$ | Ph | (S)- |
| II-167 | Me | Et | Me | N(Me) | Ph | CH$_2$ | Ph | racemic |
| II-168 | Me | Et | Me | N(Me) | Ph | CH$_2$ | Ph | (S)- |
| II-169 | Me | Me | Me | NH | Ph | C(Me)$_2$ | H | racemic |
| II-170 | Me | Me | Me | NH | Ph | C(Me)$_2$ | H | (S)- |
| II-171 | Me | Et | Me | NH | Ph | C(Me)$_2$ | H | racemic |
| II-172 | Me | Et | Me | NH | Ph | C(Me)$_2$ | H | (S)- |
| II-173 | Me | Me | Me | N(Me) | Ph | C(Me)$_2$ | H | racemic |
| II-174 | Me | Me | Me | N(Me) | Ph | C(Me)$_2$ | H | (S)- |
| II-175 | Me | Et | Me | N(Me) | Ph | C(Me)$_2$ | H | racemic |
| II-176 | Me | Et | Me | N(Me) | Ph | C(Me)$_2$ | H | (S)- |
| II-177 | Me | Me | Me | NH | Ph | C(Me)$_2$ | Me | racemic |
| II-178 | Me | Me | Me | NH | Ph | C(Me)$_2$ | Me | (S)- |
| II-179 | Me | Et | Me | NH | Ph | C(Me)$_2$ | Me | racemic |
| II-180 | Me | Et | Me | NH | Ph | C(Me)$_2$ | Me | (S)- |
| II-181 | Me | Me | Me | N(Me) | Ph | C(Me)$_2$ | Me | racemic |
| II-182 | Me | Me | Me | N(Me) | Ph | C(Me)$_2$ | Me | (S)- |
| II-183 | Me | Et | Me | N(Me) | Ph | C(Me)$_2$ | Me | racemic |
| II-184 | Me | Et | Me | N(Me) | Ph | C(Me)$_2$ | Me | (S)- |
| II-185 | Me | Me | Me | NH | Ph | C(Me)$_2$ | CHF$_2$ | racemic |
| II-186 | Me | Me | Me | NH | Ph | C(Me)$_2$ | CHF$_2$ | (S)- |
| II-187 | Me | Et | Me | NH | Ph | C(Me)$_2$ | CHF$_2$ | racemic |
| II-188 | Me | Et | Me | NH | Ph | C(Me)$_2$ | CHF$_2$ | (S)- |
| II-189 | Me | Me | Me | N(Me) | Ph | C(Me)$_2$ | CHF$_2$ | racemic |
| II-190 | Me | Me | Me | N(Me) | Ph | C(Me)$_2$ | CHF$_2$ | (S)- |
| II-191 | Me | Et | Me | N(Me) | Ph | C(Me)$_2$ | CHF$_2$ | racemic |
| II-192 | Me | Et | Me | N(Me) | Ph | C(Me)$_2$ | CHF$_2$ | (S)- |
| II-193 | Me | Me | Me | NH | Ph | C(Me)$_2$ | Et | racemic |
| II-194 | Me | Me | Me | NH | Ph | C(Me)$_2$ | Et | (S)- |
| II-195 | Me | Et | Me | NH | Ph | C(Me)$_2$ | Et | racemic |
| II-196 | Me | Et | Me | NH | Ph | C(Me)$_2$ | Et | (S)- |
| II-197 | Me | Me | Me | N(Me) | Ph | C(Me)$_2$ | Et | racemic |
| II-198 | Me | Me | Me | N(Me) | Ph | C(Me)$_2$ | Et | (S)- |
| II-199 | Me | Et | Me | N(Me) | Ph | C(Me)$_2$ | Et | racemic |
| II-200 | Me | Et | Me | N(Me) | Ph | C(Me)$_2$ | Et | (S)- |

TABLE 13

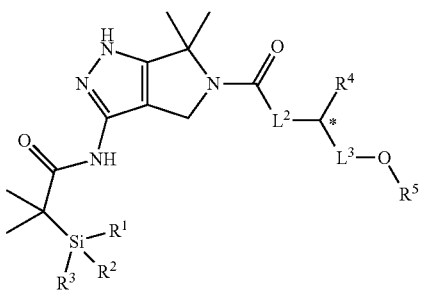

(II)

| Compound No. | R¹ | R² | R³ | L² | R⁴ | L³ | R⁵ | Configuration |
|---|---|---|---|---|---|---|---|---|
| II-201 | Me | Me | Me | NH | Ph | C(Me)$_2$ | iPr | racemic |
| II-202 | Me | Me | Me | NH | Ph | C(Me)$_2$ | iPr | (S)- |
| II-203 | Me | Et | Me | NH | Ph | C(Me)$_2$ | iPr | racemic |
| II-204 | Me | Et | Me | NH | Ph | C(Me)$_2$ | iPr | (S)- |
| II-205 | Me | Me | Me | N(Me) | Ph | C(Me)$_2$ | iPr | racemic |
| II-206 | Me | Me | Me | N(Me) | Ph | C(Me)$_2$ | iPr | (S)- |
| II-207 | Me | Et | Me | N(Me) | Ph | C(Me)$_2$ | iPr | racemic |
| II-208 | Me | Et | Me | N(Me) | Ph | C(Me)$_2$ | iPr | (S)- |
| II-209 | Me | Me | Me | NH | Ph | C(Me)$_2$ | cPr | racemic |
| II-210 | Me | Me | Me | NH | Ph | C(Me)$_2$ | cPr | (S)- |
| II-211 | Me | Et | Me | NH | Ph | C(Me)$_2$ | cPr | racemic |
| II-212 | Me | Et | Me | NH | Ph | C(Me)$_2$ | cPr | (S)- |
| II-213 | Me | Me | Me | N(Me) | Ph | C(Me)$_2$ | cPr | racemic |
| II-214 | Me | Me | Me | N(Me) | Ph | C(Me)$_2$ | cPr | (S)- |
| II-215 | Me | Et | Me | N(Me) | Ph | C(Me)$_2$ | cPr | racemic |
| II-216 | Me | Et | Me | N(Me) | Ph | C(Me)$_2$ | cPr | (S)- |
| II-217 | Me | Me | Me | NH | Ph | C(Me)$_2$ | Ph | racemic |
| II-218 | Me | Me | Me | NH | Ph | C(Me)$_2$ | Ph | (S)- |
| II-219 | Me | Et | Me | NH | Ph | C(Me)$_2$ | Ph | racemic |
| II-220 | Me | Et | Me | NH | Ph | C(Me)$_2$ | Ph | (S)- |
| II-221 | Me | Me | Me | N(Me) | Ph | C(Me)$_2$ | Ph | racemic |
| II-222 | Me | Me | Me | N(Me) | Ph | C(Me)$_2$ | Ph | (S)- |
| II-223 | Me | Et | Me | N(Me) | Ph | C(Me)$_2$ | Ph | racemic |
| II-224 | Me | Et | Me | N(Me) | Ph | C(Me)$_2$ | Ph | (S)- |
| II-225 | Me | Me | Me | NH | Ph | (CH$_2$)$_2$ | H | racemic |
| II-226 | Me | Me | Me | NH | Ph | (CH$_2$)$_2$ | H | (R)- |
| II-227 | Me | Et | Me | NH | Ph | (CH$_2$)$_2$ | H | racemic |
| II-228 | Me | Et | Me | NH | Ph | (CH$_2$)$_2$ | H | (R)- |
| II-229 | Me | Me | Me | N(Me) | Ph | (CH$_2$)$_2$ | H | racemic |
| II-230 | Me | Me | Me | N(Me) | Ph | (CH$_2$)$_2$ | H | (R)- |
| II-231 | Me | Et | Me | N(Me) | Ph | (CH$_2$)$_2$ | H | racemic |
| II-232 | Me | Et | Me | N(Me) | Ph | (CH$_2$)$_2$ | H | (R)- |
| II-233 | Me | Me | Me | NH | Ph | (CH$_2$)$_2$ | Me | racemic |
| II-234 | Me | Me | Me | NH | Ph | (CH$_2$)$_2$ | Me | (R)- |
| II-235 | Me | Et | Me | NH | Ph | (CH$_2$)$_2$ | Me | racemic |
| II-236 | Me | Et | Me | NH | Ph | (CH$_2$)$_2$ | Me | (R)- |
| II-237 | Me | Me | Me | N(Me) | Ph | (CH$_2$)$_2$ | Me | racemic |
| II-238 | Me | Me | Me | N(Me) | Ph | (CH$_2$)$_2$ | Me | (R)- |
| II-239 | Me | Et | Me | N(Me) | Ph | (CH$_2$)$_2$ | Me | racemic |
| II-240 | Me | Et | Me | N(Me) | Ph | (CH$_2$)$_2$ | Me | (R)- |
| II-241 | Me | Me | Me | NH | Ph | (CH$_2$)$_2$ | CHF$_2$ | racemic |
| II-242 | Me | Me | Me | NH | Ph | (CH$_2$)$_2$ | CHF$_2$ | (R)- |
| II-243 | Me | Et | Me | NH | Ph | (CH$_2$)$_2$ | CHF$_2$ | racemic |
| II-244 | Me | Et | Me | NH | Ph | (CH$_2$)$_2$ | CHF$_2$ | (R)- |
| II-245 | Me | Me | Me | N(Me) | Ph | (CH$_2$)$_2$ | CHF$_2$ | racemic |
| II-246 | Me | Me | Me | N(Me) | Ph | (CH$_2$)$_2$ | CHF$_2$ | (R)- |
| II-247 | Me | Et | Me | N(Me) | Ph | (CH$_2$)$_2$ | CHF$_2$ | racemic |
| II-248 | Me | Et | Me | N(Me) | Ph | (CH$_2$)$_2$ | CHF$_2$ | (R)- |
| II-249 | Me | Me | Me | NH | Ph | (CH$_2$)$_2$ | Et | racemic |
| II-250 | Me | Me | Me | NH | Ph | (CH$_2$)$_2$ | Et | (R)- |

TABLE 14

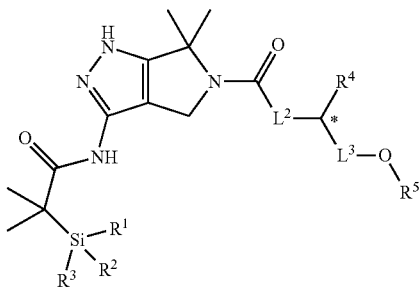

(II)

| Compound No. | R¹ | R² | R³ | L² | R⁴ | L³ | R⁵ | Configuration |
|---|---|---|---|---|---|---|---|---|
| II-251 | Me | Et | Me | NH | Ph | (CH₂)₂ | Et | racemic |
| II-252 | Me | Et | Me | NH | Ph | (CH₂)₂ | Et | (R)- |
| II-253 | Me | Me | Me | N(Me) | Ph | (CH₂)₂ | Et | racemic |
| II-254 | Me | Me | Me | N(Me) | Ph | (CH₂)₂ | Et | (R)- |
| II-255 | Me | Et | Me | N(Me) | Ph | (CH₂)₂ | Et | racemic |
| II-256 | Me | Et | Me | N(Me) | Ph | (CH₂)₂ | Et | (R)- |
| II-257 | Me | Me | Me | NH | Ph | (CH₂)₂ | iPr | racemic |
| II-258 | Me | Me | Me | NH | Ph | (CH₂)₂ | iPr | (R)- |
| II-259 | Me | Et | Me | NH | Ph | (CH₂)₂ | iPr | racemic |
| II-260 | Me | Et | Me | NH | Ph | (CH₂)₂ | iPr | (R)- |
| II-261 | Me | Me | Me | N(Me) | Ph | (CH₂)₂ | iPr | racemic |
| II-262 | Me | Me | Me | N(Me) | Ph | (CH₂)₂ | iPr | (R)- |
| II-263 | Me | Et | Me | N(Me) | Ph | (CH₂)₂ | iPr | racemic |
| II-264 | Me | Et | Me | N(Me) | Ph | (CH₂)₂ | iPr | (R)- |
| II-265 | Me | Me | Me | NH | Ph | (CH₂)₂ | cPr | racemic |
| II-266 | Me | Me | Me | NH | Ph | (CH₂)₂ | cPr | (R)- |
| II-267 | Me | Et | Me | NH | Ph | (CH₂)₂ | cPr | racemic |
| II-268 | Me | Et | Me | NH | Ph | (CH₂)₂ | cPr | (R)- |
| II-269 | Me | Me | Me | N(Me) | Ph | (CH₂)₂ | cPr | racemic |
| II-270 | Me | Me | Me | N(Me) | Ph | (CH₂)₂ | cPr | (R)- |
| II-271 | Me | Et | Me | N(Me) | Ph | (CH₂)₂ | cPr | racemic |
| II-272 | Me | Et | Me | N(Me) | Ph | (CH₂)₂ | cPr | (R)- |
| II-273 | Me | Me | Me | NH | Ph | (CH₂)₂ | Ph | racemic |
| II-274 | Me | Me | Me | NH | Ph | (CH₂)₂ | Ph | (R)- |
| II-275 | Me | Et | Me | NH | Ph | (CH₂)₂ | Ph | racemic |
| II-276 | Me | Et | Me | NH | Ph | (CH₂)₂ | Ph | (R)- |
| II-277 | Me | Me | Me | N(Me) | Ph | (CH₂)₂ | Ph | racemic |
| II-278 | Me | Me | Me | N(Me) | Ph | (CH₂)₂ | Ph | (R)- |
| II-279 | Me | Et | Me | N(Me) | Ph | (CH₂)₂ | Ph | racemic |
| II-280 | Me | Et | Me | N(Me) | Ph | (CH₂)₂ | Ph | (R)- |
| II-281 | Me | Me | Me | NH | Ph | (CH₂)₃ | H | racemic |
| II-282 | Me | Me | Me | NH | Ph | (CH₂)₃ | H | (R)- |
| II-283 | Me | Et | Me | NH | Ph | (CH₂)₃ | H | racemic |
| II-284 | Me | Et | Me | NH | Ph | (CH₂)₃ | H | (R)- |
| II-285 | Me | Me | Me | N(Me) | Ph | (CH₂)₃ | H | racemic |
| II-286 | Me | Me | Me | N(Me) | Ph | (CH₂)₃ | H | (R)- |
| II-287 | Me | Et | Me | N(Me) | Ph | (CH₂)₃ | H | racemic |
| II-288 | Me | Et | Me | N(Me) | Ph | (CH₂)₃ | H | (R)- |
| II-289 | Me | Me | Me | NH | Ph | (CH₂)₄ | H | racemic |
| II-290 | Me | Me | Me | NH | Ph | (CH₂)₄ | H | (R)- |
| II-291 | Me | Et | Me | NH | Ph | (CH₂)₄ | H | racemic |
| II-292 | Me | Et | Me | NH | Ph | (CH₂)₄ | H | (R)- |
| II-293 | Me | Me | Me | N(Me) | Ph | (CH₂)₄ | H | racemic |
| II-294 | Me | Me | Me | N(Me) | Ph | (CH₂)₄ | H | (R)- |
| II-295 | Me | Et | Me | N(Me) | Ph | (CH₂)₄ | H | racemic |
| II-296 | Me | Et | Me | N(Me) | Ph | (CH₂)₄ | H | (R)- |
| II-297 | Me | Me | Me | NH | Ph | CH₂C(Me)₂ | H | racemic |
| II-298 | Me | Me | Me | NH | Ph | CH₂C(Me)₂ | H | (R)- |
| II-299 | Me | Et | Me | NH | Ph | CH₂C(Me)₂ | H | racemic |
| II-300 | Me | Et | Me | NH | Ph | CH₂C(Me)₂ | H | (R)- |

TABLE 15

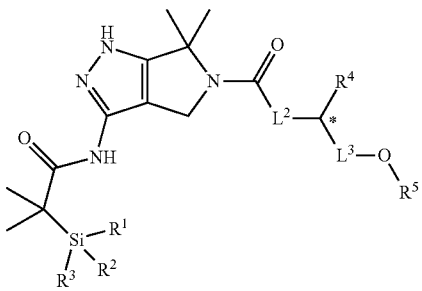

(II)

| Compound No. | R¹ | R² | R³ | L² | R⁴ | L³ | R⁵ | Configuration |
|---|---|---|---|---|---|---|---|---|
| II-301 | Me | Me | Me | N(Me) | Ph | CH₂C(Me)₂ | H | racemic |
| II-302 | Me | Me | Me | N(Me) | Ph | CH₂C(Me)₂ | H | (R)- |
| II-303 | Me | Et | Me | N(Me) | Ph | CH₂C(Me)₂ | H | racemic |
| II-304 | Me | Et | Me | N(Me) | Ph | CH₂C(Me)₂ | H | (R)- |
| II-305 | Me | Me | Me | NH | Ph | CH₂C(Me)₂ | Me | racemic |
| II-306 | Me | Me | Me | NH | Ph | CH₂C(Me)₂ | Me | (R)- |
| II-307 | Me | Et | Me | NH | Ph | CH₂C(Me)₂ | Me | racemic |
| II-308 | Me | Et | Me | NH | Ph | CH₂C(Me)₂ | Me | (R)- |
| II-309 | Me | Me | Me | N(Me) | Ph | CH₂C(Me)₂ | Me | racemic |
| II-310 | Me | Me | Me | N(Me) | Ph | CH₂C(Me)₂ | Me | (R)- |
| II-311 | Me | Et | Me | N(Me) | Ph | CH₂C(Me)₂ | Me | racemic |
| II-312 | Me | Et | Me | N(Me) | Ph | CH₂C(Me)₂ | Me | (R)- |
| II-313 | Me | Me | Me | NH | Ph | CH₂C(Me)₂ | CHF₂ | racemic |
| II-314 | Me | Me | Me | NH | Ph | CH₂C(Me)₂ | CHF₂ | (R)- |
| II-315 | Me | Et | Me | NH | Ph | CH₂C(Me)₂ | CHF₂ | racemic |
| II-316 | Me | Et | Me | NH | Ph | CH₂C(Me)₂ | CHF₂ | (R)- |
| II-317 | Me | Me | Me | N(Me) | Ph | CH₂C(Me)₂ | CHF₂ | racemic |
| II-318 | Me | Me | Me | N(Me) | Ph | CH₂C(Me)₂ | CHF₂ | (R)- |
| II-319 | Me | Et | Me | N(Me) | Ph | CH₂C(Me)₂ | CHF₂ | racemic |
| II-320 | Me | Et | Me | N(Me) | Ph | CH₂C(Me)₂ | CHF₂ | (R)- |
| II-321 | Me | Me | Me | NH | Ph | CH₂C(Me)₂ | Et | racemic |
| II-322 | Me | Me | Me | NH | Ph | CH₂C(Me)₂ | Et | (R)- |
| II-323 | Me | Et | Me | NH | Ph | CH₂C(Me)₂ | Et | racemic |
| II-324 | Me | Et | Me | NH | Ph | CH₂C(Me)₂ | Et | (R)- |
| II-325 | Me | Me | Me | N(Me) | Ph | CH₂C(Me)₂ | Et | racemic |
| II-326 | Me | Me | Me | N(Me) | Ph | CH₂C(Me)₂ | Et | (R)- |
| II-327 | Me | Et | Me | N(Me) | Ph | CH₂C(Me)₂ | Et | racemic |
| II-328 | Me | Et | Me | N(Me) | Ph | CH₂C(Me)₂ | Et | (R)- |
| II-329 | Me | Me | Me | NH | Ph | CH₂C(Me)₂ | iPr | racemic |
| II-330 | Me | Me | Me | NH | Ph | CH₂C(Me)₂ | iPr | (R)- |
| II-331 | Me | Et | Me | NH | Ph | CH₂C(Me)₂ | iPr | racemic |
| II-332 | Me | Et | Me | NH | Ph | CH₂C(Me)₂ | iPr | (R)- |
| II-333 | Me | Me | Me | N(Me) | Ph | CH₂C(Me)₂ | iPr | racemic |
| II-334 | Me | Me | Me | N(Me) | Ph | CH₂C(Me)₂ | iPr | (R)- |
| II-335 | Me | Et | Me | N(Me) | Ph | CH₂C(Me)₂ | iPr | racemic |
| II-336 | Me | Et | Me | N(Me) | Ph | CH₂C(Me)₂ | iPr | (R)- |
| II-337 | Me | Me | Me | NH | Ph | CH₂C(Me)₂ | cPr | racemic |
| II-338 | Me | Me | Me | NH | Ph | CH₂C(Me)₂ | cPr | (R)- |
| II-339 | Me | Et | Me | NH | Ph | CH₂C(Me)₂ | cPr | racemic |
| II-340 | Me | Et | Me | NH | Ph | CH₂C(Me)₂ | cPr | (R)- |
| II-341 | Me | Me | Me | N(Me) | Ph | CH₂C(Me)₂ | cPr | racemic |
| II-342 | Me | Me | Me | N(Me) | Ph | CH₂C(Me)₂ | cPr | (R)- |
| II-343 | Me | Et | Me | N(Me) | Ph | CH₂C(Me)₂ | cPr | racemic |
| II-344 | Me | Et | Me | N(Me) | Ph | CH₂C(Me)₂ | cPr | (R)- |
| II-345 | Me | Me | Me | NH | Ph | CH₂C(Me)₂ | Ph | racemic |
| II-346 | Me | Me | Me | NH | Ph | CH₂C(Me)₂ | Ph | (R)- |
| II-347 | Me | Et | Me | NH | Ph | CH₂C(Me)₂ | Ph | racemic |
| II-348 | Me | Et | Me | NH | Ph | CH₂C(Me)₂ | Ph | (R)- |
| II-349 | Me | Me | Me | N(Me) | Ph | CH₂C(Me)₂ | Ph | racemic |
| II-350 | Me | Me | Me | N(Me) | Ph | CH₂C(Me)₂ | Ph | (R)- |

TABLE 16

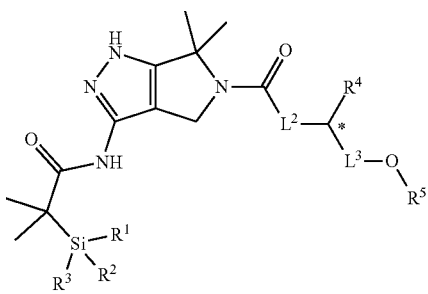

(II)

| Compound No. | R¹ | R² | R³ | L² | R⁴ | L³ | R⁵ | Configuration |
|---|---|---|---|---|---|---|---|---|
| II-351 | Me | Et | Me | N(Me) | Ph | CH₂C(Me)₂ | Ph | racemic |
| II-352 | Me | Et | Me | N(Me) | Ph | CH₂C(Me)₂ | Ph | (R)- |
| II-353 | Me | Me | Me | NH | Ph | C(Me)₂CH₂ | H | racemic |
| II-354 | Me | Me | Me | NH | Ph | C(Me)₂CH₂ | H | (S)- |
| II-355 | Me | Et | Me | NH | Ph | C(Me)₂CH₂ | H | racemic |
| II-356 | Me | Et | Me | NH | Ph | C(Me)₂CH₂ | H | (S)- |
| II-357 | Me | Me | Me | N(Me) | Ph | C(Me)₂CH₂ | H | racemic |
| II-358 | Me | Me | Me | N(Me) | Ph | C(Me)₂CH₂ | H | (S)- |
| II-359 | Me | Et | Me | N(Me) | Ph | C(Me)₂CH₂ | H | racemic |
| II-360 | Me | Et | Me | N(Me) | Ph | C(Me)₂CH₂ | H | (S)- |
| II-361 | Me | Me | Me | NH | Ph | CF₂CH₂ | H | racemic |
| II-362 | Me | Me | Me | NH | Ph | CF₂CH₂ | H | (S)- |
| II-363 | Me | Et | Me | NH | Ph | CF₂CH₂ | H | racemic |
| II-364 | Me | Et | Me | NH | Ph | CF₂CH₂ | H | (S)- |
| II-365 | Me | Me | Me | N(Me) | Ph | CF₂CH₂ | H | racemic |
| II-366 | Me | Me | Me | N(Me) | Ph | CF₂CH₂ | H | (S)- |
| II-367 | Me | Et | Me | N(Me) | Ph | CF₂CH₂ | H | racemic |
| II-368 | Me | Et | Me | N(Me) | Ph | CF₂CH₂ | H | (S)- |
| II-369 | Me | Me | Me | NH | Ph | CH=CHCH₂ | H | racemic |
| II-370 | Me | Me | Me | NH | Ph | CH=CHCH₂ | H | (S)- |
| II-371 | Me | Et | Me | NH | Ph | CH=CHCH₂ | H | racemic |
| II-372 | Me | Et | Me | NH | Ph | CH=CHCH₂ | H | (S)- |
| II-373 | Me | Me | Me | N(Me) | Ph | CH=CHCH₂ | H | racemic |
| II-374 | Me | Me | Me | N(Me) | Ph | CH=CHCH₂ | H | (S)- |
| II-375 | Me | Et | Me | N(Me) | Ph | CH=CHCH₂ | H | racemic |
| II-376 | Me | Et | Me | N(Me) | Ph | CH=CHCH₂ | H | (S)- |
| II-377 | Me | Me | Me | NH | Ph | C≡CCH₂ | H | racemic |
| II-378 | Me | Me | Me | NH | Ph | C≡CCH₂ | H | (S)- |
| II-379 | Me | Et | Me | NH | Ph | C≡CCH₂ | H | racemic |
| II-380 | Me | Et | Me | NH | Ph | C≡CCH₂ | H | (S)- |
| II-381 | Me | Me | Me | N(Me) | Ph | C≡CCH₂ | H | racemic |
| II-382 | Me | Me | Me | N(Me) | Ph | C≡CCH₂ | H | (S)- |
| II-383 | Me | Et | Me | N(Me) | Ph | C≡CCH₂ | H | racemic |
| II-384 | Me | Et | Me | N(Me) | Ph | C≡CCH₂ | H | (S)- |
| II-385 | Me | Me | Me | NH | Ph | 1,1-Cyclopropylene | H | racemic |
| II-386 | Me | Me | Me | NH | Ph | 1,1-Cyclopropylene | H | (S)- |
| II-387 | Me | Et | Me | NH | Ph | 1,1-Cyclopropylene | H | racemic |
| II-388 | Me | Et | Me | NH | Ph | 1,1-Cyclopropylene | H | (S)- |
| II-389 | Me | Me | Me | N(Me) | Ph | 1,1-Cyclopropylene | H | racemic |
| II-390 | Me | Me | Me | N(Me) | Ph | 1,1-Cyclopropylene | H | (S)- |
| II-391 | Me | Et | Me | N(Me) | Ph | 1,1-Cyclopropylene | H | racemic |
| II-392 | Me | Et | Me | N(Me) | Ph | 1,1-Cyclopropylene | H | (S)- |
| II-393 | Me | Me | Me | NH | Ph | 1,2-Cyclopropynylene | H | racemic |
| II-394 | Me | Me | Me | NH | Ph | 1,2-Cyclopropynylene | H | (S)- |
| II-395 | Me | Et | Me | NH | Ph | 1,2-Cyclopropynylene | H | racemic |
| II-396 | Me | Et | Me | NH | Ph | 1,2-Cyclopropynylene | H | (S)- |
| II-397 | Me | Me | Me | N(Me) | Ph | 1,2-Cyclopropynylene | H | racemic |
| II-398 | Me | Me | Me | N(Me) | Ph | 1,2-Cyclopropynylene | H | (S)- |
| II-399 | Me | Et | Me | N(Me) | Ph | 1,2-Cyclopropynylene | H | racemic |
| II-400 | Me | Et | Me | N(Me) | Ph | 1,2-Cyclopropynylene | H | (S)- |

TABLE 17

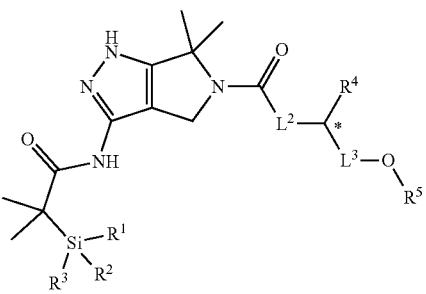

(II)

| Compound No. | R¹ | R² | R³ | L² | R⁴ | L³ | R⁵ | Configuration |
|---|---|---|---|---|---|---|---|---|
| II-401 | Me | Me | Me | NH | Ph | C(=O) | H | racemic |
| II-402 | Me | Me | Me | NH | Ph | C(=O) | H | (S)- |
| II-403 | Me | Et | Me | NH | Ph | C(=O) | H | racemic |
| II-404 | Me | Et | Me | NH | Ph | C(=O) | H | (S)- |
| II-405 | Me | Me | Me | N(Me) | Ph | C(=O) | H | racemic |
| II-406 | Me | Me | Me | N(Me) | Ph | C(=O) | H | (S)- |
| II-407 | Me | Et | Me | N(Me) | Ph | C(=O) | H | racemic |
| II-408 | Me | Et | Me | N(Me) | Ph | C(=O) | H | (S)- |
| II-409 | Me | Me | Me | NH | Ph | C(=O) | Bn | racemic |
| II-410 | Me | Me | Me | NH | Ph | C(=O) | Bn | (S)- |
| II-411 | Me | Et | Me | NH | Ph | C(=O) | Bn | racemic |
| II-412 | Me | Et | Me | NH | Ph | C(=O) | Bn | (S)- |
| II-413 | Me | Me | Me | N(Me) | Ph | C(=O) | Bn | racemic |
| II-414 | Me | Me | Me | N(Me) | Ph | C(=O) | Bn | (S)- |
| II-415 | Me | Et | Me | N(Me) | Ph | C(=O) | Bn | racemic |
| II-416 | Me | Et | Me | N(Me) | Ph | C(=O) | Bn | (S)- |
| II-417 | Me | Me | Me | NH | Ph | C(=O) | Me | racemic |
| II-418 | Me | Me | Me | NH | Ph | C(=O) | Me | (S)- |
| II-419 | Me | Et | Me | NH | Ph | C(=O) | Me | racemic |
| II-420 | Me | Et | Me | NH | Ph | C(=O) | Me | (S)- |
| II-421 | Me | Me | Me | N(Me) | Ph | C(=O) | Me | racemic |
| II-422 | Me | Me | Me | N(Me) | Ph | C(=O) | Me | (S)- |
| II-423 | Me | Et | Me | N(Me) | Ph | C(=O) | Me | racemic |
| II-424 | Me | Et | Me | N(Me) | Ph | C(=O) | Me | (S)- |
| II-425 | Me | Me | Me | NH | H | CH₂ | H | |
| II-426 | Me | Et | Me | NH | H | CH₂ | H | |
| II-427 | Me | Me | Me | N(Me) | H | CH₂ | H | |
| II-428 | Me | Et | Me | N(Me) | H | CH₂ | H | |
| II-429 | Me | Me | Me | NH | H | CH(Me) | H | |
| II-430 | Me | Et | Me | NH | H | CH(Me) | H | |
| II-431 | Me | Me | Me | N(Me) | H | CH(Me) | H | |
| II-432 | Me | Et | Me | N(Me) | H | CH(Me) | H | |
| II-433 | Me | Me | Me | NH | H | CH(iPr) | H | |
| II-434 | Me | Et | Me | NH | H | CH(iPr) | H | |
| II-435 | Me | Me | Me | N(Me) | H | CH(iPr) | H | |
| II-436 | Me | Et | Me | N(Me) | H | CH(iPr) | H | |
| II-437 | Me | Me | Me | NH | H | CH(Ph) | H | |
| II-438 | Me | Et | Me | NH | H | CH(Ph) | H | |
| II-439 | Me | Me | Me | N(Me) | H | CH(Ph) | H | |
| II-440 | Me | Et | Me | N(Me) | H | CH(Ph) | H | |
| II-441 | Me | Me | Me | NH | Me | CH₂ | H | racemic |
| II-442 | Me | Me | Me | NH | Me | CH₂ | H | (S)- |
| II-443 | Me | Et | Me | NH | Me | CH₂ | H | racemic |
| II-444 | Me | Et | Me | NH | Me | CH₂ | H | (S)- |
| II-445 | Me | Me | Me | N(Me) | Me | CH₂ | H | racemic |
| II-446 | Me | Me | Me | N(Me) | Me | CH₂ | H | (S)- |
| II-447 | Me | Et | Me | N(Me) | Me | CH₂ | H | racemic |
| II-448 | Me | Et | Me | N(Me) | Me | CH₂ | H | (S)- |
| II-449 | Me | Me | Me | NH | iPr | CH₂ | H | racemic |
| II-450 | Me | Me | Me | NH | iPr | CH₂ | H | (S)- |

TABLE 18

(II)

| Compound No. | R¹ | R² | R³ | L² | R⁴ | L³ | R⁵ | Configuration |
|---|---|---|---|---|---|---|---|---|
| II-451 | Me | Et | Me | NH | iPr | $CH_2$ | H | racemic |
| II-452 | Me | Et | Me | NH | iPr | $CH_2$ | H | (S)- |
| II-453 | Me | Me | Me | N(Me) | iPr | $CH_2$ | H | racemic |
| II-454 | Me | Me | Me | N(Me) | iPr | $CH_2$ | H | (S)- |
| II-455 | Me | Et | Me | N(Me) | iPr | $CH_2$ | H | racemic |
| II-456 | Me | Et | Me | N(Me) | iPr | $CH_2$ | H | (S)- |
| II-457 | Me | Me | Me | NH | cHex | $CH_2$ | H | racemic |
| II-458 | Me | Me | Me | NH | cHex | $CH_2$ | H | (S)- |
| II-459 | Me | Et | Me | NH | cHex | $CH_2$ | H | racemic |
| II-460 | Me | Et | Me | NH | cHex | $CH_2$ | H | (S)- |
| II-461 | Me | Me | Me | N(Me) | cHex | $CH_2$ | H | racemic |
| II-462 | Me | Me | Me | N(Me) | cHex | $CH_2$ | H | (S)- |
| II-463 | Me | Et | Me | N(Me) | cHex | $CH_2$ | H | racemic |
| II-464 | Me | Et | Me | N(Me) | cHex | $CH_2$ | H | (S)- |
| II-465 | Me | Me | Me | NH | 1,3-Benzodioxol-4-yl | $CH_2$ | H | racemic |
| II-466 | Me | Me | Me | NH | 1,3-Benzodioxol-4-yl | $CH_2$ | H | (S)- |
| II-467 | Me | Et | Me | NH | 1,3-Benzodioxol-4-yl | $CH_2$ | H | racemic |
| II-468 | Me | Et | Me | NH | 1,3-Benzodioxol-4-yl | $CH_2$ | H | (S)- |
| II-469 | Me | Me | Me | N(Me) | 1,3-Benzodioxol-4-yl | $CH_2$ | H | racemic |
| II-470 | Me | Me | Me | N(Me) | 1,3-Benzodioxol-4-yl | $CH_2$ | H | (S)- |
| II-471 | Me | Et | Me | N(Me) | 1,3-Benzodioxol-4-yl | $CH_2$ | H | racemic |
| II-472 | Me | Et | Me | N(Me) | 1,3-Benzodioxol-4-yl | $CH_2$ | H | (S)- |
| II-473 | Me | Me | Me | NH | 2-F—Ph | $CH_2$ | H | racemic |
| II-474 | Me | Me | Me | NH | 2-F—Ph | $CH_2$ | H | (S)- |
| II-475 | Me | Et | Me | NH | 2-F—Ph | $CH_2$ | H | racemic |
| II-476 | Me | Et | Me | NH | 2-F—Ph | $CH_2$ | H | (S)- |
| II-477 | Me | Me | Me | N(Me) | 2-F—Ph | $CH_2$ | H | racemic |
| II-478 | Me | Me | Me | N(Me) | 2-F—Ph | $CH_2$ | H | (S)- |
| II-479 | Me | Et | Me | N(Me) | 2-F—Ph | $CH_2$ | H | racemic |
| II-480 | Me | Et | Me | N(Me) | 2-F—Ph | $CH_2$ | H | (S)- |
| II-481 | Me | Me | Me | NH | 3-F—Ph | $CH_2$ | H | racemic |
| II-482 | Me | Me | Me | NH | 3-F—Ph | $CH_2$ | H | (S)- |
| II-483 | Me | Et | Me | NH | 3-F—Ph | $CH_2$ | H | racemic |
| II-484 | Me | Et | Me | NH | 3-F—Ph | $CH_2$ | H | (S)- |
| II-485 | Me | Me | Me | N(Me) | 3-F—Ph | $CH_2$ | H | racemic |
| II-486 | Me | Me | Me | N(Me) | 3-F—Ph | $CH_2$ | H | (S)- |
| II-487 | Me | Et | Me | N(Me) | 3-F—Ph | $CH_2$ | H | racemic |
| II-488 | Me | Et | Me | N(Me) | 3-F—Ph | $CH_2$ | H | (S)- |
| II-489 | Me | Me | Me | NH | 4-F—Ph | $CH_2$ | H | racemic |
| II-490 | Me | Me | Me | NH | 4-F—Ph | $CH_2$ | H | (S)- |
| II-491 | Me | Et | Me | NH | 4-F—Ph | $CH_2$ | H | racemic |
| II-492 | Me | Et | Me | NH | 4-F—Ph | $CH_2$ | H | (S)- |
| II-493 | Me | Me | Me | N(Me) | 4-F—Ph | $CH_2$ | H | racemic |
| II-494 | Me | Me | Me | N(Me) | 4-F—Ph | $CH_2$ | H | (S)- |
| II-495 | Me | Et | Me | N(Me) | 4-F—Ph | $CH_2$ | H | racemic |
| II-496 | Me | Et | Me | N(Me) | 4-F—Ph | $CH_2$ | H | (S)- |
| II-497 | Me | Me | Me | NH | 2-Py | $CH_2$ | H | racemic |
| II-498 | Me | Me | Me | NH | 2-Py | $CH_2$ | H | (S)- |
| II-499 | Me | Et | Me | NH | 2-Py | $CH_2$ | H | racemic |
| II-500 | Me | Et | Me | NH | 2-Py | $CH_2$ | H | (S)- |

TABLE 19

(II)

| Compound No. | R¹ | R² | R³ | L² | R⁴ | L³ | R⁵ | Configuration |
|---|---|---|---|---|---|---|---|---|
| II-501 | Me | Me | Me | N(Me) | 2-Py | $CH_2$ | H | racemic |
| II-502 | Me | Me | Me | N(Me) | 2-Py | $CH_2$ | H | (S)- |
| II-503 | Me | Et | Me | N(Me) | 2-Py | $CH_2$ | H | racemic |
| II-504 | Me | Et | Me | N(Me) | 2-Py | $CH_2$ | H | (S)- |
| II-505 | Me | Me | Me | NH | 3-Py | $CH_2$ | H | racemic |
| II-506 | Me | Me | Me | NH | 3-Py | $CH_2$ | H | (S)- |
| II-507 | Me | Et | Me | NH | 3-Py | $CH_2$ | H | racemic |
| II-508 | Me | Et | Me | NH | 3-Py | $CH_2$ | H | (S)- |
| II-509 | Me | Me | Me | N(Me) | 3-Py | $CH_2$ | H | racemic |
| II-510 | Me | Me | Me | N(Me) | 3-Py | $CH_2$ | H | (S)- |
| II-511 | Me | Et | Me | N(Me) | 3-Py | $CH_2$ | H | racemic |
| II-512 | Me | Et | Me | N(Me) | 3-Py | $CH_2$ | H | (S)- |
| II-513 | Me | Me | Me | NH | 4-Py | $CH_2$ | H | racemic |
| II-514 | Me | Me | Me | NH | 4-Py | $CH_2$ | H | (S)- |
| II-515 | Me | Et | Me | NH | 4-Py | $CH_2$ | H | racemic |
| II-516 | Me | Et | Me | NH | 4-Py | $CH_2$ | H | (S)- |
| II-517 | Me | Me | Me | N(Me) | 4-Py | $CH_2$ | H | racemic |
| II-518 | Me | Me | Me | N(Me) | 4-Py | $CH_2$ | H | (S)- |
| II-519 | Me | Et | Me | N(Me) | 4-Py | $CH_2$ | H | racemic |
| II-520 | Me | Et | Me | N(Me) | 4-Py | $CH_2$ | H | (S)- |
| II-521 | Me | Me | Me | $CH_2$ | Ph | $CH_2$ | H | racemic |
| II-522 | Me | Me | Me | $CH_2$ | Ph | $CH_2$ | H | (S)- |
| II-523 | Me | Et | Me | $CH_2$ | Ph | $CH_2$ | H | racemic |
| II-524 | Me | Et | Me | $CH_2$ | Ph | $CH_2$ | H | (S)- |
| II-525 | Me | Me | Me | $CH_2$ | Ph | — | H | racemic |
| II-526 | Me | Me | Me | $CH_2$ | Ph | — | H | (S)- |
| II-527 | Me | Et | Me | $CH_2$ | Ph | — | H | racemic |
| II-528 | Me | Et | Me | $CH_2$ | Ph | — | H | (S)- |
| II-529 | Me | Me | Me | $CH_2$ | Ph | $CH_2$ | Me | racemic |
| II-530 | Me | Me | Me | $CH_2$ | Ph | $CH_2$ | Me | (S)- |
| II-531 | Me | Et | Me | $CH_2$ | Ph | $CH_2$ | Me | racemic |
| II-532 | Me | Et | Me | $CH_2$ | Ph | $CH_2$ | Me | (S)- |
| II-533 | Me | Me | Me | $CH_2$ | Ph | $C(Me)_2$ | H | racemic |
| II-534 | Me | Me | Me | $CH_2$ | Ph | $C(Me)_2$ | H | (S)- |
| II-535 | Me | Et | Me | $CH_2$ | Ph | $C(Me)_2$ | H | racemic |
| II-536 | Me | Et | Me | $CH_2$ | Ph | $C(Me)_2$ | H | (S)- |
| II-537 | Me | Me | Me | $CH_2$ | Ph | $C(Me)_2$ | Me | racemic |
| II-538 | Me | Me | Me | $CH_2$ | Ph | $C(Me)_2$ | Me | (S)- |
| II-539 | Me | Et | Me | $CH_2$ | Ph | $C(Me)_2$ | Me | racemic |
| II-540 | Me | Et | Me | $CH_2$ | Ph | $C(Me)_2$ | Me | (S)- |
| II-541 | Me | Me | Me | $CH_2$ | Ph | $(CH_2)_2$ | H | racemic |
| II-542 | Me | Me | Me | $CH_2$ | Ph | $(CH_2)_2$ | H | (S)- |
| II-543 | Me | Et | Me | $CH_2$ | Ph | $(CH_2)_2$ | H | racemic |
| II-544 | Me | Et | Me | $CH_2$ | Ph | $(CH_2)_2$ | H | (S)- |
| II-545 | Me | Me | Me | $CH_2$ | Ph | $(CH_2)_2$ | Me | racemic |
| II-546 | Me | Me | Me | $CH_2$ | Ph | $(CH_2)_2$ | Me | (S)- |
| II-547 | Me | Et | Me | $CH_2$ | Ph | $(CH_2)_2$ | Me | racemic |
| II-548 | Me | Et | Me | $CH_2$ | Ph | $(CH_2)_2$ | Me | (S)- |
| II-549 | Me | Me | Me | $CH_2$ | Ph | $CH_2C(Me)_2$ | H | racemic |
| II-550 | Me | Me | Me | $CH_2$ | Ph | $CH_2C(Me)_2$ | H | (S)- |

TABLE 20

(II)

| Compound No. | R¹ | R² | R³ | L² | R⁴ | L³ | R⁵ | Configuration |
|---|---|---|---|---|---|---|---|---|
| II-551 | Me | Et | Me | $CH_2$ | Ph | $CH_2C(Me)_2$ | H | racemic |
| II-552 | Me | Et | Me | $CH_2$ | Ph | $CH_2C(Me)_2$ | H | (S)- |
| II-553 | Me | Me | Me | $CH_2$ | Ph | $CH_2C(Me)_2$ | Me | racemic |
| II-554 | Me | Me | Me | $CH_2$ | Ph | $CH_2C(Me)_2$ | Me | (S)- |
| II-555 | Me | Et | Me | $CH_2$ | Ph | $CH_2C(Me)_2$ | Me | racemic |
| II-556 | Me | Et | Me | $CH_2$ | Ph | $CH_2C(Me)_2$ | Me | (S)- |
| II-557 | Me | Me | Me | — | Ph | $CH_2$ | H | racemic |
| II-558 | Me | Me | Me | — | Ph | $CH_2$ | H | (S)- |
| II-559 | Me | Me | Me | — | Ph | $CH_2$ | Me | racemic |
| II-560 | Me | Me | Me | — | Ph | $CH_2$ | Me | (S)- |
| II-561 | Me | Me | Me | CH=CH | Ph | $CH_2$ | H | racemic |
| II-562 | Me | Me | Me | CH=CH | Ph | $CH_2$ | H | (S)- |
| II-563 | Me | Me | Me | CH=CH | Ph | $CH_2$ | Me | racemic |
| II-564 | Me | Me | Me | CH=CH | Ph | $CH_2$ | Me | (S)- |
| II-565 | Me | Me | Me | C≡C | Ph | $CH_2$ | H | racemic |
| II-566 | Me | Me | Me | C≡C | Ph | $CH_2$ | H | (S)- |
| II-567 | Me | Me | Me | C≡C | Ph | $CH_2$ | Me | racemic |
| II-568 | Me | Me | Me | C≡C | Ph | $CH_2$ | Me | (S)- |
| II-569 | Me | Me | Me | 1,2-Cyclo-propylene | Ph | $CH_2$ | H | racemic |
| II-570 | Me | Me | Me | 1,2-Cyclo-propylene | Ph | $CH_2$ | H | (S)- |
| II-571 | Me | Me | Me | 1,2-Cyclo-propylene | Ph | $CH_2$ | Me | racemic |
| II-572 | Me | Me | Me | 1,2-Cyclo-propylene | Ph | $CH_2$ | Me | (S)- |
| II-573 | Me | Me | Me | 1,2-Cyclo-propynylene | Ph | $CH_2$ | H | racemic |
| II-574 | Me | Me | Me | 1,2-Cyclo-propynylene | Ph | $CH_2$ | H | (S)- |
| II-575 | Me | Me | Me | 1,2-Cyclo-propynylene | Ph | $CH_2$ | Me | racemic |
| II-576 | Me | Me | Me | 1,2-Cyclo-propynylene | Ph | $CH_2$ | Me | (S)- |

TABLE 21

(II)

| Compound No. | R¹ | R² | R³ | L² | R⁴ | L³ | R⁵ | Configuration |
|---|---|---|---|---|---|---|---|---|
| II-577 | Me | Me | Me | O | Ph | $C(Me)_2CH_2$ | H | racemic |
| II-578 | Me | Me | Me | O | Ph | $C(Me)_2CH_2$ | H | (+) |
| II-579 | Me | Me | Me | O | Ph | $C(Me)_2CH_2$ | H | (−) |
| II-580 | Me | Et | Me | O | Ph | $C(Me)_2CH_2$ | H | racemic |
| II-581 | Me | Et | Me | O | Ph | $C(Me)_2CH_2$ | H | (+) |
| II-582 | Me | Et | Me | O | Ph | $C(Me)_2CH_2$ | H | (−) |
| II-583 | Me | Me | Me | O | Ph | $C(Me)_2CH_2$ | Me | racemic |
| II-584 | Me | Me | Me | O | Ph | $C(Me)_2CH_2$ | Me | (+) |
| II-585 | Me | Me | Me | O | Ph | $C(Me)_2CH_2$ | Me | (−) |
| II-586 | Me | Et | Me | O | Ph | $C(Me)_2CH_2$ | Me | racemic |
| II-587 | Me | Et | Me | O | Ph | $C(Me)_2CH_2$ | Me | (+) |
| II-588 | Me | Et | Me | O | Ph | $C(Me)_2CH_2$ | Me | (−) |
| II-589 | Me | Me | Me | O | Ph | $C(Me)_2CH_2$ | $CHF_2$ | racemic |
| II-590 | Me | Me | Me | O | Ph | $C(Me)_2CH_2$ | $CHF_2$ | (+) |
| II-591 | Me | Me | Me | O | Ph | $C(Me)_2CH_2$ | $CHF_2$ | (−) |
| II-592 | Me | Me | Me | O | Ph | $C(Me)_2CH_2$ | Et | racemic |
| II-593 | Me | Me | Me | O | Ph | $C(Me)_2CH_2$ | Et | (+) |
| II-594 | Me | Me | Me | O | Ph | $C(Me)_2CH_2$ | Et | (−) |
| II-595 | Me | Me | Me | NH | Ph | $C(Me)_2CH_2$ | H | (+) |
| II-596 | Me | Me | Me | NH | Ph | $C(Me)_2CH_2$ | H | (−) |
| II-597 | Me | Et | Me | NH | Ph | $C(Me)_2CH_2$ | H | (+) |
| II-598 | Me | Et | Me | NH | Ph | $C(Me)_2CH_2$ | H | (−) |
| II-599 | Me | Me | Me | NH | Ph | $C(Me)_2CH_2$ | Me | racemic |
| II-600 | Me | Me | Me | NH | Ph | $C(Me)_2CH_2$ | Me | (+) |
| II-601 | Me | Me | Me | NH | Ph | $C(Me)_2CH_2$ | Me | (−) |
| II-602 | Me | Et | Me | NH | Ph | $C(Me)_2CH_2$ | Me | racemic |
| II-603 | Me | Et | Me | NH | Ph | $C(Me)_2CH_2$ | Me | (+) |
| II-604 | Me | Et | Me | NH | Ph | $C(Me)_2CH_2$ | Me | (−) |
| II-605 | Me | Me | Me | NH | Ph | $C(Me)_2CH_2$ | $CHF_2$ | racemic |
| II-606 | Me | Me | Me | NH | Ph | $C(Me)_2CH_2$ | $CHF_2$ | (+) |
| II-607 | Me | Me | Me | NH | Ph | $C(Me)_2CH_2$ | $CHF_2$ | (−) |
| II-608 | Me | Et | Me | NH | Ph | $C(Me)_2CH_2$ | $CHF_2$ | racemic |
| II-609 | Me | Et | Me | NH | Ph | $C(Me)_2CH_2$ | $CHF_2$ | (+) |
| II-610 | Me | Et | Me | NH | Ph | $C(Me)_2CH_2$ | $CHF_2$ | (−) |
| II-611 | Me | Me | Me | NH | Ph | $C(Me)_2CH_2$ | Et | racemic |
| II-612 | Me | Me | Me | NH | Ph | $C(Me)_2CH_2$ | Et | (+) |
| II-613 | Me | Me | Me | NH | Ph | $C(Me)_2CH_2$ | Et | (−) |
| II-614 | Me | Et | Me | NH | Ph | $C(Me)_2CH_2$ | Et | racemic |
| II-615 | Me | Et | Me | NH | Ph | $C(Me)_2CH_2$ | Et | (+) |
| II-616 | Me | Et | Me | NH | Ph | $C(Me)_2CH_2$ | Et | (−) |
| II-617 | Me | Me | Me | NH | Ph | $C(Me)_2CH_2$ | iPr | racemic |
| II-618 | Me | Me | Me | NH | Ph | $C(Me)_2CH_2$ | iPr | (+) |
| II-619 | Me | Me | Me | NH | Ph | $C(Me)_2CH_2$ | iPr | (−) |
| II-620 | Me | Et | Me | NH | Ph | $C(Me)_2CH_2$ | iPr | racemic |
| II-621 | Me | Et | Me | NH | Ph | $C(Me)_2CH_2$ | iPr | (+) |
| II-622 | Me | Et | Me | NH | Ph | $C(Me)_2CH_2$ | iPr | (−) |
| II-623 | Me | Me | Me | NH | Ph | $C(Me)_2CH_2$ | cPr | racemic |
| II-624 | Me | Me | Me | NH | Ph | $C(Me)_2CH_2$ | cPr | (+) |
| II-625 | Me | Me | Me | NH | Ph | $C(Me)_2CH_2$ | cPr | (−) |
| II-626 | Me | Et | Me | NH | Ph | $C(Me)_2CH_2$ | cPr | racemic |

TABLE 22

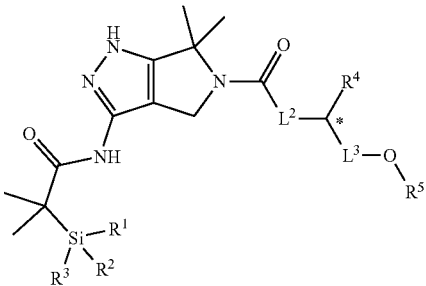

(II)

| Compound No. | R¹ | R² | R³ | L² | R⁴ | L³ | R⁵ | Configuration |
|---|---|---|---|---|---|---|---|---|
| II-627 | Me | Et | Me | NH | Ph | C(Me)₂CH₂ | cPr | (+) |
| II-628 | Me | Et | Me | NH | Ph | C(Me)₂CH₂ | cPr | (−) |
| II-629 | Me | Me | Me | NH | Ph | 1,1-Cyclopropylene-CH₂ | H | racemic |
| II-630 | Me | Me | Me | NH | Ph | 1,1-Cyclopropylene-CH₂ | H | (+) |
| II-631 | Me | Me | Me | NH | Ph | 1,1-Cyclopropylene-CH₂ | H | (−) |
| II-632 | Me | Et | Me | NH | Ph | 1,1-Cyclopropylene-CH₂ | H | racemic |
| II-633 | Me | Et | Me | NH | Ph | 1,1-Cyclopropylene-CH₂ | H | (+) |
| II-634 | Me | Et | Me | NH | Ph | 1,1-Cyclopropylene-CH₂ | H | (−) |
| II-635 | Me | Me | Me | NH | Ph | 1,1-Cyclopropylene-CH₂ | Me | racemic |
| II-636 | Me | Me | Me | NH | Ph | 1,1-Cyclopropylene-CH₂ | Me | (+) |
| II-637 | Me | Me | Me | NH | Ph | 1,1-Cyclopropylene-CH₂ | Me | (−) |
| II-638 | Me | Et | Me | NH | Ph | 1,1-Cyclopropylene-CH₂ | Me | racemic |
| II-639 | Me | Et | Me | NH | Ph | 1,1-Cyclopropylene-CH₂ | Me | (+) |
| II-640 | Me | Et | Me | NH | Ph | 1,1-Cyclopropylene-CH₂ | Me | (−) |
| II-641 | Me | Me | Me | NH | Ph | 1,1-Cyclobutylene-CH₂ | H | racemic |
| II-642 | Me | Me | Me | NH | Ph | 1,1-Cyclobutylene-CH₂ | H | (+) |
| II-643 | Me | Me | Me | NH | Ph | 1,1-Cyclobutylene-CH₂ | H | (−) |
| II-644 | Me | Et | Me | NH | Ph | 1,1-Cyclobutylene-CH₂ | H | racemic |
| II-645 | Me | Et | Me | NH | Ph | 1,1-Cyclobutylene-CH₂ | H | (+) |
| II-646 | Me | Et | Me | NH | Ph | 1,1-Cyclobutylene-CH₂ | H | (−) |
| II-647 | Me | Me | Me | NH | Ph | 1,1-Cyclobutylene-CH₂ | Me | racemic |
| II-648 | Me | Me | Me | NH | Ph | 1,1-Cyclobutylene-CH₂ | Me | (+) |
| II-649 | Me | Me | Me | NH | Ph | 1,1-Cyclobutylene-CH₂ | Me | (−) |
| II-650 | Me | Et | Me | NH | Ph | 1,1-Cyclobutylene-CH₂ | Me | racemic |
| II-651 | Me | Et | Me | NH | Ph | 1,1-Cyclobutylene-CH₂ | Me | (+) |
| II-652 | Me | Et | Me | NH | Ph | 1,1-Cyclobutylene-CH₂ | Me | (−) |
| II-653 | Me | Me | Me | NH | Ph | C(Et)₂CH₂ | H | racemic |
| II-654 | Me | Me | Me | NH | Ph | C(Et)₂CH₂ | H | (+) |
| II-655 | Me | Me | Me | NH | Ph | C(Et)₂CH₂ | H | (−) |
| II-656 | Me | Et | Me | NH | Ph | C(Et)₂CH₂ | H | racemic |
| II-657 | Me | Et | Me | NH | Ph | C(Et)₂CH₂ | H | (+) |
| II-658 | Me | Et | Me | NH | Ph | C(Et)₂CH₂ | H | (−) |
| II-659 | Me | Me | Me | NH | Ph | C(Et)₂CH₂ | Me | racemic |
| II-660 | Me | Me | Me | NH | Ph | C(Et)₂CH₂ | Me | (+) |
| II-661 | Me | Me | Me | NH | Ph | C(Et)₂CH₂ | Me | (−) |
| II-662 | Me | Et | Me | NH | Ph | C(Et)₂CH₂ | Me | racemic |
| II-663 | Me | Et | Me | NH | Ph | C(Et)₂CH₂ | Me | (+) |
| II-664 | Me | Et | Me | NH | Ph | C(Et)₂CH₂ | Me | (−) |
| II-665 | Me | Me | Me | NH | Ph | CH₂-1,1-Cyclopropylene | H | racemic |
| II-666 | Me | Me | Me | NH | Ph | CH₂-1,1-Cyclopropylene | H | (R)- |
| II-667 | Me | Et | Me | NH | Ph | CH₂-1,1-Cyclopropylene | H | racemic |
| II-668 | Me | Et | Me | NH | Ph | CH₂-1,1-Cyclopropylene | H | (R)- |
| II-669 | Me | Me | Me | NH | Ph | CH₂-1,1-Cyclopropylene | Me | racemic |
| II-670 | Me | Me | Me | NH | Ph | CH₂-1,1-Cyclopropylene | Me | (R)- |
| II-671 | Me | Et | Me | NH | Ph | CH₂-1,1-Cyclopropylene | Me | racemic |
| II-672 | Me | Et | Me | NH | Ph | CH₂-1,1-Cyclopropylene | Me | (R)- |
| II-673 | Me | Me | Me | NH | Ph | CH₂-1,1-cyclobutylene | H | racemic |
| II-674 | Me | Me | Me | NH | Ph | CH₂-1,1-cyclobutylene | H | (R)- |
| II-675 | Me | Et | Me | NH | Ph | CH₂-1,1-cyclobutylene | H | racemic |
| II-676 | Me | Et | Me | NH | Ph | CH₂-1,1-cyclobutylene | H | (R)- |

TABLE 23

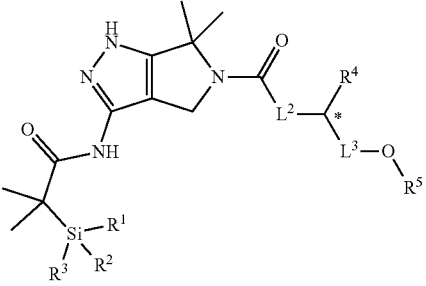

(II)

| Compound No. | R¹ | R² | R³ | L² | R⁴ | L³ | R⁵ | Configuration |
|---|---|---|---|---|---|---|---|---|
| II-677 | Me | Me | Me | NH | Ph | CH₂-1,1-cyclobutylene | Me | racemic |
| II-678 | Me | Me | Me | NH | Ph | CH₂-1,1-cyclobutylene | Me | (R)- |
| II-679 | Me | Et | Me | NH | Ph | CH₂-1,1-cyclobutylene | Me | racemic |
| II-680 | Me | Et | Me | NH | Ph | CH₂-1,1-cyclobutylene | Me | (R)- |
| II-681 | Me | Me | Me | NH | Ph | CH₂C(Et)₂ | H | racemic |
| II-682 | Me | Me | Me | NH | Ph | CH₂C(Et)₂ | H | (R)- |
| II-683 | Me | Et | Me | NH | Ph | CH₂C(Et)₂ | H | racemic |
| II-684 | Me | Et | Me | NH | Ph | CH₂C(Et)₂ | H | (R)- |
| II-685 | Me | Me | Me | NH | Ph | CH₂C(Et)₂ | Me | racemic |
| II-686 | Me | Me | Me | NH | Ph | CH₂C(Et)₂ | Me | (R)- |
| II-687 | Me | Et | Me | NH | Ph | CH₂C(Et)₂ | Me | racemic |
| II-688 | Me | Et | Me | NH | Ph | CH₂C(Et)₂ | Me | (R)- |
| II-689 | Me | Me | Me | NH | iPr | CH₂ | Me | racemic |
| II-690 | Me | Me | Me | NH | iPr | CH₂ | Me | (S)- |
| II-691 | Me | Et | Me | NH | iPr | CH₂ | Me | racemic |
| II-692 | Me | Et | Me | NH | iPr | CH₂ | Me | (S)- |
| II-693 | Me | Me | Me | NH | iPr | (CH₂)₂ | H | racemic |
| II-694 | Me | Me | Me | NH | iPr | (CH₂)₂ | H | (R)- |
| II-695 | Me | Et | Me | NH | iPr | (CH₂)₂ | H | racemic |
| II-696 | Me | Et | Me | NH | iPr | (CH₂)₂ | H | (R)- |
| II-697 | Me | Me | Me | NH | iPr | (CH₂)₂ | Me | racemic |
| II-698 | Me | Me | Me | NH | iPr | (CH₂)₂ | Me | (R)- |
| II-699 | Me | Et | Me | NH | iPr | (CH₂)₂ | Me | racemic |
| II-700 | Me | Et | Me | NH | iPr | (CH₂)₂ | Me | (R)- |
| II-701 | Me | Me | Me | NH | CF₃ | CH₂ | H | racemic |
| II-702 | Me | Me | Me | NH | CF₃ | CH₂ | H | (S)- |
| II-703 | Me | Et | Me | NH | CF₃ | CH₂ | H | racemic |
| II-704 | Me | Et | Me | NH | CF₃ | CH₂ | H | (S)- |
| II-705 | Me | Me | Me | NH | CH₂OH | CH₂ | H | |
| II-706 | Me | Et | Me | NH | CH₂OH | CH₂ | H | |
| II-707 | Me | Me | Me | NH | CH₂OMe | CH₂ | H | racemic |
| II-708 | Me | Me | Me | NH | CH₂OMe | CH₂ | H | (R)- |
| II-709 | Me | Et | Me | NH | CH₂OMe | CH₂ | H | racemic |
| II-710 | Me | Et | Me | NH | CH₂OMe | CH₂ | H | (R)- |
| II-711 | Me | Me | Me | NH | CH₂Ph | CH₂ | H | racemic |
| II-712 | Me | Me | Me | NH | CH₂Ph | CH₂ | H | (R)- |
| II-713 | Me | Me | Me | NH | CH₂Ph | CH₂ | H | (S)- |
| II-714 | Me | Et | Me | NH | CH₂Ph | CH₂ | H | racemic |
| II-715 | Me | Et | Me | NH | CH₂Ph | CH₂ | H | (S)- |
| II-716 | Me | Me | Me | NH | 2-F—Ph | CH₂ | Me | racemic |
| II-717 | Me | Me | Me | NH | 2-F—Ph | CH₂ | Me | (S)- |
| II-718 | Me | Et | Me | NH | 2-F—Ph | CH₂ | Me | racemic |
| II-719 | Me | Et | Me | NH | 2-F—Ph | CH₂ | Me | (S)- |
| II-720 | Me | Me | Me | NH | 2-F—Ph | (CH₂)₂ | H | racemic |
| II-721 | Me | Me | Me | NH | 2-F—Ph | (CH₂)₂ | H | (R)- |
| II-722 | Me | Et | Me | NH | 2-F—Ph | (CH₂)₂ | H | racemic |
| II-723 | Me | Et | Me | NH | 2-F—Ph | (CH₂)₂ | H | (R)- |
| II-724 | Me | Me | Me | NH | 2-F—Ph | (CH₂)₂ | Me | racemic |
| II-725 | Me | Me | Me | NH | 2-F—Ph | (CH₂)₂ | Me | (R)- |
| II-726 | Me | Et | Me | NH | 2-F—Ph | (CH₂)₂ | Me | racemic |

TABLE 24

(II)

| Compound No. | R¹ | R² | R³ | L² | R⁴ | L³ | R⁵ | Configuration |
|---|---|---|---|---|---|---|---|---|
| II-727 | Me | Et | Me | NH | 2-F—Ph | (CH$_2$)$_2$ | Me | (R)- |
| II-728 | Me | Me | Me | NH | 2-F—Ph | CH$_2$C(Me)$_2$ | H | racemic |
| II-729 | Me | Me | Me | NH | 2-F—Ph | CH$_2$C(Me)$_2$ | H | (R)- |
| II-730 | Me | Et | Me | NH | 2-F—Ph | CH$_2$C(Me)$_2$ | H | racemic |
| II-731 | Me | Et | Me | NH | 2-F—Ph | CH$_2$C(Me)$_2$ | H | (R)- |
| II-732 | Me | Me | Me | NH | 2-F—Ph | CH$_2$C(Me)$_2$ | Me | racemic |
| II-733 | Me | Me | Me | NH | 2-F—Ph | CH$_2$C(Me)$_2$ | Me | (R)- |
| II-734 | Me | Et | Me | NH | 2-F—Ph | CH$_2$C(Me)$_2$ | Me | racemic |
| II-735 | Me | Et | Me | NH | 2-F—Ph | CH$_2$C(Me)$_2$ | Me | (R)- |
| II-736 | Me | Me | Me | NH | 2-F—Ph | C(Me)$_2$CH$_2$ | H | racemic |
| II-737 | Me | Me | Me | NH | 2-F—Ph | C(Me)$_2$CH$_2$ | H | (+) |
| II-738 | Me | Me | Me | NH | 2-F—Ph | C(Me)$_2$CH$_2$ | H | (−) |
| II-739 | Me | Et | Me | NH | 2-F—Ph | C(Me)$_2$CH$_2$ | H | racemic |
| II-740 | Me | Et | Me | NH | 2-F—Ph | C(Me)$_2$CH$_2$ | H | (+) |
| II-741 | Me | Et | Me | NH | 2-F—Ph | C(Me)$_2$CH$_2$ | H | (−) |
| II-742 | Me | Me | Me | NH | 2-F—Ph | C(Me)$_2$CH$_2$ | Me | racemic |
| II-743 | Me | Me | Me | NH | 2-F—Ph | C(Me)$_2$CH$_2$ | Me | (+) |
| II-744 | Me | Me | Me | NH | 2-F—Ph | C(Me)$_2$CH$_2$ | Me | (−) |
| II-745 | Me | Et | Me | NH | 2-F—Ph | C(Me)$_2$CH$_2$ | Me | racemic |
| II-746 | Me | Et | Me | NH | 2-F—Ph | C(Me)$_2$CH$_2$ | Me | (+) |
| II-747 | Me | Et | Me | NH | 2-F—Ph | C(Me)$_2$CH$_2$ | Me | (−) |
| II-748 | Me | Me | Me | NH | 3-F—Ph | (CH$_2$)$_2$ | H | racemic |
| II-749 | Me | Me | Me | NH | 3-F—Ph | (CH$_2$)$_2$ | H | (R)- |
| II-750 | Me | Et | Me | NH | 3-F—Ph | (CH$_2$)$_2$ | H | racemic |
| II-751 | Me | Et | Me | NH | 3-F—Ph | (CH$_2$)$_2$ | H | (R)- |
| II-752 | Me | Me | Me | NH | 3-F—Ph | (CH$_2$)$_2$ | Me | racemic |
| II-753 | Me | Me | Me | NH | 3-F—Ph | (CH$_2$)$_2$ | Me | (R)- |
| II-754 | Me | Et | Me | NH | 3-F—Ph | (CH$_2$)$_2$ | Me | racemic |
| II-755 | Me | Et | Me | NH | 3-F—Ph | (CH$_2$)$_2$ | Me | (R)- |
| II-756 | Me | Me | Me | NH | 3-F—Ph | CH$_2$C(Me)$_2$ | H | racemic |
| II-757 | Me | Me | Me | NH | 3-F—Ph | CH$_2$C(Me)$_2$ | H | (R)- |
| II-758 | Me | Et | Me | NH | 3-F—Ph | CH$_2$C(Me)$_2$ | H | racemic |
| II-759 | Me | Et | Me | NH | 3-F—Ph | CH$_2$C(Me)$_2$ | H | (R)- |
| II-760 | Me | Me | Me | NH | 3-F—Ph | CH$_2$C(Me)$_2$ | Me | racemic |
| II-761 | Me | Me | Me | NH | 3-F—Ph | CH$_2$C(Me)$_2$ | Me | (R)- |
| II-762 | Me | Et | Me | NH | 3-F—Ph | CH$_2$C(Me)$_2$ | Me | racemic |
| II-763 | Me | Et | Me | NH | 3-F—Ph | CH$_2$C(Me)$_2$ | Me | (R)- |
| II-764 | Me | Me | Me | NH | 3-F—Ph | C(Me)$_2$CH$_2$ | H | racemic |
| II-765 | Me | Me | Me | NH | 3-F—Ph | C(Me)$_2$CH$_2$ | H | (+) |
| II-766 | Me | Me | Me | NH | 3-F—Ph | C(Me)$_2$CH$_2$ | H | (−) |
| II-767 | Me | Et | Me | NH | 3-F—Ph | C(Me)$_2$CH$_2$ | H | racemic |
| II-768 | Me | Et | Me | NH | 3-F—Ph | C(Me)$_2$CH$_2$ | H | (+) |
| II-769 | Me | Et | Me | NH | 3-F—Ph | C(Me)$_2$CH$_2$ | H | (−) |
| II-770 | Me | Me | Me | NH | 3-F—Ph | C(Me)$_2$CH$_2$ | Me | racemic |
| II-771 | Me | Me | Me | NH | 3-F—Ph | C(Me)$_2$CH$_2$ | Me | (+) |
| II-772 | Me | Me | Me | NH | 3-F—Ph | C(Me)$_2$CH$_2$ | Me | (−) |
| II-773 | Me | Et | Me | NH | 3-F—Ph | C(Me)$_2$CH$_2$ | Me | racemic |
| II-774 | Me | Et | Me | NH | 3-F—Ph | C(Me)$_2$CH$_2$ | Me | (+) |
| II-775 | Me | Et | Me | NH | 3-F—Ph | C(Me)$_2$CH$_2$ | Me | (−) |
| II-776 | Me | Me | Me | NH | 4-F—Ph | (CH$_2$)$_2$ | H | racemic |

TABLE 25

(II)

| Compound No. | R¹ | R² | R³ | L² | R⁴ | L³ | R⁵ | Configuration |
|---|---|---|---|---|---|---|---|---|
| II-777 | Me | Me | Me | NH | 4-F—Ph | (CH$_2$)$_2$ | H | (R)- |
| II-778 | Me | Et | Me | NH | 4-F—Ph | (CH$_2$)$_2$ | H | racemic |
| II-779 | Me | Et | Me | NH | 4-F—Ph | (CH$_2$)$_2$ | H | (R)- |
| II-780 | Me | Me | Me | NH | 4-F—Ph | (CH$_2$)$_2$ | Me | racemic |
| II-781 | Me | Me | Me | NH | 4-F—Ph | (CH$_2$)$_2$ | Me | (R)- |
| II-782 | Me | Et | Me | NH | 4-F—Ph | (CH$_2$)$_2$ | Me | racemic |
| II-783 | Me | Et | Me | NH | 4-F—Ph | (CH$_2$)$_2$ | Me | (R)- |
| II-784 | Me | Me | Me | NH | 4-F—Ph | CH$_2$C(Me)$_2$ | H | racemic |
| II-785 | Me | Me | Me | NH | 4-F—Ph | CH$_2$C(Me)$_2$ | H | (R)- |
| II-786 | Me | Et | Me | NH | 4-F—Ph | CH$_2$C(Me)$_2$ | H | racemic |
| II-787 | Me | Et | Me | NH | 4-F—Ph | CH$_2$C(Me)$_2$ | H | (R)- |
| II-788 | Me | Me | Me | NH | 4-F—Ph | CH$_2$C(Me)$_2$ | Me | racemic |
| II-789 | Me | Me | Me | NH | 4-F—Ph | CH$_2$C(Me)$_2$ | Me | (R)- |
| II-790 | Me | Et | Me | NH | 4-F—Ph | CH$_2$C(Me)$_2$ | Me | racemic |
| II-791 | Me | Et | Me | NH | 4-F—Ph | CH$_2$C(Me)$_2$ | Me | (R)- |
| II-792 | Me | Me | Me | NH | 4-F—Ph | C(Me)$_2$CH$_2$ | H | racemic |
| II-793 | Me | Me | Me | NH | 4-F—Ph | C(Me)$_2$CH$_2$ | H | (+) |
| II-794 | Me | Me | Me | NH | 4-F—Ph | C(Me)$_2$CH$_2$ | H | (−) |
| II-795 | Me | Et | Me | NH | 4-F—Ph | C(Me)$_2$CH$_2$ | H | racemic |
| II-796 | Me | Et | Me | NH | 4-F—Ph | C(Me)$_2$CH$_2$ | H | (+) |
| II-797 | Me | Et | Me | NH | 4-F—Ph | C(Me)$_2$CH$_2$ | H | (−) |
| II-798 | Me | Me | Me | NH | 4-F—Ph | C(Me)$_2$CH$_2$ | Me | racemic |
| II-799 | Me | Me | Me | NH | 4-F—Ph | C(Me)$_2$CH$_2$ | Me | (+) |
| II-800 | Me | Me | Me | NH | 4-F—Ph | C(Me)$_2$CH$_2$ | Me | (−) |
| II-801 | Me | Et | Me | NH | 4-F—Ph | C(Me)$_2$CH$_2$ | Me | racemic |
| II-802 | Me | Et | Me | NH | 4-F—Ph | C(Me)$_2$CH$_2$ | Me | (+) |
| II-803 | Me | Et | Me | NH | 4-F—Ph | C(Me)$_2$CH$_2$ | Me | (−) |
| II-804 | Me | Me | Me | NH | 2-Cl—Ph | CH$_2$ | H | racemic |
| II-805 | Me | Me | Me | NH | 2-Cl—Ph | CH$_2$ | H | (S)- |
| II-806 | Me | Et | Me | NH | 2-Cl—Ph | CH$_2$ | H | racemic |
| II-807 | Me | Et | Me | NH | 2-Cl—Ph | CH$_2$ | H | (S)- |
| II-808 | Me | Me | Me | NH | 2-Cl—Ph | CH$_2$ | Me | racemic |
| II-809 | Me | Me | Me | NH | 2-Cl—Ph | CH$_2$ | Me | (S)- |
| II-810 | Me | Et | Me | NH | 2-Cl—Ph | CH$_2$ | Me | racemic |
| II-811 | Me | Et | Me | NH | 2-Cl—Ph | CH$_2$ | Me | (S)- |
| II-812 | Me | Me | Me | NH | 2-Cl—Ph | (CH$_2$)$_2$ | H | racemic |
| II-813 | Me | Me | Me | NH | 2-Cl—Ph | (CH$_2$)$_2$ | H | (R)- |
| II-814 | Me | Et | Me | NH | 2-Cl—Ph | (CH$_2$)$_2$ | H | racemic |
| II-815 | Me | Et | Me | NH | 2-Cl—Ph | (CH$_2$)$_2$ | H | (R)- |
| II-816 | Me | Me | Me | NH | 2-Cl—Ph | (CH$_2$)$_2$ | Me | racemic |
| II-817 | Me | Me | Me | NH | 2-Cl—Ph | (CH$_2$)$_2$ | Me | (R)- |
| II-818 | Me | Et | Me | NH | 2-Cl—Ph | (CH$_2$)$_2$ | Me | racemic |
| II-819 | Me | Et | Me | NH | 2-Cl—Ph | (CH$_2$)$_2$ | Me | (R)- |
| II-820 | Me | Me | Me | NH | 2-Cl—Ph | CH$_2$C(Me)$_2$ | H | racemic |
| II-821 | Me | Me | Me | NH | 2-Cl—Ph | CH$_2$C(Me)$_2$ | H | (R)- |
| II-822 | Me | Et | Me | NH | 2-Cl—Ph | CH$_2$C(Me)$_2$ | H | racemic |
| II-823 | Me | Et | Me | NH | 2-Cl—Ph | CH$_2$C(Me)$_2$ | H | (R)- |
| II-824 | Me | Me | Me | NH | 2-Cl—Ph | CH$_2$C(Me)$_2$ | Me | racemic |
| II-825 | Me | Me | Me | NH | 2-Cl—Ph | CH$_2$C(Me)$_2$ | Me | (R)- |
| II-826 | Me | Et | Me | NH | 2-Cl—Ph | CH$_2$C(Me)$_2$ | Me | racemic |

TABLE 26

(II)

| Compound No. | R¹ | R² | R³ | L² | R⁴ | L³ | R⁵ | Configuration |
|---|---|---|---|---|---|---|---|---|
| II-827 | Me | Et | Me | NH | 2-Cl—Ph | CH₂C(Me)₂ | Me | (R)- |
| II-828 | Me | Me | Me | NH | 2-Cl—Ph | C(Me)₂CH₂ | H | racemic |
| II-829 | Me | Me | Me | NH | 2-Cl—Ph | C(Me)₂CH₂ | H | (+) |
| II-830 | Me | Me | Me | NH | 2-Cl—Ph | C(Me)₂CH₂ | H | (−) |
| II-831 | Me | Et | Me | NH | 2-Cl—Ph | C(Me)₂CH₂ | H | racemic |
| II-832 | Me | Et | Me | NH | 2-Cl—Ph | C(Me)₂CH₂ | H | (+) |
| II-833 | Me | Et | Me | NH | 2-Cl—Ph | C(Me)₂CH₂ | H | (−) |
| II-834 | Me | Me | Me | NH | 2-Cl—Ph | C(Me)₂CH₂ | Me | racemic |
| II-835 | Me | Me | Me | NH | 2-Cl—Ph | C(Me)₂CH₂ | Me | (+) |
| II-836 | Me | Me | Me | NH | 2-Cl—Ph | C(Me)₂CH₂ | Me | (−) |
| II-837 | Me | Et | Me | NH | 2-Cl—Ph | C(Me)₂CH₂ | Me | racemic |
| II-838 | Me | Et | Me | NH | 2-Cl—Ph | C(Me)₂CH₂ | Me | (+) |
| II-839 | Me | Et | Me | NH | 2-Cl—Ph | C(Me)₂CH₂ | Me | (−) |
| II-840 | Me | Me | Me | NH | 3-Cl—Ph | CH₂ | H | racemic |
| II-841 | Me | Me | Me | NH | 3-Cl—Ph | CH₂ | H | (S)- |
| II-842 | Me | Et | Me | NH | 3-Cl—Ph | CH₂ | H | racemic |
| II-843 | Me | Et | Me | NH | 3-Cl—Ph | CH₂ | H | (S)- |
| II-844 | Me | Me | Me | NH | 3-Cl—Ph | CH₂ | Me | racemic |
| II-845 | Me | Me | Me | NH | 3-Cl—Ph | CH₂ | Me | (S)- |
| II-846 | Me | Et | Me | NH | 3-Cl—Ph | CH₂ | Me | racemic |
| II-847 | Me | Et | Me | NH | 3-Cl—Ph | CH₂ | Me | (S)- |
| II-848 | Me | Me | Me | NH | 3-Cl—Ph | (CH₂)₂ | H | racemic |
| II-849 | Me | Me | Me | NH | 3-Cl—Ph | (CH₂)₂ | H | (R)- |
| II-850 | Me | Et | Me | NH | 3-Cl—Ph | (CH₂)₂ | H | racemic |
| II-851 | Me | Et | Me | NH | 3-Cl—Ph | (CH₂)₂ | H | (R)- |
| II-852 | Me | Me | Me | NH | 3-Cl—Ph | (CH₂)₂ | Me | racemic |
| II-853 | Me | Me | Me | NH | 3-Cl—Ph | (CH₂)₂ | Me | (R)- |
| II-854 | Me | Et | Me | NH | 3-Cl—Ph | (CH₂)₂ | Me | racemic |
| II-855 | Me | Et | Me | NH | 3-Cl—Ph | (CH₂)₂ | Me | (R)- |
| II-856 | Me | Me | Me | NH | 3-Cl—Ph | CH₂C(Me)₂ | H | racemic |
| II-857 | Me | Me | Me | NH | 3-Cl—Ph | CH₂C(Me)₂ | H | (R)- |
| II-858 | Me | Et | Me | NH | 3-Cl—Ph | CH₂C(Me)₂ | H | racemic |
| II-859 | Me | Et | Me | NH | 3-Cl—Ph | CH₂C(Me)₂ | H | (R)- |
| II-860 | Me | Me | Me | NH | 3-Cl—Ph | CH₂C(Me)₂ | Me | racemic |
| II-861 | Me | Me | Me | NH | 3-Cl—Ph | CH₂C(Me)₂ | Me | (R)- |
| II-862 | Me | Et | Me | NH | 3-Cl—Ph | CH₂C(Me)₂ | Me | racemic |
| II-863 | Me | Et | Me | NH | 3-Cl—Ph | CH₂C(Me)₂ | Me | (R)- |
| II-864 | Me | Me | Me | NH | 3-Cl—Ph | C(Me)₂CH₂ | H | racemic |
| II-865 | Me | Me | Me | NH | 3-Cl—Ph | C(Me)₂CH₂ | H | (+) |
| II-866 | Me | Me | Me | NH | 3-Cl—Ph | C(Me)₂CH₂ | H | (−) |
| II-867 | Me | Et | Me | NH | 3-Cl—Ph | C(Me)₂CH₂ | H | racemic |
| II-868 | Me | Et | Me | NH | 3-Cl—Ph | C(Me)₂CH₂ | H | (+) |
| II-869 | Me | Et | Me | NH | 3-Cl—Ph | C(Me)₂CH₂ | H | (−) |
| II-870 | Me | Me | Me | NH | 3-Cl—Ph | C(Me)₂CH₂ | Me | racemic |
| II-871 | Me | Me | Me | NH | 3-Cl—Ph | C(Me)₂CH₂ | Me | (+) |
| II-872 | Me | Me | Me | NH | 3-Cl—Ph | C(Me)₂CH₂ | Me | (−) |
| II-873 | Me | Et | Me | NH | 3-Cl—Ph | C(Me)₂CH₂ | Me | racemic |
| II-874 | Me | Et | Me | NH | 3-Cl—Ph | C(Me)₂CH₂ | Me | (+) |
| II-875 | Me | Et | Me | NH | 3-Cl—Ph | C(Me)₂CH₂ | Me | (−) |
| II-876 | Me | Me | Me | NH | 4-Cl—Ph | CH₂ | H | racemic |

TABLE 27

(II)

| Compound No. | R¹ | R² | R³ | L² | R⁴ | L³ | R⁵ | Configuration |
|---|---|---|---|---|---|---|---|---|
| II-877 | Me | Me | Me | NH | 4-Cl—Ph | CH₂ | H | (S)- |
| II-878 | Me | Et | Me | NH | 4-Cl—Ph | CH₂ | H | racemic |
| II-879 | Me | Et | Me | NH | 4-Cl—Ph | CH₂ | H | (S)- |
| II-880 | Me | Me | Me | NH | 4-Cl—Ph | CH₂ | Me | racemic |
| II-881 | Me | Me | Me | NH | 4-Cl—Ph | CH₂ | Me | (S)- |
| II-882 | Me | Et | Me | NH | 4-Cl—Ph | CH₂ | Me | racemic |
| II-883 | Me | Et | Me | NH | 4-Cl—Ph | CH₂ | Me | (S)- |
| II-884 | Me | Me | Me | NH | 4-Cl—Ph | (CH₂)₂ | H | racemic |
| II-885 | Me | Me | Me | NH | 4-Cl—Ph | (CH₂)₂ | H | (R)- |
| II-886 | Me | Et | Me | NH | 4-Cl—Ph | (CH₂)₂ | H | racemic |
| II-887 | Me | Et | Me | NH | 4-Cl—Ph | (CH₂)₂ | H | (R)- |
| II-888 | Me | Me | Me | NH | 4-Cl—Ph | (CH₂)₂ | Me | racemic |
| II-889 | Me | Me | Me | NH | 4-Cl—Ph | (CH₂)₂ | Me | (R)- |
| II-890 | Me | Et | Me | NH | 4-Cl—Ph | (CH₂)₂ | Me | racemic |
| II-891 | Me | Et | Me | NH | 4-Cl—Ph | (CH₂)₂ | Me | (R)- |
| II-892 | Me | Me | Me | NH | 4-Cl—Ph | CH₂C(Me)₂ | H | racemic |
| II-893 | Me | Me | Me | NH | 4-Cl—Ph | CH₂C(Me)₂ | H | (R)- |
| II-894 | Me | Et | Me | NH | 4-Cl—Ph | CH₂C(Me)₂ | H | racemic |
| II-895 | Me | Et | Me | NH | 4-Cl—Ph | CH₂C(Me)₂ | H | (R)- |
| II-896 | Me | Me | Me | NH | 4-Cl—Ph | CH₂C(Me)₂ | Me | racemic |
| II-897 | Me | Me | Me | NH | 4-Cl—Ph | CH₂C(Me)₂ | Me | (R)- |
| II-898 | Me | Et | Me | NH | 4-Cl—Ph | CH₂C(Me)₂ | Me | racemic |
| II-899 | Me | Et | Me | NH | 4-Cl—Ph | CH₂C(Me)₂ | Me | (R)- |
| II-900 | Me | Me | Me | NH | 4-Cl—Ph | C(Me)₂CH₂ | H | racemic |
| II-901 | Me | Me | Me | NH | 4-Cl—Ph | C(Me)₂CH₂ | H | (+) |
| II-902 | Me | Me | Me | NH | 4-Cl—Ph | C(Me)₂CH₂ | H | (−) |
| II-903 | Me | Et | Me | NH | 4-Cl—Ph | C(Me)₂CH₂ | H | racemic |
| II-904 | Me | Et | Me | NH | 4-Cl—Ph | C(Me)₂CH₂ | H | (+) |
| II-905 | Me | Et | Me | NH | 4-Cl—Ph | C(Me)₂CH₂ | H | (−) |
| II-906 | Me | Me | Me | NH | 4-Cl—Ph | C(Me)₂CH₂ | Me | racemic |
| II-907 | Me | Me | Me | NH | 4-Cl—Ph | C(Me)₂CH₂ | Me | (+) |
| II-908 | Me | Me | Me | NH | 4-Cl—Ph | C(Me)₂CH₂ | Me | (−) |
| II-909 | Me | Et | Me | NH | 4-Cl—Ph | C(Me)₂CH₂ | Me | racemic |
| II-910 | Me | Et | Me | NH | 4-Cl—Ph | C(Me)₂CH₂ | Me | (+) |
| II-911 | Me | Et | Me | NH | 4-Cl—Ph | C(Me)₂CH₂ | Me | (−) |
| II-912 | Me | Me | Me | NH | 2-Me—Ph | CH₂ | H | racemic |
| II-913 | Me | Me | Me | NH | 2-Me—Ph | CH₂ | H | (S)- |
| II-914 | Me | Et | Me | NH | 2-Me—Ph | CH₂ | H | racemic |
| II-915 | Me | Et | Me | NH | 2-Me—Ph | CH₂ | H | (S)- |
| II-916 | Me | Me | Me | NH | 2-Me—Ph | CH₂ | Me | racemic |
| II-917 | Me | Me | Me | NH | 2-Me—Ph | CH₂ | Me | (S)- |
| II-918 | Me | Et | Me | NH | 2-Me—Ph | CH₂ | Me | racemic |
| II-919 | Me | Et | Me | NH | 2-Me—Ph | CH₂ | Me | (S)- |
| II-920 | Me | Me | Me | NH | 2-Me—Ph | (CH₂)₂ | H | racemic |
| II-921 | Me | Me | Me | NH | 2-Me—Ph | (CH₂)₂ | H | (R)- |
| II-922 | Me | Et | Me | NH | 2-Me—Ph | (CH₂)₂ | H | racemic |
| II-923 | Me | Et | Me | NH | 2-Me—Ph | (CH₂)₂ | H | (R)- |
| II-924 | Me | Me | Me | NH | 2-Me—Ph | (CH₂)₂ | Me | racemic |
| II-925 | Me | Me | Me | NH | 2-Me—Ph | (CH₂)₂ | Me | (R)- |
| II-926 | Me | Et | Me | NH | 2-Me—Ph | (CH₂)₂ | Me | racemic |

TABLE 28

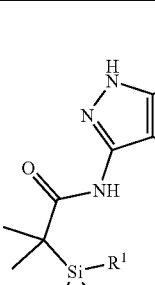

(II)

| Compound No. | R¹ | R² | R³ | L² | R⁴ | L³ | R⁵ | Configuration |
|---|---|---|---|---|---|---|---|---|
| II-927 | Me | Et | Me | NH | 2-Me—Ph | (CH$_2$)$_2$ | Me | (R)- |
| II-928 | Me | Me | Me | NH | 2-Me—Ph | CH$_2$C(Me)$_2$ | H | racemic |
| II-929 | Me | Me | Me | NH | 2-Me—Ph | CH$_2$C(Me)$_2$ | H | (R)- |
| II-930 | Me | Et | Me | NH | 2-Me—Ph | CH$_2$C(Me)$_2$ | H | racemic |
| II-931 | Me | Et | Me | NH | 2-Me—Ph | CH$_2$C(Me)$_2$ | H | (R)- |
| II-932 | Me | Me | Me | NH | 2-Me—Ph | CH$_2$C(Me)$_2$ | Me | racemic |
| II-933 | Me | Me | Me | NH | 2-Me—Ph | CH$_2$C(Me)$_2$ | Me | (R)- |
| II-934 | Me | Et | Me | NH | 2-Me—Ph | CH$_2$C(Me)$_2$ | Me | racemic |
| II-935 | Me | Et | Me | NH | 2-Me—Ph | CH$_2$C(Me)$_2$ | Me | (R)- |
| II-936 | Me | Me | Me | NH | 2-Me—Ph | C(Me)$_2$CH$_2$ | H | racemic |
| II-937 | Me | Me | Me | NH | 2-Me—Ph | C(Me)$_2$CH$_2$ | H | (+) |
| II-938 | Me | Me | Me | NH | 2-Me—Ph | C(Me)$_2$CH$_2$ | H | (−) |
| II-939 | Me | Et | Me | NH | 2-Me—Ph | C(Me)$_2$CH$_2$ | H | racemic |
| II-940 | Me | Et | Me | NH | 2-Me—Ph | C(Me)$_2$CH$_2$ | H | (+) |
| II-941 | Me | Et | Me | NH | 2-Me—Ph | C(Me)$_2$CH$_2$ | H | (−) |
| II-942 | Me | Me | Me | NH | 2-Me—Ph | C(Me)$_2$CH$_2$ | Me | racemic |
| II-943 | Me | Me | Me | NH | 2-Me—Ph | C(Me)$_2$CH$_2$ | Me | (+) |
| II-944 | Me | Me | Me | NH | 2-Me—Ph | C(Me)$_2$CH$_2$ | Me | (−) |
| II-945 | Me | Et | Me | NH | 2-Me—Ph | C(Me)$_2$CH$_2$ | Me | racemic |
| II-946 | Me | Et | Me | NH | 2-Me—Ph | C(Me)$_2$CH$_2$ | Me | (+) |
| II-947 | Me | Et | Me | NH | 2-Me—Ph | C(Me)$_2$CH$_2$ | Me | (−) |
| II-948 | Me | Me | Me | NH | 3-Me—Ph | CH$_2$ | H | racemic |
| II-949 | Me | Me | Me | NH | 3-Me—Ph | CH$_2$ | H | (S)- |
| II-950 | Me | Et | Me | NH | 3-Me—Ph | CH$_2$ | H | racemic |
| II-951 | Me | Et | Me | NH | 3-Me—Ph | CH$_2$ | H | (S)- |
| II-952 | Me | Me | Me | NH | 3-Me—Ph | CH$_2$ | Me | racemic |
| II-953 | Me | Me | Me | NH | 3-Me—Ph | CH$_2$ | Me | (S)- |
| II-954 | Me | Et | Me | NH | 3-Me—Ph | CH$_2$ | Me | racemic |
| II-955 | Me | Et | Me | NH | 3-Me—Ph | CH$_2$ | Me | (S)- |
| II-956 | Me | Me | Me | NH | 3-Me—Ph | (CH$_2$)$_2$ | H | racemic |
| II-957 | Me | Me | Me | NH | 3-Me—Ph | (CH$_2$)$_2$ | H | (R)- |
| II-958 | Me | Et | Me | NH | 3-Me—Ph | (CH$_2$)$_2$ | H | racemic |
| II-959 | Me | Et | Me | NH | 3-Me—Ph | (CH$_2$)$_2$ | H | (R)- |
| II-960 | Me | Me | Me | NH | 3-Me—Ph | (CH$_2$)$_2$ | Me | racemic |
| II-961 | Me | Me | Me | NH | 3-Me—Ph | (CH$_2$)$_2$ | Me | (R)- |
| II-962 | Me | Et | Me | NH | 3-Me—Ph | (CH$_2$)$_2$ | Me | racemic |
| II-963 | Me | Et | Me | NH | 3-Me—Ph | (CH$_2$)$_2$ | Me | (R)- |
| II-964 | Me | Me | Me | NH | 3-Me—Ph | CH$_2$C(Me)$_2$ | H | racemic |
| II-965 | Me | Me | Me | NH | 3-Me—Ph | CH$_2$C(Me)$_2$ | H | (R)- |
| II-966 | Me | Et | Me | NH | 3-Me—Ph | CH$_2$C(Me)$_2$ | H | racemic |
| II-967 | Me | Et | Me | NH | 3-Me—Ph | CH$_2$C(Me)$_2$ | H | (R)- |
| II-968 | Me | Me | Me | NH | 3-Me—Ph | CH$_2$C(Me)$_2$ | Me | racemic |
| II-969 | Me | Me | Me | NH | 3-Me—Ph | CH$_2$C(Me)$_2$ | Me | (R)- |
| II-970 | Me | Et | Me | NH | 3-Me—Ph | CH$_2$C(Me)$_2$ | Me | racemic |
| II-971 | Me | Et | Me | NH | 3-Me—Ph | CH$_2$C(Me)$_2$ | Me | (R)- |
| II-972 | Me | Me | Me | NH | 3-Me—Ph | C(Me)$_2$CH$_2$ | H | racemic |
| II-973 | Me | Me | Me | NH | 3-Me—Ph | C(Me)$_2$CH$_2$ | H | (+) |
| II-974 | Me | Me | Me | NH | 3-Me—Ph | C(Me)$_2$CH$_2$ | H | (−) |
| II-975 | Me | Et | Me | NH | 3-Me—Ph | C(Me)$_2$CH$_2$ | H | racemic |
| II-976 | Me | Et | Me | NH | 3-Me—Ph | C(Me)$_2$CH$_2$ | H | (+) |

TABLE 29

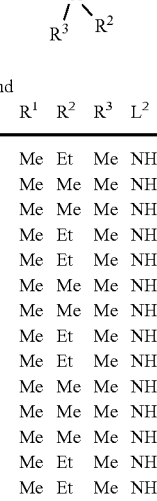

(II)

| Compound No. | R¹ | R² | R³ | L² | R⁴ | L³ | R⁵ | Configuration |
|---|---|---|---|---|---|---|---|---|
| II-977 | Me | Et | Me | NH | 3-Me—Ph | C(Me)$_2$CH$_2$ | H | (−) |
| II-978 | Me | Me | Me | NH | 3-Me—Ph | C(Me)$_2$CH$_2$ | Me | racemic |
| II-979 | Me | Me | Me | NH | 3-Me—Ph | C(Me)$_2$CH$_2$ | Me | (+) |
| II-980 | Me | Me | Me | NH | 3-Me—Ph | C(Me)$_2$CH$_2$ | Me | (−) |
| II-981 | Me | Et | Me | NH | 3-Me—Ph | C(Me)$_2$CH$_2$ | Me | racemic |
| II-982 | Me | Et | Me | NH | 3-Me—Ph | C(Me)$_2$CH$_2$ | Me | (+) |
| II-983 | Me | Et | Me | NH | 3-Me—Ph | C(Me)$_2$CH$_2$ | Me | (−) |
| II-984 | Me | Me | Me | NH | 4-Me—Ph | CH$_2$ | H | racemic |
| II-985 | Me | Me | Me | NH | 4-Me—Ph | CH$_2$ | H | (S)- |
| II-986 | Me | Et | Me | NH | 4-Me—Ph | CH$_2$ | H | racemic |
| II-987 | Me | Et | Me | NH | 4-Me—Ph | CH$_2$ | H | (S)- |
| II-988 | Me | Me | Me | NH | 4-Me—Ph | CH$_2$ | Me | racemic |
| II-989 | Me | Me | Me | NH | 4-Me—Ph | CH$_2$ | Me | (S)- |
| II-990 | Me | Et | Me | NH | 4-Me—Ph | CH$_2$ | Me | racemic |
| II-991 | Me | Et | Me | NH | 4-Me—Ph | CH$_2$ | Me | (S)- |
| II-992 | Me | Me | Me | NH | 4-Me—Ph | (CH$_2$)$_2$ | H | racemic |
| II-993 | Me | Me | Me | NH | 4-Me—Ph | (CH$_2$)$_2$ | H | (R)- |
| II-994 | Me | Et | Me | NH | 4-Me—Ph | (CH$_2$)$_2$ | H | racemic |
| II-995 | Me | Et | Me | NH | 4-Me—Ph | (CH$_2$)$_2$ | H | (R)- |
| II-996 | Me | Me | Me | NH | 4-Me—Ph | (CH$_2$)$_2$ | Me | racemic |
| II-997 | Me | Me | Me | NH | 4-Me—Ph | (CH$_2$)$_2$ | Me | (R)- |
| II-998 | Me | Et | Me | NH | 4-Me—Ph | (CH$_2$)$_2$ | Me | racemic |
| II-999 | Me | Et | Me | NH | 4-Me—Ph | (CH$_2$)$_2$ | Me | (R)- |
| II-1000 | Me | Me | Me | NH | 4-Me—Ph | CH$_2$C(Me)$_2$ | H | racemic |
| II-1001 | Me | Me | Me | NH | 4-Me—Ph | CH$_2$C(Me)$_2$ | H | (R)- |
| II-1002 | Me | Et | Me | NH | 4-Me—Ph | CH$_2$C(Me)$_2$ | H | racemic |
| II-1003 | Me | Et | Me | NH | 4-Me—Ph | CH$_2$C(Me)$_2$ | H | (R)- |
| II-1004 | Me | Me | Me | NH | 4-Me—Ph | CH$_2$C(Me)$_2$ | Me | racemic |
| II-1005 | Me | Me | Me | NH | 4-Me—Ph | CH$_2$C(Me)$_2$ | Me | (R)- |
| II-1006 | Me | Et | Me | NH | 4-Me—Ph | CH$_2$C(Me)$_2$ | Me | racemic |
| II-1007 | Me | Et | Me | NH | 4-Me—Ph | CH$_2$C(Me)$_2$ | Me | (R)- |
| II-1008 | Me | Me | Me | NH | 4-Me—Ph | C(Me)$_2$CH$_2$ | H | racemic |
| II-1009 | Me | Me | Me | NH | 4-Me—Ph | C(Me)$_2$CH$_2$ | H | (+) |
| II-1010 | Me | Me | Me | NH | 4-Me—Ph | C(Me)$_2$CH$_2$ | H | (−) |
| II-1011 | Me | Et | Me | NH | 4-Me—Ph | C(Me)$_2$CH$_2$ | H | racemic |
| II-1012 | Me | Et | Me | NH | 4-Me—Ph | C(Me)$_2$CH$_2$ | H | (+) |
| II-1013 | Me | Et | Me | NH | 4-Me—Ph | C(Me)$_2$CH$_2$ | H | (−) |
| II-1014 | Me | Me | Me | NH | 4-Me—Ph | C(Me)$_2$CH$_2$ | Me | racemic |
| II-1015 | Me | Me | Me | NH | 4-Me—Ph | C(Me)$_2$CH$_2$ | Me | (+) |
| II-1016 | Me | Me | Me | NH | 4-Me—Ph | C(Me)$_2$CH$_2$ | Me | (−) |
| II-1017 | Me | Et | Me | NH | 4-Me—Ph | C(Me)$_2$CH$_2$ | Me | racemic |
| II-1018 | Me | Et | Me | NH | 4-Me—Ph | C(Me)$_2$CH$_2$ | Me | (+) |
| II-1019 | Me | Et | Me | NH | 4-Me—Ph | C(Me)$_2$CH$_2$ | Me | (−) |
| II-1020 | Me | Me | Me | — | Ph | — | H | racemic |
| II-1021 | Me | Me | Me | — | Ph | — | H | (R)- |
| II-1022 | Me | Et | Me | — | Ph | — | H | racemic |
| II-1023 | Me | Et | Me | — | Ph | — | H | (R)- |
| II-1024 | Me | Me | Me | — | Ph | — | Me | racemic |
| II-1025 | Me | Me | Me | — | Ph | — | Me | (R)- |
| II-1026 | Me | Et | Me | — | Ph | — | Me | racemic |

TABLE 30 (II)

| Compound No. | R¹ | R² | R³ | L² | R⁴ | L³ | R⁵ | Configuration |
|---|---|---|---|---|---|---|---|---|
| II-1027 | Me | Et | Me | — | Ph | — | Me | (R)- |
| II-1028 | Me | Me | Me | — | Ph | — | $CHF_2$ | racemic |
| II-1029 | Me | Me | Me | — | Ph | — | $CHF_2$ | (R)- |
| II-1030 | Me | Et | Me | — | Ph | — | $CHF_2$ | racemic |
| II-1031 | Me | Et | Me | — | Ph | — | $CHF_2$ | (R)- |
| II-1032 | Me | Me | Me | — | Ph | — | $CF_3$ | racemic |
| II-1033 | Me | Me | Me | — | Ph | — | $CF_3$ | (R)- |
| II-1034 | Me | Et | Me | — | Ph | — | $CF_3$ | racemic |
| II-1035 | Me | Et | Me | — | Ph | — | $CF_3$ | (R)- |
| II-1036 | Me | Me | Me | — | Ph | — | Et | racemic |
| II-1037 | Me | Me | Me | — | Ph | — | Et | (R)- |
| II-1038 | Me | Et | Me | — | Ph | — | Et | racemic |
| II-1039 | Me | Et | Me | — | Ph | — | Et | (R)- |
| II-1040 | Me | Me | Me | — | Ph | — | $CF_2CH_3$ | racemic |
| II-1041 | Me | Me | Me | — | Ph | — | $CF_2CH_3$ | (R)- |
| II-1042 | Me | Et | Me | — | Ph | — | $CF_2CH_3$ | racemic |
| II-1043 | Me | Et | Me | — | Ph | — | $CF_2CH_3$ | (R)- |
| II-1044 | Me | Me | Me | — | Ph | — | nPr | racemic |
| II-1045 | Me | Me | Me | — | Ph | — | nPr | (R)- |
| II-1046 | Me | Et | Me | — | Ph | — | nPr | racemic |
| II-1047 | Me | Et | Me | — | Ph | — | nPr | (R)- |
| II-1048 | Me | Me | Me | — | Ph | — | nBu | racemic |
| II-1049 | Me | Me | Me | — | Ph | — | nBu | (R)- |
| II-1050 | Me | Et | Me | — | Ph | — | nBu | racemic |
| II-1051 | Me | Et | Me | — | Ph | — | nBu | (R)- |
| II-1052 | Me | Me | Me | — | Ph | — | iPr | racemic |
| II-1053 | Me | Me | Me | — | Ph | — | iPr | (R)- |
| II-1054 | Me | Et | Me | — | Ph | — | iPr | racemic |
| II-1055 | Me | Et | Me | — | Ph | — | iPr | (R)- |
| II-1056 | Me | Me | Me | — | Ph | — | cPr | racemic |
| II-1057 | Me | Me | Me | — | Ph | — | cPr | (R)- |
| II-1058 | Me | Et | Me | — | Ph | — | cPr | racemic |
| II-1059 | Me | Et | Me | — | Ph | — | cPr | (R)- |
| II-1060 | Me | Me | Me | — | Ph | — | Ph | racemic |
| II-1061 | Me | Me | Me | — | Ph | — | Ph | (R)- |
| II-1062 | Me | Et | Me | — | Ph | — | Ph | racemic |
| II-1063 | Me | Et | Me | — | Ph | — | Ph | (R)- |
| II-1064 | Me | Me | Me | — | Ph | $CH_2$ | $CHF_2$ | racemic |
| II-1065 | Me | Me | Me | — | Ph | $CH_2$ | $CHF_2$ | (S)- |
| II-1066 | Me | Me | Me | — | Ph | $CH_2$ | Et | racemic |
| II-1067 | Me | Me | Me | — | Ph | $CH_2$ | Et | (S)- |
| II-1068 | Me | Me | Me | — | Ph | $CH_2$ | Ph | racemic |
| II-1069 | Me | Me | Me | — | Ph | $CH_2$ | Ph | (R)- |
| II-1070 | Me | Me | Me | — | Ph | $(CH_2)_2$ | H | racemic |
| II-1071 | Me | Me | Me | — | Ph | $(CH_2)_2$ | H | (S)- |
| II-1072 | Me | Me | Me | — | Ph | $(CH_2)_2$ | Me | racemic |
| II-1073 | Me | Me | Me | — | Ph | $(CH_2)_2$ | Me | (S)- |
| II-1074 | Me | Me | Me | — | Ph | $(CH_2)_2$ | $CHF_2$ | racemic |
| II-1075 | Me | Me | Me | — | Ph | $(CH_2)_2$ | $CHF_2$ | (S)- |
| II-1076 | Me | Me | Me | — | Ph | $(CH_2)_2$ | Et | racemic |

TABLE 31 (II)

| Compound No. | R¹ | R² | R³ | L² | R⁴ | L³ | R⁵ | Configuration |
|---|---|---|---|---|---|---|---|---|
| II-1077 | Me | Me | Me | — | Ph | $(CH_2)_2$ | Et | (S)- |
| II-1078 | Me | Me | Me | — | H | — | H | |
| II-1079 | Me | Me | Me | — | H | — | Me | |
| II-1080 | Me | Me | Me | — | H | — | $CHF_2$ | |
| II-1081 | Me | Me | Me | — | H | — | $CF_3$ | |
| II-1082 | Me | Me | Me | — | H | — | Et | |
| II-1083 | Me | Me | Me | — | H | — | nPr | |
| II-1084 | Me | Me | Me | — | H | — | iPr | |
| II-1085 | Me | Me | Me | — | H | — | cPr | |
| II-1086 | Me | Me | Me | — | H | — | Ph | |
| II-1087 | Me | Me | Me | — | Me | — | H | racemic |
| II-1088 | Me | Me | Me | — | Me | — | H | (R)- |
| II-1089 | Me | Me | Me | — | Me | — | Me | racemic |
| II-1090 | Me | Me | Me | — | Me | — | Me | (R)- |
| II-1091 | Me | Me | Me | — | Me | — | $CHF_2$ | racemic |
| II-1092 | Me | Me | Me | — | Me | — | $CHF_2$ | (R)- |
| II-1093 | Me | Me | Me | — | Me | — | $CF_3$ | racemic |
| II-1094 | Me | Me | Me | — | Me | — | $CF_3$ | (R)- |
| II-1095 | Me | Me | Me | — | Me | — | Et | racemic |
| II-1096 | Me | Me | Me | — | Me | — | Et | (R)- |
| II-1097 | Me | Me | Me | — | Me | — | nPr | racemic |
| II-1098 | Me | Me | Me | — | Me | — | nPr | (R)- |
| II-1099 | Me | Me | Me | — | Me | — | iPr | racemic |
| II-1100 | Me | Me | Me | — | Me | — | iPr | (R)- |
| II-1101 | Me | Me | Me | — | Me | — | cPr | racemic |
| II-1102 | Me | Me | Me | — | Me | — | cPr | (R)- |
| II-1103 | Me | Me | Me | — | Me | — | cHex | racemic |
| II-1104 | Me | Me | Me | — | Me | — | cHex | (R)- |
| II-1105 | Me | Me | Me | — | Me | — | Ph | racemic |
| II-1106 | Me | Me | Me | — | Me | — | Ph | (R)- |
| II-1107 | Me | Me | Me | — | Me | — | 2-F—Ph | racemic |
| II-1108 | Me | Me | Me | — | Me | — | 2-F—Ph | (R)- |
| II-1109 | Me | Me | Me | — | Me | — | 3-F—Ph | racemic |
| II-1110 | Me | Me | Me | — | Me | — | 3-F—Ph | (R)- |
| II-1111 | Me | Me | Me | — | Me | — | 4-F—Ph | racemic |
| II-1112 | Me | Me | Me | — | Me | — | 4-F—Ph | (R)- |
| II-1113 | Me | Me | Me | — | Me | — | 2-Cl—Ph | racemic |
| II-1114 | Me | Me | Me | — | Me | — | 2-Cl—Ph | (R)- |
| II-1115 | Me | Me | Me | — | Me | — | 3-Cl—Ph | racemic |
| II-1116 | Me | Me | Me | — | Me | — | 3-Cl—Ph | (R)- |
| II-1117 | Me | Me | Me | — | Me | — | 4-Cl—Ph | racemic |
| II-1118 | Me | Me | Me | — | Me | — | 4-Cl—Ph | (R)- |
| II-1119 | Me | Me | Me | — | Me | — | 2-Py | racemic |
| II-1120 | Me | Me | Me | — | Me | — | 2-Py | (R)- |
| II-1121 | Me | Me | Me | — | Me | — | 3-Py | racemic |
| II-1122 | Me | Me | Me | — | Me | — | 3-Py | (R)- |
| II-1123 | Me | Me | Me | — | Me | — | 4-Py | racemic |
| II-1124 | Me | Me | Me | — | Me | — | 4-Py | (R)- |
| II-1125 | Me | Me | Me | — | iPr | — | H | racemic |
| II-1126 | Me | Me | Me | — | iPr | — | H | (R)- |

TABLE 32

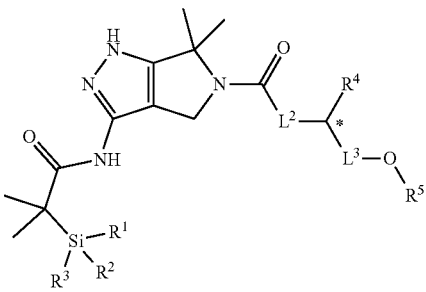

(II)

| Compound No. | R¹ | R² | R³ | L² | R⁴ | L³ | R⁵ | Configuration |
|---|---|---|---|---|---|---|---|---|
| II-1127 | Me | Me | Me | — | iPr | — | Me | racemic |
| II-1128 | Me | Me | Me | — | iPr | — | Me | (R)- |
| II-1129 | Me | Me | Me | — | iPr | — | CHF₂ | racemic |
| II-1130 | Me | Me | Me | — | iPr | — | CHF₂ | (R)- |
| II-1131 | Me | Me | Me | — | iPr | — | CF₃ | racemic |
| II-1132 | Me | Me | Me | — | iPr | — | CF₃ | (R)- |
| II-1133 | Me | Me | Me | — | iPr | — | Et | racemic |
| II-1134 | Me | Me | Me | — | iPr | — | Et | (R)- |
| II-1135 | Me | Me | Me | — | iPr | — | nPr | racemic |
| II-1136 | Me | Me | Me | — | iPr | — | nPr | (R)- |
| II-1137 | Me | Me | Me | — | iPr | — | iPr | racemic |
| II-1138 | Me | Me | Me | — | iPr | — | iPr | (R)- |
| II-1139 | Me | Me | Me | — | iPr | — | cPr | racemic |
| II-1140 | Me | Me | Me | — | iPr | — | cPr | (R)- |
| II-1141 | Me | Me | Me | — | iPr | — | Ph | racemic |
| II-1142 | Me | Me | Me | — | iPr | — | Ph | (R)- |
| II-1143 | Me | Me | Me | — | CF₃ | — | H | racemic |
| II-1144 | Me | Me | Me | — | CF₃ | — | H | (R)- |
| II-1145 | Me | Me | Me | — | CF₃ | — | Me | racemic |
| II-1146 | Me | Me | Me | — | CF₃ | — | Me | (R)- |
| II-1147 | Me | Me | Me | — | CF₃ | — | CHF₂ | racemic |
| II-1148 | Me | Me | Me | — | CF₃ | — | CHF₂ | (R)- |
| II-1149 | Me | Me | Me | — | CF₃ | — | CF₃ | racemic |
| II-1150 | Me | Me | Me | — | CF₃ | — | CF₃ | (R)- |
| II-1151 | Me | Me | Me | — | CF₃ | — | Et | racemic |
| II-1152 | Me | Me | Me | — | CF₃ | — | Et | (R)- |
| II-1153 | Me | Me | Me | — | CF₃ | — | nPr | racemic |
| II-1154 | Me | Me | Me | — | CF₃ | — | nPr | (R)- |
| II-1155 | Me | Me | Me | — | CF₃ | — | iPr | racemic |
| II-1156 | Me | Me | Me | — | CF₃ | — | iPr | (R)- |
| II-1157 | Me | Me | Me | — | CF₃ | — | cPr | racemic |
| II-1158 | Me | Me | Me | — | CF₃ | — | cPr | (R)- |
| II-1159 | Me | Me | Me | — | CF₃ | — | Ph | racemic |
| II-1160 | Me | Me | Me | — | CF₃ | — | Ph | (R)- |
| II-1161 | Me | Me | Me | — | CH₂OH | — | H | racemic |
| II-1162 | Me | Me | Me | — | CH₂OH | — | H | (R)- |
| II-1163 | Me | Me | Me | — | CH₂OH | — | Me | racemic |
| II-1164 | Me | Me | Me | — | CH₂OH | — | Me | (R)- |
| II-1165 | Me | Me | Me | — | CH₂OH | — | CHF₂ | racemic |
| II-1166 | Me | Me | Me | — | CH₂OH | — | CHF₂ | (R)- |
| II-1167 | Me | Me | Me | — | CH₂OH | — | CF₃ | racemic |
| II-1168 | Me | Me | Me | — | CH₂OH | — | CF₃ | (R)- |
| II-1169 | Me | Me | Me | — | CH₂OH | — | Et | racemic |
| II-1170 | Me | Me | Me | — | CH₂OH | — | Et | (R)- |
| II-1171 | Me | Me | Me | — | CH₂OH | — | nPr | racemic |
| II-1172 | Me | Me | Me | — | CH₂OH | — | nPr | (R)- |
| II-1173 | Me | Me | Me | — | CH₂OH | — | iPr | racemic |
| II-1174 | Me | Me | Me | — | CH₂OH | — | iPr | (R)- |
| II-1175 | Me | Me | Me | — | CH₂OH | — | cPr | racemic |
| II-1176 | Me | Me | Me | — | CH₂OH | — | cPr | (R)- |

TABLE 33

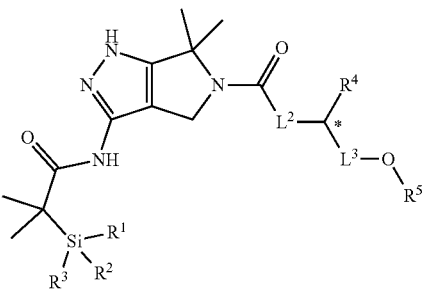

(II)

| Compound No. | R¹ | R² | R³ | L² | R⁴ | L³ | R⁵ | Configuration |
|---|---|---|---|---|---|---|---|---|
| II-1177 | Me | Me | Me | — | CH₂OH | — | Ph | racemic |
| II-1178 | Me | Me | Me | — | CH₂OH | — | Ph | (R)- |
| II-1179 | Me | Me | Me | — | CH₂OMe | — | H | racemic |
| II-1180 | Me | Me | Me | — | CH₂OMe | — | H | (R)- |
| II-1181 | Me | Me | Me | — | CH₂OMe | — | Me | racemic |
| II-1182 | Me | Me | Me | — | CH₂OMe | — | Me | (R)- |
| II-1183 | Me | Me | Me | — | CH₂OMe | — | CHF₂ | racemic |
| II-1184 | Me | Me | Me | — | CH₂OMe | — | CHF₂ | (R)- |
| II-1185 | Me | Me | Me | — | CH₂OMe | — | CF₃ | racemic |
| II-1186 | Me | Me | Me | — | CH₂OMe | — | CF₃ | (R)- |
| II-1187 | Me | Me | Me | — | CH₂OMe | — | Et | racemic |
| II-1188 | Me | Me | Me | — | CH₂OMe | — | Et | (R)- |
| II-1189 | Me | Me | Me | — | CH₂OMe | — | nPr | racemic |
| II-1190 | Me | Me | Me | — | CH₂OMe | — | nPr | (R)- |
| II-1191 | Me | Me | Me | — | CH₂OMe | — | iPr | racemic |
| II-1192 | Me | Me | Me | — | CH₂OMe | — | iPr | (R)- |
| II-1193 | Me | Me | Me | — | CH₂OMe | — | cPr | racemic |
| II-1194 | Me | Me | Me | — | CH₂OMe | — | cPr | (R)- |
| II-1195 | Me | Me | Me | — | CH₂OMe | — | Ph | racemic |
| II-1196 | Me | Me | Me | — | CH₂OMe | — | Ph | (R)- |
| II-1197 | Me | Me | Me | — | CH₂OBn | — | H | racemic |
| II-1198 | Me | Me | Me | — | CH₂OBn | — | H | (R)- |
| II-1199 | Me | Me | Me | — | CH₂OBn | — | Me | racemic |
| II-1200 | Me | Me | Me | — | CH₂OBn | — | Me | (R)- |
| II-1201 | Me | Me | Me | — | CH₂OBn | — | Ph | racemic |
| II-1202 | Me | Me | Me | — | CH₂OBn | — | Ph | (R)- |
| II-1203 | Me | Me | Me | — | CH₂NMe₂ | — | H | racemic |
| II-1204 | Me | Me | Me | — | CH₂NMe₂ | — | H | (R)- |
| II-1205 | Me | Me | Me | — | CH₂NMe₂ | — | Me | racemic |
| II-1206 | Me | Me | Me | — | CH₂NMe₂ | — | Me | (R)- |
| II-1207 | Me | Me | Me | — | CH₂NMe₂ | — | CHF₂ | racemic |
| II-1208 | Me | Me | Me | — | CH₂NMe₂ | — | CHF₂ | (R)- |
| II-1209 | Me | Me | Me | — | CH₂NMe₂ | — | CF₃ | racemic |
| II-1210 | Me | Me | Me | — | CH₂NMe₂ | — | CF₃ | (R)- |
| II-1211 | Me | Me | Me | — | CH₂NMe₂ | — | Et | racemic |
| II-1212 | Me | Me | Me | — | CH₂NMe₂ | — | Et | (R)- |
| II-1213 | Me | Me | Me | — | CH₂NMe₂ | — | nPr | racemic |
| II-1214 | Me | Me | Me | — | CH₂NMe₂ | — | nPr | (R)- |
| II-1215 | Me | Me | Me | — | CH₂NMe₂ | — | iPr | racemic |
| II-1216 | Me | Me | Me | — | CH₂NMe₂ | — | iPr | (R)- |
| II-1217 | Me | Me | Me | — | CH₂NMe₂ | — | cPr | racemic |
| II-1218 | Me | Me | Me | — | CH₂NMe₂ | — | cPr | (R)- |
| II-1219 | Me | Me | Me | — | CH₂NMe₂ | — | Ph | racemic |
| II-1220 | Me | Me | Me | — | CH₂NMe₂ | — | Ph | (R)- |
| II-1221 | Me | Me | Me | — | CH₂-(3,3-difluoropyrrolidyl) | — | H | racemic |
| II-1222 | Me | Me | Me | — | CH₂-(3,3-difluoropyrrolidyl) | — | H | (R)- |
| II-1223 | Me | Me | Me | — | CH₂-(3,3-difluoropyrrolidyl) | — | Me | racemic |
| II-1224 | Me | Me | Me | — | CH₂-(3,3-difluoropyrrolidyl) | — | Me | (R)- |
| II-1225 | Me | Me | Me | — | CH₂-(3,3-difluoropyrrolidyl) | — | Ph | racemic |
| II-1226 | Me | Me | Me | — | CH₂-(3,3-difluoropyrrolidyl) | — | Ph | (R)- |

TABLE 34

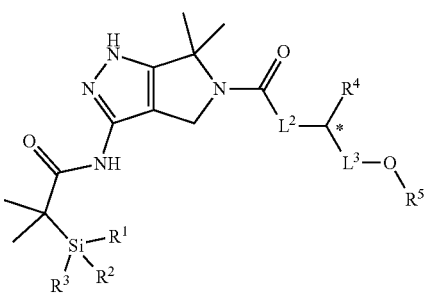

(II)

| Compound No. | R¹ | R² | R³ | L² | R⁴ | L³ | R⁵ | Configuration |
|---|---|---|---|---|---|---|---|---|
| II-1227 | Me | Me | Me | — | 2-F—Ph | — | H | racemic |
| II-1228 | Me | Me | Me | — | 2-F—Ph | — | H | (R)- |
| II-1229 | Me | Me | Me | — | 2-F—Ph | — | Me | racemic |
| II-1230 | Me | Me | Me | — | 2-F—Ph | — | Me | (R)- |
| II-1231 | Me | Me | Me | — | 2-F—Ph | — | $CHF_2$ | racemic |
| II-1232 | Me | Me | Me | — | 2-F—Ph | — | $CHF_2$ | (R)- |
| II-1233 | Me | Me | Me | — | 2-F—Ph | — | $CF_3$ | racemic |
| II-1234 | Me | Me | Me | — | 2-F—Ph | — | $CF_3$ | (R)- |
| II-1235 | Me | Me | Me | — | 2-F—Ph | — | Et | racemic |
| II-1236 | Me | Me | Me | — | 2-F—Ph | — | Et | (R)- |
| II-1237 | Me | Me | Me | — | 2-F—Ph | — | nPr | racemic |
| II-1238 | Me | Me | Me | — | 2-F—Ph | — | nPr | (R)- |
| II-1239 | Me | Me | Me | — | 2-F—Ph | — | iPr | racemic |
| II-1240 | Me | Me | Me | — | 2-F—Ph | — | iPr | (R)- |
| II-1241 | Me | Me | Me | — | 2-F—Ph | — | cPr | racemic |
| II-1242 | Me | Me | Me | — | 2-F—Ph | — | cPr | (R)- |
| II-1243 | Me | Me | Me | — | 3-F—Ph | — | H | racemic |
| II-1244 | Me | Me | Me | — | 3-F—Ph | — | H | (R)- |
| II-1245 | Me | Me | Me | — | 3-F—Ph | — | Me | racemic |
| II-1246 | Me | Me | Me | — | 3-F—Ph | — | Me | (R)- |
| II-1247 | Me | Me | Me | — | 3-F—Ph | — | $CHF_2$ | racemic |
| II-1248 | Me | Me | Me | — | 3-F—Ph | — | $CHF_2$ | (R)- |
| II-1249 | Me | Me | Me | — | 3-F—Ph | — | $CF_3$ | racemic |
| II-1250 | Me | Me | Me | — | 3-F—Ph | — | $CF_3$ | (R)- |
| II-1251 | Me | Me | Me | — | 3-F—Ph | — | Et | racemic |
| II-1252 | Me | Me | Me | — | 3-F—Ph | — | Et | (R)- |
| II-1253 | Me | Me | Me | — | 3-F—Ph | — | nPr | racemic |
| II-1254 | Me | Me | Me | — | 3-F—Ph | — | nPr | (R)- |
| II-1255 | Me | Me | Me | — | 3-F—Ph | — | iPr | racemic |
| II-1256 | Me | Me | Me | — | 3-F—Ph | — | iPr | (R)- |
| II-1257 | Me | Me | Me | — | 3-F—Ph | — | cPr | racemic |
| II-1258 | Me | Me | Me | — | 3-F—Ph | — | cPr | (R)- |
| II-1259 | Me | Me | Me | — | 4-F—Ph | — | H | racemic |
| II-1260 | Me | Me | Me | — | 4-F—Ph | — | H | (R)- |
| II-1261 | Me | Me | Me | — | 4-F—Ph | — | Me | racemic |
| II-1262 | Me | Me | Me | — | 4-F—Ph | — | Me | (R)- |
| II-1263 | Me | Me | Me | — | 4-F—Ph | — | $CHF_2$ | racemic |
| II-1264 | Me | Me | Me | — | 4-F—Ph | — | $CHF_2$ | (R)- |
| II-1265 | Me | Me | Me | — | 4-F—Ph | — | $CF_3$ | racemic |
| II-1266 | Me | Me | Me | — | 4-F—Ph | — | $CF_3$ | (R)- |
| II-1267 | Me | Me | Me | — | 4-F—Ph | — | Et | racemic |
| II-1268 | Me | Me | Me | — | 4-F—Ph | — | Et | (R)- |
| II-1269 | Me | Me | Me | — | 4-F—Ph | — | nPr | racemic |
| II-1270 | Me | Me | Me | — | 4-F—Ph | — | nPr | (R)- |
| II-1271 | Me | Me | Me | — | 4-F—Ph | — | iPr | racemic |
| II-1272 | Me | Me | Me | — | 4-F—Ph | — | iPr | (R)- |
| II-1273 | Me | Me | Me | — | 4-F—Ph | — | cPr | racemic |
| II-1274 | Me | Me | Me | — | 4-F—Ph | — | cPr | (R)- |
| II-1275 | Me | Me | Me | — | 2-thienyl | — | H | racemic |
| II-1276 | Me | Me | Me | — | 2-thienyl | — | H | (S)- |

TABLE 35

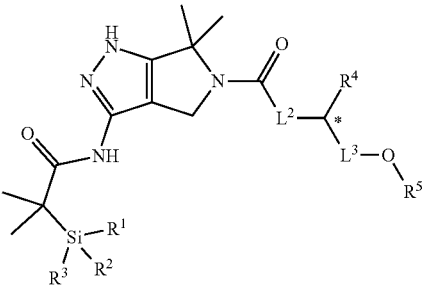

(II)

| Compound No. | R¹ | R² | R³ | L² | R⁴ | L³ | R⁵ | Configuration |
|---|---|---|---|---|---|---|---|---|
| II-1277 | Me | Me | Me | — | 2-thienyl | — | Me | racemic |
| II-1278 | Me | Me | Me | — | 2-thienyl | — | Me | (S)- |
| II-1279 | Me | Me | Me | — | 2-thienyl | — | $CHF_2$ | racemic |
| II-1280 | Me | Me | Me | — | 2-thienyl | — | $CHF_2$ | (S)- |
| II-1281 | Me | Me | Me | — | 2-thienyl | — | $CF_3$ | racemic |
| II-1282 | Me | Me | Me | — | 2-thienyl | — | $CF_3$ | (S)- |
| II-1283 | Me | Me | Me | — | 2-thienyl | — | Et | racemic |
| II-1284 | Me | Me | Me | — | 2-thienyl | — | Et | (S)- |
| II-1285 | Me | Me | Me | — | 2-thienyl | — | nPr | racemic |
| II-1286 | Me | Me | Me | — | 2-thienyl | — | nPr | (S)- |
| II-1287 | Me | Me | Me | — | 2-thienyl | — | iPr | racemic |
| II-1288 | Me | Me | Me | — | 2-thienyl | — | iPr | (S)- |
| II-1289 | Me | Me | Me | — | 2-thienyl | — | cPr | racemic |
| II-1290 | Me | Me | Me | — | 2-thienyl | — | cPr | (S)- |
| II-1291 | Me | Me | Me | — | 3-thienyl | — | H | racemic |
| II-1292 | Me | Me | Me | — | 3-thienyl | — | H | (R)- |
| II-1293 | Me | Me | Me | — | 3-thienyl | — | Me | racemic |
| II-1294 | Me | Me | Me | — | 3-thienyl | — | Me | (R)- |
| II-1295 | Me | Me | Me | — | 3-thienyl | — | $CHF_2$ | racemic |
| II-1296 | Me | Me | Me | — | 3-thienyl | — | $CHF_2$ | (R)- |
| II-1297 | Me | Me | Me | — | 3-thienyl | — | $CF_3$ | racemic |
| II-1298 | Me | Me | Me | — | 3-thienyl | — | $CF_3$ | (R)- |
| II-1299 | Me | Me | Me | — | 3-thienyl | — | Et | racemic |
| II-1300 | Me | Me | Me | — | 3-thienyl | — | Et | (R)- |
| II-1301 | Me | Me | Me | — | 3-thienyl | — | nPr | racemic |
| II-1302 | Me | Me | Me | — | 3-thienyl | — | nPr | (R)- |
| II-1303 | Me | Me | Me | — | 3-thienyl | — | iPr | racemic |
| II-1304 | Me | Me | Me | — | 3-thienyl | — | iPr | (R)- |
| II-1305 | Me | Me | Me | — | 3-thienyl | — | cPr | racemic |
| II-1306 | Me | Me | Me | — | 3-thienyl | — | cPr | (R)- |

TABLE 36

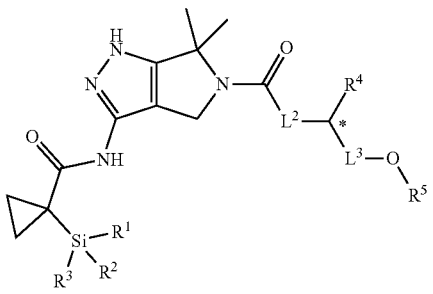

(III)

| Compound No. | R¹ | R² | R³ | L² | R⁴ | L³ | R⁵ | Configuration |
|---|---|---|---|---|---|---|---|---|
| III-1 | Me | Me | Me | O | Ph | $CH_2$ | H | racemic |
| III-2 | Me | Me | Me | O | Ph | $CH_2$ | H | (S)- |
| III-3 | Me | Et | Me | O | Ph | $CH_2$ | H | racemic |
| III-4 | Me | Et | Me | O | Ph | $CH_2$ | H | (S)- |
| III-5 | Me | Me | Me | O | Ph | $CH_2$ | Me | racemic |

TABLE 36-continued

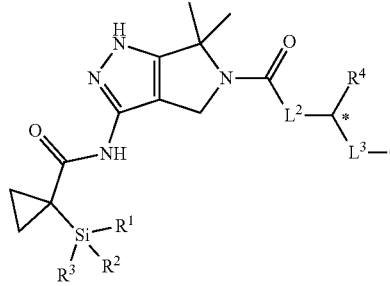

(III)

| Compound No. | R¹ | R² | R³ | L² | R⁴ | L³ | R⁵ | Configuration |
|---|---|---|---|---|---|---|---|---|
| III-6 | Me | Me | Me | O | Ph | CH₂ | Me | (S)- |
| III-7 | Me | Et | Me | O | Ph | CH₂ | Me | racemic |
| III-8 | Me | Et | Me | O | Ph | CH₂ | Me | (S)- |
| III-9 | Me | Me | Me | O | Ph | CH₂ | CHF₂ | racemic |
| III-10 | Me | Me | Me | O | Ph | CH₂ | CHF₂ | (S)- |
| III-11 | Me | Et | Me | O | Ph | CH₂ | CHF₂ | racemic |
| III-12 | Me | Et | Me | O | Ph | CH₂ | CHF₂ | (S)- |
| III-13 | Me | Me | Me | O | Ph | CH₂ | Et | racemic |
| III-14 | Me | Me | Me | O | Ph | CH₂ | Et | (S)- |
| III-15 | Me | Et | Me | O | Ph | CH₂ | Et | racemic |
| III-16 | Me | Et | Me | O | Ph | CH₂ | Et | (S)- |
| III-17 | Me | Me | Me | O | Ph | CH₂ | iPr | racemic |
| III-18 | Me | Me | Me | O | Ph | CH₂ | iPr | (S)- |
| III-19 | Me | Et | Me | O | Ph | CH₂ | iPr | racemic |
| III-20 | Me | Et | Me | O | Ph | CH₂ | iPr | (S)- |
| III-21 | Me | Me | Me | O | Ph | CH₂ | cPr | racemic |
| III-22 | Me | Me | Me | O | Ph | CH₂ | cPr | (S)- |
| III-23 | Me | Et | Me | O | Ph | CH₂ | cPr | racemic |
| III-24 | Me | Et | Me | O | Ph | CH₂ | cPr | (S)- |
| III-25 | Me | Me | Me | O | Ph | CH₂ | Ph | racemic |
| III-26 | Me | Me | Me | O | Ph | CH₂ | Ph | (S)- |
| III-27 | Me | Et | Me | O | Ph | CH₂ | Ph | racemic |
| III-28 | Me | Et | Me | O | Ph | CH₂ | Ph | (S)- |
| III-29 | Me | Me | Me | O | Ph | C(Me)₂ | H | racemic |
| III-30 | Me | Me | Me | O | Ph | C(Me)₂ | H | (S)- |
| III-31 | Me | Et | Me | O | Ph | C(Me)₂ | H | racemic |
| III-32 | Me | Et | Me | O | Ph | C(Me)₂ | H | (S)- |
| III-33 | Me | Me | Me | O | Ph | C(Me)₂ | Me | racemic |
| III-34 | Me | Me | Me | O | Ph | C(Me)₂ | Me | (S)- |
| III-35 | Me | Et | Me | O | Ph | C(Me)₂ | Me | racemic |
| III-36 | Me | Et | Me | O | Ph | C(Me)₂ | Me | (S)- |
| III-37 | Me | Me | Me | O | Ph | C(Me)₂ | CHF₂ | racemic |
| III-38 | Me | Me | Me | O | Ph | C(Me)₂ | CHF₂ | (S)- |
| III-39 | Me | Et | Me | O | Ph | C(Me)₂ | CHF₂ | racemic |
| III-40 | Me | Et | Me | O | Ph | C(Me)₂ | CHF₂ | (S)- |
| III-41 | Me | Me | Me | O | Ph | C(Me)₂ | Et | racemic |
| III-42 | Me | Me | Me | O | Ph | C(Me)₂ | Et | (S)- |
| III-43 | Me | Et | Me | O | Ph | C(Me)₂ | Et | racemic |
| III-44 | Me | Et | Me | O | Ph | C(Me)₂ | Et | (S)- |
| III-45 | Me | Me | Me | O | Ph | C(Me)₂ | iPr | racemic |
| III-46 | Me | Me | Me | O | Ph | C(Me)₂ | iPr | (S)- |
| III-47 | Me | Et | Me | O | Ph | C(Me)₂ | iPr | racemic |
| III-48 | Me | Et | Me | O | Ph | C(Me)₂ | iPr | (S)- |
| III-49 | Me | Me | Me | O | Ph | C(Me)₂ | cPr | racemic |
| III-50 | Me | Me | Me | O | Ph | C(Me)₂ | cPr | (S)- |

TABLE 37

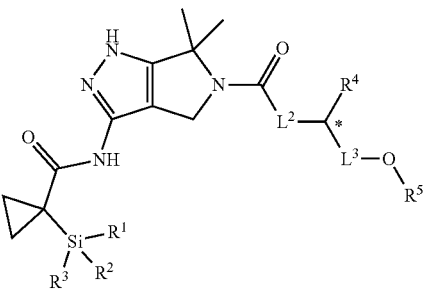

(III)

| Compound No. | R¹ | R² | R³ | L² | R⁴ | L³ | R⁵ | Configuration |
|---|---|---|---|---|---|---|---|---|
| III-51 | Me | Et | Me | O | Ph | C(Me)₂ | cPr | racemic |
| III-52 | Me | Et | Me | O | Ph | C(Me)₂ | cPr | (S)- |
| III-53 | Me | Me | Me | O | Ph | C(Me)₂ | Ph | racemic |
| III-54 | Me | Me | Me | O | Ph | C(Me)₂ | Ph | (S)- |
| III-55 | Me | Et | Me | O | Ph | C(Me)₂ | Ph | racemic |
| III-56 | Me | Et | Me | O | Ph | C(Me)₂ | Ph | (S)- |
| III-57 | Me | Me | Me | O | Ph | (CH₂)₂ | H | racemic |
| III-58 | Me | Me | Me | O | Ph | (CH₂)₂ | H | (R)- |
| III-59 | Me | Et | Me | O | Ph | (CH₂)₂ | H | racemic |
| III-60 | Me | Et | Me | O | Ph | (CH₂)₂ | H | (R)- |
| III-61 | Me | Me | Me | O | Ph | (CH₂)₂ | Me | racemic |
| III-62 | Me | Me | Me | O | Ph | (CH₂)₂ | Me | (R)- |
| III-63 | Me | Et | Me | O | Ph | (CH₂)₂ | Me | racemic |
| III-64 | Me | Et | Me | O | Ph | (CH₂)₂ | Me | (R)- |
| III-65 | Me | Me | Me | O | Ph | (CH₂)₂ | CHF₂ | racemic |
| III-66 | Me | Me | Me | O | Ph | (CH₂)₂ | CHF₂ | (R)- |
| III-67 | Me | Et | Me | O | Ph | (CH₂)₂ | CHF₂ | racemic |
| III-68 | Me | Et | Me | O | Ph | (CH₂)₂ | CHF₂ | (R)- |
| III-69 | Me | Me | Me | O | Ph | (CH₂)₂ | Et | racemic |
| III-70 | Me | Me | Me | O | Ph | (CH₂)₂ | Et | (R)- |
| III-71 | Me | Et | Me | O | Ph | (CH₂)₂ | Et | racemic |
| III-72 | Me | Et | Me | O | Ph | (CH₂)₂ | Et | (R)- |
| III-73 | Me | Me | Me | O | Ph | (CH₂)₂ | iPr | racemic |
| III-74 | Me | Me | Me | O | Ph | (CH₂)₂ | iPr | (R)- |
| III-75 | Me | Et | Me | O | Ph | (CH₂)₂ | iPr | racemic |
| III-76 | Me | Et | Me | O | Ph | (CH₂)₂ | iPr | (R)- |
| III-77 | Me | Me | Me | O | Ph | (CH₂)₂ | cPr | racemic |
| III-78 | Me | Me | Me | O | Ph | (CH₂)₂ | cPr | (R)- |
| III-79 | Me | Et | Me | O | Ph | (CH₂)₂ | cPr | racemic |
| III-80 | Me | Et | Me | O | Ph | (CH₂)₂ | cPr | (R)- |
| III-81 | Me | Me | Me | O | Ph | (CH₂)₂ | Ph | racemic |
| III-82 | Me | Me | Me | O | Ph | (CH₂)₂ | Ph | (R)- |
| III-83 | Me | Et | Me | O | Ph | (CH₂)₂ | Ph | racemic |
| III-84 | Me | Et | Me | O | Ph | (CH₂)₂ | Ph | (R)- |
| III-85 | Me | Me | Me | O | Ph | CH₂C(Me)₂ | H | racemic |
| III-86 | Me | Me | Me | O | Ph | CH₂C(Me)₂ | H | (R)- |
| III-87 | Me | Et | Me | O | Ph | CH₂C(Me)₂ | H | racemic |
| III-88 | Me | Et | Me | O | Ph | CH₂C(Me)₂ | H | (R)- |
| III-89 | Me | Me | Me | O | Ph | CH₂C(Me)₂ | Me | racemic |
| III-90 | Me | Me | Me | O | Ph | CH₂C(Me)₂ | Me | (R)- |
| III-91 | Me | Et | Me | O | Ph | CH₂C(Me)₂ | Me | racemic |
| III-92 | Me | Et | Me | O | Ph | CH₂C(Me)₂ | Me | (R)- |
| III-93 | Me | Me | Me | O | Ph | CH₂C(Me)₂ | CHF₂ | racemic |
| III-94 | Me | Me | Me | O | Ph | CH₂C(Me)₂ | CHF₂ | (R)- |
| III-95 | Me | Et | Me | O | Ph | CH₂C(Me)₂ | CHF₂ | racemic |
| III-96 | Me | Et | Me | O | Ph | CH₂C(Me)₂ | CHF₂ | (R)- |
| III-97 | Me | Me | Me | O | Ph | CH₂C(Me)₂ | Et | racemic |
| III-98 | Me | Me | Me | O | Ph | CH₂C(Me)₂ | Et | (R)- |
| III-99 | Me | Et | Me | O | Ph | CH₂C(Me)₂ | Et | racemic |
| III-100 | Me | Et | Me | O | Ph | CH₂C(Me)₂ | Et | (R)- |

TABLE 38

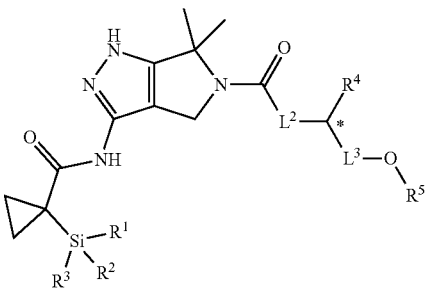

(III)

| Compound No. | R¹ | R² | R³ | L² | R⁴ | L³ | R⁵ | Configuration |
|---|---|---|---|---|---|---|---|---|
| III-101 | Me | Me | Me | O | Ph | CH$_2$C(Me)$_2$ | iPr | racemic |
| III-102 | Me | Me | Me | O | Ph | CH$_2$C(Me)$_2$ | iPr | (R)- |
| III-103 | Me | Et | Me | O | Ph | CH$_2$C(Me)$_2$ | iPr | racemic |
| III-104 | Me | Et | Me | O | Ph | CH$_2$C(Me)$_2$ | iPr | (R)- |
| III-105 | Me | Me | Me | O | Ph | CH$_2$C(Me)$_2$ | cPr | racemic |
| III-106 | Me | Me | Me | O | Ph | CH$_2$C(Me)$_2$ | cPr | (R)- |
| III-107 | Me | Et | Me | O | Ph | CH$_2$C(Me)$_2$ | cPr | racemic |
| III-108 | Me | Et | Me | O | Ph | CH$_2$C(Me)$_2$ | cPr | (R)- |
| III-109 | Me | Me | Me | O | Ph | CH$_2$C(Me)$_2$ | Ph | racemic |
| III-110 | Me | Me | Me | O | Ph | CH$_2$C(Me)$_2$ | Ph | (R)- |
| III-111 | Me | Et | Me | O | Ph | CH$_2$C(Me)$_2$ | Ph | racemic |
| III-112 | Me | Et | Me | O | Ph | CH$_2$C(Me)$_2$ | Ph | (R)- |
| III-113 | Me | Me | Me | NH | Ph | CH$_2$ | H | racemic |
| III-114 | Me | Me | Me | NH | Ph | CH$_2$ | H | (S)- |
| III-115 | Me | Et | Me | NH | Ph | CH$_2$ | H | racemic |
| III-116 | Me | Et | Me | NH | Ph | CH$_2$ | H | (S)- |
| III-117 | Me | Me | Me | N(Me) | Ph | CH$_2$ | H | racemic |
| III-118 | Me | Me | Me | N(Me) | Ph | CH$_2$ | H | (S)- |
| III-119 | Me | Et | Me | N(Me) | Ph | CH$_2$ | H | racemic |
| III-120 | Me | Et | Me | N(Me) | Ph | CH$_2$ | H | (S)- |
| III-121 | Me | Me | Me | NH | Ph | CH$_2$ | Me | racemic |
| III-122 | Me | Me | Me | NH | Ph | CH$_2$ | Me | (S)- |
| III-123 | Me | Et | Me | NH | Ph | CH$_2$ | Me | racemic |
| III-124 | Me | Et | Me | NH | Ph | CH$_2$ | Me | (S)- |
| III-125 | Me | Me | Me | N(Me) | Ph | CH$_2$ | Me | racemic |
| III-126 | Me | Me | Me | N(Me) | Ph | CH$_2$ | Me | (S)- |
| III-127 | Me | Et | Me | N(Me) | Ph | CH$_2$ | Me | racemic |
| III-128 | Me | Et | Me | N(Me) | Ph | CH$_2$ | Me | (S)- |
| III-129 | Me | Me | Me | NH | Ph | CH$_2$ | CHF$_2$ | racemic |
| III-130 | Me | Me | Me | NH | Ph | CH$_2$ | CHF$_2$ | (S)- |
| III-131 | Me | Et | Me | NH | Ph | CH$_2$ | CHF$_2$ | racemic |
| III-132 | Me | Et | Me | NH | Ph | CH$_2$ | CHF$_2$ | (S)- |
| III-133 | Me | Me | Me | N(Me) | Ph | CH$_2$ | CHF$_2$ | racemic |
| III-134 | Me | Me | Me | N(Me) | Ph | CH$_2$ | CHF$_2$ | (S)- |
| III-135 | Me | Et | Me | N(Me) | Ph | CH$_2$ | CHF$_2$ | racemic |
| III-136 | Me | Et | Me | N(Me) | Ph | CH$_2$ | CHF$_2$ | (S)- |
| III-137 | Me | Me | Me | NH | Ph | CH$_2$ | Et | racemic |
| III-138 | Me | Me | Me | NH | Ph | CH$_2$ | Et | (S)- |
| III-139 | Me | Et | Me | NH | Ph | CH$_2$ | Et | racemic |
| III-140 | Me | Et | Me | NH | Ph | CH$_2$ | Et | (S)- |
| III-141 | Me | Me | Me | N(Me) | Ph | CH$_2$ | Et | racemic |
| III-142 | Me | Me | Me | N(Me) | Ph | CH$_2$ | Et | (S)- |
| III-143 | Me | Et | Me | N(Me) | Ph | CH$_2$ | Et | racemic |
| III-144 | Me | Et | Me | N(Me) | Ph | CH$_2$ | Et | (S)- |
| III-145 | Me | Me | Me | NH | Ph | CH$_2$ | iPr | racemic |
| III-146 | Me | Me | Me | NH | Ph | CH$_2$ | iPr | (S)- |
| III-147 | Me | Et | Me | NH | Ph | CH$_2$ | iPr | racemic |
| III-148 | Me | Et | Me | NH | Ph | CH$_2$ | iPr | (S)- |
| III-149 | Me | Me | Me | N(Me) | Ph | CH$_2$ | iPr | racemic |
| III-150 | Me | Me | Me | N(Me) | Ph | CH$_2$ | iPr | (S)- |

TABLE 39

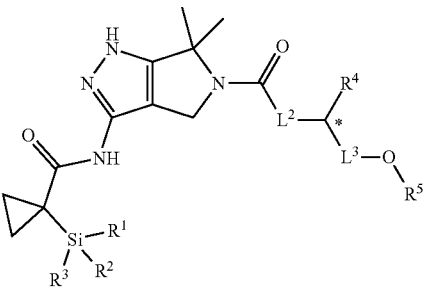

(III)

| Compound No. | R¹ | R² | R³ | L² | R⁴ | L³ | R⁵ | Configuration |
|---|---|---|---|---|---|---|---|---|
| III-151 | Me | Et | Me | N(Me) | Ph | CH$_2$ | iPr | racemic |
| III-152 | Me | Et | Me | N(Me) | Ph | CH$_2$ | iPr | (S)- |
| III-153 | Me | Me | Me | NH | Ph | CH$_2$ | cPr | racemic |
| III-154 | Me | Me | Me | NH | Ph | CH$_2$ | cPr | (S)- |
| III-155 | Me | Et | Me | NH | Ph | CH$_2$ | cPr | racemic |
| III-156 | Me | Et | Me | NH | Ph | CH$_2$ | cPr | (S)- |
| III-157 | Me | Me | Me | N(Me) | Ph | CH$_2$ | cPr | racemic |
| III-158 | Me | Me | Me | N(Me) | Ph | CH$_2$ | cPr | (S)- |
| III-159 | Me | Et | Me | N(Me) | Ph | CH$_2$ | cPr | racemic |
| III-160 | Me | Et | Me | N(Me) | Ph | CH$_2$ | cPr | (S)- |
| III-161 | Me | Me | Me | NH | Ph | CH$_2$ | Ph | racemic |
| III-162 | Me | Me | Me | NH | Ph | CH$_2$ | Ph | (S)- |
| III-163 | Me | Et | Me | NH | Ph | CH$_2$ | Ph | racemic |
| III-164 | Me | Et | Me | NH | Ph | CH$_2$ | Ph | (S)- |
| III-165 | Me | Me | Me | N(Me) | Ph | CH$_2$ | Ph | racemic |
| III-166 | Me | Me | Me | N(Me) | Ph | CH$_2$ | Ph | (S)- |
| III-167 | Me | Et | Me | N(Me) | Ph | CH$_2$ | Ph | racemic |
| III-168 | Me | Et | Me | N(Me) | Ph | CH$_2$ | Ph | (S)- |
| III-169 | Me | Me | Me | NH | Ph | C(Me)$_2$ | H | racemic |
| III-170 | Me | Me | Me | NH | Ph | C(Me)$_2$ | H | (S)- |
| III-171 | Me | Et | Me | NH | Ph | C(Me)$_2$ | H | racemic |
| III-172 | Me | Et | Me | NH | Ph | C(Me)$_2$ | H | (S)- |
| III-173 | Me | Me | Me | N(Me) | Ph | C(Me)$_2$ | H | racemic |
| III-174 | Me | Me | Me | N(Me) | Ph | C(Me)$_2$ | H | (S)- |
| III-175 | Me | Et | Me | N(Me) | Ph | C(Me)$_2$ | H | racemic |
| III-176 | Me | Et | Me | N(Me) | Ph | C(Me)$_2$ | H | (S)- |
| III-177 | Me | Me | Me | NH | Ph | C(Me)$_2$ | Me | racemic |
| III-178 | Me | Me | Me | NH | Ph | C(Me)$_2$ | Me | (S)- |
| III-179 | Me | Et | Me | NH | Ph | C(Me)$_2$ | Me | racemic |
| III-180 | Me | Et | Me | NH | Ph | C(Me)$_2$ | Me | (S)- |
| III-181 | Me | Me | Me | N(Me) | Ph | C(Me)$_2$ | Me | racemic |
| III-182 | Me | Me | Me | N(Me) | Ph | C(Me)$_2$ | Me | (S)- |
| III-183 | Me | Et | Me | N(Me) | Ph | C(Me)$_2$ | Me | racemic |
| III-184 | Me | Et | Me | N(Me) | Ph | C(Me)$_2$ | Me | (S)- |
| III-185 | Me | Me | Me | NH | Ph | C(Me)$_2$ | CHF$_2$ | racemic |
| III-186 | Me | Me | Me | NH | Ph | C(Me)$_2$ | CHF$_2$ | (S)- |
| III-187 | Me | Et | Me | NH | Ph | C(Me)$_2$ | CHF$_2$ | racemic |
| III-188 | Me | Et | Me | NH | Ph | C(Me)$_2$ | CHF$_2$ | (S)- |
| III-189 | Me | Me | Me | N(Me) | Ph | C(Me)$_2$ | CHF$_2$ | racemic |
| III-190 | Me | Me | Me | N(Me) | Ph | C(Me)$_2$ | CHF$_2$ | (S)- |
| III-191 | Me | Et | Me | N(Me) | Ph | C(Me)$_2$ | CHF$_2$ | racemic |
| III-192 | Me | Et | Me | N(Me) | Ph | C(Me)$_2$ | CHF$_2$ | (S)- |
| III-193 | Me | Me | Me | NH | Ph | C(Me)$_2$ | Et | racemic |
| III-194 | Me | Me | Me | NH | Ph | C(Me)$_2$ | Et | (S)- |
| III-195 | Me | Et | Me | NH | Ph | C(Me)$_2$ | Et | racemic |
| III-196 | Me | Et | Me | NH | Ph | C(Me)$_2$ | Et | (S)- |
| III-197 | Me | Me | Me | N(Me) | Ph | C(Me)$_2$ | Et | racemic |
| III-198 | Me | Me | Me | N(Me) | Ph | C(Me)$_2$ | Et | (S)- |
| III-199 | Me | Et | Me | N(Me) | Ph | C(Me)$_2$ | Et | racemic |
| III-200 | Me | Et | Me | N(Me) | Ph | C(Me)$_2$ | Et | (S)- |

TABLE 40

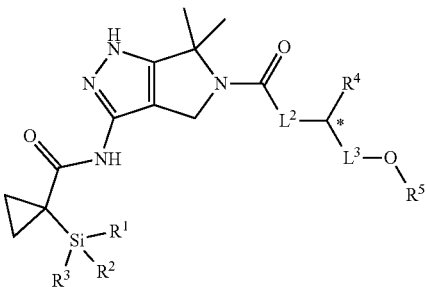

(III)

| Compound No. | R¹ | R² | R³ | L² | R⁴ | L³ | R⁵ | Configuration |
|---|---|---|---|---|---|---|---|---|
| III-201 | Me | Me | Me | NH | Ph | C(Me)₂ | iPr | racemic |
| III-202 | Me | Me | Me | NH | Ph | C(Me)₂ | iPr | (S)- |
| III-203 | Me | Et | Me | NH | Ph | C(Me)₂ | iPr | racemic |
| III-204 | Me | Et | Me | NH | Ph | C(Me)₂ | iPr | (S)- |
| III-205 | Me | Me | Me | N(Me) | Ph | C(Me)₂ | iPr | racemic |
| III-206 | Me | Me | Me | N(Me) | Ph | C(Me)₂ | iPr | (S)- |
| III-207 | Me | Et | Me | N(Me) | Ph | C(Me)₂ | iPr | racemic |
| III-208 | Me | Et | Me | N(Me) | Ph | C(Me)₂ | iPr | (S)- |
| III-209 | Me | Me | Me | NH | Ph | C(Me)₂ | cPr | racemic |
| III-210 | Me | Me | Me | NH | Ph | C(Me)₂ | cPr | (S)- |
| III-211 | Me | Et | Me | NH | Ph | C(Me)₂ | cPr | racemic |
| III-212 | Me | Et | Me | NH | Ph | C(Me)₂ | cPr | (S)- |
| III-213 | Me | Me | Me | N(Me) | Ph | C(Me)₂ | cPr | racemic |
| III-214 | Me | Me | Me | N(Me) | Ph | C(Me)₂ | cPr | (S)- |
| III-215 | Me | Et | Me | N(Me) | Ph | C(Me)₂ | cPr | racemic |
| III-216 | Me | Et | Me | N(Me) | Ph | C(Me)₂ | cPr | (S)- |
| III-217 | Me | Me | Me | NH | Ph | C(Me)₂ | Ph | racemic |
| III-218 | Me | Me | Me | NH | Ph | C(Me)₂ | Ph | (S)- |
| III-219 | Me | Et | Me | NH | Ph | C(Me)₂ | Ph | racemic |
| III-220 | Me | Et | Me | NH | Ph | C(Me)₂ | Ph | (S)- |
| III-221 | Me | Me | Me | N(Me) | Ph | C(Me)₂ | Ph | racemic |
| III-222 | Me | Me | Me | N(Me) | Ph | C(Me)₂ | Ph | (S)- |
| III-223 | Me | Et | Me | N(Me) | Ph | C(Me)₂ | Ph | racemic |
| III-224 | Me | Et | Me | N(Me) | Ph | C(Me)₂ | Ph | (S)- |
| III-225 | Me | Me | Me | NH | Ph | C(Me)₂ | H | racemic |
| III-226 | Me | Me | Me | NH | Ph | C(Me)₂ | H | (R)- |
| III-227 | Me | Et | Me | NH | Ph | C(Me)₂ | H | racemic |
| III-228 | Me | Et | Me | NH | Ph | C(Me)₂ | H | (R)- |
| III-229 | Me | Me | Me | N(Me) | Ph | C(Me)₂ | H | racemic |
| III-230 | Me | Me | Me | N(Me) | Ph | C(Me)₂ | H | (R)- |
| III-231 | Me | Et | Me | N(Me) | Ph | C(Me)₂ | H | racemic |
| III-232 | Me | Et | Me | N(Me) | Ph | C(Me)₂ | H | (R)- |
| III-233 | Me | Me | Me | NH | Ph | C(Me)₂ | Me | racemic |
| III-234 | Me | Me | Me | NH | Ph | C(Me)₂ | Me | (R)- |
| III-235 | Me | Et | Me | NH | Ph | C(Me)₂ | Me | racemic |
| III-236 | Me | Et | Me | NH | Ph | C(Me)₂ | Me | (R)- |
| III-237 | Me | Me | Me | N(Me) | Ph | C(Me)₂ | Me | racemic |
| III-238 | Me | Me | Me | N(Me) | Ph | C(Me)₂ | Me | (R)- |
| III-239 | Me | Et | Me | N(Me) | Ph | C(Me)₂ | Me | racemic |
| III-240 | Me | Et | Me | N(Me) | Ph | C(Me)₂ | Me | (R)- |
| III-241 | Me | Me | Me | NH | Ph | C(Me)₂ | CHF₂ | racemic |
| III-242 | Me | Me | Me | NH | Ph | C(Me)₂ | CHF₂ | (R)- |
| III-243 | Me | Et | Me | NH | Ph | C(Me)₂ | CHF₂ | racemic |
| III-244 | Me | Et | Me | NH | Ph | C(Me)₂ | CHF₂ | (R)- |
| III-245 | Me | Me | Me | N(Me) | Ph | C(Me)₂ | CHF₂ | racemic |
| III-246 | Me | Me | Me | N(Me) | Ph | C(Me)₂ | CHF₂ | (R)- |
| III-247 | Me | Et | Me | N(Me) | Ph | C(Me)₂ | CHF₂ | racemic |
| III-248 | Me | Et | Me | N(Me) | Ph | C(Me)₂ | CHF₂ | (R)- |
| III-249 | Me | Me | Me | NH | Ph | C(Me)₂ | Et | racemic |
| III-250 | Me | Me | Me | NH | Ph | C(Me)₂ | Et | (R)- |

TABLE 41

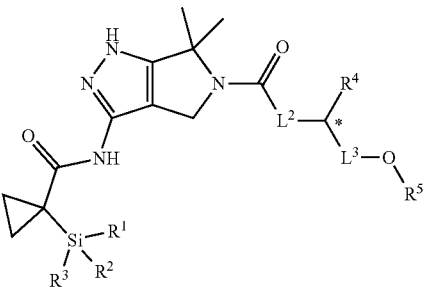

(III)

| Compound No. | R¹ | R² | R³ | L² | R⁴ | L³ | R⁵ | Configuration |
|---|---|---|---|---|---|---|---|---|
| III-251 | Me | Et | Me | NH | Ph | (CH₂)₂ | Et | racemic |
| III-252 | Me | Et | Me | NH | Ph | (CH₂)₂ | Et | (R)- |
| III-253 | Me | Me | Me | N(Me) | Ph | (CH₂)₂ | Et | racemic |
| III-254 | Me | Me | Me | N(Me) | Ph | (CH₂)₂ | Et | (R)- |
| III-255 | Me | Et | Me | N(Me) | Ph | (CH₂)₂ | Et | racemic |
| III-256 | Me | Et | Me | N(Me) | Ph | (CH₂)₂ | Et | (R)- |
| III-257 | Me | Me | Me | NH | Ph | (CH₂)₂ | iPr | racemic |
| III-258 | Me | Me | Me | NH | Ph | (CH₂)₂ | iPr | (R)- |
| III-259 | Me | Et | Me | NH | Ph | (CH₂)₂ | iPr | racemic |
| III-260 | Me | Et | Me | NH | Ph | (CH₂)₂ | iPr | (R)- |
| III-261 | Me | Me | Me | N(Me) | Ph | (CH₂)₂ | iPr | racemic |
| III-262 | Me | Me | Me | N(Me) | Ph | (CH₂)₂ | iPr | (R)- |
| III-263 | Me | Et | Me | N(Me) | Ph | (CH₂)₂ | iPr | racemic |
| III-264 | Me | Et | Me | N(Me) | Ph | (CH₂)₂ | iPr | (R)- |
| III-265 | Me | Me | Me | NH | Ph | (CH₂)₂ | cPr | racemic |
| III-266 | Me | Me | Me | NH | Ph | (CH₂)₂ | cPr | (R)- |
| III-267 | Me | Et | Me | NH | Ph | (CH₂)₂ | cPr | racemic |
| III-268 | Me | Et | Me | NH | Ph | (CH₂)₂ | cPr | (R)- |
| III-269 | Me | Me | Me | N(Me) | Ph | (CH₂)₂ | cPr | racemic |
| III-270 | Me | Me | Me | N(Me) | Ph | (CH₂)₂ | cPr | (R)- |
| III-271 | Me | Et | Me | N(Me) | Ph | (CH₂)₂ | cPr | racemic |
| III-272 | Me | Et | Me | N(Me) | Ph | (CH₂)₂ | cPr | (R)- |
| III-273 | Me | Me | Me | NH | Ph | (CH₂)₂ | Ph | racemic |
| III-274 | Me | Me | Me | NH | Ph | (CH₂)₂ | Ph | (R)- |
| III-275 | Me | Et | Me | NH | Ph | (CH₂)₂ | Ph | racemic |
| III-276 | Me | Et | Me | NH | Ph | (CH₂)₂ | Ph | (R)- |
| III-277 | Me | Me | Me | N(Me) | Ph | (CH₂)₂ | Ph | racemic |
| III-278 | Me | Me | Me | N(Me) | Ph | (CH₂)₂ | Ph | (R)- |
| III-279 | Me | Et | Me | N(Me) | Ph | (CH₂)₂ | Ph | racemic |
| III-280 | Me | Et | Me | N(Me) | Ph | (CH₂)₂ | Ph | (R)- |
| III-281 | Me | Me | Me | NH | Ph | (CH₂)₃ | H | racemic |
| III-282 | Me | Me | Me | NH | Ph | (CH₂)₃ | H | (R)- |
| III-283 | Me | Et | Me | NH | Ph | (CH₂)₃ | H | racemic |
| III-284 | Me | Et | Me | NH | Ph | (CH₂)₃ | H | (R)- |
| III-285 | Me | Me | Me | N(Me) | Ph | (CH₂)₃ | H | racemic |
| III-286 | Me | Me | Me | N(Me) | Ph | (CH₂)₃ | H | (R)- |
| III-287 | Me | Et | Me | N(Me) | Ph | (CH₂)₃ | H | racemic |
| III-288 | Me | Et | Me | N(Me) | Ph | (CH₂)₃ | H | (R)- |
| III-289 | Me | Me | Me | NH | Ph | (CH₂)₄ | H | racemic |
| III-290 | Me | Me | Me | NH | Ph | (CH₂)₄ | H | (R)- |
| III-291 | Me | Et | Me | NH | Ph | (CH₂)₄ | H | racemic |
| III-292 | Me | Et | Me | NH | Ph | (CH₂)₄ | H | (R)- |
| III-293 | Me | Me | Me | N(Me) | Ph | (CH₂)₄ | H | racemic |
| III-294 | Me | Me | Me | N(Me) | Ph | (CH₂)₄ | H | (R)- |
| III-295 | Me | Et | Me | N(Me) | Ph | (CH₂)₄ | H | racemic |
| III-296 | Me | Et | Me | N(Me) | Ph | (CH₂)₄ | H | (R)- |
| III-297 | Me | Me | Me | NH | Ph | CH₂C(Me)₂ | H | racemic |
| III-298 | Me | Me | Me | NH | Ph | CH₂C(Me)₂ | H | (R)- |
| III-299 | Me | Et | Me | NH | Ph | CH₂C(Me)₂ | H | racemic |
| III-300 | Me | Et | Me | NH | Ph | CH₂C(Me)₂ | H | (R)- |

TABLE 42

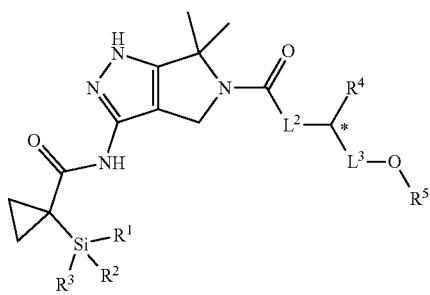

(III)

| Compound No. | R¹ | R² | R³ | L² | R⁴ | L³ | R⁵ | Configuration |
|---|---|---|---|---|---|---|---|---|
| III-301 | Me | Me | Me | N(Me) | Ph | CH$_2$C(Me)$_2$ | H | racemic |
| III-302 | Me | Me | Me | N(Me) | Ph | CH$_2$C(Me)$_2$ | H | (R)- |
| III-303 | Me | Et | Me | N(Me) | Ph | CH$_2$C(Me)$_2$ | H | racemic |
| III-304 | Me | Et | Me | N(Me) | Ph | CH$_2$C(Me)$_2$ | H | (R)- |
| III-305 | Me | Me | Me | NH | Ph | CH$_2$C(Me)$_2$ | Me | racemic |
| III-306 | Me | Me | Me | NH | Ph | CH$_2$C(Me)$_2$ | Me | (R)- |
| III-307 | Me | Et | Me | NH | Ph | CH$_2$C(Me)$_2$ | Me | racemic |
| III-308 | Me | Et | Me | NH | Ph | CH$_2$C(Me)$_2$ | Me | (R)- |
| III-309 | Me | Me | Me | N(Me) | Ph | CH$_2$C(Me)$_2$ | Me | racemic |
| III-310 | Me | Me | Me | N(Me) | Ph | CH$_2$C(Me)$_2$ | Me | (R)- |
| III-311 | Me | Et | Me | N(Me) | Ph | CH$_2$C(Me)$_2$ | Me | racemic |
| III-312 | Me | Et | Me | N(Me) | Ph | CH$_2$C(Me)$_2$ | Me | (R)- |
| III-313 | Me | Me | Me | NH | Ph | CH$_2$C(Me)$_2$ | CHF$_2$ | racemic |
| III-314 | Me | Me | Me | NH | Ph | CH$_2$C(Me)$_2$ | CHF$_2$ | (R)- |
| III-315 | Me | Et | Me | NH | Ph | CH$_2$C(Me)$_2$ | CHF$_2$ | racemic |
| III-316 | Me | Et | Me | NH | Ph | CH$_2$C(Me)$_2$ | CHF$_2$ | (R)- |
| III-317 | Me | Me | Me | N(Me) | Ph | CH$_2$C(Me)$_2$ | CHF$_2$ | racemic |
| III-318 | Me | Me | Me | N(Me) | Ph | CH$_2$C(Me)$_2$ | CHF$_2$ | (R)- |
| III-319 | Me | Et | Me | N(Me) | Ph | CH$_2$C(Me)$_2$ | CHF$_2$ | racemic |
| III-320 | Me | Et | Me | N(Me) | Ph | CH$_2$C(Me)$_2$ | CHF$_2$ | (R)- |
| III-321 | Me | Me | Me | NH | Ph | CH$_2$C(Me)$_2$ | Et | racemic |
| III-322 | Me | Me | Me | NH | Ph | CH$_2$C(Me)$_2$ | Et | (R)- |
| III-323 | Me | Et | Me | NH | Ph | CH$_2$C(Me)$_2$ | Et | racemic |
| III-324 | Me | Et | Me | NH | Ph | CH$_2$C(Me)$_2$ | Et | (R)- |
| III-325 | Me | Me | Me | N(Me) | Ph | CH$_2$C(Me)$_2$ | Et | racemic |
| III-326 | Me | Me | Me | N(Me) | Ph | CH$_2$C(Me)$_2$ | Et | (R)- |
| III-327 | Me | Et | Me | N(Me) | Ph | CH$_2$C(Me)$_2$ | Et | racemic |
| III-328 | Me | Et | Me | N(Me) | Ph | CH$_2$C(Me)$_2$ | Et | (R)- |
| III-329 | Me | Me | Me | NH | Ph | CH$_2$C(Me)$_2$ | iPr | racemic |
| III-330 | Me | Me | Me | NH | Ph | CH$_2$C(Me)$_2$ | iPr | (R)- |
| III-331 | Me | Et | Me | NH | Ph | CH$_2$C(Me)$_2$ | iPr | racemic |
| III-332 | Me | Et | Me | NH | Ph | CH$_2$C(Me)$_2$ | iPr | (R)- |
| III-333 | Me | Me | Me | N(Me) | Ph | CH$_2$C(Me)$_2$ | iPr | racemic |
| III-334 | Me | Me | Me | N(Me) | Ph | CH$_2$C(Me)$_2$ | iPr | (R)- |
| III-335 | Me | Et | Me | N(Me) | Ph | CH$_2$C(Me)$_2$ | iPr | racemic |
| III-336 | Me | Et | Me | N(Me) | Ph | CH$_2$C(Me)$_2$ | iPr | (R)- |
| III-337 | Me | Me | Me | NH | Ph | CH$_2$C(Me)$_2$ | cPr | racemic |
| III-338 | Me | Me | Me | NH | Ph | CH$_2$C(Me)$_2$ | cPr | (R)- |
| III-339 | Me | Et | Me | NH | Ph | CH$_2$C(Me)$_2$ | cPr | racemic |
| III-340 | Me | Et | Me | NH | Ph | CH$_2$C(Me)$_2$ | cPr | (R)- |
| III-341 | Me | Me | Me | N(Me) | Ph | CH$_2$C(Me)$_2$ | cPr | racemic |
| III-342 | Me | Me | Me | N(Me) | Ph | CH$_2$C(Me)$_2$ | cPr | (R)- |
| III-343 | Me | Et | Me | N(Me) | Ph | CH$_2$C(Me)$_2$ | cPr | racemic |
| III-344 | Me | Et | Me | N(Me) | Ph | CH$_2$C(Me)$_2$ | cPr | (R)- |
| III-345 | Me | Me | Me | NH | Ph | CH$_2$C(Me)$_2$ | Ph | racemic |
| III-346 | Me | Me | Me | NH | Ph | CH$_2$C(Me)$_2$ | Ph | (R)- |
| III-347 | Me | Et | Me | NH | Ph | CH$_2$C(Me)$_2$ | Ph | racemic |
| III-348 | Me | Et | Me | NH | Ph | CH$_2$C(Me)$_2$ | Ph | (R)- |
| III-349 | Me | Me | Me | N(Me) | Ph | CH$_2$C(Me)$_2$ | Ph | racemic |
| III-350 | Me | Me | Me | N(Me) | Ph | CH$_2$C(Me)$_2$ | Ph | (R)- |

TABLE 43

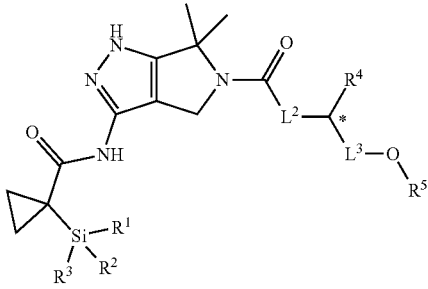

(III)

| Compound No. | R¹ | R² | R³ | L² | R⁴ | L³ | R⁵ | Configuration |
|---|---|---|---|---|---|---|---|---|
| III-351 | Me | Et | Me | N(Me) | Ph | CH$_2$C(Me)$_2$ | Ph | racemic |
| III-352 | Me | Et | Me | N(Me) | Ph | CH$_2$C(Me)$_2$ | Ph | (R)- |
| III-353 | Me | Me | Me | NH | Ph | CH$_2$C(Me)$_2$ | H | racemic |
| III-354 | Me | Me | Me | NH | Ph | CH$_2$C(Me)$_2$ | H | (S)- |
| III-355 | Me | Et | Me | NH | Ph | CH$_2$C(Me)$_2$ | H | racemic |
| III-356 | Me | Et | Me | NH | Ph | CH$_2$C(Me)$_2$ | H | (S)- |
| III-357 | Me | Me | Me | N(Me) | Ph | CH$_2$C(Me)$_2$ | H | racemic |
| III-358 | Me | Me | Me | N(Me) | Ph | CH$_2$C(Me)$_2$ | H | (S)- |
| III-359 | Me | Et | Me | N(Me) | Ph | CH$_2$C(Me)$_2$ | H | racemic |
| III-360 | Me | Et | Me | N(Me) | Ph | CH$_2$C(Me)$_2$ | H | (S)- |
| III-361 | Me | Me | Me | NH | Ph | CF$_2$CH$_2$ | H | racemic |
| III-362 | Me | Me | Me | NH | Ph | CF$_2$CH$_2$ | H | (S)- |
| III-363 | Me | Et | Me | NH | Ph | CF$_2$CH$_2$ | H | racemic |
| III-364 | Me | Et | Me | NH | Ph | CF$_2$CH$_2$ | H | (S)- |
| III-365 | Me | Me | Me | N(Me) | Ph | CF$_2$CH$_2$ | H | racemic |
| III-366 | Me | Me | Me | N(Me) | Ph | CF$_2$CH$_2$ | H | (S)- |
| III-367 | Me | Et | Me | N(Me) | Ph | CF$_2$CH$_2$ | H | racemic |
| III-368 | Me | Et | Me | N(Me) | Ph | CF$_2$CH$_2$ | H | (S)- |
| III-369 | Me | Me | Me | NH | Ph | CH=CHCH$_2$ | H | racemic |
| III-370 | Me | Me | Me | NH | Ph | CH=CHCH$_2$ | H | (S)- |
| III-371 | Me | Et | Me | NH | Ph | CH=CHCH$_2$ | H | racemic |
| III-372 | Me | Et | Me | NH | Ph | CH=CHCH$_2$ | H | (S)- |
| III-373 | Me | Me | Me | N(Me) | Ph | CH=CHCH$_2$ | H | racemic |
| III-374 | Me | Me | Me | N(Me) | Ph | CH=CHCH$_2$ | H | (S)- |
| III-375 | Me | Et | Me | N(Me) | Ph | CH=CHCH$_2$ | H | racemic |
| III-376 | Me | Et | Me | N(Me) | Ph | CH=CHCH$_2$ | H | (S)- |
| III-377 | Me | Me | Me | NH | Ph | C≡CH$_2$ | H | racemic |
| III-378 | Me | Me | Me | NH | Ph | C≡CH$_2$ | H | (S)- |
| III-379 | Me | Et | Me | NH | Ph | C≡CH$_2$ | H | racemic |
| III-380 | Me | Et | Me | NH | Ph | C≡CH$_2$ | H | (S)- |
| III-381 | Me | Me | Me | N(Me) | Ph | C≡CH$_2$ | H | racemic |
| III-382 | Me | Me | Me | N(Me) | Ph | C≡CH$_2$ | H | (S)- |
| III-383 | Me | Et | Me | N(Me) | Ph | C≡CH$_2$ | H | racemic |
| III-384 | Me | Et | Me | N(Me) | Ph | C≡CH$_2$ | H | (S)- |
| III-385 | Me | Me | Me | NH | Ph | 1,1-Cyclopropylene | H | racemic |
| III-386 | Me | Me | Me | NH | Ph | 1,1-Cyclopropylene | H | (S)- |
| III-387 | Me | Et | Me | NH | Ph | 1,1-Cyclopropylene | H | racemic |
| III-388 | Me | Et | Me | NH | Ph | 1,1-Cyclopropylene | H | (S)- |
| III-389 | Me | Me | Me | N(Me) | Ph | 1,1-Cyclopropylene | H | racemic |
| III-390 | Me | Me | Me | N(Me) | Ph | 1,1-Cyclopropylene | H | (S)- |
| III-391 | Me | Et | Me | N(Me) | Ph | 1,1-Cyclopropylene | H | racemic |
| III-392 | Me | Et | Me | N(Me) | Ph | 1,1-Cyclopropylene | H | (S)- |
| III-393 | Me | Me | Me | NH | Ph | 1,2-Cyclopropynylene | H | racemic |
| III-394 | Me | Me | Me | NH | Ph | 1,2-Cyclopropynylene | H | (S)- |
| III-395 | Me | Et | Me | NH | Ph | 1,2-Cyclopropynylene | H | racemic |
| III-396 | Me | Et | Me | NH | Ph | 1,2-Cyclopropynylene | H | (S)- |
| III-397 | Me | Me | Me | N(Me) | Ph | 1,2-Cyclopropynylene | H | racemic |

TABLE 43-continued

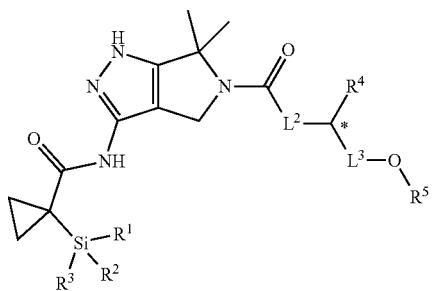
(III)

| Compound No. | R¹ | R² | R³ | L² | R⁴ | L³ | R⁵ | Configuration |
|---|---|---|---|---|---|---|---|---|
| III-398 | Me | Me | Me | N(Me) | Ph | 1,2-Cyclopropynylene | H | (S)- |
| III-399 | Me | Et | Me | N(Me) | Ph | 1,2-Cyclopropynylene | H | racemic |
| III-400 | Me | Et | Me | N(Me) | Ph | 1,2-Cyclopropynylene | H | (S)- |

TABLE 44

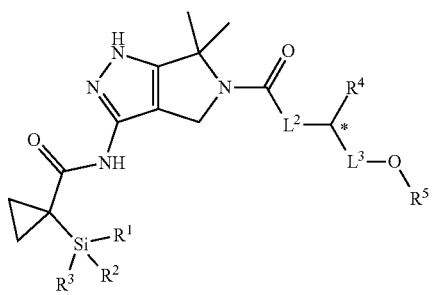
(III)

| Compound No. | R¹ | R² | R³ | L² | R⁴ | L³ | R⁵ | Configuration |
|---|---|---|---|---|---|---|---|---|
| III-401 | Me | Me | Me | NH | Ph | C(=O) | H | racemic |
| III-402 | Me | Me | Me | NH | Ph | C(=O) | H | (S)- |
| III-403 | Me | Et | Me | NH | Ph | C(=O) | H | racemic |
| III-404 | Me | Et | Me | NH | Ph | C(=O) | H | (S)- |
| III-405 | Me | Me | Me | N(Me) | Ph | C(=O) | H | racemic |
| III-406 | Me | Me | Me | N(Me) | Ph | C(=O) | H | (S)- |
| III-407 | Me | Et | Me | N(Me) | Ph | C(=O) | H | racemic |
| III-408 | Me | Et | Me | N(Me) | Ph | C(=O) | H | (S)- |
| III-409 | Me | Me | Me | NH | Ph | C(=O) | Bn | racemic |
| III-410 | Me | Me | Me | NH | Ph | C(=O) | Bn | (S)- |
| III-411 | Me | Et | Me | NH | Ph | C(=O) | Bn | racemic |
| III-412 | Me | Et | Me | NH | Ph | C(=O) | Bn | (S)- |
| III-413 | Me | Me | Me | N(Me) | Ph | C(=O) | Bn | racemic |
| III-414 | Me | Me | Me | N(Me) | Ph | C(=O) | Bn | (S)- |
| III-415 | Me | Et | Me | N(Me) | Ph | C(=O) | Bn | racemic |
| III-416 | Me | Et | Me | N(Me) | Ph | C(=O) | Bn | (S)- |
| III-417 | Me | Me | Me | NH | Ph | C(=O) | Me | racemic |
| III-418 | Me | Me | Me | NH | Ph | C(=O) | Me | (S)- |
| III-419 | Me | Et | Me | NH | Ph | C(=O) | Me | racemic |
| III-420 | Me | Et | Me | NH | Ph | C(=O) | Me | (S)- |
| III-421 | Me | Me | Me | N(Me) | Ph | C(=O) | Me | racemic |
| III-422 | Me | Me | Me | N(Me) | Ph | C(=O) | Me | (S)- |
| III-423 | Me | Et | Me | N(Me) | Ph | C(=O) | Me | racemic |
| III-424 | Me | Et | Me | N(Me) | Ph | C(=O) | Me | (S)- |
| III-425 | Me | Me | Me | NH | H | CH₂ | H | |
| III-426 | Me | Et | Me | NH | H | CH₂ | H | |
| III-427 | Me | Me | Me | N(Me) | H | CH₂ | H | |
| III-428 | Me | Et | Me | N(Me) | H | CH₂ | H | |
| III-429 | Me | Me | Me | NH | H | CH(Me) | H | |

TABLE 44-continued

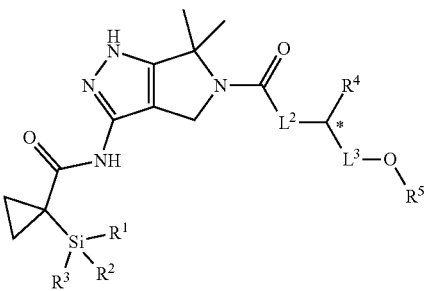
(III)

| Compound No. | R¹ | R² | R³ | L² | R⁴ | L³ | R⁵ | Configuration |
|---|---|---|---|---|---|---|---|---|
| III-430 | Me | Et | Me | NH | H | CH(Me) | H | |
| III-431 | Me | Me | Me | N(Me) | H | CH(Me) | H | |
| III-432 | Me | Et | Me | N(Me) | H | CH(Me) | H | |
| III-433 | Me | Me | Me | NH | H | CH(iPr) | H | |
| III-434 | Me | Et | Me | NH | H | CH(iPr) | H | |
| III-435 | Me | Me | Me | N(Me) | H | CH(iPr) | H | |
| III-436 | Me | Et | Me | N(Me) | H | CH(iPr) | H | |
| III-437 | Me | Me | Me | NH | H | CH(Ph) | H | |
| III-438 | Me | Et | Me | NH | H | CH(Ph) | H | |
| III-439 | Me | Me | Me | N(Me) | H | CH(Ph) | H | |
| III-440 | Me | Et | Me | N(Me) | H | CH(Ph) | H | |
| III-441 | Me | Me | Me | NH | Me | CH₂ | H | racemic |
| III-442 | Me | Me | Me | NH | Me | CH₂ | H | (S)- |
| III-443 | Me | Et | Me | NH | Me | CH₂ | H | racemic |
| III-444 | Me | Et | Me | NH | Me | CH₂ | H | (S)- |
| III-445 | Me | Me | Me | N(Me) | Me | CH₂ | H | racemic |
| III-446 | Me | Me | Me | N(Me) | Me | CH₂ | H | (S)- |
| III-447 | Me | Et | Me | N(Me) | Me | CH₂ | H | racemic |
| III-448 | Me | Et | Me | N(Me) | Me | CH₂ | H | (S)- |
| III-449 | Me | Me | Me | NH | iPr | CH₂ | H | racemic |
| III-450 | Me | Me | Me | NH | iPr | CH₂ | H | (S)- |

TABLE 45

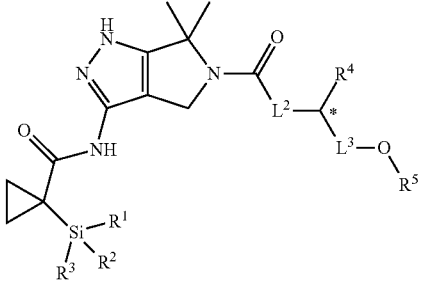
(III)

| Compound No. | R¹ | R² | R³ | L² | R⁴ | L³ | R⁵ | Configuration |
|---|---|---|---|---|---|---|---|---|
| III-451 | Me | Et | Me | NH | iPr | CH₂ | H | racemic |
| III-452 | Me | Et | Me | NH | iPr | CH₂ | H | (S)- |
| III-453 | Me | Me | Me | N(Me) | iPr | CH₂ | H | racemic |
| III-454 | Me | Me | Me | N(Me) | iPr | CH₂ | H | (S)- |
| III-455 | Me | Et | Me | N(Me) | iPr | CH₂ | H | racemic |
| III-456 | Me | Et | Me | N(Me) | iPr | CH₂ | H | (S)- |
| III-457 | Me | Me | Me | NH | cHex | CH₂ | H | racemic |
| III-458 | Me | Me | Me | NH | cHex | CH₂ | H | (S)- |
| III-459 | Me | Et | Me | NH | cHex | CH₂ | H | racemic |
| III-460 | Me | Et | Me | NH | cHex | CH₂ | H | (S)- |
| III-461 | Me | Me | Me | N(Me) | cHex | CH₂ | H | racemic |
| III-462 | Me | Me | Me | N(Me) | cHex | CH₂ | H | (S)- |
| III-463 | Me | Et | Me | N(Me) | cHex | CH₂ | H | racemic |
| III-464 | Me | Et | Me | N(Me) | cHex | CH₂ | H | (S)- |
| III-465 | Me | Me | Me | NH | 1,3-Benzodioxol-4-yl | CH₂ | H | racemic |

TABLE 45-continued (III)

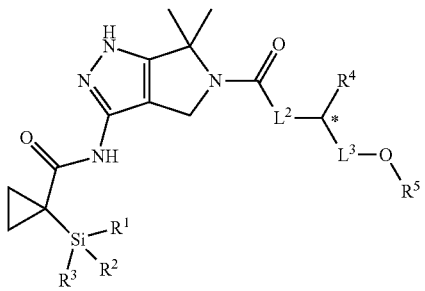

| Compound No. | R¹ | R² | R³ | L² | R⁴ | L³ | R⁵ | Configuration |
|---|---|---|---|---|---|---|---|---|
| III-466 | Me | Me | Me | NH | 1,3-Benzo-dioxol-4-yl | CH₂ | H | (S)- |
| III-467 | Me | Et | Me | NH | 1,3-Benzo-dioxol-4-yl | CH₂ | H | racemic |
| III-468 | Me | Et | Me | NH | 1,3-Benzo-dioxol-4-yl | CH₂ | H | (S)- |
| III-469 | Me | Me | Me | N(Me) | 1,3-Benzo-dioxol-4-yl | CH₂ | H | racemic |
| III-470 | Me | Me | Me | N(Me) | 1,3-Benzo-dioxol-4-yl | CH₂ | H | (S)- |
| III-471 | Me | Et | Me | N(Me) | 1,3-Benzo-diox-4-yl | CH₂ | H | racemic |
| III-472 | Me | Et | Me | N(Me) | 1,3-Benzo-dioxol | CH₂ | H | (S)- |
| III-473 | Me | Me | Me | NH | 2-F—Ph | CH₂ | H | racemic |
| III-474 | Me | Me | Me | NH | 2-F—Ph | CH₂ | H | (S)- |
| III-475 | Me | Et | Me | NH | 2-F—Ph | CH₂ | H | racemic |
| III-476 | Me | Et | Me | NH | 2-F—Ph | CH₂ | H | (S)- |
| III-477 | Me | Me | Me | N(Me) | 2-F—Ph | CH₂ | H | racemic |
| III-478 | Me | Me | Me | N(Me) | 2-F—Ph | CH₂ | H | (S)- |
| III-479 | Me | Et | Me | N(Me) | 2-F—Ph | CH₂ | H | racemic |
| III-480 | Me | Et | Me | N(Me) | 2-F—Ph | CH₂ | H | (S)- |
| III-481 | Me | Me | Me | NH | 3-F—Ph | CH₂ | H | racemic |
| III-482 | Me | Me | Me | NH | 3-F—Ph | CH₂ | H | (S)- |
| III-483 | Me | Et | Me | NH | 3-F—Ph | CH₂ | H | racemic |
| III-484 | Me | Et | Me | NH | 3-F—Ph | CH₂ | H | (S)- |
| III-485 | Me | Me | Me | N(Me) | 3-F—Ph | CH₂ | H | racemic |
| III-486 | Me | Me | Me | N(Me) | 3-F—Ph | CH₂ | H | (S)- |
| III-487 | Me | Et | Me | N(Me) | 3-F—Ph | CH₂ | H | racemic |
| III-488 | Me | Et | Me | N(Me) | 3-F—Ph | CH₂ | H | (S)- |
| III-489 | Me | Me | Me | NH | 4-F—Ph | CH₂ | H | racemic |
| III-490 | Me | Me | Me | NH | 4-F—Ph | CH₂ | H | (S)- |
| III-491 | Me | Et | Me | NH | 4-F—Ph | CH₂ | H | racemic |
| III-492 | Me | Et | Me | NH | 4-F—Ph | CH₂ | H | (S)- |
| III-493 | Me | Me | Me | N(Me) | 4-F—Ph | CH₂ | H | racemic |
| III-494 | Me | Me | Me | N(Me) | 4-F—Ph | CH₂ | H | (S)- |
| III-495 | Me | Et | Me | N(Me) | 4-F—Ph | CH₂ | H | racemic |
| III-496 | Me | Et | Me | N(Me) | 4-F—Ph | CH₂ | H | (S)- |
| III-497 | Me | Me | Me | NH | 2-Py | CH₂ | H | racemic |
| III-498 | Me | Me | Me | NH | 2-Py | CH₂ | H | (S)- |
| III-499 | Me | Et | Me | NH | 2-Py | CH₂ | H | racemic |
| III-500 | Me | Et | Me | NH | 2-Py | CH₂ | H | (S)- |

TABLE 46

(III)

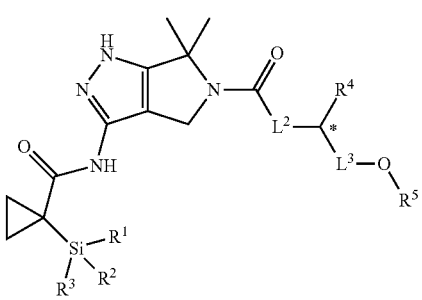

| Compound No. | R¹ | R² | R³ | L² | R⁴ | L³ | R⁵ | Configuration |
|---|---|---|---|---|---|---|---|---|
| III-501 | Me | Me | Me | N(Me) | 2-Py | CH₂ | H | racemic |
| III-502 | Me | Me | Me | N(Me) | 2-Py | CH₂ | H | (S)- |
| III-503 | Me | Et | Me | N(Me) | 2-Py | CH₂ | H | racemic |
| III-504 | Me | Et | Me | N(Me) | 2-Py | CH₂ | H | (S)- |
| III-505 | Me | Me | Me | NH | 3-Py | CH₂ | H | racemic |
| III-506 | Me | Me | Me | NH | 3-Py | CH₂ | H | (S)- |
| III-507 | Me | Et | Me | NH | 3-Py | CH₂ | H | racemic |
| III-508 | Me | Et | Me | NH | 3-Py | CH₂ | H | (S)- |
| III-509 | Me | Me | Me | N(Me) | 3-Py | CH₂ | H | racemic |
| III-510 | Me | Me | Me | N(Me) | 3-Py | CH₂ | H | (S)- |
| III-511 | Me | Et | Me | N(Me) | 3-Py | CH₂ | H | racemic |
| III-512 | Me | Et | Me | N(Me) | 3-Py | CH₂ | H | (S)- |
| III-513 | Me | Me | Me | NH | 4-Py | CH₂ | H | racemic |
| III-514 | Me | Me | Me | NH | 4-Py | CH₂ | H | (S)- |
| III-515 | Me | Et | Me | NH | 4-Py | CH₂ | H | racemic |
| III-516 | Me | Et | Me | NH | 4-Py | CH₂ | H | (S)- |
| III-517 | Me | Me | Me | N(Me) | 4-Py | CH₂ | H | racemic |
| III-518 | Me | Me | Me | N(Me) | 4-Py | CH₂ | H | (S)- |
| III-519 | Me | Et | Me | N(Me) | 4-Py | CH₂ | H | racemic |
| III-520 | Me | Et | Me | N(Me) | 4-Py | CH₂ | H | (S)- |
| III-521 | Me | Me | Me | CH₂ | Ph | CH₂ | H | racemic |
| III-522 | Me | Me | Me | CH₂ | Ph | CH₂ | H | (S)- |
| III-523 | Me | Et | Me | CH₂ | Ph | CH₂ | H | racemic |
| III-524 | Me | Et | Me | CH₂ | Ph | CH₂ | H | (S)- |
| III-525 | Me | Me | Me | CH₂ | Ph | — | H | racemic |
| III-526 | Me | Me | Me | CH₂ | Ph | — | H | (S)- |
| III-527 | Me | Et | Me | CH₂ | Ph | — | H | racemic |
| III-528 | Me | Et | Me | CH₂ | Ph | — | H | (S)- |
| III-529 | Me | Me | Me | CH₂ | Ph | CH₂ | Me | racemic |
| III-530 | Me | Me | Me | CH₂ | Ph | CH₂ | Me | (S)- |
| III-531 | Me | Et | Me | CH₂ | Ph | CH₂ | Me | racemic |
| III-532 | Me | Et | Me | CH₂ | Ph | CH₂ | Me | (S)- |
| III-533 | Me | Me | Me | CH₂ | Ph | CH₂ | CHF₂ | racemic |
| III-534 | Me | Me | Me | CH₂ | Ph | CH₂ | CHF₂ | (S)- |
| III-535 | Me | Et | Me | CH₂ | Ph | CH₂ | CHF₂ | racemic |
| III-536 | Me | Et | Me | CH₂ | Ph | CH₂ | CHF₂ | (S)- |
| III-537 | Me | Me | Me | CH₂ | Ph | CH₂ | Et | racemic |
| III-538 | Me | Me | Me | CH₂ | Ph | CH₂ | Et | (S)- |
| III-539 | Me | Et | Me | CH₂ | Ph | CH₂ | Et | racemic |
| III-540 | Me | Et | Me | CH₂ | Ph | CH₂ | Et | (S)- |
| III-541 | Me | Me | Me | CH₂ | Ph | CH₂ | cPr | racemic |
| III-542 | Me | Me | Me | CH₂ | Ph | CH₂ | cPr | (S)- |
| III-543 | Me | Me | Me | CH₂ | Ph | CH₂ | Ph | racemic |
| III-544 | Me | Me | Me | CH₂ | Ph | CH₂ | Ph | (S)- |
| III-545 | Me | Me | Me | CH₂ | Ph | C(Me)₂ | H | racemic |
| III-546 | Me | Me | Me | CH₂ | Ph | C(Me)₂ | H | (S)- |
| III-547 | Me | Et | Me | CH₂ | Ph | C(Me)₂ | H | racemic |
| III-548 | Me | Et | Me | CH₂ | Ph | C(Me)₂ | H | (S)- |
| III-549 | Me | Me | Me | CH₂ | Ph | C(Me)₂ | Me | racemic |
| III-550 | Me | Me | Me | CH₂ | Ph | C(Me)₂ | Me | (S)- |

TABLE 47

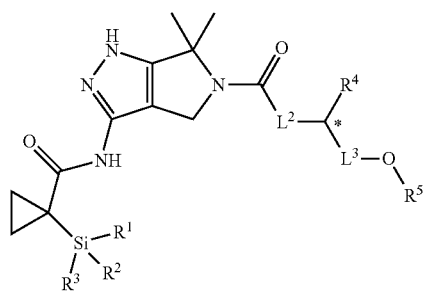
(III)

| Compound No. | R¹ | R² | R³ | L² | R⁴ | L³ | R⁵ | Configuration |
|---|---|---|---|---|---|---|---|---|
| III-551 | Me | Et | Me | CH₂ | Ph | C(Me)₂ | Me | racemic |
| III-552 | Me | Et | Me | CH₂ | Ph | C(Me)₂ | Me | (S)- |
| III-553 | Me | Me | Me | CH₂ | Ph | C(Me)₂ | CHF₂ | racemic |
| III-554 | Me | Me | Me | CH₂ | Ph | C(Me)₂ | CHF₂ | (S)- |
| III-555 | Me | Me | Me | CH₂ | Ph | C(Me)₂ | Et | racemic |
| III-556 | Me | Me | Me | CH₂ | Ph | C(Me)₂ | Et | (S)- |
| III-557 | Me | Me | Me | CH₂ | Ph | C(Me)₂ | cPr | racemic |
| III-558 | Me | Me | Me | CH₂ | Ph | C(Me)₂ | cPr | (S)- |
| III-559 | Me | Me | Me | CH₂ | Ph | C(Me)₂ | Ph | racemic |
| III-560 | Me | Me | Me | CH₂ | Ph | C(Me)₂ | Ph | (S)- |
| III-561 | Me | Me | Me | CH₂ | Ph | (CH₂)₂ | H | racemic |
| III-562 | Me | Me | Me | CH₂ | Ph | (CH₂)₂ | H | (S)- |
| III-563 | Me | Et | Me | CH₂ | Ph | (CH₂)₂ | H | racemic |
| III-564 | Me | Et | Me | CH₂ | Ph | (CH₂)₂ | H | (S)- |
| III-565 | Me | Me | Me | CH₂ | Ph | (CH₂)₂ | Me | racemic |
| III-566 | Me | Me | Me | CH₂ | Ph | (CH₂)₂ | Me | (S)- |
| III-567 | Me | Me | Me | CH₂ | Ph | (CH₂)₂ | CHF₂ | racemic |
| III-568 | Me | Me | Me | CH₂ | Ph | (CH₂)₂ | CHF₂ | (S)- |
| III-569 | Me | Me | Me | CH₂ | Ph | (CH₂)₂ | Et | racemic |
| III-570 | Me | Me | Me | CH₂ | Ph | (CH₂)₂ | Et | (S)- |
| III-571 | Me | Me | Me | CH₂ | Ph | (CH₂)₂ | cPr | racemic |
| III-572 | Me | Me | Me | CH₂ | Ph | (CH₂)₂ | cPr | (S)- |
| III-573 | Me | Me | Me | CH₂ | Ph | (CH₂)₂ | Ph | racemic |
| III-574 | Me | Me | Me | CH₂ | Ph | (CH₂)₂ | Ph | (S)- |
| III-575 | Me | Me | Me | CH₂ | Ph | CH₂C(Me)₂ | H | racemic |
| III-576 | Me | Me | Me | CH₂ | Ph | CH₂C(Me)₂ | H | (S)- |
| III-577 | Me | Et | Me | CH₂ | Ph | CH₂C(Me)₂ | H | racemic |
| III-578 | Me | Et | Me | CH₂ | Ph | CH₂C(Me)₂ | H | (S)- |
| III-579 | Me | Me | Me | CH₂ | Ph | CH₂C(Me)₂ | Me | racemic |
| III-580 | Me | Me | Me | CH₂ | Ph | CH₂C(Me)₂ | Me | (S)- |
| III-581 | Me | Et | Me | CH₂ | Ph | CH₂C(Me)₂ | Me | racemic |
| III-582 | Me | Et | Me | CH₂ | Ph | CH₂C(Me)₂ | Me | (S)- |
| III-583 | Me | Me | Me | CH₂ | Ph | CH₂C(Me)₂ | CHF₂ | racemic |
| III-584 | Me | Me | Me | CH₂ | Ph | CH₂C(Me)₂ | CHF₂ | (S)- |
| III-585 | Me | Me | Me | CH₂ | Ph | CH₂C(Me)₂ | Et | racemic |
| III-586 | Me | Me | Me | CH₂ | Ph | CH₂C(Me)₂ | Et | (S)- |
| III-587 | Me | Me | Me | CH₂ | Ph | CH₂C(Me)₂ | cPr | racemic |
| III-588 | Me | Me | Me | CH₂ | Ph | CH₂C(Me)₂ | cPr | (S)- |
| III-589 | Me | Me | Me | CH₂ | Ph | CH₂C(Me)₂ | Ph | racemic |
| III-590 | Me | Me | Me | CH₂ | Ph | CH₂C(Me)₂ | Ph | (S)- |
| III-591 | Me | Me | Me | — | Ph | CH₂ | H | racemic |
| III-592 | Me | Me | Me | — | Ph | CH₂ | H | (S)- |
| III-593 | Me | Me | Me | — | Ph | CH₂ | Me | racemic |
| III-594 | Me | Me | Me | — | Ph | CH₂ | Me | (S)- |
| III-595 | Me | Me | Me | CH=CH | Ph | CH₂ | H | racemic |
| III-596 | Me | Me | Me | CH=CH | Ph | CH₂ | H | (S)- |
| III-597 | Me | Me | Me | CH=CH | Ph | CH₂ | Me | racemic |
| III-598 | Me | Me | Me | CH=CH | Ph | CH₂ | Me | (S)- |
| III-599 | Me | Me | Me | C≡C | Ph | CH₂ | H | racemic |
| III-600 | Me | Me | Me | C≡C | Ph | CH₂ | H | (S)- |

TABLE 48

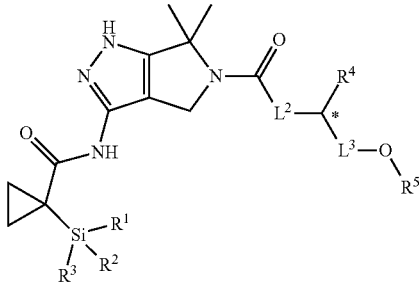
(III)

| Compound No. | R¹ | R² | R³ | L² | R⁴ | L³ | R⁵ | Configuration |
|---|---|---|---|---|---|---|---|---|
| III-601 | Me | Me | Me | C≡C | Ph | CH₂ | Me | racemic |
| III-602 | Me | Me | Me | C≡C | Ph | CH₂ | Me | (S)- |
| III-603 | Me | Me | Me | 1,2-Cyclopropylene | Ph | CH₂ | H | racemic |
| III-604 | Me | Me | Me | 1,2-Cyclopropylene | Ph | CH₂ | H | (S)- |
| III-605 | Me | Me | Me | 1,2-Cyclopropylene | Ph | CH₂ | Me | racemic |
| III-606 | Me | Me | Me | 1,2-Cyclopropylene | Ph | CH₂ | Me | (S)- |
| III-607 | Me | Me | Me | 1,2-Cyclopropynylene | Ph | CH₂ | H | racemic |
| III-608 | Me | Me | Me | 1,2-Cyclopropynylene | Ph | CH₂ | H | (S)- |
| III-609 | Me | Me | Me | 1,2-Cyclopropynylene | Ph | CH₂ | Me | racemic |
| III-610 | Me | Me | Me | 1,2-Cyclopropynylene | Ph | CH₂ | Me | (S)- |

TABLE 49

(III)

| Compound No. | R¹ | R² | R³ | L² | R⁴ | L³ | R⁵ | Configuration |
|---|---|---|---|---|---|---|---|---|
| III-611 | Me | Me | Me | O | Ph | C(Me)₂CH₂ | H | racemic |
| III-612 | Me | Me | Me | O | Ph | C(Me)₂CH₂ | H | (+) |
| III-613 | Me | Me | Me | O | Ph | C(Me)₂CH₂ | H | (−) |
| III-614 | Me | Et | Me | O | Ph | C(Me)₂CH₂ | H | racemic |
| III-615 | Me | Et | Me | O | Ph | C(Me)₂CH₂ | H | (+) |
| III-616 | Me | Et | Me | O | Ph | C(Me)₂CH₂ | H | (−) |
| III-617 | Me | Me | Me | O | Ph | C(Me)₂CH₂ | Me | racemic |
| III-618 | Me | Me | Me | O | Ph | C(Me)₂CH₂ | Me | (+) |
| III-619 | Me | Me | Me | O | Ph | C(Me)₂CH₂ | Me | (−) |
| III-620 | Me | Et | Me | O | Ph | C(Me)₂CH₂ | Me | racemic |
| III-621 | Me | Et | Me | O | Ph | C(Me)₂CH₂ | Me | (+) |
| III-622 | Me | Et | Me | O | Ph | C(Me)₂CH₂ | Me | (−) |
| III-623 | Me | Me | Me | O | Ph | C(Me)₂CH₂ | CHF₂ | racemic |
| III-624 | Me | Me | Me | O | Ph | C(Me)₂CH₂ | CHF₂ | (+) |
| III-625 | Me | Me | Me | O | Ph | C(Me)₂CH₂ | CHF₂ | (−) |
| III-626 | Me | Me | Me | O | Ph | C(Me)₂CH₂ | Et | racemic |
| III-627 | Me | Me | Me | O | Ph | C(Me)₂CH₂ | Et | (+) |
| III-628 | Me | Me | Me | O | Ph | C(Me)₂CH₂ | Et | (−) |
| III-629 | Me | Me | Me | NH | Ph | C(Me)₂CH₂ | H | (+) |
| III-630 | Me | Me | Me | NH | Ph | C(Me)₂CH₂ | H | (−) |
| III-631 | Me | Et | Me | NH | Ph | C(Me)₂CH₂ | H | (+) |
| III-632 | Me | Et | Me | NH | Ph | C(Me)₂CH₂ | H | (−) |
| III-633 | Me | Me | Me | NH | Ph | C(Me)₂CH₂ | Me | racemic |
| III-634 | Me | Me | Me | NH | Ph | C(Me)₂CH₂ | Me | (+) |
| III-635 | Me | Me | Me | NH | Ph | C(Me)₂CH₂ | Me | (−) |
| III-636 | Me | Et | Me | NH | Ph | C(Me)₂CH₂ | Me | racemic |
| III-637 | Me | Et | Me | NH | Ph | C(Me)₂CH₂ | Me | (+) |

TABLE 49-continued

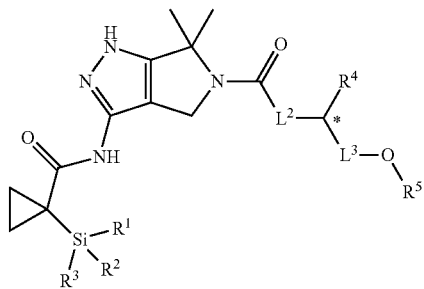

(III)

| Compound No. | R¹ | R² | R³ | L² | R⁴ | L³ | R⁵ | Configuration |
|---|---|---|---|---|---|---|---|---|
| III-638 | Me | Et | Me | NH | Ph | C(Me)₂CH₂ | Me | (−) |
| III-639 | Me | Me | Me | NH | Ph | C(Me)₂CH₂ | CHF₂ | racemic |
| III-640 | Me | Me | Me | NH | Ph | C(Me)₂CH₂ | CHF₂ | (+) |
| III-641 | Me | Me | Me | NH | Ph | C(Me)₂CH₂ | CHF₂ | (−) |
| III-642 | Me | Et | Me | NH | Ph | C(Me)₂CH₂ | CHF₂ | racemic |
| III-643 | Me | Et | Me | NH | Ph | C(Me)₂CH₂ | CHF₂ | (+) |
| III-644 | Me | Et | Me | NH | Ph | C(Me)₂CH₂ | CHF₂ | (−) |
| III-645 | Me | Me | Me | NH | Ph | C(Me)₂CH₂ | Et | racemic |
| III-646 | Me | Me | Me | NH | Ph | C(Me)₂CH₂ | Et | (+) |
| III-647 | Me | Me | Me | NH | Ph | C(Me)₂CH₂ | Et | (−) |
| III-648 | Me | Et | Me | NH | Ph | C(Me)₂CH₂ | Et | racemic |
| III-649 | Me | Et | Me | NH | Ph | C(Me)₂CH₂ | Et | (+) |
| III-650 | Me | Et | Me | NH | Ph | C(Me)₂CH₂ | Et | (−) |

TABLE 50

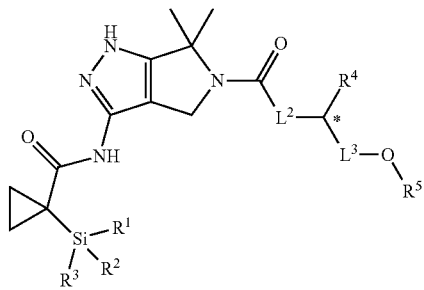

(III)

| Compound No. | R¹ | R² | R³ | L² | R⁴ | L³ | R⁵ | Configuration |
|---|---|---|---|---|---|---|---|---|
| III-651 | Me | Me | Me | NH | Ph | C(Me)₂CH₂ | iPr | racemic |
| III-652 | Me | Me | Me | NH | Ph | C(Me)₂CH₂ | iPr | (+) |
| III-653 | Me | Me | Me | NH | Ph | C(Me)₂CH₂ | iPr | (−) |
| III-654 | Me | Et | Me | NH | Ph | C(Me)₂CH₂ | iPr | racemic |
| III-655 | Me | Et | Me | NH | Ph | C(Me)₂CH₂ | iPr | (+) |
| III-656 | Me | Et | Me | NH | Ph | C(Me)₂CH₂ | iPr | (−) |
| III-657 | Me | Me | Me | NH | Ph | C(Me)₂CH₂ | cPr | racemic |
| III-658 | Me | Me | Me | NH | Ph | C(Me)₂CH₂ | cPr | (+) |
| III-659 | Me | Me | Me | NH | Ph | C(Me)₂CH₂ | cPr | (−) |
| III-660 | Me | Et | Me | NH | Ph | C(Me)₂CH₂ | cPr | racemic |
| III-661 | Me | Et | Me | NH | Ph | C(Me)₂CH₂ | cPr | (+) |
| III-662 | Me | Et | Me | NH | Ph | C(Me)₂CH₂ | cPr | (−) |
| III-663 | Me | Me | Me | NH | Ph | 1,1-Cyclopropylene-CH₂ | H | racemic |
| III-664 | Me | Me | Me | NH | Ph | 1,1-Cyclopropylene-CH₂ | H | (+) |
| III-665 | Me | Me | Me | NH | Ph | 1,1-Cyclopropylene-CH₂ | H | (−) |
| III-666 | Me | Et | Me | NH | Ph | 1,1-Cyclopropylene-CH₂ | H | racemic |
| III-667 | Me | Et | Me | NH | Ph | 1,1-Cyclopropylene-CH₂ | H | (+) |
| III-668 | Me | Et | Me | NH | Ph | 1,1-Cyclopropylene-CH₂ | H | (−) |

TABLE 50-continued

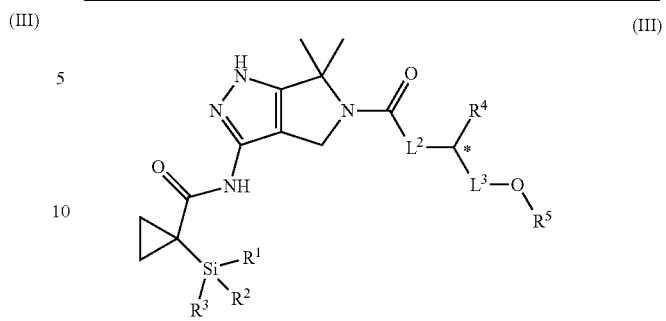

(III)

| Compound No. | R¹ | R² | R³ | L² | R⁴ | L³ | R⁵ | Configuration |
|---|---|---|---|---|---|---|---|---|
| III-669 | Me | Me | Me | NH | Ph | 1,1-Cyclopropylene-CH₂ | Me | racemic |
| III-670 | Me | Me | Me | NH | Ph | 1,1-Cyclopropylene-CH₂ | Me | (+) |
| III-671 | Me | Me | Me | NH | Ph | 1,1-Cyclopropylene-CH₂ | Me | (−) |
| III-672 | Me | Et | Me | NH | Ph | 1,1-Cyclopropylene-CH₂ | Me | racemic |
| III-673 | Me | Et | Me | NH | Ph | 1,1-Cyclopropylene-CH₂ | Me | (+) |
| III-674 | Me | Et | Me | NH | Ph | 1,1-Cyclopropylene-CH₂ | Me | (−) |
| III-675 | Me | Me | Me | NH | Ph | 1,1-Cyclobutylene-CH₂ | H | racemic |
| III-676 | Me | Me | Me | NH | Ph | 1,1-Cyclobutylene-CH₂ | H | (+) |
| III-677 | Me | Me | Me | NH | Ph | 1,1-Cyclobutylene-CH₂ | H | (−) |
| III-678 | Me | Et | Me | NH | Ph | 1,1-Cyclobutylene-CH₂ | H | racemic |
| III-679 | Me | Et | Me | NH | Ph | 1,1-Cyclobutylene-CH₂ | H | (+) |
| III-680 | Me | Et | Me | NH | Ph | 1,1-Cyclobutylene-CH₂ | H | (−) |
| III-681 | Me | Me | Me | NH | Ph | 1,1-Cyclobutylene-CH₂ | Me | racemic |
| III-682 | Me | Me | Me | NH | Ph | 1,1-Cyclobutylene-CH₂ | Me | (+) |
| III-683 | Me | Me | Me | NH | Ph | 1,1-Cyclobutylene-CH₂ | Me | (−) |
| III-684 | Me | Et | Me | NH | Ph | 1,1-Cyclobutylene-CH₂ | Me | racemic |
| III-685 | Me | Et | Me | NH | Ph | 1,1-Cyclobutylene-CH₂ | Me | (+) |
| III-686 | Me | Et | Me | NH | Ph | 1,1-Cyclobutylene-CH₂ | Me | (−) |
| III-687 | Me | Me | Me | NH | Ph | C(Et)₂CH₂ | H | racemic |
| III-688 | Me | Me | Me | NH | Ph | C(Et)₂CH₂ | H | (+) |
| III-689 | Me | Me | Me | NH | Ph | C(Et)₂CH₂ | H | (−) |
| III-690 | Me | Et | Me | NH | Ph | C(Et)₂CH₂ | H | racemic |
| III-691 | Me | Et | Me | NH | Ph | C(Et)₂CH₂ | H | (+) |
| III-692 | Me | Et | Me | NH | Ph | C(Et)₂CH₂ | H | (−) |
| III-693 | Me | Me | Me | NH | Ph | C(Et)₂CH₂ | Me | racemic |
| III-694 | Me | Me | Me | NH | Ph | C(Et)₂CH₂ | Me | (+) |
| III-695 | Me | Me | Me | NH | Ph | C(Et)₂CH₂ | Me | (−) |
| III-696 | Me | Et | Me | NH | Ph | C(Et)₂CH₂ | Me | racemic |
| III-697 | Me | Et | Me | NH | Ph | C(Et)₂CH₂ | Me | (+) |
| III-698 | Me | Et | Me | NH | Ph | C(Et)₂CH₂ | Me | (−) |
| III-699 | Me | Me | Me | NH | Ph | CH₂-1,1-Cyclopropylene | H | racemic |
| III-700 | Me | Me | Me | NH | Ph | CH₂-1,1-Cyclopropylene | H | (R)- |

TABLE 51

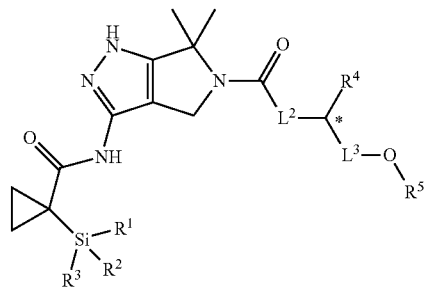

(III)

| Compound No. | R¹ | R² | R³ | L² | R⁴ | L³ | R⁵ | Configuration |
|---|---|---|---|---|---|---|---|---|
| III-701 | Me | Et | Me | NH | Ph | CH₂-1,1-Cyclopropylene | H | racemic |
| III-702 | Me | Et | Me | NH | Ph | CH₂-1,1-Cyclopropylene | H | (R)- |
| III-703 | Me | Me | Me | NH | Ph | CH₂-1,1-Cyclopropylene | Me | racemic |
| III-704 | Me | Me | Me | NH | Ph | CH₂-1,1-Cyclopropylene | Me | (R)- |
| III-705 | Me | Et | Me | NH | Ph | CH₂-1,1-Cyclopropylene | Me | racemic |
| III-706 | Me | Et | Me | NH | Ph | CH₂-1,1-Cyclopropylene | Me | (R)- |
| III-707 | Me | Me | Me | NH | Ph | CH₂-1,1-cyclobutylene | H | racemic |
| III-708 | Me | Me | Me | NH | Ph | CH₂-1,1-cyclobutylene | H | (R)- |
| III-709 | Me | Et | Me | NH | Ph | CH₂-1,1-cyclobutylene | H | racemic |
| III-710 | Me | Et | Me | NH | Ph | CH₂-1,1-cyclobutylene | H | (R)- |
| III-711 | Me | Me | Me | NH | Ph | CH₂-1,1-cyclobutylene | Me | racemic |
| III-712 | Me | Me | Me | NH | Ph | CH₂-1,1-cyclobutylene | Me | (R)- |
| III-713 | Me | Et | Me | NH | Ph | CH₂-1,1-cyclobutylene | Me | racemic |
| III-714 | Me | Et | Me | NH | Ph | CH₂-1,1-cyclobutylene | Me | (R)- |
| III-715 | Me | Me | Me | NH | Ph | CH₂C(Et)₂ | H | racemic |
| III-716 | Me | Me | Me | NH | Ph | CH₂C(Et)₂ | H | (R)- |
| III-717 | Me | Et | Me | NH | Ph | CH₂C(Et)₂ | H | racemic |
| III-718 | Me | Et | Me | NH | Ph | CH₂C(Et)₂ | H | (R)- |
| III-719 | Me | Me | Me | NH | Ph | CH₂C(Et)₂ | Me | racemic |
| III-720 | Me | Me | Me | NH | Ph | CH₂C(Et)₂ | Me | (R)- |
| III-721 | Me | Et | Me | NH | Ph | CH₂C(Et)₂ | Me | racemic |
| III-722 | Me | Et | Me | NH | Ph | CH₂C(Et)₂ | Me | (R)- |
| III-723 | Me | Me | Me | NH | iPr | CH₂ | Me | racemic |
| III-724 | Me | Me | Me | NH | iPr | CH₂ | Me | (S)- |
| III-725 | Me | Et | Me | NH | iPr | CH₂ | Me | racemic |
| III-726 | Me | Et | Me | NH | iPr | CH₂ | Me | (S)- |
| III-727 | Me | Me | Me | NH | iPr | (CH₂)₂ | H | racemic |
| III-728 | Me | Me | Me | NH | iPr | (CH₂)₂ | H | (R)- |
| III-729 | Me | Et | Me | NH | iPr | (CH₂)₂ | H | racemic |
| III-730 | Me | Et | Me | NH | iPr | (CH₂)₂ | H | (R)- |
| III-731 | Me | Me | Me | NH | iPr | (CH₂)₂ | Me | racemic |
| III-732 | Me | Me | Me | NH | iPr | (CH₂)₂ | Me | (R)- |
| III-733 | Me | Et | Me | NH | iPr | (CH₂)₂ | Me | racemic |
| III-734 | Me | Et | Me | NH | iPr | (CH₂)₂ | Me | (R)- |
| III-735 | Me | Me | Me | NH | CF₃ | CH₂ | H | racemic |
| III-736 | Me | Me | Me | NH | CF₃ | CH₂ | H | (S)- |
| III-737 | Me | Et | Me | NH | CF₃ | CH₂ | H | racemic |
| III-738 | Me | Et | Me | NH | CF₃ | CH₂ | H | (S)- |
| III-739 | Me | Me | Me | NH | CH₂OH | CH₂ | H | |
| III-740 | Me | Et | Me | NH | CH₂OH | CH₂ | H | |
| III-741 | Me | Me | Me | NH | CH₂OMe | CH₂ | H | racemic |
| III-742 | Me | Me | Me | NH | CH₂OMe | CH₂ | H | (R)- |
| III-743 | Me | Et | Me | NH | CH₂OMe | CH₂ | H | racemic |
| III-744 | Me | Et | Me | NH | CH₂OMe | CH₂ | H | (R)- |
| III-745 | Me | Me | Me | NH | CH₂Ph | CH₂ | H | racemic |
| III-746 | Me | Me | Me | NH | CH₂Ph | CH₂ | H | (R)- |

TABLE 51-continued

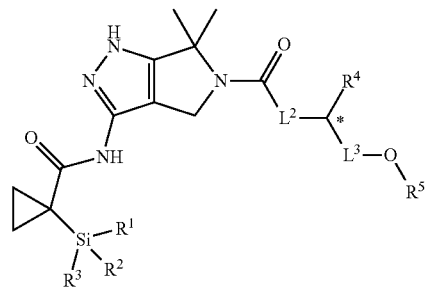

(III)

| Compound No. | R¹ | R² | R³ | L² | R⁴ | L³ | R⁵ | Configuration |
|---|---|---|---|---|---|---|---|---|
| III-747 | Me | Me | Me | NH | CH₂Ph | CH₂ | H | (S)- |
| III-748 | Me | Et | Me | NH | CH₂Ph | CH₂ | H | racemic |
| III-749 | Me | Et | Me | NH | CH₂Ph | CH₂ | H | (S)- |
| III-750 | Me | Me | Me | NH | 2-F—Ph | CH₂ | Me | racemic |

TABLE 52

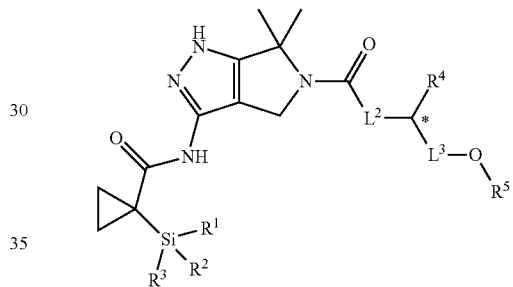

(III)

| Compound No. | R¹ | R² | R³ | L² | R⁴ | L³ | R⁵ | Configuration |
|---|---|---|---|---|---|---|---|---|
| III-751 | Me | Me | Me | NH | 2-F—Ph | CH₂ | Me | (S)- |
| III-752 | Me | Et | Me | NH | 2-F—Ph | CH₂ | Me | racemic |
| III-753 | Me | Et | Me | NH | 2-F—Ph | CH₂ | Me | (S)- |
| III-754 | Me | Me | Me | NH | 2-F—Ph | (CH₂)₂ | H | racemic |
| III-755 | Me | Me | Me | NH | 2-F—Ph | (CH₂)₂ | H | (R)- |
| III-756 | Me | Et | Me | NH | 2-F—Ph | (CH₂)₂ | H | racemic |
| III-757 | Me | Et | Me | NH | 2-F—Ph | (CH₂)₂ | H | (R)- |
| III-758 | Me | Me | Me | NH | 2-F—Ph | (CH₂)₂ | Me | racemic |
| III-759 | Me | Me | Me | NH | 2-F—Ph | (CH₂)₂ | Me | (R)- |
| III-760 | Me | Et | Me | NH | 2-F—Ph | (CH₂)₂ | Me | racemic |
| III-761 | Me | Et | Me | NH | 2-F—Ph | (CH₂)₂ | Me | (R)- |
| III-762 | Me | Me | Me | NH | 2-F—Ph | CH₂C(Me)₂ | H | racemic |
| III-763 | Me | Me | Me | NH | 2-F—Ph | CH₂C(Me)₂ | H | (R)- |
| III-764 | Me | Et | Me | NH | 2-F—Ph | CH₂C(Me)₂ | H | racemic |
| III-765 | Me | Et | Me | NH | 2-F—Ph | CH₂C(Me)₂ | H | (R)- |
| III-766 | Me | Me | Me | NH | 2-F—Ph | CH₂C(Me)₂ | Me | racemic |
| III-767 | Me | Me | Me | NH | 2-F—Ph | CH₂C(Me)₂ | Me | (R)- |
| III-768 | Me | Et | Me | NH | 2-F—Ph | CH₂C(Me)₂ | Me | racemic |
| III-769 | Me | Et | Me | NH | 2-F—Ph | CH₂C(Me)₂ | Me | (R)- |
| III-770 | Me | Me | Me | NH | 2-F—Ph | C(Me)₂CH₂ | H | racemic |
| III-771 | Me | Me | Me | NH | 2-F—Ph | C(Me)₂CH₂ | H | (+) |
| III-772 | Me | Me | Me | NH | 2-F—Ph | C(Me)₂CH₂ | H | (−) |
| III-773 | Me | Et | Me | NH | 2-F—Ph | C(Me)₂CH₂ | H | racemic |
| III-774 | Me | Et | Me | NH | 2-F—Ph | C(Me)₂CH₂ | H | (+) |
| III-775 | Me | Et | Me | NH | 2-F—Ph | C(Me)₂CH₂ | H | (−) |
| III-776 | Me | Me | Me | NH | 2-F—Ph | C(Me)₂CH₂ | Me | racemic |
| III-777 | Me | Me | Me | NH | 2-F—Ph | C(Me)₂CH₂ | Me | (+) |
| III-778 | Me | Me | Me | NH | 2-F—Ph | C(Me)₂CH₂ | Me | (−) |
| III-779 | Me | Et | Me | NH | 2-F—Ph | C(Me)₂CH₂ | Me | racemic |
| III-780 | Me | Et | Me | NH | 2-F—Ph | C(Me)₂CH₂ | Me | (+) |
| III-781 | Me | Et | Me | NH | 2-F—Ph | C(Me)₂CH₂ | Me | (−) |
| III-782 | Me | Me | Me | NH | 3-F—Ph | (CH₂)₂ | H | racemic |
| III-783 | Me | Me | Me | NH | 3-F—Ph | (CH₂)₂ | H | (R)- |

TABLE 52-continued

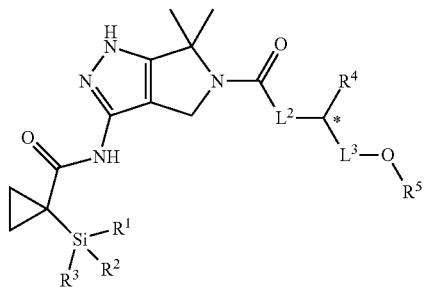
(III)

| Compound No. | R¹ | R² | R³ | L² | R⁴ | L³ | R⁵ | Configuration |
|---|---|---|---|---|---|---|---|---|
| III-784 | Me | Et | Me | NH | 3-F—Ph | (CH₂)₂ | H | racemic |
| III-785 | Me | Et | Me | NH | 3-F—Ph | (CH₂)₂ | H | (R)- |
| III-786 | Me | Me | Me | NH | 3-F—Ph | (CH₂)₂ | Me | racemic |
| III-787 | Me | Me | Me | NH | 3-F—Ph | (CH₂)₂ | Me | (R)- |
| III-788 | Me | Et | Me | NH | 3-F—Ph | (CH₂)₂ | Me | racemic |
| III-789 | Me | Et | Me | NH | 3-F—Ph | (CH₂)₂ | Me | (R)- |
| III-790 | Me | Me | Me | NH | 3-F—Ph | CH₂C(Me)₂ | H | racemic |
| III-791 | Me | Me | Me | NH | 3-F—Ph | CH₂C(Me)₂ | H | (R)- |
| III-792 | Me | Et | Me | NH | 3-F—Ph | CH₂C(Me)₂ | H | racemic |
| III-793 | Me | Et | Me | NH | 3-F—Ph | CH₂C(Me)₂ | H | (R)- |
| III-794 | Me | Me | Me | NH | 3-F—Ph | CH₂C(Me)₂ | Me | racemic |
| III-795 | Me | Me | Me | NH | 3-F—Ph | CH₂C(Me)₂ | Me | (R)- |
| III-796 | Me | Et | Me | NH | 3-F—Ph | CH₂C(Me)₂ | Me | racemic |
| III-797 | Me | Et | Me | NH | 3-F—Ph | CH₂C(Me)₂ | Me | (R)- |
| III-798 | Me | Me | Me | NH | 3-F—Ph | C(Me)₂CH₂ | H | racemic |
| III-799 | Me | Me | Me | NH | 3-F—Ph | C(Me)₂CH₂ | H | (+) |
| III-800 | Me | Me | Me | NH | 3-F—Ph | C(Me)₂CH₂ | H | (−) |

TABLE 53

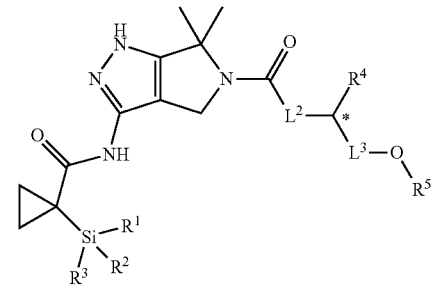
(III)

| Compound No. | R¹ | R² | R³ | L² | R⁴ | L³ | R⁵ | Configuration |
|---|---|---|---|---|---|---|---|---|
| III-801 | Me | Et | Me | NH | 3-F—Ph | C(Me)₂CH₂ | H | racemic |
| III-802 | Me | Et | Me | NH | 3-F—Ph | C(Me)₂CH₂ | H | (+) |
| III-803 | Me | Et | Me | NH | 3-F—Ph | C(Me)₂CH₂ | H | (−) |
| III-804 | Me | Me | Me | NH | 3-F—Ph | C(Me)₂CH₂ | Me | racemic |
| III-805 | Me | Me | Me | NH | 3-F—Ph | C(Me)₂CH₂ | Me | (+) |
| III-806 | Me | Me | Me | NH | 3-F—Ph | C(Me)₂CH₂ | Me | (−) |
| III-807 | Me | Et | Me | NH | 3-F—Ph | C(Me)₂CH₂ | Me | racemic |
| III-808 | Me | Et | Me | NH | 3-F—Ph | C(Me)₂CH₂ | Me | (+) |
| III-809 | Me | Et | Me | NH | 3-F—Ph | C(Me)₂CH₂ | Me | (−) |
| III-810 | Me | Me | Me | NH | 4-F—Ph | (CH₂)₂ | H | racemic |
| III-811 | Me | Me | Me | NH | 4-F—Ph | (CH₂)₂ | H | (R)- |
| III-812 | Me | Et | Me | NH | 4-F—Ph | (CH₂)₂ | H | racemic |
| III-813 | Me | Et | Me | NH | 4-F—Ph | (CH₂)₂ | H | (R)- |
| III-814 | Me | Me | Me | NH | 4-F—Ph | (CH₂)₂ | Me | racemic |
| III-815 | Me | Me | Me | NH | 4-F—Ph | (CH₂)₂ | Me | (R)- |
| III-816 | Me | Et | Me | NH | 4-F—Ph | (CH₂)₂ | Me | racemic |
| III-817 | Me | Et | Me | NH | 4-F—Ph | (CH₂)₂ | Me | (R)- |
| III-818 | Me | Me | Me | NH | 4-F—Ph | CH₂C(Me)₂ | H | racemic |
| III-819 | Me | Me | Me | NH | 4-F—Ph | CH₂C(Me)₂ | H | (R)- |
| III-820 | Me | Et | Me | NH | 4-F—Ph | CH₂C(Me)₂ | H | racemic |
| III-821 | Me | Et | Me | NH | 4-F—Ph | CH₂C(Me)₂ | H | (R)- |

TABLE 53-continued

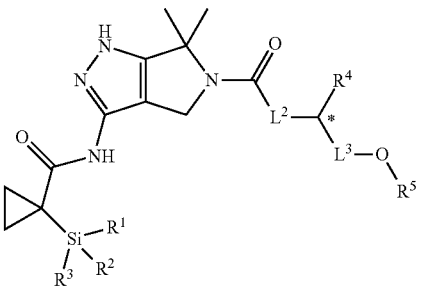
(III)

| Compound No. | R¹ | R² | R³ | L² | R⁴ | L³ | R⁵ | Configuration |
|---|---|---|---|---|---|---|---|---|
| III-822 | Me | Me | Me | NH | 4-F—Ph | CH₂C(Me)₂ | Me | racemic |
| III-823 | Me | Me | Me | NH | 4-F—Ph | CH₂C(Me)₂ | Me | (R)- |
| III-824 | Me | Et | Me | NH | 4-F—Ph | CH₂C(Me)₂ | Me | racemic |
| III-825 | Me | Et | Me | NH | 4-F—Ph | CH₂C(Me)₂ | Me | (R)- |
| III-826 | Me | Me | Me | NH | 4-F—Ph | C(Me)₂CH₂ | H | racemic |
| III-827 | Me | Me | Me | NH | 4-F—Ph | C(Me)₂CH₂ | H | (+) |
| III-828 | Me | Me | Me | NH | 4-F—Ph | C(Me)₂CH₂ | H | (−) |
| III-829 | Me | Et | Me | NH | 4-F—Ph | C(Me)₂CH₂ | H | racemic |
| III-830 | Me | Et | Me | NH | 4-F—Ph | C(Me)₂CH₂ | H | (+) |
| III-831 | Me | Et | Me | NH | 4-F—Ph | C(Me)₂CH₂ | H | (−) |
| III-832 | Me | Me | Me | NH | 4-F—Ph | C(Me)₂CH₂ | Me | racemic |
| III-833 | Me | Me | Me | NH | 4-F—Ph | C(Me)₂CH₂ | Me | (+) |
| III-834 | Me | Me | Me | NH | 4-F—Ph | C(Me)₂CH₂ | Me | (−) |
| III-835 | Me | Et | Me | NH | 4-F—Ph | C(Me)₂CH₂ | Me | racemic |
| III-836 | Me | Et | Me | NH | 4-F—Ph | C(Me)₂CH₂ | Me | (+) |
| III-837 | Me | Et | Me | NH | 4-F—Ph | C(Me)₂CH₂ | Me | (−) |
| III-838 | Me | Me | Me | NH | 2-Cl—Ph | CH₂ | H | racemic |
| III-839 | Me | Me | Me | NH | 2-Cl—Ph | CH₂ | H | (S)- |
| III-840 | Me | Et | Me | NH | 2-Cl—Ph | CH₂ | H | racemic |
| III-841 | Me | Et | Me | NH | 2-Cl—Ph | CH₂ | H | (S)- |
| III-842 | Me | Me | Me | NH | 2-Cl—Ph | CH₂ | Me | racemic |
| III-843 | Me | Me | Me | NH | 2-Cl—Ph | CH₂ | Me | (S)- |
| III-844 | Me | Et | Me | NH | 2-Cl—Ph | CH₂ | Me | racemic |
| III-845 | Me | Et | Me | NH | 2-Cl—Ph | CH₂ | Me | (S)- |
| III-846 | Me | Me | Me | NH | 2-Cl—Ph | (CH₂)₂ | H | racemic |
| III-847 | Me | Me | Me | NH | 2-Cl—Ph | (CH₂)₂ | H | (R)- |
| III-848 | Me | Et | Me | NH | 2-Cl—Ph | (CH₂)₂ | H | racemic |
| III-849 | Me | Et | Me | NH | 2-Cl—Ph | (CH₂)₂ | H | (R)- |
| III-850 | Me | Me | Me | NH | 2-Cl—Ph | (CH₂)₂ | Me | racemic |

TABLE 54

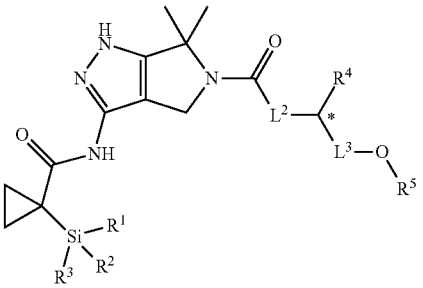
(III)

| Compound No. | R¹ | R² | R³ | L² | R⁴ | L³ | R⁵ | Configuration |
|---|---|---|---|---|---|---|---|---|
| III-851 | Me | Me | Me | NH | 2-Cl—Ph | (CH₂)₂ | Me | (R)- |
| III-852 | Me | Et | Me | NH | 2-Cl—Ph | (CH₂)₂ | Me | racemic |
| III-853 | Me | Et | Me | NH | 2-Cl—Ph | (CH₂)₂ | Me | (R)- |
| III-854 | Me | Me | Me | NH | 2-Cl—Ph | CH₂C(Me)₂ | H | racemic |
| III-855 | Me | Me | Me | NH | 2-Cl—Ph | CH₂C(Me)₂ | H | (R)- |
| III-856 | Me | Et | Me | NH | 2-Cl—Ph | CH₂C(Me)₂ | H | racemic |
| III-857 | Me | Et | Me | NH | 2-Cl—Ph | CH₂C(Me)₂ | H | (R)- |
| III-858 | Me | Me | Me | NH | 2-Cl—Ph | CH₂C(Me)₂ | Me | racemic |
| III-859 | Me | Me | Me | NH | 2-Cl—Ph | CH₂C(Me)₂ | Me | (R)- |

TABLE 54-continued (III)

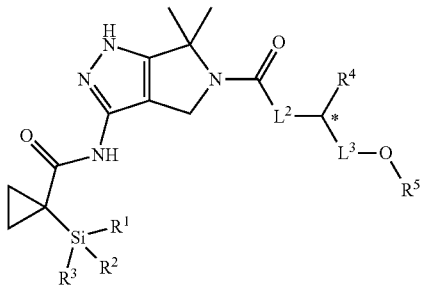

| Compound No. | R¹ | R² | R³ | L² | R⁴ | L³ | R⁵ | Configuration |
|---|---|---|---|---|---|---|---|---|
| III-860 | Me | Et | Me | NH | 2-Cl—Ph | CH₂C(Me)₂ | Me | racemic |
| III-861 | Me | Et | Me | NH | 2-Cl—Ph | CH₂C(Me)₂ | Me | (R)- |
| III-862 | Me | Me | Me | NH | 2-Cl—Ph | C(Me)₂CH₂ | H | racemic |
| III-863 | Me | Me | Me | NH | 2-Cl—Ph | C(Me)₂CH₂ | H | (+) |
| III-864 | Me | Me | Me | NH | 2-Cl—Ph | C(Me)₂CH₂ | H | (−) |
| III-865 | Me | Et | Me | NH | 2-Cl—Ph | C(Me)₂CH₂ | H | racemic |
| III-866 | Me | Et | Me | NH | 2-Cl—Ph | C(Me)₂CH₂ | H | (+) |
| III-867 | Me | Et | Me | NH | 2-Cl—Ph | C(Me)₂CH₂ | H | (−) |
| III-868 | Me | Me | Me | NH | 2-Cl—Ph | C(Me)₂CH₂ | Me | racemic |
| III-869 | Me | Me | Me | NH | 2-Cl—Ph | C(Me)₂CH₂ | Me | (+) |
| III-870 | Me | Me | Me | NH | 2-Cl—Ph | C(Me)₂CH₂ | Me | (−) |
| III-871 | Me | Et | Me | NH | 2-Cl—Ph | C(Me)₂CH₂ | Me | racemic |
| III-872 | Me | Et | Me | NH | 2-Cl—Ph | C(Me)₂CH₂ | Me | (+) |
| III-873 | Me | Et | Me | NH | 2-Cl—Ph | C(Me)₂CH₂ | Me | (−) |
| III-874 | Me | Me | Me | NH | 3-Cl—Ph | CH₂ | H | racemic |
| III-875 | Me | Me | Me | NH | 3-Cl—Ph | CH₂ | H | (S)- |
| III-876 | Me | Et | Me | NH | 3-Cl—Ph | CH₂ | H | racemic |
| III-877 | Me | Et | Me | NH | 3-Cl—Ph | CH₂ | H | (S)- |
| III-878 | Me | Me | Me | NH | 3-Cl—Ph | CH₂ | Me | racemic |
| III-879 | Me | Me | Me | NH | 3-Cl—Ph | CH₂ | Me | (S)- |
| III-880 | Me | Et | Me | NH | 3-Cl—Ph | CH₂ | Me | racemic |
| III-881 | Me | Et | Me | NH | 3-Cl—Ph | CH₂ | Me | (S)- |
| III-882 | Me | Me | Me | NH | 3-Cl—Ph | (CH₂)₂ | H | racemic |
| III-883 | Me | Me | Me | NH | 3-Cl—Ph | (CH₂)₂ | H | (R)- |
| III-884 | Me | Et | Me | NH | 3-Cl—Ph | (CH₂)₂ | H | racemic |
| III-885 | Me | Et | Me | NH | 3-Cl—Ph | (CH₂)₂ | H | (R)- |
| III-886 | Me | Me | Me | NH | 3-Cl—Ph | (CH₂)₂ | Me | racemic |
| III-887 | Me | Me | Me | NH | 3-Cl—Ph | (CH₂)₂ | Me | (R)- |
| III-888 | Me | Et | Me | NH | 3-Cl—Ph | (CH₂)₂ | Me | racemic |
| III-889 | Me | Et | Me | NH | 3-Cl—Ph | (CH₂)₂ | Me | (R)- |
| III-890 | Me | Me | Me | NH | 3-Cl—Ph | CH₂C(Me)₂ | H | racemic |
| III-891 | Me | Me | Me | NH | 3-Cl—Ph | CH₂C(Me)₂ | H | (R)- |
| III-892 | Me | Et | Me | NH | 3-Cl—Ph | CH₂C(Me)₂ | H | racemic |
| III-893 | Me | Et | Me | NH | 3-Cl—Ph | CH₂C(Me)₂ | H | (R)- |
| III-894 | Me | Me | Me | NH | 3-Cl—Ph | CH₂C(Me)₂ | Me | racemic |
| III-895 | Me | Me | Me | NH | 3-Cl—Ph | CH₂C(Me)₂ | Me | (R)- |
| III-896 | Me | Et | Me | NH | 3-Cl—Ph | CH₂C(Me)₂ | Me | racemic |
| III-897 | Me | Et | Me | NH | 3-Cl—Ph | CH₂C(Me)₂ | Me | (R)- |
| III-898 | Me | Me | Me | NH | 3-Cl—Ph | C(Me)₂CH₂ | H | racemic |
| III-899 | Me | Me | Me | NH | 3-Cl—Ph | C(Me)₂CH₂ | H | (+) |
| III-900 | Me | Me | Me | NH | 3-Cl—Ph | C(Me)₂CH₂ | H | (−) |

TABLE 55

(III)

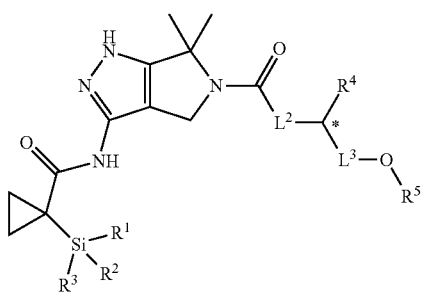

| Compound No. | R¹ | R² | R³ | L² | R⁴ | L³ | R⁵ | Configuration |
|---|---|---|---|---|---|---|---|---|
| III-901 | Me | Et | Me | NH | 3-Cl—Ph | C(Me)₂CH₂ | H | racemic |
| III-902 | Me | Et | Me | NH | 3-Cl—Ph | C(Me)₂CH₂ | H | (+) |
| III-903 | Me | Et | Me | NH | 3-Cl—Ph | C(Me)₂CH₂ | H | (−) |
| III-904 | Me | Me | Me | NH | 3-Cl—Ph | C(Me)₂CH₂ | Me | racemic |
| III-905 | Me | Me | Me | NH | 3-Cl—Ph | C(Me)₂CH₂ | Me | (+) |
| III-906 | Me | Me | Me | NH | 3-Cl—Ph | C(Me)₂CH₂ | Me | (−) |
| III-907 | Me | Et | Me | NH | 3-Cl—Ph | C(Me)₂CH₂ | Me | racemic |
| III-908 | Me | Et | Me | NH | 3-Cl—Ph | C(Me)₂CH₂ | Me | (+) |
| III-909 | Me | Et | Me | NH | 3-Cl—Ph | C(Me)₂CH₂ | Me | (−) |
| III-910 | Me | Me | Me | NH | 4-Cl—Ph | CH₂ | H | racemic |
| III-911 | Me | Me | Me | NH | 4-Cl—Ph | CH₂ | H | (S)- |
| III-912 | Me | Et | Me | NH | 4-Cl—Ph | CH₂ | H | racemic |
| III-913 | Me | Et | Me | NH | 4-Cl—Ph | CH₂ | H | (S)- |
| III-914 | Me | Me | Me | NH | 4-Cl—Ph | CH₂ | Me | racemic |
| III-915 | Me | Me | Me | NH | 4-Cl—Ph | CH₂ | Me | (S)- |
| III-916 | Me | Et | Me | NH | 4-Cl—Ph | CH₂ | Me | racemic |
| III-917 | Me | Et | Me | NH | 4-Cl—Ph | CH₂ | Me | (S)- |
| III-918 | Me | Me | Me | NH | 4-Cl—Ph | (CH₂)₂ | H | racemic |
| III-919 | Me | Me | Me | NH | 4-Cl—Ph | (CH₂)₂ | H | (R)- |
| III-920 | Me | Et | Me | NH | 4-Cl—Ph | (CH₂)₂ | H | racemic |
| III-921 | Me | Et | Me | NH | 4-Cl—Ph | (CH₂)₂ | H | (R)- |
| III-922 | Me | Me | Me | NH | 4-Cl—Ph | (CH₂)₂ | Me | racemic |
| III-923 | Me | Me | Me | NH | 4-Cl—Ph | (CH₂)₂ | Me | (R)- |
| III-924 | Me | Et | Me | NH | 4-Cl—Ph | (CH₂)₂ | Me | racemic |
| III-925 | Me | Et | Me | NH | 4-Cl—Ph | (CH₂)₂ | Me | (R)- |
| III-926 | Me | Me | Me | NH | 4-Cl—Ph | CH₂C(Me)₂ | H | racemic |
| III-927 | Me | Me | Me | NH | 4-Cl—Ph | CH₂C(Me)₂ | H | (R)- |
| III-928 | Me | Et | Me | NH | 4-Cl—Ph | CH₂C(Me)₂ | H | racemic |
| III-929 | Me | Et | Me | NH | 4-Cl—Ph | CH₂C(Me)₂ | H | (R)- |
| III-930 | Me | Me | Me | NH | 4-Cl—Ph | CH₂C(Me)₂ | Me | racemic |
| III-931 | Me | Me | Me | NH | 4-Cl—Ph | CH₂C(Me)₂ | Me | (R)- |
| III-932 | Me | Et | Me | NH | 4-Cl—Ph | CH₂C(Me)₂ | Me | racemic |
| III-933 | Me | Et | Me | NH | 4-Cl—Ph | CH₂C(Me)₂ | Me | (R)- |
| III-934 | Me | Me | Me | NH | 4-Cl—Ph | C(Me)₂CH₂ | H | racemic |
| III-935 | Me | Me | Me | NH | 4-Cl—Ph | C(Me)₂CH₂ | H | (+) |
| III-936 | Me | Me | Me | NH | 4-Cl—Ph | C(Me)₂CH₂ | H | (−) |
| III-937 | Me | Et | Me | NH | 4-Cl—Ph | C(Me)₂CH₂ | H | racemic |
| III-938 | Me | Et | Me | NH | 4-Cl—Ph | C(Me)₂CH₂ | H | (+) |
| III-939 | Me | Et | Me | NH | 4-Cl—Ph | C(Me)₂CH₂ | H | (−) |
| III-940 | Me | Me | Me | NH | 4-Cl—Ph | C(Me)₂CH₂ | Me | racemic |
| III-941 | Me | Me | Me | NH | 4-Cl—Ph | C(Me)₂CH₂ | Me | (+) |
| III-942 | Me | Me | Me | NH | 4-Cl—Ph | C(Me)₂CH₂ | Me | (−) |
| III-943 | Me | Et | Me | NH | 4-Cl—Ph | C(Me)₂CH₂ | Me | racemic |
| III-944 | Me | Et | Me | NH | 4-Cl—Ph | C(Me)₂CH₂ | Me | (+) |
| III-945 | Me | Et | Me | NH | 4-Cl—Ph | C(Me)₂CH₂ | Me | (−) |
| III-946 | Me | Me | Me | NH | 2-Me—Ph | CH₂ | H | racemic |
| III-947 | Me | Me | Me | NH | 2-Me—Ph | CH₂ | H | (S)- |
| III-948 | Me | Et | Me | NH | 2-Me—Ph | CH₂ | H | racemic |
| III-949 | Me | Et | Me | NH | 2-Me—Ph | CH₂ | H | (S)- |
| III-950 | Me | Me | Me | NH | 2-Me—Ph | CH₂ | Me | racemic |

TABLE 56

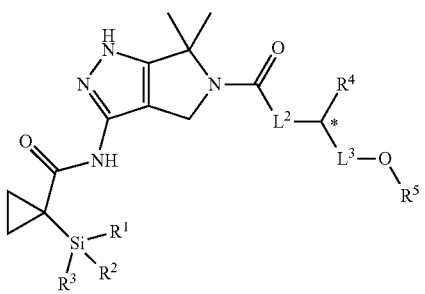

(III)

| Compound No. | R¹ | R² | R³ | L² | R⁴ | L³ | R⁵ | Configuration |
|---|---|---|---|---|---|---|---|---|
| III-951 | Me | Me | Me | NH | 2-Me—Ph | CH₂ | Me | (S)- |
| III-952 | Me | Et | Me | NH | 2-Me—Ph | CH₂ | Me | racemic |
| III-953 | Me | Et | Me | NH | 2-Me—Ph | CH₂ | Me | (S)- |
| III-954 | Me | Me | Me | NH | 2-Me—Ph | (CH₂)₂ | H | racemic |
| III-955 | Me | Me | Me | NH | 2-Me—Ph | (CH₂)₂ | H | (R)- |
| III-956 | Me | Et | Me | NH | 2-Me—Ph | (CH₂)₂ | H | racemic |
| III-957 | Me | Et | Me | NH | 2-Me—Ph | (CH₂)₂ | H | (R)- |
| III-958 | Me | Me | Me | NH | 2-Me—Ph | (CH₂)₂ | Me | racemic |
| III-959 | Me | Me | Me | NH | 2-Me—Ph | (CH₂)₂ | Me | (R)- |
| III-960 | Me | Et | Me | NH | 2-Me—Ph | (CH₂)₂ | Me | racemic |
| III-961 | Me | Et | Me | NH | 2-Me—Ph | (CH₂)₂ | Me | (R)- |
| III-962 | Me | Me | Me | NH | 2-Me—Ph | CH₂C(Me)₂ | H | racemic |
| III-963 | Me | Me | Me | NH | 2-Me—Ph | CH₂C(Me)₂ | H | (R)- |
| III-964 | Me | Et | Me | NH | 2-Me—Ph | CH₂C(Me)₂ | H | racemic |
| III-965 | Me | Et | Me | NH | 2-Me—Ph | CH₂C(Me)₂ | H | (R)- |
| III-966 | Me | Me | Me | NH | 2-Me—Ph | CH₂C(Me)₂ | Me | racemic |
| III-967 | Me | Me | Me | NH | 2-Me—Ph | CH₂C(Me)₂ | Me | (R)- |
| III-968 | Me | Et | Me | NH | 2-Me—Ph | CH₂C(Me)₂ | Me | racemic |
| III-969 | Me | Et | Me | NH | 2-Me—Ph | CH₂C(Me)₂ | Me | (R)- |
| III-970 | Me | Me | Me | NH | 2-Me—Ph | C(Me)₂CH₂ | H | racemic |
| III-971 | Me | Me | Me | NH | 2-Me—Ph | C(Me)₂CH₂ | H | (+) |
| III-972 | Me | Me | Me | NH | 2-Me—Ph | C(Me)₂CH₂ | H | (−) |
| III-973 | Me | Et | Me | NH | 2-Me—Ph | C(Me)₂CH₂ | H | racemic |
| III-974 | Me | Et | Me | NH | 2-Me—Ph | C(Me)₂CH₂ | H | (+) |
| III-975 | Me | Et | Me | NH | 2-Me—Ph | C(Me)₂CH₂ | H | (−) |
| III-976 | Me | Me | Me | NH | 2-Me—Ph | C(Me)₂CH₂ | Me | racemic |
| III-977 | Me | Me | Me | NH | 2-Me—Ph | C(Me)₂CH₂ | Me | (+) |
| III-978 | Me | Me | Me | NH | 2-Me—Ph | C(Me)₂CH₂ | Me | (−) |
| III-979 | Me | Et | Me | NH | 2-Me—Ph | C(Me)₂CH₂ | Me | racemic |
| III-980 | Me | Et | Me | NH | 2-Me—Ph | C(Me)₂CH₂ | Me | (+) |
| III-981 | Me | Et | Me | NH | 2-Me—Ph | C(Me)₂CH₂ | Me | (−) |
| III-982 | Me | Me | Me | NH | 3-Me—Ph | CH₂ | H | racemic |
| III-983 | Me | Me | Me | NH | 3-Me—Ph | CH₂ | H | (S)- |
| III-984 | Me | Et | Me | NH | 3-Me—Ph | CH₂ | H | racemic |
| III-985 | Me | Et | Me | NH | 3-Me—Ph | CH₂ | H | (S)- |
| III-986 | Me | Me | Me | NH | 3-Me—Ph | CH₂ | Me | racemic |
| III-987 | Me | Me | Me | NH | 3-Me—Ph | CH₂ | Me | (S)- |
| III-988 | Me | Et | Me | NH | 3-Me—Ph | CH₂ | Me | racemic |
| III-989 | Me | Et | Me | NH | 3-Me—Ph | CH₂ | Me | (S)- |
| III-990 | Me | Me | Me | NH | 3-Me—Ph | (CH₂)₂ | H | racemic |
| III-991 | Me | Me | Me | NH | 3-Me—Ph | (CH₂)₂ | H | (R)- |
| III-992 | Me | Et | Me | NH | 3-Me—Ph | (CH₂)₂ | H | racemic |
| III-993 | Me | Et | Me | NH | 3-Me—Ph | (CH₂)₂ | H | (R)- |
| III-994 | Me | Me | Me | NH | 3-Me—Ph | (CH₂)₂ | Me | racemic |
| III-995 | Me | Me | Me | NH | 3-Me—Ph | (CH₂)₂ | Me | (R)- |
| III-996 | Me | Et | Me | NH | 3-Me—Ph | (CH₂)₂ | Me | racemic |
| III-997 | Me | Et | Me | NH | 3-Me—Ph | (CH₂)₂ | Me | (R)- |
| III-998 | Me | Me | Me | NH | 3-Me—Ph | CH₂C(Me)₂ | H | racemic |
| III-999 | Me | Me | Me | NH | 3-Me—Ph | CH₂C(Me)₂ | H | (R)- |
| III-1000 | Me | Et | Me | NH | 3-Me—Ph | CH₂C(Me)₂ | H | racemic |

TABLE 57

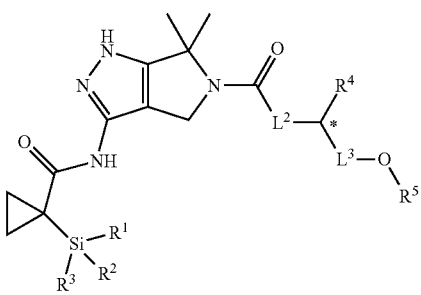

(III)

| Compound No. | R¹ | R² | R³ | L² | R⁴ | L³ | R⁵ | Configuration |
|---|---|---|---|---|---|---|---|---|
| III-1001 | Me | Et | Me | NH | 3-Me—Ph | CH₂C(Me)₂ | H | (R)- |
| III-1002 | Me | Me | Me | NH | 3-Me—Ph | CH₂C(Me)₂ | Me | racemic |
| III-1003 | Me | Me | Me | NH | 3-Me—Ph | CH₂C(Me)₂ | Me | (R)- |
| III-1004 | Me | Et | Me | NH | 3-Me—Ph | CH₂C(Me)₂ | Me | racemic |
| III-1005 | Me | Et | Me | NH | 3-Me—Ph | CH₂C(Me)₂ | Me | (R)- |
| III-1006 | Me | Me | Me | NH | 3-Me—Ph | C(Me)₂CH₂ | H | racemic |
| III-1007 | Me | Me | Me | NH | 3-Me—Ph | C(Me)₂CH₂ | H | (+) |
| III-1008 | Me | Me | Me | NH | 3-Me—Ph | C(Me)₂CH₂ | H | (−) |
| III-1009 | Me | Et | Me | NH | 3-Me—Ph | C(Me)₂CH₂ | H | racemic |
| III-1010 | Me | Et | Me | NH | 3-Me—Ph | C(Me)₂CH₂ | H | (+) |
| III-1011 | Me | Et | Me | NH | 3-Me—Ph | C(Me)₂CH₂ | H | (−) |
| III-1012 | Me | Me | Me | NH | 3-Me—Ph | C(Me)₂CH₂ | Me | racemic |
| III-1013 | Me | Me | Me | NH | 3-Me—Ph | C(Me)₂CH₂ | Me | (+) |
| III-1014 | Me | Me | Me | NH | 3-Me—Ph | C(Me)₂CH₂ | Me | (−) |
| III-1015 | Me | Et | Me | NH | 3-Me—Ph | C(Me)₂CH₂ | Me | racemic |
| III-1016 | Me | Et | Me | NH | 3-Me—Ph | C(Me)₂CH₂ | Me | (+) |
| III-1017 | Me | Et | Me | NH | 3-Me—Ph | C(Me)₂CH₂ | Me | (−) |
| III-1018 | Me | Me | Me | NH | 4-Me—Ph | CH₂ | H | racemic |
| III-1019 | Me | Me | Me | NH | 4-Me—Ph | CH₂ | H | (S)- |
| III-1020 | Me | Et | Me | NH | 4-Me—Ph | CH₂ | H | racemic |
| III-1021 | Me | Et | Me | NH | 4-Me—Ph | CH₂ | H | (S)- |
| III-1022 | Me | Me | Me | NH | 4-Me—Ph | CH₂ | Me | racemic |
| III-1023 | Me | Me | Me | NH | 4-Me—Ph | CH₂ | Me | (S)- |
| III-1024 | Me | Et | Me | NH | 4-Me—Ph | CH₂ | Me | racemic |
| III-1025 | Me | Et | Me | NH | 4-Me—Ph | CH₂ | Me | (S)- |
| III-1026 | Me | Me | Me | NH | 4-Me—Ph | (CH₂)₂ | H | racemic |
| III-1027 | Me | Me | Me | NH | 4-Me—Ph | (CH₂)₂ | H | (R)- |
| III-1028 | Me | Et | Me | NH | 4-Me—Ph | (CH₂)₂ | H | racemic |
| III-1029 | Me | Et | Me | NH | 4-Me—Ph | (CH₂)₂ | H | (R)- |
| III-1030 | Me | Me | Me | NH | 4-Me—Ph | (CH₂)₂ | Me | racemic |
| III-1031 | Me | Me | Me | NH | 4-Me—Ph | (CH₂)₂ | Me | (R)- |
| III-1032 | Me | Et | Me | NH | 4-Me—Ph | (CH₂)₂ | Me | racemic |
| III-1033 | Me | Et | Me | NH | 4-Me—Ph | (CH₂)₂ | Me | (R)- |
| III-1034 | Me | Me | Me | NH | 4-Me—Ph | CH₂C(Me)₂ | H | racemic |
| III-1035 | Me | Me | Me | NH | 4-Me—Ph | CH₂C(Me)₂ | H | (R)- |
| III-1036 | Me | Et | Me | NH | 4-Me—Ph | CH₂C(Me)₂ | H | racemic |
| III-1037 | Me | Et | Me | NH | 4-Me—Ph | CH₂C(Me)₂ | H | (R)- |
| III-1038 | Me | Me | Me | NH | 4-Me—Ph | CH₂C(Me)₂ | Me | racemic |
| III-1039 | Me | Me | Me | NH | 4-Me—Ph | CH₂C(Me)₂ | Me | (R)- |
| III-1040 | Me | Et | Me | NH | 4-Me—Ph | CH₂C(Me)₂ | Me | racemic |
| III-1041 | Me | Et | Me | NH | 4-Me—Ph | CH₂C(Me)₂ | Me | (R)- |
| III-1042 | Me | Me | Me | NH | 4-Me—Ph | C(Me)₂CH₂ | H | racemic |
| III-1043 | Me | Me | Me | NH | 4-Me—Ph | C(Me)₂CH₂ | H | (+) |
| III-1044 | Me | Me | Me | NH | 4-Me—Ph | C(Me)₂CH₂ | H | (−) |
| III-1045 | Me | Et | Me | NH | 4-Me—Ph | C(Me)₂CH₂ | H | racemic |
| III-1046 | Me | Et | Me | NH | 4-Me—Ph | C(Me)₂CH₂ | H | (+) |
| III-1047 | Me | Et | Me | NH | 4-Me—Ph | C(Me)₂CH₂ | H | (−) |
| III-1048 | Me | Me | Me | NH | 4-Me—Ph | C(Me)₂CH₂ | Me | racemic |
| III-1049 | Me | Me | Me | NH | 4-Me—Ph | C(Me)₂CH₂ | Me | (+) |
| III-1050 | Me | Me | Me | NH | 4-Me—Ph | C(Me)₂CH₂ | Me | (−) |

TABLE 58

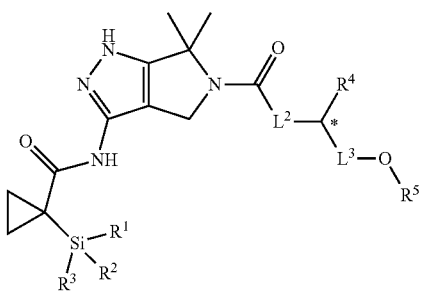

(III)

| Compound No. | R¹ | R² | R³ | L² | R⁴ | L³ | R⁵ | Configuration |
|---|---|---|---|---|---|---|---|---|
| III-1051 | Me | Et | Me | NH | 4-Me—Ph | C(Me)₂CH₂ | Me | racemic |
| III-1052 | Me | Et | Me | NH | 4-Me—Ph | C(Me)₂CH₂ | Me | (+) |
| III-1053 | Me | Et | Me | NH | 4-Me—Ph | C(Me)₂CH₂ | Me | (−) |
| III-1054 | Me | Me | Me | — | Ph | — | H | racemic |
| III-1055 | Me | Me | Me | — | Ph | — | H | (R)- |
| III-1056 | Me | Et | Me | — | Ph | — | H | racemic |
| III-1057 | Me | Et | Me | — | Ph | — | H | (R)- |
| III-1058 | Me | Me | Me | — | Ph | — | Me | racemic |
| III-1059 | Me | Me | Me | — | Ph | — | Me | (R)- |
| III-1060 | Me | Et | Me | — | Ph | — | Me | racemic |
| III-1061 | Me | Et | Me | — | Ph | — | Me | (R)- |
| III-1062 | Me | Me | Me | — | Ph | — | CHF₂ | racemic |
| III-1063 | Me | Me | Me | — | Ph | — | CHF₂ | (R)- |
| III-1064 | Me | Et | Me | — | Ph | — | CHF₂ | racemic |
| III-1065 | Me | Et | Me | — | Ph | — | CHF₂ | (R)- |
| III-1066 | Me | Me | Me | — | Ph | — | CF₃ | racemic |
| III-1067 | Me | Me | Me | — | Ph | — | CF₃ | (R)- |
| III-1068 | Me | Et | Me | — | Ph | — | CF₃ | racemic |
| III-1069 | Me | Et | Me | — | Ph | — | CF₃ | (R)- |
| III-1070 | Me | Me | Me | — | Ph | — | Et | racemic |
| III-1071 | Me | Me | Me | — | Ph | — | Et | (R)- |
| III-1072 | Me | Et | Me | — | Ph | — | Et | racemic |
| III-1073 | Me | Et | Me | — | Ph | — | Et | (R)- |
| III-1074 | Me | Me | Me | — | Ph | — | CF₂CH₃ | racemic |
| III-1075 | Me | Me | Me | — | Ph | — | CF₂CH₃ | (R)- |
| III-1076 | Me | Et | Me | — | Ph | — | CF₂CH₃ | racemic |
| III-1077 | Me | Et | Me | — | Ph | — | CF₂CH₃ | (R)- |
| III-1078 | Me | Me | Me | — | Ph | — | nPr | racemic |
| III-1079 | Me | Me | Me | — | Ph | — | nPr | (R)- |
| III-1080 | Me | Et | Me | — | Ph | — | nPr | racemic |
| III-1081 | Me | Et | Me | — | Ph | — | nPr | (R)- |
| III-1082 | Me | Me | Me | — | Ph | — | nBu | racemic |
| III-1083 | Me | Me | Me | — | Ph | — | nBu | (R)- |
| III-1084 | Me | Et | Me | — | Ph | — | nBu | racemic |
| III-1085 | Me | Et | Me | — | Ph | — | nBu | (R)- |
| III-1086 | Me | Me | Me | — | Ph | — | iPr | racemic |
| III-1087 | Me | Me | Me | — | Ph | — | iPr | (R)- |
| III-1088 | Me | Et | Me | — | Ph | — | iPr | racemic |
| III-1089 | Me | Et | Me | — | Ph | — | iPr | (R)- |
| III-1090 | Me | Me | Me | — | Ph | — | cPr | racemic |
| III-1091 | Me | Me | Me | — | Ph | — | cPr | (R)- |
| III-1092 | Me | Et | Me | — | Ph | — | cPr | racemic |
| III-1093 | Me | Et | Me | — | Ph | — | cPr | (R)- |
| III-1094 | Me | Me | Me | — | Ph | — | Ph | racemic |
| III-1095 | Me | Me | Me | — | Ph | — | Ph | (R)- |
| III-1096 | Me | Et | Me | — | Ph | — | Ph | racemic |
| III-1097 | Me | Et | Me | — | Ph | — | Ph | (R)- |
| III-1098 | Me | Me | Me | — | Ph | CH₂ | CHF₂ | racemic |
| III-1099 | Me | Me | Me | — | Ph | CH₂ | CHF₂ | (S)- |
| III-1100 | Me | Me | Me | — | Ph | CH₂ | Et | racemic |

TABLE 59

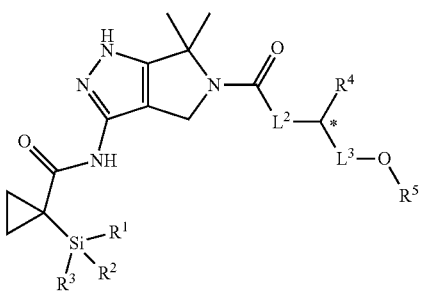

(III)

| Compound No. | R¹ | R² | R³ | L² | R⁴ | L³ | R⁵ | Configuration |
|---|---|---|---|---|---|---|---|---|
| III-1101 | Me | Me | Me | — | Ph | CH₂ | Et | (S)- |
| III-1102 | Me | Me | Me | — | Ph | CH₂ | Ph | racemic |
| III-1103 | Me | Me | Me | — | Ph | CH₂ | Ph | (R)- |
| III-1104 | Me | Me | Me | — | Ph | (CH₂)₂ | H | racemic |
| III-1105 | Me | Me | Me | — | Ph | (CH₂)₂ | H | (S)- |
| III-1106 | Me | Me | Me | — | Ph | (CH₂)₂ | Me | racemic |
| III-1107 | Me | Me | Me | — | Ph | (CH₂)₂ | Me | (S)- |
| III-1108 | Me | Me | Me | — | Ph | (CH₂)₂ | CHF₂ | racemic |
| III-1109 | Me | Me | Me | — | Ph | (CH₂)₂ | CHF₂ | (S)- |
| III-1110 | Me | Me | Me | — | Ph | (CH₂)₂ | Et | racemic |
| III-1111 | Me | Me | Me | — | Ph | (CH₂)₂ | Et | (S)- |
| III-1112 | Me | Me | Me | — | H | — | H | |
| III-1113 | Me | Me | Me | — | H | — | Me | |
| III-1114 | Me | Me | Me | — | H | — | CHF₂ | |
| III-1115 | Me | Me | Me | — | H | — | CF₃ | |
| III-1116 | Me | Me | Me | — | H | — | Et | |
| III-1117 | Me | Me | Me | — | H | — | nPr | |
| III-1118 | Me | Me | Me | — | H | — | iPr | |
| III-1119 | Me | Me | Me | — | H | — | cPr | |
| III-1120 | Me | Me | Me | — | H | — | Ph | |
| III-1121 | Me | Me | Me | — | Me | — | H | racemic |
| III-1122 | Me | Me | Me | — | Me | — | H | (R)- |
| III-1123 | Me | Me | Me | — | Me | — | Me | racemic |
| III-1124 | Me | Me | Me | — | Me | — | Me | (R)- |
| III-1125 | Me | Me | Me | — | Me | — | CHF₂ | racemic |
| III-1126 | Me | Me | Me | — | Me | — | CHF₂ | (R)- |
| III-1127 | Me | Me | Me | — | Me | — | CF₃ | racemic |
| III-1128 | Me | Me | Me | — | Me | — | CF₃ | (R)- |
| III-1129 | Me | Me | Me | — | Me | — | Et | racemic |
| III-1130 | Me | Me | Me | — | Me | — | Et | (R)- |
| III-1131 | Me | Me | Me | — | Me | — | nPr | racemic |
| III-1132 | Me | Me | Me | — | Me | — | nPr | (R)- |
| III-1133 | Me | Me | Me | — | Me | — | iPr | racemic |
| III-1134 | Me | Me | Me | — | Me | — | iPr | (R)- |
| III-1135 | Me | Me | Me | — | Me | — | cPr | racemic |
| III-1136 | Me | Me | Me | — | Me | — | cPr | (R)- |
| III-1137 | Me | Me | Me | — | Me | — | cHex | racemic |
| III-1138 | Me | Me | Me | — | Me | — | cHex | (R)- |
| III-1139 | Me | Me | Me | — | Me | — | Ph | racemic |
| III-1140 | Me | Me | Me | — | Me | — | Ph | (R)- |
| III-1141 | Me | Me | Me | — | Me | — | 2-F—Ph | racemic |
| III-1142 | Me | Me | Me | — | Me | — | 2-F—Ph | (R)- |
| III-1143 | Me | Me | Me | — | Me | — | 3-F—Ph | racemic |
| III-1144 | Me | Me | Me | — | Me | — | 3-F—Ph | (R)- |
| III-1145 | Me | Me | Me | — | Me | — | 4-F—Ph | racemic |
| III-1146 | Me | Me | Me | — | Me | — | 4-F—Ph | (R)- |
| III-1147 | Me | Me | Me | — | Me | — | 2-Cl—Ph | racemic |
| III-1148 | Me | Me | Me | — | Me | — | 2-Cl—Ph | (R)- |
| III-1149 | Me | Me | Me | — | Me | — | 3-Cl—Ph | racemic |
| III-1150 | Me | Me | Me | — | Me | — | 3-Cl—Ph | (R)- |

TABLE 60

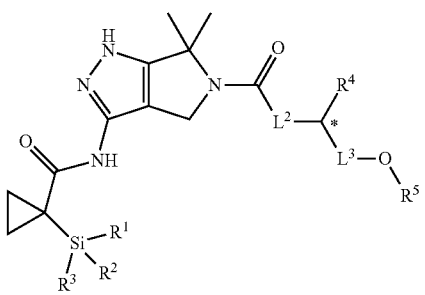

(III)

| Compound No. | R¹ | R² | R³ | L² | R⁴ | L³ | R⁵ | Configuration |
|---|---|---|---|---|---|---|---|---|
| III-1151 | Me | Me | Me | — | Me | — | 4-Cl—Ph | racemic |
| III-1152 | Me | Me | Me | — | Me | — | 4-Cl—Ph | (R)- |
| III-1153 | Me | Me | Me | — | Me | — | 2-Py | racemic |
| III-1154 | Me | Me | Me | — | Me | — | 2-Py | (R)- |
| III-1155 | Me | Me | Me | — | Me | — | 3-Py | racemic |
| III-1156 | Me | Me | Me | — | Me | — | 3-Py | (R)- |
| III-1157 | Me | Me | Me | — | Me | — | 4-Py | racemic |
| III-1158 | Me | Me | Me | — | Me | — | 4-Py | (R)- |
| III-1159 | Me | Me | Me | — | iPr | — | H | racemic |
| III-1160 | Me | Me | Me | — | iPr | — | H | (R)- |
| III-1161 | Me | Me | Me | — | iPr | — | Me | racemic |
| III-1162 | Me | Me | Me | — | iPr | — | Me | (R)- |
| III-1163 | Me | Me | Me | — | iPr | — | CHF₂ | racemic |
| III-1164 | Me | Me | Me | — | iPr | — | CHF₂ | (R)- |
| III-1165 | Me | Me | Me | — | iPr | — | CF₃ | racemic |
| III-1166 | Me | Me | Me | — | iPr | — | CF₃ | (R)- |
| III-1167 | Me | Me | Me | — | iPr | — | Et | racemic |
| III-1168 | Me | Me | Me | — | iPr | — | Et | (R)- |
| III-1169 | Me | Me | Me | — | iPr | — | nPr | racemic |
| III-1170 | Me | Me | Me | — | iPr | — | nPr | (R)- |
| III-1171 | Me | Me | Me | — | iPr | — | iPr | racemic |
| III-1172 | Me | Me | Me | — | iPr | — | iPr | (R)- |
| III-1173 | Me | Me | Me | — | iPr | — | cPr | racemic |
| III-1174 | Me | Me | Me | — | iPr | — | cPr | (R)- |
| III-1175 | Me | Me | Me | — | iPr | — | Ph | racemic |
| III-1176 | Me | Me | Me | — | iPr | — | Ph | (R)- |
| III-1177 | Me | Me | Me | — | CF₃ | — | H | racemic |
| III-1178 | Me | Me | Me | — | CF₃ | — | H | (R)- |
| III-1179 | Me | Me | Me | — | CF₃ | — | Me | racemic |
| III-1180 | Me | Me | Me | — | CF₃ | — | Me | (R)- |
| III-1181 | Me | Me | Me | — | CF₃ | — | CHF₂ | racemic |
| III-1182 | Me | Me | Me | — | CF₃ | — | CHF₂ | (R)- |
| III-1183 | Me | Me | Me | — | CF₃ | — | CF₃ | racemic |
| III-1184 | Me | Me | Me | — | CF₃ | — | CF₃ | (R)- |
| III-1185 | Me | Me | Me | — | CF₃ | — | Et | racemic |
| III-1186 | Me | Me | Me | — | CF₃ | — | Et | (R)- |
| III-1187 | Me | Me | Me | — | CF₃ | — | nPr | racemic |
| III-1188 | Me | Me | Me | — | CF₃ | — | nPr | (R)- |
| III-1189 | Me | Me | Me | — | CF₃ | — | iPr | racemic |
| III-1190 | Me | Me | Me | — | CF₃ | — | iPr | (R)- |
| III-1191 | Me | Me | Me | — | CF₃ | — | cPr | racemic |
| III-1192 | Me | Me | Me | — | CF₃ | — | cPr | (R)- |
| III-1193 | Me | Me | Me | — | CF₃ | — | Ph | racemic |
| III-1194 | Me | Me | Me | — | CF₃ | — | Ph | (R)- |
| III-1195 | Me | Me | Me | — | CH₂OH | — | H | racemic |
| III-1196 | Me | Me | Me | — | CH₂OH | — | H | (R)- |
| III-1197 | Me | Me | Me | — | CH₂OH | — | Me | racemic |
| III-1198 | Me | Me | Me | — | CH₂OH | — | Me | (R)- |
| III-1199 | Me | Me | Me | — | CH₂OH | — | CHF₂ | racemic |
| III-1200 | Me | Me | Me | — | CH₂OH | — | CHF₂ | (R)- |

TABLE 61

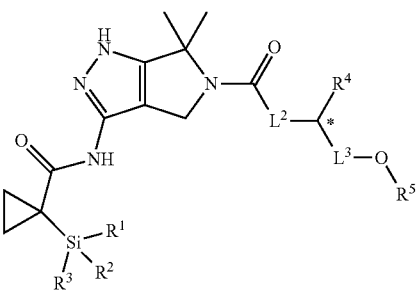

(III)

| Compound No. | R¹ | R² | R³ | L² | R⁴ | L³ | R⁵ | Configuration |
|---|---|---|---|---|---|---|---|---|
| III-1201 | Me | Me | Me | — | CH₂OH | — | CF₃ | racemic |
| III-1202 | Me | Me | Me | — | CH₂OH | — | CF₃ | (R)- |
| III-1203 | Me | Me | Me | — | CH₂OH | — | Et | racemic |
| III-1204 | Me | Me | Me | — | CH₂OH | — | Et | (R)- |
| III-1205 | Me | Me | Me | — | CH₂OH | — | nPr | racemic |
| III-1206 | Me | Me | Me | — | CH₂OH | — | nPr | (R)- |
| III-1207 | Me | Me | Me | — | CH₂OH | — | iPr | racemic |
| III-1208 | Me | Me | Me | — | CH₂OH | — | iPr | (R)- |
| III-1209 | Me | Me | Me | — | CH₂OH | — | cPr | racemic |
| III-1210 | Me | Me | Me | — | CH₂OH | — | cPr | (R)- |
| III-1211 | Me | Me | Me | — | CH₂OH | — | Ph | racemic |
| III-1212 | Me | Me | Me | — | CH₂OH | — | Ph | (R)- |
| III-1213 | Me | Me | Me | — | CH₂OMe | — | H | racemic |
| III-1214 | Me | Me | Me | — | CH₂OMe | — | H | (R)- |
| III-1215 | Me | Me | Me | — | CH₂OMe | — | Me | racemic |
| III-1216 | Me | Me | Me | — | CH₂OMe | — | Me | (R)- |
| III-1217 | Me | Me | Me | — | CH₂OMe | — | CHF₂ | racemic |
| III-1218 | Me | Me | Me | — | CH₂OMe | — | CHF₂ | (R)- |
| III-1219 | Me | Me | Me | — | CH₂OMe | — | CF₃ | racemic |
| III-1220 | Me | Me | Me | — | CH₂OMe | — | CF₃ | (R)- |
| III-1221 | Me | Me | Me | — | CH₂OMe | — | Et | racemic |
| III-1222 | Me | Me | Me | — | CH₂OMe | — | Et | (R)- |
| III-1223 | Me | Me | Me | — | CH₂OMe | — | nPr | racemic |
| III-1224 | Me | Me | Me | — | CH₂OMe | — | nPr | (R)- |
| III-1225 | Me | Me | Me | — | CH₂OMe | — | iPr | racemic |
| III-1226 | Me | Me | Me | — | CH₂OMe | — | iPr | (R)- |
| III-1227 | Me | Me | Me | — | CH₂OMe | — | cPr | racemic |
| III-1228 | Me | Me | Me | — | CH₂OMe | — | cPr | (R)- |
| III-1229 | Me | Me | Me | — | CH₂OMe | — | Ph | racemic |
| III-1230 | Me | Me | Me | — | CH₂OMe | — | Ph | (R)- |
| III-1231 | Me | Me | Me | — | CH₂OBn | — | H | racemic |
| III-1232 | Me | Me | Me | — | CH₂OBn | — | H | (R)- |
| III-1233 | Me | Me | Me | — | CH₂OBn | — | Me | racemic |
| III-1234 | Me | Me | Me | — | CH₂OBn | — | Me | (R)- |
| III-1235 | Me | Me | Me | — | CH₂OBn | — | Ph | racemic |
| III-1236 | Me | Me | Me | — | CH₂OBn | — | Ph | (R)- |
| III-1237 | Me | Me | Me | — | CH₂NMe₂ | — | H | racemic |
| III-1238 | Me | Me | Me | — | CH₂NMe₂ | — | H | (R)- |
| III-1239 | Me | Me | Me | — | CH₂NMe₂ | — | Me | racemic |
| III-1240 | Me | Me | Me | — | CH₂NMe₂ | — | Me | (R)- |
| III-1241 | Me | Me | Me | — | CH₂NMe₂ | — | CHF₂ | racemic |
| III-1242 | Me | Me | Me | — | CH₂NMe₂ | — | CHF₂ | (R)- |
| III-1243 | Me | Me | Me | — | CH₂NMe₂ | — | CF₃ | racemic |
| III-1244 | Me | Me | Me | — | CH₂NMe₂ | — | CF₃ | (R)- |
| III-1245 | Me | Me | Me | — | CH₂NMe₂ | — | Et | racemic |
| III-1246 | Me | Me | Me | — | CH₂NMe₂ | — | Et | (R)- |
| III-1247 | Me | Me | Me | — | CH₂NMe₂ | — | nPr | racemic |
| III-1248 | Me | Me | Me | — | CH₂NMe₂ | — | nPr | (R)- |
| III-1249 | Me | Me | Me | — | CH₂NMe₂ | — | iPr | racemic |
| III-1250 | Me | Me | Me | — | CH₂NMe₂ | — | iPr | (R)- |

TABLE 62

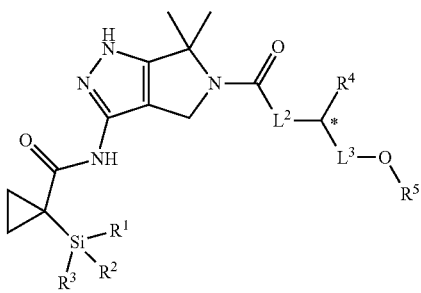

(III)

| Compound No. | R¹ | R² | R³ | L² | R⁴ | L³ | R⁵ | Configuration |
|---|---|---|---|---|---|---|---|---|
| III-1251 | Me | Me | Me | — | CH₂NMe₂ | — | cPr | racemic |
| III-1252 | Me | Me | Me | — | CH₂NMe₂ | — | cPr | (R)- |
| III-1253 | Me | Me | Me | — | CH₂NMe₂ | — | Ph | racemic |
| III-1254 | Me | Me | Me | — | CH₂NMe₂ | — | Ph | (R)- |
| III-1255 | Me | Me | Me | — | CH₂-(3,3-difluoro-pyrrolidyl) | — | H | racemic |
| III-1256 | Me | Me | Me | — | CH₂-(3,3-difluoro-pyrrolidyl) | — | H | (R)- |
| III-1257 | Me | Me | Me | — | CH₂-(3,3-difluoro-pyrrolidyl) | — | Me | racemic |
| III-1258 | Me | Me | Me | — | CH₂-(3,3-difluoro-pyrrolidyl) | — | Me | (R)- |
| III-1259 | Me | Me | Me | — | CH₂-(3,3-difluoro-pyrrolidyl) | — | Ph | racemic |
| III-1260 | Me | Me | Me | — | CH₂-(3,3-difluoro-pyrrolidyl) | — | Ph | (R)- |
| III-1261 | Me | Me | Me | — | 2-F—Ph | — | H | racemic |
| III-1262 | Me | Me | Me | — | 2-F—Ph | — | H | (R)- |
| III-1263 | Me | Me | Me | — | 2-F—Ph | — | Me | racemic |
| III-1264 | Me | Me | Me | — | 2-F—Ph | — | Me | (R)- |
| III-1265 | Me | Me | Me | — | 2-F—Ph | — | CHF₂ | racemic |
| III-1266 | Me | Me | Me | — | 2-F—Ph | — | CHF₂ | (R)- |
| III-1267 | Me | Me | Me | — | 2-F—Ph | — | CF₃ | racemic |
| III-1268 | Me | Me | Me | — | 2-F—Ph | — | CF₃ | (R)- |
| III-1269 | Me | Me | Me | — | 2-F—Ph | — | Et | racemic |
| III-1270 | Me | Me | Me | — | 2-F—Ph | — | Et | (R)- |
| III-1271 | Me | Me | Me | — | 2-F—Ph | — | nPr | racemic |
| III-1272 | Me | Me | Me | — | 2-F—Ph | — | nPr | (R)- |
| III-1273 | Me | Me | Me | — | 2-F—Ph | — | iPr | racemic |
| III-1274 | Me | Me | Me | — | 2-F—Ph | — | iPr | (R)- |
| III-1275 | Me | Me | Me | — | 2-F—Ph | — | cPr | racemic |
| III-1276 | Me | Me | Me | — | 2-F—Ph | — | cPr | (R)- |
| III-1277 | Me | Me | Me | — | 3-F—Ph | — | H | racemic |
| III-1278 | Me | Me | Me | — | 3-F—Ph | — | H | (R)- |
| III-1279 | Me | Me | Me | — | 3-F—Ph | — | Me | racemic |
| III-1280 | Me | Me | Me | — | 3-F—Ph | — | Me | (R)- |
| III-1281 | Me | Me | Me | — | 3-F—Ph | — | CHF₂ | racemic |
| III-1282 | Me | Me | Me | — | 3-F—Ph | — | CHF₂ | (R)- |
| III-1283 | Me | Me | Me | — | 3-F—Ph | — | CF₃ | racemic |
| III-1284 | Me | Me | Me | — | 3-F—Ph | — | CF₃ | (R)- |
| III-1285 | Me | Me | Me | — | 3-F—Ph | — | Et | racemic |
| III-1286 | Me | Me | Me | — | 3-F—Ph | — | Et | (R)- |
| III-1287 | Me | Me | Me | — | 3-F—Ph | — | nPr | racemic |
| III-1288 | Me | Me | Me | — | 3-F—Ph | — | nPr | (R)- |
| III-1289 | Me | Me | Me | — | 3-F—Ph | — | iPr | racemic |
| III-1290 | Me | Me | Me | — | 3-F—Ph | — | iPr | (R)- |
| III-1291 | Me | Me | Me | — | 3-F—Ph | — | cPr | racemic |
| III-1292 | Me | Me | Me | — | 3-F—Ph | — | cPr | (R)- |
| III-1293 | Me | Me | Me | — | 4-F—Ph | — | H | racemic |
| III-1294 | Me | Me | Me | — | 4-F—Ph | — | H | (R)- |
| III-1295 | Me | Me | Me | — | 4-F—Ph | — | Me | racemic |
| III-1296 | Me | Me | Me | — | 4-F—Ph | — | Me | (R)- |
| III-1297 | Me | Me | Me | — | 4-F—Ph | — | CHF₂ | racemic |
| III-1298 | Me | Me | Me | — | 4-F—Ph | — | CHF₂ | (R)- |
| III-1299 | Me | Me | Me | — | 4-F—Ph | — | CF₃ | racemic |
| III-1300 | Me | Me | Me | — | 4-F—Ph | — | CF₃ | (R)- |

TABLE 63

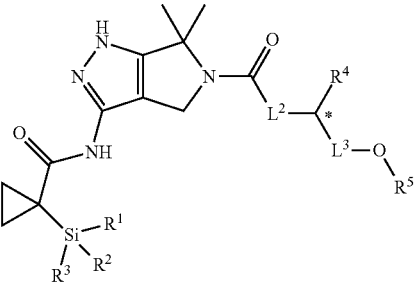

(III)

| Compound No. | R¹ | R² | R³ | L² | R⁴ | L³ | R⁵ | Configuration |
|---|---|---|---|---|---|---|---|---|
| III-1301 | Me | Me | Me | — | 4-F—Ph | — | Et | racemic |
| III-1302 | Me | Me | Me | — | 4-F—Ph | — | Et | (R)- |
| III-1303 | Me | Me | Me | — | 4-F—Ph | — | nPr | racemic |
| III-1304 | Me | Me | Me | — | 4-F—Ph | — | nPr | (R)- |
| III-1305 | Me | Me | Me | — | 4-F—Ph | — | iPr | racemic |
| III-1306 | Me | Me | Me | — | 4-F—Ph | — | iPr | (R)- |
| III-1307 | Me | Me | Me | — | 4-F—Ph | — | cPr | racemic |
| III-1308 | Me | Me | Me | — | 4-F—Ph | — | cPr | (R)- |
| III-1309 | Me | Me | Me | — | 2-thienyl | — | H | racemic |
| III-1310 | Me | Me | Me | — | 2-thienyl | — | H | (S)- |
| III-1311 | Me | Me | Me | — | 2-thienyl | — | Me | racemic |
| III-1312 | Me | Me | Me | — | 2-thienyl | — | Me | (S)- |
| III-1313 | Me | Me | Me | — | 2-thienyl | — | CHF₂ | racemic |
| III-1314 | Me | Me | Me | — | 2-thienyl | — | CHF₂ | (S)- |
| III-1315 | Me | Me | Me | — | 2-thienyl | — | CF₃ | racemic |
| III-1316 | Me | Me | Me | — | 2-thienyl | — | CF₃ | (S)- |
| III-1317 | Me | Me | Me | — | 2-thienyl | — | Et | racemic |
| III-1318 | Me | Me | Me | — | 2-thienyl | — | Et | (S)- |
| III-1319 | Me | Me | Me | — | 2-thienyl | — | nPr | racemic |
| III-1320 | Me | Me | Me | — | 2-thienyl | — | nPr | (S)- |
| III-1321 | Me | Me | Me | — | 2-thienyl | — | iPr | racemic |
| III-1322 | Me | Me | Me | — | 2-thienyl | — | iPr | (S)- |
| III-1323 | Me | Me | Me | — | 2-thienyl | — | cPr | racemic |
| III-1324 | Me | Me | Me | — | 2-thienyl | — | cPr | (S)- |
| III-1325 | Me | Me | Me | — | 3-thienyl | — | H | racemic |
| III-1326 | Me | Me | Me | — | 3-thienyl | — | H | (R)- |
| III-1327 | Me | Me | Me | — | 3-thienyl | — | Me | racemic |
| III-1328 | Me | Me | Me | — | 3-thienyl | — | Me | (R)- |
| III-1329 | Me | Me | Me | — | 3-thienyl | — | CHF₂ | racemic |
| III-1330 | Me | Me | Me | — | 3-thienyl | — | CHF₂ | (R)- |
| III-1331 | Me | Me | Me | — | 3-thienyl | — | CF₃ | racemic |
| III-1332 | Me | Me | Me | — | 3-thienyl | — | CF₃ | (R)- |
| III-1333 | Me | Me | Me | — | 3-thienyl | — | Et | racemic |
| III-1334 | Me | Me | Me | — | 3-thienyl | — | Et | (R)- |
| III-1335 | Me | Me | Me | — | 3-thienyl | — | nPr | racemic |
| III-1336 | Me | Me | Me | — | 3-thienyl | — | nPr | (R)- |
| III-1337 | Me | Me | Me | — | 3-thienyl | — | iPr | racemic |
| III-1338 | Me | Me | Me | — | 3-thienyl | — | iPr | (R)- |
| III-1339 | Me | Me | Me | — | 3-thienyl | — | cPr | racemic |
| III-1340 | Me | Me | Me | — | 3-thienyl | — | cPr | (R)- |

TABLE 64

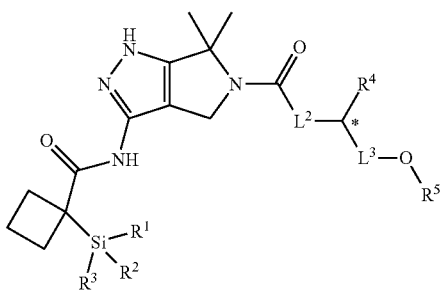

(IV)

| Compound No. | R¹ | R² | R³ | L² | R⁴ | L³ | R⁵ | Configuration |
|---|---|---|---|---|---|---|---|---|
| IV-1 | Me | Me | Me | O | Ph | CH₂ | H | racemic |
| IV-2 | Me | Me | Me | O | Ph | CH₂ | H | (S)- |
| IV-3 | Me | Et | Me | O | Ph | CH₂ | H | racemic |
| IV-4 | Me | Et | Me | O | Ph | CH₂ | H | (S)- |
| IV-5 | Me | Me | Me | O | Ph | CH₂ | Me | racemic |
| IV-6 | Me | Me | Me | O | Ph | CH₂ | Me | (S)- |
| IV-7 | Me | Et | Me | O | Ph | CH₂ | Me | racemic |
| IV-8 | Me | Et | Me | O | Ph | CH₂ | Me | (S)- |
| IV-9 | Me | Me | Me | O | Ph | CH₂ | CHF₂ | racemic |
| IV-10 | Me | Me | Me | O | Ph | CH₂ | CHF₂ | (S)- |
| IV-11 | Me | Et | Me | O | Ph | CH₂ | CHF₂ | racemic |
| IV-12 | Me | Et | Me | O | Ph | CH₂ | CHF₂ | (S)- |
| IV-13 | Me | Me | Me | O | Ph | CH₂ | Et | racemic |
| IV-14 | Me | Me | Me | O | Ph | CH₂ | Et | (S)- |
| IV-15 | Me | Et | Me | O | Ph | CH₂ | Et | racemic |
| IV-16 | Me | Et | Me | O | Ph | CH₂ | Et | (S)- |
| IV-17 | Me | Me | Me | O | Ph | CH₂ | iPr | racemic |
| IV-18 | Me | Me | Me | O | Ph | CH₂ | iPr | (S)- |
| IV-19 | Me | Et | Me | O | Ph | CH₂ | iPr | racemic |
| IV-20 | Me | Et | Me | O | Ph | CH₂ | iPr | (S)- |
| IV-21 | Me | Me | Me | O | Ph | CH₂ | cPr | racemic |
| IV-22 | Me | Me | Me | O | Ph | CH₂ | cPr | (S)- |
| IV-23 | Me | Et | Me | O | Ph | CH₂ | cPr | racemic |
| IV-24 | Me | Et | Me | O | Ph | CH₂ | cPr | (S)- |
| IV-25 | Me | Me | Me | O | Ph | CH₂ | Ph | racemic |
| IV-26 | Me | Me | Me | O | Ph | CH₂ | Ph | (S)- |
| IV-27 | Me | Et | Me | O | Ph | CH₂ | Ph | racemic |
| IV-28 | Me | Et | Me | O | Ph | CH₂ | Ph | (S)- |
| IV-29 | Me | Me | Me | O | Ph | C(Me)₂ | H | racemic |
| IV-30 | Me | Me | Me | O | Ph | C(Me)₂ | H | (S)- |
| IV-31 | Me | Et | Me | O | Ph | C(Me)₂ | H | racemic |
| IV-32 | Me | Et | Me | O | Ph | C(Me)₂ | H | (S)- |
| IV-33 | Me | Me | Me | O | Ph | C(Me)₂ | Me | racemic |
| IV-34 | Me | Me | Me | O | Ph | C(Me)₂ | Me | (S)- |
| IV-35 | Me | Et | Me | O | Ph | C(Me)₂ | Me | racemic |
| IV-36 | Me | Et | Me | O | Ph | C(Me)₂ | Me | (S)- |
| IV-37 | Me | Me | Me | O | Ph | C(Me)₂ | CHF₂ | racemic |
| IV-38 | Me | Me | Me | O | Ph | C(Me)₂ | CHF₂ | (S)- |
| IV-39 | Me | Et | Me | O | Ph | C(Me)₂ | CHF₂ | racemic |
| IV-40 | Me | Et | Me | O | Ph | C(Me)₂ | CHF₂ | (S)- |
| IV-41 | Me | Me | Me | O | Ph | C(Me)₂ | Et | racemic |
| IV-42 | Me | Me | Me | O | Ph | C(Me)₂ | Et | (S)- |
| IV-43 | Me | Et | Me | O | Ph | C(Me)₂ | Et | racemic |
| IV-44 | Me | Et | Me | O | Ph | C(Me)₂ | Et | (S)- |
| IV-45 | Me | Me | Me | O | Ph | C(Me)₂ | iPr | racemic |
| IV-46 | Me | Me | Me | O | Ph | C(Me)₂ | iPr | (S)- |
| IV-47 | Me | Et | Me | O | Ph | C(Me)₂ | iPr | racemic |
| IV-48 | Me | Et | Me | O | Ph | C(Me)₂ | iPr | (S)- |
| IV-49 | Me | Me | Me | O | Ph | C(Me)₂ | cPr | racemic |
| IV-50 | Me | Me | Me | O | Ph | C(Me)₂ | cPr | (S)- |

TABLE 65

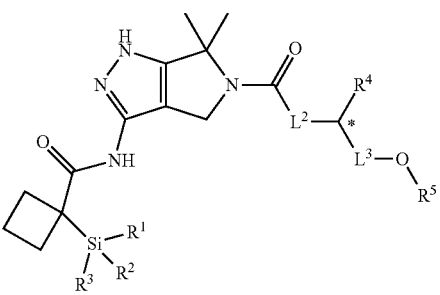

(IV)

| Compound No. | R¹ | R² | R³ | L² | R⁴ | L³ | R⁵ | Configuration |
|---|---|---|---|---|---|---|---|---|
| IV-51 | Me | Et | Me | O | Ph | C(Me)₂ | cPr | racemic |
| IV-52 | Me | Et | Me | O | Ph | C(Me)₂ | cPr | (S)- |
| IV-53 | Me | Me | Me | O | Ph | C(Me)₂ | Ph | racemic |
| IV-54 | Me | Me | Me | O | Ph | C(Me)₂ | Ph | (S)- |
| IV-55 | Me | Et | Me | O | Ph | C(Me)₂ | Ph | racemic |
| IV-56 | Me | Et | Me | O | Ph | C(Me)₂ | Ph | (S)- |
| IV-57 | Me | Me | Me | O | Ph | (CH₂)₂ | H | racemic |
| IV-58 | Me | Me | Me | O | Ph | (CH₂)₂ | H | (R)- |
| IV-59 | Me | Et | Me | O | Ph | (CH₂)₂ | H | racemic |
| IV-60 | Me | Et | Me | O | Ph | (CH₂)₂ | H | (R)- |
| IV-61 | Me | Me | Me | O | Ph | (CH₂)₂ | Me | racemic |
| IV-62 | Me | Me | Me | O | Ph | (CH₂)₂ | Me | (R)- |
| IV-63 | Me | Et | Me | O | Ph | (CH₂)₂ | Me | racemic |
| IV-64 | Me | Et | Me | O | Ph | (CH₂)₂ | Me | (R)- |
| IV-65 | Me | Me | Me | O | Ph | (CH₂)₂ | CHF₂ | racemic |
| IV-66 | Me | Me | Me | O | Ph | (CH₂)₂ | CHF₂ | (R)- |
| IV-67 | Me | Et | Me | O | Ph | (CH₂)₂ | CHF₂ | racemic |
| IV-68 | Me | Et | Me | O | Ph | (CH₂)₂ | CHF₂ | (R)- |
| IV-69 | Me | Me | Me | O | Ph | (CH₂)₂ | Et | racemic |
| IV-70 | Me | Me | Me | O | Ph | (CH₂)₂ | Et | (R)- |
| IV-71 | Me | Et | Me | O | Ph | (CH₂)₂ | Et | racemic |
| IV-72 | Me | Et | Me | O | Ph | (CH₂)₂ | Et | (R)- |
| IV-73 | Me | Me | Me | O | Ph | (CH₂)₂ | iPr | racemic |
| IV-74 | Me | Me | Me | O | Ph | (CH₂)₂ | iPr | (R)- |
| IV-75 | Me | Et | Me | O | Ph | (CH₂)₂ | iPr | racemic |
| IV-76 | Me | Et | Me | O | Ph | (CH₂)₂ | iPr | (R)- |
| IV-77 | Me | Me | Me | O | Ph | (CH₂)₂ | cPr | racemic |
| IV-78 | Me | Me | Me | O | Ph | (CH₂)₂ | cPr | (R)- |
| IV-79 | Me | Et | Me | O | Ph | (CH₂)₂ | cPr | racemic |
| IV-80 | Me | Et | Me | O | Ph | (CH₂)₂ | cPr | (R)- |
| IV-81 | Me | Me | Me | O | Ph | (CH₂)₂ | Ph | racemic |
| IV-82 | Me | Me | Me | O | Ph | (CH₂)₂ | Ph | (R)- |
| IV-83 | Me | Et | Me | O | Ph | (CH₂)₂ | Ph | racemic |
| IV-84 | Me | Et | Me | O | Ph | (CH₂)₂ | Ph | (R)- |
| IV-85 | Me | Me | Me | O | Ph | CH₂C(Me)₂ | H | racemic |
| IV-86 | Me | Me | Me | O | Ph | CH₂C(Me)₂ | H | (R)- |
| IV-87 | Me | Et | Me | O | Ph | CH₂C(Me)₂ | H | racemic |
| IV-88 | Me | Et | Me | O | Ph | CH₂C(Me)₂ | H | (R)- |
| IV-89 | Me | Me | Me | O | Ph | CH₂C(Me)₂ | Me | racemic |
| IV-90 | Me | Me | Me | O | Ph | CH₂C(Me)₂ | Me | (R)- |
| IV-91 | Me | Et | Me | O | Ph | CH₂C(Me)₂ | Me | racemic |
| IV-92 | Me | Et | Me | O | Ph | CH₂C(Me)₂ | Me | (R)- |
| IV-93 | Me | Me | Me | O | Ph | CH₂C(Me)₂ | CHF₂ | racemic |
| IV-94 | Me | Me | Me | O | Ph | CH₂C(Me)₂ | CHF₂ | (R)- |
| IV-95 | Me | Et | Me | O | Ph | CH₂C(Me)₂ | CHF₂ | racemic |
| IV-96 | Me | Et | Me | O | Ph | CH₂C(Me)₂ | CHF₂ | (R)- |
| IV-97 | Me | Me | Me | O | Ph | CH₂C(Me)₂ | Et | racemic |
| IV-98 | Me | Me | Me | O | Ph | CH₂C(Me)₂ | Et | (R)- |
| IV-99 | Me | Et | Me | O | Ph | CH₂C(Me)₂ | Et | racemic |
| IV-100 | Me | Et | Me | O | Ph | CH₂C(Me)₂ | Et | (R)- |

TABLE 66

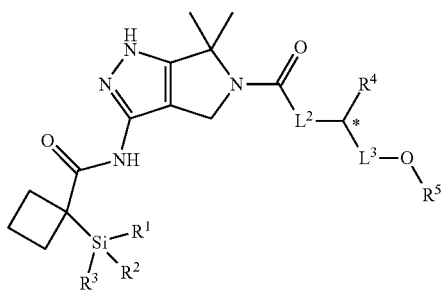

(IV)

| Compound No. | R¹ | R² | R³ | L² | R⁴ | L³ | R⁵ | Configuration |
|---|---|---|---|---|---|---|---|---|
| IV-101 | Me | Me | Me | O | Ph | CH$_2$C(Me)$_2$ | iPr | racemic |
| IV-102 | Me | Me | Me | O | Ph | CH$_2$C(Me)$_2$ | iPr | (R)- |
| IV-103 | Me | Et | Me | O | Ph | CH$_2$C(Me)$_2$ | iPr | racemic |
| IV-104 | Me | Et | Me | O | Ph | CH$_2$C(Me)$_2$ | iPr | (R)- |
| IV-105 | Me | Me | Me | O | Ph | CH$_2$C(Me)$_2$ | cPr | racemic |
| IV-106 | Me | Me | Me | O | Ph | CH$_2$C(Me)$_2$ | cPr | (R)- |
| IV-107 | Me | Et | Me | O | Ph | CH$_2$C(Me)$_2$ | cPr | racemic |
| IV-108 | Me | Et | Me | O | Ph | CH$_2$C(Me)$_2$ | cPr | (R)- |
| IV-109 | Me | Me | Me | O | Ph | CH$_2$C(Me)$_2$ | Ph | racemic |
| IV-110 | Me | Me | Me | O | Ph | CH$_2$C(Me)$_2$ | Ph | (R)- |
| IV-111 | Me | Et | Me | O | Ph | CH$_2$C(Me)$_2$ | Ph | racemic |
| IV-112 | Me | Et | Me | O | Ph | CH$_2$C(Me)$_2$ | Ph | (R)- |
| IV-113 | Me | Me | Me | NH | Ph | CH$_2$ | H | racemic |
| IV-114 | Me | Me | Me | NH | Ph | CH$_2$ | H | (S)- |
| IV-115 | Me | Me | Me | NH | Ph | CH$_2$ | H | (R)- |
| IV-116 | Me | Et | Me | NH | Ph | CH$_2$ | H | racemic |
| IV-117 | Me | Et | Me | NH | Ph | CH$_2$ | H | (S)- |
| IV-118 | Me | Me | Me | N(Me) | Ph | CH$_2$ | H | racemic |
| IV-119 | Me | Me | Me | N(Me) | Ph | CH$_2$ | H | (S)- |
| IV-120 | Me | Et | Me | N(Me) | Ph | CH$_2$ | H | racemic |
| IV-121 | Me | Et | Me | N(Me) | Ph | CH$_2$ | H | (S)- |
| IV-122 | Me | Me | Me | NH | Ph | CH$_2$ | Me | racemic |
| IV-123 | Me | Me | Me | NH | Ph | CH$_2$ | Me | (S)- |
| IV-124 | Me | Et | Me | NH | Ph | CH$_2$ | Me | racemic |
| IV-125 | Me | Et | Me | NH | Ph | CH$_2$ | Me | (S)- |
| IV-126 | Me | Me | Me | N(Me) | Ph | CH$_2$ | Me | racemic |
| IV-127 | Me | Me | Me | N(Me) | Ph | CH$_2$ | Me | (S)- |
| IV-128 | Me | Et | Me | N(Me) | Ph | CH$_2$ | Me | racemic |
| IV-129 | Me | Et | Me | N(Me) | Ph | CH$_2$ | Me | (S)- |
| IV-130 | Me | Me | Me | NH | Ph | CH$_2$ | CHF$_2$ | racemic |
| IV-131 | Me | Me | Me | NH | Ph | CH$_2$ | CHF$_2$ | (S)- |
| IV-132 | Me | Et | Me | NH | Ph | CH$_2$ | CHF$_2$ | racemic |
| IV-133 | Me | Et | Me | NH | Ph | CH$_2$ | CHF$_2$ | (S)- |
| IV-134 | Me | Me | Me | N(Me) | Ph | CH$_2$ | CHF$_2$ | racemic |
| IV-135 | Me | Me | Me | N(Me) | Ph | CH$_2$ | CHF$_2$ | (S)- |
| IV-136 | Me | Et | Me | N(Me) | Ph | CH$_2$ | CHF$_2$ | racemic |
| IV-137 | Me | Et | Me | N(Me) | Ph | CH$_2$ | CHF$_2$ | (S)- |
| IV-138 | Me | Me | Me | NH | Ph | CH$_2$ | Et | racemic |
| IV-139 | Me | Me | Me | NH | Ph | CH$_2$ | Et | (S)- |
| IV-140 | Me | Et | Me | NH | Ph | CH$_2$ | Et | racemic |
| IV-141 | Me | Et | Me | NH | Ph | CH$_2$ | Et | (S)- |
| IV-142 | Me | Me | Me | N(Me) | Ph | CH$_2$ | Et | racemic |
| IV-143 | Me | Me | Me | N(Me) | Ph | CH$_2$ | Et | (S)- |
| IV-144 | Me | Et | Me | N(Me) | Ph | CH$_2$ | Et | racemic |
| IV-145 | Me | Et | Me | N(Me) | Ph | CH$_2$ | Et | (S)- |
| IV-146 | Me | Me | Me | NH | Ph | CH$_2$ | iPr | racemic |
| IV-147 | Me | Me | Me | NH | Ph | CH$_2$ | iPr | (S)- |
| IV-148 | Me | Et | Me | NH | Ph | CH$_2$ | iPr | racemic |
| IV-149 | Me | Et | Me | NH | Ph | CH$_2$ | iPr | (S)- |
| IV-150 | Me | Me | Me | N(Me) | Ph | CH$_2$ | iPr | racemic |

TABLE 67

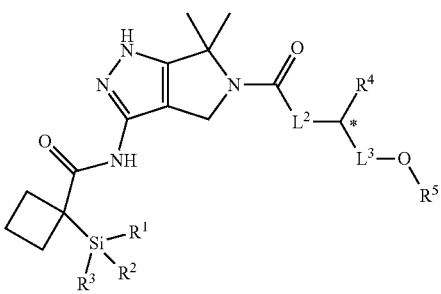

(IV)

| Compound No. | R¹ | R² | R³ | L² | R⁴ | L³ | R⁵ | Configuration |
|---|---|---|---|---|---|---|---|---|
| IV-151 | Me | Me | Me | N(Me) | Ph | CH$_2$ | iPr | (S)- |
| IV-152 | Me | Et | Me | N(Me) | Ph | CH$_2$ | iPr | racemic |
| IV-153 | Me | Et | Me | N(Me) | Ph | CH$_2$ | iPr | (S)- |
| IV-154 | Me | Me | Me | NH | Ph | CH$_2$ | cPr | racemic |
| IV-155 | Me | Me | Me | NH | Ph | CH$_2$ | cPr | (S)- |
| IV-156 | Me | Et | Me | NH | Ph | CH$_2$ | cPr | racemic |
| IV-157 | Me | Et | Me | NH | Ph | CH$_2$ | cPr | (S)- |
| IV-158 | Me | Me | Me | N(Me) | Ph | CH$_2$ | cPr | racemic |
| IV-159 | Me | Me | Me | N(Me) | Ph | CH$_2$ | cPr | (S)- |
| IV-160 | Me | Et | Me | N(Me) | Ph | CH$_2$ | cPr | racemic |
| IV-161 | Me | Et | Me | N(Me) | Ph | CH$_2$ | cPr | (S)- |
| IV-162 | Me | Me | Me | NH | Ph | CH$_2$ | Ph | racemic |
| IV-163 | Me | Me | Me | NH | Ph | CH$_2$ | Ph | (S)- |
| IV-164 | Me | Et | Me | NH | Ph | CH$_2$ | Ph | racemic |
| IV-165 | Me | Et | Me | NH | Ph | CH$_2$ | Ph | (S)- |
| IV-166 | Me | Me | Me | N(Me) | Ph | CH$_2$ | Ph | racemic |
| IV-167 | Me | Me | Me | N(Me) | Ph | CH$_2$ | Ph | (S)- |
| IV-168 | Me | Et | Me | N(Me) | Ph | CH$_2$ | Ph | racemic |
| IV-169 | Me | Et | Me | N(Me) | Ph | CH$_2$ | Ph | (S)- |
| IV-170 | Me | Me | Me | NH | Ph | C(Me)$_2$ | H | racemic |
| IV-171 | Me | Me | Me | NH | Ph | C(Me)$_2$ | H | (S)- |
| IV-172 | Me | Et | Me | NH | Ph | C(Me)$_2$ | H | racemic |
| IV-173 | Me | Et | Me | NH | Ph | C(Me)$_2$ | H | (S)- |
| IV-174 | Me | Me | Me | N(Me) | Ph | C(Me)$_2$ | H | racemic |
| IV-175 | Me | Me | Me | N(Me) | Ph | C(Me)$_2$ | H | (S)- |
| IV-176 | Me | Et | Me | N(Me) | Ph | C(Me)$_2$ | H | racemic |
| IV-177 | Me | Et | Me | N(Me) | Ph | C(Me)$_2$ | H | (S)- |
| IV-178 | Me | Me | Me | NH | Ph | C(Me)$_2$ | Me | racemic |
| IV-179 | Me | Me | Me | NH | Ph | C(Me)$_2$ | Me | (S)- |
| IV-180 | Me | Et | Me | NH | Ph | C(Me)$_2$ | Me | racemic |
| IV-181 | Me | Et | Me | NH | Ph | C(Me)$_2$ | Me | (S)- |
| IV-182 | Me | Me | Me | N(Me) | Ph | C(Me)$_2$ | Me | racemic |
| IV-183 | Me | Me | Me | N(Me) | Ph | C(Me)$_2$ | Me | (S)- |
| IV-184 | Me | Et | Me | N(Me) | Ph | C(Me)$_2$ | Me | racemic |
| IV-185 | Me | Et | Me | N(Me) | Ph | C(Me)$_2$ | Me | (S)- |
| IV-186 | Me | Me | Me | NH | Ph | C(Me)$_2$ | CHF$_2$ | racemic |
| IV-187 | Me | Me | Me | NH | Ph | C(Me)$_2$ | CHF$_2$ | (S)- |
| IV-188 | Me | Et | Me | NH | Ph | C(Me)$_2$ | CHF$_2$ | racemic |
| IV-189 | Me | Et | Me | NH | Ph | C(Me)$_2$ | CHF$_2$ | (S)- |
| IV-190 | Me | Me | Me | N(Me) | Ph | C(Me)$_2$ | CHF$_2$ | (S)- |
| IV-191 | Me | Me | Me | N(Me) | Ph | C(Me)$_2$ | CHF$_2$ | (S)- |
| IV-192 | Me | Et | Me | N(Me) | Ph | C(Me)$_2$ | CHF$_2$ | racemic |
| IV-193 | Me | Et | Me | N(Me) | Ph | C(Me)$_2$ | CHF$_2$ | (S)- |
| IV-194 | Me | Me | Me | NH | Ph | C(Me)$_2$ | Et | racemic |
| IV-195 | Me | Me | Me | NH | Ph | C(Me)$_2$ | Et | (S)- |
| IV-196 | Me | Et | Me | NH | Ph | C(Me)$_2$ | Et | racemic |
| IV-197 | Me | Et | Me | NH | Ph | C(Me)$_2$ | Et | (S)- |
| IV-198 | Me | Me | Me | N(Me) | Ph | C(Me)$_2$ | Et | racemic |
| IV-199 | Me | Me | Me | N(Me) | Ph | C(Me)$_2$ | Et | (S)- |
| IV-200 | Me | Et | Me | N(Me) | Ph | C(Me)$_2$ | Et | racemic |

TABLE 68

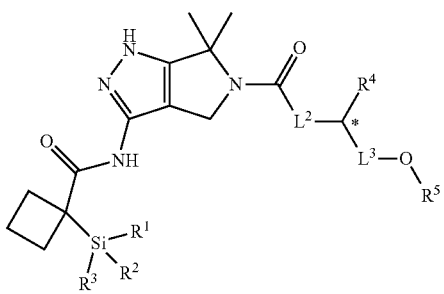

(IV)

| Compound No. | R¹ | R² | R³ | L² | R⁴ | L³ | R⁵ | Configuration |
|---|---|---|---|---|---|---|---|---|
| IV-201 | Me | Et | Me | N(Me) | Ph | C(Me)₂ | Et | (S)- |
| IV-202 | Me | Me | Me | NH | Ph | C(Me)₂ | iPr | racemic |
| IV-203 | Me | Me | Me | NH | Ph | C(Me)₂ | iPr | (S)- |
| IV-204 | Me | Et | Me | NH | Ph | C(Me)₂ | iPr | racemic |
| IV-205 | Me | Et | Me | NH | Ph | C(Me)₂ | iPr | (S)- |
| IV-206 | Me | Me | Me | N(Me) | Ph | C(Me)₂ | iPr | racemic |
| IV-207 | Me | Me | Me | N(Me) | Ph | C(Me)₂ | iPr | (S)- |
| IV-208 | Me | Et | Me | N(Me) | Ph | C(Me)₂ | iPr | racemic |
| IV-209 | Me | Et | Me | N(Me) | Ph | C(Me)₂ | iPr | (S)- |
| IV-210 | Me | Me | Me | NH | Ph | C(Me)₂ | cPr | racemic |
| IV-211 | Me | Me | Me | NH | Ph | C(Me)₂ | cPr | (S)- |
| IV-212 | Me | Et | Me | NH | Ph | C(Me)₂ | cPr | racemic |
| IV-213 | Me | Et | Me | NH | Ph | C(Me)₂ | cPr | (S)- |
| IV-214 | Me | Me | Me | N(Me) | Ph | C(Me)₂ | cPr | racemic |
| IV-215 | Me | Me | Me | N(Me) | Ph | C(Me)₂ | cPr | (S)- |
| IV-216 | Me | Et | Me | N(Me) | Ph | C(Me)₂ | cPr | racemic |
| IV-217 | Me | Et | Me | N(Me) | Ph | C(Me)₂ | cPr | (S)- |
| IV-218 | Me | Me | Me | NH | Ph | C(Me)₂ | Ph | racemic |
| IV-219 | Me | Me | Me | NH | Ph | C(Me)₂ | Ph | (S)- |
| IV-220 | Me | Et | Me | NH | Ph | C(Me)₂ | Ph | racemic |
| IV-221 | Me | Et | Me | NH | Ph | C(Me)₂ | Ph | (S)- |
| IV-222 | Me | Me | Me | N(Me) | Ph | C(Me)₂ | Ph | racemic |
| IV-223 | Me | Me | Me | N(Me) | Ph | C(Me)₂ | Ph | (S)- |
| IV-224 | Me | Et | Me | N(Me) | Ph | C(Me)₂ | Ph | racemic |
| IV-225 | Me | Et | Me | N(Me) | Ph | C(Me)₂ | Ph | (S)- |
| IV-226 | Me | Me | Me | NH | Ph | (CH₂)₂ | H | racemic |
| IV-227 | Me | Me | Me | NH | Ph | (CH₂)₂ | H | (R)- |
| IV-228 | Me | Et | Me | NH | Ph | (CH₂)₂ | H | racemic |
| IV-229 | Me | Et | Me | NH | Ph | (CH₂)₂ | H | (R)- |
| IV-230 | Me | Me | Me | N(Me) | Ph | (CH₂)₂ | H | racemic |
| IV-231 | Me | Me | Me | N(Me) | Ph | (CH₂)₂ | H | (R)- |
| IV-232 | Me | Et | Me | N(Me) | Ph | (CH₂)₂ | H | racemic |
| IV-233 | Me | Et | Me | N(Me) | Ph | (CH₂)₂ | H | (R)- |
| IV-234 | Me | Me | Me | NH | Ph | (CH₂)₂ | Me | racemic |
| IV-235 | Me | Me | Me | NH | Ph | (CH₂)₂ | Me | (R)- |
| IV-236 | Me | Et | Me | NH | Ph | (CH₂)₂ | Me | racemic |
| IV-237 | Me | Et | Me | NH | Ph | (CH₂)₂ | Me | (R)- |
| IV-238 | Me | Me | Me | N(Me) | Ph | (CH₂)₂ | Me | racemic |
| IV-239 | Me | Me | Me | N(Me) | Ph | (CH₂)₂ | Me | (R)- |
| IV-240 | Me | Et | Me | N(Me) | Ph | (CH₂)₂ | Me | racemic |
| IV-241 | Me | Et | Me | N(Me) | Ph | (CH₂)₂ | Me | (R)- |
| IV-242 | Me | Me | Me | NH | Ph | (CH₂)₂ | CHF₂ | racemic |
| IV-243 | Me | Me | Me | NH | Ph | (CH₂)₂ | CHF₂ | (R)- |
| IV-244 | Me | Et | Me | NH | Ph | (CH₂)₂ | CHF₂ | racemic |
| IV-245 | Me | Et | Me | NH | Ph | (CH₂)₂ | CHF₂ | (R)- |
| IV-246 | Me | Me | Me | N(Me) | Ph | (CH₂)₂ | CHF₂ | racemic |
| IV-247 | Me | Me | Me | N(Me) | Ph | (CH₂)₂ | CHF₂ | (R)- |
| IV-248 | Me | Et | Me | N(Me) | Ph | (CH₂)₂ | CHF₂ | racemic |
| IV-249 | Me | Et | Me | N(Me) | Ph | (CH₂)₂ | CHF₂ | (R)- |
| IV-250 | Me | Me | Me | NH | Ph | (CH₂)₂ | Et | racemic |

TABLE 69

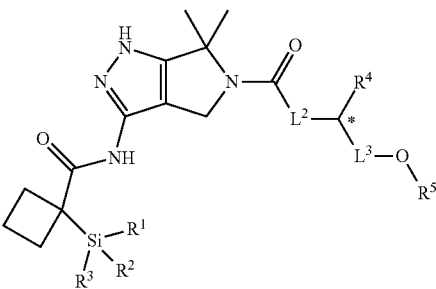

(IV)

| Compound No. | R¹ | R² | R³ | L² | R⁴ | L³ | R⁵ | Configuration |
|---|---|---|---|---|---|---|---|---|
| IV-251 | Me | Me | Me | NH | Ph | (CH₂)₂ | Et | (R)- |
| IV-252 | Me | Et | Me | NH | Ph | (CH₂)₂ | Et | racemic |
| IV-253 | Me | Et | Me | NH | Ph | (CH₂)₂ | Et | (R)- |
| IV-254 | Me | Me | Me | N(Me) | Ph | (CH₂)₂ | Et | racemic |
| IV-255 | Me | Me | Me | N(Me) | Ph | (CH₂)₂ | Et | (R)- |
| IV-256 | Me | Et | Me | N(Me) | Ph | (CH₂)₂ | Et | racemic |
| IV-257 | Me | Et | Me | N(Me) | Ph | (CH₂)₂ | Et | (R)- |
| IV-258 | Me | Me | Me | NH | Ph | (CH₂)₂ | iPr | racemic |
| IV-259 | Me | Me | Me | NH | Ph | (CH₂)₂ | iPr | (R)- |
| IV-260 | Me | Et | Me | NH | Ph | (CH₂)₂ | iPr | racemic |
| IV-261 | Me | Et | Me | NH | Ph | (CH₂)₂ | iPr | (R)- |
| IV-262 | Me | Me | Me | N(Me) | Ph | (CH₂)₂ | iPr | racemic |
| IV-263 | Me | Me | Me | N(Me) | Ph | (CH₂)₂ | iPr | (R)- |
| IV-264 | Me | Et | Me | N(Me) | Ph | (CH₂)₂ | iPr | racemic |
| IV-265 | Me | Et | Me | N(Me) | Ph | (CH₂)₂ | iPr | (R)- |
| IV-266 | Me | Me | Me | NH | Ph | (CH₂)₂ | cPr | racemic |
| IV-267 | Me | Me | Me | NH | Ph | (CH₂)₂ | cPr | (R)- |
| IV-268 | Me | Et | Me | NH | Ph | (CH₂)₂ | cPr | racemic |
| IV-269 | Me | Et | Me | NH | Ph | (CH₂)₂ | cPr | (R)- |
| IV-270 | Me | Me | Me | N(Me) | Ph | (CH₂)₂ | cPr | racemic |
| IV-271 | Me | Me | Me | N(Me) | Ph | (CH₂)₂ | cPr | (R)- |
| IV-272 | Me | Et | Me | N(Me) | Ph | (CH₂)₂ | cPr | racemic |
| IV-273 | Me | Et | Me | N(Me) | Ph | (CH₂)₂ | cPr | (R)- |
| IV-274 | Me | Me | Me | NH | Ph | (CH₂)₂ | Ph | racemic |
| IV-275 | Me | Me | Me | NH | Ph | (CH₂)₂ | Ph | (R)- |
| IV-276 | Me | Et | Me | NH | Ph | (CH₂)₂ | Ph | racemic |
| IV-277 | Me | Et | Me | NH | Ph | (CH₂)₂ | Ph | (R)- |
| IV-278 | Me | Me | Me | N(Me) | Ph | (CH₂)₂ | Ph | racemic |
| IV-279 | Me | Me | Me | N(Me) | Ph | (CH₂)₂ | Ph | (R)- |
| IV-280 | Me | Et | Me | N(Me) | Ph | (CH₂)₂ | Ph | racemic |
| IV-281 | Me | Et | Me | N(Me) | Ph | (CH₂)₂ | Ph | (R)- |
| IV-282 | Me | Me | Me | NH | Ph | (CH₂)₃ | H | racemic |
| IV-283 | Me | Me | Me | NH | Ph | (CH₂)₃ | H | (R)- |
| IV-284 | Me | Et | Me | NH | Ph | (CH₂)₃ | H | racemic |
| IV-285 | Me | Et | Me | NH | Ph | (CH₂)₃ | H | (R)- |
| IV-286 | Me | Me | Me | N(Me) | Ph | (CH₂)₃ | H | racemic |
| IV-287 | Me | Me | Me | N(Me) | Ph | (CH₂)₃ | H | (R)- |
| IV-288 | Me | Et | Me | N(Me) | Ph | (CH₂)₃ | H | racemic |
| IV-289 | Me | Et | Me | N(Me) | Ph | (CH₂)₃ | H | (R)- |
| IV-290 | Me | Me | Me | NH | Ph | (CH₂)₄ | H | racemic |
| IV-291 | Me | Me | Me | NH | Ph | (CH₂)₄ | H | (R)- |
| IV-292 | Me | Et | Me | NH | Ph | (CH₂)₄ | H | racemic |
| IV-293 | Me | Et | Me | NH | Ph | (CH₂)₄ | H | (R)- |
| IV-294 | Me | Me | Me | N(Me) | Ph | (CH₂)₄ | H | racemic |
| IV-295 | Me | Me | Me | N(Me) | Ph | (CH₂)₄ | H | (R)- |
| IV-296 | Me | Et | Me | N(Me) | Ph | (CH₂)₄ | H | racemic |
| IV-297 | Me | Et | Me | N(Me) | Ph | (CH₂)₄ | H | (R)- |
| IV-298 | Me | Me | Me | NH | Ph | CH₂C(Me)₂ | H | racemic |
| IV-299 | Me | Me | Me | NH | Ph | CH₂C(Me)₂ | H | (R)- |
| IV-300 | Me | Et | Me | NH | Ph | CH₂C(Me)₂ | H | racemic |

TABLE 70

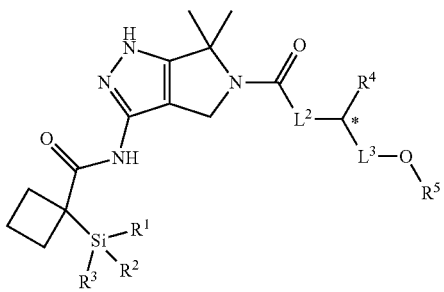

(IV)

| Compound No. | R¹ | R² | R³ | L² | R⁴ | L³ | R⁵ | Configuration |
|---|---|---|---|---|---|---|---|---|
| IV-301 | Me | Et | Me | NH | Ph | CH$_2$C(Me)$_2$ | H | (R)- |
| IV-302 | Me | Me | Me | N(Me) | Ph | CH$_2$C(Me)$_2$ | H | racemic |
| IV-303 | Me | Me | Me | N(Me) | Ph | CH$_2$C(Me)$_2$ | H | (R)- |
| IV-304 | Me | Et | Me | N(Me) | Ph | CH$_2$C(Me)$_2$ | H | racemic |
| IV-305 | Me | Et | Me | N(Me) | Ph | CH$_2$C(Me)$_2$ | H | (R)- |
| IV-306 | Me | Me | Me | NH | Ph | CH$_2$C(Me)$_2$ | Me | racemic |
| IV-307 | Me | Me | Me | NH | Ph | CH$_2$C(Me)$_2$ | Me | (R)- |
| IV-308 | Me | Et | Me | NH | Ph | CH$_2$C(Me)$_2$ | Me | racemic |
| IV-309 | Me | Et | Me | NH | Ph | CH$_2$C(Me)$_2$ | Me | (R)- |
| IV-310 | Me | Me | Me | N(Me) | Ph | CH$_2$C(Me)$_2$ | Me | racemic |
| IV-311 | Me | Me | Me | N(Me) | Ph | CH$_2$C(Me)$_2$ | Me | (R)- |
| IV-312 | Me | Et | Me | N(Me) | Ph | CH$_2$C(Me)$_2$ | Me | racemic |
| IV-313 | Me | Et | Me | N(Me) | Ph | CH$_2$C(Me)$_2$ | Me | (R)- |
| IV-314 | Me | Me | Me | NH | Ph | CH$_2$C(Me)$_2$ | CHF$_2$ | racemic |
| IV-315 | Me | Me | Me | NH | Ph | CH$_2$C(Me)$_2$ | CHF$_2$ | (R)- |
| IV-316 | Me | Et | Me | NH | Ph | CH$_2$C(Me)$_2$ | CHF$_2$ | racemic |
| IV-317 | Me | Et | Me | NH | Ph | CH$_2$C(Me)$_2$ | CHF$_2$ | (R)- |
| IV-318 | Me | Me | Me | N(Me) | Ph | CH$_2$C(Me)$_2$ | CHF$_2$ | racemic |
| IV-319 | Me | Me | Me | N(Me) | Ph | CH$_2$C(Me)$_2$ | CHF$_2$ | (R)- |
| IV-320 | Me | Et | Me | N(Me) | Ph | CH$_2$C(Me)$_2$ | CHF$_2$ | racemic |
| IV-321 | Me | Et | Me | N(Me) | Ph | CH$_2$C(Me)$_2$ | CHF$_2$ | (R)- |
| IV-322 | Me | Me | Me | NH | Ph | CH$_2$C(Me)$_2$ | Et | racemic |
| IV-323 | Me | Me | Me | NH | Ph | CH$_2$C(Me)$_2$ | Et | (R)- |
| IV-324 | Me | Et | Me | NH | Ph | CH$_2$C(Me)$_2$ | Et | racemic |
| IV-325 | Me | Et | Me | NH | Ph | CH$_2$C(Me)$_2$ | Et | (R)- |
| IV-326 | Me | Me | Me | N(Me) | Ph | CH$_2$C(Me)$_2$ | Et | racemic |
| IV-327 | Me | Me | Me | N(Me) | Ph | CH$_2$C(Me)$_2$ | Et | (R)- |
| IV-328 | Me | Et | Me | N(Me) | Ph | CH$_2$C(Me)$_2$ | Et | racemic |
| IV-329 | Me | Et | Me | N(Me) | Ph | CH$_2$C(Me)$_2$ | Et | (R)- |
| IV-330 | Me | Me | Me | NH | Ph | CH$_2$C(Me)$_2$ | iPr | racemic |
| IV-331 | Me | Me | Me | NH | Ph | CH$_2$C(Me)$_2$ | iPr | (R)- |
| IV-332 | Me | Et | Me | NH | Ph | CH$_2$C(Me)$_2$ | iPr | racemic |
| IV-333 | Me | Et | Me | NH | Ph | CH$_2$C(Me)$_2$ | iPr | (R)- |
| IV-334 | Me | Me | Me | N(Me) | Ph | CH$_2$C(Me)$_2$ | iPr | racemic |
| IV-335 | Me | Me | Me | N(Me) | Ph | CH$_2$C(Me)$_2$ | iPr | (R)- |
| IV-336 | Me | Et | Me | N(Me) | Ph | CH$_2$C(Me)$_2$ | iPr | racemic |
| IV-337 | Me | Et | Me | N(Me) | Ph | CH$_2$C(Me)$_2$ | iPr | (R)- |
| IV-338 | Me | Me | Me | NH | Ph | CH$_2$C(Me)$_2$ | cPr | racemic |
| IV-339 | Me | Me | Me | NH | Ph | CH$_2$C(Me)$_2$ | cPr | (R)- |
| IV-340 | Me | Et | Me | NH | Ph | CH$_2$C(Me)$_2$ | cPr | racemic |
| IV-341 | Me | Et | Me | NH | Ph | CH$_2$C(Me)$_2$ | cPr | (R)- |
| IV-342 | Me | Me | Me | N(Me) | Ph | CH$_2$C(Me)$_2$ | cPr | racemic |
| IV-343 | Me | Me | Me | N(Me) | Ph | CH$_2$C(Me)$_2$ | cPr | (R)- |
| IV-344 | Me | Et | Me | N(Me) | Ph | CH$_2$C(Me)$_2$ | cPr | racemic |
| IV-345 | Me | Et | Me | N(Me) | Ph | CH$_2$C(Me)$_2$ | cPr | (R)- |
| IV-346 | Me | Me | Me | NH | Ph | CH$_2$C(Me)$_2$ | Ph | racemic |
| IV-347 | Me | Me | Me | NH | Ph | CH$_2$C(Me)$_2$ | Ph | (R)- |
| IV-348 | Me | Et | Me | NH | Ph | CH$_2$C(Me)$_2$ | Ph | racemic |
| IV-349 | Me | Et | Me | NH | Ph | CH$_2$C(Me)$_2$ | Ph | (R)- |
| IV-350 | Me | Me | Me | N(Me) | Ph | CH$_2$C(Me)$_2$ | Ph | racemic |

TABLE 71

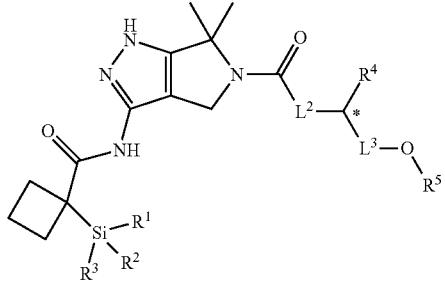

(IV)

| Compound No. | R¹ | R² | R³ | L² | R⁴ | L³ | R⁵ | Configuration |
|---|---|---|---|---|---|---|---|---|
| IV-351 | Me | Me | Me | N(Me) | Ph | CH$_2$C(Me)$_2$ | Ph | (R)- |
| IV-352 | Me | Et | Me | N(Me) | Ph | CH$_2$C(Me)$_2$ | Ph | racemic |
| IV-353 | Me | Et | Me | N(Me) | Ph | CH$_2$C(Me)$_2$ | Ph | (R)- |
| IV-354 | Me | Me | Me | NH | Ph | C(Me)$_2$CH$_2$ | H | racemic |
| IV-355 | Me | Me | Me | NH | Ph | C(Me)$_2$CH$_2$ | H | (S)- |
| IV-356 | Me | Et | Me | NH | Ph | C(Me)$_2$CH$_2$ | H | racemic |
| IV-357 | Me | Et | Me | NH | Ph | C(Me)$_2$CH$_2$ | H | (S)- |
| IV-358 | Me | Me | Me | N(Me) | Ph | C(Me)$_2$CH$_2$ | H | racemic |
| IV-359 | Me | Me | Me | N(Me) | Ph | C(Me)$_2$CH$_2$ | H | (S)- |
| IV-360 | Me | Et | Me | N(Me) | Ph | C(Me)$_2$CH$_2$ | H | racemic |
| IV-361 | Me | Et | Me | N(Me) | Ph | C(Me)$_2$CH$_2$ | H | (S)- |
| IV-362 | Me | Me | Me | NH | Ph | CF$_2$CH$_2$ | H | racemic |
| IV-363 | Me | Me | Me | NH | Ph | CF$_2$CH$_2$ | H | (S)- |
| IV-364 | Me | Et | Me | NH | Ph | CF$_2$CH$_2$ | H | racemic |
| IV-365 | Me | Et | Me | NH | Ph | CF$_2$CH$_2$ | H | (S)- |
| IV-366 | Me | Me | Me | N(Me) | Ph | CF$_2$CH$_2$ | H | racemic |
| IV-367 | Me | Me | Me | N(Me) | Ph | CF$_2$CH$_2$ | H | (S)- |
| IV-368 | Me | Et | Me | N(Me) | Ph | CF$_2$CH$_2$ | H | racemic |
| IV-369 | Me | Et | Me | N(Me) | Ph | CF$_2$CH$_2$ | H | (S)- |
| IV-370 | Me | Me | Me | NH | Ph | CH=CHCH$_2$ | H | racemic |
| IV-371 | Me | Me | Me | NH | Ph | CH=CHCH$_2$ | H | (S)- |
| IV-372 | Me | Et | Me | NH | Ph | CH=CHCH$_2$ | H | racemic |
| IV-373 | Me | Et | Me | NH | Ph | CH=CHCH$_2$ | H | (S)- |
| IV-374 | Me | Me | Me | N(Me) | Ph | CH=CHCH$_2$ | H | racemic |
| IV-375 | Me | Me | Me | N(Me) | Ph | CH=CHCH$_2$ | H | (S)- |
| IV-376 | Me | Et | Me | N(Me) | Ph | CH=CHCH$_2$ | H | racemic |
| IV-377 | Me | Et | Me | N(Me) | Ph | CH=CHCH$_2$ | H | (S)- |
| IV-378 | Me | Me | Me | NH | Ph | C≡CCH$_2$ | H | racemic |
| IV-379 | Me | Me | Me | NH | Ph | C≡CCH$_2$ | H | (S)- |
| IV-380 | Me | Et | Me | NH | Ph | C≡CCH$_2$ | H | racemic |
| IV-381 | Me | Et | Me | NH | Ph | C≡CCH$_2$ | H | (S)- |
| IV-382 | Me | Me | Me | N(Me) | Ph | C≡CCH$_2$ | H | racemic |
| IV-383 | Me | Me | Me | N(Me) | Ph | C≡CCH$_2$ | H | (S)- |
| IV-384 | Me | Et | Me | N(Me) | Ph | C≡CCH$_2$ | H | racemic |
| IV-385 | Me | Et | Me | N(Me) | Ph | C≡CCH$_2$ | H | (S)- |
| IV-386 | Me | Me | Me | NH | Ph | 1,1-Cyclopropylene | H | racemic |
| IV-387 | Me | Me | Me | NH | Ph | 1,1-Cyclopropylene | H | (S)- |
| IV-388 | Me | Et | Me | NH | Ph | 1,1-Cyclopropylene | H | racemic |
| IV-389 | Me | Et | Me | NH | Ph | 1,1-Cyclopropylene | H | (S)- |
| IV-390 | Me | Me | Me | N(Me) | Ph | 1,1-Cyclopropylene | H | racemic |
| IV-391 | Me | Me | Me | N(Me) | Ph | 1,1-Cyclopropylene | H | (S)- |
| IV-392 | Me | Et | Me | N(Me) | Ph | 1,1-Cyclopropylene | H | racemic |
| IV-393 | Me | Et | Me | N(Me) | Ph | 1,1-Cyclopropylene | H | (S)- |
| IV-394 | Me | Me | Me | NH | Ph | 1,2-Cyclopropynylene | H | racemic |
| IV-395 | Me | Me | Me | NH | Ph | 1,2-Cyclopropynylene | H | (S)- |
| IV-396 | Me | Et | Me | NH | Ph | 1,2-Cyclopropynylene | H | racemic |
| IV-397 | Me | Et | Me | NH | Ph | 1,2-Cyclopropynylene | H | (S)- |
| IV-398 | Me | Me | Me | N(Me) | Ph | 1,2-Cyclopropynylene | H | racemic |
| IV-399 | Me | Me | Me | N(Me) | Ph | 1,2-Cyclopropynylene | H | (S)- |
| IV-400 | Me | Et | Me | N(Me) | Ph | 1,2-Cyclopropynylene | H | racemic |

TABLE 72

(IV)

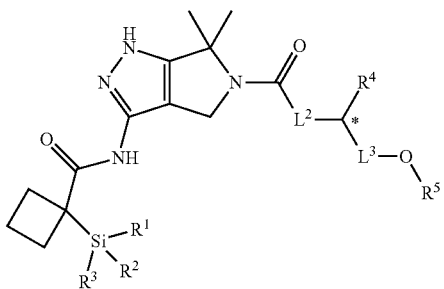

| Compound No. | R¹ | R² | R³ | L² | R⁴ | L³ | R⁵ | Configuration |
|---|---|---|---|---|---|---|---|---|
| IV-401 | Me | Et | Me | N(Me) | Ph | 1,2-Cyclopropynylene | H | (S)- |
| IV-402 | Me | Me | Me | NH | Ph | C(=O) | H | racemic |
| IV-403 | Me | Me | Me | NH | Ph | C(=O) | H | (S)- |
| IV-404 | Me | Et | Me | NH | Ph | C(=O) | H | racemic |
| IV-405 | Me | Et | Me | NH | Ph | C(=O) | H | (S)- |
| IV-406 | Me | Me | Me | N(Me) | Ph | C(=O) | H | racemic |
| IV-407 | Me | Me | Me | N(Me) | Ph | C(=O) | H | (S)- |
| IV-408 | Me | Et | Me | N(Me) | Ph | C(=O) | H | racemic |
| IV-409 | Me | Et | Me | N(Me) | Ph | C(=O) | H | (S)- |
| IV-410 | Me | Me | Me | NH | Ph | C(=O) | Bn | racemic |
| IV-411 | Me | Me | Me | NH | Ph | C(=O) | Bn | (S)- |
| IV-412 | Me | Et | Me | NH | Ph | C(=O) | Bn | racemic |
| IV-413 | Me | Et | Me | NH | Ph | C(=O) | Bn | (S)- |
| IV-414 | Me | Me | Me | N(Me) | Ph | C(=O) | Bn | racemic |
| IV-415 | Me | Me | Me | N(Me) | Ph | C(=O) | Bn | (S)- |
| IV-416 | Me | Et | Me | N(Me) | Ph | C(=O) | Bn | racemic |
| IV-417 | Me | Et | Me | N(Me) | Ph | C(=O) | Bn | (S)- |
| IV-418 | Me | Me | Me | NH | Ph | C(=O) | Me | racemic |
| IV-419 | Me | Me | Me | NH | Ph | C(=O) | Me | (S)- |
| IV-420 | Me | Et | Me | NH | Ph | C(=O) | Me | racemic |
| IV-421 | Me | Et | Me | NH | Ph | C(=O) | Me | (S)- |
| IV-422 | Me | Me | Me | N(Me) | Ph | C(=O) | Me | racemic |
| IV-423 | Me | Me | Me | N(Me) | Ph | C(=O) | Me | (S)- |
| IV-424 | Me | Et | Me | N(Me) | Ph | C(=O) | Me | racemic |
| IV-425 | Me | Et | Me | N(Me) | Ph | C(=O) | Me | (S)- |
| IV-426 | Me | Me | Me | NH | Ph | CH(Me) | H | racemic |
| IV-427 | Me | Me | Me | NH | Ph | CH(Me) | H | (S)- |
| IV-428 | Me | Et | Me | NH | Ph | CH(Me) | H | racemic |
| IV-429 | Me | Et | Me | NH | Ph | CH(Me) | H | (S)- |
| IV-430 | Me | Me | Me | NH | Ph | CH(iPr) | H | racemic |
| IV-431 | Me | Me | Me | NH | Ph | CH(iPr) | H | (S)- |
| IV-432 | Me | Et | Me | NH | Ph | CH(iPr) | H | racemic |
| IV-433 | Me | Et | Me | NH | Ph | CH(iPr) | H | (S)- |
| IV-434 | Me | Me | Me | NH | Ph | CH(Ph) | H | racemic |
| IV-435 | Me | Me | Me | NH | Ph | CH(Ph) | H | (S)- |
| IV-436 | Me | Et | Me | NH | Ph | CH(Ph) | H | racemic |
| IV-437 | Me | Et | Me | NH | Ph | CH(Ph) | H | (S)- |
| IV-438 | Me | Me | Me | NH | H | CH₂ | H | |
| IV-439 | Me | Et | Me | NH | H | CH₂ | H | |
| IV-440 | Me | Me | Me | N(Me) | H | CH₂ | H | |
| IV-441 | Me | Et | Me | N(Me) | H | CH₂ | H | |
| IV-442 | Me | Me | Me | NH | H | CH(Me) | H | |
| IV-443 | Me | Et | Me | NH | H | CH(Me) | H | |
| IV-444 | Me | Me | Me | N(Me) | H | CH(Me) | H | |
| IV-445 | Me | Et | Me | N(Me) | H | CH(Me) | H | |
| IV-446 | Me | Me | Me | NH | H | CH(iPr) | H | |
| IV-447 | Me | Et | Me | NH | H | CH(iPr) | H | |
| IV-448 | Me | Me | Me | N(Me) | H | CH(iPr) | H | |
| IV-449 | Me | Et | Me | N(Me) | H | CH(iPr) | H | |
| IV-450 | Me | Me | Me | NH | H | CH(Ph) | H | |

TABLE 73

(IV)

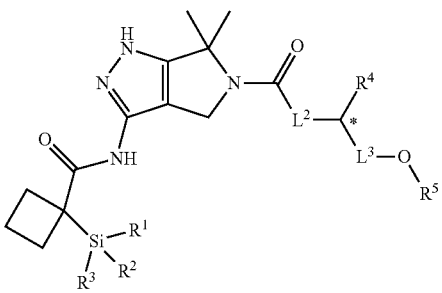

| Compound No. | R¹ | R² | R³ | L² | R⁴ | L³ | R⁵ | Configuration |
|---|---|---|---|---|---|---|---|---|
| IV-451 | Me | Et | Me | N(Me) | H | CH(Ph) | H | |
| IV-452 | Me | Me | Me | N(Me) | H | CH(Ph) | H | |
| IV-453 | Me | Et | Me | N(Me) | H | CH(Ph) | H | |
| IV-454 | Me | Me | Me | NH | Me | CH₂ | H | racemic |
| IV-455 | Me | Me | Me | NH | Me | CH₂ | H | (S)- |
| IV-456 | Me | Et | Me | NH | Me | CH₂ | H | racemic |
| IV-457 | Me | Et | Me | NH | Me | CH₂ | H | (S)- |
| IV-458 | Me | Me | Me | NH | Me | CH(Me) | H | racemic |
| IV-459 | Me | Me | Me | NH | Me | CH(Me) | H | (S)- |
| IV-460 | Me | Et | Me | NH | Me | CH(Me) | H | racemic |
| IV-461 | Me | Et | Me | NH | Me | CH(Me) | H | (S)- |
| IV-462 | Me | Me | Me | NH | Me | CH(iPr) | H | racemic |
| IV-463 | Me | Me | Me | NH | Me | CH(iPr) | H | (S)- |
| IV-464 | Me | Et | Me | NH | Me | CH(iPr) | H | racemic |
| IV-465 | Me | Et | Me | NH | Me | CH(iPr) | H | (S)- |
| IV-466 | Me | Me | Me | NH | Me | CH(Ph) | H | racemic |
| IV-467 | Me | Me | Me | NH | Me | CH(Ph) | H | (S)- |
| IV-468 | Me | Et | Me | NH | Me | CH(Ph) | H | racemic |
| IV-469 | Me | Et | Me | NH | Me | CH(Ph) | H | (S)- |
| IV-470 | Me | Me | Me | N(Me) | Me | CH₂ | H | racemic |
| IV-471 | Me | Me | Me | N(Me) | Me | CH₂ | H | (S)- |
| IV-472 | Me | Et | Me | N(Me) | Me | CH₂ | H | racemic |
| IV-473 | Me | Et | Me | N(Me) | Me | CH₂ | H | (S)- |
| IV-474 | Me | Me | Me | NH | iPr | CH₂ | H | racemic |
| IV-475 | Me | Me | Me | NH | iPr | CH₂ | H | (S)- |
| IV-476 | Me | Et | Me | NH | iPr | CH₂ | H | racemic |
| IV-477 | Me | Et | Me | NH | iPr | CH₂ | H | (S)- |
| IV-478 | Me | Me | Me | NH | iPr | CH(Me) | H | racemic |
| IV-479 | Me | Me | Me | NH | iPr | CH(Me) | H | (S)- |
| IV-480 | Me | Et | Me | NH | iPr | CH(Me) | H | racemic |
| IV-481 | Me | Et | Me | NH | iPr | CH(Me) | H | (S)- |
| IV-482 | Me | Me | Me | NH | iPr | CH(iPr) | H | racemic |
| IV-483 | Me | Me | Me | NH | iPr | CH(iPr) | H | (S)- |
| IV-484 | Me | Et | Me | NH | iPr | CH(iPr) | H | racemic |
| IV-485 | Me | Et | Me | NH | iPr | CH(iPr) | H | (S)- |
| IV-486 | Me | Me | Me | NH | iPr | CH(Ph) | H | racemic |
| IV-487 | Me | Me | Me | NH | iPr | CH(Ph) | H | (S)- |
| IV-488 | Me | Et | Me | NH | iPr | CH(Ph) | H | racemic |
| IV-489 | Me | Et | Me | NH | iPr | CH(Ph) | H | (S)- |
| IV-490 | Me | Me | Me | N(Me) | iPr | CH₂ | H | racemic |
| IV-491 | Me | Me | Me | N(Me) | iPr | CH₂ | H | (S)- |
| IV-492 | Me | Et | Me | N(Me) | iPr | CH₂ | H | racemic |
| IV-493 | Me | Et | Me | N(Me) | iPr | CH₂ | H | (S)- |
| IV-494 | Me | Me | Me | NH | cHex | CH₂ | H | racemic |
| IV-495 | Me | Me | Me | NH | cHex | CH₂ | H | (S)- |
| IV-496 | Me | Et | Me | NH | cHex | CH₂ | H | racemic |
| IV-497 | Me | Et | Me | NH | cHex | CH₂ | H | (S)- |
| IV-498 | Me | Me | Me | N(Me) | cHex | CH₂ | H | racemic |
| IV-499 | Me | Me | Me | N(Me) | cHex | CH₂ | H | (S)- |
| IV-500 | Me | Et | Me | N(Me) | cHex | CH₂ | H | racemic |

TABLE 74

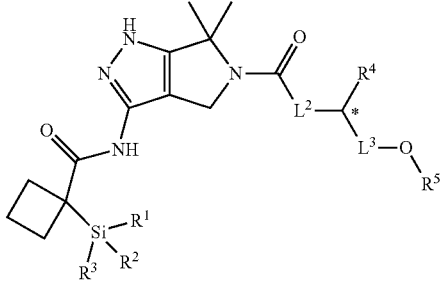

(IV)

| Compound No. | R¹ | R² | R³ | L² | R⁴ | L³ | R⁵ | Configuration |
|---|---|---|---|---|---|---|---|---|
| IV-501 | Me | Et | Me | N(Me) | cHex | CH₂ | H | (S)- |
| IV-502 | Me | Me | Me | NH | 1,3-Benzodioxol-4-yl | CH₂ | H | racemic |
| IV-503 | Me | Me | Me | NH | 1,3-Benzodioxol-4-yl | CH₂ | H | (S)- |
| IV-504 | Me | Et | Me | NH | 1,3-Benzodioxol-4-yl | CH₂ | H | racemic |
| IV-505 | Me | Et | Me | NH | 1,3-Benzodioxol-4-yl | CH₂ | H | (S)- |
| IV-506 | Me | Me | Me | N(Me) | 1,3-Benzodioxol-4-yl | CH₂ | H | racemic |
| IV-507 | Me | Me | Me | N(Me) | 1,3-Benzodioxol-4-yl | CH₂ | H | (S)- |
| IV-508 | Me | Et | Me | N(Me) | 1,3-Benzodioxol-4-yl | CH₂ | H | racemic |
| IV-509 | Me | Et | Me | N(Me) | 1,3-Benzodioxol-4-yl | CH₂ | H | (S)- |
| IV-510 | Me | Me | Me | NH | 2-F—Ph | CH₂ | H | racemic |
| IV-511 | Me | Me | Me | NH | 2-F—Ph | CH₂ | H | (S)- |
| IV-512 | Me | Et | Me | NH | 2-F—Ph | CH₂ | H | racemic |
| IV-513 | Me | Et | Me | NH | 2-F—Ph | CH₂ | H | (S)- |
| IV-514 | Me | Me | Me | N(Me) | 2-F—Ph | CH₂ | H | racemic |
| IV-515 | Me | Me | Me | N(Me) | 2-F—Ph | CH₂ | H | (S)- |
| IV-516 | Me | Et | Me | N(Me) | 2-F—Ph | CH₂ | H | racemic |
| IV-517 | Me | Et | Me | N(Me) | 2-F—Ph | CH₂ | H | (S)- |
| IV-518 | Me | Me | Me | NH | 3-F—Ph | CH₂ | H | racemic |
| IV-519 | Me | Me | Me | NH | 3-F—Ph | CH₂ | H | (S)- |
| IV-520 | Me | Et | Me | NH | 3-F—Ph | CH₂ | H | racemic |
| IV-521 | Me | Et | Me | NH | 3-F—Ph | CH₂ | H | (S)- |
| IV-522 | Me | Me | Me | N(Me) | 3-F—Ph | CH₂ | H | racemic |
| IV-523 | Me | Me | Me | N(Me) | 3-F—Ph | CH₂ | H | (S)- |
| IV-524 | Me | Et | Me | N(Me) | 3-F—Ph | CH₂ | H | racemic |
| IV-525 | Me | Et | Me | N(Me) | 3-F—Ph | CH₂ | H | (S)- |
| IV-526 | Me | Me | Me | NH | 4-F—Ph | CH₂ | H | racemic |
| IV-527 | Me | Me | Me | NH | 4-F—Ph | CH₂ | H | (S)- |
| IV-528 | Me | Et | Me | NH | 4-F—Ph | CH₂ | H | racemic |
| IV-529 | Me | Et | Me | NH | 4-F—Ph | CH₂ | H | (S)- |
| IV-530 | Me | Me | Me | N(Me) | 4-F—Ph | CH₂ | H | racemic |
| IV-531 | Me | Me | Me | N(Me) | 4-F—Ph | CH₂ | H | (S)- |
| IV-532 | Me | Et | Me | N(Me) | 4-F—Ph | CH₂ | H | racemic |
| IV-533 | Me | Et | Me | N(Me) | 4-F—Ph | CH₂ | H | (S)- |
| IV-534 | Me | Me | Me | NH | 2-Py | CH₂ | H | racemic |
| IV-535 | Me | Me | Me | NH | 2-Py | CH₂ | H | (S)- |
| IV-536 | Me | Et | Me | NH | 2-Py | CH₂ | H | racemic |
| IV-537 | Me | Et | Me | NH | 2-Py | CH₂ | H | (S)- |
| IV-538 | Me | Me | Me | N(Me) | 2-Py | CH₂ | H | racemic |
| IV-539 | Me | Me | Me | N(Me) | 2-Py | CH₂ | H | (S)- |
| IV-540 | Me | Et | Me | N(Me) | 2-Py | CH₂ | H | racemic |
| IV-541 | Me | Et | Me | N(Me) | 2-Py | CH₂ | H | (S)- |
| IV-542 | Me | Me | Me | NH | 3-Py | CH₂ | H | racemic |
| IV-543 | Me | Me | Me | NH | 3-Py | CH₂ | H | (S)- |
| IV-544 | Me | Et | Me | NH | 3-Py | CH₂ | H | racemic |
| IV-545 | Me | Et | Me | NH | 3-Py | CH₂ | H | (S)- |
| IV-546 | Me | Me | Me | N(Me) | 3-Py | CH₂ | H | racemic |
| IV-547 | Me | Me | Me | N(Me) | 3-Py | CH₂ | H | (S)- |
| IV-548 | Me | Et | Me | N(Me) | 3-Py | CH₂ | H | racemic |
| IV-549 | Me | Et | Me | N(Me) | 3-Py | CH₂ | H | (S)- |
| IV-550 | Me | Me | Me | NH | 4-Py | CH₂ | H | racemic |

TABLE 75

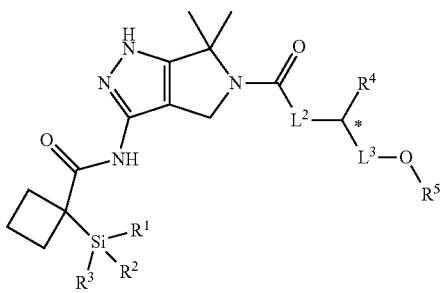

(IV)

| Compound No. | R¹ | R² | R³ | L² | R⁴ | L³ | R⁵ | Configuration |
|---|---|---|---|---|---|---|---|---|
| IV-551 | Me | Me | Me | NH | 4-Py | CH₂ | H | (S)- |
| IV-552 | Me | Et | Me | NH | 4-Py | CH₂ | H | racemic |
| IV-553 | Me | Et | Me | NH | 4-Py | CH₂ | H | (S)- |
| IV-554 | Me | Me | Me | N(Me) | 4-Py | CH₂ | H | racemic |
| IV-555 | Me | Me | Me | N(Me) | 4-Py | CH₂ | H | (S)- |
| IV-556 | Me | Et | Me | N(Me) | 4-Py | CH₂ | H | racemic |
| IV-557 | Me | Et | Me | N(Me) | 4-Py | CH₂ | H | (S)- |
| IV-558 | Me | Me | Me | CH₂ | Ph | CH₂ | H | racemic |
| IV-559 | Me | Me | Me | CH₂ | Ph | CH₂ | H | (S)- |
| IV-560 | Me | Et | Me | CH₂ | Ph | CH₂ | H | racemic |
| IV-561 | Me | Et | Me | CH₂ | Ph | CH₂ | H | (S)- |
| IV-562 | Me | Me | Me | CH₂ | Ph | — | H | racemic |
| IV-563 | Me | Me | Me | CH₂ | Ph | — | H | (S)- |
| IV-564 | Me | Et | Me | CH₂ | Ph | — | H | racemic |
| IV-565 | Me | Et | Me | CH₂ | Ph | — | H | (S)- |
| IV-566 | Me | Me | Me | CH₂ | Ph | CH₂ | Me | racemic |
| IV-567 | Me | Me | Me | CH₂ | Ph | CH₂ | Me | (S)- |
| IV-568 | Me | Et | Me | CH₂ | Ph | CH₂ | Me | racemic |
| IV-569 | Me | Et | Me | CH₂ | Ph | CH₂ | Me | (S)- |
| IV-570 | Me | Me | Me | CH₂ | Ph | CH₂ | CHF₂ | racemic |
| IV-571 | Me | Me | Me | CH₂ | Ph | CH₂ | CHF₂ | (S)- |
| IV-572 | Me | Me | Me | CH₂ | Ph | CH₂ | Et | racemic |
| IV-573 | Me | Me | Me | CH₂ | Ph | CH₂ | Et | (S)- |
| IV-574 | Me | Et | Me | CH₂ | Ph | CH₂ | Et | racemic |
| IV-575 | Me | Et | Me | CH₂ | Ph | CH₂ | Et | (S)- |
| IV-576 | Me | Me | Me | CH₂ | Ph | CH₂ | cPr | racemic |
| IV-577 | Me | Me | Me | CH₂ | Ph | CH₂ | cPr | (S)- |
| IV-578 | Me | Et | Me | CH₂ | Ph | CH₂ | cPr | racemic |
| IV-579 | Me | Et | Me | CH₂ | Ph | CH₂ | cPr | (S)- |
| IV-580 | Me | Me | Me | CH₂ | Ph | CH₂ | Ph | racemic |
| IV-581 | Me | Me | Me | CH₂ | Ph | CH₂ | Ph | (S)- |
| IV-582 | Me | Et | Me | CH₂ | Ph | CH₂ | Ph | racemic |
| IV-583 | Me | Et | Me | CH₂ | Ph | CH₂ | Ph | (S)- |
| IV-584 | Me | Me | Me | CH₂ | Ph | C(Me)₂ | H | racemic |
| IV-585 | Me | Me | Me | CH₂ | Ph | C(Me)₂ | H | (S)- |
| IV-586 | Me | Et | Me | CH₂ | Ph | C(Me)₂ | H | racemic |
| IV-587 | Me | Et | Me | CH₂ | Ph | C(Me)₂ | H | (S)- |
| IV-588 | Me | Me | Me | CH₂ | Ph | C(Me)₂ | Me | racemic |
| IV-589 | Me | Me | Me | CH₂ | Ph | C(Me)₂ | Me | (S)- |
| IV-590 | Me | Et | Me | CH₂ | Ph | C(Me)₂ | Me | racemic |
| IV-591 | Me | Et | Me | CH₂ | Ph | C(Me)₂ | Me | (S)- |
| IV-592 | Me | Me | Me | CH₂ | Ph | C(Me)₂ | CHF₂ | racemic |
| IV-593 | Me | Me | Me | CH₂ | Ph | C(Me)₂ | CHF₂ | (S)- |
| IV-594 | Me | Me | Me | CH₂ | Ph | C(Me)₂ | Et | racemic |
| IV-595 | Me | Me | Me | CH₂ | Ph | C(Me)₂ | Et | (S)- |
| IV-596 | Me | Me | Me | CH₂ | Ph | C(Me)₂ | cPr | racemic |
| IV-597 | Me | Me | Me | CH₂ | Ph | C(Me)₂ | cPr | (S)- |
| IV-598 | Me | Me | Me | CH₂ | Ph | C(Me)₂ | Ph | racemic |
| IV-599 | Me | Me | Me | CH₂ | Ph | C(Me)₂ | Ph | (S)- |
| IV-600 | Me | Me | Me | CH₂ | Ph | (CH₂)₂ | H | racemic |

TABLE 76

(IV)

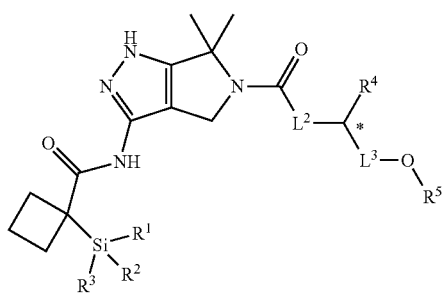

| Compound No. | R¹ | R² | R³ | L² | R⁴ | L³ | R⁵ | Configuration |
|---|---|---|---|---|---|---|---|---|
| IV-601 | Me | Me | Me | CH₂ | Ph | (CH₂)₂ | H | (S)- |
| IV-602 | Me | Et | Me | CH₂ | Ph | (CH₂)₂ | H | racemic |
| IV-603 | Me | Et | Me | CH₂ | Ph | (CH₂)₂ | H | (S)- |
| IV-604 | Me | Me | Me | CH₂ | Ph | (CH₂)₂ | Me | racemic |
| IV-605 | Me | Me | Me | CH₂ | Ph | (CH₂)₂ | Me | (S)- |
| IV-606 | Me | Et | Me | CH₂ | Ph | (CH₂)₂ | Me | racemic |
| IV-607 | Me | Et | Me | CH₂ | Ph | (CH₂)₂ | Me | (S)- |
| IV-608 | Me | Me | Me | CH₂ | Ph | (CH₂)₂ | CHF₂ | racemic |
| IV-609 | Me | Me | Me | CH₂ | Ph | (CH₂)₂ | CHF₂ | (S)- |
| IV-610 | Me | Me | Me | CH₂ | Ph | (CH₂)₂ | Et | racemic |
| IV-611 | Me | Me | Me | CH₂ | Ph | (CH₂)₂ | Et | (S)- |
| IV-612 | Me | Me | Me | CH₂ | Ph | (CH₂)₂ | cPr | racemic |
| IV-613 | Me | Me | Me | CH₂ | Ph | (CH₂)₂ | cPr | (S)- |
| IV-614 | Me | Me | Me | CH₂ | Ph | (CH₂)₂ | Ph | racemic |
| IV-615 | Me | Me | Me | CH₂ | Ph | (CH₂)₂ | Ph | (S)- |
| IV-616 | Me | Me | Me | CH₂ | Ph | CH₂C(Me)₂ | H | racemic |
| IV-617 | Me | Me | Me | CH₂ | Ph | CH₂C(Me)₂ | H | (S)- |
| IV-618 | Me | Et | Me | CH₂ | Ph | CH₂C(Me)₂ | H | racemic |
| IV-619 | Me | Et | Me | CH₂ | Ph | CH₂C(Me)₂ | H | (S)- |
| IV-620 | Me | Me | Me | CH₂ | Ph | CH₂C(Me)₂ | Me | racemic |
| IV-621 | Me | Me | Me | CH₂ | Ph | CH₂C(Me)₂ | Me | (S)- |
| IV-622 | Me | Et | Me | CH₂ | Ph | CH₂C(Me)₂ | Me | racemic |
| IV-623 | Me | Et | Me | CH₂ | Ph | CH₂C(Me)₂ | Me | (S)- |
| IV-624 | Me | Me | Me | CH₂ | Ph | CH₂C(Me)₂ | CHF₂ | racemic |
| IV-625 | Me | Me | Me | CH₂ | Ph | CH₂C(Me)₂ | CHF₂ | (S)- |
| IV-626 | Me | Me | Me | CH₂ | Ph | CH₂C(Me)₂ | Et | racemic |
| IV-627 | Me | Me | Me | CH₂ | Ph | CH₂C(Me)₂ | Et | (S)- |
| IV-628 | Me | Me | Me | CH₂ | Ph | CH₂C(Me)₂ | cPr | racemic |
| IV-629 | Me | Me | Me | CH₂ | Ph | CH₂C(Me)₂ | cPr | (S)- |
| IV-630 | Me | Me | Me | CH₂ | Ph | CH₂C(Me)₂ | Ph | racemic |
| IV-631 | Me | Me | Me | CH₂ | Ph | CH₂C(Me)₂ | Ph | (S)- |
| IV-632 | Me | Me | Me | — | Ph | CH₂ | H | racemic |
| IV-633 | Me | Me | Me | — | Ph | CH₂ | H | (S)- |
| IV-634 | Me | Me | Me | — | Ph | CH₂ | Me | racemic |
| IV-635 | Me | Me | Me | — | Ph | CH₂ | Me | (S)- |
| IV-636 | Me | Me | Me | CH=CH | Ph | CH₂ | H | racemic |
| IV-637 | Me | Me | Me | CH=CH | Ph | CH₂ | H | (S)- |
| IV-638 | Me | Me | Me | CH=CH | Ph | CH₂ | Me | racemic |
| IV-639 | Me | Me | Me | CH=CH | Ph | CH₂ | Me | (S)- |
| IV-640 | Me | Me | Me | C≡C | Ph | CH₂ | H | racemic |
| IV-641 | Me | Me | Me | C≡C | Ph | CH₂ | H | (S)- |
| IV-642 | Me | Me | Me | C≡C | Ph | CH₂ | Me | racemic |
| IV-643 | Me | Me | Me | C≡C | Ph | CH₂ | Me | (S)- |
| IV-644 | Me | Me | Me | 1,2-Cyclopropylene | Ph | CH₂ | H | racemic |
| IV-645 | Me | Me | Me | 1,2-Cyclopropylene | Ph | CH₂ | H | (S)- |
| IV-646 | Me | Me | Me | 1,2-Cyclopropylene | Ph | CH₂ | Me | racemic |
| IV-647 | Me | Me | Me | 1,2-Cyclopropylene | Ph | CH₂ | Me | (S)- |
| IV-648 | Me | Me | Me | 1,2-Cyclopropynylene | Ph | CH₂ | H | racemic |
| IV-649 | Me | Me | Me | 1,2-Cyclopropynylene | Ph | CH₂ | H | (S)- |
| IV-650 | Me | Me | Me | 1,2-Cyclopropynylene | Ph | CH₂ | Me | racemic |
| IV-651 | Me | Me | Me | 1,2-Cyclopropynylene | Ph | CH₂ | Me | (S)- |

TABLE 77

(IV)

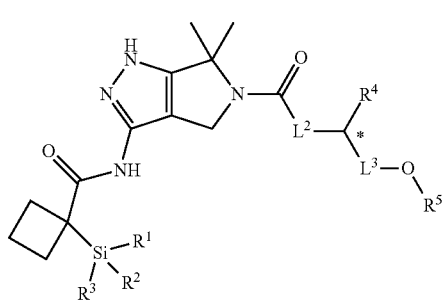

| Compound No. | R¹ | R² | R³ | L² | R⁴ | L³ | R⁵ | Configuration |
|---|---|---|---|---|---|---|---|---|
| IV-652 | Me | Me | Me | O | Ph | C(Me)₂CH₂ | H | racemic |
| IV-653 | Me | Me | Me | O | Ph | C(Me)₂CH₂ | H | (+) |
| IV-654 | Me | Me | Me | O | Ph | C(Me)₂CH₂ | H | (−) |
| IV-655 | Me | Et | Me | O | Ph | C(Me)₂CH₂ | H | racemic |
| IV-656 | Me | Et | Me | O | Ph | C(Me)₂CH₂ | H | (+) |
| IV-657 | Me | Et | Me | O | Ph | C(Me)₂CH₂ | H | (−) |
| IV-658 | Me | Me | Me | O | Ph | C(Me)₂CH₂ | Me | racemic |
| IV-659 | Me | Me | Me | O | Ph | C(Me)₂CH₂ | Me | (+) |
| IV-660 | Me | Me | Me | O | Ph | C(Me)₂CH₂ | Me | (−) |
| IV-661 | Me | Et | Me | O | Ph | C(Me)₂CH₂ | Me | racemic |
| IV-662 | Me | Et | Me | O | Ph | C(Me)₂CH₂ | Me | (+) |
| IV-663 | Me | Et | Me | O | Ph | C(Me)₂CH₂ | Me | (−) |
| IV-664 | Me | Me | Me | O | Ph | C(Me)₂CH₂ | CHF₂ | racemic |
| IV-665 | Me | Me | Me | O | Ph | C(Me)₂CH₂ | CHF₂ | (+) |
| IV-666 | Me | Me | Me | O | Ph | C(Me)₂CH₂ | CHF₂ | (−) |
| IV-667 | Me | Me | Me | O | Ph | C(Me)₂CH₂ | Et | racemic |
| IV-668 | Me | Me | Me | O | Ph | C(Me)₂CH₂ | Et | (+) |
| IV-669 | Me | Me | Me | O | Ph | C(Me)₂CH₂ | Et | (−) |
| IV-670 | Me | Me | Me | O | H | CH(Ph) | H | |
| IV-671 | Me | Et | Me | O | H | CH(Ph) | H | |
| IV-672 | Me | Me | Me | NH | Ph | C(Me)₂CH₂ | H | (+) |
| IV-673 | Me | Me | Me | NH | Ph | C(Me)₂CH₂ | H | (−) |
| IV-674 | Me | Et | Me | NH | Ph | C(Me)₂CH₂ | H | (+) |
| IV-675 | Me | Et | Me | NH | Ph | C(Me)₂CH₂ | H | (−) |
| IV-676 | Me | Me | Me | NH | Ph | C(Me)₂CH₂ | Me | racemic |
| IV-677 | Me | Me | Me | NH | Ph | C(Me)₂CH₂ | Me | (+) |
| IV-678 | Me | Me | Me | NH | Ph | C(Me)₂CH₂ | Me | (−) |
| IV-679 | Me | Et | Me | NH | Ph | C(Me)₂CH₂ | Me | racemic |
| IV-680 | Me | Et | Me | NH | Ph | C(Me)₂CH₂ | Me | (+) |
| IV-681 | Me | Et | Me | NH | Ph | C(Me)₂CH₂ | Me | (−) |
| IV-682 | Me | Me | Me | NH | Ph | C(Me)₂CH₂ | CHF₂ | racemic |
| IV-683 | Me | Me | Me | NH | Ph | C(Me)₂CH₂ | CHF₂ | (+) |
| IV-684 | Me | Me | Me | NH | Ph | C(Me)₂CH₂ | CHF₂ | (−) |
| IV-685 | Me | Et | Me | NH | Ph | C(Me)₂CH₂ | CHF₂ | racemic |
| IV-686 | Me | Et | Me | NH | Ph | C(Me)₂CH₂ | CHF₂ | (+) |
| IV-687 | Me | Et | Me | NH | Ph | C(Me)₂CH₂ | CHF₂ | (−) |
| IV-688 | Me | Me | Me | NH | Ph | C(Me)₂CH₂ | Et | racemic |
| IV-689 | Me | Me | Me | NH | Ph | C(Me)₂CH₂ | Et | (+) |
| IV-690 | Me | Me | Me | NH | Ph | C(Me)₂CH₂ | Et | (−) |
| IV-691 | Me | Et | Me | NH | Ph | C(Me)₂CH₂ | Et | racemic |
| IV-692 | Me | Et | Me | NH | Ph | C(Me)₂CH₂ | Et | (+) |
| IV-693 | Me | Et | Me | NH | Ph | C(Me)₂CH₂ | Et | (−) |
| IV-694 | Me | Me | Me | NH | Ph | C(Me)₂CH₂ | iPr | racemic |
| IV-695 | Me | Me | Me | NH | Ph | C(Me)₂CH₂ | iPr | (+) |
| IV-696 | Me | Me | Me | NH | Ph | C(Me)₂CH₂ | iPr | (−) |
| IV-697 | Me | Et | Me | NH | Ph | C(Me)₂CH₂ | iPr | racemic |
| IV-698 | Me | Et | Me | NH | Ph | C(Me)₂CH₂ | iPr | (+) |
| IV-699 | Me | Et | Me | NH | Ph | C(Me)₂CH₂ | iPr | (−) |
| IV-700 | Me | Me | Me | NH | Ph | C(Me)₂CH₂ | cPr | racemic |
| IV-701 | Me | Me | Me | NH | Ph | C(Me)₂CH₂ | cPr | (+) |

TABLE 78

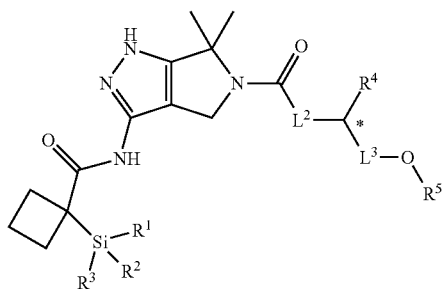

(IV)

| Compound No. | R¹ | R² | R³ | L² | R⁴ | L³ | R⁵ | Configuration |
|---|---|---|---|---|---|---|---|---|
| IV-702 | Me | Me | Me | NH | Ph | C(Me)₂CH₂ | cPr | (−) |
| IV-703 | Me | Et | Me | NH | Ph | C(Me)₂CH₂ | cPr | racemic |
| IV-704 | Me | Et | Me | NH | Ph | C(Me)₂CH₂ | cPr | (+) |
| IV-705 | Me | Et | Me | NH | Ph | C(Me)₂CH₂ | cPr | (−) |
| IV-706 | Me | Me | Me | NH | Ph | 1,1-Cyclopropylene-CH₂ | H | racemic |
| IV-707 | Me | Me | Me | NH | Ph | 1,1-Cyclopropylene-CH₂ | H | (+) |
| IV-708 | Me | Me | Me | NH | Ph | 1,1-Cyclopropylene-CH₂ | H | (+) |
| IV-709 | Me | Et | Me | NH | Ph | 1,1-Cyclopropylene-CH₂ | H | racemic |
| IV-710 | Me | Et | Me | NH | Ph | 1,1-Cyclopropylene-CH₂ | H | (+) |
| IV-711 | Me | Et | Me | NH | Ph | 1,1-Cyclopropylene-CH₂ | H | (−) |
| IV-712 | Me | Me | Me | NH | Ph | 1,1-Cyclopropylene-CH₂ | Me | racemic |
| IV-713 | Me | Me | Me | NH | Ph | 1,1-Cyclopropylene-CH₂ | Me | (+) |
| IV-714 | Me | Me | Me | NH | Ph | 1,1-Cyclopropylene-CH₂ | Me | (−) |
| IV-715 | Me | Et | Me | NH | Ph | 1,1-Cyclopropylene-CH₂ | Me | racemic |
| IV-716 | Me | Et | Me | NH | Ph | 1,1-Cyclopropylene-CH₂ | Me | (+) |
| IV-717 | Me | Et | Me | NH | Ph | 1,1-Cyclopropylene-CH₂ | Me | (−) |
| IV-718 | Me | Me | Me | NH | Ph | 1,1-Cyclobutylene-CH₂ | H | racemic |
| IV-719 | Me | Me | Me | NH | Ph | 1,1-Cyclobutylene-CH₂ | H | (+) |
| IV-720 | Me | Me | Me | NH | Ph | 1,1-Cyclobutylene-CH₂ | H | (−) |
| IV-721 | Me | Et | Me | NH | Ph | 1,1-Cyclobutylene-CH₂ | H | racemic |
| IV-722 | Me | Et | Me | NH | Ph | 1,1-Cyclobutylene-CH₂ | H | (+) |
| IV-723 | Me | Et | Me | NH | Ph | 1,1-Cyclobutylene-CH₂ | H | (−) |
| IV-724 | Me | Me | Me | NH | Ph | 1,1-Cyclobutylene-CH₂ | Me | racemic |
| IV-725 | Me | Me | Me | NH | Ph | 1,1-Cyclobutylene-CH₂ | Me | (+) |
| IV-726 | Me | Me | Me | NH | Ph | 1,1-Cyclobutylene-CH₂ | Me | (−) |
| IV-727 | Me | Et | Me | NH | Ph | 1,1-Cyclobutylene-CH₂ | Me | racemic |
| IV-728 | Me | Et | Me | NH | Ph | 1,1-Cyclobutylene-CH₂ | Me | (+) |
| IV-729 | Me | Et | Me | NH | Ph | 1,1-Cyclobutylene-CH₂ | Me | (−) |
| IV-730 | Me | Me | Me | NH | Ph | C(Et)₂CH₂ | H | racemic |
| IV-731 | Me | Me | Me | NH | Ph | C(Et)₂CH₂ | H | (+) |
| IV-732 | Me | Me | Me | NH | Ph | C(Et)₂CH₂ | H | (−) |
| IV-733 | Me | Et | Me | NH | Ph | C(Et)₂CH₂ | H | racemic |
| IV-734 | Me | Et | Me | NH | Ph | C(Et)₂CH₂ | H | (+) |
| IV-735 | Me | Et | Me | NH | Ph | C(Et)₂CH₂ | H | (−) |
| IV-736 | Me | Me | Me | NH | Ph | C(Et)₂CH₂ | Me | racemic |
| IV-737 | Me | Me | Me | NH | Ph | C(Et)₂CH₂ | Me | (+) |
| IV-738 | Me | Me | Me | NH | Ph | C(Et)₂CH₂ | Me | (−) |
| IV-739 | Me | Et | Me | NH | Ph | C(Et)₂CH₂ | Me | racemic |
| IV-740 | Me | Et | Me | NH | Ph | C(Et)₂CH₂ | Me | (+) |
| IV-741 | Me | Et | Me | NH | Ph | C(Et)₂CH₂ | Me | (−) |
| IV-742 | Me | Me | Me | NH | Ph | CH₂-1,1-Cyclopropylene | H | racemic |
| IV-743 | Me | Me | Me | NH | Ph | CH₂-1,1-Cyclopropylene | H | (R)- |
| IV-744 | Me | Et | Me | NH | Ph | CH₂-1,1-Cyclopropylene | H | racemic |
| IV-745 | Me | Et | Me | NH | Ph | CH₂-1,1-Cyclopropylene | H | (R)- |
| IV-746 | Me | Me | Me | NH | Ph | CH₂-1,1-Cyclopropylene | Me | racemic |
| IV-747 | Me | Me | Me | NH | Ph | CH₂-1,1-Cyclopropylene | Me | (R)- |
| IV-748 | Me | Et | Me | NH | Ph | CH₂-1,1-Cyclopropylene | Me | racemic |
| IV-749 | Me | Et | Me | NH | Ph | CH₂-1,1-Cyclopropylene | Me | (R)- |
| IV-750 | Me | Me | Me | NH | Ph | CH₂-1,1-cyclobutylene | H | racemic |
| IV-751 | Me | Me | Me | NH | Ph | CH₂-1,1-cyclobutylene | H | (R)- |

TABLE 79

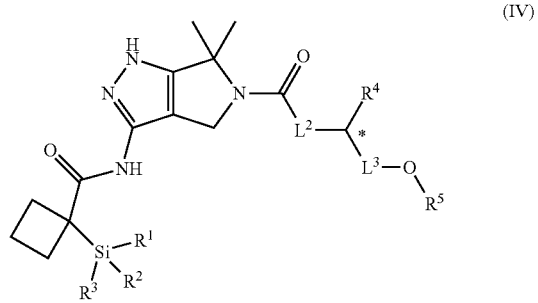

(IV)

| Compound No. | R¹ | R² | R³ | L² | R⁴ | L³ | R⁵ | Configuration |
|---|---|---|---|---|---|---|---|---|
| IV-752 | Me | Et | Me | NH | Ph | CH₂-1,1-cyclobutylene | H | racemic |
| IV-753 | Me | Et | Me | NH | Ph | CH₂-1,1-cyclobutylene | H | (R)- |
| IV-754 | Me | Me | Me | NH | Ph | CH₂-1,1-cyclobutylene | Me | racemic |
| IV-755 | Me | Me | Me | NH | Ph | CH₂-1,1-cyclobutylene | Me | (R)- |
| IV-756 | Me | Et | Me | NH | Ph | CH₂-1,1-cyclobutylene | Me | racemic |
| IV-757 | Me | Et | Me | NH | Ph | CH₂-1,1-cyclobutylene | Me | (R)- |
| IV-758 | Me | Me | Me | NH | Ph | CH₂C(Et)₂ | H | racemic |
| IV-759 | Me | Me | Me | NH | Ph | CH₂C(Et)₂ | H | (R)- |
| IV-760 | Me | Et | Me | NH | Ph | CH₂C(Et)₂ | H | racemic |
| IV-761 | Me | Et | Me | NH | Ph | CH₂C(Et)₂ | H | (R)- |
| IV-762 | Me | Me | Me | NH | Ph | CH₂C(Et)₂ | Me | racemic |
| IV-763 | Me | Me | Me | NH | Ph | CH₂C(Et)₂ | Me | (R)- |
| IV-764 | Me | Et | Me | NH | Ph | CH₂C(Et)₂ | Me | racemic |
| IV-765 | Me | Et | Me | NH | Ph | CH₂C(Et)₂ | Me | (R)- |
| IV-766 | Me | Me | Me | NH | Ph | (R)-CH(Me) | H | (S)- |
| IV-767 | Me | Me | Me | NH | Ph | (S)-CH(Me) | H | (S)- |
| IV-768 | Me | Et | Me | NH | Ph | (R)-CH(Me) | H | (S)- |
| IV-769 | Me | Et | Me | NH | Ph | (S)-CH(Me) | H | (S)- |
| IV-770 | Me | Me | Me | NH | Ph | (R)-CH(iPr) | H | (S)- |
| IV-771 | Me | Me | Me | NH | Ph | (S)-CH(iPr) | H | (S)- |
| IV-772 | Me | Et | Me | NH | Ph | (R)-CH(iPr) | H | (S)- |
| IV-773 | Me | Et | Me | NH | Ph | (S)-CH(iPr) | H | (S)- |
| IV-774 | Me | Me | Me | NH | Ph | (R)-CH(Ph) | H | (S)- |
| IV-775 | Me | Me | Me | NH | Ph | (S)-CH(Ph) | H | (S)- |
| IV-776 | Me | Et | Me | NH | Ph | (R)-CH(Ph) | H | (S)- |
| IV-777 | Me | Et | Me | NH | Ph | (S)-CH(Ph) | H | (S)- |
| IV-778 | Me | Me | Me | NH | H | (R)-CH(Me) | H | |
| IV-779 | Me | Me | Me | NH | H | (S)-CH(Me) | H | |
| IV-780 | Me | Et | Me | NH | H | (R)-CH(Me) | H | |
| IV-781 | Me | Et | Me | NH | H | (S)-CH(Me) | H | |
| IV-782 | Me | Me | Me | NH | H | (R)-CH(iPr) | H | |
| IV-783 | Me | Me | Me | NH | H | (S)-CH(iPr) | H | |
| IV-784 | Me | Et | Me | NH | H | (R)-CH(iPr) | H | |
| IV-785 | Me | Et | Me | NH | H | (S)-CH(iPr) | H | |
| IV-786 | Me | Me | Me | NH | H | (R)-CH(Ph) | H | |
| IV-787 | Me | Me | Me | NH | H | (S)-CH(Ph) | H | |
| IV-788 | Me | Et | Me | NH | H | (R)-CH(Ph) | H | |
| IV-789 | Me | Et | Me | NH | H | (S)-CH(Ph) | H | |
| IV-790 | Me | Me | Me | NH | Me | (R)-CH(Me) | H | (S)- |
| IV-791 | Me | Me | Me | NH | Me | (S)-CH(Me) | H | (S)- |
| IV-792 | Me | Et | Me | NH | Me | (R)-CH(Me) | H | (S)- |
| IV-793 | Me | Et | Me | NH | Me | (S)-CH(Me) | H | (S)- |
| IV-794 | Me | Me | Me | NH | Me | (R)-CH(iPr) | H | (S)- |
| IV-795 | Me | Me | Me | NH | Me | (S)-CH(iPr) | H | (S)- |
| IV-796 | Me | Et | Me | NH | Me | (R)-CH(iPr) | H | (S)- |
| IV-797 | Me | Et | Me | NH | Me | (S)-CH(iPr) | H | (S)- |
| IV-798 | Me | Me | Me | NH | Me | (R)-CH(Ph) | H | (S)- |
| IV-799 | Me | Me | Me | NH | Me | (S)-CH(Ph) | H | (S)- |

TABLE 79-continued

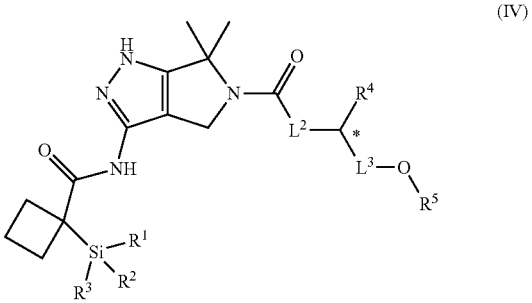

(IV)

| Compound No. | R¹ | R² | R³ | L² | R⁴ | L³ | R⁵ | Configuration |
|---|---|---|---|---|---|---|---|---|
| IV-800 | Me | Et | Me | NH | Me | (R)-CH(Ph) | H | (S)- |
| IV-801 | Me | Et | Me | NH | Me | (S)-CH(Ph) | H | (S)- |

TABLE 80

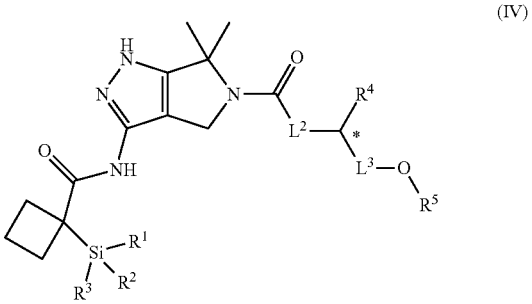

(IV)

| Compound No. | R¹ | R² | R³ | L² | R⁴ | L³ | R⁵ | Configuration |
|---|---|---|---|---|---|---|---|---|
| IV-802 | Me | Me | Me | NH | iPr | CH₂ | Me | racemic |
| IV-803 | Me | Me | Me | NH | iPr | CH₂ | Me | (S)- |
| IV-804 | Me | Et | Me | NH | iPr | CH₂ | Me | racemic |
| IV-805 | Me | Et | Me | NH | iPr | CH₂ | Me | (S)- |
| IV-806 | Me | Me | Me | NH | iPr | (CH₂)₂ | H | racemic |
| IV-807 | Me | Me | Me | NH | iPr | (CH₂)₂ | H | (R)- |
| IV-808 | Me | Et | Me | NH | iPr | (CH₂)₂ | H | racemic |
| IV-809 | Me | Et | Me | NH | iPr | (CH₂)₂ | H | (R)- |
| IV-810 | Me | Me | Me | NH | iPr | (CH₂)₂ | Me | racemic |
| IV-811 | Me | Me | Me | NH | iPr | (CH₂)₂ | Me | (R)- |
| IV-812 | Me | Et | Me | NH | iPr | (CH₂)₂ | Me | racemic |
| IV-813 | Me | Et | Me | NH | iPr | (CH₂)₂ | Me | (R)- |
| IV-814 | Me | Me | Me | NH | iPr | CH₂C(Me)₂ | H | racemic |
| IV-815 | Me | Me | Me | NH | iPr | CH₂C(Me)₂ | H | (R)- |
| IV-816 | Me | Et | Me | NH | iPr | CH₂C(Me)₂ | H | racemic |
| IV-817 | Me | Et | Me | NH | iPr | CH₂C(Me)₂ | H | (R)- |
| IV-818 | Me | Me | Me | NH | iPr | CH₂C(Me)₂ | Me | racemic |
| IV-819 | Me | Me | Me | NH | iPr | CH₂C(Me)₂ | Me | (R)- |
| IV-820 | Me | Et | Me | NH | iPr | CH₂C(Me)₂ | Me | racemic |
| IV-821 | Me | Et | Me | NH | iPr | CH₂C(Me)₂ | Me | (R)- |
| IV-822 | Me | Me | Me | NH | iPr | C(Me)₂CH₂ | H | racemic |
| IV-823 | Me | Me | Me | NH | iPr | C(Me)₂CH₂ | H | (+) |
| IV-824 | Me | Me | Me | NH | iPr | C(Me)₂CH₂ | H | (−) |
| IV-825 | Me | Et | Me | NH | iPr | C(Me)₂CH₂ | H | racemic |
| IV-826 | Me | Et | Me | NH | iPr | C(Me)₂CH₂ | H | (+) |
| IV-827 | Me | Et | Me | NH | iPr | C(Me)₂CH₂ | H | (−) |
| IV-828 | Me | Me | Me | NH | iPr | C(Me)₂CH₂ | Me | racemic |
| IV-829 | Me | Me | Me | NH | iPr | C(Me)₂CH₂ | Me | (+) |
| IV-830 | Me | Me | Me | NH | iPr | C(Me)₂CH₂ | Me | (−) |
| IV-831 | Me | Et | Me | NH | iPr | C(Me)₂CH₂ | Me | racemic |
| IV-832 | Me | Et | Me | NH | iPr | C(Me)₂CH₂ | Me | (+) |
| IV-833 | Me | Et | Me | NH | iPr | C(Me)₂CH₂ | Me | (−) |
| IV-834 | Me | Me | Me | NH | iPr | (R)-CH(Me) | H | (S)- |
| IV-835 | Me | Me | Me | NH | iPr | (S)-CH(Me) | H | (S)- |
| IV-836 | Me | Et | Me | NH | iPr | (R)-CH(Me) | H | (S)- |

TABLE 80-continued

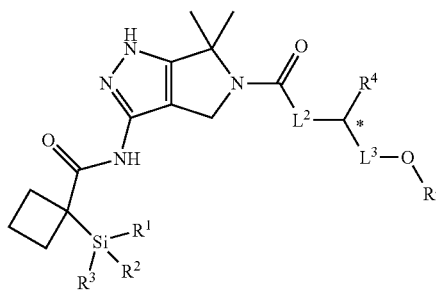

(IV)

| Compound No. | R¹ | R² | R³ | L² | R⁴ | L³ | R⁵ | Configuration |
|---|---|---|---|---|---|---|---|---|
| IV-837 | Me | Et | Me | NH | iPr | (S)-CH(Me) | H | (S)- |
| IV-838 | Me | Me | Me | NH | iPr | (R)-CH(iPr) | H | (S)- |
| IV-839 | Me | Me | Me | NH | iPr | (S)-CH(iPr) | H | (S)- |
| IV-840 | Me | Et | Me | NH | iPr | (R)-CH(iPr) | H | (S)- |
| IV-841 | Me | Et | Me | NH | iPr | (S)-CH(iPr) | H | (S)- |
| IV-842 | Me | Me | Me | NH | iPr | (R)-CH(Ph) | H | (S)- |
| IV-843 | Me | Me | Me | NH | iPr | (S)-CH(Ph) | H | (S)- |
| IV-844 | Me | Et | Me | NH | iPr | (R)-CH(Ph) | H | (S)- |
| IV-845 | Me | Et | Me | NH | iPr | (S)-CH(Ph) | H | (S)- |
| IV-846 | Me | Me | Me | NH | CF₃ | CH₂ | H | racemic |
| IV-847 | Me | Me | Me | NH | CF₃ | CH₂ | H | (S)- |
| IV-848 | Me | Et | Me | NH | CF₃ | CH₂ | H | racemic |
| IV-849 | Me | Et | Me | NH | CF₃ | CH₂ | H | (S)- |
| IV-850 | Me | Me | Me | N(Me) | CF₃ | CH₂ | H | racemic |
| IV-851 | Me | Me | Me | N(Me) | CF₃ | CH₂ | H | (S)- |

TABLE 81

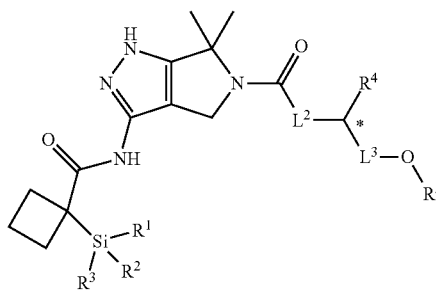

(IV)

| Compound No. | R¹ | R² | R³ | L² | R⁴ | L³ | R⁵ | Configuration |
|---|---|---|---|---|---|---|---|---|
| IV-852 | Me | Et | Me | N(Me) | CF₃ | CH₂ | H | racemic |
| IV-853 | Me | Et | Me | N(Me) | CF₃ | CH₂ | H | (S)- |
| IV-854 | Me | Me | Me | NH | CH₂OH | CH₂ | H | |
| IV-855 | Me | Et | Me | NH | CH₂OH | CH₂ | H | |
| IV-856 | Me | Me | Me | NH | CH₂OMe | CH₂ | H | racemic |
| IV-857 | Me | Me | Me | NH | CH₂OMe | CH₂ | H | (R)- |
| IV-858 | Me | Et | Me | NH | CH₂OMe | CH₂ | H | racemic |
| IV-859 | Me | Et | Me | NH | CH₂OMe | CH₂ | H | (R)- |
| IV-860 | Me | Me | Me | NH | CH₂Ph | CH₂ | H | racemic |
| IV-861 | Me | Me | Me | NH | CH₂Ph | CH₂ | H | (R)- |
| IV-862 | Me | Me | Me | NH | CH₂Ph | CH₂ | H | (S)- |
| IV-863 | Me | Et | Me | NH | CH₂Ph | CH₂ | H | racemic |
| IV-864 | Me | Et | Me | NH | CH₂Ph | CH₂ | H | (S)- |
| IV-865 | Me | Me | Me | N(Me) | CH₂Ph | CH₂ | H | racemic |
| IV-866 | Me | Me | Me | N(Me) | CH₂Ph | CH₂ | H | (S)- |
| IV-867 | Me | Et | Me | N(Me) | CH₂Ph | CH₂ | H | racemic |
| IV-868 | Me | Et | Me | N(Me) | CH₂Ph | CH₂ | H | (S)- |
| IV-869 | Me | Me | Me | NH | 2-F—Ph | CH₂ | Me | racemic |
| IV-870 | Me | Me | Me | NH | 2-F—Ph | CH₂ | Me | (S)- |
| IV-871 | Me | Et | Me | NH | 2-F—Ph | CH₂ | Me | racemic |
| IV-872 | Me | Et | Me | NH | 2-F—Ph | CH₂ | Me | (S)- |
| IV-873 | Me | Me | Me | NH | 2-F—Ph | (CH₂)₂ | H | racemic |

TABLE 81-continued (IV)

| Compound No. | R¹ | R² | R³ | L² | R⁴ | L³ | R⁵ | Configuration |
|---|---|---|---|---|---|---|---|---|
| IV-874 | Me | Me | Me | NH | 2-F—Ph | (CH₂)₂ | H | (+)- |
| IV-875 | Me | Me | Me | NH | 2-F—Ph | (CH₂)₂ | H | (−)- |
| IV-876 | Me | Et | Me | NH | 2-F—Ph | (CH₂)₂ | H | racemic |
| IV-877 | Me | Et | Me | NH | 2-F—Ph | (CH₂)₂ | H | (R)- |
| IV-878 | Me | Me | Me | NH | 2-F—Ph | (CH₂)₂ | Me | racemic |
| IV-879 | Me | Me | Me | NH | 2-F—Ph | (CH₂)₂ | Me | (R)- |
| IV-880 | Me | Et | Me | NH | 2-F—Ph | (CH₂)₂ | Me | racemic |
| IV-881 | Me | Et | Me | NH | 2-F—Ph | (CH₂)₂ | Me | (R)- |
| IV-882 | Me | Me | Me | NH | 2-F—Ph | CH₂C(Me)₂ | H | racemic |
| IV-883 | Me | Me | Me | NH | 2-F—Ph | CH₂C(Me)₂ | H | (R)- |
| IV-884 | Me | Et | Me | NH | 2-F—Ph | CH₂C(Me)₂ | H | racemic |
| IV-885 | Me | Et | Me | NH | 2-F—Ph | CH₂C(Me)₂ | H | (R)- |
| IV-886 | Me | Me | Me | NH | 2-F—Ph | CH₂C(Me)₂ | Me | racemic |
| IV-887 | Me | Me | Me | NH | 2-F—Ph | CH₂C(Me)₂ | Me | (R)- |
| IV-888 | Me | Et | Me | NH | 2-F—Ph | CH₂C(Me)₂ | Me | racemic |
| IV-889 | Me | Et | Me | NH | 2-F—Ph | CH₂C(Me)₂ | Me | (R)- |
| IV-890 | Me | Me | Me | NH | 2-F—Ph | C(Me)₂CH₂ | H | racemic |
| IV-891 | Me | Me | Me | NH | 2-F—Ph | C(Me)₂CH₂ | H | (+) |
| IV-892 | Me | Me | Me | NH | 2-F—Ph | C(Me)₂CH₂ | H | (−) |
| IV-893 | Me | Et | Me | NH | 2-F—Ph | C(Me)₂CH₂ | H | racemic |
| IV-894 | Me | Et | Me | NH | 2-F—Ph | C(Me)₂CH₂ | H | (+) |
| IV-895 | Me | Et | Me | NH | 2-F—Ph | C(Me)₂CH₂ | H | (−) |
| IV-896 | Me | Me | Me | NH | 2-F—Ph | C(Me)₂CH₂ | Me | racemic |
| IV-897 | Me | Me | Me | NH | 2-F—Ph | C(Me)₂CH₂ | Me | (+) |
| IV-898 | Me | Me | Me | NH | 2-F—Ph | C(Me)₂CH₂ | Me | (−) |
| IV-899 | Me | Et | Me | NH | 2-F—Ph | C(Me)₂CH₂ | Me | racemic |
| IV-900 | Me | Et | Me | NH | 2-F—Ph | C(Me)₂CH₂ | Me | (+) |
| IV-901 | Me | Et | Me | NH | 2-F—Ph | C(Me)₂CH₂ | Me | (−) |

TABLE 82

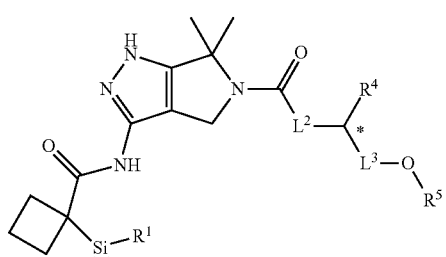

(IV)

| Compound No. | R¹ | R² | R³ | L² | R⁴ | L³ | R⁵ | Configuration |
|---|---|---|---|---|---|---|---|---|
| IV-902 | Me | Me | Me | NH | 3-F—Ph | (CH₂)₂ | H | racemic |
| IV-903 | Me | Me | Me | NH | 3-F—Ph | (CH₂)₂ | H | (R)- |
| IV-904 | Me | Et | Me | NH | 3-F—Ph | (CH₂)₂ | H | racemic |
| IV-905 | Me | Et | Me | NH | 3-F—Ph | (CH₂)₂ | H | (R)- |
| IV-906 | Me | Me | Me | NH | 3-F—Ph | (CH₂)₂ | Me | racemic |
| IV-907 | Me | Me | Me | NH | 3-F—Ph | (CH₂)₂ | Me | (R)- |
| IV-908 | Me | Et | Me | NH | 3-F—Ph | (CH₂)₂ | Me | racemic |
| IV-909 | Me | Et | Me | NH | 3-F—Ph | (CH₂)₂ | Me | (R)- |

TABLE 82-continued

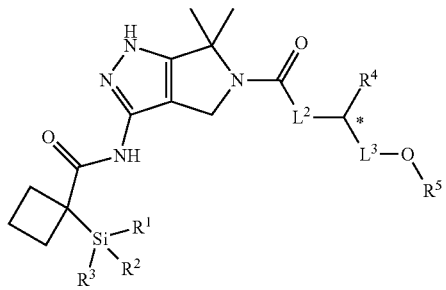

(IV)

| Compound No. | R¹ | R² | R³ | L² | R⁴ | L³ | R⁵ | Configuration |
|---|---|---|---|---|---|---|---|---|
| IV-910 | Me | Me | Me | NH | 3-F—Ph | CH₂C(Me)₂ | H | racemic |
| IV-911 | Me | Me | Me | NH | 3-F—Ph | CH₂C(Me)₂ | H | (R)- |
| IV-912 | Me | Et | Me | NH | 3-F—Ph | CH₂C(Me)₂ | H | racemic |
| IV-913 | Me | Et | Me | NH | 3-F—Ph | CH₂C(Me)₂ | H | (R)- |
| IV-914 | Me | Me | Me | NH | 3-F—Ph | CH₂C(Me)₂ | Me | racemic |
| IV-915 | Me | Me | Me | NH | 3-F—Ph | CH₂C(Me)₂ | Me | (R)- |
| IV-916 | Me | Et | Me | NH | 3-F—Ph | CH₂C(Me)₂ | Me | racemic |
| IV-917 | Me | Et | Me | NH | 3-F—Ph | CH₂C(Me)₂ | Me | (R)- |
| IV-918 | Me | Me | Me | NH | 3-F—Ph | C(Me)₂CH₂ | H | racemic |
| IV-919 | Me | Me | Me | NH | 3-F—Ph | C(Me)₂CH₂ | H | (+) |
| IV-920 | Me | Me | Me | NH | 3-F—Ph | C(Me)₂CH₂ | H | (−) |
| IV-921 | Me | Et | Me | NH | 3-F—Ph | C(Me)₂CH₂ | H | racemic |
| IV-922 | Me | Et | Me | NH | 3-F—Ph | C(Me)₂CH₂ | H | (+) |
| IV-923 | Me | Et | Me | NH | 3-F—Ph | C(Me)₂CH₂ | H | (−) |
| IV-924 | Me | Me | Me | NH | 3-F—Ph | C(Me)₂CH₂ | Me | racemic |
| IV-925 | Me | Me | Me | NH | 3-F—Ph | C(Me)₂CH₂ | Me | (+) |
| IV-926 | Me | Me | Me | NH | 3-F—Ph | C(Me)₂CH₂ | Me | (−) |
| IV-927 | Me | Et | Me | NH | 3-F—Ph | C(Me)₂CH₂ | Me | racemic |
| IV-928 | Me | Et | Me | NH | 3-F—Ph | C(Me)₂CH₂ | Me | (+) |
| IV-929 | Me | Et | Me | NH | 3-F—Ph | C(Me)₂CH₂ | Me | (−) |
| IV-930 | Me | Me | Me | NH | 4-F—Ph | (CH₂)₂ | H | racemic |
| IV-931 | Me | Me | Me | NH | 4-F—Ph | (CH₂)₂ | H | (R)- |
| IV-932 | Me | Et | Me | NH | 4-F—Ph | (CH₂)₂ | H | racemic |
| IV-933 | Me | Et | Me | NH | 4-F—Ph | (CH₂)₂ | H | (R)- |
| IV-934 | Me | Me | Me | NH | 4-F—Ph | (CH₂)₂ | Me | racemic |
| IV-935 | Me | Me | Me | NH | 4-F—Ph | (CH₂)₂ | Me | (R)- |
| IV-936 | Me | Et | Me | NH | 4-F—Ph | (CH₂)₂ | Me | racemic |
| IV-937 | Me | Et | Me | NH | 4-F—Ph | (CH₂)₂ | Me | (R)- |
| IV-938 | Me | Me | Me | NH | 4-F—Ph | CH₂C(Me)₂ | H | racemic |
| IV-939 | Me | Me | Me | NH | 4-F—Ph | CH₂C(Me)₂ | H | (R)- |
| IV-940 | Me | Et | Me | NH | 4-F—Ph | CH₂C(Me)₂ | H | racemic |
| IV-941 | Me | Et | Me | NH | 4-F—Ph | CH₂C(Me)₂ | H | (R)- |
| IV-942 | Me | Me | Me | NH | 4-F—Ph | CH₂C(Me)₂ | Me | racemic |
| IV-943 | Me | Me | Me | NH | 4-F—Ph | CH₂C(Me)₂ | Me | (R)- |
| IV-944 | Me | Et | Me | NH | 4-F—Ph | CH₂C(Me)₂ | Me | racemic |
| IV-945 | Me | Et | Me | NH | 4-F—Ph | CH₂C(Me)₂ | Me | (R)- |
| IV-946 | Me | Me | Me | NH | 4-F—Ph | C(Me)₂CH₂ | H | racemic |
| IV-947 | Me | Me | Me | NH | 4-F—Ph | C(Me)₂CH₂ | H | (+) |
| IV-948 | Me | Me | Me | NH | 4-F—Ph | C(Me)₂CH₂ | H | (−) |
| IV-949 | Me | Et | Me | NH | 4-F—Ph | C(Me)₂CH₂ | H | racemic |
| IV-950 | Me | Et | Me | NH | 4-F—Ph | C(Me)₂CH₂ | H | (+) |
| IV-951 | Me | Et | Me | NH | 4-F—Ph | C(Me)₂CH₂ | H | (−) |

TABLE 83

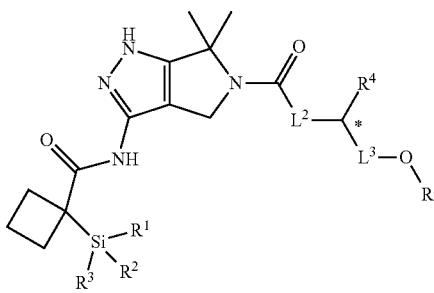

(IV)

| Compound No. | R¹ | R² | R³ | L² | R⁴ | L³ | R⁵ | Configuration |
|---|---|---|---|---|---|---|---|---|
| IV-952 | Me | Me | Me | NH | 4-F—Ph | C(Me)₂CH₂ | Me | racemic |
| IV-953 | Me | Me | Me | NH | 4-F—Ph | C(Me)₂CH₂ | Me | (+) |
| IV-954 | Me | Me | Me | NH | 4-F—Ph | C(Me)₂CH₂ | Me | (−) |
| IV-955 | Me | Et | Me | NH | 4-F—Ph | C(Me)₂CH₂ | Me | racemic |
| IV-956 | Me | Et | Me | NH | 4-F—Ph | C(Me)₂CH₂ | Me | (+) |
| IV-957 | Me | Et | Me | NH | 4-F—Ph | C(Me)₂CH₂ | Me | (−) |
| IV-958 | Me | Me | Me | NH | 2-Cl—Ph | CH₂ | H | racemic |
| IV-959 | Me | Me | Me | NH | 2-Cl—Ph | CH₂ | H | (S)- |
| IV-960 | Me | Et | Me | NH | 2-Cl—Ph | CH₂ | H | racemic |
| IV-961 | Me | Et | Me | NH | 2-Cl—Ph | CH₂ | H | (S)- |
| IV-962 | Me | Me | Me | NH | 2-Cl—Ph | CH₂ | Me | racemic |
| IV-963 | Me | Me | Me | NH | 2-Cl—Ph | CH₂ | Me | (S)- |
| IV-964 | Me | Et | Me | NH | 2-Cl—Ph | CH₂ | Me | racemic |
| IV-965 | Me | Et | Me | NH | 2-Cl—Ph | CH₂ | Me | (S)- |
| IV-966 | Me | Me | Me | NH | 2-Cl—Ph | (CH₂)₂ | H | racemic |
| IV-967 | Me | Me | Me | NH | 2-Cl—Ph | (CH₂)₂ | H | (R)- |
| IV-968 | Me | Et | Me | NH | 2-Cl—Ph | (CH₂)₂ | H | racemic |
| IV-969 | Me | Et | Me | NH | 2-Cl—Ph | (CH₂)₂ | H | (R)- |
| IV-970 | Me | Me | Me | NH | 2-Cl—Ph | (CH₂)₂ | Me | racemic |
| IV-971 | Me | Me | Me | NH | 2-Cl—Ph | (CH₂)₂ | Me | (R)- |
| IV-972 | Me | Et | Me | NH | 2-Cl—Ph | (CH₂)₂ | Me | racemic |
| IV-973 | Me | Et | Me | NH | 2-Cl—Ph | (CH₂)₂ | Me | (R)- |
| IV-974 | Me | Me | Me | NH | 2-Cl—Ph | CH₂C(Me)₂ | H | racemic |
| IV-975 | Me | Me | Me | NH | 2-Cl—Ph | CH₂C(Me)₂ | H | (R)- |
| IV-976 | Me | Et | Me | NH | 2-Cl—Ph | CH₂C(Me)₂ | H | racemic |
| IV-977 | Me | Et | Me | NH | 2-Cl—Ph | CH₂C(Me)₂ | H | (R)- |
| IV-978 | Me | Me | Me | NH | 2-Cl—Ph | CH₂C(Me)₂ | Me | racemic |
| IV-979 | Me | Me | Me | NH | 2-Cl—Ph | CH₂C(Me)₂ | Me | (R)- |
| IV-980 | Me | Et | Me | NH | 2-Cl—Ph | CH₂C(Me)₂ | Me | racemic |
| IV-981 | Me | Et | Me | NH | 2-Cl—Ph | CH₂C(Me)₂ | Me | (R)- |
| IV-982 | Me | Me | Me | NH | 2-Cl—Ph | C(Me)₂CH₂ | H | racemic |
| IV-983 | Me | Me | Me | NH | 2-Cl—Ph | C(Me)₂CH₂ | H | (+) |
| IV-984 | Me | Me | Me | NH | 2-Cl—Ph | C(Me)₂CH₂ | H | (−) |
| IV-985 | Me | Et | Me | NH | 2-Cl—Ph | C(Me)₂CH₂ | H | racemic |
| IV-986 | Me | Et | Me | NH | 2-Cl—Ph | C(Me)₂CH₂ | H | (+) |
| IV-987 | Me | Et | Me | NH | 2-Cl—Ph | C(Me)₂CH₂ | H | (−) |
| IV-988 | Me | Me | Me | NH | 2-Cl—Ph | C(Me)₂CH₂ | Me | racemic |
| IV-989 | Me | Me | Me | NH | 2-Cl—Ph | C(Me)₂CH₂ | Me | (+) |
| IV-990 | Me | Me | Me | NH | 2-Cl—Ph | C(Me)₂CH₂ | Me | (−) |
| IV-991 | Me | Et | Me | NH | 2-Cl—Ph | C(Me)₂CH₂ | Me | racemic |
| IV-992 | Me | Et | Me | NH | 2-Cl—Ph | C(Me)₂CH₂ | Me | (+) |
| IV-993 | Me | Et | Me | NH | 2-Cl—Ph | C(Me)₂CH₂ | Me | (−) |
| IV-994 | Me | Me | Me | NH | 3-Cl—Ph | CH₂ | H | racemic |
| IV-995 | Me | Me | Me | NH | 3-Cl—Ph | CH₂ | H | (S)- |
| IV-996 | Me | Et | Me | NH | 3-Cl—Ph | CH₂ | H | racemic |
| IV-997 | Me | Et | Me | NH | 3-Cl—Ph | CH₂ | H | (S)- |
| IV-998 | Me | Me | Me | NH | 3-Cl—Ph | CH₂ | Me | racemic |
| IV-999 | Me | Me | Me | NH | 3-Cl—Ph | CH₂ | Me | (S)- |
| IV-1000 | Me | Et | Me | NH | 3-Cl—Ph | CH₂ | Me | racemic |
| IV-1001 | Me | Et | Me | NH | 3-Cl—Ph | CH₂ | Me | (S)- |

TABLE 84

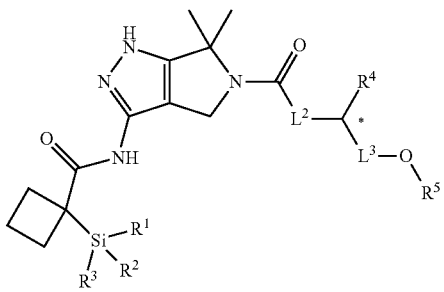

(IV)

| Compound No. | R¹ | R² | R³ | L² | R⁴ | L³ | R⁵ | Configuration |
|---|---|---|---|---|---|---|---|---|
| IV-1002 | Me | Me | Me | NH | 3-Cl—Ph | (CH₂)₂ | H | racemic |
| IV-1003 | Me | Me | Me | NH | 3-Cl—Ph | (CH₂)₂ | H | (R)- |
| IV-1004 | Me | Et | Me | NH | 3-Cl—Ph | (CH₂)₂ | H | racemic |
| IV-1005 | Me | Et | Me | NH | 3-Cl—Ph | (CH₂)₂ | H | (R)- |
| IV-1006 | Me | Me | Me | NH | 3-Cl—Ph | (CH₂)₂ | Me | racemic |
| IV-1007 | Me | Me | Me | NH | 3-Cl—Ph | (CH₂)₂ | Me | (R)- |
| IV-1008 | Me | Et | Me | NH | 3-Cl—Ph | (CH₂)₂ | Me | racemic |
| IV-1009 | Me | Et | Me | NH | 3-Cl—Ph | (CH₂)₂ | Me | (R)- |
| IV-1010 | Me | Me | Me | NH | 3-Cl—Ph | CH₂C(Me)₂ | H | racemic |
| IV-1011 | Me | Me | Me | NH | 3-Cl—Ph | CH₂C(Me)₂ | H | (R)- |
| IV-1012 | Me | Et | Me | NH | 3-Cl—Ph | CH₂C(Me)₂ | H | racemic |
| IV-1013 | Me | Et | Me | NH | 3-Cl—Ph | CH₂C(Me)₂ | H | (R)- |
| IV-1014 | Me | Me | Me | NH | 3-Cl—Ph | CH₂C(Me)₂ | Me | racemic |
| IV-1015 | Me | Me | Me | NH | 3-Cl—Ph | CH₂C(Me)₂ | Me | (R)- |
| IV-1016 | Me | Et | Me | NH | 3-Cl—Ph | CH₂C(Me)₂ | Me | racemic |
| IV-1017 | Me | Et | Me | NH | 3-Cl—Ph | CH₂C(Me)₂ | Me | (R)- |
| IV-1018 | Me | Me | Me | NH | 3-Cl—Ph | C(Me)₂CH₂ | H | racemic |
| IV-1019 | Me | Me | Me | NH | 3-Cl—Ph | C(Me)₂CH₂ | H | (+) |
| IV-1020 | Me | Me | Me | NH | 3-Cl—Ph | C(Me)₂CH₂ | H | (−) |
| IV-1021 | Me | Et | Me | NH | 3-Cl—Ph | C(Me)₂CH₂ | H | racemic |
| IV-1022 | Me | Et | Me | NH | 3-Cl—Ph | C(Me)₂CH₂ | H | (+30) |
| IV-1023 | Me | Et | Me | NH | 3-Cl—Ph | C(Me)₂CH₂ | H | (-) |
| IV-1024 | Me | Me | Me | NH | 3-Cl—Ph | C(Me)₂CH₂ | Me | racemic |
| IV-1025 | Me | Me | Me | NH | 3-Cl—Ph | C(Me)₂CH₂ | Me | (+) |
| IV-1026 | Me | Me | Me | NH | 3-Cl—Ph | C(Me)₂CH₂ | Me | (−) |
| IV-1027 | Me | Et | Me | NH | 3-Cl—Ph | C(Me)₂CH₂ | Me | racemic |
| IV-1028 | Me | Et | Me | NH | 3-Cl—Ph | C(Me)₂CH₂ | Me | (+) |
| IV-1029 | Me | Et | Me | NH | 3-Cl—Ph | C(Me)₂CH₂ | Me | (−) |
| IV-1030 | Me | Me | Me | NH | 3-Cl—Ph | CH₂ | H | racemic |
| IV-1031 | Me | Me | Me | NH | 3-Cl—Ph | CH₂ | H | (S)- |
| IV-1032 | Me | Et | Me | NH | 3-Cl—Ph | CH₂ | H | racemic |
| IV-1033 | Me | Et | Me | NH | 3-Cl—Ph | CH₂ | H | (S)- |
| IV-1034 | Me | Me | Me | NH | 3-Cl—Ph | CH₂ | Me | racemic |
| IV-1035 | Me | Me | Me | NH | 3-Cl—Ph | CH₂ | Me | (S)- |
| IV-1036 | Me | Et | Me | NH | 3-Cl—Ph | CH₂ | Me | racemic |
| IV-1037 | Me | Et | Me | NH | 3-Cl—Ph | CH₂ | Me | (S)- |
| IV-1038 | Me | Me | Me | NH | 3-Cl—Ph | (CH₂)₂ | H | racemic |
| IV-1039 | Me | Me | Me | NH | 3-Cl—Ph | (CH₂)₂ | H | (R)- |
| IV-1040 | Me | Et | Me | NH | 3-Cl—Ph | (CH₂)₂ | H | racemic |
| IV-1041 | Me | Et | Me | NH | 3-Cl—Ph | (CH₂)₂ | H | (R)- |
| IV-1042 | Me | Me | Me | NH | 3-Cl—Ph | (CH₂)₂ | Me | racemic |
| IV-1043 | Me | Me | Me | NH | 3-Cl—Ph | (CH₂)₂ | Me | (R)- |
| IV-1044 | Me | Et | Me | NH | 3-Cl—Ph | (CH₂)₂ | Me | racemic |
| IV-1045 | Me | Et | Me | NH | 3-Cl—Ph | (CH₂)₂ | Me | (R)- |
| IV-1046 | Me | Me | Me | NH | 3-Cl—Ph | CH₂C(Me)₂ | H | racemic |
| IV-1047 | Me | Me | Me | NH | 3-Cl—Ph | CH₂C(Me)₂ | H | (R)- |
| IV-1048 | Me | Et | Me | NH | 3-Cl—Ph | CH₂C(Me)₂ | H | racemic |
| IV-1049 | Me | Et | Me | NH | 3-Cl—Ph | CH₂C(Me)₂ | H | (R)- |
| IV-1050 | Me | Me | Me | NH | 3-Cl—Ph | CH₂C(Me)₂ | Me | racemic |
| IV-1051 | Me | Me | Me | NH | 3-Cl—Ph | CH₂C(Me)₂ | Me | (R)- |

TABLE 85

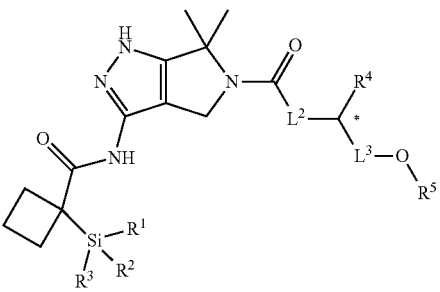

(IV)

| Compound No. | R¹ | R² | R³ | L² | R⁴ | L³ | R⁵ | Configuration |
|---|---|---|---|---|---|---|---|---|
| IV-1052 | Me | Et | Me | NH | 4-Cl—Ph | CH₂C(Me)₂ | Me | racemic |
| IV-1053 | Me | Et | Me | NH | 4-Cl—Ph | CH₂C(Me)₂ | Me | (R)- |
| IV-1054 | Me | Me | Me | NH | 4-Cl—Ph | CH₂C(Me)₂ | H | racemic |
| IV-1055 | Me | Me | Me | NH | 4-Cl—Ph | CH₂C(Me)₂ | H | (+) |
| IV-1056 | Me | Me | Me | NH | 4-Cl—Ph | CH₂C(Me)₂ | H | (−) |
| IV-1057 | Me | Et | Me | NH | 4-Cl—Ph | CH₂C(Me)₂ | H | racemic |
| IV-1058 | Me | Et | Me | NH | 4-Cl—Ph | CH₂C(Me)₂ | H | (+) |
| IV-1059 | Me | Et | Me | NH | 4-Cl—Ph | CH₂C(Me)₂ | H | (−) |
| IV-1060 | Me | Me | Me | NH | 4-Cl—Ph | CH₂C(Me)₂ | Me | racemic |
| IV-1061 | Me | Me | Me | NH | 4-Cl—Ph | CH₂C(Me)₂ | Me | (+) |
| IV-1062 | Me | Me | Me | NH | 4-Cl—Ph | CH₂C(Me)₂ | Me | (−) |
| IV-1063 | Me | Et | Me | NH | 4-Cl—Ph | CH₂C(Me)₂ | Me | racemic |
| IV-1064 | Me | Et | Me | NH | 4-Cl—Ph | CH₂C(Me)₂ | Me | (+) |
| IV-1065 | Me | Et | Me | NH | 4-Cl—Ph | CH₂C(Me)₂ | Me | (−) |
| IV-1066 | Me | Me | Me | NH | 2-Me—Ph | CH₂ | H | racemic |
| IV-1067 | Me | Me | Me | NH | 2-Me—Ph | CH₂ | H | (S)- |
| IV-1068 | Me | Et | Me | NH | 2-Me—Ph | CH₂ | H | racemic |
| IV-1069 | Me | Et | Me | NH | 2-Me—Ph | CH₂ | H | (S)- |
| IV-1070 | Me | Me | Me | NH | 2-Me—Ph | CH₂ | Me | racemic |
| IV-1071 | Me | Me | Me | NH | 2-Me—Ph | CH₂ | Me | (S)- |
| IV-1072 | Me | Et | Me | NH | 2-Me—Ph | CH₂ | Me | racemic |
| IV-1073 | Me | Et | Me | NH | 2-Me—Ph | CH₂ | Me | (S)- |
| IV-1074 | Me | Me | Me | NH | 2-Me—Ph | (CH₂)₂ | H | racemic |
| IV-1075 | Me | Me | Me | NH | 2-Me—Ph | (CH₂)₂ | H | (R)- |
| IV-1076 | Me | Et | Me | NH | 2-Me—Ph | (CH₂)₂ | H | racemic |
| IV-1077 | Me | Et | Me | NH | 2-Me—Ph | (CH₂)₂ | H | (R)- |
| IV-1078 | Me | Me | Me | NH | 2-Me—Ph | (CH₂)₂ | Me | racemic |
| IV-1079 | Me | Me | Me | NH | 2-Me—Ph | (CH₂)₂ | Me | (R)- |
| IV-1080 | Me | Et | Me | NH | 2-Me—Ph | (CH₂)₂ | Me | racemic |
| IV-1081 | Me | Et | Me | NH | 2-Me—Ph | (CH₂)₂ | Me | (R)- |
| IV-1082 | Me | Me | Me | NH | 2-Me—Ph | CH₂C(Me)₂ | H | racemic |
| IV-1083 | Me | Me | Me | NH | 2-Me—Ph | CH₂C(Me)₂ | H | (R)- |
| IV-1084 | Me | Et | Me | NH | 2-Me—Ph | CH₂C(Me)₂ | H | racemic |
| IV-1085 | Me | Et | Me | NH | 2-Me—Ph | CH₂C(Me)₂ | H | (R)- |
| IV-1086 | Me | Me | Me | NH | 2-Me—Ph | CH₂C(Me)₂ | Me | racemic |
| IV-1087 | Me | Me | Me | NH | 2-Me—Ph | CH₂C(Me)₂ | Me | (R)- |
| IV-1088 | Me | Et | Me | NH | 2-Me—Ph | CH₂C(Me)₂ | Me | racemic |
| IV-1089 | Me | Et | Me | NH | 2-Me—Ph | CH₂C(Me)₂ | Me | (R)- |
| IV-1090 | Me | Me | Me | NH | 2-Me—Ph | CH₂C(Me)₂ | H | racemic |
| IV-1091 | Me | Me | Me | NH | 2-Me—Ph | CH₂C(Me)₂ | H | (+) |
| IV-1092 | Me | Me | Me | NH | 2-Me—Ph | CH₂C(Me)₂ | H | (−) |
| IV-1093 | Me | Et | Me | NH | 2-Me—Ph | CH₂C(Me)₂ | H | racemic |
| IV-1094 | Me | Et | Me | NH | 2-Me—Ph | CH₂C(Me)₂ | H | (+) |
| IV-1095 | Me | Et | Me | NH | 2-Me—Ph | CH₂C(Me)₂ | H | (−) |
| IV-1096 | Me | Me | Me | NH | 2-Me—Ph | CH₂C(Me)₂ | Me | racemic |
| IV-1097 | Me | Me | Me | NH | 2-Me—Ph | CH₂C(Me)₂ | Me | (+) |
| IV-1098 | Me | Me | Me | NH | 2-Me—Ph | CH₂C(Me)₂ | Me | (−) |
| IV-1099 | Me | Et | Me | NH | 2-Me—Ph | CH₂C(Me)₂ | Me | racemic |
| IV-1100 | Me | Et | Me | NH | 2-Me—Ph | CH₂C(Me)₂ | Me | (+) |
| IV-1101 | Me | Et | Me | NH | 2-Me—Ph | CH₂C(Me)₂ | Me | (−) |

TABLE 86

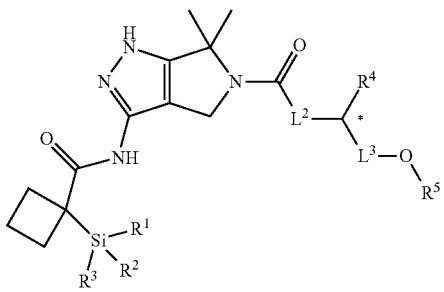

(IV)

| Compound No. | R¹ | R² | R³ | L² | R⁴ | L³ | R⁵ | Configuration |
|---|---|---|---|---|---|---|---|---|
| IV-1102 | Me | Me | Me | NH | 3-Me—Ph | CH₂ | H | racemic |
| IV-1103 | Me | Me | Me | NH | 3-Me—Ph | CH₂ | H | (S)- |
| IV-1104 | Me | Et | Me | NH | 3-Me—Ph | CH₂ | H | racemic |
| IV-1105 | Me | Et | Me | NH | 3-Me—Ph | CH₂ | H | (S)- |
| IV-1106 | Me | Me | Me | NH | 3-Me—Ph | CH₂ | Me | racemic |
| IV-1107 | Me | Me | Me | NH | 3-Me—Ph | CH₂ | Me | (S)- |
| IV-1108 | Me | Et | Me | NH | 3-Me—Ph | CH₂ | Me | racemic |
| IV-1109 | Me | Et | Me | NH | 3-Me—Ph | CH₂ | Me | (S)- |
| IV-1110 | Me | Me | Me | NH | 3-Me—Ph | (CH₂)₂ | H | racemic |
| IV-1111 | Me | Me | Me | NH | 3-Me—Ph | (CH₂)₂ | H | (R)- |
| IV-1112 | Me | Et | Me | NH | 3-Me—Ph | (CH₂)₂ | H | racemic |
| IV-1113 | Me | Et | Me | NH | 3-Me—Ph | (CH₂)₂ | H | (R)- |
| IV-1114 | Me | Me | Me | NH | 3-Me—Ph | (CH₂)₂ | Me | racemic |
| IV-1115 | Me | Me | Me | NH | 3-Me—Ph | (CH₂)₂ | Me | (R)- |
| IV-1116 | Me | Et | Me | NH | 3-Me—Ph | (CH₂)₂ | Me | racemic |
| IV-1117 | Me | Et | Me | NH | 3-Me—Ph | (CH₂)₂ | Me | (R)- |
| IV-1118 | Me | Me | Me | NH | 3-Me—Ph | CH₂C(Me)₂ | H | racemic |
| IV-1119 | Me | Me | Me | NH | 3-Me—Ph | CH₂C(Me)₂ | H | (R)- |
| IV-1120 | Me | Et | Me | NH | 3-Me—Ph | CH₂C(Me)₂ | H | racemic |
| IV-1121 | Me | Et | Me | NH | 3-Me—Ph | CH₂C(Me)₂ | H | (R)- |
| IV-1122 | Me | Me | Me | NH | 3-Me—Ph | CH₂C(Me)₂ | Me | racemic |
| IV-1123 | Me | Me | Me | NH | 3-Me—Ph | CH₂C(Me)₂ | Me | (R)- |
| IV-1124 | Me | Et | Me | NH | 3-Me—Ph | CH₂C(Me)₂ | Me | racemic |
| IV-1125 | Me | Et | Me | NH | 3-Me—Ph | CH₂C(Me)₂ | Me | (R)- |
| IV-1126 | Me | Me | Me | NH | 3-Me—Ph | C(Me)₂CH₂ | H | racemic |
| IV-1127 | Me | Me | Me | NH | 3-Me—Ph | C(Me)₂CH₂ | H | (+) |
| IV-1128 | Me | Me | Me | NH | 3-Me—Ph | C(Me)₂CH₂ | H | (−) |
| IV-1129 | Me | Et | Me | NH | 3-Me—Ph | C(Me)₂CH₂ | H | racemic |
| IV-1130 | Me | Et | Me | NH | 3-Me—Ph | C(Me)₂CH₂ | H | (+) |
| IV-1131 | Me | Et | Me | NH | 3-Me—Ph | C(Me)₂CH₂ | H | (−) |
| IV-1132 | Me | Me | Me | NH | 3-Me—Ph | C(Me)₂CH₂ | Me | racemic |
| IV-1133 | Me | Me | Me | NH | 3-Me—Ph | C(Me)₂CH₂ | Me | (+) |
| IV-1134 | Me | Me | Me | NH | 3-Me—Ph | C(Me)₂CH₂ | Me | (−) |
| IV-1135 | Me | Et | Me | NH | 3-Me—Ph | C(Me)₂CH₂ | Me | racemic |
| IV-1136 | Me | Et | Me | NH | 3-Me—Ph | C(Me)₂CH₂ | Me | (+) |
| IV-1137 | Me | Et | Me | NH | 3-Me—Ph | C(Me)₂CH₂ | Me | (−) |
| IV-1138 | Me | Me | Me | NH | 3-Me—Ph | CH₂ | H | racemic |
| IV-1139 | Me | Me | Me | NH | 3-Me—Ph | CH₂ | H | (S)- |
| IV-1140 | Me | Et | Me | NH | 3-Me—Ph | CH₂ | H | racemic |
| IV-1141 | Me | Et | Me | NH | 3-Me—Ph | CH₂ | H | (S)- |
| IV-1142 | Me | Me | Me | NH | 3-Me—Ph | CH₂ | Me | racemic |
| IV-1143 | Me | Me | Me | NH | 3-Me—Ph | CH₂ | Me | (S)- |
| IV-1144 | Me | Et | Me | NH | 3-Me—Ph | CH₂ | Me | racemic |
| IV-1145 | Me | Et | Me | NH | 3-Me—Ph | CH₂ | Me | (S)- |
| IV-1146 | Me | Me | Me | NH | 3-Me—Ph | (CH₂)₂ | H | racemic |
| IV-1147 | Me | Me | Me | NH | 3-Me—Ph | (CH₂)₂ | H | (R)- |
| IV-1148 | Me | Et | Me | NH | 3-Me—Ph | (CH₂)₂ | H | racemic |
| IV-1149 | Me | Et | Me | NH | 3-Me—Ph | (CH₂)₂ | Me | (R)- |
| IV-1150 | Me | Me | Me | NH | 3-Me—Ph | CH₂C(Me)₂ | H | racemic |
| IV-1151 | Me | Me | Me | NH | 3-Me—Ph | CH₂C(Me)₂ | H | (R)- |

TABLE 87

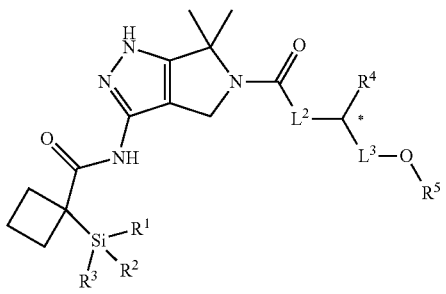

(IV)

| Compound No. | R¹ | R² | R³ | L² | R⁴ | L³ | R⁵ | Configuration |
|---|---|---|---|---|---|---|---|---|
| IV-1152 | Me | Et | Me | NH | 4-Me—Ph | CH₂C(Me)₂ | H | racemic |
| IV-1153 | Me | Et | Me | NH | 4-Me—Ph | CH₂C(Me)₂ | H | (R)- |
| IV-1154 | Me | Me | Me | NH | 4-Me—Ph | CH₂C(Me)₂ | Me | racemic |
| IV-1155 | Me | Me | Me | NH | 4-Me—Ph | CH₂C(Me)₂ | Me | (R)- |
| IV-1156 | Me | Et | Me | NH | 4-Me—Ph | CH₂C(Me)₂ | Me | racemic |
| IV-1157 | Me | Et | Me | NH | 4-Me—Ph | CH₂C(Me)₂ | Me | (R)- |
| IV-1158 | Me | Me | Me | NH | 4-Me—Ph | C(Me)₂CH₂ | H | racemic |
| IV-1159 | Me | Me | Me | NH | 4-Me—Ph | C(Me)₂CH₂ | H | (+) |
| IV-1160 | Me | Me | Me | NH | 4-Me—Ph | C(Me)₂CH₂ | H | (−) |
| IV-1161 | Me | Et | Me | NH | 4-Me—Ph | C(Me)₂CH₂ | H | racemic |
| IV-1162 | Me | Et | Me | NH | 4-Me—Ph | C(Me)₂CH₂ | H | (+) |
| IV-1163 | Me | Et | Me | NH | 4-Me—Ph | C(Me)₂CH₂ | H | (−) |
| IV-1164 | Me | Me | Me | NH | 4-Me—Ph | C(Me)₂CH₂ | Me | racemic |
| IV-1165 | Me | Me | Me | NH | 4-Me—Ph | C(Me)₂CH₂ | Me | (+) |
| IV-1166 | Me | Me | Me | NH | 4-Me—Ph | C(Me)₂CH₂ | Me | (−) |
| IV-1167 | Me | Et | Me | NH | 4-Me—Ph | C(Me)₂CH₂ | Me | racemic |
| IV-1168 | Me | Et | Me | NH | 4-Me—Ph | C(Me)₂CH₂ | Me | (+) |
| IV-1169 | Me | Et | Me | NH | 4-Me—Ph | C(Me)₂CH₂ | Me | (−) |
| IV-1170 | Me | Me | Me | — | Ph | — | H | racemic |
| IV-1171 | Me | Me | Me | — | Ph | — | H | (R)- |
| IV-1172 | Me | Et | Me | — | Ph | — | H | racemic |
| IV-1173 | Me | Et | Me | — | Ph | — | H | (R)- |
| IV-1174 | Me | Me | Me | — | Ph | — | Me | racemic |
| IV-1175 | Me | Me | Me | — | Ph | — | Me | (R)- |
| IV-1176 | Me | Me | Me | — | Ph | — | Me | (S)- |
| IV-1177 | Me | Et | Me | — | Ph | — | Me | racemic |
| IV-1178 | Me | Et | Me | — | Ph | — | Me | (R)- |
| IV-1179 | Me | Me | Me | — | Ph | — | CHF₂ | racemic |
| IV-1180 | Me | Me | Me | — | Ph | — | CHF₂ | (R)- |
| IV-1181 | Me | Et | Me | — | Ph | — | CHF₂ | racemic |
| IV-1182 | Me | Et | Me | — | Ph | — | CHF₂ | (R)- |
| IV-1183 | Me | Me | Me | — | Ph | — | CF₃ | racemic |
| IV-1184 | Me | Me | Me | — | Ph | — | CF₃ | (R)- |
| IV-1185 | Me | Et | Me | — | Ph | — | CF₃ | racemic |
| IV-1186 | Me | Et | Me | — | Ph | — | CF₃ | (R)- |
| IV-1187 | Me | Me | Me | — | Ph | — | Et | racemic |
| IV-1188 | Me | Me | Me | — | Ph | — | Et | (R)- |
| IV-1189 | Me | Et | Me | — | Ph | — | Et | racemic |
| IV-1190 | Me | Et | Me | — | Ph | — | Et | (R)- |
| IV-1191 | Me | Me | Me | — | Ph | — | CF₂CH₃ | racemic |
| IV-1192 | Me | Me | Me | — | Ph | — | CF₂CH₃ | (R)- |
| IV-1193 | Me | Et | Me | — | Ph | — | CF₂CH₃ | racemic |
| IV-1194 | Me | Et | Me | — | Ph | — | CF₂CH₃ | (R)- |
| IV-1195 | Me | Me | Me | — | Ph | — | nPr | racemic |
| IV-1196 | Me | Me | Me | — | Ph | — | nPr | (R)- |
| IV-1197 | Me | Et | Me | — | Ph | — | nPr | racemic |
| IV-1198 | Me | Et | Me | — | Ph | — | nPr | (R)- |
| IV-1199 | Me | Me | Me | — | Ph | — | nBu | racemic |
| IV-1200 | Me | Me | Me | — | Ph | — | nBu | (R)- |
| IV-1201 | Me | Et | Me | — | Ph | — | nBu | racemic |

TABLE 88

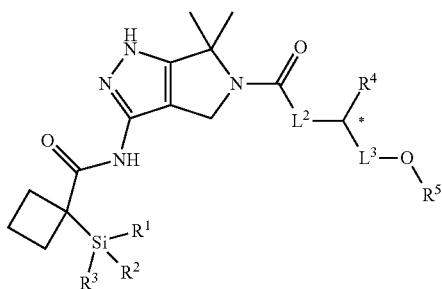

(IV)

| Compound No. | R¹ | R² | R³ | L² | R⁴ | L³ | R⁵ | Configuration |
|---|---|---|---|---|---|---|---|---|
| IV-1202 | Me | Et | Me | — | Ph | — | nBu | (R)- |
| IV-1203 | Me | Me | Me | — | Ph | — | iPr | racemic |
| IV-1204 | Me | Me | Me | — | Ph | — | iPr | (R)- |
| IV-1205 | Me | Et | Me | — | Ph | — | iPr | racemic |
| IV-1206 | Me | Et | Me | — | Ph | — | iPr | (R)- |
| IV-1207 | Me | Me | Me | — | Ph | — | cPr | racemic |
| IV-1208 | Me | Me | Me | — | Ph | — | cPr | (R)- |
| IV-1209 | Me | Et | Me | — | Ph | — | cPr | racemic |
| IV-1210 | Me | Et | Me | — | Ph | — | cPr | (R)- |
| IV-1211 | Me | Me | Me | — | Ph | — | Ph | racemic |
| IV-1212 | Me | Me | Me | — | Ph | — | Ph | (R)- |
| IV-1213 | Me | Me | Me | — | Ph | — | 2,2-diF-cPr | racemic |
| IV-1214 | Me | Me | Me | — | Ph | — | 2,2-diF-cPr | (R)- |
| IV-1215 | Me | Me | Me | — | Ph | CH₂ | H | (R)- |
| IV-1216 | Me | Me | Me | — | Ph | CH₂ | CHF₂ | racemic |
| IV-1217 | Me | Me | Me | — | Ph | CH₂ | CHF₂ | (S)- |
| IV-1218 | Me | Me | Me | — | Ph | CH₂ | Et | racemic |
| IV-1219 | Me | Me | Me | — | Ph | CH₂ | Et | (S)- |
| IV-1220 | Me | Me | Me | — | Ph | CH₂ | Bn | racemic |
| IV-1221 | Me | Me | Me | — | Ph | CH₂ | Bn | (R)- |
| IV-1222 | Me | Me | Me | — | Ph | (CH₂)₂ | H | racemic |
| IV-1223 | Me | Me | Me | — | Ph | (CH₂)₂ | H | (S)- |
| IV-1224 | Me | Me | Me | — | Ph | (CH₂)₂ | Me | racemic |
| IV-1225 | Me | Me | Me | — | Ph | (CH₂)₂ | Me | (S)- |
| IV-1226 | Me | Me | Me | — | Ph | (CH₂)₂ | CHF₂ | racemic |
| IV-1227 | Me | Me | Me | — | Ph | (CH₂)₂ | CHF₂ | (S)- |
| IV-1228 | Me | Me | Me | — | Ph | (CH₂)₂ | Et | racemic |
| IV-1229 | Me | Me | Me | — | Ph | (CH₂)₂ | Et | (S)- |
| IV-1230 | Me | Me | Me | — | H | — | H | |
| IV-1231 | Me | Me | Me | — | H | — | Me | |
| IV-1232 | Me | Me | Me | — | H | — | CHF₂ | |
| IV-1233 | Me | Me | Me | — | H | — | CF₃ | |
| IV-1234 | Me | Me | Me | — | H | — | Et | |
| IV-1235 | Me | Me | Me | — | H | — | nPr | |
| IV-1236 | Me | Me | Me | — | H | — | iPr | |
| IV-1237 | Me | Me | Me | — | H | — | cPr | |
| IV-1238 | Me | Me | Me | — | H | — | Ph | |
| IV-1239 | Me | Me | Me | — | Me | — | H | racemic |
| IV-1240 | Me | Me | Me | — | Me | — | H | (R)- |
| IV-1241 | Me | Me | Me | — | Me | — | Me | racemic |
| IV-1242 | Me | Me | Me | — | Me | — | Me | (R)- |
| IV-1243 | Me | Me | Me | — | Me | — | CHF₂ | racemic |
| IV-1244 | Me | Me | Me | — | Me | — | CHF₂ | (R)- |
| IV-1245 | Me | Me | Me | — | Me | — | CF₃ | racemic |
| IV-1246 | Me | Me | Me | — | Me | — | CF₃ | (R)- |
| IV-1247 | Me | Me | Me | — | Me | — | Et | racemic |
| IV-1248 | Me | Me | Me | — | Me | — | Et | (R)- |
| IV-1249 | Me | Me | Me | — | Me | — | nPr | racemic |
| IV-1250 | Me | Me | Me | — | Me | — | nPr | (R)- |
| IV-1251 | Me | Me | Me | — | Me | — | iPr | racemic |

TABLE 89

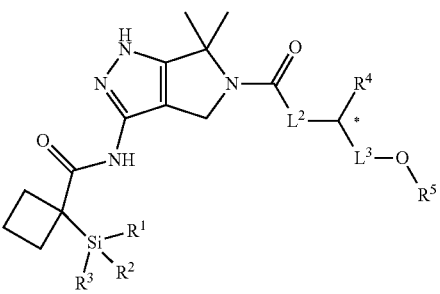

(IV)

| Compound No. | R¹ | R² | R³ | L² | R⁴ | L³ | R⁵ | Configuration |
|---|---|---|---|---|---|---|---|---|
| IV-1252 | Me | Me | Me | — | Me | — | iPr | (R)- |
| IV-1253 | Me | Me | Me | — | Me | — | cPr | racemic |
| IV-1254 | Me | Me | Me | — | Me | — | cPr | (R)- |
| IV-1255 | Me | Me | Me | — | Me | — | cHex | racemic |
| IV-1256 | Me | Me | Me | — | Me | — | cHex | (R)- |
| IV-1257 | Me | Me | Me | — | Me | — | Ph | racemic |
| IV-1258 | Me | Me | Me | — | Me | — | Ph | (R)- |
| IV-1259 | Me | Me | Me | — | Me | — | Ph | (S)- |
| IV-1260 | Me | Me | Me | — | Me | — | 2-F—Ph | racemic |
| IV-1261 | Me | Me | Me | — | Me | — | 2-F—Ph | (R)- |
| IV-1262 | Me | Me | Me | — | Me | — | 2-F—Ph | racemic |
| IV-1263 | Me | Me | Me | — | Me | — | 2-F—Ph | (R)- |
| IV-1264 | Me | Me | Me | — | Me | — | 2-F—Ph | racemic |
| IV-1265 | Me | Me | Me | — | Me | — | 2-F—Ph | (R)- |
| IV-1266 | Me | Me | Me | — | Me | — | 2-Cl—Ph | racemic |
| IV-1267 | Me | Me | Me | — | Me | — | 2-Cl—Ph | (R)- |
| IV-1268 | Me | Me | Me | — | Me | — | 2-Cl—Ph | racemic |
| IV-1269 | Me | Me | Me | — | Me | — | 2-Cl—Ph | (R)- |
| IV-1270 | Me | Me | Me | — | Me | — | 2-Cl—Ph | racemic |
| IV-1271 | Me | Me | Me | — | Me | — | 2-Cl—Ph | (R)- |
| IV-1272 | Me | Me | Me | — | Me | — | 2-Py | racemic |
| IV-1273 | Me | Me | Me | — | Me | — | 2-Py | (R)- |
| IV-1274 | Me | Me | Me | — | Me | — | 3-Py | racemic |
| IV-1275 | Me | Me | Me | — | Me | — | 3-Py | (R)- |
| IV-1276 | Me | Me | Me | — | Me | — | 4-Py | racemic |
| IV-1277 | Me | Me | Me | — | Me | — | 4-Py | (R)- |
| IV-1278 | Me | Me | Me | — | iPr | — | H | racemic |
| IV-1279 | Me | Me | Me | — | iPr | — | H | (R)- |
| IV-1280 | Me | Me | Me | — | iPr | — | Me | racemic |
| IV-1281 | Me | Me | Me | — | iPr | — | Me | (R)- |
| IV-1282 | Me | Me | Me | — | iPr | — | CHF₂ | racemic |
| IV-1283 | Me | Me | Me | — | iPr | — | CHF₂ | (R)- |
| IV-1284 | Me | Me | Me | — | iPr | — | CF₃ | racemic |
| IV-1285 | Me | Me | Me | — | iPr | — | CF₃ | (R)- |
| IV-1286 | Me | Me | Me | — | iPr | — | Et | racemic |
| IV-1287 | Me | Me | Me | — | iPr | — | Et | (R)- |
| IV-1288 | Me | Me | Me | — | iPr | — | nPr | racemic |
| IV-1289 | Me | Me | Me | — | iPr | — | nPr | (R)- |
| IV-1290 | Me | Me | Me | — | iPr | — | iPr | racemic |
| IV-1291 | Me | Me | Me | — | iPr | — | iPr | (R)- |
| IV-1292 | Me | Me | Me | — | iPr | — | cPr | racemic |
| IV-1293 | Me | Me | Me | — | iPr | — | cPr | (R)- |
| IV-1294 | Me | Me | Me | — | iPr | — | Ph | racemic |
| IV-1295 | Me | Me | Me | — | iPr | — | Ph | (R)- |
| IV-1296 | Me | Me | Me | — | CF₃ | — | H | racemic |
| IV-1297 | Me | Me | Me | — | CF₃ | — | H | (R)- |
| IV-1298 | Me | Me | Me | — | CF₃ | — | Me | racemic |
| IV-1299 | Me | Me | Me | — | CF₃ | — | Me | (R)- |
| IV-1300 | Me | Me | Me | — | CF₃ | — | CHF₂ | racemic |
| IV-1301 | Me | Me | Me | — | CF₃ | — | CHF₂ | (R)- |

TABLE 90

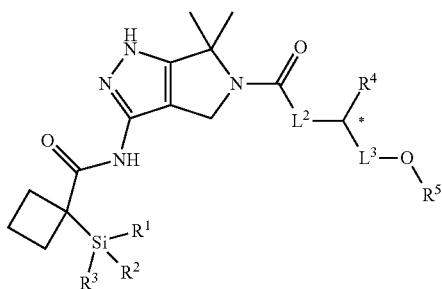

(IV)

| Compound No. | R¹ | R² | R³ | L² | R⁴ | L³ | R⁵ | Configuration |
|---|---|---|---|---|---|---|---|---|
| IV-1302 | Me | Me | Me | — | CF₃ | — | CF₃ | racemic |
| IV-1303 | Me | Me | Me | — | CF₃ | — | CF₃ | (R)- |
| IV-1304 | Me | Me | Me | — | CF₃ | — | Et | racemic |
| IV-1305 | Me | Me | Me | — | CF₃ | — | Et | (R)- |
| IV-1306 | Me | Me | Me | — | CF₃ | — | nPr | racemic |
| IV-1307 | Me | Me | Me | — | CF₃ | — | nPr | (R)- |
| IV-1308 | Me | Me | Me | — | CF₃ | — | iPr | racemic |
| IV-1309 | Me | Me | Me | — | CF₃ | — | iPr | (R)- |
| IV-1310 | Me | Me | Me | — | CF₃ | — | cPr | racemic |
| IV-1311 | Me | Me | Me | — | CF₃ | — | cPr | (R)- |
| IV-1312 | Me | Me | Me | — | CF₃ | — | Ph | racemic |
| IV-1313 | Me | Me | Me | — | CF₃ | — | Ph | (R)- |
| IV-1314 | Me | Me | Me | — | CH₂OH | — | H | racemic |
| IV-1315 | Me | Me | Me | — | CH₂OH | — | H | (R)- |
| IV-1316 | Me | Me | Me | — | CH₂OH | — | Me | racemic |
| IV-1317 | Me | Me | Me | — | CH₂OH | — | Me | (R)- |
| IV-1318 | Me | Me | Me | — | CH₂OH | — | CHF₂ | racemic |
| IV-1319 | Me | Me | Me | — | CH₂OH | — | CHF₂ | (R)- |
| IV-1320 | Me | Me | Me | — | CH₂OH | — | CF₃ | racemic |
| IV-1321 | Me | Me | Me | — | CH₂OH | — | CF₃ | (R)- |
| IV-1322 | Me | Me | Me | — | CH₂OH | — | Et | racemic |
| IV-1323 | Me | Me | Me | — | CH₂OH | — | Et | (R)- |
| IV-1324 | Me | Me | Me | — | CH₂OH | — | nPr | racemic |
| IV-1325 | Me | Me | Me | — | CH₂OH | — | nPr | (R)- |
| IV-1326 | Me | Me | Me | — | CH₂OH | — | iPr | racemic |
| IV-1327 | Me | Me | Me | — | CH₂OH | — | iPr | (R)- |
| IV-1328 | Me | Me | Me | — | CH₂OH | — | cPr | racemic |
| IV-1329 | Me | Me | Me | — | CH₂OH | — | cPr | (R)- |
| IV-1330 | Me | Me | Me | — | CH₂OH | — | Ph | racemic |
| IV-1331 | Me | Me | Me | — | CH₂OH | — | Ph | (R)- |
| IV-1332 | Me | Me | Me | — | CH₂OMe | — | H | racemic |
| IV-1333 | Me | Me | Me | — | CH₂OMe | — | H | (R)- |
| IV-1334 | Me | Me | Me | — | CH₂OMe | — | Me | racemic |
| IV-1335 | Me | Me | Me | — | CH₂OMe | — | Me | (R)- |
| IV-1336 | Me | Me | Me | — | CH₂OMe | — | CHF₂ | racemic |
| IV-1337 | Me | Me | Me | — | CH₂OMe | — | CHF₂ | (R)- |
| IV-1338 | Me | Me | Me | — | CH₂OMe | — | CF₃ | racemic |
| IV-1339 | Me | Me | Me | — | CH₂OMe | — | CF₃ | (R)- |
| IV-1340 | Me | Me | Me | — | CH₂OMe | — | Et | racemic |
| IV-1341 | Me | Me | Me | — | CH₂OMe | — | Et | (R)- |
| IV-1342 | Me | Me | Me | — | CH₂OMe | — | nPr | racemic |
| IV-1343 | Me | Me | Me | — | CH₂OMe | — | nPr | (R)- |
| IV-1344 | Me | Me | Me | — | CH₂OMe | — | iPr | racemic |
| IV-1345 | Me | Me | Me | — | CH₂OMe | — | iPr | (R)- |
| IV-1346 | Me | Me | Me | — | CH₂OMe | — | cPr | racemic |
| IV-1347 | Me | Me | Me | — | CH₂OMe | — | cPr | (R)- |
| IV-1348 | Me | Me | Me | — | CH₂OMe | — | Ph | racemic |
| IV-1349 | Me | Me | Me | — | CH₂OMe | — | Ph | (R)- |
| IV-1350 | Me | Me | Me | — | CH₂OBn | — | H | racemic |
| IV-1351 | Me | Me | Me | — | CH₂OBn | — | H | (R)- |

TABLE 91

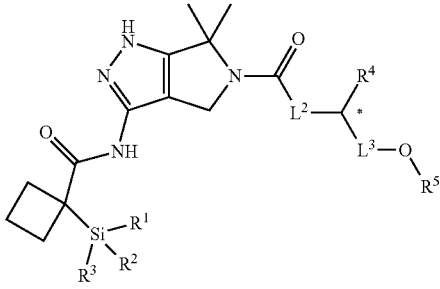

(IV)

| Compound No. | R¹ | R² | R³ | L² | R⁴ | L³ | R⁵ | Configuration |
|---|---|---|---|---|---|---|---|---|
| IV-1352 | Me | Me | Me | — | CH₂OBn | — | Me | racemic |
| IV-1353 | Me | Me | Me | — | CH₂OBn | — | Me | (R)- |
| IV-1354 | Me | Me | Me | — | CH₂OBn | — | Ph | racemic |
| IV-1355 | Me | Me | Me | — | CH₂OBn | — | Ph | (R)- |
| IV-1356 | Me | Me | Me | — | CH₂NMe₂ | — | H | racemic |
| IV-1357 | Me | Me | Me | — | CH₂NMe₂ | — | H | (R)- |
| IV-1358 | Me | Me | Me | — | CH₂NMe₂ | — | Me | racemic |
| IV-1359 | Me | Me | Me | — | CH₂NMe₂ | — | Me | (R)- |
| IV-1360 | Me | Me | Me | — | CH₂NMe₂ | — | CHF₂ | racemic |
| IV-1361 | Me | Me | Me | — | CH₂NMe₂ | — | CHF₂ | (R)- |
| IV-1362 | Me | Me | Me | — | CH₂NMe₂ | — | CF₃ | racemic |
| IV-1363 | Me | Me | Me | — | CH₂NMe₂ | — | CF₃ | (R)- |
| IV-1364 | Me | Me | Me | — | CH₂NMe₂ | — | Et | racemic |
| IV-1365 | Me | Me | Me | — | CH₂NMe₂ | — | Et | (R)- |
| IV-1366 | Me | Me | Me | — | CH₂NMe₂ | — | nPr | racemic |
| IV-1367 | Me | Me | Me | — | CH₂NMe₂ | — | nPr | (R)- |
| IV-1368 | Me | Me | Me | — | CH₂NMe₂ | — | iPr | racemic |
| IV-1369 | Me | Me | Me | — | CH₂NMe₂ | — | iPr | (R)- |
| IV-1370 | Me | Me | Me | — | CH₂NMe₂ | — | cPr | racemic |
| IV-1371 | Me | Me | Me | — | CH₂NMe₂ | — | cPr | (R)- |
| IV-1372 | Me | Me | Me | — | CH₂NMe₂ | — | Ph | racemic |
| IV-1373 | Me | Me | Me | — | CH₂NMe₂ | — | Ph | (R)- |
| IV-1374 | Me | Me | Me | — | CH₂-3-(3,3-(3, pyrrolidyl) | — | H | racemic |
| IV-1375 | Me | Me | Me | — | CH₂-3-(3,3-(3, pyrrolidyl) | — | H | (R)- |
| IV-1376 | Me | Me | Me | — | CH₂-3-(3,3-(3, pyrrolidyl) | — | Me | racemic |
| IV-1377 | Me | Me | Me | — | CH₂-3-(3,3-(3, pyrrolidyl) | — | Me | (R)- |
| IV-1378 | Me | Me | Me | — | CH₂-3-(3,3-(3, pyrrolidyl) | — | Ph | racemic |
| IV-1379 | Me | Me | Me | — | CH₂-3-(3,3-(3, pyrrolidyl) | — | Ph | (R)- |
| IV-1380 | Me | Me | Me | — | 2-F—Ph | — | H | racemic |
| IV-1381 | Me | Me | Me | — | 2-F—Ph | — | H | (R)- |
| IV-1382 | Me | Me | Me | — | 2-F—Ph | — | Me | racemic |
| IV-1383 | Me | Me | Me | — | 2-F—Ph | — | Me | (R)- |
| IV-1384 | Me | Me | Me | — | 2-F—Ph | — | Me | (S)- |
| IV-1385 | Me | Me | Me | — | 2-F—Ph | — | CHF₂ | racemic |
| IV-1386 | Me | Me | Me | — | 2-F—Ph | — | CHF₂ | (R)- |
| IV-1387 | Me | Me | Me | — | 2-F—Ph | — | CHF₂ | (S)- |
| IV-1388 | Me | Me | Me | — | 2-F—Ph | — | CF₃ | racemic |
| IV-1389 | Me | Me | Me | — | 2-F—Ph | — | CF₃ | (R)- |
| IV-1390 | Me | Me | Me | — | 2-F—Ph | — | CF₃ | (S)- |
| IV-1391 | Me | Me | Me | — | 2-F—Ph | — | Et | racemic |
| IV-1392 | Me | Me | Me | — | 2-F—Ph | — | Et | (R)- |
| IV-1393 | Me | Me | Me | — | 2-F—Ph | — | Et | (S)- |
| IV-1394 | Me | Me | Me | — | 2-F—Ph | — | nPr | racemic |
| IV-1395 | Me | Me | Me | — | 2-F—Ph | — | nPr | (R)- |
| IV-1396 | Me | Me | Me | — | 2-F—Ph | — | iPr | racemic |
| IV-1397 | Me | Me | Me | — | 2-F—Ph | — | iPr | (R)- |
| IV-1398 | Me | Me | Me | — | 2-F—Ph | — | iPr | (S)- |
| IV-1399 | Me | Me | Me | — | 2-F—Ph | — | cPr | racemic |
| IV-1400 | Me | Me | Me | — | 2-F—Ph | — | cPr | (R)- |
| IV-1401 | Me | Me | Me | — | 2-F—Ph | — | cPr | (S)- |

TABLE 92

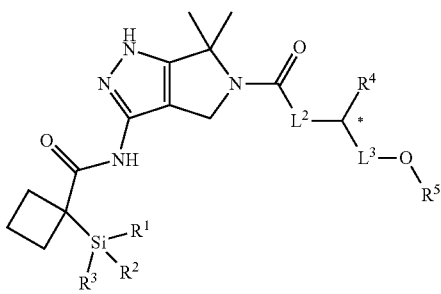

(IV)

| Compound No. | R¹ | R² | R³ | L² | R⁴ | L³ | R⁵ | Configuration |
|---|---|---|---|---|---|---|---|---|
| IV-1402 | Me | Me | Me | — | 3-F—Ph | — | H | racemic |
| IV-1403 | Me | Me | Me | — | 3-F—Ph | — | H | (R)- |
| IV-1404 | Me | Me | Me | — | 3-F—Ph | — | Me | racemic |
| IV-1405 | Me | Me | Me | — | 3-F—Ph | — | Me | (R)- |
| IV-1406 | Me | Me | Me | — | 3-F—Ph | — | Me | (S)- |
| IV-1407 | Me | Me | Me | — | 3-F—Ph | — | CHF₂ | racemic |
| IV-1408 | Me | Me | Me | — | 3-F—Ph | — | CHF₂ | (R)- |
| IV-1409 | Me | Me | Me | — | 3-F—Ph | — | CHF₂ | (S)- |
| IV-1410 | Me | Me | Me | — | 3-F—Ph | — | CF₃ | racemic |
| IV-1411 | Me | Me | Me | — | 3-F—Ph | — | CF₃ | (R)- |
| IV-1412 | Me | Me | Me | — | 3-F—Ph | — | CF₃ | (S)- |
| IV-1413 | Me | Me | Me | — | 3-F—Ph | — | Et | racemic |
| IV-1414 | Me | Me | Me | — | 3-F—Ph | — | Et | (R)- |
| IV-1415 | Me | Me | Me | — | 3-F—Ph | — | Et | (S)- |
| IV-1416 | Me | Me | Me | — | 3-F—Ph | — | nPr | racemic |
| IV-1417 | Me | Me | Me | — | 3-F—Ph | — | nPr | (R)- |
| IV-1418 | Me | Me | Me | — | 3-F—Ph | — | nPr | (S)- |
| IV-1419 | Me | Me | Me | — | 3-F—Ph | — | iPr | racemic |
| IV-1420 | Me | Me | Me | — | 3-F—Ph | — | iPr | (R)- |
| IV-1421 | Me | Me | Me | — | 3-F—Ph | — | iPr | (S)- |
| IV-1422 | Me | Me | Me | — | 3-F—Ph | — | cPr | racemic |
| IV-1423 | Me | Me | Me | — | 3-F—Ph | — | cPr | (R)- |
| IV-1424 | Me | Me | Me | — | 3-F—Ph | — | cPr | (S)- |
| IV-1425 | Me | Me | Me | — | 4-F—Ph | — | H | racemic |
| IV-1426 | Me | Me | Me | — | 4-F—Ph | — | H | (R)- |
| IV-1427 | Me | Me | Me | — | 4-F—Ph | — | Me | racemic |
| IV-1428 | Me | Me | Me | — | 4-F—Ph | — | Me | (R)- |
| IV-1429 | Me | Me | Me | — | 4-F—Ph | — | Me | (S)- |
| IV-1430 | Me | Me | Me | — | 4-F—Ph | — | CHF₂ | racemic |
| IV-1431 | Me | Me | Me | — | 4-F—Ph | — | CHF₂ | (R)- |
| IV-1432 | Me | Me | Me | — | 4-F—Ph | — | CHF₂ | (S)- |
| IV-1433 | Me | Me | Me | — | 4-F—Ph | — | CF₃ | racemic |
| IV-1434 | Me | Me | Me | — | 4-F—Ph | — | CF₃ | (R)- |
| IV-1435 | Me | Me | Me | — | 4-F—Ph | — | CF₃ | (S)- |
| IV-1436 | Me | Me | Me | — | 4-F—Ph | — | Et | racemic |
| IV-1437 | Me | Me | Me | — | 4-F—Ph | — | Et | (R)- |
| IV-1438 | Me | Me | Me | — | 4-F—Ph | — | Et | (S)- |
| IV-1439 | Me | Me | Me | — | 4-F—Ph | — | nPr | racemic |
| IV-1440 | Me | Me | Me | — | 4-F—Ph | — | nPr | (R)- |
| IV-1441 | Me | Me | Me | — | 4-F—Ph | — | nPr | (S)- |
| IV-1442 | Me | Me | Me | — | 4-F—Ph | — | iPr | racemic |
| IV-1443 | Me | Me | Me | — | 4-F—Ph | — | iPr | (R)- |
| IV-1444 | Me | Me | Me | — | 4-F—Ph | — | iPr | (S)- |
| IV-1445 | Me | Me | Me | — | 4-F—Ph | — | cPr | racemic |
| IV-1446 | Me | Me | Me | — | 4-F—Ph | — | cPr | (R)- |
| IV-1447 | Me | Me | Me | — | 4-F—Ph | — | cPr | (S)- |
| IV-1448 | Me | Me | Me | — | 2-Cl—Ph | — | H | racemic |
| IV-1449 | Me | Me | Me | — | 2-Cl—Ph | — | H | (R)- |
| IV-1450 | Me | Me | Me | — | 2-Cl—Ph | — | Me | racemic |
| IV-1451 | Me | Me | Me | — | 2-Cl—Ph | — | Me | (R)- |

TABLE 93

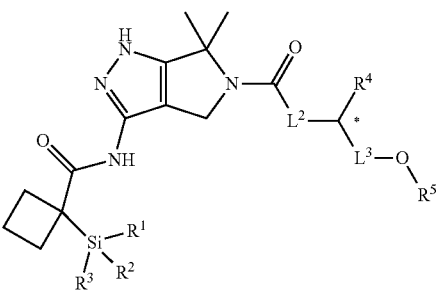

(IV)

| Compound No. | R¹ | R² | R³ | L² | R⁴ | L³ | R⁵ | Configuration |
|---|---|---|---|---|---|---|---|---|
| IV-1452 | Me | Me | Me | — | 2-Cl—Ph | — | CHF₂ | racemic |
| IV-1453 | Me | Me | Me | — | 2-Cl—Ph | — | CHF₂ | (R)- |
| IV-1454 | Me | Me | Me | — | 2-Cl—Ph | — | CF₃ | racemic |
| IV-1455 | Me | Me | Me | — | 2-Cl—Ph | — | CF₃ | (R)- |
| IV-1456 | Me | Me | Me | — | 2-Cl—Ph | — | Et | racemic |
| IV-1457 | Me | Me | Me | — | 2-Cl—Ph | — | Et | (R)- |
| IV-1458 | Me | Me | Me | — | 2-Cl—Ph | — | nPr | racemic |
| IV-1459 | Me | Me | Me | — | 2-Cl—Ph | — | nPr | (R)- |
| IV-1460 | Me | Me | Me | — | 2-Cl—Ph | — | iPr | racemic |
| IV-1461 | Me | Me | Me | — | 2-Cl—Ph | — | iPr | (R)- |
| IV-1462 | Me | Me | Me | — | 2-Cl—Ph | — | cPr | racemic |
| IV-1463 | Me | Me | Me | — | 2-Cl—Ph | — | cPr | (R)- |
| IV-1464 | Me | Me | Me | — | 2-Cl—Ph | — | H | racemic |
| IV-1465 | Me | Me | Me | — | 2-Cl—Ph | — | H | (R)- |
| IV-1466 | Me | Me | Me | — | 2-Cl—Ph | — | Me | racemic |
| IV-1467 | Me | Me | Me | — | 2-Cl—Ph | — | Me | (R)- |
| IV-1468 | Me | Me | Me | — | 2-Cl—Ph | — | CHF₂ | racemic |
| IV-1469 | Me | Me | Me | — | 2-Cl—Ph | — | CHF₂ | (R)- |
| IV-1470 | Me | Me | Me | — | 2-Cl—Ph | — | CF₃ | racemic |
| IV-1471 | Me | Me | Me | — | 2-Cl—Ph | — | CF₃ | (R)- |
| IV-1472 | Me | Me | Me | — | 2-Cl—Ph | — | Et | racemic |
| IV-1473 | Me | Me | Me | — | 2-Cl—Ph | — | Et | (R)- |
| IV-1474 | Me | Me | Me | — | 2-Cl—Ph | — | nPr | racemic |
| IV-1475 | Me | Me | Me | — | 2-Cl—Ph | — | nPr | (R)- |
| IV-1476 | Me | Me | Me | — | 2-Cl—Ph | — | iPr | racemic |
| IV-1477 | Me | Me | Me | — | 2-Cl—Ph | — | iPr | (R)- |
| IV-1478 | Me | Me | Me | — | 2-Cl—Ph | — | cPr | racemic |
| IV-1479 | Me | Me | Me | — | 2-Cl—Ph | — | cPr | (R)- |
| IV-1480 | Me | Me | Me | — | 4-Cl—Ph | — | H | racemic |
| IV-1481 | Me | Me | Me | — | 4-Cl—Ph | — | H | (R)- |
| IV-1482 | Me | Me | Me | — | 4-Cl—Ph | — | Me | racemic |
| IV-1483 | Me | Me | Me | — | 4-Cl—Ph | — | Me | (R)- |
| IV-1484 | Me | Me | Me | — | 4-Cl—Ph | — | CHF₂ | racemic |
| IV-1485 | Me | Me | Me | — | 4-Cl—Ph | — | CHF₂ | (R)- |
| IV-1486 | Me | Me | Me | — | 4-Cl—Ph | — | CF₃ | racemic |
| IV-1487 | Me | Me | Me | — | 4-Cl—Ph | — | CF₃ | (R)- |
| IV-1488 | Me | Me | Me | — | 4-Cl—Ph | — | Et | racemic |
| IV-1489 | Me | Me | Me | — | 4-Cl—Ph | — | Et | (R)- |
| IV-1490 | Me | Me | Me | — | 4-Cl—Ph | — | nPr | racemic |
| IV-1491 | Me | Me | Me | — | 4-Cl—Ph | — | nPr | (R)- |
| IV-1492 | Me | Me | Me | — | 4-Cl—Ph | — | iPr | racemic |
| IV-1493 | Me | Me | Me | — | 4-Cl—Ph | — | iPr | (R)- |
| IV-1494 | Me | Me | Me | — | 4-Cl—Ph | — | cPr | racemic |
| IV-1495 | Me | Me | Me | — | 4-Cl—Ph | — | cPr | (R)- |
| IV-1496 | Me | Me | Me | — | 2-Me—Ph | — | H | racemic |
| IV-1497 | Me | Me | Me | — | 2-Me—Ph | — | H | (R)- |
| IV-1498 | Me | Me | Me | — | 2-Me—Ph | — | Me | racemic |
| IV-1499 | Me | Me | Me | — | 2-Me—Ph | — | Me | (R)- |
| IV-1500 | Me | Me | Me | — | 2-Me—Ph | — | CHF₂ | racemic |
| IV-1501 | Me | Me | Me | — | 2-Me—Ph | — | CHF₂ | (R)- |

TABLE 94

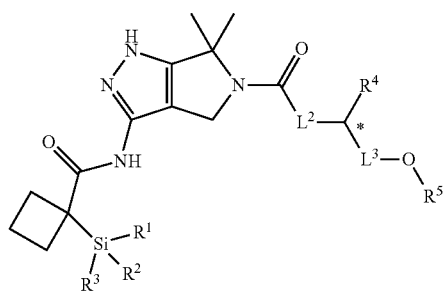

(IV)

| Compound No. | R¹ | R² | R³ | L² | R⁴ | L³ | R⁵ | Configuration |
|---|---|---|---|---|---|---|---|---|
| IV-1502 | Me | Me | Me | — | 2-Me—Ph | — | CF₃ | racemic |
| IV-1503 | Me | Me | Me | — | 2-Me—Ph | — | CF₃ | (R)- |
| IV-1504 | Me | Me | Me | — | 2-Me—Ph | — | Et | racemic |
| IV-1505 | Me | Me | Me | — | 2-Me—Ph | — | Et | (R)- |
| IV-1506 | Me | Me | Me | — | 2-Me—Ph | — | nPr | racemic |
| IV-1507 | Me | Me | Me | — | 2-Me—Ph | — | nPr | (R)- |
| IV-1508 | Me | Me | Me | — | 2-Me—Ph | — | iPr | racemic |
| IV-1509 | Me | Me | Me | — | 2-Me—Ph | — | iPr | (R)- |
| IV-1510 | Me | Me | Me | — | 2-Me—Ph | — | cPr | racemic |
| IV-1511 | Me | Me | Me | — | 2-Me—Ph | — | cPr | (R)- |
| IV-1512 | Me | Me | Me | — | 3-Me—Ph | — | H | racemic |
| IV-1513 | Me | Me | Me | — | 3-Me—Ph | — | H | (R)- |
| IV-1514 | Me | Me | Me | — | 3-Me—Ph | — | Me | racemic |
| IV-1515 | Me | Me | Me | — | 3-Me—Ph | — | Me | (R)- |
| IV-1516 | Me | Me | Me | — | 3-Me—Ph | — | CHF₂ | racemic |
| IV-1517 | Me | Me | Me | — | 3-Me—Ph | — | CHF₂ | (R)- |
| IV-1518 | Me | Me | Me | — | 3-Me—Ph | — | CF₃ | racemic |
| IV-1519 | Me | Me | Me | — | 3-Me—Ph | — | CF₃ | (R)- |
| IV-1520 | Me | Me | Me | — | 3-Me—Ph | — | Et | racemic |
| IV-1521 | Me | Me | Me | — | 3-Me—Ph | — | Et | (R)- |
| IV-1522 | Me | Me | Me | — | 3-Me—Ph | — | nPr | racemic |
| IV-1523 | Me | Me | Me | — | 3-Me—Ph | — | nPr | (R)- |
| IV-1524 | Me | Me | Me | — | 3-Me—Ph | — | iPr | racemic |
| IV-1525 | Me | Me | Me | — | 3-Me—Ph | — | iPr | (R)- |
| IV-1526 | Me | Me | Me | — | 3-Me—Ph | — | cPr | racemic |
| IV-1527 | Me | Me | Me | — | 3-Me—Ph | — | cPr | (R)- |
| IV-1528 | Me | Me | Me | — | 4-Me—Ph | — | H | racemic |
| IV-1529 | Me | Me | Me | — | 4-Me—Ph | — | H | (R)- |
| IV-1530 | Me | Me | Me | — | 4-Me—Ph | — | Me | racemic |
| IV-1531 | Me | Me | Me | — | 4-Me—Ph | — | Me | (R)- |
| IV-1532 | Me | Me | Me | — | 4-Me—Ph | — | CHF₂ | racemic |
| IV-1533 | Me | Me | Me | — | 4-Me—Ph | — | CHF₂ | (R)- |
| IV-1534 | Me | Me | Me | — | 4-Me—Ph | — | CF₃ | racemic |
| IV-1535 | Me | Me | Me | — | 4-Me—Ph | — | CF₃ | (R)- |
| IV-1536 | Me | Me | Me | — | 4-Me—Ph | — | Et | racemic |
| IV-1537 | Me | Me | Me | — | 4-Me—Ph | — | Et | (R)- |
| IV-1538 | Me | Me | Me | — | 4-Me—Ph | — | nPr | racemic |
| IV-1539 | Me | Me | Me | — | 4-Me—Ph | — | nPr | (R)- |
| IV-1540 | Me | Me | Me | — | 4-Me—Ph | — | iPr | racemic |
| IV-1541 | Me | Me | Me | — | 4-Me—Ph | — | iPr | (R)- |
| IV-1542 | Me | Me | Me | — | 4-Me—Ph | — | cPr | racemic |
| IV-1543 | Me | Me | Me | — | 4-Me—Ph | — | cPr | (R)- |
| IV-1544 | Me | Me | Me | — | 2-thienyl | — | H | racemic |
| IV-1545 | Me | Me | Me | — | 2-thienyl | — | H | (S)- |
| IV-1546 | Me | Me | Me | — | 2-thienyl | — | Me | racemic |
| IV-1547 | Me | Me | Me | — | 2-thienyl | — | Me | (+)- |
| IV-1548 | Me | Me | Me | — | 2-thienyl | — | Me | (−)- |
| IV-1549 | Me | Me | Me | — | 2-thienyl | — | CHF₂ | racemic |
| IV-1550 | Me | Me | Me | — | 2-thienyl | — | CHF₂ | (+)- |
| IV-1551 | Me | Me | Me | — | 2-thienyl | — | CHF₂ | (−)- |

TABLE 95

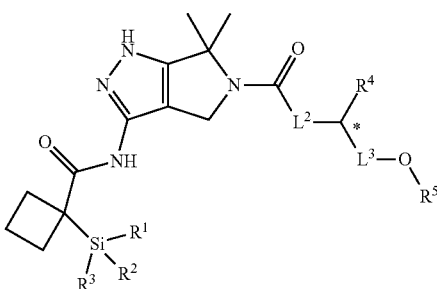

(IV)

| Compound No. | R¹ | R² | R³ | L² | R⁴ | L³ | R⁵ | Configuration |
|---|---|---|---|---|---|---|---|---|
| IV-1552 | Me | Me | Me | — | 2-thienyl | — | CF₃ | racemic |
| IV-1553 | Me | Me | Me | — | 2-thienyl | — | CF₃ | (+)- |
| IV-1554 | Me | Me | Me | — | 2-thienyl | — | CF₃ | (−)- |
| IV-1555 | Me | Me | Me | — | 2-thienyl | — | Et | racemic |
| IV-1556 | Me | Me | Me | — | 2-thienyl | — | Et | (+)- |
| IV-1557 | Me | Me | Me | — | 2-thienyl | — | Et | (−)- |
| IV-1558 | Me | Me | Me | — | 2-thienyl | — | nPr | racemic |
| IV-1559 | Me | Me | Me | — | 2-thienyl | — | nPr | (+)- |
| IV-1560 | Me | Me | Me | — | 2-thienyl | — | nPr | (−)- |
| IV-1561 | Me | Me | Me | — | 2-thienyl | — | iPr | racemic |
| IV-1562 | Me | Me | Me | — | 2-thienyl | — | iPr | (+)- |
| IV-1563 | Me | Me | Me | — | 2-thienyl | — | iPr | (−)- |
| IV-1564 | Me | Me | Me | — | 2-thienyl | — | cPr | racemic |
| IV-1565 | Me | Me | Me | — | 2-thienyl | — | cPr | (+)- |
| IV-1566 | Me | Me | Me | — | 2-thienyl | — | cPr | (−)- |
| IV-1567 | Me | Me | Me | — | 3-F-2-thienyl | — | H | racemic |
| IV-1568 | Me | Me | Me | — | 3-F-2-thienyl | — | H | (S)- |
| IV-1569 | Me | Me | Me | — | 3-F-2-thienyl | — | Me | racemic |
| IV-1570 | Me | Me | Me | — | 3-F-2-thienyl | — | Me | (S)- |
| IV-1571 | Me | Me | Me | — | 3-F-2-thienyl | — | CHF₂ | racemic |
| IV-1572 | Me | Me | Me | — | 3-F-2-thienyl | — | CHF₂ | (S)- |
| IV-1573 | Me | Me | Me | — | 3-F-2-thienyl | — | CF₃ | racemic |
| IV-1574 | Me | Me | Me | — | 3-F-2-thienyl | — | CF₃ | (S)- |
| IV-1575 | Me | Me | Me | — | 3-F-2-thienyl | — | Et | racemic |
| IV-1576 | Me | Me | Me | — | 3-F-2-thienyl | — | Et | (S)- |
| IV-1577 | Me | Me | Me | — | 3-F-2-thienyl | — | nPr | racemic |
| IV-1578 | Me | Me | Me | — | 3-F-2-thienyl | — | nPr | (S)- |
| IV-1579 | Me | Me | Me | — | 3-F-2-thienyl | — | iPr | racemic |
| IV-1580 | Me | Me | Me | — | 3-F-2-thienyl | — | iPr | (S)- |
| IV-1581 | Me | Me | Me | — | 3-F-2-thienyl | — | cPr | racemic |
| IV-1582 | Me | Me | Me | — | 3-F-2-thienyl | — | cPr | (S)- |
| IV-1583 | Me | Me | Me | — | 4-F-2-thienyl | — | H | racemic |
| IV-1584 | Me | Me | Me | — | 4-F-2-thienyl | — | H | (S)- |
| IV-1585 | Me | Me | Me | — | 4-F-2-thienyl | — | Me | racemic |
| IV-1586 | Me | Me | Me | — | 4-F-2-thienyl | — | Me | (S)- |
| IV-1587 | Me | Me | Me | — | 4-F-2-thienyl | — | CHF₂ | racemic |
| IV-1588 | Me | Me | Me | — | 4-F-2-thienyl | — | CHF₂ | (S)- |
| IV-1589 | Me | Me | Me | — | 4-F-2-thienyl | — | CF₃ | racemic |
| IV-1590 | Me | Me | Me | — | 4-F-2-thienyl | — | CF₃ | (S)- |
| IV-1591 | Me | Me | Me | — | 4-F-2-thienyl | — | Et | racemic |
| IV-1592 | Me | Me | Me | — | 4-F-2-thienyl | — | Et | (S)- |
| IV-1593 | Me | Me | Me | — | 4-F-2-thienyl | — | nPr | racemic |
| IV-1594 | Me | Me | Me | — | 4-F-2-thienyl | — | nPr | (S)- |
| IV-1595 | Me | Me | Me | — | 4-F-2-thienyl | — | iPr | racemic |
| IV-1596 | Me | Me | Me | — | 4-F-2-thienyl | — | iPr | (S)- |
| IV-1597 | Me | Me | Me | — | 4-F-2-thienyl | — | cPr | racemic |
| IV-1598 | Me | Me | Me | — | 4-F-2-thienyl | — | cPr | (S)- |
| IV-1599 | Me | Me | Me | — | 4-F-2-thienyl | — | H | racemic |
| IV-1600 | Me | Me | Me | — | 4-F-2-thienyl | — | H | (S)- |
| IV-1601 | Me | Me | Me | — | 4-F-2-thienyl | — | Me | racemic |

TABLE 96

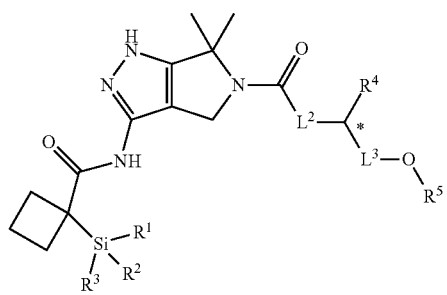

(IV)

| Compound No. | R¹ | R² | R³ | L² | R⁴ | L³ | R⁵ | Configuration |
|---|---|---|---|---|---|---|---|---|
| IV-1602 | Me | Me | Me | — | 5-F-2-thienyl | — | Me | (S)- |
| IV-1603 | Me | Me | Me | — | 5-F-2-thienyl | — | CHF₂ | racemic |
| IV-1604 | Me | Me | Me | — | 5-F-2-thienyl | — | CHF₂ | (S)- |
| IV-1605 | Me | Me | Me | — | 5-F-2-thienyl | — | CF₃ | racemic |
| IV-1606 | Me | Me | Me | — | 5-F-2-thienyl | — | CF₃ | (S)- |
| IV-1607 | Me | Me | Me | — | 5-F-2-thienyl | — | Et | racemic |
| IV-1608 | Me | Me | Me | — | 5-F-2-thienyl | — | Et | (S)- |
| IV-1609 | Me | Me | Me | — | 5-F-2-thienyl | — | nPr | racemic |
| IV-1610 | Me | Me | Me | — | 5-F-2-thienyl | — | nPr | (S)- |
| IV-1611 | Me | Me | Me | — | 5-F-2-thienyl | — | iPr | racemic |
| IV-1612 | Me | Me | Me | — | 5-F-2-thienyl | — | iPr | (S)- |
| IV-1613 | Me | Me | Me | — | 5-F-2-thienyl | — | cPr | racemic |
| IV-1614 | Me | Me | Me | — | 5-F-2-thienyl | — | cPr | (S)- |
| IV-1615 | Me | Me | Me | — | 3-Cl-2-thienyl | — | H | racemic |
| IV-1616 | Me | Me | Me | — | 3-Cl-2-thienyl | — | H | (S)- |
| IV-1617 | Me | Me | Me | — | 3-Cl-2-thienyl | — | Me | racemic |
| IV-1618 | Me | Me | Me | — | 3-Cl-2-thienyl | — | Me | (S)- |
| IV-1619 | Me | Me | Me | — | 3-Cl-2-thienyl | — | CHF₂ | racemic |
| IV-1620 | Me | Me | Me | — | 3-Cl-2-thienyl | — | CHF₂ | (S)- |
| IV-1621 | Me | Me | Me | — | 3-Cl-2-thienyl | — | CF₃ | racemic |
| IV-1622 | Me | Me | Me | — | 3-Cl-2-thienyl | — | CF₃ | (S)- |
| IV-1623 | Me | Me | Me | — | 3-Cl-2-thienyl | — | Et | racemic |
| IV-1624 | Me | Me | Me | — | 3-Cl-2-thienyl | — | Et | (S)- |
| IV-1625 | Me | Me | Me | — | 3-Cl-2-thienyl | — | nPr | racemic |
| IV-1626 | Me | Me | Me | — | 3-Cl-2-thienyl | — | nPr | (S)- |
| IV-1627 | Me | Me | Me | — | 3-Cl-2-thienyl | — | iPr | racemic |
| IV-1628 | Me | Me | Me | — | 3-Cl-2-thienyl | — | iPr | (S)- |
| IV-1629 | Me | Me | Me | — | 3-Cl-2-thienyl | — | cPr | racemic |
| IV-1630 | Me | Me | Me | — | 3-Cl-2-thienyl | — | cPr | (S)- |
| IV-1631 | Me | Me | Me | — | 4-Cl-2-thienyl | — | H | racemic |
| IV-1632 | Me | Me | Me | — | 4-Cl-2-thienyl | — | H | (S)- |
| IV-1633 | Me | Me | Me | — | 4-Cl-2-thienyl | — | Me | racemic |
| IV-1634 | Me | Me | Me | — | 4-Cl-2-thienyl | — | Me | (S)- |
| IV-1635 | Me | Me | Me | — | 4-Cl-2-thienyl | — | CHF₂ | racemic |
| IV-1636 | Me | Me | Me | — | 4-Cl-2-thienyl | — | CHF₂ | (S)- |
| IV-1637 | Me | Me | Me | — | 4-Cl-2-thienyl | — | CF₃ | racemic |
| IV-1638 | Me | Me | Me | — | 4-Cl-2-thienyl | — | CF₃ | (S)- |
| IV-1639 | Me | Me | Me | — | 4-Cl-2-thienyl | — | Et | racemic |
| IV-1640 | Me | Me | Me | — | 4-Cl-2-thienyl | — | Et | (S)- |
| IV-1641 | Me | Me | Me | — | 4-Cl-2-thienyl | — | nPr | racemic |
| IV-1642 | Me | Me | Me | — | 4-Cl-2-thienyl | — | nPr | (S)- |
| IV-1643 | Me | Me | Me | — | 4-Cl-2-thienyl | — | iPr | racemic |
| IV-1644 | Me | Me | Me | — | 4-Cl-2-thienyl | — | iPr | (S)- |
| IV-1645 | Me | Me | Me | — | 4-Cl-2-thienyl | — | cPr | racemic |
| IV-1646 | Me | Me | Me | — | 4-Cl-2-thienyl | — | cPr | (S)- |
| IV-1647 | Me | Me | Me | — | 5-Cl-2-thienyl | — | H | racemic |
| IV-1648 | Me | Me | Me | — | 5-Cl-2-thienyl | — | H | (S)- |
| IV-1649 | Me | Me | Me | — | 5-Cl-2-thienyl | — | Me | racemic |
| IV-1650 | Me | Me | Me | — | 5-Cl-2-thienyl | — | Me | (S)- |
| IV-1651 | Me | Me | Me | — | 5-Cl-2-thienyl | — | CHF₂ | racemic |

TABLE 97

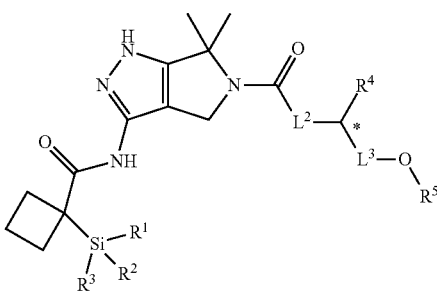

(IV)

| Compound No. | R¹ | R² | R³ | L² | R⁴ | L³ | R⁵ | Configuration |
|---|---|---|---|---|---|---|---|---|
| IV-1652 | Me | Me | Me | — | 5-Cl-2-thienyl | — | CHF₂ | (S)- |
| IV-1653 | Me | Me | Me | — | 5-Cl-2-thienyl | — | CF₃ | racemic |
| IV-1654 | Me | Me | Me | — | 5-Cl-2-thienyl | — | CF₃ | (S)- |
| IV-1655 | Me | Me | Me | — | 5-Cl-2-thienyl | — | Et | racemic |
| IV-1656 | Me | Me | Me | — | 5-Cl-2-thienyl | — | Et | (S)- |
| IV-1657 | Me | Me | Me | — | 5-Cl-2-thienyl | — | nPr | racemic |
| IV-1658 | Me | Me | Me | — | 5-Cl-2-thienyl | — | nPr | (S)- |
| IV-1659 | Me | Me | Me | — | 5-Cl-2-thienyl | — | iPr | racemic |
| IV-1660 | Me | Me | Me | — | 5-Cl-2-thienyl | — | iPr | (S)- |
| IV-1661 | Me | Me | Me | — | 5-Cl-2-thienyl | — | cPr | racemic |
| IV-1662 | Me | Me | Me | — | 5-Cl-2-thienyl | — | cPr | (S)- |
| IV-1663 | Me | Me | Me | — | 3-Me-2-thienyl | — | H | racemic |
| IV-1664 | Me | Me | Me | — | 3-Me-2-thienyl | — | H | (S)- |
| IV-1665 | Me | Me | Me | — | 3-Me-2-thienyl | — | Me | racemic |
| IV-1666 | Me | Me | Me | — | 3-Me-2-thienyl | — | Me | (S)- |
| IV-1667 | Me | Me | Me | — | 3-Me-2-thienyl | — | CHF₂ | racemic |
| IV-1668 | Me | Me | Me | — | 3-Me-2-thienyl | — | CHF₂ | (S)- |
| IV-1669 | Me | Me | Me | — | 3-Me-2-thienyl | — | CF₃ | racemic |
| IV-1670 | Me | Me | Me | — | 3-Me-2-thienyl | — | CF₃ | (S)- |
| IV-1671 | Me | Me | Me | — | 3-Me-2-thienyl | — | Et | racemic |
| IV-1672 | Me | Me | Me | — | 3-Me-2-thienyl | — | Et | (S)- |
| IV-1673 | Me | Me | Me | — | 3-Me-2-thienyl | — | nPr | racemic |
| IV-1674 | Me | Me | Me | — | 3-Me-2-thienyl | — | nPr | (S)- |
| IV-1675 | Me | Me | Me | — | 3-Me-2-thienyl | — | iPr | racemic |
| IV-1676 | Me | Me | Me | — | 3-Me-2-thienyl | — | iPr | (S)- |
| IV-1677 | Me | Me | Me | — | 3-Me-2-thienyl | — | cPr | racemic |
| IV-1678 | Me | Me | Me | — | 3-Me-2-thienyl | — | cPr | (S)- |
| IV-1679 | Me | Me | Me | — | 4-Me-2-thienyl | — | H | racemic |
| IV-1680 | Me | Me | Me | — | 4-Me-2-thienyl | — | H | (S)- |
| IV-1681 | Me | Me | Me | — | 4-Me-2-thienyl | — | Me | racemic |
| IV-1682 | Me | Me | Me | — | 4-Me-2-thienyl | — | Me | (S)- |
| IV-1683 | Me | Me | Me | — | 4-Me-2-thienyl | — | CHF₂ | racemic |
| IV-1684 | Me | Me | Me | — | 4-Me-2-thienyl | — | CHF₂ | (S)- |
| IV-1685 | Me | Me | Me | — | 4-Me-2-thienyl | — | CF₃ | racemic |
| IV-1686 | Me | Me | Me | — | 4-Me-2-thienyl | — | CF₃ | (S)- |
| IV-1687 | Me | Me | Me | — | 4-Me-2-thienyl | — | Et | racemic |
| IV-1688 | Me | Me | Me | — | 4-Me-2-thienyl | — | Et | (S)- |
| IV-1689 | Me | Me | Me | — | 4-Me-2-thienyl | — | nPr | racemic |
| IV-1690 | Me | Me | Me | — | 4-Me-2-thienyl | — | nPr | (S)- |
| IV-1691 | Me | Me | Me | — | 4-Me-2-thienyl | — | iPr | racemic |
| IV-1692 | Me | Me | Me | — | 4-Me-2-thienyl | — | iPr | (S)- |
| IV-1693 | Me | Me | Me | — | 4-Me-2-thienyl | — | cPr | racemic |
| IV-1694 | Me | Me | Me | — | 4-Me-2-thienyl | — | cPr | (S)- |
| IV-1695 | Me | Me | Me | — | 5-Me-2-thienyl | — | H | racemic |
| IV-1696 | Me | Me | Me | — | 5-Me-2-thienyl | — | H | (S)- |
| IV-1697 | Me | Me | Me | — | 5-Me-2-thienyl | — | Me | racemic |
| IV-1698 | Me | Me | Me | — | 5-Me-2-thienyl | — | Me | (S)- |
| IV-1699 | Me | Me | Me | — | 5-Me-2-thienyl | — | CHF₂ | racemic |
| IV-1700 | Me | Me | Me | — | 5-Me-2-thienyl | — | CHF₂ | (S)- |
| IV-1701 | Me | Me | Me | — | 5-Me-2-thienyl | — | CF₃ | racemic |

TABLE 98

(IV)

| Compound No. | R¹ | R² | R³ | L² | R⁴ | L³ | R⁵ | Configuration |
|---|---|---|---|---|---|---|---|---|
| IV-1702 | Me | Me | Me | — | 5-Me-2-thienyl | — | CF₃ | (S)- |
| IV-1703 | Me | Me | Me | — | 5-Me-2-thienyl | — | Et | racemic |
| IV-1704 | Me | Me | Me | — | 5-Me-2-thienyl | — | Et | (S)- |
| IV-1705 | Me | Me | Me | — | 5-Me-2-thienyl | — | nPr | racemic |
| IV-1706 | Me | Me | Me | — | 5-Me-2-thienyl | — | nPr | (S)- |
| IV-1707 | Me | Me | Me | — | 5-Me-2-thienyl | — | iPr | racemic |
| IV-1708 | Me | Me | Me | — | 5-Me-2-thienyl | — | iPr | (S)- |
| IV-1709 | Me | Me | Me | — | 5-Me-2-thienyl | — | cPr | racemic |
| IV-1710 | Me | Me | Me | — | 5-Me-2-thienyl | — | cPr | (S)- |
| IV-1711 | Me | Me | Me | — | 3-thienyl | — | H | racemic |
| IV-1712 | Me | Me | Me | — | 3-thienyl | — | H | (R)- |
| IV-1713 | Me | Me | Me | — | 3-thienyl | — | Me | racemic |
| IV-1714 | Me | Me | Me | — | 3-thienyl | — | Me | (R)- |
| IV-1715 | Me | Me | Me | — | 3-thienyl | — | CHF₂ | racemic |
| IV-1716 | Me | Me | Me | — | 3-thienyl | — | CHF₂ | (R)- |
| IV-1717 | Me | Me | Me | — | 3-thienyl | — | CF₃ | racemic |
| IV-1718 | Me | Me | Me | — | 3-thienyl | — | CF₃ | (R)- |
| IV-1719 | Me | Me | Me | — | 3-thienyl | — | Et | racemic |
| IV-1720 | Me | Me | Me | — | 3-thienyl | — | Et | (R)- |
| IV-1721 | Me | Me | Me | — | 3-thienyl | — | nPr | racemic |
| IV-1722 | Me | Me | Me | — | 3-thienyl | — | nPr | (R)- |
| IV-1723 | Me | Me | Me | — | 3-thienyl | — | iPr | racemic |
| IV-1724 | Me | Me | Me | — | 3-thienyl | — | iPr | (R)- |
| IV-1725 | Me | Me | Me | — | 3-thienyl | — | cPr | racemic |
| IV-1726 | Me | Me | Me | — | 3-thienyl | — | cPr | (R)- |

TABLE 99

(Va)

| Compound No. | R¹ | R² | R³ | L² | R⁴ | L³ | R⁵ | Configuration |
|---|---|---|---|---|---|---|---|---|
| V-1 | Me | Me | Me | O | Ph | CH₂ | Me | racemic |
| V-2 | Me | Me | Me | O | Ph | CH₂ | Me | (S)- |
| V-3 | Me | Et | Me | O | Ph | CH₂ | Me | racemic |
| V-4 | Me | Et | Me | O | Ph | CH₂ | Me | (S)- |
| V-5 | Me | Me | Me | O | Ph | CH₂ | Et | racemic |
| V-6 | Me | Me | Me | O | Ph | CH₂ | Et | (S)- |
| V-7 | Me | Et | Me | O | Ph | CH₂ | Et | racemic |
| V-8 | Me | Et | Me | O | Ph | CH₂ | Et | (S)- |
| V-9 | Me | Me | Me | O | Ph | CH₂ | nPr | racemic |
| V-10 | Me | Me | Me | O | Ph | CH₂ | nPr | (S)- |
| V-11 | Me | Et | Me | O | Ph | CH₂ | nPr | racemic |

TABLE 99-continued (Va)

| Compound No. | R¹ | R² | R³ | L² | R⁴ | L³ | R⁵ | Configuration |
|---|---|---|---|---|---|---|---|---|
| V-12 | Me | Et | Me | O | Ph | CH₂ | nPr | (S)- |
| V-13 | Me | Me | Me | O | Ph | CH₂ | iPr | racemic |
| V-14 | Me | Me | Me | O | Ph | CH₂ | iPr | (S)- |
| V-15 | Me | Et | Me | O | Ph | CH₂ | iPr | racemic |
| V-16 | Me | Et | Me | O | Ph | CH₂ | iPr | (S)- |
| V-17 | Me | Me | Me | O | Ph | CH₂ | nBu | racemic |
| V-18 | Me | Me | Me | O | Ph | CH₂ | nBu | (S)- |
| V-19 | Me | Et | Me | O | Ph | CH₂ | nBu | racemic |
| V-20 | Me | Et | Me | O | Ph | CH₂ | nBu | (S)- |
| V-21 | Me | Me | Me | O | Ph | CH₂ | tBu | racemic |
| V-22 | Me | Me | Me | O | Ph | CH₂ | tBu | (S)- |
| V-23 | Me | Et | Me | O | Ph | CH₂ | tBu | racemic |
| V-24 | Me | Et | Me | O | Ph | CH₂ | tBu | (S)- |
| V-25 | Me | Me | Me | O | Ph | CH₂ | iBu | racemic |
| V-26 | Me | Me | Me | O | Ph | CH₂ | iBu | (S)- |
| V-27 | Me | Et | Me | O | Ph | CH₂ | iBu | racemic |
| V-28 | Me | Et | Me | O | Ph | CH₂ | iBu | (S)- |
| V-29 | Me | Me | Me | O | Ph | CH₂ | n-Heptyl | racemic |
| V-30 | Me | Me | Me | O | Ph | CH₂ | n-Heptyl | (S)- |
| V-31 | Me | Et | Me | O | Ph | CH₂ | n-Heptyl | racemic |
| V-32 | Me | Et | Me | O | Ph | CH₂ | n-Heptyl | (S)- |
| V-33 | Me | Me | Me | O | Ph | CH₂ | n-Undecyl | racemic |
| V-34 | Me | Me | Me | O | Ph | CH₂ | n-Undecyl | (S)- |
| V-35 | Me | Et | Me | O | Ph | CH₂ | n-Undecyl | racemic |
| V-36 | Me | Et | Me | O | Ph | CH₂ | n-Undecyl | (S)- |
| V-37 | Me | Me | Me | O | Ph | CH₂ | Ph | racemic |
| V-38 | Me | Me | Me | O | Ph | CH₂ | Ph | (S)- |
| V-39 | Me | Et | Me | O | Ph | CH₂ | Ph | racemic |
| V-40 | Me | Et | Me | O | Ph | CH₂ | Ph | (S)- |
| V-41 | Me | Me | Me | O | Ph | CH₂ | OEt | racemic |
| V-42 | Me | Me | Me | O | Ph | CH₂ | OEt | (S)- |
| V-43 | Me | Et | Me | O | Ph | CH₂ | OEt | racemic |
| V-44 | Me | Et | Me | O | Ph | CH₂ | OEt | (S)- |
| V-45 | Me | Me | Me | O | Ph | CH₂ | (CH₂)₂COOH | racemic |
| V-46 | Me | Me | Me | O | Ph | CH₂ | (CH₂)₂COOH | (S)- |
| V-47 | Me | Et | Me | O | Ph | CH₂ | (CH₂)₂COOH | racemic |
| V-48 | Me | Et | Me | O | Ph | CH₂ | (CH₂)₂COOH | (S)- |
| V-49 | Me | Me | Me | O | Ph | C(Me)₂ | Me | racemic |
| V-50 | Me | Me | Me | O | Ph | C(Me)₂ | Me | (S)- |

TABLE 100

(Va)

| Compound No. | R¹ | R² | R³ | L² | R⁴ | L³ | R⁵ | Configuration |
|---|---|---|---|---|---|---|---|---|
| V-51 | Me | Et | Me | O | Ph | C(Me)₂ | Me | racemic |
| V-52 | Me | Et | Me | O | Ph | C(Me)₂ | Me | (S)- |
| V-53 | Me | Me | Me | O | Ph | C(Me)₂ | Et | racemic |
| V-54 | Me | Me | Me | O | Ph | C(Me)₂ | Et | (S)- |
| V-55 | Me | Et | Me | O | Ph | C(Me)₂ | Et | racemic |
| V-56 | Me | Et | Me | O | Ph | C(Me)₂ | Et | (S)- |
| V-57 | Me | Me | Me | O | Ph | C(Me)₂ | nPr | racemic |
| V-58 | Me | Me | Me | O | Ph | C(Me)₂ | nPr | (S)- |
| V-59 | Me | Et | Me | O | Ph | C(Me)₂ | nPr | racemic |
| V-60 | Me | Et | Me | O | Ph | C(Me)₂ | nPr | (S)- |
| V-61 | Me | Me | Me | O | Ph | C(Me)₂ | iPr | racemic |
| V-62 | Me | Me | Me | O | Ph | C(Me)₂ | iPr | (S)- |
| V-63 | Me | Et | Me | O | Ph | C(Me)₂ | iPr | racemic |
| V-64 | Me | Et | Me | O | Ph | C(Me)₂ | iPr | (S)- |
| V-65 | Me | Me | Me | O | Ph | C(Me)₂ | nBu | racemic |
| V-66 | Me | Me | Me | O | Ph | C(Me)₂ | nBu | (S)- |
| V-67 | Me | Et | Me | O | Ph | C(Me)₂ | nBu | racemic |
| V-68 | Me | Et | Me | O | Ph | C(Me)₂ | nBu | (S)- |
| V-69 | Me | Me | Me | O | Ph | C(Me)₂ | tBu | racemic |
| V-70 | Me | Me | Me | O | Ph | C(Me)₂ | tBu | (S)- |
| V-71 | Me | Et | Me | O | Ph | C(Me)₂ | tBu | racemic |
| V-72 | Me | Et | Me | O | Ph | C(Me)₂ | tBu | (S)- |
| V-73 | Me | Me | Me | O | Ph | C(Me)₂ | iBu | racemic |
| V-74 | Me | Me | Me | O | Ph | C(Me)₂ | iBu | (S)- |
| V-75 | Me | Et | Me | O | Ph | C(Me)₂ | iBu | racemic |
| V-76 | Me | Et | Me | O | Ph | C(Me)₂ | iBu | (S)- |
| V-77 | Me | Me | Me | O | Ph | C(Me)₂ | n-Heptyl | racemic |
| V-78 | Me | Me | Me | O | Ph | C(Me)₂ | n-Heptyl | (S)- |
| V-79 | Me | Et | Me | O | Ph | C(Me)₂ | n-Heptyl | racemic |
| V-80 | Me | Et | Me | O | Ph | C(Me)₂ | n-Heptyl | (S)- |
| V-81 | Me | Me | Me | O | Ph | C(Me)₂ | n-Undecyl | racemic |
| V-82 | Me | Me | Me | O | Ph | C(Me)₂ | n-Undecyl | (S)- |
| V-83 | Me | Et | Me | O | Ph | C(Me)₂ | n-Undecyl | racemic |
| V-84 | Me | Et | Me | O | Ph | C(Me)₂ | n-Undecyl | (S)- |
| V-85 | Me | Me | Me | O | Ph | C(Me)₂ | Ph | racemic |
| V-86 | Me | Me | Me | O | Ph | C(Me)₂ | Ph | (S)- |
| V-87 | Me | Et | Me | O | Ph | C(Me)₂ | Ph | racemic |
| V-88 | Me | Et | Me | O | Ph | C(Me)₂ | Ph | (S)- |
| V-89 | Me | Me | Me | O | Ph | C(Me)₂ | OEt | racemic |
| V-90 | Me | Me | Me | O | Ph | C(Me)₂ | OEt | (S)- |
| V-91 | Me | Et | Me | O | Ph | C(Me)₂ | OEt | racemic |
| V-92 | Me | Et | Me | O | Ph | C(Me)₂ | OEt | (S)- |
| V-93 | Me | Me | Me | O | Ph | C(Me)₂ | (CH₂)₂COOH | racemic |
| V-94 | Me | Me | Me | O | Ph | C(Me)₂ | (CH₂)₂COOH | (S)- |
| V-95 | Me | Et | Me | O | Ph | C(Me)₂ | (CH₂)₂COOH | racemic |
| V-96 | Me | Et | Me | O | Ph | C(Me)₂ | (CH₂)₂COOH | (S)- |
| V-97 | Me | Me | Me | O | Ph | (CH₂)₂ | Me | racemic |
| V-98 | Me | Me | Me | O | Ph | (CH₂)₂ | Me | (R)- |
| V-99 | Me | Et | Me | O | Ph | (CH₂)₂ | Me | racemic |
| V-100 | Me | Et | Me | O | Ph | (CH₂)₂ | Me | (R)- |

TABLE 101

(Va)

| Compound No. | R¹ | R² | R³ | L² | R⁴ | L³ | R⁵ | Configuration |
|---|---|---|---|---|---|---|---|---|
| V-101 | Me | Me | Me | O | Ph | (CH₂)₂ | Et | racemic |
| V-102 | Me | Me | Me | O | Ph | (CH₂)₂ | Et | (R)- |
| V-103 | Me | Et | Me | O | Ph | (CH₂)₂ | Et | racemic |
| V-104 | Me | Et | Me | O | Ph | (CH₂)₂ | Et | (R)- |
| V-105 | Me | Me | Me | O | Ph | (CH₂)₂ | nPr | racemic |
| V-106 | Me | Me | Me | O | Ph | (CH₂)₂ | nPr | (R)- |
| V-107 | Me | Et | Me | O | Ph | (CH₂)₂ | nPr | racemic |
| V-108 | Me | Et | Me | O | Ph | (CH₂)₂ | nPr | (R)- |
| V-109 | Me | Me | Me | O | Ph | (CH₂)₂ | iPr | racemic |
| V-110 | Me | Me | Me | O | Ph | (CH₂)₂ | iPr | (R)- |
| V-111 | Me | Et | Me | O | Ph | (CH₂)₂ | iPr | racemic |
| V-112 | Me | Et | Me | O | Ph | (CH₂)₂ | iPr | (R)- |
| V-113 | Me | Me | Me | O | Ph | (CH₂)₂ | nBu | racemic |
| V-114 | Me | Me | Me | O | Ph | (CH₂)₂ | nBu | (R)- |
| V-115 | Me | Et | Me | O | Ph | (CH₂)₂ | nBu | racemic |
| V-116 | Me | Et | Me | O | Ph | (CH₂)₂ | nBu | (R)- |
| V-117 | Me | Me | Me | O | Ph | (CH₂)₂ | tBu | racemic |
| V-118 | Me | Me | Me | O | Ph | (CH₂)₂ | tBu | (R)- |
| V-119 | Me | Et | Me | O | Ph | (CH₂)₂ | tBu | racemic |
| V-120 | Me | Et | Me | O | Ph | (CH₂)₂ | tBu | (R)- |
| V-121 | Me | Me | Me | O | Ph | (CH₂)₂ | iBu | racemic |
| V-122 | Me | Me | Me | O | Ph | (CH₂)₂ | iBu | (R)- |
| V-123 | Me | Et | Me | O | Ph | (CH₂)₂ | iBu | racemic |
| V-124 | Me | Et | Me | O | Ph | (CH₂)₂ | iBu | (R)- |
| V-125 | Me | Me | Me | O | Ph | (CH₂)₂ | n-Heptyl | racemic |
| V-126 | Me | Me | Me | O | Ph | (CH₂)₂ | n-Heptyl | (R)- |
| V-127 | Me | Et | Me | O | Ph | (CH₂)₂ | n-Heptyl | racemic |
| V-128 | Me | Et | Me | O | Ph | (CH₂)₂ | n-Heptyl | (R)- |
| V-129 | Me | Me | Me | O | Ph | (CH₂)₂ | n-Undecyl | racemic |
| V-130 | Me | Me | Me | O | Ph | (CH₂)₂ | n-Undecyl | (R)- |
| V-131 | Me | Et | Me | O | Ph | (CH₂)₂ | n-Undecyl | racemic |
| V-132 | Me | Et | Me | O | Ph | (CH₂)₂ | n-Undecyl | (R)- |
| V-133 | Me | Me | Me | O | Ph | (CH₂)₂ | Ph | racemic |
| V-134 | Me | Me | Me | O | Ph | (CH₂)₂ | Ph | (R)- |
| V-135 | Me | Et | Me | O | Ph | (CH₂)₂ | Ph | racemic |
| V-136 | Me | Et | Me | O | Ph | (CH₂)₂ | Ph | (R)- |
| V-137 | Me | Me | Me | O | Ph | (CH₂)₂ | OEt | racemic |
| V-138 | Me | Me | Me | O | Ph | (CH₂)₂ | OEt | (R)- |
| V-139 | Me | Et | Me | O | Ph | (CH₂)₂ | OEt | racemic |
| V-140 | Me | Et | Me | O | Ph | (CH₂)₂ | OEt | (R)- |
| V-141 | Me | Me | Me | O | Ph | (CH₂)₂ | (CH₂)₂COOH | racemic |
| V-142 | Me | Me | Me | O | Ph | (CH₂)₂ | (CH₂)₂COOH | (R)- |
| V-143 | Me | Et | Me | O | Ph | (CH₂)₂ | (CH₂)₂COOH | racemic |
| V-144 | Me | Et | Me | O | Ph | (CH₂)₂ | (CH₂)₂COOH | (R)- |
| V-145 | Me | Me | Me | O | Ph | CH₂C(Me)₂ | Me | racemic |
| V-146 | Me | Me | Me | O | Ph | CH₂C(Me)₂ | Me | (R)- |
| V-147 | Me | Et | Me | O | Ph | CH₂C(Me)₂ | Me | racemic |
| V-148 | Me | Et | Me | O | Ph | CH₂C(Me)₂ | Me | (R)- |
| V-149 | Me | Me | Me | O | Ph | CH₂C(Me)₂ | Et | racemic |
| V-150 | Me | Me | Me | O | Ph | CH₂C(Me)₂ | Et | (R)- |

TABLE 102

(Va)

| Compound No. | R¹ | R² | R³ | L² | R⁴ | L³ | R⁵ | Configuration |
|---|---|---|---|---|---|---|---|---|
| V-151 | Me | Et | Me | O | Ph | CH$_2$C(Me)$_2$ | Et | racemic |
| V-152 | Me | Et | Me | O | Ph | CH$_2$C(Me)$_2$ | Et | (R)- |
| V-153 | Me | Me | Me | O | Ph | CH$_2$C(Me)$_2$ | nPr | racemic |
| V-154 | Me | Me | Me | O | Ph | CH$_2$C(Me)$_2$ | nPr | (R)- |
| V-155 | Me | Et | Me | O | Ph | CH$_2$C(Me)$_2$ | nPr | racemic |
| V-156 | Me | Et | Me | O | Ph | CH$_2$C(Me)$_2$ | nPr | (R)- |
| V-157 | Me | Me | Me | O | Ph | CH$_2$C(Me)$_2$ | iPr | racemic |
| V-158 | Me | Me | Me | O | Ph | CH$_2$C(Me)$_2$ | iPr | (R)- |
| V-159 | Me | Et | Me | O | Ph | CH$_2$C(Me)$_2$ | iPr | racemic |
| V-160 | Me | Et | Me | O | Ph | CH$_2$C(Me)$_2$ | iPr | (R)- |
| V-161 | Me | Me | Me | O | Ph | CH$_2$C(Me)$_2$ | nBu | racemic |
| V-162 | Me | Me | Me | O | Ph | CH$_2$C(Me)$_2$ | nBu | (R)- |
| V-163 | Me | Et | Me | O | Ph | CH$_2$C(Me)$_2$ | nBu | racemic |
| V-164 | Me | Et | Me | O | Ph | CH$_2$C(Me)$_2$ | nBu | (R)- |
| V-165 | Me | Me | Me | O | Ph | CH$_2$C(Me)$_2$ | tBu | racemic |
| V-166 | Me | Me | Me | O | Ph | CH$_2$C(Me)$_2$ | tBu | (R)- |
| V-167 | Me | Et | Me | O | Ph | CH$_2$C(Me)$_2$ | tBu | racemic |
| V-168 | Me | Et | Me | O | Ph | CH$_2$C(Me)$_2$ | tBu | (R)- |
| V-169 | Me | Me | Me | O | Ph | CH$_2$C(Me)$_2$ | iBu | racemic |
| V-170 | Me | Me | Me | O | Ph | CH$_2$C(Me)$_2$ | iBu | (R)- |
| V-171 | Me | Et | Me | O | Ph | CH$_2$C(Me)$_2$ | iBu | racemic |
| V-172 | Me | Et | Me | O | Ph | CH$_2$C(Me)$_2$ | iBu | (R)- |
| V-173 | Me | Me | Me | O | Ph | CH$_2$C(Me)$_2$ | n-Heptyl | racemic |
| V-174 | Me | Me | Me | O | Ph | CH$_2$C(Me)$_2$ | n-Heptyl | (R)- |
| V-175 | Me | Et | Me | O | Ph | CH$_2$C(Me)$_2$ | n-Heptyl | racemic |
| V-176 | Me | Et | Me | O | Ph | CH$_2$C(Me)$_2$ | n-Heptyl | (R)- |
| V-177 | Me | Me | Me | O | Ph | CH$_2$C(Me)$_2$ | n-Undecyl | racemic |
| V-178 | Me | Me | Me | O | Ph | CH$_2$C(Me)$_2$ | n-Undecyl | (R)- |
| V-179 | Me | Et | Me | O | Ph | CH$_2$C(Me)$_2$ | n-Undecyl | racemic |
| V-180 | Me | Et | Me | O | Ph | CH$_2$C(Me)$_2$ | n-Undecyl | (R)- |
| V-181 | Me | Me | Me | O | Ph | CH$_2$C(Me)$_2$ | Ph | racemic |
| V-182 | Me | Me | Me | O | Ph | CH$_2$C(Me)$_2$ | Ph | (R)- |
| V-183 | Me | Et | Me | O | Ph | CH$_2$C(Me)$_2$ | Ph | racemic |
| V-184 | Me | Et | Me | O | Ph | CH$_2$C(Me)$_2$ | Ph | (R)- |
| V-185 | Me | Me | Me | O | Ph | CH$_2$C(Me)$_2$ | OEt | racemic |
| V-186 | Me | Me | Me | O | Ph | CH$_2$C(Me)$_2$ | OEt | (R)- |
| V-187 | Me | Et | Me | O | Ph | CH$_2$C(Me)$_2$ | OEt | racemic |
| V-188 | Me | Et | Me | O | Ph | CH$_2$C(Me)$_2$ | OEt | (R)- |
| V-189 | Me | Me | Me | O | Ph | CH$_2$C(Me)$_2$ | (CH$_2$)$_2$COOH | racemic |
| V-190 | Me | Me | Me | O | Ph | CH$_2$C(Me)$_2$ | (CH$_2$)$_2$COOH | (R)- |
| V-191 | Me | Et | Me | O | Ph | CH$_2$C(Me)$_2$ | (CH$_2$)$_2$COOH | racemic |
| V-192 | Me | Et | Me | O | Ph | CH$_2$C(Me)$_2$ | (CH$_2$)$_2$COOH | (R)- |
| V-193 | Me | Me | Me | NH | Ph | CH$_2$ | Me | racemic |
| V-194 | Me | Me | Me | NH | Ph | CH$_2$ | Me | (S)- |
| V-195 | Me | Et | Me | NH | Ph | CH$_2$ | Me | racemic |
| V-196 | Me | Et | Me | NH | Ph | CH$_2$ | Me | (S)- |
| V-197 | Me | Me | Me | NH | Ph | CH$_2$ | Et | racemic |
| V-198 | Me | Me | Me | NH | Ph | CH$_2$ | Et | (S)- |
| V-199 | Me | Et | Me | NH | Ph | CH$_2$ | Et | racemic |
| V-200 | Me | Et | Me | NH | Ph | CH$_2$ | Et | (S)- |

TABLE 103

(Va)

| Compound No. | R¹ | R² | R³ | L² | R⁴ | L³ | R⁵ | Configuration |
|---|---|---|---|---|---|---|---|---|
| V-201 | Me | Me | Me | NH | Ph | CH$_2$ | nPr | racemic |
| V-202 | Me | Me | Me | NH | Ph | CH$_2$ | nPr | (S)- |
| V-203 | Me | Et | Me | NH | Ph | CH$_2$ | nPr | racemic |
| V-204 | Me | Et | Me | NH | Ph | CH$_2$ | nPr | (S)- |
| V-205 | Me | Me | Me | NH | Ph | CH$_2$ | iPr | racemic |
| V-206 | Me | Me | Me | NH | Ph | CH$_2$ | iPr | (S)- |
| V-207 | Me | Et | Me | NH | Ph | CH$_2$ | iPr | racemic |
| V-208 | Me | Et | Me | NH | Ph | CH$_2$ | iPr | (S)- |
| V-209 | Me | Me | Me | NH | Ph | CH$_2$ | nBu | racemic |
| V-210 | Me | Me | Me | NH | Ph | CH$_2$ | nBu | (S)- |
| V-211 | Me | Et | Me | NH | Ph | CH$_2$ | nBu | racemic |
| V-212 | Me | Et | Me | NH | Ph | CH$_2$ | nBu | (S)- |
| V-213 | Me | Me | Me | NH | Ph | CH$_2$ | tBu | racemic |
| V-214 | Me | Me | Me | NH | Ph | CH$_2$ | tBu | (S)- |
| V-215 | Me | Et | Me | NH | Ph | CH$_2$ | tBu | racemic |
| V-216 | Me | Et | Me | NH | Ph | CH$_2$ | tBu | (S)- |
| V-217 | Me | Me | Me | NH | Ph | CH$_2$ | iBu | racemic |
| V-218 | Me | Me | Me | NH | Ph | CH$_2$ | iBu | (S)- |
| V-219 | Me | Et | Me | NH | Ph | CH$_2$ | iBu | racemic |
| V-220 | Me | Et | Me | NH | Ph | CH$_2$ | iBu | (S)- |
| V-221 | Me | Me | Me | NH | Ph | CH$_2$ | n-Heptyl | racemic |
| V-222 | Me | Me | Me | NH | Ph | CH$_2$ | n-Heptyl | (S)- |
| V-223 | Me | Et | Me | NH | Ph | CH$_2$ | n-Heptyl | racemic |
| V-224 | Me | Et | Me | NH | Ph | CH$_2$ | n-Heptyl | (S)- |
| V-225 | Me | Me | Me | NH | Ph | CH$_2$ | n-Undecyl | racemic |
| V-226 | Me | Me | Me | NH | Ph | CH$_2$ | n-Undecyl | (S)- |
| V-227 | Me | Et | Me | NH | Ph | CH$_2$ | n-Undecyl | racemic |
| V-228 | Me | Et | Me | NH | Ph | CH$_2$ | n-Undecyl | (S)- |
| V-229 | Me | Me | Me | NH | Ph | CH$_2$ | Ph | racemic |
| V-230 | Me | Me | Me | NH | Ph | CH$_2$ | Ph | (S)- |
| V-231 | Me | Et | Me | NH | Ph | CH$_2$ | Ph | racemic |
| V-232 | Me | Et | Me | NH | Ph | CH$_2$ | Ph | (S)- |
| V-233 | Me | Me | Me | NH | Ph | CH$_2$ | OEt | racemic |
| V-234 | Me | Me | Me | NH | Ph | CH$_2$ | OEt | (S)- |
| V-235 | Me | Et | Me | NH | Ph | CH$_2$ | OEt | racemic |
| V-236 | Me | Et | Me | NH | Ph | CH$_2$ | OEt | (S)- |
| V-237 | Me | Me | Me | NH | Ph | CH$_2$ | (CH$_2$)$_2$COOH | racemic |
| V-238 | Me | Me | Me | NH | Ph | CH$_2$ | (CH$_2$)$_2$COOH | (S)- |
| V-239 | Me | Et | Me | NH | Ph | CH$_2$ | (CH$_2$)$_2$COOH | racemic |
| V-240 | Me | Et | Me | NH | Ph | CH$_2$ | (CH$_2$)$_2$COOH | (S)- |
| V-241 | Me | Me | Me | NH | Ph | C(Me)$_2$ | Me | racemic |
| V-242 | Me | Me | Me | NH | Ph | C(Me)$_2$ | Me | (S)- |
| V-243 | Me | Et | Me | NH | Ph | C(Me)$_2$ | Me | racemic |
| V-244 | Me | Et | Me | NH | Ph | C(Me)$_2$ | Me | (S)- |
| V-245 | Me | Me | Me | NH | Ph | C(Me)$_2$ | Et | racemic |
| V-246 | Me | Me | Me | NH | Ph | C(Me)$_2$ | Et | (S)- |
| V-247 | Me | Et | Me | NH | Ph | C(Me)$_2$ | Et | racemic |
| V-248 | Me | Et | Me | NH | Ph | C(Me)$_2$ | Et | (S)- |
| V-249 | Me | Me | Me | NH | Ph | C(Me)$_2$ | nPr | racemic |
| V-250 | Me | Me | Me | NH | Ph | C(Me)$_2$ | nPr | (S)- |

TABLE 104

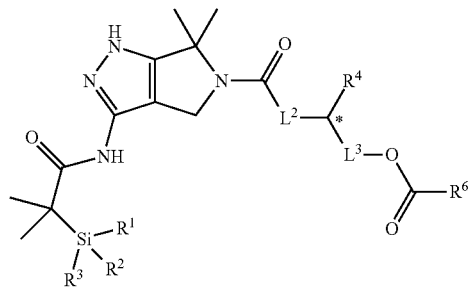

(Va)

| Compound No. | R¹ | R² | R³ | L² | R⁴ | L³ | R⁶ | Configuration |
|---|---|---|---|---|---|---|---|---|
| V-251 | Me | Et | Me | NH | Ph | C(Me)$_2$ | nPr | racemic |
| V-252 | Me | Et | Me | NH | Ph | C(Me)$_2$ | nPr | (S)- |
| V-253 | Me | Me | Me | NH | Ph | C(Me)$_2$ | iPr | racemic |
| V-254 | Me | Me | Me | NH | Ph | C(Me)$_2$ | iPr | (S)- |
| V-255 | Me | Et | Me | NH | Ph | C(Me)$_2$ | iPr | racemic |
| V-256 | Me | Et | Me | NH | Ph | C(Me)$_2$ | iPr | (S)- |
| V-257 | Me | Me | Me | NH | Ph | C(Me)$_2$ | nBu | racemic |
| V-258 | Me | Me | Me | NH | Ph | C(Me)$_2$ | nBu | (S)- |
| V-259 | Me | Et | Me | NH | Ph | C(Me)$_2$ | nBu | racemic |
| V-260 | Me | Et | Me | NH | Ph | C(Me)$_2$ | nBu | (S)- |
| V-261 | Me | Me | Me | NH | Ph | C(Me)$_2$ | tBu | racemic |
| V-262 | Me | Me | Me | NH | Ph | C(Me)$_2$ | tBu | (S)- |
| V-263 | Me | Et | Me | NH | Ph | C(Me)$_2$ | tBu | racemic |
| V-264 | Me | Et | Me | NH | Ph | C(Me)$_2$ | tBu | (S)- |
| V-265 | Me | Me | Me | NH | Ph | C(Me)$_2$ | iBu | racemic |
| V-266 | Me | Me | Me | NH | Ph | C(Me)$_2$ | iBu | (S)- |
| V-267 | Me | Et | Me | NH | Ph | C(Me)$_2$ | iBu | racemic |
| V-268 | Me | Et | Me | NH | Ph | C(Me)$_2$ | iBu | (S)- |
| V-269 | Me | Me | Me | NH | Ph | C(Me)$_2$ | n-Heptyl | racemic |
| V-270 | Me | Me | Me | NH | Ph | C(Me)$_2$ | n-Heptyl | (S)- |
| V-271 | Me | Et | Me | NH | Ph | C(Me)$_2$ | n-Heptyl | racemic |
| V-272 | Me | Et | Me | NH | Ph | C(Me)$_2$ | n-Heptyl | (S)- |
| V-273 | Me | Me | Me | NH | Ph | C(Me)$_2$ | n-Undecyl | racemic |
| V-274 | Me | Me | Me | NH | Ph | C(Me)$_2$ | n-Undecyl | (S)- |
| V-275 | Me | Et | Me | NH | Ph | C(Me)$_2$ | n-Undecyl | racemic |
| V-276 | Me | Et | Me | NH | Ph | C(Me)$_2$ | n-Undecyl | (S)- |
| V-277 | Me | Me | Me | NH | Ph | C(Me)$_2$ | Ph | racemic |
| V-278 | Me | Me | Me | NH | Ph | C(Me)$_2$ | Ph | (S)- |
| V-279 | Me | Et | Me | NH | Ph | C(Me)$_2$ | Ph | racemic |
| V-280 | Me | Et | Me | NH | Ph | C(Me)$_2$ | Ph | (S)- |
| V-281 | Me | Me | Me | NH | Ph | C(Me)$_2$ | OEt | racemic |
| V-282 | Me | Me | Me | NH | Ph | C(Me)$_2$ | OEt | (S)- |
| V-283 | Me | Et | Me | NH | Ph | C(Me)$_2$ | OEt | racemic |
| V-284 | Me | Et | Me | NH | Ph | C(Me)$_2$ | OEt | (S)- |
| V-285 | Me | Me | Me | NH | Ph | C(Me)$_2$ | (CH$_2$)$_2$COOH | racemic |
| V-286 | Me | Me | Me | NH | Ph | C(Me)$_2$ | (CH$_2$)$_2$COOH | (S)- |
| V-287 | Me | Et | Me | NH | Ph | C(Me)$_2$ | (CH$_2$)$_2$COOH | racemic |
| V-288 | Me | Et | Me | NH | Ph | C(Me)$_2$ | (CH$_2$)$_2$COOH | (S)- |
| V-289 | Me | Me | Me | NH | Ph | (CH$_2$)$_2$ | Me | racemic |
| V-290 | Me | Me | Me | NH | Ph | (CH$_2$)$_2$ | Me | (R)- |
| V-291 | Me | Et | Me | NH | Ph | (CH$_2$)$_2$ | Me | racemic |
| V-292 | Me | Et | Me | NH | Ph | (CH$_2$)$_2$ | Me | (R)- |
| V-293 | Me | Me | Me | NH | Ph | (CH$_2$)$_2$ | Et | racemic |
| V-294 | Me | Me | Me | NH | Ph | (CH$_2$)$_2$ | Et | (R)- |
| V-295 | Me | Et | Me | NH | Ph | (CH$_2$)$_2$ | Et | racemic |
| V-296 | Me | Et | Me | NH | Ph | (CH$_2$)$_2$ | Et | (R)- |
| V-297 | Me | Me | Me | NH | Ph | (CH$_2$)$_2$ | nPr | racemic |
| V-298 | Me | Me | Me | NH | Ph | (CH$_2$)$_2$ | nPr | (R)- |
| V-299 | Me | Et | Me | NH | Ph | (CH$_2$)$_2$ | nPr | racemic |
| V-300 | Me | Et | Me | NH | Ph | (CH$_2$)$_2$ | nPr | (R)- |

TABLE 105

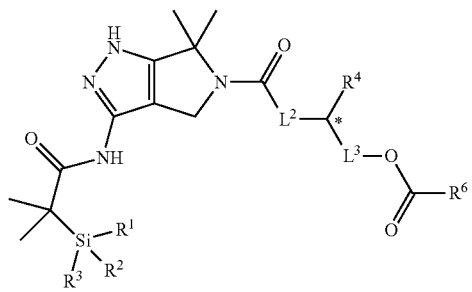

(Va)

| Compound No. | R¹ | R² | R³ | L² | R⁴ | L³ | R⁶ | Configuration |
|---|---|---|---|---|---|---|---|---|
| V-301 | Me | Me | Me | NH | Ph | (CH$_2$)$_2$ | iPr | racemic |
| V-302 | Me | Me | Me | NH | Ph | (CH$_2$)$_2$ | iPr | (R)- |
| V-303 | Me | Et | Me | NH | Ph | (CH$_2$)$_2$ | iPr | racemic |
| V-304 | Me | Et | Me | NH | Ph | (CH$_2$)$_2$ | iPr | (R)- |
| V-305 | Me | Me | Me | NH | Ph | (CH$_2$)$_2$ | nBu | racemic |
| V-306 | Me | Me | Me | NH | Ph | (CH$_2$)$_2$ | nBu | (R)- |
| V-307 | Me | Et | Me | NH | Ph | (CH$_2$)$_2$ | nBu | racemic |
| V-308 | Me | Et | Me | NH | Ph | (CH$_2$)$_2$ | nBu | (R)- |
| V-309 | Me | Me | Me | NH | Ph | (CH$_2$)$_2$ | tBu | racemic |
| V-310 | Me | Me | Me | NH | Ph | (CH$_2$)$_2$ | tBu | (R)- |
| V-311 | Me | Et | Me | NH | Ph | (CH$_2$)$_2$ | tBu | racemic |
| V-312 | Me | Et | Me | NH | Ph | (CH$_2$)$_2$ | tBu | (R)- |
| V-313 | Me | Me | Me | NH | Ph | (CH$_2$)$_2$ | iBu | racemic |
| V-314 | Me | Me | Me | NH | Ph | (CH$_2$)$_2$ | iBu | (R)- |
| V-315 | Me | Et | Me | NH | Ph | (CH$_2$)$_2$ | iBu | racemic |
| V-316 | Me | Et | Me | NH | Ph | (CH$_2$)$_2$ | iBu | (R)- |
| V-317 | Me | Me | Me | NH | Ph | (CH$_2$)$_2$ | n-Heptyl | racemic |
| V-318 | Me | Me | Me | NH | Ph | (CH$_2$)$_2$ | n-Heptyl | (R)- |
| V-319 | Me | Et | Me | NH | Ph | (CH$_2$)$_2$ | n-Heptyl | racemic |
| V-320 | Me | Et | Me | NH | Ph | (CH$_2$)$_2$ | n-Heptyl | (R)- |
| V-321 | Me | Me | Me | NH | Ph | (CH$_2$)$_2$ | n-Undecyl | racemic |
| V-322 | Me | Me | Me | NH | Ph | (CH$_2$)$_2$ | n-Undecyl | (R)- |
| V-323 | Me | Et | Me | NH | Ph | (CH$_2$)$_2$ | n-Undecyl | racemic |
| V-324 | Me | Et | Me | NH | Ph | (CH$_2$)$_2$ | n-Undecyl | (R)- |
| V-325 | Me | Me | Me | NH | Ph | (CH$_2$)$_2$ | Ph | racemic |
| V-326 | Me | Me | Me | NH | Ph | (CH$_2$)$_2$ | Ph | (R)- |
| V-327 | Me | Et | Me | NH | Ph | (CH$_2$)$_2$ | Ph | racemic |
| V-328 | Me | Et | Me | NH | Ph | (CH$_2$)$_2$ | Ph | (R)- |
| V-329 | Me | Me | Me | NH | Ph | (CH$_2$)$_2$ | OEt | racemic |
| V-330 | Me | Me | Me | NH | Ph | (CH$_2$)$_2$ | OEt | (R)- |
| V-331 | Me | Et | Me | NH | Ph | (CH$_2$)$_2$ | OEt | racemic |
| V-332 | Me | Et | Me | NH | Ph | (CH$_2$)$_2$ | OEt | (R)- |
| V-333 | Me | Me | Me | NH | Ph | (CH$_2$)$_2$ | (CH$_2$)$_2$COOH | racemic |
| V-334 | Me | Me | Me | NH | Ph | (CH$_2$)$_2$ | (CH$_2$)$_2$COOH | (R)- |
| V-335 | Me | Et | Me | NH | Ph | (CH$_2$)$_2$ | (CH$_2$)$_2$COOH | racemic |
| V-336 | Me | Et | Me | NH | Ph | (CH$_2$)$_2$ | (CH$_2$)$_2$COOH | (R)- |
| V-337 | Me | Me | Me | NH | Ph | CH$_2$C(Me)$_2$ | Me | racemic |
| V-338 | Me | Me | Me | NH | Ph | CH$_2$C(Me)$_2$ | Me | (R)- |
| V-339 | Me | Et | Me | NH | Ph | CH$_2$C(Me)$_2$ | Me | racemic |
| V-340 | Me | Et | Me | NH | Ph | CH$_2$C(Me)$_2$ | Me | (R)- |
| V-341 | Me | Me | Me | NH | Ph | CH$_2$C(Me)$_2$ | Et | racemic |
| V-342 | Me | Me | Me | NH | Ph | CH$_2$C(Me)$_2$ | Et | (R)- |
| V-343 | Me | Et | Me | NH | Ph | CH$_2$C(Me)$_2$ | Et | racemic |
| V-344 | Me | Et | Me | NH | Ph | CH$_2$C(Me)$_2$ | Et | (R)- |
| V-345 | Me | Me | Me | NH | Ph | CH$_2$C(Me)$_2$ | nPr | racemic |
| V-346 | Me | Me | Me | NH | Ph | CH$_2$C(Me)$_2$ | nPr | (R)- |
| V-347 | Me | Et | Me | NH | Ph | CH$_2$C(Me)$_2$ | nPr | racemic |
| V-348 | Me | Et | Me | NH | Ph | CH$_2$C(Me)$_2$ | nPr | (R)- |
| V-349 | Me | Me | Me | NH | Ph | CH$_2$C(Me)$_2$ | iPr | racemic |
| V-350 | Me | Me | Me | NH | Ph | CH$_2$C(Me)$_2$ | iPr | (R)- |

TABLE 106

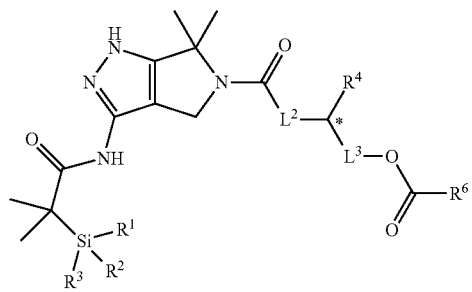
(Va)

| Compound No. | R¹ | R² | R³ | L² | R⁴ | L³ | R⁶ | Configuration |
|---|---|---|---|---|---|---|---|---|
| V-351 | Me | Et | Me | NH | Ph | CH₂C(Me)₂ | iPr | racemic |
| V-352 | Me | Et | Me | NH | Ph | CH₂C(Me)₂ | iPr | (R)- |
| V-353 | Me | Me | Me | NH | Ph | CH₂C(Me)₂ | nBu | racemic |
| V-354 | Me | Me | Me | NH | Ph | CH₂C(Me)₂ | nBu | (R)- |
| V-355 | Me | Et | Me | NH | Ph | CH₂C(Me)₂ | nBu | racemic |
| V-356 | Me | Et | Me | NH | Ph | CH₂C(Me)₂ | nBu | (R)- |
| V-357 | Me | Me | Me | NH | Ph | CH₂C(Me)₂ | tBu | racemic |
| V-358 | Me | Me | Me | NH | Ph | CH₂C(Me)₂ | tBu | (R)- |
| V-359 | Me | Et | Me | NH | Ph | CH₂C(Me)₂ | tBu | racemic |
| V-360 | Me | Et | Me | NH | Ph | CH₂C(Me)₂ | tBu | (R)- |
| V-361 | Me | Me | Me | NH | Ph | CH₂C(Me)₂ | iBu | racemic |
| V-362 | Me | Me | Me | NH | Ph | CH₂C(Me)₂ | iBu | (R)- |
| V-363 | Me | Et | Me | NH | Ph | CH₂C(Me)₂ | iBu | racemic |
| V-364 | Me | Et | Me | NH | Ph | CH₂C(Me)₂ | iBu | (R)- |
| V-365 | Me | Me | Me | NH | Ph | CH₂C(Me)₂ | n-Heptyl | racemic |
| V-366 | Me | Me | Me | NH | Ph | CH₂C(Me)₂ | n-Heptyl | (R)- |
| V-367 | Me | Et | Me | NH | Ph | CH₂C(Me)₂ | n-Heptyl | racemic |
| V-368 | Me | Et | Me | NH | Ph | CH₂C(Me)₂ | n-Heptyl | (R)- |
| V-369 | Me | Me | Me | NH | Ph | CH₂C(Me)₂ | n-Undecyl | racemic |
| V-370 | Me | Me | Me | NH | Ph | CH₂C(Me)₂ | n-Undecyl | (R)- |
| V-371 | Me | Et | Me | NH | Ph | CH₂C(Me)₂ | n-Undecyl | racemic |
| V-372 | Me | Et | Me | NH | Ph | CH₂C(Me)₂ | n-Undecyl | (R)- |
| V-373 | Me | Me | Me | NH | Ph | CH₂C(Me)₂ | Ph | racemic |
| V-374 | Me | Me | Me | NH | Ph | CH₂C(Me)₂ | Ph | (R)- |
| V-375 | Me | Et | Me | NH | Ph | CH₂C(Me)₂ | Ph | racemic |
| V-376 | Me | Et | Me | NH | Ph | CH₂C(Me)₂ | Ph | (R)- |
| V-377 | Me | Me | Me | NH | Ph | CH₂C(Me)₂ | OEt | racemic |
| V-378 | Me | Me | Me | NH | Ph | CH₂C(Me)₂ | OEt | (R)- |
| V-379 | Me | Et | Me | NH | Ph | CH₂C(Me)₂ | OEt | racemic |
| V-380 | Me | Et | Me | NH | Ph | CH₂C(Me)₂ | OEt | (R)- |
| V-381 | Me | Me | Me | NH | Ph | CH₂C(Me)₂ | (CH₂)₂COOH | racemic |
| V-382 | Me | Me | Me | NH | Ph | CH₂C(Me)₂ | (CH₂)₂COOH | (R)- |
| V-383 | Me | Et | Me | NH | Ph | CH₂C(Me)₂ | (CH₂)₂COOH | racemic |
| V-384 | Me | Et | Me | NH | Ph | CH₂C(Me)₂ | (CH₂)₂COOH | (R)- |
| V-385 | Me | Me | Me | CH₂ | Ph | CH₂ | Me | racemic |
| V-386 | Me | Me | Me | CH₂ | Ph | CH₂ | Me | (S)- |
| V-387 | Me | Et | Me | CH₂ | Ph | CH₂ | Me | racemic |
| V-388 | Me | Et | Me | CH₂ | Ph | CH₂ | Me | (S)- |
| V-389 | Me | Me | Me | CH₂ | Ph | CH₂ | Et | racemic |
| V-390 | Me | Me | Me | CH₂ | Ph | CH₂ | Et | (S)- |
| V-391 | Me | Et | Me | CH₂ | Ph | CH₂ | Et | racemic |
| V-392 | Me | Et | Me | CH₂ | Ph | CH₂ | Et | (S)- |
| V-393 | Me | Me | Me | CH₂ | Ph | CH₂ | nPr | racemic |
| V-394 | Me | Me | Me | CH₂ | Ph | CH₂ | nPr | (S)- |
| V-395 | Me | Et | Me | CH₂ | Ph | CH₂ | nPr | racemic |
| V-396 | Me | Et | Me | CH₂ | Ph | CH₂ | nPr | (S)- |
| V-397 | Me | Me | Me | CH₂ | Ph | CH₂ | iPr | racemic |
| V-398 | Me | Me | Me | CH₂ | Ph | CH₂ | iPr | (S)- |
| V-399 | Me | Et | Me | CH₂ | Ph | CH₂ | iPr | racemic |
| V-400 | Me | Et | Me | CH₂ | Ph | CH₂ | iPr | (S)- |

TABLE 107

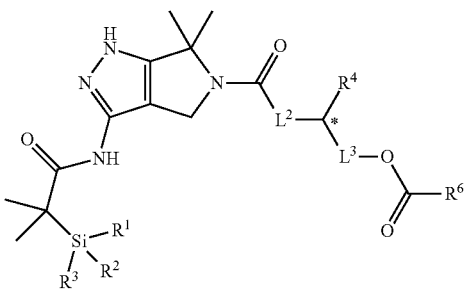
(Va)

| Compound No. | R¹ | R² | R³ | L² | R⁴ | L³ | R⁶ | Configuration |
|---|---|---|---|---|---|---|---|---|
| V-401 | Me | Me | Me | CH₂ | Ph | CH₂ | nBu | racemic |
| V-402 | Me | Me | Me | CH₂ | Ph | CH₂ | nBu | (S)- |
| V-403 | Me | Et | Me | CH₂ | Ph | CH₂ | nBu | racemic |
| V-404 | Me | Et | Me | CH₂ | Ph | CH₂ | nBu | (S)- |
| V-405 | Me | Me | Me | CH₂ | Ph | CH₂ | tBu | racemic |
| V-406 | Me | Me | Me | CH₂ | Ph | CH₂ | tBu | (S)- |
| V-407 | Me | Et | Me | CH₂ | Ph | CH₂ | tBu | racemic |
| V-408 | Me | Et | Me | CH₂ | Ph | CH₂ | tBu | (S)- |
| V-409 | Me | Me | Me | CH₂ | Ph | CH₂ | iBu | racemic |
| V-410 | Me | Me | Me | CH₂ | Ph | CH₂ | iBu | (S)- |
| V-411 | Me | Et | Me | CH₂ | Ph | CH₂ | iBu | racemic |
| V-412 | Me | Et | Me | CH₂ | Ph | CH₂ | iBu | (S)- |
| V-413 | Me | Me | Me | CH₂ | Ph | CH₂ | n-Heptyl | racemic |
| V-414 | Me | Me | Me | CH₂ | Ph | CH₂ | n-Heptyl | (S)- |
| V-415 | Me | Et | Me | CH₂ | Ph | CH₂ | n-Heptyl | racemic |
| V-416 | Me | Et | Me | CH₂ | Ph | CH₂ | n-Heptyl | (S)- |
| V-417 | Me | Me | Me | CH₂ | Ph | CH₂ | n-Undecyl | racemic |
| V-418 | Me | Me | Me | CH₂ | Ph | CH₂ | n-Undecyl | (S)- |
| V-419 | Me | Et | Me | CH₂ | Ph | CH₂ | n-Undecyl | racemic |
| V-420 | Me | Et | Me | CH₂ | Ph | CH₂ | n-Undecyl | (S)- |
| V-421 | Me | Me | Me | CH₂ | Ph | CH₂ | Ph | racemic |
| V-422 | Me | Me | Me | CH₂ | Ph | CH₂ | Ph | (S)- |
| V-423 | Me | Et | Me | CH₂ | Ph | CH₂ | Ph | racemic |
| V-424 | Me | Et | Me | CH₂ | Ph | CH₂ | Ph | (S)- |
| V-425 | Me | Me | Me | CH₂ | Ph | CH₂ | OEt | racemic |
| V-426 | Me | Me | Me | CH₂ | Ph | CH₂ | OEt | (S)- |
| V-427 | Me | Et | Me | CH₂ | Ph | CH₂ | OEt | racemic |
| V-428 | Me | Et | Me | CH₂ | Ph | CH₂ | OEt | (S)- |
| V-429 | Me | Me | Me | CH₂ | Ph | CH₂ | (CH₂)₂COOH | racemic |
| V-430 | Me | Me | Me | CH₂ | Ph | CH₂ | (CH₂)₂COOH | (S)- |
| V-431 | Me | Et | Me | CH₂ | Ph | CH₂ | (CH₂)₂COOH | racemic |
| V-432 | Me | Et | Me | CH₂ | Ph | CH₂ | (CH₂)₂COOH | (S)- |
| V-433 | Me | Me | Me | CH₂ | Ph | — | Me | racemic |
| V-434 | Me | Me | Me | CH₂ | Ph | — | Me | (S)- |
| V-435 | Me | Et | Me | CH₂ | Ph | — | Me | racemic |
| V-436 | Me | Et | Me | CH₂ | Ph | — | Me | (S)- |
| V-437 | Me | Me | Me | CH₂ | Ph | — | Et | racemic |
| V-438 | Me | Me | Me | CH₂ | Ph | — | Et | (S)- |
| V-439 | Me | Et | Me | CH₂ | Ph | — | Et | racemic |
| V-440 | Me | Et | Me | CH₂ | Ph | — | Et | (S)- |
| V-441 | Me | Me | Me | CH₂ | Ph | — | nPr | racemic |
| V-442 | Me | Me | Me | CH₂ | Ph | — | nPr | (S)- |
| V-443 | Me | Et | Me | CH₂ | Ph | — | nPr | racemic |
| V-444 | Me | Et | Me | CH₂ | Ph | — | nPr | (S)- |
| V-445 | Me | Me | Me | CH₂ | Ph | — | iPr | racemic |
| V-446 | Me | Me | Me | CH₂ | Ph | — | iPr | (S)- |
| V-447 | Me | Et | Me | CH₂ | Ph | — | iPr | racemic |
| V-448 | Me | Et | Me | CH₂ | Ph | — | iPr | (S)- |
| V-449 | Me | Me | Me | CH₂ | Ph | — | nBu | racemic |
| V-450 | Me | Me | Me | CH₂ | Ph | — | nBu | (S)- |

TABLE 108

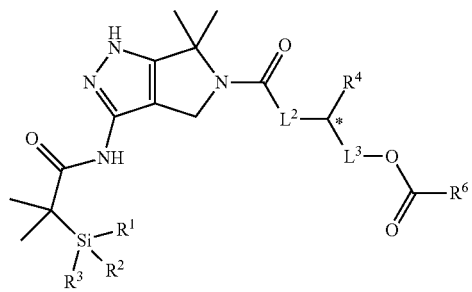

(Va)

| Compound No. | R¹ | R² | R³ | L² | R⁴ | L³ | R⁶ | Configuration |
|---|---|---|---|---|---|---|---|---|
| V-451 | Me | Et | Me | CH₂ | Ph | — | nBu | racemic |
| V-452 | Me | Et | Me | CH₂ | Ph | — | nBu | (S)- |
| V-453 | Me | Me | Me | CH₂ | Ph | — | tBu | racemic |
| V-454 | Me | Me | Me | CH₂ | Ph | — | tBu | (S)- |
| V-455 | Me | Et | Me | CH₂ | Ph | — | tBu | racemic |
| V-456 | Me | Et | Me | CH₂ | Ph | — | tBu | (S)- |
| V-457 | Me | Me | Me | CH₂ | Ph | — | iBu | racemic |
| V-458 | Me | Me | Me | CH₂ | Ph | — | iBu | (S)- |
| V-459 | Me | Et | Me | CH₂ | Ph | — | iBu | racemic |
| V-460 | Me | Et | Me | CH₂ | Ph | — | iBu | (S)- |
| V-461 | Me | Me | Me | CH₂ | Ph | — | n-Heptyl | racemic |
| V-462 | Me | Me | Me | CH₂ | Ph | — | n-Heptyl | (S)- |
| V-463 | Me | Et | Me | CH₂ | Ph | — | n-Heptyl | racemic |
| V-464 | Me | Et | Me | CH₂ | Ph | — | n-Heptyl | (S)- |
| V-465 | Me | Me | Me | CH₂ | Ph | — | n-Undecyl | racemic |
| V-466 | Me | Me | Me | CH₂ | Ph | — | n-Undecyl | (S)- |
| V-467 | Me | Et | Me | CH₂ | Ph | — | n-Undecyl | racemic |
| V-468 | Me | Et | Me | CH₂ | Ph | — | n-Undecyl | (S)- |
| V-469 | Me | Me | Me | CH₂ | Ph | — | Ph | racemic |
| V-470 | Me | Me | Me | CH₂ | Ph | — | Ph | (S)- |
| V-471 | Me | Et | Me | CH₂ | Ph | — | Ph | racemic |
| V-472 | Me | Et | Me | CH₂ | Ph | — | Ph | (S)- |
| V-473 | Me | Me | Me | CH₂ | Ph | — | OEt | racemic |
| V-474 | Me | Me | Me | CH₂ | Ph | — | OEt | (S)- |
| V-475 | Me | Et | Me | CH₂ | Ph | — | OEt | racemic |
| V-476 | Me | Et | Me | CH₂ | Ph | — | OEt | (S)- |
| V-477 | Me | Me | Me | CH₂ | Ph | — | (CH₂)₂COOH | racemic |
| V-478 | Me | Me | Me | CH₂ | Ph | — | (CH₂)₂COOH | (S)- |
| V-479 | Me | Et | Me | CH₂ | Ph | — | (CH₂)₂COOH | racemic |
| V-480 | Me | Et | Me | CH₂ | Ph | — | (CH₂)₂COOH | (S)- |
| V-481 | Me | Me | Me | CH₂ | Ph | C(Me)₂ | Me | racemic |
| V-482 | Me | Me | Me | CH₂ | Ph | C(Me)₂ | Me | (S)- |
| V-483 | Me | Et | Me | CH₂ | Ph | C(Me)₂ | Me | racemic |
| V-484 | Me | Et | Me | CH₂ | Ph | C(Me)₂ | Me | (S)- |
| V-485 | Me | Me | Me | CH₂ | Ph | C(Me)₂ | Et | racemic |
| V-486 | Me | Me | Me | CH₂ | Ph | C(Me)₂ | Et | (S)- |
| V-487 | Me | Et | Me | CH₂ | Ph | C(Me)₂ | Et | racemic |
| V-488 | Me | Et | Me | CH₂ | Ph | C(Me)₂ | Et | (S)- |
| V-489 | Me | Me | Me | CH₂ | Ph | C(Me)₂ | nPr | racemic |
| V-490 | Me | Me | Me | CH₂ | Ph | C(Me)₂ | nPr | (S)- |
| V-491 | Me | Et | Me | CH₂ | Ph | C(Me)₂ | nPr | racemic |
| V-492 | Me | Et | Me | CH₂ | Ph | C(Me)₂ | nPr | (S)- |
| V-493 | Me | Me | Me | CH₂ | Ph | C(Me)₂ | iPr | racemic |
| V-494 | Me | Me | Me | CH₂ | Ph | C(Me)₂ | iPr | (S)- |
| V-495 | Me | Et | Me | CH₂ | Ph | C(Me)₂ | iPr | racemic |
| V-496 | Me | Et | Me | CH₂ | Ph | C(Me)₂ | iPr | (S)- |
| V-497 | Me | Me | Me | CH₂ | Ph | C(Me)₂ | nBu | racemic |
| V-498 | Me | Me | Me | CH₂ | Ph | C(Me)₂ | nBu | (S)- |
| V-499 | Me | Et | Me | CH₂ | Ph | C(Me)₂ | nBu | racemic |
| V-500 | Me | Et | Me | CH₂ | Ph | C(Me)₂ | nBu | (S)- |

TABLE 109

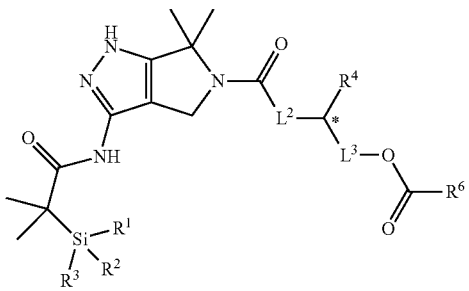

(Va)

| Compound No. | R¹ | R² | R³ | L² | R⁴ | L³ | R⁶ | Configuration |
|---|---|---|---|---|---|---|---|---|
| V-501 | Me | Me | Me | CH₂ | Ph | C(Me)₂ | tBu | racemic |
| V-502 | Me | Me | Me | CH₂ | Ph | C(Me)₂ | tBu | (S)- |
| V-503 | Me | Et | Me | CH₂ | Ph | C(Me)₂ | tBu | racemic |
| V-504 | Me | Et | Me | CH₂ | Ph | C(Me)₂ | tBu | (S)- |
| V-505 | Me | Me | Me | CH₂ | Ph | C(Me)₂ | iBu | racemic |
| V-506 | Me | Me | Me | CH₂ | Ph | C(Me)₂ | iBu | (S)- |
| V-507 | Me | Et | Me | CH₂ | Ph | C(Me)₂ | iBu | racemic |
| V-508 | Me | Et | Me | CH₂ | Ph | C(Me)₂ | iBu | (S)- |
| V-509 | Me | Me | Me | CH₂ | Ph | C(Me)₂ | n-Heptyl | racemic |
| V-510 | Me | Me | Me | CH₂ | Ph | C(Me)₂ | n-Heptyl | (S)- |
| V-511 | Me | Et | Me | CH₂ | Ph | C(Me)₂ | n-Heptyl | racemic |
| V-512 | Me | Et | Me | CH₂ | Ph | C(Me)₂ | n-Heptyl | (S)- |
| V-513 | Me | Me | Me | CH₂ | Ph | C(Me)₂ | n-Undecyl | racemic |
| V-514 | Me | Me | Me | CH₂ | Ph | C(Me)₂ | n-Undecyl | (S)- |
| V-515 | Me | Et | Me | CH₂ | Ph | C(Me)₂ | n-Undecyl | racemic |
| V-516 | Me | Et | Me | CH₂ | Ph | C(Me)₂ | n-Undecyl | (S)- |
| V-517 | Me | Me | Me | CH₂ | Ph | C(Me)₂ | Ph | racemic |
| V-518 | Me | Me | Me | CH₂ | Ph | C(Me)₂ | Ph | (S)- |
| V-519 | Me | Et | Me | CH₂ | Ph | C(Me)₂ | Ph | racemic |
| V-520 | Me | Et | Me | CH₂ | Ph | C(Me)₂ | Ph | (S)- |
| V-521 | Me | Me | Me | CH₂ | Ph | C(Me)₂ | OEt | racemic |
| V-522 | Me | Me | Me | CH₂ | Ph | C(Me)₂ | OEt | (S)- |
| V-523 | Me | Et | Me | CH₂ | Ph | C(Me)₂ | OEt | racemic |
| V-524 | Me | Et | Me | CH₂ | Ph | C(Me)₂ | OEt | (S)- |
| V-525 | Me | Me | Me | CH₂ | Ph | C(Me)₂ | (CH₂)₂COOH | racemic |
| V-526 | Me | Me | Me | CH₂ | Ph | C(Me)₂ | (CH₂)₂COOH | (S)- |
| V-527 | Me | Et | Me | CH₂ | Ph | C(Me)₂ | (CH₂)₂COOH | racemic |
| V-528 | Me | Et | Me | CH₂ | Ph | C(Me)₂ | (CH₂)₂COOH | (S)- |
| V-529 | Me | Me | Me | CH₂ | Ph | (CH₂)₂ | Me | racemic |
| V-530 | Me | Me | Me | CH₂ | Ph | (CH₂)₂ | Me | (S)- |
| V-531 | Me | Et | Me | CH₂ | Ph | (CH₂)₂ | Me | racemic |
| V-532 | Me | Et | Me | CH₂ | Ph | (CH₂)₂ | Me | (S)- |
| V-533 | Me | Me | Me | CH₂ | Ph | (CH₂)₂ | Et | racemic |
| V-534 | Me | Me | Me | CH₂ | Ph | (CH₂)₂ | Et | (S)- |
| V-535 | Me | Et | Me | CH₂ | Ph | (CH₂)₂ | Et | racemic |
| V-536 | Me | Et | Me | CH₂ | Ph | (CH₂)₂ | Et | (S)- |
| V-537 | Me | Me | Me | CH₂ | Ph | (CH₂)₂ | nPr | racemic |
| V-538 | Me | Me | Me | CH₂ | Ph | (CH₂)₂ | nPr | (S)- |
| V-539 | Me | Et | Me | CH₂ | Ph | (CH₂)₂ | nPr | racemic |
| V-540 | Me | Et | Me | CH₂ | Ph | (CH₂)₂ | nPr | (S)- |
| V-541 | Me | Me | Me | CH₂ | Ph | (CH₂)₂ | iPr | racemic |
| V-542 | Me | Me | Me | CH₂ | Ph | (CH₂)₂ | iPr | (S)- |
| V-543 | Me | Et | Me | CH₂ | Ph | (CH₂)₂ | iPr | racemic |
| V-544 | Me | Et | Me | CH₂ | Ph | (CH₂)₂ | iPr | (S)- |
| V-545 | Me | Me | Me | CH₂ | Ph | (CH₂)₂ | nBu | racemic |
| V-546 | Me | Me | Me | CH₂ | Ph | (CH₂)₂ | nBu | (S)- |
| V-547 | Me | Et | Me | CH₂ | Ph | (CH₂)₂ | nBu | racemic |
| V-548 | Me | Et | Me | CH₂ | Ph | (CH₂)₂ | nBu | (S)- |
| V-549 | Me | Me | Me | CH₂ | Ph | (CH₂)₂ | tBu | racemic |
| V-550 | Me | Me | Me | CH₂ | Ph | (CH₂)₂ | tBu | (S)- |

TABLE 110

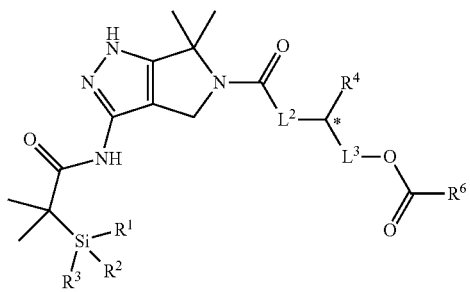

(Va)

| Compound No. | R¹ | R² | R³ | L² | R⁴ | L³ | R⁶ | Configuration |
|---|---|---|---|---|---|---|---|---|
| V-551 | Me | Et | Me | CH₂ | Ph | (CH₂)₂ | tBu | racemic |
| V-552 | Me | Et | Me | CH₂ | Ph | (CH₂)₂ | tBu | (S)- |
| V-553 | Me | Me | Me | CH₂ | Ph | (CH₂)₂ | iBu | racemic |
| V-554 | Me | Me | Me | CH₂ | Ph | (CH₂)₂ | iBu | (S)- |
| V-555 | Me | Et | Me | CH₂ | Ph | (CH₂)₂ | iBu | racemic |
| V-556 | Me | Et | Me | CH₂ | Ph | (CH₂)₂ | iBu | (S)- |
| V-557 | Me | Me | Me | CH₂ | Ph | (CH₂)₂ | n-Heptyl | racemic |
| V-558 | Me | Me | Me | CH₂ | Ph | (CH₂)₂ | n-Heptyl | (S)- |
| V-559 | Me | Et | Me | CH₂ | Ph | (CH₂)₂ | n-Heptyl | racemic |
| V-560 | Me | Et | Me | CH₂ | Ph | (CH₂)₂ | n-Heptyl | (S)- |
| V-561 | Me | Me | Me | CH₂ | Ph | (CH₂)₂ | n-Undecyl | racemic |
| V-562 | Me | Me | Me | CH₂ | Ph | (CH₂)₂ | n-Undecyl | (S)- |
| V-563 | Me | Et | Me | CH₂ | Ph | (CH₂)₂ | n-Undecyl | racemic |
| V-564 | Me | Et | Me | CH₂ | Ph | (CH₂)₂ | n-Undecyl | (S)- |
| V-565 | Me | Me | Me | CH₂ | Ph | (CH₂)₂ | Ph | racemic |
| V-566 | Me | Me | Me | CH₂ | Ph | (CH₂)₂ | Ph | (S)- |
| V-567 | Me | Et | Me | CH₂ | Ph | (CH₂)₂ | Ph | racemic |
| V-568 | Me | Et | Me | CH₂ | Ph | (CH₂)₂ | Ph | (S)- |
| V-569 | Me | Me | Me | CH₂ | Ph | (CH₂)₂ | OEt | racemic |
| V-570 | Me | Me | Me | CH₂ | Ph | (CH₂)₂ | OEt | (S)- |
| V-571 | Me | Et | Me | CH₂ | Ph | (CH₂)₂ | OEt | racemic |
| V-572 | Me | Et | Me | CH₂ | Ph | (CH₂)₂ | OEt | (S)- |
| V-573 | Me | Me | Me | CH₂ | Ph | (CH₂)₂ | (CH₂)₂COOH | racemic |
| V-574 | Me | Me | Me | CH₂ | Ph | (CH₂)₂ | (CH₂)₂COOH | (S)- |
| V-575 | Me | Et | Me | CH₂ | Ph | (CH₂)₂ | (CH₂)₂COOH | racemic |
| V-576 | Me | Et | Me | CH₂ | Ph | (CH₂)₂ | (CH₂)₂COOH | (S)- |
| V-577 | Me | Me | Me | CH₂ | Ph | CH₂C(Me)₂ | Me | racemic |
| V-578 | Me | Me | Me | CH₂ | Ph | CH₂C(Me)₂ | Me | (S)- |
| V-579 | Me | Et | Me | CH₂ | Ph | CH₂C(Me)₂ | Me | racemic |
| V-580 | Me | Et | Me | CH₂ | Ph | CH₂C(Me)₂ | Me | (S)- |
| V-581 | Me | Me | Me | CH₂ | Ph | CH₂C(Me)₂ | Et | racemic |
| V-582 | Me | Me | Me | CH₂ | Ph | CH₂C(Me)₂ | Et | (S)- |
| V-583 | Me | Et | Me | CH₂ | Ph | CH₂C(Me)₂ | Et | racemic |
| V-584 | Me | Et | Me | CH₂ | Ph | CH₂C(Me)₂ | Et | (S)- |
| V-585 | Me | Me | Me | CH₂ | Ph | CH₂C(Me)₂ | nPr | racemic |
| V-586 | Me | Me | Me | CH₂ | Ph | CH₂C(Me)₂ | nPr | (S)- |
| V-587 | Me | Et | Me | CH₂ | Ph | CH₂C(Me)₂ | nPr | racemic |
| V-588 | Me | Et | Me | CH₂ | Ph | CH₂C(Me)₂ | nPr | (S)- |
| V-589 | Me | Me | Me | CH₂ | Ph | CH₂C(Me)₂ | iPr | racemic |
| V-590 | Me | Me | Me | CH₂ | Ph | CH₂C(Me)₂ | iPr | (S)- |
| V-591 | Me | Et | Me | CH₂ | Ph | CH₂C(Me)₂ | iPr | racemic |
| V-592 | Me | Et | Me | CH₂ | Ph | CH₂C(Me)₂ | iPr | (S)- |
| V-593 | Me | Me | Me | CH₂ | Ph | CH₂C(Me)₂ | nBu | racemic |
| V-594 | Me | Me | Me | CH₂ | Ph | CH₂C(Me)₂ | nBu | (S)- |
| V-595 | Me | Et | Me | CH₂ | Ph | CH₂C(Me)₂ | nBu | racemic |
| V-596 | Me | Et | Me | CH₂ | Ph | CH₂C(Me)₂ | nBu | (S)- |
| V-597 | Me | Me | Me | CH₂ | Ph | CH₂C(Me)₂ | tBu | racemic |
| V-598 | Me | Me | Me | CH₂ | Ph | CH₂C(Me)₂ | tBu | (S)- |
| V-599 | Me | Et | Me | CH₂ | Ph | CH₂C(Me)₂ | tBu | racemic |
| V-600 | Me | Et | Me | CH₂ | Ph | CH₂C(Me)₂ | tBu | (S)- |

TABLE 111

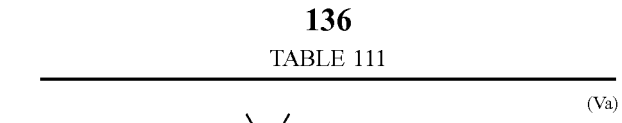

(Va)

| Compound No. | R¹ | R² | R³ | L² | R⁴ | L³ | R⁶ | Configuration |
|---|---|---|---|---|---|---|---|---|
| V-601 | Me | Me | Me | CH₂ | Ph | CH₂C(Me)₂ | iBu | racemic |
| V-602 | Me | Me | Me | CH₂ | Ph | CH₂C(Me)₂ | iBu | (S)- |
| V-603 | Me | Et | Me | CH₂ | Ph | CH₂C(Me)₂ | iBu | racemic |
| V-604 | Me | Et | Me | CH₂ | Ph | CH₂C(Me)₂ | iBu | (S)- |
| V-605 | Me | Me | Me | CH₂ | Ph | CH₂C(Me)₂ | n-Heptyl | racemic |
| V-606 | Me | Me | Me | CH₂ | Ph | CH₂C(Me)₂ | n-Heptyl | (S)- |
| V-607 | Me | Et | Me | CH₂ | Ph | CH₂C(Me)₂ | n-Heptyl | racemic |
| V-608 | Me | Et | Me | CH₂ | Ph | CH₂C(Me)₂ | n-Heptyl | (S)- |
| V-609 | Me | Me | Me | CH₂ | Ph | CH₂C(Me)₂ | n-Undecyl | racemic |
| V-610 | Me | Me | Me | CH₂ | Ph | CH₂C(Me)₂ | n-Undecyl | (S)- |
| V-611 | Me | Et | Me | CH₂ | Ph | CH₂C(Me)₂ | n-Undecyl | racemic |
| V-612 | Me | Et | Me | CH₂ | Ph | CH₂C(Me)₂ | n-Undecyl | (S)- |
| V-613 | Me | Me | Me | CH₂ | Ph | CH₂C(Me)₂ | Ph | racemic |
| V-614 | Me | Me | Me | CH₂ | Ph | CH₂C(Me)₂ | Ph | (S)- |
| V-615 | Me | Et | Me | CH₂ | Ph | CH₂C(Me)₂ | Ph | racemic |
| V-616 | Me | Et | Me | CH₂ | Ph | CH₂C(Me)₂ | Ph | (S)- |
| V-617 | Me | Me | Me | CH₂ | Ph | CH₂C(Me)₂ | OEt | racemic |
| V-618 | Me | Me | Me | CH₂ | Ph | CH₂C(Me)₂ | OEt | (S)- |
| V-619 | Me | Et | Me | CH₂ | Ph | CH₂C(Me)₂ | OEt | racemic |
| V-620 | Me | Et | Me | CH₂ | Ph | CH₂C(Me)₂ | OEt | (S)- |
| V-621 | Me | Me | Me | CH₂ | Ph | CH₂C(Me)₂ | (CH₂)₂COOH | racemic |
| V-622 | Me | Me | Me | CH₂ | Ph | CH₂C(Me)₂ | (CH₂)₂COOH | (S)- |
| V-623 | Me | Et | Me | CH₂ | Ph | CH₂C(Me)₂ | (CH₂)₂COOH | racemic |
| V-624 | Me | Et | Me | CH₂ | Ph | CH₂C(Me)₂ | (CH₂)₂COOH | (S)- |

TABLE 112

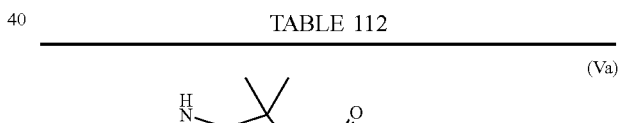

(Va)

| Compound No. | R¹ | R² | R³ | L² | R⁴ | L³ | R⁶ | Configuration |
|---|---|---|---|---|---|---|---|---|
| V-1884 | Me | Me | Me | — | Ph | — | Me | racemic |
| V-1885 | Me | Me | Me | — | Ph | — | Me | (R)- |
| V-1886 | Me | Et | Me | — | Ph | — | Me | racemic |
| V-1887 | Me | Et | Me | — | Ph | — | Me | (R)- |
| V-1888 | Me | Me | Me | — | Ph | — | Et | racemic |
| V-1889 | Me | Me | Me | — | Ph | — | Et | (R)- |
| V-1890 | Me | Et | Me | — | Ph | — | Et | racemic |
| V-1891 | Me | Et | Me | — | Ph | — | Et | (R)- |
| V-1892 | Me | Me | Me | — | Ph | — | nPr | racemic |
| V-1893 | Me | Me | Me | — | Ph | — | nPr | (R)- |
| V-1894 | Me | Et | Me | — | Ph | — | nPr | racemic |
| V-1895 | Me | Et | Me | — | Ph | — | nPr | (R)- |

TABLE 112-continued

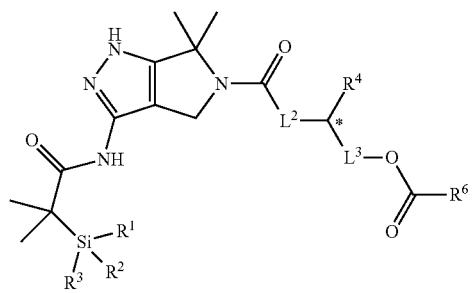

(Va)

| Compound No. | R¹ | R² | R³ | L² | R⁴ | L³ | R⁶ | Configuration |
|---|---|---|---|---|---|---|---|---|
| V-1896 | Me | Me | Me | — | Ph | — | iPr | racemic |
| V-1897 | Me | Me | Me | — | Ph | — | iPr | (R)- |
| V-1898 | Me | Et | Me | — | Ph | — | iPr | racemic |
| V-1899 | Me | Et | Me | — | Ph | — | iPr | (R)- |
| V-1900 | Me | Me | Me | — | Ph | — | nBu | racemic |
| V-1901 | Me | Me | Me | — | Ph | — | nBu | (R)- |
| V-1902 | Me | Et | Me | — | Ph | — | nBu | racemic |
| V-1903 | Me | Et | Me | — | Ph | — | nBu | (R)- |
| V-1904 | Me | Me | Me | — | Ph | — | tBu | racemic |
| V-1905 | Me | Me | Me | — | Ph | — | tBu | (R)- |
| V-1906 | Me | Et | Me | — | Ph | — | tBu | racemic |
| V-1907 | Me | Et | Me | — | Ph | — | tBu | (R)- |
| V-1908 | Me | Me | Me | — | Ph | — | iBu | racemic |
| V-1909 | Me | Me | Me | — | Ph | — | iBu | (R)- |
| V-1910 | Me | Et | Me | — | Ph | — | iBu | racemic |
| V-1911 | Me | Et | Me | — | Ph | — | iBu | (R)- |
| V-1912 | Me | Me | Me | — | Ph | — | n-Heptyl | racemic |
| V-1913 | Me | Me | Me | — | Ph | — | n-Heptyl | (R)- |
| V-1914 | Me | Et | Me | — | Ph | — | n-Heptyl | racemic |
| V-1915 | Me | Et | Me | — | Ph | — | n-Heptyl | (R)- |
| V-1916 | Me | Me | Me | — | Ph | — | n-Undecyl | racemic |
| V-1917 | Me | Me | Me | — | Ph | — | n-Undecyl | (R)- |
| V-1918 | Me | Et | Me | — | Ph | — | n-Undecyl | racemic |
| V-1919 | Me | Et | Me | — | Ph | — | n-Undecyl | (R)- |
| V-1920 | Me | Me | Me | — | Ph | — | OEt | racemic |
| V-1921 | Me | Me | Me | — | Ph | — | OEt | (R)- |
| V-1922 | Me | Et | Me | — | Ph | — | OEt | racemic |
| V-1923 | Me | Et | Me | — | Ph | — | OEt | (R)- |
| V-1924 | Me | Me | Me | — | Ph | — | (CH₂)₂COONa | racemic |
| V-1925 | Me | Me | Me | — | Ph | — | (CH₂)₂COONa | (R)- |
| V-1926 | Me | Et | Me | — | Ph | — | (CH₂)₂COONa | racemic |
| V-1927 | Me | Et | Me | — | Ph | — | (CH₂)₂COONa | (R)- |
| V-1928 | Me | Me | Me | — | Ph | CH₂ | Me | racemic |
| V-1929 | Me | Me | Me | — | Ph | CH₂ | Me | (S)- |
| V-1930 | Me | Et | Me | — | Ph | CH₂ | Me | racemic |
| V-1931 | Me | Et | Me | — | Ph | CH₂ | Me | (S)- |
| V-1932 | Me | Me | Me | — | Ph | CH₂ | Et | racemic |
| V-1933 | Me | Me | Me | — | Ph | CH₂ | Et | (S)- |

TABLE 113

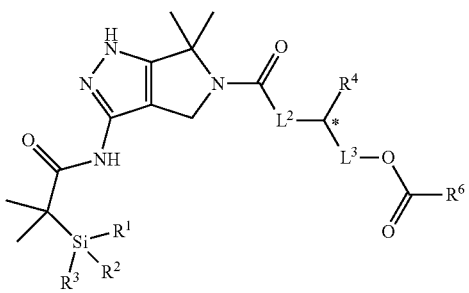

(Va)

| Compound No. | R¹ | R² | R³ | L² | R⁴ | L³ | R⁶ | Configuration |
|---|---|---|---|---|---|---|---|---|
| V-1934 | Me | Et | Me | — | Ph | CH₂ | Et | racemic |
| V-1935 | Me | Et | Me | — | Ph | CH₂ | Et | (S)- |
| V-1936 | Me | Me | Me | — | Ph | CH₂ | nPr | racemic |
| V-1937 | Me | Me | Me | — | Ph | CH₂ | nPr | (S)- |
| V-1938 | Me | Et | Me | — | Ph | CH₂ | nPr | racemic |
| V-1939 | Me | Et | Me | — | Ph | CH₂ | nPr | (S)- |
| V-1940 | Me | Me | Me | — | Ph | CH₂ | iPr | racemic |
| V-1941 | Me | Me | Me | — | Ph | CH₂ | iPr | (S)- |
| V-1942 | Me | Et | Me | — | Ph | CH₂ | iPr | racemic |
| V-1943 | Me | Et | Me | — | Ph | CH₂ | iPr | (S)- |
| V-1944 | Me | Me | Me | — | Ph | CH₂ | nBu | racemic |
| V-1945 | Me | Me | Me | — | Ph | CH₂ | nBu | (S)- |
| V-1946 | Me | Et | Me | — | Ph | CH₂ | nBu | racemic |
| V-1947 | Me | Et | Me | — | Ph | CH₂ | nBu | (S)- |
| V-1948 | Me | Me | Me | — | Ph | CH₂ | tBu | racemic |
| V-1949 | Me | Me | Me | — | Ph | CH₂ | tBu | (S)- |
| V-1950 | Me | Et | Me | — | Ph | CH₂ | tBu | racemic |
| V-1951 | Me | Et | Me | — | Ph | CH₂ | tBu | (S)- |
| V-1952 | Me | Me | Me | — | Ph | CH₂ | iBu | racemic |
| V-1953 | Me | Me | Me | — | Ph | CH₂ | iBu | (S)- |
| V-1954 | Me | Et | Me | — | Ph | CH₂ | iBu | racemic |
| V-1955 | Me | Et | Me | — | Ph | CH₂ | iBu | (S)- |
| V-1956 | Me | Me | Me | — | Ph | CH₂ | n-Heptyl | racemic |
| V-1957 | Me | Me | Me | — | Ph | CH₂ | n-Heptyl | (S)- |
| V-1958 | Me | Et | Me | — | Ph | CH₂ | n-Heptyl | racemic |
| V-1959 | Me | Et | Me | — | Ph | CH₂ | n-Heptyl | (S)- |
| V-1960 | Me | Me | Me | — | Ph | CH₂ | n-Undecyl | racemic |
| V-1961 | Me | Me | Me | — | Ph | CH₂ | n-Undecyl | (S)- |
| V-1962 | Me | Et | Me | — | Ph | CH₂ | n-Undecyl | racemic |
| V-1963 | Me | Et | Me | — | Ph | CH₂ | n-Undecyl | (S)- |
| V-1964 | Me | Me | Me | — | Ph | CH₂ | OEt | racemic |
| V-1965 | Me | Me | Me | — | Ph | CH₂ | OEt | (S)- |
| V-1966 | Me | Et | Me | — | Ph | CH₂ | OEt | racemic |
| V-1967 | Me | Et | Me | — | Ph | CH₂ | OEt | (S)- |
| V-1968 | Me | Me | Me | — | Ph | CH₂ | (CH₂)₂COONa | racemic |
| V-1969 | Me | Me | Me | — | Ph | CH₂ | (CH₂)₂COONa | (S)- |
| V-1970 | Me | Et | Me | — | Ph | CH₂ | (CH₂)₂COONa | racemic |
| V-1971 | Me | Et | Me | — | Ph | CH₂ | (CH₂)₂COONa | (S)- |

TABLE 114

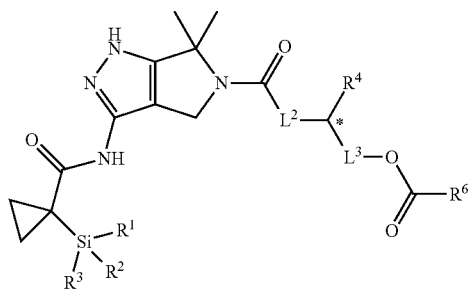
(Vb)

| Compound No. | R¹ | R² | R³ | L² | R⁴ | L³ | R⁶ | Configuration |
|---|---|---|---|---|---|---|---|---|
| V-625 | Me | Me | Me | O | Ph | CH₂ | Me | racemic |
| V-626 | Me | Me | Me | O | Ph | CH₂ | Me | (S)- |
| V-627 | Me | Et | Me | O | Ph | CH₂ | Me | racemic |
| V-628 | Me | Et | Me | O | Ph | CH₂ | Me | (S)- |
| V-629 | Me | Me | Me | O | Ph | CH₂ | Et | racemic |
| V-630 | Me | Me | Me | O | Ph | CH₂ | Et | (S)- |
| V-631 | Me | Et | Me | O | Ph | CH₂ | Et | racemic |
| V-632 | Me | Et | Me | O | Ph | CH₂ | Et | (S)- |
| V-633 | Me | Me | Me | O | Ph | CH₂ | nPr | racemic |
| V-634 | Me | Me | Me | O | Ph | CH₂ | nPr | (S)- |
| V-635 | Me | Et | Me | O | Ph | CH₂ | nPr | racemic |
| V-636 | Me | Et | Me | O | Ph | CH₂ | nPr | (S)- |
| V-637 | Me | Me | Me | O | Ph | CH₂ | iPr | racemic |
| V-638 | Me | Me | Me | O | Ph | CH₂ | iPr | (S)- |
| V-639 | Me | Et | Me | O | Ph | CH₂ | iPr | racemic |
| V-640 | Me | Et | Me | O | Ph | CH₂ | iPr | (S)- |
| V-641 | Me | Me | Me | O | Ph | CH₂ | nBu | racemic |
| V-642 | Me | Me | Me | O | Ph | CH₂ | nBu | (S)- |
| V-643 | Me | Et | Me | O | Ph | CH₂ | nBu | racemic |
| V-644 | Me | Et | Me | O | Ph | CH₂ | nBu | (S)- |
| V-645 | Me | Me | Me | O | Ph | CH₂ | tBu | racemic |
| V-646 | Me | Me | Me | O | Ph | CH₂ | tBu | (S)- |
| V-647 | Me | Et | Me | O | Ph | CH₂ | tBu | racemic |
| V-648 | Me | Et | Me | O | Ph | CH₂ | tBu | (S)- |
| V-649 | Me | Me | Me | O | Ph | CH₂ | iBu | racemic |
| V-650 | Me | Me | Me | O | Ph | CH₂ | iBu | (S)- |
| V-651 | Me | Et | Me | O | Ph | CH₂ | iBu | racemic |
| V-652 | Me | Et | Me | O | Ph | CH₂ | iBu | (S)- |
| V-653 | Me | Me | Me | O | Ph | CH₂ | n-Heptyl | racemic |
| V-654 | Me | Me | Me | O | Ph | CH₂ | n-Heptyl | (S)- |
| V-655 | Me | Et | Me | O | Ph | CH₂ | n-Heptyl | racemic |
| V-656 | Me | Et | Me | O | Ph | CH₂ | n-Heptyl | (S)- |
| V-657 | Me | Me | Me | O | Ph | CH₂ | n-Undecyl | racemic |
| V-658 | Me | Me | Me | O | Ph | CH₂ | n-Undecyl | (S)- |
| V-659 | Me | Et | Me | O | Ph | CH₂ | n-Undecyl | racemic |
| V-660 | Me | Et | Me | O | Ph | CH₂ | n-Undecyl | (S)- |
| V-661 | Me | Me | Me | O | Ph | CH₂ | Ph | racemic |
| V-662 | Me | Me | Me | O | Ph | CH₂ | Ph | (S)- |
| V-663 | Me | Et | Me | O | Ph | CH₂ | Ph | racemic |
| V-664 | Me | Et | Me | O | Ph | CH₂ | Ph | (S)- |
| V-665 | Me | Me | Me | O | Ph | CH₂ | OEt | racemic |
| V-666 | Me | Me | Me | O | Ph | CH₂ | OEt | (S)- |
| V-667 | Me | Et | Me | O | Ph | CH₂ | OEt | racemic |
| V-668 | Me | Et | Me | O | Ph | CH₂ | OEt | (S)- |
| V-669 | Me | Me | Me | O | Ph | CH₂ | (CH₂)₂COOH | racemic |
| V-670 | Me | Me | Me | O | Ph | CH₂ | (CH₂)₂COOH | (S)- |
| V-671 | Me | Et | Me | O | Ph | CH₂ | (CH₂)₂COOH | racemic |
| V-672 | Me | Et | Me | O | Ph | CH₂ | (CH₂)₂COOH | (S)- |
| V-673 | Me | Me | Me | O | Ph | C(Me)₂ | Me | racemic |
| V-674 | Me | Me | Me | O | Ph | C(Me)₂ | Me | (S)- |
| V-675 | Me | Et | Me | O | Ph | C(Me)₂ | Me | racemic |

TABLE 115

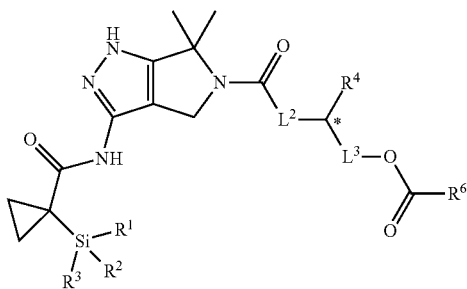
(Vb)

| Compound No. | R¹ | R² | R³ | L² | R⁴ | L³ | R⁶ | Configuration |
|---|---|---|---|---|---|---|---|---|
| V-676 | Me | Et | Me | O | Ph | C(Me)₂ | Me | (S)- |
| V-677 | Me | Me | Me | O | Ph | C(Me)₂ | Et | racemic |
| V-678 | Me | Me | Me | O | Ph | C(Me)₂ | Et | (S)- |
| V-679 | Me | Et | Me | O | Ph | C(Me)₂ | Et | racemic |
| V-680 | Me | Et | Me | O | Ph | C(Me)₂ | Et | (S)- |
| V-681 | Me | Me | Me | O | Ph | C(Me)₂ | nPr | racemic |
| V-682 | Me | Me | Me | O | Ph | C(Me)₂ | nPr | (S)- |
| V-683 | Me | Et | Me | O | Ph | C(Me)₂ | nPr | racemic |
| V-684 | Me | Et | Me | O | Ph | C(Me)₂ | nPr | (S)- |
| V-685 | Me | Me | Me | O | Ph | C(Me)₂ | iPr | racemic |
| V-686 | Me | Me | Me | O | Ph | C(Me)₂ | iPr | (S)- |
| V-687 | Me | Et | Me | O | Ph | C(Me)₂ | iPr | racemic |
| V-688 | Me | Et | Me | O | Ph | C(Me)₂ | iPr | (S)- |
| V-689 | Me | Me | Me | O | Ph | C(Me)₂ | nBu | racemic |
| V-690 | Me | Me | Me | O | Ph | C(Me)₂ | nBu | (S)- |
| V-691 | Me | Et | Me | O | Ph | C(Me)₂ | nBu | racemic |
| V-692 | Me | Et | Me | O | Ph | C(Me)₂ | nBu | (S)- |
| V-693 | Me | Me | Me | O | Ph | C(Me)₂ | tBu | racemic |
| V-694 | Me | Me | Me | O | Ph | C(Me)₂ | tBu | (S)- |
| V-695 | Me | Et | Me | O | Ph | C(Me)₂ | tBu | racemic |
| V-696 | Me | Et | Me | O | Ph | C(Me)₂ | tBu | (S)- |
| V-697 | Me | Me | Me | O | Ph | C(Me)₂ | iBu | racemic |
| V-698 | Me | Me | Me | O | Ph | C(Me)₂ | iBu | (S)- |
| V-699 | Me | Et | Me | O | Ph | C(Me)₂ | iBu | racemic |
| V-700 | Me | Et | Me | O | Ph | C(Me)₂ | iBu | (S)- |
| V-701 | Me | Me | Me | O | Ph | C(Me)₂ | n-Heptyl | racemic |
| V-702 | Me | Me | Me | O | Ph | C(Me)₂ | n-Heptyl | (S)- |
| V-703 | Me | Et | Me | O | Ph | C(Me)₂ | n-Heptyl | racemic |
| V-704 | Me | Et | Me | O | Ph | C(Me)₂ | n-Heptyl | (S)- |
| V-705 | Me | Me | Me | O | Ph | C(Me)₂ | n-Undecyl | racemic |
| V-706 | Me | Me | Me | O | Ph | C(Me)₂ | n-Undecyl | (S)- |
| V-707 | Me | Et | Me | O | Ph | C(Me)₂ | n-Undecyl | racemic |
| V-708 | Me | Et | Me | O | Ph | C(Me)₂ | n-Undecyl | (S)- |
| V-709 | Me | Me | Me | O | Ph | C(Me)₂ | Ph | racemic |
| V-710 | Me | Me | Me | O | Ph | C(Me)₂ | Ph | (S)- |
| V-711 | Me | Et | Me | O | Ph | C(Me)₂ | Ph | racemic |
| V-712 | Me | Et | Me | O | Ph | C(Me)₂ | Ph | (S)- |
| V-713 | Me | Me | Me | O | Ph | C(Me)₂ | OEt | racemic |
| V-714 | Me | Me | Me | O | Ph | C(Me)₂ | OEt | (S)- |
| V-715 | Me | Et | Me | O | Ph | C(Me)₂ | OEt | racemic |
| V-716 | Me | Et | Me | O | Ph | C(Me)₂ | OEt | (S)- |
| V-717 | Me | Me | Me | O | Ph | C(Me)₂ | (CH₂)₂COOH | racemic |
| V-718 | Me | Me | Me | O | Ph | C(Me)₂ | (CH₂)₂COOH | (S)- |
| V-719 | Me | Et | Me | O | Ph | C(Me)₂ | (CH₂)₂COOH | racemic |
| V-720 | Me | Et | Me | O | Ph | C(Me)₂ | (CH₂)₂COOH | (S)- |
| V-721 | Me | Me | Me | O | Ph | (CH₂)₂ | Me | racemic |
| V-722 | Me | Me | Me | O | Ph | (CH₂)₂ | Me | (R)- |
| V-723 | Me | Et | Me | O | Ph | (CH₂)₂ | Me | racemic |
| V-724 | Me | Et | Me | O | Ph | (CH₂)₂ | Me | (R)- |
| V-725 | Me | Me | Me | O | Ph | (CH₂)₂ | Et | racemic |

TABLE 116

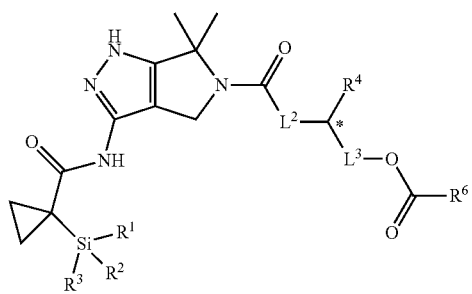

(Vb)

| Compound No. | R¹ | R² | R³ | L² | R⁴ | L³ | R⁶ | Configuration |
|---|---|---|---|---|---|---|---|---|
| V-726 | Me | Me | Me | O | Ph | (CH₂)₂ | Et | (R)- |
| V-727 | Me | Et | Me | O | Ph | (CH₂)₂ | Et | racemic |
| V-728 | Me | Et | Me | O | Ph | (CH₂)₂ | Et | (R)- |
| V-729 | Me | Me | Me | O | Ph | (CH₂)₂ | nPr | racemic |
| V-730 | Me | Me | Me | O | Ph | (CH₂)₂ | nPr | (R)- |
| V-731 | Me | Et | Me | O | Ph | (CH₂)₂ | nPr | racemic |
| V-732 | Me | Et | Me | O | Ph | (CH₂)₂ | nPr | (R)- |
| V-733 | Me | Me | Me | O | Ph | (CH₂)₂ | iPr | racemic |
| V-734 | Me | Me | Me | O | Ph | (CH₂)₂ | iPr | (R)- |
| V-735 | Me | Et | Me | O | Ph | (CH₂)₂ | iPr | racemic |
| V-736 | Me | Et | Me | O | Ph | (CH₂)₂ | iPr | (R)- |
| V-737 | Me | Me | Me | O | Ph | (CH₂)₂ | nBu | racemic |
| V-738 | Me | Me | Me | O | Ph | (CH₂)₂ | nBu | (R)- |
| V-739 | Me | Et | Me | O | Ph | (CH₂)₂ | nBu | racemic |
| V-740 | Me | Et | Me | O | Ph | (CH₂)₂ | nBu | (R)- |
| V-741 | Me | Me | Me | O | Ph | (CH₂)₂ | tBu | racemic |
| V-742 | Me | Me | Me | O | Ph | (CH₂)₂ | tBu | (R)- |
| V-743 | Me | Et | Me | O | Ph | (CH₂)₂ | tBu | racemic |
| V-744 | Me | Et | Me | O | Ph | (CH₂)₂ | tBu | (R)- |
| V-745 | Me | Me | Me | O | Ph | (CH₂)₂ | iBu | racemic |
| V-746 | Me | Me | Me | O | Ph | (CH₂)₂ | iBu | (R)- |
| V-747 | Me | Et | Me | O | Ph | (CH₂)₂ | iBu | racemic |
| V-748 | Me | Et | Me | O | Ph | (CH₂)₂ | iBu | (R)- |
| V-749 | Me | Me | Me | O | Ph | (CH₂)₂ | n-Heptyl | racemic |
| V-750 | Me | Me | Me | O | Ph | (CH₂)₂ | n-Heptyl | (R)- |
| V-751 | Me | Et | Me | O | Ph | (CH₂)₂ | n-Heptyl | racemic |
| V-752 | Me | Et | Me | O | Ph | (CH₂)₂ | n-Heptyl | (R)- |
| V-753 | Me | Me | Me | O | Ph | (CH₂)₂ | n-Undecyl | racemic |
| V-754 | Me | Me | Me | O | Ph | (CH₂)₂ | n-Undecyl | (R)- |
| V-755 | Me | Et | Me | O | Ph | (CH₂)₂ | n-Undecyl | racemic |
| V-756 | Me | Et | Me | O | Ph | (CH₂)₂ | n-Undecyl | (R)- |
| V-757 | Me | Me | Me | O | Ph | (CH₂)₂ | Ph | racemic |
| V-758 | Me | Me | Me | O | Ph | (CH₂)₂ | Ph | (R)- |
| V-759 | Me | Et | Me | O | Ph | (CH₂)₂ | Ph | racemic |
| V-760 | Me | Et | Me | O | Ph | (CH₂)₂ | Ph | (R)- |
| V-761 | Me | Me | Me | O | Ph | (CH₂)₂ | OEt | racemic |
| V-762 | Me | Me | Me | O | Ph | (CH₂)₂ | OEt | (R)- |
| V-763 | Me | Et | Me | O | Ph | (CH₂)₂ | OEt | racemic |
| V-764 | Me | Et | Me | O | Ph | (CH₂)₂ | OEt | (R)- |
| V-765 | Me | Me | Me | O | Ph | (CH₂)₂ | (CH₂)₂COOH | racemic |
| V-766 | Me | Me | Me | O | Ph | (CH₂)₂ | (CH₂)₂COOH | (R)- |
| V-767 | Me | Et | Me | O | Ph | (CH₂)₂ | (CH₂)₂COOH | racemic |
| V-768 | Me | Et | Me | O | Ph | (CH₂)₂ | (CH₂)₂COOH | (R)- |
| V-769 | Me | Me | Me | O | Ph | CH₂C(Me)₂ | Me | racemic |
| V-770 | Me | Me | Me | O | Ph | CH₂C(Me)₂ | Me | (R)- |
| V-771 | Me | Et | Me | O | Ph | CH₂C(Me)₂ | Me | racemic |
| V-772 | Me | Et | Me | O | Ph | CH₂C(Me)₂ | Me | (R)- |
| V-773 | Me | Me | Me | O | Ph | CH₂C(Me)₂ | Et | racemic |
| V-774 | Me | Me | Me | O | Ph | CH₂C(Me)₂ | Et | (R)- |
| V-775 | Me | Et | Me | O | Ph | CH₂C(Me)₂ | Et | racemic |

TABLE 117

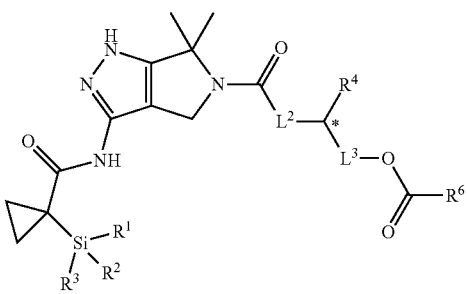

(Vb)

| Compound No. | R¹ | R² | R³ | L² | R⁴ | L³ | R⁶ | Configuration |
|---|---|---|---|---|---|---|---|---|
| V-776 | Me | Et | Me | O | Ph | CH₂C(Me)₂ | Et | (R)- |
| V-777 | Me | Me | Me | O | Ph | CH₂C(Me)₂ | nPr | racemic |
| V-778 | Me | Me | Me | O | Ph | CH₂C(Me)₂ | nPr | (R)- |
| V-779 | Me | Et | Me | O | Ph | CH₂C(Me)₂ | nPr | racemic |
| V-780 | Me | Et | Me | O | Ph | CH₂C(Me)₂ | nPr | (R)- |
| V-781 | Me | Me | Me | O | Ph | CH₂C(Me)₂ | iPr | racemic |
| V-782 | Me | Me | Me | O | Ph | CH₂C(Me)₂ | iPr | (R)- |
| V-783 | Me | Et | Me | O | Ph | CH₂C(Me)₂ | iPr | racemic |
| V-784 | Me | Et | Me | O | Ph | CH₂C(Me)₂ | iPr | (R)- |
| V-785 | Me | Me | Me | O | Ph | CH₂C(Me)₂ | nBu | racemic |
| V-786 | Me | Me | Me | O | Ph | CH₂C(Me)₂ | nBu | (R)- |
| V-787 | Me | Et | Me | O | Ph | CH₂C(Me)₂ | nBu | racemic |
| V-788 | Me | Et | Me | O | Ph | CH₂C(Me)₂ | nBu | (R)- |
| V-789 | Me | Me | Me | O | Ph | CH₂C(Me)₂ | tBu | racemic |
| V-790 | Me | Me | Me | O | Ph | CH₂C(Me)₂ | tBu | (R)- |
| V-791 | Me | Et | Me | O | Ph | CH₂C(Me)₂ | tBu | racemic |
| V-792 | Me | Et | Me | O | Ph | CH₂C(Me)₂ | tBu | (R)- |
| V-793 | Me | Me | Me | O | Ph | CH₂C(Me)₂ | iBu | racemic |
| V-794 | Me | Me | Me | O | Ph | CH₂C(Me)₂ | iBu | (R)- |
| V-795 | Me | Et | Me | O | Ph | CH₂C(Me)₂ | iBu | racemic |
| V-796 | Me | Et | Me | O | Ph | CH₂C(Me)₂ | iBu | (R)- |
| V-797 | Me | Me | Me | O | Ph | CH₂C(Me)₂ | n-Heptyl | racemic |
| V-798 | Me | Me | Me | O | Ph | CH₂C(Me)₂ | n-Heptyl | (R)- |
| V-799 | Me | Et | Me | O | Ph | CH₂C(Me)₂ | n-Heptyl | racemic |
| V-800 | Me | Et | Me | O | Ph | CH₂C(Me)₂ | n-Heptyl | (R)- |
| V-801 | Me | Me | Me | O | Ph | CH₂C(Me)₂ | n-Undecyl | racemic |
| V-802 | Me | Me | Me | O | Ph | CH₂C(Me)₂ | n-Undecyl | (R)- |
| V-803 | Me | Et | Me | O | Ph | CH₂C(Me)₂ | n-Undecyl | racemic |
| V-804 | Me | Et | Me | O | Ph | CH₂C(Me)₂ | n-Undecyl | (R)- |
| V-805 | Me | Me | Me | O | Ph | CH₂C(Me)₂ | Ph | racemic |
| V-806 | Me | Me | Me | O | Ph | CH₂C(Me)₂ | Ph | (R)- |
| V-807 | Me | Et | Me | O | Ph | CH₂C(Me)₂ | Ph | racemic |
| V-808 | Me | Et | Me | O | Ph | CH₂C(Me)₂ | Ph | (R)- |
| V-809 | Me | Me | Me | O | Ph | CH₂C(Me)₂ | OEt | racemic |
| V-810 | Me | Me | Me | O | Ph | CH₂C(Me)₂ | OEt | (R)- |
| V-811 | Me | Et | Me | O | Ph | CH₂C(Me)₂ | OEt | racemic |
| V-812 | Me | Et | Me | O | Ph | CH₂C(Me)₂ | OEt | (R)- |
| V-813 | Me | Me | Me | O | Ph | CH₂C(Me)₂ | (CH₂)₂COOH | racemic |
| V-814 | Me | Me | Me | O | Ph | CH₂C(Me)₂ | (CH₂)₂COOH | (R)- |
| V-815 | Me | Et | Me | O | Ph | CH₂C(Me)₂ | (CH₂)₂COOH | racemic |
| V-816 | Me | Et | Me | O | Ph | CH₂C(Me)₂ | (CH₂)₂COOH | (R)- |
| V-817 | Me | Me | Me | NH | Ph | CH₂ | Me | racemic |
| V-818 | Me | Me | Me | NH | Ph | CH₂ | Me | (S)- |
| V-819 | Me | Et | Me | NH | Ph | CH₂ | Me | racemic |
| V-820 | Me | Et | Me | NH | Ph | CH₂ | Me | (S)- |
| V-821 | Me | Me | Me | NH | Ph | CH₂ | Et | racemic |
| V-822 | Me | Me | Me | NH | Ph | CH₂ | Et | (S)- |
| V-823 | Me | Et | Me | NH | Ph | CH₂ | Et | racemic |
| V-824 | Me | Et | Me | NH | Ph | CH₂ | Et | (S)- |
| V-825 | Me | Me | Me | NH | Ph | CH₂ | nPr | racemic |

TABLE 118

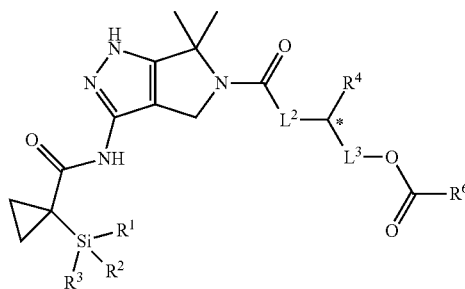

(Vb)

| Compound No. | R¹ | R² | R³ | L² | R⁴ | L³ | R⁶ | Configuration |
|---|---|---|---|---|---|---|---|---|
| V-826 | Me | Me | Me | NH | Ph | CH₂ | nPr | (S)- |
| V-827 | Me | Et | Me | NH | Ph | CH₂ | nPr | racemic |
| V-828 | Me | Et | Me | NH | Ph | CH₂ | nPr | (S)- |
| V-829 | Me | Me | Me | NH | Ph | CH₂ | iPr | racemic |
| V-830 | Me | Me | Me | NH | Ph | CH₂ | iPr | (S)- |
| V-831 | Me | Et | Me | NH | Ph | CH₂ | iPr | racemic |
| V-832 | Me | Et | Me | NH | Ph | CH₂ | iPr | (S)- |
| V-833 | Me | Me | Me | NH | Ph | CH₂ | nBu | racemic |
| V-834 | Me | Me | Me | NH | Ph | CH₂ | nBu | (S)- |
| V-835 | Me | Et | Me | NH | Ph | CH₂ | nBu | racemic |
| V-836 | Me | Et | Me | NH | Ph | CH₂ | nBu | (S)- |
| V-837 | Me | Me | Me | NH | Ph | CH₂ | tBu | racemic |
| V-838 | Me | Me | Me | NH | Ph | CH₂ | tBu | (S)- |
| V-839 | Me | Et | Me | NH | Ph | CH₂ | tBu | racemic |
| V-840 | Me | Et | Me | NH | Ph | CH₂ | tBu | (S)- |
| V-841 | Me | Me | Me | NH | Ph | CH₂ | iBu | racemic |
| V-842 | Me | Me | Me | NH | Ph | CH₂ | iBu | (S)- |
| V-843 | Me | Et | Me | NH | Ph | CH₂ | iBu | racemic |
| V-844 | Me | Et | Me | NH | Ph | CH₂ | iBu | (S)- |
| V-845 | Me | Me | Me | NH | Ph | CH₂ | n-Heptyl | racemic |
| V-846 | Me | Me | Me | NH | Ph | CH₂ | n-Heptyl | (S)- |
| V-847 | Me | Et | Me | NH | Ph | CH₂ | n-Heptyl | racemic |
| V-848 | Me | Et | Me | NH | Ph | CH₂ | n-Heptyl | (S)- |
| V-849 | Me | Me | Me | NH | Ph | CH₂ | n-Undecyl | racemic |
| V-850 | Me | Me | Me | NH | Ph | CH₂ | n-Undecyl | (S)- |
| V-851 | Me | Et | Me | NH | Ph | CH₂ | n-Undecyl | racemic |
| V-852 | Me | Et | Me | NH | Ph | CH₂ | n-Undecyl | (S)- |
| V-853 | Me | Me | Me | NH | Ph | CH₂ | Ph | racemic |
| V-854 | Me | Me | Me | NH | Ph | CH₂ | Ph | (S)- |
| V-855 | Me | Et | Me | NH | Ph | CH₂ | Ph | racemic |
| V-856 | Me | Et | Me | NH | Ph | CH₂ | Ph | (S)- |
| V-857 | Me | Me | Me | NH | Ph | CH₂ | OEt | racemic |
| V-858 | Me | Me | Me | NH | Ph | CH₂ | OEt | (S)- |
| V-859 | Me | Et | Me | NH | Ph | CH₂ | OEt | racemic |
| V-860 | Me | Et | Me | NH | Ph | CH₂ | OEt | (S)- |
| V-861 | Me | Me | Me | NH | Ph | CH₂ | (CH₂)₂COOH | racemic |
| V-862 | Me | Me | Me | NH | Ph | CH₂ | (CH₂)₂COOH | (S)- |
| V-863 | Me | Et | Me | NH | Ph | CH₂ | (CH₂)₂COOH | racemic |
| V-864 | Me | Et | Me | NH | Ph | CH₂ | (CH₂)₂COOH | (S)- |
| V-865 | Me | Me | Me | NH | Ph | C(Me)₂ | Me | racemic |
| V-866 | Me | Me | Me | NH | Ph | C(Me)₂ | Me | (S)- |
| V-867 | Me | Et | Me | NH | Ph | C(Me)₂ | Me | racemic |
| V-868 | Me | Et | Me | NH | Ph | C(Me)₂ | Me | (S)- |
| V-869 | Me | Me | Me | NH | Ph | C(Me)₂ | Et | racemic |
| V-870 | Me | Me | Me | NH | Ph | C(Me)₂ | Et | (S)- |
| V-871 | Me | Et | Me | NH | Ph | C(Me)₂ | Et | racemic |
| V-872 | Me | Et | Me | NH | Ph | C(Me)₂ | Et | (S)- |
| V-873 | Me | Me | Me | NH | Ph | C(Me)₂ | nPr | racemic |
| V-874 | Me | Me | Me | NH | Ph | C(Me)₂ | nPr | (S)- |
| V-875 | Me | Et | Me | NH | Ph | C(Me)₂ | nPr | racemic |

TABLE 119

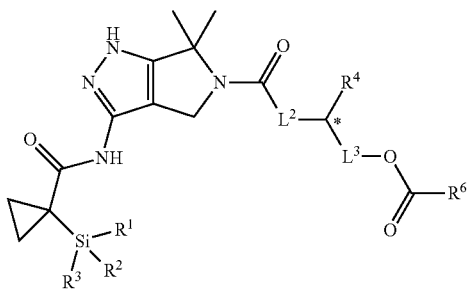

(Vb)

| Compound No. | R¹ | R² | R³ | L² | R⁴ | L³ | R⁶ | Configuration |
|---|---|---|---|---|---|---|---|---|
| V-876 | Me | Et | Me | NH | Ph | C(Me)₂ | nPr | (S)- |
| V-877 | Me | Me | Me | NH | Ph | C(Me)₂ | iPr | racemic |
| V-878 | Me | Me | Me | NH | Ph | C(Me)₂ | iPr | (S)- |
| V-879 | Me | Et | Me | NH | Ph | C(Me)₂ | iPr | racemic |
| V-880 | Me | Et | Me | NH | Ph | C(Me)₂ | iPr | (S)- |
| V-881 | Me | Me | Me | NH | Ph | C(Me)₂ | nBu | racemic |
| V-882 | Me | Me | Me | NH | Ph | C(Me)₂ | nBu | (S)- |
| V-883 | Me | Et | Me | NH | Ph | C(Me)₂ | nBu | racemic |
| V-884 | Me | Et | Me | NH | Ph | C(Me)₂ | nBu | (S)- |
| V-885 | Me | Me | Me | NH | Ph | C(Me)₂ | tBu | racemic |
| V-886 | Me | Me | Me | NH | Ph | C(Me)₂ | tBu | (S)- |
| V-887 | Me | Et | Me | NH | Ph | C(Me)₂ | tBu | racemic |
| V-888 | Me | Et | Me | NH | Ph | C(Me)₂ | tBu | (S)- |
| V-889 | Me | Me | Me | NH | Ph | C(Me)₂ | iBu | racemic |
| V-890 | Me | Me | Me | NH | Ph | C(Me)₂ | iBu | (S)- |
| V-891 | Me | Et | Me | NH | Ph | C(Me)₂ | iBu | racemic |
| V-892 | Me | Et | Me | NH | Ph | C(Me)₂ | iBu | (S)- |
| V-893 | Me | Me | Me | NH | Ph | C(Me)₂ | n-Heptyl | racemic |
| V-894 | Me | Me | Me | NH | Ph | C(Me)₂ | n-Heptyl | (S)- |
| V-895 | Me | Et | Me | NH | Ph | C(Me)₂ | n-Heptyl | racemic |
| V-896 | Me | Et | Me | NH | Ph | C(Me)₂ | n-Heptyl | (S)- |
| V-897 | Me | Me | Me | NH | Ph | C(Me)₂ | n-Undecyl | racemic |
| V-898 | Me | Me | Me | NH | Ph | C(Me)₂ | n-Undecyl | (S)- |
| V-899 | Me | Et | Me | NH | Ph | C(Me)₂ | n-Undecyl | racemic |
| V-900 | Me | Et | Me | NH | Ph | C(Me)₂ | n-Undecyl | (S)- |
| V-901 | Me | Me | Me | NH | Ph | C(Me)₂ | Ph | racemic |
| V-902 | Me | Me | Me | NH | Ph | C(Me)₂ | Ph | (S)- |
| V-903 | Me | Et | Me | NH | Ph | C(Me)₂ | Ph | racemic |
| V-904 | Me | Et | Me | NH | Ph | C(Me)₂ | Ph | (S)- |
| V-905 | Me | Me | Me | NH | Ph | C(Me)₂ | OEt | racemic |
| V-906 | Me | Me | Me | NH | Ph | C(Me)₂ | OEt | (S)- |
| V-907 | Me | Et | Me | NH | Ph | C(Me)₂ | OEt | racemic |
| V-908 | Me | Et | Me | NH | Ph | C(Me)₂ | OEt | (S)- |
| V-909 | Me | Me | Me | NH | Ph | C(Me)₂ | (CH₂)₂COOH | racemic |
| V-910 | Me | Me | Me | NH | Ph | C(Me)₂ | (CH₂)₂COOH | (S)- |
| V-911 | Me | Et | Me | NH | Ph | C(Me)₂ | (CH₂)₂COOH | racemic |
| V-912 | Me | Et | Me | NH | Ph | C(Me)₂ | (CH₂)₂COOH | (S)- |
| V-913 | Me | Me | Me | NH | Ph | (CH₂)₂ | Me | racemic |
| V-914 | Me | Me | Me | NH | Ph | (CH₂)₂ | Me | (R)- |
| V-915 | Me | Et | Me | NH | Ph | (CH₂)₂ | Me | racemic |
| V-916 | Me | Et | Me | NH | Ph | (CH₂)₂ | Me | (R)- |
| V-917 | Me | Me | Me | NH | Ph | (CH₂)₂ | Et | racemic |
| V-918 | Me | Me | Me | NH | Ph | (CH₂)₂ | Et | (R)- |
| V-919 | Me | Et | Me | NH | Ph | (CH₂)₂ | Et | racemic |
| V-920 | Me | Et | Me | NH | Ph | (CH₂)₂ | Et | (R)- |
| V-921 | Me | Me | Me | NH | Ph | (CH₂)₂ | nPr | racemic |
| V-922 | Me | Me | Me | NH | Ph | (CH₂)₂ | nPr | (R)- |
| V-923 | Me | Et | Me | NH | Ph | (CH₂)₂ | nPr | racemic |
| V-924 | Me | Et | Me | NH | Ph | (CH₂)₂ | nPr | (R)- |
| V-925 | Me | Me | Me | NH | Ph | (CH₂)₂ | iPr | racemic |

TABLE 120

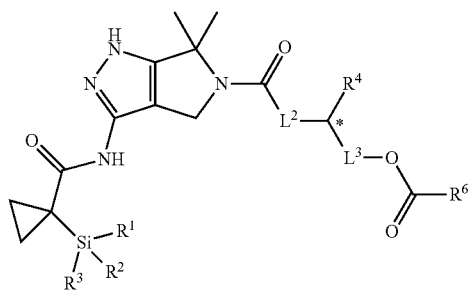

(Vb)

| Compound No. | R¹ | R² | R³ | L² | R⁴ | L³ | R⁶ | Configuration |
|---|---|---|---|---|---|---|---|---|
| V-926 | Me | Me | Me | NH | Ph | (CH₂)₂ | iPr | (R)- |
| V-927 | Me | Et | Me | NH | Ph | (CH₂)₂ | iPr | racemic |
| V-928 | Me | Et | Me | NH | Ph | (CH₂)₂ | iPr | (R)- |
| V-929 | Me | Me | Me | NH | Ph | (CH₂)₂ | nBu | racemic |
| V-930 | Me | Me | Me | NH | Ph | (CH₂)₂ | nBu | (R)- |
| V-931 | Me | Et | Me | NH | Ph | (CH₂)₂ | nBu | racemic |
| V-932 | Me | Et | Me | NH | Ph | (CH₂)₂ | nBu | (R)- |
| V-933 | Me | Me | Me | NH | Ph | (CH₂)₂ | tBu | racemic |
| V-934 | Me | Me | Me | NH | Ph | (CH₂)₂ | tBu | (R)- |
| V-935 | Me | Et | Me | NH | Ph | (CH₂)₂ | tBu | racemic |
| V-936 | Me | Et | Me | NH | Ph | (CH₂)₂ | tBu | (R)- |
| V-937 | Me | Me | Me | NH | Ph | (CH₂)₂ | iBu | racemic |
| V-938 | Me | Me | Me | NH | Ph | (CH₂)₂ | iBu | (R)- |
| V-939 | Me | Et | Me | NH | Ph | (CH₂)₂ | iBu | racemic |
| V-940 | Me | Et | Me | NH | Ph | (CH₂)₂ | iBu | (R)- |
| V-941 | Me | Me | Me | NH | Ph | (CH₂)₂ | n-Heptyl | racemic |
| V-942 | Me | Me | Me | NH | Ph | (CH₂)₂ | n-Heptyl | (R)- |
| V-943 | Me | Et | Me | NH | Ph | (CH₂)₂ | n-Heptyl | racemic |
| V-944 | Me | Et | Me | NH | Ph | (CH₂)₂ | n-Heptyl | (R)- |
| V-945 | Me | Me | Me | NH | Ph | (CH₂)₂ | n-Undecyl | racemic |
| V-946 | Me | Me | Me | NH | Ph | (CH₂)₂ | n-Undecyl | (R)- |
| V-947 | Me | Et | Me | NH | Ph | (CH₂)₂ | n-Undecyl | racemic |
| V-948 | Me | Et | Me | NH | Ph | (CH₂)₂ | n-Undecyl | (R)- |
| V-949 | Me | Me | Me | NH | Ph | (CH₂)₂ | Ph | racemic |
| V-950 | Me | Me | Me | NH | Ph | (CH₂)₂ | Ph | (R)- |
| V-951 | Me | Et | Me | NH | Ph | (CH₂)₂ | Ph | racemic |
| V-952 | Me | Et | Me | NH | Ph | (CH₂)₂ | Ph | (R)- |
| V-953 | Me | Me | Me | NH | Ph | (CH₂)₂ | OEt | racemic |
| V-954 | Me | Me | Me | NH | Ph | (CH₂)₂ | OEt | (R)- |
| V-955 | Me | Et | Me | NH | Ph | (CH₂)₂ | OEt | racemic |
| V-956 | Me | Et | Me | NH | Ph | (CH₂)₂ | OEt | (R)- |
| V-957 | Me | Me | Me | NH | Ph | (CH₂)₂ | (CH₂)₂COOH | racemic |
| V-958 | Me | Me | Me | NH | Ph | (CH₂)₂ | (CH₂)₂COOH | (R)- |
| V-959 | Me | Et | Me | NH | Ph | (CH₂)₂ | (CH₂)₂COOH | racemic |
| V-960 | Me | Et | Me | NH | Ph | (CH₂)₂ | (CH₂)₂COOH | (R)- |
| V-961 | Me | Me | Me | NH | Ph | CH₂C(Me)₂ | Me | racemic |
| V-962 | Me | Me | Me | NH | Ph | CH₂C(Me)₂ | Me | (R)- |
| V-963 | Me | Et | Me | NH | Ph | CH₂C(Me)₂ | Me | racemic |
| V-964 | Me | Et | Me | NH | Ph | CH₂C(Me)₂ | Me | (R)- |
| V-965 | Me | Me | Me | NH | Ph | CH₂C(Me)₂ | Et | racemic |
| V-966 | Me | Me | Me | NH | Ph | CH₂C(Me)₂ | Et | (R)- |
| V-967 | Me | Et | Me | NH | Ph | CH₂C(Me)₂ | Et | racemic |
| V-968 | Me | Et | Me | NH | Ph | CH₂C(Me)₂ | Et | (R)- |
| V-969 | Me | Me | Me | NH | Ph | CH₂C(Me)₂ | nPr | racemic |
| V-970 | Me | Me | Me | NH | Ph | CH₂C(Me)₂ | nPr | (R)- |
| V-971 | Me | Et | Me | NH | Ph | CH₂C(Me)₂ | nPr | racemic |
| V-972 | Me | Et | Me | NH | Ph | CH₂C(Me)₂ | nPr | (R)- |
| V-973 | Me | Me | Me | NH | Ph | CH₂C(Me)₂ | iPr | racemic |
| V-974 | Me | Me | Me | NH | Ph | CH₂C(Me)₂ | iPr | (R)- |
| V-975 | Me | Et | Me | NH | Ph | CH₂C(Me)₂ | iPr | racemic |

TABLE 121

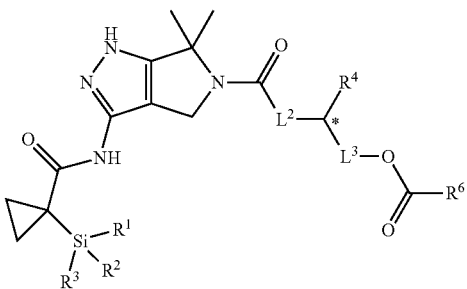

(Vb)

| Compound No. | R¹ | R² | R³ | L² | R⁴ | L³ | R⁶ | Configuration |
|---|---|---|---|---|---|---|---|---|
| V-976 | Me | Et | Me | NH | Ph | CH₂C(Me)₂ | iPr | (R)- |
| V-977 | Me | Me | Me | NH | Ph | CH₂C(Me)₂ | nBu | racemic |
| V-978 | Me | Me | Me | NH | Ph | CH₂C(Me)₂ | nBu | (R)- |
| V-979 | Me | Et | Me | NH | Ph | CH₂C(Me)₂ | nBu | racemic |
| V-980 | Me | Et | Me | NH | Ph | CH₂C(Me)₂ | nBu | (R)- |
| V-981 | Me | Me | Me | NH | Ph | CH₂C(Me)₂ | tBu | racemic |
| V-982 | Me | Me | Me | NH | Ph | CH₂C(Me)₂ | tBu | (R)- |
| V-983 | Me | Et | Me | NH | Ph | CH₂C(Me)₂ | tBu | racemic |
| V-984 | Me | Et | Me | NH | Ph | CH₂C(Me)₂ | tBu | (R)- |
| V-985 | Me | Me | Me | NH | Ph | CH₂C(Me)₂ | iBu | racemic |
| V-986 | Me | Me | Me | NH | Ph | CH₂C(Me)₂ | iBu | (R)- |
| V-987 | Me | Et | Me | NH | Ph | CH₂C(Me)₂ | iBu | racemic |
| V-988 | Me | Et | Me | NH | Ph | CH₂C(Me)₂ | iBu | (R)- |
| V-989 | Me | Me | Me | NH | Ph | CH₂C(Me)₂ | n-Heptyl | racemic |
| V-990 | Me | Me | Me | NH | Ph | CH₂C(Me)₂ | n-Heptyl | (R)- |
| V-991 | Me | Et | Me | NH | Ph | CH₂C(Me)₂ | n-Heptyl | racemic |
| V-992 | Me | Et | Me | NH | Ph | CH₂C(Me)₂ | n-Heptyl | (R)- |
| V-993 | Me | Me | Me | NH | Ph | CH₂C(Me)₂ | n-Undecyl | racemic |
| V-994 | Me | Me | Me | NH | Ph | CH₂C(Me)₂ | n-Undecyl | (R)- |
| V-995 | Me | Et | Me | NH | Ph | CH₂C(Me)₂ | n-Undecyl | racemic |
| V-996 | Me | Et | Me | NH | Ph | CH₂C(Me)₂ | n-Undecyl | (R)- |
| V-997 | Me | Me | Me | NH | Ph | CH₂C(Me)₂ | Ph | racemic |
| V-998 | Me | Me | Me | NH | Ph | CH₂C(Me)₂ | Ph | (R)- |
| V-999 | Me | Et | Me | NH | Ph | CH₂C(Me)₂ | Ph | racemic |
| V-1000 | Me | Et | Me | NH | Ph | CH₂C(Me)₂ | Ph | (R)- |
| V-1001 | Me | Me | Me | NH | Ph | CH₂C(Me)₂ | OEt | racemic |
| V-1002 | Me | Me | Me | NH | Ph | CH₂C(Me)₂ | OEt | (R)- |
| V-1003 | Me | Et | Me | NH | Ph | CH₂C(Me)₂ | OEt | racemic |
| V-1004 | Me | Et | Me | NH | Ph | CH₂C(Me)₂ | OEt | (R)- |
| V-1005 | Me | Me | Me | NH | Ph | CH₂C(Me)₂ | (CH₂)₂COOH | racemic |
| V-1006 | Me | Me | Me | NH | Ph | CH₂C(Me)₂ | (CH₂)₂COOH | (R)- |
| V-1007 | Me | Et | Me | NH | Ph | CH₂C(Me)₂ | (CH₂)₂COOH | racemic |
| V-1008 | Me | Et | Me | NH | Ph | CH₂C(Me)₂ | (CH₂)₂COOH | (R)- |
| V-1009 | Me | Me | Me | CH₂ | Ph | CH₂ | Me | racemic |
| V-1010 | Me | Me | Me | CH₂ | Ph | CH₂ | Me | (S)- |
| V-1011 | Me | Et | Me | CH₂ | Ph | CH₂ | Me | racemic |
| V-1012 | Me | Et | Me | CH₂ | Ph | CH₂ | Me | (S)- |
| V-1013 | Me | Me | Me | CH₂ | Ph | CH₂ | Et | racemic |
| V-1014 | Me | Me | Me | CH₂ | Ph | CH₂ | Et | (S)- |
| V-1015 | Me | Et | Me | CH₂ | Ph | CH₂ | Et | racemic |
| V-1016 | Me | Et | Me | CH₂ | Ph | CH₂ | Et | (S)- |
| V-1017 | Me | Me | Me | CH₂ | Ph | CH₂ | nPr | racemic |
| V-1018 | Me | Me | Me | CH₂ | Ph | CH₂ | nPr | (S)- |
| V-1019 | Me | Et | Me | CH₂ | Ph | CH₂ | nPr | racemic |
| V-1020 | Me | Et | Me | CH₂ | Ph | CH₂ | nPr | (S)- |
| V-1021 | Me | Me | Me | CH₂ | Ph | CH₂ | iPr | racemic |
| V-1022 | Me | Me | Me | CH₂ | Ph | CH₂ | iPr | (S)- |
| V-1023 | Me | Et | Me | CH₂ | Ph | CH₂ | iPr | racemic |
| V-1024 | Me | Et | Me | CH₂ | Ph | CH₂ | iPr | (S)- |
| V-1025 | Me | Me | Me | CH₂ | Ph | CH₂ | nBu | racemic |

TABLE 122

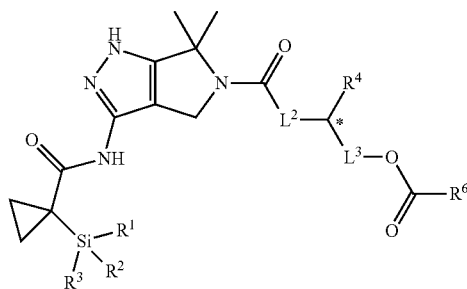

(Vb)

| Compound No. | R¹ | R² | R³ | L² | R⁴ | L³ | R⁶ | Configuration |
|---|---|---|---|---|---|---|---|---|
| V-1026 | Me | Me | Me | CH₂ | Ph | CH₂ | nBu | (S)- |
| V-1027 | Me | Et | Me | CH₂ | Ph | CH₂ | nBu | racemic |
| V-1028 | Me | Et | Me | CH₂ | Ph | CH₂ | nBu | (S)- |
| V-1029 | Me | Me | Me | CH₂ | Ph | CH₂ | tBu | racemic |
| V-1030 | Me | Me | Me | CH₂ | Ph | CH₂ | tBu | (S)- |
| V-1031 | Me | Et | Me | CH₂ | Ph | CH₂ | tBu | racemic |
| V-1032 | Me | Et | Me | CH₂ | Ph | CH₂ | tBu | (S)- |
| V-1033 | Me | Me | Me | CH₂ | Ph | CH₂ | iBu | racemic |
| V-1034 | Me | Me | Me | CH₂ | Ph | CH₂ | iBu | (S)- |
| V-1035 | Me | Et | Me | CH₂ | Ph | CH₂ | iBu | racemic |
| V-1036 | Me | Et | Me | CH₂ | Ph | CH₂ | iBu | (S)- |
| V-1037 | Me | Me | Me | CH₂ | Ph | CH₂ | n-Heptyl | racemic |
| V-1038 | Me | Me | Me | CH₂ | Ph | CH₂ | n-Heptyl | (S)- |
| V-1039 | Me | Et | Me | CH₂ | Ph | CH₂ | n-Heptyl | racemic |
| V-1040 | Me | Et | Me | CH₂ | Ph | CH₂ | n-Heptyl | (S)- |
| V-1041 | Me | Me | Me | CH₂ | Ph | CH₂ | n-Undecyl | racemic |
| V-1042 | Me | Me | Me | CH₂ | Ph | CH₂ | n-Undecyl | (S)- |
| V-1043 | Me | Et | Me | CH₂ | Ph | CH₂ | n-Undecyl | racemic |
| V-1044 | Me | Et | Me | CH₂ | Ph | CH₂ | n-Undecyl | (S)- |
| V-1045 | Me | Me | Me | CH₂ | Ph | CH₂ | Ph | racemic |
| V-1046 | Me | Me | Me | CH₂ | Ph | CH₂ | Ph | (S)- |
| V-1047 | Me | Et | Me | CH₂ | Ph | CH₂ | Ph | racemic |
| V-1048 | Me | Et | Me | CH₂ | Ph | CH₂ | Ph | (S)- |
| V-1049 | Me | Me | Me | CH₂ | Ph | CH₂ | OEt | racemic |
| V-1050 | Me | Me | Me | CH₂ | Ph | CH₂ | OEt | (S)- |
| V-1051 | Me | Et | Me | CH₂ | Ph | CH₂ | OEt | racemic |
| V-1052 | Me | Et | Me | CH₂ | Ph | CH₂ | OEt | (S)- |
| V-1053 | Me | Me | Me | CH₂ | Ph | CH₂ | (CH₂)₂COOH | racemic |
| V-1054 | Me | Me | Me | CH₂ | Ph | CH₂ | (CH₂)₂COOH | (S)- |
| V-1055 | Me | Et | Me | CH₂ | Ph | CH₂ | (CH₂)₂COOH | racemic |
| V-1056 | Me | Et | Me | CH₂ | Ph | CH₂ | (CH₂)₂COOH | (S)- |
| V-1057 | Me | Me | Me | CH₂ | Ph | — | Me | racemic |
| V-1058 | Me | Me | Me | CH₂ | Ph | — | Me | (S)- |
| V-1059 | Me | Et | Me | CH₂ | Ph | — | Me | racemic |
| V-1060 | Me | Et | Me | CH₂ | Ph | — | Me | (S)- |
| V-1061 | Me | Me | Me | CH₂ | Ph | — | Et | racemic |
| V-1062 | Me | Me | Me | CH₂ | Ph | — | Et | (S)- |
| V-1063 | Me | Et | Me | CH₂ | Ph | — | Et | racemic |
| V-1064 | Me | Et | Me | CH₂ | Ph | — | Et | (S)- |
| V-1065 | Me | Me | Me | CH₂ | Ph | — | nPr | racemic |
| V-1066 | Me | Me | Me | CH₂ | Ph | — | nPr | (S)- |
| V-1067 | Me | Et | Me | CH₂ | Ph | — | nPr | racemic |
| V-1068 | Me | Et | Me | CH₂ | Ph | — | nPr | (S)- |
| V-1069 | Me | Me | Me | CH₂ | Ph | — | iPr | racemic |
| V-1070 | Me | Me | Me | CH₂ | Ph | — | iPr | (S)- |
| V-1071 | Me | Et | Me | CH₂ | Ph | — | iPr | racemic |
| V-1072 | Me | Et | Me | CH₂ | Ph | — | iPr | (S)- |
| V-1073 | Me | Me | Me | CH₂ | Ph | — | nBu | racemic |
| V-1074 | Me | Me | Me | CH₂ | Ph | — | nBu | (S)- |
| V-1075 | Me | Et | Me | CH₂ | Ph | — | nBu | racemic |

TABLE 123

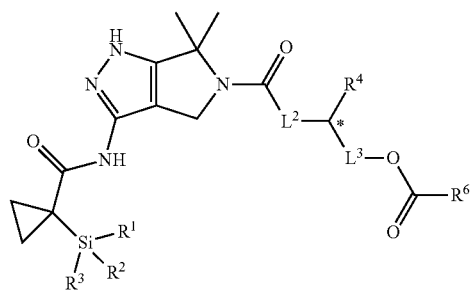

(Vb)

| Compound No. | R¹ | R² | R³ | L² | R⁴ | L³ | R⁶ | Configuration |
|---|---|---|---|---|---|---|---|---|
| V-1076 | Me | Et | Me | CH₂ | Ph | — | nBu | (S)- |
| V-1077 | Me | Me | Me | CH₂ | Ph | — | tBu | racemic |
| V-1078 | Me | Me | Me | CH₂ | Ph | — | tBu | (S)- |
| V-1079 | Me | Et | Me | CH₂ | Ph | — | tBu | racemic |
| V-1080 | Me | Et | Me | CH₂ | Ph | — | tBu | (S)- |
| V-1081 | Me | Me | Me | CH₂ | Ph | — | iBu | racemic |
| V-1082 | Me | Me | Me | CH₂ | Ph | — | iBu | (S)- |
| V-1083 | Me | Et | Me | CH₂ | Ph | — | iBu | racemic |
| V-1084 | Me | Et | Me | CH₂ | Ph | — | iBu | (S)- |
| V-1085 | Me | Me | Me | CH₂ | Ph | — | n-Heptyl | racemic |
| V-1086 | Me | Me | Me | CH₂ | Ph | — | n-Heptyl | (S)- |
| V-1087 | Me | Et | Me | CH₂ | Ph | — | n-Heptyl | racemic |
| V-1088 | Me | Et | Me | CH₂ | Ph | — | n-Heptyl | (S)- |
| V-1089 | Me | Me | Me | CH₂ | Ph | — | n-Undecyl | racemic |
| V-1090 | Me | Me | Me | CH₂ | Ph | — | n-Undecyl | (S)- |
| V-1091 | Me | Et | Me | CH₂ | Ph | — | n-Undecyl | racemic |
| V-1092 | Me | Et | Me | CH₂ | Ph | — | n-Undecyl | (S)- |
| V-1093 | Me | Me | Me | CH₂ | Ph | — | Ph | racemic |
| V-1094 | Me | Me | Me | CH₂ | Ph | — | Ph | (S)- |
| V-1095 | Me | Et | Me | CH₂ | Ph | — | Ph | racemic |
| V-1096 | Me | Et | Me | CH₂ | Ph | — | Ph | (S)- |
| V-1097 | Me | Me | Me | CH₂ | Ph | — | OEt | racemic |
| V-1098 | Me | Me | Me | CH₂ | Ph | — | OEt | (S)- |
| V-1099 | Me | Et | Me | CH₂ | Ph | — | OEt | racemic |
| V-1100 | Me | Et | Me | CH₂ | Ph | — | OEt | (S)- |
| V-1101 | Me | Me | Me | CH₂ | Ph | — | (CH₂)₂COOH | racemic |
| V-1102 | Me | Me | Me | CH₂ | Ph | — | (CH₂)₂COOH | (S)- |
| V-1103 | Me | Et | Me | CH₂ | Ph | — | (CH₂)₂COOH | racemic |
| V-1104 | Me | Et | Me | CH₂ | Ph | — | (CH₂)₂COOH | (S)- |
| V-1105 | Me | Me | Me | CH₂ | Ph | C(Me)₂ | Me | racemic |
| V-1106 | Me | Me | Me | CH₂ | Ph | C(Me)₂ | Me | (S)- |
| V-1107 | Me | Et | Me | CH₂ | Ph | C(Me)₂ | Me | racemic |
| V-1108 | Me | Et | Me | CH₂ | Ph | C(Me)₂ | Me | (S)- |
| V-1109 | Me | Me | Me | CH₂ | Ph | C(Me)₂ | Et | racemic |
| V-1110 | Me | Me | Me | CH₂ | Ph | C(Me)₂ | Et | (S)- |
| V-1111 | Me | Et | Me | CH₂ | Ph | C(Me)₂ | Et | racemic |
| V-1112 | Me | Et | Me | CH₂ | Ph | C(Me)₂ | Et | (S)- |
| V-1113 | Me | Me | Me | CH₂ | Ph | C(Me)₂ | nPr | racemic |
| V-1114 | Me | Me | Me | CH₂ | Ph | C(Me)₂ | nPr | (S)- |
| V-1115 | Me | Et | Me | CH₂ | Ph | C(Me)₂ | nPr | racemic |
| V-1116 | Me | Et | Me | CH₂ | Ph | C(Me)₂ | nPr | (S)- |
| V-1117 | Me | Me | Me | CH₂ | Ph | C(Me)₂ | iPr | racemic |
| V-1118 | Me | Me | Me | CH₂ | Ph | C(Me)₂ | iPr | (S)- |
| V-1119 | Me | Et | Me | CH₂ | Ph | C(Me)₂ | iPr | racemic |
| V-1120 | Me | Et | Me | CH₂ | Ph | C(Me)₂ | iPr | (S)- |
| V-1121 | Me | Me | Me | CH₂ | Ph | C(Me)₂ | nBu | racemic |
| V-1122 | Me | Me | Me | CH₂ | Ph | C(Me)₂ | nBu | (S)- |
| V-1123 | Me | Et | Me | CH₂ | Ph | C(Me)₂ | nBu | racemic |
| V-1124 | Me | Et | Me | CH₂ | Ph | C(Me)₂ | nBu | (S)- |
| V-1125 | Me | Me | Me | CH₂ | Ph | C(Me)₂ | tBu | racemic |

TABLE 124

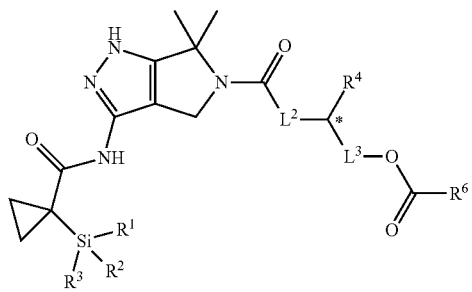

(Vb)

| Compound No. | R¹ | R² | R³ | L² | R⁴ | L³ | R⁶ | Configuration |
|---|---|---|---|---|---|---|---|---|
| V-1126 | Me | Me | Me | CH₂ | Ph | C(Me)₂ | tBu | (S)- |
| V-1127 | Me | Et | Me | CH₂ | Ph | C(Me)₂ | tBu | racemic |
| V-1128 | Me | Et | Me | CH₂ | Ph | C(Me)₂ | tBu | (S)- |
| V-1129 | Me | Me | Me | CH₂ | Ph | C(Me)₂ | iBu | racemic |
| V-1130 | Me | Me | Me | CH₂ | Ph | C(Me)₂ | iBu | (S)- |
| V-1131 | Me | Et | Me | CH₂ | Ph | C(Me)₂ | iBu | racemic |
| V-1132 | Me | Et | Me | CH₂ | Ph | C(Me)₂ | iBu | (S)- |
| V-1133 | Me | Me | Me | CH₂ | Ph | C(Me)₂ | n-Heptyl | racemic |
| V-1134 | Me | Me | Me | CH₂ | Ph | C(Me)₂ | n-Heptyl | (S)- |
| V-1135 | Me | Et | Me | CH₂ | Ph | C(Me)₂ | n-Heptyl | racemic |
| V-1136 | Me | Et | Me | CH₂ | Ph | C(Me)₂ | n-Heptyl | (S)- |
| V-1137 | Me | Me | Me | CH₂ | Ph | C(Me)₂ | n-Undecyl | racemic |
| V-1138 | Me | Me | Me | CH₂ | Ph | C(Me)₂ | n-Undecyl | (S)- |
| V-1139 | Me | Et | Me | CH₂ | Ph | C(Me)₂ | n-Undecyl | racemic |
| V-1140 | Me | Et | Me | CH₂ | Ph | C(Me)₂ | n-Undecyl | (S)- |
| V-1141 | Me | Me | Me | CH₂ | Ph | C(Me)₂ | Ph | racemic |
| V-1142 | Me | Me | Me | CH₂ | Ph | C(Me)₂ | Ph | (S)- |
| V-1143 | Me | Et | Me | CH₂ | Ph | C(Me)₂ | Ph | racemic |
| V-1144 | Me | Et | Me | CH₂ | Ph | C(Me)₂ | Ph | (S)- |
| V-1145 | Me | Me | Me | CH₂ | Ph | C(Me)₂ | OEt | racemic |
| V-1146 | Me | Me | Me | CH₂ | Ph | C(Me)₂ | OEt | (S)- |
| V-1147 | Me | Et | Me | CH₂ | Ph | C(Me)₂ | OEt | racemic |
| V-1148 | Me | Et | Me | CH₂ | Ph | C(Me)₂ | OEt | (S)- |
| V-1149 | Me | Me | Me | CH₂ | Ph | C(Me)₂ | (CH₂)₂COOH | racemic |
| V-1150 | Me | Me | Me | CH₂ | Ph | C(Me)₂ | (CH₂)₂COOH | (S)- |
| V-1151 | Me | Et | Me | CH₂ | Ph | C(Me)₂ | (CH₂)₂COOH | racemic |
| V-1152 | Me | Et | Me | CH₂ | Ph | C(Me)₂ | (CH₂)₂COOH | (S)- |
| V-1153 | Me | Me | Me | CH₂ | Ph | (CH₂)₂ | Me | racemic |
| V-1154 | Me | Me | Me | CH₂ | Ph | (CH₂)₂ | Me | (S)- |
| V-1155 | Me | Et | Me | CH₂ | Ph | (CH₂)₂ | Me | racemic |
| V-1156 | Me | Et | Me | CH₂ | Ph | (CH₂)₂ | Me | (S)- |
| V-1157 | Me | Me | Me | CH₂ | Ph | (CH₂)₂ | Et | racemic |
| V-1158 | Me | Me | Me | CH₂ | Ph | (CH₂)₂ | Et | (S)- |
| V-1159 | Me | Et | Me | CH₂ | Ph | (CH₂)₂ | Et | racemic |
| V-1160 | Me | Et | Me | CH₂ | Ph | (CH₂)₂ | Et | (S)- |
| V-1161 | Me | Me | Me | CH₂ | Ph | (CH₂)₂ | nPr | racemic |
| V-1162 | Me | Me | Me | CH₂ | Ph | (CH₂)₂ | nPr | (S)- |
| V-1163 | Me | Et | Me | CH₂ | Ph | (CH₂)₂ | nPr | racemic |
| V-1164 | Me | Et | Me | CH₂ | Ph | (CH₂)₂ | nPr | (S)- |
| V-1165 | Me | Me | Me | CH₂ | Ph | (CH₂)₂ | iPr | racemic |
| V-1166 | Me | Me | Me | CH₂ | Ph | (CH₂)₂ | iPr | (S)- |
| V-1167 | Me | Et | Me | CH₂ | Ph | (CH₂)₂ | iPr | racemic |
| V-1168 | Me | Et | Me | CH₂ | Ph | (CH₂)₂ | iPr | (S)- |
| V-1169 | Me | Me | Me | CH₂ | Ph | (CH₂)₂ | nBu | racemic |
| V-1170 | Me | Me | Me | CH₂ | Ph | (CH₂)₂ | nBu | (S)- |
| V-1171 | Me | Et | Me | CH₂ | Ph | (CH₂)₂ | nBu | racemic |
| V-1172 | Me | Et | Me | CH₂ | Ph | (CH₂)₂ | nBu | (S)- |
| V-1173 | Me | Me | Me | CH₂ | Ph | (CH₂)₂ | tBu | racemic |
| V-1174 | Me | Me | Me | CH₂ | Ph | (CH₂)₂ | tBu | (S)- |
| V-1175 | Me | Et | Me | CH₂ | Ph | (CH₂)₂ | tBu | racemic |

TABLE 125

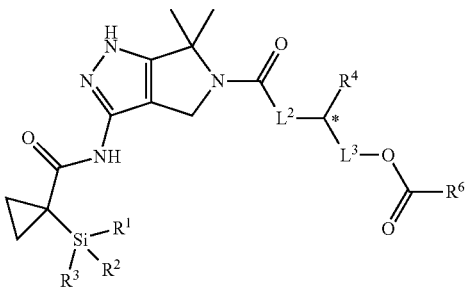

(Vb)

| Compound No. | R¹ | R² | R³ | L² | R⁴ | L³ | R⁶ | Configuration |
|---|---|---|---|---|---|---|---|---|
| V-1176 | Me | Et | Me | CH₂ | Ph | (CH₂)₂ | tBu | (S)- |
| V-1177 | Me | Me | Me | CH₂ | Ph | (CH₂)₂ | iBu | racemic |
| V-1178 | Me | Me | Me | CH₂ | Ph | (CH₂)₂ | iBu | (S)- |
| V-1179 | Me | Et | Me | CH₂ | Ph | (CH₂)₂ | iBu | racemic |
| V-1180 | Me | Et | Me | CH₂ | Ph | (CH₂)₂ | iBu | (S)- |
| V-1181 | Me | Me | Me | CH₂ | Ph | (CH₂)₂ | n-Heptyl | racemic |
| V-1182 | Me | Me | Me | CH₂ | Ph | (CH₂)₂ | n-Heptyl | (S)- |
| V-1183 | Me | Et | Me | CH₂ | Ph | (CH₂)₂ | n-Heptyl | racemic |
| V-1184 | Me | Et | Me | CH₂ | Ph | (CH₂)₂ | n-Heptyl | (S)- |
| V-1185 | Me | Me | Me | CH₂ | Ph | (CH₂)₂ | n-Undecyl | racemic |
| V-1186 | Me | Me | Me | CH₂ | Ph | (CH₂)₂ | n-Undecyl | (S)- |
| V-1187 | Me | Et | Me | CH₂ | Ph | (CH₂)₂ | n-Undecyl | racemic |
| V-1188 | Me | Et | Me | CH₂ | Ph | (CH₂)₂ | n-Undecyl | (S)- |
| V-1189 | Me | Me | Me | CH₂ | Ph | (CH₂)₂ | Ph | racemic |
| V-1190 | Me | Me | Me | CH₂ | Ph | (CH₂)₂ | Ph | (S)- |
| V-1191 | Me | Et | Me | CH₂ | Ph | (CH₂)₂ | Ph | racemic |
| V-1192 | Me | Et | Me | CH₂ | Ph | (CH₂)₂ | Ph | (S)- |
| V-1193 | Me | Me | Me | CH₂ | Ph | (CH₂)₂ | OEt | racemic |
| V-1194 | Me | Me | Me | CH₂ | Ph | (CH₂)₂ | OEt | (S)- |
| V-1195 | Me | Et | Me | CH₂ | Ph | (CH₂)₂ | OEt | racemic |
| V-1196 | Me | Et | Me | CH₂ | Ph | (CH₂)₂ | OEt | (S)- |
| V-1197 | Me | Me | Me | CH₂ | Ph | (CH₂)₂ | (CH₂)₂COOH | racemic |
| V-1198 | Me | Me | Me | CH₂ | Ph | (CH₂)₂ | (CH₂)₂COOH | (S)- |
| V-1199 | Me | Et | Me | CH₂ | Ph | (CH₂)₂ | (CH₂)₂COOH | racemic |
| V-1200 | Me | Et | Me | CH₂ | Ph | (CH₂)₂ | (CH₂)₂COOH | (S)- |
| V-1201 | Me | Me | Me | CH₂ | Ph | CH₂C(Me)₂ | Me | racemic |
| V-1202 | Me | Me | Me | CH₂ | Ph | CH₂C(Me)₂ | Me | (S)- |
| V-1203 | Me | Et | Me | CH₂ | Ph | CH₂C(Me)₂ | Me | racemic |
| V-1204 | Me | Et | Me | CH₂ | Ph | CH₂C(Me)₂ | Me | (S)- |
| V-1205 | Me | Me | Me | CH₂ | Ph | CH₂C(Me)₂ | Et | racemic |
| V-1206 | Me | Me | Me | CH₂ | Ph | CH₂C(Me)₂ | Et | (S)- |
| V-1207 | Me | Et | Me | CH₂ | Ph | CH₂C(Me)₂ | Et | racemic |
| V-1208 | Me | Et | Me | CH₂ | Ph | CH₂C(Me)₂ | Et | (S)- |
| V-1209 | Me | Me | Me | CH₂ | Ph | CH₂C(Me)₂ | nPr | racemic |
| V-1210 | Me | Me | Me | CH₂ | Ph | CH₂C(Me)₂ | nPr | (S)- |
| V-1211 | Me | Et | Me | CH₂ | Ph | CH₂C(Me)₂ | nPr | racemic |
| V-1212 | Me | Et | Me | CH₂ | Ph | CH₂C(Me)₂ | nPr | (S)- |
| V-1213 | Me | Me | Me | CH₂ | Ph | CH₂C(Me)₂ | iPr | racemic |
| V-1214 | Me | Me | Me | CH₂ | Ph | CH₂C(Me)₂ | iPr | (S)- |
| V-1215 | Me | Et | Me | CH₂ | Ph | CH₂C(Me)₂ | iPr | racemic |
| V-1216 | Me | Et | Me | CH₂ | Ph | CH₂C(Me)₂ | iPr | (S)- |
| V-1217 | Me | Me | Me | CH₂ | Ph | CH₂C(Me)₂ | nBu | racemic |
| V-1218 | Me | Me | Me | CH₂ | Ph | CH₂C(Me)₂ | nBu | (S)- |
| V-1219 | Me | Et | Me | CH₂ | Ph | CH₂C(Me)₂ | nBu | racemic |
| V-1220 | Me | Et | Me | CH₂ | Ph | CH₂C(Me)₂ | nBu | (S)- |
| V-1221 | Me | Me | Me | CH₂ | Ph | CH₂C(Me)₂ | tBu | racemic |
| V-1222 | Me | Me | Me | CH₂ | Ph | CH₂C(Me)₂ | tBu | (S)- |
| V-1223 | Me | Et | Me | CH₂ | Ph | CH₂C(Me)₂ | tBu | racemic |
| V-1224 | Me | Et | Me | CH₂ | Ph | CH₂C(Me)₂ | tBu | (S)- |
| V-1225 | Me | Me | Me | CH₂ | Ph | CH₂C(Me)₂ | iBu | racemic |

TABLE 126

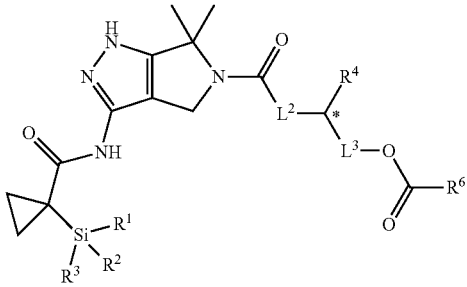
(Vb)

| Compound No. | R¹ | R² | R³ | L² | R⁴ | L³ | R⁶ | Configuration |
|---|---|---|---|---|---|---|---|---|
| V-1226 | Me | Me | Me | CH₂ | Ph | CH₂C(Me)₂ | iBu | (S)- |
| V-1227 | Me | Et | Me | CH₂ | Ph | CH₂C(Me)₂ | iBu | racemic |
| V-1228 | Me | Et | Me | CH₂ | Ph | CH₂C(Me)₂ | iBu | (S)- |
| V-1229 | Me | Me | Me | CH₂ | Ph | CH₂C(Me)₂ | n-Heptyl | racemic |
| V-1230 | Me | Me | Me | CH₂ | Ph | CH₂C(Me)₂ | n-Heptyl | (S)- |
| V-1231 | Me | Et | Me | CH₂ | Ph | CH₂C(Me)₂ | n-Heptyl | racemic |
| V-1232 | Me | Et | Me | CH₂ | Ph | CH₂C(Me)₂ | n-Heptyl | (S)- |
| V-1233 | Me | Me | Me | CH₂ | Ph | CH₂C(Me)₂ | n-Undecyl | racemic |
| V-1234 | Me | Me | Me | CH₂ | Ph | CH₂C(Me)₂ | n-Undecyl | (S)- |
| V-1235 | Me | Et | Me | CH₂ | Ph | CH₂C(Me)₂ | n-Undecyl | racemic |
| V-1236 | Me | Et | Me | CH₂ | Ph | CH₂C(Me)₂ | n-Undecyl | (S)- |
| V-1237 | Me | Me | Me | CH₂ | Ph | CH₂C(Me)₂ | Ph | racemic |
| V-1238 | Me | Me | Me | CH₂ | Ph | CH₂C(Me)₂ | Ph | (S)- |
| V-1239 | Me | Et | Me | CH₂ | Ph | CH₂C(Me)₂ | Ph | racemic |
| V-1240 | Me | Et | Me | CH₂ | Ph | CH₂C(Me)₂ | Ph | (S)- |
| V-1241 | Me | Me | Me | CH₂ | Ph | CH₂C(Me)₂ | OEt | racemic |
| V-1242 | Me | Me | Me | CH₂ | Ph | CH₂C(Me)₂ | OEt | (S)- |
| V-1243 | Me | Et | Me | CH₂ | Ph | CH₂C(Me)₂ | OEt | racemic |
| V-1244 | Me | Et | Me | CH₂ | Ph | CH₂C(Me)₂ | OEt | (S)- |
| V-1245 | Me | Me | Me | CH₂ | Ph | CH₂C(Me)₂ | (CH₂)₂COOH | racemic |
| V-1246 | Me | Me | Me | CH₂ | Ph | CH₂C(Me)₂ | (CH₂)₂COOH | (S)- |
| V-1247 | Me | Et | Me | CH₂ | Ph | CH₂C(Me)₂ | (CH₂)₂COOH | racemic |
| V-1248 | Me | Et | Me | CH₂ | Ph | CH₂C(Me)₂ | (CH₂)₂COOH | (S)- |

TABLE 127

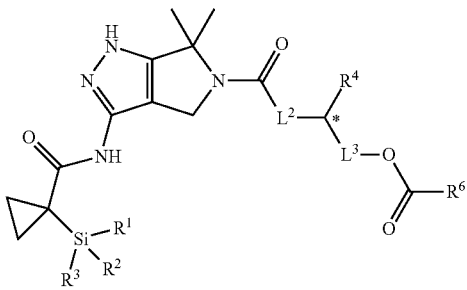
(Vb)

| Compound No. | R¹ | R² | R³ | L² | R⁴ | L³ | R⁶ | Configuration |
|---|---|---|---|---|---|---|---|---|
| V-1972 | Me | Me | Me | — | Ph | — | Me | racemic |
| V-1973 | Me | Me | Me | — | Ph | — | Me | (R)- |
| V-1974 | Me | Et | Me | — | Ph | — | Me | racemic |
| V-1975 | Me | Et | Me | — | Ph | — | Me | (R)- |
| V-1976 | Me | Me | Me | — | Ph | — | Et | racemic |
| V-1977 | Me | Me | Me | — | Ph | — | Et | (R)- |
| V-1978 | Me | Et | Me | — | Ph | — | Et | racemic |
| V-1979 | Me | Et | Me | — | Ph | — | Et | (R)- |
| V-1980 | Me | Me | Me | — | Ph | — | nPr | racemic |
| V-1981 | Me | Me | Me | — | Ph | — | nPr | (R)- |
| V-1982 | Me | Et | Me | — | Ph | — | nPr | racemic |
| V-1983 | Me | Et | Me | — | Ph | — | nPr | (R)- |
| V-1984 | Me | Me | Me | — | Ph | — | iPr | racemic |
| V-1985 | Me | Me | Me | — | Ph | — | iPr | (R)- |

TABLE 127-continued

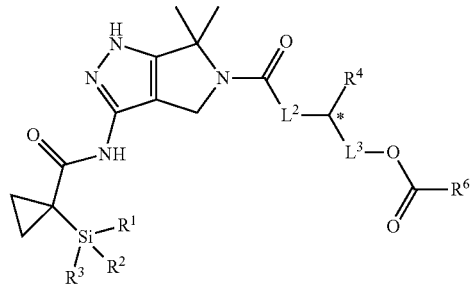
(Vb)

| Compound No. | R¹ | R² | R³ | L² | R⁴ | L³ | R⁶ | Configuration |
|---|---|---|---|---|---|---|---|---|
| V-1986 | Me | Et | Me | — | Ph | — | iPr | racemic |
| V-1987 | Me | Et | Me | — | Ph | — | iPr | (R)- |
| V-1988 | Me | Me | Me | — | Ph | — | nBu | racemic |
| V-1989 | Me | Me | Me | — | Ph | — | nBu | (R)- |
| V-1990 | Me | Et | Me | — | Ph | — | nBu | racemic |
| V-1991 | Me | Et | Me | — | Ph | — | nBu | (R)- |
| V-1992 | Me | Me | Me | — | Ph | — | tBu | racemic |
| V-1993 | Me | Me | Me | — | Ph | — | tBu | (R)- |
| V-1994 | Me | Et | Me | — | Ph | — | tBu | racemic |
| V-1995 | Me | Et | Me | — | Ph | — | tBu | (R)- |
| V-1996 | Me | Me | Me | — | Ph | — | iBu | racemic |
| V-1997 | Me | Me | Me | — | Ph | — | iBu | (R)- |
| V-1998 | Me | Et | Me | — | Ph | — | iBu | racemic |
| V-1999 | Me | Et | Me | — | Ph | — | iBu | (R)- |
| V-2000 | Me | Me | Me | — | Ph | — | n-Heptyl | racemic |
| V-2001 | Me | Me | Me | — | Ph | — | n-Heptyl | (R)- |
| V-2002 | Me | Et | Me | — | Ph | — | n-Heptyl | racemic |
| V-2003 | Me | Et | Me | — | Ph | — | n-Heptyl | (R)- |
| V-2004 | Me | Me | Me | — | Ph | — | n-Undecyl | racemic |
| V-2005 | Me | Me | Me | — | Ph | — | n-Undecyl | (R)- |
| V-2006 | Me | Et | Me | — | Ph | — | n-Undecyl | racemic |
| V-2007 | Me | Et | Me | — | Ph | — | n-Undecyl | (R)- |
| V-2008 | Me | Me | Me | — | Ph | — | OEt | racemic |
| V-2009 | Me | Me | Me | — | Ph | — | OEt | (R)- |
| V-2010 | Me | Et | Me | — | Ph | — | OEt | racemic |
| V-2011 | Me | Et | Me | — | Ph | — | OEt | (R)- |
| V-2012 | Me | Me | Me | — | Ph | — | (CH₂)₂COONa | racemic |
| V-2013 | Me | Me | Me | — | Ph | — | (CH₂)₂COONa | (R)- |
| V-2014 | Me | Et | Me | — | Ph | — | (CH₂)₂COONa | racemic |
| V-2015 | Me | Et | Me | — | Ph | — | (CH₂)₂COONa | (R)- |
| V-2016 | Me | Me | Me | — | Ph | CH₂ | Me | racemic |
| V-2017 | Me | Me | Me | — | Ph | CH₂ | Me | (S)- |
| V-2018 | Me | Et | Me | — | Ph | CH₂ | Me | racemic |
| V-2019 | Me | Et | Me | — | Ph | CH₂ | Me | (S)- |
| V-2020 | Me | Me | Me | — | Ph | CH₂ | Et | racemic |
| V-2021 | Me | Me | Me | — | Ph | CH₂ | Et | (S)- |

TABLE 128

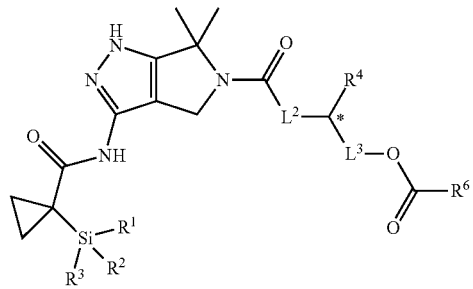
(Vb)

| Compound No. | R¹ | R² | R³ | L² | R⁴ | L³ | R⁶ | Configuration |
|---|---|---|---|---|---|---|---|---|
| V-2022 | Me | Et | Me | — | Ph | CH₂ | Et | racemic |
| V-2023 | Me | Et | Me | — | Ph | CH₂ | Et | (S)- |

TABLE 128-continued (Vb)

| Compound No. | R¹ | R² | R³ | L² | R⁴ | L³ | R⁶ | Configuration |
|---|---|---|---|---|---|---|---|---|
| V-2024 | Me | Me | Me | — | Ph | CH₂ | nPr | racemic |
| V-2025 | Me | Me | Me | — | Ph | CH₂ | nPr | (S)- |
| V-2026 | Me | Et | Me | — | Ph | CH₂ | nPr | racemic |
| V-2027 | Me | Et | Me | — | Ph | CH₂ | nPr | (S)- |
| V-2028 | Me | Me | Me | — | Ph | CH₂ | iPr | racemic |
| V-2029 | Me | Me | Me | — | Ph | CH₂ | iPr | (S)- |
| V-2030 | Me | Et | Me | — | Ph | CH₂ | iPr | racemic |
| V-2031 | Me | Et | Me | — | Ph | CH₂ | iPr | (S)- |
| V-2032 | Me | Me | Me | — | Ph | CH₂ | nBu | racemic |
| V-2033 | Me | Me | Me | — | Ph | CH₂ | nBu | (S)- |
| V-2034 | Me | Et | Me | — | Ph | CH₂ | nBu | racemic |
| V-2035 | Me | Et | Me | — | Ph | CH₂ | nBu | (S)- |
| V-2036 | Me | Me | Me | — | Ph | CH₂ | tBu | racemic |
| V-2037 | Me | Me | Me | — | Ph | CH₂ | tBu | (S)- |
| V-2038 | Me | Et | Me | — | Ph | CH₂ | tBu | racemic |
| V-2039 | Me | Et | Me | — | Ph | CH₂ | tBu | (S)- |
| V-2040 | Me | Me | Me | — | Ph | CH₂ | iBu | racemic |
| V-2041 | Me | Me | Me | — | Ph | CH₂ | iBu | (S)- |
| V-2042 | Me | Et | Me | — | Ph | CH₂ | iBu | racemic |
| V-2043 | Me | Et | Me | — | Ph | CH₂ | iBu | (S)- |
| V-2044 | Me | Me | Me | — | Ph | CH₂ | n-Heptyl | racemic |
| V-2045 | Me | Me | Me | — | Ph | CH₂ | n-Heptyl | (S)- |
| V-2046 | Me | Et | Me | — | Ph | CH₂ | n-Heptyl | racemic |
| V-2047 | Me | Et | Me | — | Ph | CH₂ | n-Heptyl | (S)- |
| V-2048 | Me | Me | Me | — | Ph | CH₂ | n-Undecyl | racemic |
| V-2049 | Me | Me | Me | — | Ph | CH₂ | n-Undecyl | (S)- |
| V-2050 | Me | Et | Me | — | Ph | CH₂ | n-Undecyl | racemic |
| V-2051 | Me | Et | Me | — | Ph | CH₂ | n-Undecyl | (S)- |
| V-2052 | Me | Me | Me | — | Ph | CH₂ | OEt | racemic |
| V-2053 | Me | Me | Me | — | Ph | CH₂ | OEt | (S)- |
| V-2054 | Me | Et | Me | — | Ph | CH₂ | OEt | racemic |
| V-2055 | Me | Et | Me | — | Ph | CH₂ | OEt | (S)- |
| V-2056 | Me | Me | Me | — | Ph | CH₂ | (CH₂)₂COONa | racemic |
| V-2057 | Me | Me | Me | — | Ph | CH₂ | (CH₂)₂COONa | (S)- |
| V-2058 | Me | Et | Me | — | Ph | CH₂ | (CH₂)₂COONa | racemic |
| V-2059 | Me | Et | Me | — | Ph | CH₂ | (CH₂)₂COONa | (S)- |

TABLE 129

(Vc)

| Compound No. | R¹ | R² | R³ | L² | R⁴ | L³ | R⁶ | Configuration |
|---|---|---|---|---|---|---|---|---|
| V-1249 | Me | Me | Me | O | Ph | CH₂ | Me | racemic |
| V-1250 | Me | Me | Me | O | Ph | CH₂ | Me | (S)- |
| V-1251 | Me | Et | Me | O | Ph | CH₂ | Me | racemic |
| V-1252 | Me | Et | Me | O | Ph | CH₂ | Me | (S)- |
| V-1253 | Me | Me | Me | O | Ph | CH₂ | Et | racemic |
| V-1254 | Me | Me | Me | O | Ph | CH₂ | Et | (S)- |
| V-1255 | Me | Et | Me | O | Ph | CH₂ | Et | racemic |
| V-1256 | Me | Et | Me | O | Ph | CH₂ | Et | (S)- |
| V-1257 | Me | Me | Me | O | Ph | CH₂ | nPr | racemic |
| V-1258 | Me | Me | Me | O | Ph | CH₂ | nPr | (S)- |
| V-1259 | Me | Et | Me | O | Ph | CH₂ | nPr | racemic |
| V-1260 | Me | Et | Me | O | Ph | CH₂ | nPr | (S)- |
| V-1261 | Me | Me | Me | O | Ph | CH₂ | iPr | racemic |
| V-1262 | Me | Me | Me | O | Ph | CH₂ | iPr | (S)- |
| V-1263 | Me | Et | Me | O | Ph | CH₂ | iPr | racemic |
| V-1264 | Me | Et | Me | O | Ph | CH₂ | iPr | (S)- |
| V-1265 | Me | Me | Me | O | Ph | CH₂ | nBu | racemic |
| V-1266 | Me | Me | Me | O | Ph | CH₂ | nBu | (S)- |
| V-1267 | Me | Et | Me | O | Ph | CH₂ | nBu | racemic |
| V-1268 | Me | Et | Me | O | Ph | CH₂ | nBu | (S)- |
| V-1269 | Me | Me | Me | O | Ph | CH₂ | tBu | racemic |
| V-1270 | Me | Me | Me | O | Ph | CH₂ | tBu | (S)- |
| V-1271 | Me | Et | Me | O | Ph | CH₂ | tBu | racemic |
| V-1272 | Me | Et | Me | O | Ph | CH₂ | tBu | (S)- |
| V-1273 | Me | Me | Me | O | Ph | CH₂ | iBu | racemic |
| V-1274 | Me | Me | Me | O | Ph | CH₂ | iBu | (S)- |
| V-1275 | Me | Et | Me | O | Ph | CH₂ | iBu | racemic |
| V-1276 | Me | Et | Me | O | Ph | CH₂ | iBu | (S)- |
| V-1277 | Me | Me | Me | O | Ph | CH₂ | n-Heptyl | racemic |
| V-1278 | Me | Me | Me | O | Ph | CH₂ | n-Heptyl | (S)- |
| V-1279 | Me | Et | Me | O | Ph | CH₂ | n-Heptyl | racemic |
| V-1280 | Me | Et | Me | O | Ph | CH₂ | n-Heptyl | (S)- |
| V-1281 | Me | Me | Me | O | Ph | CH₂ | n-Undecyl | racemic |
| V-1282 | Me | Me | Me | O | Ph | CH₂ | n-Undecyl | (S)- |
| V-1283 | Me | Et | Me | O | Ph | CH₂ | n-Undecyl | racemic |
| V-1284 | Me | Et | Me | O | Ph | CH₂ | n-Undecyl | (S)- |
| V-1285 | Me | Me | Me | O | Ph | CH₂ | Ph | racemic |
| V-1286 | Me | Me | Me | O | Ph | CH₂ | Ph | (S)- |
| V-1287 | Me | Et | Me | O | Ph | CH₂ | Ph | racemic |
| V-1288 | Me | Et | Me | O | Ph | CH₂ | Ph | (S)- |
| V-1289 | Me | Me | Me | O | Ph | CH₂ | OEt | racemic |
| V-1290 | Me | Me | Me | O | Ph | CH₂ | OEt | (S)- |
| V-1291 | Me | Et | Me | O | Ph | CH₂ | OEt | racemic |
| V-1292 | Me | Et | Me | O | Ph | CH₂ | OEt | (S)- |
| V-1293 | Me | Me | Me | O | Ph | CH₂ | (CH₂)₂COOH | racemic |
| V-1294 | Me | Me | Me | O | Ph | CH₂ | (CH₂)₂COOH | (S)- |
| V-1295 | Me | Et | Me | O | Ph | CH₂ | (CH₂)₂COOH | racemic |
| V-1296 | Me | Et | Me | O | Ph | CH₂ | (CH₂)₂COOH | (S)- |
| V-1297 | Me | Me | Me | O | Ph | C(Me)₂ | Me | racemic |
| V-1298 | Me | Me | Me | O | Ph | C(Me)₂ | Me | (S)- |

TABLE 130

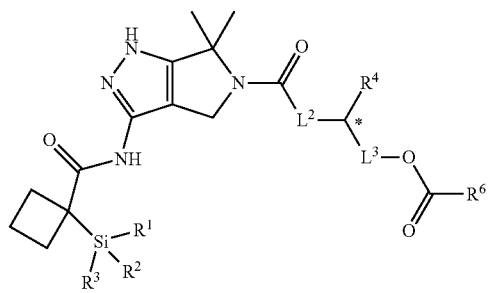

(Vc)

| Compound No. | R¹ | R² | R³ | L² | R⁴ | L³ | R⁶ | Configuration |
|---|---|---|---|---|---|---|---|---|
| V-1299 | Me | Et | Me | O | Ph | C(Me)₂ | Me | racemic |
| V-1300 | Me | Et | Me | O | Ph | C(Me)₂ | Me | (S)- |
| V-1301 | Me | Me | Me | O | Ph | C(Me)₂ | Et | racemic |
| V-1302 | Me | Me | Me | O | Ph | C(Me)₂ | Et | (S)- |
| V-1303 | Me | Et | Me | O | Ph | C(Me)₂ | Et | racemic |
| V-1304 | Me | Et | Me | O | Ph | C(Me)₂ | Et | (S)- |
| V-1305 | Me | Me | Me | O | Ph | C(Me)₂ | nPr | racemic |
| V-1306 | Me | Me | Me | O | Ph | C(Me)₂ | nPr | (S)- |
| V-1307 | Me | Et | Me | O | Ph | C(Me)₂ | nPr | racemic |
| V-1308 | Me | Et | Me | O | Ph | C(Me)₂ | nPr | (S)- |
| V-1309 | Me | Me | Me | O | Ph | C(Me)₂ | iPr | racemic |
| V-1310 | Me | Me | Me | O | Ph | C(Me)₂ | iPr | (S)- |
| V-1311 | Me | Et | Me | O | Ph | C(Me)₂ | iPr | racemic |
| V-1312 | Me | Et | Me | O | Ph | C(Me)₂ | iPr | (S)- |
| V-1313 | Me | Me | Me | O | Ph | C(Me)₂ | nBu | racemic |
| V-1314 | Me | Me | Me | O | Ph | C(Me)₂ | nBu | (S)- |
| V-1315 | Me | Et | Me | O | Ph | C(Me)₂ | nBu | racemic |
| V-1316 | Me | Et | Me | O | Ph | C(Me)₂ | nBu | (S)- |
| V-1317 | Me | Me | Me | O | Ph | C(Me)₂ | tBu | racemic |
| V-1318 | Me | Me | Me | O | Ph | C(Me)₂ | tBu | (S)- |
| V-1319 | Me | Et | Me | O | Ph | C(Me)₂ | tBu | racemic |
| V-1320 | Me | Et | Me | O | Ph | C(Me)₂ | tBu | (S)- |
| V-1321 | Me | Me | Me | O | Ph | C(Me)₂ | iBu | racemic |
| V-1322 | Me | Me | Me | O | Ph | C(Me)₂ | iBu | (S)- |
| V-1323 | Me | Et | Me | O | Ph | C(Me)₂ | iBu | racemic |
| V-1324 | Me | Et | Me | O | Ph | C(Me)₂ | iBu | (S)- |
| V-1325 | Me | Me | Me | O | Ph | C(Me)₂ | n-Heptyl | racemic |
| V-1326 | Me | Me | Me | O | Ph | C(Me)₂ | n-Heptyl | (S)- |
| V-1327 | Me | Et | Me | O | Ph | C(Me)₂ | n-Heptyl | racemic |
| V-1328 | Me | Et | Me | O | Ph | C(Me)₂ | n-Heptyl | (S)- |
| V-1329 | Me | Me | Me | O | Ph | C(Me)₂ | n-Undecyl | racemic |
| V-1330 | Me | Me | Me | O | Ph | C(Me)₂ | n-Undecyl | (S)- |
| V-1331 | Me | Et | Me | O | Ph | C(Me)₂ | n-Undecyl | racemic |
| V-1332 | Me | Et | Me | O | Ph | C(Me)₂ | n-Undecyl | (S)- |
| V-1333 | Me | Me | Me | O | Ph | C(Me)₂ | Ph | racemic |
| V-1334 | Me | Me | Me | O | Ph | C(Me)₂ | Ph | (S)- |
| V-1335 | Me | Et | Me | O | Ph | C(Me)₂ | Ph | racemic |
| V-1336 | Me | Et | Me | O | Ph | C(Me)₂ | Ph | (S)- |
| V-1337 | Me | Me | Me | O | Ph | C(Me)₂ | OEt | racemic |
| V-1338 | Me | Me | Me | O | Ph | C(Me)₂ | OEt | (S)- |
| V-1339 | Me | Et | Me | O | Ph | C(Me)₂ | OEt | racemic |
| V-1340 | Me | Et | Me | O | Ph | C(Me)₂ | OEt | (S)- |
| V-1341 | Me | Me | Me | O | Ph | C(Me)₂ | (CH₂)₂COOH | racemic |
| V-1342 | Me | Me | Me | O | Ph | C(Me)₂ | (CH₂)₂COOH | (S)- |
| V-1343 | Me | Et | Me | O | Ph | C(Me)₂ | (CH₂)₂COOH | racemic |
| V-1344 | Me | Et | Me | O | Ph | C(Me)₂ | (CH₂)₂COOH | (S)- |
| V-1345 | Me | Me | Me | O | Ph | (CH₂)₂ | Me | racemic |
| V-1346 | Me | Me | Me | O | Ph | (CH₂)₂ | Me | (R)- |
| V-1347 | Me | Et | Me | O | Ph | (CH₂)₂ | Me | racemic |
| V-1348 | Me | Et | Me | O | Ph | (CH₂)₂ | Me | (R)- |

TABLE 131

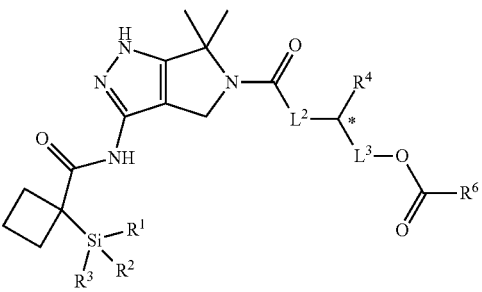

(Vc)

| Compound No. | R¹ | R² | R³ | L² | R⁴ | L³ | R⁶ | Configuration |
|---|---|---|---|---|---|---|---|---|
| V-1349 | Me | Me | Me | O | Ph | (CH₂)₂ | Et | racemic |
| V-1350 | Me | Me | Me | O | Ph | (CH₂)₂ | Et | (R)- |
| V-1351 | Me | Et | Me | O | Ph | (CH₂)₂ | Et | racemic |
| V-1352 | Me | Et | Me | O | Ph | (CH₂)₂ | Et | (R)- |
| V-1353 | Me | Me | Me | O | Ph | (CH₂)₂ | nPr | racemic |
| V-1354 | Me | Me | Me | O | Ph | (CH₂)₂ | nPr | (R)- |
| V-1355 | Me | Et | Me | O | Ph | (CH₂)₂ | nPr | racemic |
| V-1356 | Me | Et | Me | O | Ph | (CH₂)₂ | nPr | (R)- |
| V-1357 | Me | Me | Me | O | Ph | (CH₂)₂ | iPr | racemic |
| V-1358 | Me | Me | Me | O | Ph | (CH₂)₂ | iPr | (R)- |
| V-1359 | Me | Et | Me | O | Ph | (CH₂)₂ | iPr | racemic |
| V-1360 | Me | Et | Me | O | Ph | (CH₂)₂ | iPr | (R)- |
| V-1361 | Me | Me | Me | O | Ph | (CH₂)₂ | nBu | racemic |
| V-1362 | Me | Me | Me | O | Ph | (CH₂)₂ | nBu | (R)- |
| V-1363 | Me | Et | Me | O | Ph | (CH₂)₂ | nBu | racemic |
| V-1364 | Me | Et | Me | O | Ph | (CH₂)₂ | nBu | (R)- |
| V-1365 | Me | Me | Me | O | Ph | (CH₂)₂ | tBu | racemic |
| V-1366 | Me | Me | Me | O | Ph | (CH₂)₂ | tBu | (R)- |
| V-1367 | Me | Et | Me | O | Ph | (CH₂)₂ | tBu | racemic |
| V-1368 | Me | Et | Me | O | Ph | (CH₂)₂ | tBu | (R)- |
| V-1369 | Me | Me | Me | O | Ph | (CH₂)₂ | iBu | racemic |
| V-1370 | Me | Me | Me | O | Ph | (CH₂)₂ | iBu | (R)- |
| V-1371 | Me | Et | Me | O | Ph | (CH₂)₂ | iBu | racemic |
| V-1372 | Me | Et | Me | O | Ph | (CH₂)₂ | iBu | (R)- |
| V-1373 | Me | Me | Me | O | Ph | (CH₂)₂ | n-Heptyl | racemic |
| V-1374 | Me | Me | Me | O | Ph | (CH₂)₂ | n-Heptyl | (R)- |
| V-1375 | Me | Et | Me | O | Ph | (CH₂)₂ | n-Heptyl | racemic |
| V-1376 | Me | Et | Me | O | Ph | (CH₂)₂ | n-Heptyl | (R)- |
| V-1377 | Me | Me | Me | O | Ph | (CH₂)₂ | n-Undecyl | racemic |
| V-1378 | Me | Me | Me | O | Ph | (CH₂)₂ | n-Undecyl | (R)- |
| V-1379 | Me | Et | Me | O | Ph | (CH₂)₂ | n-Undecyl | racemic |
| V-1380 | Me | Et | Me | O | Ph | (CH₂)₂ | n-Undecyl | (R)- |
| V-1381 | Me | Me | Me | O | Ph | (CH₂)₂ | Ph | racemic |
| V-1382 | Me | Me | Me | O | Ph | (CH₂)₂ | Ph | (R)- |
| V-1383 | Me | Et | Me | O | Ph | (CH₂)₂ | Ph | racemic |
| V-1384 | Me | Et | Me | O | Ph | (CH₂)₂ | Ph | (R)- |
| V-1385 | Me | Me | Me | O | Ph | (CH₂)₂ | OEt | racemic |
| V-1386 | Me | Me | Me | O | Ph | (CH₂)₂ | OEt | (R)- |
| V-1387 | Me | Et | Me | O | Ph | (CH₂)₂ | OEt | racemic |
| V-1388 | Me | Et | Me | O | Ph | (CH₂)₂ | OEt | (R)- |
| V-1389 | Me | Me | Me | O | Ph | (CH₂)₂ | (CH₂)₂COOH | racemic |
| V-1390 | Me | Me | Me | O | Ph | (CH₂)₂ | (CH₂)₂COOH | (R)- |
| V-1391 | Me | Et | Me | O | Ph | (CH₂)₂ | (CH₂)₂COOH | racemic |
| V-1392 | Me | Et | Me | O | Ph | (CH₂)₂ | (CH₂)₂COOH | (R)- |
| V-1393 | Me | Me | Me | O | Ph | CH₂C(Me)₂ | Me | racemic |
| V-1394 | Me | Me | Me | O | Ph | CH₂C(Me)₂ | Me | (R)- |
| V-1395 | Me | Et | Me | O | Ph | CH₂C(Me)₂ | Me | racemic |
| V-1396 | Me | Et | Me | O | Ph | CH₂C(Me)₂ | Me | (R)- |
| V-1397 | Me | Me | Me | O | Ph | CH₂C(Me)₂ | Et | racemic |
| V-1398 | Me | Me | Me | O | Ph | CH₂C(Me)₂ | Et | (R)- |

TABLE 132

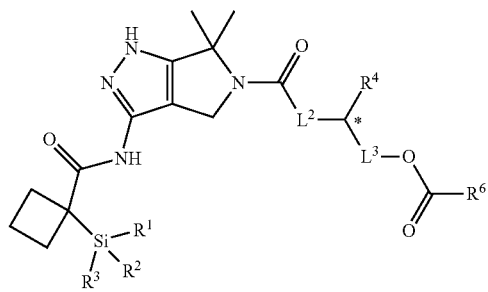

(Vc)

| Compound No. | R¹ | R² | R³ | L² | R⁴ | L³ | R⁶ | Configuration |
|---|---|---|---|---|---|---|---|---|
| V-1399 | Me | Et | Me | O | Ph | CH₂C(Me)₂ | Et | racemic |
| V-1400 | Me | Et | Me | O | Ph | CH₂C(Me)₂ | Et | (R)- |
| V-1401 | Me | Me | Me | O | Ph | CH₂C(Me)₂ | nPr | racemic |
| V-1402 | Me | Me | Me | O | Ph | CH₂C(Me)₂ | nPr | (R)- |
| V-1403 | Me | Et | Me | O | Ph | CH₂C(Me)₂ | nPr | racemic |
| V-1404 | Me | Et | Me | O | Ph | CH₂C(Me)₂ | nPr | (R)- |
| V-1405 | Me | Me | Me | O | Ph | CH₂C(Me)₂ | iPr | racemic |
| V-1406 | Me | Me | Me | O | Ph | CH₂C(Me)₂ | iPr | (R)- |
| V-1407 | Me | Et | Me | O | Ph | CH₂C(Me)₂ | iPr | racemic |
| V-1408 | Me | Et | Me | O | Ph | CH₂C(Me)₂ | iPr | (R)- |
| V-1409 | Me | Me | Me | O | Ph | CH₂C(Me)₂ | nBu | racemic |
| V-1410 | Me | Me | Me | O | Ph | CH₂C(Me)₂ | nBu | (R)- |
| V-1411 | Me | Et | Me | O | Ph | CH₂C(Me)₂ | nBu | racemic |
| V-1412 | Me | Et | Me | O | Ph | CH₂C(Me)₂ | nBu | (R)- |
| V-1413 | Me | Me | Me | O | Ph | CH₂C(Me)₂ | tBu | racemic |
| V-1414 | Me | Me | Me | O | Ph | CH₂C(Me)₂ | tBu | (R)- |
| V-1415 | Me | Et | Me | O | Ph | CH₂C(Me)₂ | tBu | racemic |
| V-1416 | Me | Et | Me | O | Ph | CH₂C(Me)₂ | tBu | (R)- |
| V-1417 | Me | Me | Me | O | Ph | CH₂C(Me)₂ | iBu | racemic |
| V-1418 | Me | Me | Me | O | Ph | CH₂C(Me)₂ | iBu | (R)- |
| V-1419 | Me | Et | Me | O | Ph | CH₂C(Me)₂ | iBu | racemic |
| V-1420 | Me | Et | Me | O | Ph | CH₂C(Me)₂ | iBu | (R)- |
| V-1421 | Me | Me | Me | O | Ph | CH₂C(Me)₂ | n-Heptyl | racemic |
| V-1422 | Me | Me | Me | O | Ph | CH₂C(Me)₂ | n-Heptyl | (R)- |
| V-1423 | Me | Et | Me | O | Ph | CH₂C(Me)₂ | n-Heptyl | racemic |
| V-1424 | Me | Et | Me | O | Ph | CH₂C(Me)₂ | n-Heptyl | (R)- |
| V-1425 | Me | Me | Me | O | Ph | CH₂C(Me)₂ | n-Undecyl | racemic |
| V-1426 | Me | Me | Me | O | Ph | CH₂C(Me)₂ | n-Undecyl | (R)- |
| V-1427 | Me | Et | Me | O | Ph | CH₂C(Me)₂ | n-Undecyl | racemic |
| V-1428 | Me | Et | Me | O | Ph | CH₂C(Me)₂ | n-Undecyl | (R)- |
| V-1429 | Me | Me | Me | O | Ph | CH₂C(Me)₂ | Ph | racemic |
| V-1430 | Me | Me | Me | O | Ph | CH₂C(Me)₂ | Ph | (R)- |
| V-1431 | Me | Et | Me | O | Ph | CH₂C(Me)₂ | Ph | racemic |
| V-1432 | Me | Et | Me | O | Ph | CH₂C(Me)₂ | Ph | (R)- |
| V-1433 | Me | Me | Me | O | Ph | CH₂C(Me)₂ | OEt | racemic |
| V-1434 | Me | Me | Me | O | Ph | CH₂C(Me)₂ | OEt | (R)- |
| V-1435 | Me | Et | Me | O | Ph | CH₂C(Me)₂ | OEt | racemic |
| V-1436 | Me | Et | Me | O | Ph | CH₂C(Me)₂ | OEt | (R)- |
| V-1437 | Me | Me | Me | O | Ph | CH₂C(Me)₂ | (CH₂)₂COOH | racemic |
| V-1438 | Me | Me | Me | O | Ph | CH₂C(Me)₂ | (CH₂)₂COOH | (R)- |
| V-1439 | Me | Et | Me | O | Ph | CH₂C(Me)₂ | (CH₂)₂COOH | racemic |
| V-1440 | Me | Et | Me | O | Ph | CH₂C(Me)₂ | (CH₂)₂COOH | (R)- |
| V-1441 | Me | Me | Me | NH | Ph | CH₂ | Me | racemic |
| V-1442 | Me | Me | Me | NH | Ph | CH₂ | Me | (S)- |
| V-1443 | Me | Et | Me | NH | Ph | CH₂ | Me | racemic |
| V-1444 | Me | Et | Me | NH | Ph | CH₂ | Me | (S)- |
| V-1445 | Me | Me | Me | NH | Ph | CH₂ | Et | racemic |
| V-1446 | Me | Me | Me | NH | Ph | CH₂ | Et | (S)- |
| V-1447 | Me | Et | Me | NH | Ph | CH₂ | Et | racemic |
| V-1448 | Me | Et | Me | NH | Ph | CH₂ | Et | (S)- |

TABLE 133

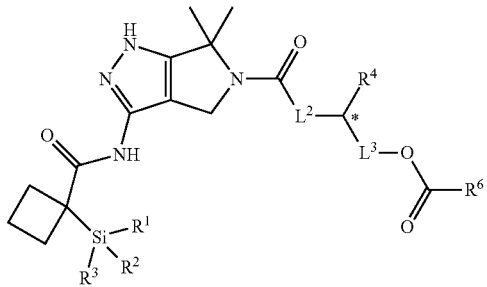

(Vc)

| Compound No. | R¹ | R² | R³ | L² | R⁴ | L³ | R⁶ | Configuration |
|---|---|---|---|---|---|---|---|---|
| V-1449 | Me | Me | Me | NH | Ph | CH₂ | nPr | racemic |
| V-1450 | Me | Me | Me | NH | Ph | CH₂ | nPr | (S)- |
| V-1451 | Me | Et | Me | NH | Ph | CH₂ | nPr | racemic |
| V-1452 | Me | Et | Me | NH | Ph | CH₂ | nPr | (S)- |
| V-1453 | Me | Me | Me | NH | Ph | CH₂ | iPr | racemic |
| V-1454 | Me | Me | Me | NH | Ph | CH₂ | iPr | (S)- |
| V-1455 | Me | Et | Me | NH | Ph | CH₂ | iPr | racemic |
| V-1456 | Me | Et | Me | NH | Ph | CH₂ | iPr | (S)- |
| V-1457 | Me | Me | Me | NH | Ph | CH₂ | nBu | racemic |
| V-1458 | Me | Me | Me | NH | Ph | CH₂ | nBu | (S)- |
| V-1459 | Me | Et | Me | NH | Ph | CH₂ | nBu | racemic |
| V-1460 | Me | Et | Me | NH | Ph | CH₂ | nBu | (S)- |
| V-1461 | Me | Me | Me | NH | Ph | CH₂ | tBu | racemic |
| V-1462 | Me | Me | Me | NH | Ph | CH₂ | tBu | (S)- |
| V-1463 | Me | Et | Me | NH | Ph | CH₂ | tBu | racemic |
| V-1464 | Me | Et | Me | NH | Ph | CH₂ | tBu | (S)- |
| V-1465 | Me | Me | Me | NH | Ph | CH₂ | iBu | racemic |
| V-1466 | Me | Me | Me | NH | Ph | CH₂ | iBu | (S)- |
| V-1467 | Me | Et | Me | NH | Ph | CH₂ | iBu | racemic |
| V-1468 | Me | Et | Me | NH | Ph | CH₂ | iBu | (S)- |
| V-1469 | Me | Me | Me | NH | Ph | CH₂ | n-Heptyl | racemic |
| V-1470 | Me | Me | Me | NH | Ph | CH₂ | n-Heptyl | (S)- |
| V-1471 | Me | Et | Me | NH | Ph | CH₂ | n-Heptyl | racemic |
| V-1472 | Me | Et | Me | NH | Ph | CH₂ | n-Heptyl | (S)- |
| V-1473 | Me | Me | Me | NH | Ph | CH₂ | n-Undecyl | racemic |
| V-1474 | Me | Me | Me | NH | Ph | CH₂ | n-Undecyl | (S)- |
| V-1475 | Me | Et | Me | NH | Ph | CH₂ | n-Undecyl | racemic |
| V-1476 | Me | Et | Me | NH | Ph | CH₂ | n-Undecyl | (S)- |
| V-1477 | Me | Me | Me | NH | Ph | CH₂ | n-Pentadecyl | racemic |
| V-1478 | Me | Me | Me | NH | Ph | CH₂ | n-Pentadecyl | (S)- |
| V-1479 | Me | Et | Me | NH | Ph | CH₂ | n-Pentadecyl | racemic |
| V-1480 | Me | Et | Me | NH | Ph | CH₂ | n-Pentadecyl | (S)- |
| V-1481 | Me | Me | Me | NH | Ph | CH₂ | Ph | racemic |
| V-1482 | Me | Me | Me | NH | Ph | CH₂ | Ph | (S)- |
| V-1483 | Me | Et | Me | NH | Ph | CH₂ | Ph | racemic |
| V-1484 | Me | Et | Me | NH | Ph | CH₂ | Ph | (S)- |
| V-1485 | Me | Me | Me | NH | Ph | CH₂ | OEt | racemic |
| V-1486 | Me | Me | Me | NH | Ph | CH₂ | OEt | (S)- |
| V-1487 | Me | Et | Me | NH | Ph | CH₂ | OEt | racemic |
| V-1488 | Me | Et | Me | NH | Ph | CH₂ | OEt | (S)- |
| V-1489 | Me | Me | Me | NH | Ph | CH₂ | (CH₂)₂COOH | racemic |
| V-1490 | Me | Me | Me | NH | Ph | CH₂ | (CH₂)₂COOH | (S)- |
| V-1491 | Me | Et | Me | NH | Ph | CH₂ | (CH₂)₂COOH | racemic |
| V-1492 | Me | Et | Me | NH | Ph | CH₂ | (CH₂)₂COOH | (S)- |
| V-1493 | Me | Me | Me | NH | Ph | CH₂ | H | racemic |
| V-1494 | Me | Me | Me | NH | Ph | CH₂ | H | (S)- |
| V-1495 | Me | Et | Me | NH | Ph | CH₂ | H | racemic |
| V-1496 | Me | Et | Me | NH | Ph | CH₂ | H | (S)- |
| V-1497 | Me | Me | Me | NH | Ph | CH₂ | (5-Methyl-2-oxo-1,3-dioxol-4-yl)methoxy | racemic |
| V-1498 | Me | Me | Me | NH | Ph | CH₂ | (5-Methyl-2-oxo-1,3-dioxol-4-yl)methoxy | (S)- |

TABLE 134

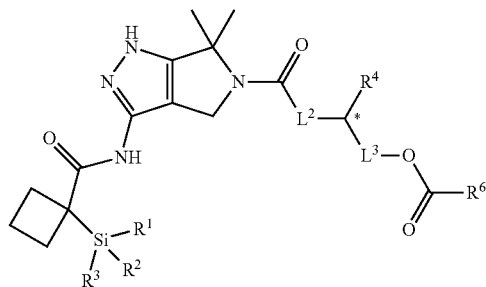
(Vc)

| Compound No. | R¹ | R² | R³ | L² | R⁴ | L³ | R⁶ | Configuration |
|---|---|---|---|---|---|---|---|---|
| V-1499 | Me | Et | Me | NH | Ph | CH₂ | (5-Methyl-2-oxo-1,3-dioxol-4-yl)methoxy | racemic |
| V-1500 | Me | Et | Me | NH | Ph | CH₂ | (5-Methyl-2-oxo-1,3-dioxol-4-yl)methoxy | (S)- |
| V-1501 | Me | Me | Me | NH | Ph | C(Me)₂ | Me | (S)- |
| V-1502 | Me | Et | Me | NH | Ph | C(Me)₂ | Me | racemic |
| V-1503 | Me | Et | Me | NH | Ph | C(Me)₂ | Me | (S)- |
| V-1504 | Me | Me | Me | NH | Ph | C(Me)₂ | Et | racemic |
| V-1505 | Me | Me | Me | NH | Ph | C(Me)₂ | Et | (S)- |
| V-1506 | Me | Et | Me | NH | Ph | C(Me)₂ | Et | racemic |
| V-1507 | Me | Et | Me | NH | Ph | C(Me)₂ | Et | (S)- |
| V-1508 | Me | Me | Me | NH | Ph | C(Me)₂ | nPr | racemic |
| V-1509 | Me | Me | Me | NH | Ph | C(Me)₂ | nPr | (S)- |
| V-1510 | Me | Et | Me | NH | Ph | C(Me)₂ | nPr | racemic |
| V-1511 | Me | Et | Me | NH | Ph | C(Me)₂ | nPr | (S)- |
| V-1512 | Me | Me | Me | NH | Ph | C(Me)₂ | iPr | racemic |
| V-1513 | Me | Me | Me | NH | Ph | C(Me)₂ | iPr | (S)- |
| V-1514 | Me | Et | Me | NH | Ph | C(Me)₂ | iPr | racemic |
| V-1515 | Me | Et | Me | NH | Ph | C(Me)₂ | iPr | (S)- |
| V-1516 | Me | Me | Me | NH | Ph | C(Me)₂ | nBu | racemic |
| V-1517 | Me | Me | Me | NH | Ph | C(Me)₂ | nBu | (S)- |
| V-1518 | Me | Et | Me | NH | Ph | C(Me)₂ | nBu | racemic |
| V-1519 | Me | Et | Me | NH | Ph | C(Me)₂ | nBu | (S)- |
| V-1520 | Me | Me | Me | NH | Ph | C(Me)₂ | tBu | racemic |
| V-1521 | Me | Me | Me | NH | Ph | C(Me)₂ | tBu | (S)- |
| V-1522 | Me | Et | Me | NH | Ph | C(Me)₂ | tBu | racemic |
| V-1523 | Me | Et | Me | NH | Ph | C(Me)₂ | tBu | (S)- |
| V-1524 | Me | Me | Me | NH | Ph | C(Me)₂ | iBu | racemic |
| V-1525 | Me | Me | Me | NH | Ph | C(Me)₂ | iBu | (S)- |
| V-1526 | Me | Et | Me | NH | Ph | C(Me)₂ | iBu | racemic |
| V-1527 | Me | Et | Me | NH | Ph | C(Me)₂ | iBu | (S)- |
| V-1528 | Me | Me | Me | NH | Ph | C(Me)₂ | n-Heptyl | racemic |
| V-1529 | Me | Me | Me | NH | Ph | C(Me)₂ | n-Heptyl | (S)- |
| V-1530 | Me | Et | Me | NH | Ph | C(Me)₂ | n-Heptyl | racemic |
| V-1531 | Me | Et | Me | NH | Ph | C(Me)₂ | n-Heptyl | (S)- |
| V-1532 | Me | Me | Me | NH | Ph | C(Me)₂ | n-Undecyl | racemic |
| V-1533 | Me | Me | Me | NH | Ph | C(Me)₂ | n-Undecyl | (S)- |
| V-1534 | Me | Et | Me | NH | Ph | C(Me)₂ | n-Undecyl | racemic |
| V-1535 | Me | Et | Me | NH | Ph | C(Me)₂ | n-Undecyl | (S)- |
| V-1536 | Me | Me | Me | NH | Ph | C(Me)₂ | Ph | racemic |
| V-1537 | Me | Me | Me | NH | Ph | C(Me)₂ | Ph | (S)- |
| V-1538 | Me | Et | Me | NH | Ph | C(Me)₂ | Ph | racemic |
| V-1539 | Me | Et | Me | NH | Ph | C(Me)₂ | Ph | (S)- |
| V-1540 | Me | Me | Me | NH | Ph | C(Me)₂ | OEt | racemic |
| V-1541 | Me | Me | Me | NH | Ph | C(Me)₂ | OEt | (S)- |
| V-1542 | Me | Et | Me | NH | Ph | C(Me)₂ | OEt | racemic |
| V-1543 | Me | Et | Me | NH | Ph | C(Me)₂ | OEt | (S)- |
| V-1544 | Me | Me | Me | NH | Ph | C(Me)₂ | (CH₂)₂COOH | racemic |
| V-1545 | Me | Me | Me | NH | Ph | C(Me)₂ | (CH₂)₂COOH | (S)- |
| V-1546 | Me | Et | Me | NH | Ph | C(Me)₂ | (CH₂)₂COOH | racemic |
| V-1547 | Me | Et | Me | NH | Ph | C(Me)₂ | (CH₂)₂COOH | (S)- |
| V-1548 | Me | Me | Me | NH | Ph | (CH₂)₂ | Me | racemic |

TABLE 135

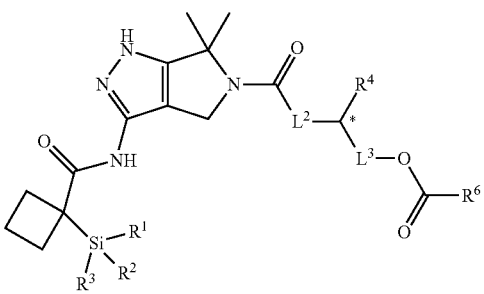
(Vc)

| Compound No. | R¹ | R² | R³ | L² | R⁴ | L³ | R⁶ | Configuration |
|---|---|---|---|---|---|---|---|---|
| V-1549 | Me | Me | Me | NH | Ph | (CH₂)₂ | Me | (R)- |
| V-1550 | Me | Et | Me | NH | Ph | (CH₂)₂ | Me | racemic |
| V-1551 | Me | Et | Me | NH | Ph | (CH₂)₂ | Me | (R)- |
| V-1552 | Me | Me | Me | NH | Ph | (CH₂)₂ | Et | racemic |
| V-1553 | Me | Me | Me | NH | Ph | (CH₂)₂ | Et | (R)- |
| V-1554 | Me | Et | Me | NH | Ph | (CH₂)₂ | Et | racemic |
| V-1555 | Me | Et | Me | NH | Ph | (CH₂)₂ | Et | (R)- |
| V-1556 | Me | Me | Me | NH | Ph | (CH₂)₂ | nPr | racemic |
| V-1557 | Me | Me | Me | NH | Ph | (CH₂)₂ | nPr | (R)- |
| V-1558 | Me | Et | Me | NH | Ph | (CH₂)₂ | nPr | racemic |
| V-1559 | Me | Et | Me | NH | Ph | (CH₂)₂ | nPr | (R)- |
| V-1560 | Me | Me | Me | NH | Ph | (CH₂)₂ | iPr | racemic |
| V-1561 | Me | Me | Me | NH | Ph | (CH₂)₂ | iPr | (R)- |
| V-1562 | Me | Et | Me | NH | Ph | (CH₂)₂ | iPr | racemic |
| V-1563 | Me | Et | Me | NH | Ph | (CH₂)₂ | iPr | (R)- |
| V-1564 | Me | Me | Me | NH | Ph | (CH₂)₂ | nBu | racemic |
| V-1565 | Me | Me | Me | NH | Ph | (CH₂)₂ | nBu | (R)- |
| V-1566 | Me | Et | Me | NH | Ph | (CH₂)₂ | nBu | racemic |
| V-1567 | Me | Et | Me | NH | Ph | (CH₂)₂ | nBu | (R)- |
| V-1568 | Me | Me | Me | NH | Ph | (CH₂)₂ | tBu | racemic |
| V-1569 | Me | Me | Me | NH | Ph | (CH₂)₂ | tBu | (R)- |
| V-1570 | Me | Et | Me | NH | Ph | (CH₂)₂ | tBu | racemic |
| V-1571 | Me | Et | Me | NH | Ph | (CH₂)₂ | tBu | (R)- |
| V-1572 | Me | Me | Me | NH | Ph | (CH₂)₂ | iBu | racemic |
| V-1573 | Me | Me | Me | NH | Ph | (CH₂)₂ | iBu | (R)- |
| V-1574 | Me | Et | Me | NH | Ph | (CH₂)₂ | iBu | racemic |
| V-1575 | Me | Et | Me | NH | Ph | (CH₂)₂ | iBu | (R)- |
| V-1576 | Me | Me | Me | NH | Ph | (CH₂)₂ | n-Heptyl | racemic |
| V-1577 | Me | Me | Me | NH | Ph | (CH₂)₂ | n-Heptyl | (R)- |
| V-1578 | Me | Et | Me | NH | Ph | (CH₂)₂ | n-Heptyl | racemic |
| V-1579 | Me | Et | Me | NH | Ph | (CH₂)₂ | n-Heptyl | (R)- |
| V-1580 | Me | Me | Me | NH | Ph | (CH₂)₂ | n-Undecyl | racemic |
| V-1581 | Me | Me | Me | NH | Ph | (CH₂)₂ | n-Undecyl | (R)- |
| V-1582 | Me | Et | Me | NH | Ph | (CH₂)₂ | n-Undecyl | racemic |
| V-1583 | Me | Et | Me | NH | Ph | (CH₂)₂ | n-Undecyl | (R)- |
| V-1584 | Me | Me | Me | NH | Ph | (CH₂)₂ | Ph | racemic |
| V-1585 | Me | Me | Me | NH | Ph | (CH₂)₂ | Ph | (R)- |
| V-1586 | Me | Et | Me | NH | Ph | (CH₂)₂ | Ph | racemic |
| V-1587 | Me | Et | Me | NH | Ph | (CH₂)₂ | Ph | (R)- |
| V-1588 | Me | Me | Me | NH | Ph | (CH₂)₂ | OEt | racemic |
| V-1589 | Me | Me | Me | NH | Ph | (CH₂)₂ | OEt | (R)- |
| V-1590 | Me | Et | Me | NH | Ph | (CH₂)₂ | OEt | racemic |
| V-1591 | Me | Et | Me | NH | Ph | (CH₂)₂ | OEt | (R)- |
| V-1592 | Me | Me | Me | NH | Ph | (CH₂)₂ | (CH₂)₂COOH | racemic |
| V-1593 | Me | Me | Me | NH | Ph | (CH₂)₂ | (CH₂)₂COOH | (R)- |
| V-1594 | Me | Et | Me | NH | Ph | (CH₂)₂ | (CH₂)₂COOH | racemic |
| V-1595 | Me | Et | Me | NH | Ph | (CH₂)₂ | (CH₂)₂COOH | (R)- |
| V-1596 | Me | Me | Me | NH | Ph | CH₂C(Me)₂ | Me | racemic |
| V-1597 | Me | Me | Me | NH | Ph | CH₂C(Me)₂ | Me | (R)- |
| V-1598 | Me | Et | Me | NH | Ph | CH₂C(Me)₂ | Me | racemic |

TABLE 136

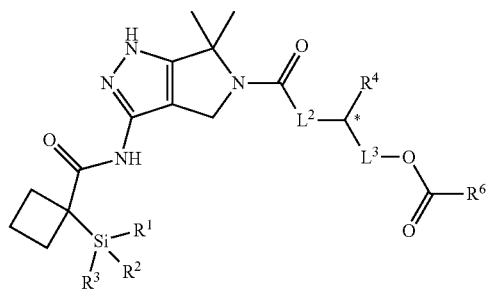
(Vc)

| Compound No. | R¹ | R² | R³ | L² | R⁴ | L³ | R⁶ | Configuration |
|---|---|---|---|---|---|---|---|---|
| V-1599 | Me | Et | Me | NH | Ph | CH₂C(Me)₂ | Me | (R)- |
| V-1600 | Me | Me | Me | NH | Ph | CH₂C(Me)₂ | Et | racemic |
| V-1601 | Me | Me | Me | NH | Ph | CH₂C(Me)₂ | Et | (R)- |
| V-1602 | Me | Et | Me | NH | Ph | CH₂C(Me)₂ | Et | racemic |
| V-1603 | Me | Et | Me | NH | Ph | CH₂C(Me)₂ | Et | (R)- |
| V-1604 | Me | Me | Me | NH | Ph | CH₂C(Me)₂ | nPr | racemic |
| V-1605 | Me | Me | Me | NH | Ph | CH₂C(Me)₂ | nPr | (R)- |
| V-1606 | Me | Et | Me | NH | Ph | CH₂C(Me)₂ | nPr | racemic |
| V-1607 | Me | Et | Me | NH | Ph | CH₂C(Me)₂ | nPr | (R)- |
| V-1608 | Me | Me | Me | NH | Ph | CH₂C(Me)₂ | iPr | racemic |
| V-1609 | Me | Me | Me | NH | Ph | CH₂C(Me)₂ | iPr | (R)- |
| V-1610 | Me | Et | Me | NH | Ph | CH₂C(Me)₂ | iPr | racemic |
| V-1611 | Me | Et | Me | NH | Ph | CH₂C(Me)₂ | iPr | (R)- |
| V-1612 | Me | Me | Me | NH | Ph | CH₂C(Me)₂ | nBu | racemic |
| V-1613 | Me | Me | Me | NH | Ph | CH₂C(Me)₂ | nBu | (R)- |
| V-1614 | Me | Et | Me | NH | Ph | CH₂C(Me)₂ | nBu | racemic |
| V-1615 | Me | Et | Me | NH | Ph | CH₂C(Me)₂ | nBu | (R)- |
| V-1616 | Me | Me | Me | NH | Ph | CH₂C(Me)₂ | tBu | racemic |
| V-1617 | Me | Me | Me | NH | Ph | CH₂C(Me)₂ | tBu | (R)- |
| V-1618 | Me | Et | Me | NH | Ph | CH₂C(Me)₂ | tBu | racemic |
| V-1619 | Me | Et | Me | NH | Ph | CH₂C(Me)₂ | tBu | (R)- |
| V-1620 | Me | Me | Me | NH | Ph | CH₂C(Me)₂ | iBu | racemic |
| V-1621 | Me | Me | Me | NH | Ph | CH₂C(Me)₂ | iBu | (R)- |
| V-1622 | Me | Et | Me | NH | Ph | CH₂C(Me)₂ | iBu | racemic |
| V-1623 | Me | Et | Me | NH | Ph | CH₂C(Me)₂ | iBu | (R)- |
| V-1624 | Me | Me | Me | NH | Ph | CH₂C(Me)₂ | n-Heptyl | racemic |
| V-1625 | Me | Me | Me | NH | Ph | CH₂C(Me)₂ | n-Heptyl | (R)- |
| V-1626 | Me | Et | Me | NH | Ph | CH₂C(Me)₂ | n-Heptyl | racemic |
| V-1627 | Me | Et | Me | NH | Ph | CH₂C(Me)₂ | n-Heptyl | (R)- |
| V-1628 | Me | Me | Me | NH | Ph | CH₂C(Me)₂ | n-Undecyl | racemic |
| V-1629 | Me | Me | Me | NH | Ph | CH₂C(Me)₂ | n-Undecyl | (R)- |
| V-1630 | Me | Et | Me | NH | Ph | CH₂C(Me)₂ | n-Undecyl | racemic |
| V-1631 | Me | Et | Me | NH | Ph | CH₂C(Me)₂ | n-Undecyl | (R)- |
| V-1632 | Me | Me | Me | NH | Ph | CH₂C(Me)₂ | Ph | racemic |
| V-1633 | Me | Me | Me | NH | Ph | CH₂C(Me)₂ | Ph | (R)- |
| V-1634 | Me | Et | Me | NH | Ph | CH₂C(Me)₂ | Ph | racemic |
| V-1635 | Me | Et | Me | NH | Ph | CH₂C(Me)₂ | Ph | (R)- |
| V-1636 | Me | Me | Me | NH | Ph | CH₂C(Me)₂ | OEt | racemic |
| V-1637 | Me | Me | Me | NH | Ph | CH₂C(Me)₂ | OEt | (R)- |
| V-1638 | Me | Et | Me | NH | Ph | CH₂C(Me)₂ | OEt | racemic |
| V-1639 | Me | Et | Me | NH | Ph | CH₂C(Me)₂ | OEt | (R)- |
| V-1640 | Me | Me | Me | NH | Ph | CH₂C(Me)₂ | (CH₂)₂COOH | racemic |
| V-1641 | Me | Me | Me | NH | Ph | CH₂C(Me)₂ | (CH₂)₂COOH | (R)- |
| V-1642 | Me | Et | Me | NH | Ph | CH₂C(Me)₂ | (CH₂)₂COOH | racemic |
| V-1643 | Me | Et | Me | NH | Ph | CH₂C(Me)₂ | (CH₂)₂COOH | (R)- |
| V-1644 | Me | Me | Me | CH₂ | Ph | CH₂ | Me | racemic |
| V-1645 | Me | Me | Me | CH₂ | Ph | CH₂ | Me | (S)- |
| V-1646 | Me | Et | Me | CH₂ | Ph | CH₂ | Me | racemic |
| V-1647 | Me | Et | Me | CH₂ | Ph | CH₂ | Me | (S)- |
| V-1648 | Me | Me | Me | CH₂ | Ph | CH₂ | Et | racemic |

TABLE 137

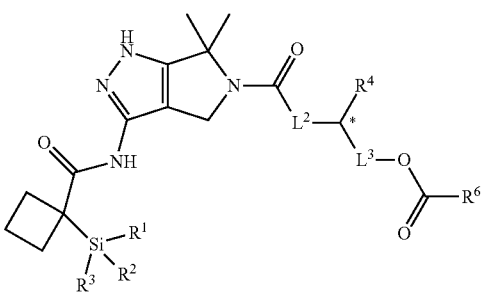
(Vc)

| Compound No. | R¹ | R² | R³ | L² | R⁴ | L³ | R⁶ | Configuration |
|---|---|---|---|---|---|---|---|---|
| V-1649 | Me | Me | Me | CH₂ | Ph | CH₂ | Et | (S)- |
| V-1650 | Me | Et | Me | CH₂ | Ph | CH₂ | Et | racemic |
| V-1651 | Me | Et | Me | CH₂ | Ph | CH₂ | Et | (S)- |
| V-1652 | Me | Me | Me | CH₂ | Ph | CH₂ | nPr | racemic |
| V-1653 | Me | Me | Me | CH₂ | Ph | CH₂ | nPr | (S)- |
| V-1654 | Me | Et | Me | CH₂ | Ph | CH₂ | nPr | racemic |
| V-1655 | Me | Et | Me | CH₂ | Ph | CH₂ | nPr | (S)- |
| V-1656 | Me | Me | Me | CH₂ | Ph | CH₂ | iPr | racemic |
| V-1657 | Me | Me | Me | CH₂ | Ph | CH₂ | iPr | (S)- |
| V-1658 | Me | Et | Me | CH₂ | Ph | CH₂ | iPr | racemic |
| V-1659 | Me | Et | Me | CH₂ | Ph | CH₂ | iPr | (S)- |
| V-1660 | Me | Me | Me | CH₂ | Ph | CH₂ | nBu | racemic |
| V-1661 | Me | Me | Me | CH₂ | Ph | CH₂ | nBu | (S)- |
| V-1662 | Me | Et | Me | CH₂ | Ph | CH₂ | nBu | racemic |
| V-1663 | Me | Et | Me | CH₂ | Ph | CH₂ | nBu | (S)- |
| V-1664 | Me | Me | Me | CH₂ | Ph | CH₂ | tBu | racemic |
| V-1665 | Me | Me | Me | CH₂ | Ph | CH₂ | tBu | (S)- |
| V-1666 | Me | Et | Me | CH₂ | Ph | CH₂ | tBu | racemic |
| V-1667 | Me | Et | Me | CH₂ | Ph | CH₂ | tBu | (S)- |
| V-1668 | Me | Me | Me | CH₂ | Ph | CH₂ | iBu | racemic |
| V-1669 | Me | Me | Me | CH₂ | Ph | CH₂ | iBu | (S)- |
| V-1670 | Me | Et | Me | CH₂ | Ph | CH₂ | iBu | racemic |
| V-1671 | Me | Et | Me | CH₂ | Ph | CH₂ | iBu | (S)- |
| V-1672 | Me | Me | Me | CH₂ | Ph | CH₂ | n-Heptyl | racemic |
| V-1673 | Me | Me | Me | CH₂ | Ph | CH₂ | n-Heptyl | (S)- |
| V-1674 | Me | Et | Me | CH₂ | Ph | CH₂ | n-Heptyl | racemic |
| V-1675 | Me | Et | Me | CH₂ | Ph | CH₂ | n-Heptyl | (S)- |
| V-1676 | Me | Me | Me | CH₂ | Ph | CH₂ | n-Undecyl | racemic |
| V-1677 | Me | Me | Me | CH₂ | Ph | CH₂ | n-Undecyl | (S)- |
| V-1678 | Me | Et | Me | CH₂ | Ph | CH₂ | n-Undecyl | racemic |
| V-1679 | Me | Et | Me | CH₂ | Ph | CH₂ | n-Undecyl | (S)- |
| V-1680 | Me | Me | Me | CH₂ | Ph | CH₂ | Ph | racemic |
| V-1681 | Me | Me | Me | CH₂ | Ph | CH₂ | Ph | (S)- |
| V-1682 | Me | Et | Me | CH₂ | Ph | CH₂ | Ph | racemic |
| V-1683 | Me | Et | Me | CH₂ | Ph | CH₂ | Ph | (S)- |
| V-1684 | Me | Me | Me | CH₂ | Ph | CH₂ | OEt | racemic |
| V-1685 | Me | Me | Me | CH₂ | Ph | CH₂ | OEt | (S)- |
| V-1686 | Me | Et | Me | CH₂ | Ph | CH₂ | OEt | racemic |
| V-1687 | Me | Et | Me | CH₂ | Ph | CH₂ | OEt | (S)- |
| V-1688 | Me | Me | Me | CH₂ | Ph | CH₂ | (CH₂)₂COOH | racemic |
| V-1689 | Me | Me | Me | CH₂ | Ph | CH₂ | (CH₂)₂COOH | (S)- |
| V-1690 | Me | Et | Me | CH₂ | Ph | CH₂ | (CH₂)₂COOH | racemic |
| V-1691 | Me | Et | Me | CH₂ | Ph | CH₂ | (CH₂)₂COOH | (S)- |
| V-1692 | Me | Me | Me | CH₂ | Ph | — | Me | racemic |
| V-1693 | Me | Me | Me | CH₂ | Ph | — | Me | (S)- |
| V-1694 | Me | Et | Me | CH₂ | Ph | — | Me | racemic |
| V-1695 | Me | Et | Me | CH₂ | Ph | — | Me | (S)- |
| V-1696 | Me | Me | Me | CH₂ | Ph | — | Et | racemic |
| V-1697 | Me | Me | Me | CH₂ | Ph | — | Et | (S)- |
| V-1698 | Me | Et | Me | CH₂ | Ph | — | Et | racemic |

TABLE 138

(Vc)

| Compound No. | R¹ | R² | R³ | L² | R⁴ | L³ | R⁶ | Configuration |
|---|---|---|---|---|---|---|---|---|
| V-1699 | Me | Et | Me | CH₂ | Ph | — | Et | (S)- |
| V-1700 | Me | Me | Me | CH₂ | Ph | — | nPr | racemic |
| V-1701 | Me | Me | Me | CH₂ | Ph | — | nPr | (S)- |
| V-1702 | Me | Et | Me | CH₂ | Ph | — | nPr | racemic |
| V-1703 | Me | Et | Me | CH₂ | Ph | — | nPr | (S)- |
| V-1704 | Me | Me | Me | CH₂ | Ph | — | iPr | racemic |
| V-1705 | Me | Me | Me | CH₂ | Ph | — | iPr | (S)- |
| V-1706 | Me | Et | Me | CH₂ | Ph | — | iPr | racemic |
| V-1707 | Me | Et | Me | CH₂ | Ph | — | iPr | (S)- |
| V-1708 | Me | Me | Me | CH₂ | Ph | — | nBu | racemic |
| V-1709 | Me | Me | Me | CH₂ | Ph | — | nBu | (S)- |
| V-1710 | Me | Et | Me | CH₂ | Ph | — | nBu | racemic |
| V-1711 | Me | Et | Me | CH₂ | Ph | — | nBu | (S)- |
| V-1712 | Me | Me | Me | CH₂ | Ph | — | tBu | racemic |
| V-1713 | Me | Me | Me | CH₂ | Ph | — | tBu | (S)- |
| V-1714 | Me | Et | Me | CH₂ | Ph | — | tBu | racemic |
| V-1715 | Me | Et | Me | CH₂ | Ph | — | tBu | (S)- |
| V-1716 | Me | Me | Me | CH₂ | Ph | — | iBu | racemic |
| V-1717 | Me | Me | Me | CH₂ | Ph | — | iBu | (S)- |
| V-1718 | Me | Et | Me | CH₂ | Ph | — | iBu | racemic |
| V-1719 | Me | Et | Me | CH₂ | Ph | — | iBu | (S)- |
| V-1720 | Me | Me | Me | CH₂ | Ph | — | n-Heptyl | racemic |
| V-1721 | Me | Me | Me | CH₂ | Ph | — | n-Heptyl | (S)- |
| V-1722 | Me | Et | Me | CH₂ | Ph | — | n-Heptyl | racemic |
| V-1723 | Me | Et | Me | CH₂ | Ph | — | n-Heptyl | (S)- |
| V-1724 | Me | Me | Me | CH₂ | Ph | — | n-Undecyl | racemic |
| V-1725 | Me | Me | Me | CH₂ | Ph | — | n-Undecyl | (S)- |
| V-1726 | Me | Et | Me | CH₂ | Ph | — | n-Undecyl | racemic |
| V-1727 | Me | Et | Me | CH₂ | Ph | — | n-Undecyl | (S)- |
| V-1728 | Me | Me | Me | CH₂ | Ph | — | Ph | racemic |
| V-1729 | Me | Me | Me | CH₂ | Ph | — | Ph | (S)- |
| V-1730 | Me | Et | Me | CH₂ | Ph | — | Ph | racemic |
| V-1731 | Me | Et | Me | CH₂ | Ph | — | Ph | (S)- |
| V-1732 | Me | Me | Me | CH₂ | Ph | — | OEt | racemic |
| V-1733 | Me | Me | Me | CH₂ | Ph | — | OEt | (S)- |
| V-1734 | Me | Et | Me | CH₂ | Ph | — | OEt | racemic |
| V-1735 | Me | Et | Me | CH₂ | Ph | — | OEt | (S)- |
| V-1736 | Me | Me | Me | CH₂ | Ph | — | (CH₂)₂COOH | racemic |
| V-1737 | Me | Me | Me | CH₂ | Ph | — | (CH₂)₂COOH | (S)- |
| V-1738 | Me | Et | Me | CH₂ | Ph | — | (CH₂)₂COOH | racemic |
| V-1739 | Me | Et | Me | CH₂ | Ph | — | (CH₂)₂COOH | (S)- |
| V-1740 | Me | Me | Me | CH₂ | Ph | C(Me)₂ | Me | racemic |
| V-1741 | Me | Me | Me | CH₂ | Ph | C(Me)₂ | Me | (S)- |
| V-1742 | Me | Et | Me | CH₂ | Ph | C(Me)₂ | Me | racemic |
| V-1743 | Me | Et | Me | CH₂ | Ph | C(Me)₂ | Me | (S)- |
| V-1744 | Me | Me | Me | CH₂ | Ph | C(Me)₂ | Et | racemic |
| V-1745 | Me | Me | Me | CH₂ | Ph | C(Me)₂ | Et | (S)- |
| V-1746 | Me | Et | Me | CH₂ | Ph | C(Me)₂ | Et | racemic |
| V-1747 | Me | Et | Me | CH₂ | Ph | C(Me)₂ | Et | (S)- |
| V-1748 | Me | Me | Me | CH₂ | Ph | C(Me)₂ | nPr | racemic |

TABLE 139

(Vc)

| Compound No. | R¹ | R² | R³ | L² | R⁴ | L³ | R⁶ | Configuration |
|---|---|---|---|---|---|---|---|---|
| V-1749 | Me | Me | Me | CH₂ | Ph | C(Me)₂ | nPr | (S)- |
| V-1750 | Me | Et | Me | CH₂ | Ph | C(Me)₂ | nPr | racemic |
| V-1751 | Me | Et | Me | CH₂ | Ph | C(Me)₂ | nPr | (S)- |
| V-1752 | Me | Me | Me | CH₂ | Ph | C(Me)₂ | iPr | racemic |
| V-1753 | Me | Me | Me | CH₂ | Ph | C(Me)₂ | iPr | (S)- |
| V-1754 | Me | Et | Me | CH₂ | Ph | C(Me)₂ | iPr | racemic |
| V-1755 | Me | Et | Me | CH₂ | Ph | C(Me)₂ | iPr | (S)- |
| V-1756 | Me | Me | Me | CH₂ | Ph | C(Me)₂ | nBu | racemic |
| V-1757 | Me | Me | Me | CH₂ | Ph | C(Me)₂ | nBu | (S)- |
| V-1758 | Me | Et | Me | CH₂ | Ph | C(Me)₂ | nBu | racemic |
| V-1759 | Me | Et | Me | CH₂ | Ph | C(Me)₂ | nBu | (S)- |
| V-1760 | Me | Me | Me | CH₂ | Ph | C(Me)₂ | tBu | racemic |
| V-1761 | Me | Me | Me | CH₂ | Ph | C(Me)₂ | tBu | (S)- |
| V-1762 | Me | Et | Me | CH₂ | Ph | C(Me)₂ | tBu | racemic |
| V-1763 | Me | Et | Me | CH₂ | Ph | C(Me)₂ | tBu | (S)- |
| V-1764 | Me | Me | Me | CH₂ | Ph | C(Me)₂ | iBu | racemic |
| V-1765 | Me | Me | Me | CH₂ | Ph | C(Me)₂ | iBu | (S)- |
| V-1766 | Me | Et | Me | CH₂ | Ph | C(Me)₂ | iBu | racemic |
| V-1767 | Me | Et | Me | CH₂ | Ph | C(Me)₂ | iBu | (S)- |
| V-1768 | Me | Me | Me | CH₂ | Ph | C(Me)₂ | n-Heptyl | racemic |
| V-1769 | Me | Me | Me | CH₂ | Ph | C(Me)₂ | n-Heptyl | (S)- |
| V-1770 | Me | Et | Me | CH₂ | Ph | C(Me)₂ | n-Heptyl | racemic |
| V-1771 | Me | Et | Me | CH₂ | Ph | C(Me)₂ | n-Heptyl | (S)- |
| V-1772 | Me | Me | Me | CH₂ | Ph | C(Me)₂ | n-Undecyl | racemic |
| V-1773 | Me | Me | Me | CH₂ | Ph | C(Me)₂ | n-Undecyl | (S)- |
| V-1774 | Me | Et | Me | CH₂ | Ph | C(Me)₂ | n-Undecyl | racemic |
| V-1775 | Me | Et | Me | CH₂ | Ph | C(Me)₂ | n-Undecyl | (S)- |
| V-1776 | Me | Me | Me | CH₂ | Ph | C(Me)₂ | Ph | racemic |
| V-1777 | Me | Me | Me | CH₂ | Ph | C(Me)₂ | Ph | (S)- |
| V-1778 | Me | Et | Me | CH₂ | Ph | C(Me)₂ | Ph | racemic |
| V-1779 | Me | Et | Me | CH₂ | Ph | C(Me)₂ | Ph | (S)- |
| V-1780 | Me | Me | Me | CH₂ | Ph | C(Me)₂ | OEt | racemic |
| V-1781 | Me | Me | Me | CH₂ | Ph | C(Me)₂ | OEt | (S)- |
| V-1782 | Me | Et | Me | CH₂ | Ph | C(Me)₂ | OEt | racemic |
| V-1783 | Me | Et | Me | CH₂ | Ph | C(Me)₂ | OEt | (S)- |
| V-1784 | Me | Me | Me | CH₂ | Ph | C(Me)₂ | (CH₂)₂COOH | racemic |
| V-1785 | Me | Me | Me | CH₂ | Ph | C(Me)₂ | (CH₂)₂COOH | (S)- |
| V-1786 | Me | Et | Me | CH₂ | Ph | C(Me)₂ | (CH₂)₂COOH | racemic |
| V-1787 | Me | Et | Me | CH₂ | Ph | C(Me)₂ | (CH₂)₂COOH | (S)- |
| V-1788 | Me | Me | Me | CH₂ | Ph | (CH₂)₂ | Me | racemic |
| V-1789 | Me | Me | Me | CH₂ | Ph | (CH₂)₂ | Me | (S)- |
| V-1790 | Me | Et | Me | CH₂ | Ph | (CH₂)₂ | Me | racemic |
| V-1791 | Me | Et | Me | CH₂ | Ph | (CH₂)₂ | Me | (S)- |
| V-1792 | Me | Me | Me | CH₂ | Ph | (CH₂)₂ | Et | racemic |
| V-1793 | Me | Me | Me | CH₂ | Ph | (CH₂)₂ | Et | (S)- |
| V-1794 | Me | Et | Me | CH₂ | Ph | (CH₂)₂ | Et | racemic |
| V-1795 | Me | Et | Me | CH₂ | Ph | (CH₂)₂ | Et | (S)- |
| V-1796 | Me | Me | Me | CH₂ | Ph | (CH₂)₂ | nPr | racemic |
| V-1797 | Me | Me | Me | CH₂ | Ph | (CH₂)₂ | nPr | (S)- |
| V-1798 | Me | Et | Me | CH₂ | Ph | (CH₂)₂ | nPr | racemic |

TABLE 140

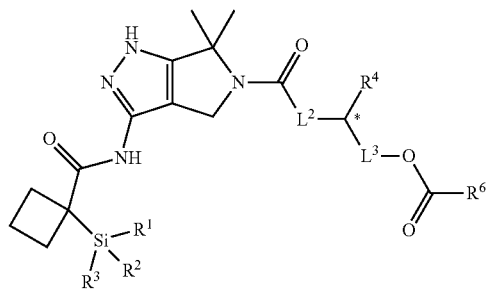

(Vc)

| Compound No. | R¹ | R² | R³ | L² | R⁴ | L³ | R⁶ | Configuration |
|---|---|---|---|---|---|---|---|---|
| V-1799 | Me | Et | Me | CH₂ | Ph | (CH₂)₂ | nPr | (S)- |
| V-1800 | Me | Me | Me | CH₂ | Ph | (CH₂)₂ | iPr | racemic |
| V-1801 | Me | Me | Me | CH₂ | Ph | (CH₂)₂ | iPr | (S)- |
| V-1802 | Me | Et | Me | CH₂ | Ph | (CH₂)₂ | iPr | racemic |
| V-1803 | Me | Et | Me | CH₂ | Ph | (CH₂)₂ | iPr | (S)- |
| V-1804 | Me | Me | Me | CH₂ | Ph | (CH₂)₂ | nBu | racemic |
| V-1805 | Me | Me | Me | CH₂ | Ph | (CH₂)₂ | nBu | (S)- |
| V-1806 | Me | Et | Me | CH₂ | Ph | (CH₂)₂ | nBu | racemic |
| V-1807 | Me | Et | Me | CH₂ | Ph | (CH₂)₂ | nBu | (S)- |
| V-1808 | Me | Me | Me | CH₂ | Ph | (CH₂)₂ | tBu | racemic |
| V-1809 | Me | Me | Me | CH₂ | Ph | (CH₂)₂ | tBu | (S)- |
| V-1810 | Me | Et | Me | CH₂ | Ph | (CH₂)₂ | tBu | racemic |
| V-1811 | Me | Et | Me | CH₂ | Ph | (CH₂)₂ | tBu | (S)- |
| V-1812 | Me | Me | Me | CH₂ | Ph | (CH₂)₂ | iBu | racemic |
| V-1813 | Me | Me | Me | CH₂ | Ph | (CH₂)₂ | iBu | (S)- |
| V-1814 | Me | Et | Me | CH₂ | Ph | (CH₂)₂ | iBu | racemic |
| V-1815 | Me | Et | Me | CH₂ | Ph | (CH₂)₂ | iBu | (S)- |
| V-1816 | Me | Me | Me | CH₂ | Ph | (CH₂)₂ | n-Heptyl | racemic |
| V-1817 | Me | Me | Me | CH₂ | Ph | (CH₂)₂ | n-Heptyl | (S)- |
| V-1818 | Me | Et | Me | CH₂ | Ph | (CH₂)₂ | n-Heptyl | racemic |
| V-1819 | Me | Et | Me | CH₂ | Ph | (CH₂)₂ | n-Heptyl | (S)- |
| V-1820 | Me | Me | Me | CH₂ | Ph | (CH₂)₂ | n-Undecyl | racemic |
| V-1821 | Me | Me | Me | CH₂ | Ph | (CH₂)₂ | n-Undecyl | (S)- |
| V-1822 | Me | Et | Me | CH₂ | Ph | (CH₂)₂ | n-Undecyl | racemic |
| V-1823 | Me | Et | Me | CH₂ | Ph | (CH₂)₂ | n-Undecyl | (S)- |
| V-1824 | Me | Me | Me | CH₂ | Ph | (CH₂)₂ | Ph | racemic |
| V-1825 | Me | Me | Me | CH₂ | Ph | (CH₂)₂ | Ph | (S)- |
| V-1826 | Me | Et | Me | CH₂ | Ph | (CH₂)₂ | Ph | racemic |
| V-1827 | Me | Et | Me | CH₂ | Ph | (CH₂)₂ | Ph | (S)- |
| V-1828 | Me | Me | Me | CH₂ | Ph | (CH₂)₂ | OEt | racemic |
| V-1829 | Me | Me | Me | CH₂ | Ph | (CH₂)₂ | OEt | (S)- |
| V-1830 | Me | Et | Me | CH₂ | Ph | (CH₂)₂ | OEt | racemic |
| V-1831 | Me | Et | Me | CH₂ | Ph | (CH₂)₂ | OEt | (S)- |
| V-1832 | Me | Me | Me | CH₂ | Ph | (CH₂)₂ | (CH₂)₂COOH | racemic |
| V-1833 | Me | Me | Me | CH₂ | Ph | (CH₂)₂ | (CH₂)₂COOH | (S)- |
| V-1834 | Me | Et | Me | CH₂ | Ph | (CH₂)₂ | (CH₂)₂COOH | racemic |
| V-1835 | Me | Et | Me | CH₂ | Ph | (CH₂)₂ | (CH₂)₂COOH | (S)- |
| V-1836 | Me | Me | Me | CH₂ | Ph | CH₂C(Me)₂ | Me | racemic |
| V-1837 | Me | Me | Me | CH₂ | Ph | CH₂C(Me)₂ | Me | (S)- |
| V-1838 | Me | Et | Me | CH₂ | Ph | CH₂C(Me)₂ | Me | racemic |
| V-1839 | Me | Et | Me | CH₂ | Ph | CH₂C(Me)₂ | Me | (S)- |
| V-1840 | Me | Me | Me | CH₂ | Ph | CH₂C(Me)₂ | Et | racemic |
| V-1841 | Me | Me | Me | CH₂ | Ph | CH₂C(Me)₂ | Et | (S)- |
| V-1842 | Me | Et | Me | CH₂ | Ph | CH₂C(Me)₂ | Et | racemic |
| V-1843 | Me | Et | Me | CH₂ | Ph | CH₂C(Me)₂ | Et | (S)- |
| V-1844 | Me | Me | Me | CH₂ | Ph | CH₂C(Me)₂ | nPr | racemic |
| V-1845 | Me | Me | Me | CH₂ | Ph | CH₂C(Me)₂ | nPr | (S)- |
| V-1846 | Me | Et | Me | CH₂ | Ph | CH₂C(Me)₂ | nPr | racemic |
| V-1847 | Me | Et | Me | CH₂ | Ph | CH₂C(Me)₂ | nPr | (S)- |
| V-1848 | Me | Me | Me | CH₂ | Ph | CH₂C(Me)₂ | iPr | racemic |

TABLE 141

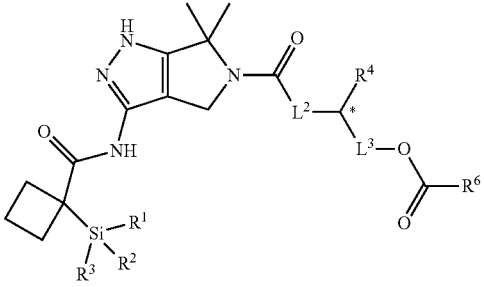

(Vc)

| Compound No. | R¹ | R² | R³ | L² | R⁴ | L³ | R⁶ | Configuration |
|---|---|---|---|---|---|---|---|---|
| V-1849 | Me | Me | Me | CH₂ | Ph | CH₂C(Me)₂ | iPr | (S)- |
| V-1850 | Me | Et | Me | CH₂ | Ph | CH₂C(Me)₂ | iPr | racemic |
| V-1851 | Me | Et | Me | CH₂ | Ph | CH₂C(Me)₂ | iPr | (S)- |
| V-1852 | Me | Me | Me | CH₂ | Ph | CH₂C(Me)₂ | nBu | racemic |
| V-1853 | Me | Me | Me | CH₂ | Ph | CH₂C(Me)₂ | nBu | (S)- |
| V-1854 | Me | Et | Me | CH₂ | Ph | CH₂C(Me)₂ | nBu | racemic |
| V-1855 | Me | Et | Me | CH₂ | Ph | CH₂C(Me)₂ | nBu | (S)- |
| V-1856 | Me | Me | Me | CH₂ | Ph | CH₂C(Me)₂ | tBu | racemic |
| V-1857 | Me | Me | Me | CH₂ | Ph | CH₂C(Me)₂ | tBu | (S)- |
| V-1858 | Me | Et | Me | CH₂ | Ph | CH₂C(Me)₂ | tBu | racemic |
| V-1859 | Me | Et | Me | CH₂ | Ph | CH₂C(Me)₂ | tBu | (S)- |
| V-1860 | Me | Me | Me | CH₂ | Ph | CH₂C(Me)₂ | iBu | racemic |
| V-1861 | Me | Me | Me | CH₂ | Ph | CH₂C(Me)₂ | iBu | (S)- |
| V-1862 | Me | Et | Me | CH₂ | Ph | CH₂C(Me)₂ | iBu | racemic |
| V-1863 | Me | Et | Me | CH₂ | Ph | CH₂C(Me)₂ | iBu | (S)- |
| V-1864 | Me | Me | Me | CH₂ | Ph | CH₂C(Me)₂ | n-Heptyl | racemic |
| V-1865 | Me | Me | Me | CH₂ | Ph | CH₂C(Me)₂ | n-Heptyl | (S)- |
| V-1866 | Me | Et | Me | CH₂ | Ph | CH₂C(Me)₂ | n-Heptyl | racemic |
| V-1867 | Me | Et | Me | CH₂ | Ph | CH₂C(Me)₂ | n-Heptyl | (S)- |
| V-1868 | Me | Me | Me | CH₂ | Ph | CH₂C(Me)₂ | n-Undecyl | racemic |
| V-1869 | Me | Me | Me | CH₂ | Ph | CH₂C(Me)₂ | n-Undecyl | (S)- |
| V-1870 | Me | Et | Me | CH₂ | Ph | CH₂C(Me)₂ | n-Undecyl | racemic |
| V-1871 | Me | Et | Me | CH₂ | Ph | CH₂C(Me)₂ | n-Undecyl | (S)- |
| V-1872 | Me | Me | Me | CH₂ | Ph | CH₂C(Me)₂ | Ph | racemic |
| V-1873 | Me | Me | Me | CH₂ | Ph | CH₂C(Me)₂ | Ph | (S)- |
| V-1874 | Me | Et | Me | CH₂ | Ph | CH₂C(Me)₂ | Ph | racemic |
| V-1875 | Me | Et | Me | CH₂ | Ph | CH₂C(Me)₂ | Ph | (S)- |
| V-1876 | Me | Me | Me | CH₂ | Ph | CH₂C(Me)₂ | OEt | racemic |
| V-1877 | Me | Me | Me | CH₂ | Ph | CH₂C(Me)₂ | OEt | (S)- |
| V-1878 | Me | Et | Me | CH₂ | Ph | CH₂C(Me)₂ | OEt | racemic |
| V-1879 | Me | Et | Me | CH₂ | Ph | CH₂C(Me)₂ | OEt | (S)- |
| V-1880 | Me | Me | Me | CH₂ | Ph | CH₂C(Me)₂ | (CH₂)₂COOH | racemic |
| V-1881 | Me | Me | Me | CH₂ | Ph | CH₂C(Me)₂ | (CH₂)₂COOH | (S)- |
| V-1882 | Me | Et | Me | CH₂ | Ph | CH₂C(Me)₂ | (CH₂)₂COOH | racemic |
| V-1883 | Me | Et | Me | CH₂ | Ph | CH₂C(Me)₂ | (CH₂)₂COOH | (S)- |

TABLE 142

(Vc)

| Compound No. | R¹ | R² | R³ | L² | R⁴ | L³ | R⁶ | Configuration |
|---|---|---|---|---|---|---|---|---|
| V-2060 | Me | Me | Me | — | Ph | — | Me | racemic |
| V-2061 | Me | Me | Me | — | Ph | — | Me | (R)- |

TABLE 142-continued (Vc)

| Compound No. | R¹ | R² | R³ | L² | R⁴ | L³ | R⁶ | Configuration |
|---|---|---|---|---|---|---|---|---|
| V-2062 | Me | Et | Me | — | Ph | — | Me | racemic |
| V-2063 | Me | Et | Me | — | Ph | — | Me | (R)- |
| V-2064 | Me | Me | Me | — | Ph | — | Et | racemic |
| V-2065 | Me | Me | Me | — | Ph | — | Et | (R)- |
| V-2066 | Me | Et | Me | — | Ph | — | Et | racemic |
| V-2067 | Me | Et | Me | — | Ph | — | Et | (R)- |
| V-2068 | Me | Me | Me | — | Ph | — | nPr | racemic |
| V-2069 | Me | Me | Me | — | Ph | — | nPr | (R)- |
| V-2070 | Me | Et | Me | — | Ph | — | nPr | racemic |
| V-2071 | Me | Et | Me | — | Ph | — | nPr | (R)- |
| V-2072 | Me | Me | Me | — | Ph | — | iPr | racemic |
| V-2073 | Me | Me | Me | — | Ph | — | iPr | (R)- |
| V-2074 | Me | Et | Me | — | Ph | — | iPr | racemic |
| V-2075 | Me | Et | Me | — | Ph | — | iPr | (R)- |
| V-2076 | Me | Me | Me | — | Ph | — | nBu | racemic |
| V-2077 | Me | Me | Me | — | Ph | — | nBu | (R)- |
| V-2078 | Me | Et | Me | — | Ph | — | nBu | racemic |
| V-2079 | Me | Et | Me | — | Ph | — | nBu | (R)- |
| V-2080 | Me | Me | Me | — | Ph | — | tBu | racemic |
| V-2081 | Me | Me | Me | — | Ph | — | tBu | (R)- |
| V-2082 | Me | Et | Me | — | Ph | — | tBu | racemic |
| V-2083 | Me | Et | Me | — | Ph | — | tBu | (R)- |
| V-2084 | Me | Me | Me | — | Ph | — | iBu | racemic |
| V-2085 | Me | Me | Me | — | Ph | — | iBu | (R)- |
| V-2086 | Me | Et | Me | — | Ph | — | iBu | racemic |
| V-2087 | Me | Et | Me | — | Ph | — | iBu | (R)- |
| V-2088 | Me | Me | Me | — | Ph | — | n-Heptyl | racemic |
| V-2089 | Me | Me | Me | — | Ph | — | n-Heptyl | (R)- |
| V-2090 | Me | Et | Me | — | Ph | — | n-Heptyl | racemic |
| V-2091 | Me | Et | Me | — | Ph | — | n-Heptyl | (R)- |
| V-2092 | Me | Me | Me | — | Ph | — | n-Undecyl | racemic |
| V-2093 | Me | Me | Me | — | Ph | — | n-Undecyl | (R)- |
| V-2094 | Me | Et | Me | — | Ph | — | n-Undecyl | racemic |
| V-2095 | Me | Et | Me | — | Ph | — | n-Undecyl | (R)- |
| V-2096 | Me | Me | Me | — | Ph | — | OEt | racemic |
| V-2097 | Me | Me | Me | — | Ph | — | OEt | (R)- |
| V-2098 | Me | Et | Me | — | Ph | — | OEt | racemic |
| V-2099 | Me | Et | Me | — | Ph | — | OEt | (R)- |
| V-2100 | Me | Me | Me | — | Ph | — | $(CH_2)_2COONa$ | racemic |
| V-2101 | Me | Me | Me | — | Ph | — | $(CH_2)_2COONa$ | (R)- |
| V-2102 | Me | Et | Me | — | Ph | — | $(CH_2)_2COONa$ | racemic |
| V-2103 | Me | Et | Me | — | Ph | — | $(CH_2)_2COONa$ | (R)- |
| V-2104 | Me | Me | Me | — | Ph | $CH_2$ | Me | racemic |
| V-2105 | Me | Me | Me | — | Ph | $CH_2$ | Me | (S)- |
| V-2106 | Me | Et | Me | — | Ph | $CH_2$ | Me | racemic |
| V-2107 | Me | Et | Me | — | Ph | $CH_2$ | Me | (S)- |
| V-2108 | Me | Me | Me | — | Ph | $CH_2$ | Et | racemic |
| V-2109 | Me | Me | Me | — | Ph | $CH_2$ | Et | (S)- |

TABLE 143

(Vc)

| Compound No. | R¹ | R² | R³ | L² | R⁴ | L³ | R⁶ | Configuration |
|---|---|---|---|---|---|---|---|---|
| V-2110 | Me | Et | Me | — | Ph | $CH_2$ | Et | racemic |
| V-2111 | Me | Et | Me | — | Ph | $CH_2$ | Et | (S)- |
| V-2112 | Me | Me | Me | — | Ph | $CH_2$ | nPr | racemic |
| V-2113 | Me | Me | Me | — | Ph | $CH_2$ | nPr | (S)- |
| V-2114 | Me | Et | Me | — | Ph | $CH_2$ | nPr | racemic |
| V-2115 | Me | Et | Me | — | Ph | $CH_2$ | nPr | (S)- |
| V-2116 | Me | Me | Me | — | Ph | $CH_2$ | iPr | racemic |
| V-2117 | Me | Me | Me | — | Ph | $CH_2$ | iPr | (S)- |
| V-2118 | Me | Et | Me | — | Ph | $CH_2$ | iPr | racemic |
| V-2119 | Me | Et | Me | — | Ph | $CH_2$ | iPr | (S)- |
| V-2120 | Me | Me | Me | — | Ph | $CH_2$ | nBu | racemic |
| V-2121 | Me | Me | Me | — | Ph | $CH_2$ | nBu | (S)- |
| V-2122 | Me | Et | Me | — | Ph | $CH_2$ | nBu | racemic |
| V-2123 | Me | Et | Me | — | Ph | $CH_2$ | nBu | (S)- |
| V-2124 | Me | Me | Me | — | Ph | $CH_2$ | tBu | racemic |
| V-2125 | Me | Me | Me | — | Ph | $CH_2$ | tBu | (S)- |
| V-2126 | Me | Et | Me | — | Ph | $CH_2$ | tBu | racemic |
| V-2127 | Me | Et | Me | — | Ph | $CH_2$ | tBu | (S)- |
| V-2128 | Me | Me | Me | — | Ph | $CH_2$ | iBu | racemic |
| V-2129 | Me | Me | Me | — | Ph | $CH_2$ | iBu | (S)- |
| V-2130 | Me | Et | Me | — | Ph | $CH_2$ | iBu | racemic |
| V-2131 | Me | Et | Me | — | Ph | $CH_2$ | iBu | (S)- |
| V-2132 | Me | Me | Me | — | Ph | $CH_2$ | n-Heptyl | racemic |
| V-2133 | Me | Me | Me | — | Ph | $CH_2$ | n-Heptyl | (S)- |
| V-2134 | Me | Et | Me | — | Ph | $CH_2$ | n-Heptyl | racemic |
| V-2135 | Me | Et | Me | — | Ph | $CH_2$ | n-Heptyl | (S)- |
| V-2136 | Me | Me | Me | — | Ph | $CH_2$ | n-Undecyl | racemic |
| V-2137 | Me | Me | Me | — | Ph | $CH_2$ | n-Undecyl | (S)- |
| V-2138 | Me | Et | Me | — | Ph | $CH_2$ | n-Undecyl | racemic |
| V-2139 | Me | Et | Me | — | Ph | $CH_2$ | n-Undecyl | (S)- |
| V-2140 | Me | Me | Me | — | Ph | $CH_2$ | OEt | racemic |
| V-2141 | Me | Me | Me | — | Ph | $CH_2$ | OEt | (S)- |
| V-2142 | Me | Et | Me | — | Ph | $CH_2$ | OEt | racemic |
| V-2143 | Me | Et | Me | — | Ph | $CH_2$ | OEt | (S)- |
| V-2144 | Me | Me | Me | — | Ph | $CH_2$ | $(CH_2)_2COONa$ | racemic |
| V-2145 | Me | Me | Me | — | Ph | $CH_2$ | $(CH_2)_2COONa$ | (S)- |
| V-2146 | Me | Et | Me | — | Ph | $CH_2$ | $(CH_2)_2COONa$ | racemic |
| V-2147 | Me | Et | Me | — | Ph | $CH_2$ | $(CH_2)_2COONa$ | (S)- |

TABLE 144

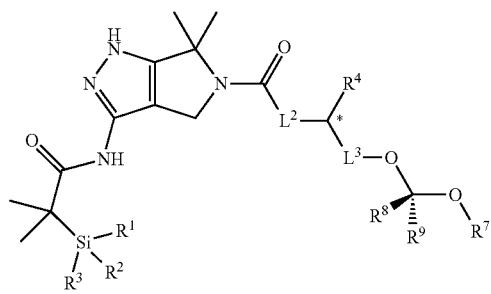

(VIa)

| Compound No. | R¹ | R² | R³ | L² | R⁴ | L³ | R⁸ | R⁹ | R⁷ | Configuration |
|---|---|---|---|---|---|---|---|---|---|---|
| VI-1 | Me | Me | Me | O | Ph | CH₂ | H | H | Me | racemic |
| VI-2 | Me | Me | Me | O | Ph | CH₂ | H | H | Me | (S)- |
| VI-3 | Me | Me | Me | O | Ph | CH₂ | Me | H | Me | racemic |
| VI-4 | Me | Me | Me | O | Ph | CH₂ | Me | H | Me | (S)- |
| VI-5 | Me | Me | Me | O | Ph | CH₂ | H | Me | Me | racemic |
| VI-6 | Me | Me | Me | O | Ph | CH₂ | H | Me | Me | (S)- |
| VI-7 | Me | Me | Me | O | Ph | CH₂ | Me | Me | Me | racemic |
| VI-8 | Me | Me | Me | O | Ph | CH₂ | Me | Me | Me | (S)- |
| VI-9 | Me | Et | Me | O | Ph | CH₂ | H | H | Me | racemic |
| VI-10 | Me | Et | Me | O | Ph | CH₂ | H | H | Me | (S)- |
| VI-11 | Me | Et | Me | O | Ph | CH₂ | Me | H | Me | racemic |
| VI-12 | Me | Et | Me | O | Ph | CH₂ | Me | H | Me | (S)- |
| VI-13 | Me | Et | Me | O | Ph | CH₂ | H | Me | Me | racemic |
| VI-14 | Me | Et | Me | O | Ph | CH₂ | H | Me | Me | (S)- |
| VI-15 | Me | Et | Me | O | Ph | CH₂ | Me | Me | Me | racemic |
| VI-16 | Me | Et | Me | O | Ph | CH₂ | Me | Me | Me | (S)- |
| VI-17 | Me | Me | Me | O | Ph | CH₂ | H | H | Et | racemic |
| VI-18 | Me | Me | Me | O | Ph | CH₂ | H | H | Et | (S)- |
| VI-19 | Me | Me | Me | O | Ph | CH₂ | Me | H | Et | racemic |
| VI-20 | Me | Me | Me | O | Ph | CH₂ | Me | H | Et | (S)- |
| VI-21 | Me | Me | Me | O | Ph | CH₂ | H | Me | Et | racemic |
| VI-22 | Me | Me | Me | O | Ph | CH₂ | H | Me | Et | (S)- |
| VI-23 | Me | Me | Me | O | Ph | CH₂ | Me | Me | Et | racemic |
| VI-24 | Me | Me | Me | O | Ph | CH₂ | Me | Me | Et | (S)- |
| VI-25 | Me | Et | Me | O | Ph | CH₂ | H | H | Et | racemic |
| VI-26 | Me | Et | Me | O | Ph | CH₂ | H | H | Et | (S)- |
| VI-27 | Me | Et | Me | O | Ph | CH₂ | Me | H | Et | racemic |
| VI-28 | Me | Et | Me | O | Ph | CH₂ | Me | H | Et | (S)- |
| VI-29 | Me | Et | Me | O | Ph | CH₂ | H | Me | Et | racemic |
| VI-30 | Me | Et | Me | O | Ph | CH₂ | H | Me | Et | (S)- |
| VI-31 | Me | Et | Me | O | Ph | CH₂ | Me | Me | Et | racemic |
| VI-32 | Me | Et | Me | O | Ph | CH₂ | Me | Me | Et | (S)- |
| VI-33 | Me | Me | Me | NH | Ph | CH₂ | H | H | Me | racemic |
| VI-34 | Me | Me | Me | NH | Ph | CH₂ | H | H | Me | (S)- |
| VI-35 | Me | Me | Me | NH | Ph | CH₂ | Me | H | Me | racemic |
| VI-36 | Me | Me | Me | NH | Ph | CH₂ | Me | H | Me | (S)- |
| VI-37 | Me | Me | Me | NH | Ph | CH₂ | H | Me | Me | racemic |
| VI-38 | Me | Me | Me | NH | Ph | CH₂ | H | Me | Me | (S)- |
| VI-39 | Me | Me | Me | NH | Ph | CH₂ | Me | Me | Me | racemic |
| VI-40 | Me | Me | Me | NH | Ph | CH₂ | Me | Me | Me | (S)- |
| VI-41 | Me | Et | Me | NH | Ph | CH₂ | H | H | Me | racemic |
| VI-42 | Me | Et | Me | NH | Ph | CH₂ | H | H | Me | (S)- |
| VI-43 | Me | Et | Me | NH | Ph | CH₂ | Me | H | Me | racemic |
| VI-44 | Me | Et | Me | NH | Ph | CH₂ | Me | H | Me | (S)- |
| VI-45 | Me | Et | Me | NH | Ph | CH₂ | H | Me | Me | racemic |
| VI-46 | Me | Et | Me | NH | Ph | CH₂ | H | Me | Me | (S)- |
| VI-47 | Me | Et | Me | NH | Ph | CH₂ | Me | Me | Me | racemic |
| VI-48 | Me | Et | Me | NH | Ph | CH₂ | Me | Me | Me | (S)- |
| VI-49 | Me | Me | Me | NH | Ph | CH₂ | H | H | Et | racemic |
| VI-50 | Me | Me | Me | NH | Ph | CH₂ | H | H | Et | (S)- |

TABLE 145

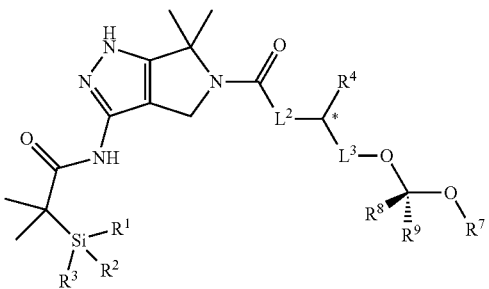

(VIa)

| Compound No. | R¹ | R² | R³ | L² | R⁴ | L³ | R⁸ | R⁹ | R⁷ | Configuration |
|---|---|---|---|---|---|---|---|---|---|---|
| VI-51 | Me | Me | Me | NH | Ph | CH₂ | Me | H | Et | racemic |
| VI-52 | Me | Me | Me | NH | Ph | CH₂ | Me | H | Et | (S)- |
| VI-53 | Me | Me | Me | NH | Ph | CH₂ | H | Me | Et | racemic |
| VI-54 | Me | Me | Me | NH | Ph | CH₂ | H | Me | Et | (S)- |
| VI-55 | Me | Me | Me | NH | Ph | CH₂ | Me | Me | Et | racemic |
| VI-56 | Me | Me | Me | NH | Ph | CH₂ | Me | Me | Et | (S)- |
| VI-57 | Me | Et | Me | NH | Ph | CH₂ | H | H | Et | racemic |
| VI-58 | Me | Et | Me | NH | Ph | CH₂ | H | H | Et | (S)- |
| VI-59 | Me | Et | Me | NH | Ph | CH₂ | Me | H | Et | racemic |
| VI-60 | Me | Et | Me | NH | Ph | CH₂ | Me | H | Et | (S)- |
| VI-61 | Me | Et | Me | NH | Ph | CH₂ | H | Me | Et | racemic |
| VI-62 | Me | Et | Me | NH | Ph | CH₂ | H | Me | Et | (S)- |
| VI-63 | Me | Et | Me | NH | Ph | CH₂ | Me | Me | Et | racemic |
| VI-64 | Me | Et | Me | NH | Ph | CH₂ | Me | Me | Et | (S)- |
| VI-65 | Me | Me | Me | NH | Ph | CH₂ | H | H | C(=O)Me | racemic |
| VI-66 | Me | Me | Me | NH | Ph | CH₂ | H | H | C(=O)Me | (S)- |
| VI-67 | Me | Me | Me | NH | Ph | CH₂ | Me | H | C(=O)Me | racemic |
| VI-68 | Me | Me | Me | NH | Ph | CH₂ | Me | H | C(=O)Me | (S)- |
| VI-69 | Me | Me | Me | NH | Ph | CH₂ | H | Me | C(=O)Me | racemic |
| VI-70 | Me | Me | Me | NH | Ph | CH₂ | H | Me | C(=O)Me | (S)- |
| VI-71 | Me | Me | Me | NH | Ph | CH₂ | Me | Me | C(=O)Me | racemic |
| VI-72 | Me | Me | Me | NH | Ph | CH₂ | Me | Me | C(=O)Me | (S)- |
| VI-73 | Me | Et | Me | NH | Ph | CH₂ | H | H | C(=O)Me | racemic |
| VI-74 | Me | Et | Me | NH | Ph | CH₂ | H | H | C(=O)Me | (S)- |
| VI-75 | Me | Et | Me | NH | Ph | CH₂ | Me | H | C(=O)Me | racemic |
| VI-76 | Me | Et | Me | NH | Ph | CH₂ | Me | H | C(=O)Me | (S)- |
| VI-77 | Me | Et | Me | NH | Ph | CH₂ | H | Me | C(=O)Me | racemic |
| VI-78 | Me | Et | Me | NH | Ph | CH₂ | H | Me | C(=O)Me | (S)- |
| VI-79 | Me | Et | Me | NH | Ph | CH₂ | Me | Me | C(=O)Me | racemic |
| VI-80 | Me | Et | Me | NH | Ph | CH₂ | Me | Me | C(=O)Me | (S)- |
| VI-81 | Me | Me | Me | NH | Ph | CH₂ | H | H | C(=O)Et | racemic |
| VI-82 | Me | Me | Me | NH | Ph | CH₂ | H | H | C(=O)Et | (S)- |
| VI-83 | Me | Me | Me | NH | Ph | CH₂ | Me | H | C(=O)Et | racemic |
| VI-84 | Me | Me | Me | NH | Ph | CH₂ | Me | H | C(=O)Et | (S)- |
| VI-85 | Me | Me | Me | NH | Ph | CH₂ | H | Me | C(=O)Et | racemic |
| VI-86 | Me | Me | Me | NH | Ph | CH₂ | H | Me | C(=O)Et | (S)- |
| VI-87 | Me | Me | Me | NH | Ph | CH₂ | Me | Me | C(=O)Et | racemic |
| VI-88 | Me | Me | Me | NH | Ph | CH₂ | Me | Me | C(=O)Et | (S)- |
| VI-89 | Me | Et | Me | NH | Ph | CH₂ | H | H | C(=O)Et | racemic |
| VI-90 | Me | Et | Me | NH | Ph | CH₂ | H | H | C(=O)Et | (S)- |
| VI-91 | Me | Et | Me | NH | Ph | CH₂ | Me | H | C(=O)Et | racemic |
| VI-92 | Me | Et | Me | NH | Ph | CH₂ | Me | H | C(=O)Et | (S)- |
| VI-93 | Me | Et | Me | NH | Ph | CH₂ | H | Me | C(=O)Et | racemic |
| VI-94 | Me | Et | Me | NH | Ph | CH₂ | H | Me | C(=O)Et | (S)- |
| VI-95 | Me | Et | Me | NH | Ph | CH₂ | Me | Me | C(=O)Et | racemic |
| VI-96 | Me | Et | Me | NH | Ph | CH₂ | Me | Me | C(=O)Et | (S)- |
| VI-97 | Me | Me | Me | NH | Ph | CH₂ | H | H | C(=O)tBu | racemic |
| VI-98 | Me | Me | Me | NH | Ph | CH₂ | H | H | C(=O)tBu | (S)- |
| VI-99 | Me | Me | Me | NH | Ph | CH₂ | Me | H | C(=O)tBu | racemic |
| VI-100 | Me | Me | Me | NH | Ph | CH₂ | Me | H | C(=O)tBu | (S)- |

TABLE 146

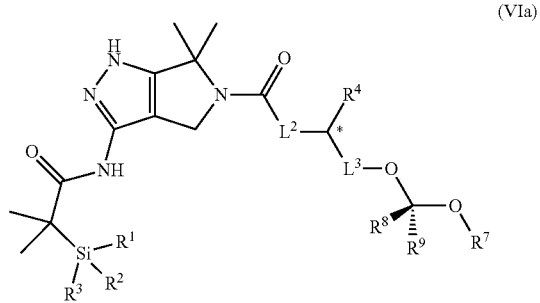
(VIa)

| Compound No. | R¹ | R² | R³ | L² | R⁴ | L³ | R⁸ | R⁹ | R⁷ | Configuration |
|---|---|---|---|---|---|---|---|---|---|---|
| VI-101 | Me | Me | Me | NH | Ph | CH₂ | H | Me | C(=O)tBu | racemic |
| VI-102 | Me | Me | Me | NH | Ph | CH₂ | H | Me | C(=O)tBu | (S)- |
| VI-103 | Me | Me | Me | NH | Ph | CH₂ | Me | Me | C(=O)tBu | racemic |
| VI-104 | Me | Me | Me | NH | Ph | CH₂ | Me | Me | C(=O)tBu | (S)- |
| VI-105 | Me | Et | Me | NH | Ph | CH₂ | H | H | C(=O)tBu | racemic |
| VI-106 | Me | Et | Me | NH | Ph | CH₂ | H | H | C(=O)tBu | (S)- |
| VI-107 | Me | Et | Me | NH | Ph | CH₂ | Me | H | C(=O)tBu | racemic |
| VI-108 | Me | Et | Me | NH | Ph | CH₂ | Me | H | C(=O)tBu | (S)- |
| VI-109 | Me | Et | Me | NH | Ph | CH₂ | H | Me | C(=O)tBu | racemic |
| VI-110 | Me | Et | Me | NH | Ph | CH₂ | H | Me | C(=O)tBu | (S)- |
| VI-111 | Me | Et | Me | NH | Ph | CH₂ | Me | Me | C(=O)tBu | racemic |
| VI-112 | Me | Et | Me | NH | Ph | CH₂ | Me | Me | C(=O)tBu | (S)- |
| VI-113 | Me | Me | Me | NH | Ph | CH₂ | H | H | C(=O)OEt | racemic |
| VI-114 | Me | Me | Me | NH | Ph | CH₂ | H | H | C(=O)OEt | (S)- |
| VI-115 | Me | Me | Me | NH | Ph | CH₂ | Me | H | C(=O)OEt | racemic |
| VI-116 | Me | Me | Me | NH | Ph | CH₂ | Me | H | C(=O)OEt | (S)- |
| VI-117 | Me | Me | Me | NH | Ph | CH₂ | H | Me | C(=O)OEt | racemic |
| VI-118 | Me | Me | Me | NH | Ph | CH₂ | H | Me | C(=O)OEt | (S)- |
| VI-119 | Me | Me | Me | NH | Ph | CH₂ | Me | Me | C(=O)OEt | racemic |
| VI-120 | Me | Me | Me | NH | Ph | CH₂ | Me | Me | C(=O)OEt | (S)- |
| VI-121 | Me | Et | Me | NH | Ph | CH₂ | H | H | C(=O)OEt | racemic |
| VI-122 | Me | Et | Me | NH | Ph | CH₂ | H | H | C(=O)OEt | (S)- |
| VI-123 | Me | Et | Me | NH | Ph | CH₂ | Me | H | C(=O)OEt | racemic |
| VI-124 | Me | Et | Me | NH | Ph | CH₂ | Me | H | C(=O)OEt | (S)- |
| VI-125 | Me | Et | Me | NH | Ph | CH₂ | H | Me | C(=O)OEt | racemic |
| VI-126 | Me | Et | Me | NH | Ph | CH₂ | H | Me | C(=O)OEt | (S)- |
| VI-127 | Me | Et | Me | NH | Ph | CH₂ | Me | Me | C(=O)OEt | racemic |
| VI-128 | Me | Et | Me | NH | Ph | CH₂ | Me | Me | C(=O)OEt | (S)- |
| VI-129 | Me | Me | Me | NH | Ph | CH₂ | H | H | C(=O)OcHex | racemic |
| VI-130 | Me | Me | Me | NH | Ph | CH₂ | H | H | C(=O)OcHex | (S)- |
| VI-131 | Me | Me | Me | NH | Ph | CH₂ | Me | H | C(=O)OcHex | racemic |
| VI-132 | Me | Me | Me | NH | Ph | CH₂ | Me | H | C(=O)OcHex | (S)- |
| VI-133 | Me | Me | Me | NH | Ph | CH₂ | H | Me | C(=O)OcHex | racemic |
| VI-134 | Me | Me | Me | NH | Ph | CH₂ | H | Me | C(=O)OcHex | (S)- |
| VI-135 | Me | Me | Me | NH | Ph | CH₂ | Me | Me | C(=O)OcHex | racemic |
| VI-136 | Me | Me | Me | NH | Ph | CH₂ | Me | Me | C(=O)OcHex | (S)- |
| VI-137 | Me | Et | Me | NH | Ph | CH₂ | H | H | C(=O)OcHex | racemic |
| VI-138 | Me | Et | Me | NH | Ph | CH₂ | H | H | C(=O)OcHex | (S)- |
| VI-139 | Me | Et | Me | NH | Ph | CH₂ | Me | H | C(=O)OcHex | racemic |
| VI-140 | Me | Et | Me | NH | Ph | CH₂ | Me | H | C(=O)OcHex | (S)- |
| VI-141 | Me | Et | Me | NH | Ph | CH₂ | H | Me | C(=O)OcHex | racemic |
| VI-142 | Me | Et | Me | NH | Ph | CH₂ | H | Me | C(=O)OcHex | (S)- |
| VI-143 | Me | Et | Me | NH | Ph | CH₂ | Me | Me | C(=O)OcHex | racemic |
| VI-144 | Me | Et | Me | NH | Ph | CH₂ | Me | Me | C(=O)OcHex | (S)- |

TABLE 146-continued

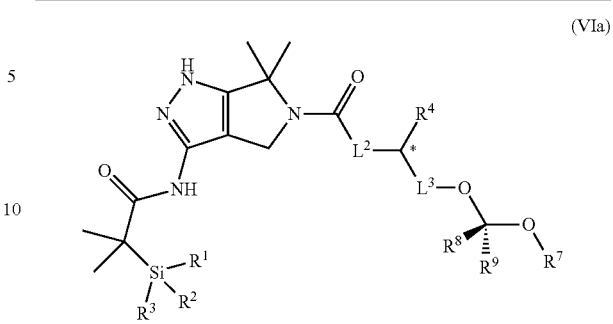
(VIa)

| Compound No. | R¹ | R² | R³ | L² | R⁴ | L³ | R⁸ | R⁹ | R⁷ | Configuration |
|---|---|---|---|---|---|---|---|---|---|---|
| VI-145 | Me | Me | Me | CH₂ | Ph | CH₂ | H | H | Me | racemic |
| VI-146 | Me | Me | Me | CH₂ | Ph | CH₂ | H | H | Me | (S)- |
| VI-147 | Me | Me | Me | CH₂ | Ph | CH₂ | Me | H | Me | racemic |
| VI-148 | Me | Me | Me | CH₂ | Ph | CH₂ | Me | H | Me | (S)- |
| VI-149 | Me | Me | Me | CH₂ | Ph | CH₂ | H | Me | Me | racemic |
| VI-150 | Me | Me | Me | CH₂ | Ph | CH₂ | H | Me | Me | (S)- |

TABLE 147

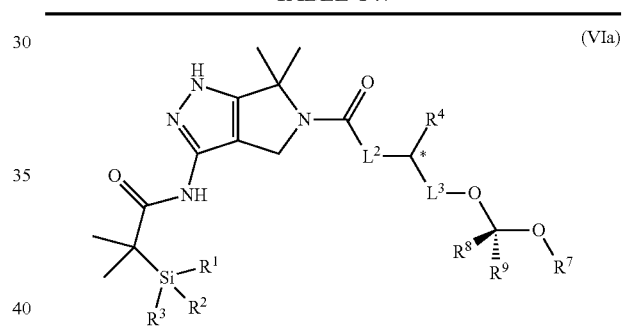
(VIa)

| Compound No. | R¹ | R² | R³ | L² | R⁴ | L³ | R⁸ | R⁹ | R⁷ | Configuration |
|---|---|---|---|---|---|---|---|---|---|---|
| VI-151 | Me | Me | Me | CH₂ | Ph | CH₂ | Me | Me | Me | racemic |
| VI-152 | Me | Me | Me | CH₂ | Ph | CH₂ | Me | Me | Me | (S)- |
| VI-153 | Me | Et | Me | CH₂ | Ph | CH₂ | H | H | Me | racemic |
| VI-154 | Me | Et | Me | CH₂ | Ph | CH₂ | H | H | Me | (S)- |
| VI-155 | Me | Et | Me | CH₂ | Ph | CH₂ | Me | H | Me | racemic |
| VI-156 | Me | Et | Me | CH₂ | Ph | CH₂ | Me | H | Me | (S)- |
| VI-157 | Me | Et | Me | CH₂ | Ph | CH₂ | H | Me | Me | racemic |
| VI-158 | Me | Et | Me | CH₂ | Ph | CH₂ | H | Me | Me | (S)- |
| VI-159 | Me | Et | Me | CH₂ | Ph | CH₂ | Me | Me | Me | racemic |
| VI-160 | Me | Et | Me | CH₂ | Ph | CH₂ | Me | Me | Me | (S)- |
| VI-161 | Me | Me | Me | CH₂ | Ph | CH₂ | H | H | Et | racemic |
| VI-162 | Me | Me | Me | CH₂ | Ph | CH₂ | H | H | Et | (S)- |
| VI-163 | Me | Me | Me | CH₂ | Ph | CH₂ | Me | H | Et | racemic |
| VI-164 | Me | Me | Me | CH₂ | Ph | CH₂ | Me | H | Et | (S)- |
| VI-165 | Me | Me | Me | CH₂ | Ph | CH₂ | H | Me | Et | racemic |
| VI-166 | Me | Me | Me | CH₂ | Ph | CH₂ | H | Me | Et | (S)- |
| VI-167 | Me | Me | Me | CH₂ | Ph | CH₂ | Me | Me | Et | racemic |
| VI-168 | Me | Me | Me | CH₂ | Ph | CH₂ | Me | Me | Et | (S)- |
| VI-169 | Me | Et | Me | CH₂ | Ph | CH₂ | H | H | Et | racemic |
| VI-170 | Me | Et | Me | CH₂ | Ph | CH₂ | H | H | Et | (S)- |
| VI-171 | Me | Et | Me | CH₂ | Ph | CH₂ | Me | H | Et | racemic |
| VI-172 | Me | Et | Me | CH₂ | Ph | CH₂ | Me | H | Et | (S)- |
| VI-173 | Me | Et | Me | CH₂ | Ph | CH₂ | H | Me | Et | racemic |
| VI-174 | Me | Et | Me | CH₂ | Ph | CH₂ | H | Me | Et | (S)- |
| VI-175 | Me | Et | Me | CH₂ | Ph | CH₂ | Me | Me | Et | racemic |
| VI-176 | Me | Et | Me | CH₂ | Ph | CH₂ | Me | Me | Et | (S)- |

TABLE 148

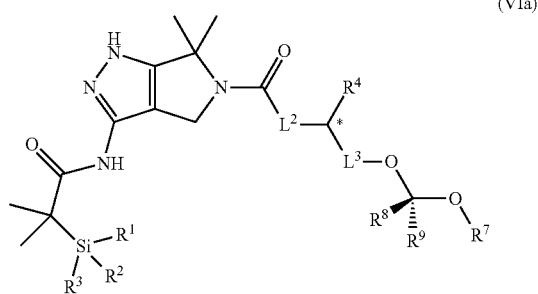

(VIa)

| Compound No. | R¹ | R² | R³ | L² | R⁴ | L³ | R⁸ | R⁹ | R⁷ | Configuration |
|---|---|---|---|---|---|---|---|---|---|---|
| VI-553 | Me | Me | Me | NH | Ph | (CH₂)₂ | H | H | Me | racemic |
| VI-554 | Me | Me | Me | NH | Ph | (CH₂)₂ | H | H | Me | (R)- |
| VI-555 | Me | Me | Me | NH | Ph | (CH₂)₂ | Me | H | Me | racemic |
| VI-556 | Me | Me | Me | NH | Ph | (CH₂)₂ | Me | H | Me | (R)- |
| VI-557 | Me | Me | Me | NH | Ph | (CH₂)₂ | H | Me | Me | racemic |
| VI-558 | Me | Me | Me | NH | Ph | (CH₂)₂ | H | Me | Me | (R)- |
| VI-559 | Me | Me | Me | NH | Ph | (CH₂)₂ | Me | Me | Me | racemic |
| VI-560 | Me | Me | Me | NH | Ph | (CH₂)₂ | Me | Me | Me | (R)- |
| VI-561 | Me | Et | Me | NH | Ph | (CH₂)₂ | H | H | Me | racemic |
| VI-562 | Me | Et | Me | NH | Ph | (CH₂)₂ | H | H | Me | (R)- |
| VI-563 | Me | Et | Me | NH | Ph | (CH₂)₂ | Me | H | Me | racemic |
| VI-564 | Me | Et | Me | NH | Ph | (CH₂)₂ | Me | H | Me | (R)- |
| VI-565 | Me | Et | Me | NH | Ph | (CH₂)₂ | H | Me | Me | racemic |
| VI-566 | Me | Et | Me | NH | Ph | (CH₂)₂ | H | Me | Me | (R)- |
| VI-567 | Me | Et | Me | NH | Ph | (CH₂)₂ | Me | Me | Me | racemic |
| VI-568 | Me | Et | Me | NH | Ph | (CH₂)₂ | Me | Me | Me | (R)- |
| VI-569 | Me | Me | Me | NH | Ph | (CH₂)₂ | H | H | C(=O)Me | racemic |
| VI-570 | Me | Me | Me | NH | Ph | (CH₂)₂ | H | H | C(=O)Me | (R)- |
| VI-571 | Me | Me | Me | NH | Ph | (CH₂)₂ | Me | H | C(=O)Me | racemic |
| VI-572 | Me | Me | Me | NH | Ph | (CH₂)₂ | Me | H | C(=O)Me | (R)- |
| VI-573 | Me | Me | Me | NH | Ph | (CH₂)₂ | H | Me | C(=O)Me | racemic |
| VI-574 | Me | Me | Me | NH | Ph | (CH₂)₂ | H | Me | C(=O)Me | (R)- |
| VI-575 | Me | Me | Me | NH | Ph | (CH₂)₂ | Me | Me | C(=O)Me | racemic |
| VI-576 | Me | Me | Me | NH | Ph | (CH₂)₂ | Me | Me | C(=O)Me | (R)- |
| VI-577 | Me | Et | Me | NH | Ph | (CH₂)₂ | H | H | C(=O)Me | racemic |
| VI-578 | Me | Et | Me | NH | Ph | (CH₂)₂ | H | H | C(=O)Me | (R)- |
| VI-579 | Me | Et | Me | NH | Ph | (CH₂)₂ | Me | H | C(=O)Me | racemic |
| VI-580 | Me | Et | Me | NH | Ph | (CH₂)₂ | Me | H | C(=O)Me | (R)- |
| VI-581 | Me | Et | Me | NH | Ph | (CH₂)₂ | H | Me | C(=O)Me | racemic |
| VI-582 | Me | Et | Me | NH | Ph | (CH₂)₂ | H | Me | C(=O)Me | (R)- |
| VI-583 | Me | Et | Me | NH | Ph | (CH₂)₂ | Me | Me | C(=O)Me | racemic |
| VI-584 | Me | Et | Me | NH | Ph | (CH₂)₂ | Me | Me | C(=O)Me | (R)- |
| VI-585 | Me | Me | Me | NH | Ph | (CH₂)₂ | H | H | C(=O)Et | racemic |
| VI-586 | Me | Me | Me | NH | Ph | (CH₂)₂ | H | H | C(=O)Et | (R)- |
| VI-587 | Me | Me | Me | NH | Ph | (CH₂)₂ | Me | H | C(=O)Et | racemic |
| VI-588 | Me | Me | Me | NH | Ph | (CH₂)₂ | Me | H | C(=O)Et | (R)- |
| VI-589 | Me | Me | Me | NH | Ph | (CH₂)₂ | H | Me | C(=O)Et | racemic |
| VI-590 | Me | Me | Me | NH | Ph | (CH₂)₂ | H | Me | C(=O)Et | (R)- |
| VI-591 | Me | Me | Me | NH | Ph | (CH₂)₂ | Me | Me | C(=O)Et | racemic |
| VI-592 | Me | Me | Me | NH | Ph | (CH₂)₂ | Me | Me | C(=O)Et | (R)- |
| VI-593 | Me | Et | Me | NH | Ph | (CH₂)₂ | H | H | C(=O)Et | racemic |
| VI-594 | Me | Et | Me | NH | Ph | (CH₂)₂ | H | H | C(=O)Et | (R)- |
| VI-595 | Me | Et | Me | NH | Ph | (CH₂)₂ | Me | H | C(=O)Et | racemic |
| VI-596 | Me | Et | Me | NH | Ph | (CH₂)₂ | Me | H | C(=O)Et | (R)- |
| VI-597 | Me | Et | Me | NH | Ph | (CH₂)₂ | H | Me | C(=O)Et | racemic |
| VI-598 | Me | Et | Me | NH | Ph | (CH₂)₂ | H | Me | C(=O)Et | (R)- |
| VI-599 | Me | Et | Me | NH | Ph | (CH₂)₂ | Me | Me | C(=O)Et | racemic |
| VI-600 | Me | Et | Me | NH | Ph | (CH₂)₂ | Me | Me | C(=O)Et | (R)- |
| VI-601 | Me | Me | Me | — | Ph | — | H | H | Me | racemic |
| VI-602 | Me | Me | Me | — | Ph | — | H | H | Me | (R)- |
| VI-603 | Me | Me | Me | — | Ph | — | Me | H | Me | racemic |

TABLE 149

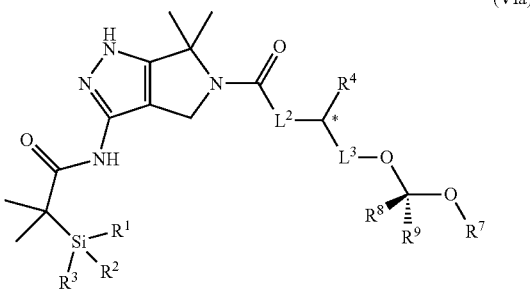

(VIa)

| Compound No. | R¹ | R² | R³ | L² | R⁴ | L³ | R⁸ | R⁹ | R⁷ | Configuration |
|---|---|---|---|---|---|---|---|---|---|---|
| VI-604 | Me | Me | Me | — | Ph | — | Me | H | Me | (R)- |
| VI-605 | Me | Me | Me | — | Ph | — | H | Me | Me | racemic |
| VI-606 | Me | Me | Me | — | Ph | — | H | Me | Me | (R)- |
| VI-607 | Me | Me | Me | — | Ph | — | Me | Me | Me | racemic |
| VI-608 | Me | Me | Me | — | Ph | — | Me | Me | Me | (R)- |
| VI-609 | Me | Et | Me | — | Ph | — | H | H | Me | racemic |
| VI-610 | Me | Et | Me | — | Ph | — | H | H | Me | (R)- |
| VI-611 | Me | Et | Me | — | Ph | — | Me | H | Me | racemic |
| VI-612 | Me | Et | Me | — | Ph | — | Me | H | Me | (R)- |
| VI-613 | Me | Et | Me | — | Ph | — | H | Me | Me | racemic |
| VI-614 | Me | Et | Me | — | Ph | — | H | Me | Me | (R)- |
| VI-615 | Me | Et | Me | — | Ph | — | Me | Me | Me | racemic |
| VI-616 | Me | Et | Me | — | Ph | — | Me | Me | Me | (R)- |
| VI-617 | Me | Me | Me | — | Ph | — | H | H | C(=O)Me | racemic |
| VI-618 | Me | Me | Me | — | Ph | — | H | H | C(=O)Me | (R)- |
| VI-619 | Me | Me | Me | — | Ph | — | Me | H | C(=O)Me | racemic |
| VI-620 | Me | Me | Me | — | Ph | — | Me | H | C(=O)Me | (R)- |
| VI-621 | Me | Me | Me | — | Ph | — | H | Me | C(=O)Me | racemic |
| VI-622 | Me | Me | Me | — | Ph | — | H | Me | C(=O)Me | (R)- |
| VI-623 | Me | Me | Me | — | Ph | — | Me | Me | C(=O)Me | racemic |
| VI-624 | Me | Me | Me | — | Ph | — | Me | Me | C(=O)Me | (R)- |
| VI-625 | Me | Et | Me | — | Ph | — | H | H | C(=O)Me | racemic |
| VI-626 | Me | Et | Me | — | Ph | — | H | H | C(=O)Me | (R)- |
| VI-627 | Me | Et | Me | — | Ph | — | Me | H | C(=O)Me | racemic |
| VI-628 | Me | Et | Me | — | Ph | — | Me | H | C(=O)Me | (R)- |
| VI-629 | Me | Et | Me | — | Ph | — | H | Me | C(=O)Me | racemic |
| VI-630 | Me | Et | Me | — | Ph | — | H | Me | C(=O)Me | (R)- |
| VI-631 | Me | Et | Me | — | Ph | — | Me | Me | C(=O)Me | racemic |
| VI-632 | Me | Et | Me | — | Ph | — | Me | Me | C(=O)Me | (R)- |
| VI-633 | Me | Me | Me | — | Ph | — | H | H | C(=O)Et | racemic |
| VI-634 | Me | Me | Me | — | Ph | — | H | H | C(=O)Et | (R)- |
| VI-635 | Me | Me | Me | — | Ph | — | Me | H | C(=O)Et | racemic |
| VI-636 | Me | Me | Me | — | Ph | — | Me | H | C(=O)Et | (R)- |
| VI-637 | Me | Me | Me | — | Ph | — | H | Me | C(=O)Et | racemic |
| VI-638 | Me | Me | Me | — | Ph | — | H | Me | C(=O)Et | (R)- |
| VI-639 | Me | Me | Me | — | Ph | — | Me | Me | C(=O)Et | racemic |
| VI-640 | Me | Me | Me | — | Ph | — | Me | Me | C(=O)Et | (R)- |
| VI-641 | Me | Et | Me | — | Ph | — | H | H | C(=O)Et | racemic |
| VI-642 | Me | Et | Me | — | Ph | — | H | H | C(=O)Et | (R)- |
| VI-643 | Me | Et | Me | — | Ph | — | Me | H | C(=O)Et | racemic |
| VI-644 | Me | Et | Me | — | Ph | — | Me | H | C(=O)Et | (R)- |
| VI-645 | Me | Et | Me | — | Ph | — | H | Me | C(=O)Et | racemic |
| VI-646 | Me | Et | Me | — | Ph | — | H | Me | C(=O)Et | (R)- |
| VI-647 | Me | Et | Me | — | Ph | — | Me | Me | C(=O)Et | racemic |
| VI-648 | Me | Et | Me | — | Ph | — | Me | Me | C(=O)Et | (R)- |
| VI-649 | Me | Me | Me | — | Ph | CH₂ | H | H | Me | racemic |
| VI-650 | Me | Me | Me | — | Ph | CH₂ | H | H | Me | (S)- |
| VI-651 | Me | Me | Me | — | Ph | CH₂ | Me | H | Me | racemic |
| VI-652 | Me | Me | Me | — | Ph | CH₂ | Me | H | Me | (S)- |
| VI-653 | Me | Me | Me | — | Ph | CH₂ | H | Me | Me | racemic |

TABLE 150

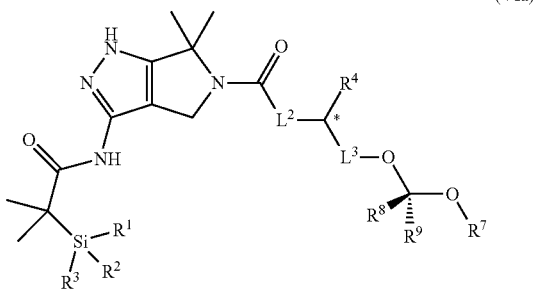

(VIa)

| Compound No. | R¹ | R² | R³ | L² | R⁴ | L³ | R⁸ | R⁹ | R⁷ | Configuration |
|---|---|---|---|---|---|---|---|---|---|---|
| VI-654 | Me | Me | Me | — | Ph | CH₂ | H | Me | Me | (S)- |
| VI-655 | Me | Me | Me | — | Ph | CH₂ | Me | Me | Me | racemic |
| VI-656 | Me | Me | Me | — | Ph | CH₂ | Me | Me | Me | (S)- |
| VI-657 | Me | Et | Me | — | Ph | CH₂ | H | H | Me | racemic |
| VI-658 | Me | Et | Me | — | Ph | CH₂ | H | H | Me | (S)- |
| VI-659 | Me | Et | Me | — | Ph | CH₂ | Me | H | Me | racemic |
| VI-660 | Me | Et | Me | — | Ph | CH₂ | Me | H | Me | (S)- |
| VI-661 | Me | Et | Me | — | Ph | CH₂ | H | Me | Me | racemic |
| VI-662 | Me | Et | Me | — | Ph | CH₂ | H | Me | Me | (S)- |
| VI-663 | Me | Et | Me | — | Ph | CH₂ | Me | Me | Me | racemic |
| VI-664 | Me | Et | Me | — | Ph | CH₂ | Me | Me | Me | (S)- |
| VI-665 | Me | Me | Me | — | Ph | CH₂ | H | H | C(=O)Me | racemic |
| VI-666 | Me | Me | Me | — | Ph | CH₂ | H | H | C(=O)Me | (S)- |
| VI-667 | Me | Me | Me | — | Ph | CH₂ | Me | H | C(=O)Me | racemic |
| VI-668 | Me | Me | Me | — | Ph | CH₂ | Me | H | C(=O)Me | (S)- |
| VI-669 | Me | Me | Me | — | Ph | CH₂ | H | Me | C(=O)Me | racemic |
| VI-670 | Me | Me | Me | — | Ph | CH₂ | H | Me | C(=O)Me | (S)- |
| VI-671 | Me | Me | Me | — | Ph | CH₂ | Me | Me | C(=O)Me | racemic |
| VI-672 | Me | Me | Me | — | Ph | CH₂ | Me | Me | C(=O)Me | (S)- |
| VI-673 | Me | Et | Me | — | Ph | CH₂ | H | H | C(=O)Me | racemic |
| VI-674 | Me | Et | Me | — | Ph | CH₂ | H | H | C(=O)Me | (S)- |
| VI-675 | Me | Et | Me | — | Ph | CH₂ | Me | H | C(=O)Me | racemic |
| VI-676 | Me | Et | Me | — | Ph | CH₂ | Me | H | C(=O)Me | (S)- |
| VI-677 | Me | Et | Me | — | Ph | CH₂ | H | Me | C(=O)Me | racemic |
| VI-678 | Me | Et | Me | — | Ph | CH₂ | H | Me | C(=O)Me | (S)- |
| VI-679 | Me | Et | Me | — | Ph | CH₂ | Me | Me | C(=O)Me | racemic |
| VI-680 | Me | Et | Me | — | Ph | CH₂ | Me | Me | C(=O)Me | (S)- |
| VI-681 | Me | Me | Me | — | Ph | CH₂ | H | H | C(=O)Et | racemic |
| VI-682 | Me | Me | Me | — | Ph | CH₂ | H | H | C(=O)Et | (S)- |
| VI-683 | Me | Me | Me | — | Ph | CH₂ | Me | H | C(=O)Et | racemic |
| VI-684 | Me | Me | Me | — | Ph | CH₂ | Me | H | C(=O)Et | (S)- |
| VI-685 | Me | Me | Me | — | Ph | CH₂ | H | Me | C(=O)Et | racemic |
| VI-686 | Me | Me | Me | — | Ph | CH₂ | H | Me | C(=O)Et | (S)- |
| VI-687 | Me | Me | Me | — | Ph | CH₂ | Me | Me | C(=O)Et | racemic |
| VI-688 | Me | Me | Me | — | Ph | CH₂ | Me | Me | C(=O)Et | (S)- |
| VI-689 | Me | Et | Me | — | Ph | CH₂ | H | H | C(=O)Et | racemic |
| VI-690 | Me | Et | Me | — | Ph | CH₂ | H | H | C(=O)Et | (S)- |
| VI-691 | Me | Et | Me | — | Ph | CH₂ | Me | H | C(=O)Et | racemic |
| VI-692 | Me | Et | Me | — | Ph | CH₂ | Me | H | C(=O)Et | (S)- |
| VI-693 | Me | Et | Me | — | Ph | CH₂ | H | Me | C(=O)Et | racemic |
| VI-694 | Me | Et | Me | — | Ph | CH₂ | H | Me | C(=O)Et | (S)- |
| VI-695 | Me | Et | Me | — | Ph | CH₂ | Me | Me | C(=O)Et | racemic |
| VI-696 | Me | Et | Me | — | Ph | CH₂ | Me | Me | C(=O)Et | (S)- |

TABLE 151

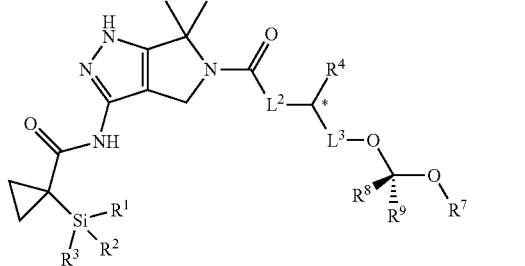

(VIb)

| Compound No. | R¹ | R² | R³ | L² | R⁴ | L³ | R⁸ | R⁹ | R⁷ | Configuration |
|---|---|---|---|---|---|---|---|---|---|---|
| VI-177 | Me | Me | Me | O | Ph | CH₂ | H | H | Me | racemic |
| VI-178 | Me | Me | Me | O | Ph | CH₂ | H | H | Me | (S)- |
| VI-179 | Me | Me | Me | O | Ph | CH₂ | Me | H | Me | racemic |
| VI-180 | Me | Me | Me | O | Ph | CH₂ | Me | H | Me | (S)- |
| VI-181 | Me | Me | Me | O | Ph | CH₂ | H | Me | Me | racemic |
| VI-182 | Me | Me | Me | O | Ph | CH₂ | H | Me | Me | (S)- |
| VI-183 | Me | Me | Me | O | Ph | CH₂ | Me | Me | Me | racemic |
| VI-184 | Me | Me | Me | O | Ph | CH₂ | Me | Me | Me | (S)- |
| VI-185 | Me | Et | Me | O | Ph | CH₂ | H | H | Me | racemic |
| VI-186 | Me | Et | Me | O | Ph | CH₂ | H | H | Me | (S)- |
| VI-187 | Me | Et | Me | O | Ph | CH₂ | Me | H | Me | racemic |
| VI-188 | Me | Et | Me | O | Ph | CH₂ | Me | H | Me | (S)- |
| VI-189 | Me | Et | Me | O | Ph | CH₂ | H | Me | Me | racemic |
| VI-190 | Me | Et | Me | O | Ph | CH₂ | H | Me | Me | (S)- |
| VI-191 | Me | Et | Me | O | Ph | CH₂ | Me | Me | Me | racemic |
| VI-192 | Me | Et | Me | O | Ph | CH₂ | Me | Me | Me | (S)- |
| VI-193 | Me | Me | Me | O | Ph | CH₂ | H | H | Et | racemic |
| VI-194 | Me | Me | Me | O | Ph | CH₂ | H | H | Et | (S)- |
| VI-195 | Me | Me | Me | O | Ph | CH₂ | Me | H | Et | racemic |
| VI-196 | Me | Me | Me | O | Ph | CH₂ | Me | H | Et | (S)- |
| VI-197 | Me | Me | Me | O | Ph | CH₂ | H | Me | Et | racemic |
| VI-198 | Me | Me | Me | O | Ph | CH₂ | H | Me | Et | (S)- |
| VI-199 | Me | Me | Me | O | Ph | CH₂ | Me | Me | Et | racemic |
| VI-200 | Me | Me | Me | O | Ph | CH₂ | Me | Me | Et | (S)- |
| VI-201 | Me | Et | Me | O | Ph | CH₂ | H | H | Et | racemic |
| VI-202 | Me | Et | Me | O | Ph | CH₂ | H | H | Et | (S)- |
| VI-203 | Me | Et | Me | O | Ph | CH₂ | Me | H | Et | racemic |
| VI-204 | Me | Et | Me | O | Ph | CH₂ | Me | H | Et | (S)- |
| VI-205 | Me | Et | Me | O | Ph | CH₂ | H | Me | Et | racemic |
| VI-206 | Me | Et | Me | O | Ph | CH₂ | H | Me | Et | (S)- |
| VI-207 | Me | Et | Me | O | Ph | CH₂ | Me | Me | Et | racemic |
| VI-208 | Me | Et | Me | O | Ph | CH₂ | Me | Me | Et | (S)- |
| VI-209 | Me | Me | Me | NH | Ph | CH₂ | H | H | Me | racemic |
| VI-210 | Me | Me | Me | NH | Ph | CH₂ | H | H | Me | (S)- |
| VI-211 | Me | Me | Me | NH | Ph | CH₂ | Me | H | Me | racemic |
| VI-212 | Me | Me | Me | NH | Ph | CH₂ | Me | H | Me | (S)- |
| VI-213 | Me | Me | Me | NH | Ph | CH₂ | H | Me | Me | racemic |
| VI-214 | Me | Me | Me | NH | Ph | CH₂ | H | Me | Me | (S)- |
| VI-215 | Me | Me | Me | NH | Ph | CH₂ | Me | Me | Me | racemic |
| VI-216 | Me | Me | Me | NH | Ph | CH₂ | Me | Me | Me | (S)- |
| VI-217 | Me | Et | Me | NH | Ph | CH₂ | H | H | Me | racemic |
| VI-218 | Me | Et | Me | NH | Ph | CH₂ | H | H | Me | (S)- |
| VI-219 | Me | Et | Me | NH | Ph | CH₂ | Me | H | Me | racemic |
| VI-220 | Me | Et | Me | NH | Ph | CH₂ | Me | H | Me | (S)- |
| VI-221 | Me | Et | Me | NH | Ph | CH₂ | H | Me | Me | racemic |
| VI-222 | Me | Et | Me | NH | Ph | CH₂ | H | Me | Me | (S)- |
| VI-223 | Me | Et | Me | NH | Ph | CH₂ | Me | Me | Me | racemic |
| VI-224 | Me | Et | Me | NH | Ph | CH₂ | Me | Me | Me | (S)- |
| VI-225 | Me | Me | Me | NH | Ph | CH₂ | H | H | Et | racemic |
| VI-226 | Me | Me | Me | NH | Ph | CH₂ | H | H | Et | (S)- |

TABLE 152

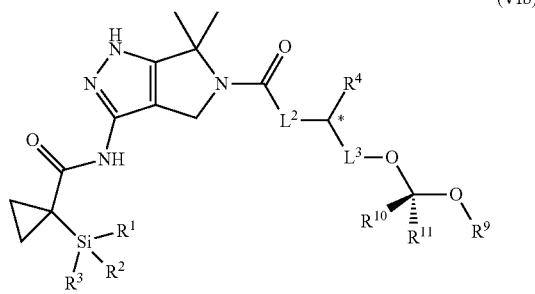

(VIb)

| Compound No. | R¹ | R² | R³ | L² | R⁴ | L³ | R¹⁰ | R¹¹ | R⁹ | Configuration |
|---|---|---|---|---|---|---|---|---|---|---|
| VI-227 | Me | Me | Me | NH | Ph | CH₂ | Me | H | Et | racemic |
| VI-228 | Me | Me | Me | NH | Ph | CH₂ | Me | H | Et | (S)- |
| VI-229 | Me | Me | Me | NH | Ph | CH₂ | H | Me | Et | racemic |
| VI-230 | Me | Me | Me | NH | Ph | CH₂ | H | Me | Et | (S)- |
| VI-231 | Me | Me | Me | NH | Ph | CH₂ | Me | Me | Et | racemic |
| VI-232 | Me | Me | Me | NH | Ph | CH₂ | Me | Me | Et | (S)- |
| VI-233 | Me | Et | Me | NH | Ph | CH₂ | H | H | Et | racemic |
| VI-234 | Me | Et | Me | NH | Ph | CH₂ | H | H | Et | (S)- |
| VI-235 | Me | Et | Me | NH | Ph | CH₂ | Me | H | Et | racemic |
| VI-236 | Me | Et | Me | NH | Ph | CH₂ | Me | H | Et | (S)- |
| VI-237 | Me | Et | Me | NH | Ph | CH₂ | H | Me | Et | racemic |
| VI-238 | Me | Et | Me | NH | Ph | CH₂ | H | Me | Et | (S)- |
| VI-239 | Me | Et | Me | NH | Ph | CH₂ | Me | Me | Et | racemic |
| VI-240 | Me | Et | Me | NH | Ph | CH₂ | Me | Me | Et | (S)- |
| VI-241 | Me | Me | Me | NH | Ph | CH₂ | H | H | C(=O)Me | racemic |
| VI-242 | Me | Me | Me | NH | Ph | CH₂ | H | H | C(=O)Me | (S)- |
| VI-243 | Me | Me | Me | NH | Ph | CH₂ | Me | H | C(=O)Me | racemic |
| VI-244 | Me | Me | Me | NH | Ph | CH₂ | Me | H | C(=O)Me | (S)- |
| VI-245 | Me | Me | Me | NH | Ph | CH₂ | H | Me | C(=O)Me | racemic |
| VI-246 | Me | Me | Me | NH | Ph | CH₂ | H | Me | C(=O)Me | (S)- |
| VI-247 | Me | Me | Me | NH | Ph | CH₂ | Me | Me | C(=O)Me | racemic |
| VI-248 | Me | Me | Me | NH | Ph | CH₂ | Me | Me | C(=O)Me | (S)- |
| VI-249 | Me | Et | Me | NH | Ph | CH₂ | H | H | C(=O)Me | racemic |
| VI-250 | Me | Et | Me | NH | Ph | CH₂ | H | H | C(=O)Me | (S)- |
| VI-251 | Me | Et | Me | NH | Ph | CH₂ | Me | H | C(=O)Me | racemic |
| VI-252 | Me | Et | Me | NH | Ph | CH₂ | Me | H | C(=O)Me | (S)- |
| VI-253 | Me | Et | Me | NH | Ph | CH₂ | H | Me | C(=O)Me | racemic |
| VI-254 | Me | Et | Me | NH | Ph | CH₂ | H | Me | C(=O)Me | (S)- |
| VI-255 | Me | Et | Me | NH | Ph | CH₂ | Me | Me | C(=O)Me | racemic |
| VI-256 | Me | Et | Me | NH | Ph | CH₂ | Me | Me | C(=O)Me | (S)- |
| VI-257 | Me | Me | Me | NH | Ph | CH₂ | H | H | C(=O)Et | racemic |
| VI-258 | Me | Me | Me | NH | Ph | CH₂ | H | H | C(=O)Et | (S)- |
| VI-259 | Me | Me | Me | NH | Ph | CH₂ | Me | H | C(=O)Et | racemic |
| VI-260 | Me | Me | Me | NH | Ph | CH₂ | Me | H | C(=O)Et | (S)- |
| VI-261 | Me | Me | Me | NH | Ph | CH₂ | H | Me | C(=O)Et | racemic |
| VI-262 | Me | Me | Me | NH | Ph | CH₂ | H | Me | C(=O)Et | (S)- |
| VI-263 | Me | Me | Me | NH | Ph | CH₂ | Me | Me | C(=O)Et | racemic |
| VI-264 | Me | Me | Me | NH | Ph | CH₂ | Me | Me | C(=O)Et | (S)- |
| VI-265 | Me | Et | Me | NH | Ph | CH₂ | H | H | C(=O)Et | racemic |
| VI-266 | Me | Et | Me | NH | Ph | CH₂ | H | H | C(=O)Et | (S)- |
| VI-267 | Me | Et | Me | NH | Ph | CH₂ | Me | H | C(=O)Et | racemic |
| VI-268 | Me | Et | Me | NH | Ph | CH₂ | Me | H | C(=O)Et | (S)- |
| VI-269 | Me | Et | Me | NH | Ph | CH₂ | H | Me | C(=O)Et | racemic |
| VI-270 | Me | Et | Me | NH | Ph | CH₂ | H | Me | C(=O)Et | (S)- |
| VI-271 | Me | Et | Me | NH | Ph | CH₂ | Me | Me | C(=O)Et | racemic |
| VI-272 | Me | Et | Me | NH | Ph | CH₂ | Me | Me | C(=O)Et | (S)- |
| VI-273 | Me | Me | Me | NH | Ph | CH₂ | H | H | C(=O)tBu | racemic |
| VI-274 | Me | Me | Me | NH | Ph | CH₂ | H | H | C(=O)tBu | (S)- |
| VI-275 | Me | Me | Me | NH | Ph | CH₂ | Me | H | C(=O)tBu | racemic |
| VI-276 | Me | Me | Me | NH | Ph | CH₂ | Me | H | C(=O)tBu | (S)- |

TABLE 153

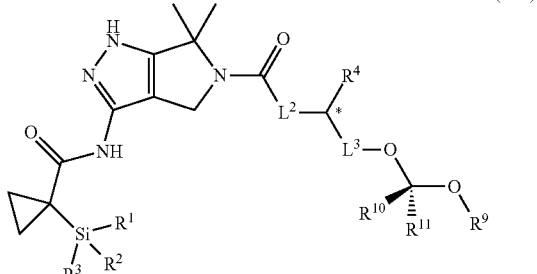

(VIb)

| Compound No. | R¹ | R² | R³ | L² | R⁴ | L³ | R¹⁰ | R¹¹ | R⁹ | Configuration |
|---|---|---|---|---|---|---|---|---|---|---|
| VI-277 | Me | Me | Me | NH | Ph | CH₂ | H | Me | C(=O)tBu | racemic |
| VI-278 | Me | Me | Me | NH | Ph | CH₂ | H | Me | C(=O)tBu | (S)- |
| VI-279 | Me | Me | Me | NH | Ph | CH₂ | Me | Me | C(=O)tBu | racemic |
| VI-280 | Me | Me | Me | NH | Ph | CH₂ | Me | Me | C(=O)tBu | (S)- |
| VI-281 | Me | Et | Me | NH | Ph | CH₂ | H | H | C(=O)tBu | racemic |
| VI-282 | Me | Et | Me | NH | Ph | CH₂ | H | H | C(=O)tBu | (S)- |
| VI-283 | Me | Et | Me | NH | Ph | CH₂ | Me | H | C(=O)tBu | racemic |
| VI-284 | Me | Et | Me | NH | Ph | CH₂ | Me | H | C(=O)tBu | (S)- |
| VI-285 | Me | Et | Me | NH | Ph | CH₂ | H | Me | C(=O)tBu | racemic |
| VI-286 | Me | Et | Me | NH | Ph | CH₂ | H | Me | C(=O)tBu | (S)- |
| VI-287 | Me | Et | Me | NH | Ph | CH₂ | Me | Me | C(=O)tBu | racemic |
| VI-288 | Me | Et | Me | NH | Ph | CH₂ | Me | Me | C(=O)tBu | (S)- |
| VI-289 | Me | Me | Me | NH | Ph | CH₂ | H | H | C(=O)OEt | racemic |
| VI-290 | Me | Me | Me | NH | Ph | CH₂ | H | H | C(=O)OEt | (S)- |
| VI-291 | Me | Me | Me | NH | Ph | CH₂ | Me | H | C(=O)OEt | racemic |
| VI-292 | Me | Me | Me | NH | Ph | CH₂ | Me | H | C(=O)OEt | (S)- |
| VI-293 | Me | Me | Me | NH | Ph | CH₂ | H | Me | C(=O)OEt | racemic |
| VI-294 | Me | Me | Me | NH | Ph | CH₂ | H | Me | C(=O)OEt | (S)- |
| VI-295 | Me | Me | Me | NH | Ph | CH₂ | Me | Me | C(=O)OEt | racemic |
| VI-296 | Me | Me | Me | NH | Ph | CH₂ | Me | Me | C(=O)OEt | (S)- |
| VI-297 | Me | Et | Me | NH | Ph | CH₂ | H | H | C(=O)OEt | racemic |
| VI-298 | Me | Et | Me | NH | Ph | CH₂ | H | H | C(=O)OEt | (S)- |
| VI-299 | Me | Et | Me | NH | Ph | CH₂ | Me | H | C(=O)OEt | racemic |
| VI-300 | Me | Et | Me | NH | Ph | CH₂ | Me | H | C(=O)OEt | (S)- |
| VI-301 | Me | Et | Me | NH | Ph | CH₂ | H | Me | C(=O)OEt | racemic |
| VI-302 | Me | Et | Me | NH | Ph | CH₂ | H | Me | C(=O)OEt | (S)- |
| VI-303 | Me | Et | Me | NH | Ph | CH₂ | Me | Me | C(=O)OEt | racemic |
| VI-304 | Me | Et | Me | NH | Ph | CH₂ | Me | Me | C(=O)OEt | (S)- |
| VI-305 | Me | Me | Me | NH | Ph | CH₂ | H | H | C(=O)OcHex | racemic |
| VI-306 | Me | Me | Me | NH | Ph | CH₂ | H | H | C(=O)OcHex | (S)- |
| VI-307 | Me | Me | Me | NH | Ph | CH₂ | Me | H | C(=O)OcHex | racemic |
| VI-308 | Me | Me | Me | NH | Ph | CH₂ | Me | H | C(=O)OcHex | (S)- |
| VI-309 | Me | Me | Me | NH | Ph | CH₂ | H | Me | C(=O)OcHex | racemic |
| VI-310 | Me | Me | Me | NH | Ph | CH₂ | H | Me | C(=O)OcHex | (S)- |
| VI-311 | Me | Me | Me | NH | Ph | CH₂ | Me | Me | C(=O)OcHex | racemic |
| VI-312 | Me | Me | Me | NH | Ph | CH₂ | Me | Me | C(=O)OcHex | (S)- |
| VI-313 | Me | Et | Me | NH | Ph | CH₂ | H | H | C(=O)OcHex | racemic |
| VI-314 | Me | Et | Me | NH | Ph | CH₂ | H | H | C(=O)OcHex | (S)- |
| VI-315 | Me | Et | Me | NH | Ph | CH₂ | Me | H | C(=O)OcHex | racemic |
| VI-316 | Me | Et | Me | NH | Ph | CH₂ | Me | H | C(=O)OcHex | (S)- |
| VI-317 | Me | Et | Me | NH | Ph | CH₂ | H | Me | C(=O)OcHex | racemic |
| VI-318 | Me | Et | Me | NH | Ph | CH₂ | H | Me | C(=O)OcHex | (S)- |
| VI-319 | Me | Et | Me | NH | Ph | CH₂ | Me | Me | C(=O)OcHex | racemic |
| VI-320 | Me | Et | Me | NH | Ph | CH₂ | Me | Me | C(=O)OcHex | (S)- |

TABLE 153-continued (VIb)

| Compound No. | R¹ | R² | R³ | L² | R⁴ | L³ | R¹⁰ | R¹¹ | R⁹ | Configuration |
|---|---|---|---|---|---|---|---|---|---|---|
| VI-321 | Me | Me | Me | CH₂ | Ph | CH₂ | H | H | Me | racemic |
| VI-322 | Me | Me | Me | CH₂ | Ph | CH₂ | H | H | Me | (S)- |
| VI-323 | Me | Me | Me | CH₂ | Ph | CH₂ | Me | H | Me | racemic |
| VI-324 | Me | Me | Me | CH₂ | Ph | CH₂ | Me | H | Me | (S)- |
| VI-325 | Me | Me | Me | CH₂ | Ph | CH₂ | H | Me | Me | racemic |
| VI-326 | Me | Me | Me | CH₂ | Ph | CH₂ | H | Me | Me | (S)- |

TABLE 154

(VIb)

| Compound No. | R¹ | R² | R³ | L² | R⁴ | L³ | R¹⁰ | R¹¹ | R⁹ | Configuration |
|---|---|---|---|---|---|---|---|---|---|---|
| VI-327 | Me | Me | Me | CH₂ | Ph | CH₂ | Me | Me | Me | racemic |
| VI-328 | Me | Me | Me | CH₂ | Ph | CH₂ | Me | Me | Me | (S)- |
| VI-329 | Me | Et | Me | CH₂ | Ph | CH₂ | H | H | Me | racemic |
| VI-330 | Me | Et | Me | CH₂ | Ph | CH₂ | H | H | Me | (S)- |
| VI-331 | Me | Et | Me | CH₂ | Ph | CH₂ | Me | H | Me | racemic |
| VI-332 | Me | Et | Me | CH₂ | Ph | CH₂ | Me | H | Me | (S)- |
| VI-333 | Me | Et | Me | CH₂ | Ph | CH₂ | H | Me | Me | racemic |
| VI-334 | Me | Et | Me | CH₂ | Ph | CH₂ | H | Me | Me | (S)- |
| VI-335 | Me | Et | Me | CH₂ | Ph | CH₂ | Me | Me | Me | racemic |
| VI-336 | Me | Et | Me | CH₂ | Ph | CH₂ | Me | Me | Me | (S)- |
| VI-337 | Me | Me | Me | CH₂ | Ph | CH₂ | H | H | Et | racemic |
| VI-338 | Me | Me | Me | CH₂ | Ph | CH₂ | H | H | Et | (S)- |
| VI-339 | Me | Me | Me | CH₂ | Ph | CH₂ | Me | H | Et | racemic |
| VI-340 | Me | Me | Me | CH₂ | Ph | CH₂ | Me | H | Et | (S)- |
| VI-341 | Me | Me | Me | CH₂ | Ph | CH₂ | H | Me | Et | racemic |
| VI-342 | Me | Me | Me | CH₂ | Ph | CH₂ | H | Me | Et | (S)- |
| VI-343 | Me | Me | Me | CH₂ | Ph | CH₂ | Me | Me | Et | racemic |
| VI-344 | Me | Me | Me | CH₂ | Ph | CH₂ | Me | Me | Et | (S)- |
| VI-345 | Me | Et | Me | CH₂ | Ph | CH₂ | H | H | Et | racemic |
| VI-346 | Me | Et | Me | CH₂ | Ph | CH₂ | H | H | Et | (S)- |
| VI-347 | Me | Et | Me | CH₂ | Ph | CH₂ | Me | H | Et | racemic |
| VI-348 | Me | Et | Me | CH₂ | Ph | CH₂ | Me | H | Et | (S)- |
| VI-349 | Me | Et | Me | CH₂ | Ph | CH₂ | H | Me | Et | racemic |
| VI-350 | Me | Et | Me | CH₂ | Ph | CH₂ | H | Me | Et | (S)- |
| VI-351 | Me | Et | Me | CH₂ | Ph | CH₂ | Me | Me | Et | racemic |
| VI-352 | Me | Et | Me | CH₂ | Ph | CH₂ | Me | Me | Et | (S)- |

TABLE 155

(VIb)

| Compound No. | R¹ | R² | R³ | L² | R⁴ | L³ | R⁸ | R⁹ | R⁷ | Configuration |
|---|---|---|---|---|---|---|---|---|---|---|
| VI-697 | Me | Me | Me | NH | Ph | (CH₂)₂ | H | H | Me | racemic |
| VI-698 | Me | Me | Me | NH | Ph | (CH₂)₂ | H | H | Me | (R)- |
| VI-699 | Me | Me | Me | NH | Ph | (CH₂)₂ | Me | H | Me | racemic |
| VI-700 | Me | Me | Me | NH | Ph | (CH₂)₂ | Me | H | Me | (R)- |
| VI-701 | Me | Me | Me | NH | Ph | (CH₂)₂ | H | Me | Me | racemic |
| VI-702 | Me | Me | Me | NH | Ph | (CH₂)₂ | H | Me | Me | (R)- |
| VI-703 | Me | Me | Me | NH | Ph | (CH₂)₂ | Me | Me | Me | racemic |
| VI-704 | Me | Me | Me | NH | Ph | (CH₂)₂ | Me | Me | Me | (R)- |
| VI-705 | Me | Et | Me | NH | Ph | (CH₂)₂ | H | H | Me | racemic |
| VI-706 | Me | Et | Me | NH | Ph | (CH₂)₂ | H | H | Me | (R)- |
| VI-707 | Me | Et | Me | NH | Ph | (CH₂)₂ | Me | H | Me | racemic |
| VI-708 | Me | Et | Me | NH | Ph | (CH₂)₂ | Me | H | Me | (R)- |
| VI-709 | Me | Et | Me | NH | Ph | (CH₂)₂ | H | Me | Me | racemic |
| VI-710 | Me | Et | Me | NH | Ph | (CH₂)₂ | H | Me | Me | (R)- |
| VI-711 | Me | Et | Me | NH | Ph | (CH₂)₂ | Me | Me | Me | racemic |
| VI-712 | Me | Et | Me | NH | Ph | (CH₂)₂ | Me | Me | Me | (R)- |
| VI-713 | Me | Me | Me | NH | Ph | (CH₂)₂ | H | H | C(=O)Me | racemic |
| VI-714 | Me | Me | Me | NH | Ph | (CH₂)₂ | H | H | C(=O)Me | (R)- |
| VI-715 | Me | Me | Me | NH | Ph | (CH₂)₂ | Me | H | C(=O)Me | racemic |
| VI-716 | Me | Me | Me | NH | Ph | (CH₂)₂ | Me | H | C(=O)Me | (R)- |
| VI-717 | Me | Me | Me | NH | Ph | (CH₂)₂ | H | Me | C(=O)Me | racemic |
| VI-718 | Me | Me | Me | NH | Ph | (CH₂)₂ | H | Me | C(=O)Me | (R)- |
| VI-719 | Me | Me | Me | NH | Ph | (CH₂)₂ | Me | Me | C(=O)Me | racemic |
| VI-720 | Me | Me | Me | NH | Ph | (CH₂)₂ | Me | Me | C(=O)Me | (R)- |
| VI-721 | Me | Et | Me | NH | Ph | (CH₂)₂ | H | H | C(=O)Me | racemic |
| VI-722 | Me | Et | Me | NH | Ph | (CH₂)₂ | H | H | C(=O)Me | (R)- |
| VI-723 | Me | Et | Me | NH | Ph | (CH₂)₂ | Me | H | C(=O)Me | racemic |
| VI-724 | Me | Et | Me | NH | Ph | (CH₂)₂ | Me | H | C(=O)Me | (R)- |
| VI-725 | Me | Et | Me | NH | Ph | (CH₂)₂ | H | Me | C(=O)Me | racemic |
| VI-726 | Me | Et | Me | NH | Ph | (CH₂)₂ | H | Me | C(=O)Me | (R)- |
| VI-727 | Me | Et | Me | NH | Ph | (CH₂)₂ | Me | Me | C(=O)Me | racemic |
| VI-728 | Me | Et | Me | NH | Ph | (CH₂)₂ | Me | Me | C(=O)Me | (R)- |
| VI-729 | Me | Me | Me | NH | Ph | (CH₂)₂ | H | H | C(=O)Et | racemic |
| VI-730 | Me | Me | Me | NH | Ph | (CH₂)₂ | H | H | C(=O)Et | (R)- |
| VI-731 | Me | Me | Me | NH | Ph | (CH₂)₂ | Me | H | C(=O)Et | racemic |
| VI-732 | Me | Me | Me | NH | Ph | (CH₂)₂ | Me | H | C(=O)Et | (R)- |
| VI-733 | Me | Me | Me | NH | Ph | (CH₂)₂ | H | Me | C(=O)Et | racemic |
| VI-734 | Me | Me | Me | NH | Ph | (CH₂)₂ | H | Me | C(=O)Et | (R)- |
| VI-735 | Me | Me | Me | NH | Ph | (CH₂)₂ | Me | Me | C(=O)Et | racemic |
| VI-736 | Me | Me | Me | NH | Ph | (CH₂)₂ | Me | Me | C(=O)Et | (R)- |
| VI-737 | Me | Et | Me | NH | Ph | (CH₂)₂ | H | H | C(=O)Et | racemic |
| VI-738 | Me | Et | Me | NH | Ph | (CH₂)₂ | H | H | C(=O)Et | (R)- |
| VI-739 | Me | Et | Me | NH | Ph | (CH₂)₂ | Me | H | C(=O)Et | racemic |
| VI-740 | Me | Et | Me | NH | Ph | (CH₂)₂ | Me | H | C(=O)Et | (R)- |
| VI-741 | Me | Et | Me | NH | Ph | (CH₂)₂ | H | Me | C(=O)Et | racemic |
| VI-742 | Me | Et | Me | NH | Ph | (CH₂)₂ | H | Me | C(=O)Et | (R)- |
| VI-743 | Me | Et | Me | NH | Ph | (CH₂)₂ | Me | Me | C(=O)Et | racemic |
| VI-744 | Me | Et | Me | NH | Ph | (CH₂)₂ | Me | Me | C(=O)Et | (R)- |
| VI-745 | Me | Me | Me | — | Ph | — | H | H | Me | racemic |
| VI-746 | Me | Me | Me | — | Ph | — | H | H | Me | (R)- |

TABLE 156

(VIb)

| Compound No. | R¹ | R² | R³ | L² | R⁴ | L³ | R⁸ | R⁹ | R⁷ | Configuration |
|---|---|---|---|---|---|---|---|---|---|---|
| VI-747 | Me | Me | Me | — | Ph | — | Me | H | Me | racemic |
| VI-748 | Me | Me | Me | — | Ph | — | Me | H | Me | (R)- |
| VI-749 | Me | Me | Me | — | Ph | — | H | Me | Me | racemic |
| VI-750 | Me | Me | Me | — | Ph | — | H | Me | Me | (R)- |
| VI-751 | Me | Me | Me | — | Ph | — | Me | Me | Me | racemic |
| VI-752 | Me | Me | Me | — | Ph | — | Me | Me | Me | (R)- |
| VI-753 | Me | Et | Me | — | Ph | — | H | H | Me | racemic |
| VI-754 | Me | Et | Me | — | Ph | — | H | H | Me | (R)- |
| VI-755 | Me | Et | Me | — | Ph | — | Me | H | Me | racemic |
| VI-756 | Me | Et | Me | — | Ph | — | Me | H | Me | (R)- |
| VI-757 | Me | Et | Me | — | Ph | — | H | Me | Me | racemic |
| VI-758 | Me | Et | Me | — | Ph | — | H | Me | Me | (R)- |
| VI-759 | Me | Et | Me | — | Ph | — | Me | Me | Me | racemic |
| VI-760 | Me | Et | Me | — | Ph | — | Me | Me | Me | (R)- |
| VI-761 | Me | Me | Me | — | Ph | — | H | H | C(=O)Me | racemic |
| VI-762 | Me | Me | Me | — | Ph | — | H | H | C(=O)Me | (R)- |
| VI-763 | Me | Me | Me | — | Ph | — | Me | H | C(=O)Me | racemic |
| VI-764 | Me | Me | Me | — | Ph | — | Me | H | C(=O)Me | (R)- |
| VI-765 | Me | Me | Me | — | Ph | — | H | Me | C(=O)Me | racemic |
| VI-766 | Me | Me | Me | — | Ph | — | H | Me | C(=O)Me | (R)- |
| VI-767 | Me | Me | Me | — | Ph | — | Me | Me | C(=O)Me | racemic |
| VI-768 | Me | Me | Me | — | Ph | — | Me | Me | C(=O)Me | (R)- |
| VI-769 | Me | Et | Me | — | Ph | — | H | H | C(=O)Me | racemic |
| VI-770 | Me | Et | Me | — | Ph | — | H | H | C(=O)Me | (R)- |
| VI-771 | Me | Et | Me | — | Ph | — | Me | H | C(=O)Me | racemic |
| VI-772 | Me | Et | Me | — | Ph | — | Me | H | C(=O)Me | (R)- |
| VI-773 | Me | Et | Me | — | Ph | — | H | Me | C(=O)Me | racemic |
| VI-774 | Me | Et | Me | — | Ph | — | H | Me | C(=O)Me | (R)- |
| VI-775 | Me | Et | Me | — | Ph | — | Me | Me | C(=O)Me | racemic |
| VI-776 | Me | Et | Me | — | Ph | — | Me | Me | C(=O)Me | (R)- |
| VI-777 | Me | Me | Me | — | Ph | — | H | H | C(=O)Et | racemic |
| VI-778 | Me | Me | Me | — | Ph | — | H | H | C(=O)Et | (R)- |
| VI-779 | Me | Me | Me | — | Ph | — | Me | H | C(=O)Et | racemic |
| VI-780 | Me | Me | Me | — | Ph | — | Me | H | C(=O)Et | (R)- |
| VI-781 | Me | Me | Me | — | Ph | — | H | Me | C(=O)Et | racemic |
| VI-782 | Me | Me | Me | — | Ph | — | H | Me | C(=O)Et | (R)- |
| VI-783 | Me | Me | Me | — | Ph | — | Me | Me | C(=O)Et | racemic |
| VI-784 | Me | Me | Me | — | Ph | — | Me | Me | C(=O)Et | (R)- |
| VI-785 | Me | Et | Me | — | Ph | — | H | H | C(=O)Et | racemic |
| VI-786 | Me | Et | Me | — | Ph | — | H | H | C(=O)Et | (R)- |
| VI-787 | Me | Et | Me | — | Ph | — | Me | H | C(=O)Et | racemic |
| VI-788 | Me | Et | Me | — | Ph | — | Me | H | C(=O)Et | (R)- |
| VI-789 | Me | Et | Me | — | Ph | — | H | Me | C(=O)Et | racemic |
| VI-790 | Me | Et | Me | — | Ph | — | H | Me | C(=O)Et | (R)- |
| VI-791 | Me | Et | Me | — | Ph | — | Me | Me | C(=O)Et | racemic |
| VI-792 | Me | Et | Me | — | Ph | — | Me | Me | C(=O)Et | (R)- |
| VI-793 | Me | Me | Me | — | Ph | CH₂ | H | H | Me | racemic |
| VI-794 | Me | Me | Me | — | Ph | CH₂ | H | H | Me | (S)- |
| VI-795 | Me | Me | Me | — | Ph | CH₂ | Me | H | Me | racemic |
| VI-796 | Me | Me | Me | — | Ph | CH₂ | Me | H | Me | (S)- |

TABLE 157

(VIb)

| Compound No. | R¹ | R² | R³ | L² | R⁴ | L³ | R⁸ | R⁹ | R⁷ | Configuration |
|---|---|---|---|---|---|---|---|---|---|---|
| VI-797 | Me | Me | Me | — | Ph | CH₂ | H | Me | Me | racemic |
| VI-798 | Me | Me | Me | — | Ph | CH₂ | H | Me | Me | (S)- |
| VI-799 | Me | Me | Me | — | Ph | CH₂ | Me | Me | Me | racemic |
| VI-800 | Me | Me | Me | — | Ph | CH₂ | Me | Me | Me | (S)- |
| VI-801 | Me | Et | Me | — | Ph | CH₂ | H | H | Me | racemic |
| VI-802 | Me | Et | Me | — | Ph | CH₂ | H | H | Me | (S)- |
| VI-803 | Me | Et | Me | — | Ph | CH₂ | Me | H | Me | racemic |
| VI-804 | Me | Et | Me | — | Ph | CH₂ | Me | H | Me | (S)- |
| VI-805 | Me | Et | Me | — | Ph | CH₂ | H | Me | Me | racemic |
| VI-806 | Me | Et | Me | — | Ph | CH₂ | H | Me | Me | (S)- |
| VI-807 | Me | Et | Me | — | Ph | CH₂ | Me | Me | Me | racemic |
| VI-808 | Me | Et | Me | — | Ph | CH₂ | Me | Me | Me | (S)- |
| VI-809 | Me | Me | Me | — | Ph | CH₂ | H | H | C(=O)Me | racemic |
| VI-810 | Me | Me | Me | — | Ph | CH₂ | H | H | C(=O)Me | (S)- |
| VI-811 | Me | Me | Me | — | Ph | CH₂ | Me | H | C(=O)Me | racemic |
| VI-812 | Me | Me | Me | — | Ph | CH₂ | Me | H | C(=O)Me | (S)- |
| VI-813 | Me | Me | Me | — | Ph | CH₂ | H | Me | C(=O)Me | racemic |
| VI-814 | Me | Me | Me | — | Ph | CH₂ | H | Me | C(=O)Me | (S)- |
| VI-815 | Me | Me | Me | — | Ph | CH₂ | Me | Me | C(=O)Me | racemic |
| VI-816 | Me | Me | Me | — | Ph | CH₂ | Me | Me | C(=O)Me | (S)- |
| VI-817 | Me | Et | Me | — | Ph | CH₂ | H | H | C(=O)Me | racemic |
| VI-818 | Me | Et | Me | — | Ph | CH₂ | H | H | C(=O)Me | (S)- |
| VI-819 | Me | Et | Me | — | Ph | CH₂ | Me | H | C(=O)Me | racemic |
| VI-820 | Me | Et | Me | — | Ph | CH₂ | Me | H | C(=O)Me | (S)- |
| VI-821 | Me | Et | Me | — | Ph | CH₂ | H | Me | C(=O)Me | racemic |
| VI-822 | Me | Et | Me | — | Ph | CH₂ | H | Me | C(=O)Me | (S)- |
| VI-823 | Me | Et | Me | — | Ph | CH₂ | Me | Me | C(=O)Me | racemic |
| VI-824 | Me | Et | Me | — | Ph | CH₂ | Me | Me | C(=O)Me | (S)- |
| VI-825 | Me | Me | Me | — | Ph | CH₂ | H | H | C(=O)Et | racemic |
| VI-826 | Me | Me | Me | — | Ph | CH₂ | H | H | C(=O)Et | (S)- |
| VI-827 | Me | Me | Me | — | Ph | CH₂ | Me | H | C(=O)Et | racemic |
| VI-828 | Me | Me | Me | — | Ph | CH₂ | Me | H | C(=O)Et | (S)- |
| VI-829 | Me | Me | Me | — | Ph | CH₂ | H | Me | C(=O)Et | racemic |
| VI-830 | Me | Me | Me | — | Ph | CH₂ | H | Me | C(=O)Et | (S)- |
| VI-831 | Me | Me | Me | — | Ph | CH₂ | Me | Me | C(=O)Et | racemic |
| VI-832 | Me | Me | Me | — | Ph | CH₂ | Me | Me | C(=O)Et | (S)- |
| VI-833 | Me | Et | Me | — | Ph | CH₂ | H | H | C(=O)Et | racemic |
| VI-834 | Me | Et | Me | — | Ph | CH₂ | H | H | C(=O)Et | (S)- |
| VI-835 | Me | Et | Me | — | Ph | CH₂ | Me | H | C(=O)Et | racemic |
| VI-836 | Me | Et | Me | — | Ph | CH₂ | Me | H | C(=O)Et | (S)- |
| VI-837 | Me | Et | Me | — | Ph | CH₂ | H | Me | C(=O)Et | racemic |
| VI-838 | Me | Et | Me | — | Ph | CH₂ | H | Me | C(=O)Et | (S)- |
| VI-839 | Me | Et | Me | — | Ph | CH₂ | Me | Me | C(=O)Et | racemic |
| VI-840 | Me | Et | Me | — | Ph | CH₂ | Me | Me | C(=O)Et | (S)- |

TABLE 158

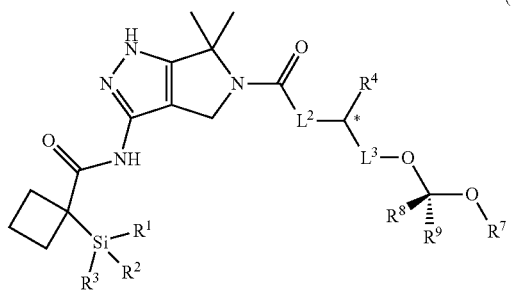

(VIc)

| Compound No. | R¹ | R² | R³ | L² | R⁴ | L³ | R⁸ | R⁹ | R⁷ | Configuration |
|---|---|---|---|---|---|---|---|---|---|---|
| VI-353 | Me | Me | Me | O | Ph | CH₂ | H | H | Me | racemic |
| VI-354 | Me | Me | Me | O | Ph | CH₂ | H | H | Me | (S)- |
| VI-355 | Me | Me | Me | O | Ph | CH₂ | Me | H | Me | racemic |
| VI-356 | Me | Me | Me | O | Ph | CH₂ | Me | H | Me | (S)- |
| VI-357 | Me | Me | Me | O | Ph | CH₂ | H | Me | Me | racemic |
| VI-358 | Me | Me | Me | O | Ph | CH₂ | H | Me | Me | (S)- |
| VI-359 | Me | Me | Me | O | Ph | CH₂ | Me | Me | Me | racemic |
| VI-360 | Me | Me | Me | O | Ph | CH₂ | Me | Me | Me | (S)- |
| VI-361 | Me | Et | Me | O | Ph | CH₂ | H | H | Me | racemic |
| VI-362 | Me | Et | Me | O | Ph | CH₂ | H | H | Me | (S)- |
| VI-363 | Me | Et | Me | O | Ph | CH₂ | Me | H | Me | racemic |
| VI-364 | Me | Et | Me | O | Ph | CH₂ | Me | H | Me | (S)- |
| VI-365 | Me | Et | Me | O | Ph | CH₂ | H | Me | Me | racemic |
| VI-366 | Me | Et | Me | O | Ph | CH₂ | H | Me | Me | (S)- |
| VI-367 | Me | Et | Me | O | Ph | CH₂ | Me | Me | Me | racemic |
| VI-368 | Me | Et | Me | O | Ph | CH₂ | Me | Me | Me | (S)- |
| VI-369 | Me | Me | Me | O | Ph | CH₂ | H | H | Et | racemic |
| VI-370 | Me | Me | Me | O | Ph | CH₂ | H | H | Et | (S)- |
| VI-371 | Me | Me | Me | O | Ph | CH₂ | Me | H | Et | racemic |
| VI-372 | Me | Me | Me | O | Ph | CH₂ | Me | H | Et | (S)- |
| VI-373 | Me | Me | Me | O | Ph | CH₂ | H | Me | Et | racemic |
| VI-374 | Me | Me | Me | O | Ph | CH₂ | H | Me | Et | (S)- |
| VI-375 | Me | Me | Me | O | Ph | CH₂ | Me | Me | Et | racemic |
| VI-376 | Me | Me | Me | O | Ph | CH₂ | Me | Me | Et | (S)- |
| VI-377 | Me | Et | Me | O | Ph | CH₂ | H | H | Et | racemic |
| VI-378 | Me | Et | Me | O | Ph | CH₂ | H | H | Et | (S)- |
| VI-379 | Me | Et | Me | O | Ph | CH₂ | Me | H | Et | racemic |
| VI-380 | Me | Et | Me | O | Ph | CH₂ | Me | H | Et | (S)- |
| VI-381 | Me | Et | Me | O | Ph | CH₂ | H | Me | Et | racemic |
| VI-382 | Me | Et | Me | O | Ph | CH₂ | H | Me | Et | (S)- |
| VI-383 | Me | Et | Me | O | Ph | CH₂ | Me | Me | Et | racemic |
| VI-384 | Me | Et | Me | O | Ph | CH₂ | Me | Me | Et | (S)- |
| VI-385 | Me | Me | Me | NH | Ph | CH₂ | H | H | Me | racemic |
| VI-386 | Me | Me | Me | NH | Ph | CH₂ | H | H | Me | (S)- |
| VI-387 | Me | Me | Me | NH | Ph | CH₂ | Me | H | Me | racemic |
| VI-388 | Me | Me | Me | NH | Ph | CH₂ | Me | H | Me | (S)- |
| VI-389 | Me | Me | Me | NH | Ph | CH₂ | H | Me | Me | racemic |
| VI-390 | Me | Me | Me | NH | Ph | CH₂ | H | Me | Me | (S)- |
| VI-391 | Me | Me | Me | NH | Ph | CH₂ | Me | Me | Me | racemic |
| VI-392 | Me | Me | Me | NH | Ph | CH₂ | Me | Me | Me | (S)- |
| VI-393 | Me | Et | Me | NH | Ph | CH₂ | H | H | Me | racemic |
| VI-394 | Me | Et | Me | NH | Ph | CH₂ | H | H | Me | (S)- |
| VI-395 | Me | Et | Me | NH | Ph | CH₂ | Me | H | Me | racemic |
| VI-396 | Me | Et | Me | NH | Ph | CH₂ | Me | H | Me | (S)- |
| VI-397 | Me | Et | Me | NH | Ph | CH₂ | H | Me | Me | racemic |
| VI-398 | Me | Et | Me | NH | Ph | CH₂ | H | Me | Me | (S)- |
| VI-399 | Me | Et | Me | NH | Ph | CH₂ | Me | Me | Me | racemic |
| VI-400 | Me | Et | Me | NH | Ph | CH₂ | Me | Me | Me | (S)- |
| VI-401 | Me | Me | Me | NH | Ph | CH₂ | H | H | Et | racemic |
| VI-402 | Me | Me | Me | NH | Ph | CH₂ | H | H | Et | (S)- |

TABLE 159

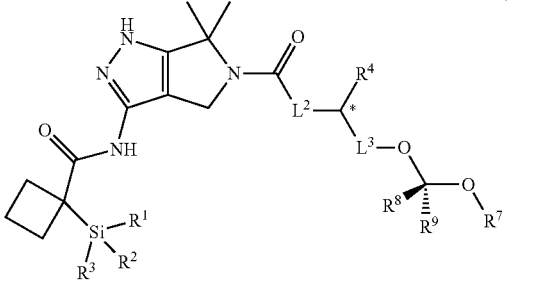

(VIc)

| Compound No. | R¹ | R² | R³ | L² | R⁴ | L³ | R⁸ | R⁹ | R⁷ | Configuration |
|---|---|---|---|---|---|---|---|---|---|---|
| VI-403 | Me | Me | Me | NH | Ph | CH₂ | Me | H | Et | racemic |
| VI-404 | Me | Me | Me | NH | Ph | CH₂ | Me | H | Et | (S)- |
| VI-405 | Me | Me | Me | NH | Ph | CH₂ | H | Me | Et | racemic |
| VI-406 | Me | Me | Me | NH | Ph | CH₂ | H | Me | Et | (S)- |
| VI-407 | Me | Me | Me | NH | Ph | CH₂ | Me | Me | Et | racemic |
| VI-408 | Me | Me | Me | NH | Ph | CH₂ | Me | Me | Et | (S)- |
| VI-409 | Me | Et | Me | NH | Ph | CH₂ | H | H | Et | racemic |
| VI-410 | Me | Et | Me | NH | Ph | CH₂ | H | H | Et | (S)- |
| VI-411 | Me | Et | Me | NH | Ph | CH₂ | Me | H | Et | racemic |
| VI-412 | Me | Et | Me | NH | Ph | CH₂ | Me | H | Et | (S)- |
| VI-413 | Me | Et | Me | NH | Ph | CH₂ | H | Me | Et | racemic |
| VI-414 | Me | Et | Me | NH | Ph | CH₂ | H | Me | Et | (S)- |
| VI-415 | Me | Et | Me | NH | Ph | CH₂ | Me | Me | Et | racemic |
| VI-416 | Me | Et | Me | NH | Ph | CH₂ | Me | Me | Et | (S)- |
| VI-417 | Me | Me | Me | NH | Ph | CH₂ | H | H | (5-Methyl-2-oxo-1,3-dioxol-4-yl)methyl | racemic |
| VI-418 | Me | Me | Me | NH | Ph | CH₂ | H | H | (5-Methyl-2-oxo-1,3-dioxol-4-yl)methyl | (S)- |
| VI-419 | Me | Me | Me | NH | Ph | CH₂ | Me | H | (5-Methyl-2-oxo-1,3-dioxol-4-yl)methyl | racemic |
| VI-420 | Me | Me | Me | NH | Ph | CH₂ | Me | H | (5-Methyl-2-oxo-1,3-dioxol-4-yl)methyl | (S)- |
| VI-421 | Me | Me | Me | NH | Ph | CH₂ | H | Me | (5-Methyl-2-oxo-1,3-dioxol-4-yl)methyl | racemic |
| VI-422 | Me | Me | Me | NH | Ph | CH₂ | H | Me | (5-Methyl-2-oxo-1,3-dioxol-4-yl)methyl | (S)- |
| VI-423 | Me | Me | Me | NH | Ph | CH₂ | Me | Me | (5-Methyl-2-oxo-1,3-dioxol-4-yl)methyl | racemic |
| VI-424 | Me | Me | Me | NH | Ph | CH₂ | Me | Me | (5-Methyl-2-oxo-1,3-dioxol-4-yl)methyl | (S)- |
| VI-425 | Me | Me | Me | NH | Ph | CH₂ | H | H | C(=O)H | racemic |
| VI-426 | Me | Me | Me | NH | Ph | CH₂ | H | H | C(=O)H | (S)- |
| VI-427 | Me | Me | Me | NH | Ph | CH₂ | Me | H | C(=O)H | racemic |
| VI-428 | Me | Me | Me | NH | Ph | CH₂ | Me | H | C(=O)H | (S)- |
| VI-429 | Me | Me | Me | NH | Ph | CH₂ | H | Me | C(=O)H | racemic |
| VI-430 | Me | Me | Me | NH | Ph | CH₂ | H | Me | C(=O)H | (S)- |
| VI-431 | Me | Me | Me | NH | Ph | CH₂ | Me | Me | C(=O)H | racemic |
| VI-432 | Me | Me | Me | NH | Ph | CH₂ | Me | Me | C(=O)H | (S)- |
| VI-433 | Me | Et | Me | NH | Ph | CH₂ | H | H | C(=O)H | racemic |
| VI-434 | Me | Et | Me | NH | Ph | CH₂ | H | H | C(=O)H | (S)- |
| VI-435 | Me | Et | Me | NH | Ph | CH₂ | Me | H | C(=O)H | racemic |
| VI-436 | Me | Et | Me | NH | Ph | CH₂ | Me | H | C(=O)H | (S)- |
| VI-437 | Me | Et | Me | NH | Ph | CH₂ | H | Me | C(=O)H | racemic |
| VI-438 | Me | Et | Me | NH | Ph | CH₂ | H | Me | C(=O)H | (S)- |

TABLE 159-continued

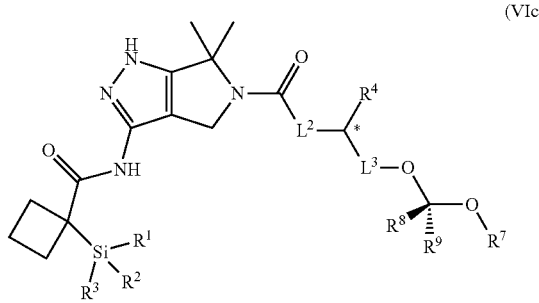

(VIc)

| Compound No. | R¹ | R² | R³ | L² | R⁴ | L³ | R⁸ | R⁹ | R⁷ | Configuration |
|---|---|---|---|---|---|---|---|---|---|---|
| VI-439 | Me | Et | Me | NH | Ph | CH₂ | Me | Me | C(=O)H | racemic |
| VI-440 | Me | Et | Me | NH | Ph | CH₂ | Me | Me | C(=O)H | (S)- |
| VI-441 | Me | Me | Me | NH | Ph | CH₂ | H | H | C(=O)Me | racemic |
| VI-442 | Me | Me | Me | NH | Ph | CH₂ | H | H | C(=O)Me | (S)- |
| VI-443 | Me | Me | Me | NH | Ph | CH₂ | Me | H | C(=O)Me | racemic |
| VI-444 | Me | Me | Me | NH | Ph | CH₂ | Me | H | C(=O)Me | (S)- |
| VI-445 | Me | Me | Me | NH | Ph | CH₂ | H | Me | C(=O)Me | racemic |
| VI-446 | Me | Me | Me | NH | Ph | CH₂ | H | Me | C(=O)Me | (S)- |
| VI-447 | Me | Me | Me | NH | Ph | CH₂ | Me | Me | C(=O)Me | racemic |
| VI-448 | Me | Me | Me | NH | Ph | CH₂ | Me | Me | C(=O)Me | (S)- |
| VI-449 | Me | Et | Me | NH | Ph | CH₂ | H | H | C(=O)Me | racemic |
| VI-450 | Me | Et | Me | NH | Ph | CH₂ | H | H | C(=O)Me | (S)- |
| VI-451 | Me | Et | Me | NH | Ph | CH₂ | Me | H | C(=O)Me | racemic |
| VI-452 | Me | Et | Me | NH | Ph | CH₂ | Me | H | C(=O)Me | (S)- |

TABLE 160

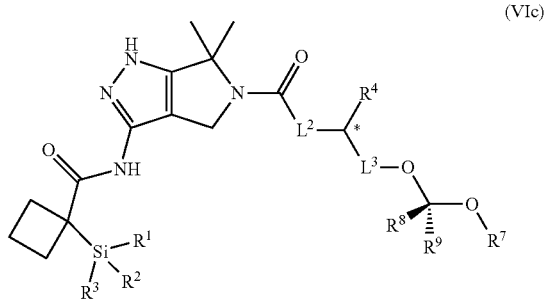

(VIc)

| Compound No. | R¹ | R² | R³ | L² | R⁴ | L³ | R⁸ | R⁹ | R⁷ | Configuration |
|---|---|---|---|---|---|---|---|---|---|---|
| VI-453 | Me | Et | Me | NH | Ph | CH₂ | H | Me | C(=O)Me | racemic |
| VI-454 | Me | Et | Me | NH | Ph | CH₂ | H | Me | C(=O)Me | (S)- |
| VI-455 | Me | Et | Me | NH | Ph | CH₂ | Me | Me | C(=O)Me | racemic |
| VI-456 | Me | Et | Me | NH | Ph | CH₂ | Me | Me | C(=O)Me | (S)- |
| VI-457 | Me | Me | Me | NH | Ph | CH₂ | H | H | C(=O)Et | racemic |
| VI-458 | Me | Me | Me | NH | Ph | CH₂ | H | H | C(=O)Et | (S)- |
| VI-459 | Me | Me | Me | NH | Ph | CH₂ | Me | H | C(=O)Et | racemic |
| VI-460 | Me | Me | Me | NH | Ph | CH₂ | Me | H | C(=O)Et | (S)- |
| VI-461 | Me | Me | Me | NH | Ph | CH₂ | H | Me | C(=O)Et | racemic |
| VI-462 | Me | Me | Me | NH | Ph | CH₂ | H | Me | C(=O)Et | (S)- |
| VI-463 | Me | Me | Me | NH | Ph | CH₂ | Me | Me | C(=O)Et | racemic |
| VI-464 | Me | Me | Me | NH | Ph | CH₂ | Me | Me | C(=O)Et | (S)- |
| VI-465 | Me | Et | Me | NH | Ph | CH₂ | H | H | C(=O)Et | racemic |
| VI-466 | Me | Et | Me | NH | Ph | CH₂ | H | H | C(=O)Et | (S)- |
| VI-467 | Me | Et | Me | NH | Ph | CH₂ | Me | H | C(=O)Et | racemic |
| VI-468 | Me | Et | Me | NH | Ph | CH₂ | Me | H | C(=O)Et | (S)- |
| VI-469 | Me | Et | Me | NH | Ph | CH₂ | H | Me | C(=O)Et | racemic |
| VI-470 | Me | Et | Me | NH | Ph | CH₂ | H | Me | C(=O)Et | (S)- |
| VI-471 | Me | Et | Me | NH | Ph | CH₂ | Me | Me | C(=O)Et | racemic |
| VI-472 | Me | Et | Me | NH | Ph | CH₂ | Me | Me | C(=O)Et | (S)- |
| VI-473 | Me | Me | Me | NH | Ph | CH₂ | H | H | C(=O)tBu | racemic |
| VI-474 | Me | Me | Me | NH | Ph | CH₂ | H | H | C(=O)tBu | (S)- |

TABLE 160-continued

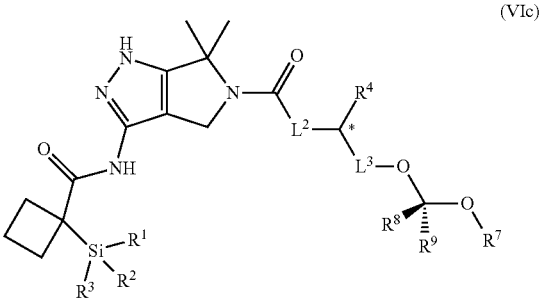

(VIc)

| Compound No. | R¹ | R² | R³ | L² | R⁴ | L³ | R⁸ | R⁹ | R⁷ | Configuration |
|---|---|---|---|---|---|---|---|---|---|---|
| VI-475 | Me | Me | Me | NH | Ph | CH₂ | Me | H | C(=O)tBu | racemic |
| VI-476 | Me | Me | Me | NH | Ph | CH₂ | Me | H | C(=O)tBu | (S)- |
| VI-477 | Me | Me | Me | NH | Ph | CH₂ | H | Me | C(=O)tBu | racemic |
| VI-478 | Me | Me | Me | NH | Ph | CH₂ | H | Me | C(=O)tBu | (S)- |
| VI-479 | Me | Me | Me | NH | Ph | CH₂ | Me | Me | C(=O)tBu | racemic |
| VI-480 | Me | Me | Me | NH | Ph | CH₂ | Me | Me | C(=O)tBu | (S)- |
| VI-481 | Me | Et | Me | NH | Ph | CH₂ | H | H | C(=O)tBu | racemic |
| VI-482 | Me | Et | Me | NH | Ph | CH₂ | H | H | C(=O)tBu | (S)- |
| VI-483 | Me | Et | Me | NH | Ph | CH₂ | Me | H | C(=O)tBu | racemic |
| VI-484 | Me | Et | Me | NH | Ph | CH₂ | Me | H | C(=O)tBu | (S)- |
| VI-485 | Me | Et | Me | NH | Ph | CH₂ | H | Me | C(=O)tBu | racemic |
| VI-486 | Me | Et | Me | NH | Ph | CH₂ | H | Me | C(=O)tBu | (S)- |
| VI-487 | Me | Et | Me | NH | Ph | CH₂ | Me | Me | C(=O)tBu | racemic |
| VI-488 | Me | Et | Me | NH | Ph | CH₂ | Me | Me | C(=O)tBu | (S)- |
| VI-489 | Me | Me | Me | NH | Ph | CH₂ | H | H | C(=O)OEt | racemic |
| VI-490 | Me | Me | Me | NH | Ph | CH₂ | H | H | C(=O)OEt | (S)- |
| VI-491 | Me | Me | Me | NH | Ph | CH₂ | Me | H | C(=O)OEt | racemic |
| VI-492 | Me | Me | Me | NH | Ph | CH₂ | Me | H | C(=O)OEt | (S)- |
| VI-493 | Me | Me | Me | NH | Ph | CH₂ | H | Me | C(=O)OEt | racemic |
| VI-494 | Me | Me | Me | NH | Ph | CH₂ | H | Me | C(=O)OEt | (S)- |
| VI-495 | Me | Me | Me | NH | Ph | CH₂ | Me | Me | C(=O)OEt | racemic |
| VI-496 | Me | Me | Me | NH | Ph | CH₂ | Me | Me | C(=O)OEt | (S)- |
| VI-497 | Me | Et | Me | NH | Ph | CH₂ | H | H | C(=O)OEt | racemic |
| VI-498 | Me | Et | Me | NH | Ph | CH₂ | H | H | C(=O)OEt | (S)- |
| VI-499 | Me | Et | Me | NH | Ph | CH₂ | Me | H | C(=O)OEt | racemic |
| VI-500 | Me | Et | Me | NH | Ph | CH₂ | Me | H | C(=O)OEt | (S)- |
| VI-501 | Me | Et | Me | NH | Ph | CH₂ | H | Me | C(=O)OEt | racemic |
| VI-502 | Me | Et | Me | NH | Ph | CH₂ | H | Me | C(=O)OEt | (S)- |

TABLE 161

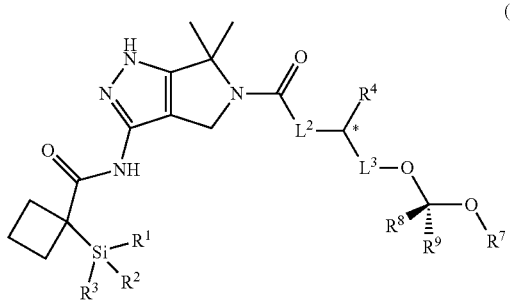

(VIc)

| Compound No. | R¹ | R² | R³ | L² | R⁴ | L³ | R⁸ | R⁹ | R⁷ | Configuration |
|---|---|---|---|---|---|---|---|---|---|---|
| VI-503 | Me | Et | Me | NH | Ph | CH₂ | Me | Me | C(=O)OEt | racemic |
| VI-504 | Me | Et | Me | NH | Ph | CH₂ | Me | Me | C(=O)OEt | (S)- |
| VI-505 | Me | Me | Me | NH | Ph | CH₂ | H | H | C(=O)OcHex | racemic |
| VI-506 | Me | Me | Me | NH | Ph | CH₂ | H | H | C(=O)OcHex | (S)- |
| VI-507 | Me | Me | Me | NH | Ph | CH₂ | Me | H | C(=O)OcHex | racemic |

TABLE 161-continued (VIc)

| Compound No. | R¹ | R² | R³ | L² | R⁴ | L³ | R⁸ | R⁹ | R⁷ | Configuration |
|---|---|---|---|---|---|---|---|---|---|---|
| VI-508 | Me | Me | Me | NH | Ph | CH₂ | Me | H | C(=O)oHex | S)- |
| VI-509 | Me | Me | Me | NH | Ph | CH₂ | H | Me | C(=O)oHex | racemic |
| VI-510 | Me | Me | Me | NH | Ph | CH₂ | H | Me | C(=O)oHex | (S)- |
| VI-511 | Me | Me | Me | NH | Ph | CH₂ | Me | Me | C(=O)oHex | racemic |
| VI-512 | Me | Me | Me | NH | Ph | CH₂ | Me | Me | C(=O)oHex | (S)- |
| VI-513 | Me | Et | Me | NH | Ph | CH₂ | H | H | C(=O)oHex | racemic |
| VI-514 | Me | Et | Me | NH | Ph | CH₂ | H | H | C(=O)oHex | (S)- |
| VI-515 | Me | Et | Me | NH | Ph | CH₂ | Me | H | C(=O)oHex | racemic |
| VI-516 | Me | Et | Me | NH | Ph | CH₂ | Me | H | C(=O)oHex | (S)- |
| VI-517 | Me | Et | Me | NH | Ph | CH₂ | H | Me | C(=O)oHex | racemic |
| VI-518 | Me | Et | Me | NH | Ph | CH₂ | H | Me | C(=O)oHex | (S)- |
| VI-519 | Me | Et | Me | NH | Ph | CH₂ | Me | Me | C(=O)oHex | racemic |
| VI-520 | Me | Et | Me | NH | Ph | CH₂ | Me | Me | C(=O)oHex | (S)- |
| VI-521 | Me | Me | Me | CH₂ | Ph | CH₂ | H | H | Me | racemic |
| VI-522 | Me | Me | Me | CH₂ | Ph | CH₂ | H | H | Me | (S)- |
| VI-523 | Me | Me | Me | CH₂ | Ph | CH₂ | Me | H | Me | racemic |
| VI-524 | Me | Me | Me | CH₂ | Ph | CH₂ | Me | H | Me | (S)- |
| VI-525 | Me | Me | Me | CH₂ | Ph | CH₂ | H | Me | Me | racemic |
| VI-526 | Me | Me | Me | CH₂ | Ph | CH₂ | H | Me | Me | (S)- |
| VI-527 | Me | Me | Me | CH₂ | Ph | CH₂ | Me | Me | Me | racemic |
| VI-528 | Me | Me | Me | CH₂ | Ph | CH₂ | Me | Me | Me | (S)- |
| VI-529 | Me | Et | Me | CH₂ | Ph | CH₂ | H | H | Me | racemic |
| VI-530 | Me | Et | Me | CH₂ | Ph | CH₂ | H | H | Me | (S)- |
| VI-531 | Me | Et | Me | CH₂ | Ph | CH₂ | Me | H | Me | racemic |
| VI-532 | Me | Et | Me | CH₂ | Ph | CH₂ | Me | H | Me | (S)- |
| VI-533 | Me | Et | Me | CH₂ | Ph | CH₂ | H | Me | Me | racemic |
| VI-534 | Me | Et | Me | CH₂ | Ph | CH₂ | H | Me | Me | (S)- |
| VI-535 | Me | Et | Me | CH₂ | Ph | CH₂ | Me | Me | Me | racemic |
| VI-536 | Me | Et | Me | CH₂ | Ph | CH₂ | Me | Me | Me | (S)- |
| VI-537 | Me | Me | Me | CH₂ | Ph | CH₂ | H | H | Et | racemic |
| VI-538 | Me | Me | Me | CH₂ | Ph | CH₂ | H | H | Et | (S)- |
| VI-539 | Me | Me | Me | CH₂ | Ph | CH₂ | Me | H | Et | racemic |
| VI-540 | Me | Me | Me | CH₂ | Ph | CH₂ | Me | H | Et | (S)- |
| VI-541 | Me | Me | Me | CH₂ | Ph | CH₂ | H | Me | Et | racemic |
| VI-542 | Me | Me | Me | CH₂ | Ph | CH₂ | H | Me | Et | (S)- |
| VI-543 | Me | Me | Me | CH₂ | Ph | CH₂ | Me | Me | Et | racemic |
| VI-544 | Me | Me | Me | CH₂ | Ph | CH₂ | Me | Me | Et | (S)- |
| VI-545 | Me | Et | Me | CH₂ | Ph | CH₂ | H | H | Et | racemic |
| VI-546 | Me | Et | Me | CH₂ | Ph | CH₂ | H | H | Et | (S)- |
| VI-547 | Me | Et | Me | CH₂ | Ph | CH₂ | Me | H | Et | racemic |
| VI-548 | Me | Et | Me | CH₂ | Ph | CH₂ | Me | H | Et | (S)- |
| VI-549 | Me | Et | Me | CH₂ | Ph | CH₂ | H | Me | Et | racemic |
| VI-550 | Me | Et | Me | CH₂ | Ph | CH₂ | H | Me | Et | (S)- |
| VI-551 | Me | Et | Me | CH₂ | Ph | CH₂ | Me | Me | Et | racemic |
| VI-552 | Me | Et | Me | CH₂ | Ph | CH₂ | Me | Me | Et | (S)- |

TABLE 162

(VIc)

| Compound No. | R¹ | R² | R³ | L² | R⁴ | L³ | R⁸ | R⁹ | R⁷ | Configuration |
|---|---|---|---|---|---|---|---|---|---|---|
| VI-841 | Me | Me | Me | NH | Ph | (CH₂)₂ | H | H | Me | racemic |
| VI-842 | Me | Me | Me | NH | Ph | (CH₂)₂ | H | H | Me | (R)- |
| VI-843 | Me | Me | Me | NH | Ph | (CH₂)₂ | Me | H | Me | racemic |
| VI-844 | Me | Me | Me | NH | Ph | (CH₂)₂ | Me | H | Me | (R)- |
| VI-845 | Me | Me | Me | NH | Ph | (CH₂)₂ | H | Me | Me | racemic |
| VI-846 | Me | Me | Me | NH | Ph | (CH₂)₂ | H | Me | Me | (R)- |
| VI-847 | Me | Me | Me | NH | Ph | (CH₂)₂ | Me | Me | Me | racemic |
| VI-848 | Me | Me | Me | NH | Ph | (CH₂)₂ | Me | Me | Me | (R)- |
| VI-849 | Me | Et | Me | NH | Ph | (CH₂)₂ | H | H | Me | racemic |
| VI-850 | Me | Et | Me | NH | Ph | (CH₂)₂ | H | H | Me | (R)- |
| VI-851 | Me | Et | Me | NH | Ph | (CH₂)₂ | Me | H | Me | racemic |
| VI-852 | Me | Et | Me | NH | Ph | (CH₂)₂ | Me | H | Me | (R)- |
| VI-853 | Me | Et | Me | NH | Ph | (CH₂)₂ | H | Me | Me | racemic |
| VI-854 | Me | Et | Me | NH | Ph | (CH₂)₂ | H | Me | Me | (R)- |
| VI-855 | Me | Et | Me | NH | Ph | (CH₂)₂ | Me | Me | Me | racemic |
| VI-856 | Me | Et | Me | NH | Ph | (CH₂)₂ | Me | Me | Me | (R)- |
| VI-857 | Me | Me | Me | NH | Ph | (CH₂)₂ | H | H | C(=O)Me | racemic |
| VI-858 | Me | Me | Me | NH | Ph | (CH₂)₂ | H | H | C(=O)Me | (R)- |
| VI-859 | Me | Me | Me | NH | Ph | (CH₂)₂ | Me | H | C(=O)Me | racemic |
| VI-860 | Me | Me | Me | NH | Ph | (CH₂)₂ | Me | H | C(=O)Me | (R)- |
| VI-861 | Me | Me | Me | NH | Ph | (CH₂)₂ | H | Me | C(=O)Me | racemic |
| VI-862 | Me | Me | Me | NH | Ph | (CH₂)₂ | H | Me | C(=O)Me | (R)- |
| VI-863 | Me | Me | Me | NH | Ph | (CH₂)₂ | Me | Me | C(=O)Me | racemic |
| VI-864 | Me | Me | Me | NH | Ph | (CH₂)₂ | Me | Me | C(=O)Me | (R)- |
| VI-865 | Me | Et | Me | NH | Ph | (CH₂)₂ | H | H | C(=O)Me | racemic |
| VI-866 | Me | Et | Me | NH | Ph | (CH₂)₂ | H | H | C(=O)Me | (R)- |
| VI-867 | Me | Et | Me | NH | Ph | (CH₂)₂ | Me | H | C(=O)Me | racemic |
| VI-868 | Me | Et | Me | NH | Ph | (CH₂)₂ | Me | H | C(=O)Me | (R)- |
| VI-869 | Me | Et | Me | NH | Ph | (CH₂)₂ | H | Me | C(=O)Me | racemic |
| VI-870 | Me | Et | Me | NH | Ph | (CH₂)₂ | H | Me | C(=O)Me | (R)- |
| VI-871 | Me | Et | Me | NH | Ph | (CH₂)₂ | Me | Me | C(=O)Me | racemic |
| VI-872 | Me | Et | Me | NH | Ph | (CH₂)₂ | Me | Me | C(=O)Me | (R)- |
| VI-873 | Me | Me | Me | NH | Ph | (CH₂)₂ | H | H | C(=O)Et | racemic |
| VI-874 | Me | Me | Me | NH | Ph | (CH₂)₂ | H | H | C(=O)Et | (R)- |
| VI-875 | Me | Me | Me | NH | Ph | (CH₂)₂ | Me | H | C(=O)Et | racemic |
| VI-876 | Me | Me | Me | NH | Ph | (CH₂)₂ | Me | H | C(=O)Et | (R)- |
| VI-877 | Me | Me | Me | NH | Ph | (CH₂)₂ | H | Me | C(=O)Et | racemic |
| VI-878 | Me | Me | Me | NH | Ph | (CH₂)₂ | H | Me | C(=O)Et | (R)- |
| VI-879 | Me | Me | Me | NH | Ph | (CH₂)₂ | Me | Me | C(=O)Et | racemic |
| VI-880 | Me | Me | Me | NH | Ph | (CH₂)₂ | Me | Me | C(=O)Et | (R)- |
| VI-881 | Me | Et | Me | NH | Ph | (CH₂)₂ | H | H | C(=O)Et | racemic |
| VI-882 | Me | Et | Me | NH | Ph | (CH₂)₂ | H | H | C(=O)Et | (R)- |
| VI-883 | Me | Et | Me | NH | Ph | (CH₂)₂ | Me | H | C(=O)Et | racemic |
| VI-884 | Me | Et | Me | NH | Ph | (CH₂)₂ | Me | H | C(=O)Et | (R)- |
| VI-885 | Me | Et | Me | NH | Ph | (CH₂)₂ | H | Me | C(=O)Et | racemic |
| VI-886 | Me | Et | Me | NH | Ph | (CH₂)₂ | H | Me | C(=O)Et | (R)- |
| VI-887 | Me | Et | Me | NH | Ph | (CH₂)₂ | Me | Me | C(=O)Et | racemic |
| VI-888 | Me | Et | Me | NH | Ph | (CH₂)₂ | Me | Me | C(=O)Et | (R)- |
| VI-889 | Me | Me | Me | — | Ph | — | H | H | Me | racemic |
| VI-890 | Me | Me | Me | — | Ph | — | H | H | Me | (R)- |

TABLE 163

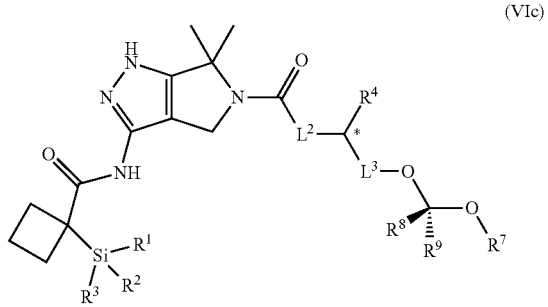

(VIc)

| Compound No. | R¹ | R² | R³ | L² | R⁴ | L³ | R⁸ | R⁹ | R⁷ | Configuration |
|---|---|---|---|---|---|---|---|---|---|---|
| VI-891 | Me | Me | Me | — | Ph | — | Me | H | Me | racemic |
| VI-892 | Me | Me | Me | — | Ph | — | Me | H | Me | (R)- |
| VI-893 | Me | Me | Me | — | Ph | — | H | Me | Me | racemic |
| VI-894 | Me | Me | Me | — | Ph | — | H | Me | Me | (R)- |
| VI-895 | Me | Me | Me | — | Ph | — | Me | Me | Me | racemic |
| VI-896 | Me | Me | Me | — | Ph | — | Me | Me | Me | (R)- |
| VI-897 | Me | Et | Me | — | Ph | — | H | H | Me | racemic |
| VI-898 | Me | Et | Me | — | Ph | — | H | H | Me | (R)- |
| VI-899 | Me | Et | Me | — | Ph | — | Me | H | Me | racemic |
| VI-900 | Me | Et | Me | — | Ph | — | Me | H | Me | (R)- |
| VI-901 | Me | Et | Me | — | Ph | — | H | Me | Me | racemic |
| VI-902 | Me | Et | Me | — | Ph | — | H | Me | Me | (R)- |
| VI-903 | Me | Et | Me | — | Ph | — | Me | Me | Me | racemic |
| VI-904 | Me | Et | Me | — | Ph | — | Me | Me | Me | (R)- |
| VI-905 | Me | Me | Me | — | Ph | — | H | H | C(=O)Me | racemic |
| VI-906 | Me | Me | Me | — | Ph | — | H | H | C(=O)Me | (R)- |
| VI-907 | Me | Me | Me | — | Ph | — | Me | H | C(=O)Me | racemic |
| VI-908 | Me | Me | Me | — | Ph | — | Me | H | C(=O)Me | (R)- |
| VI-909 | Me | Me | Me | — | Ph | — | H | Me | C(=O)Me | racemic |
| VI-910 | Me | Me | Me | — | Ph | — | H | Me | C(=O)Me | (R)- |
| VI-911 | Me | Me | Me | — | Ph | — | Me | Me | C(=O)Me | racemic |
| VI-912 | Me | Me | Me | — | Ph | — | Me | Me | C(=O)Me | (R)- |
| VI-913 | Me | Et | Me | — | Ph | — | H | H | C(=O)Me | racemic |
| VI-914 | Me | Et | Me | — | Ph | — | H | H | C(=O)Me | (R)- |
| VI-915 | Me | Et | Me | — | Ph | — | Me | H | C(=O)Me | racemic |
| VI-916 | Me | Et | Me | — | Ph | — | Me | H | C(=O)Me | (R)- |
| VI-917 | Me | Et | Me | — | Ph | — | H | Me | C(=O)Me | racemic |
| VI-918 | Me | Et | Me | — | Ph | — | H | Me | C(=O)Me | (R)- |
| VI-919 | Me | Et | Me | — | Ph | — | Me | Me | C(=O)Me | racemic |
| VI-920 | Me | Et | Me | — | Ph | — | Me | Me | C(=O)Me | (R)- |
| VI-921 | Me | Me | Me | — | Ph | — | H | H | C(=O)Et | racemic |
| VI-922 | Me | Me | Me | — | Ph | — | H | H | C(=O)Et | (R)- |
| VI-923 | Me | Me | Me | — | Ph | — | Me | H | C(=O)Et | racemic |
| VI-924 | Me | Me | Me | — | Ph | — | Me | H | C(=O)Et | (R)- |
| VI-925 | Me | Me | Me | — | Ph | — | H | Me | C(=O)Et | racemic |
| VI-926 | Me | Me | Me | — | Ph | — | H | Me | C(=O)Et | (R)- |
| VI-927 | Me | Me | Me | — | Ph | — | Me | Me | C(=O)Et | racemic |
| VI-928 | Me | Me | Me | — | Ph | — | Me | Me | C(=O)Et | (R)- |
| VI-929 | Me | Et | Me | — | Ph | — | H | H | C(=O)Et | racemic |
| VI-930 | Me | Et | Me | — | Ph | — | H | H | C(=O)Et | (R)- |
| VI-931 | Me | Et | Me | — | Ph | — | Me | H | C(=O)Et | racemic |
| VI-932 | Me | Et | Me | — | Ph | — | Me | H | C(=O)Et | (R)- |
| VI-933 | Me | Et | Me | — | Ph | — | H | Me | C(=O)Et | racemic |
| VI-934 | Me | Et | Me | — | Ph | — | H | Me | C(=O)Et | (R)- |
| VI-935 | Me | Et | Me | — | Ph | — | Me | Me | C(=O)Et | racemic |
| VI-936 | Me | Et | Me | — | Ph | — | Me | Me | C(=O)Et | (R)- |
| VI-937 | Me | Me | Me | — | Ph | CH₂ | H | H | Me | racemic |
| VI-938 | Me | Me | Me | — | Ph | CH₂ | H | H | Me | (S)- |
| VI-939 | Me | Me | Me | — | Ph | CH₂ | Me | H | Me | racemic |
| VI-940 | Me | Me | Me | — | Ph | CH₂ | Me | H | Me | (S)- |

TABLE 164

(VIc)

| Compound No. | R¹ | R² | R³ | L² | R⁴ | L³ | R⁸ | R⁹ | R⁷ | Configuration |
|---|---|---|---|---|---|---|---|---|---|---|
| VI-941 | Me | Me | Me | — | Ph | CH₂ | H | Me | Me | racemic |
| VI-942 | Me | Me | Me | — | Ph | CH₂ | H | Me | Me | (S)- |
| VI-943 | Me | Me | Me | — | Ph | CH₂ | Me | Me | Me | racemic |
| VI-944 | Me | Me | Me | — | Ph | CH₂ | Me | Me | Me | (S)- |
| VI-945 | Me | Et | Me | — | Ph | CH₂ | H | H | Me | racemic |
| VI-946 | Me | Et | Me | — | Ph | CH₂ | H | H | Me | (S)- |
| VI-947 | Me | Et | Me | — | Ph | CH₂ | Me | H | Me | racemic |
| VI-948 | Me | Et | Me | — | Ph | CH₂ | Me | H | Me | (S)- |
| VI-949 | Me | Et | Me | — | Ph | CH₂ | H | Me | Me | racemic |
| VI-950 | Me | Et | Me | — | Ph | CH₂ | H | Me | Me | (S)- |
| VI-951 | Me | Et | Me | — | Ph | CH₂ | Me | Me | Me | racemic |
| VI-952 | Me | Et | Me | — | Ph | CH₂ | Me | Me | Me | (S)- |
| VI-953 | Me | Me | Me | — | Ph | CH₂ | H | H | C(=O)Me | racemic |
| VI-954 | Me | Me | Me | — | Ph | CH₂ | H | H | C(=O)Me | (S)- |
| VI-955 | Me | Me | Me | — | Ph | CH₂ | Me | H | C(=O)Me | racemic |
| VI-956 | Me | Me | Me | — | Ph | CH₂ | Me | H | C(=O)Me | (S)- |
| VI-957 | Me | Me | Me | — | Ph | CH₂ | H | Me | C(=O)Me | racemic |
| VI-958 | Me | Me | Me | — | Ph | CH₂ | H | Me | C(=O)Me | (S)- |
| VI-959 | Me | Me | Me | — | Ph | CH₂ | Me | Me | C(=O)Me | racemic |
| VI-960 | Me | Me | Me | — | Ph | CH₂ | Me | Me | C(=O)Me | (S)- |
| VI-961 | Me | Et | Me | — | Ph | CH₂ | H | H | C(=O)Me | racemic |
| VI-962 | Me | Et | Me | — | Ph | CH₂ | H | H | C(=O)Me | (S)- |
| VI-963 | Me | Et | Me | — | Ph | CH₂ | Me | H | C(=O)Me | racemic |
| VI-964 | Me | Et | Me | — | Ph | CH₂ | Me | H | C(=O)Me | (S)- |
| VI-965 | Me | Et | Me | — | Ph | CH₂ | H | Me | C(=O)Me | racemic |
| VI-966 | Me | Et | Me | — | Ph | CH₂ | H | Me | C(=O)Me | (S)- |
| VI-967 | Me | Et | Me | — | Ph | CH₂ | Me | Me | C(=O)Me | racemic |
| VI-968 | Me | Et | Me | — | Ph | CH₂ | Me | Me | C(=O)Me | (S)- |
| VI-969 | Me | Me | Me | — | Ph | CH₂ | H | H | C(=O)Et | racemic |
| VI-970 | Me | Me | Me | — | Ph | CH₂ | H | H | C(=O)Et | (S)- |
| VI-971 | Me | Me | Me | — | Ph | CH₂ | Me | H | C(=O)Et | racemic |
| VI-972 | Me | Me | Me | — | Ph | CH₂ | Me | H | C(=O)Et | (S)- |
| VI-973 | Me | Me | Me | — | Ph | CH₂ | H | Me | C(=O)Et | racemic |
| VI-974 | Me | Me | Me | — | Ph | CH₂ | H | Me | C(=O)Et | (S)- |
| VI-975 | Me | Me | Me | — | Ph | CH₂ | Me | Me | C(=O)Et | racemic |
| VI-976 | Me | Me | Me | — | Ph | CH₂ | Me | Me | C(=O)Et | (S)- |
| VI-977 | Me | Et | Me | — | Ph | CH₂ | H | H | C(=O)Et | racemic |
| VI-978 | Me | Et | Me | — | Ph | CH₂ | H | H | C(=O)Et | (S)- |
| VI-979 | Me | Et | Me | — | Ph | CH₂ | Me | H | C(=O)Et | racemic |
| VI-980 | Me | Et | Me | — | Ph | CH₂ | Me | H | C(=O)Et | (S)- |
| VI-981 | Me | Et | Me | — | Ph | CH₂ | H | Me | C(=O)Et | racemic |
| VI-982 | Me | Et | Me | — | Ph | CH₂ | H | Me | C(=O)Et | (S)- |
| VI-983 | Me | Et | Me | — | Ph | CH₂ | Me | Me | C(=O)Et | racemic |
| VI-984 | Me | Et | Me | — | Ph | CH₂ | Me | Me | C(=O)Et | (S)- |

Advantageous Effects of Invention

As for a novel substituted dihydropyrrolopyrazole compound having a particular structure represented by formula (I) of the present invention or a pharmacologically acceptable salt thereof, the compound itself or a metabolite thereof has excellent CDK7 inhibitory activity, high selectivity for a kinase inhibitory effect, and excellent safety. Thus, the compound represented by formula (I) or the pharmacologically acceptable salt thereof is pharmaceutically useful as a therapeutic agent and/or a prophylactic agent for cancers or inflammatory diseases.

DESCRIPTION OF EMBODIMENTS

One embodiment of the present invention will be described below. In the present specification, each "compound represented by formula (I)", etc. is also referred to as "compound (I)", etc. for the sake of convenience. Various substituents defined or illustrated below can be arbitrarily selected and combined.

In the present specification, the "prodrug" means a compound or a salt thereof which forms a compound having a CDK7 inhibitory effect by undergoing metabolic reaction when administered into an animal body.

One embodiment of the present invention is a compound represented by formula (I) or a pharmaceutically acceptable salt thereof.

[Chemical Formula 6]

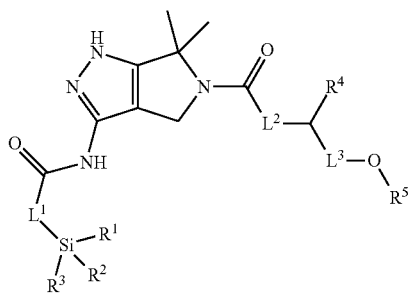

(I)

In formula (I), $L^1$ is an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group, $L^2$ is a single bond, an oxygen atom, an optionally substituted nitrogen atom, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group, $L^3$ is a single bond, an optionally substituted linear or branched $C_{1-6}$ alkylene group, an optionally substituted linear or branched $C_{2-6}$ alkenyl group, an optionally substituted linear or branched $C_{2-6}$ alkynyl group, an optionally substituted $C_{3-6}$ cycloalkylene group, or an optionally substituted $C_{3-6}$ cycloalkenylene group, $R^1$, $R^2$, and $R^3$ each independently are an optionally substituted linear or branched $C_{1-4}$ alkyl group, an optionally substituted linear or branched $C_{2-4}$ alkenyl group, an optionally substituted linear or branched $C_{2-4}$ alkynyl group, an optionally substituted $C_{6-10}$ aryl group, or an optionally substituted heterocyclic group, $R^4$ is a hydrogen atom, an optionally substituted linear or branched $C_{1-6}$ alkyl group, an optionally substituted linear or branched $C_{2-6}$ alkenyl group, an optionally substituted linear or branched $C_{2-6}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group, and $R^5$ is a hydrogen atom, an optionally substituted linear or branched $C_{1-16}$ alkyl group, an optionally substituted linear or branched $C_{2-16}$ alkenyl group, an optionally substituted linear or branched $C_{2-16}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group.

In the present specification, the term "optionally substituted" means that the group concerned may be unsubstituted or may be further substituted by a substituent.

The substituent means a monovalent group, and examples thereof include linear or branched $C_{1-6}$ alkyl groups, $C_{3-6}$ cycloalkyl groups, linear or branched $C_{2-6}$ alkenyl groups, $C_{3-6}$ cycloalkenyl groups, linear or branched $C_{2-6}$ alkynyl groups, $C_{1-6}$ alkoxy groups, halogen atoms, a hydroxy group, a cyano group, an oxo group (=O), an amino group, $C_{1-6}$ alkylamino groups, a nitro group, a carboxy group (—COOH), a carbamoyl group (—CONH$_2$), N-mono-$C_{1-6}$ alkylcarbamoyl groups, N,N-di-$C_{1-6}$ alkylcarbamoyl groups, $C_{1-6}$ alkanoyloxy groups (—OCOR; R is a $C_{1-6}$ alkyl group), $C_{6-10}$ aryl groups, heterocyclic groups, $C_{6-10}$ aryloxy groups, $C_{7-12}$ aralkyl groups, and $C_{7-12}$ aralkyloxy groups. The substituent may be further substituted by a halogen atom, a hydroxy group, an amino group, a cyano group, an oxo group (=O), a linear or branched $C_{1-6}$ alkyl group, or the like. In the case where the substituent is an amino group or a carboxy group, the form may be a salt thereof.

In the case where the group concerned has two or more substituents, two substituents may be bonded to each other to form a cyclic structure. Examples of the case where two substituents are bonded to each other to form a cyclic structure include a cyclopropyl group, a cyclobutyl group, and a methylenedioxy group. Specifically, in the case where a methylenedioxy group is bonded to a benzene ring, the substituent becomes a 1,3-benzodioxole group; in the case where the same carbon atom of a 1,2-ethylene group has two methyl groups which are bonded to each other, the group becomes a group represented by the following formula (M-1) or (M-2); and in the case where the same carbon atom of a 1,2-ethylene group has a methyl group and an ethyl group and 2-position of the ethyl group is bonded to the methyl group, the group becomes a group represented by the following formula (N-1) or (N-2).

[Chemical Formula 7]

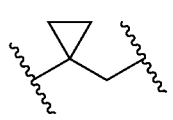

(M-1)

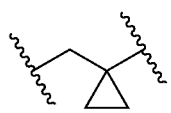

(M-2)

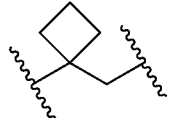

(N-1)

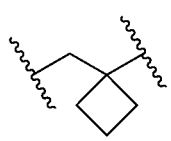

(N-2)

The linear or branched $C_{1-6}$ alkyl group described in the present specification means a linear or branched alkyl group having 1 to 6 carbon atoms. Examples of the linear or branched $C_{1-6}$ alkyl group include $C_{1-6}$ alkyl groups such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-ethylpropyl group, a 1-methylbutyl group, a 2-methylbutyl group, a 1,2-dimethylpropyl group, a hexyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 2,2-dimethylbutyl group, a 3,3-dimethylbutyl group, a 1,2-dimethylbutyl group, a 1,3-dimethylbutyl group, and a 2,3-dimethylbutyl group. The substituent is preferably a methyl group, an ethyl group, a propyl group, an isopropyl group, a butyl group, an isobutyl group, a sec-butyl group, or a tert-butyl group.

Examples of a $C_{1-6}$ alkyl group substituted by a halogen atom include a chloromethyl group, a bromomethyl group, an iodomethyl group, a difluoromethyl group, a dichloromethyl group, a dibromomethyl group, a diiodomethyl group, a trifluoromethyl group, a trichloromethyl group, a 1-fluoroethyl group, a 2-fluoroethyl group, a 2-chloroethyl group, a 2-bromoethyl group, a 2,2-difluoroethyl group, a 2,2,2-trifluoroethyl group, a pentafluoroethyl group, a 2,2-dichloroethyl group, a 2,2,2-trichloroethyl group, a 1-fluoropropyl group, a 2-fluoropropyl group, a 3-fluoropropyl group, a 3,3,3-trifluoropropyl group, a perfluoropropyl group, a 1-fluoromethylethyl group, a 1-difluoromethylethyl group, a 1-trifluoromethylethyl group, a 1-fluoro-1-methylethyl group, a 4-fluorobutyl group, a perfluorobutyl group, a 5-fluoropentyl group, a perfluoropentyl group, a 6-fluorohexyl group, and a perfluorohexyl group.

A $C_{1-6}$ alkyl group substituted by an aryl group may be, for example, a $C_{7-11}$ aralkyl group. The $C_{7-11}$ aralkyl group means an alkyl group having an aryl group and having a total of 7 to 11 carbon atoms, and examples thereof include a benzyl group, a phenylethyl group, and a naphthylmethyl group.

The $C_{3-6}$ cycloalkyl group described in the present specification means a cyclic alkyl group having 3 to 6 carbon atoms. Examples of the $C_{3-6}$ cycloalkyl group include: monocyclic rings such as a cyclopropyl group, a cyclobutyl group, a cyclopentyl group, and a cyclohexyl group; condensed rings such as a bicyclo[3.1.0]hexyl group; and spiro rings such as a spiro[2.3]hexyl group. The substituent is preferably a cyclopropyl group or a cyclobutyl group.

The linear or branched $C_{2-6}$ alkenyl group described in the present specification means a linear or branched alkenyl group having 2 to 6 carbon atoms. Examples of the linear or branched $C_{2-6}$ alkenyl group include alkenyl groups such as a vinyl group, a propen-1-yl group, a propen-2-yl group, a 1-butenyl group, a 2-butenyl group, a 3-butenyl group, a 1-methyl-1-propenyl group, a 2-methyl-1-propenyl group, a 1-pentenyl group, a 2-pentenyl group, a 3-pentenyl group, a 4-pentenyl group, a 5-pentenyl group, a 1-methyl-1-butenyl group, a 2-methyl-1-butenyl group, a 3-methyl-1-butenyl group, a 4-methyl-1-butenyl group, a 1-methyl-2-butenyl group, a 2-methyl-2-butenyl group, a 3-methyl-2-butenyl group, a 4-methyl-2-butenyl group, a 1-methyl-3-butenyl group, a 2-methyl-3-butenyl group, a 3-methyl-3-butenyl group, a 4-methyl-3-butenyl group, a 1,2-dimethyl-1-propenyl group, a 1-hexenyl group, a 2-hexenyl group, a 3-hexenyl group, a 4-hexenyl group, a 5-hexenyl group, a 6-hexenyl group, and structural isomers thereof.

The $C_{3-6}$ cycloalkenyl group described in the present specification means a cycloalkenyl group having 3 to 6 carbon atoms. Examples of the $C_{3-6}$ cycloalkenyl group include a cyclopropenyl group, a cyclobutenyl group, a cyclopentenyl group, and a cyclohexenyl group.

The $C_{2-6}$ alkynyl group described in the present specification means an alkynyl group having 2 to 6 carbon atoms. Examples of the $C_{2-6}$ alkynyl group include an ethynyl group, a propargyl group, a butynyl group, a pentynyl group, and a hexynyl group.

The $C_{1-6}$ alkoxy group described in the present specification means a group consisting of an oxy group (—O—) and a linear or branched $C_{1-6}$ alkyl group or a $C_{3-6}$ cycloalkyl group bonded to the oxy group. Examples of the $C_{1-6}$ alkoxy group include a methoxy group, an ethoxy group, a propyloxy group, an isopropyloxy group, a cyclopropyloxy group, a butoxy group, a cyclobutyloxy group, a pentyloxy group, a cyclopentyloxy group, a hexyloxy group, and a cyclohexyloxy group.

The $C_{1-6}$ alkylamino group described in the present specification means an amino group substituted by one or two independently selected aforementioned linear or branched $C_{1-6}$ alkyl groups or $C_{3-6}$ cycloalkyl groups. Examples of the $C_{1-6}$ alkylamino group include a methylamino group, an ethylamino group, a propylamino group, an isopropylamino group, a cyclopropylamino group, a butoxy group, a cyclobutylamino group, a pentylamino group, a cyclopentylamino group, a hexylamino group, a cyclohexylamino group, a dimethylamino group, a diethylamino group, an ethylmethylamino group, an isopropylmethylamino group, and a cyclopropylmethylamino group.

The halogen atom described in the present specification means a fluorine atom, a chlorine atom, a bromine atom, or an iodine atom.

The $C_{6-10}$ aryl group described in the present specification means an aryl group having 6 to 10 carbon atoms. Examples of the $C_{6-10}$ aryl group include a phenyl group and a naphthyl group.

The heterocyclic group described in the present specification means a cyclic group having at least one nitrogen atom, oxygen atom, or sulfur atom and may be an aromatic heterocyclic group or may be a nonaromatic heterocyclic group. Examples of the aromatic heterocyclic group include a pyridine group, a pyrimidine group, a pyridazine group, a pyrazine group, a triazine group, a pyrrole group, an imidazole group, a pyrazole group, an indole group, an indazole group, a furan group, a benzofuran group, a thiophene group, a benzothiophene group, a thiazole group, an isothiazole group, an oxazole group, an isoxazole group, and an oxadiazole group. Examples of the nonaromatic heterocyclic group include a pyrrolidinyl group, a piperidinyl group, a piperazinyl group, a morpholinyl group, and a thiomorpholinyl group.

The $C_{6-10}$ aryloxy group described in the present specification means a group consisting of an oxy group (—O—) and the aforementioned $C_{6-10}$ aryl group bonded to the oxy group. Examples of the $C_{6-10}$ aryloxy group include a phenyloxy group, a 1-naphthyloxy group, and a 2-naphthyloxy group.

The $C_{7-12}$ aralkyl group described in the present specification means the aforementioned $C_{1-6}$ alkyl group substituted by the aforementioned $C_{6-10}$ aryl group. Examples of the $C_{7-12}$ aralkyl group include a benzyl group, a phenylethyl group, a naphthylmethyl group, and a naphthylethyl group.

The $C_{7-12}$ aralkyloxy group described in the present specification means a group consisting of an oxy group (—O—) and the aforementioned $C_{7-12}$ aralkyl group bonded to the oxy group. Examples of the $C_{7-12}$ aralkyloxy group include a benzyloxy group, a phenylethyloxy group, a naphthylmethyloxy group, and a naphthylethyloxy group.

The linear or branched $C_{1-6}$ alkylene group as $L^1$, $L^2$, or $L^3$ means a divalent group prepared by further removing one hydrogen atom from the aforementioned $C_{1-6}$ alkyl group. Examples of the $C_{1-6}$ alkylene group include a methylene group, a 1,1-ethylene group, a 1,2-ethylene group, a 1,1-propylene group, a 1,2-propylene group, a 2,2-propylene group, and a 1,3-propylene group.

The linear or branched $C_{2-6}$ alkenylene group as $L^1$, $L^2$, or $L^3$ means a divalent group prepared by further removing one hydrogen atom from the aforementioned $C_{2-6}$ alkenyl group. Examples of the $C_{2-6}$ alkenylene group include a vinylene group and a propenylene group.

The linear or branched $C_{2-6}$ alkynylene group as $L^1$, $L^2$, or $L^3$ means a divalent group prepared by further removing one hydrogen atom from the aforementioned $C_{2-6}$ alkynyl group. Examples of the $C_{2-6}$ alkynylene group include an ethynylene group and a propynylene group.

The $C_{3-6}$ cycloalkylene group as $L^1$, $L^2$, or $L^3$ means a divalent group prepared by further removing one hydrogen atom from the aforementioned $C_{3-6}$ cycloalkyl group, and examples thereof include a 1,1-cyclopropylene group, a 1,2-cyclopropylene group, a 1,1-cyclobutylene group, a 1,2-cyclobutylene group, a 1,3-cyclobutylene group, a 1,4-cyclobutylene group, a 1,1-cyclopentylene group, a 1,2-cyclopentylene group, a 1,3-cyclopentylene group, a 1,1-cyclohexylene group, a 1,2-cyclohexylene group, a 1,3-cyclohexylene group, a 1,4-cyclohexylene group, a 5,5-spiro[2.3]hexylene group, and a 6,6-bicyclo[3.1.0]hexylene group.

The $C_{3-6}$ cycloalkenylene group as $L^1$, $L^2$, or $L^3$ means a divalent group prepared by further removing one hydrogen atom from the aforementioned $C_{3-6}$ cycloalkenyl group, and examples thereof include a 1,2-cyclopropenylene group, a 1,2-cyclobutenylene group, a 1,3-cyclobutenylene group, a 3,3-cyclobutenylene group, a 1,2-cyclopentenylene group, a 1,2-cyclopentenylene group, a 1,3-cyclopentenylene group, a 3,3-cyclopentenylene group, a 4,4-cyclopentenylene group, a 1,2-cyclohexenylene group, a 1,3-cyclohexenylene group, a 1,3-cyclohexenylene group, a 1,3-cyclohexenylene group, a 3,3-cyclohexenylene group, and a 4,4-cyclohexenylene group.

The optionally substituted nitrogen atom as $L^2$ may be an unsubstituted nitrogen atom (divalent amino group represented by —NH—) or may be a divalent amino group having the aforementioned substituent bonded to the nitrogen atom.

The linear or branched $C_{1-4}$ alkyl group as $R^1$, $R^2$, or $R^3$ is a linear or branched alkyl group having 1 to 4 carbon atoms and corresponds to one having 1 to 4 carbon atoms among the $C_{1-6}$ alkyl groups described above.

The linear or branched $C_{2-4}$ alkenyl group as $R^1$, $R^2$, or $R^3$ is a linear or branched alkenyl group having 2 to 4 carbon atoms and corresponds to one having 2 to 4 carbon atoms among the $C_{2-6}$ alkenyl groups described above.

The linear or branched $C_{2-4}$ alkynyl group as $R^1$, $R^2$, or $R^3$ is a linear or branched alkynyl group having 2 to 4 carbon atoms and corresponds to one having 2 to 4 carbon atoms among the $C_{2-6}$ alkynyl groups described above.

The linear or branched $C_{1-6}$ alkyl group, the linear or branched $C_{2-6}$ alkenyl group, the linear or branched $C_{2-6}$ alkynyl group, the $C_{6-10}$ aryl group, and the heterocyclic group as $R^4$ are defined as in the substituents described above.

The linear or branched $C_{1-16}$ alkyl group as $R^5$ means an alkyl group having 1 to 16 carbon atoms. Examples of the linear or branched $C_{1-16}$ alkyl group include $C_{1-16}$ alkyl groups such as a methyl group, an ethyl group, a propyl group, a butyl group, an isobutyl group, a pentyl group, an isopentyl group, a neopentyl group, a hexyl group, a heptyl group, an octyl group, a nonyl group, a decyl group, an undecyl group, a dodecyl group, a tridecyl group, a tetradecyl group, a pentadecyl group, and a hexadecyl group.

The linear or branched $C_{2-16}$ alkenyl group as $R^5$ means a monovalent linear or branched alkenyl group having 2 to 16 carbon atoms, and the linear or branched $C_{2-16}$ alkynyl group means a monovalent linear or branched alkynyl group having 2 to 16 carbon atoms. The $C_{3-6}$ cycloalkyl group, the $C_{3-6}$ cycloalkenyl group, the $C_{6-10}$ aryl group, and the heterocyclic group as $R^5$ are defined as in the substituents described above and $L^1$, etc.

The compound according to the present embodiment may be a compound represented by any chemical formula of formula (II), formula (III), or formula (IV).

[Chemical Formula 8]

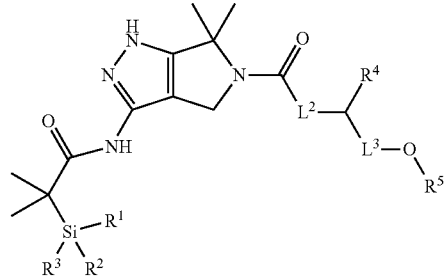

(II)

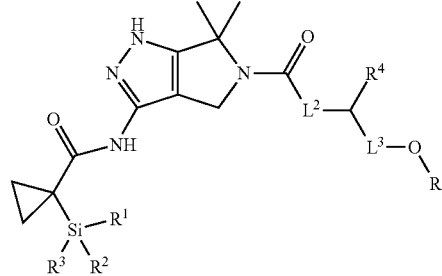

(III)

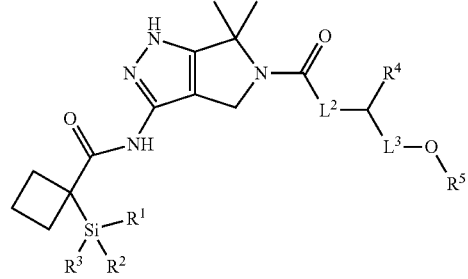

(IV)

In formula (II), formula (III), and formula (IV), $L^2$, $L^3$, $R^1$, $R^2$, $R^3$, $R^4$, and $R^5$ are defined as in formula (I).

In the formulas (I) to (IV), $L^2$ may be an oxygen atom, an unsubstituted nitrogen atom, or a methylene group. $L^3$ may be a single bond, or an optionally substituted linear or branched $C_{1-6}$ alkylene group or $C_{2-6}$ alkynylene group, or may be a linear or branched $C_{1-6}$ alkylene group, $C_{2-6}$ alkenylene group, or $C_{2-6}$ alkynylene group substituted by an oxo group which forms an ester group together with the oxygen atom bonded to $R^5$.

In the formulas (I) to (IV), $R^1$, $R^2$, and $R^3$ may each independently be an optionally substituted linear or branched $C_{1-4}$ alkyl group. $R^4$ may be a hydrogen atom, an optionally substituted linear or branched $C_{1-6}$ alkyl group, an optionally substituted $C_{3-6}$ cycloalkyl group, an optionally substituted $C_{6-10}$ aryl group, or an optionally substituted heterocyclic group. $R^5$ may be a hydrogen atom, an optionally substituted linear or branched $C_{1-16}$ alkyl group, an optionally substituted $C_{3-6}$ cycloalkyl group, an optionally substituted $C_{6-10}$ aryl group, or an optionally substituted heterocyclic group.

In the formulas (I) to (IV), preferably, $L^2$ is a single bond or an unsubstituted nitrogen atom, $L^3$ is a single bond or an optionally substituted linear or branched $C_{1-6}$ alkylene group, $R^1$, $R^2$, and $R^3$ are each independently an optionally substituted linear or branched $C_{1-4}$ alkyl group, $R^4$ is an optionally substituted linear or branched $C_{1-6}$ alkyl group, an optionally substituted $C_{6-10}$ aryl group, or an optionally substituted heterocyclic group, and $R^5$ is a hydrogen atom, an optionally substituted linear or branched $C_{1-16}$ alkyl group, or an optionally substituted $C_{3-6}$ cycloalkyl group.

In the formulas (I) to (IV), more preferably, $L^2$ is a single bond or an unsubstituted nitrogen atom, $L^3$ is a single bond or an optionally substituted linear or branched $C_{1-6}$ alkylene group, $R^1$, $R^2$, and $R^3$ are each independently a linear or branched $C_{1-4}$ alkyl group, $R^4$ is an optionally substituted linear or branched $C_{1-6}$ alkyl group, an optionally substituted $C_{6-10}$ aryl group, or an optionally substituted heterocyclic group, and $R^5$ is a hydrogen atom, a linear or branched $C_{1-16}$ alkyl group, a linear or branched $C_{1-16}$ alkyl group substituted by a halogen atom, an oxo group, or a linear or branched $C_{1-6}$ alkyl group, or a $C_{3-6}$ cycloalkyl group optionally substituted by a halogen atom.

In the formulas (I) to (IV), particularly preferably, $L^2$ is a single bond or an unsubstituted nitrogen atom, $L^3$ is a single bond or a group represented by the following formula (O-1), (O-2), (O-3), or (O-4), $R^1$, $R^2$, and $R^3$ are each independently a linear or branched $C_{1-4}$ alkyl group, $R^4$ is an optionally substituted phenyl group or thienyl group, and $R^5$ is a hydrogen atom, a linear or branched $C_{1-16}$ alkyl group, a linear or branched $C_{1-16}$ alkyl group substituted by a halogen atom, or a $C_{3-6}$ cycloalkyl group. In the present specification, the chemical formula represented by formula (O-1) is also referred to as "C(Me)$_2$CH$_2$", the chemical formula represented by formula (O-2) is also referred to as "CH$_2$C(Me)$_2$", the chemical formula represented by formula (M-2) is also referred to as "CH$_2$-1,1-cyclopropylene", and the chemical formula represented by formula (N-1) is also referred to as "1,1-cyclobutylene-CH$_2$".

[Chemical Formula 9]

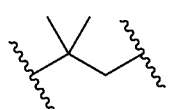

(O-1)

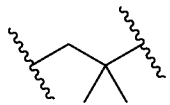

(O-2)

-continued

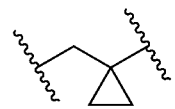

(M-2)

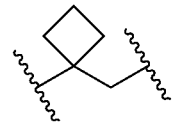

(N-1)

Among compounds (I) according to the present embodiment or pharmacologically acceptable salts thereof, a compound as represented by formula (V) wherein $R^5$ is substituted by an oxo group, and the oxo group and the oxygen atom bonded to $R^5$ form an ester bond, or a compound as represented by formula (VI) wherein $R^5$ is an alkylene group substituted by a substituent containing an oxygen atom, and an acetal group containing the oxygen atom and the oxygen atom bonded to $R^5$ is formed can be a compound that acts as a prodrug. The compound (V) or the compound (VI) tends to have better oral absorbability and skin penetration and can form compound (I) (wherein $R^5$ is a hydrogen atom) by metabolism.

[Chemical Formula 10]

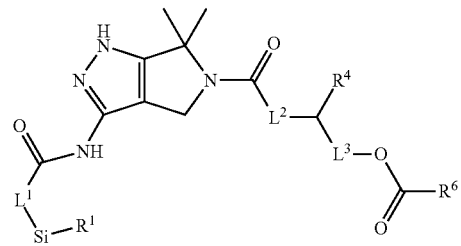

(V)

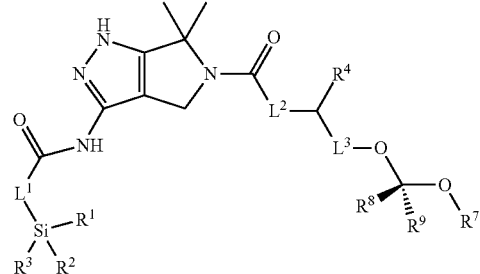

(VI)

In formula (V) and formula (VI), $R^1$, $R^2$, $R^3$, $R^4$, $L^1$, $L^2$, and $L^3$ are defined as in formula (I). $R^6$ is a hydrogen atom, an optionally substituted linear or branched $C_{1-15}$ alkyl group, an optionally substituted linear or branched $C_{2-15}$ alkenyl group, an optionally substituted linear or branched $C_{2-15}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group, and $R^8$ and $R^9$ are each independently a hydrogen atom or a $C_{1-4}$ alkyl group. $R^7$ is a linear or branched $C_{1-15}$ alkyl group optionally having a substituent, an optionally substituted linear or branched $C_{2-15}$ alkenyl group, an optionally substituted linear or branched $C_{2-15}$ alkynyl group, an optionally substituted $C_{3-6}$ cycloalkyl group, or an optionally substituted $C_{3-6}$ cycloalkenyl group. The linear or branched $C_{1-15}$ alkyl group, the linear or branched $C_{2-15}$ alkenyl group, the linear or branched $C_{2-15}$ alkynyl group, the $C_{3-6}$ cycloalkyl group, the $C_{3-6}$ cycloalkenyl group, the $C_{6-10}$ aryl group, and the heterocyclic group as $R^6$ or $R^7$, and substituents added to these are defined as in the groups in the formulas (I) to (IV).

$R^6$ may be an optionally substituted linear or branched $C_{1-15}$ alkyl group, an optionally substituted $C_{6-10}$ aryl group, or an optionally substituted $C_{1-15}$ alkoxy group. $R^7$ may be an optionally substituted linear or branched $C_{1-16}$ alkyl group.

In formula (V), preferably, $L^1$ is a cyclopropylene group or a cyclobutylene group, $L^2$ is a single bond or an unsubstituted nitrogen atom, $L^3$ is a single bond or an optionally substituted linear or branched $C_{1-6}$ alkylene group, $R^1$, $R^2$, and $R^3$ are each independently an optionally substituted linear or branched $C_{1-4}$ alkyl group, $R^4$ is an optionally substituted linear or branched $C_{1-6}$ alkyl group, an optionally substituted $C_{6-10}$ aryl group, or an optionally substituted heterocyclic group, and $R^6$ is an optionally substituted linear or branched $C_{1-15}$ alkyl group.

In formula (V), more preferably, $L^1$ is a cyclobutylene group, $L^2$ is a single bond or an unsubstituted nitrogen atom, $L^3$ is a single bond or an optionally substituted linear or branched $C_{1-6}$ alkylene group, $R^1$, $R^2$, and $R^3$ are each independently a linear or branched $C_{1-4}$ alkyl group, $R^4$ is an optionally substituted linear or branched $C_{1-6}$ alkyl group, an optionally substituted $C_{6-10}$ aryl group, or an optionally substituted heterocyclic group, and $R^6$ is an optionally substituted linear or branched $C_{1-15}$ alkyl group.

The compound according to the present embodiment or a pharmacologically acceptable salt thereof is specifically a compound selected from a compound group shown below or a pharmacologically acceptable salt thereof.

(S)—N-(2-hydroxy-1-phenylethyl)-6,6-dimethyl-3-[1-(trimethylsilyl)cyclobutanecarboxamido]-4,6-dihydropyrrolo[3,4-c]pyrazole-5(1H)-carboxamide,
(S)—N-(2-hydroxy-1-phenylethyl)-6,6-dimethyl-3-[1-(trimethylsilyl)cyclopropanecarboxamido]-4,6-dihydropyrrolo[3,4-c]pyrazole-5(1H)-carboxamide,
(S)—N-(2-hydroxy-1-phenylethyl)-6,6-dimethyl-3-[2-methyl-2-(trimethylsilyl)propaneamido]-4,6-dihydropyrrolo[3,4-c]pyrazole-5(1H)-carboxamide,
(S)-3-[1-(ethyldimethylsilyl)cyclobutanecarboxamido]-N-(2-hydroxy-1-phenylethyl)-6,6-dimethyl-4,6-dihydropyrrolo[3,4-c]pyrazole-5(1H)-carboxamide,
(S)-3-[2-(ethyldimethylsilyl)-2-methylpropaneamido]-N-(2-hydroxy-1-phenylethyl)-6,6-dimethyl-4,6-dihydropyrrolo[3,4-c]pyrazole-5(1H)-carboxamide,
(S)—N-(2-hydroxy-1-phenylethyl)-N,6,6-trimethyl-3-[1-(trimethylsilyl)cyclobutanecarboxamido]-4,6-dihydropyrrolo[3,4-c]pyrazole-5(1H)-carboxamide,
(S)-2-[(2-methoxypropan-2-yl)oxy]-1-phenylethyl6,6-dimethyl-3-[1-(trimethylsilyl)cyclobutanecarboxamido]-4,6-dihydropyrrolo[3,4-c]pyrazole-5(1H)-carboxylate,
(S)-2-hydroxy-1-phenylethyl 6,6-dimethyl-3-[1-(trimethylsilyl)cyclobutanecarboxamido]-4,6-dihydropyrrolo[3,4-c]pyrazole-5(1H)-carboxylate,
2-Methoxy-1-phenylethyl 6,6-dimethyl-3-[1-(trimethylsilyl)cyclopropanecarboxamido]-4,6-dihydropyrrolo[3,4-c]pyrazole-5(1H)-carboxylate,
N-[5-(4-hydroxy-3-phenylbutanoyl)-6,6-dimethyl-1,4,5,6-tetrahydropyrrolo[3,4-c]pyrazol-3-yl]-1-(trimethylsilyl)cyclobutanecarboxamide,
N-[5-(3-hydroxy-3-phenylpropanoyl)-6,6-dimethyl-1,4,5,6-tetrahydropyrrolo[3,4-c]pyrazol-3-yl]-1-(trimethylsilyl)cyclobutanecarboxamide,
(R)—N-(3-hydroxy-1-phenylpropyl)-6,6-dimethyl-3-[1-(trimethylsilyl)cyclobutanecarboxamido]-4,6-dihydropyrrolo[3,4-c]pyrazole-5(1H)-carboxamide,
(R)—N-(3-hydroxy-1-phenylpropyl)-6,6-dimethyl-3-[1-(trimethylsilyl)cyclopropanecarboxamido]-4,6-dihydropyrrolo[3,4-c]pyrazole-5(1H)-carboxamide,
(R)—N-(4-hydroxy-1-phenylbutyl)-6,6-dimethyl-3-[1-(trimethylsilyl)cyclobutanecarboxamido]-4,6-dihydropyrrolo[3,4-c]pyrazole-5(1H)-carboxamide,
(R)—N-(5-hydroxy-1-phenylpentyl)-6,6-dimethyl-3-[1-(trimethylsilyl)cyclobutanecarboxamido]-4,6-dihydropyrrolo[3,4-c]pyrazole-5(1H)-carboxamide,
(S)—N-(2-hydroxy-2-methyl-1-phenylpropyl)-6,6-dimethyl-3-[1-(trimethylsilyl)cyclobutanecarboxamido]-4,6-dihydropyrrolo[3,4-c]pyrazole-5(1H)-carboxamide,
(S)—N-(2-hydroxy-2-methyl-1-phenylpropyl)-6,6-dimethyl-3-[1-(trimethylsilyl)cyclopropanecarboxamido]-4,6-dihydropyrrolo[3,4-c]pyrazole-5(1H)-carboxamide,
N-(3-hydroxy-2,2-dimethyl-1-phenylpropyl)-6,6-dimethyl-3-[1-(trimethylsilyl)cyclobutanecarboxamido]-4,6-dihydropyrrolo[3,4-c]pyrazole-5(1H)-carboxamide,
(R)—N-(3-hydroxy-3-methyl-1-phenylbutyl)-6,6-dimethyl-3-[1-(trimethylsilyl)cyclobutanecarboxamido]-4,6-dihydropyrrolo[3,4-c]pyrazole-5(1H)-carboxamide,
(S)—N-(2-methoxy-1-phenylethyl)-6,6-dimethyl-3-[1-(trimethylsilyl)cyclobutanecarboxamido]-4,6-dihydropyrrolo[3,4-c]pyrazole-5(1H)-carboxamide,
(S)—N-[2-(difluoromethoxy)-1-phenylethyl]-6,6-dimethyl-3-[1-(trimethylsilyl)cyclobutanecarboxamido]-4,6-dihydropyrrolo[3,4-c]pyrazole-5(1H)-carboxamide,
(S)—N-(2-ethoxy-1-phenylethyl)-6,6-dimethyl-3-[1-(trimethylsilyl)cyclobutanecarboxamido]-4,6-dihydropyrrolo[3,4-c]pyrazole-5(1H)-carboxamide,
(R)—N-(3-methoxy-1-phenylpropyl)-6,6-dimethyl-3-[1-(trimethylsilyl)cyclobutanecarboxamido]-4,6-dihydropyrrolo[3,4-c]pyrazole-5(1H)-carboxamide,
Sodium (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylacetate,
(R)—N-(2-hydroxy-1-phenylethyl)-6,6-dimethyl-3-[1-(trimethylsilyl)cyclobutanecarboxamido]-4,6-dihydropyrrolo[3,4-c]pyrazole-5(1H)-carboxamide,
N-[1-(2-fluorophenyl)-2-hydroxyethyl]-6,6-dimethyl-3-[1-(trimethylsilyl)cyclobutanecarboxamido]-4,6-dihydropyrrolo[3,4-c]pyrazole-5(1H)-carboxamide,
(S)—N-[1-(3-fluorophenyl)-2-hydroxyethyl]-6,6-dimethyl-3-[1-(trimethylsilyl)cyclobutanecarboxamido]-4,6-dihydropyrrolo[3,4-c]pyrazole-5(1H)-carboxamide,
(S)—N-[1-(4-fluorophenyl)-2-hydroxyethyl]-6,6-dimethyl-3-[1-(trimethylsilyl)cyclobutanecarboxamido]-4,6-dihydropyrrolo[3,4-c]pyrazole-5(1H)-carboxamide,
N-[2-hydroxy-1-(pyridin-2-yl)ethyl]-6,6-dimethyl-3-[1-(trimethylsilyl)cyclobutanecarboxamido]-4,6-dihydropyrrolo[3,4-c]pyrazole-5(1H)-carboxamide,
N-[2-hydroxy-1-(pyridin-3-yl)ethyl]-6,6-dimethyl-3-[1-(trimethylsilyl)cyclobutanecarboxamido]-4,6-dihydropyrrolo[3,4-c]pyrazole-5(1H)-carboxamide,
N-[1-(benzo[d][1,3]dioxol-4-yl)-2-hydroxyethyl]-6,6-dimethyl-3-[1-(trimethylsilyl)cyclobutanecarboxamido]-4,6-dihydropyrrolo[3,4-c]pyrazole-5(1H)-carboxamide,
(S)—N-(1-cyclohexyl-2-hydroxyethyl)-6,6-dimethyl-3-[1-(trimethylsilyl)cyclobutanecarboxamido]-4,6-dihydropyrrolo[3,4-c]pyrazole-5(1H)-carboxamide, (S)—N-(1-hydroxy-3-methylbutan-2-yl)-6,6-dimethyl-3-[1-(trimethylsilyl)cyclobutanecarboxamido]-4,6-dihydropyrrolo[3,4-c]pyrazole-5(1H)-carboxamide, (S)—N-(1-hydroxypropan-2-yl)-6,6-dimethyl-3-[1-(trimethylsilyl)cyclobutanecarboxamido]-4,6-dihydropyrrolo[3,4-c]pyrazole-5(1H)-carboxamide, N-(2-hydroxyethyl)-6,6-dimethyl-3-[1-(trimethylsilyl)cyclobutanecarboxamido]-4,6-dihydropyrrolo[3,4-c]pyrazole-5(1H)-carboxamide, N-(2-hydroxy-2-phenylethyl)-6,6-dimethyl-3-[1-(trimethylsilyl)cyclobutanecarboxamido]-4,6-dihydropyrrolo[3,4-c]pyrazole-5(1H)-carboxamide, N-(2-hydroxypropyl)-6,6-dimethyl-3-[1-(trimethylsilyl)cyclobutanecarboxamido]-4,6-dihydropyrrolo[3,4-c]pyrazole-5(1H)-carboxamide, N-[(2S)-1-hydroxy-3-methyl-1-phenylbutan-2-yl]-6,6-dimethyl-3-[1-(trimethylsilyl)cyclobutanecarboxamido]-4,6-dihydropyrrolo[3,4-c]pyrazole-5(1H)-carboxamide, N-(4-hydroxy-1-phenyl-2-butyn-1-yl)-6,6-dimethyl-3-[1-(trimethylsilyl)cyclobutanecarboxamido]-4,6-dihydropyrrolo[3,4-c]pyrazole-5(1H)-carboxamide, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl acetate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl propionate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl butanoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl pentanoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl octanoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl dodecanoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl palmitate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl isobutanoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl pivalate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl 3-methylbutanoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl benzoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl ethylcarbonate, Sodium (S)-4-(2-{6,6-dimethyl-3-[1-(trimethylsilyl)cyclobutanecarboxamido]-1,4,5,6-tetrahydropyrrolo[3,4-c]pyrazole-5-carboxamido}-2-phenylethoxy)-4-oxobutanoate, (S)-(2-{6,6-dimethyl-3-[1-(trimethylsilyl)cyclobutanecarboxamido]-1,4,5,6-tetrahydropyrrolo[3,4-c]pyrazole-5-carboxamido}-2-phenylethoxy)methyl pivalate, (S)-2-acetoxy-1-phenylethyl 6,6-dimethyl-3-[1-(trimethylsilyl)cyclobutanecarboxamido]-4,6-dihydro pyrrolo[3,4-c]pyrazole-5(1H)-carboxylate, (S)-benzyl 2-{6,6-dimethyl-3-[1-(trimethylsilyl)cyclobutanecarboxamido]-1,4,5,6-tetrahydropyrrolo[3,4-c]pyrazole-5-carboxamido}-2-phenylacetate, (S)-methyl 2-{6,6-dimethyl-3-[1-(trimethylsilyl)cyclobutanecarboxamido]-1,4,5,6-tetrahydropyrrolo[3,4-c]pyrazole-5-carboxamido}-2-phenylacetate, N-(2,2-difluoro-3-hydroxy-1-phenylpropyl)-6,6-dimethyl-3-[1-(trimethylsilyl)cyclobutanecarboxamido]-4,6-dihydropyrrolo[3,4-c]pyrazole-5(1H)-carboxamide, N-(2-isopropoxy-1-phenylethyl)-6,6-dimethyl-3-[1-(trimethylsilyl)cyclobutanecarboxamido]-4,6-dihydropyrrolo[3,4-c]pyrazole-5(1H)-carboxamide, 6,6-Dimethyl-N-(2-phenoxy-1-phenylethyl)-3-[1-(trimethylsilyl)cyclobutanecarboxamido]-4,6-dihydropyrrolo[3,4-c]pyrazole-5(1H)-carboxamide, (S)—N-[1-(2-chlorophenyl)-2-hydroxyethyl]-6,6-dimethyl-3-[1-(trimethylsilyl)cyclobutanecarboxamido]-4,6-dihydropyrrolo[3,4-c]pyrazole-5(1H)-carboxamide, (S)—N-[2-hydroxy-1-(o-tolyl)ethyl]-6,6-dimethyl-3-[1-(trimethylsilyl)cyclobutanecarboxamido]-4,6-dihydropyrrolo[3,4-c]pyrazole-5(1H)-carboxamide, (S)—N-(1-hydroxy-3-phenylpropan-2-yl)-6,6-dimethyl-3-[1-(trimethylsilyl)cyclobutanecarboxamido]-4,6-dihydropyrrolo[3,4-c]pyrazole-5(1H)-carboxamide, N-(2-hydroxy-3-methylbutyl)-6,6-dimethyl-3-[1-(trimethylsilyl)cyclobutanecarboxamido]-4,6-dihydropyrrolo[3,4-c]pyrazole-5(1H)-carboxamide, (R)—N-(1-hydroxy-3-phenylpropan-2-yl)-6,6-dimethyl-3-[1-(trimethylsilyl)cyclobutanecarboxamido]-4,6-dihydropyrrolo[3,4-c]pyrazole-5(1H)-carboxamide, (R)—N-(2-hydroxy-2-phenylethyl)-6,6-dimethyl-3-[1-(trimethylsilyl)cyclobutanecarboxamido]-4,6-dihydropyrrolo[3,4-c]pyrazole-5(1H)-carboxamide, (S)—N-(2-hydroxy-2-phenylethyl)-6,6-dimethyl-3-[1-(trimethylsilyl)cyclobutanecarboxamido]-4,6-dihydropyrrolo[3,4-c]pyrazole-5(1H)-carboxamide, 2-Hydroxy-2-phenylethyl 6,6-dimethyl-3-[1-(trimethylsilyl)cyclobutanecarboxamido]-4,6-dihydropyrrolo[3,4-c]pyrazole-5(1H)-carboxylate, (R)—N-[6,6-dimethyl-5-(2-phenoxypropanoyl)-1,4,5,6-tetrahydropyrrolo[3,4-c]pyrazol-3-yl]-1-(trimethylsilyl)cyclobutanecarboxamide, (S)—N-[6,6-dimethyl-5-(2-phenoxypropanoyl)-1,4,5,6-tetrahydropyrrolo[3,4-c]pyrazol-3-yl]-1-(trimethylsilyl)cyclobutanecarboxamide, N-[6,6-dimethyl-5-(2-phenoxyacetyl)-1,4,5,6-tetrahydropyrrolo[3,4-c]pyrazol-3-yl]-1-(trimethylsilyl)cyclobutanecarboxamide, (R)—N-[6,6-dimethyl-5-(2-phenoxypropanoyl)-1,4,5,6-tetrahydropyrrolo[3,4-c]pyrazol-3-yl]-1-(trimethylsilyl)cyclopropanecarboxamide, N-{5-[3-(benzyloxy)-2-phenoxypropanoyl]-6,6-dimethyl-1,4,5,6-tetrahydropyrrolo[3,4-c]pyrazol-3-yl}-1-(trimethylsilyl)cyclobutanecarboxamide, N-[5-(3-hydroxy-2-phenoxypropanoyl)-6,6-dimethyl-1,4,5,6-tetrahydropyrrolo[3,4-c]pyrazol-3-yl]-1-(trimethylsilyl)cyclobutanecarboxamide, N-{5-[2-(4-chlorophenoxy)propanoyl]-6,6-dimethyl-1,4,5,6-tetrahydropyrrolo[3,4-c]pyrazol-3-yl}-1-(trimethylsilyl)cyclobutanecarboxamide, N-{5-[2-(2-chlorophenoxy)propanoyl]-6,6-dimethyl-1,4,5,6-tetrahydropyrrolo[3,4-c]pyrazol-3-yl}-1-(trimethylsilyl)cyclobutanecarboxamide, N-{5-[2-(cyclohexyloxy)propanoyl]-6,6-dimethyl-1,4,5,6-tetrahydropyrrolo[3,4-c]pyrazol-3-yl}-1-(trimethylsilyl)cyclobutanecarboxamide, N-{5-[2-(3-chlorophenoxy)propanoyl]-6,6-dimethyl-1,4,5,6-tetrahydropyrrolo[3,4-c]pyrazol-3-yl}-1-(trimethylsilyl)cyclobutanecarboxamide, N-[5-(2-methoxypropanoyl)-6,6-dimethyl-1,4,5,6-tetrahydropyrrolo[3,4-c]pyrazol-3-yl]-1-(trimethylsilyl)cyclobutanecarboxamide, N-[5-(3-methoxy-2-phenoxypropanoyl)-6,6-dimethyl-1,4,5,6-tetrahydropyrrolo[3,4-c]pyrazol-3-yl]-1-(trimethylsilyl)cyclobutanecarboxamide, N-{6,6-dimethyl-5-[2-(pyridin-3-yloxy)propanoyl]-1,4,5,6-tetrahydropyrrolo[3,4-c]pyrazol-3-yl}-1-(trimethylsilyl)cyclobutanecarboxamide, N-{5-[3-(dimethylamino)-2-phenoxypropanoyl]-6,6-dimethyl-1,4,5,6-tetrahydropyrrolo[3,4-c]pyrazol-3-yl}-1-(trimethylsilyl)cyclobutanecarboxamide, N-[6,6-dimethyl-5-(2-phenoxy-2-phenylacetyl)-1,4,5,6-tetrahydropyrrolo[3,4-c]pyrazol-3-yl]-1-(trimethylsilyl)cyclobutanecarboxamide, N-{5-[3-(3,3-difluoropyrrolidin-1-yl)-2-phenoxypropanoyl]-6,6-dimethyl-1,4,5,6-tetrahydropyrrolo[3,4-c]pyrazol-3-yl}-1-(trimethylsilyl)cyclobutanecarboxamide, N-[5-(3-hydroxy-2-phenylpropanoyl)-6,6-dimethyl-1,4,5,6-tetrahydropyrrolo[3,4-c]pyrazol-3-yl]-1-(trimethylsilyl)cyclobutanecarboxamide, (S)—N-[5-(3-hydroxy-2-phenylpropanoyl)-6,6-dimethyl-1,4,5,6-tetrahydropyrrolo[3,4-c]pyrazol-3-yl]-1-(trimethylsilyl)cyclobutanecarboxamide, (R)—N-{5-[3-(benzyloxy)-2-phenylpropanoyl]-6,6-dimethyl-1,4,5,6-tetrahydropyrrolo[3,4-c]pyrazol-3-yl}-1-(trimethylsilyl)cyclobutanecarboxamide, (R)—N-[5-(3-hydroxy-2-phenylpropanoyl)-6,6-dimethyl-1,4,5,6-tetrahydropyrrolo[3,4-c]pyrazol-3-yl]-1-(trimethylsilyl)cyclobutanecarboxamide (R)—N-[5-(2-methoxy-2-phenylacetyl)-6,6-dimethyl-1,4,5,6-tetrahydropyrrolo[3,4-c]pyrazol-3-yl]-1-(trimethylsilyl)cyclobutanecarboxamide, (S)—N-[5-(2-methoxy-2-phenylacetyl)-6,6-dimethyl-1,4,5,6-tetrahydropyrrolo[3,4-c]pyrazol-3-yl]-1-(trimethylsilyl)cyclobutanecarboxamide, N-[5-(3-methoxy-2-phenylpropanoyl)-6,6-dimethyl-1,4,5,6-tetrahydropyrrolo[3,4-c]pyrazol-3-yl]-1-(trimethylsilyl)cyclobutanecarboxamide, N-[5-(4-methoxy-2-phenylbutanoyl)-6,6-dimethyl-1,4,5,6-tetrahydropyrrolo[3,4-c]pyrazol-3-yl]-1-(trimethylsilyl)cyclobutanecarboxamide, (S)—N-[5-(3-hydroxy-2-phenylpropanoyl)-6,6-dimethyl-1,4,5,6-tetrahydropyrrolo[3,4-c]pyrazol-3-yl]-1-(trimethylsilyl)cyclopropanecarboxamide, (R)—N-[5-(2-methoxy-2-phenylacetyl)-6,6-dimethyl-1,4,5,6-tetrahydropyrrolo[3,4-c]pyrazol-3-yl]-1-(trimethylsilyl)cyclopropanecarboxamide, (R)—N-{5-[2-(difluoromethoxy)-2-phenylacetyl]-6,6-dimethyl-1,4,5,6-tetrahydropyrrolo[3,4-c]pyrazol-3-yl}-1-(trimethylsilyl)cyclobutanecarboxamide, (R)—N-[5-(2-ethoxy-2-phenylacetyl)-6,6-dimethyl-1,4,5,6-tetrahydropyrrolo[3,4-c]pyrazol-3-yl]-1-(trimethylsilyl)cyclobutanecarboxamide, (R)-1-(ethyldimethylsilyl)-N-[5-(2-methoxy-2-phenylacetyl)-6,6-dimethyl-1,4,5,6-tetrahydropyrrolo[3,4-c]pyrazol-3-yl]cyclobutanecarboxamide, (R)—N-[5-(2-cyclopropoxy-2-phenylacetyl)-6,6-dimethyl-1,4,5,6-tetrahydropyrrolo[3,4-c]pyrazol-3-yl]-1-(trimethylsilyl)cyclobutanecarboxamide, (R)—N-[5-(2-isopropoxy-2-phenylacetyl)-6,6-dimethyl-1,4,5,6-tetrahydropyrrolo[3,4-c]pyrazol-3-yl]-1-(trimethylsilyl)cyclobutanecarboxamide, (R)—N-{6,6-dimethyl-5-[2-phenyl-2-(trifluoromethoxy)acetyl]-1,4,5,6-tetrahydropyrrolo[3,4-c]pyrazol-3-yl}-1-(trimethylsilyl)cyclobutanecarboxamide, (R)—N-[6,6-dimethyl-5-(2-phenyl-2-propoxyacetyl)-1,4,5,6-tetrahydropyrrolo[3,4-c]pyrazol-3-yl]-1-(trimethylsilyl)cyclobutanecarboxamide, N-{5-[2-(4-fluorophenyl)-2-methoxyacetyl]-6,6-dimethyl-1,4,5,6-tetrahydropyrrolo[3,4-c]pyrazol-3-yl}-1-(trimethylsilyl)cyclobutanecarboxamide, N-{5-[2-(3-fluorophenyl)-2-methoxyacetyl]-6,6-dimethyl-1,4,5,6-tetrahydropyrrolo[3,4-c]pyrazol-3-yl}-1-(trimethylsilyl)cyclobutanecarboxamide, (R)—N-{5-[2-(2-fluorophenyl)-2-methoxyacetyl]-6,6-dimethyl-1,4,5,6-tetrahydropyrrolo[3,4-c]pyrazol-3-yl}-1-(trimethylsilyl)cyclobutanecarboxamide, N-{5-[2-methoxy-2-(thiophen-2-yl)acetyl]-6,6-dimethyl-1,4,5,6-tetrahydropyrrolo[3,4-c]pyrazol-3-yl}-1-(trimethylsilyl)cyclobutanecarboxamide, (−)-N-{5-[2-methoxy-2-(thiophen-2-yl)acetyl]-6,6-dimethyl-1,4,5,6-tetrahydropyrrolo[3,4-c]pyrazol-3-yl}-1-(trimethylsilyl)cyclobutanecarboxamide, (+)-N-{5-[2-methoxy-2-(thiophen-2-yl)acetyl]-6,6-dimethyl-1,4,5,6-tetrahydropyrrolo[3,4-c]pyrazol-3-yl}-1-(trimethylsilyl)cyclobutanecarboxamide, N-{[1-(hydroxymethyl)cyclobutyl](phenyl)methyl}-6,6-dimethyl-3-[1-(trimethylsilyl)cyclobutanecarboxamido]-4,6-dihydropyrrolo[3,4-c]pyrazole-5(1H)-carboxamide, (R)—N-[2-(1-hydroxycyclopropyl)-1-phenylethyl]-6,6-dimethyl-3-[1-(trimethylsilyl)cyclobutanecarboxamido]-4,6-dihydropyrrolo[3,4-c]pyrazole-5(1H)-carboxamide, (R)—N-(3-ethyl-3-hydroxy-1-phenylpentyl)-6,6-dimethyl-3-[1-(trimethylsilyl)cyclobutanecarboxamido]-4,6-dihydropyrrolo[3,4-c]pyrazole-5(1H)-carboxamide, (R)—N-[1-(4-fluorophenyl)-3-hydroxy-3-methylbutyl]-6,6-dimethyl-3-[1-(trimethylsilyl)cyclobutanecarboxamido]-4,6-dihydropyrrolo[3,4-c]pyrazole-5(1H)-carboxamide, (R)—N-[1-(3-fluorophenyl)-3-hydroxy-3-methylbutyl]-6,6-dimethyl-3-[1-(trimethylsilyl)cyclobutanecarboxamido]-4,6-dihydropyrrolo[3,4-c]pyrazole-5(1H)-carboxamide, (R)—N-[1-(2-fluorophenyl)-3-hydroxy-3-methylbutyl]-6,6-dimethyl-3-[1-(trimethylsilyl)cyclobutanecarboxamido]-4,6-dihydropyrrolo[3,4-c]pyrazole-5(1H)-carboxamide, (R)—N-(5-hydroxy-2,5-dimethylhexan-3-yl)-6,6-dimethyl-3-[1-(trimethylsilyl)cyclobutanecarboxamido]-4,6-dihydropyrrolo[3,4-c]pyrazole-5(1H)-carboxamide, N-[1-(4-fluorophenyl)-3-hydroxy2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide, N-[1-(3-fluorophenyl)-3-hydroxy-2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide, (−)-N-[1-(3-fluorophenyl)-3-hydroxy-2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide, (+)-N-[1-(3-fluorophenyl)-3-hydroxy-2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide, N-[1-(2-fluorophenyl)-3-hydroxy-2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide, N-(1-hydroxy-2,2,4-trimethylpentan-3-yl)-6,6-dimethyl-3-[1-(trimethylsilyl)cyclobutanecarboxamido]-4,6-dihydropyrrolo[3,4-c]pyrazole-5(1H)-carboxamide, (R)—N-(3-hydroxy-3-methyl-1-phenylbutyl)-6,6-dimethyl-3-[1-(trimethylsilyl)cyclopropanecarboxamido]-4,6-dihydropyrrolo[3,4-c]pyrazole-5(1H)-carboxamide,
N-(3-hydroxy-2,2-dimethyl-1-phenylpropyl)-6,6-dimethyl-3-[1-(trimethylsilyl)cyclopropanecarboxamido]-4,6-dihydropyrrolo[3,4-c]pyrazole-5(1H)-carboxamide,
(−)-N-(3-hydroxy-2,2-dimethyl-1-phenylpropyl)-6,6-dimethyl-3-[1-(trimethylsilyl)cyclobutanecarboxamido]-4,6-dihydropyrrolo[3,4-c]pyrazole-5(1H)-carboxamide,
(+)-N-(3-hydroxy-2,2-dimethyl-1-phenylpropyl)-6,6-dimethyl-3-[1-(trimethylsilyl)cyclobutanecarboxamido]-4,6-dihydropyrrolo[3,4-c]pyrazole-5(1H)-carboxamide,
(R)—N-[5-(2-butoxy-2-phenylacetyl)-6,6-dimethyl-1,4,5,6-tetrahydropyrrolo[3,4-c]pyrazol-3-yl]-1-(trimethylsilyl)cyclobutanecarboxamide, and
N-(3-methoxy-2,2-dimethyl-1-phenylpropyl)-6,6-dimethyl-3-[1-(trimethylsilyl)cyclobutanecarboxamido]-4,6-dihydropyrrolo[3,4-c]pyrazole-5(1H)-carboxamide.

The compound or the pharmacologically acceptable salt thereof according to the present embodiment may be a single optically active form or may be a mixture of a plurality of optically active forms.

In the case where geometric isomers or rotational isomers are present in the compound according to the present embodiment, these isomers are also included in the scope of the present invention, and in the case where proton tautomers are present, these tautomers are also encompassed in the present invention.

The "pharmacologically acceptable salt" according to the present embodiment is not particularly limited as long as being a salt acceptable as a drug, and examples thereof include: salts with inorganic acids such as hydrochloric acid, hydrobromic acid, hydroiodic acid, nitric acid, sulfuric acid, and phosphoric acid; salts with organic carboxylic acids such as acetic acid, fumaric acid, maleic acid, succinic acid, citric acid, tartaric acid, adipic acid, lactic acid, and trifluoroacetic acid; salts with organic sulfonic acids such as methanesulfonic acid, trifluoromethanesulfonic acid, benzenesulfonic acid, p-toluenesulfonic acid, and naphthalenesulfonic acid; salts with alkali metals such as lithium, sodium, and potassium; salts with alkaline earth metals such as calcium and magnesium; and quaternary ammonium salts such as ammonia, morpholine, glucosamine, ethylenediamine, guanidine, diethylamine, triethylamine, dicyclohexylamine, diethanolamine, and piperazine.

The compound or the pharmacologically acceptable salt thereof according to the present embodiment can form a hydrate or a solvate, and each one or a mixture thereof is encompassed in the present invention.

The compound according to the present embodiment may contain a non-natural ratio of an atomic isotope for one or more of the constituting atoms. Examples of the atomic isotope include deuterium ($^2H$), tritium ($^3H$), carbon-14 ($^{14}C$), fluorine-18 ($^{18}F$), sulfur-35 ($^{35}S$), and iodine-125 ($^{125}I$). These compounds are useful as therapeutic or prophylactic agents, research reagents, for example, assay reagents, and diagnostic agents, for example, in vivo diagnostic imaging agents. All isotopic variants of the compound according to the present embodiment are encompassed in the present invention, regardless of whether to be radioactive.

The compound or the pharmacologically acceptable salt thereof according to the present embodiment can be used as a pharmaceutical composition, if necessary, by adding an excipient, a lubricant, a binder, a disintegrant, a coating agent, a stabilizer, a tonicity agent, a buffer, a pH adjuster, a solubilizer, a thickener, a preservative, an antioxidant, a sweetener, a colorant, a flavor, and the like. The pharmaceutical composition can be appropriately prepared according to a purpose by a known method described in, for example, General Rules for Preparations, Japanese Pharmacopoeia 16th edition.

In the pharmaceutical composition, the content of the compound or the pharmacologically acceptable salt thereof according to the present embodiment can be appropriately adjusted.

The pharmaceutical composition can be in a dosage form described in General Rules for Preparations, Japanese Pharmacopoeia 16th edition, for example, a preparation for oral administration such as tablets, capsules, granules, or powders, or a preparation for parenteral administration such as injections (e.g., intravenous administration, subcutaneous administration, intramuscular administration, and intraperitoneal administration), eye drops, nasal drops, suppositories, ointments, lotions, creams, gels, sprays, patches, inhalants, or percutaneous absorption preparations.

Examples of the excipient include lactose, mannitol, starch, crystalline cellulose, light anhydrous silicic acid, calcium carbonate, and calcium hydrogen phosphate, and examples of the lubricant include stearic acid, magnesium stearate, and talc. Examples of the binder include starch, hydroxypropylcellulose, hydroxypropylmethylcellulose, and polyvinylpyrrolidone, and examples of the disintegrant include carboxymethylcellulose, low-substituted hydroxypropylmethylcellulose, and calcium citrate. Examples of the coating agent include hydroxypropylmethylcellulose, macrogol, and silicone resins, and examples of the stabilizer include ethyl p-hydroxybenzoate and benzyl alcohol.

Examples of the tonicity agent include glycerin, propylene glycol, sodium chloride, potassium chloride, sorbitol, and mannitol, examples of the buffer include boric acid, boric acid salts, phosphoric acid, phosphoric acid salts, citric acid, citric acid salts, acetic acid, acetic acid salts, ε-aminocaproic acid, and trometamol, and examples of the pH adjuster include hydrochloric acid, citric acid, phosphoric acid, glacial acetic acid, sodium hydroxide, potassium hydroxide, sodium carbonate, and sodium bicarbonate. Examples of the solubilizer include polysorbate 80, polyoxyethylene hydrogenated castor oil 60, macrogol 4000, purified soybean lecithin, and polyoxyethylene (160) polyoxypropylene (30) glycol, and examples of the thickener include cellulose polymers such as hydroxypropylmethylcellulose and hydroxypropylcellulose, polyvinyl alcohol, and polyvinylpyrrolidone. Examples of the stabilizer include edetic acid and sodium edetate, and examples of the preservative include sorbic acid, potassium sorbate, benzalkonium chloride, benzethonium chloride, methyl p-hydroxybenzoate, propyl p-hydroxybenzoate, and chlorobutanol.

Examples of ingredients that may be contained in pharmaceutical compositions for percutaneous administration such as ointments, lotions, creams, gels, patches, and sprays include: absorption promoters such as lauryl alcohol, myristyl alcohol, salicylic acid ethylene glycol, and pyrrothiodecane; fatty acid esters such as diisopropyl adipate, isopropyl myristate, cetyl lactate, myristyl lactate, isopropyl palmitate, diethyl sebacate, hexyl laurate, and cetyl isooctanoate; aliphatic alcohols such as cetyl alcohol, stearyl alcohol, oleyl alcohol, hexadecyl alcohol, and behenyl alcohol; glycols such as propylene glycol, propylenediol, polyethylene glycol, and dipropylene glycol; and surfactants such as sorbitan fatty acid ester, glycerin fatty acid ester, polyoxyethylene sorbitan fatty acid ester, polyoxyethylene glycerin fatty acid ester, polyethylene glycol fatty acid ester, polyoxyethylene alkyl ether, polyoxyethylene castor oil, and polyoxyethylene hydrogenated castor oil.

The dose of the compound or the pharmacologically acceptable salt thereof according to the present embodiment can be appropriately varied according to symptoms, age, a dosage form, etc. In the case of, for example, oral administration, it can usually be administered in one portion or several divided portions of 0.01 to 2000 mg, preferably 1 to 500 mg per day.

As for ointments, lotions, creams, or gels, one having a concentration of 0.00001% (w/v) to 10% (w/v), preferably 0.001% (w/v) to 5% (w/v) can usually be administered in one portion or several divided portions.

Next, a method for producing the compound or the pharmacologically acceptable salt thereof according to the present embodiment will be described. The compound or the pharmacologically acceptable salt thereof according to the present invention is not limited to compounds or pharmacologically acceptable salts thereof produced by production methods described below.

In the production methods given below, in the case where partial structures that inhibit the desired reactions or receive side reactions (e.g., a hydroxy group, an amino group, a carbonyl group, a carboxyl group, an amide group, a thiol group and the like) are present in compounds, the compounds of interest can be obtained by introducing protective groups to these partial structures, performing the desired reactions, and then removing the protective groups.

The introduction reaction and removal reaction of a protective group can be carried out according to a method routinely used in organic synthetic chemistry (e.g., a method described in, for example, Protective Groups in Organic Synthesis, 4th ed., T.W. Greene, P.G.M. Wuts, John Wiley & Sons Inc. (2006)).

Specific methods for producing the individual compounds of the present invention will be described in detail in Examples mentioned later.

Compound (I) can be produced, for example, by methods of production methods 1 to 4 given below with compound (A) as a starting material. A method for producing the compound (A) will be mentioned later.

<Production Method 1 for Compound (I)>

Production method 1 is a method for producing compound (I) through steps 1 to 3 with compound (A) as a starting material. Production method 1 is a suitable production method in the case where $L^2$ is an oxygen atom or an optionally substituted nitrogen atom. In production method 1, $R^1$, $R^2$, $R^3$, $R^4$, $R^5$, $L^1$, $L^2$, and $L^3$ are defined as in formula (I). $P^1$ group is a protective group for the amino group, and X is a leaving group. The $P^1$ group can substitute an acidic proton of pyrazole in the 4,6-dihydropyrrolo[3,4-c]pyrazole skeleton. Thus, the $P^1$ group may be added to position 1 of the 4,6-dihydropyrrolo[3,4-c]pyrazole skeleton or may be added to 2-position. Compound (A) will be described by using a chemical formula wherein it is added to 1-position of the 4,6-dihydropyrrolo[3,4-c]pyrazole skeleton, for the sake of convenience.

[Chemical Formula 11]

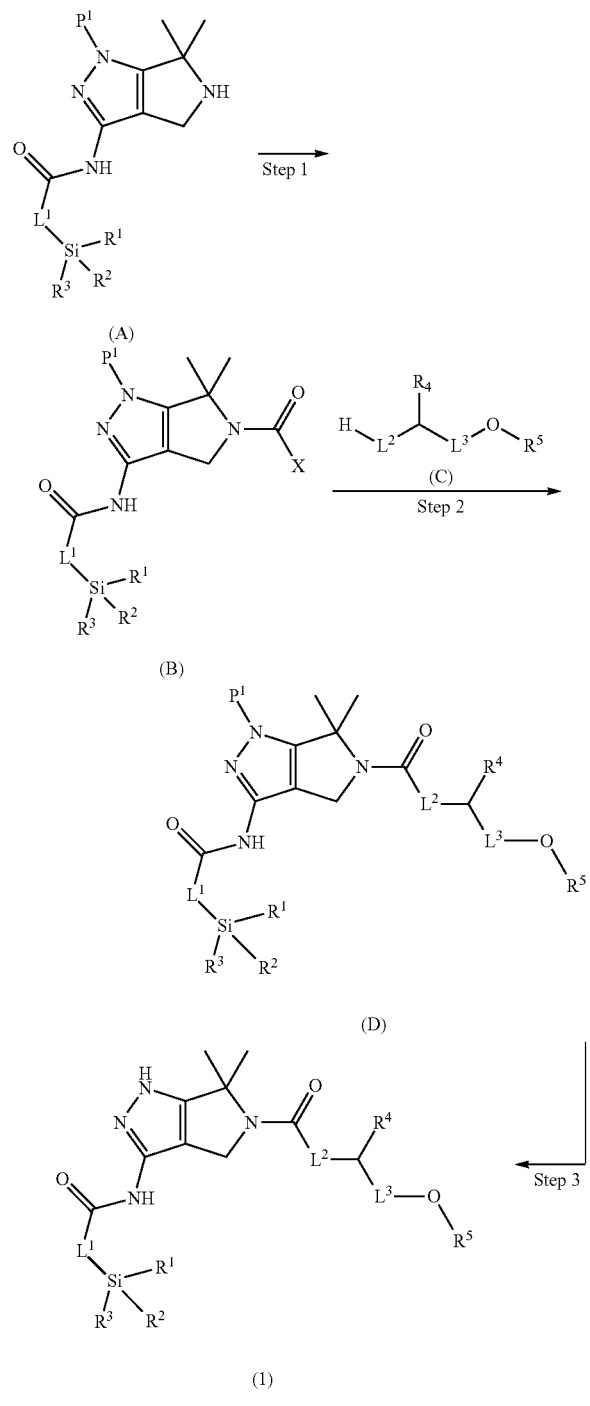

The $P^1$ group is not particularly limited as long as being a substituent known as a protective group for the amino group to those skilled in the art. Examples of the $P^1$ group include: optionally substituted $C_{7-11}$ aralkyl groups such as a benzyl group, a p-methoxyphenylmethyl group, and a o-nitrophenylmethyl group; optionally substituted acyl groups such as an acetyl group, a trifluoroacetyl group, and a benzoyl group; optionally substituted $C_{1-6}$ alkoxycarbonyl groups such as a methoxycarbonyl group, an ethoxycarbonyl group, a Boc group (tert-butoxycarbonyl group), a Cbz group (benzyloxycarbonyl group), a Fmoc group (fluorenylmethyloxycarbonyl group), and a Teoc group (trimethylsilylethyloxycarbonyl group); alkenyloxycarbonyl groups such as an Alloc group (allyloxycarbonyl group); alkylsulfonyl groups such as a methanesulfonyl group; and $C_{6-10}$ arylsulfonyl groups such as a p-toluenesulfonyl group.

The X group is not particularly limited as long as being a substituent known as a leaving group to those skilled in the art. Examples of X include: halogen atoms; an imidazolyl group; aminooxy groups such as a succinyl-N-oxy group and a benzotriazolyl-N-oxy group; and acyloxy groups such as a pivaloyloxy group and a benzoyloxy group. Alternatively, X may be a hydroxy group.

(Step 1)

Step 1 is the step of reacting compound (A) with an acylating agent to obtain compound (B).

As the acylating agent, for example, phosgene, diphosgene, triphosgene, carbonyldiimidazole (CDI), N,N'-disuccinimidyl carbonate, or carbonic acid ester can be used.

The amount of the acylating agent used is preferably 0.4 to 3.0 mol, more preferably 0.7 to 1.5 mol, with respect to 1 mol of the compound (A).

The reaction of step 1 may be performed in a solvent or may be performed without a solvent. In the case of using a solvent, there is no limitation as long as the solvent does not have influence on the reaction, and an organic solvent is preferred. Examples of the organic solvent include dichloromethane, 1,2-dichloroethane, diethyl ether, 1,2-dimethoxyethane, tetrahydrofuran (THF), N,N-dimethylformamide (DMF), and dimethyl sulfoxide (DMSO).

In step 1, a base can be further added in order to accelerate the reaction. Examples of the base include organic amines such as triethylamine, diisopropylethylamine (DIPEA), 1,5-diazabicyclo[4.3.0]nonene (DBN), 1,8-diazabicyclo[5.4.0]undecene (DBU), pyridine, and 4-dimethylaminopyridine (DMAP).

The amount of the base added is preferably 1 to 10 mol, more preferably 3 to 6 mol, with respect to 1 mol of the compound (A).

The reaction temperature of step 1 can be appropriately set by those skilled in the art. The reaction temperature is usually −100 to −20° C., preferably −80 to −60° C.

(Step 2)

Step 2 is the step of reacting compound (B) with compound (C) to obtain compound (D).

In step 2, the $L^2$ group is an oxygen atom or an optionally substituted nitrogen atom. Specifically, the compound (C) is an alcohol or an amine The amount of the compound (C) used is preferably 1 to 20 mol, more preferably 2 to 5 mol, with respect to 1 mol of the compound (B). The compound (C) and the compound (B) may be dissolved in an organic solvent and added to the reaction solution.

The reaction of step 2 may be performed in a solvent or may be performed without a solvent. In the case of using a solvent, there is no limitation as long as the solvent does not have influence on the reaction, and an organic solvent is preferred. Examples of the organic solvent include dichloromethane, 1,2-dichloroethane, diethyl ether, 1,2-dimethoxyethane, tetrahydrofuran (THF), 1,4-dioxane, N,N-dimethylformamide (DMF), and dimethyl sulfoxide (DMSO).

In step 2, a base can be further added in order to accelerate the reaction. Examples of the base include: organic amines such as triethylamine, diisopropylethylamine (DIPEA), 1,5-diazabicyclo[4.3.0]nonene (DBN), 1,8-diazabicyclo[5.4.0]undecene (DBU), pyridine, and 4-dimethylaminopyridine (DMAP); and inorganic bases such as potassium carbonate and sodium carbonate.

The amount of the base added is preferably 1 to 20 mol, more preferably 2 to 5 mol, with respect to 1 mol of the compound (A).

The reaction temperature of step 2 can be appropriately set by those skilled in the art. The reaction temperature is usually 0 to 120° C., preferably 25 to 100° C.

(Step 3)

Step 3 is the step of removing the $P^1$ group of compound (D) to produce compound (I).

The reaction conditions of step 3 can be appropriately selected by those skilled in the art according to the type of the $P^1$ group used. In the case where the $P^1$ group is, for example, an aralkyl group, it may be performed by hydrogenolysis or may be performed by using protonic acid or Lewis acid. In the case where the $P^1$ group is a Boc group, it can be performed by treatment with protonic acid or Lewis acid; in the case where the $P^1$ group is a Cbz group, it can be performed by hydrogenolysis or treatment with a base; and in the case where the $P^1$ group is a Teoc group, a reagent that forms a fluoride ion such as tetrabutylammonium fluoride can be used. In the case where the $P^1$ group is an alkoxycarbonyl group such as a methoxycarbonyl group or an ethoxycarbonyl group, it may be performed by heating in the presence of an organic amine such as triethylamine or diisopropylethylamine (DIPEA), or an inorganic base such as potassium carbonate or sodium carbonate.

The compound (I) obtained by step 3 can be converted to a pharmacologically acceptable salt thereof by a method well known to those skilled in the art.

<Production Method 2 for Compound (I)>

Production method 2 is a method for obtaining compound (D) through steps 4 and 5 with compound (C) as a starting material, followed by conversion to compound (1) according to step 3 of production method 1 described above. Production method 2 is a suitable production method in the case where $L^2$ is an oxygen atom or an optionally substituted nitrogen atom. In production method 2, $R^1$, $R^2$, $R^3$, $R^4$, $R^5$, $L^1$, $L^2$, $L^3$, $P^1$, and X are defined as in production method 1 described above.

[Chemical Formula 12]

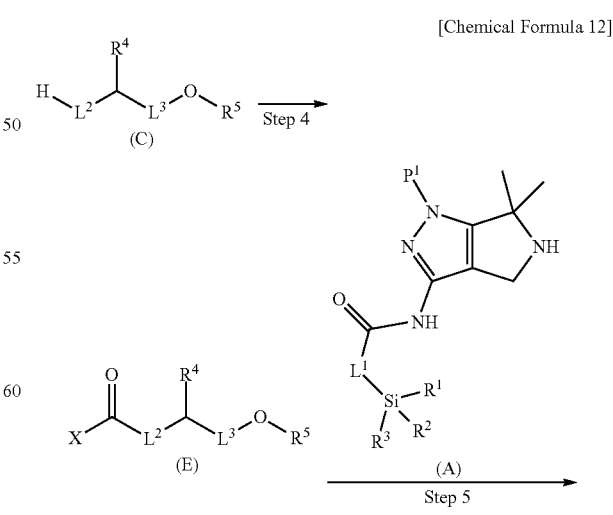

-continued

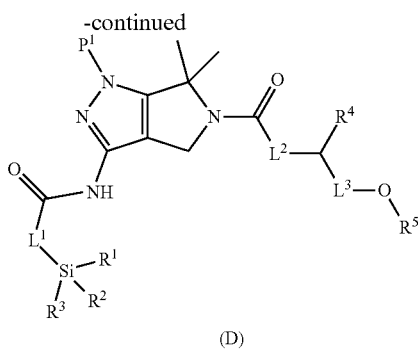

(D)

(Step 4)

Step 4 is the step of reacting compound (C) with an acylating agent to obtain compound (E).

In step 4, the $L^2$ group is an oxygen atom or an optionally substituted nitrogen atom. Specifically, the compound (C) is an alcohol or an amine As the acylating agent, for example, phosgene, diphosgene, triphosgene, carbonyldiimidazole (CDI), N,N'-disuccinimidyl carbonate, or carbonic acid ester can be used.

The amount of the acylating agent used is preferably 1 to 5 mol, more preferably 1 to 2 mol, with respect to 1 mol of the compound (C).

The reaction of step 4 may be performed in a solvent or may be performed without a solvent. In the case of using a solvent, there is no limitation as long as the solvent does not have influence on the reaction, and an organic solvent is preferred. Examples of the organic solvent include acetonitrile, dichloromethane, diethyl ether, tetrahydrofuran (THF), N,N-dimethylformamide (DMF), and dimethyl sulfoxide (DMSO).

In step 4, a base can be further added in order to accelerate the reaction. Examples of the base include organic amines such as triethylamine, diisopropylethylamine (DIPEA), 1,5-diazabicyclo[4.3.0]nonene (DBN), 1,8-diazabicyclo[5.4.0]undecene (DBU), pyridine, and 4-dimethylaminopyridine (DMAP).

The amount of the base added is preferably 1 to 5 mol, more preferably 1 to 2 mol, with respect to 1 mol of the compound (C).

The reaction temperature of step 4 can be appropriately set by those skilled in the art. The reaction temperature is usually 0 to 100° C., preferably 20 to 40° C.

(Step 5)

Step 5 is the step of reacting compound (E) with compound (A) to obtain compound (D).

The amount of the compound (E) used is preferably 1 to 5 mol, more preferably 1 to 2 mol, with respect to 1 mol of the compound (A). The compound (E) and the compound (A) may be dissolved in an organic solvent and added to the reaction solution.

The reaction of step 5 may be performed in a solvent or may be performed without a solvent. In the case of using a solvent, there is no limitation as long as the solvent does not have influence on the reaction, and an organic solvent is preferred. Examples of the organic solvent include dichloromethane, diethyl ether, tetrahydrofuran (THF), N,N-dimethylformamide (DMF), and dimethyl sulfoxide (DMSO).

In step 5, a base can be further added in order to accelerate the reaction. Examples of the base include organic amines such as triethylamine, diisopropylethylamine (DIPEA), 1,5-diazabicyclo[4.3.0]nonene (DBN), 1,8-diazabicyclo[5.4.0]undecene (DBU), pyridine, and 4-dimethylaminopyridine (DMAP).

The amount of the base added is preferably 1 to 10 mol, more preferably 1 to 5 mol, with respect to 1 mol of the compound (A).

The reaction temperature of step 5 can be appropriately set by those skilled in the art. The reaction temperature is usually 0 to 100° C., preferably 20 to 40° C.

<Production Method 3 for Compound (I)>

Production method 3 is a method for reacting compound (A) with compound (F) to obtain compound (D), followed by conversion to compound (I) according to step 3 of production method 1 described above. Production method 3 is a suitable production method in the case where $L^2$ is a single bond, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group. In production method 3, $R^1$, $R^2$, $R^3$, $R^4$, $R^5$, $L^1$, $L^3$, and $P^1$ are defined as in production method 1 described above.

[Chemical Formula 13]

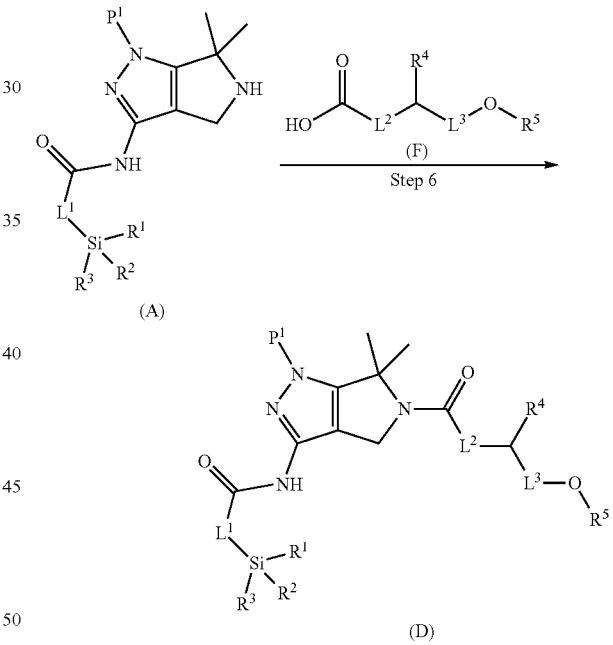

(Step 6)

Step 6 is the step of condensing compound (A) with compound (F) to obtain compound (D). The condensation reaction involves converting the compound (F) to an acid halide, a carboxylic anhydride, an acid azide, or an active ester by using a reagent used in amide bond formation reaction, followed by reaction with the compound (A). The reagent used in amide bond formation reaction is not particularly limited as long as being a reagent known as a reagent used in amide bond formation reaction to those skilled in the art.

The amount of the compound (F) used is preferably 1 to 10 mol, more preferably 1 to 5 mol, with respect to 1 mol of the compound (A). The compound (F) may be dissolved in an organic solvent and added to the reaction solution.

The reaction of step 6 may be performed in a solvent or may be performed without a solvent. In the case of using a solvent, there is no limitation as long as the solvent does not have influence on the reaction, and an organic solvent is preferred. Examples of the organic solvent include dichloromethane, 1,2-dichloroethane, diethyl ether, tetrahydrofuran (THF), N,N-dimethylformamide (DMF), and dimethyl sulfoxide (DMSO).

In step 6, a base can be further added in order to accelerate the reaction. Examples of the base include organic amines such as triethylamine, diisopropylethylamine (DIPEA), 1,5-diazabicyclo[4.3.0]nonene (DBN), 1,8-diazabicyclo[5.4.0]undecene (DBU), pyridine, and 4-dimethylaminopyridine (DMAP).

The amount of the base added is preferably 1 to 10 mol, more preferably 1 to 5 mol, with respect to 1 mol of the compound (A).

The reaction temperature of step 6 can be appropriately set by those skilled in the art. The reaction temperature is usually 0 to 100° C., preferably 20 to 40° C.

<Production Method 4 for Compound (I)>

Production method 4 is a method for obtaining compound (D) through step 7 and step 8 with compound (H) as a starting material, followed by conversion to compound (I) according to step 3 of production method 1 described above. In production method 4, $R^1$, $R^2$, $R^3$, $R^4$, $L^1$, $L^2$, and $L^3$ are defined as in formula (I). $P^1$ group is a protective group for the amino group, and $P^2$ is a protective group for the hydroxy group. The $P^1$ group is defined as in production method 1 described above.

[Chemical Formula 14]

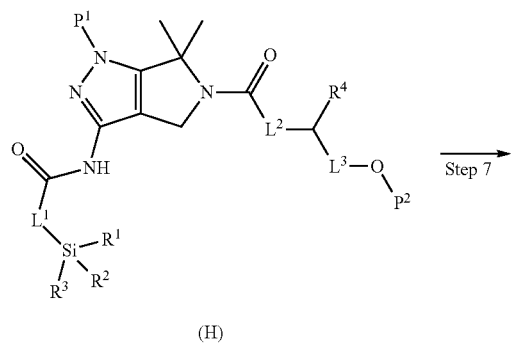

(H)

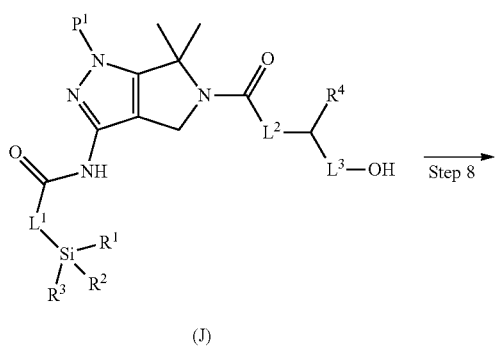

(J)

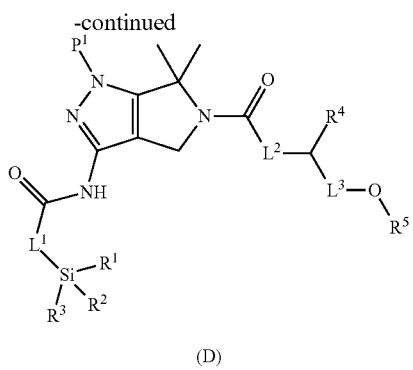

(D)

The $P^2$ group is not particularly limited as long as being a substituent known as a protective group for the hydroxy group to those skilled in the art. Examples of the $P^2$ group include: optionally substituted $C_{7-11}$ aralkyl groups such as a benzyl group, a p-methoxyphenylmethyl group, and a o-nitrophenylmethyl group; optionally substituted acyl groups such as an acetyl group, a trifluoroacetyl group, and a benzoyl group; and substituted silyl groups such as a trimethylsilyl group, a tert-butyldimethylsilyl group, a triethylsilyl group, a triisopropylsilyl group, and a tert-butyldiphenylsilyl group.

(Step 7)

Step 7 is the step of performing the deprotection reaction of compound (H) to obtain compound (J). The removal reaction of the $P^2$ group can also be performed by a method well known to those skilled in the art (e.g., a method described in, for example, Protective Groups in Organic Synthesis, 4th ed., T.W. Greene, P.G.M. Wuts, John Wiley & Sons Inc. (2006)).

(Step 8)

Step 8 is the step of reacting compound (J) with an acid halide, an acid anhydride, or an alkyl halide to obtain compound (D).

The amount of the acid halide, the acid anhydride, or the alkyl halide used is preferably 1 to 10 mol, more preferably 1 to 2 mol, with respect to 1 mol of the compound (J).

The reaction of step 7 may be performed in a solvent or may be performed without a solvent. In the case of using a solvent, there is no limitation as long as the solvent does not have influence on the reaction, and an organic solvent is preferred. Examples of the organic solvent include dichloromethane, diethyl ether, tetrahydrofuran (THF), 1,4-dioxane, N,N-dimethylformamide (DMF), and dimethyl sulfoxide (DMSO).

In step 8, a base can be further added in order to accelerate the reaction. Examples of the base include organic amines such as triethylamine, diisopropylethylamine (DIPEA), 1,5-diazabicyclo[4.3.0]nonene (DBN), 1,8-diazabicyclo[5.4.0]undecene (DBU), pyridine, and 4-dimethylaminopyridine (DMAP).

The amount of the base added is preferably 1 to 20 mol, more preferably 1 to 5 mol, with respect to 1 mol of the compound (J).

The reaction temperature of step 8 can be appropriately set by those skilled in the art. The reaction temperature is usually −20 to 120° C., preferably 15 to 100° C.

<Method for Producing Compound (A)>

The compound (A) can be produced, for example, by the following method with compound (A1) as a starting material. Compound (A1) can be produced, for example, with reference to WO2007/72153 or through the following steps 11 to 15.

[Chemical Formula 15]

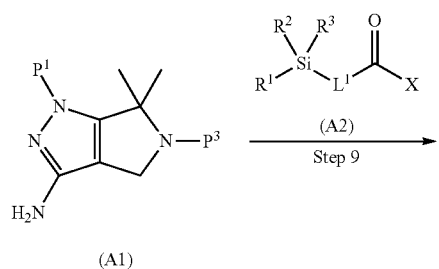

(A1)

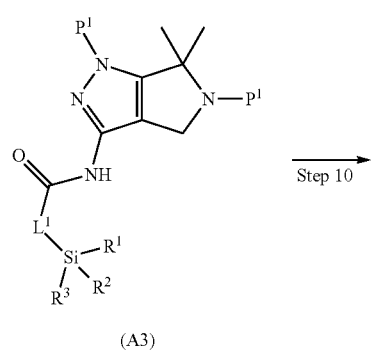

(A3)

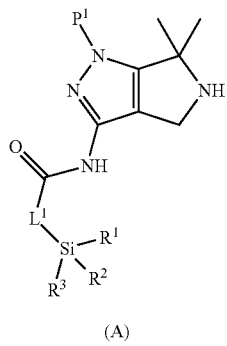

(A)

The compound (A1) is 3-amino-6,6-dimethyl-4,6-dihydropyrrolo[3,4-c]pyrazole in which the nitrogen atom on the pyrazole skeleton may be substituted by $P^1$ group, and the nitrogen atom at 5-position may be substituted by $P^3$ group. The $P^1$ group can substitute an acidic proton of pyrazole in the 4,6-dihydropyrrolo[3,4-c]pyrazole skeleton. Thus, the $P^1$ group may be added to position 1 of the 4,6-dihydropyrrolo[3,4-c]pyrazole skeleton or may be added to 2-position. Compound (A1) and compound (A2) will be described by using a chemical formula wherein it is added to 1-position of the 4,6-dihydropyrrolo[3,4-c]pyrazole skeleton, for the sake of convenience.

In the compound (A1), $P^1$ has the same meaning as defined in compound (A). The $P^3$ group is not particularly limited as long as being a substituent known as a protective group for the amino group to those skilled in the art. Examples of the $P^3$ group include: optionally substituted $C_{7-11}$ aralkyl groups such as a benzyl group, a p-methoxyphenylmethyl group, and a o-nitrophenylmethyl group; optionally substituted $C_{1-6}$ alkylcarbonyl groups such as an acetyl group and a trifluoroacetyl group; optionally substituted $C_{6-10}$ arylcarbonyl groups such as a benzoyl group; optionally substituted C1-6 alkoxycarbonyl groups such as a methoxycarbonyl group, an ethoxycarbonyl group, a Boc group (tert-butoxycarbonyl group), a Cbz group (benzyloxycarbonyl group), a Fmoc group (fluorenylmethyloxycarbonyl group), and a Teoc group (trimethylsilylethyloxycarbonyl group); alkenyloxycarbonyl groups such as an Alloc group (allyloxycarbonyl group); alkylsulfonyl groups such as a methanesulfonyl group; and optionally substituted $C_{6-10}$ arylsulfonyl groups such as a p-toluenesulfonyl group.

In the formulas (A2) and (A3), $R^1$, $R^2$, $R^3$, and $L^1$ have the same meanings as defined in compound (I). The group X is not particularly limited as long as being a substituent known as a leaving group to those skilled in the art. Examples of X include: halogen atoms; an imidazolyl group; aminooxy groups such as a succinyl-N-oxy group and a benzotriazolyl-N-oxy group; and acyloxy groups such as a pivaloyloxy group and a benzoyloxy group. Alternatively, X may be a hydroxy group.

In the case where the compound (A2) is a carboxylic acid (i.e., X is a hydroxy group), it may be converted to an acid anhydride by a method well known to those skilled in the art and then reacted with the compound (A1), or may be reacted with the compound (A1) by using a reagent known as a condensing agent used in amide bond formation reaction to those skilled in the art.

(Step 9)

Step 9 is the step of reacting compound (A1) with compound (A2) to obtain compound (A3).

The amount of the compound (A2) used is preferably 1 to 10 mol, more preferably 1 to 3 mol, with respect to 1 mol of the compound (A1).

The reaction of step 9 may be performed in a solvent or may be performed without a solvent. In the case of using a solvent, there is no limitation as long as the solvent does not have influence on the reaction, and an organic solvent is preferred. Examples of the organic solvent include dichloromethane, diethyl ether, tetrahydrofuran (THF), N,N-dimethylformamide (DMF), and dimethyl sulfoxide (DMSO).

In step 9, a base can be further added in order to accelerate the reaction. Examples of the base include organic amines such as triethylamine, diisopropylethylamine (DIPEA), 1,5-diazabicyclo[4.3.0]nonene (DBN), 1,8-diazabicyclo[5.4.0]undecene (DBU), pyridine, and 4-dimethylaminopyridine (DMAP).

The amount of the base added is preferably 1 to 20 mol, more preferably 1 to 5 mol, with respect to 1 mol of the compound (A1).

The reaction temperature of step 9 can be appropriately set by those skilled in the art. The reaction temperature is usually −40 to 100° C., preferably −20 to 20° C.

(Step 10)

Step 10 is the step of performing the deprotection reaction of compound (A3) to obtain compound (A). The removal reaction of the $P^3$ group can also be performed by a method well known to those skilled in the art (e.g., a method described in, for example, Protective Groups in Organic Synthesis, 4th ed., T.W. Greene, P.G.M. Wuts, John Wiley & Sons Inc. (2006)).

<Method for Producing Compound (A1)>

[Chemical Formula 16]

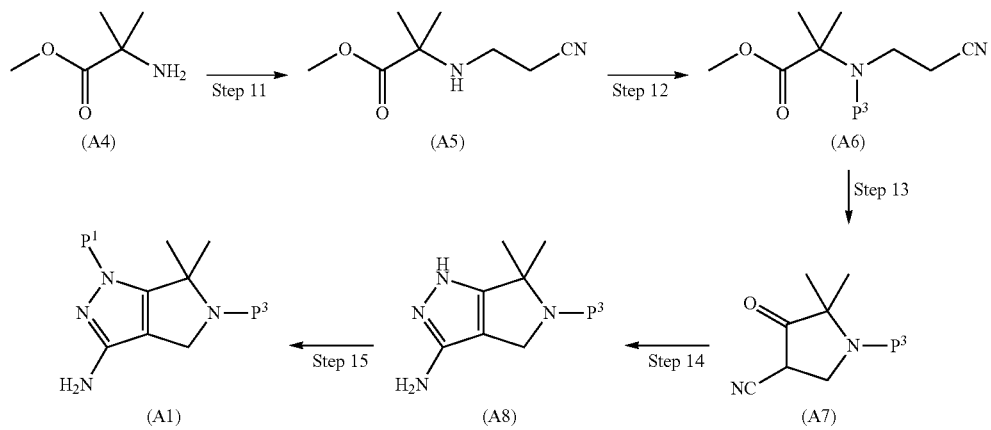

In the formulas (A6), (A7), and (A8), $P^3$ has the same meaning as defined in compound (A1).

(Step 11)

Step 11 is the step of reacting compound (A4) with acrylonitrile to obtain compound (A5).

The amount of the acrylonitrile used is preferably 1 to 10 mol, more preferably 1 to 3 mol, with respect to 1 mol of the compound (A4).

In step 11, there is no limitation as long as a solvent does not have influence on the reaction, and an aqueous solvent is preferred.

In step 11, a base can be further added in order to accelerate the reaction. Examples of the base include inorganic bases such as potassium hydroxide. The amount of the base added is preferably 0.8 to 2 mol, with respect to 1 mol of the compound (A1).

The reaction temperature of step 11 can be appropriately set by those skilled in the art. The reaction temperature is usually 0 to 100° C., preferably 50 to 90° C.

(Step 12)

Step 12 is the step of protecting the amino group of compound (A5) with $P^3$ group to obtain compound (A6). The protection reaction of the amino group with the $P^3$ group can be performed by a method well known to those skilled in the art (e.g., a method described in, for example, Protective Groups in Organic Synthesis, 4th ed., T.W. Greene, P.G.M. Wuts, John Wiley & Sons Inc. (2006)).

(Step 13)

Step 13 is the step of performing the cyclization reaction of compound (A6) to obtain compound (A7).

The reaction of step 13 may be performed in a solvent or may be performed without a solvent. In the case of using a solvent, there is no limitation as long as the solvent does not have influence on the reaction, and an organic solvent is preferred. Examples of the organic solvent include diethyl ether, tetrahydrofuran (THF), 1,4-dioxane, N,N-dimethylformamide (DMF) toluene.

In step 13, a base can be further added in order to accelerate the reaction. Examples of the base include sodium hydride, potassium hydride, sodium methoxide, sodiumethoxide, n-butyllithium, and tert-butoxy potassium. The amount of the base added is preferably 1 to 3 mol with respect to 1 mol of the compound (A6).

The reaction temperature of step 13 can be appropriately set by those skilled in the art. The reaction temperature is usually 20 to 150° C., preferably 50 to 100° C.

(Step 14)

Step 14 is the step of reacting compound (A7) with hydrazine to obtain compound (A8).

The reaction of step 14 may be performed in a solvent or may be performed without a solvent. In the case of using a solvent, there is no limitation as long as the solvent does not have influence on the reaction, and an organic solvent is preferred. Examples of the organic solvent include ethanol, n-propanol, and n-butanol.

In step 14, an acid can be further added in order to accelerate the reaction. Examples of the acid include acetic acid, hydrochloric acid, and sulfuric acid. The amount of the acid added is preferably 1 to 10 mol with respect to 1 mol of the compound (A7).

The reaction temperature of step 14 can be appropriately set by those skilled in the art. The reaction temperature is usually 20 to 150° C., preferably 50 to 120° C.

(Step 15)

Step 15 is the step of protecting the amino group of compound (A7) with $P^1$ group to obtain compound (A1). The protection reaction of the amino group with the $P^1$ group can be performed by a method well known to those skilled in the art (e.g., a method described in, for example, Protective Groups in Organic Synthesis, 4th ed., T.W. Greene, P.G.M. Wuts, John Wiley & Sons Inc. (2006)).

Example

Hereinafter, the present invention will be described further specifically as to the compound according to the present embodiment or the pharmaceutically acceptable salt thereof by showing Examples (Examples 1 to 125), Reference Examples (Reference Examples 1 to 137), and Test Examples (Test Examples 1 to 12); however, these examples are given for more understanding the present invention and does not limit the scope of the present invention.

DIOL silica gel in silica gel column chromatography represents CHROMATOREX (trade name) DIOL MB 100-40/75 manufactured by Fuji Silysia Chemical Ltd.

DNH silica gel in silica gel column chromatography represents CHROMATOREX (trade name) DNH MB 100-40/75 manufactured by Fuji Silysia Chemical Ltd.

219

In the case where a plurality of values of mass spectra are observed due to the presence of isotopes, only one having minimum m/z was described. DUIS in an ionization mode of a mass spectrum is a mixed mode of ESI and APCI.

$^1$H-NMR is indicated by chemical shift (δ) with tetramethylsilane as an internal standard (0 ppm), and a coupling constant (J value) is indicated by Hz unit, unless otherwise specified. An abbreviation for the split pattern of each peak has the following meaning: s: singlet, d: doublet, t: triplet, q: quartet, and br: broad.

Abbreviations described in Examples and Reference Examples are usually used as meanings generally used in the fields of organic chemistry and pharmacy. Each abbreviation is specifically understood by those skilled in the art as follows.

ATP: adenosine triphosphate
Boc: tert-butyloxycarbonyl
DIPEA: N,N-diisopropylethylamine
DMF: N,N-dimethylformamide
DMSO: dimethyl sulfoxide
DTT: dithiothreitol
Et: ethyl
FBS: fetal bovine serum
HEPES: N-2-hydroxyethylpiperazine-N'-2-ethanesulfonic acid
MBP: myelin basic protein
n-: normal
NADPH: nicotinamide adenine dinucleotide phosphate
PBMC: peripheral blood mononuclear cell
PBS: aqueous solution of phosphate-buffered sodium chloride
TBME: tert-butyl methyl ether
TBS: tert-butyldimethylsilyl
tert-: tertiary
THF: tetrahydrofuran
Tris: trishydroxyaminomethane Example 1

(S)—N-(2-Hydroxy-1-phenylethyl)-6,6-dimethyl-3-[1-(trimethylsilyl)cyclobutanecarboxamido]-4,6-dihydropyrrolo[3,4-c]pyrazole-5(1H)-carboxamide (Compound No. IV-114)

[Chemical Formula 17]

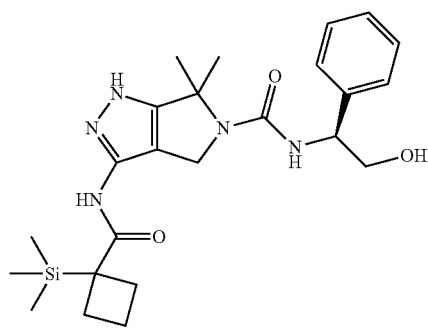

To a solution of 308 mg (0.698 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 6 ml of THF, 0.23 ml (1.4 mmol) of DIPEA and 472 mg (3.44 mmol) of (S)-(+)-2-phenylglycinol were added at room temperature, then applied to a microwave reaction apparatus, and reacted at 80° C. for 1 hour. Subsequently, 2.7 ml (67 mmol) of methanol and 2.7 ml (19 mmol) of triethylamine were added to the reaction solution, then applied to a microwave reaction apparatus, and reacted at 80° C. for 0.5 hours.

After the completion of the reaction, the reaction solution was concentrated under reduced pressure. The obtained concentration residue was subjected to silica gel column chromatography (DIOL silica gel, elution solvent: 1,2-dichloroethane:methanol=100:0 to 98:2 (V/V)), and a fraction containing the compound of interest was concentrated under reduced pressure. For the obtained concentration residue, crystallization was performed with ethyl acetate/diethyl ether, and the obtained solid was collected by filtration. 20 ml of water was added to the obtained solid and stirred, and then, insoluble matter was collected by filtration and dried under reduced pressure to obtain 152 mg of the title compound (yield: 46%) as a white solid.

Mass spectrum (DUIS, m/z): 470 [M+1]$^+$.

$^1$H-NMR spectrum (400 MHz, DMSO-d$_6$) δ: 12.20 & 11.65 (br s, total 1H), 9.66-9.46 (m, 1H), 7.41-7.25 (m, 4H), 7.22-7.15 (m, 1H), 6.18 & 6.06 (d, J=7.7 Hz, total 1H), 4.88 (t, J=5.9 Hz, 1H), 4.83-4.71 (m, 1H), 4.62-4.41 (m, 2H), 3.69-3.52 (m, 2H), 2.49-2.41 (m, 2H), 2.30-2.12 (m, 2H), 1.93-1.73 (m, 2H), 1.68-1.44 (m, 6H), 0.17-0.04 (m, 9H).

Example 2

(S)—N-(2-Hydroxy-1-phenylethyl)-6,6-dimethyl-3-[1-(trimethylsilyl)cyclopropanecarboxamido]-4,6-dihydropyrrolo[3,4-c]pyrazole-5(1H)-carboxamide (Compound No. III-114)

[Chemical Formula 18]

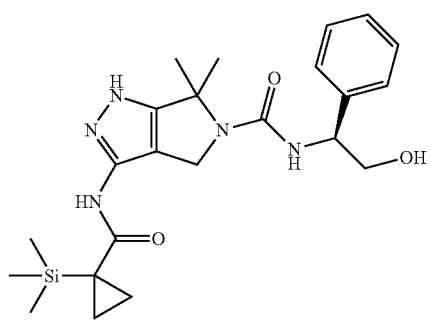

To a solution of 433 mg (1.08 mmol) of ethyl 6,6-dimethyl-3-[1-(trimethylsilyl)cyclopropanecarboxamido]-5,6-dihydropyrrolo[3,4-c]pyrazole-2(4H)-carboxylate hydrochloride synthesized in the similar manner as in Reference Example 7 in 7.5 ml of dehydrated dichloromethane, 0.90 ml (5.2 mmol) of DIPEA was added at room temperature in a nitrogen atmosphere, and then, a solution of 275 mg (0.928 mmol) of bis(trichloromethyl)carbonate in 2.5 ml of dehydrated dichloromethane was added dropwise at −78° C. and stirred at the same temperature as above for 2.5 hours.

After the completion of the reaction, 10 ml of a saturated aqueous solution of sodium bicarbonate was added to the reaction solution and stirred while the temperature was raised to room temperature for a while. The organic layer and the aqueous layer were separated, and then, the aqueous layer was subjected to extraction with dichloromethane twice. All of the obtained organic layers were dried over anhydrous magnesium sulfate, filtered, and concentrated under reduced pressure. The obtained concentration residue was subjected to silica gel column chromatography (elution solvent: n-hexane:ethyl acetate=90:10 to 80:20 (V/V)), and a fraction containing the compound of interest was concentrated under reduced pressure and dried under reduced pressure to obtain a concentration residue.

To a solution of 457 mg of the obtained concentration residue in 4 ml of dehydrated THF, 0.40 ml (2.2 mmol) of DIPEA and 528 mg (3.85 mmol) of (S)-(+)-2-phenylglycinol were added at room temperature in a nitrogen atmosphere and then stirred for 3.75 hours while heated to reflux. Subsequently, 0.90 ml (6.5 mmol) of triethylamine and 0.90 ml (22 mmol) of methanol were added to the reaction solution and then stirred for 1 hour while heated to reflux.

After the completion of the reaction, water was added to the reaction solution, followed by extraction with dichloromethane three times. All of the obtained organic layers were dried over anhydrous magnesium sulfate, filtered, and concentrated under reduced pressure. The obtained concentration residue was subjected to silica gel column chromatography (DNH silica gel, elution solvent: dichloromethane:methanol=100:0 to 97:3 (V/V)), and a fraction containing the compound of interest was concentrated under reduced pressure. For the obtained concentration residue, crystallization was performed with ethyl acetate/diisopropyl ether/n-hexane, and the deposited solid was collected by filtration, washed by sousing with n-hexane, and then dried under reduced pressure to obtain 388 mg of the title compound (yield: 79% [2 steps]) as a white solid.

Mass spectrum (CI, m/z): 456 [M+1]$^+$.

$^1$H-NMR spectrum (400 MHz, DMSO-d$_6$) δ: 12.02 & 11.54 (br s, total 1H), 9.44 & 9.25 (br s, total 1H), 7.40-7.33 (m, 2H), 7.33-7.24 (m, 2H), 7.23-7.16 (m, 1H), 5.88-5.69 (m, 1H), 4.86-4.79 (m, 1H), 4.61 (t, J=5.6 Hz, 1H), 4.55-4.37 (m, 2H), 3.71-3.64 (m, 2H), 1.63 (s, 3H), 1.57 (s, 3H), 1.08-1.01 (m, 2H), 0.83-0.60 (m, 2H), 0.07 (s, 9H).

Example 3

(S)—N-(2-Hydroxy-1-phenylethyl)-6,6-dimethyl-3-[2-methyl-2-(trimethylsilyl)propanamido]-4,6-dihydropyrrolo[3,4-c]pyrazole-5(1H)-carboxamide (Compound No. II-114)

[Chemical Formula 19]

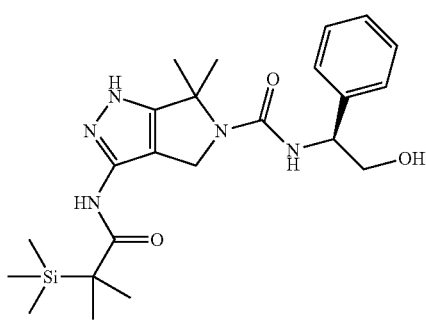

To a solution of 337 mg (0.714 mmol) of 5-tert-butyl 1-ethyl 6,6-dimethyl-3-[2-methyl-2-(trimethylsilyl)propanamido]pyrrolo[3,4-c]pyrazole-1,5(4H,6H)-dicarboxylate synthesized in the similar manner as in Reference Example 9 in 3 ml of dehydrated dichloromethane, 0.25 ml (2.2 mmol) of 2,6-lutidine and 0.39 ml (2.2 mmol) of trimethylsilyl trifluoromethanesulfonate were added in this order at 0° C. in a nitrogen atmosphere and stirred at the same temperature as above for 1.5 hours.

After the completion of the reaction, the reaction solution was diluted with dichloromethane and subsequently washed with a saturated aqueous solution of sodium bicarbonate. The organic layer and the aqueous layer were separated, and then, the aqueous layer was subjected to extraction with dichloromethane twice. All of the obtained organic layers were dried over anhydrous magnesium sulfate, filtered, and concentrated under reduced pressure. The operation of adding 25 ml of toluene to the obtained concentration residue and concentrating it under reduced pressure was repeated three times, followed by drying under reduced pressure to obtain a concentration residue.

To a solution of 292 mg of the obtained concentration residue in 5 ml of dehydrated dichloromethane, 0.38 ml (2.2 mmol) of DIPEA was added at room temperature in a nitrogen atmosphere, and then, 149 mg (0.502 mmol) of bis(trichloromethyl)carbonate was added at −78° C. and stirred at the same temperature as above for 2.5 hours.

After the completion of the reaction, 7 ml of a saturated aqueous solution of sodium bicarbonate was added to the reaction solution and stirred while the temperature was raised to room temperature for a while. The organic layer and the aqueous layer were separated, and then, the aqueous layer was subjected to extraction with dichloromethane once. All of the organic layers were dried over anhydrous magnesium sulfate, filtered, and concentrated under reduced pressure. The obtained concentration residue was subjected to silica gel column chromatography (elution solvent: n-hexane:ethyl acetate=90:10 to 85:15 (V/V)), and a fraction containing the compound of interest was concentrated under reduced pressure and dried under reduced pressure to obtain a concentration residue.

To a solution of 262 mg of the obtained concentration residue in 3 ml of dehydrated THF, 0.27 ml (1.6 mmol) of DIPEA and 255 mg (1.86 mmol) of (S)-(+)-2-phenylglycinol were added at room temperature in a nitrogen atmosphere and then stirred for 2.5 hours while heated to reflux. Subsequently, 1.0 ml (7.2 mmol) of triethylamine and 1.0 ml (25 mmol) of methanol were added to the reaction solution and then stirred for 5.5 hours while heated to reflux.

After the completion of the reaction, water was added to the reaction solution, followed by extraction with dichloromethane three times. All of the obtained organic layers were dried over anhydrous magnesium sulfate, filtered, and concentrated under reduced pressure. 0.10 ml of acetic acid was added to the obtained concentration residue and then subjected to silica gel column chromatography (DIOL silica gel, elution solvent: dichloromethane:methanol=100:0 to 97:3 (V/V)), and a fraction containing the compound of interest was concentrated under reduced pressure. For the obtained concentration residue, crystallization was performed with ethyl acetate/n-hexane, and the obtained solid was collected by filtration, washed by sousing with n-hexane, and then dried under reduced pressure to obtain 206 mg of the title compound (yield: 63% [3 steps]) as a pale yellow solid.

Mass spectrum (CI, m/z): 458 [M+1]$^+$.

$^1$H-NMR spectrum (400 MHz, DMSO-d$_6$) δ: 12.25 & 11.64 (br s, total 1H), 9.42-9.11 (m, 1H), 7.38-7.25 (m, 4H), 7.23-7.15 (m, 1H), 6.21-6.05 (m, 1H), 4.87 (t, J=5.9 Hz, 1H), 4.81-4.73 (m, 1H), 4.57-4.41 (m, 2H), 3.70-3.54 (m, 2H), 1.66-1.47 (m, 6H), 1.25 (s, 6H), 0.04 (s, 9H).

Example 4

(S)-3-[1-(Ethyldimethylsilyl)cyclobutanecarboxamido]-N-(2-hydroxy-1-phenylethyl)-6,6-dimethyl-4,6-dihydropyrrolo[3,4-c]pyrazole-5(1H)-carboxamide (Compound No. IV-117)

[Chemical Formula 20]

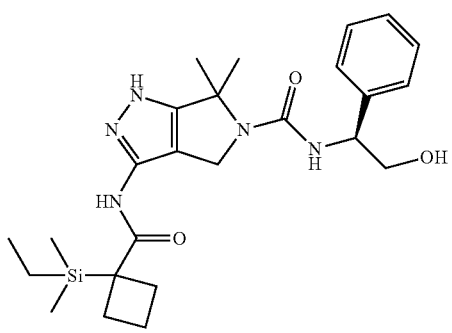

To a solution of 454 mg (0.997 mmol) of ethyl 5-(chlorocarbonyl)-3-[1-(ethyl dimethylsilyl)cyclobutanecarboxamido]-6,6-dimethyl-5,6-dihydropyrrolo[3,4-c]pyrazole-2(4H)-carboxylate synthesized in the similar manner as in Reference Example 13 in 10 ml of dehydrated THF, 700 mg (5.10 mmol) of (S)-(+)-2-phenylglycinol and 0.35 ml (2.0 mmol) of DIPEA were added at room temperature in an argon atmosphere and then stirred at 60° C. for 4 hours. Subsequently, 6 ml of methanol and 2 ml of triethylamine were added to the reaction solution and stirred at 60° C. for 2 hours.

After the completion of the reaction, the reaction solution was concentrated under reduced pressure, a saturated aqueous solution of sodium bicarbonate was added to the obtained concentration residue, and the mixed solution was subjected to extraction with dichloromethane three times. All of the obtained organic layers were dried over anhydrous magnesium sulfate and filtered, and then, the filtrate was concentrated under reduced pressure. The obtained concentration residue was subjected to silica gel column chromatography (DIOL silica gel, elution solvent: 1,2-dichloroethane:methanol=100:0 to 98:2 (V/V)), and a fraction containing the compound of interest was concentrated under reduced pressure. For the concentration residue, crystallization was performed with dichloromethane/diisopropyl ether, and the deposited solid was collected by filtration and subsequently dried under reduced pressure to obtain 404 mg of the title compound (yield: 84%) as a white solid.

Mass spectrum (DUIS, m/z): 484 [M+1]$^+$.

$^1$H-NMR spectrum (400 MHz, DMSO-d$_6$) δ: 12.20 & 11.66 (br s, total 1H), 9.64-9.47 (m, 1H), 7.40-7.14 (m, 5H), 6.26-6.01 (m, 1H), 4.88 (t, J=5.8 Hz, 1H), 4.83-4.71 (m, 1H), 4.60-4.43 (m, 2H), 3.66-3.54 (m, 2H), 2.48-2.42 (m, 2H), 2.33-2.14 (m, 2H), 1.93-1.72 (m, 2H), 1.67-1.45 (m, 6H), 0.92 (t, J=7.9 Hz, 3H), 0.60 (q, J=7.9 Hz, 2H), 0.08 (s, 6H).

Example 5

(S)-3-[2-(Ethyldimethylsilyl)-2-methylpropanamido]-N-(2-hydroxy-1-phenylethyl)-6,6-dimethyl-4,6-dihydropyrrolo[3,4-c]pyrazole-5(1H)-carboxamide (Compound No. II-116)

[Chemical Formula 21]

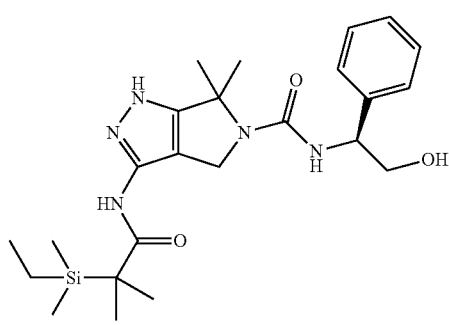

To a solution of 2.44 g (6.41 mmol) of ethyl 3-[2-(ethyldimethylsilyl)-2-methylpropanamido]-6,6-dimethyl-5,6-dihydropyrrolo[3,4-c]pyrazole-1(4H)-carboxylate synthesized in the similar manner as in Reference Example 16 in 30 ml of dehydrated dichloromethane, 5.6 ml (32 mmol) of DIPEA and a solution of 1.33 g (4.48 mmol) of bis(trichloromethyl)carbonate in 10 ml of dehydrated dichloromethane were added in this order at −78° C. in a nitrogen atmosphere and stirred at the same temperature as above for 1 hour.

After the completion of the reaction, a saturated aqueous solution of sodium bicarbonate was added to the reaction solution, and the temperature was raised to room temperature for a while with stirring. After separation into an aqueous layer and an organic layer, the aqueous layer was subjected to extraction with dichloromethane. All of the obtained organic layers were dried over anhydrous magnesium sulfate and filtered, and the filtrate was concentrated under reduced pressure. The obtained concentration residue was subjected to silica gel column chromatography (elution solvent: n-hexane:ethyl acetate=95:5 to 70:30 (V/V)), and a fraction containing the compound of interest was concentrated under reduced pressure to obtain 2.51 g of a concentration residue.

To a solution of 474 mg of the obtained concentration residue in ml of dehydrated THF, 700 mg (5.10 mmol) of (S)-2-amino-2-phenylethanol and 0.35 ml (2.0 mmol) of DIPEA were added at room temperature in an argon atmosphere, then applied to a microwave reaction apparatus, and reacted at 100° C. for 2 hours. After standing to cool, 6 ml of methanol and 2 ml of triethylamine were added, applied to a microwave reaction apparatus, and reacted at 80° C. for 3 hours.

After the completion of the reaction, the reaction solution was concentrated under reduced pressure, a saturated aqueous solution of sodium bicarbonate was added to the obtained concentration residue, and the mixed solution was subjected to extraction with dichloromethane three times. All of the obtained organic layers were dried over anhydrous magnesium sulfate and filtered, and the filtrate was concentrated under reduced pressure. The obtained concentration residue was subjected to silica gel column chromatography (DIOL silica gel, elution solvent: 1,2-dichloroethane:methanol=100:0 to 98:2 (V/V)), and a fraction containing the compound of interest was concentrated under reduced pressure. For the concentration residue, crystallization was performed with dichloromethane/diisopropyl ether, and the deposited solid was collected by filtration and subsequently dried under reduced pressure to obtain 321 mg of the title compound (yield: 56% [2 steps]) as a white solid.

Mass spectrum (DUIS, m/z): 472 [M+1]$^+$.

$^1$H-NMR spectrum (400 MHz, DMSO-d$_6$) δ: 12.26 & 11.67 (br s, total 1H), 9.42-9.16 (m, 1H), 7.38-7.25 (m, 4H), 7.25-7.14 (m, 1H), 6.20-6.04 (m, 1H), 4.88 (t, J=5.8 Hz, 1H), 4.82-4.72 (m, 1H), 4.55-4.42 (m, 2H), 3.66-3.55 (m, 2H), 1.64-1.48 (m, 6H), 1.26 (s, 6H), 0.90 (t, J=7.9 Hz, 3H), 0.56 (q, J=7.9 Hz, 2H), 0.02 (s, 6H).

Example 6

(S)—N-(2-Hydroxy-1-phenylethyl)-N,6,6-trimethyl-3-[1-(trimethylsilyl)cyclobutanecarboxamido]-4,6-dihydropyrrolo[3,4-c]pyrazole-5(1H)-carboxamide (Compound No. IV-119)

[Chemical Formula 22]

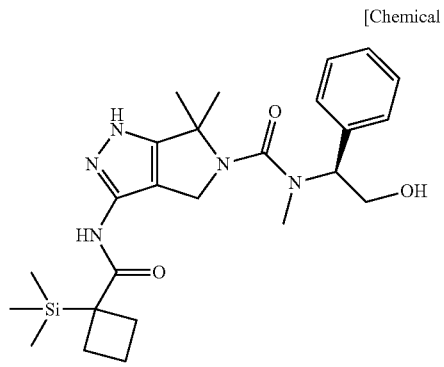

To a solution of 210 mg (1.39 mmol) of (S)-2-(methylamino)-2-phenylethanol [synthesized according to the method described in J. Org. Chem., 1992, 57, 5383-5394] in 3 ml of dehydrated 1,4-dioxane, 0.24 ml (1.37 mmol) of DIPEA and 200 mg (0.454 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 were added in an argon atmosphere and stirred at 100° C. for 3 hours. Subsequently, 1 ml of triethylamine and 1 ml of methanol were added to the reaction solution and stirred at room temperature for 16 hours.

After the completion of the reaction, water was added to the reaction solution, followed by extraction from the mixed solution with ethyl acetate. The obtained organic layer was washed with a saturated aqueous solution of sodium chloride, dried over anhydrous sodium sulfate, filtered, and concentrated under reduced pressure. The obtained concentration residue was subjected to silica gel chromatography (elution solvent: n-hexane:ethyl acetate=90:10 to 0:100 (V/V)), and a fraction containing the compound of interest was concentrated under reduced pressure. The obtained concentration residue was subjected again to silica gel chromatography (elution solvent: n-hexane:ethyl acetate=50:50 to 0:100 (V/V)), and a fraction containing the compound of interest was concentrated under reduced pressure. The obtained concentration residue was repulp-washed in hexane, and the solid was collected by filtration and then dried under reduced pressure to obtain 105 mg of the title compound (yield: 48%) as a white solid.

Mass spectrum (CI, m/z): 484 [M+1]$^+$ $^1$H-NMR spectrum (400 MHz, DMSO-d$_6$) δ: 12.21 & 11.84 (br s, total 1H), 9.75-9.42 (m, 1H), 7.41-7.21 (m, 5H), 4.85 (t, J=5.2 Hz, 1H), 4.82-4.76 (m, 1H), 4.58-4.35 (m, 2H), 3.96-3.78 (m, 2H), 2.52 (s, 3H), 2.47-2.38 (m, 2H), 2.23-2.11 (m, 2H), 1.87-1.72 (m, 2H), 1.71-1.52 (m, 6H), 0.05 (s, 9H).

Example 7

(S)-2-[(2-Methoxypropan-2-yl)oxy]-1-phenylethyl 6,6-dimethyl-3-[1-(trimethylsilyl)cyclobutanecarboxamido]-4,6-dihydropyrrolo[3,4-c]pyrazole-5(1H)-carboxylate (Compound No. VI-360)

[Chemical Formula 23]

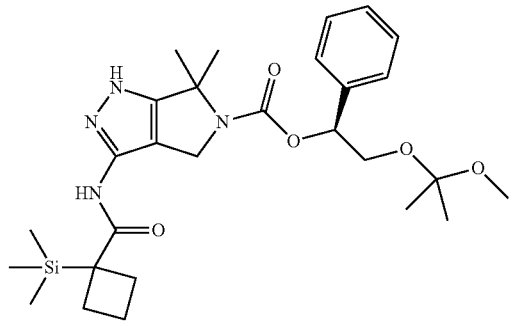

To 205 mg of crude ethyl 6,6-dimethyl-3-[1-(trimethylsilyl)cyclobutanecarboxamido]-5,6-dihydropyrrolo[3,4-c]pyrazole-1(4H)-carboxylate [containing impurities] obtained through the same reaction as in Reference Example 5 from 225 mg (0.470 mmol) of 5-tert-butyl 1-ethyl 6,6-dimethyl-3-[1-(trimethylsilyl)cyclobutanecarboxamido]pyrrolo[3,4-c]pyrazole-1,5(4H,6H)-dicarboxylate synthesized in the similar manner as in Reference Example 4, a solution of 187 mg (0.533 mmol) of (S)-2,5-dioxopyrrolidin-1-yl {2-[(2-methoxypropan-2-yl)oxy]-1-phenylethyl}carbonate synthesized in the similar manner as in Reference Example 18 in 3 ml of THF and 0.28 ml (1.6 mmol) of DIPEA were added at room temperature in a nitrogen atmosphere and stirred at the same temperature as above for 15 hours. Subsequently, 1.0 ml (7.2 mmol) of triethylamine and 0.70 ml (17 mmol) of methanol were added to the reaction solution and stirred at room temperature 4.5 hours and for 2 hours while heated to reflux, and then, 247 mg (1.80 mmol) of (S)-2-amino-2-phenylethanol was added to the reaction solution and stirred for 4.5 hours while heated to reflux.

After the completion of the reaction, water was added to the reaction solution, followed by extraction with dichloromethane three times. All of the obtained organic layers were dried over anhydrous magnesium sulfate, filtered, and concentrated under reduced pressure. The obtained concentration residue was subjected to silica gel column chromatography (elution solvent: n-hexane:ethyl acetate=80:20 to 50:50 (V/V)), and a fraction containing the compound of interest was concentrated under reduced pressure. For the obtained concentration residue, crystallization was performed with ethyl acetate/n-hexane, and the deposited solid was collected by filtration, washed by sousing with n-hexane, and then dried under reduced pressure to obtain 22.7 mg of the title compound (yield: 9% [2 steps]) as a white solid. The filtrate was further concentrated under reduced pressure and dried under reduced pressure to obtain 178 mg of the title compound (yield: 70% [2 steps]) as a white foam.

Mass spectrum (ESI, m/z): 565 [M+23(Na)]⁺, 541 [M−1]⁻.

¹H-NMR spectrum (400 MHz, DMSO-d₆) δ: 12.35-12.19 & 11.96-11.80 (m, total 1H), 9.85-9.44 (m, 1H), 7.45-7.26 (m, 5H), 5.81-5.68 (m, 1H), 4.63-4.18 (m, 2H), 3.72-3.50 (m, 2H), 3.08-2.94 (m, 3H), 2.56-2.38 (m, 2H), 2.30-2.10 (m, 2H), 1.94-1.75 (m, 2H), 1.73-1.45 (m, 6H), 1.32-1.18 (m, 6H), 0.13-0.02 (m, 9H).

Example 8

(S)-2-Hydroxy-1-phenylethyl 6,6-dimethyl-3-[1-(trimethylsilyl)cyclobutanecarboxamido]-4,6-dihydropyrrolo[3,4-c]pyrazole-5(1H)-carboxylate (Compound No. IV-2)

[Chemical Formula 24]

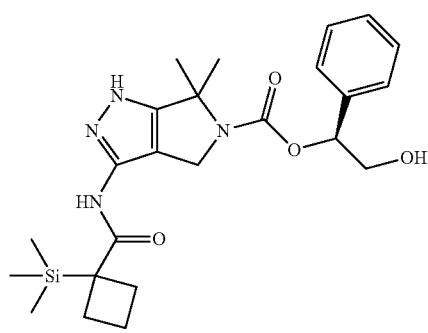

To a solution of 175 mg (0.322 mmol) of (S)-2-[(2-methoxypropan-2-yl)oxy]-1-phenylethyl 6,6-dimethyl-3-[1-(trimethylsilyl)cyclobutanecarboxamido]-4,6-dihydropyrrolo[3,4-c]pyrazole-5(1H)-carboxylate synthesized in the similar manner as in Example 7 in 2.5 ml of methanol, 9.6 mg (0.038 mmol) of pyridinium p-toluenesulfonate was added at 0° C. in a nitrogen atmosphere and stirred at the same temperature as above for 70 minutes.

After the completion of the reaction, 0.1 ml of triethylamine was added to the reaction solution and then concentrated under reduced pressure. The obtained concentration residue was subjected to silica gel column chromatography (elution solvent: n-hexane:ethyl acetate=65:35 to 25:75 (V/V)), and a fraction containing the compound of interest was concentrated under reduced pressure. For the obtained concentration residue, crystallization was performed with ethyl acetate/n-hexane, and the deposited solid was collected by filtration, washed by sousing with n-hexane, and then dried under reduced pressure to obtain 124 mg of the title compound (yield: 82%) as a white solid.

Mass spectrum (CI, m/z): 471 [M+1]⁺.

¹H-NMR spectrum (400 MHz, DMSO-d₆) δ: 12.35-12.11 & 11.97-11.79 (m, total 1H), 9.84-9.46 (m, 1H), 7.46-7.20 (m, 5H), 5.71-5.58 (m, 1H), 5.12-4.95 (m, 1H), 4.72-4.18 (m, 2H), 3.80-3.54 (m, 2H), 2.60-2.38 (m, 2H), 2.30-2.10 (m, 2H), 1.93-1.74 (m, 2H), 1.74-1.43 (m, 6H), 0.16-0.02 (m, 9H).

Example 9

2-Methoxy-1-phenylethyl 6,6-dimethyl-3-[1-(trimethylsilyl)cyclopropanecarboxamido]-4,6-dihydropyrrolo[3,4-c]pyrazole-5(1H)-carboxylate (Compound No. III-5)

[Chemical Formula 25]

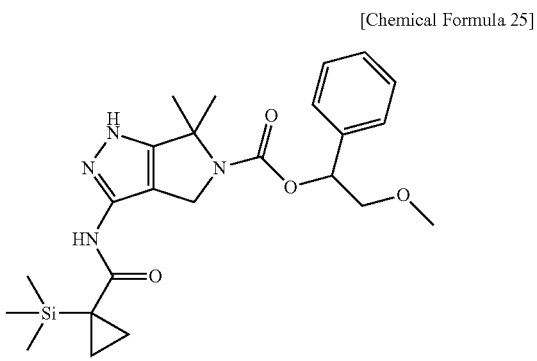

To a solution of 2.15 g (5.36 mmol) of ethyl 6,6-dimethyl-3-[1-(trimethylsilyl)cyclopropanecarboxamido]-5,6-dihydropyrrolo[3,4-c]pyrazole-2(4H)-carboxylate hydrochloride synthesized in the similar manner as in Reference Example 7 in 72 ml of dehydrated dichloromethane, 3.6 ml (21 mmol) of DIPEA was added at room temperature and subsequently cooled in a dry ice/acetone coolant, and then, a solution of 1.17 g (3.94 mmol) of bis(trichloromethyl)carbonate in 12 ml of dehydrated dichloromethane was added dropwise over 30 minutes and stirred at the same temperature as above for 6 hours. During this reaction, 3.6 ml (21 mmol) of DIPEA 4 times and DIPEA (1.0 ml, 5.7 mmol) once were added in this order.

After the completion of the reaction, 46 ml of a saturated aqueous solution of sodium bicarbonate was added at −78° C., and then, the temperature was raised to room temperature for a while. The reaction solution was separated into an aqueous layer and an organic layer, then the aqueous layer was subjected to extraction with 50 ml of dichloromethane twice, all of the obtained organic layers were dried over anhydrous magnesium sulfate and filtered, and then, the filtrate was concentrated under reduced pressure. The obtained concentration residue was subjected to silica gel column chromatography (elution solvent: n-hexane:ethyl acetate=78:22 to 57:43 (V/V)), and a fraction containing the compound of interest was concentrated under reduced pressure. 20 ml of n-hexane was added to the concentration residue and cooled in ice, and then, the deposited solid was collected by filtration and dried under reduced pressure to obtain 1.96 g of white solid.

To 40.4 mg (0.0946 mmol) of the obtained white solid, 224 mg (1.48 mmol) of 2-methoxy-1-phenylethanol [synthesized according to the method described in WO 2012/138648], 26.0 mg (0.188 mmol) of potassium carbonate, 0.8 ml of 1,2-dimethoxyethane, and 80 mg of molecular sieve 4A (powder) were added at room temperature and then stirred at 80° C. for 26 hours.

After the completion of the reaction, insoluble matter was filtered, and 10 ml of ethyl acetate, 5 ml of water, and 5 ml of a saturated aqueous solution of sodium chloride were added to the filtrate and then the aqueous layer and the organic layer were separated. The obtained organic layer was dried over anhydrous magnesium sulfate and filtered, and then, the filtrate was concentrated under reduced pressure. The obtained concentration residue was subjected to silica gel column chromatography four times (silica gel (1st run), elution solvent: 1,2-dichloroethane:methanol=100:0 to 93:7 (V/V); silica gel (2nd run), elution solvent: ethyl acetate:methanol=98:2 to 95:5 (V/V); silica gel (3rd run), elution solvent: 1,2-dichloroethane:methanol=98:2 to 95:5 (V/V); and DNH silica gel, elution solvent: 1,2-dichloroethane:methanol=98:2 to 95:5 (V/V)) and preparative HPLC (column: X-Bridge (trade name) ODS, elution solvent: 0.1% aqueous formic acid solution: 0.1% formic acid:acetonitrile=50:50 to 5:95 (V/V))), and a fraction containing the compound of interest was neutralized with dilute aqueous ammonia solution and then concentrated under reduced pressure. The obtained concentration residue was dissolved by adding acetonitrile and water and then freeze-dried to obtain 4.1 mg of the title compound (yield: 8% [2 steps]) as a white foam.

Mass spectrum (DUIS, m/z): 471 [M+1]$^+$.

$^1$H-NMR spectrum (400 MHz, DMSO-d$_6$) δ: 12.40-11.86 (m, 1H), 10.11-9.61 (m, 1H), 7.49-7.22 (m, 5H), 5.90-5.71 (m, 1H), 4.63-4.14 (m, 2H), 3.77-3.51 (m, 2H), 3.30-3.29 (m, 3H), 1.78-1.40 (m, 6H), 1.11-0.92 (m, 2H), 0.81-0.59 (m, 2H), 0.11-0.04 (m, 9H).

Example 10

N-[5-(4-Hydroxy-3-phenylbutanoyl)-6,6-dimethyl-1,4,5,6-tetrahydropyrrolo[3,4-c]pyrazol-3-yl]-1-(trimethylsilyl)cyclobutanecarboxamide (Compound No. IV-558)

[Chemical Formula 26]

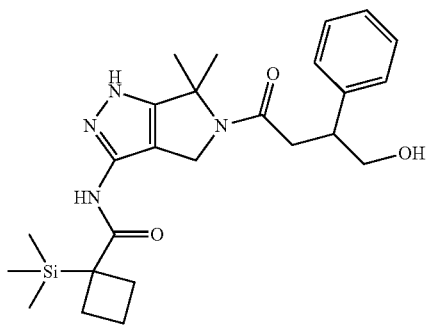

To a solution of 160 mg (0.536 mmol) of ethyl 4-(benzyloxy)-3-phenylbutanoate synthesized in the similar manner as in Reference Example 19 in a mixture of 3 ml of THF/1.5 ml of water, 48 mg (1.1 mmol) of lithium hydroxide monohydrate was added at room temperature in an argon atmosphere, stirred at the same temperature as above for 2 hours, and then stirred at 60° C. for 3 hours. The reaction solution was concentrated under reduced pressure, and 3 ml of ethanol and 1.0 ml (2.0 mmol) of a 2 N aqueous sodium hydroxide solution were added to the obtained concentration residue at room temperature and heated and stirred at 60° C. for 1 hour.

After the completion of the reaction, 1 N hydrochloric acid was added to the reaction solution, followed by extraction from the mixed solution with ethyl acetate. The obtained organic layer was washed with a saturated aqueous solution of sodium chloride, then dried over anhydrous magnesium sulfate, filtered, and concentrated under reduced pressure. The obtained concentration residue was subjected to silica gel chromatography (elution solvent: n-hexane:ethyl acetate=90:10 to 50:50 (V/V)), and a fraction containing 4-(benzyloxy)-3-phenylbutanoic acid was concentrated under reduced pressure and dried under reduced pressure to obtain a concentration residue.

To a solution of 137 mg of the obtained concentration residue, 165 mg (0.436 mmol) of ethyl 6,6-dimethyl-3-[1-(trimethylsilyl)cyclobutanecarboxamido]-5,6-dihydropyrrolo[3,4-c]pyrazole-1(4H)-carboxylate synthesized in the similar manner as in Reference Example 5, and 201 mg (0.529 mmol) of O-(7-azabenzotriazol-1-yl)-N,N,N',N'-tetramethyluronium hexafluorophosphate in 3 ml of dehydrated dichloromethane, 0.185 ml (1.06 mmol) of DIPEA was added at room temperature in an argon atmosphere and stirred at room temperature for 16 hours.

After the completion of the reaction, water was added to the reaction solution, followed by extraction from the mixed solution with ethyl acetate. The obtained organic layer was washed with a saturated aqueous solution of sodium chloride, then dried over anhydrous sodium sulfate, filtered, and concentrated under reduced pressure. The obtained residue was subjected to silica gel chromatography (elution solvent: n-hexane:ethyl acetate=70:30 to 0:100 (V/V)), and a fraction containing ethyl 5-[4-(benzyloxy)-3-phenylbutanoyl]-6,6-dimethyl-3-[1-(trimethylsilyl)cyclobutanecarboxamido]-5,6-dihydropyrrolo[3,4-c]pyrazole-1(4H)-carboxylate was concentrated under reduced pressure and dried under reduced pressure to obtain a concentration residue.

To a solution of 256 mg of the obtained concentration residue in a mixture of 2 ml of THF/2 ml of methanol, 2 ml of triethylamine was added at room temperature in an argon atmosphere and stirred at the same temperature as above for 16 hours. Subsequently, 0.20 ml (3.3 mmol) of 2-aminoethanol was added at room temperature and stirred at the same temperature as above for 30 minutes.

After the completion of the reaction, water was added to the reaction solution, followed by extraction from the mixed solution with ethyl acetate. The obtained organic layer was washed with a saturated aqueous solution of sodium chloride, then dried over anhydrous sodium sulfate, filtered, and concentrated under reduced pressure to obtain a concentration residue.

To a solution of 250 mg of the obtained concentration residue in 3 ml of ethanol, 25 mg of 20% palladium hydroxide/carbon (containing 50% water) was added in an argon atmosphere and after replacement with a hydrogen atmosphere under reduced pressure, stirred at room temperature for 2 hours.

After the completion of the reaction, replacement with an argon atmosphere was performed, and the reaction solution was filtered through celite. The solid on the celite was washed with ethanol, and all of the filtrates were concentrated under reduced pressure. The obtained concentration residue was subjected to silica gel chromatography (DIOL silica gel, elution solvent: n-hexane:ethyl acetate=50:50 to 0:100 (V/V)), and a fraction containing the compound of interest was concentrated under reduced pressure and dried under reduced pressure to obtain 93 mg of the title compound (yield: 45% [3 steps]) as a white solid.

Mass spectrum (CI, m/z): 469 [M+1]$^+$ $^1$H-NMR spectrum (400 MHz, DMSO-d$_6$) δ: 12.19 & 11.83 (br s, total 1H), 9.84-9.47 (m, 1H), 7.27-7.21 (m, 4H), 7.18-7.12 (m, 1H), 4.72 (t, J=5.3 Hz, 1H), 4.57 (d, J=12.4 Hz, 1H), 4.44 (d, J=12.4 Hz, 1H), 3.60-3.52 (m, 2H), 3.27-3.19 (m, 1H), 2.75 (dd, J=6.0, 15.9 Hz, 1H), 2.58-2.52

(m, 1H), 2.48-2.40 (m, 2H), 2.25-2.12 (m, 2H), 1.89-1.72 (m, 2H), 1.61 (s, 3H), 1.49 (s, 3H), 0.08 (s, 9H).

Example 11

N-[5-(3-Hydroxy-3-phenylpropanoyl)-6,6-dimethyl-1,4,5,6-tetrahydropyrrolo[3,4-c]pyrazol-3-yl]-1-(trimethylsilyl)cyclobutanecarboxamide (Compound No. IV-562)

[Chemical Formula 27]

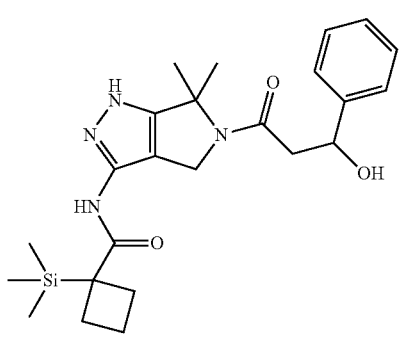

To a solution of 285 mg (0.543 mmol) of a mixture of ethyl 6,6-dimethyl-5-(3-oxo-3-phenylpropanoyl)-3-[1-(trimethylsilyl)cyclobutanecarboxamido]-5,6-dihydropyrrolo[3,4-c]pyrazole-2(4H)-carboxylate synthesized in the similar manner as in Reference Example 20 and (Z)-ethyl 5-(3-hydroxy-3-phenylacryloyl)-6,6-dimethyl-3-[1-(trimethylsilyl)cyclobutanecarboxamido]-5,6-dihydropyrrolo[3,4-c]pyrazole-2(4H)-carboxylate as a tautomer in 5 ml of methanol, 9.2 mg (0.24 mmol) of sodium borohydride was added at 0° C. in a nitrogen atmosphere and stirred for 1.5 hours after the temperature was raised to room temperature.

After the completion of the reaction, 10 ml of a saturated aqueous solution of ammonium chloride and dichloromethane were added to the reaction solution and then the aqueous layer and the organic layer were separated. The aqueous layer was subjected to extraction with dichloromethane, all of the obtained organic layers were dried over anhydrous magnesium sulfate and filtered, and then, the filtrate was concentrated under reduced pressure. The obtained concentration residue was subjected to silica gel column chromatography (DIOL silica gel, elution solvent: 1,2-dichloroethane:methanol=100:0 to 98:2 (V/V)), and a fraction containing the compound of interest was concentrated under reduced pressure. For the obtained concentration residue, crystallization was performed with dichloromethane/n-hexane, and the deposited solid was collected by filtration and dried under reduced pressure to obtain 88 mg of the title compound (yield: 35%) as a white solid.

Mass spectrum (DUIS, m/z): 455 [M+1]$^+$.

$^1$H-NMR spectrum (400 MHz, DMSO-d$_6$) δ: 12.23 & 11.85 (br s, total 1H), 9.75-9.43 (m, 1H), 7.44-7.13 (m, 5H), 5.35 (d, J=4.1 Hz, 1H), 5.05-4.98 (m, 1H), 4.57 (d, J=11.7 Hz, 1H), 4.35 (d, J=11.7 Hz, 1H), 2.65 (dd, J=8.9, 15.1 Hz, 1H), 2.57-2.35 (m, 3H), 2.25-2.09 (m, 2H), 1.89-1.72 (m, 2H), 1.65 (s, 3H), 1.61 (s, 3H), 0.06 (s, 9H).

Example 12

(R)-N-(3-Hydroxy-1-phenylpropyl)-6,6-dimethyl-3-[1-(trimethylsilyl)cyclobutanecarboxamido]-4,6-dihydropyrrolo[3,4-c]pyrazole-5(1H)-carboxamide (Compound No. IV-227)

[Chemical Formula 28]

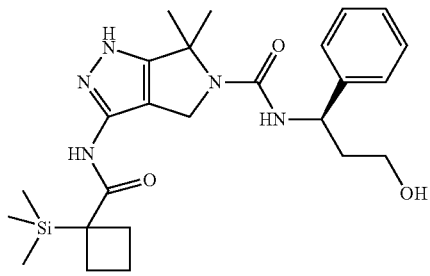

To a solution of 216 mg (0.489 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2 (4H)-carboxylate synthesized in the similar manner as in Reference Example 3 in 4.5 ml of 1,4-dioxane, 379 mg (2.51 mmol) of (R)-3-amino-3-phenylpropan-1-ol [purchased from Ark Pharm, Inc.] and 0.17 ml (0.99 mmol) of DIPEA were added at room temperature in an argon atmosphere, then applied to a microwave reaction apparatus, and reacted at 100° C. for 1 hour. After standing to cool, 1.0 ml of methanol and 0.5 ml of triethylamine were added, applied to a microwave reaction apparatus, and reacted at 80° C. for 1 hour.

After the completion of the reaction, the reaction solution was concentrated under reduced pressure, and ethyl acetate, water, and a saturated aqueous solution of sodium chloride were added thereto and then the aqueous layer and the organic layer were separated. The organic layer was dried over anhydrous magnesium sulfate and filtered, and then, the filtrate was concentrated under reduced pressure. The obtained concentration residue was subjected to silica gel column chromatography (DIOL silica gel, elution solvent: 1,2-dichloroethane:methanol=99:1 to 96:4 (V/V)), and a fraction containing the compound of interest was concentrated under reduced pressure. For the obtained concentration residue, crystallization was performed with ethyl acetate/diisopropyl ether, and the deposited solid was collected by filtration and dried under reduced pressure to obtain 173 mg of the title compound (yield: 73%) as a white solid.

Mass spectrum (CI, m/z): 484 [M+1]$^+$.

$^1$H-NMR spectrum (400 MHz, DMSO-d$_6$) δ: 12.19 & 11.66 (s, total 1H), 9.61-9.47 (m, 1H), 7.39-7.13 (m, 5H), 6.46 & 6.38 (d, J=8.0 Hz, total 1H), 4.92-4.83 (m, 1H), 4.66-4.33 (m, 3H), 3.46-3.34 (m, 2H), 2.50-2.41 (m, 2H), 2.26-2.13 (m, 2H), 2.01-1.72 (m, 4H), 1.65-1.47 (m, 6H), 0.12-0.06 (m, 9H).

Example 13

(R)—N-(3-Hydroxy-1-phenylpropyl)-6,6-dimethyl-3-[1-(trimethylsilyl)cyclopropanecarboxamido]-4,6-dihydropyrrolo[3,4-c]pyrazole-5(1H)-carboxamide (Compound No. III-226)

[Chemical Formula 29]

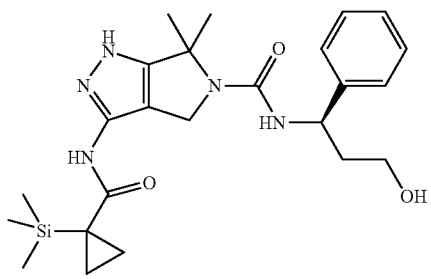

To a solution of 468 mg (1.17 mmol) of ethyl 6,6-dimethyl-3-[1-(trimethylsilyl)cyclopropanecarboxamido]-5,6-dihydropyrrolo[3,4-c]pyrazole-2(4H)-carboxylate hydrochloride synthesized in the similar manner as in Reference Example 7 in 10 ml of dehydrated dichloromethane, 0.72 ml (4.1 mmol) of DIPEA was added at room temperature in a nitrogen atmosphere, and then, 235 mg (0.791 mmol) of bis(trichloromethyl)carbonate was added at −78° C. and stirred at the same temperature as above for 3 hours.

After the completion of the reaction, 20 ml of a saturated aqueous solution of sodium bicarbonate was added to the reaction solution and stirred while the temperature was raised to room temperature for a while. The organic layer and the aqueous layer were separated, and then, the aqueous layer was subjected to extraction with dichloromethane twice. All of the obtained organic layers were dried over anhydrous magnesium sulfate, filtered, and concentrated under reduced pressure. The obtained concentration residue was subjected to silica gel column chromatography (elution solvent: n-hexane:ethyl acetate=90:10 to 75:25 (V/V)), and a fraction containing ethyl 5-(chlorocarbonyl)-6,6-dimethyl-3-[1-(trimethylsilyl)cyclopropanecarboxamido]-5,6-dihydropyrrolo[3,4-c]pyrazole-2 (4H)-carboxylate was concentrated under reduced pressure and dried under reduced pressure to obtain 490 mg of a concentration residue.

To a solution of 113 mg of the obtained concentration residue in 2 ml of dehydrated THF, 0.14 ml (0.80 mmol) of DIPEA and 105 mg (0.692 mmol) of (R)-3-amino-3-phenylpropan-1-ol [purchased from Ark Pharm, Inc.] were added at room temperature in a nitrogen atmosphere and then stirred for 2.5 hours while heated to reflux. Subsequently, 0.10 ml (1.7 mmol) of 2-aminoethanol was added and then stirred for 2 hours while heated to reflux.

After the completion of the reaction, a saturated aqueous solution of sodium bicarbonate was added to the reaction solution, followed by extraction with dichloromethane three times. All of the obtained organic layers were dried over anhydrous magnesium sulfate, filtered, and concentrated under reduced pressure. 0.1 ml of acetic acid was added to the obtained concentration residue and then subjected to silica gel column chromatography (DIOL silica gel, elution solvent: n-hexane:ethyl acetate=50:50 to 15:85 (V/V)), and a fraction containing the compound of interest was concentrated under reduced pressure. The obtained concentration residue was subjected again to silica gel column chromatography (elution solvent: dichloromethane:methanol=99:1 to 95:5 (V/V)), and a fraction containing the compound of interest was concentrated under reduced pressure. For the obtained concentration residue, crystallization was performed with ethyl acetate/n-hexane, and the deposited solid was collected by filtration, washed by sousing with n-hexane, and then dried under reduced pressure to obtain 49 mg of the title compound (yield: 39% [2 steps]) as a white solid.

Mass spectrum (CI, m/z): 470 [M+1]$^+$.

$^1$H-NMR spectrum (400 MHz, DMSO-d$_6$) δ: 12.22 & 11.84 (br s, total 1H), 9.91-9.66 (m, 1H), 7.37-7.26 (m, 4H), 7.21-7.14 (m, 1H), 6.50-6.28 (m, 1H), 4.92-4.80 (m, 1H), 4.65-4.52 (m, 1H), 4.49-4.31 (m, 2H), 3.44-3.36 (m, 2H), 2.00-1.77 (m, 2H), 1.59 (br s, 3H), 1.51 (br s, 3H), 1.06-0.93 (m, 2H), 0.81-0.61 (m, 2H), 0.03 (s, 9H).

Example 14

(R)—N-(4-Hydroxy-1-phenylbutyl)-6,6-dimethyl-3-[1-(trimethylsilyl)cyclobutanecarboxamido]-4,6-dihydropyrrolo[3,4-c]pyrazole-5(1H)-carboxamide (Compound No. IV-283)

[Chemical Formula 30]

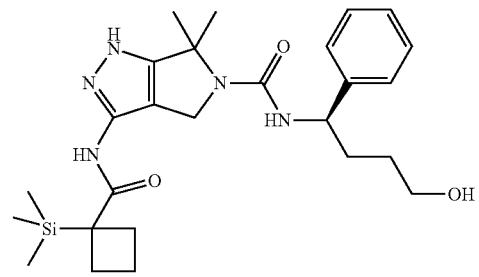

To a solution of 100 mg (0.227 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2 (4H)-carboxylate synthesized in the similar manner as in Reference Example 3 and 138 mg (0.684 mmol) of (R)-4-amino-4-phenylbutan-1-ol hydrochloride [purchased from NetChem, Inc.] in 2 ml of dehydrated 1,4-dioxane, 0.24 ml (1.4 mmol) of DIPEA was added at room temperature in an argon atmosphere and stirred at 100° C. for 3 hours. Subsequently, 1 ml of triethylamine and 1 ml of ethanol were added to the reaction solution and heated and stirred at 80° C. for 5 hours.

After the completion of the reaction, water was added to the reaction solution, followed by extraction from the mixed solution with ethyl acetate. The obtained organic layer was washed with a saturated aqueous solution of sodium chloride, dried by adding anhydrous sodium sulfate, filtered, and concentrated under reduced pressure. The obtained concentration residue was subjected to silica gel chromatography (DIOL silica gel, elution solvent: n-hexane:ethyl acetate=50:50 to 0:100 (V/V)), and a fraction containing the compound of interest was concentrated under reduced pressure and dried under reduced pressure to obtain 91.3 mg of the title compound (yield: 81%) as a white solid.

Mass spectrum (CI, m/z): 498 [M+1]$^+$ $^1$H-NMR spectrum (400 MHz, DMSO-d$_6$) δ: 12.18 & 11.73 (s, total 1H), 9.66-9.40 (m, 1H), 7.38-7.33 (m, 2H), 7.33-7.26 (m, 2H), 7.21-7.13 (m, 1H), 6.43-6.16 (m, 1H), 4.75-4.66 (m, 1H), 4.47 (br s, 2H), 4.38 (t, J=5.2 Hz, 1H), 3.45-3.35 (m, 2H), 2.49-2.42 (m, 2H), 2.25-2.14 (m, 2H), 1.88-1.64 (m, 4H), 1.60 (br s, 3H), 1.55-1.28 (m, 5H), 0.09 (s, 9H).

Example 15

(R)—N-(5-Hydroxy-1-phenylpentyl)-6,6-dimethyl-3-[1-(trimethylsilyl)cyclobutanecarboxamido]-4,6-dihydropyrrolo[3,4-c]pyrazole-5(1H)-carboxamide (Compound No. IV-291)

[Chemical Formula 31]

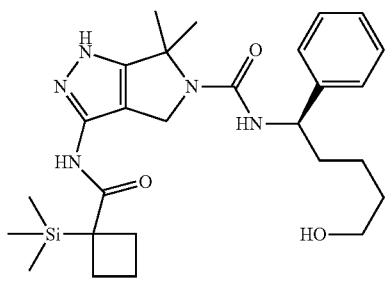

To a solution of 9.50 ml (9.50 mmol) of 1 M lithium aluminum hydride/THF solution in 40 ml of dehydrated THF, a solution of 2.02 g (6.28 mmol) of (R)-ethyl 5-[(tert-butoxycarbonyl)amino]-5-phenylpentanoate [synthesized according to the method described in Tetrahedron Lett., 1998, 39, 5951-5954] in 20 ml of dehydrated THF was added dropwise with stirring at 0° C. in an argon atmosphere and stirred at the same temperature as above for 2 hours.

After the completion of the reaction, 50 ml of THF was added, and then, 0.4 ml of water and 1.6 ml (1.6 mmol) of a 1 N aqueous sodium hydroxide solution were added and stirred at the same temperature as above for 30 minutes. The deposited solid was filtered using a celite filter, and the solid was washed with ethyl acetate. The obtained filtrate was concentrated under reduced pressure and dried under reduced pressure to obtain a concentration residue.

To a solution of 1.68 g of the obtained concentration residue in 20 ml of dichloromethane, 2 ml of trifluoroacetic acid was added at room temperature in an argon atmosphere and stirred at the same temperature as above for 2 hours.

After the completion of the reaction, the reaction solution was concentrated under reduced pressure and dried under reduced pressure to obtain 1.35 g of a concentration residue.

To a solution of 905 mg of the obtained concentration residue in 3 ml of dehydrated THF, 0.60 ml (3.4 mmol) of DIPEA was added with stirring in an argon atmosphere, and then, 205 mg (0.465 mmol) of ethyl 5-(chlorocarbonyl)-6,6-dimethyl-3-[1-(trimethylsilyl)cyclobutanecarbox amido]-5,6-dihydropyrrolo[3,4-c]pyrazole-2(4H)-carboxylate synthesized in the similar manner as in Reference Example 3 was added at room temperature and stirred at 60° C. for 4 hours. Subsequently, 0.5 ml of triethylamine and 1 ml of methanol were added to the reaction solution, heated and stirred at 60° C. for 3 hours, and subsequently stirred at room temperature for 15 hours.

After the completion of the reaction, the reaction solution was concentrated under reduced pressure. The obtained concentration residue was subjected to silica gel chromatography (DIOL silica gel, elution solvent: dichloromethane:methanol=100:0 to 90:10 (V/V)), and a fraction containing the compound of interest was concentrated under reduced pressure and dried under reduced pressure. The obtained concentration residue was further subjected to silica gel chromatography (DNH silica gel, elution solvent: dichloromethane:methanol=100:0 to 93:7 (V/V)), and a fraction containing the compound of interest was concentrated under reduced pressure and dried under reduced pressure. The obtained concentration residue was subjected to silica gel chromatography (DIOL silica gel, elution solvent: n-hexane:ethyl acetate=70:30 to 0:100 (V/V)), and a fraction containing the compound of interest was concentrated under reduced pressure and dried under reduced pressure to obtain 131 mg of the title compound (yield: 55%) as a white solid.

Mass spectrum (CI, m/z): 512 [M+1]$^+$ $^1$H-NMR spectrum (400 MHz, DMSO-d$_6$) δ: 12.18 & 11.64 (br s, total 1H), 9.58-9.47 (m, 1H), 7.38-7.33 (m, 2H), 7.32-7.25 (m, 2H), 7.21-7.14 (m, 1H), 6.38-6.15 (m, 1H), 4.75-4.65 (m, 1H), 4.52-4.38 (m, 2H), 4.33 (t, J=5.2 Hz, 1H), 3.39-3.33 (m, 2H), 2.49-2.42 (m, 2H), 2.26-2.14 (m, 2H), 1.88-1.72 (m, 3H), 1.72-1.30 (m, 10H), 1.27-1.14 (m, 1H), 0.13-0.06 (m, 9H).

Example 16

(S)—N-(2-Hydroxy-2-methyl-1-phenylpropyl)-6,6-dimethyl-3-[1-(trimethylsilyl)cyclobutanecarboxamido]-4,6-dihydropyrrolo[3,4-c]pyrazole-5(1H)-carboxamide (Compound No. IV-171)

[Chemical Formula 32]

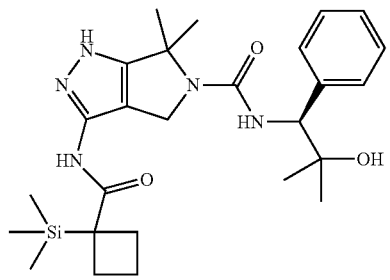

To a solution of 200 mg (0.454 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 3 ml of dehydrated THF, 0.16 ml (0.92 mmol) of DIPEA and 385 mg (2.33 mmol) of (S)-1-amino-2-methyl-1-phenylpropan-2-ol [purchased from IS Chemical Technology Ltd.] were added at room temperature in an argon atmosphere and stirred at 60° C. for 4 hours. Subsequently, 1 ml of methanol and 1 ml of triethylamine were added at room temperature and stirred at the same temperature as above for 15 hours.

After the completion of the reaction, water was added to the reaction solution, followed by extraction from the mixed solution with ethyl acetate. The obtained organic layer was washed with a saturated aqueous solution of sodium chloride, dried by adding anhydrous sodium sulfate, filtered, and concentrated under reduced pressure. The obtained concentration residue was subjected to silica gel chromatography (DIOL silica gel, elution solvent: dichloromethane:methanol=100:0 to 90:10 (V/V)), and a fraction containing the compound of interest was concentrated under reduced pressure and dried under reduced pressure. The obtained concentration residue was subjected again to silica gel chromatography (DIOL silica gel, elution solvent: dichloromethane:methanol=100:0 to 90:10 (V/V)), and a fraction containing the compound of interest was concentrated under reduced pressure and dried under reduced pressure to obtain 182 mg of the title compound (yield: 81%) as a white solid.

Mass spectrum (DUIS, m/z): 498 [M+1]$^+$ $^1$H-NMR spectrum (400 MHz, DMSO-d$_6$) δ: 12.22 & 11.78 (br s, total 1H), 9.74-9.49 (m, 1H), 7.38-7.16 (m, 5H), 5.90-5.74 (m, 1H), 4.85 (s, 1H), 4.65-4.35 (m, 3H), 2.49-2.41 (m, 2H), 2.28-2.15 (m, 2H), 1.91-1.73 (m, 2H), 1.67-1.44 (m, 6H), 1.22 (s, 3H), 0.91 (s, 3H), 0.09 s, 9H).

Example 17

(S)—N-(2-Hydroxy-2-methyl-1-phenylpropyl)-6,6-dimethyl-3-[1-(trimethylsilyl)cyclopropanecarboxamido]-4,6-dihydropyrrolo[3,4-c]pyrazole-5(1H)-carboxamide (Compound No. III-170)

[Chemical Formula 33]

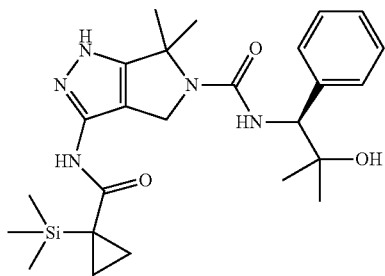

To a solution of 468 mg (1.17 mmol) of ethyl 6,6-dimethyl-3-[1-(trimethylsilyl)cyclopropanecarboxamido]-5,6-dihydropyrrolo[3,4-c]pyrazole-2(4H)-carboxylate hydrochloride synthesized in the similar manner as in Reference Example 7 in 10 ml of dehydrated dichloromethane, 0.72 ml (4.1 mmol) of DIPEA was added at room temperature in a nitrogen atmosphere, and then, 235 mg (0.791 mmol) of bis(trichloromethyl)carbonate was added at −78° C. and stirred at the same temperature as above for 3 hours.

After the completion of the reaction, 20 ml of a saturated aqueous solution of sodium bicarbonate was added to the reaction solution and stirred while the temperature was raised to room temperature for a while. The organic layer and the aqueous layer were separated, and then, the aqueous layer was subjected to extraction with dichloromethane twice. All of the obtained organic layers were dried over anhydrous magnesium sulfate, filtered, and concentrated under reduced pressure. The obtained concentration residue was subjected to silica gel column chromatography (elution solvent: n-hexane:ethyl acetate=90:10 to 75:25 (V/V)), and a fraction containing the compound of interest was concentrated under reduced pressure and dried under reduced pressure to obtain 490 mg of a concentration residue.

To a solution of 112 mg of the obtained concentration residue in 2 ml of dehydrated THF, 0.14 ml (0.80 mmol) of DIPEA and 109 mg (0.660 mmol) of (S)-1-amino-2-methyl-1-phenylpropan-2-ol [purchased from IS Chemical Technology Ltd.] were added in this order at room temperature in a nitrogen atmosphere and then stirred for 3 hours while heated to reflux. Subsequently, 0.10 ml (1.7 mmol) of 2-aminoethanol was added and then stirred for 2.5 hours while heated to reflux.

After the completion of the reaction, a saturated aqueous solution of sodium bicarbonate was added to the reaction solution, followed by extraction with dichloromethane three times. All of the obtained organic layers were dried over anhydrous magnesium sulfate, filtered, and concentrated under reduced pressure. 0.1 ml of acetic acid was added to the obtained concentration residue and then subjected to silica gel column chromatography (DIOL silica gel, elution solvent: n-hexane:ethyl acetate=50:50 to 20:80 (V/V)), and a fraction containing the compound of interest was concentrated under reduced pressure. For the obtained concentration residue, crystallization was performed with ethyl acetate/n-hexane, and the deposited solid was collected by filtration, washed by sousing with n-hexane, and then dried under reduced pressure to obtain 100 mg of the title compound (yield: 77% [2 steps]) as a white solid.

Mass spectrum (CI, m/z): 484 [M+1]$^+$.

$^1$H-NMR spectrum (400 MHz, DMSO-d$_6$) δ: 12.24 & 11.90 (br s, total 1H), 10.02-9.68 (m, 1H), 7.38-7.16 (m, 5H), 5.89-5.71 (m, 1H), 4.82 (s, 1H), 4.59 (d, J=8.4 Hz, 1H), 4.56-4.31 (m, 2H), 1.66-1.43 (m, 6H), 1.21 (s, 3H), 1.06-0.97 (m, 2H), 0.91 (s, 3H), 0.81-0.61 (m, 2H), 0.04 (s, 9H).

Example 18

N-(3-Hydroxy-2,2-dimethyl-1-phenylpropyl)-6,6-dimethyl-3-[1-(trimethylsilyl)cyclobutanecarboxamido]-4,6-dihydropyrrolo[3,4-c]pyrazole-5(1H)-carboxamide (Compound No. IV-354)

[Chemical Formula 34]

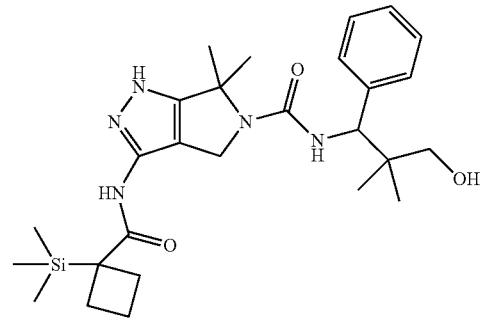

To a solution of 152 mg (0.346 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 and 201 mg (1.12 mmol) of 3-amino-2,2-dimethyl-3-phenylpropan-1-ol [synthesized according to the method described in Synthetic Communications 1994, 24 (7), 899-906] in 4 ml of 1,4-dioxane, 0.18 ml (1.0 mmol) of DIPEA was added at room temperature in an argon atmosphere, then applied to a microwave reaction apparatus, and reacted at 100° C. for 1 hour. After standing to cool, the reaction solution was concentrated under reduced pressure, and 4 ml of methanol and 1 ml of triethylamine were added to the obtained concentration residue and stirred at room temperature for 15 hours.

After the completion of the reaction, the reaction solution was concentrated under reduced pressure, the obtained concentration residue was subjected to silica gel column chromatography (DIOL silica gel, elution solvent: ethyl acetate:methanol=99:1 to 97:3 (V/V)), and a fraction containing the compound of interest was concentrated under reduced pressure. The obtained concentration residue was subjected again to silica gel column chromatography (DIOL silica gel, elution solvent: 1,2-dichloroethane:methanol=99:1 to 92:8 (V/V)), and a fraction containing the compound of interest was concentrated under reduced pressure. For the obtained concentration residue, crystallization was performed with dichloromethane/n-hexane, and the deposited solid was collected by filtration and dried under reduced pressure to obtain 55 mg of the title compound (yield: 31%) as a white solid.

Mass spectrum (DUIS, m/z): 512 [M+1]$^+$.

$^1$H-NMR spectrum (400 MHz, DMSO-$d_6$) δ: 12.21 & 11.95 (br s, total 1H), 9.89-9.36 (m, 1H), 7.36-7.17 (m, 5H), 6.85 (d, J=8.1 Hz, 1H), 5.50-5.39 (m, 1H), 4.64 (d, J=8.1 Hz, 1H), 4.47-4.28 (m, 2H), 3.30-3.22 (m, 1H), 3.03 (dd, J=4.1, 10.4 Hz, 1H), 2.49-2.40 (m, 2H), 2.28-2.13 (m, 2H), 1.92-1.71 (m, 2H), 1.60 (br s, 3H), 1.53 (s, 3H), 1.06 (s, 3H), 0.64 (s, 3H), 0.09 (s, 9H).

Example 19

(R)—N-(3-Hydroxy-3-methyl-1-phenylbutyl)-6,6-dimethyl-3-[1-(trimethylsilyl)cyclobutanecarboxamido]-4,6-dihydropyrrolo[3,4-c]pyrazole-5(1H)-carboxamide (Compound No. IV-299)

[Chemical Formula 35]

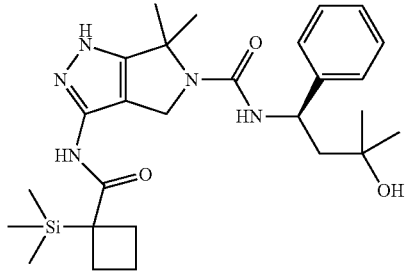

To a solution of 132 mg (0.300 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 and 155 mg (0.865 mmol) of (R)-4-amino-2-methyl-4-phenylbutan-2-ol synthesized in the similar manner as in Reference Example 23 in 4 ml of 1,4-dioxane, 0.15 ml (0.86 mmol) of DIPEA was added at room temperature in an argon atmosphere and then stirred at 100° C. for 2 hours. After standing to cool, the reaction solution was concentrated under reduced pressure, and 4 ml of methanol and 1 ml of triethylamine were added to the obtained concentration residue and stirred at room temperature for 18 hours.

After the completion of the reaction, the reaction solution was concentrated under reduced pressure, and ethyl acetate, water, and a saturated aqueous solution of sodium chloride were added to the obtained concentration residue and then the aqueous layer and the organic layer were separated. The obtained organic layer was dried over anhydrous magnesium sulfate and filtered, and then, the filtrate was concentrated under reduced pressure. The obtained concentration residue was subjected to silica gel column chromatography (DIOL silica gel, elution solvent: 1,2-dichloroethane:methanol=98:2 to 91:9 (V/V)), and a fraction containing the compound of interest was concentrated under reduced pressure. For the obtained concentration residue, crystallization was performed with dichloromethane/diethyl ether/n-hexane, and the deposited solid was collected by filtration and dried under reduced pressure to obtain 104 mg of the title compound (yield: 68%) as a white solid.

Mass spectrum (DUIS, m/z): 512 [M+1]$^+$.

$^1$H-NMR spectrum (400 MHz, DMSO-$d_6$) δ: 12.20 & 11.73 (br s, 1H), 9.66-9.40 (m, 1H), 7.37-7.25 (m, 4H), 7.19-7.13 (m, 1H), 6.54 (d, J=5.3 Hz, 1H), 4.95-4.84 (m, 1H), 4.75-4.57 (m, 1H), 4.45 (br s, 2H), 2.47-2.42 (m, 2H), 2.25-2.14 (m, 2H), 2.02-1.74 (m, 3H), 1.65 (dd, J=3.3, 14.3 Hz, 1H), 1.58 (s, 3H), 1.53 (s, 3H), 1.16 (s, 3H), 1.13 (s, 3H), 0.09 (s, 9H).

Example 20

(S)—N-(2-Methoxy-1-phenylethyl)-6,6-dimethyl-3-[1-(trimethylsilyl)cyclobutanecarboxamido]-4,6-dihydropyrrolo[3,4-c]pyrazole-5(1H)-carboxamide (Compound No. IV-123)

[Chemical Formula 36]

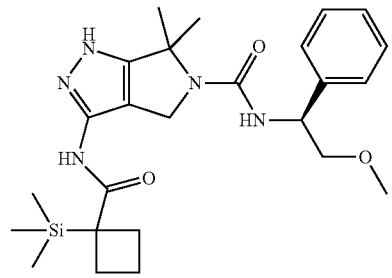

To a solution of 201 mg (0.456 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2 (4H)-carboxylate synthesized in the similar manner as in Reference Example 3 in 4.5 ml of 1,4-dioxane, 0.16 ml (0.91 mmol) of DIPEA and 213 mg (1.41 mmol) of (S)-2-methoxy-1-phenylamine [synthesized according to the method described in J. Chem. Soc., Perkin Transactions 1, 2002, 20, 2237-2242] were added at room temperature, then applied to a microwave reaction apparatus, and reacted at 100° C. for 1 hour. Subsequently, 1 ml of methanol and 0.5 ml of triethylamine were added and then reacted at 80° C. for 1 hour in a microwave reaction apparatus again.

After the completion of the reaction, 8 ml of ethyl acetate, 0.4 ml of water, and 8 ml of a saturated aqueous solution of sodium chloride were added to the reaction solution and then the aqueous layer and the organic layer were separated. The aqueous layer was subjected to extraction with 10 ml of dichloromethane. All of the obtained organic layers were dried over anhydrous magnesium sulfate, then filtered, and concentrated under reduced pressure. The obtained concentration residue was subjected to silica gel column chromatography (DIOL silica gel, elution solvent: 1,2-dichloroethane:methanol=100:0 to 95:5 (V/V)), and a fraction containing the compound of interest was concentrated under reduced pressure. Diethyl ether was added to the obtained concentration residue and ultrasonicated, and then, the deposited insoluble matter was collected by filtration and dried under reduced pressure to obtain 180 mg of the title compound (yield: 82%) as a white solid.

Mass spectrum (CI, m/z): 484 [M+1]$^+$.

$^1$H-NMR spectrum (400 MHz, DMSO-d$_6$) δ: 12.20 & 11.67 (br s, total 1H), 9.68-9.41 (m, 1H), 7.41-7.35 (m, 2H), 7.34-7.27 (m, 2H), 7.25-7.17 (m, 1H), 6.44-6.13 (m, 1H), 5.02-4.92 (m, 1H), 4.57-4.39 (m, 2H), 3.63 (dd, J=7.9, 9.9 Hz, 1H), 3.50 (dd, J=6.0, 9.9 Hz, 1H), 3.26 (s, 3H), 2.49-2.42 (m, 2H), 2.26-2.15 (m, 2H), 1.92-1.73 (m, 2H), 1.60 (br s, 3H), 1.53 (br s, 3H), 0.09 (s, 9H).

Example 21

(S)—N-[2-(Difluoromethoxy)-1-phenylethyl]-6,6-dimethyl-3-[1-(trimethylsilyl)cyclobutanecarboxamido]-4,6-dihydropyrrolo[3,4-c]pyrazole-5(1H)-carboxamide (Compound No. IV-131)

[Chemical Formula 37]

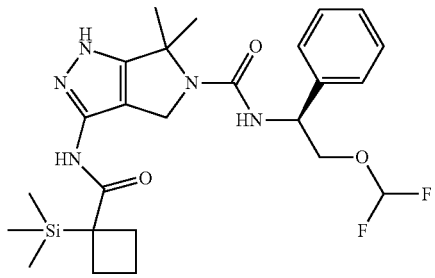

To a solution of 210 mg (0.697 mmol) of (S)-2-(difluoromethoxy)-1-phenylethanamine trifluoroacetate synthesized in the similar manner as in Reference Example 25 and 0.425 ml (2.43 mmol) of DIPEA in 3 ml of dehydrated 1,4-dioxane, 107 mg (0.243 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2 (4H)-carboxylate synthesized in the similar manner as in Reference Example 3 was added at room temperature in an argon atmosphere and heated and stirred at 100° C. for 1 hour. Subsequently, 1 ml of triethylamine and 1 ml of methanol were added to the reaction solution and heated and stirred at 80° C. for 1 hour.

After the completion of the reaction, water was added to the reaction solution, followed by extraction from the mixed solution with ethyl acetate. The obtained organic layer was washed with a saturated aqueous solution of sodium chloride, dried by adding anhydrous sodium sulfate, filtered, and concentrated under reduced pressure. The obtained concentration residue was subjected to silica gel chromatography (DIOL silica gel, elution solvent: n-hexane:ethyl acetate=50:50 to 0:100 (V/V)), and a fraction containing the compound of interest was concentrated under reduced pressure and dried under reduced pressure to obtain 40.5 mg of the title compound (yield: 32%) as a white solid.

Mass spectrum (CI, m/z): 520 [M+1]$^+$ $^1$H-NMR spectrum (400 MHz, DMSO-d$_6$) δ: 12.20 (br s, 1H), 10.12-9.41 (m, 1H), 7.43-7.38 (m, 2H), 7.38-7.32 (m, 2H), 7.28-7.23 (m, 1H), 6.70 (t, J=76.0 Hz, 1H), 6.59-6.46 (m, 1H), 5.10-5.01 (m, 1H), 4.52-4.43 (m, 2H), 4.13 (dd, J=8.3, 10.4 Hz, 1H), 4.05-3.99 (m, 1H), 2.48-2.42 (m, 2H), 2.24-2.15 (m, 2H), 1.88-1.75 (m, 2H), 1.60 (s, 3H), 1.53 (s, 3H), 0.09 (s, 9H).

Example 22

(S)—N-(2-Ethoxy-1-phenylethyl)-6,6-dimethyl-3-[1-(trimethylsilyl)cyclobutanecarboxamido]-4,6-dihydropyrrolo[3,4-c]pyrazole-5(1H)-carboxamide (Compound No. IV-139)

[Chemical Formula 38]

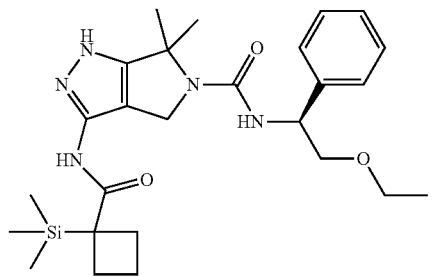

To a solution of 136 mg (0.308 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2 (4H)-carboxylate synthesized in the similar manner as in Reference Example 3 and 162 mg (0.979 mmol) of (S)-2-ethoxy-1-phenylethanamine synthesized in the similar manner as in Reference Example 26 in 4 ml of 1,4-dioxane, 0.16 ml (0.92 mmol) of DIPEA was added at room temperature in an argon atmosphere and then stirred at 100° C. for 2 hours. After standing to cool, the reaction solution was concentrated under reduced pressure, and 4 ml of methanol and 1 ml of triethylamine were added to the obtained concentration residue, applied to a microwave reaction apparatus, and reacted at 80° C. for 1 hour.

After the completion of the reaction, the reaction solution was concentrated under reduced pressure, ethyl acetate was added to the obtained concentration residue, then the organic layer obtained by washing with a 10% aqueous potassium dihydrogen phosphate solution, a saturated aqueous solution of sodium bicarbonate, and a saturated aqueous solution of sodium chloride in this order was dried over anhydrous magnesium sulfate and filtered, and then, the filtrate was concentrated under reduced pressure. The obtained residue was subjected to silica gel column chromatography (DIOL silica gel, elution solvent: 1,2-dichloroethane:methanol=98:2 to 91:9 (V/V)), and a fraction containing the compound of interest was concentrated under reduced pressure. For the obtained concentration residue, crystallization was performed with dichloromethane/diethyl ether/n-hexane, and the deposited solid was collected by filtration. The obtained solid was subjected again to silica gel column chromatography (DIOL silica gel, elution solvent: 1,2-dichloroethane:methanol=100:0 to 93:7 (V/V)), and a fraction containing the compound of interest was concentrated under reduced pressure. The obtained concentration residue was subjected again to silica gel column chromatography (DIOL silica gel, elution solvent: 1,2-dichloroethane:ethyl acetate=100:0 to 67:33 (V/V)), and a fraction containing the compound of interest was concentrated under reduced pressure. Diethyl ether and n-hexane were added to the obtained concentration residue, and after ultrasonication, the deposited solid was collected by filtration and dried under reduced pressure to obtain 81 mg of the title compound (yield: 53%) as a white solid.

Mass spectrum (DUIS, m/z): 498 [M+1]$^+$.

$^1$H-NMR spectrum (400 MHz, DMSO-d$_6$) δ: 12.20 & 11.71 (br s, total 1H), 9.67-9.47 (m, 1H), 7.41-7.34 (m, 2H), 7.34-7.27 (m, 2H), 7.25-7.17 (m, 1H), 6.38-6.11 (m, 1H), 4.99-4.91 (m, 1H), 4.56-4.38 (m, 2H), 3.65 (dd, J=8.0, 9.9 Hz, 1H), 3.54 (dd, J=6.0, 9.9 Hz, 1H), 3.51-3.41 (m, 2H), 2.49-2.41 (m, 2H), 2.28-2.14 (m, 2H), 1.91-1.71 (m, 2H), 1.61 (br s, 3H), 1.54 (br s, 3H), 1.08 (t, J=7.0 Hz, 3H), 0.09 (s, 9H).

Example 23

(R)—N-(3-Methoxy-1-phenylpropyl)-6,6-dimethyl-3-[1-(trimethylsilyl)cyclobutanecarboxamido]-4,6-dihydropyrrolo[3,4-c]pyrazole-5(1H)-carboxamide (Compound No. IV-235)

[Chemical Formula 39]

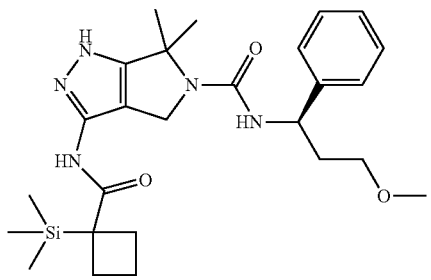

To a solution of 138 mg (0.314 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2 (4H)-carboxylate synthesized in the similar manner as in Reference Example 3 and 163 mg (0.987 mmol) of (R)-3-methoxy-1-phenylpropan-1-amine synthesized in the similar manner as in Reference Example 27 in 4 ml of 1,4-dioxane, 0.16 ml (0.92 mmol) of DIPEA was added at room temperature in an argon atmosphere and then stirred at 100° C. for 2 hours. After standing to cool, the reaction solution was concentrated under reduced pressure, and 4 ml of methanol and 1 ml of triethylamine were added to the obtained residue and stirred at room temperature for 18 hours.

After the completion of the reaction, the reaction solution was concentrated under reduced pressure, ethyl acetate was added to the obtained concentration residue, then the organic layer obtained by washing with a 10% aqueous potassium dihydrogen phosphate solution, a saturated aqueous solution of sodium bicarbonate, and a saturated aqueous solution of sodium chloride in this order was dried over anhydrous magnesium sulfate and filtered, and then, the filtrate was concentrated under reduced pressure. The obtained residue was subjected to silica gel column chromatography (DIOL silica gel, elution solvent: 1,2-dichloroethane:methanol=95:5 to 88:12 (V/V)), and a fraction containing the compound of interest was concentrated under reduced pressure. Diethyl ether and n-hexane were added to the obtained concentration residue and ultrasonicated, and then, the deposited solid was collected by filtration and dried under reduced pressure to obtain 88 mg of the title compound (yield: 56%) as a white solid.

Mass spectrum (DUIS, m/z): 498 [M+1]$^+$.

$^1$H-NMR spectrum (400 MHz, DMSO-d$_6$) δ: 12.18 & 11.73 (br s, total 1H), 9.54 (br s, 1H), 7.35-7.28 (m, 4H), 7.22-7.16 (m, 1H), 6.41 (br s, 1H), 4.91-4.79 (m, 1H), 4.53-4.40 (m, 2H), 3.32-3.27 (m, 2H), 3.23 (s, 3H), 2.50-2.42 (m, 2H), 2.26-2.15 (m, 2H), 2.08-1.70 (m, 4H), 1.60 (s, 3H), 1.52 (s, 3H), 0.09 (s, 9H).

Example 24

Sodium (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylacetate (Sodium Salt of Compound No. IV-403)

[Chemical Formula 40]

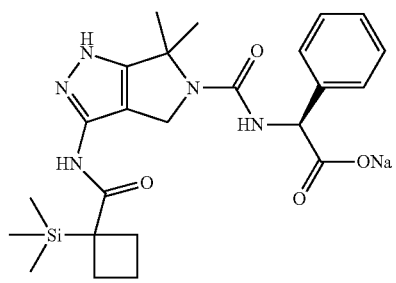

To a solution of 98.0 mg (0.171 mmol) of (S)-benzyl 2-{6,6-dimethyl-3-[1-(trimethylsilyl)cyclobutanecarboxamido]-1,4,5,6-tetrahydropyrrolo[3,4-c]pyrazole-5-carboxamido}-2-phenylacetate synthesized in the similar manner as in Example 55 in 15 ml of ethanol, 19.9 mg of palladium/carbon [ASCA2 (trade name), manufactured by N.E. Chemcat Corp., containing 52% water] was added in a nitrogen atmosphere and then, after replacement with a hydrogen atmosphere under reduced pressure, stirred at room temperature for 50 minutes.

After the completion of the reaction, replacement with an argon atmosphere was performed, and the reaction solution was filtered through celite. 14.8 mg (0.176 mmol) of sodium bicarbonate was added to the obtained filtrate and concentrated under reduced pressure. Purified water and diethyl ether were added to the obtained concentration residue and then dried under reduced pressure to obtain 82 mg of the title compound (yield: 95%) as a white solid.

$^1$H-NMR spectrum (400 MHz, DMSO-d$_6$) δ: 12.41 (br s, 1H), 9.95 (br. s, 1H), 7.38-7.30 (m, 2H), 7.24-7.17 (m, 2H), 7.14-7.08 (m, 1H), 6.42 (d, J=4.6 Hz, 1H), 4.68 (d, J=4.6 Hz, 1H), 4.48 (d, J=11.3 Hz, 1H), 4.45 (d, J=11.3 Hz, 1H), 2.51-2.41 (m, 2H), 2.28-2.14 (m, 2H), 1.90-1.74 (m, 2H), 1.59 (s, 3H), 1.55 (s, 3H), 0.08 (s, 9H).

Example 25

(R)—N-(2-Hydroxy-1-phenylethyl)-6,6-dimethyl-3-[1-(trimethylsilyl)cyclobutanecarboxamido]-4,6-dihydropyrrolo[3,4-c]pyrazole-5(1H)-carboxamide (Compound No. IV-115)

[Chemical Formula 41]

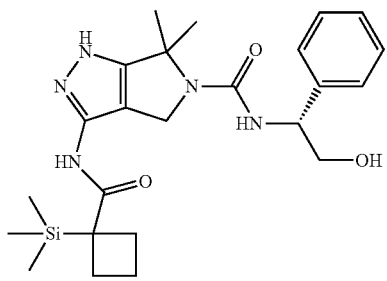

To a solution of 127 mg (0.287 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 and 203 mg (1.48 mmol) of (R)-2-amino-2-phenylethanol in 3 ml of THF, 0.15 ml (0.86 mmol) of DIPEA was added at room temperature in an argon atmosphere and then stirred at 60° C. for 3 hours.

After the completion of the reaction, ethyl acetate, water, and a saturated aqueous solution of sodium chloride were added to the reaction solution and then the aqueous layer and the organic layer were separated. The obtained organic layer was dried over anhydrous magnesium sulfate and filtered, and then, the filtrate was concentrated under reduced pressure. The obtained concentration residue was subjected to silica gel column chromatography (DIOL silica gel, elution solvent: 1,2-dichloroethane:methanol=100:0 to 98:2 (V/V)), and a fraction containing the compound of interest was concentrated under reduced pressure. The obtained concentration residue was subjected again to silica gel column chromatography (elution solvent: ethyl acetate:a mixed solution of 28% aqueous ammonia solution/ethanol [1:5 (V/V)]=98:2 to 95:5 (V/V)), and a fraction containing the compound of interest was concentrated under reduced pressure and dried under reduced pressure to obtain 82 mg of the title compound (yield: 61%) as a white foam.

Mass spectrum (DUIS, m/z): 470 [M+1]$^+$.

$^1$H-NMR spectrum (400 MHz, DMSO-d$_6$) δ: 12.20 & 11.79 (br s, total 1H), 9.73-9.49 (m, 1H), 7.44-7.11 (m, 5H), 6.25-6.00 (m, 1H), 4.95-4.70 (m, 2H), 4.62-4.41 (m, 2H), 3.71-3.52 (m, 2H), 2.48-2.41 (m, 2H), 2.27-2.13 (m, 2H), 1.93-1.73 (m, 2H), 1.71-1.43 (m, 6H), 0.09 (br s, 9H).

Example 26

N-[1-(2-Fluorophenyl)-2-hydroxyethyl]-6,6-dimethyl-3-[1-(trimethylsilyl)cyclobutanecarboxamido]-4,6-dihydropyrrolo[3,4-c]pyrazole-5(1H)-carboxamide (Compound No. IV-510)

[Chemical Formula 42]

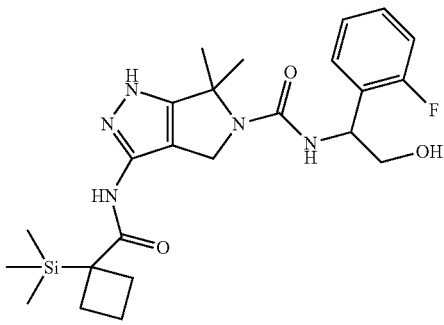

To a solution of 201 mg (0.456 mmol) of ethyl 5-(chlorocarbonyl)-6,6-dimethyl-3-[1-(trimethylsilyl)cyclobutanecarbox amido]-5,6-dihydropyrrolo[3,4-c]pyrazole-2 (4H)-carboxylate synthesized in the similar manner as in Reference Example 3 in 5 ml of 1,4-dioxane, 0.23 ml (1.4 mmol) of DIPEA and 212 mg (1.37 mmol) of 2-amino-2-(2-fluorophenyl)ethanol [purchased from Amatek Chemical Co., Ltd.] were added at room temperature in an argon atmosphere and then reacted at 100° C. for 1 hour. The reaction solution was concentrated under reduced pressure, and then, 4 ml of methanol and 1 ml of triethylamine were added to the concentration residue and reacted at 65° C. for 4.5 hours and further at 70° C. for 1.5 hours.

After the completion of the reaction, the reaction solution was concentrated under reduced pressure, and the obtained concentration residue was dissolved in 5 ml of ethyl acetate and washed with 10 ml of a 5% aqueous potassium bisulfate solution twice. All of the obtained organic layers were washed with 10 ml of a saturated aqueous solution of sodium bicarbonate, then dried over anhydrous magnesium sulfate, filtered, and concentrated under reduced pressure. The obtained concentration residue was subjected to silica gel column chromatography (DIOL silica gel, elution solvent: 1,2-dichloroethane:methanol=100:0 to 98:2 (V/V)), and a fraction containing the compound of interest was concentrated under reduced pressure and dried under reduced pressure to obtain 131 mg of the title compound (yield: 59%) as a white foam.

Mass spectrum (CI, m/z): 488 [M+1]$^+$.

$^1$H-NMR spectrum (400 MHz, DMSO-d$_6$) δ: 12.41-11.66 (m, 1H), 9.94-9.30 (m, 1H), 7.51-7.42 (m, 1H), 7.31-7.06 (m, 3H), 6.19 (br s, 1H), 5.15-5.04 (m, 1H), 4.98 (t, J=6.0 Hz, 1H), 4.54 (br s, 2H), 3.64-3.54 (m, 2H), 2.49-2.42 (m, 2H), 2.26-2.15 (m, 2H), 1.87-1.76 (m, 2H), 1.60 (s, 3H), 1.51 (s, 3H), 0.10 (s, 9H).

Example 27

(S)—N-[1-(3-Fluorophenyl)-2-hydroxyethyl]-6,6-dimethyl-3-[1-(trimethylsilyl)cyclobutanecarboxamido]-4,6-dihydropyrrolo[3,4-c]pyrazole-5(1H)-carboxamide (Compound No. IV-519)

[Chemical Formula 43]

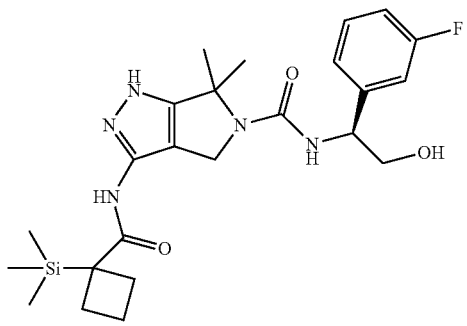

To a solution of 201 mg (0.456 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 5.0 ml of 1,4-dioxane, 0.23 ml (1.4 mmol) of DIPEA and 212 mg (1.37 mmol) of (S)-2-amino-2-(3-fluorophenyl)ethanol [purchased from Amatek Chemical Co., Ltd.] were added at room temperature in an argon atmosphere and then reacted at 100° C. for 1 hour. The reaction solution was concentrated under reduced pressure, and then, 4 ml of methanol and 1 ml of triethylamine were added to the concentration residue and reacted at room temperature for 17 hours.

After the completion of the reaction, the reaction solution was concentrated under reduced pressure, and the obtained concentration residue was dissolved in 5 ml of ethyl acetate, washed with 10 ml of a 5% aqueous potassium dihydrogen phosphate solution twice and 10 ml of a saturated aqueous solution of sodium bicarbonate once, then dried over anhydrous magnesium sulfate, filtered, and concentrated under reduced pressure. The obtained concentration residue was subjected to silica gel column chromatography (DIOL silica gel, elution solvent: 1,2-dichloroethane:methanol=100:0 to 98:2 (V/V)), and a fraction containing the compound of interest was concentrated under reduced pressure and dried under reduced pressure to obtain 128 mg of the title compound (yield: 58%) as a white foam.

Mass spectrum (CI, m/z): 488 [M+1]$^+$.

$^1$H-NMR spectrum (400 MHz, DMSO-$d_6$) δ: 12.35-11.70 (m, 1H), 9.84-9.41 (m, 1H), 7.38-7.29 (m, 1H), 7.21-7.15 (m, 2H), 7.05-6.98 (m, 1H), 6.21 (br s, 1H), 4.92 (t, J=5.8 Hz, 1H), 4.83-4.74 (m, 1H), 4.58-4.45 (m, 2H), 3.67-3.55 (m, 2H), 2.49-2.42 (m, 2H), 2.26-2.15 (m, 2H), 1.89-1.73 (m, 2H), 1.60 (s, 3H), 1.53 (s, 3H), 0.09 (s, 9H).

Example 28

(S)—N-[1-(4-Fluorophenyl)-2-hydroxyethyl]-6,6-dimethyl-3-[1-(trimethylsilyl)cyclobutanecarboxamido]-4,6-dihydropyrrolo[3,4-c]pyrazole-5(1H)-carboxamide (Compound No. IV-527)

[Chemical Formula 44]

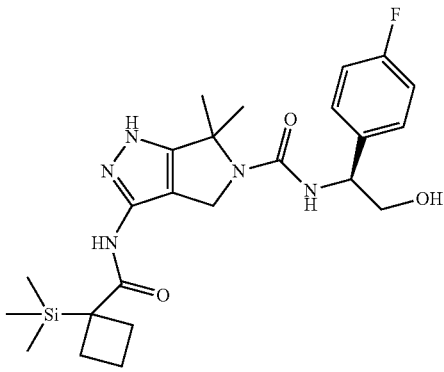

To a solution of 201 mg (0.456 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2 (4H)-carboxylate synthesized in the similar manner as in Reference Example 3 in 5.0 ml of 1,4-dioxane, 0.23 ml (1.4 mmol) of DIPEA and 212 mg (1.37 mmol) of (S)-2-amino-2-(4-fluorophenyl)ethanol [purchased from Amatek Chemical Co., Ltd.] were added at room temperature in an argon atmosphere and then reacted at 100° C. for 1 hour. The reaction solution was concentrated under reduced pressure, and then, 4 ml of methanol and 1 ml of triethylamine were added to the concentration residue and reacted at room temperature for 15 hours.

After the completion of the reaction, the reaction solution was concentrated under reduced pressure, and the obtained concentration residue was dissolved in 5 ml of ethyl acetate, washed with 10 ml of a 5% aqueous potassium dihydrogen phosphate solution twice and 10 ml of a saturated aqueous solution of sodium bicarbonate once, then dried over anhydrous magnesium sulfate, filtered, and concentrated under reduced pressure. The obtained concentration residue was subjected to silica gel column chromatography (DIOL silica gel, elution solvent: 1,2-dichloroethane:methanol=100:0 to 98:2 (V/V)), and a fraction containing the compound of interest was concentrated under reduced pressure. The obtained concentration residue was subjected again to silica gel column chromatography (DIOL silica gel, elution solvent: 1,2-dichloroethane:methanol=100:0 to 98:2 (V/V)), and a fraction containing the compound of interest was concentrated under reduced pressure and dried under reduced pressure to obtain 139 mg of the title compound (yield: 63%) as a pale yellow foam.

Mass spectrum (CI, m/z): 488 [M+1]$^+$.

$^1$H-NMR spectrum (400 MHz, DMSO-$d_6$) δ: 12.20 & 11.71 (br s, total 1H), 9.75-9.43 (m, 1H), 7.42-7.33 (m, 2H), 7.15-7.06 (m, 2H), 6.28-6.02 (m, 1H), 4.89 (t, J=5.8 Hz, 1H), 4.81-4.72 (m, 1H), 4.51 (br s, 2H), 3.66-3.53 (m, 2H), 2.49-2.42 (m, 2H), 2.26-2.15 (m, 2H), 1.90-1.74 (m, 2H), 1.60 (br s, 3H), 1.53 (br s, 3H), 0.09 (s, 9H).

Example 29

N-[2-Hydroxy-1-(pyridin-2-yl)ethyl]-6,6-dimethyl-3-[1-(trimethylsilyl)cyclobutanecarboxamido]-4,6-dihydropyrrolo[3,4-c]pyrazole-5(1H)-carboxamide (Compound No. IV-534)

[Chemical Formula 45]

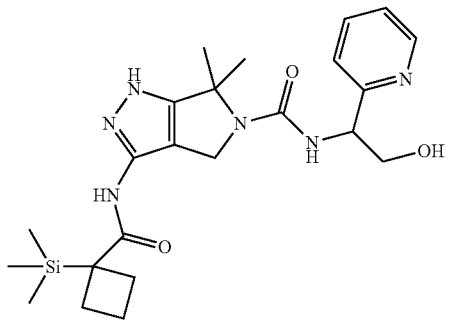

To a solution of 152 mg (0.344 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2 (4H)-carboxylate synthesized in the similar manner as in Reference Example 3 and 223 mg (1.06 mmol) of 2-amino-2-(pyridin-2-yl)ethanol dihydrochloride [purchased from J&W PharmLab, LLC] in 4 ml of 1,4-dioxane, 0.60 ml (3.4 mmol) of DIPEA was added at room temperature in an argon atmosphere, then applied to a microwave reaction apparatus, and reacted at 100° C. for 1 hour.

After the completion of the reaction, the reaction solution was concentrated under reduced pressure, and a saturated aqueous solution of sodium bicarbonate was added to the concentration residue, followed by extraction with dichloromethane. The obtained organic layer was dried over anhydrous sodium sulfate and filtered, and then, the filtrate was concentrated under reduced pressure. The obtained residue was subjected to silica gel column chromatography (DNH silica gel, elution solvent: 1,2-dichloroethane:methanol=100:0 to 93:7 (V/V)), and a fraction containing the compound of interest was concentrated under reduced pressure. The obtained residue was subjected again to silica gel column chromatography (DIOL silica gel, elution solvent: ethyl acetate:methanol=100:0 to 78:22 (V/V)), and a fraction containing the compound of interest was concentrated under reduced pressure and dried under reduced pressure to obtain 78 mg of the title compound (yield: 48%) as a white foam.

Mass spectrum (DUIS, m/z): 469 [M−1]$^-$.

$^1$H-NMR spectrum (400 MHz, DMSO-d$_6$) δ: 12.22 & 11.78 (br s, total 1H), 9.79-9.45 (m, 1H), 8.54-8.49 (m, 1H), 7.74 (dt, J=1.7, 7.7 Hz, 1H), 7.42-7.36 (m, 1H), 7.28-7.21 (m, 1H), 6.19-6.00 (m, 1H), 4.92-4.82 (m, 2H), 4.62-4.43 (m, 2H), 3.76-3.65 (m, 2H), 2.49-2.42 (m, 2H), 2.27-2.15 (m, 2H), 1.92-1.72 (m, 2H), 1.68-1.50 (m, 6H), 0.10 (s, 9H).

Example 30

N-[2-Hydroxy-1-(pyridin-3-yl)ethyl]-6,6-dimethyl-3-[1-(trimethylsilyl)cyclobutanecarboxamido]-4,6-dihydropyrrolo[3,4-c]pyrazole-5(1H)-carboxamide (Compound No. IV-542)

[Chemical Formula 46]

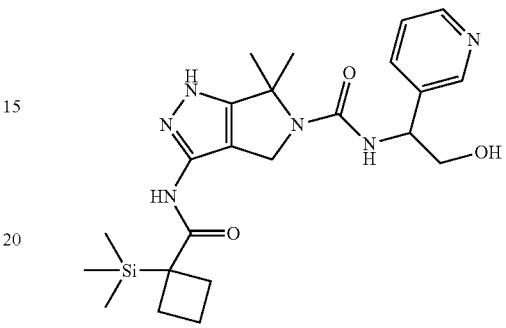

To a solution of 150 mg (0.341 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 and 218 mg (1.03 mmol) of 2-amino-2-(pyridin-3-yl)ethanol dihydrochloride [purchased from J&W PharmLab, LLC] in 4 ml of 1,4-dioxane, 0.60 ml (3.4 mmol) of DIPEA was added at room temperature in an argon atmosphere and then stirred at 100° C. for 1 hour.

After the completion of the reaction, the reaction solution was concentrated under reduced pressure, and a saturated aqueous solution of sodium bicarbonate was added to the concentration residue, followed by extraction with dichloromethane. The obtained organic layer was dried over anhydrous magnesium sulfate and filtered, and then, the filtrate was concentrated under reduced pressure. 4 ml of methanol and 1 ml of triethylamine were added to the obtained concentration residue, applied to a microwave reaction apparatus, and reacted at 80° C. for 1 hour.

After the completion of the reaction, the reaction solution was concentrated under reduced pressure, the obtained concentration residue was subjected to silica gel column chromatography (DNH silica gel, elution solvent: 1,2-dichloroethane:methanol=95:5 to 88:12 (V/V)), and a fraction containing the compound of interest was concentrated under reduced pressure. The obtained residue was subjected again to silica gel column chromatography (DNH silica gel, elution solvent: ethyl acetate:methanol=96:4 to 70:30 (V/V)), and a fraction containing the compound of interest was concentrated under reduced pressure. The obtained residue was subjected again to silica gel column chromatography (DIOL silica gel, elution solvent: ethyl acetate:methanol=99:1 to 73:27 (V/V)), and a fraction containing the compound of interest was concentrated under reduced pressure and dried under reduced pressure to obtain 27 mg of the title compound (yield: 17%) as a white foam.

Mass spectrum (DUIS, m/z): 471 [M+1]$^+$.

$^1$H-NMR spectrum (400 MHz, DMSO-d$_6$) δ: 12.20 & 11.77 (br s, total 1H), 9.75-9.47 (m, 1H), 8.54 (d, J=2.0 Hz, 1H), 8.41 (dd, J=2.0, 4.7 Hz, 1H), 7.75 (ddd, J=2.0, 2.0, 7.6 Hz, 1H), 7.32 (dd, J=4.7, 7.6 Hz, 1H), 6.39-6.13 (m, 1H), 4.97 (t, J=5.8 Hz, 1H), 4.84-4.76 (m, 1H), 4.61-4.42 (m, 2H), 3.71-3.59 (m, 2H), 2.49-2.42 (m, 2H), 2.27-2.14 (m, 2H), 1.89-1.72 (m, 2H), 1.60 (br s, 3H), 1.52 (br s, 3H), 0.09 (s, 9H).

Example 31

N-[1-(Benzo[d][1,3]dioxol-4-yl)-2-hydroxyethyl]-6,6-dimethyl-3-[1-(trimethylsilyl)cyclobutanecarboxamido]-4,6-dihydropyrrolo[3,4-c]pyrazole-5(1H)-carboxamide (Compound No. IV-502)

[Chemical Formula 47]

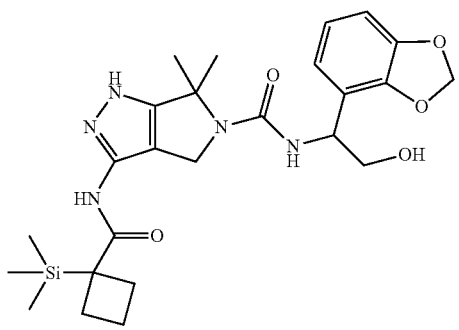

To a solution of 240 mg (0.815 mmol) of 1-(benzo[d][1,3]dioxol-4-yl)-2-[(tert-butyldimethylsilyl)oxy]ethanamine synthesized in the similar manner as in Reference Example 32 in 10 ml of dichloromethane, 1 ml (4 mmol) of 4 N hydrogen chloride/1,4-dioxane solution was added at room temperature and stirred at room temperature for 2 hours. The reaction solution was concentrated under reduced pressure, and 3 ml of THF, 0.210 ml (1.24 mmol) of DIPEA, and 93.0 mg (0.211 mmol) of ethyl 5-(chlorocarbonyl)-6,6-dimethyl-3-[1-(trimethylsilyl)cyclobutanecarbox amido]-5,6-dihydropyrrolo[3,4-c]pyrazole-2(4H)-carboxylate synthesized in the similar manner as in Reference Example 3 were added to the obtained residue at room temperature and stirred at 60° C. for 8 hours.

After the completion of the reaction, the reaction solution was concentrated under reduced pressure, and ethyl acetate, a saturated aqueous solution of sodium chloride, and water were added thereto and then the aqueous layer and the organic layer were separated. The obtained organic layer was dried over anhydrous magnesium sulfate, filtered, and then concentrated under reduced pressure. 2 ml of methanol and 2 ml of triethylamine were added to the obtained concentration residue, applied to a microwave reaction apparatus, and reacted at 80° C. for 30 minutes.

After the completion of the reaction, the concentration residue obtained by concentration under reduced pressure was subjected to silica gel column chromatography (elution solvent: ethyl acetate: a mixed solution of 28% aqueous ammonia solution/ethanol [1:5 (V/V)]=98:2 to 95:5 (V/V)), and a fraction containing N-{1-(benzo[d][1,3]dioxol-4-yl)-2-[(tert-butyldimethylsilyl)oxy]ethyl}-6,6-dimethyl-3-[1-(trimethylsilyl)cyclobutanecarboxamido]-4,6-dihydropyrrolo[3,4-c]pyrazole-5(1H)-carboxamide was concentrated under reduced pressure to obtain a concentration residue.

To a solution of 119 mg (0.190 mmol) of the obtained concentration residue in 3.5 ml of dehydrated dichloromethane, 0.18 ml (1.0 mmol) of trimethylsilyl trifluoromethanesulfonate was added at 0° C. and stirred at the same temperature as above for 5 minutes, and then, 0.17 ml (1.5 mmol) of 2,6-lutidine and 0.18 ml (1.0 mmol) of trimethylsilyl trifluoromethanesulfonate were added at 0° C. and stirred at the same temperature as above for 5 minutes. Subsequently, 1 ml of methanol and 0.17 ml (1.5 mmol) of 2,6-lutidine were added, and then, the reaction solution was concentrated under reduced pressure. To a solution of the obtained concentration residue in 1 ml of dehydrated dichloromethane, 0.18 ml (1.0 mmol) of trimethylsilyl trifluoromethanesulfonate was added at 0° C. and stirred at the same temperature as above for 5 minutes, and then, 1.0 ml of dehydrated acetonitrile was added at 0° C. and stirred at the same temperature as above for 10 minutes.

After the completion of the reaction, 1 ml of methanol and 0.17 ml (1.5 mmol) of 2,6-lutidine were added to the reaction solution and then concentrated under reduced pressure. The obtained concentration residue was subjected to silica gel column chromatography (elution solvent: ethyl acetate:a mixed solution of 28% aqueous ammonia solution/ethanol [1:5 (V/V)]=98:2 to 95:5 (V/V)), and a fraction containing the compound of interest was concentrated under reduced pressure. The obtained concentration residue was subjected again to silica gel column chromatography (DIOL silica gel, elution solvent: ethyl acetate:methanol=100:0 to 95:5 (V/V)), and a fraction containing the compound of interest was concentrated under reduced pressure and dried under reduced pressure to obtain 52 mg of the title compound (yield: 48%) as a white solid.

Mass spectrum (DUIS, m/z): 514 [M+1]$^+$.

$^1$H-NMR spectrum (400 MHz, DMSO-d$_6$) δ: 12.21 & 11.72 (br s, total 1H), 9.69-9.50 (m, 1H), 6.89-6.83 (m, 1H), 6.81-6.76 (m, 2H), 6.12-5.94 (m, 3H), 4.96-4.90 (m, 2H), 4.59-4.43 (m, 2H), 3.62-3.56 (m, 2H), 2.49-2.42 (m, 2H), 2.26-2.15 (m, 2H), 1.90-1.74 (m, 2H), 1.60 (br s, 3H), 1.54 (br s, 3H), 0.10 (s, 9H).

Example 32

(S)—N-(1-Cyclohexyl-2-hydroxyethyl)-6,6-dimethyl-3-[1-(trimethylsilyl)cyclobutanecarboxamido]-4,6-dihydropyrrolo[3,4-c]pyrazole-5(1H)-carboxamide (Compound No. IV-495)

[Chemical Formula 48]

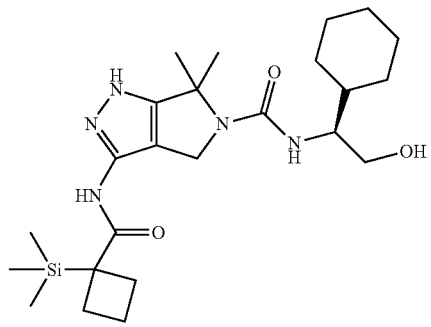

To a solution of 326 mg (0.739 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 4 ml of dehydrated THF, 0.33 ml (1.9 mmol) of DIPEA and 304 mg (2.12 mmol) of (S)-2-amino-2-cyclohexylethanol [synthesized according to the method described in Bioorg. Med. Chem. Lett., 2009, 19, 926-929] were added at room temperature in a nitrogen atmosphere and then stirred for 1.5 hours while heated to reflux. Subsequently, 0.90 ml (6.5 mmol) of triethylamine and 0.90 ml (22 mmol) of methanol were added to the reaction solution and then stirred for 1.5 hours while heated to reflux.

After the completion of the reaction, water was added to the reaction solution, followed by extraction with dichloromethane three times. All of the obtained organic layers were dried over anhydrous magnesium sulfate, filtered, and concentrated under reduced pressure. 85 μl of acetic acid was added to the obtained concentration residue and then subjected to silica gel column chromatography (DIOL silica gel, elution solvent: dichloromethane:methanol=100:0 to 97:3 (V/V)), and a fraction containing the compound of interest was concentrated under reduced pressure. For the obtained concentration residue, crystallization was performed with dichloromethane/n-hexane, and the deposited solid was collected by filtration, washed by sousing with n-hexane, and then dried under reduced pressure to obtain 295 mg of the title compound (yield: 84%) as a white solid.

Mass spectrum (CI, m/z): 476 [M+1]$^+$.

$^1$H-NMR spectrum (400 MHz, DMSO-$d_6$) δ: 12.20 & 11.71 (br s, total 1H), 9.70-9.44 (m, 1H), 5.46-5.15 (m, 1H), 4.54 (t, J=5.0 Hz, 1H), 4.49-4.21 (m, 2H), 3.53-3.40 (m, 3H), 2.48-2.40 (m, 2H), 2.27-2.10 (m, 2H), 1.88-1.45 (m, 14H), 1.28-1.03 (m, 3H), 1.03-0.83 (m, 2H), 0.08 (s, 9H).

Example 33

(S)—N-(1-Hydroxy-3-methylbutan-2-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-475)

[Chemical Formula 49]

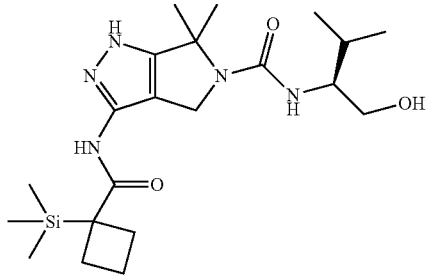

To a solution of 201 mg (0.456 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 4.5 ml of 1,4-dioxane, 235 mg (2.27 mmol) of (S)-2-amino-3-methylbutan-1-ol and 0.16 ml (0.91 mmol) of DIPEA were added at room temperature in a nitrogen atmosphere and then stirred at 100° C. for 1 hour.

After the completion of the reaction, the reaction solution was concentrated under reduced pressure, and ethyl acetate, water, and a saturated aqueous solution of sodium chloride were added to the concentration residue and then the aqueous layer and the organic layer were separated. The aqueous layer was subjected to extraction with ethyl acetate, all of the obtained organic layers were dried over anhydrous magnesium sulfate and filtered, and then, the filtrate was concentrated under reduced pressure. The obtained concentration residue was subjected to silica gel column chromatography (DIOL silica gel, elution solvent: 1,2-dichloroethane:methanol=99:1 to 96:4 (V/V)), and a fraction containing the compound of interest was concentrated under reduced pressure. Acetone was added to the obtained concentration residue and then ultrasonicated, and the deposited solid was collected by filtration and dried under reduced pressure to obtain 129 mg of the title compound (yield: 65%) as a white solid.

Mass spectrum (CI, m/z): 436 [M+1]$^+$.

$^1$H-NMR spectrum (400 MHz, DMSO-$d_6$) δ: 12.20 & 11.67 (br s, total 1H), 9.60-9.48 (m, 1H), 5.45-5.20 (m, 1H), 4.62-4.24 (m, 3H), 3.52-3.39 (m, 3H), 2.49-2.41 (m, 2H), 2.24-2.13 (m, 2H), 1.91-1.73 (m, 3H), 1.60 (br s, 6H), 0.92-0.82 (m, 6H), 0.08 (s, 9H).

Example 34

(S)—N-(1-Hydroxypropan-2-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-455)

[Chemical Formula 50]

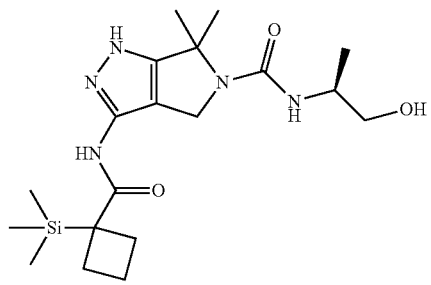

To a solution of 200 mg (0.454 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 4.5 ml of 1,4-dioxane, 170 mg (2.26 mmol) of (S)-2-aminopropan-1-ol and 0.16 ml (0.91 mmol) of DIPEA were added at room temperature, then applied to a microwave reaction apparatus, and reacted at 100° C. for 1 hour.

After the completion of the reaction, the reaction solution was concentrated under reduced pressure, and ethyl acetate, water, and a saturated aqueous solution of sodium chloride were added to the concentration residue and then the aqueous layer and the organic layer were separated. The aqueous layer was subjected to extraction with ethyl acetate, all of the obtained organic layers were dried over anhydrous magnesium sulfate and filtered, and then, the filtrate was concentrated under reduced pressure. The obtained concentration residue was subjected to silica gel column chromatography (DIOL silica gel, elution solvent: 1,2-dichloroethane:methanol=99:1 to 95:5 (V/V)), and a fraction containing the compound of interest was concentrated under reduced pressure. Ethyl acetate was added to the obtained concentration residue and ultrasonicated, and the deposited solid was

Example 35

N-(2-Hydroxyethyl)-6,6-dimethyl-3-[1-(trimethylsilyl)cyclobutanecarboxamido]-4,6-dihydropyrrolo[3,4-c]pyrazole-5(1H)-carboxamide (Compound No. IV-438)

[Chemical Formula 51]

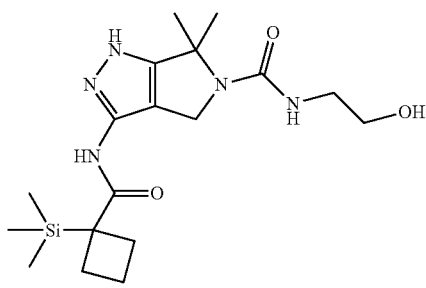

To a solution of 200 mg (0.454 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 3 ml of dehydrated THF, 0.16 ml (0.92 mmol) of DIPEA and 0.14 ml (2.3 mmol) of 2-aminoethanol were added at room temperature in an argon atmosphere and stirred at 60° C. for 3 hours.

After the completion of the reaction, water was added to the reaction solution, followed by extraction from the mixed solution with ethyl acetate. The obtained organic layer was washed with a saturated aqueous solution of sodium chloride, then dried by adding anhydrous sodium sulfate, filtered, and concentrated under reduced pressure. The obtained concentration residue was subjected to silica gel chromatography (DIOL silica gel, elution solvent: n-hexane: ethyl acetate=90:10 to 50:50 (V/V)), and a fraction containing the compound of interest was concentrated under reduced pressure and dried under reduced pressure to obtain 135 mg of the title compound (yield: 76%) as a white solid.

Mass spectrum (DUIS, m/z): 394 [M+1]+

$^1$H-NMR spectrum (400 MHz, DMSO-$d_6$) δ: 12.19 & 11.60 (br s, total 1H), 9.54 (s, 1H), 6.05-5.85 (m, 1H), 4.66 (t, J=5.5 Hz, 1H), 4.42-4.28 (m, 2H), 3.45-3.36 (in 2H), 3.17-3.02 (m, 2H), 2.48-2.39 (m, 2H), 2.25-2.12 (m, 2H), 1.91-1.71 (m, 2H), 1.67-1.52 (m, 6H), 0.08 (s, 9H).

Example 36

N-(2-Hydroxy-2-phenylethyl)-6,6-dimethyl-3-[1-(trimethylsilyl)cyclobutanecarboxamido]-4,6-dihydropyrrolo[3,4-c]pyrazole-5(1H)-carboxamide (Compound No. IV-450)

[Chemical Formula 52]

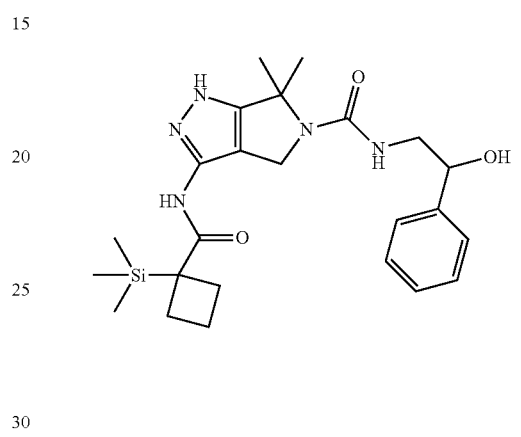

To a solution of 100 mg (0.227 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 2 ml of dehydrated 1,4-dioxane, 0.20 ml (1.1 mmol) of DIPEA and 160 mg (1.17 mmol) of 2-amino-1-phenylethanol were added at room temperature in an argon atmosphere and stirred at the same temperature as above for 1 hour.

After the completion of the reaction, water was added to the reaction solution, followed by extraction from the mixed solution with ethyl acetate. The obtained organic layer was washed with a saturated aqueous solution of sodium chloride, then dried by adding anhydrous sodium sulfate, filtered, and concentrated under reduced pressure. The obtained concentration residue was subjected to silica gel chromatography (DIOL silica gel, elution solvent: n-hexane: ethyl acetate=50:50 to 0:100 (V/V)), and a fraction containing the compound of interest was concentrated under reduced pressure and dried under reduced pressure to obtain 82.0 mg of the title compound (yield: 77%) as a white solid.

Mass spectrum (CI, m/z): 470 [M+1]+

$^1$H-NMR spectrum (400 MHz, DMSO-$d_6$) δ: 12.38-11.74 (m, 1H), 9.59 (br s, 1H), 7.36-7.29 (m, 4H), 7.26-7.20 (m, 1H), 6.14-5.98 (m, 1H), 5.58 (d, J=4.0 Hz, 1H), 4.70-4.62 (m, 1H), 4.42-4.28 (m, 2H), 3.29-3.23 (m, 1H), 3.10 (ddd, J=4.8, 8.0, 13.2 Hz, 1H), 2.48-2.40 (m, 2H), 2.23-2.14 (m, 2H), 1.88-1.74 (m, 2H), 1.60 (s, 6H), 0.08 (s, 9H).

---

Above text continues from previous page:

collected by filtration and dried under reduced pressure to obtain 145 mg of the title compound (yield: 78%) as a white solid.

Mass spectrum (CI, m/z): 408 [M+1]+.

$^1$H-NMR spectrum (400 MHz, DMSO-$d_6$) δ: 12.18 & 11.64 (br s, total 1H), 9.52 (s, 1H), 5.70-5.32 (m, 1H), 4.65 (t, J=5.6 Hz, 1H), 4.44-4.28 (m, 2H), 3.77-3.64 (m, 1H), 3.41-3.34 (m, 1H), 3.30-3.23 (m, 1H), 2.49-2.40 (m, 2H), 2.24-2.13 (m, 2H), 1.88-1.72 (m, 2H), 1.60 (s, 6H), 1.05 (d, J=6.7 Hz, 3H), 0.08 (s, 9H).

Example 37

N-(2-Hydroxypropyl)-6,6-dimethyl-3-[1-(trimethylsilyl)cyclobutanecarboxamido]-4,6-dihydropyrrolo[3,4-c]pyrazole-5(1H)-carboxamide (Compound No. IV-442)

[Chemical Formula 53]

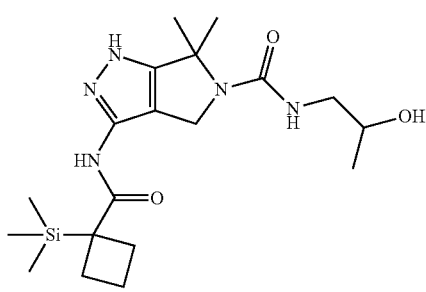

To a solution of 100 mg (0.227 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 and 85 μl (1.1 mmol) of 1-amino-2-propanol in 2 ml of dehydrated 1,4-dioxane, 0.20 ml (1.1 mmol) of DIPEA was added at room temperature in an argon atmosphere and stirred at the same temperature as above for 1.5 hours.

After the completion of the reaction, water was added to the reaction solution, followed by extraction from the mixed solution with ethyl acetate. The obtained organic layer was washed with a saturated aqueous solution of sodium chloride, then dried by adding anhydrous sodium sulfate, filtered, and concentrated under reduced pressure. The obtained concentration residue was subjected to silica gel chromatography (DIOL silica gel, elution solvent: n-hexane:ethyl acetate=50:50 to 0:100 (V/V)), and a fraction containing the compound of interest was concentrated under reduced pressure and dried under reduced pressure to obtain 61.1 mg of the title compound (yield: 66%) as a white solid.

Mass spectrum (CI, m/z): 408 [M+1]$^+$ $^1$H-NMR spectrum (400 MHz, DMSO-$d_6$) δ: 12.19 & 11.78 (br s, total 1H), 9.71-9.46 (m, 1H), 6.05-5.78 (m, 1H), 4.76 (d, J=4.4 Hz, 1H), 4.38 (br s, 2H), 3.71-3.61 (m, 1H), 3.09-2.99 (m, 1H), 2.97-2.88 (m, 1H), 2.49-2.39 (m, 2H), 2.25-2.13 (m, 2H), 1.88-1.71 (m, 2H), 1.60 (br s, 6H), 1.01 (d, J=6.3 Hz, 3H), 0.08 (s, 9H).

Example 38

N-[(2S)-1-Hydroxy-3-methyl-1-phenylbutan-2-yl]-6,6-dimethyl-3-[1-(trimethylsilyl)cyclobutanecarboxamido]-4,6-dihydropyrrolo[3,4-c]pyrazole-5(1H)-carboxamide (compound No. IV-487)

[Chemical Formula 54]

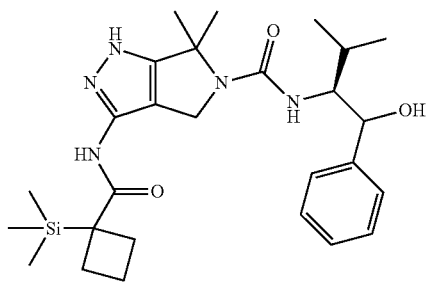

To a solution of 1.25 g (6.21 mmol) of (S)-tert-butyl (3-methyl-1-oxobutan-2-yl)carbamate [synthesized according to the method described in J. Am. Chem. Soc., 2004, 126, 11440-11441] in 15 ml of dehydrated THF, 6.60 ml (6.60 mmol) of 1 M phenyl magnesium bromide/THF solution was added dropwise at an internal temperature of 15° C. or lower in an argon atmosphere and, after the completion of the dropwise addition, stirred at room temperature for 1.5 hours.

After the completion of the reaction, the reaction solution was cooled in ice water, and 20 ml of a saturated aqueous solution of ammonium chloride was added and stirred at room temperature. Ethyl acetate and a saturated aqueous solution of sodium chloride were further added thereto and then the aqueous layer and the organic layer were separated. The obtained organic layer was dried over anhydrous magnesium sulfate and filtered, and then, the filtrate was concentrated under reduced pressure. The obtained residue was subjected to silica gel column chromatography (elution solvent: n-hexane:ethyl acetate=90:10 to 70:30 (V/V)), and a fraction containing tert-butyl[(2S)-1-hydroxy-3-methyl-1-phenylbutan-2-yl]carbamate was concentrated under reduced pressure to obtain a concentration residue.

To a solution of 0.90 g of the obtained concentration residue in 10 ml of dichloromethane, 1.2 ml (10 mmol) of 2,6-lutidine and 1.8 ml (10 mmol) of trimethylsilyl trifluoromethanesulfonate were added dropwise at 0° C. in a nitrogen atmosphere and stirred at the same temperature as above for 2 hours.

After the completion of the reaction, 50 ml of a saturated aqueous solution of sodium bicarbonate was added thereto, stirred, and then the aqueous layer and the organic layer were separated. The aqueous layer was subjected to extraction with dichloromethane, all of the obtained organic layers were dried over anhydrous sodium sulfate and filtered, and then, the filtrate was concentrated under reduced pressure. The operation of adding toluene to the obtained concentration residue and concentrating the resultant under reduced pressure was repeated several times. The obtained concentration residue was subjected to silica gel column chromatography (DNH silica gel, elution solvent: 1,2-dichloroethane:methanol=100:0 to 95:5 (V/V)), and a fraction containing (2S)-2-amino-3-methyl-1-phenylbutan-1-ol was concentrated under reduced pressure. The obtained concentration residue was subjected again to silica gel column chromatography (DIOL silica gel, elution solvent: 1,2-dichloroethane:methanol=100:0 to 95:5 (V/V)), and a fraction containing (2S)-2-amino-3-methyl-1-phenylbutan-1-ol was concentrated under reduced pressure to obtain a concentration residue.

To a solution of 111 mg (0.251 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2 (4H)-carboxylate synthesized in the similar manner as in Reference Example 3 in 4.0 ml of 1,4-dioxane, 97 mg of the concentration residue of (2S)-2-amino-3-methyl-1-phenylbutan-1-ol described above and 0.11 ml (0.63 mmol) of DIPEA were added at room temperature, then applied to a microwave reaction apparatus, and reacted at 100° C. for 1 hour. After the reaction, the reaction solution was concentrated under reduced pressure, and 4 ml of methanol and 1 ml of triethylamine were added to the obtained concentration residue, applied to a microwave reaction apparatus, and reacted at 80° C. for 1 hour.

After the completion of the reaction, the reaction solution was concentrated under reduced pressure, the obtained concentration residue was subjected to silica gel column chromatography (DIOL silica gel, elution solvent: 1,2-dichloroethane:methanol=100:0 to 95:5 (V/V)), and a fraction containing the compound of interest was concentrated under reduced pressure. Diethyl ether and n-hexane were added to the obtained concentration residue and ultrasonicated, and the deposited solid was collected by filtration. The obtained solid was subjected again to silica gel column chromatography (DIOL silica gel, elution solvent: 1,2-dichloroethane: methanol=100:0 to 95:5 (V/V)), and a fraction containing the compound of interest was concentrated under reduced pressure. For the obtained concentration residue, crystallization was performed with acetone/n-heptane, and the deposited solid was collected by filtration. The obtained solid was subjected again to silica gel column chromatography (elution solvent: hexane:ethyl acetate=38:62 to 17:83 (V/V)), and a fraction containing the compound of interest was concentrated under reduced pressure. n-Hexane was added to the obtained concentration residue, and after ultrasonication, the deposited solid was collected by filtration and dried under reduced pressure to obtain 55 mg of the title compound (yield: 42%) as a white solid.

Mass spectrum (CI, m/z): 512 [M+1]$^+$.

$^1$H-NMR spectrum (400 MHz, DMSO-d$_6$) δ: 12.15 & 11.74 (br s, total 1H), 9.85-9.20 (m, 1H), 7.33-7.19 (m, 4H), 7.17-7.10 (m, 1H), 5.68 (d, J=5.8 Hz, 1H), 5.32-5.16 (m, 1H), 4.82 (dd, J=2.6, 5.8 Hz, 1H), 4.37-4.23 (m, 2H), 3.52 (ddd, J=2.6, 8.7, 8.7 Hz, 1H), 2.49-2.39 (m, 2H), 2.26-2.13 (m, 2H), 2.00-1.72 (m, 3H), 1.52 (br s, 3H), 1.31 (br s, 3H), 1.03 (d, J=6.7 Hz, 3H), 0.90 (d, J=6.7 Hz, 3H), 0.09 (s, 9H).

Example 39

N-(4-Hydroxy-1-phenyl-2-butyn-1-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-378)

[Chemical Formula 55]

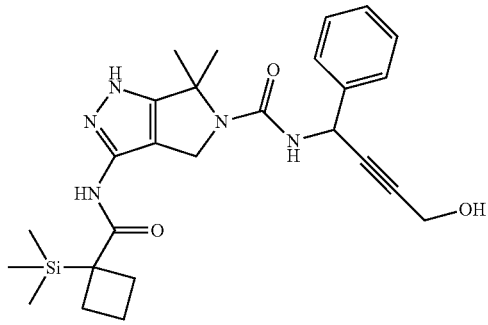

To a solution of 106 mg (0.240 mmol) of ethyl 5-(chlorocarbonyl)-6,6-dimethyl-3-[1-(trimethylsilyl)cyclobutanecarbox amido]-5,6-dihydropyrrolo[3,4-c]pyrazole-2(4H)-carboxylate synthesized in the similar manner as in Reference Example 3 in 3 ml of dehydrated 1,4-dioxane, 0.24 ml (1.4 mmol) of DIPEA and 146 mg (0.739 mmol) of 4-amino-4-phenyl-2-butyn-1-ol hydrochloride synthesized in the similar manner as in Reference Example 33 were added in an argon atmosphere and stirred at 100° C. for 2 hours. Subsequently, 1 ml of triethylamine and 1 ml of methanol were added to the reaction solution and stirred at 80° C. for 1 hour.

After the completion of the reaction, water was added to the reaction solution, followed by extraction from the mixed solution with ethyl acetate. The obtained organic layer was washed with a saturated aqueous solution of sodium chloride, dried over anhydrous sodium sulfate, filtered, and concentrated under reduced pressure. The obtained concentration residue was subjected to silica gel chromatography (DIOL column, elution solvent: dichloromethane:methanol=100:0 to 90:10 (V/V)), and a fraction containing the compound of interest was concentrated under reduced pressure. The obtained concentration residue was subjected again to silica gel chromatography (elution solvent: dichloromethane:methanol=100:0 to 90:10 (V/V)), and a fraction containing the compound of interest was concentrated under reduced pressure and dried under reduced pressure to obtain 79.6 mg of the title compound (yield: 67%) as a light brown solid.

Mass spectrum (CI, m/z): 494 [M+1]$^+$ $^1$H-NMR spectrum (400 MHz, DMSO-d$_6$) δ: 12.21 & 11.70 (br s, total 1H), 9.54 (br s, 1H), 7.53-7.47 (m, 2H), 7.38-7.32 (m, 2H), 7.29-7.23 (m, 1H), 7.20-6.97 (m, 1H), 5.89-5.84 (m, 1H), 5.20 (t, J=5.9 Hz, 1H), 4.45 (br s, 2H), 4.15 (dd, J=1.9, 5.9 Hz, 2H), 2.48-2.40 (m, 2H), 2.24-2.12 (m, 2H), 1.87-1.73 (m, 2H), 1.63 (s, 3H), 1.59 (s, 3H), 0.08 (s, 9H).

Example 40

(S)-2-{6,6-Dimethyl-3-[1-(trimethylsilyl)cyclobutanecarboxamido]-1,4,5,6-tetrahydropyrrolo[3,4-c]pyrazole-5-carboxamido}-2-phenylethyl acetate (Compound No. V-1442)

[Chemical Formula 56]

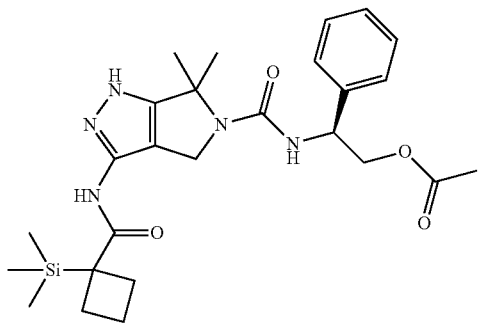

To a solution of 360 mg (0.816 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 10 ml of THF, 883 mg (4.09 mmol) of (S)-2-amino-2-phenylethyl acetate hydrochloride synthesized in the similar manner as in Reference Example 35 and 2.0 ml (12 mmol) of DIPEA were added at room temperature, applied to a microwave reaction apparatus, and reacted at 100° C. for 2 hours. Subsequently, 1.1 ml (27 mmol) of methanol was added, then applied to a microwave reaction apparatus, and reacted at 80° C. for 1 hour. 2.0 ml (49 mmol) of methanol and 1.0 ml (7.2 mmol) of triethylamine were further added, then applied to a microwave reaction apparatus, and reacted at 80° C. for 1 hour.

After the completion of the reaction, the reaction solution was concentrated under reduced pressure, and 15 ml of ethyl acetate and 15 ml of a saturated aqueous solution of sodium chloride were added to the obtained concentration residue and then the aqueous layer and the organic layer were separated. The aqueous layer was subjected to extraction with 15 ml of dichloromethane. All of the obtained organic layers were dried over anhydrous magnesium sulfate, filtered, and concentrated under reduced pressure. The obtained concentration residue was subjected to silica gel column chromatography (DIOL silica gel, elution solvent: 1,2-dichloroethane:methanol=100:0 to 90:10 (V/V)), and a fraction containing the compound of interest was concentrated under reduced pressure. Ethyl acetate and diethyl ether were added in small amounts to the obtained concentration residue, then ultrasonicated, cooled in ice water, and then filtered. The obtained solid was subjected again to silica gel column chromatography (DIOL silica gel, elution solvent: ethyl acetate:methanol=100:0 to 99:1 (V/V)), and a fraction containing the compound of interest was concentrated under reduced pressure. Ethyl acetate and diethyl ether were added in small amounts to the obtained concentration residue, then ultrasonicated, cooled in ice water, and then filtered to obtain white solid A. The filtrate was concentrated under reduced pressure, the obtained concentration residue was subjected to silica gel column chromatography (elution solvent: ethyl acetate:methanol=100:0 to 99:1 (V/V)), and a fraction containing the compound of interest was concentrated under reduced pressure. Ethyl acetate and diethyl ether were added in small amounts to the obtained concentration residue, then ultrasonicated, cooled in ice water, and then filtered to obtain white solid B. The white solids A and B were dissolved in ethyl acetate, then diethyl ether was added, and the deposited solid was filtered and dried under reduced pressure to obtain 142 mg of the title compound (yield: 34%) as a white solid.

Mass spectrum (DUIS, m/z): 512 [M+1]$^+$.

$^1$H-NMR spectrum (400 MHz, DMSO-d$_6$) δ: 12.21 & 11.71 (br s, total 1H), 9.76-9.33 (m, 1H), 7.43-7.37 (m, 2H), 7.37-7.31 (m, 2H), 7.28-7.22 (m, 1H), 6.65-6.38 (m, 1H), 5.12-5.03 (m, 1H), 4.49 (br s, 2H), 4.30-4.19 (m, 2H), 2.49-2.41 (m, 2H), 2.25-2.14 (m, 2H), 1.98 (s, 3H), 1.89-1.74 (m, 2H), 1.61 (br s, 3H), 1.53 (br s, 3H), 0.09 (s, 9H).

Example 41

(S)-2-{6,6-Dimethyl-3-[1-(trimethylsilyl)cyclobutanecarboxamido]-1,4,5,6-tetrahydropyrrolo[3,4-c]pyrazole-5-carboxamido}-2-phenylethyl propionate (Compound No. V-1446)

[Chemical Formula 57]

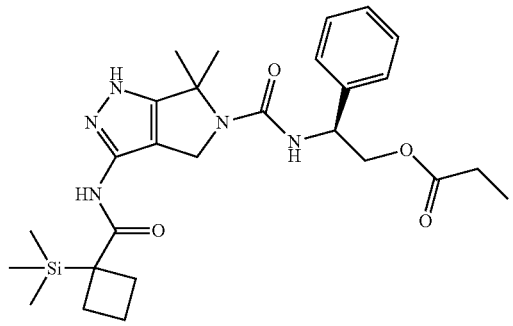

To a solution of 200 mg (0.369 mmol) of (S)-ethyl 5-[(2-hydroxy-1-phenylethyl)carbamoyl]-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 38 and 0.10 ml (0.74 mmol) of triethylamine in 3 ml of dehydrated dichloromethane, 0.071 ml (0.55 mmol) of propionic anhydride and 9.7 mg (0.079 mmol) of 4-dimethylaminopyridine were added in this order at room temperature in an argon atmosphere and then reacted at room temperature for 5 hours. Subsequently, 1 ml of methanol and 0.5 ml of triethylamine were added and reacted at room temperature for 2 hours.

After the completion of the reaction, the reaction solution was concentrated under reduced pressure, and 10 ml of ethyl acetate, 0.5 ml of water, and 10 ml of a saturated aqueous solution of sodium chloride were added to the obtained concentration residue, and then the aqueous layer and the organic layer were separated. The aqueous layer was subjected to extraction with 10 ml of dichloromethane twice, and all of the obtained organic layers were dried over anhydrous magnesium sulfate, then filtered, and concentrated under reduced pressure. The obtained concentration residue was subjected to silica gel column chromatography (DIOL silica gel, elution solvent: 1,2-dichloroethane:methanol=100:0 to 95:5 (V/V)), and a fraction containing the compound of interest was concentrated under reduced pressure. Diethyl ether was added to the obtained concentration residue, and after ultrasonication, insoluble matter was filtered and dried under reduced pressure to obtain 138 mg of the title compound (yield: 71%) as a white solid.

Mass spectrum (CI, m/z): 526 [M+1]$^+$.

$^1$H-NMR spectrum (400 MHz, DMSO-d$_6$) δ: 12.20 & 11.66 (br s, total 1H), 9.70-9.39 (m, 1H), 7.45-7.30 (m, 4H), 7.28-7.21 (m, 1H), 6.64-6.39 (m, 1H), 5.16-5.03 (m, 1H), 4.57-4.39 (m, 2H), 4.32-4.19 (m, 2H), 2.49-2.41 (m, 2H), 2.27 (q, J=7.5 Hz, 2H), 2.24-2.14 (m, 2H), 1.91-1.72 (m, 2H), 1.67-1.47 (m, 6H), 0.99 (t, J=7.5 Hz, 3H), 0.09 (s, 9H).

Example 42

(S)-2-{6,6-Dimethyl-3-[1-(trimethylsilyl)cyclobutanecarboxamido]-1,4,5,6-tetrahydropyrrolo[3,4-c]pyrazole-5-carboxamido}-2-phenylethyl butanoate (Compound No. V-1450)

[Chemical Formula 58]

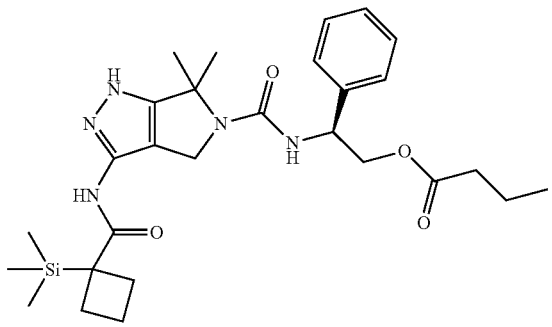

To a solution of 250 mg (0.461 mmol) of a mixture of (S)-ethyl 5-[(2-hydroxy-1-phenylethyl)carbamoyl]-6,6-dimethyl-3-[1-(trimethylsilyl)cyclobutanecarboxamido]-5,6-dihydropyrrolo[3,4-c]pyrazole-1(4H)-carboxylate synthesized in the similar manner as in Reference Example and (S)-ethyl 5-[(2-hydroxy-1-phenylethyl)carbamoyl]-6,6-dimethyl-3-[1-(trimethylsilyl)cyclobutanecarboxamido]-5,6-dihydropyrrolo[3,4-c]pyrazole-2(4H)-carboxylate and 0.10 ml (0.74 mmol) of triethylamine in 4.5 ml of 1,4-dioxane, 0.09 ml (0.6 mmol) of butyric anhydride and 9.0 mg (0.074 mmol) of 4-dimethylaminopyridine were added in this order at room temperature in an argon atmosphere and then reacted at 100° C. for 1.5 hours. Subsequently, 1.5 ml (37 mmol) of methanol and 0.75 ml (5.4 mmol) of triethylamine were added, applied to a microwave reaction apparatus, and reacted at 80° C. for 2 hours.

After the completion of the reaction, the reaction solution was concentrated under reduced pressure, and 8 ml of ethyl acetate, 0.4 ml of water, and 8 ml of a saturated aqueous solution of sodium chloride were added to the obtained concentration residue, and then the aqueous layer and the organic layer were separated. The aqueous layer was subjected to extraction with 10 ml of dichloromethane twice, and all of the obtained organic layers were dried over anhydrous magnesium sulfate, then filtered, and concentrated under reduced pressure. The obtained concentration residue was subjected to silica gel column chromatography (DIOL silica gel, elution solvent: 1,2-dichloroethane:methanol=100:0 to 95:5 (V/V)), a fraction containing the compound of interest was concentrated under reduced pressure, then the obtained concentration residue was subjected again to silica gel column chromatography (DIOL silica gel, elution solvent: 1,2-dichloroethane:ethyl acetate=100:0 to 51:49 (V/V)), and a fraction containing the compound of interest was concentrated under reduced pressure. Water was added to the concentration residue, and after ultrasonication, insoluble matter was filtered and dried under reduced pressure to obtain 80 mg of the title compound (yield: 32%) as a white solid.

Mass spectrum (CI, m/z): 540 [M+1]$^+$.

$^1$H-NMR spectrum (400 MHz, DMSO-d$_6$) δ: 12.20 & 11.65 (br s, total 1H), 9.69-9.40 (m, 1H), 7.45-7.37 (m, 2H), 7.37-7.29 (m, 2H), 7.28-7.21 (m, 1H), 6.64-6.39 (m, 1H), 5.15-5.04 (m, 1H), 4.57-4.38 (m, 2H), 4.31-4.20 (m, 2H), 2.49-2.41 (m, 2H), 2.28-2.14 (m, 4H), 1.92-1.73 (m, 2H), 1.64-1.44 (m, 8H), 0.83 (t, J=7.4 Hz, 3H), 0.09 (s, 9H).

Example 43

(S)-2-{6,6-Dimethyl-3-[1-(trimethylsilyl)cyclobutanecarboxamido]-1,4,5,6-tetrahydropyrrolo[3,4-c]pyrazole-5-carboxamido}-2-phenylethyl pentanoate (Compound No. V-1458)

[Chemical Formula 59]

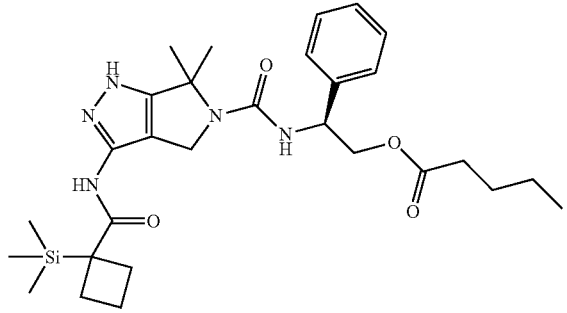

To a solution of 200 mg (0.369 mmol) of (S)-ethyl 5-[(2-hydroxy-1-phenylethyl)carbamoyl]-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 38 and 0.10 ml (0.74 mmol) of triethylamine in 3 ml of 1,4-dioxane, 0.09 ml (0.5 mmol) of valeric anhydride and 9.0 mg (0.074 mmol) of 4-dimethylaminopyridine were added at room temperature in an argon atmosphere and then reacted at 100° C. for 1 hour. Subsequently, 1 ml of methanol and 0.5 ml of triethylamine were added, applied to a microwave reaction apparatus, and reacted at 80° C. for 1 hour.

After the completion of the reaction, the reaction solution was concentrated under reduced pressure, and 10 ml of ethyl acetate and 10 ml of 10% potassium dihydrogen phosphate were added to the obtained concentration residue, and then the aqueous layer and the organic layer were separated. The aqueous layer was subjected to extraction with 10 ml of dichloromethane twice, and all of the obtained organic layers were washed with 10 ml of water, 10 ml of a saturated aqueous solution of sodium bicarbonate, and 10 ml of a saturated aqueous solution of sodium chloride in this order, then dried over anhydrous magnesium sulfate, filtered, and concentrated under reduced pressure. The obtained concentration residue was subjected to silica gel column chromatography (DIOL silica gel, elution solvent: 1,2-dichloroethane:ethyl acetate=100:0 to 51:49 (V/V)), and a fraction containing the compound of interest was concentrated under reduced pressure. Purified water was added to the obtained concentration residue, and after ultrasonication, insoluble matter was filtered and dried under reduced pressure to obtain 39 mg of the title compound (yield: 19%) as a white solid.

Mass spectrum (CI, m/z): 554 [M+1]$^+$.

$^1$H-NMR spectrum (400 MHz, DMSO-d$_6$) δ: 12.20 & 11.63 (br s, total 1H), 9.54 (s, 1H), 7.44-7.37 (m, 2H), 7.36-7.30 (m, 2H), 7.28-7.21 (m, 1H), 6.66-6.39 (m, 1H), 5.14-5.04 (m, 1H), 4.59-4.40 (m, 2H), 4.25 (d, J=7.5 Hz, 2H), 2.49-2.41 (m, 2H), 2.29-2.14 (m, 4H), 1.92-1.73 (m, 2H), 1.61 (br s, 3H), 1.56-1.41 (m, 5H), 1.29-1.18 (m, 2H), 0.80 (t, J=7.3 Hz, 3H), 0.09 (s, 9H).

Example 44

(S)-2-{6,6-Dimethyl-3-[1-(trimethylsilyl)cyclobutanecarboxamido]-1,4,5,6-tetrahydropyrrolo[3,4-c]pyrazole-5-carboxamido}-2-phenylethyl octanoate (Compound No. V-1470)

[Chemical Formula 60]

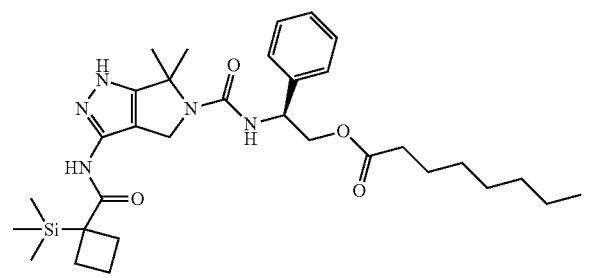

To a solution of 183 mg (0.329 mmol) of a mixture of (S)-ethyl 5-[(2-hydroxy-1-phenylethyl)carbamoyl]-6,6-dimethyl-3-[1-(trimethylsilyl)cyclobutanecarboxamido]-5,6-dihydropyrrolo[3,4-c]pyrazole-1(4H)-carboxylate synthesized in the similar manner as in Reference Example 38 and (S)-ethyl 5-[(2-hydroxy-1-phenylethyl)carbamoyl]-6,6-dimethyl-3-[1-(trimethylsilyl)cyclobutanecarboxamido]-5,6-dihydropyrrolo[3,4-c]pyrazole-2(4H)-carboxylate in a 3 ml of dehydrated dichloromethane, 0.10 ml (0.72 mmol) of triethylamine, 0.15 ml (0.51 mmol) of n-octanoic anhydride, and 10.6 mg (0.087 mmol) of 4-dimethylaminopyridine were added in this order at room temperature in a nitrogen atmosphere and then stirred at the same temperature as above for 2 hours. Subsequently, 1.0 ml (7.2 mmol) of triethylamine and 1.0 ml (25 mmol) of methanol were added to the reaction solution and then stirred at room temperature for 20.5 hours. 1.0 ml (7.2 mmol) of triethylamine and 1.0 ml (25 mmol) of methanol were added to the reaction solution, stirred at 50° C. for 2 hours, and then stirred for 4 hours after the temperature was raised to 60° C.

After the completion of the reaction, water was added to the reaction solution, followed by extraction with dichloromethane three times. All of the obtained organic layers were dried over anhydrous magnesium sulfate, filtered, and concentrated under reduced pressure. The obtained concentration residue was subjected to silica gel column chromatography (elution solvent: dichloromethane:methanol=100:0 to 97:3 (V/V)), and a fraction containing the compound of interest was concentrated under reduced pressure. n-Hexane was added to the obtained concentration residue, and after ultrasonication, the deposited solid was collected by filtration, washed by sousing with n-hexane, and then dried under reduced pressure to obtain 115 mg of the title compound (yield: 58%) as a white solid.

Mass spectrum (CI, m/z): 596 [M+1]$^+$.

$^1$H-NMR spectrum (400 MHz, DMSO-d$_6$) δ: 12.16 & 11.77 (br s, total 1H), 9.55 (br s, 1H), 7.47-7.37 (m, 2H), 7.37-7.29 (m, 2H), 7.29-7.20 (m, 1H), 6.64-6.43 (m, 1H), 5.16-5.02 (m, 1H), 4.49 (s, 2H), 4.34-4.18 (m, 2H), 2.49-2.41 (m, 2H), 2.28-2.14 (m, 4H), 1.89-1.73 (m, 2H), 1.60 (s, 3H), 1.53 (s, 3H), 1.50-1.43 (m, 2H), 1.24-1.13 (m, 8H), 0.83-0.75 (m, 3H), 0.09 (s, 9H).

Example 45

(S)-2-{6,6-Dimethyl-3-[1-(trimethylsilyl)cyclobutanecarboxamido]-1,4,5,6-tetrahydropyrrolo[3,4-c]pyrazole-5-carboxamido}-2-phenylethyl dodecanoate (Compound No. V-1474)

[Chemical Formula 61]

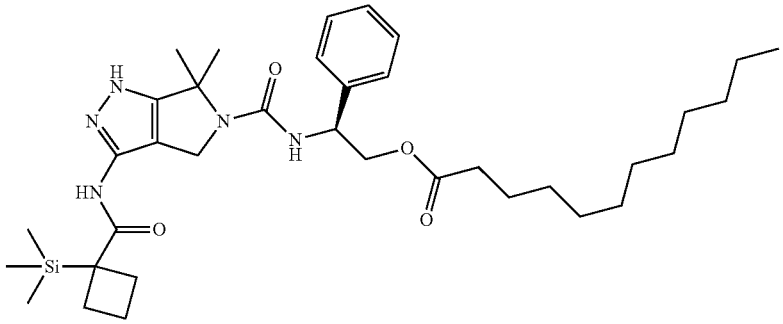

To a solution of 202 mg (0.373 mmol) of (S)-ethyl 5-[(2-hydroxy-1-phenylethyl)carbamoyl]-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 38, 0.11 ml (0.79 mmol) of triethylamine, and 10 mg (0.082 mmol) of 4-dimethylaminopyridine in 2 ml of dehydrated dichloromethane, 224 mg (0.585 mmol) of dodecanoic anhydride was added at room temperature in an argon atmosphere and stirred at room temperature for 1 hour. Subsequently, 1 ml of triethylamine and 1 ml of methanol were added to the reaction solution and stirred at room temperature for 16 hours.

After the completion of the reaction, the reaction solution was concentrated under reduced pressure. The obtained concentration residue was subjected to silica gel chromatography (elution solvent: n-hexane:ethyl acetate=95:5 to 50:50 (V/V)), and a fraction containing the compound of interest was concentrated under reduced pressure and dried under reduced pressure to obtain 139 mg of the title compound (yield: 57%) as a white solid.

Mass spectrum (CI, m/z): 652 $[M+1]^+$ $^1$H-NMR spectrum (400 MHz, DMSO-$d_6$) δ: 12.18 & 11.66 (br s, total 1H), 9.83-9.28 (m, 1H), 7.42-7.37 (m, 2H), 7.37-7.30 (m, 2H), 7.28-7.21 (m, 1H), 6.67-6.35 (m, 1H), 5.14-5.03 (m, 1H), 4.56-4.42 (m, 2H), 4.30-4.20 (m, 2H), 2.49-2.42 (m, 2H), 2.28-2.13 (m, 4H), 1.89-1.73 (m, 2H), 1.60 (br s, 3H), 1.57-1.43 (m, 5H), 1.30-1.14 (m, 16H), 0.85 (t, J=6.9 Hz, 3H), 0.09 (s, 9H).

Example 46

(S)-2-{6,6-Dimethyl-3-[1-(trimethylsilyl)cyclobutanecarboxamido]-1,4,5,6-tetrahydropyrrolo[3,4-c]pyrazole-5-carboxamido}-2-phenylethyl palmitate
(Compound No. V-1478)

[Chemical Formula 62]

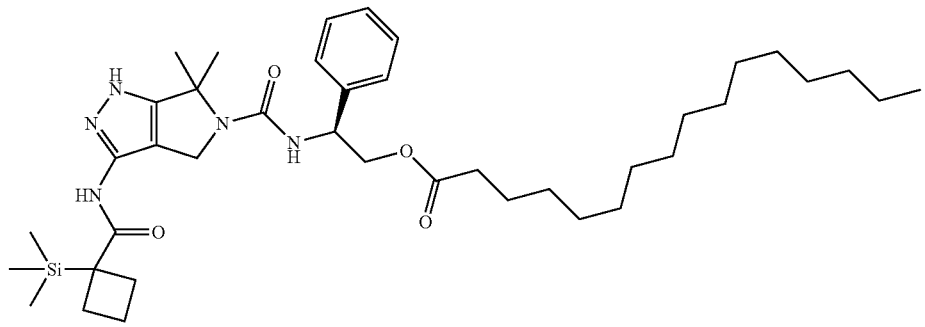

To a solution of 220 mg (0.406 mmol) of (S)-ethyl 5-[(2-hydroxy-1-phenylethyl)carbamoyl]-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 38, 0.115 ml (0.825 mmol) of triethylamine, and 300 mg (0.606 mmol) of palmitic anhydride in 3 ml of dichloromethane, 10 mg (0.082 mmol) of 4-dimethylaminopyridine was added at room temperature in an argon atmosphere and stirred at the same temperature as above for 1.5 hours. Subsequently, 1.0 ml of methanol and 0.5 ml of triethylamine were added to the reaction solution and stirred at room temperature for 15 hours.

After the completion of the reaction, the reaction solution was concentrated under reduced pressure. The obtained concentration residue was subjected to silica gel chromatography (elution solvent: n-hexane:ethyl acetate=90:10 to 50:50 (V/V)), and a fraction containing the compound of interest was concentrated under reduced pressure and dried under reduced pressure to obtain 195 mg of the title compound (yield: 68%) as a white solid.

Mass spectrum (DUIS, m/z): 708 $[M+1]^+$ $^1$H-NMR spectrum (400 MHz, DMSO-$d_6$) δ: 12.18 & 11.64 (br s, total 1H), 9.64-9.50 (m, 1H), 7.43-7.38 (m, 2H), 7.36-7.30 (m, 2H), 7.27-7.21 (m, 1H), 6.63-6.39 (m, 1H), 5.13-5.04 (m, 1H), 4.55-4.42 (m, 2H), 4.30-4.20 (m, 2H), 2.48-2.40 (m, 2H), 2.29-2.14 (m, 4H), 1.89-1.74 (m, 2H), 1.60 (br s, 3H), 1.57-1.43 (m, 5H), 1.29-1.14 (m, 24H), 0.89-0.81 (m, 3H), 0.09 (s, 9H).

Example 47

(S)-2-{6,6-Dimethyl-3-[1-(trimethylsilyl)cyclobutanecarboxamido]-1,4,5,6-tetrahydropyrrolo[3,4-c]pyrazole-5-carboxamido}-2-phenylethyl isobutanoate (Compound No. V-1454)

[Chemical Formula 63]

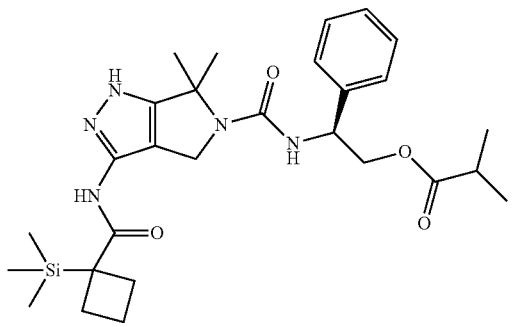

To a solution of 247 mg (0.456 mmol) of (S)-ethyl 5-[(2-hydroxy-1-phenylethyl)carbamoyl]-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 38 in 3 ml of dehydrated dichloromethane, 0.15 ml (1.1 mmol) of triethylamine and 0.060 ml (0.57 mmol) of isobutyryl chloride were added in this order at room temperature in a nitrogen atmosphere and then stirred at the same temperature as above for 100 minutes. Subsequently, 1.0 ml (7.2 mmol) of triethylamine and 1.0 ml (25 mmol) of methanol were added to the reaction solution and then stirred at room temperature for 4.5 hours.

After the completion of the reaction, water was added to the reaction solution, followed by extraction with dichloromethane three times. All of the obtained organic layers were dried over anhydrous magnesium sulfate, filtered, and concentrated under reduced pressure. The obtained concentration residue was subjected to silica gel column chromatography (DIOL silica gel, elution solvent: dichloromethane:methanol=100:0 to 99:1 (V/V)), and a fraction containing the compound of interest was concentrated under reduced pressure. For the obtained concentration residue, crystallization was performed with ethyl acetate/n-hexane, and the obtained solid was collected by filtration, washed by sousing with n-hexane, and then dried under reduced pressure to obtain 202 mg of the title compound (yield: 82%) as a white solid.

Mass spectrum (CI, m/z): 540 [M+1]$^+$.

$^1$H-NMR spectrum (400 MHz, DMSO-d$_6$) δ: 12.20 & 11.61 (br s, total 1H), 9.53 (s, 1H), 7.47-7.38 (m, 2H), 7.38-7.29 (m, 2H), 7.29-7.20 (m, 1H), 6.71-6.34 (m, 1H), 5.20-5.03 (m, 1H), 4.57-4.38 (m, 2H), 4.33-4.15 (m, 2H), 2.48-2.42 (m, 3H), 2.27-2.13 (m, 2H), 1.92-1.73 (m, 2H), 1.65-1.47 (m, 6H), 1.08-0.99 (m, 6H), 0.14-0.05 (m, 9H).

Example 48

(S)-2-{6,6-Dimethyl-3-[1-(trimethylsilyl)cyclobutanecarboxamido]-1,4,5,6-tetrahydropyrrolo[3,4-c]pyrazole-5-carboxamido}-2-phenylethyl pivalate (Compound No. V-1462)

[Chemical Formula 64]

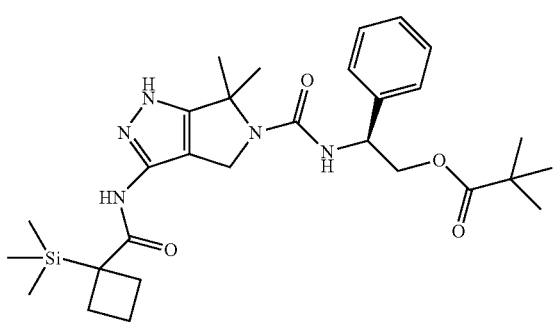

To a solution of 210 mg (0.387 mmol) of (S)-ethyl 5-[(2-hydroxy-1-phenylethyl)carbamoyl]-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 38 and 0.11 ml (0.79 mmol) of triethylamine in 3 ml of dehydrated dichloromethane, 0.12 ml (0.59 mmol) of pivalic anhydride and 10.5 mg (0.086 mmol) of 4-dimethylaminopyridine were added in an argon atmosphere and stirred at room temperature for 4.5 hours. Subsequently, 0.5 ml of triethylamine and 1 ml of methanol were added to the reaction solution and reacted at room temperature for 14 hours.

After the completion of the reaction, the reaction solution was concentrated under reduced pressure. The obtained concentration residue was subjected to silica gel chromatography (elution solvent: n-hexane:ethyl acetate=90:10 to 50:50 (V/V)), and a fraction containing the compound of interest was concentrated under reduced pressure and dried under reduced pressure. Diisopropyl ether was added to the obtained concentration residue, and after ultrasonication, insoluble matter was collected by filtration and dried under reduced pressure to obtain 144 mg of the title compound (yield: 67%) as a white solid.

Mass spectrum (CI, m/z): 554 [M+1]$^+$ $^1$H-NMR spectrum (400 MHz, DMSO-d$_6$) δ: 12.20 & 11.66 (br s, total 1H), 9.55 (s, 1H), 7.45-7.38 (m, 2H), 7.37-7.31 (m, 2H), 7.28-7.22 (m, 1H), 6.68-6.40 (m, 1H), 5.20-5.09 (m, 1H), 4.48 (br s, 2H), 4.29-4.19 (m, 2H), 2.49-2.41 (m, 2H), 2.26-2.14 (m, 2H), 1.90-1.74 (m, 2H), 1.59 (s, 3H), 1.55 (s, 3H), 1.08 (s, 9H), 0.09 (s, 9H).

Example 49

(S)-2-{6,6-Dimethyl-3-[1-(trimethylsilyl)cyclobutanecarboxamido]-1,4,5,6-tetrahydropyrrolo[3,4-c]pyrazole-5-carboxamido}-2-phenylethyl 3-methylbutanoate (Compound No. V-1466)

[Chemical Formula 65]

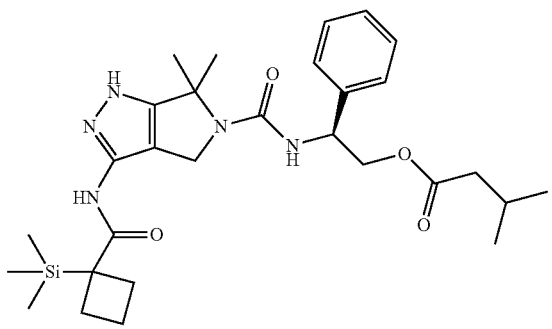

To a solution of 201 mg (0.371 mmol) of a mixture of (S)-ethyl 5-[(2-hydroxy-1-phenylethyl)carbamoyl]-6,6-dimethyl-3-[1-(trimethylsilyl)cyclobutanecarboxamido]-5,6-dihydropyrrolo[3,4-c]pyrazole-1(4H)-carboxylate synthesized in the similar manner as in Reference Example and (S)-ethyl 5-[(2-hydroxy-1-phenylethyl)carbamoyl]-6,6-dimethyl-3-[1-(trimethylsilyl)cyclobutanecarboxamido]-5,6-dihydropyrrolo[3,4-c]pyrazole-2(4H)-carboxylate and 0.10 ml (0.74 mmol) of triethylamine in 3 ml of dichloromethane, 0.11 ml (0.56 mmol) of isovaleric anhydride and 10.6 mg (0.087 mmol) of 4-dimethylaminopyridine were added at room temperature in an argon atmosphere and then reacted at the same temperature as above for 3 hours. Subsequently, 1.0 ml of methanol and 0.5 ml of triethylamine were added and reacted at room temperature for 15.5 hours, then the reaction solution was concentrated under reduced pressure, and 1.0 ml of methanol and 0.5 ml of triethylamine were added again to the obtained concentration residue and reacted at 40° C. for 6 hours.

After the completion of the reaction, the reaction solution was concentrated under reduced pressure, and 8 ml of ethyl acetate, 0.4 ml of water, and 8 ml of a saturated aqueous solution of sodium chloride were added to the obtained concentration residue, and then the aqueous layer and the organic layer were separated. The aqueous layer was subjected to extraction with 10 ml of dichloromethane twice, and all of the obtained organic layers were dried over anhydrous magnesium sulfate, then filtered, and concentrated under reduced pressure. The obtained concentration residue was subjected to silica gel column chromatography (DIOL silica gel, elution solvent: 1,2-dichloroethane:methanol=100:0 to 95:5 (V/V)), and a fraction containing the compound of interest was concentrated under reduced pressure. Diethyl ether was added to the obtained concentration residue, ultrasonicated, and then concentrated under reduced pressure. Water was added to the obtained concentration residue, ultrasonicated, and left standing overnight, and then, insoluble matter was filtered and dried under reduced pressure to obtain 97 mg of the title compound (yield: 47%) as a white solid.

Mass spectrum (CI, m/z): 554 [M+1]$^+$.

$^1$H-NMR spectrum (400 MHz, DMSO-$d_6$) δ: 12.50-11.49 (m, 1H), 9.55 (s, 1H), 7.44-7.38 (m, 2H), 7.37-7.30 (m, 2H), 7.29-7.22 (m, 1H), 6.84-6.25 (m, 1H), 5.13-5.06 (m, 1H), 4.55-4.41 (m, 2H), 4.31-4.21 (m, 2H), 2.49-2.42 (m, 2H), 2.26-2.11 (m, 4H), 2.01-1.87 (m, 1H), 1.87-1.74 (m, 2H), 1.59 (s, 3H), 1.53 (s, 3H), 0.87-0.82 (m, 6H), 0.09 (s, 9H).

Example 50

(S)-2-{6,6-Dimethyl-3-[1-(trimethylsilyl)cyclobutanecarboxamido]-1,4,5,6-tetrahydropyrrolo[3,4-c]pyrazole-5-carboxamido}-2-phenylethyl benzoate (Compound No. V-1482)

[Chemical Formula 66]

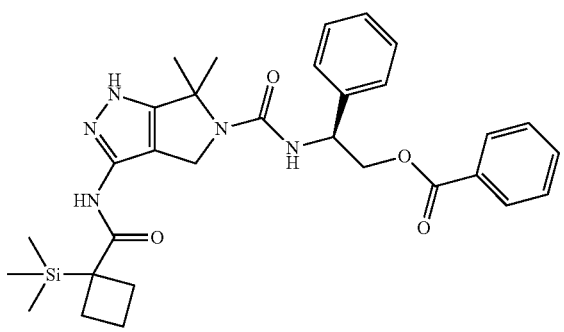

To a solution of 132 mg (0.244 mmol) of (S)-ethyl 5-[(2-hydroxy-1-phenylethyl)carbamoyl]-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 38 and 0.068 ml (0.49 mmol) of triethylamine in 2.5 ml of dehydrated dichloromethane, 0.042 ml (0.36 mmol) of benzoyl chloride was added at room temperature in an argon atmosphere and stirred at the same temperature as above for 1 hour. Subsequently, 0.5 ml of triethylamine and 0.5 ml of methanol were added to the reaction solution and stirred at room temperature for 20 hours.

After the completion of the reaction, the reaction solution was concentrated under reduced pressure. The obtained concentration residue was subjected to silica gel chromatography (elution solvent: n-hexane:ethyl acetate=90:10 to 50:50 (V/V)), and a fraction containing the compound of interest was concentrated under reduced pressure and dried under reduced pressure to obtain 94 mg of the title compound (yield: 67%) as a white solid.

Mass spectrum (CI, m/z): 574 [M+1]$^+$ $^1$H-NMR spectrum (400 MHz, DMSO-$d_6$) δ: 12.19 & 11.71 (br s, total 1H), 9.55 (br s, 1H), 7.95-7.91 (m, 2H), 7.66-7.60 (m, 1H), 7.52-7.46 (m, 4H), 7.39-7.33 (m, 2H), 7.30-7.24 (m, 1H), 6.73-6.59 (m, 1H), 5.35-5.26 (m, 1H), 4.57-4.44 (m, 4H), 2.48-2.42 (m, 2H), 2.23-2.15 (m, 2H), 1.87-1.73 (m, 2H), 1.57 (s, 3H), 1.55 (s, 3H), 0.08 (s, 9H).

Example 51

(S)-2-{6,6-Dimethyl-3-[1-(trimethylsilyl)cyclobutanecarboxamido]-1,4,5,6-tetrahydropyrrolo[3,4-c]pyrazole-5-carboxamido}-2-phenylethyl ethyl carbonate (Compound No. V-1486)

[Chemical Formula 67]

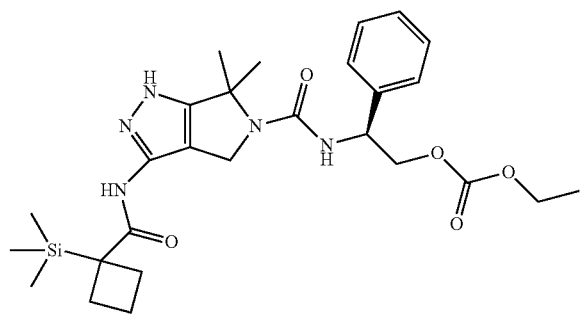

To a solution of 265 mg (0.490 mmol) of (S)-ethyl 5-[(2-hydroxy-1-phenylethyl)carbamoyl]-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 38 in 4 ml of dehydrated dichloromethane, 0.14 ml (1.0 mmol) of triethylamine and 0.060 ml (0.63 mmol) of ethyl chloroformate were added in this order at room temperature in a nitrogen atmosphere and then stirred at the same temperature as above for 2 hours. Then, 0.20 ml (1.4 mmol) of triethylamine and 0.10 ml (1.1 mmol) of ethyl chloroformate were added at room temperature and stirred at the same temperature as above for 1.5 hours. 0.20 ml (1.4 mmol) of triethylamine and 0.10 ml (1.1 mmol) of ethyl chloroformate were further added again at room temperature and stirred at the same temperature as above for 1 hour. Subsequently, 1.0 ml (7.2 mmol) of triethylamine and 1.0 ml (25 mmol) of methanol were added to the reaction solution and then stirred at room temperature for 4 hours.

After the completion of the reaction, water was added to the reaction solution, followed by extraction with dichloromethane three times. All of the obtained organic layers were dried over anhydrous magnesium sulfate, filtered, and concentrated under reduced pressure. The obtained concentration residue was subjected to silica gel column chromatography (DIOL silica gel, elution solvent: dichloromethane:methanol=100:0 to 98:2 (V/V)), and a fraction containing the compound of interest was concentrated under reduced pressure. The obtained concentration residue was subjected to preparative HPLC (column: X-Bridge (trade name) ODS, elution solvent: acetonitrile:1 mM aqueous dipotassium hydrogen phosphate solution=45:55 (V/V)), a fraction containing the compound of interest was concentrated under reduced pressure, and acetonitrile was distilled off. The deposited solid was collected by filtration, washed by sousing with pure water, and then dried under reduced pressure to obtain 60 mg of the title compound (yield: 23%) as a white solid.

Mass spectrum (ESI, m/z): 542 [M+1]$^+$.

$^1$H-NMR spectrum (400 MHz, DMSO-$d_6$) δ: 12.20 & 11.65 (br s, total 1H), 9.62-9.49 (m, 1H), 7.44-7.31 (m, 4H), 7.28-7.21 (m, 1H), 6.68-6.45 (m, 1H), 5.21-4.99 (m, 1H), 4.59-4.40 (m, 2H), 4.38-4.22 (m, 2H), 4.10 (q, J=7.0 Hz, 2H), 2.56-2.42 (m, 2H), 2.27-2.14 (m, 2H), 1.93-1.73 (m, 2H), 1.69-1.45 (m, 6H), 1.18 (t, J=7.0 Hz, 3H), 0.17-0.04 (m, 9H).

Example 52

Sodium (S)-4-(2-{6,6-dimethyl-3-[1-(trimethylsilyl)cyclobutanecarboxamido]-1,4,5,6-tetrahydropyrrolo[3,4-c]pyrazole-5-carboxamido}-2-phenylethoxy)-4-oxobutanoate (Sodium Salt of Compound No. V-1490)

[Chemical Formula 68]

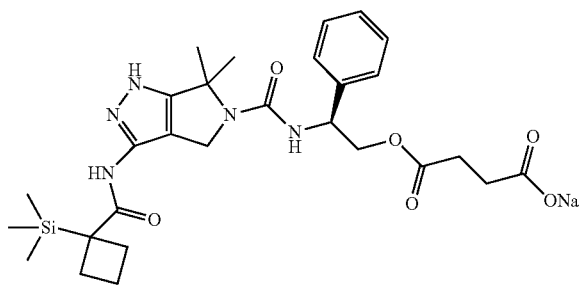

To a solution of 201 mg (0.456 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 7.0 ml of 1,4-dioxane, 628 mg of (S)-2-amino-2-phenylethyl benzyl succinate trifluoroacetate (containing impurities) synthesized in the similar manner as in Reference Example 40 and 1.0 ml (5.7 mmol) of DIPEA were added, applied to a microwave reaction apparatus, and reacted at 100° C. for 1 hour. Subsequently, 1 ml of methanol and 1 ml of triethylamine were added, applied to a microwave reaction apparatus, and reacted at 80° C. for 3 hours.

After the completion of the reaction, the reaction solution was concentrated under reduced pressure, ethyl acetate was added to the obtained concentration residue, washed with a 10% aqueous potassium dihydrogen phosphate solution, water, a saturated aqueous solution of sodium bicarbonate, and a saturated aqueous solution of sodium chloride in this order, then dried over anhydrous magnesium sulfate, and filtered, and then, the filtrate was concentrated under reduced pressure. The obtained concentration residue was subjected to silica gel column chromatography (DIOL silica gel, elution solvent: 1,2-dichloroethane:ethyl acetate=100:0 to 70:30 (V/V)), and a fraction containing (S)-benzyl (2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl)succinate was concentrated under reduced pressure to obtain a concentration residue.

To a solution of 171 mg of the obtained concentration residue in 20 ml of ethanol, 25.4 mg of palladium/carbon (ASCA2 (trade name), manufactured by N.E. Chemcat Corp., containing 52% water) was added in a nitrogen atmosphere and then, after replacement with a hydrogen atmosphere under reduced pressure, stirred at room temperature for 2 hours.

After the completion of the reaction, replacement with an argon atmosphere was performed, and the reaction solution was filtered through celite. 0.26 ml (0.26 mmol) of a 1 N aqueous sodium hydroxide solution was added to the filtrate and concentrated under reduced pressure. Diethyl ether was added to the obtained residue and then ultrasonicated, and the deposited solid was collected by filtration and dried under reduced pressure to obtain 147 mg of the title compound (yield: 54% [2 steps]) as a white solid.

$^1$H-NMR spectrum (400 MHz, DMSO-d$_6$) δ: 13.32 (br s, 1H), 10.75 (br s, 1H), 7.44-7.38 (m, 2H), 7.36-7.29 (m, 2H), 7.28-7.19 (m, 1H), 6.47 (d, J=7.3 Hz, 1H), 5.11-5.02 (m, 1H), 4.57-4.41 (m, 2H), 4.28 (dd, J=5.6, 10.8 Hz, 1H), 4.17 (dd, J=8.0, 10.8 Hz, 1H), 2.49-2.42 (m, 2H), 2.35 (t, J=7.2 Hz, 2H), 2.25-2.16 (m, 2H), 2.11 (t, J=7.2 Hz, 2H), 1.87-1.71 (m, 2H), 1.58 (s, 3H), 1.51 (s, 3H), 0.08 (s, 9H).

Example 53

(S)-(2-{6,6-Dimethyl-3-[1-(trimethylsilyl)cyclobutanecarboxamido]-1,4,5,6-tetrahydropyrrolo[3,4-c]pyrazole-5-carboxamido}-2-phenylethoxy) methyl pivalate (Compound No. VI-474)

[Chemical Formula 69]

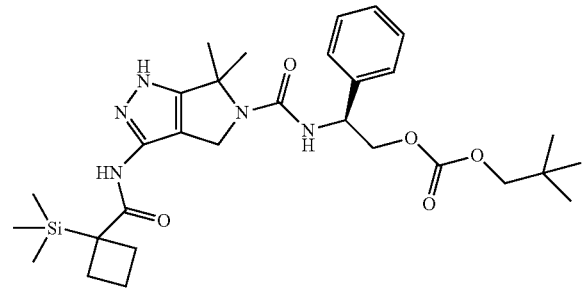

To a solution of 272 mg (1.08 mmol) of (S)-(2-amino-2-phenylethoxy)methyl pivalate synthesized in the similar manner as in Reference Example 42 in 2 ml of dehydrated THF, 0.15 ml (0.86 mmol) of DIPEA and 162 mg (0.368 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 were added in this order at room temperature in a nitrogen atmosphere and then stirred for 130 minutes while heated to reflux. Subsequently, 1.0 ml of triethylamine and 0.8 ml of methanol were added to the reaction solution and then stirred for 70 minutes while heated to reflux.

After the completion of the reaction, water was added to the reaction solution, followed by extraction with dichloromethane three times. All of the obtained organic layers were dried over anhydrous magnesium sulfate, filtered, and concentrated under reduced pressure. The obtained concentration residue was subjected to silica gel column chromatography (DNH silica gel, elution solvent: dichloromethane:methanol=100:0 to 98:2 (V/V)), and a fraction containing the compound of interest was concentrated under reduced pressure. For the obtained concentration residue, crystallization was performed with ethyl acetate/n-hexane, and the deposited solid was collected by filtration, washed by sousing with n-hexane, and then dried under reduced pressure to obtain 176 mg of the title compound (yield: 82%) as a white solid.

Mass spectrum (CI, m/z): 584 [M+1]$^+$.

$^1$H-NMR spectrum (400 MHz, DMSO-d$_6$) δ: 12.20 & 11.64 (br s, total 1H), 9.59-9.49 (m, 1H), 7.41-7.35 (m, 2H), 7.35-7.27 (m, 2H), 7.25-7.19 (m, 1H), 6.42 & 6.28 (d, J=8.0 Hz, total 1H), 5.29 (d, J=6.2 Hz, 1H), 5.22 (d, J=6.2 Hz, 1H), 5.02-4.94 (m, 1H), 4.57-4.37 (m, 2H), 3.91-3.83 (m, 1H), 3.79 (dd, J=6.0, 10.0 Hz, 1H), 2.49-2.40 (m, 2H), 2.28-2.13 (m, 2H), 1.92-1.73 (m, 2H), 1.67-1.45 (m, 6H), 1.13 (s, 9H), 0.14-0.06 (m, 9H).

Example 54

(S)-2-Acetoxy-1-phenylethyl 6,6-dimethyl-3-[1-(trimethylsilyl)cyclobutanecarboxamido]-4,6-dihydropyrrolo[3,4-c]pyrazole-5(1H)-carboxylate (Compound No. V-1250)

[Chemical Formula 70]

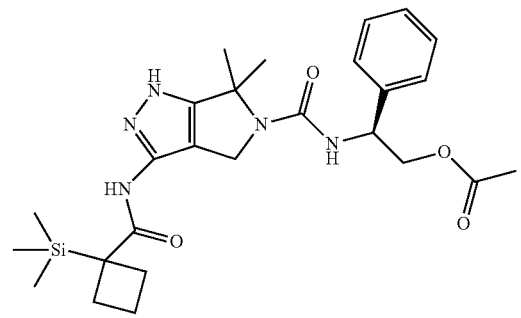

To a solution of 412 mg of ethyl 6,6-dimethyl-3-[1-(trimethylsilyl)cyclobutanecarboxamido]-5,6-dihydropyrrolo[3,4-c]pyrazole-2(4H)-carboxylate (containing impurities) synthesized in the similar manner as in Reference Example 3 by using 506 mg (1.06 mmol) of 5-tert-butyl 2-ethyl 6,6-dimethyl-3-[1-(trimethylsilyl)cyclobutanecarboxamido]pyrrolo[3,4-c]pyrazole-2,5(4H,6H)-dicarboxylate synthesized in the similar manner as in Reference Example 84 in 4 ml of dehydrated THF, 0.70 ml (4.0 mmol) of DIPEA and 1.30 g (3.84 mmol) of (S)-2-({[(2,5-dioxopyrrolidin-1-yl)oxy]carbonyl}oxy)-2-phenylethyl acetate synthesized in the similar manner as in Reference Example 43 were added in this order at room temperature in a nitrogen atmosphere and then stirred for 1.5 hours while heated to reflux. Subsequently, 2.0 ml (14 mmol) of triethylamine and 1.5 ml (37 mmol) of methanol were added to the reaction solution and then stirred for 3.5 hours while heated to reflux.

After the completion of the reaction, water was added to the reaction solution, followed by extraction with dichloromethane three times. All of the obtained organic layers were dried over anhydrous magnesium sulfate, filtered, and concentrated under reduced pressure. The obtained concentration residue was subjected to silica gel column chromatography (DIOL silica gel, elution solvent: n-hexane:ethyl acetate=80:20 to 50:50 (V/V)), and a fraction containing the compound of interest was concentrated under reduced pressure to obtain 225 mg of a concentration residue.

Approximately 50 mg of the obtained concentration residue was subjected to preparative HPLC (column: X-Bridge (trade name) ODS, elution solvent: acetonitrile:1 mM aqueous dipotassium hydrogen phosphate solution=50:50 (V/V)), a fraction containing the compound of interest was concentrated under reduced pressure, and acetonitrile was distilled off. The concentration residue was subjected to extraction with ethyl acetate twice, and all of the obtained organic layers were dried over anhydrous magnesium sulfate, filtered, and concentrated under reduced pressure. For the obtained concentration residue, crystallization was performed with ethyl acetate/diisopropyl ether/n-hexane, and the deposited solid was collected by filtration, washed by sousing with n-hexane, and then dried under reduced pressure to obtain 11.6 mg of the title compound (yield: 2% [2 steps]) as a white solid.

Mass spectrum (CI, m/z): 513 [M+1]$^+$.

$^1$H-NMR spectrum (400 MHz, DMSO-$d_6$) δ: 12.35-12.21 & 11.97-11.83 (m, total 1H), 9.87-9.45 (m, 1H), 7.47-7.24 (m, 5H), 5.99-5.85 (m, 1H), 4.65-4.17 (m, 4H), 2.48-2.36 (m, 2H), 2.28-2.10 (m, 2H), 2.05-1.95 (m, 3H), 1.92-1.72 (m, 2H), 1.71-1.43 (m, 6H), 0.16-0.02 (m, 9H).

Example 55

(S)-Benzyl 2-{6,6-dimethyl-3-[1-(trimethylsilyl)cyclobutanecarboxamido]-1,4,5,6-tetrahydropyrrolo[3,4-c]pyrazole-5-carboxamido}-2-phenylacetate (Compound No. IV-411)

[Chemical Formula 71]

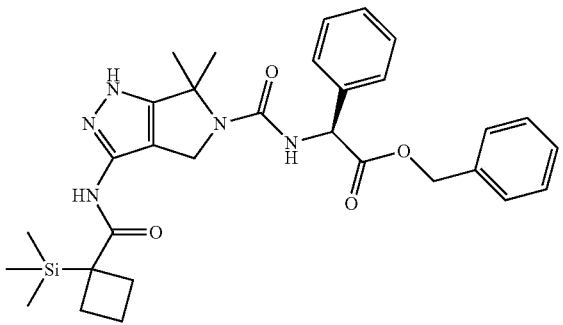

To a solution of 195 mg (0.442 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2 (4H)-carboxylate synthesized in the similar manner as in Reference Example 3 in 7 ml of 1,4-dioxane, 565 mg of (S)-benzyl 2-amino-2-phenylacetate trifluoroacetate (containing impurities) synthesized in the similar manner as in Reference Example 45 and 0.50 ml (2.9 mmol) of DIPEA were added at room temperature in an argon atmosphere, then applied to a microwave reaction apparatus, and stirred at 100° C. for 1 hour. After the reaction, the reaction solution was concentrated under reduced pressure, and 4 ml of methanol and 1 ml of triethylamine were added to the obtained concentration residue, applied to a microwave reaction apparatus, and reacted at 80° C. for 1 hour.

After the completion of the reaction, the reaction solution was concentrated under reduced pressure, ethyl acetate was added to the obtained concentration residue, the organic layer after washing with a 10% aqueous potassium dihydrogen phosphate solution, a saturated aqueous solution of sodium bicarbonate, and a saturated aqueous solution of sodium chloride in this order was dried over anhydrous magnesium sulfate and filtered, and then, the filtrate was concentrated under reduced pressure. The obtained concentration residue was subjected to silica gel column chromatography (DIOL silica gel, elution solvent: 1,2-dichloroethane:ethyl acetate=100:0 to 55:45 (V/V)), and a fraction composed mainly of the title compound and a fraction composed mainly of a by-product [(S)-methyl 2-{6,6-dimethyl-3-[1-(trimethylsilyl)cyclobutanecarboxamido]-1,4,5,6-tetrahydropyrrolo[3,4-c]pyrazole-5-carboxamido}-2-phenylacetate] were each concentrated under reduced pressure. The concentration residue of the fraction composed mainly of the title compound was subjected again to silica gel column chromatography (DIOL silica gel, elution solvent: 1,2-dichloroethane:ethyl acetate=100:0 to 55:45 (V/V)), and a fraction containing the compound of interest was concentrated under reduced pressure to obtain 99 mg of the title compound (yield: 39%) as a white foam.

Mass spectrum (DUIS, m/z): 574 [M+1]$^+$.

$^1$H-NMR spectrum (400 MHz, DMSO-$d_6$) δ: 12.21 & 11.70 (br s, total 1H), 9.63-9.44 (m, 1H), 7.51-7.41 (m, 2H), 7.38-7.23 (m, 8H), 6.81-6.47 (m, 1H), 5.42 (d, J=7.2 Hz, 1H), 5.17 (d, J=12.7 Hz, 1H), 5.11 (d, J=12.7 Hz, 1H), 4.61-4.39 (m, 2H), 2.49-2.38 (m, 2H), 2.25-2.12 (m, 2H), 1.91-1.72 (m, 2H), 1.68-1.52 (m, 6H), 0.07 (s, 9H).

Example 56

(S)-Methyl 2-{6,6-dimethyl-3-[1-(trimethylsilyl)cyclobutanecarboxamido]-1,4,5,6-tetrahydropyrrolo[3,4-c]pyrazole-5-carboxamido}-2-phenylacetate (Compound No. IV-419)

[Chemical Formula 72]

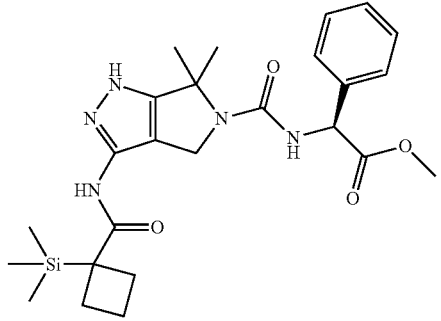

The concentration residue of the fraction composed mainly of the title compound collected at the time of the first purification of silica gel column chromatography in the operational steps of Example 55 was subjected again to silica gel column chromatography (DIOL silica gel, elution solvent: 1,2-dichloroethane:ethyl acetate=100:0 to 55:45 (V/V)), and a fraction containing the compound of interest was concentrated under reduced pressure to obtain 29 mg of the title compound (yield: 13%) as a white foam.

Mass spectrum (DUIS, m/z): 498 [M+1]$^+$.

$^1$H-NMR spectrum (400 MHz, DMSO-$d_6$) δ: 12.21 & 11.71 (br s, total 1H), 9.63-9.46 (m, 1H), 7.48-7.41 (m, 2H), 7.40-7.28 (m, 3H), 6.73-6.56 (m, 1H), 5.36 (d, J=7.2 Hz, 1H), 4.61-4.38 (m, 2H), 3.62 (s, 3H), 2.49-2.38 (m, 2H), 2.27-2.10 (m, 2H), 1.92-1.71 (m, 2H), 1.67-1.51 (m, 6H), 0.08 (s, 9H).

Example 57

N-(2,2-Difluoro-3-hydroxy-1-phenylpropyl)-6,6-dimethyl-3-[1-(trimethylsilyl)cyclobutanecarboxamido]-4,6-dihydropyrrolo[3,4-c]pyrazole-5(1H)-carboxamide (Compound No. IV-362)

[Chemical Formula 73]

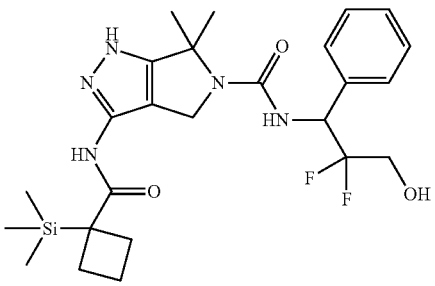

To a solution of 249 mg (1.33 mmol) of 3-amino-2,2-difluoro-3-phenylpropan-1-ol synthesized in the similar manner as in Reference Example 48 in 2 ml of dehydrated 1,4-dioxane, 0.30 ml (1.7 mmol) of DIPEA and 178 mg (0.403 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 were added in this order at room temperature in a nitrogen atmosphere and then stirred at 80° C. for 7 hours. Subsequently, 0.10 ml (1.7 mmol) of 2-aminoethanol was added to the reaction solution allowed to cool to room temperature, and then stirred at room temperature for 1.5 hours.

After the completion of the reaction, a saturated aqueous solution of sodium bicarbonate was added to the reaction solution and stirred, followed by extraction with dichloromethane three times. All of the organic layers were dried over anhydrous magnesium sulfate, then filtered, and concentrated under reduced pressure. The obtained concentration residue was subjected to silica gel column chromatography (DIOL silica gel, elution solvent: n-hexane:ethyl acetate=60:40 to 30:70 (V/V)), and a fraction containing the compound of interest was concentrated under reduced pressure. The obtained concentration residue was dissolved in ethyl acetate, then n-hexane was added, and the deposited solid was collected by filtration, washed with n-hexane, and then dried under reduced pressure to obtain 155 mg of the title compound (yield: 74%) as a white solid.

Mass spectrum (CI, m/z): 520 [M+1]$^+$.

$^1$H-NMR spectrum (400 MHz, DMSO-d$_6$) δ: 12.43-11.84 (m, 1H), 10.02-9.36 (m, 1H), 7.56-7.50 (m, 2H), 7.40-7.27 (m, 3H), 6.61 (br s, 1H), 5.71 (br s, 1H), 5.49-5.34 (m, 1H), 4.70-4.56 (m, 1H), 4.47 (br d, J=12.0 Hz, 1H), 3.73-3.45 (m, 2H), 2.57-2.42 (m, 2H), 2.26-2.15 (m, 2H), 1.90-1.74 (m, 2H), 1.61 (s, 3H), 1.51 (s, 3H), 0.09 (s, 9H).

Example 58

N-(2-Isopropoxy-1-phenylethyl)-6,6-dimethyl-3-[1-(trimethylsilyl)cyclobutanecarboxamido]-4,6-dihydropyrrolo[3,4-c]pyrazole-5(1H)-carboxamide (Compound No. IV-146)

[Chemical Formula 74]

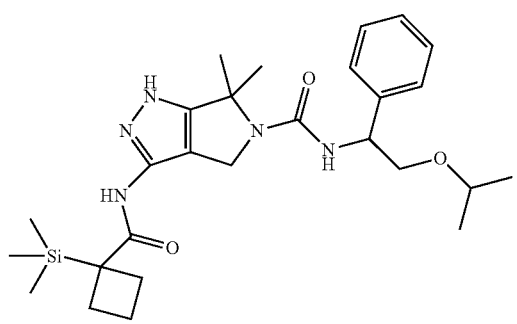

To a solution of 0.102 g (0.231 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2 (4H)-carboxylate synthesized in the similar manner as in Reference Example 3 and 0.127 g (0.709 mmol) of 2-isopropoxy-1-phenylethanamine synthesized in the similar manner as in Reference Example 50 in 2.5 ml of dehydrated 1,4-dioxane, 0.200 ml (1.15 mmol) of DIPEA was added at room temperature in a nitrogen atmosphere and then heated and stirred at 100° C. for 1 hour. After standing to cool, 0.50 ml (12 mmol) of methanol and 0.070 ml (1.2 mmol) of 2-aminoethanol were added to the reaction solution and stirred at room temperature for 1 hour.

After the completion of the reaction, ethyl acetate was added to the residue obtained by concentration under reduced pressure, the organic layer after washing with a 10% aqueous potassium dihydrogen phosphate solution, a saturated aqueous solution of sodium bicarbonate, and a saturated aqueous solution of sodium chloride in this order was dried over anhydrous magnesium sulfate and filtered, and then, the filtrate was concentrated under reduced pressure. The residue was subjected to silica gel column chromatography (DIOL silica gel, elution solvent: 1,2-dichloroethane:ethyl acetate=100:0 to 50:50 (V/V)), a fraction containing the compound of interest was concentrated under reduced pressure, the residue was dissolved in a small amount of dichloromethane, and after addition of n-hexane and ultrasonication, the deposited solid was collected by filtration and dried under reduced pressure to obtain 0.106 g of the title compound (yield: 90%) as a white solid.

Mass spectrum (CI, m/z): 512 [M+1]$^+$.

$^1$H-NMR spectrum (400 MHz, DMSO-d$_6$) δ: 12.21 & 11.76 (br s, total 1H), 9.68-9.50 (m, 1H), 7.42-7.16 (m, 5H), 6.31-6.08 (m, 1H), 4.94-4.84 (m, 1H), 4.56-4.37 (m, 2H), 3.67-3.51 (m, 3H), 2.51-2.40 (m, 2H), 2.27-2.13 (m, 2H), 1.92-1.71 (m, 2H), 1.65-1.48 (m, 6H), 1.08-1.03 (m, 6H), 0.09 (s, 9H).

Example 59

6,6-Dimethyl-N-(2-phenoxy-1-phenylethyl)-3-[1-(trimethylsilyl)cyclobutanecarboxamido]-4,6-dihydropyrrolo[3,4-c]pyrazole-5(1H)-carboxamide (Compound No. IV-162)

[Chemical Formula 75]

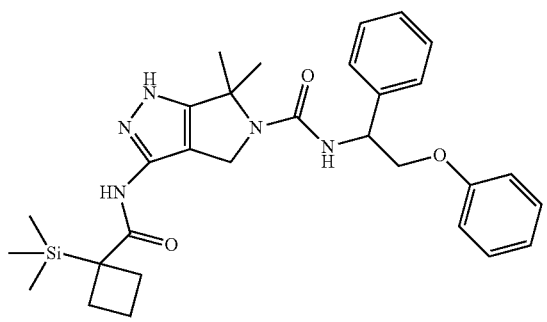

To a solution of 0.101 g (0.230 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 and 0.145 g (0.681 mmol) of 2-phenoxy-1-phenylethanamine synthesized in the similar manner as in Reference Example 52 in 2.5 ml of dehydrated 1,4-dioxane, 0.200 ml (1.15 mmol) of DIPEA was added at room temperature in a nitrogen atmosphere and then stirred at 100° C. for 1 hour. After standing to cool, 0.50 ml (12 mmol) of methanol and 0.070 ml (1.2 mmol) of 2-aminoethanol were added and stirred at room temperature for 1 hour.

After the completion of the reaction, the reaction solution was concentrated under reduced pressure, ethyl acetate was added, the organic layer after washing with a 10% aqueous potassium dihydrogen phosphate solution, a saturated aqueous solution of sodium bicarbonate, and a saturated aqueous solution of sodium chloride in this order was dried over anhydrous magnesium sulfate and filtered, and then, the filtrate was concentrated under reduced pressure. The residue was subjected to silica gel column chromatography (DIOL silica gel, elution solvent: 1,2-dichloroethane:ethyl acetate=100:0 to 67:33 (V/V)), a fraction containing the compound of interest was concentrated under reduced pressure, the residue was dissolved in a small amount of dichloromethane, and after addition of n-hexane and ultrasonication, the deposited solid was collected by filtration and dried under reduced pressure to obtain 0.112 g of the title compound (yield: 89%) as a white solid.

Mass spectrum (CI, m/z): 546 [M+1]$^+$.

$^1$H-NMR spectrum (400 MHz, DMSO-d$_6$) δ: 12.21 & 11.70 (br s, total 1H), 9.57 (br s, 1H), 7.51-7.18 (m, 7H), 7.03-6.86 (m, 3H), 6.68-6.40 (m, 1H), 5.23-5.11 (m, 1H), 4.57-4.38 (m, 2H), 4.34-4.22 (m, 1H), 4.16 (dd, J=5.9, 9.8 Hz, 1H), 2.57-2.39 (m, 2H), 2.25-2.11 (m, 2H), 1.90-1.71 (m, 2H), 1.62 (br s, 3H), 1.54 (br s, 3H), 0.08 (s, 9H).

Example 60

(S)—N-[1-(2-Chlorophenyl)-2-hydroxyethyl]-6,6-dimethyl-3-[1-(trimethylsilyl)cyclobutanecarboxamido]-4,6-dihydropyrrolo[3,4-c]pyrazole-5(1H)-carboxamide (Compound No. IV-959)

[Chemical Formula 76]

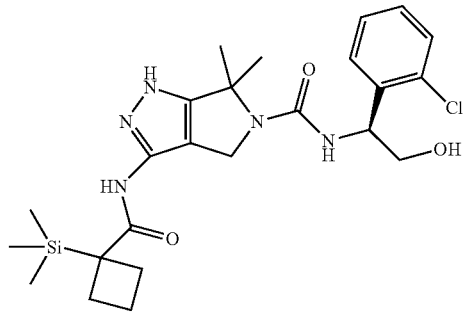

To a solution of 0.105 g (0.238 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 and 0.124 g (0.723 mmol) of (S)-2-amino-2-(2-chlorophenyl)ethanol [purchased from Amatek Chemical Co., Ltd.] in 2.5 ml of dehydrated 1,4-dioxane, 0.200 ml (1.15 mmol) of DIPEA was added at room temperature in a nitrogen atmosphere and then stirred at 100° C. for 1 hour. After standing to cool, 0.50 ml (12 mmol) of methanol and 0.070 ml (1.2 mmol) of 2-aminoethanol were added and stirred at room temperature for 1 hour.

After the completion of the reaction, the reaction solution was concentrated under reduced pressure, ethyl acetate was added to the residue, the organic layer after washing with a 10% aqueous potassium dihydrogen phosphate solution, a saturated aqueous solution of sodium bicarbonate, and a saturated aqueous solution of sodium chloride in this order was dried over anhydrous magnesium sulfate and filtered, and then, the filtrate was concentrated under reduced pressure. The residue was subjected to silica gel column chromatography (DIOL silica gel, elution solvent: 1,2-dichloroethane:ethyl acetate=84:16 to 33:67 (V/V)), a fraction containing the compound of interest was concentrated under reduced pressure, the residue was dissolved in a small amount of dichloromethane, and after addition of n-hexane and ultrasonication, the deposited solid was collected by filtration and dried under reduced pressure to obtain 0.0958 g of the title compound (yield: 80%) as a white solid.

Mass spectrum (DUIS, m/z): 504 [M+1]$^+$.

$^1$H-NMR spectrum (400 MHz, DMSO-d$_6$) δ: 12.21 & 11.75 (br s, total 1H), 9.71-9.52 (m, 1H), 7.51 (dd, J=1.6, 7.7 Hz, 1H), 7.38 (dd, J=1.2, 7.8 Hz, 1H), 7.33-7.20 (m, 2H), 6.36-6.14 (m, 1H), 5.21-5.12 (m, 1H), 5.04 (t, J=6.0 Hz, 1H), 4.66-4.45 (m, 2H), 3.64-3.48 (m, 2H), 2.57-2.41 (m, 2H), 2.28-2.13 (m, 2H), 1.91-1.72 (m, 2H), 1.66-1.42 (m, 6H), 0.10 (s, 9H).

Example 61

(S)—N-[2-Hydroxy-1-(o-tolyl)ethyl]-6,6-dimethyl-3-[1-(trimethylsilyl)cyclobutanecarboxamido]-4,6-dihydropyrrolo[3,4-c]pyrazole-5(1H)-carboxamide (Compound No. IV-1067)

[Chemical Formula 77]

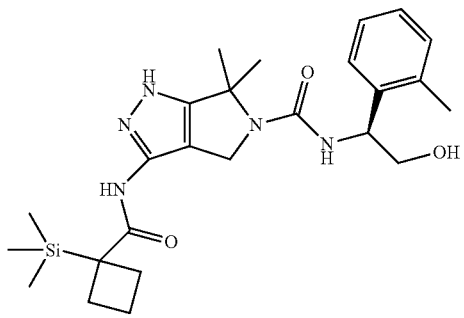

To a solution of 0.104 g (0.235 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 and 0.131 g (0.696 mmol) of (S)-2-amino-2-(o-tolyl)ethanol hydrochloride [purchased from Acesys Pharmatech Ltd.] in 2.5 ml of dehydrated 1,4-dioxane, 0.400 ml (2.30 mmol) of DIPEA was added at room temperature in a nitrogen atmosphere and then heated and stirred at 100° C. for 1 hour. After standing to cool, 0.50 ml (12 mmol) of methanol and 0.070 ml (1.2 mmol) of 2-aminoethanol were added and stirred at room temperature for 1 hour.

After the completion of the reaction, the reaction solution was concentrated under reduced pressure, ethyl acetate was added, the organic layer after washing with a 10% aqueous potassium dihydrogen phosphate solution, a saturated aqueous solution of sodium bicarbonate, and a saturated aqueous solution of sodium chloride in this order was dried over anhydrous magnesium sulfate and filtered, and then, the filtrate was concentrated under reduced pressure. The residue was subjected to silica gel column chromatography (DIOL silica gel, elution solvent: 1,2-dichloroethane:ethyl acetate=84:16 to 33:67 (V/V)), a fraction containing the compound of interest was concentrated under reduced pressure, the residue was dissolved in a small amount of dichloromethane, and after addition of n-hexane and ultrasonication, the deposited solid was collected by filtration and dried under reduced pressure to obtain 0.0738 g of the title compound (yield: 65%) as a white solid.

Mass spectrum (CI, m/z): 484 [M+1]$^+$.

$^1$H-NMR spectrum (400 MHz, DMSO-d$_6$) δ: 12.20 & 11.66 (br s, total 1H), 9.63-9.50 (m, 1H), 7.40 (d, J=7.4 Hz, 1H), 7.18-7.03 (m, 3H), 6.28-6.05 (m, 1H), 5.04-4.95 (m, 1H), 4.89 (t, J=6.0 Hz, 1H), 4.58-4.41 (m, 2H), 3.61-3.43 (m, 2H), 2.56-2.41 (m, 2H), 2.36 (s, 3H), 2.27-2.11 (m, 2H), 1.93-1.70 (m, 2H), 1.69-1.41 (m, 6H), 0.10 (s, 9H).

Example 62

(S)—N-(1-Hydroxy-3-phenylpropan-2-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-862)

[Chemical Formula 78]

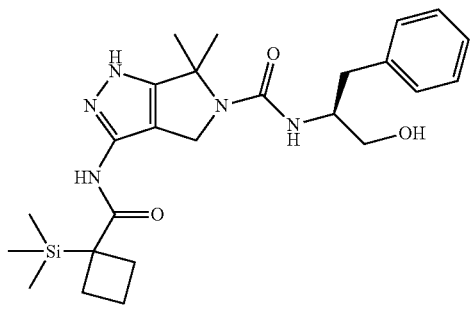

To a solution of 101 mg (0.229 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 3 ml of 1,4-dioxane, 0.115 ml (0.673 mmol) of DIPEA and 102 mg (0.675 mmol) of (S)-2-amino-3-phenylpropan-1-ol were added in this order in an argon atmosphere and then stirred at 100° C. for 1 hour. Subsequently, the reaction solution was concentrated under reduced pressure, and 2 ml of methanol and 0.5 ml of triethylamine were added in this order at room temperature and stirred at 80° C. for 1 hour in a microwave reaction apparatus.

After the completion of the reaction, the reaction solution was concentrated under reduced pressure, the concentration residue was dissolved in 5 ml of ethyl acetate and washed with a 5% aqueous potassium dihydrogen phosphate solution twice, and then, the organic layer was washed with 5 ml of a saturated aqueous solution of sodium bicarbonate. The organic layer was dried over anhydrous magnesium sulfate, then filtered, and concentrated under reduced pressure. The obtained concentration residue was subjected to silica gel column chromatography (DIOL silica gel, elution solvent: ethyl acetate:methanol=100:0 to 86:14 (V/V)), and a fraction containing the compound of interest was concentrated under reduced pressure and subsequently dried under reduced pressure at 50° C. to obtain 88.5 mg of the title compound (yield: 80%) as a white solid.

Mass spectrum (CI, m/z): 484 [M+1]$^+$.

$^1$H-NMR spectrum (400 MHz, DMSO-d$_6$) δ: 12.19 & 11.71 (br s, total 1H), 9.54 (br s, 1H), 7.28-7.18 (m, 4H), 7.18-7.12 (m, 1H), 5.72-5.45 (m, 1H), 4.77 (t, J=5.5 Hz, 1H), 4.46-4.17 (m, 2H), 3.90-3.77 (m, 1H), 3.44-3.28 (m, 2H), 2.87-2.70 (m, 2H), 2.54-2.40 (m, 2H), 2.25-2.13 (m, 2H), 1.92-1.70 (m, 2H), 1.58 (br s, 3H), 1.50 (br s, 3H), 0.09 (s, 9H).

Example 63

N-(2-Hydroxy-3-methylbutyl)-6,6-dimethyl-3-[1-(trimethylsilyl)cyclobutanecarboxamido]-4,6-dihydropyrrolo[3,4-c]pyrazole-5(1H)-carboxamide (Compound No. IV-446)

[Chemical Formula 79]

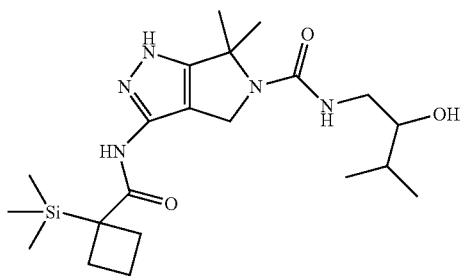

To a solution of 103 mg (0.234 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2 (4H)-carboxylate synthesized in the similar manner as in Reference Example 3 in 3 ml of 1,4-dioxane, 69.8 mg (0.677 mmol) of 1-amino-3-methylbutan-2-ol [purchased from Life Chemicals Inc.] and 0.115 ml (0.673 mmol) of DIPEA were added in this order at room temperature in an argon atmosphere and then stirred at 100° C. for 2.5 hours.

After the completion of the reaction, the reaction solution was concentrated under reduced pressure, the concentration residue was dissolved in 5 ml of ethyl acetate and washed with a 5% aqueous potassium dihydrogen phosphate solution twice, and then, the organic layer was washed with 5 ml of a saturated aqueous solution of sodium bicarbonate. The organic layer was dried over anhydrous magnesium sulfate, then filtered, and concentrated under reduced pressure. The obtained concentration residue was subjected to silica gel column chromatography (DIOL silica gel, elution solvent: ethyl acetate:methanol=100:0 to 86:14 (V/V)), and a fraction containing the compound of interest was concentrated under reduced pressure. The obtained concentration residue was dissolved in dichloromethane, n-hexane was added, and then, the deposited solid was collected by filtration and dried under reduced pressure to obtain 71.9 mg of the title compound (yield: 71%) as a white solid.

Mass spectrum (CI, m/z): 436 [M+1]$^+$.

$^1$H-NMR spectrum (400 MHz, DMSO-d$_6$) δ: 12.20 & 11.72 (br s, total 1H), 9.56 (br s, 1H), 6.03-5.75 (m, 1H), 4.79 (d, J=4.5 Hz, 1H), 4.48-4.27 (m, 2H), 3.29-3.17 (m, 2H), 2.96-2.85 (m, 1H), 2.56-2.39 (m, 2H), 2.25-2.12 (m, 2H), 1.91-1.72 (m, 2H), 1.68-1.50 (m, 7H), 0.86 (d, J=6.8 Hz, 6H), 0.08 (s, 9H).

Example 64

(R)—N-(1-Hydroxy-3-phenylpropan-2-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-861)

[Chemical Formula 80]

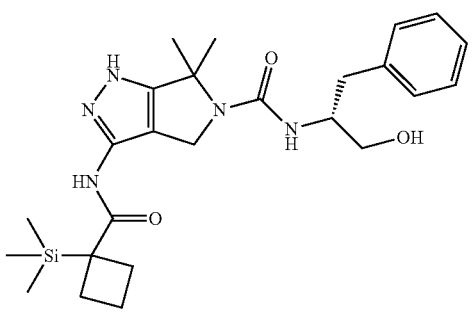

To a solution of 0.102 g (0.232 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 and 0.110 g (0.729 mmol) of (R)-2-amino-3-phenylpropan-1-ol in 2.5 ml of dehydrated 1,4-dioxane, 0.20 ml (1.1 mmol) of DIPEA was added at room temperature in an argon atmosphere and then heated and stirred at 100° C. for 1.5 hours. After standing to cool, the resultant was concentrated under reduced pressure, and 4 ml of methanol and 1 ml of triethylamine were added to the residue, applied to a microwave reaction apparatus, and reacted at 80° C. for 1 hour.

After the completion of the reaction, the reaction solution was concentrated under reduced pressure, ethyl acetate was added, the organic layer after washing with a 10% aqueous potassium dihydrogen phosphate solution, a saturated aqueous solution of sodium bicarbonate, and a saturated aqueous solution of sodium chloride in this order was dried over anhydrous magnesium sulfate and filtered, and then, the filtrate was concentrated under reduced pressure. The residue was subjected to silica gel column chromatography (DIOL silica gel, elution solvent: ethyl acetate:methanol=100:0 to 90:10 (V/V)), a fraction containing the compound of interest was concentrated under reduced pressure, small amounts of dichloromethane and n-hexane were added to the residue, and after ultrasonication, the deposited solid was collected by filtration and dried under reduced pressure to obtain 0.0454 g of the title compound (yield: 40%) as a white solid.

Mass spectrum (CI, m/z): 484 [M+1]$^+$.

$^1$H-NMR spectrum (400 MHz, DMSO-d$_6$) δ: 12.19 & 11.65 (br s, total 1H), 9.54 (s, 1H), 7.28-7.18 (m, 4H), 7.18-7.12 (m, 1H), 5.70-5.47 (m, 1H), 4.77 (t, J=5.5 Hz, 1H), 4.45-4.19 (m, 2H), 3.90-3.77 (m, 1H), 3.46-3.29 (m, 2H), 2.87-2.70 (m, 2H), 2.56-2.38 (m, 2H), 2.26-2.11 (m, 2H), 1.92-1.71 (m, 2H), 1.65-1.40 (m, 6H), 0.09 (s, 9H).

Example 65

(R)—N-(2-Hydroxy-2-phenylethyl)-6,6-dimethyl-3-[1-(trimethylsilyl)cyclobutanecarboxamido]-4,6-dihydropyrrolo[3,4-c]pyrazole-5(1H)-carboxamide (Compound No. IV-786)

[Chemical Formula 81]

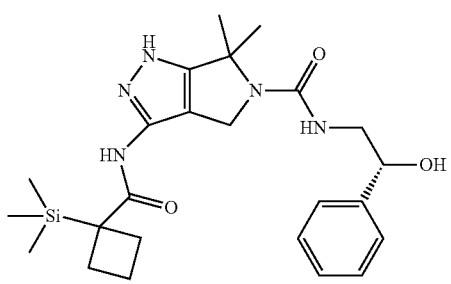

To a solution of 101 mg (0.229 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 2 ml of dehydrated THF, 0.20 ml (1.1 mmol) of DIPEA and 151 mg (1.10 mmol) of (R)-2-amino-1-phenylethanol were added in this order at room temperature in a nitrogen atmosphere and then stirred for 3 hours then with the temperature unchanged.

After the completion of the reaction, a saturated aqueous solution of sodium bicarbonate was added to the reaction solution and stirred, followed by extraction with dichloromethane three times. All of the organic layers were dried over anhydrous magnesium sulfate, then filtered, and concentrated under reduced pressure. The obtained concentration residue was subjected to silica gel column chromatography (DIOL silica gel, elution solvent: n-hexane:ethyl acetate=70:30 to 20:80 (V/V)), and a fraction containing the compound of interest was concentrated under reduced pressure. The obtained concentration residue was subjected to preparative HPLC (column: X-Bridge (trade name) ODS, elution solvent: acetonitrile:1 mM aqueous dipotassium hydrogen phosphate solution=40:60 (V/V)), a fraction containing the compound of interest was concentrated under reduced pressure, and acetonitrile was distilled off. The solid deposited in the course of concentration was collected by filtration, washed with pure water, and then dried under reduced pressure to obtain 55 mg of the title compound (yield: 51%) as a white solid.

Mass spectrum (EI, m/z): 469 [M]$^+$.

$^1$H-NMR spectrum (400 MHz, DMSO-d$_6$) δ: 12.21 & 11.67 (br s, total 1H), 9.56 (s, 1H), 7.36-7.28 (m, 4H), 7.27-7.19 (m, 1H), 6.19-5.94 (m, 1H), 5.59 (d, J=4.0 Hz, 1H), 4.66 (td, J=4.0, 8.0 Hz, 1H), 4.48-4.24 (m, 2H), 3.44-3.22 (m, 1H), 3.09 (ddd, J=4.8, 8.0, 13.2 Hz, 1H), 2.56-2.38 (m, 2H), 2.26-2.12 (m, 2H), 1.90-1.72 (m, 2H), 1.60 (br s, 6H), 0.08 (s, 9H).

Example 66

(S)—N-(2-Hydroxy-2-phenylethyl)-6,6-dimethyl-3-[1-(trimethylsilyl)cyclobutanecarboxamido]-4,6-dihydropyrrolo[3,4-c]pyrazole-5(1H)-carboxamide (Compound No. IV-787)

[Chemical Formula 82]

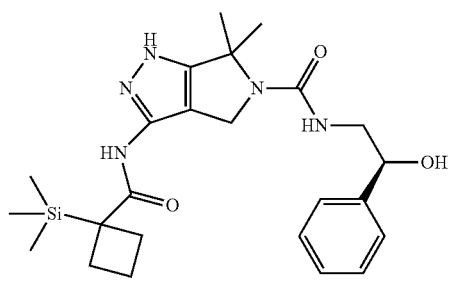

To a solution of 102 mg (0.231 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 2 ml of dehydrated THF, 0.20 ml (1.1 mmol) of DIPEA and 129 mg (0.943 mmol) of (S)-2-amino-1-phenylethanol were added in this order at room temperature in a nitrogen atmosphere and then stirred for 4 hours with the temperature unchanged.

After the completion of the reaction, a saturated aqueous solution of sodium bicarbonate was added to the reaction solution and stirred, followed by extraction with dichloromethane three times. All of the organic layers were dried over anhydrous magnesium sulfate, then filtered, and concentrated under reduced pressure. The obtained concentration residue was subjected to silica gel column chromatography (DIOL silica gel, elution solvent: dichloromethane:methanol=100:0 to 98:2 (V/V)), and a fraction containing the compound of interest was concentrated under reduced pressure. The obtained concentration residue was subjected to preparative HPLC (column: X-Bridge (trade name) ODS, elution solvent: acetonitrile:1 mM aqueous dipotassium hydrogen phosphate solution=45:55 (V/V)), a fraction containing the compound of interest was concentrated under reduced pressure, and acetonitrile was distilled off. The solid deposited in the course of concentration was collected by filtration, washed with pure water, and then dried under reduced pressure. Ethyl acetate was added to the obtained solid, then insoluble matter was removed by filtration, and the filtrate was concentrated under reduced pressure. The obtained concentration residue was dissolved in ethyl acetate, then n-hexane was added, and the deposited solid was collected by filtration, washed with n-hexane, and then dried under reduced pressure to obtain 52 mg of the title compound (yield: 48%) as a white solid.

Mass spectrum (EI, m/z): 469 [M]$^+$.

$^1$H-NMR spectrum (400 MHz, DMSO-d$_6$) δ: 12.21 & 11.70 (br s, total 1H), 9.63-9.53 (m, 1H), 7.36-7.28 (m, 4H), 7.27-7.19 (m, 1H), 6.19-5.94 (m, 1H), 5.59 (d, J=4.0 Hz, 1H), 4.66 (td, J=4.0, 8.0 Hz, 1H), 4.48-4.24 (m, 2H), 3.44-3.22 (m, 1H), 3.15-3.04 (m, 1H), 2.56-2.38 (m, 2H), 2.26-2.12 (m, 2H), 1.90-1.72 (m, 2H), 1.60 (br s, 6H), 0.08 (s, 9H).

Example 67

2-Hydroxy-2-phenylethyl 6,6-dimethyl-3-[1-(trimethylsilyl)cyclobutanecarboxamido]-4,6-dihydropyrrolo[3,4-c]pyrazole-5(1H)-carboxylate (Compound No. IV-670)

[Chemical Formula 83]

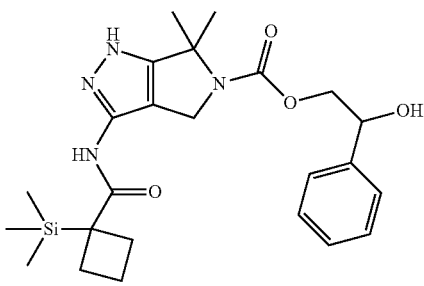

To a solution of 0.125 g of 2-[(2-methoxypropan-2-yl)oxy]-2-phenylethyl 6,6-dimethyl-3-[1-(trimethylsilyl)cyclobutanecarboxamido]-4,6-dihydropyrrolo[3,4-c]pyrazole-5(1H)-carboxylate (containing impurities) synthesized in Reference Example 56 in 3 ml of methanol, 0.0077 g (0.031 mmol) of pyridinium p-toluenesulfonate was added at 0° C. in a nitrogen atmosphere and stirred at the same temperature as above for 3.5 hours, and then, 0.020 ml of triethylamine was added and concentrated under reduced pressure.

The residue was subjected to silica gel column chromatography (DIOL silica gel, elution solvent: 1,2-dichloroethane:ethyl acetate=77:23 to 26:74 (V/V)), and a fraction containing the compound of interest was concentrated under reduced pressure to obtain 0.0837 g of the title compound (yield: 66% [2 steps]) as a white foam.

Mass spectrum (CI, m/z): 471 [M+1]$^+$.

$^1$H-NMR spectrum (400 MHz, DMSO-d$_6$) δ: 12.25 & 12.19 & 11.83 (br s, total 1H), 9.73-9.49 (m, 1H), 7.47-7.19 (m, 5H), 5.58 (d, J=4.5 Hz, 1H), 4.89-4.74 (m, 1H), 4.50-4.23 (m, 2H), 4.21-3.91 (m, 2H), 2.57-2.35 (m, 2H), 2.27-2.09 (m, 2H), 1.93-1.68 (m, 2H), 1.66-1.30 (m, 6H), 0.17-0.01 (m, 9H).

Example 68

(R)—N-[6,6-Dimethyl-5-(2-phenoxypropanoyl)-1,4,5,6-tetrahydropyrrolo[3,4-c]pyrazol-3-yl]-1-(trimethylsilyl)cyclobutanecarboxamide (Compound No. IV-1258)

[Chemical Formula 84]

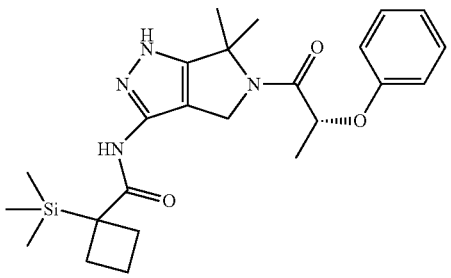

To a solution of 58.3 mg (0.351 mmol) of (R)-2-phenoxypropanoic acid in 2 ml of dehydrated DMF, 0.12 ml (0.69 mmol) of DIPEA and 152 mg (0.354 mmol) of (1-cyano-2-ethoxy-2-oxoethylideneaminooxy)dimethylaminomorpholinocarbenium hexafluorophosphate [COMU (trade name)] were added in this order at 0° C. in a nitrogen atmosphere and then stirred for 20 minutes with the temperature unchanged. Subsequently, 104 mg (0.274 mmol) of ethyl 6,6-dimethyl-3-[1-(trimethylsilyl)cyclobutanecarboxamido]-5,6-dihydropyrrolo[3,4-c]pyrazole-1(4H)-carboxylate synthesized in the similar manner as in Reference Example 5 was added at 0° C. and then stirred at room temperature for 15.5 hours. Subsequently, 0.10 ml (1.7 mmol) of 2-aminoethanol was added to the reaction solution at room temperature and then stirred for 2.5 hours with the temperature unchanged.

After the completion of the reaction, a saturated aqueous solution of sodium bicarbonate was added to the reaction solution and stirred, followed by extraction with dichloromethane three times. All of the obtained organic layers were dried over anhydrous magnesium sulfate, then filtered, and concentrated under reduced pressure. The operation of adding toluene to the obtained concentration residue, followed by concentration under reduced pressure again was repeated twice, then the resultant was subjected to silica gel column chromatography (DIOL silica gel, elution solvent: n-hexane:ethyl acetate=75:25 to 50:50 (V/V)), and a fraction containing the compound of interest was concentrated under reduced pressure. The obtained concentration residue was dissolved in ethyl acetate, then n-hexane was added, and the deposited solid was collected by filtration, washed with n-hexane, and then dried under reduced pressure to obtain 75 mg of the title compound (yield: 60%) as a white solid.

Mass spectrum (EI, m/z): 454 [M]$^+$.

$^1$H-NMR spectrum (400 MHz, DMSO-d$_6$) δ: 12.53-11.80 (m, 1H), 9.69 (br s, 1H), 7.30-7.21 (m, 2H), 6.94-6.87 (m, 1H), 6.85-6.78 (m, 2H), 4.90 (q, J=6.5 Hz, 1H), 4.87-4.78 (m, 1H), 4.67-4.57 (m, 1H), 2.56-2.38 (m, 2H), 2.25-2.12 (m, 2H), 1.87-1.74 (m, 2H), 1.67-1.58 (m, 6H), 1.46 (d, J=6.5 Hz, 3H), 0.06 (s, 9H).

Example 69

(S)—N-[6,6-Dimethyl-5-(2-phenoxypropanoyl)-1,4,5,6-tetrahydropyrrolo[3,4-c]pyrazol-3-yl]-1-(trimethylsilyl)cyclobutanecarboxamide (Compound No. IV-1259)

[Chemical Formula 85]

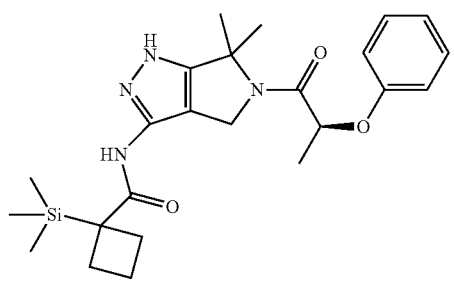

To a solution of 58.6 mg (0.353 mmol) of (S)-2-phenoxypropanoic acid in 2 ml of dehydrated DMF, 0.12 ml (0.69 mmol) of DIPEA and 153 mg (0.356 mmol) of (1-cyano-2-ethoxy-2-oxoethylideneaminooxy)dimethylaminomorpholinocarbenium hexafluorophosphate [COMU (trade name)] were added in this order at 0° C. in a nitrogen atmosphere and then stirred for 20 minutes with the temperature unchanged. Subsequently, 104 mg (0.275 mmol) of ethyl 6,6-dimethyl-3-[1-(trimethylsilyl)cyclobutanecarboxamido]-5,6-dihydropyrrolo[3,4-c]pyrazole-1(4H)-carboxylate synthesized in the similar manner as in Reference Example 5 was added at 0° C. and then stirred at room temperature for 3 hours. Subsequently, 0.10 ml (1.7 mmol) of 2-aminoethanol was added to the reaction solution at room temperature and then stirred for 2 hours with the temperature unchanged.

After the completion of the reaction, a saturated aqueous solution of sodium bicarbonate was added to the reaction solution and stirred, followed by extraction with dichloromethane three times. All of the obtained organic layers were dried over anhydrous magnesium sulfate, then filtered, and concentrated under reduced pressure. The operation of adding toluene to the obtained concentration residue, followed by concentration under reduced pressure again was repeated twice, then the resultant was subjected to silica gel column chromatography (DIOL silica gel, elution solvent: n-hexane:ethyl acetate=75:25 to 50:50 (V/V)), and a fraction containing the compound of interest was concentrated under reduced pressure. The obtained concentration residue was dissolved in ethyl acetate, then n-hexane was added, and the deposited solid was collected by filtration, washed with n-hexane, and then dried under reduced pressure to obtain 75 mg of the title compound (yield: 60%) as a white solid.

Mass spectrum (EI, m/z): 454 [M]$^+$.

$^1$H-NMR spectrum (400 MHz, DMSO-d$_6$) δ: 12.32 & 11.92 (br s, total 1H), 9.81-9.55 (m, 1H), 7.30-7.21 (m, 2H), 6.94-6.87 (m, 1H), 6.85-6.78 (m, 2H), 4.96-4.74 (m, 2H), 4.71-4.54 (m, 1H), 2.56-2.38 (m, 2H), 2.26-2.10 (m, 2H), 1.91-1.72 (m, 2H), 1.69-1.54 (m, 6H), 1.46 (d, J=6.5 Hz, 3H), 0.06 (br s, 9H).

Example 70

N-[6,6-Dimethyl-5-(2-phenoxyacetyl)-1,4,5,6-tetrahydropyrrolo[3,4-c]pyrazol-3-yl]-1-(trimethylsilyl)cyclobutanecarboxamide (Compound No. IV-1238)

[Chemical Formula 86]

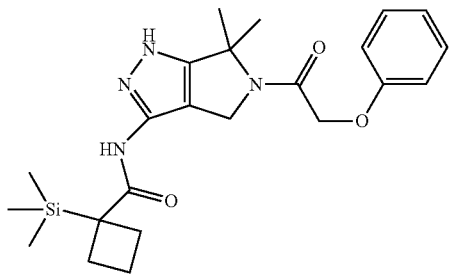

To a solution of 0.143 g (0.279 mmol) of ethyl 6,6-dimethyl-5-(2-phenoxyacetyl)-3-[1-(trimethylsilyl)cyclobutanecarboxamido]-5,6-dihydropyrrolo[3,4-c]pyrazole-2(4H)-carboxylate synthesized in the similar manner as in Reference Example 57 in 3 ml of methanol, 0.150 ml (1.38 mmol) of N,N-dimethylethane-1,2-diamine was added at room temperature in a nitrogen atmosphere and then stirred at room temperature for 30 minutes.

After the completion of the reaction, the reaction solution was concentrated under reduced pressure, ethyl acetate was added to the residue, the organic layer after washing with a 10% aqueous potassium dihydrogen phosphate solution, a saturated aqueous solution of sodium bicarbonate, and a saturated aqueous solution of sodium chloride in this order was dried over anhydrous magnesium sulfate and filtered, and then, the filtrate was concentrated under reduced pressure. The residue was subjected to silica gel column chromatography (DIOL silica gel, elution solvent: 1,2-dichloroethane:ethyl acetate=100:0 to 62:38 (V/V)), a fraction containing the compound of interest was concentrated under reduced pressure, the residue was dissolved in a small amount of dichloromethane, and after addition of n-hexane and ultrasonication, the deposited solid was collected by filtration and dried under reduced pressure to obtain 0.0876 g of the title compound (yield: 71%) as a white solid.

Mass spectrum (CI, m/z): 441 [M+1]$^+$.

$^1$H-NMR spectrum (400 MHz, DMSO-d$_6$) δ: 12.29 & 11.89 (br s, total 1H), 9.84-9.56 (m, 1H), 7.30-7.24 (m, 2H), 6.95-6.89 (m, 3H), 4.78 (s, 2H), 4.73-4.56 (m, 2H), 2.56-2.35 (m, 2H), 2.27-2.08 (m, 2H), 1.93-1.54 (m, 8H), 0.08 (s, 9H).

Example 71

(R)—N-[6,6-Dimethyl-5-(2-phenoxypropanoyl)-1,4,5,6-tetrahydropyrrolo[3,4-c]pyrazol-3-yl]-1-(trimethylsilyl)cyclopropanecarboxamide (Compound No. III-1140)

[Chemical Formula 87]

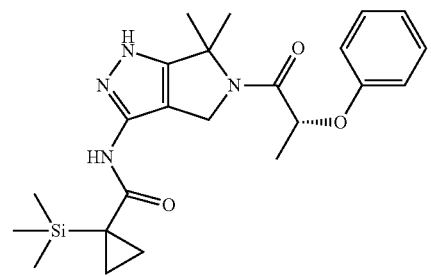

To a solution of 143 mg (0.861 mmol) of (R)-2-phenoxypropanoic acid in 3 ml of dehydrated dichloromethane, 0.12 ml (1.4 mmol) of oxalyl chloride and 0.0050 ml (0.065 mmol) of dehydrated DMF were added in this order at 0° C. in a nitrogen atmosphere and then stirred for 2 hours with the temperature unchanged.

After the completion of the reaction, the reaction solution was concentrated under reduced pressure to obtain a concentration residue.

To a solution of 154 mg (0.424 mmol) of ethyl 6,6-dimethyl-3-[1-(trimethylsilyl)cyclopropanecarboxamido]-5,6-dihydropyrrolo[3,4-c]pyrazole-2(4H)-carboxylate synthesized in the similar manner as in Reference Example 46 and 0.38 ml (2.2 mmol) of DIPEA in 2 ml of dehydrated dichloromethane, a solution of the obtained concentration residue in 1 ml of dehydrated dichloromethane was added at 0° C. in a nitrogen atmosphere and then stirred for 1.5 hours with the temperature unchanged. Subsequently, 0.24 ml (2.2 mmol) of N,N-dimethylethane-1,2-diamine was added to the reaction solution at 0° C. and then stirred at room temperature for 2 hours.

After the completion of the reaction, the reaction solution diluted with dichloromethane was washed with a 5% aqueous potassium bisulfate solution and then separated into an aqueous layer and an organic layer. The aqueous layer was subjected to extraction with dichloromethane twice, and then, all of the obtained organic layers were dried over anhydrous magnesium sulfate, filtered, and concentrated under reduced pressure. The obtained concentration residue was subjected to silica gel column chromatography (DIOL silica gel, elution solvent: n-hexane:ethyl acetate=80:20 to 50:50 (V/V)), and a fraction containing the compound of interest was concentrated under reduced pressure. The obtained concentration residue was dissolved in ethyl acetate, then n-hexane was added, and the deposited solid was collected by filtration, washed with n-hexane, and then dried under reduced pressure to obtain 155 mg of the title compound (yield: 83%) as a white solid.

Mass spectrum (CI, m/z): 441 [M+1]$^+$.

$^1$H-NMR spectrum (400 MHz, DMSO-d$_6$) δ: 12.33 & 12.02 (br s, total 1H), 10.03-9.76 (m, 1H), 7.30-7.22 (m, 2H), 6.94-6.87 (m, 1H), 6.85-6.78 (m, 2H), 4.95-4.70 (m, 2H), 4.67-4.51 (m, 1H), 1.70-1.52 (m, 6H), 1.45 (d, J=6.4 Hz, 3H), 0.98 (br s, 2H), 0.80-0.59 (m, 2H), 0.01 (br s, 9H).

Example 72

N-{5-[3-(Benzyloxy)-2-phenoxypropanoyl]-6,6-dimethyl-1,4,5,6-tetrahydropyrrolo[3,4-c]pyrazol-3-yl}-1-(trimethylsilyl)cyclobutanecarboxamide (Compound No. IV-1354)

[Chemical Formula 88]

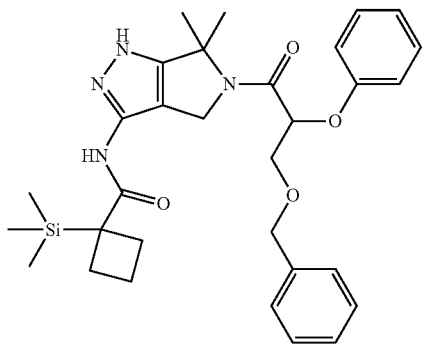

To a solution of 340 mg of 3-(benzyloxy)-2-phenoxypropanoic acid (containing impurities) synthesized in the similar manner as in Reference Example 60 in 3 ml of dehydrated dichloromethane, 0.005 ml (0.07 mmol) of DMF and 0.140 ml (1.63 mmol) of oxalyl chloride were added dropwise with stirring at 0° C. in an argon atmosphere and stirred at the same temperature as above for 2 hours.

After the completion of the reaction, the reaction solution was concentrated under reduced pressure to obtain a concentration residue.

To a solution of 236 mg (0.625 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.550 ml (3.16 mmol) of DIPEA in 3 ml of dehydrated dichloromethane, a solution of the obtained concentration residue in 1 ml of dehydrated dichloromethane was added dropwise with stirring at 0° C. in an argon atmosphere and stirred at the same temperature as above for 1 hour. Subsequently, 0.340 ml (3.12 mmol) of N,N-dimethylethane-1,2-diamine was added to the reaction solution at room temperature and then reacted with stirring at room temperature for 16 hours.

After the completion of the reaction, a saturated aqueous solution of sodium bicarbonate was added to the reaction solution, followed by extraction with dichloromethane. The obtained organic layer was washed with a saturated aqueous solution of sodium chloride, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=60:40 to 30:70 (V/V)), and a fraction containing the compound of interest was concentrated under reduced pressure. The obtained concentration residue was subjected again to silica gel column chromatography (DNH silica gel, elution solvent: 1,2-dichloroethane:methanol=100:0 to 90:10), and some fractions containing the compound of interest at high purity were concentrated under reduced pressure. The obtained concentration residue was dissolved by adding methanol and then added to water, and the deposited solid was collected by filtration and dried under reduced pressure to obtain 11.7 mg of the title compound (yield: 3.3%) as a white solid. Also, the remaining fractions containing the compound of interest obtained by silica gel column chromatography were combined, concentrated under reduced pressure, and dried under reduced pressure to obtain 162 mg of the title compound (yield: 46%) as a white solid.

Mass spectrum (CI, m/z): 561 [M+1]$^+$.

$^1$H-NMR spectrum (400 MHz, DMSO-d$_6$) δ: 12.30 & 11.92 (br s, total 1H), 9.82-9.54 (m, 1H), 7.38-7.20 (m, 7H), 6.97-6.88 (m, 1H), 6.88-6.80 (m, 2H), 5.03-4.66 (m, 3H), 4.60 (s, 2H), 3.93-3.81 (m, 2H), 2.57-2.39 (m, 2H), 2.29-2.11 (m, 2H), 1.91-1.71 (m, 2H), 1.70-1.50 (m, 6H), 0.07 (s, 9H).

Example 73

N-[5-(3-Hydroxy-2-phenoxypropanoyl)-6,6-dimethyl-1,4,5,6-tetrahydropyrrolo[3,4-c]pyrazol-3-yl]-1-(trimethylsilyl)cyclobutanecarboxamide (Compound No. IV-1330)

[Chemical Formula 89]

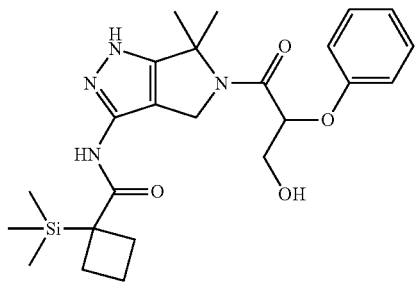

To a solution of 162 mg (0.289 mmol) of N-{5-[3-(benzyloxy)-2-phenoxypropanoyl]-6,6-dimethyl-1,4,5,6-tetrahydropyrrolo[3,4-c]pyrazol-3-yl}-1-(trimethylsilyl)cyclobutanecarboxamide synthesized in the similar manner as in Example 72 in 5 ml of ethanol, 30 mg of 20% palladium hydroxide/carbon (containing 50 wt % water) was added in an argon atmosphere and after replacement with a hydrogen atmosphere under reduced pressure, stirred at room temperature for 5 hours.

After the completion of the reaction, replacement with an argon atmosphere was performed, and the reaction solution was filtered through celite. The solid on the celite was washed with ethanol, and all of the filtrates were concentrated under reduced pressure. The obtained concentration residue was subjected to silica gel column chromatography (elution solvent: 1,2-dichloroethane:methanol=100:0 to 95:5 (V/V)), and a fraction containing the compound of interest was concentrated under reduced pressure. The obtained concentration residue was dissolved by adding methanol and then added to water, and the deposited solid was collected by filtration and dried under reduced pressure to obtain 61 mg of the title compound (yield: 45%) as a white solid.

Mass spectrum (CI, m/z): 471 [M+1]$^+$.

$^1$H-NMR spectrum (400 MHz, DMSO-d$_6$) δ: 12.39-11.82 (m, 1H), 9.70 (br s, 1H), 7.32-7.22 (m, 2H), 6.95-6.88 (m, 1H), 6.85-6.78 (m, 2H), 5.34-5.23 (m, 1H), 4.92-4.82 (m, 1H), 4.81-4.69 (m, 2H), 3.85-3.71 (m, 2H), 2.60-2.39 (m, 2H), 2.26-2.12 (m, 2H), 1.89-1.71 (m, 2H), 1.62 (s, 3H), 1.60 (s, 3H), 0.08 (s, 9H).

Example 74

N-{5-[2-(4-Chlorophenoxy)propanoyl]-6,6-dimethyl-1,4,5,6-tetrahydropyrrolo[3,4-c]pyrazol-3-yl}-1-(trimethylsilyl)cyclobutanecarboxamide (Compound No. IV-1270)

[Chemical Formula 90]

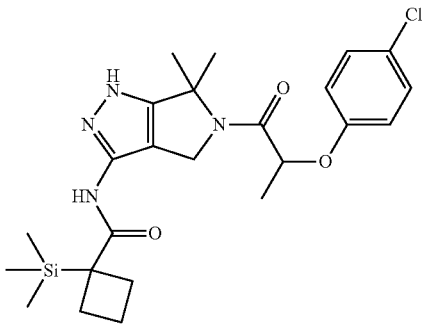

To a solution of 150 mg (0.748 mmol) of 2-(4-chlorophenoxy)propanoic acid [purchased from AK Scientific, Inc.] in 3 ml of dehydrated dichloromethane, 0.080 ml (0.93 mmol) of oxalyl chloride and 0.004 ml (0.05 mmol) of DMF were added dropwise with stirring at 0° C. in an argon atmosphere and stirred at the same temperature as above for 2 hours.

After the completion of the reaction, the reaction solution was concentrated under reduced pressure to obtain a concentration residue.

To a solution of 129 mg (0.341 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.300 ml (1.72 mmol) of DIPEA in 3 ml of dehydrated dichloromethane, a solution of the obtained concentration residue in 1 ml of dehydrated dichloromethane was added dropwise with stirring at 0° C. in an argon atmosphere and stirred at the same temperature as above for 3 hours.

Subsequently, 0.200 ml (1.84 mmol) of N,N-dimethylethane-1,2-diamine was added to the reaction solution at room temperature and then reacted with stirring at room temperature for 16 hours.

After the completion of the reaction, a saturated aqueous solution of sodium bicarbonate was added to the reaction solution, followed by extraction with dichloromethane. The obtained organic layer was washed with a saturated aqueous solution of sodium chloride, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=60:40 to 30:70 (V/V)), and a fraction containing the compound of interest was concentrated under reduced pressure. The obtained concentration residue was dissolved by adding methanol and then added to water, and the deposited solid was collected by filtration and dried under reduced pressure to obtain a solid. The obtained solid was subjected again to silica gel column chromatography (DNH silica gel, elution solvent: n-hexane:ethyl acetate=50:50 to 0:100 (V/V)), and a fraction containing the compound of interest was concentrated under reduced pressure. The obtained concentration residue was dissolved by adding methanol and then added to water, and the deposited solid was collected by filtration and dried under reduced pressure to obtain 39 mg of the title compound (yield: 23%) as a white solid.

Mass spectrum (CI, m/z): 489 [M+1]$^+$.

$^1$H-NMR spectrum (400 MHz, DMSO-d$_6$) δ: 12.32 & 11.89 (br s, total 1H), 9.79-9.53 (m, 1H), 7.34-7.24 (m, 2H), 6.90-6.77 (m, 2H), 4.93 (q, J=6.4 Hz, 1H), 4.90-4.72 (m, 1H), 4.70-4.50 (m, 1H), 2.60-2.36 (m, 2H), 2.28-2.10 (m, 2H), 1.93-1.70 (m, 2H), 1.70-1.53 (m, 6H), 1.46 (d, J=6.4 Hz, 3H), 0.06 (s, 9H).

Example 75

N-{5-[2-(2-Chlorophenoxy)propanoyl]-6,6-dimethyl-1,4,5,6-tetrahydropyrrolo[3,4-c]pyrazol-3-yl}-1-(trimethylsilyl)cyclobutanecarboxamide (Compound No. IV-1266)

[Chemical Formula 91]

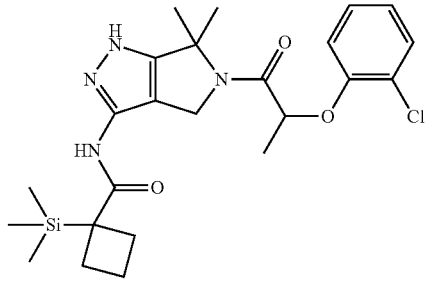

To a solution of 150 mg (0.748 mmol) of 2-(2-chlorophenoxy)propanoic acid in 3 ml of dehydrated dichloromethane, 0.080 ml (0.93 mmol) of oxalyl chloride and 0.004 ml (0.05 mmol) of DMF were added dropwise with stirring at 0° C. in an argon atmosphere and stirred at the same temperature as above for 2 hours.

After the completion of the reaction, the reaction solution was concentrated under reduced pressure to obtain a concentration residue.

To a solution of 129 mg (0.341 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.300 ml (1.72 mmol) of DIPEA in 3 ml of dehydrated dichloromethane, a solution of the obtained concentration residue in 1 ml of dehydrated dichloromethane was added dropwise with stirring at 0° C. in an argon atmosphere and stirred at the same temperature as above for 3 hours. Subsequently, 0.200 ml (1.84 mmol) of N,N-dimethylethane-1,2-diamine was added to the reaction solution at room temperature and then reacted with stirring at room temperature for 16 hours.

After the completion of the reaction, a saturated aqueous solution of sodium bicarbonate was added to the reaction solution, followed by extraction with dichloromethane. The obtained organic layer was washed with a saturated aqueous solution of sodium chloride, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=60:40 to 30:70 (V/V)), and a fraction containing the compound of interest was concentrated under reduced pressure. The obtained concentration residue was dissolved by adding methanol and then added to water, and the deposited solid was collected by filtration and dried under reduced pressure to obtain a solid. The obtained solid was subjected again to silica gel column chromatography (DNH silica gel, elution solvent: n-hexane:ethyl acetate=100:0 to 0:100 (V/V)), and a fraction containing the compound of interest was concentrated under reduced pressure. The obtained concentration residue was dissolved by adding methanol and then added to water, and the deposited solid was collected by filtration and dried under reduced pressure to obtain 16 mg of the title compound (yield: 10%) as a white solid.

Mass spectrum (CI, m/z): 489 [M+1]$^+$.

$^1$H-NMR spectrum (400 MHz, DMSO-d$_6$) δ: 12.32 & 11.92 (br s, total 1H), 9.80-9.54 (m, 1H), 7.45-7.38 (m, 1H), 7.29-7.20 (m, 1H), 6.96-6.89 (m, 1H), 6.89-6.83 (m, 1H), 5.01 (q, J=6.5 Hz, 1H), 4.92-4.74 (m, 1H), 4.72-4.52 (m, 1H), 2.58-2.37 (m, 2H), 2.27-2.10 (m, 2H), 1.93-1.71 (m, 2H), 1.71-1.55 (m, 6H), 1.51 (d, J=6.5 Hz, 3H), 0.06 (s, 9H).

To a solution of 120 mg (0.697 mmol) of 2-(cyclohexyloxy)propanoic acid [purchased from Enamine Ltd.] in 3 ml of dehydrated dichloromethane, 0.080 ml (0.93 mmol) of oxalyl chloride and 0.005 ml (0.07 mmol) of DMF were added dropwise with stirring at 0° C. in an argon atmosphere and stirred at the same temperature as above for 2 hours.

After the completion of the reaction, the reaction solution was concentrated under reduced pressure to obtain a concentration residue.

To a solution of 129 mg (0.341 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.300 ml (1.72 mmol) of DIPEA in 3 ml of dehydrated dichloromethane, a solution of the obtained concentration residue in 1 ml of dehydrated dichloromethane was added dropwise with stirring at 0° C. in an argon atmosphere and stirred at the same temperature as above for 2 hours. Subsequently, 0.200 ml (1.84 mmol) of N,N-dimethylethane-1,2-diamine was added to the reaction solution at room temperature and then reacted with stirring at room temperature for 16 hours.

After the completion of the reaction, a saturated aqueous solution of sodium bicarbonate was added to the reaction solution, followed by extraction with dichloromethane. The obtained organic layer was washed with a saturated aqueous solution of sodium chloride, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=60:40 to 30:70 (V/V)), and a fraction containing the compound of interest was concentrated under reduced pressure. The obtained concentration residue was dissolved by adding methanol and then added to water, and the deposited solid was collected by filtration and dried under reduced pressure to obtain 37 mg of the title compound (yield: 24%) as a white solid.

Mass spectrum (CI, m/z): 461 [M+1]$^+$.

$^1$H-NMR spectrum (400 MHz, DMSO-d$_6$) δ: 12.39-11.73 (m, 1H), 9.63 (br s, 1H), 4.78-4.55 (m, 2H), 4.23 (q, J=6.5 Hz, 1H), 3.41-3.26 (m, 1H), 2.58-2.37 (m, 2H), 2.25-2.12 (m, 2H), 1.90-1.72 (m, 4H), 1.71-1.55 (m, 8H), 1.50-1.39 (m, 1H), 1.28-1.05 (m, 8H), 0.07 (s, 9H).

Example 76

N-{5-[2-(Cyclohexyloxy)propanoyl]-6,6-dimethyl-1,4,5,6-tetrahydropyrrolo[3,4-c]pyrazol-3-yl}-1-(trimethylsilyl)cyclobutanecarboxamide (Compound No. IV-1255)

Example 77

N-{5-[2-(3-Chlorophenoxy)propanoyl]-6,6-dimethyl-1,4,5,6-tetrahydropyrrolo[3,4-c]pyrazol-3-yl}-1-(trimethylsilyl)cyclobutanecarboxamide (Compound No. IV-1268)

[Chemical Formula 92]

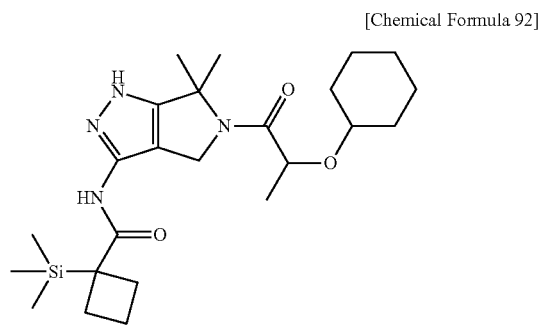 [SMILES: CC(OC1CCCCC1)C(=O)N1Cc2c(NC(=O)C3([Si](C)(C)C)CCC3)n[nH]c2C1(C)C]

[Chemical Formula 93]

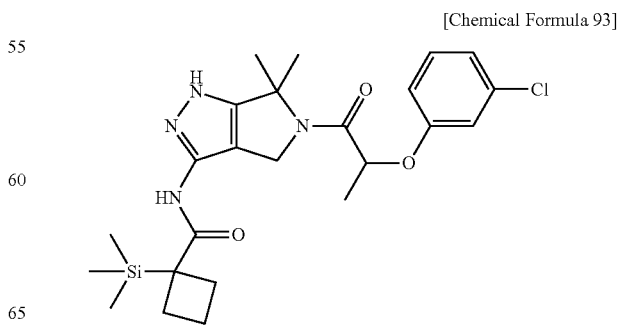

To a solution of 150 mg (0.748 mmol) of 2-(3-chlorophenoxy)propanoic acid [purchased from Combi-Blocks Inc.] in 3 ml of dehydrated dichloromethane, 0.080 ml (0.93 mmol) of oxalyl chloride and 0.005 ml (0.07 mmol) of DMF were added dropwise with stirring at 0° C. in an argon atmosphere and stirred at the same temperature as above for 2 hours.

After the completion of the reaction, the reaction solution was concentrated under reduced pressure to obtain a concentration residue.

To a solution of 129 mg (0.341 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.300 ml (1.72 mmol) of DIPEA in 3 ml of dehydrated dichloromethane, a solution of the obtained concentration residue in 1 ml of dehydrated dichloromethane was added dropwise with stirring at 0° C. in an argon atmosphere and stirred at the same temperature as above for 2 hours. Subsequently, 0.200 ml (1.84 mmol) of N,N-dimethylethane-1,2-diamine was added to the reaction solution at room temperature and then reacted with stirring at room temperature for 16 hours.

After the completion of the reaction, a saturated aqueous solution of sodium bicarbonate was added to the reaction solution, followed by extraction with dichloromethane. The obtained organic layer was washed with a saturated aqueous solution of sodium chloride, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=60:40 to 30:70 (V/V)), and a fraction containing the compound of interest was concentrated under reduced pressure. The obtained concentration residue was dissolved by adding methanol and then added to water, and the deposited solid was collected by filtration and dried under reduced pressure. The obtained solid was subjected again to silica gel column chromatography (DNH silica gel, elution solvent: n-hexane:ethyl acetate=100:0 to 0:100 (V/V)), and a fraction containing the compound of interest was concentrated under reduced pressure. The obtained concentration residue was dissolved by adding methanol and then added to water, and the deposited solid was collected by filtration and dried under reduced pressure to obtain 30 mg of the title compound (yield: 18%) as a white solid.

Mass spectrum (CI, m/z): 489 [M+1]$^+$.

$^1$H-NMR spectrum (400 MHz, DMSO-d$_6$) δ: 12.32 & 11.93 (br s, total 1H), 9.79-9.56 (m, 1H), 7.29 (t, J=8.3 Hz, 1H), 7.00-6.94 (m, 1H), 6.86 (t, J=2.1 Hz, 1H), 6.83-6.77 (m, 1H), 5.00 (q, J=6.4 Hz, 1H), 4.90-4.73 (m, 1H), 4.71-4.51 (m, 1H), 2.57-2.37 (m, 2H), 2.27-2.10 (m, 2H), 1.92-1.71 (m, 2H), 1.70-1.53 (m, 6H), 1.47 (d, J=6.4 Hz, 3H), 0.06 (s, 9H).

Example 78

N-[5-(2-Methoxypropanoyl)-6,6-dimethyl-1,4,5,6-tetrahydropyrrolo[3,4-c]pyrazol-3-yl]-1-(trimethylsilyl)cyclobutanecarboxamide (Compound No. IV-1241)

[Chemical Formula 94]

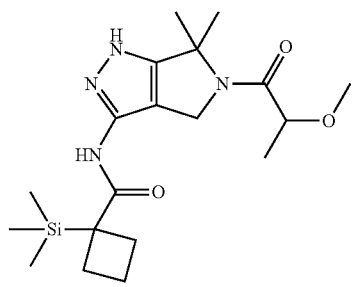

To a solution of 65.0 mg (0.624 mmol) of 2-methoxypropanoic acid [purchased from Combi-Blocks Inc.] in 3 ml of dehydrated dichloromethane, 0.200 ml (1.15 mmol) of DIPEA and 220 mg (0.514 mmol) of (1-cyano-2-ethoxy-2-oxoethylideneaminooxy)dimethylaminomorpholinocarbenium hexafluorophosphate [COMU (trade name)] were added in this order with stirring at 0° C. in an argon atmosphere and then stirred at the same temperature as above for 15 minutes. Subsequently, 129 mg (0.341 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 was added at 0° C. and stirred at room temperature for 16 hours. Subsequently, 0.220 ml (2.02 mmol) of N,N-dimethylethane-1,2-diamine was added to the reaction solution at room temperature and then reacted with stirring at room temperature for 4 hours.

The reaction solution was subjected to silica gel column chromatography (DIOL silica gel, elution solvent: n-hexane:ethyl acetate=60:40 to 30:70 (V/V)), and a fraction containing the compound of interest was concentrated under reduced pressure to obtain 61 mg of the title compound (yield: 46%) as a white solid.

Mass spectrum (CI, m/z): 393 [M+1]$^+$.

$^1$H-NMR spectrum (400 MHz, DMSO-d$_6$) δ: 12.28 & 11.86 (br s, total 1H), 9.80-9.53 (m, 1H), 4.82-4.44 (m, 2H), 4.06 (q, J=6.4 Hz, 1H), 3.20 (s, 3H), 2.57-2.37 (m, 2H), 2.29-2.10 (m, 2H), 1.93-1.55 (m, 8H), 1.21 (d, J=6.4 Hz, 3H), 0.08 (s, 9H).

301

Example 79

N-[5-(3-Methoxy-2-phenoxypropanoyl)-6,6-dimethyl-1,4,5,6-tetrahydropyrrolo[3,4-c]pyrazol-3-yl]-1-(trimethylsilyl)cyclobutanecarboxamide (Compound No. IV-1348)

[Chemical Formula 95]

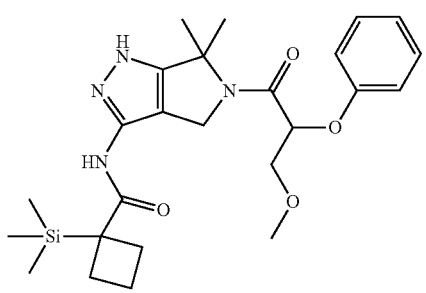

To a solution of 116 mg of 3-methoxy-2-phenoxypropanoic acid (containing impurities) synthesized in the similar manner as in Reference Example 63 in 3 ml of dehydrated dichloromethane, 0.004 ml (0.05 mmol) of DMF and 0.070 ml (0.82 mmol) of oxalyl chloride were added dropwise with stirring at 0° C. in an argon atmosphere and stirred at the same temperature as above for 2 hours.

After the completion of the reaction, the reaction solution was concentrated under reduced pressure to obtain a concentration residue.

To a solution of 124 mg (0.329 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.300 ml (1.72 mmol) of DIPEA in 3 ml of dehydrated dichloromethane, a solution of the obtained concentration residue in 1 ml of dehydrated dichloromethane was added dropwise with stirring at 0° C. in an argon atmosphere and stirred at the same temperature as above for 2 hours. Subsequently, 0.200 ml (1.84 mmol) of N,N-dimethylethane-1,2-diamine was added to the reaction solution at room temperature and then reacted with stirring at room temperature for 16 hours.

The reaction solution was subjected to silica gel column chromatography (DIOL silica gel, elution solvent: n-hexane:ethyl acetate=60:40 to 30:70 (V/V)), and a fraction containing the compound of interest was concentrated under reduced pressure. The obtained concentration residue was dissolved by adding methanol and then added to water, and the deposited solid was collected by filtration and dried under reduced pressure to obtain 75 mg of the title compound (yield: 47%) as a white solid.

Mass spectrum (CI, m/z): 485 [M+1]$^+$.

$^1$H-NMR spectrum (400 MHz, DMSO-d$_6$) δ: 12.32 & 11.94 (br s, total 1H), 9.85-9.57 (m, 1H), 7.34-7.21 (m, 2H), 6.97-6.89 (m, 1H), 6.88-6.78 (m, 2H), 4.98-4.79 (m, 2H), 4.78-4.59 (m, 1H), 3.83-3.68 (m, 2H), 3.34 (s, 3H), 2.58-2.37 (m, 2H), 2.28-2.10 (m, 2H), 1.92-1.71 (m, 2H), 1.69-1.49 (m, 6H), 0.08 (s, 9H).

302

Example 80

N-{6,6-Dimethyl-5-[2-(pyridin-3-yloxy)propanoyl]-1,4,5,6-tetrahydropyrrolo[3,4-c]pyrazol-3-yl}-1-(trimethylsilyl)cyclobutanecarboxamide (Compound No. IV-1274)

[Chemical Formula 96]

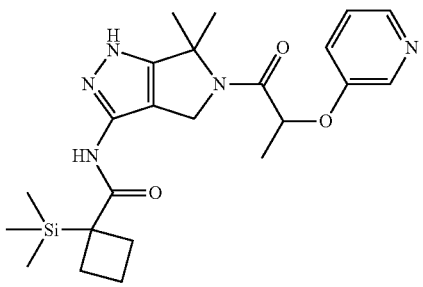

To a solution of 114 mg (0.682 mmol) of 2-(pyridin-3-yloxy)propanoic acid [purchased from Enamine Ltd.] in 3 ml of dehydrated dichloromethane, 0.200 ml (1.15 mmol) of DIPEA and 250 mg (0.584 mmol) of (1-cyano-2-ethoxy-2-oxoethylideneaininooxy)dimethylaminomorpholinocarbenium hexafluorophosphate [COMU (trade name)] were added in this order with stirring at 0° C. in an argon atmosphere and then stirred at the same temperature as above for 15 minutes. Subsequently, 172 mg (0.454 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 was added at 0° C. and stirred at room temperature for 16 hours. Subsequently, 0.250 ml (2.30 mmol) of N,N-dimethylethane-1,2-diamine was added to the reaction solution at room temperature and then reacted with stirring at room temperature for 4 hours.

The reaction solution was subjected to silica gel column chromatography (DIOL silica gel, elution solvent: n-hexane:ethyl acetate=60:40 to 30:70 (V/V)), and a fraction containing the compound of interest was concentrated under reduced pressure. The obtained concentration residue was dissolved by adding methanol and then added to water, and the deposited solid was collected by filtration and dried under reduced pressure to obtain 89 mg of the title compound (yield: 43%) as a white solid.

Mass spectrum (CI, m/z): 456 [M+1]$^+$.

$^1$H-NMR spectrum (400 MHz, DMSO-d$_6$) δ: 12.32 & 11.88 (s, total 1H), 9.76-9.60 (m, 1H), 8.24-8.17 (m, 1H), 8.17-8.09 (m, 1H), 7.33-7.27 (m, 1H), 7.25-7.20 (m, 1H), 5.06 (q, J=6.3 Hz, 1H), 4.93-4.79 (m, 1H), 4.70-4.54 (m, 1H), 2.57-2.38 (m, 2H), 2.27-2.13 (m, 2H), 1.91-1.71 (m, 2H), 1.69-1.54 (m, 6H), 1.50 (d, J=6.3 Hz, 3H), 0.13-0.02 (m, 9H).

Example 81

N-{5-[3-(Dimethylamino)-2-phenoxypropanoyl]-6,6-dimethyl-1,4,5,6-tetrahydropyrrolo[3,4-c]pyrazol-3-yl}-1-(trimethylsilyl)cyclobutanecarboxamide (Compound No. IV-1372)

[Chemical Formula 97]

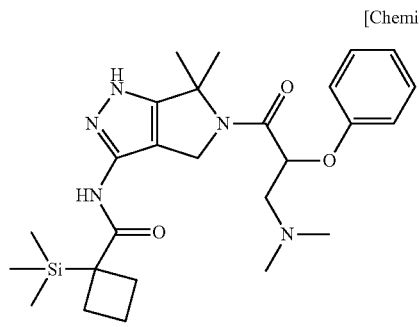

To a solution of 70.0 mg (0.335 mmol) of 3-(dimethylamino)-2-phenoxypropanoic acid synthesized in the similar manner as in Reference Example 66 in 3 ml of dehydrated DMF, 0.150 ml (0.861 mmol) of DIPEA and 200 mg (0.467 mmol) of (1-cyano-2-ethoxy-2-oxoethylideneaminooxy)dimethylaminomorpholinocarbenium hexafluorophosphate [COMU (trade name)] were added in this order with stirring at 0° C. in an argon atmosphere and then stirred at the same temperature as above for 15 minutes. Subsequently, 115 mg (0.304 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 was added at 0° C. and stirred at room temperature for 3 hours. Subsequently, 0.200 ml (1.84 mmol) of N,N-dimethylethane-1,2-diamine was added to the reaction solution at room temperature and then reacted with stirring at room temperature for 16 hours.

After the completion of the reaction, a saturated aqueous solution of sodium bicarbonate was added to the reaction solution, followed by extraction with dichloromethane. The obtained organic layer was washed with a saturated aqueous solution of sodium chloride, then dried over anhydrous sodium sulfate, and filtered, and the filtrate was concentrated under reduced pressure. The obtained concentration residue was subjected to silica gel column chromatography (elution solvent: 1,2-dichloroethane:methanol=100:0 to 90:10 (V/V)), and a fraction containing the compound of interest was concentrated under reduced pressure. The obtained concentration residue was dissolved by adding methanol and then added to water, and the deposited solid was collected by filtration and dried under reduced pressure to obtain 57 mg of the title compound (yield: 38%) as a white solid.

Mass spectrum (CI, m/z): 498 [M+1]$^+$.

$^1$H-NMR spectrum (400 MHz, DMSO-d$_6$) δ: 12.48-11.69 (m, 1H), 9.67 (br s, 1H), 7.32-7.23 (m, 2H), 6.96-6.88 (m, 1H), 6.84-6.77 (m, 2H), 4.87 (br d, J=12.0 Hz, 1H), 4.81 (dd, J=4.5, 6.6 Hz, 1H), 4.66 (br d, J=12.0 Hz, 1H), 2.82-2.70 (m, 2H), 2.57-2.39 (m, 2H), 2.26 (s, 6H), 2.24-2.12 (m, 2H), 1.89-1.73 (m, 2H), 1.62 (s, 3H), 1.61 (s, 3H), 0.07 (s, 9H).

Example 82

N-[6,6-Dimethyl-5-(2-phenoxy-2-phenylacetyl)-1,4,5,6-tetrahydropyrrolo[3,4-c]pyrazol-3-yl]-1-(trimethylsilyl)cyclobutanecarboxamide (Compound No. IV-1211)

[Chemical Formula 98]

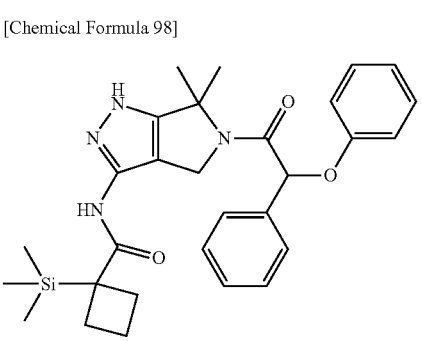

To a solution of 140 mg (0.613 mmol) of 2-phenoxy-2-phenylacetic acid [purchased from Enamine Ltd.] in 3 ml of dehydrated dichloromethane, 0.080 ml (0.93 mmol) of oxalyl chloride and 0.005 ml (0.07 mmol) of DMF were added dropwise with stirring at 0° C. in an argon atmosphere and stirred at the same temperature as above for 2 hours.

After the completion of the reaction, the reaction solution was concentrated under reduced pressure to obtain a concentration residue.

To a solution of 129 mg (0.341 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.300 ml (1.72 mmol) of DIPEA in 3 ml of dehydrated dichloromethane, a solution of the obtained concentration residue in 1 ml of dehydrated dichloromethane was added dropwise with stirring at 0° C. in an argon atmosphere and stirred at the same temperature as above for 3 hours. Subsequently, 0.200 ml (1.84 mmol) of N,N-dimethylethane-1,2-diamine was added to the reaction solution at room temperature and then reacted with stirring at room temperature for 16 hours.

The reaction solution was subjected to silica gel column chromatography (DIOL silica gel, elution solvent: n-hexane:ethyl acetate=60:40 to 30:70 (V/V)), and a fraction containing the compound of interest was concentrated under reduced pressure. The obtained concentration residue was dissolved by adding methanol and then added to water, and the deposited solid was collected by filtration and dried under reduced pressure to obtain 94 mg of the title compound (yield: 53%) as a white solid.

Mass spectrum (CI, m/z): 517 [M+1]$^+$.

$^1$H-NMR spectrum (400 MHz, DMSO-d$_6$) δ: 12.30 & 11.91 (br s, total 1H), 9.57 (br s, 1H), 7.57-7.50 (m, 2H), 7.48-7.36 (m, 3H), 7.31-7.23 (m, 2H), 6.97-6.88 (m, 3H), 5.91 (s, 1H), 4.98-4.72 (m, 1H), 4.40-4.21 (m, 1H), 2.48-2.35 (m, 2H), 2.27-2.08 (m, 2H), 1.91-1.73 (m, 2H), 1.67 (s, 3H), 1.60 (s, 3H), 0.04 (s, 9H).

Example 83

N-{5-[3-(3,3-Difluoropyrrolidin-1-yl)-2-phenoxy-propanoyl]-6,6-dimethyl-1,4,5,6-tetrahydropyrrolo[3,4-c]pyrazol-3-yl}-1-(trimethylsilyl)cyclobutanecarboxamide (Compound No. IV-1378)

[Chemical Formula 99]

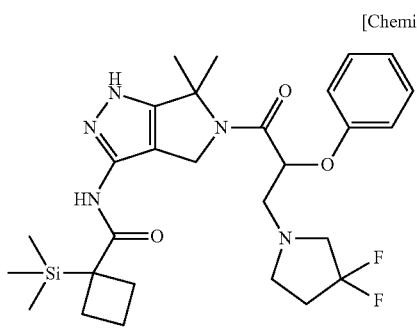

To a solution of 170 mg of 3-(3,3-difluoropyrrolidin-1-yl)-2-phenoxypropanoic acid (containing impurities) synthesized in the similar manner as in Reference Example 69 in 3 ml of dehydrated DMF, 0.250 ml (1.44 mmol) of DIPEA and 300 mg (0.700 mmol) of (1-cyano-2-ethoxy-2-oxoethylideneaminooxy)dimethylaminomorpholinocarbenium hexafluorophosphate [COMU (trade name)] were added in this order with stirring at 0° C. in an argon atmosphere and then stirred at the same temperature as above for 15 minutes. Subsequently, 129 mg (0.341 mmol) of ethyl 6,6-dimethyl-3-[1-(trimethylsilyl)cyclobutanecarboxamido]-5,6-dihydro-pyrrolo[3,4-c]pyrazole-2(4H)-carboxylate synthesized in the similar manner as in Reference Example 84 was added at 0° C. and stirred at room temperature for 16 hours. Subsequently, 0.200 ml (1.84 mmol) of N,N-dimethylethane-1,2-diamine was added to the reaction solution at room temperature and then reacted with stirring at room temperature for 64 hours.

The reaction solution was subjected to silica gel column chromatography (elution solvent: 1,2-dichloroethane:methanol=100:0 to 90:10 (V/V)), and a fraction containing the compound of interest was concentrated under reduced pressure. The obtained concentration residue was subjected to preparative HPLC (column: X-Bridge (trade name) ODS, elution solvent: acetonitrile:1 mM aqueous potassium dihydrogen phosphate solution=50:50 (V/V)), and ethyl acetate and water were added to a fraction containing the compound of interest, then an organic layer and an aqueous layer were separated. The obtained organic layer was concentrated under reduced pressure. The obtained concentration residue was dissolved by adding methanol and then added to water, and the deposited solid was collected by filtration and dried under reduced pressure to obtain 49 mg of the title compound (yield: 26%) as a white solid.

Mass spectrum (CI, m/z): 560 [M+1]$^+$.

$^1$H-NMR spectrum (400 MHz, DMSO-d$_6$) δ: 12.32 & 11.94 (br s, total 1H), 9.84-9.59 (m, 1H), 7.32-7.23 (m, 2H), 6.97-6.89 (m, 1H), 6.85-6.78 (m, 2H), 4.97-4.80 (m, 2H), 4.74-4.57 (m, 1H), 3.14-2.80 (m, 6H), 2.58-2.37 (m, 2H), 2.29-2.10 (m, 4H), 1.92-1.72 (m, 2H), 1.70-1.52 (m, 6H), 0.14-0.03 (m, 9H).

Example 84

N-[5-(3-Hydroxy-2-phenylpropanoyl)-6,6-dimethyl-1,4,5,6-tetrahydropyrrolo[3,4-c]pyrazol-3-yl]-1-(trimethylsilyl)cyclobutanecarboxamide (Compound No. IV-632)

[Chemical Formula 100]

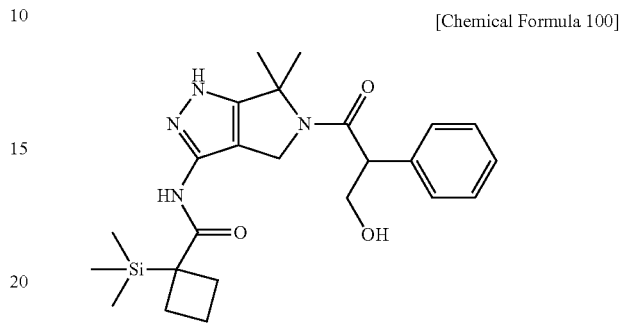

To a solution of 139 mg (0.540 mmol) of 3-(benzyloxy)-2-phenylpropanoic acid synthesized according to the method described in Tetrahedron Lett., 2002 (43), 9691-9693] in 3 ml of dehydrated DMF, 0.18 ml (1.0 mmol) of DIPEA and 233 mg (0.544 mmol) of (1-cyano-2-ethoxy-2-oxoethylideneaminooxy)dimethylaminomorpholinocarbenium hexafluorophosphate [COMU (trade name)] were added in this order at 0° C. in a nitrogen atmosphere and then stirred for 15 minutes with the temperature unchanged. Subsequently, 158 mg (0.418 mmol) of ethyl 6,6-dimethyl-3-[1-(trimethylsilyl)cyclobutanecarboxamido]-5,6-dihydro-pyrrolo[3,4-c]pyrazole-1(4H)-carboxylate synthesized in the similar manner as in Reference Example 5 was added at 0° C. and then stirred at room temperature for 3.5 hours.

After the completion of the reaction, a saturated aqueous solution of sodium bicarbonate was added to the reaction solution and stirred, followed by extraction with ethyl acetate three times. All of the obtained organic layers were dried over anhydrous magnesium sulfate, then filtered, and concentrated under reduced pressure to obtain a concentration residue.

To a solution of the obtained concentration residue in 4 ml of THF, 0.25 ml (1.8 mmol) of triethylamine and 0.10 ml (1.7 mmol) of 2-aminoethanol were added in this order at room temperature in a nitrogen atmosphere and then stirred for 1.5 hours with the temperature unchanged.

After the completion of the reaction, a saturated aqueous solution of sodium bicarbonate was added to the reaction solution and stirred, followed by extraction with dichloromethane three times. All of the obtained organic layers were dried over anhydrous magnesium sulfate, then filtered, and concentrated under reduced pressure. The obtained concentration residue was subjected to silica gel column chromatography (DIOL silica gel, elution solvent: n-hexane:ethyl acetate=70:30 to 50:50 (V/V)), subsequently concentrated under reduced pressure, and dried under reduced pressure to obtain a concentration residue.

To a solution of the obtained concentration residue in 2 ml of ethanol, 25.4 mg of 20% palladium hydroxide/carbon [containing 50 wt % water] was added at room temperature in a nitrogen atmosphere and then, after replacement with a hydrogen atmosphere under reduced pressure, stirred at room temperature for 1.5 hours. The inside of the reaction container was replaced with a nitrogen atmosphere under reduced pressure, and subsequently, 68.3 mg of 20% palladium hydroxide/carbon [containing 50 wt % water] was added at room temperature and then, after replacement with a hydrogen atmosphere again under reduced pressure, stirred at room temperature for 3.5 hours.

After the completion of the reaction, the inside of the reaction container was replaced with a nitrogen atmosphere under reduced pressure. The reaction solution was filtered using a celite filter, subsequently the removed solid was washed with ethanol, and then, the filtrate was concentrated under reduced pressure. The obtained concentration residue was subjected to silica gel column chromatography (DIOL silica gel, elution solvent: n-hexane:ethyl acetate=70:30 to 30:70 (V/V)), and a fraction containing the compound of interest was concentrated under reduced pressure. The obtained concentration residue was dissolved in ethyl acetate, then n-hexane was added, and the deposited solid was collected by filtration, washed with n-hexane, and then dried under reduced pressure to obtain 104 mg of the title compound (yield: 55% [2 steps]) as a white solid.

Mass spectrum (EI, m/z): 454 [M]$^+$.

$^1$H-NMR spectrum (400 MHz, DMSO-d$_6$) δ: 12.45-11.70 (m, 1H), 9.58 (br s, 1H), 7.35-7.20 (m, 5H), 4.81-4.64 (m, 2H), 4.23 (d, J=12.0 Hz, 1H), 3.98-3.89 (m, 1H), 3.84 (dd, J=5.4, 8.2 Hz, 1H), 3.52-3.44 (m, 1H), 2.58-2.37 (m, 2H), 2.24-2.12 (m, 2H), 1.87-1.73 (m, 2H), 1.69 (s, 3H), 1.58 (s, 3H), 0.05 (s, 9H).

Example 85

(S)—N-[5-(3-Hydroxy-2-phenylpropanoyl)-6,6-dimethyl-1,4,5,6-tetrahydropyrrolo[3,4-c]pyrazol-3-yl]-1-(trimethylsilyl)cyclobutanecarboxamide (Compound No. IV-633)

[Chemical Formula 101]

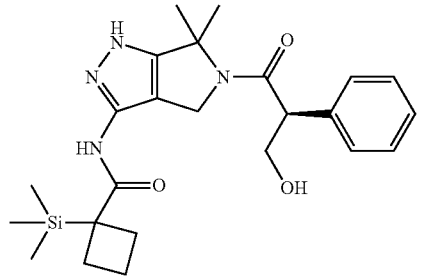

To a solution of 139 mg (0.256 mmol) of (S)—N-{5-[3-(benzyloxy)-2-phenylpropanoyl]-6,6-dimethyl-1,4,5,6-tetrahydropyrrolo[3,4-c]pyrazol-3-yl}-1-(trimethylsilyl)cyclobutanecarboxamide synthesized in the similar manner as in Reference Example 70 in 2 ml of ethanol, 58.4 mg of 20% palladium hydroxide/carbon [containing 50 wt % water] was added at room temperature in a nitrogen atmosphere and then, after replacement with a hydrogen atmosphere under reduced pressure, stirred at room temperature for 3 hours.

After the completion of the reaction, the inside of the reaction container was replaced with a nitrogen atmosphere under reduced pressure. The reaction solution was filtered using a celite filter, subsequently the removed solid was washed with ethyl acetate, and then, the filtrate was concentrated under reduced pressure. The obtained concentration residue was subjected to silica gel column chromatography (DIOL silica gel, elution solvent: n-hexane:ethyl acetate=85:15 to 35:65 (V/V)), and a fraction containing the compound of interest was concentrated under reduced pressure. The obtained concentration residue was dissolved in ethyl acetate, then n-hexane was added, and the deposited solid was collected by filtration, washed with n-hexane, and then dried under reduced pressure to obtain 55 mg of the title compound (yield: 47%) as a white solid.

Mass spectrum (CI, m/z): 455 [M+1]$^+$.

$^1$H-NMR spectrum (400 MHz, DMSO-d$_6$) δ: 12.24 & 11.85 (br s, total 1H), 9.73-9.44 (m, 1H), 7.35-7.20 (m, 5H), 4.81-4.63 (m, 2H), 4.33-4.11 (m, 1H), 3.98-3.89 (m, 1H), 3.88-3.80 (m, 1H), 3.52-3.44 (m, 1H), 2.60-2.36 (m, 2H), 2.26-2.10 (m, 2H), 1.89-1.64 (m, 5H), 1.58 (br s, 3H), 0.05 (s, 9H).

Example 86

(R)—N-{5-[3-(Benzyloxy)-2-phenylpropanoyl]-6,6-dimethyl-1,4,5,6-tetrahydropyrrolo[3,4-c]pyrazol-3-yl}-1-(trimethylsilyl)cyclobutanecarboxamide (Compound No. IV-1221)

[Chemical Formula 102]

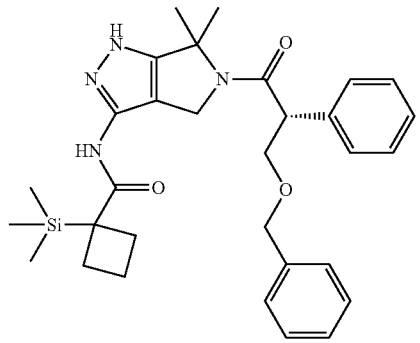

To a solution of 1.22 g (4.76 mmol) of (R)-3-(benzyloxy)-2-phenylpropanoic acid [synthesized according to the method described in Tetrahedron Lett., 2002, 43, 9691-9693] in 20 ml of dehydrated dichloromethane, 0.55 ml (6.4 mmol) of oxalyl chloride and 0.030 ml (0.39 mmol) of dehydrated DMF were added in this order at 0° C. in a nitrogen atmosphere and then stirred for 2 hours with the temperature unchanged.

After the completion of the reaction, the reaction solution was concentrated under reduced pressure to obtain a concentration residue.

To a solution of 903 mg (2.39 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 1.70 ml (9.76 mmol) of DIPEA in 15 ml of dehydrated dichloromethane, a solution of the obtained concentration residue in 5 ml of dehydrated dichloromethane was added at 0° C. in a nitrogen atmosphere and then stirred for 2 hours with the temperature unchanged. Subsequently, 1.0 ml (9.2 mmol) of N,N-dimethylethane-1,2-diamine was added to the reaction solution at 0° C. and then stirred at room temperature for 1.5 hours.

After the completion of the reaction, the reaction solution diluted with dichloromethane was washed with a 5% aqueous potassium bisulfate solution and then the aqueous layer and the organic layer were separated. The aqueous layer was subjected to extraction with dichloromethane twice, and then, all of the obtained organic layers were dried over anhydrous magnesium sulfate, filtered, and concentrated under reduced pressure. The obtained concentration residue was subjected to silica gel column chromatography (DIOL silica gel, elution solvent: n-hexane:ethyl acetate=85:15 to 50:50 (V/V)), and some fractions containing the compound of interest at high purity were concentrated under reduced pressure. The obtained concentration residue was dissolved in ethyl acetate, then n-hexane was added, and the deposited solid was collected by filtration, washed with n-hexane, and then dried under reduced pressure to obtain 43 mg of the title compound (yield: 3%) as a white solid. Also, the remaining fractions containing the compound of interest obtained by silica gel column chromatography were concentrated under reduced pressure and dried under reduced pressure to obtain 1.10 g of the title compound (yield: 85%) as a pale yellow foam.

Mass spectrum (CI, m/z): 545 [M+1]$^+$.

$^1$H-NMR spectrum (400 MHz, DMSO-d$_6$) δ: 12.25 & 11.85 (s, total 1H), 9.65-9.47 (m, 1H), 7.38-7.20 (m, 10H), 4.79-4.62 (m, 1H), 4.52 (d, J=12.6 Hz, 1H), 4.47 (d, J=12.6 Hz, 1H), 4.31-4.15 (m, 1H), 4.07-3.94 (m, 2H), 3.57-3.47 (m, 1H), 2.57-2.36 (m, 2H), 2.25-2.09 (m, 2H), 1.89-1.64 (m, 5H), 1.63-1.50 (m, 3H), 0.09-0.02 (m, 9H).

Example 87

(R)—N-[5-(3-Hydroxy-2-phenylpropanoyl)-6,6-dimethyl-1,4,5,6-tetrahydropyrrolo[3,4-c]pyrazol-3-yl]-1-(trimethylsilyl)cyclobutanecarboxamide (Compound No. IV-1215)

[Chemical Formula 103]

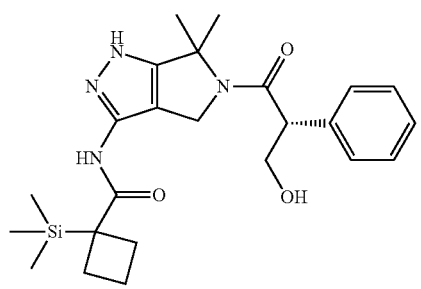

To a solution of 1.10 g (2.02 mmol) of (R)—N-{5-[3-(benzyloxy)-2-phenylpropanoyl]-6,6-dimethyl-1,4,5,6-tetrahydropyrrolo[3,4-c]pyrazol-3-yl}-1-(trimethylsilyl)cyclobutanecarboxamide synthesized in the similar manner as in Example 86 in 15 ml of ethanol, 326 mg of 20% palladium hydroxide/carbon [containing 50 wt % water] was added at room temperature in a nitrogen atmosphere and then, after replacement with a hydrogen atmosphere under reduced pressure, stirred at room temperature for 3.5 hours.

After the completion of the reaction, the inside of the reaction container was replaced with a nitrogen atmosphere under reduced pressure. The reaction solution was filtered using a celite filter, subsequently the removed solid was washed with ethyl acetate, and then, the filtrate was concentrated under reduced pressure. The obtained concentration residue was subjected to silica gel column chromatography (DIOL silica gel, elution solvent: n-hexane:ethyl acetate=70:30 to 10:90 (V/V)), and a fraction containing the compound of interest was concentrated under reduced pressure. The obtained concentration residue was subjected again to silica gel column chromatography (elution solvent: dichloromethane:methanol=100:0 to 96:4 (V/V)), and a fraction containing the compound of interest was concentrated under reduced pressure. The obtained concentration residue was dissolved in ethyl acetate, then n-hexane was added, and the deposited solid was collected by filtration, washed with n-hexane, and then dried under reduced pressure to obtain 708 mg of the title compound (yield: 77%) as a white solid.

Mass spectrum (CI, m/z): 455 [M+1]$^+$.

$^1$H-NMR spectrum (400 MHz, DMSO-d$_6$) δ: 12.25 & 11.82 (s, total 1H), 9.66-9.47 (m, 1H), 7.36-7.20 (m, 5H), 4.83-4.62 (m, 2H), 4.32-4.13 (m, 1H), 3.99-3.90 (m, 1H), 3.89-3.79 (m, 1H), 3.53-3.42 (m, 1H), 2.57-2.35 (m, 2H), 2.25-2.09 (m, 2H), 1.91-1.64 (m, 5H), 1.63-1.52 (m, 3H), 0.13-0.01 (m, 9H).

Example 88

(R)—N-[5-(2-Methoxy-2-phenylacetyl)-6,6-dimethyl-1,4,5,6-tetrahydropyrrolo[3,4-c]pyrazol-3-yl]-1-(trimethylsilyl)cyclobutanecarboxamide (Compound No. IV-1175)

[Chemical Formula 104]

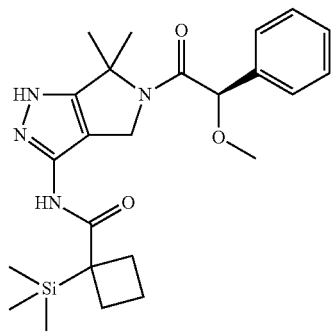

To a solution of 263 mg (1.58 mmol) of (R)-2-methoxy-2-phenylacetic acid in 5 ml of dehydrated dichloromethane, 0.24 ml (2.8 mmol) of oxalyl chloride and 0.025 ml (0.32 mmol) of DMF were added in this order at 0° C. in an argon atmosphere and then stirred for 3 hours with the temperature unchanged.

After the completion of the reaction, the reaction solution was concentrated under reduced pressure at room temperature to obtain a concentration residue.

To a solution of 300 mg (0.793 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.55 ml (3.2 mmol) of DIPEA in 5 ml of dehydrated dichloromethane, a solution of the obtained concentration residue in 3 ml of dehydrated dichloromethane was added dropwise at 0° C. in an argon atmosphere and then stirred at room temperature for 15 hours. Subsequently, 0.37 ml (4.0 mmol) of N,N-dimethylethane-1,2-diamine was added to the reaction solution at room temperature and then stirred for 3 hours with the temperature unchanged.

After the completion of the reaction, a saturated aqueous solution of sodium bicarbonate was added to the reaction solution, followed by extraction with ethyl acetate. All of the obtained organic layers were washed with a saturated aqueous solution of ammonium chloride and a saturated aqueous solution of sodium chloride in this order, dried over anhydrous magnesium sulfate, then filtered, and concentrated under reduced pressure. The obtained concentration residue was subjected to silica gel column chromatography (DIOL silica gel, elution solvent: n-hexane:ethyl acetate=50:50 to 35:65 (V/V)), and a fraction containing the compound of interest was concentrated under reduced pressure. The obtained concentration residue was dissolved by adding ethyl acetate, then n-hexane was added, and the deposited solid was collected by filtration and dried under reduced pressure to obtain 224 mg of the title compound (yield: 62%) as a white solid.

Mass spectrum (CI, m/z): 455 [M+1]$^+$.

$^1$H-NMR spectrum (400 MHz, DMSO-d$_6$) δ: 12.26 & 11.86 (br s, total 1H), 9.71-9.47 (m, 1H), 7.44-7.27 (m, 5H), 4.96 (s, 1H), 4.74-4.52 (m, 1H), 4.39-4.21 (m, 1H), 3.31 (s, 3H), 2.48-2.36 (m, 2H), 2.26-2.07 (m, 2H), 1.92-1.53 (m, 8H), 0.05 (s, 9H).

Example 89

(S)—N-[5-(2-Methoxy-2-phenylacetyl)-6,6-dimethyl-1,4,5,6-tetrahydropyrrolo[3,4-c]pyrazol-3-yl]-1-(trimethylsilyl)cyclobutanecarboxamide (Compound No. IV-1176)

[Chemical Formula 105]

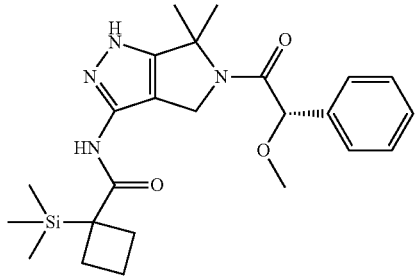

To a solution of 263 mg (1.58 mmol) of (S)-2-methoxy-2-phenylacetic acid in 5 ml of dehydrated dichloromethane, 0.24 ml (2.8 mmol) of oxalyl chloride and 0.025 ml (0.32 mmol) of DMF were added in this order at 0° C. in an argon atmosphere and then stirred for 3 hours with the temperature unchanged.

After the completion of the reaction, the reaction solution was concentrated under reduced pressure at room temperature to obtain a concentration residue.

To a solution of 300 mg (0.793 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.55 ml (3.2 mmol) of DIPEA in 5 ml of dehydrated dichloromethane, a solution of the obtained concentration residue in 3 ml of dehydrated dichloromethane was added dropwise at 0° C. in an argon atmosphere and then stirred at room temperature for 15 hours. Subsequently, 0.37 ml (4.0 mmol) of N,N-dimethylethane-1,2-diamine was added to the reaction solution at room temperature and stirred for 3 hours with the temperature unchanged.

After the completion of the reaction, a saturated aqueous solution of sodium bicarbonate was added to the reaction solution, followed by extraction with ethyl acetate. All of the obtained organic layers were washed with a saturated aqueous solution of ammonium chloride and a saturated aqueous solution of sodium chloride in this order, dried over anhydrous magnesium sulfate, then filtered, and concentrated under reduced pressure. The obtained concentration residue was subjected to silica gel column chromatography (DIOL silica gel, elution solvent: n-hexane:ethyl acetate=50:50 to 35:65 (V/V)), and a fraction containing the compound of interest was concentrated under reduced pressure. The obtained concentration residue was dissolved by adding ethyl acetate, then n-hexane was added, and the deposited solid was collected by filtration and dried under reduced pressure to obtain 206 mg of the title compound (yield: 57%) as a white solid.

Mass spectrum (CI, m/z): 455 [M+1]$^+$.

$^1$H-NMR spectrum (400 MHz, DMSO-d$_6$) δ: 12.26 & 11.86 (br s, total 1H), 9.71-9.45 (m, 1H), 7.46-7.26 (m, 5H), 4.96 (s, 1H), 4.73-4.53 (m, 1H), 4.30 (br d, J=12.3 Hz, 1H), 3.31 (s, 3H), 2.47-2.36 (m, 2H), 2.24-2.11 (m, 2H), 1.89-1.53 (m, 8H), 0.05 (s, 9H).

Example 90

N-[5-(3-Methoxy-2-phenylpropanoyl)-6,6-dimethyl-1,4,5,6-tetrahydropyrrolo[3,4-c]pyrazol-3-yl]-1-(trimethylsilyl)cyclobutanecarboxamide (Compound No. IV-634)

[Chemical Formula 106]

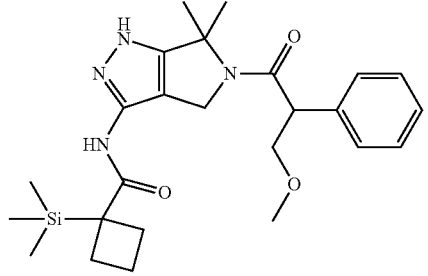

To a solution of 212 mg (1.18 mmol) of 3-methoxy-2-phenylpropanoic acid synthesized in the similar manner as in Reference Example 72 in 6 ml of dehydrated dichloromethane, 0.14 ml (1.6 mmol) of oxalyl chloride and 0.0060 ml (0.077 mmol) of dehydrated DMF were added in this order at 0° C. in a nitrogen atmosphere and then stirred for 2.5 hours with the temperature unchanged.

After the completion of the reaction, the reaction solution was concentrated under reduced pressure to obtain a concentration residue.

To a solution of 156 mg (0.413 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.36 ml (2.1 mmol) of DIPEA in 3 ml of dehydrated dichloromethane, a solution of the obtained concentration residue in 1 ml of dehydrated dichloromethane was added at 0° C. in a nitrogen atmosphere and then stirred for 1.5 hours with the temperature unchanged. Subsequently, 0.23 ml (2.1 mmol) of N,N-dimethylethane-1,2-diamine was added to the reaction solution at 0° C. and then stirred at room temperature for 2 hours.

After the completion of the reaction, the reaction solution diluted with dichloromethane was washed with a 5% aqueous potassium bisulfate solution, and then the aqueous layer and the organic layer were separated. The aqueous layer was subjected to extraction with dichloromethane twice, and then, all of the obtained organic layers were dried over anhydrous magnesium sulfate, filtered, and concentrated under reduced pressure. The obtained concentration residue was subjected to silica gel column chromatography (DIOL silica gel, elution solvent: n-hexane:ethyl acetate=70:30 to 50:50 (V/V)), and a fraction containing the compound of interest was concentrated under reduced pressure. The obtained concentration residue was subjected again to silica gel column chromatography (elution solvent: dichloromethane:methanol=100:0 to 95:5 (V/V)), and a fraction containing the compound of interest was concentrated under reduced pressure. The obtained concentration residue was subjected to preparative HPLC (column: X-Bridge (trade name) ODS, elution solvent: acetonitrile:1 mM aqueous dipotassium hydrogen phosphate solution=40:60 (V/V)), a fraction containing the compound of interest was concentrated under reduced pressure, and acetonitrile was distilled off. The obtained concentration residue was subjected to extraction with ethyl acetate three times, and then, all of the obtained organic layers were washed with a saturated aqueous solution of sodium chloride, subsequently dried over anhydrous magnesium sulfate, filtered, and concentrated under reduced pressure. The obtained concentration residue was dissolved in ethyl acetate, then n-hexane was added, and the deposited solid was collected by filtration, washed with n-hexane, and then dried under reduced pressure to obtain 101 mg of the title compound (yield: 52%) as a white solid.

Mass spectrum (CI, m/z): 469 [M+1]$^+$.

$^1$H-NMR spectrum (400 MHz, DMSO-d$_6$) δ: 12.50-11.61 (m, 1H), 9.57 (br s, 1H), 7.36-7.22 (m, 5H), 4.70 (d, J=12.3 Hz, 1H), 4.22 (d, J=12.3 Hz, 1H), 3.99-3.92 (m, 1H), 3.90-3.83 (m, 1H), 3.40 (dd, J=5.7, 8.8 Hz, 1H), 3.23 (s, 3H), 2.57-2.37 (m, 2H), 2.22-2.12 (m, 2H), 1.86-1.74 (m, 2H), 1.68 (s, 3H), 1.57 (s, 3H), 0.05 (s, 9H).

Example 91

N-[5-(4-Methoxy-2-phenylbutanoyl)-6,6-dimethyl-1,4,5,6-tetrahydropyrrolo[3,4-c]pyrazol-3-yl]-1-(trimethylsilyl)cyclobutanecarboxamide (Compound No. IV-1224)

[Chemical Formula 107]

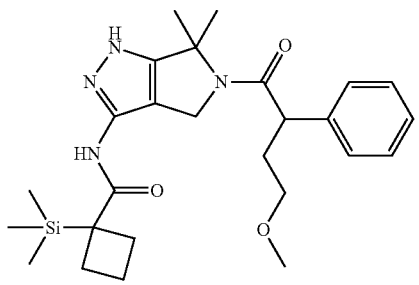

To a solution of 154 mg (0.793 mmol) of 4-methoxy-2-phenylbutanoic acid synthesized in the similar manner as in Reference Example 74 in 3 ml of dehydrated dichloromethane, 0.14 ml (1.6 mmol) of oxalyl chloride and 0.0092 ml (0.12 mmol) of DMF were added in this order at 0° C. in an argon atmosphere and then stirred for 1 hour with the temperature unchanged.

After the completion of the reaction, the reaction solution was concentrated under reduced pressure at room temperature to obtain a concentration residue.

To a solution of 150 mg (0.396 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.28 ml (1.6 mmol) of DIPEA in 3 ml of dehydrated dichloromethane, a solution of the obtained concentration residue in 3 ml of dehydrated dichloromethane was added dropwise at 0° C. in an argon atmosphere and then stirred at room temperature for 3 hours. Subsequently, 0.185 ml (1.98 mmol) of N,N-dimethylethane-1,2-diamine was added to the reaction solution at room temperature and then stirred for 14 hours with the temperature unchanged.

After the completion of the reaction, a saturated aqueous solution of sodium bicarbonate was added to the reaction solution, followed by extraction with ethyl acetate. All of the obtained organic layers were washed with a saturated aqueous solution of ammonium chloride and a saturated aqueous solution of sodium chloride in this order, dried over anhydrous magnesium sulfate, then filtered, and concentrated under reduced pressure. The obtained concentration residue was subjected to silica gel column chromatography (DIOL silica gel, elution solvent: n-hexane:ethyl acetate=60:40 to 40:60 (V/V)), and a fraction containing the compound of interest was concentrated under reduced pressure. The obtained concentration residue was subjected to preparative HPLC (column: XSelect (trade name) HSS C18, elution solvent: acetonitrile:1 mM aqueous potassium dihydrogen phosphate solution=50:50 (V/V)), a fraction containing the compound of interest was concentrated under reduced pressure, and acetonitrile was distilled off. The obtained concentration residue was subjected to extraction with ethyl acetate, and all of the obtained organic layers were washed with a saturated aqueous solution of sodium chloride, dried over anhydrous magnesium sulfate, then filtered, and concentrated under reduced pressure. The obtained concentration residue was dissolved by adding ethyl acetate, then n-hexane was added, and the deposited solid was collected by filtration and dried under reduced pressure to obtain 78 mg of the title compound (yield: 41%) as a white solid.

Mass spectrum (CI, m/z): 483 [M+1]$^+$.

$^1$H-NMR spectrum (400 MHz, DMSO-d$_6$) δ: 12.24 & 11.95 (br s, total 1H), 9.78-9.46 (m, 1H), 7.39-7.18 (m, 5H), 4.79-4.57 (m, 1H), 4.24 (br d, J=12.2 Hz, 1H), 3.92-3.75 (m, 1H), 3.29-3.21 (m, 2H), 3.20 (s, 3H), 2.59-2.37 (m, 2H), 2.25-2.11 (m, 3H), 1.88-1.62 (m, 6H), 1.57 (br s, 3H), 0.05 (s, 9H).

Example 92

(S)—N-[5-(3-Hydroxy-2-phenylpropanoyl)-6,6-dimethyl-1,4,5,6-tetrahydropyrrolo[3,4-c]pyrazol-3-yl]-1-(trimethylsilyl)cyclopropanecarboxamide (Compound No. III-592)

[Chemical Formula 108]

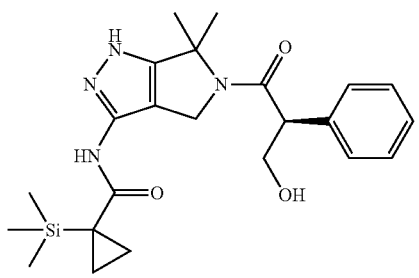

To a solution of 45.8 mg (0.0864 mmol) of (S)—N-{5-[3-(benzyloxy)-2-phenylpropanoyl]-6,6-dimethyl-1,4,5,6-tetrahydropyrrolo[3,4-c]pyrazol-3-yl}-1-(trimethylsilyl)cyclopropanecarboxamide synthesized in the similar manner as in Reference Example 75 in 1 ml of ethanol, 13.6 mg of 20% palladium hydroxide/carbon [containing 50 wt % water] was added at room temperature in a nitrogen atmosphere and then, after replacement with a hydrogen atmosphere under reduced pressure, stirred at room temperature for 2.5 hours.

After the completion of the reaction, the inside of the reaction container was replaced with a nitrogen atmosphere under reduced pressure. The reaction solution was filtered using a celite filter, subsequently the removed solid was washed with ethyl acetate, and then, the filtrate was concentrated under reduced pressure. The obtained concentration residue was subjected to silica gel column chromatography (DIOL silica gel, elution solvent: n-hexane:ethyl acetate=70:30 to 30:70 (V/V)), and a fraction containing the compound of interest was concentrated under reduced pressure. The obtained concentration residue was subjected again to silica gel column chromatography (elution solvent: dichloromethane:methanol=99:1 to 95:5 (V/V)), and a fraction containing the compound of interest was concentrated under reduced pressure. The obtained concentration residue was dissolved in ethyl acetate, then n-hexane was added, and the deposited solid was collected by filtration, washed with n-hexane, and then dried under reduced pressure to obtain 19 mg of the title compound (yield: 50%) as a white solid.

Mass spectrum (CI, m/z): 441 [M+1]$^+$.

$^1$H-NMR spectrum (400 MHz, DMSO-$d_6$) δ: 12.25 & 11.96 (br s, total 1H), 9.98-9.65 (m, 1H), 7.37-7.19 (m, 5H), 4.80-4.58 (m, 2H), 4.33-4.10 (m, 1H), 3.98-3.88 (m, 1H), 3.88-3.80 (m, 1H), 3.52-3.43 (m, 1H), 1.68 (br s, 3H), 1.57 (br s, 3H), 1.05-0.91 (m, 2H), 0.80-0.56 (m, 2H), 0.01 (s, 9H).

Example 93

(R)—N-[5-(2-Methoxy-2-phenylacetyl)-6,6-dimethyl-1,4,5,6-tetrahydropyrrolo[3,4-c]pyrazol-3-yl]-1-(trimethylsilyl)cyclopropanecarboxamide (Compound No. III-1059)

[Chemical Formula 109]

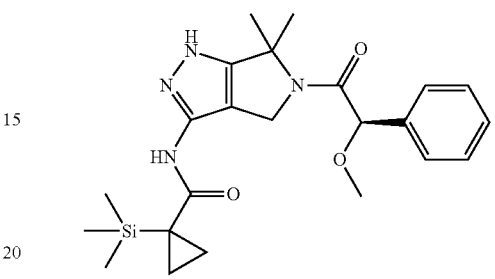

To a solution of 182 mg (1.10 mmol) of (R)-2-methoxy-2-phenylacetic acid in 5 ml of dehydrated dichloromethane, 0.165 ml (1.92 mmol) of oxalyl chloride and 0.017 ml (0.22 mmol) of DMF were added in this order at 0° C. in an argon atmosphere and then stirred for 1 hour with the temperature unchanged.

After the completion of the reaction, the reaction solution was concentrated under reduced pressure at room temperature to obtain a concentration residue.

To a solution of 200 mg (0.549 mmol) of ethyl 6,6-dimethyl-3-[1-(trimethylsilyl)cyclopropanecarboxamido]-5,6-dihydropyrrolo[3,4-c]pyrazole-2(4H)-carboxylate synthesized in the similar manner as in Reference Example 46 and 0.38 ml (2.2 mmol) of DIPEA in 5 ml of dehydrated dichloromethane, a solution of the obtained concentration residue in 3 ml of dehydrated dichloromethane was added dropwise at 0° C. in an argon atmosphere and then stirred at room temperature for 1.5 hours. Subsequently, 0.26 ml (2.7 mmol) of N,N-dimethylethane-1,2-diamine was added to the reaction solution at room temperature and then stirred for 1 hour with the temperature unchanged.

After the completion of the reaction, a saturated aqueous solution of sodium bicarbonate was added to the reaction solution, followed by extraction with ethyl acetate. All of the obtained organic layers were washed with a saturated aqueous solution of ammonium chloride and a saturated aqueous solution of sodium chloride in this order, dried over anhydrous magnesium sulfate, then filtered, and concentrated under reduced pressure. The obtained concentration residue was subjected to silica gel column chromatography (DIOL silica gel, elution solvent: n-hexane:ethyl acetate=70:30 to 50:50 (V/V)), and a fraction containing the compound of interest was concentrated under reduced pressure. The obtained concentration residue was subjected again to silica gel column chromatography (elution solvent: 1,2-dichloroethane:methanol=97:3 to 90:10 (V/V)), and a fraction containing the compound of interest was concentrated under reduced pressure and dried under reduced pressure to obtain 191 mg of the title compound (yield: 79%) as a white solid.

Mass spectrum (CI, m/z): 441 [M+1]$^+$.

$^1$H-NMR spectrum (400 MHz, DMSO-$d_6$) δ: 12.38-11.88 (m, 1H), 9.97-9.65 (m, 1H), 7.45-7.27 (m, 5H), 4.96 (s, 1H), 4.71-4.49 (m, 1H), 4.29 (br d, J=12.8 Hz, 1H), 3.31 (s, 3H), 1.68 (br s, 3H), 1.59 (s, 3H), 1.05-0.91 (m, 2H), 0.78-0.58 (m, 2H), 0.01 (s, 9H).

Example 94

(R)—N-{5-[2-(Difluoromethoxy)-2-phenylacetyl]-6,6-dimethyl-1,4,5,6-tetrahydropyrrolo[3,4-c]pyrazol-3-yl}-1-(trimethylsilyl)cyclobutanecarboxamide (Compound No. IV-1180)

[Chemical Formula 110]

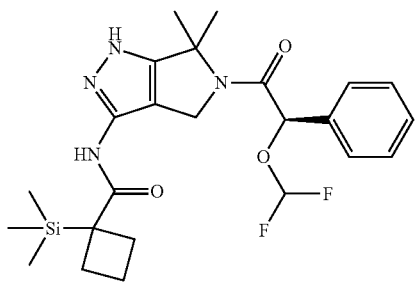

To a solution of 1.01 g (4.17 mmol) of (R)-benzyl 2-hydroxy-2-phenylacetate and 158 mg (0.83 mmol) of copper(I) iodide in 15 ml of acetonitrile, a solution of 2.2 ml (17 mmol) of 2,2-difluoro-2-(fluorosulfonyl)acetic acid in 20 ml of acetonitrile was dividedly added (2 ml each) every 5 minutes at 60° C. in an argon atmosphere and stirred for 2 hours with the temperature unchanged.

After the completion of the reaction, the reaction solution allowed to cool to room temperature was concentrated under reduced pressure and diluted with ethyl acetate. The organic layer was washed with a saturated aqueous solution of sodium bicarbonate and a saturated aqueous solution of sodium chloride in this order, then dried over anhydrous magnesium sulfate, filtered, and concentrated under reduced pressure. The obtained concentration residue was subjected to silica gel column chromatography (elution solvent: n-hexane:ethyl acetate=90:10 to 70:30 (V/V)), and subsequently, a fraction containing the compound of interest was concentrated under reduced pressure to obtain 0.67 g of a concentration residue as a colorless oil.

To a solution of 0.67 g of the obtained concentration residue in 20 ml of methanol, 70 mg of palladium/carbon (ASCA2 (trade name), manufactured by N.E. Chemcat Corp., containing 54% water) was added in an argon atmosphere and then, after replacement with a hydrogen atmosphere under reduced pressure, stirred at room temperature for 2 hours.

After the completion of the reaction, replacement with a nitrogen atmosphere was performed, the reaction solution was filtered through celite, the solid component was washed with methanol, and then, the filtrate was concentrated under reduced pressure to obtain 0.42 g of a concentration residue as a pale yellow solid.

To a solution of 115 mg of the obtained concentration residue in 3 ml of dehydrated dichloromethane, 0.072 ml (0.82 mmol) of oxalyl chloride and 0.010 ml (0.13 mmol) of dehydrated DMF were added in this order at room temperature in an argon atmosphere and then stirred for 15 minutes with the temperature unchanged.

After the completion of the reaction, the reaction solution was concentrated under reduced pressure to obtain a concentration residue.

To a solution of 103 mg (0.273 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.24 ml (1.4 mmol) of DIPEA in 3 ml of dehydrated dichloromethane, a solution of the obtained concentration residue in 1 ml of dehydrated dichloromethane was added at room temperature in an argon atmosphere and then stirred for 3.5 hours with the temperature unchanged. Subsequently, 0.15 ml (1.4 mmol) of N,N-dimethylethane-1,2-diamine was added to the reaction solution at room temperature and then stirred at room temperature for 1 hour.

After the completion of the reaction, a 5% aqueous potassium bisulfate solution was added, followed by extraction with ethyl acetate. The organic layer was washed with a saturated aqueous solution of sodium bicarbonate and a saturated aqueous solution of sodium chloride in this order, dried by adding anhydrous magnesium sulfate, filtered, and concentrated under reduced pressure. The obtained concentration residue was subjected to silica gel column chromatography (DIOL silica gel, elution solvent: n-hexane:ethyl acetate=50:50 to 0:100 (V/V)), and a fraction containing the compound of interest was concentrated under reduced pressure. The obtained concentration residue was dissolved in ethyl acetate, and n-hexane was added. The deposited solid was collected by filtration and dried under reduced pressure to obtain 48.1 mg of the title compound (yield: 36%) as a white solid.

Mass spectrum (CI, m/z): 491 [M+1]$^+$.

$^1$H-NMR spectrum (400 MHz, DMSO-d$_6$) δ: 12.30 & 11.86 (br s, total 1H), 9.67-9.51 (m, 1H), 7.48-7.37 (m, 5H), 6.83 (t, J=76.0 Hz, 1H), 5.78 (s, 1H), 4.83-4.61 (m, 1H), 4.24-4.07 (m, 1H), 2.56-2.35 (m, 2H), 2.24-2.10 (m, 2H), 1.91-1.50 (m, 8H), 0.04 (s, 9H).

Example 95

(R)—N-[5-(2-Ethoxy-2-phenylacetyl)-6,6-dimethyl-1,4,5,6-tetrahydropyrrolo[3,4-c]pyrazol-3-yl]-1-(trimethylsilyl)cyclobutanecarboxamide (Compound No. IV-1188)

[Chemical Formula 111]

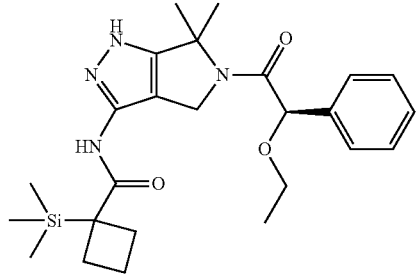

To a solution of 128 mg (0.710 mmol) of (R)-2-ethoxy-2-phenylacetic acid obtained in the similar manner as in Reference Example 77 in 3 ml of dehydrated dichloromethane, 0.090 ml (1.0 mmol) of oxalyl chloride and 0.010 ml (0.13 mmol) of dehydrated DMF were added in this order at 0° C. in an argon atmosphere and then stirred for 1 hour with the temperature unchanged.

After the completion of the reaction, the reaction solution was concentrated under reduced pressure to obtain a concentration residue.

To a solution of 112 mg (0.295 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.30 ml (1.7 mmol) of DIPEA in 3 ml of dehydrated dichloromethane, a solution of the obtained concentration residue in 1 ml of dehydrated dichloromethane was added at 0° C. in an argon atmosphere and then stirred for 30 minutes with the temperature unchanged. Subsequently, 0.11 ml (1.01 mmol) of N,N-dimethylethane-1,2-diamine was added to the reaction solution at 0° C. and then stirred at room temperature for 1 hour.

After the completion of the reaction, water was added, followed by extraction with ethyl acetate. The organic layer was washed with a 5% aqueous potassium bisulfate solution and a saturated aqueous solution of sodium chloride in this order, dried by adding anhydrous magnesium sulfate, filtered, and concentrated under reduced pressure. The obtained concentration residue was subjected to silica gel column chromatography (DIOL silica gel, elution solvent: n-hexane:ethyl acetate=50:50 to 0:100 (V/V)), and a fraction containing the compound of interest was concentrated under reduced pressure. The obtained concentration residue was dissolved in ethyl acetate, n-hexane was added, and the deposited solid was collected by filtration and dried under reduced pressure to obtain 69.7 mg of the title compound (yield: 50%) as a white solid.

Mass spectrum (CI, m/z): 469 $[M+1]^+$.
$^1$H-NMR spectrum (400 MHz, DMSO-$d_6$) δ: 12.26 & 11.85 (br s, total 1H), 9.67-9.48 (m, 1H), 7.43-7.27 (m, 5H), 5.04 (s, 1H), 4.73-4.47 (m, 1H), 4.44-4.24 (m, 1H), 3.62-3.40 (m, 2H), 2.58-2.36 (m, 2H), 2.25-2.10 (m, 2H), 1.90-1.53 (m, 8H), 1.14 (t, J=7.0 Hz, 3H), 0.05 (s, 9H).

Example 96

(R)-1-(Ethyldimethylsilyl)-N-[5-(2-methoxy-2-phenylacetyl)-6,6-dimethyl-1,4,5,6-tetrahydropyrrolo[3,4-c]pyrazol-3-yl] cyclobutanecarboxamide (Compound No. IV-1178)

[Chemical Formula 112]

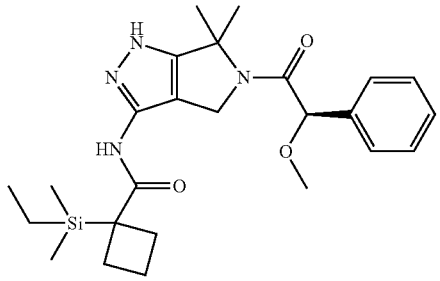

To a solution of 107 mg (0.646 mmol) of (R)-2-methoxy-2-phenylacetic acid in 2 ml of dehydrated dichloromethane, 0.080 ml (0.93 mmol) of oxalyl chloride and 0.0050 ml (0.065 mmol) of dehydrated DMF were added in this order at 0° C. in a nitrogen atmosphere and then stirred for 3 hours with the temperature unchanged.

After the completion of the reaction, the reaction solution was concentrated under reduced pressure to obtain a concentration residue.

To a solution of 117 mg (0.299 mmol) of ethyl 3-[1-(ethyldimethylsilyl)cyclobutanecarboxamido]-6,6-dimethyl-5,6-dihydropyrrolo[3,4-c]pyrazole-2(4H)-carboxylate synthesized in the similar manner as in Reference Example 12 and 0.21 ml (1.2 mmol) of DIPEA in 1 ml of dehydrated dichloromethane, a solution of the obtained concentration residue in 1 ml of dehydrated dichloromethane was added at 0° C. in a nitrogen atmosphere and then stirred for 2.5 hours with the temperature unchanged. Subsequently, 0.16 ml (1.5 mmol) of N,N-dimethylethane-1,2-diamine was added to the reaction solution at 0° C. and then stirred at room temperature for 1.5 hours.

After the completion of the reaction, the reaction solution diluted with dichloromethane was washed with a 5% aqueous potassium bisulfate solution and then the aqueous layer and the organic layer were separated. The aqueous layer was subjected to extraction with dichloromethane twice, and then, all of the obtained organic layers were dried over anhydrous magnesium sulfate, filtered, and concentrated under reduced pressure. The obtained concentration residue was subjected to silica gel column chromatography (DIOL silica gel, elution solvent: n-hexane:ethyl acetate=80:20 to 50:50 (V/V)), and a fraction containing the compound of interest was concentrated under reduced pressure. The obtained concentration residue was dissolved in ethyl acetate, then n-hexane was added, and the deposited solid was collected by filtration, washed with n-hexane, and then dried under reduced pressure to obtain 115 mg of the title compound (yield: 82%) as a white solid.

Mass spectrum (CI, m/z): 469 $[M+1]^+$.
$^1$H-NMR spectrum (400 MHz, DMSO-$d_6$) δ: 12.26 & 11.84 (s, total 1H), 9.67-9.48 (m, 1H), 7.42-7.27 (m, 5H), 4.95 (s, 1H), 4.71-4.52 (m, 1H), 4.35-4.23 (m, 1H), 3.30 (s, 3H), 2.56-2.37 (m, 2H), 2.26-2.11 (m, 2H), 1.90-1.52 (m, 8H), 0.88 (t, J=7.8 Hz, 3H), 0.53 (q, J=7.8 Hz, 2H), 0.09-0.01 (m, 6H).

Example 97

(R)—N-[5-(2-Cyclopropoxy-2-phenylacetyl)-6,6-dimethyl-1,4,5,6-tetrahydropyrrolo[3,4-c]pyrazol-3-yl]-1-(trimethylsilyl)cyclobutanecarboxamide (Compound No. IV-1208)

[Chemical Formula 113]

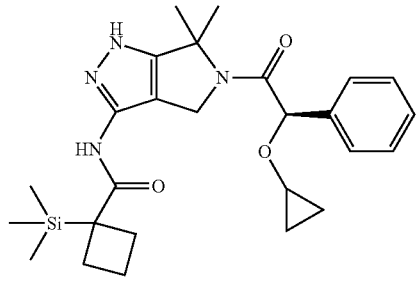

To a solution of 140 mg (0.728 mmol) of (R)-2-cyclopropoxy-2-phenylacetic acid synthesized in the similar manner as in Reference Example 86 in 2 ml of dehydrated dichloromethane, 0.006 ml (0.08 mmol) of DMF and 0.083 ml (0.95 mmol) of oxalyl chloride were added with stirring at 0° C. in an argon atmosphere and stirred at room temperature for 1.5 hours.

After the completion of the reaction, the reaction solution was concentrated under reduced pressure to obtain a concentration residue.

To a solution of 150 mg (0.396 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.350 ml (2.00 mmol) of DIPEA in 2 ml of dehydrated dichloromethane, a solution of the obtained concentration residue in 3 ml of dehydrated dichloromethane was added dropwise with stirring at 0° C. in an argon atmosphere and stirred at room temperature for 2 hours.

After the completion of the reaction, a saturated aqueous solution of sodium bicarbonate was added to the reaction solution, followed by extraction with dichloromethane. The obtained organic layer was washed with water, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=100:0 to 70:30 (V/V)), subsequently concentrated under reduced pressure, and dried under reduced pressure to obtain a concentration residue.

To a solution of the obtained concentration residue in 2 ml of dehydrated dichloromethane, 0.130 ml (1.19 mmol) of N,N-dimethylethane-1,2-diamine was added at room temperature in an argon atmosphere and then stirred at room temperature for 16 hours.

After the completion of the reaction, a 5% aqueous potassium bisulfate solution was added to the reaction solution and stirred, followed by extraction with dichloromethane. The obtained organic layer was washed with a saturated aqueous solution of sodium bicarbonate and a saturated aqueous solution of sodium chloride in this order, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=100:0 to 50:50 (V/V)), and a fraction containing the compound of interest was concentrated under reduced pressure. The obtained concentration residue was dissolved in ethyl acetate and then added to n-hexane, and the deposited solid was collected by filtration and dried under reduced pressure to obtain 80 mg of the title compound (yield: 42%) as a white solid.

Mass spectrum (CI, m/z): 481 [M+1]$^+$.

$^1$H-NMR spectrum (400 MHz, DMSO-d$_6$) δ: 12.37-11.83 (m, 1H), 9.59 (br s, 1H), 7.42-7.28 (m, 5H), 5.10 (s, 1H), 4.73-4.54 (m, 1H), 4.35 (d, J=12.4 Hz, 1H), 3.40 (tt, J=3.0, 6.1 Hz, 1H), 2.59-2.37 (m, 2H), 2.24-2.12 (m, 2H), 1.90-1.74 (m, 2H), 1.70 (s, 3H), 1.61 (s, 3H), 0.69-0.53 (m, 2H), 0.51-0.39 (m, 2H), 0.05 (s, 9H).

Example 98

(R)—N-[5-(2-Isopropoxy-2-phenylacetyl)-6,6-dimethyl-1,4,5,6-tetrahydropyrrolo[3,4-c]pyrazol-3-yl]-1-(trimethylsilyl)cyclobutanecarboxamide (Compound No. IV-1204)

[Chemical Formula 114]

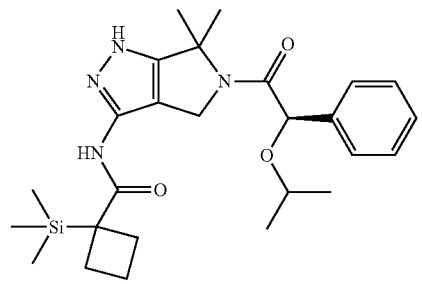

To a solution of 165 mg (0.849 mmol) of (R)-2-isopropoxy-2-phenylacetic acid synthesized in the similar manner as in Reference Example 87 in 2 ml of dehydrated dichloromethane, 0.10 ml (1.2 mmol) of oxalyl chloride and 0.0050 ml (0.065 mmol) of dehydrated DMF were added in this order at 0° C. in an argon atmosphere and then stirred for 2.5 hours with the temperature unchanged.

After the completion of the reaction, the reaction solution was concentrated under reduced pressure and dried under reduced pressure to obtain a concentration residue.

To a solution of 128 mg (0.338 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.30 ml (1.7 mmol) of DIPEA in 1 ml of dehydrated dichloromethane, a solution of the obtained concentration residue in 1 ml of dehydrated dichloromethane was added at 0° C. in an argon atmosphere and then stirred for 1.5 hours with the temperature unchanged.

After the completion of the reaction, ethyl acetate and a saturated aqueous solution of sodium bicarbonate were added to the reaction solution and stirred. After separation into an aqueous layer and an organic layer, the aqueous layer was subjected to extraction with ethyl acetate twice. All of the organic layers were dried over anhydrous magnesium sulfate, then filtered, and concentrated under reduced pressure. The obtained concentration residue was subjected to silica gel column chromatography (elution solvent: n-hexane:ethyl acetate=80:20 to 60:40 (V/V)), subsequently concentrated under reduced pressure, and dried under reduced pressure to obtain a concentration residue.

To a solution of the obtained concentration residue in 2 ml of THF, 0.15 ml (1.4 mmol) of N,N-dimethylethane-1,2-diamine was added at room temperature in an argon atmosphere and then stirred at room temperature for 2 hours.

After the completion of the reaction, a 5% aqueous potassium bisulfate solution was added to the reaction solution and stirred, followed by extraction with ethyl acetate three times. All of the obtained organic layers were dried over anhydrous magnesium sulfate, filtered, and concentrated under reduced pressure. The obtained concentration residue was subjected to silica gel column chromatography (DIOL silica gel, elution solvent: n-hexane:ethyl acetate=80:20 to 50:50 (V/V)), and a fraction containing the compound of interest was concentrated under reduced pressure. The obtained concentration residue was dissolved in ethyl acetate, then n-hexane was added, and the deposited solid was collected by filtration, washed with n-hexane, and then dried under reduced pressure to obtain 135 mg of the title compound (yield: 83%) as a white solid.

Mass spectrum (CI, m/z): 483 [M+1]$^+$.

$^1$H-NMR spectrum (400 MHz, DMSO-d$_6$) δ: 12.40-11.82 (m, 1H), 9.75-9.42 (m, 1H), 7.40-7.27 (m, 5H), 5.11 (s, 1H), 4.65-4.38 (m, 2H), 3.68 (spt, J=6.0 Hz, 1H), 2.47-2.35 (m, 2H), 2.23-2.09 (m, 2H), 1.87-1.71 (m, 2H), 1.67 (s, 3H), 1.61 (s, 3H), 1.16 (d, J=6.0 Hz, 3H), 1.13 (d, J=6.0 Hz, 3H), 0.04 (s, 9H).

Example 99

(R)—N-{6,6-Dimethyl-5-[2-phenyl-2-(trifluoromethoxy)acetyl]-1,4,5,6-tetrahydropyrrolo[3,4-c]pyrazol-3-yl}-1-(trimethylsilyl)cyclobutanecarboxamide (Compound No. Iv-1184)

[Chemical Formula 115]

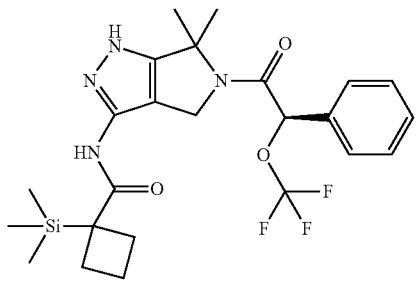

To a solution of 160 mg of (R)-2-phenyl-2-(trifluoromethoxy)acetic acid (containing impurities) synthesized in the similar manner as in Reference Example 89 in 2 ml of dehydrated dichloromethane, 0.083 ml (0.95 mmol) of oxalyl chloride and 0.006 ml (0.08 mmol) of DMF were added with stirring at 0° C. in an argon atmosphere and stirred at room temperature for 1.5 hours.

After the completion of the reaction, the reaction solution was concentrated under reduced pressure to obtain a concentration residue.

To a solution of 150 mg (0.396 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.350 ml (2.00 mmol) of DIPEA in 2 ml of dehydrated dichloromethane, a solution of the obtained concentration residue in 3 ml of dehydrated dichloromethane was added dropwise with stirring at 0° C. in an argon atmosphere and stirred at room temperature for 2 hours.

After the completion of the reaction, a saturated aqueous solution of sodium bicarbonate was added to the reaction solution, followed by extraction with dichloromethane. The obtained organic layer was washed with water, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=100:0 to 70:30 (V/V)), subsequently concentrated under reduced pressure, and dried under reduced pressure to obtain a concentration residue.

To a solution of the obtained concentration residue in 2 ml of dehydrated dichloromethane, 0.130 ml (1.19 mmol) of N,N-dimethylethane-1,2-diamine was added at room temperature in an argon atmosphere and then stirred at room temperature for 2 hours.

After the completion of the reaction, a 5% aqueous potassium bisulfate solution was added to the reaction solution and stirred, followed by extraction with dichloromethane. The obtained organic layer was washed with a saturated aqueous solution of sodium bicarbonate and a saturated aqueous solution of sodium chloride in this order, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=100:0 to 50:50 (V/V)), and a fraction containing the compound of interest was concentrated under reduced pressure. The obtained concentration residue was dissolved in ethyl acetate and then added to n-hexane, and the deposited solid was collected by filtration and dried under reduced pressure to obtain 97.6 mg of the title compound (yield: 48%) as a white solid.

Mass spectrum (CI, m/z): 509 [M+1]$^+$.

$^1$H-NMR spectrum (400 MHz, DMSO-d$_6$) δ: 12.39-11.84 (m, 1H), 9.58 (br s, 1H), 7.54-7.41 (m, 5H), 6.06 (s, 1H), 4.78 (br d, J=11.9 Hz, 1H), 4.08 (br d, J=11.9 Hz, 1H), 2.58-2.35 (m, 2H), 2.23-2.10 (m, 2H), 1.88-1.73 (m, 2H), 1.70 (s, 3H), 1.60 (s, 3H), 0.04 (s, 9H).

Example 100

(R)—N-[6,6-Dimethyl-5-(2-phenyl-2-propoxyacetyl)-1,4,5,6-tetrahydropyrrolo[3,4-c]pyrazol-3-yl]-1-(trimethylsilyl)cyclobutanecarboxamide (Compound No. Iv-1196)

[Chemical Formula 116]

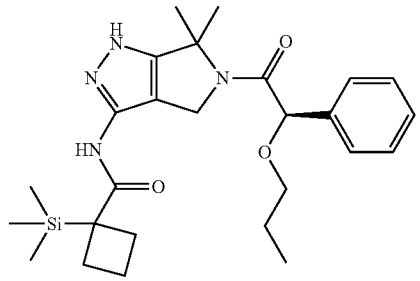

To a solution of 146 mg (0.753 mmol) of (R)-2-phenyl-2-propoxyacetic acid synthesized in the similar manner as in Reference Example 91 in 2 ml of dehydrated dichloromethane, 0.10 ml (1.2 mmol) of oxalyl chloride and 0.0050 ml (0.065 mmol) of dehydrated DMF were added in this order at 0° C. in an argon atmosphere and then stirred for 1.5 hours with the temperature unchanged.

After the completion of the reaction, the reaction solution was concentrated under reduced pressure and dried under reduced pressure to obtain a concentration residue.

To a solution of 144 mg (0.380 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.33 ml (1.9 mmol) of DIPEA in 1 ml of dehydrated dichloromethane, a solution of the obtained concentration residue in 1 ml of dehydrated dichloromethane was added at 0° C. in an argon atmosphere and then stirred for 1.5 hours with the temperature unchanged.

After the completion of the reaction, ethyl acetate and a saturated aqueous solution of sodium bicarbonate were added to the reaction solution and stirred. After separation into an aqueous layer and an organic layer, the aqueous layer was subjected to extraction with ethyl acetate twice. All of the organic layers were dried over anhydrous magnesium sulfate, then filtered, and concentrated under reduced pressure. The obtained concentration residue was subjected to silica gel column chromatography (elution solvent: n-hexane:ethyl acetate=85:15 to 60:40 (V/V)), subsequently concentrated under reduced pressure, and dried under reduced pressure to obtain a concentration residue.

To a solution of the obtained concentration residue in 2 ml of THF, 0.17 ml (1.6 mmol) of N,N-dimethylethane-1,2-diamine was added at room temperature in an argon atmosphere and then stirred at room temperature for 3 hours.

After the completion of the reaction, a 5% aqueous potassium bisulfate solution was added to the reaction solution and stirred, followed by extraction with ethyl acetate three times. All of the obtained organic layers were dried over anhydrous magnesium sulfate, filtered, and concentrated under reduced pressure. The obtained concentration residue was subjected to silica gel column chromatography (DIOL silica gel, elution solvent: n-hexane:ethyl acetate=85:15 to 60:40 (V/V)), and a fraction containing the compound of interest was concentrated under reduced pressure. The obtained concentration residue was dissolved in ethyl acetate, then n-hexane was added, and the deposited solid was collected by filtration, washed with n-hexane, and then dried under reduced pressure to obtain 144 mg of the title compound (yield: 80%) as a white solid.

Mass spectrum (CI, m/z): 483 [M+1]$^+$.

$^1$H-NMR spectrum (400 MHz, DMSO-d$_6$) δ: 12.43-11.75 (m, 1H), 9.56 (br s, 1H), 7.43-7.27 (m, 5H), 5.03 (s, 1H), 4.71-4.47 (m, 1H), 4.39 (br d, J=12.5 Hz, 1H), 3.51-3.43 (m, 1H), 3.41-3.24 (m, 1H), 2.60-2.36 (m, 2H), 2.25-2.10 (m, 2H), 1.88-1.72 (m, 2H), 1.68 (s, 3H), 1.65-1.48 (m, 5H), 0.87 (t, J=7.4 Hz, 3H), 0.04 (s, 9H).

Example 101

N-{5-[2-(4-Fluorophenyl)-2-methoxyacetyl]-6,6-dimethyl-1,4,5,6-tetrahydropyrrolo[3,4-c]pyrazol-3-yl}-1-(trimethylsilyl)cyclobutanecarboxamide
(Compound No. IV-1427)

[Chemical Formula 117]

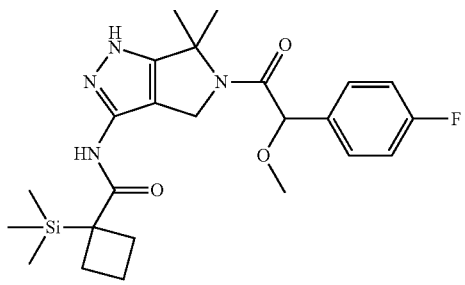

To a suspension of 229 mg of 2-(4-fluorophenyl)-2-methoxyacetic acid (containing impurities) synthesized in the similar manner as in Reference Example 93 in 2 ml of dehydrated dichloromethane, 0.150 ml (1.71 mmol) of oxalyl chloride and 0.011 ml (0.14 mmol) of DMF were added with stirring at 0° C. in an argon atmosphere and stirred at room temperature for 1.5 hours.

After the completion of the reaction, the reaction solution was concentrated under reduced pressure to obtain a concentration residue.

To a solution of 265 mg (0.700 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.620 ml (3.55 mmol) of DIPEA in 2 ml of dehydrated dichloromethane, a solution of the obtained concentration residue in 3 ml of dehydrated dichloromethane was added dropwise with stirring at 0° C. in an argon atmosphere and stirred at room temperature for 1 hour.

After the completion of the reaction, a saturated aqueous solution of sodium bicarbonate was added to the reaction solution, followed by extraction with dichloromethane. The obtained organic layer was washed with water, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=100:0 to 70:30 (V/V)), subsequently concentrated under reduced pressure, and dried under reduced pressure to obtain a concentration residue.

To a solution of the obtained concentration residue in 2 ml of dehydrated dichloromethane, 0.230 ml (2.11 mmol) of N,N-dimethylethane-1,2-diamine was added at room temperature in an argon atmosphere and then stirred at room temperature for 1 hour.

After the completion of the reaction, a 5% aqueous potassium bisulfate solution was added to the reaction solution and stirred, followed by extraction with dichloromethane. The obtained organic layer was washed with a saturated aqueous solution of sodium bicarbonate and a saturated aqueous solution of sodium chloride in this order, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=100:0 to 50:50 (V/V)), and a fraction containing the compound of interest was concentrated under reduced pressure. The obtained concentration residue was dissolved in dichloromethane, and then, a 5% aqueous potassium bisulfate solution was added thereto, stirred, and separated into an aqueous layer and an organic layer. The obtained organic layer was washed with a saturated aqueous solution of sodium bicarbonate and a saturated aqueous solution of sodium chloride in this order, then dried over anhydrous sodium sulfate, and filtered, and the filtrate was concentrated under reduced pressure. The obtained concentration residue was dissolved in ethyl acetate and then added to n-hexane, and the deposited solid was collected by filtration and dried under reduced pressure to obtain 174 mg of the title compound (yield: 53%) as a white solid.

Mass spectrum (CI, m/z): 473 [M+1]$^+$.

$^1$H-NMR spectrum (400 MHz, DMSO-d$_6$) δ: 12.27 & 11.91 (br s, total 1H), 9.58 (br s, 1H), 7.47-7.36 (m, 2H), 7.26-7.14 (m, 2H), 4.99 (s, 1H), 4.76-4.53 (m, 1H), 4.32 (br d, J=12.4 Hz, 1H), 3.29 (s, 3H), 2.58-2.36 (m, 2H), 2.25-2.10 (m, 2H), 1.88-1.72 (m, 2H), 1.69 (br s, 3H), 1.60 (s, 3H), 0.05 (s, 9H).

Example 102

N-{5-[2-(3-Fluorophenyl)-2-methoxyacetyl]-6,6-dimethyl-1,4,5,6-tetrahydropyrrolo[3,4-c]pyrazol-3-yl}-1-(trimethylsilyl)cyclobutanecarboxamide (Compound No. IV-1404)

[Chemical Formula 118]

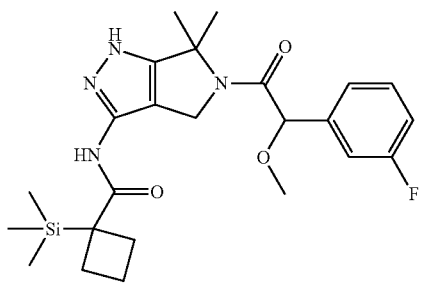

To a suspension of 146 mg of 2-(3-fluorophenyl)-2-methoxyacetic acid (containing impurities) synthesized in the similar manner as in Reference Example 96 in 2 ml of dehydrated dichloromethane, 0.080 ml (0.91 mmol) of oxalyl chloride and 0.010 ml (0.13 mmol) of DMF were added with stirring at 0° C. in an argon atmosphere and stirred at room temperature for 1.5 hours.

After the completion of the reaction, the reaction solution was concentrated under reduced pressure to obtain a concentration residue.

To a solution of 200 mg (0.528 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.462 ml (2.65 mmol) of DIPEA in 2 ml of dehydrated dichloromethane, a solution of the obtained concentration residue in 3 ml of dehydrated dichloromethane was added dropwise with stirring at room temperature in an argon atmosphere and stirred at room temperature for 1 hour.

After the completion of the reaction, a saturated aqueous solution of sodium bicarbonate was added to the reaction solution, followed by extraction with dichloromethane. The obtained organic layer was washed with water, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=100:0 to 70:30 (V/V)), subsequently concentrated under reduced pressure, and dried under reduced pressure to obtain a concentration residue.

To a solution of the obtained concentration residue in 2 ml of dehydrated dichloromethane, 0.173 ml (1.59 mmol) of N,N-dimethylethane-1,2-diamine was added at room temperature in an argon atmosphere and then stirred at room temperature for 16 hours.

After the completion of the reaction, a 5% aqueous potassium bisulfate solution was added to the reaction solution and stirred, followed by extraction with dichloromethane. The obtained organic layer was washed with a saturated aqueous solution of sodium bicarbonate and a saturated aqueous solution of sodium chloride in this order, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=100:0 to 50:50 (V/V)), and a fraction containing the compound of interest was concentrated under reduced pressure. The obtained concentration residue was dissolved in methanol and then added to water, and the deposited solid was collected by filtration and dried under reduced pressure to obtain 187 mg of the title compound (yield: 75%) as a white solid.

Mass spectrum (CI, m/z): 473 [M+1]$^+$.

$^1$H-NMR spectrum (400 MHz, DMSO-$d_6$) δ: 12.40-11.81 (m, 1H), 9.60 (br s, 1H), 7.48-7.38 (m, 1H), 7.24-7.13 (m, 3H), 5.03 (s, 1H), 4.75-4.54 (m, 1H), 4.39 (br d, J=12.7 Hz, 1H), 3.32 (s, 3H), 2.59-2.36 (m, 2H), 2.24-2.10 (m, 2H), 1.88-1.72 (m, 2H), 1.69 (s, 3H), 1.60 (s, 3H), 0.05 (s, 9H).

Example 103

(R)—N-{5-[2-(2-Fluorophenyl)-2-methoxyacetyl]-6,6-dimethyl-1,4,5,6-tetrahydropyrrolo[3,4-c]pyrazol-3-yl}-1-(trimethylsilyl)cyclobutanecarboxamide (Compound No. IV-1383)

[Chemical Formula 119]

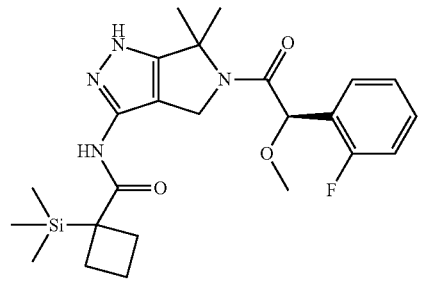

To a suspension of 200 mg (1.09 mmol) of (R)-2-(2-fluorophenyl)-2-methoxyacetic acid synthesized in the similar manner as in Reference Example 98 in 2 ml of dehydrated dichloromethane, 0.111 ml (1.27 mmol) of oxalyl chloride and 0.010 ml (0.13 mmol) of DMF were added with stirring at 0° C. in an argon atmosphere and stirred at room temperature for 1.5 hours.

After the completion of the reaction, the reaction solution was concentrated under reduced pressure to obtain a concentration residue.

To a solution of 200 mg (0.528 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.500 ml (2.86 mmol) of DIPEA in 2 ml of dehydrated dichloromethane, a solution of the obtained concentration residue in 3 ml of dehydrated dichloromethane was added dropwise with stirring at room temperature in an argon atmosphere and stirred at room temperature for 2 hours.

After the completion of the reaction, a saturated aqueous solution of sodium bicarbonate was added to the reaction solution, followed by extraction with dichloromethane. The obtained organic layer was washed with water, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=100:0 to 70:30 (V/V)), subsequently concentrated under reduced pressure, and dried under reduced pressure to obtain a concentration residue.

To a solution of the obtained concentration residue in 2 ml of dehydrated dichloromethane, 0.173 ml (1.59 mmol) of N,N-dimethylethane-1,2-diamine was added at room temperature in an argon atmosphere and then stirred at room temperature for 3 hours.

After the completion of the reaction, a 5% aqueous potassium bisulfate solution was added to the reaction solution and stirred, followed by extraction with dichloromethane. The obtained organic layer was washed with a saturated aqueous solution of sodium bicarbonate and a saturated aqueous solution of sodium chloride in this order, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=100:0 to 50:50 (V/V)), and a fraction containing the compound of interest was concentrated under reduced pressure. The obtained concentration residue was dissolved in methanol and then added to water, and the deposited solid was collected by filtration and dried under reduced pressure to obtain 164 mg of the title compound (yield: 66%) as a white solid.

Mass spectrum (CI, m/z): 473 [M+1]$^+$.

$^1$H-NMR spectrum (400 MHz, DMSO-d$_6$) δ: 12.42-11.83 (m, 1H), 9.60 (br s, 1H), 7.46-7.34 (m, 2H), 7.27-7.18 (m, 2H), 5.22 (s, 1H), 4.75 (d, J=12.3 Hz, 1H), 4.20 (d, J=12.3 Hz, 1H), 3.32 (s, 3H), 2.58-2.37 (m, 2H), 2.25-2.11 (m, 2H), 1.88-1.73 (m, 2H), 1.70 (s, 3H), 1.60 (s, 3H), 0.05 (s, 9H).

Example 104

N-{5-[2-Methoxy-2-(thiophen-2-yl)acetyl]-6,6-dimethyl-1,4,5,6-tetrahydropyrrolo[3,4-c]pyrazol-3-yl}-1-(trimethylsilyl)cyclobutanecarboxamide (Compound No. IV-1546)

[Chemical Formula 120]

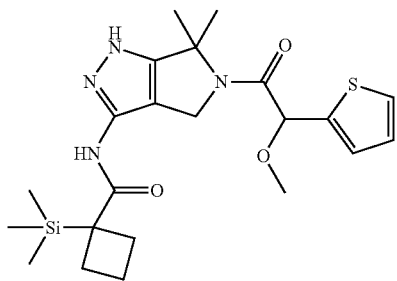

To a suspension of 60 mg of 2-methoxy-2-(thiophen-2-yl)acetic acid (containing impurities) synthesized in the similar manner as in Reference Example 101 in 2 ml of dehydrated dichloromethane, 0.036 ml (0.41 mmol) of oxalyl chloride and 0.005 ml (0.07 mmol) of DMF were added with stirring at 0° C. in an argon atmosphere and stirred at room temperature for 1.5 hours.

After the completion of the reaction, the reaction solution was concentrated under reduced pressure to obtain a concentration residue.

To a solution of 120 mg (0.317 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.166 ml (0.950 mmol) of DIPEA in 2 ml of dehydrated dichloromethane, a solution of the obtained concentration residue in 3 ml of dehydrated dichloromethane was added dropwise with stirring at 0° C. in an argon atmosphere and stirred at room temperature for 2 hours.

After the completion of the reaction, a saturated aqueous solution of sodium bicarbonate was added to the reaction solution, followed by extraction with dichloromethane. The obtained organic layer was washed with water, then dried over anhydrous sodium sulfate, and filtered, and the filtrate was concentrated under reduced pressure. The obtained concentration residue was subjected to silica gel column chromatography (DIOL silica gel, elution solvent: n-hexane: ethyl acetate=100:0 to 70:30 (V/V)), subsequently concentrated under reduced pressure, and dried under reduced pressure to obtain a concentration residue.

To a solution of the obtained concentration residue in 2 ml of dehydrated dichloromethane, 0.104 ml (0.954 mmol) of N,N-dimethylethane-1,2-diamine was added at room temperature in an argon atmosphere and then stirred at room temperature for 16 hours.

After the completion of the reaction, a 5% aqueous potassium bisulfate solution was added to the reaction solution and stirred, followed by extraction with dichloromethane. The obtained organic layer was washed with a saturated aqueous solution of sodium bicarbonate and a saturated aqueous solution of sodium chloride in this order, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=100:0 to 50:50 (V/V)), and a fraction containing the compound of interest was concentrated under reduced pressure. The obtained concentration residue was dissolved in methanol and then added to water, and the deposited solid was collected by filtration and dried under reduced pressure to obtain 62 mg of the title compound (yield: 42%) as a white solid.

Mass spectrum (CI, m/z): 461 [M+1]$^+$.

$^1$H-NMR spectrum (400 MHz, DMSO-d$_6$) δ: 12.41-11.86 (m, 1H), 9.82-9.47 (m, 1H), 7.57 (dd, J=1.3, 5.0 Hz, 1H), 7.13-7.06 (m, 1H), 7.01 (dd, J=3.5, 5.0 Hz, 1H), 5.26 (s, 1H), 4.84-4.64 (m, 1H), 4.41 (br d, J=12.4 Hz, 1H), 3.28 (s, 3H), 2.58-2.37 (m, 2H), 2.26-2.10 (m, 2H), 1.89-1.73 (m, 2H), 1.70 (s, 3H), 1.62 (s, 3H), 0.06 (s, 9H).

Example 105

(−)-N-{5-[2-Methoxy-2-(thiophen-2-yl)acetyl]-6,6-dimethyl-1,4,5,6-tetrahydropyrrolo[3,4-c]pyrazol-3-yl}-1-(trimethylsilyl)cyclobutanecarboxamide (Compound No. IV-1548)

0.041 g (0.089 mmol) of N-{5-[2-methoxy-2-(thiophen-2-yl)acetyl]-6,6-dimethyl-1,4,5,6-tetrahydropyrrolo[3,4-c]pyrazol-3-yl}-1-(trimethylsilyl)cyclobutanecarboxamide synthesized in the similar manner as in Example 104 was subjected to optical resolution preparative chromatography (column: CHIRALPAK (trade name) ID, elution solvent: n-hexane:ethanol=85:15 (V/V)), and a fraction containing an optically active form eluted first was concentrated under reduced pressure to obtain 17 mg of the title compound (yield: 41%) as a white solid.

Specific optical rotation: $[\alpha]_D^{20}$=−51° (c=0.20, methanol).

Mass spectrum (CI, m/z): 461 [M+1]$^+$.

$^1$H-NMR spectrum (400 MHz, DMSO-d$_6$) δ: 12.23 (br s, 1H), 9.67 (br s, 1H), 7.57 (dd, J=1.2, 5.0 Hz, 1H), 7.13-7.06 (m, 1H), 7.01 (dd, J=3.5, 5.0 Hz, 1H), 5.26 (s, 1H), 4.74 (br d, J=12.5 Hz, 1H), 4.41 (d, J=12.5 Hz, 1H), 3.28 (s, 3H), 2.58-2.37 (m, 2H), 2.24-2.11 (m, 2H), 1.89-1.74 (m, 2H), 1.70 (s, 3H), 1.62 (s, 3H), 0.06 (s, 9H).
HPLC analysis:
Column: CHIRALPAK (trade name) ID 4.6×250 mm
Eluent: n-hexane/ethanol=85/15 (V/V)
Flow rate: 1.0 ml/min
Temperature: 40° C.
Detection wavelength: 254 nm
Retention time: 7.6 min.
Optical purity: >99% ee Example 106

(+)-N-{5-[2-Methoxy-2-(thiophen-2-yl)acetyl]-6,6-dimethyl-1,4,5,6-tetrahydropyrrolo[3,4-c]pyrazol-3-yl}-1-(trimethylsilyl)cyclobutanecarboxamide (Compound No. IV-1547)

A fraction containing an optically active form eluted later in the optical resolution preparative chromatography operation of Example 105 was concentrated under reduced pressure to obtain 14 mg of the title compound (yield: 34%) as a white solid.
Specific optical rotation: [α]$_D^{20}$=+66° (c=0.20, methanol).
Mass spectrum (CI, m/z): 461 [M+1]$^+$.
$^1$H-NMR spectrum (400 MHz, DMSO-d$_6$) δ: 12.23 (br s, 1H), 9.66 (br s, 1H), 7.57 (dd, J=1.2, 5.0 Hz, 1H), 7.14-7.06 (m, 1H), 7.01 (dd, J=3.5, 5.0 Hz, 1H), 5.26 (s, 1H), 4.74 (br d, J=12.4 Hz, 1H), 4.41 (d, J=12.4 Hz, 1H), 3.28 (s, 3H), 2.58-2.37 (m, 2H), 2.26-2.10 (m, 2H), 1.89-1.74 (m, 2H), 1.70 (s, 3H), 1.62 (s, 3H), 0.06 (s, 9H).
HPLC analysis:
Column: CHIRALPAK (trade name) ID 4.6×250 mm
Eluent: n-hexane/ethanol=85/15 (V/V)
Flow rate: 1.0 ml/min
Temperature: 40° C.
Detection wavelength: 254 nm
Retention time: 9.7 min.
Optical purity: >99% ee Example 107

N-{[1-(Hydroxymethyl)cyclobutyl](phenyl)methyl}-6,6-dimethyl-3-[1-(trimethylsilyl)cyclobutanecarboxamido]-4,6-dihydropyrrolo[3,4-c]pyrazole-5(1H)-carboxamide (Compound No. IV-718)

[Chemical Formula 121]

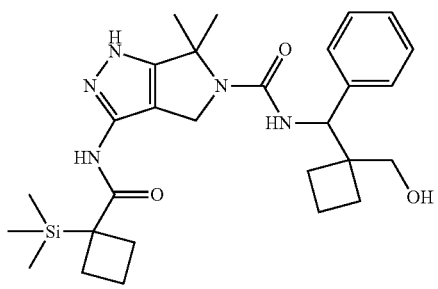

To a solution of a mixture of 131 mg (0.243 mmol) of 2-ethyl 5-(trichloromethyl) 6,6-dimethyl-3-[1-(trimethylsilyl)cyclobutanecarboxamido]pyrrolo[3,4-c]pyrazole-2,5 (4H,6H)-dicarboxylate synthesized in the similar manner as in Reference Example 102 and 79 mg (0.18 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate in 3 ml of dehydrated 1,4-dioxane, 0.34 ml (2.0 mmol) of DIPEA and 235 mg (1.23 mmol) of {1-[amino(phenyl)methyl] cyclobutyl}methanol synthesized in the similar manner as in Reference Example 103 were added in this order at room temperature in an argon atmosphere and then stirred at 90° C. for 1.5 hours. After standing to cool until the reaction solution becomes room temperature, 0.21 ml (1.9 mmol) of N,N-dimethylethane-1,2-diamine was added at room temperature and stirred for 2 hours with the temperature unchanged.

After the completion of the reaction, a 5% aqueous potassium bisulfate solution was added to the reaction solution and stirred, followed by extraction with ethyl acetate three times. All of the organic layers were dried over anhydrous magnesium sulfate, then filtered, and concentrated under reduced pressure. The obtained concentration residue was subjected to silica gel column chromatography (DIOL silica gel, elution solvent: n-hexane:ethyl acetate=60:40 to 30:70 (V/V)), and a fraction containing the compound of interest was concentrated under reduced pressure. The obtained concentration residue was dissolved in ethyl acetate, then n-hexane was added, and the deposited solid was collected by filtration, washed with n-hexane, and then dried under reduced pressure to obtain 187 mg of a white solid. The obtained solid was subjected to preparative HPLC (column: X-Bridge (trade name) ODS, elution solvent: acetonitrile:1 mM aqueous potassium dihydrogen phosphate solution=50:50 (V/V)), a fraction containing the compound of interest was concentrated under reduced pressure, and acetonitrile was distilled off. The solid deposited in the course of concentration was collected by filtration, washed with water, and then dried under reduced pressure to obtain 156 mg of the title compound (yield: 70%) as a white solid.

Mass spectrum (CI, m/z): 524 [M+1]$^+$.
$^1$H-NMR spectrum (400 MHz, DMSO-d$_6$) δ: 12.34-11.78 (m, 1H), 9.87-9.34 (m, 1H), 7.35-7.27 (m, 4H), 7.24-7.16 (m, 1H), 6.75 (d, J=7.9 Hz, 1H), 5.49 (br s, 1H), 4.95 (d, J=7.9 Hz, 1H), 4.47-4.20 (m, 2H), 3.49-3.41 (m, 1H), 3.26-3.18 (m, 1H), 2.57-2.39 (m, 2H), 2.26-2.14 (m, 2H), 2.11-1.99 (m, 2H), 1.98-1.74 (m, 5H), 1.61 (s, 3H), 1.53 (s, 3H), 1.26-1.13 (m, 1H), 0.08 (s, 9H).

Example 108

(R)—N-[2-(1-Hydroxycyclopropyl)-1-phenylethyl]-6,6-dimethyl-3-[1-(trimethylsilyl)cyclobutanecarboxamido]-4,6-dihydropyrrolo[3,4-c]pyrazole-5(1H)-carboxamide (Compound No. IV-743)

[Chemical Formula 122]

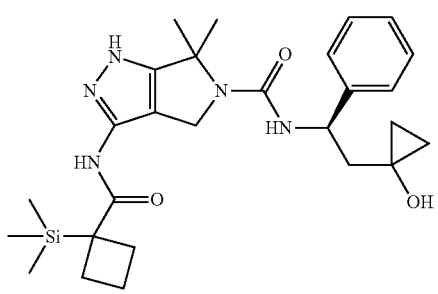

To a solution of 128 mg of (R)-1-(2-amino-2-phenylethyl)cyclopropanol (containing impurities) synthesized in the similar manner as in Reference Example 105 in 2 ml of dehydrated 1,4-dioxane, 0.26 ml (1.5 mmol) of DIPEA and 154 mg (0.349 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 were added in this order at room temperature in an argon atmosphere and then stirred at 90° C. for 2 hours. After standing to cool until the reaction solution becomes room temperature, 0.16 ml (1.5 mmol) of N,N-dimethylethane-1,2-diamine was added at room temperature and stirred for 2 hours with the temperature unchanged.

After the completion of the reaction, a 5% aqueous potassium bisulfate solution was added to the reaction solution and stirred, followed by extraction with ethyl acetate twice. All of the obtained organic layers were dried over anhydrous magnesium sulfate, filtered, and concentrated under reduced pressure. The obtained concentration residue was subjected to silica gel column chromatography (DIOL silica gel, elution solvent: n-hexane:ethyl acetate=70:30 to 40:60 (V/V)), and a fraction containing the compound of interest was concentrated under reduced pressure. The obtained concentration residue was suspended in an ethyl acetate/n-hexane mixed solvent and stirred, and then, insoluble matter was collected by filtration, washed with n-hexane, and then dried under reduced pressure to obtain 139 mg of the title compound (yield: 79%) as a white solid.

Mass spectrum (CI, m/z): 510 [M+1]$^+$.

$^1$H-NMR spectrum (400 MHz, DMSO-d$_6$) δ: 12.23 & 11.80 (br s, total 1H), 9.75-9.47 (m, 1H), 7.43-7.37 (m, 2H), 7.34-7.27 (m, 2H), 7.23-7.17 (m, 1H), 6.51-6.33 (m, 1H), 5.54-5.37 (m, 1H), 5.14-5.05 (m, 1H), 4.66-4.29 (m, 2H), 2.61-2.39 (m, 2H), 2.26-2.06 (m, 3H), 1.90-1.50 (m, 9H), 0.55-0.37 (m, 3H), 0.18-0.04 (m, 10H).

Example 109

(R)—N-(3-Ethyl-3-Hydroxy-1-phenylpentyl)-6,6-dimethyl-3-[1-(trimethylsilyl)cyclobutanecarboxamido]-4,6-dihydropyrrolo[3,4-c]pyrazole-5(1H)-carboxamide (Compound No. IV-759)

[Chemical Formula 123]

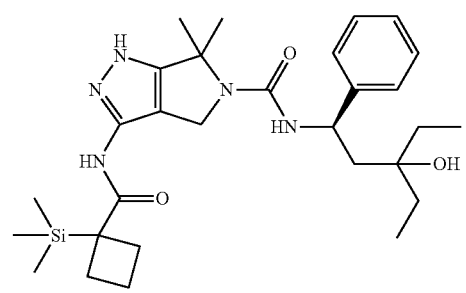

To a solution of 118 mg (0.568 mmol) of (R)-1-amino-3-ethyl-1-phenylpentan-3-ol synthesized in the similar manner as in Reference Example 107 in 2 ml of dehydrated 1,4-dioxane, 0.20 ml (1.1 mmol) of DIPEA and 128 mg (0.290 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 were added in this order at room temperature in an argon atmosphere and then stirred at 90° C. for 2 hours.

After the completion of the reaction, a saturated aqueous solution of sodium bicarbonate was added to the reaction solution and stirred, followed by extraction with ethyl acetate three times. All of the organic layers were dried over anhydrous magnesium sulfate, then filtered, and concentrated under reduced pressure. The obtained concentration residue was subjected to silica gel column chromatography (elution solvent: n-hexane:ethyl acetate=75:25 to 40:60 (V/V)), subsequently concentrated under reduced pressure, and dried under reduced pressure to obtain a concentration residue.

To a solution of the obtained concentration residue in 2 ml of THF, 0.13 ml (1.2 mmol) of N,N-dimethylethane-1,2-diamine was added at room temperature in an argon atmosphere and then stirred at room temperature for 2 hours.

After the completion of the reaction, a 5% aqueous potassium bisulfate solution was added to the reaction solution and stirred, followed by extraction with ethyl acetate three times. All of the obtained organic layers were dried over anhydrous magnesium sulfate, filtered, and concentrated under reduced pressure. The obtained concentration residue was subjected to silica gel column chromatography (DIOL silica gel, elution solvent: n-hexane:ethyl acetate=70:30 to 30:70 (V/V)), and a fraction containing the compound of interest was concentrated under reduced pressure. The obtained concentration residue was suspended in an ethyl acetate/n-hexane mixed solvent and stirred at room temperature, and then, insoluble matter was collected by filtration, washed with n-hexane, and then dried under reduced pressure to obtain 123 mg of the title compound (yield: 79%) as a white solid.

Mass spectrum (CI, m/z): 540 [M+1]$^+$.

$^1$H-NMR spectrum (400 MHz, DMSO-d$_6$) δ: 12.35-11.68 (m, 1H), 9.56 (br s, 1H), 7.37-7.24 (m, 4H), 7.19-7.13 (m, 1H), 6.56 (d, J=5.8 Hz, 1H), 4.91-4.81 (m, 1H), 4.54-4.31 (m, 3H), 2.58-2.41 (m, 2H), 2.26-2.13 (m, 2H), 1.95-1.73 (m, 3H), 1.63-1.55 (m, 4H), 1.53 (s, 3H), 1.49-1.33 (m, 4H), 0.82 (t, J=7.4 Hz, 3H), 0.77 (t, J=7.4 Hz, 3H), 0.09 (s, 9H).

Example 110

(R)—N-[1-(4-Fluorophenyl)-3-hydroxy-3-methylbutyl]-6,6-dimethyl-3-[1-(trimethylsilyl)cyclobutanecarboxamido]-4,6-dihydropyrrolo[3,4-c]pyrazole-5(1H)-carboxamide (Compound No. IV-939)

[Chemical Formula 124]

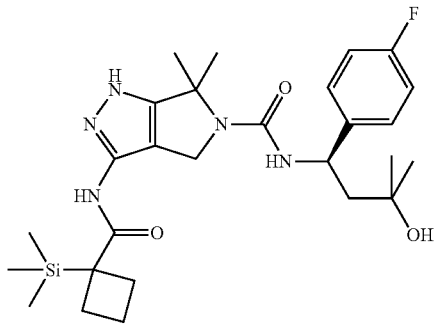

To a solution of 599 mg (1.36 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 3 ml of 1,4-dioxane, 134 mg of (R)-4-amino-4-(4-fluorophenyl)-2-methylbutan-2-ol (containing impurities) synthesized in the similar manner as in Reference Example 111 and 0.602 ml (3.40 mmol) of DIPEA were added in this order at room temperature under argon stream and then stirred at 100° C. for 1 hour. Subsequently, 0.318 ml (3.40 mmol) of N,N-dimethylethane-1,2-diamine was added at room temperature and stirred for 2 hours with the temperature unchanged.

After the completion of the reaction, a 5% aqueous potassium bisulfate solution was added to the reaction solution, followed by extraction with ethyl acetate. The obtained organic layer was washed with a saturated aqueous solution of sodium chloride in this order, dried over anhydrous magnesium sulfate, then filtered, and concentrated under reduced pressure. The obtained concentration residue was subjected to silica gel column chromatography (DIOL silica gel, elution solvent: ethyl acetate:methanol=100:0 to 90:10 (V/V)), and a fraction containing the compound of interest was concentrated under reduced pressure. The obtained concentration residue was subjected to preparative HPLC (column: X-Bridge (trade name) ODS, elution solvent: acetonitrile:1 mM aqueous potassium dihydrogen phosphate solution=30:70 to 50:50 (V/V)), a fraction containing the compound of interest was concentrated under reduced pressure, and acetonitrile was distilled off, followed by extraction with ethyl acetate. The obtained organic layer was washed with a saturated aqueous solution of sodium chloride, dried over anhydrous magnesium sulfate, then filtered, concentrated under reduced pressure, and dried under reduced pressure to obtain 48 mg of the title compound (yield: 8% [2 steps]) as a white solid.

Mass spectrum (CI, m/z): 530 [M+1]$^+$.

$^1$H-NMR spectrum (400 MHz, DMSO-d$_6$) δ: 12.20 & 11.77 (br s, total 1H), 9.74-9.41 (m, 1H), 7.40-7.32 (m, 2H), 7.14-7.05 (m, 2H), 6.66-6.44 (m, 1H), 4.94-4.84 (m, 1H), 4.75-4.60 (m, 1H), 4.52-4.31 (m, 2H), 2.59-2.39 (m, 2H), 2.27-2.11 (m, 2H), 2.04-1.73 (m, 3H), 1.70-1.45 (m, 7H), 1.15 (s, 3H), 1.13 (s, 3H), 0.09 (s, 9H).

Example 111

(R)—N-[1-(3-Fluorophenyl)-3-hydroxy-3-methylbutyl]-6,6-dimethyl-3-[1-(trimethylsilyl)cyclobutanecarboxamido]-4,6-dihydropyrrolo[3,4-c]pyrazole-5(1H)-carboxamide (Compound No. IV-911)

[Chemical Formula 125]

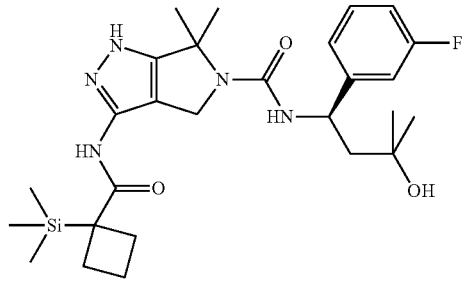

To a solution of 149 mg (0.248 mmol) of (R)-ethyl 5-{[1-(3-fluorophenyl)-3-hydroxy-3-methylbutyl]carbamoyl}-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 116 in 3 ml of dichloromethane, 0.108 ml (0.992 mmol) of N,N-dimethylethane-1,2-diamine was added in one portion with stirring at room temperature under argon stream and stirred at room temperature for 1 hour.

After the completion of the reaction, a 5% aqueous potassium bisulfate solution was added to the reaction solution, followed by extraction from the mixed solution with ethyl acetate twice. The organic layer was washed with a 5% aqueous potassium bisulfate solution, dried over anhydrous magnesium sulfate, filtered, and concentrated under reduced pressure. The obtained concentration residue was subjected to silica gel column chromatography (DIOL silica gel, elution solvent: n-hexane:ethyl acetate=70:30 to 17:83 (V/V)), and a fraction containing the compound of interest was concentrated under reduced pressure. The obtained concentration residue was dissolved in a small amount of ethyl acetate, and a solid was deposited by adding n-hexane. The solid was collected by filtration, washed with n-hexane, and dried under reduced pressure at 50° C. to obtain 101 mg of the title compound (yield: 77%) as a white solid.

Mass spectrum (CI, m/z): 530 [M+1]$^+$.

$^1$H-NMR spectrum (400 MHz, DMSO-d$_6$) δ: 12.21 & 11.77 (br s, total 1H), 9.71-9.47 (m, 1H), 7.37-7.26 (m, 1H), 7.22-7.11 (m, 2H), 7.02-6.92 (m, 1H), 6.65-6.51 (m, 1H), 4.95-4.87 (m, 1H), 4.76-4.60 (m, 1H), 4.55-4.35 (m, 2H), 2.57-2.40 (m, 2H), 2.27-2.12 (m, 2H), 2.03-1.74 (m, 3H), 1.66 (dd, J=3.1, 14.2 Hz, 1H), 1.59 (br s, 3H), 1.54 (br s, 3H), 1.16 (s, 3H), 1.13 (s, 3H), 0.09 (s, 9H).

Example 112

(R)—N-[1-(2-Fluorophenyl)-3-hydroxy-3-methylbutyl]-6,6-dimethyl-3-[1-(trimethylsilyl)cyclobutanecarboxamido]-4,6-dihydropyrrolo[3,4-c]pyrazole-5(1H)-carboxamide (Compound No. IV-883)

[Chemical Formula 126]

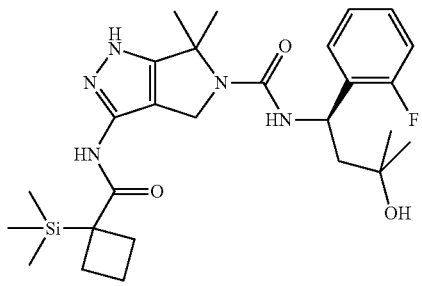

To a solution of 150 mg (0.249 mmol) of (R)-ethyl 5-{[1-(2-fluorophenyl)-3-hydroxy-3-methylbutyl]carbamoyl}-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 121 in 3 ml of dichloromethane, 0.109 ml (1.00 mmol) of N,N-dimethylethane-1,2-diamine was added in one portion with stirring at room temperature under argon stream and stirred at room temperature for 1 hour.

After the completion of the reaction, a 5% aqueous potassium bisulfate solution was added to the reaction solution, followed by extraction from the mixed solution with ethyl acetate twice. The organic layer was washed with a 5% aqueous potassium bisulfate solution, dried over anhydrous magnesium sulfate, filtered, and concentrated under reduced pressure. The obtained concentration residue was subjected to silica gel column chromatography (DIOL silica gel, elution solvent: n-hexane:ethyl acetate=70:30 to 17:83 (V/V)), and a fraction containing the compound of interest was concentrated under reduced pressure. The obtained concentration residue was dissolved in a small amount of ethyl acetate, and a solid was deposited by adding n-hexane. The solid was collected by filtration, washed with n-hexane, and dried under reduced pressure at 50° C. to obtain 112 mg of the title compound (yield: 85%) as a white solid.

Mass spectrum (CI, m/z): 530 [M+1]$^+$.

$^1$H-NMR spectrum (400 MHz, DMSO-d$_6$) δ: 12.20 & 11.76 (br s, total 1H), 9.72-9.46 (m, 1H), 7.54-7.43 (m, 1H), 7.26-7.17 (m, 1H), 7.17-7.04 (m, 2H), 6.62-6.47 (m, 1H), 5.23-5.14 (m, 1H), 4.78-4.62 (m, 1H), 4.55-4.35 (m, 2H), 2.58-2.40 (m, 2H), 2.27-2.12 (m, 2H), 2.02-1.73 (m, 3H), 1.67-1.45 (m, 7H), 1.18 (s, 3H), 1.15 (s, 3H), 0.09 (s, 9H)

Example 113

(R)—N-(5-Hydroxy-2,5-dimethylhexan-3-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-815)

[Chemical Formula 127]

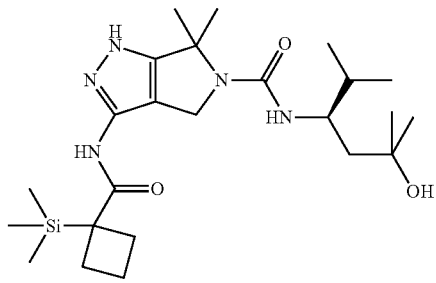

To a solution of 99 mg (0.18 mmol) of (R)-ethyl 5-[(5-hydroxy-2,5-dimethylhexan-3-yl)carbamoyl]-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 125 in 3 ml of dichloromethane, 0.078 ml (0.72 mmol) of N,N-dimethylethane-1,2-diamine was added in one portion with stirring at room temperature under argon stream and stirred at room temperature for 1 hour.

After the completion of the reaction, a 5% aqueous potassium bisulfate solution was added to the reaction solution, followed by extraction from the mixed solution with ethyl acetate twice. The organic layer was washed with a 5% aqueous potassium bisulfate solution, dried over anhydrous magnesium sulfate, filtered, and concentrated under reduced pressure. The obtained concentration residue was subjected to silica gel column chromatography (DIOL silica gel, elution solvent: n-hexane:ethyl acetate=50:50 to 16:84 (V/V)), and a fraction containing the compound of interest was concentrated under reduced pressure. The obtained concentration residue was dissolved in a small amount of ethyl acetate, and a solid was deposited by adding n-hexane. The solid was collected by filtration, washed with n-hexane, and dried under reduced pressure at 50° C. to obtain 72 mg of the title compound (yield: 84%) as a white solid.

Mass spectrum (CI, m/z): 478 [M+1]$^+$.

$^1$H-NMR spectrum (400 MHz, DMSO-d$_6$) δ: 12.19 & 11.81 (br s, total 1H), 9.71-9.44 (m, 1H), 5.63 (br s, 1H), 4.47-4.25 (m, 3H), 3.71-3.60 (m, 1H), 2.57-2.39 (m, 2H), 2.27-2.11 (m, 2H), 1.90-1.66 (m, 3H), 1.65-1.52 (m, 7H), 1.49-1.42 (m, 1H), 1.10 (s, 3H), 1.09 (s, 3H), 0.82 (d, J=6.8 Hz, 6H), 0.08 (s, 9H).

Example 114

N-[1-(4-Fluorophenyl)-3-hydroxy-2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide (Compound No. IV-946)

[Chemical Formula 128]

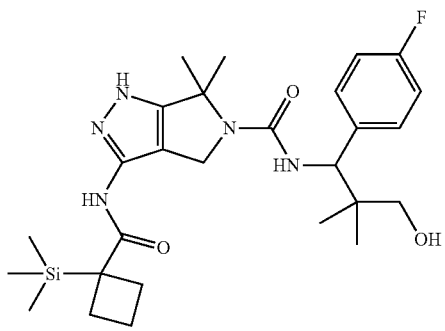

To a solution of 0.745 g (1.69 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 8 ml of 1,4-dioxane, 1.47 ml (8.44 mmol) of DIPEA and 1.00 g (5.07 mmol) of 3-amino-3-(4-fluorophenyl)-2,2-dimethylpropan-1-ol synthesized in the similar manner as in Reference Example 127 were added in this order with stirring at room temperature under argon stream and stirred at 90° C. for 1.5 hours. Subsequently, the reaction solution was allowed to cool to room temperature, and then, 0.738 ml (6.78 mmol) of N,N-dimethylethane-1,2-diamine was added dropwise at room temperature and stirred at room temperature for 4 hours.

After the completion of the reaction, a 5% aqueous potassium bisulfate solution was added to the reaction solution, followed by extraction from the mixed solution with ethyl acetate twice. The organic layer was washed with a saturated aqueous solution of sodium chloride, dried over anhydrous magnesium sulfate, filtered, and concentrated under reduced pressure. The obtained concentration residue was subjected to silica gel column chromatography (DIOL silica gel, elution solvent: n-hexane:ethyl acetate=70:30 to 19:81 (V/V)), and a fraction containing the compound of interest was concentrated under reduced pressure. The concentration residue was dissolved in 60 ml of ethyl acetate and washed with 10 ml of a 5% aqueous potassium bisulfate solution three times. The organic layer was washed with a saturated aqueous solution of sodium chloride, dried over anhydrous magnesium sulfate, filtered, and concentrated under reduced pressure. The obtained concentration residue was dissolved in a small amount of ethyl acetate, and a solid was deposited by adding n-hexane. The solid was collected by filtration, washed with n-hexane, and dried under reduced pressure at 50° C. to obtain 509 mg of the title compound (yield: 57%) as a white solid.

Mass spectrum (ESI, m/z): 530 [M+1]$^+$.

$^1$H-NMR spectrum (400 MHz, DMSO-d$_6$) δ: 12.21 & 11.80 (br s, total 1H), 9.68-9.44 (m, 1H), 7.39-7.32 (m, 2H), 7.17-7.09 (m, 2H), 6.91-6.78 (m, 1H), 5.46 (br s, 1H), 4.65 (d, J=7.9 Hz, 1H), 4.45-4.28 (m, 2H), 3.23 (dd, J=4.2, 10.6 Hz, 1H), 3.08-2.99 (m, 1H), 2.60-2.39 (m, 2H), 2.27-2.14 (m, 2H), 1.91-1.73 (m, 2H), 1.65-1.49 (m, 6H), 1.05 (s, 3H), 0.64 (s, 3H), 0.09 (s, 9H).

Example 115

N-[1-(3-Fluorophenyl)-3-hydroxy-2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide (Compound No. IV-918)

[Chemical Formula 129]

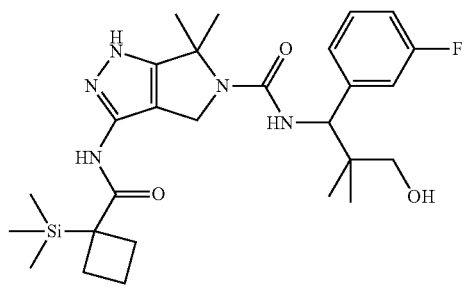

To a solution of 162 mg (0.367 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 4 ml of 1,4-dioxane, 0.32 ml (1.9 mmol) of DIPEA and 227 mg (1.15 mmol) of 3-amino-3-(3-fluorophenyl)-2,2-dimethylpropan-1-ol synthesized in the similar manner as in Reference Example 129 were added at room temperature in an argon atmosphere and then reacted at 100° C. for 2.5 hours. After standing to cool, 0.12 ml (1.1 mmol) of N,N-dimethyl-1,2-diamine was added and stirred at room temperature for 1 hour.

After the completion of the reaction, the reaction solution was concentrated under reduced pressure, 20 ml of ethyl acetate was added to the residue, the organic layer after washing with 10 ml of a 5% aqueous potassium bisulfate solution, 10 ml of a saturated aqueous solution of sodium bicarbonate, and 10 ml of a saturated aqueous solution of sodium chloride in this order was dried over anhydrous magnesium sulfate and filtered, and then, the filtrate was concentrated under reduced pressure. The residue was subjected to silica gel column chromatography (DIOL silica gel, elution solvent: 1,2-dichloroethane:ethyl acetate=81:19 to 30:70 (V/V)), and a fraction containing the compound of interest was concentrated under reduced pressure. The obtained concentration residue was dissolved in a small amount of dichloromethane, then n-hexane was added, and the deposited solid was collected by filtration and dried under reduced pressure to obtain 159 mg of the title compound (yield: 82%) as a white solid.

Mass spectrum (CI, m/z): 530 [M+1]$^+$.

$^1$H-NMR spectrum (400 MHz, DMSO-d$_6$) δ: 12.22 & 11.89 (br s, total 1H), 9.79-9.40 (m, 1H), 7.39-7.29 (m, 1H), 7.22-7.13 (m, 2H), 7.08-7.01 (m, 1H), 6.86 (d, J=8.0 Hz, 1H), 5.56-5.41 (m, 1H), 4.67 (d, J=8.0 Hz, 1H), 4.49-4.27 (m, 2H), 3.25 (dd, J=4.0, 10.6 Hz, 1H), 3.05 (dd, J=4.0, 10.6 Hz, 1H), 2.56-2.40 (m, 2H), 2.29-2.13 (m, 2H), 1.92-1.72 (m, 2H), 1.60 (br s, 3H), 1.52 (br s, 3H), 1.05 (s, 3H), 0.67 (s, 3H), 0.09 (s, 9H).

Example 116

(−)-N-[1-(3-Fluorophenyl)-3-hydroxy-2,2-dimethylpropyl]-6,6-dimethyl-3-[1-(trimethyl silyl)cyclobutanecarboxamido]-4,6-dihydropyrrolo[3,4-c]pyrazole-5(1H)-carboxamide (Compound No. IV-920)

0.129 g (0.244 mmol) of N-[1-(3-fluorophenyl)-3-hydroxy-2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide synthesized in the similar manner as in Example 115 was subjected to optical resolution preparative chromatography (column: CHIRALPAK (trade name) ID, elution solvent: n-hexane:ethanol:methanol=95:5:1 (V/V)), and a fraction containing an optically active form eluted first was concentrated under reduced pressure to obtain 47 mg of the title compound (yield: 36%) as a white solid.

Specific optical rotation: $[\alpha]_D^{20}=-53°$ (c=0.23, methanol).

Mass spectrum (CI, m/z): 530 [M+1]$^+$.

$^1$H-NMR spectrum (400 MHz, DMSO-d$_6$) δ: 12.21 & 11.88 (br s, total 1H), 9.78-9.41 (m, 1H), 7.38-7.30 (m, 1H), 7.21-7.13 (m, 2H), 7.08-7.01 (m, 1H), 6.86 (br d, J=8.3 Hz, 1H), 5.56-5.40 (m, 1H), 4.67 (d, J=8.3 Hz, 1H), 4.47-4.30 (m, 2H), 3.25 (br dd, J=3.9, 10.5 Hz, 1H), 3.05 (br dd, J=3.9, 10.5 Hz, 1H), 2.60-2.40 (m, 2H), 2.26-2.13 (m, 2H), 1.90-1.73 (m, 2H), 1.60 (br s, 3H), 1.52 (s, 3H), 1.05 (s, 3H), 0.67 (s, 3H), 0.09 (s, 9H).

HPLC analysis:
Column: CHIRALPAK (trade name) ID 4.6×250 mm
Eluent: n-hexane/ethanol/methanol=95/5/1 (V/V)
Flow rate: 1.0 ml/min
Temperature: 40° C.
Detection wavelength: 254 nm
Retention time: 8.8 min.
Optical purity: >99% ee

Example 117

(+)-N-[1-(3-Fluorophenyl)-3-hydroxy-2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide (Compound No. IV-919)

A fraction containing an optically active form eluted later in the optical resolution preparative chromatography operation of Example 116 was concentrated under reduced pressure to obtain 45 mg of the title compound (yield: 35%) as a white solid.

Specific optical rotation: $[\alpha]_D^{20}=+59°$ (c=0.22, methanol).

Mass spectrum (CI, m/z): 530 [M+1]$^+$.

$^1$H-NMR spectrum (400 MHz, DMSO-d$_6$) δ: 12.21 & 11.94 (br s, total 1H), 9.78-9.41 (m, 1H), 7.38-7.30 (m, 1H), 7.21-7.13 (m, 2H), 7.08-7.01 (m, 1H), 6.86 (br d, J=8.1 Hz, 1H), 5.56-5.39 (m, 1H), 4.67 (d, J=8.1 Hz, 1H), 4.47-4.30 (m, 2H), 3.25 (br dd, J=3.8, 10.5 Hz, 1H), 3.05 (br dd, J=3.8, 10.5 Hz, 1H), 2.59-2.40 (m, 2H), 2.27-2.13 (m, 2H), 1.90-1.73 (m, 2H), 1.60 (br s, 3H), 1.52 (s, 3H), 1.05 (s, 3H), 0.67 (s, 3H), 0.09 (s, 9H).

HPLC analysis:
Column: CHIRALPAK (trade name) ID 4.6×250 mm
Elution solvent: n-hexane/ethanol/methanol=95/5/1 (V/V)
Flow rate: 1.0 ml/min
Temperature: 40° C.
Detection wavelength: 254 nm
Retention time: 11.6 min
Optical purity: >98% ee

Example 118

N-[1-(2-Fluorophenyl)-3-hydroxy-2,2-dimethylpropyl]-6,6-dimethyl-3-[1-(trimethylsilyl)cyclobutanecarboxamido]-4,6-dihydropyrrolo[3,4-c]pyrazole-5(1H)-carboxamide (Compound No. IV-890)

[Chemical Formula 130]

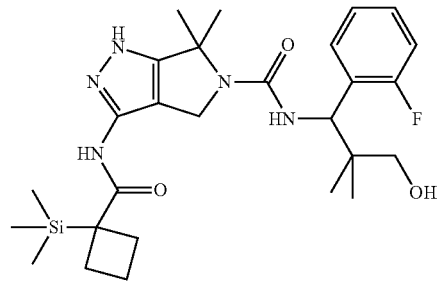

To a solution of 225 mg (1.14 mmol) of 3-amino-3-(2-fluorophenyl)-2,2-dimethylpropan-1-ol synthesized in the similar manner as in Reference Example 130 in 4 ml of 1,4-dioxane, 0.32 ml (1.9 mmol) of DIPEA and 166 mg (0.376 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2 (4H)-carboxylate synthesized in the similar manner as in Reference Example 3 were added at room temperature in an argon atmosphere and then reacted at 100° C. for 2.5 hours. After standing to cool, 0.12 ml (1.1 mmol) of N,N-dimethylethane-1,2-diamine was added and stirred at room temperature for 1 hour.

After the completion of the reaction, the reaction solution was concentrated under reduced pressure, 20 ml of ethyl acetate was added to the residue, the organic layer after washing with 10 ml of a 5% aqueous potassium bisulfate solution, 10 ml of a saturated aqueous solution of sodium bicarbonate, and 10 ml of a saturated aqueous solution of sodium chloride in this order was dried over anhydrous magnesium sulfate and filtered, and then, the filtrate was concentrated under reduced pressure. The residue was subjected to silica gel column chromatography (DIOL silica gel, elution solvent: 1,2-dichloroethane:ethyl acetate=81:19 to 30:70 (V/V)), and a fraction containing the compound of interest was concentrated under reduced pressure. The obtained concentration residue was dissolved in a small amount of dichloromethane, then n-hexane was added, and the deposited solid was collected by filtration and dried under reduced pressure to obtain 154 mg of the title compound (yield: 77%) as a white solid.

Mass spectrum (CI, m/z): 530 [M+1]$^+$.

$^1$H-NMR spectrum (400 MHz, DMSO-d$_6$) δ: 12.22 & 11.87 (br s, total 1H), 9.75-9.42 (m, 1H), 7.53-7.44 (m, 1H), 7.32-7.24 (m, 1H), 7.23-7.17 (m, 1H), 7.17-7.08 (m, 1H), 6.96-6.85 (m, 1H), 5.53 (br s, 1H), 5.03 (d, J=7.9 Hz, 1H), 4.46-4.26 (m, 2H), 3.40-3.28 (m, 1H), 3.08 (dd, J=4.0, 10.5 Hz, 1H), 2.56-2.39 (m, 2H), 2.27-2.12 (m, 2H), 1.92-1.72 (m, 2H), 1.65-1.47 (m, 6H), 1.10 (s, 3H), 0.69-0.60 (m, 3H), 0.09 (s, 9H).

Example 119

N-(1-Hydroxy-2,2,4-trimethylpentan-3-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-822)

[Chemical Formula 131]

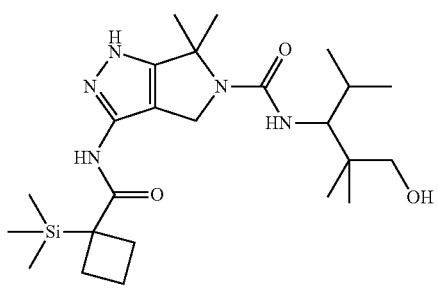

To a solution of a mixture of 133 mg (0.246 mmol) of 2-ethyl 5-(trichloromethyl) 6,6-dimethyl-3-[1-(trimethylsilyl)cyclobutanecarboxamido]pyrrolo[3,4-c]pyrazole-2,5(4H,6H)-dicarboxylate synthesized in the similar manner as in Reference Example 102 and 80 mg (0.18 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate in 3 ml of dehydrated 1,4-dioxane, 0.37 ml (2.1 mmol) of DIPEA and 189 mg (1.30 mmol) of 3-amino-2,2,4-trimethylpentan-1-ol synthesized in the similar manner as in Reference Example 132 were added in this order at room temperature in an argon atmosphere and then stirred at 90° C. for 2.5 hours. After standing to cool until the reaction solution becomes room temperature, 0.23 ml (2.1 mmol) of N,N-dimethylethane-1,2-diamine was added at room temperature and stirred for 14 hours with the temperature unchanged.

After the completion of the reaction, a 5% aqueous potassium bisulfate solution was added to the reaction solution and stirred, followed by extraction with ethyl acetate three times. All of the organic layers were dried over anhydrous magnesium sulfate, then filtered, and concentrated under reduced pressure. The obtained concentration residue was subjected to silica gel column chromatography (DIOL silica gel, elution solvent: n-hexane:ethyl acetate=60:40 to 30:70 (V/V)), and a fraction containing the compound of interest was concentrated under reduced pressure. The obtained concentration residue was dissolved in ethyl acetate, then n-hexane was added, and the deposited solid was collected by filtration, washed with n-hexane, and then dried under reduced pressure to obtain 107 mg of the title compound (yield: 52%) as a white solid.

Mass spectrum (CI, m/z): 478 [M+1]$^+$.

$^1$H-NMR spectrum (400 MHz, DMSO-$d_6$) δ: 12.42-11.70 (m, 1H), 9.86-9.33 (m, 1H), 5.48 (br d, J=9.2 Hz, 1H), 5.13-4.93 (m, 1H), 4.48-4.22 (m, 2H), 3.55-3.48 (m, 1H), 3.45 (dd, J=3.9, 10.7 Hz, 1H), 3.04 (dd, J=5.4, 10.7 Hz, 1H), 2.58-2.38 (m, 2H), 2.26-2.12 (m, 2H), 2.05-1.92 (m, 1H), 1.88-1.73 (m, 2H), 1.61 (br s, 3H), 1.59 (br s, 3H), 0.93 (s, 3H), 0.89 (d, J=6.7 Hz, 6H), 0.79 (s, 3H), 0.07 (s, 9H).

Example 120

(R)—N-(3-Hydroxy-3-methyl-1-phenylbutyl)-6,6-dimethyl-3-[1-(trimethylsilyl)cyclopropanecarboxamido]-4,6-dihydropyrrolo[3,4-c]pyrazole-5(1H)-carboxamide (Compound No. III-298)

[Chemical Formula 132]

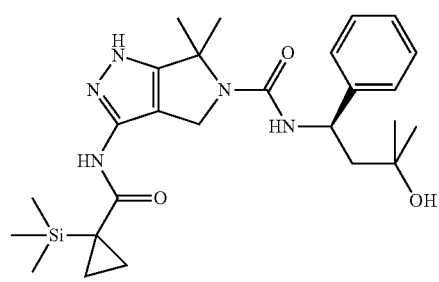

To a solution of 1.53 g (4.19 mmol) of ethyl 6,6-dimethyl-3-[1-(trimethylsilyl)cyclopropanecarboxamido]-5,6-dihydropyrrolo[3,4-c]pyrazole-2(4H)-carboxylate synthesized in the similar manner as in Reference Example 46 in 20 ml of dehydrated dichloromethane, 2.60 ml (14.9 mmol) of DIPEA was added at room temperature in an argon atmosphere. Subsequently, a solution of 700 mg (2.36 mmol) of bis(trichloromethyl) carbonate in 5 ml of dehydrated dichloromethane was added dropwise at −78° C. and then stirred for 0.5 hours with the temperature unchanged and further for 2 hours after the temperature was raised to room temperature.

After the completion of the reaction, a saturated aqueous solution of sodium bicarbonate and dichloromethane were added to the reaction solution at −78° C. and then stirred for 1.5 hours while the temperature was raised to room temperature for a while. The reaction solution was separated into an aqueous layer and an organic layer, and then, the aqueous layer was subjected to extraction with ethyl acetate twice. All of the organic layers were washed with a saturated aqueous solution of sodium chloride, then dried over anhydrous magnesium sulfate, filtered, and concentrated under reduced pressure. The obtained concentration residue was subjected to silica gel column chromatography (elution solvent: n-hexane:ethyl acetate=85:15 to 75:25 (V/V)), subsequently concentrated under reduced pressure, and dried under reduced pressure to obtain 1.75 g of a white solid.

To a solution of 97.1 mg (0.542 mmol) of (R)-4-amino-2-methyl-4-phenylbutan-2-ol synthesized in the similar manner as in Reference Example 23 in 2 ml of dehydrated 1,4-dioxane, 0.18 ml (1.0 mmol) of DIPEA and 130 mg of a portion of the solid obtained by the operation described above were added in this order at room temperature in an argon atmosphere and then stirred at 90° C. for 1.5 hours.

After the completion of the reaction, a saturated aqueous solution of sodium bicarbonate was added to the reaction solution and stirred, followed by extraction with ethyl acetate three times. All of the organic layers were dried over anhydrous magnesium sulfate, then filtered, and concentrated under reduced pressure. The obtained concentration residue was subjected to silica gel column chromatography (elution solvent: n-hexane:ethyl acetate=70:30 to 30:70 (V/V)), subsequently concentrated under reduced pressure, and dried under reduced pressure to obtain a concentration residue.

To a solution of the obtained concentration residue in 2 ml of THF, 0.12 ml (1.1 mmol) of N,N-dimethylethane-1,2-diamine was added at room temperature in an argon atmosphere and then stirred for 2 hours with the temperature unchanged.

After the completion of the reaction, a 5% aqueous potassium bisulfate solution was added to the reaction solution and stirred, followed by extraction with ethyl acetate three times. All of the organic layers were dried over anhydrous magnesium sulfate, then filtered, and concentrated under reduced pressure. The obtained concentration residue was subjected to silica gel column chromatography (DIOL silica gel, elution solvent: n-hexane:ethyl acetate=50:50 to 25:75 (V/V)), and a fraction containing the compound of interest was concentrated under reduced pressure. The obtained concentration residue was dissolved in ethyl acetate, then n-hexane was added, and the deposited solid was collected by filtration, washed with n-hexane, and then dried under reduced pressure to obtain 96 mg of the title compound (yield: 62% [2 steps]) as a white solid.

Mass spectrum (CI, m/z): 498 [M+1]$^+$.

$^1$H-NMR spectrum (400 MHz, DMSO-$d_6$) δ: 12.35-11.77 (m, 1H), 9.95-9.67 (m, 1H), 7.36-7.23 (m, 4H), 7.19-7.11 (m, 1H), 6.58-6.44 (m, 1H), 4.94-4.84 (m, 1H), 4.64 (br s, 1H), 4.40 (br s, 2H), 2.00-1.88 (m, 1H), 1.65 (dd, J=3.2, 14.2 Hz, 1H), 1.57 (br s, 3H), 1.52 (br s, 3H), 1.16 (s, 3H), 1.13 (s, 3H), 0.97 (br s, 2H), 0.98 (br s, 2H), 0.03 (s, 9H).

Example 121

N-(3-Hydroxy-2,2-dimethyl-1-phenylpropyl)-6,6-dimethyl-3-[1-(trimethylsilyl)cyclopropanecarboxamido]-4,6-dihydropyrrolo[3,4-c]pyrazole-5(1H)-carboxamide (Compound No. III-353)

[Chemical Formula 133]

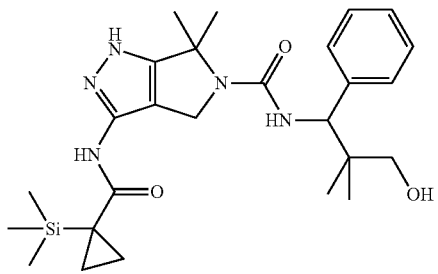

To a solution of 1.53 g (4.19 mmol) of ethyl 6,6-dimethyl-3-[1-(trimethylsilyl)cyclopropanecarboxamido]-5,6-dihydropyrrolo[3,4-c]pyrazole-2(4H)-carboxylate synthesized in the similar manner as in Reference Example 46 in 20 ml of dehydrated dichloromethane, 2.60 ml (14.9 mmol) of DIPEA was added at room temperature in an argon atmosphere. Subsequently, a solution of 700 mg (2.36 mmol) of bis(trichloromethyl) carbonate in 5 ml of dehydrated dichloromethane was added dropwise at −78° C. and then stirred for 0.5 hours with the temperature unchanged and further for 2 hours after the temperature was raised to room temperature.

After the completion of the reaction, a saturated aqueous solution of sodium bicarbonate and dichloromethane were added to the reaction solution at −78° C. and then stirred for 1.5 hours while the temperature was raised to room temperature for a while. The reaction solution was separated into an aqueous layer and an organic layer, and then, the aqueous layer was subjected to extraction with ethyl acetate twice. All of the organic layers were washed with a saturated aqueous solution of sodium chloride, then dried over anhydrous magnesium sulfate, filtered, and concentrated under reduced pressure. The obtained concentration residue was subjected to silica gel column chromatography (elution solvent: n-hexane:ethyl acetate=85:15 to 75:25 (V/V)), subsequently concentrated under reduced pressure, and dried under reduced pressure to obtain 1.75 g of a white solid.

To a solution of 109 mg (0.608 mmol) of 3-amino-2,2-dimethyl-3-phenylpropan-1-ol [synthesized according to the method described in Synthetic Communications 1994, 24 (7), 899-906] in 2 ml of dehydrated 1,4-dioxane, 0.20 ml (1.1 mmol) of DIPEA and 142 mg of a portion of the solid obtained by the operation described above were added in this order at room temperature in an argon atmosphere and then stirred at 90° C. for 2.5 hours. After standing to cool until the reaction solution becomes room temperature, 0.13 ml (1.2 mmol) of N,N-dimethylethane-1,2-diamine was added at room temperature and stirred for 2 hours with the temperature unchanged.

After the completion of the reaction, a 5% aqueous potassium bisulfate solution was added to the reaction solution and stirred, followed by extraction with ethyl acetate three times. All of the organic layers were dried over anhydrous magnesium sulfate, then filtered, and concentrated under reduced pressure. The obtained concentration residue was subjected to silica gel column chromatography (DIOL silica gel, elution solvent: n-hexane:ethyl acetate=60:40 to 40:60 (V/V)), and a fraction containing the compound of interest was concentrated under reduced pressure. The obtained concentration residue was dissolved in ethyl acetate, then n-hexane was added, and the deposited solid was collected by filtration, washed with n-hexane, and then dried under reduced pressure to obtain 112 mg of the title compound (yield: 66% [2 steps]) as a white solid. Mass spectrum (CI, m/z): 498 [M+1]$^+$.

$^1$H-NMR spectrum (400 MHz, DMSO-$d_6$) δ: 12.40-11.84 (m, 1H), 10.11-9.58 (m, 1H), 7.37-7.26 (m, 4H), 7.25-7.18 (m, 1H), 6.85 (br d, J=8.2 Hz, 1H), 5.53-5.39 (m, 1H), 4.63 (d, J=8.2 Hz, 1H), 4.45-4.25 (m, 2H), 3.29-3.22 (m, 1H), 3.07-2.98 (m, 1H), 1.58 (s, 3H), 1.51 (s, 3H), 1.06 (s, 3H), 1.03-0.94 (m, 2H), 0.76-0.58 (m, 5H), 0.03 (s, 9H).

Example 122

(−)-N-(3-Hydroxy-2,2-dimethyl-1-phenylpropyl)-6,6-dimethyl-3-[1-(trimethylsilyl)cyclobutanecarboxamido]-4,6-dihydropyrrolo[3,4-c]pyrazole-5(1H)-carboxamide (Compound No. IV-673)

To a solution of a mixture of 545 mg (1.16 mmol) of 2-ethyl 5-(trichloromethyl) 6,6-dimethyl-3-[1-(trimethylsilyl)cyclobutanecarboxamido]pyrrolo[3,4-c]pyrazole-2,5(4H,6H)-dicarboxylate synthesized in the similar manner as in Reference Example 102 and 329 mg (0.853 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate in 7 ml of dehydrated 1,4-dioxane, 1.80 ml (10.3 mmol) of DIPEA and 1.16 g (6.47 mmol) of 3-amino-2,2-dimethyl-3-phenylpropan-1-ol [synthesized according to the method described in Synthetic Communications 1994, 24 (7), 899-906] were added in this order at room temperature in an argon atmosphere and then stirred at 90° C. for 2 hours. After standing to cool until the reaction solution becomes room temperature, 0.90 ml (8.3 mmol) of N,N-dimethylethane-1,2-diamine was added at room temperature and stirred for 2.5 hours with the temperature unchanged.

After the completion of the reaction, a 5% aqueous potassium bisulfate solution was added to the reaction solution and stirred, followed by extraction with ethyl acetate three times. All of the organic layers were dried over anhydrous magnesium sulfate, then filtered, and concentrated under reduced pressure. The obtained concentration residue was subjected to silica gel column chromatography (DIOL silica gel, elution solvent: n-hexane:ethyl acetate=60:40 to 40:60 (V/V)), and a fraction containing the compound of interest was concentrated under reduced pressure. The obtained concentration residue was subjected again to silica gel column chromatography (DIOL silica gel, elution solvent: 1,2-dichloroethane:ethyl acetate=100:0 to 85:15 (V/V)), and a fraction containing the compound of interest was concentrated under reduced pressure. The obtained concentration residue was dissolved in an ethyl acetate/ethanol mixed solvent, then n-hexane was added, and the deposited solid was collected by filtration, washed with n-hexane, and then dried under reduced pressure to obtain 802 mg of a white solid.

0.50 g of a portion of the obtained solid was subjected to optical resolution preparative chromatography (column: CHIRALPAK (trade name) ID, elution solvent: n-hexane:ethanol=90:10 (V/V)), and a fraction containing an optically active form eluted first was concentrated under reduced pressure. The obtained concentration residue was dissolved in an acetonitrile/water mixed solvent and then freeze-dried to obtain 225 mg of the title compound (yield: 35%) as a white solid.

Specific optical rotation: $[\alpha]_D^{20}=-66°$ (c=0.50, methanol).

Mass spectrum (CI, m/z): 512 [M+1]$^+$.

$^1$H-NMR spectrum (400 MHz, DMSO-d$_6$) δ: 12.35-11.77 (m, 1H), 9.86-9.35 (m, 1H), 7.36-7.27 (m, 4H), 7.25-7.17 (m, 1H), 6.86 (br d, J=8.2 Hz, 1H), 5.45 (br s, 1H), 4.64 (d, J=8.2 Hz, 1H), 4.46-4.30 (m, 2H), 3.45-3.23 (m, 1H), 3.06-2.99 (m, 1H), 2.58-2.40 (m, 2H), 2.26-2.14 (m, 2H), 1.90-1.73 (m, 2H), 1.60 (s, 3H), 1.52 (s, 3H), 1.06 (s, 3H), 0.64 (s, 3H), 0.09 (s, 9H).

SFC (supercritical fluid chromatography) analysis:
Column: CHIRALPAK (trade name) ID 2.1×150 mm (particle size: 3 um)
Eluent: CO$_2$/methanol=90/10 (V/V)
Flow rate: 0.85 ml/min
Temperature: 40° C.
Detection wavelength: 240 nm
Retention time: 5.3 min.
Optical purity: >99% ee Example 123

(+)-N-(3-Hydroxy-2,2-dimethyl-1-phenylpropyl)-6,6-dimethyl-3-[1-(trimethylsilyl)cyclobutanecarboxamido]-4,6-dihydropyrrolo[3,4-c]pyrazole-5(1H)-carboxamide (Compound No. IV-672)

A fraction containing an optically active form eluted later in the optical resolution preparative chromatography operation of Example 122 was concentrated under reduced pressure. The obtained concentration residue was dissolved in an acetonitrile/water mixed solvent and then freeze-dried to obtain 223 mg of the title compound (yield: 35%) as a white solid.

Specific optical rotation: $[\alpha]_D^{20}=+60°$ (c=0.50, methanol).

Mass spectrum (CI, m/z): 512 [M+1]$^+$.

$^1$H-NMR spectrum (400 MHz, DMSO-d$_6$) δ: 12.42-11.76 (m, 1H), 9.57 (br s, 1H), 7.35-7.27 (m, 4H), 7.25-7.18 (m, 1H), 6.86 (br d, J=8.2 Hz, 1H), 5.45 (br s, 1H), 4.64 (d, J=8.2 Hz, 1H), 4.44-4.30 (m, 2H), 3.44-3.23 (m, 1H), 3.06-2.98 (m, 1H), 2.59-2.40 (m, 2H), 2.26-2.14 (m, 2H), 1.89-1.74 (m, 2H), 1.60 (s, 3H), 1.52 (s, 3H), 1.06 (s, 3H), 0.64 (s, 3H), 0.09 (s, 9H).

SFC (supercritical fluid chromatography) analysis:
Column: CHIRALPAK (trade name) ID 2.1×150 mm (particle size: 3 um)
Eluent: CO$_2$/methanol=90/10 (V/V)
Flow rate: 0.85 ml/min
Temperature: 40° C.
Detection wavelength: 240 nm
Retention time: 6.5 min.
Optical purity: >99% ee Example 124

(R)—N-[5-(2-Butoxy-2-phenylacetyl)-6,6-dimethyl-1,4,5,6-tetrahydropyrrolo[3,4-c]pyrazol-3-yl]-1-(trimethylsilyl)cyclobutanecarboxamide (Compound No. IV-1200)

[Chemical Formula 134]

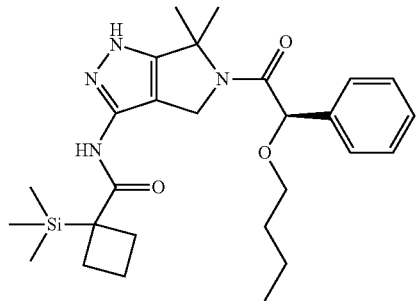

To a solution of 1.65 g (5.53 mmol) of (R)-benzyl 2-butoxy-2-phenylacetate synthesized in the similar manner as in Reference Example 133 in 8 ml of methanol/8 ml of water, 300 mg (7.15 mmol) of lithium hydroxide monohydrate was added at room temperature and then reacted with stirring at room temperature for 3 hours.

After the completion of the reaction, diethyl ether was added to the reaction solution and separated into an aqueous layer and an organic layer. The aqueous layer was adjusted to pH 2 by adding 2 N hydrochloric acid, followed by extraction with ethyl acetate three times. All of the obtained organic layers were washed with saturated saline, then dried over anhydrous magnesium sulfate, filtered, and concentrated under reduced pressure to obtain 1.34 g of a concentration residue.

To a solution of 150 mg of a portion of the obtained concentration residue in 2 ml of dehydrated dichloromethane, 0.006 ml (0.08 mmol) of DMF and 0.083 ml (0.95 mmol) of oxalyl chloride were added with stirring at 0° C. in an argon atmosphere and stirred at room temperature for 1.5 hours.

After the completion of the reaction, the reaction solution was concentrated under reduced pressure to obtain a concentration residue.

To a solution of 150 mg (0.396 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.350 ml (2.00 mmol) of DIPEA in 2 ml of dehydrated dichloromethane, a solution of the obtained concentration residue in 3 ml of dehydrated dichloromethane was added dropwise with stirring at 0° C. in an argon atmosphere and stirred at room temperature for 3 hours.

After the completion of the reaction, a saturated aqueous solution of sodium bicarbonate was added to the reaction solution, followed by extraction with dichloromethane. The obtained organic layer was washed with water, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=100:0 to 70:30 (V/V)) and subsequently concentrated under reduced pressure to obtain a concentration residue.

To a solution of the obtained concentration residue in 2 ml of dehydrated dichloromethane, 0.130 ml (1.19 mmol) of N,N-dimethylethane-1,2-diamine was added at room temperature in an argon atmosphere and then stirred at room temperature for 16 hours.

After the completion of the reaction, a 5% aqueous potassium bisulfate solution was added to the reaction solution and stirred, followed by extraction with dichloromethane. The obtained organic layer was washed with a saturated aqueous solution of sodium bicarbonate and saturated saline in this order, then dried over anhydrous sodium sulfate, and filtered, and the filtrate was concentrated under reduced pressure. The obtained concentration residue was subjected to silica gel column chromatography (DIOL silica gel, elution solvent: n-hexane:ethyl acetate=100:0 to 50:50 (V/V)), and a fraction containing the compound of interest was concentrated under reduced pressure. The obtained concentration residue was subjected to preparative HPLC (column: X-Bridge (trade name) ODS, elution solvent: acetonitrile:1 mM aqueous potassium dihydrogen phosphate solution=50:50 (V/V)), and ethyl acetate and water were added to a fraction containing the compound of interest to separate an organic layer and an aqueous layer. The obtained organic layer was concentrated under reduced pressure. The obtained concentration residue was dissolved in ethyl acetate and then added to n-hexane, and the deposited solid was collected by filtration and dried under reduced pressure to obtain 77 mg of the title compound (yield: 39%) as a white solid.

Mass spectrum (CI, m/z): 497 [M+1]$^+$.

$^1$H-NMR spectrum (400 MHz, DMSO-d$_6$) δ: 12.34-11.89 (m, 1H), 9.56 (br s, 1H), 7.45-7.25 (m, 5H), 5.02 (s, 1H), 4.68-4.49 (m, 1H), 4.40 (br d, J=12.7 Hz, 1H), 3.57-3.39 (m, 2H), 2.59-2.35 (m, 2H), 2.24-2.09 (m, 2H), 1.87-1.73 (m, 2H), 1.68 (s, 3H), 1.61 (s, 3H), 1.56-1.45 (m, 2H), 1.40-1.28 (m, 2H), 0.86 (t, J=7.3 Hz, 3H), 0.05 (s, 9H).

Example 125

N-(3-Methoxy-2,2-dimethyl-1-phenylpropyl)-6,6-dimethyl-3-[1-(trimethylsilyl)cyclobutanecarboxamido]-4,6-dihydropyrrolo[3,4-c]pyrazole-5(1H)-carboxamide (Compound No. IV-676)

[Chemical Formula 135]

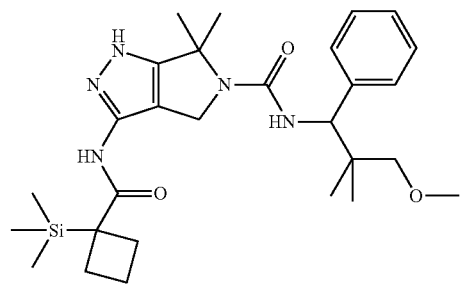

To a solution of 131 mg (0.219 mmol) of ethyl 5-[(3-methoxy-2,2-dimethyl-1-phenylpropyl)carbamoyl]-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 137 in 3 ml of dichloromethane, 0.095 ml (0.87 mol) of N,N-dimethylethane-1,2-diamine was added in one portion with stirring at room temperature under argon stream and stirred at room temperature for 1 hour.

After the completion of the reaction, a 5% aqueous potassium bisulfate solution was added to the reaction solution, followed by extraction from the mixed solution with ethyl acetate twice. The organic layer was washed with a 5% aqueous potassium bisulfate solution, dried over anhydrous magnesium sulfate, filtered, and concentrated under reduced pressure. The obtained concentration residue was subjected to silica gel column chromatography (DIOL silica gel, elution solvent: n-hexane:ethyl acetate=70:30 to 13:87 (V/V)), and a fraction containing the compound of interest was concentrated under reduced pressure. The obtained concentration residue was dissolved in a small amount of ethyl acetate, and a solid was deposited by adding n-hexane. The solid was collected by filtration, washed with n-hexane, and dried under reduced pressure at 50° C. to obtain 62 mg of the title compound (yield: 54%) as a white solid.

Mass spectrum (CI, m/z): 526 [M+1]$^+$.

$^1$H-NMR spectrum (400 MHz, DMSO-d$_6$) δ: 12.21 & 11.76 (br s, total 1H), 9.58 (br s, 1H), 7.38-7.18 (m, 5H), 6.75-6.52 (m, 1H), 4.59 (d, J=7.7 Hz, 1H), 4.52-4.30 (m, 2H), 3.38 (s, 3H), 3.13 (d, J=9.3 Hz, 1H), 2.92 (d, J=9.3 Hz, 1H), 2.58-2.40 (m, 2H), 2.29-2.12 (m, 2H), 1.91-1.74 (m, 2H), 1.59 (br s, 3H), 1.50 (s, 3H), 1.12 (s, 3H), 0.68 (s, 3H), 0.09 (s, 9H).

Reference Example 1

1-(Trimethylsilyl)cyclobutanecarboxylic acid

[Chemical Formula 136]

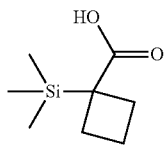

To 200 ml of dehydrated THF, 214 ml (428 mmol) of 2 M lithium diisopropylamide/THF solution was added in an argon atmosphere, and then, 10.1 ml (107 mmol) of cyclobutanecarboxylic acid was added dropwise with stirring under cooling in ice water and stirred for 4 hours while the temperature was raised to room temperature for a while. Subsequently, 20 ml (116 mmol) of hexamethylphosphoric acid triamide was added, and 51 ml (490 mmol) of chlorotrimethylsilane was added dropwise with stirring while the internal temperature was kept at −60° C. or lower under cooling in a dry ice/acetone coolant, and then stirred at −78° C. for 16.5 hours.

After the completion of the reaction, 67 ml of methanol was added to the reaction solution, and 134 ml of cold water was added after the temperature was raised to 0° C. The pH was adjusted to 2.1 by adding 2 N hydrochloric acid, 268 ml of diethyl ether was added thereto and then the aqueous layer and the organic layer were separated, and the organic layer was washed with 268 ml of a saturated aqueous solution of sodium chloride. The organic layer was dried over anhydrous magnesium sulfate, filtered, and concentrated under reduced pressure. 50 ml of a 2 N aqueous sodium hydroxide solution and 267 ml of n-hexane were added to the obtained concentration residue and then the aqueous layer and the organic layer were separated. Subsequently, the aqueous layer was adjusted to pH 2.7 by adding 1 N hydrochloric acid, and 267 ml of ethyl acetate was added to this solution and then the aqueous layer and the organic layer were separated. The obtained organic layer was dried over anhydrous magnesium sulfate, filtered, and concentrated under reduced pressure. n-Hexane was added to the obtained concentration residue and cooled in an ice water bath. The resulting solid was filtered, washed by sousing with cooled n-hexane, and then dried under reduced pressure to obtain 6.24 g of the title compound (yield: 34%) as a white solid. The filtrate was further concentrated under reduced pressure, and the obtained residue was subjected to silica gel column chromatography (elution solvent: 1,2-dichloroethane:methanol=100:0 to 95:5 (V/V)), and a fraction containing the compound of interest was concentrated under reduced pressure and dried under reduced pressure to obtain 4.33 g of the title compound (yield: 23%) as a white solid.

Mass spectrum (CI, m/z): 173 [M+1]$^+$.

$^1$H-NMR spectrum (400 MHz, DMSO-d$_6$) δ: 11.64 (br s, 1H), 2.45-2.34 (m, 2H), 2.17-2.06 (m, 2H), 1.91-1.70 (m, 2H), 0.06 (s, 9H).

Reference Example 2

5-tert-Butyl 2-ethyl 6,6-dimethyl-3-[1-(trimethylsilyl)cyclobutanecarboxamido]pyrrolo[3,4-c]pyrazole-2,5(4H,6H)-dicarboxylate

[Chemical Formula 137]

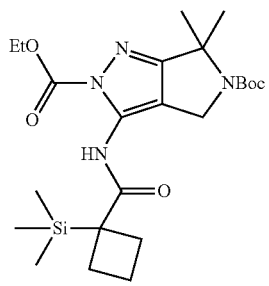

To a solution of 13.9 g (80.4 mmol) of 1-(trimethylsilyl)cyclobutanecarboxylic acid synthesized in the similar manner as in Reference Example 1 in 105 ml of dehydrated dichloromethane, 6.96 ml (81.2 mmol) of oxalyl chloride and 0.32 ml (4.14 mmol) of DMF were added dropwise in this order between −25° C. and −10° C. in an argon atmosphere and then stirred for 2 hours after the temperature was raised to 0° C. To a solution of 8.74 g (26.9 mmol) of 5-tert-butyl 2-ethyl 3-amino-6,6-dimethylpyrrolo[3,4-c]pyrazole-2,5(4H,6H)-dicarboxylate [synthesized according to the method described in Journal of Medicinal Chemistry 2012, 55 (10), 4728-4739] and 23.5 ml (135 mmol) of DIPEA in 122 ml of dehydrated dichloromethane, the resulting reaction solution was added dropwise at 0° C. in an argon atmosphere and stirred at the same temperature as above for 16 hours.

After the completion of the reaction, 486 ml of a 5% aqueous potassium bisulfate solution was added to the reaction solution and then the aqueous layer and the organic layer were separated. The aqueous layer was subjected to extraction with 200 ml of dichloromethane twice. All of the obtained organic layers were dried over anhydrous magnesium sulfate, filtered, and concentrated under reduced pressure. The obtained concentration residue was subjected to silica gel column chromatography (elution solvent: n-hexane:ethyl acetate=86:14 to 53:47 (V/V)), and a fraction containing the compound of interest was concentrated under reduced pressure and dried under reduced pressure to obtain 8.30 g of the title compound (yield: 64%) as a white foam.

Mass spectrum (CI, m/z): 479 [M+1]$^+$.

$^1$H-NMR spectrum (400 MHz, DMSO-d$_6$) δ: 9.98 & 9.72 & 9.71 (s, total 1H), 4.50-4.37 (m, 4H), 2.53-2.43 (m, 2H), 2.32-2.07 (m, 2H), 2.02-1.72 (m, 2H), 1.65-1.55 (m, 6H), 1.51-1.42 (m, 9H), 1.38-1.31 (m, 3H), 0.10 & 0.06 & 0.01 (s, total 9H).

Reference Example 3

Ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate

[Chemical Formula 138]

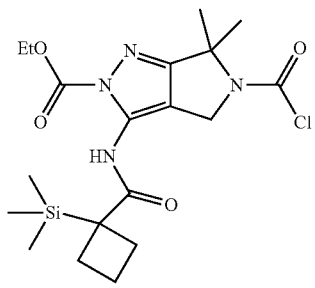

To a solution of 8.30 g (17.3 mmol) of 5-tert-butyl 2-ethyl 6,6-dimethyl-3-[1-(trimethylsilyl)cyclobutanecarboxamido] pyrrolo[3,4-c]pyrazole-2,5(4H,6H)-dicarboxylate synthesized in the similar manner as in Reference Example 2 in 81 ml of dehydrated dichloromethane, 6.0 ml (52 mmol) of 2,6-lutidine and 9.2 ml (51 mmol) of trimethylsilyl trifluoromethanesulfonate were added dropwise in this order at 0° C. in an argon atmosphere and stirred at the same temperature as above for 2 hours.

After the completion of the reaction, 64 ml of a saturated aqueous solution of sodium bicarbonate and 64 ml of dichloromethane were added to the reaction solution and then the aqueous layer and the organic layer were separated. The aqueous layer was subjected to extraction with 72 ml of dichloromethane twice, and then, all of the obtained organic layers were washed with 72 ml of a saturated aqueous solution of sodium bicarbonate and 72 ml of a saturated aqueous solution of sodium chloride in this order, subsequently dried over anhydrous magnesium sulfate, filtered, and concentrated under reduced pressure. The operation of adding 5 ml of toluene to the obtained concentration residue and concentrating the resultant under reduced pressure was repeated five times to obtain crude ethyl 6,6-dimethyl-3-[1-(trimethylsilyl)cyclobutanecarboxamido]-5,6-dihydropyrrolo[3,4-c]pyrazole-2(4H)-carboxylate.

To a solution of 6.70 g of the obtained crude ethyl 6,6-dimethyl-3-[1-(trimethylsilyl)cyclobutanecarboxamido]-5,6-dihydropyrrolo[3,4-c]pyrazole-2(4H)-carboxylate in 235 ml of dehydrated dichloromethane, 8.8 ml (51 mmol) of DIPEA was added at room temperature in an argon atmosphere, and then, a solution of 3.79 g (12.8 mmol) of bis(trichloromethyl)carbonate in 38 ml of dehydrated dichloromethane was added dropwise at −78° C. and stirred at the same temperature as above for 3 hours. At each point in time of 1 hour, 2 hours, and 2.6 hours after the start of this reaction, 1.0 ml (5.7 mmol) of DIPEA was added thereto.

After the completion of the reaction, 150 ml of a saturated aqueous solution of sodium bicarbonate was added to the reaction solution and stirred while the temperature was raised to room temperature for a while. After separation into an aqueous layer and an organic layer, the aqueous layer was subjected to extraction with 130 ml of dichloromethane twice. All of the obtained organic layers were dried over anhydrous magnesium sulfate, filtered, and concentrated under reduced pressure. The obtained concentration residue was subjected to silica gel column chromatography (elution solvent: n-hexane:ethyl acetate=78:22 to 57:43 (V/V)), and a fraction containing the compound of interest was concentrated under reduced pressure. n-Hexane was added to the obtained concentration residue and ultrasonicated. After cooling in a refrigerator, the deposited solid was filtered and dried under reduced pressure to obtain 3.51 g of the title compound (yield: 46% [2 steps]) as a white solid.

Mass spectrum (CI, m/z): 441 [M+1]$^+$.

$^1$H-NMR spectrum (400 MHz, DMSO-d$_6$) δ: 9.83-9.65 (m, 1H), 4.84 (s, 2H), 4.49-4.37 (m, 2H), 2.54-2.43 (m, 2H), 2.31-2.21 (m, 2H), 1.95-1.83 (m, 2H), 1.71-1.58 (m, 6H), 1.35 (t, J=7.1 Hz, 3H), 0.13-0.08 (m, 9H).

Reference Example 4

5-tert-Butyl 1-ethyl 6,6-dimethyl-3-[1-(trimethylsilyl)cyclobutanecarboxamido]pyrrolo[3,4-c]pyrazole-1,5(4H,6H)-dicarboxylate

[Chemical Formula 139]

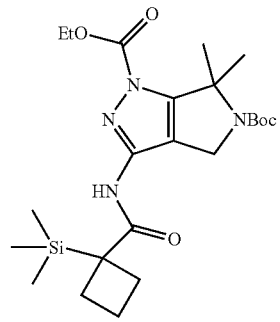

To a solution of 24.52 g (142 mmol) of 1-(trimethylsilyl) cyclobutanecarboxylic acid synthesized in the similar manner as in Reference Example 1 in 180 ml of dehydrated dichloromethane, 0.55 ml (7.1 mmol) of DMF and 12.2 ml (142 mmol) of oxalyl chloride were added dropwise at 0° C. in an argon atmosphere and stirred at the same temperature as above for 2 hours.

After the completion of the reaction, the reaction solution was concentrated under reduced pressure (hot water bath temperature: 30° C.) to obtain a concentration residue.

To a solution of 15.39 g (47.4 mmol) of 5-tert-butyl 1-ethyl 3-amino-6,6-dimethylpyrrolo[3,4-c]pyrazole-1,5 (4H,6H)-dicarboxylate [synthesized according to the method described in Journal of Medicinal Chemistry 2012, 55 (10), 4728-4739] and 40.6 ml (238 mmol) of DIPEA in 180 ml of dehydrated dichloromethane, a solution of the obtained concentration residue in 120 ml of dehydrated dichloromethane was added dropwise at 0° C. in an argon atmosphere and stirred at the same temperature as above for 20 hours.

After the completion of the reaction, the reaction solution was poured to 800 ml of a 5% aqueous potassium bisulfate solution, stirred, and then the aqueous layer and the organic layer were separated. The aqueous layer was subjected to extraction with 250 ml of dichloromethane twice. All of the obtained organic layers were dried over anhydrous magnesium sulfate, filtered, and concentrated under reduced pressure. The obtained concentration residue was subjected to silica gel column chromatography (elution solvent: n-hexane:ethyl acetate=91:9 to 70:30 (V/V)), and a fraction containing the compound of interest was concentrated under reduced pressure and dried under reduced pressure to obtain 14.6 g of the title compound (yield: 64%) as a white foam.

Mass spectrum (EI, m/z): 478 [M]+.

¹H-NMR spectrum (400 MHz, DMSO-d₆) δ: 10.32-10.20 (m, 1H), 4.46-4.32 (m, 4H), 2.48-2.39 (m, 2H), 2.24-2.14 (m, 2H), 1.84-1.68 (m, 8H), 1.52-1.40 (m, 9H), 1.32 (t, J=7.1 Hz, 3H), 0.07 (s, 9H).

Reference Example 5

Ethyl 6,6-dimethyl-3-[1-(trimethylsilyl)cyclobutanecarboxamido]-5,6-dihydropyrrolo[3,4-c]pyrazole-1(4H)-carboxylate

[Chemical Formula 140]

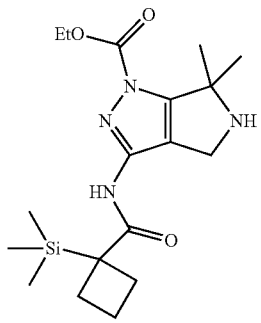

To a solution of 10.02 g (20.9 mmol) of 5-tert-butyl 1-ethyl 6,6-dimethyl-3-[1-(trimethylsilyl)cyclobutanecarboxamido]pyrrolo[3,4-c]pyrazole-1,5(4H,6H)-dicarboxylate synthesized in the similar manner as in Reference Example 4 in 100 ml of dehydrated dichloromethane, 7.26 ml (62.7 mmol) of 2,6-lutidine and 11.3 ml (62.7 mmol) of trimethylsilyl trifluoromethanesulfonate were added dropwise at 0° C. in an argon atmosphere and stirred at the same temperature as above for 1.5 hours.

After the completion of the reaction, 60 ml of a saturated aqueous solution of sodium bicarbonate and 60 ml of dichloromethane were added to the reaction solution. After separation into an aqueous layer and an organic layer, the aqueous layer was subjected to extraction with 60 ml of dichloromethane twice. All of the obtained organic layers were washed with 60 ml of a saturated aqueous solution of sodium bicarbonate and 60 ml of a saturated aqueous solution of sodium chloride in this order, then dried over anhydrous magnesium sulfate, filtered, and concentrated under reduced pressure. The operation of adding toluene to the obtained concentration residue and concentrating it under reduced pressure was repeated three times to obtain 7.43 g of the title compound (yield: 94%) as a pale yellow solid.

Mass spectrum (EI, m/z): 378 [M]+.

¹H-NMR spectrum (400 MHz, DMSO-d₆) δ: 10.03 (s, 1H), 4.37 (q, J=7.1 Hz, 2H), 3.85 (s, 2H), 2.48-2.38 (m, 2H), 2.23-2.12 (m, 2H), 1.85-1.72 (m, 2H), 1.41 (s, 6H), 1.31 (t, J=7.1 Hz, 3H), 0.06 (s, 9H).

Reference Example 6

5-tert-Butyl 2-ethyl 6,6-dimethyl-3-[1-(trimethylsilyl)cyclopropanecarboxamido]pyrrolo[3,4-c]pyrazole-2,5(4H,6H)-dicarboxylate

[Chemical Formula 141]

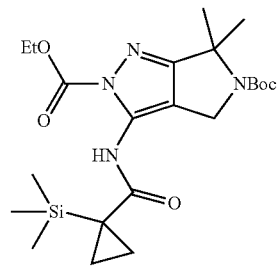

To a solution of 1.05 g (6.63 mmol) of 1-(trimethylsilyl)cyclopropanecarboxylic acid [synthesized according to the method described in J. Org. Chem., 1982, 47 (5), 893-895] in 20 ml of dehydrated dichloromethane, 0.70 ml (8.2 mmol) of oxalyl chloride and 0.020 ml (0.26 mmol) of DMF were added at 0° C. in a nitrogen atmosphere and stirred at the same temperature as above for 3 hours.

After the completion of the reaction, the reaction solution was concentrated under reduced pressure (hot water bath temperature: 25° C.) to obtain a concentration residue.

To a solution of the obtained concentration residue in 15 ml of dehydrated dichloromethane, 1.80 ml (10.3 mmol) of DIPEA and 839 mg (2.59 mmol) of 5-tert-butyl 2-ethyl 3-amino-6,6-dimethylpyrrolo[3,4-c]pyrazole-2,5(4H,6H)-dicarboxylate [synthesized according to the method described in Journal of Medicinal Chemistry 2012, 55 (10), 4728-4739] were added at 0° C. in a nitrogen atmosphere and stirred at the same temperature as above for 20.5 hours.

After the completion of the reaction, a saturated aqueous solution of sodium bicarbonate was added to the reaction solution, followed by extraction with dichloromethane twice. All of the obtained organic layers were dried over anhydrous magnesium sulfate, filtered, and concentrated under reduced pressure. The obtained concentration residue was subjected to silica gel column chromatography (elution solvent: n-hexane:ethyl acetate=90:10 to 75:25 (V/V)), and a fraction containing the compound of interest was concentrated under reduced pressure and dried under reduced pressure to obtain 1.19 g of the title compound (containing impurities) as a pale yellow foam.

Mass spectrum (CI, m/z): 465 [M+1]+.

¹H-NMR spectrum (400 MHz, CDCl₃) δ: 10.09 & 9.92 (s, total 1H), 4.70-4.46 (m, 4H), 1.72 (s, 3H), 1.65 (s, 3H), 1.54-1.44 (m, 12H), 1.15-1.07 (m, 2H), 0.84-0.78 (m, 2H), 0.17-0.07 (m, 9H).

Reference Example 7

Ethyl 6,6-dimethyl-3-[1-(trimethylsilyl)cyclopropanecarboxamido]-5,6-dihydropyrrolo[3,4-c]pyrazole-2(4H)-carboxylate hydrochloride

[Chemical Formula 142]

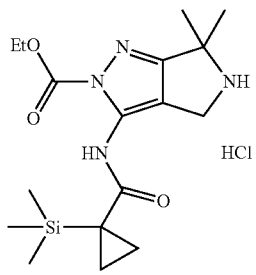

To a solution of 1.19 g of 5-tert-butyl 2-ethyl 6,6-dimethyl-3-[1-(trimethylsilyl)cyclopropanecarboxamido]pyrrolo[3,4-c]pyrazole-2,5(4H,6H)-dicarboxylate (containing impurities) synthesized in the similar manner as in Reference Example 6 in 20 ml of ethyl acetate, 4.0 ml (16 mmol) of 4 N hydrogen chloride/ethyl acetate was added at room temperature in a nitrogen atmosphere and stirred at the same temperature as above for 6.5 hours. Then, 2.0 ml (8.0 mmol) of 4 N hydrogen chloride/ethyl acetate was added thereto and further stirred at room temperature for 14.5 hours.

After the completion of the reaction, the reaction solution was concentrated under reduced pressure, and the obtained concentration residue was suspended in diisopropyl ether and stirred at room temperature. Insoluble matter was collected by filtration, and the obtained solid was washed by sousing with diisopropyl ether and then dried under reduced pressure to obtain 0.91 g of the title compound (yield: 88% [2 steps]) as a white solid.

Mass spectrum (CI, m/z): 365 [M+1]$^+$.

$^1$H-NMR spectrum (400 MHz, DMSO-d$_6$) δ: 9.99 (br s, 2H), 9.91 (s, 1H), 4.51-4.39 (m, 4H), 1.63 (s, 6H), 1.35 (t, J=7.2 Hz, 3H), 1.08 (dd, J=4.2, 6.0 Hz, 2H), 0.87 (dd, J=4.2, 6.0 Hz, 2H), 0.08 (s, 9H).

Reference Example 8

2-Methyl-2-(trimethylsilyl)propanoic acid

[Chemical Formula 143]

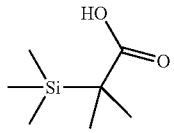

To 100 ml of dehydrated THF, 200 ml (400 mmol) of 2 M lithium diisopropylamide/THF solution was added in an argon atmosphere, and subsequently, 4.7 ml (51 mmol) of isobutanoic acid was added dropwise at 0° C. and then stirred at room temperature for 4 hours. 10 ml (58 mmol) of hexamethylphosphoric acid triamide was added thereto, and then, 29 ml (230 mmol) of chlorotrimethylsilane was added thereto dropwise at −78° C. and stirred for 24 hours while the temperature was gradually raised to room temperature.

After the completion of the reaction, 25 ml of methanol and 50 ml of water were added to the reaction solution. Subsequently, the solution was rendered acidic by adding 2 N hydrochloric acid, followed by extraction with diethyl ether. All of the obtained organic layers were washed with a saturated aqueous solution of sodium chloride, then dried over anhydrous magnesium sulfate, filtered, and concentrated under reduced pressure. The obtained concentration residue was dissolved in a 2 N aqueous sodium hydroxide solution and washed with ethyl acetate. After separation into an aqueous layer and an organic layer, the aqueous layer was rendered acidic by adding 1 N hydrochloric acid, followed by extraction with ethyl acetate. All of the obtained organic layers were dried over anhydrous magnesium sulfate, filtered, and concentrated under reduced pressure. The obtained concentration residue was suspended in n-hexane, and after ultrasonication, insoluble matter was collected by filtration. The filtrate was concentrated under reduced pressure, the obtained concentration residue was subjected to silica gel column chromatography (elution solvent: 1,2-dichloroethane:methanol=100:0 to 99:1 (V/V)), and a fraction containing the compound of interest and the aforementioned solid collected by filtration were combined, concentrated under reduced pressure, and dried under reduced pressure to obtain 2.66 g of the title compound (yield: 32%) as a white solid.

Mass spectrum (CI, m/z): 161 [M+1]$^+$.

$^1$H-NMR spectrum (400 MHz, CDCl$_3$) δ: 1.22 (s, 6H), 0.08 (s, 9H).

Reference Example 9

5-tert-Butyl 1-ethyl 6,6-dimethyl-3-[2-methyl-2-(trimethylsilyl)propanamido]pyrrolo[3,4-c]pyrazole-1,5(4H,6H)-dicarboxylate

[Chemical Formula 144]

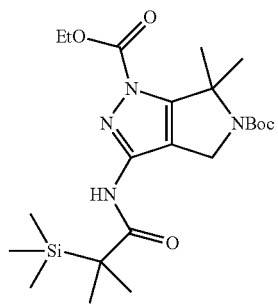

To a solution of 1.30 g (8.11 mmol) of 2-methyl-2-(trimethylsilyl)propanoic acid synthesized in the similar manner as in Reference Example 8 in 25 ml of dehydrated dichloromethane, 0.85 ml (9.9 mmol) of oxalyl chloride and 0.040 ml (0.52 mmol) of DMF were added in this order at 0° C. in a nitrogen atmosphere and stirred at the same temperature as above for 3.5 hours.

After the completion of the reaction, the reaction solution was concentrated under reduced pressure (hot water bath temperature: 25° C.) to obtain a concentration residue.

To a solution of the obtained concentration residue in 15 ml of dehydrated dichloromethane, 2.30 ml (13.2 mmol) of DIPEA and 1.08 g (3.33 mmol) of 5-tert-butyl 1-ethyl 3-amino-6,6-dimethylpyrrolo[3,4-c]pyrazole-1,5(4H,6H)-dicarboxylate [synthesized according to the method described in Journal of Medicinal Chemistry 2012, 55 (10), 4728-4739] were added in this order at 0° C. in a nitrogen atmosphere and stirred at the same temperature as above for 17.5 hours.

After the completion of the reaction, a saturated aqueous solution of sodium bicarbonate was added to the reaction solution and stirred, followed by extraction with dichloromethane three times. All of the organic layers were dried over anhydrous magnesium sulfate, filtered, and concentrated under reduced pressure. The obtained concentration residue was subjected to silica gel column chromatography (elution solvent: n-hexane:ethyl acetate=93:7 to 80:20 (V/V)), and a fraction containing the compound of interest was concentrated under reduced pressure and dried under reduced pressure to obtain 1.28 g of the title compound (yield: 82%) as a pale yellow foam.

Mass spectrum (CI, m/z): 467 [M+1]$^+$.

$^1$H-NMR spectrum (400 MHz, CDCl$_3$) δ: 7.87-7.74 (m, 1H), 4.60-4.47 (m, 4H), 1.84 & 1.78 (s, total 6H), 1.55-1.48 (m, 9H), 1.47 (t, J=7.2 Hz, 3H), 1.31-1.25 (m, 6H), 0.10-0.04 (m, 9H).

Reference Example 10

1-(Ethyldimethylsilyl)cyclobutanecarboxylic acid

[Chemical Formula 145]

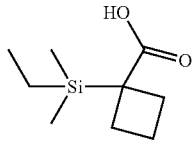

To 200 ml of dehydrated THF, 214 ml (428 mmol) of 2 M lithium diisopropylamide/THF solution was added in an argon atmosphere, and then, 10.7 ml (112 mmol) of cyclobutanecarboxylic acid was added dropwise under cooling in ice water and stirred while the temperature was raised to room temperature for a while. Subsequently, 20 ml (120 mmol) of hexamethylphosphoric acid triamide was added. After cooling in a dry ice/ethanol coolant, 67.6 ml (485 mmol) of chloro(ethyl)dimethylsilane was added dropwise at −75° C. to −69° C. and stirred overnight at a temperature of −60° C. or lower.

After the completion of the reaction, 67 ml of methanol and subsequently 134 ml of cold water were added dropwise to the reaction solution and then brought to room temperature. 240 ml of 2 N hydrochloric acid was added for acidity (pH 2.0), and 200 ml of diethyl ether was added thereto and then the aqueous layer and the organic layer were separated. The obtained organic layer was washed with 250 ml of a saturated aqueous solution of sodium chloride, then dried over anhydrous magnesium sulfate, filtered, and concentrated under reduced pressure. 41 ml of a 2 N aqueous sodium hydroxide solution was added to the obtained concentration residue and washed with 250 ml of n-hexane. The aqueous layer was rendered acidic (pH 2.0) again by adding 82 ml of 1 N hydrochloric acid. This solution was subjected to extraction with 250 ml of ethyl acetate, and the organic layer was concentrated under reduced pressure. The obtained residue was subjected to silica gel column chromatography (elution solvent: 1,2-dichloroethane:methanol=100:0 to 95:5 (V/V)), and a fraction containing the compound of interest was concentrated under reduced pressure and dried under reduced pressure to obtain 11.7 g of the title compound (yield: 59%) as a white solid.

$^1$H-NMR spectrum (400 MHz, DMSO-d$_6$) δ: 11.71 (br s, 1H), 2.44-2.33 (m, 2H), 2.19-2.08 (m, 2H), 1.91-1.73 (m, 2H), 0.92 (t, J=7.9 Hz, 3H), 0.55 (q, J=7.9 Hz, 2H), 0.05 (s, 6H).

Reference Example 11

5-tert-Butyl 2-ethyl 3-[1-(ethyldimethylsilyl)cyclobutanecarboxamido]-6,6-dimethylpyrrolo[3,4-c]pyrazole-2,5(4H,6H)-dicarboxylate

[Chemical Formula 146]

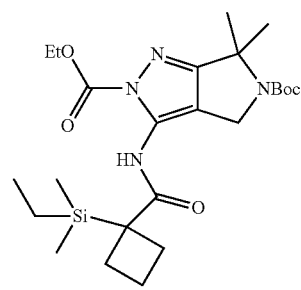

To a solution of 11.7 g (62.8 mmol) of 1-(ethyldimethylsilyl)cyclobutanecarboxylic acid synthesized in the similar manner as in Reference Example 10 in 81 ml of dehydrated dichloromethane, 5.3 ml (62 mmol) of oxalyl chloride and 0.24 ml (3.1 mmol) of DMF were added in this order under cooling in ice water in an argon atmosphere and stirred at the same temperature as above for 2 hours.

After the completion of the reaction, the reaction solution was concentrated under reduced pressure at room temperature to obtain a concentration residue.

To a solution of 6.73 g (20.7 mmol) of 5-tert-butyl 2-ethyl 3-amino-6,6-dimethylpyrrolo[3,4-c]pyrazole-2,5(4H,6H)-dicarboxylate [synthesized according to the method described in Journal of Medicinal Chemistry 2012, 55 (10), 4728-4739] and 18 ml (100 mmol) of DIPEA in 94 ml of dehydrated dichloromethane, a solution of the obtained concentration residue in 5 ml of dehydrated dichloromethane was added dropwise under cooling in ice water in a nitrogen atmosphere and stirred at the same temperature as above for 16 hours.

After the completion of the reaction, 350 ml of a 5% aqueous potassium bisulfate solution was added to the reaction solution and separated into an aqueous layer and an organic layer, and then, the aqueous layer was subjected to extraction with 150 ml of dichloromethane twice. All of the obtained organic layers were dried over anhydrous magnesium sulfate and then filtered, and the filtrate was concentrated under reduced pressure. The obtained residue was subjected to silica gel column chromatography (elution solvent: n-hexane:ethyl acetate=86:14 to 53:47 (V/V)), and a fraction containing the compound of interest was concentrated under reduced pressure to obtain 7.51 g of the title compound (yield: 74%) as a pale yellow oil.

Mass spectrum (DUIS, m/z): 493 [M+1]$^+$.

$^1$H-NMR spectrum (400 MHz, DMSO-$d_6$) δ: 9.82-9.69 (m, 1H), 4.51-4.36 (m, 4H), 2.49-2.42 (m, 2H), 2.32-2.23 (m, 2H), 1.95-1.84 (m, 2H), 1.62-1.55 (m, 6H), 1.49-1.42 (m, 9H), 1.38-1.31 (m, 3H), 0.91 (t, J=7.9 Hz, 3H), 0.57 (q, J=7.9 Hz, 2H), 0.09 (s, 6H).

Reference Example 12

Ethyl 3-[1-(ethyldimethylsilyl)cyclobutanecarboxamido]-6,6-dimethyl-5,6-dihydropyrrolo[3,4-c]pyrazole-2(4H)-carboxylate

[Chemical Formula 147]

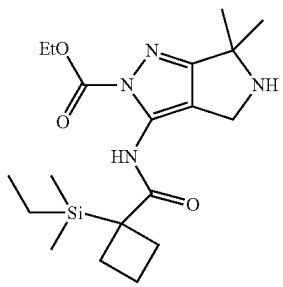

To a solution of 7.27 g (14.8 mmol) of 5-tert-butyl 2-ethyl 3-[1-(ethyl dimethylsilyl)cyclobutanecarboxamido]-6,6-dimethylpyrrolo[3,4-c]pyrazole-2,5(4H,6H)-dicarboxylate synthesized in the similar manner as in Reference Example 11 in 70 ml of dehydrated dichloromethane, 5.1 ml (44 mmol) of 2,6-lutidine and 7.8 ml (43 mmol) of trimethylsilyl trifluoromethanesulfonate were added dropwise in this order under ice cooling in an argon atmosphere and stirred at the same temperature as above for 2 hours.

After the completion of the reaction, 57 ml of a saturated aqueous solution of sodium bicarbonate and 57 ml of dichloromethane were added to the reaction solution, and then the aqueous layer and the organic layer were separated. The aqueous layer was subjected to extraction with 60 ml of dichloromethane twice, all of the obtained organic layers were washed with 60 ml of a saturated aqueous solution of sodium bicarbonate and 60 ml of a saturated aqueous solution of sodium chloride in this order, then dried over anhydrous magnesium sulfate, and filtered, and the filtrate was concentrated under reduced pressure. The operation of adding toluene to the obtained concentration residue and concentrating the resultant under reduced pressure was performed five times to obtain 5.92 g of the title compound (containing impurities) as a yellow oil.

Mass spectrum (DUIS, m/z): 393 [M+1]$^+$.

$^1$H-NMR spectrum (400 MHz, DMSO-$d_6$) δ: 9.68 (s, 1H), 4.39 (q, J=7.0 Hz, 2H), 3.92 (s, 2H), 2.48-2.40 (m, 2H), 2.29-2.22 (m, 2H), 1.93-1.82 (m, 2H), 1.33 (t, J=7.0 Hz, 3H), 1.29 (s, 6H), 0.91 (t, J=8.1 Hz, 3H), 0.56 (q, J=8.1 Hz, 2H), 0.08 (s, 6H).

Reference Example 13

Ethyl 5-(chlorocarbonyl)-3-[1-(ethyldimethylsilyl) cyclobutanecarboxamido]-6,6-dimethyl-5,6-dihydropyrrolo[3,4-c]pyrazole-2(4H)-carboxylate

[Chemical Formula 148]

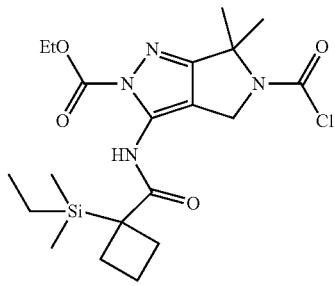

To a solution of 5.92 g of ethyl 3-[1-(ethyldimethylsilyl) cyclobutanecarboxamido]-6,6-dimethyl-5,6-dihydropyrrolo [3,4-c]pyrazole-2(4H)-carboxylate (containing impurities) synthesized in the similar manner as in Reference Example 12 by using 7.27 g (14.8 mmol) of 5-tert-butyl 2-ethyl 3-[1-(ethyldimethylsilyl)cyclobutanecarboxamido]-6,6-dimethylpyrrolo[3,4-c]pyrazole-2,5(4H,6H)-dicarboxylate synthesized in the similar manner as in Reference Example 11 in 200 ml of dehydrated dichloromethane, 7.3 ml (43 mmol) of DIPEA was added at room temperature in an argon atmosphere, and then, a solution of 3.24 g (10.9 mmol) of bis(trichloromethyl)carbonate in 33 ml of dehydrated dichloromethane was added dropwise at −60° C. or lower and stirred at the same temperature as above for 2 hours.

After the completion of the reaction, 130 ml of a saturated aqueous solution of sodium bicarbonate was added to the reaction solution, and the temperature was raised to room temperature for a while with stirring. After separation into an aqueous layer and an organic layer, the aqueous layer was subjected to extraction with 100 ml of dichloromethane twice. All of the obtained organic layers were dried over anhydrous magnesium sulfate and filtered, and the filtrate was concentrated under reduced pressure. The obtained concentration residue was subjected to silica gel column chromatography (elution solvent: n-hexane:ethyl acetate=78:22 to 57:43 (V/V)), and a fraction containing the compound of interest was concentrated under reduced pressure. n-Hexane was added to the concentration residue and concentrated again under reduced pressure to obtain 5.13 g of the title compound (yield: 76% [2 steps]) as a white solid.

Mass spectrum (CI, m/z): 455 [M+1]$^+$.

$^1$H-NMR spectrum (400 MHz, DMSO-$d_6$) δ: 9.85-9.76 (m, 1H), 4.88-4.81 & 4.53-4.48 (m, total 2H), 4.44 (q, J=7.1 Hz, 2H), 2.55-2.44 (m, 2H), 2.35-2.24 (m, 2H), 1.96-1.85 (m, 2H), 1.69-1.61 (m, 6H), 1.34 (t, J=7.1 Hz, 3H), 0.92 (t, J=7.9 Hz, 3H), 0.58 (q, J=7.9 Hz, 2H), 0.13-0.07 (m, 6H).

Reference Example 14

2-(Ethyldimethylsilyl)-2-methylpropanoic acid

[Chemical Formula 149]

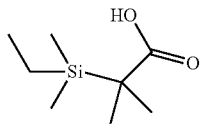

To 100 ml of dehydrated THF, 100 ml (200 mmol) of 2 M lithium diisopropylamide/THF solution was added in an argon atmosphere, and then, 4.7 ml (51 mmol) of isobutanoic acid was added dropwise at 0° C. and stirred for 4 hours after the temperature was raised to room temperature. Subsequently, 10 ml (58 mmol) of hexamethylphosphoric acid triamide was added thereto, and then, 32 ml (230 mmol) of chloro(ethyl)dimethylsilane was added thereto dropwise at −78° C. After the completion of the dropwise addition, the resultant was stirred for 1 day while the temperature was raised to room temperature for a while.

After the completion of the reaction, 25 ml of methanol and subsequently 50 ml of water were added under cooling in ice water. Then, 2 N hydrochloric acid was added for acidity, followed by extraction with diethyl ether. The obtained organic layer was washed with a saturated aqueous solution of sodium chloride, then dried over anhydrous magnesium sulfate, and filtered, and the filtrate was concentrated under reduced pressure. A 2 N aqueous sodium hydroxide solution was added to the concentration residue, and it was washed with ethyl acetate. Subsequently, the aqueous layer was rendered acidic by adding a 1 N aqueous hydrochloric acid solution, followed by extraction with ethyl acetate. The obtained organic layer was dried over anhydrous magnesium sulfate and filtered, and the filtrate was concentrated under reduced pressure. The obtained residue was subjected to silica gel column chromatography (elution solvent: 1,2-dichloroethane:methanol=100:0 to 99:1 (V/V)), and a fraction containing the compound of interest was concentrated under reduced pressure and dried under reduced pressure to obtain 2.24 g of the title compound (yield: 25%) as a white solid.

Mass spectrum (CI, m/z): 175 [M+1]$^+$.

$^1$H-NMR spectrum (400 MHz, CDCl$_3$) δ: 11.57 (br s, 1H), 1.23 (s, 6H), 0.95 (t, J=8.0 Hz, 3H), 0.62 (q, J=8.0 Hz, 2H), 0.06 (s, 6H).

Reference Example 15

5-tert-Butyl 1-ethyl 3-[2-(ethyldimethylsilyl)-2-methylpropanamido]-6,6-dimethylpyrrolo[3,4-c]pyrazole-1,5(4H,6H)-dicarboxylate

[Chemical Formula 150]

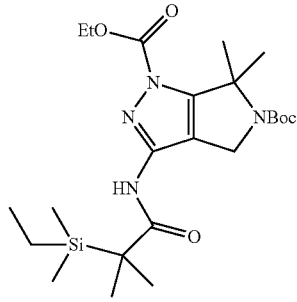

To a solution of 4.7 g (27 mmol) of 2-(ethyldimethylsilyl)-2-methylpropanoic acid synthesized in the similar manner as in Reference Example 14 in 40 ml of dehydrated dichloromethane, 2.3 ml (27 mmol) of oxalyl chloride was added dropwise at 0° C. in an argon atmosphere and stirred at the same temperature as above for 10 minutes. Subsequently, 0.10 ml (1.3 mmol) of DMF was added at 0° C. and stirred at the same temperature as above for 4 hours.

After the completion of the reaction, the reaction solution was concentrated under reduced pressure at room temperature to obtain a concentration residue.

To a solution of 2.9 g (8.9 mmol) of 5-tert-butyl 1-ethyl 3-amino-6,6-dimethylpyrrolo[3,4-c]pyrazole-1,5(4H,6H)-dicarboxylate [synthesized according to the method described in Journal of Medicinal Chemistry 2012, 55 (10), 4728-4739] in 10 ml of dehydrated dichloromethane, a solution of the obtained concentration residue in 20 ml of dehydrated dichloromethane was added dropwise at 0° C. in an argon atmosphere, and subsequently, 7.9 ml (45 mmol) of DIPEA was added and stirred at 0° C. for 24 hours.

After the completion of the reaction, water was added to the reaction solution, followed by extraction with dichloromethane. The obtained organic layer was washed with a saturated aqueous solution of sodium chloride, then dried over anhydrous sodium sulfate, and filtered, and the filtrate was concentrated under reduced pressure. The obtained residue was subjected to silica gel column chromatography (elution solvent: n-hexane:ethyl acetate=98:2 to 80:20 (V/V)), and a fraction containing the compound of interest was concentrated under reduced pressure to obtain 3.18 g of the title compound (yield: 74%) as a pale yellow oil.

Mass spectrum (CI, m/z): 481 [M+1]⁺.
¹H-NMR spectrum (400 MHz, CDCl₃) δ: 7.88-7.73 (m, 1H), 4.62-4.46 (m, 4H), 1.87-1.75 (m, 6H), 1.55-1.41 (m, 12H), 1.31-1.26 (m, 6H), 0.99-0.88 (m, 3H), 0.66-0.53 (m, 2H), 0.09-0.02 (m, 6H).

Reference Example 16

Ethyl 3-[2-(ethyldimethylsilyl)-2-methylpropanamido]-6,6-dimethyl-5,6-dihydropyrrolo[3,4-c]pyrazole-1(4H)-carboxylate

[Chemical Formula 151]

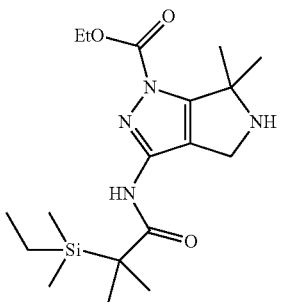

To a solution of 3.18 g (6.62 mmol) of 5-tert-butyl 1-ethyl 3-[2-(ethyldimethylsilyl)-2-methylpropanamido]-6,6-dimethylpyrrolo[3,4-c]pyrazole-1,5(4H,6H)-dicarboxylate synthesized in the similar manner as in Reference Example 15 in 30 ml of dehydrated dichloromethane, 2.3 ml (20 mmol) of 2,6-lutidine and 3.6 ml (20 mmol) of trimethylsilyl trifluoromethanesulfonate were added dropwise in this order at 0° C. in an argon atmosphere and stirred at the same temperature as above for 1 hour.

After the completion of the reaction, a saturated aqueous solution of sodium bicarbonate was added to the reaction solution, followed by extraction with dichloromethane. The obtained organic layer was washed with a saturated aqueous solution of sodium chloride, then dried over anhydrous magnesium sulfate, and filtered, and the filtrate was concentrated under reduced pressure. Toluene was added to the residue, and then, concentration under reduced pressure was performed to obtain 2.44 g of the title compound (yield: 97%) as a pale yellow solid.

Mass spectrum (CI, m/z): 381 [M+1]⁺.
¹H-NMR spectrum (400 MHz, CDCl₃) δ: 7.77 (s, 1H), 4.50 (q, J=7.2 Hz, 2H), 4.15 (s, 2H), 1.55 (s, 6H), 1.46 (t, J=7.2 Hz, 3H), 1.32-1.25 (m, 6H), 0.93 (t, J=8.0 Hz, 3H), 0.60 (q, J=8.0 Hz, 2H), 0.05 (s, 6H).

Reference Example 17

(S)-2-[(2-Methoxypropan-2-yl)oxy]-1-phenylethanol

[Chemical Formula 152]

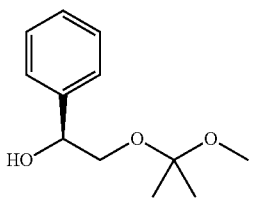

To a solution of 664 mg (2.63 mmol) of (S)-2-[(tert-butyldimethylsilyl)oxy]-2-phenylethanol [synthesized according to the method described in Angew. Chem. Int. Ed., 2012, 51 (31), 7825-7829] in 15 ml of dichloromethane, 0.33 ml (3.5 mmol) of 2-methoxy-1-propene and 68.3 mg (0.272 mmol) of pyridinium p-toluenesulfonate were added at 0° C. in a nitrogen atmosphere and stirred at the same temperature as above for 2 hours.

After the completion of the reaction, a saturated aqueous solution of sodium bicarbonate was added to the reaction solution and stirred, followed by extraction with dichloromethane twice. All of the organic layers were dried over anhydrous magnesium sulfate, filtered, and concentrated under reduced pressure. The obtained concentration residue was subjected to silica gel column chromatography (elution solvent: n-hexane:ethyl acetate=98:2 to 97:3 (V/V)), and a fraction containing (S)-3,3,8,8,9,9-hexamethyl-6-phenyl-2,4,7-trioxa-8-siladecane was concentrated under reduced pressure and dried under reduced pressure to obtain a concentration residue.

To a solution of 347 mg of the obtained concentration residue in 10 ml of THF, 428 mg (1.64 mmol) of tetrabutylammonium fluoride was added at 0° C. in a nitrogen atmosphere and stirred at the same temperature as above for 3.5 hours.

After the completion of the reaction, a saturated aqueous solution of sodium bicarbonate was added to the reaction solution and stirred, followed by extraction with an ethyl acetate/n-hexane mixed solvent twice. All of the obtained organic layers were dried over anhydrous magnesium sulfate, filtered, and concentrated under reduced pressure. The obtained concentration residue was subjected to silica gel column chromatography (elution solvent: n-hexane:ethyl acetate=90:10 to 85:15 (V/V)), and a fraction containing the compound of interest was concentrated under reduced pressure and dried under reduced pressure to obtain 160 mg of the title compound (yield: 29% [2 steps]) as a colorless oil.

¹H-NMR spectrum (400 MHz, CDCl₃) δ: 7.43-7.27 (m, 5H), 4.89-4.83 (m, 1H), 3.59 (dd, J=3.2, 9.8 Hz, 1H), 3.45 (dd, J=9.0, 9.8 Hz, 1H), 3.19 (s, 3H), 2.82 (d, J=2.4 Hz, 1H), 1.38 (s, 3H), 1.37 (s, 3H).

Reference Example 18

(S)-2,5-Dioxopyrrolidin-1-yl {2-[(2-methoxypropan-2-yl)oxy]-1-phenylethyl}carbonate

[Chemical Formula 153]

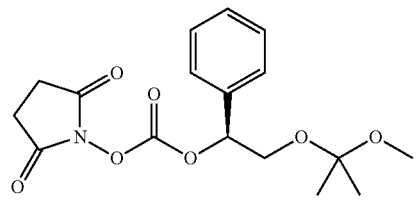

To a solution of 157 mg (0.747 mmol) of (S)-2-[(2-methoxypropan-2-yl)oxy]-1-phenylethanol synthesized in the similar manner as in Reference Example 17 in 4 ml of dehydrated acetonitrile, 0.16 ml (1.2 mmol) of triethylamine and 233 mg (0.908 mmol) of N,N'-disuccinimidyl carbonate were added at room temperature in a nitrogen atmosphere and stirred at the same temperature as above for 6 hours.

After the completion of the reaction, the reaction solution was concentrated under reduced pressure. The obtained concentration residue was dissolved in ethyl acetate, and it was washed with water. After separation into an aqueous layer and an organic layer, the aqueous layer was subjected to extraction with ethyl acetate twice. All of the obtained organic layers were dried over anhydrous magnesium sulfate, filtered, and concentrated under reduced pressure. The obtained concentration residue was subjected to silica gel column chromatography (elution solvent: n-hexane:ethyl acetate=90:10 to 65:35 (V/V)), and a fraction containing the compound of interest was concentrated under reduced pressure and dried under reduced pressure to obtain 190 mg of the title compound (yield: 72%) as a colorless oil.

$^1$H-NMR spectrum (400 MHz, CDCl$_3$) δ: 7.42-7.33 (m, 5H), 5.86 (dd, J=3.4, 8.8 Hz, 1H), 3.83 (dd, J=8.8, 11.0 Hz, 1H), 3.64 (dd, J=3.4, 11.0 Hz, 1H), 3.20 (s, 3H), 2.81 (s, 4H), 1.38 (s, 3H), 1.34 (s, 3H).

Reference Example 19

Ethyl 4-(benzyloxy)-3-phenylbutanoate

[Chemical Formula 154]

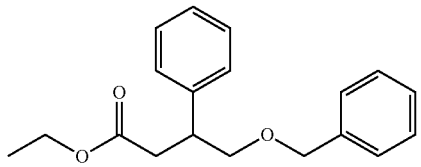

To a solution of 8.9 mg (0.023 mmol) of bis(acetonitrile)(1,5-cyclooctadiene)rhodium(I) tetrafluoroborate in 3 ml of 1,4-dioxane/0.3 ml of water, 23 mg (0.41 mmol) of potassium hydroxide, 128 mg (1.05 mmol) of phenylboronic acid, and 120 mg (0.545 mmol) of (E)-ethyl 4-(benzyloxy)-2-butenoate [synthesized according to the method described in Tetrahedron Lett., 1982, 37, 9033-9036] were added in this order with stirring at room temperature in an argon atmosphere, stirred at the same temperature as above for 30 minutes, and then stirred at 60° C. for 6 hours.

After the completion of the reaction, water was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained residue was subjected to silica gel chromatography (elution solvent: n-hexane:ethyl acetate=95:5 to 50:50 (V/V)), and a fraction containing the compound of interest was concentrated under reduced pressure to obtain 160 mg of the title compound (yield: 98%) as a pale yellow oil.

$^1$H-NMR spectrum (400 MHz, DMSO-d$_6$) δ: 7.36-7.18 (m, 10H), 4.45 (s, 2H), 3.97-3.89 (m, 2H), 3.59-3.52 (m, 2H), 3.39-3.33 (m, 1H), 2.81 (dd, J=6.3, 15.6 Hz, 1H), 2.59 (dd, J=8.5, 15.6 Hz, 1H), 1.04 (t, J=7.1 Hz, 3H).

Reference Example 20

Ethyl 6,6-dimethyl-5-(3-oxo-3-phenylpropanoyl)-3-[1-(trimethylsilyl)cyclobutanecarboxamido]-5,6-dihydropyrrolo[3,4-c]pyrazole-2(4H)-carboxylate and (Z)-ethyl 5-(3-hydroxy-3-phenylacryloyl)-6,6-dimethyl-3-[1-(trimethylsilyl)cyclobutanecarboxamido]-5,6-dihydropyrrolo[3,4-c]pyrazole-2(4H)-carboxylate as tautomer

[Chemical Formula 155]

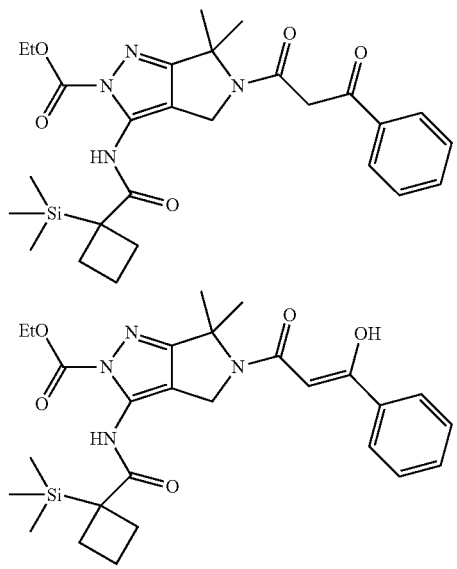

To a solution of 487 mg (2.39 mmol) of 3-oxo-3-phenylpropanoic acid [synthesized according to the method described in Chem. Pharm. Bull., 29 (10), 2762 (1981)] and 10 μl (0.13 mmol) of DMF in 5 ml of dehydrated dichloromethane, 205 μl (2.39 mmol) of oxalyl chloride was added dropwise with stirring at 0° C. in an argon atmosphere and stirred for 1.5 hours after the temperature was raised to room temperature.

After the completion of the reaction, the reaction solution was concentrated under reduced pressure at room temperature to obtain a concentration residue.

To a solution of 299 mg (0.790 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.70 ml (4.1 mmol) of DIPEA in 5 ml of 1,2-dichloroethane, a solution of the obtained concentration residue in 5 ml of 1,2-dichloroethane was added dropwise with stirring at room temperature in an argon atmosphere and stirred at the same temperature as above for 5 hours.

After the completion of the reaction, 5 ml of 2-propanol was added and stirred at room temperature for 14 hours, and then, the reaction solution was concentrated under reduced pressure. The obtained residue was subjected to silica gel column chromatography (elution solvent: n-hexane:ethyl acetate=87:13 to 0:100 (V/V)), and a fraction containing the compound of interest was concentrated under reduced pressure to obtain 293 mg of the title compound (yield: 71%) (containing the tautomer) as a pale yellow solid.

Mass spectrum (DUIS, m/z): 525 [M+1]$^+$.

$^1$H-NMR spectrum (400 MHz, DMSO-$d_6$) δ: 15.71 (s, 0.3H), 9.79 (s, 0.3H), 9.75 (s, 0.7H), 8.01-7.42 (m, total 5H), 5.82 (s, 0.3H), 4.85 (s, 0.6H), 4.78 (s, 1.4H), 4.47-4.38 (m, total 2H), 4.18 (s, 1.4H), 2.57-2.41 (m, total 2H), 2.33-2.12 (m, total 2H), 1.93-1.81 (m, total 2H), 1.75 & 1.64 (s, total 6H), 1.38-1.31 (m, total 3H), 0.11 & 0.08 (s, total 9H)

Reference Example 21

(R)-Methyl 3-amino-3-phenylpropanoate hydrochloride

[Chemical Formula 156]

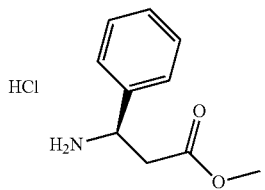

To a solution of 2.01 g (12.2 mmol) of (R)-3-amino-3-phenylpropanoic acid [purchased from Shanghai HC Biotech Co., Ltd.] in 100 ml of dehydrated methanol, 1.32 ml (18.2 mmol) of thionyl chloride was added dropwise with stirring at room temperature in a nitrogen atmosphere and then stirred at the same temperature as above for 24 hours. Then, the temperature was raised to 65° C., and the resultant was stirred for 9.5 hours.

After standing to cool, the reaction solution was concentrated under reduced pressure, diethyl ether was added to the obtained concentration residue and ultrasonicated, and the deposited solid was collected by filtration and dried under reduced pressure to obtain 2.55 g of the title compound (yield: 97%) as a white solid.

Mass spectrum (DUIS, m/z): 180 [M+1]$^+$.

$^1$H-NMR spectrum (400 MHz, DMSO-$d_6$) δ: 8.67 (br s, 3H), 7.57-7.50 (m, 2H), 7.45-7.36 (m, 3H), 4.58 (dd, J=6.0, 8.6 Hz, 1H), 3.35 (br s, 3H), 3.20 (dd, J=6.0, 16.3 Hz, 1H), 3.00 (dd, J=8.6, 16.3 Hz, 1H).

Reference Example 22

(R)-Methyl 3-phenyl-3-(2,2,2-trifluoroacetamido)propanoate

[Chemical Formula 157]

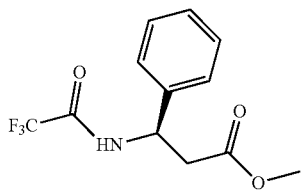

To a solution of 2.55 g (11.8 mmol) of (R)-methyl 3-amino-3-phenylpropanoate hydrochloride synthesized in the similar manner as in Reference Example 21 in 50 ml of dichloromethane, 10.5 ml (60.3 mmol) of DIPEA and 1.75 ml (12.4 mmol) of trifluoroacetic anhydride were added dropwise in this order with stirring at 0° C. in an argon atmosphere, stirred at the same temperature as above for 2 hours, and further stirred overnight at room temperature.

After the completion of the reaction, the reaction solution was concentrated under reduced pressure. Ethyl acetate was added to the concentration residue, washed with a saturated aqueous solution of sodium bicarbonate and a saturated aqueous solution of sodium chloride in this order, then dried over anhydrous magnesium sulfate, and filtered, and the filtrate was concentrated under reduced pressure. The obtained residue was subjected to silica gel column chromatography (elution solvent: n-hexane:ethyl acetate=91:9 to 70:30 (V/V)), and a fraction containing the compound of interest was concentrated under reduced pressure to obtain 2.75 g of the title compound (yield: 85%) as a white solid.

Mass spectrum (DUIS, m/z): 276 [M+1]$^+$.

$^1$H-NMR spectrum (400 MHz, CDCl$_3$) δ: 7.80-7.64 (m, 1H), 7.39-7.25 (m, 5H), 5.46-5.39 (m, 1H), 3.65 (s, 3H), 3.00 (dd, J=5.5, 16.2 Hz, 1H), 2.93 (dd, J=5.5, 16.2 Hz, 1H).

Reference Example 23

(R)-4-Amino-2-methyl-4-phenylbutan-2-ol

[Chemical Formula 158]

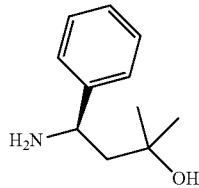

To a solution of 506 mg (1.84 mmol) of (R)-methyl 3-phenyl-3-(2,2,2-trifluoroacetamido)propanoate synthesized in the similar manner as in Reference Example 22 in 5 ml of dehydrated THF, 6.60 ml (9.24 mmol) of 1.4 M methyl magnesium bromide/THF solution was added dropwise with stirring at room temperature in an argon atmosphere and stirred at room temperature for 3.5 hours.

After the completion of the reaction, 10 ml of a saturated aqueous solution of ammonium chloride was added dropwise to the reaction solution under ice cooling, brought back to room temperature, and stirred for a while. Dichloromethane and water, and further an aqueous solution of dilute sodium hydroxide were added to the reaction solution to adjust the pH of the aqueous layer to 10, followed by separation into an aqueous layer and an organic layer. The aqueous layer was subjected to extraction with dichloromethane, all of the obtained organic layers were dried over anhydrous sodium sulfate and filtered, and the filtrate was concentrated under reduced pressure. The obtained residue was subjected to silica gel column chromatography (DNH silica gel, elution solvent: 1,2-dichloroethane:methanol=100:0 to 95:5 (V/V)), and a fraction containing (R)-2,2,2-trifluoro-N-(3-hydroxy-3-methyl-1-phenylbutyl)acetamide was concentrated under reduced pressure to obtain a concentration residue.

To a solution of 427 mg of the obtained concentration residue in 5 ml of ethanol, 64.6 mg (1.71 mmol) of sodium borohydride was added in several divided portions at room temperature and then stirred at room temperature for 14 hours. 77.0 mg (2.04 mmol) of sodium borohydride was further added in several divided portions, stirred at room temperature for 2 hours, and then stirred at 75° C. for 2 hours.

After the completion of the reaction, the reaction solution was cooled in ice, and 10 ml of a saturated aqueous solution of ammonium chloride was added thereto dropwise and then stirred at room temperature. Dichloromethane and water were added thereto, and an aqueous solution of dilute sodium hydroxide was added thereto to adjust the pH of the aqueous layer to 10, followed by separation into an aqueous layer and an organic layer. The aqueous layer was subjected to extraction with dichloromethane, all of the obtained organic layers were dried over anhydrous sodium sulfate and filtered, and the filtrate was concentrated under reduced pressure. The concentration residue was subjected to silica gel column chromatography (DNH silica gel, elution solvent: 1,2-dichloroethane:methanol=100:0 to 95:5 (V/V)), and a fraction containing the compound of interest was concentrated under reduced pressure to obtain 160 mg of the title compound (yield: 49%) as a colorless oil.

Mass spectrum (DUIS, m/z): 180 [M+1]$^+$.
$^1$H-NMR spectrum (400 MHz, DMSO-d$_6$) δ: 7.37-7.26 (m, 4H), 7.21-7.15 (m, 1H), 4.05 (dd, J=2.8, 10.7 Hz, 1H), 1.66 (dd, J=10.7, 14.0 Hz, 1H), 1.52 (dd, J=2.8, 14.0 Hz, 1H), 1.22 (s, 3H), 1.10 (s, 3H).

Reference Example 24

(S)-tert-Butyl [2-(difluoromethoxy)-1-phenylethyl]carbamate

[Chemical Formula 159]

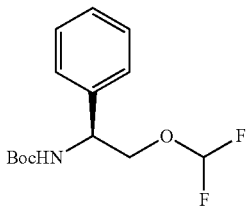

To a solution of 1.00 g (4.21 mmol) of (S)-tert-butyl (2-hydroxy-1-phenylethyl)carbamate [purchased from Novo Cherry Ltd.] in 30 ml of dehydrated acetonitrile, 165 mg (0.866 mmol) of copper(I) iodide was added at room temperature in an argon atmosphere and stirred at the same temperature as above for 30 minutes. Subsequently, a solution of 0.87 ml (8.4 mmol) of 2-(fluorosulfonyl)difluoroacetic acid in 10 ml of dehydrated acetonitrile was dividedly added (1 ml each) at 45° C. over 40 minutes and stirred at the same temperature as above for 1 hour.

After the completion of the reaction, the reaction solution allowed to cool to room temperature was concentrated under reduced pressure. Water and ethyl acetate were added to the obtained concentration residue, followed by extraction from the mixed solution with ethyl acetate. The obtained organic layer was washed with water, then dried over anhydrous magnesium sulfate, filtered, and concentrated under reduced pressure. The obtained concentration residue was subjected to silica gel chromatography (elution solvent: n-hexane:ethyl acetate=95:5 to 50:50 (V/V)), and a fraction containing the compound of interest was concentrated under reduced pressure. The obtained concentration residue was subjected again to silica gel chromatography (elution solvent: n-hexane:ethyl acetate=95:5 to 50:50 (V/V)), and a fraction containing the compound of interest was concentrated under reduced pressure and dried under reduced pressure to obtain 213 mg of the title compound (yield: 18%) as a yellow solid.

Mass spectrum (CI, m/z): 288 [M+1]$^+$.
$^1$H-NMR spectrum (400 MHz, DMSO-d$_6$) δ: 7.55 (d, J=8.7 Hz, 1H), 7.37-7.24 (m, 5H), 6.67 (t, J=75.9 Hz, 1H), 4.83-4.73 (m, 1H), 3.95-3.86 (m, 2H), 1.42-1.23 (m, 9H).

Reference Example 25

(S)-2-(Difluoromethoxy)-1-phenylethanamine trifluoroacetate

[Chemical Formula 160]

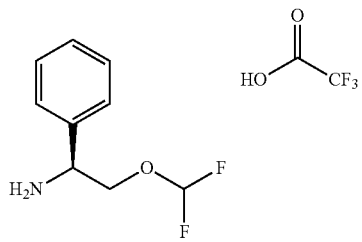

To a solution of 210 mg (0.731 mmol) of (S)-tert-butyl [2-(difluoromethoxy)-1-phenylethyl]carbamate synthesized in the similar manner as in Reference Example 24 in 4 ml of dehydrated dichloromethane, 1 ml of trifluoroacetic acid was added at room temperature in an argon atmosphere and stirred at the same temperature as above for 2 hours.

After the completion of the reaction, the reaction solution was concentrated under reduced pressure and dried under reduced pressure to obtain 210 mg of the title compound (yield: 95%) as a yellow oil.

$^1$H-NMR spectrum (400 MHz, DMSO-d$_6$) δ: 8.59 (br s, 3H), 7.54-7.40 (m, 5H), 6.76 (t, J=74.8 Hz, 1H), 4.70-4.59 (m, 1H), 4.19-4.11 (m, 2H).

Reference Example 26

(S)-2-Ethoxy-1-phenylethanamine

[Chemical Formula 161]

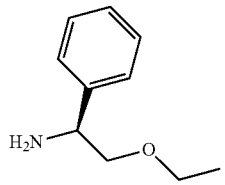

To a solution of 1.40 g (10.2 mmol) of (S)-2-amino-2-phenylethanol and 3.0 ml (15 mmol) of 1,4,7,10,13-pentaoxacyclopentadecane in 10 ml of dehydrated THF, 481 mg (11.0 mmol) of 55% sodium hydride was dividedly added with stirring at room temperature in an argon atmosphere and stirred at the same temperature as above until foaming settled. Subsequently, 0.82 ml (10 mmol) of ethyl iodide was added dropwise at room temperature and stirred at the same temperature as above for 24 hours.

After the completion of the reaction, water and diethyl ether were added to the reaction solution and then the aqueous layer and the organic layer were separated. The aqueous layer was subjected to extraction with diethyl ether, then all of the organic layers were washed with a saturated aqueous solution of sodium chloride, dried over anhydrous sodium sulfate, and filtered, and the filtrate was concentrated under reduced pressure. The obtained residue was subjected to silica gel column chromatography (DNH silica gel, elution solvent: 1,2-dichloroethane:methanol=100:0 to 95:5 (V/V)), and a fraction containing the compound of interest was concentrated under reduced pressure to obtain 1.17 g of the title compound (yield: 69%) as a pale yellow oil.

Mass spectrum (CI, m/z): 166 [M+1]$^+$.

$^1$H-NMR spectrum (400 MHz, DMSO-d$_6$) δ: 7.39-7.33 (m, 2H), 7.33-7.25 (m, 2H), 7.25-7.19 (m, 1H), 4.01 (dd, J=4.9, 8.0 Hz, 1H), 3.53-3.35 (m, 3H), 3.28 (dd, J=8.0, 9.3 Hz, 1H), 1.82 (br s, 2H), 1.09 (t, J=7.0 Hz, 3H).

Reference Example 27

(R)-3-Methoxy-1-phenylpropan-1-amine

[Chemical Formula 162]

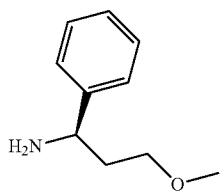

To a solution of 1.53 g (10.1 mmol) of (R)-3-amino-3-phenylpropan-1-ol [purchased from Ark Pharm, Inc.] and 3.0 ml (15 mmol) of 1,4,7,10,13-pentaoxacyclopentadecane in 10 ml of dehydrated THF, 473 mg (10.9 mmol) of 55% sodium hydride was dividedly added with stirring at room temperature in an argon atmosphere and stirred at the same temperature as above until foaming settled. Subsequently, 0.62 ml (10 mmol) of methyl iodide was added thereto dropwise at 0° C. and then stirred at room temperature for 17 hours.

After the completion of the reaction, water and diethyl ether were added to the reaction solution and then the aqueous layer and the organic layer were separated. The aqueous layer was subjected to extraction with diethyl ether, then all of the organic layers were washed with a saturated aqueous solution of sodium chloride, dried over anhydrous sodium sulfate, and filtered, and the filtrate was concentrated under reduced pressure. The obtained residue was subjected to silica gel column chromatography (DNH silica gel, elution solvent: 1,2-dichloroethane:methanol=100:0 to 95:5 (V/V)), and a fraction containing the compound of interest was concentrated under reduced pressure to obtain 1.49 g of the title compound (yield: 89%) as a colorless oil.

Mass spectrum (CI, m/z): 166 [M+1]$^+$.

$^1$H-NMR spectrum (400 MHz, DMSO-d$_6$) δ: 7.35-7.26 (m, 4H), 7.24-7.15 (m, 1H), 3.85 (dd, J=6.4, 7.4 Hz, 1H), 3.38-3.20 (m, 2H), 3.19 (s, 3H), 1.93-1.63 (m, 4H).

Reference Example 28

2-(Benzo[d][1,3]dioxol-4-yl)-2-[(tert-butoxycarbonyl)amino]acetic acid

[Chemical Formula 163]

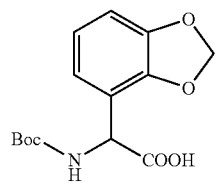

To a solution of 7.09 g (47.2 mmol) of benzo[d][1,3]dioxole-4-carbaldehyde in 15 ml of methanol, 67.5 ml (472 mmol) of 7 M aqueous ammonia solution/methanol solution was gradually added at room temperature and then stirred at room temperature for 18 minutes. The reaction solution was cooled in ice water, and 14.1 ml (113 mmol) of trimethylsilane carbonitrile was added dropwise. After the completion of the dropwise addition, the resultant was stirred overnight at room temperature.

After the completion of the reaction, the reaction solution was concentrated under reduced pressure to obtain a concentration residue.

To 9.30 g of the obtained concentration residue, 17 ml of acetic acid and 66.7 ml (776 mmol) of concentrated hydrochloric acid were added and stirred for 9 hours while heated to reflux.

After standing to cool, the reaction solution was concentrated under reduced pressure to obtain a concentration residue.

To 8.33 g of the obtained concentration residue, 35.2 ml (141 mmol) of a 4 N aqueous sodium hydroxide solution, 65 ml of 1,4-dioxane, and 14.7 ml (64.1 mmol) of di-tert-butyl dicarbonate were added in this order at room temperature and stirred at room temperature.

After the completion of the reaction, the reaction solution was concentrated under reduced pressure, 100 ml of dichloromethane was added thereto, and then, the pH was adjusted to 1.75 by using concentrated hydrochloric acid. Methanol was added thereto until insoluble matter was dissolved, and then the aqueous layer and the organic layer were separated. The aqueous layer was subjected to extraction with 100 ml of dichloromethane twice, all of the obtained organic layers were dried over anhydrous magnesium sulfate and filtered, and the filtrate was concentrated under reduced pressure. The obtained residue was subjected to silica gel column chromatography (elution solvent: ethyl acetate), and a fraction containing the compound of interest was concentrated under reduced pressure. The obtained residue was subjected again to silica gel column chromatography (elution solvent: ethyl acetate), and a fraction containing the compound of interest was concentrated under reduced pressure to obtain 10.22 g of the title compound (yield: 73% [3 steps]) as a black viscous liquid.

Mass spectrum (DUIS, m/z): 296 [M+1]$^+$.

$^1$H-NMR spectrum (400 MHz, DMSO-d$_6$) δ: 13.24-12.32 (m, 1H), 7.48 (d, J=8.5 Hz, 1H), 6.88-6.77 (m, 3H), 6.04-6.01 (m, 2H), 5.22 (d, J=8.5 Hz, 1H), 1.38 (s, 9H).

Reference Example 29

Methyl 2-(benzo[d][1,3]dioxol-4-yl)-2-[(tert-butoxycarbonyl)amino]acetate

[Chemical Formula 164]

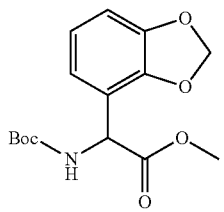

To a solution of 3.93 g (13.3 mmol) of 2-(benzo[d][1,3]dioxol-4-yl)-2-[(tert-butoxycarbonyl)amino]acetic acid synthesized in the similar manner as in Reference Example 28 in 8 ml of DMF, 3.86 g (27.9 mmol) of potassium carbonate and 1.3 ml (21 mmol) of methyl iodide were added in this order at room temperature, stirred at the same temperature as above for 1 hour, and then left standing overnight.

After the completion of the reaction, the reaction solution was poured to 100 ml of a saturated aqueous solution of sodium chloride, and water was added until insoluble matter was dissolved, followed by extraction with toluene twice. The obtained organic layer was dried over anhydrous sodium sulfate and filtered, and then, the filtrate was concentrated under reduced pressure. The obtained residue was subjected to silica gel column chromatography (elution solvent: hexane:ethyl acetate=95:5 to 70:30 (V/V)), and a fraction containing the compound of interest was concentrated under reduced pressure to obtain 2.83 g of the title compound (yield: 69%) as a white solid.

Mass spectrum (EI, m/z): 309 [M]$^+$.

$^1$H-NMR spectrum (400 MHz, CDCl$_3$) δ: 6.85-6.76 (m, 3H), 6.03-5.97 (m, 2H), 5.71-5.61 (m, 1H), 5.49-5.39 (m, 1H), 3.73 (s, 3H), 1.47-1.39 (m, 9H).

Reference Example 30 tert-Butyl [1-(benzo[d][1,3]dioxol-4-yl)-2-hydroxyethyl]carbamate

[Chemical Formula 165]

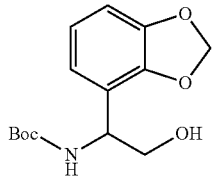

To a solution of 2.82 g (9.13 mmol) of methyl 2-(benzo[d][1,3]dioxol-4-yl)-2-[(tert-butoxycarbonyl)amino]acetate synthesized in the similar manner as in Reference Example 29 in 30 ml of dehydrated THF, 716 mg (32.9 mmol) of lithium borohydride was added under cooling in ice water and stirred at room temperature.

After the completion of the reaction, the reaction solution was poured to 150 ml of a saturated aqueous solution of ammonium chloride, followed by extraction with ethyl acetate. The obtained organic layer was dried over anhydrous magnesium sulfate and filtered, and the filtrate was concentrated under reduced pressure. Diethyl ether and n-hexane were added to the concentration residue, and the formed solid was filtered, washed by sousing with diethyl ether, and then dried under reduced pressure to obtain 1.54 g of the title compound (yield: 60%) as a white solid.

Mass spectrum (CI, m/z): 282 [M+1]$^+$.

$^1$H-NMR spectrum (400 MHz, DMSO-d$_6$) δ: 7.13 (d, J=8.3 Hz, 1H), 6.84-6.75 (m, 3H), 6.02-5.96 (m, 2H), 4.82 (t, J=5.6 Hz, 1H), 4.74-4.64 (m, 1H), 3.54-3.40 (m, 2H), 1.37 (s, 9H).

Reference Example 31

2-Amino-2-(benzo[d][1,3] dioxol-4-yl)ethanol

[Chemical Formula 166]

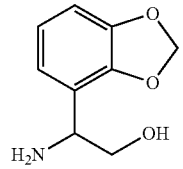

To a solution of 1.04 g (3.69 mmol) of tert-butyl[1-(benzo[d][1,3]dioxol-4-yl)-2-hydroxyethyl]carbamate synthesized in the similar manner as in Reference Example 30 in 17 ml of dichloromethane, 1.3 ml (11 mmol) of 2,6-lutidine and 2.0 ml (11 mmol) of trimethylsilyl trifluoromethanesulfonate were added in this order under cooling in ice water and stirred at the same temperature as above for 3 hours.

After the completion of the reaction, 14 ml of a saturated aqueous solution of sodium bicarbonate and 14 ml of dichloromethane were added to the reaction solution. The pH was adjusted to 10 to 11 by further adding a 4 N aqueous sodium hydroxide solution, followed by separation into an aqueous layer and an organic layer. The aqueous layer was subjected to extraction with dichloromethane twice, all of the obtained organic layers were dried over anhydrous sodium carbonate and filtered, and then, the filtrate was concentrated under reduced pressure. 2.5 ml of methanol and 2.5 ml of triethylamine were added to the obtained residue and stirred at room temperature for 7 hours. 5 ml of methanol was further added, then applied to a microwave reaction apparatus, and reacted at 80° C. for 1 hour. After the completion of the reaction, the reaction solution was concentrated under reduced pressure to obtain 0.696 g of the title compound (containing impurities) as a pale yellow solid.

$^1$H-NMR spectrum (400 MHz, DMSO-d$_6$) δ: 6.95-6.91 (m, 1H), 6.81-6.75 (m, 2H), 5.98 (d, J=0.9 Hz, 1H), 5.95 (d, J=0.9 Hz, 1H), 4.86-4.63 (m, 1H), 3.96 (dd, J=4.4, 7.9 Hz, 1H), 3.51 (dd, J=4.4, 10.2 Hz, 1H), 3.40-3.21 (m, 1H), 1.98-1.72 (m, 2H).

Reference Example 32

1-(Benzo[d][1,3]dioxol-4-yl)-2-[(tert-butyldimethyl-silyl)oxy]ethanamine

[Chemical Formula 167]

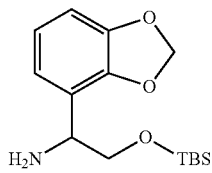

To a solution of 0.691 g of 2-amino-2-(benzo[d][1,3]dioxol-4-yl)ethanol (containing impurities) synthesized in the similar manner as in Reference Example 31 by using 1.04 g (3.69 mmol) of tert-butyl [1-(benzo[d][1,3]dioxol-4-yl)-2-hydroxyethyl] carbamate synthesized in the similar manner as in Reference Example 30, and 95.9 mg (0.785 mmol) of 4-(N,N-dimethylamino)pyridine in 7 ml of dichloromethane, 1.10 ml (7.89 mmol) of triethylamine and 580 mg (3.85 mmol) of chloro(tert-butyl)dimethylsilane were added and stirred at room temperature for 14 hours.

After the completion of the reaction, water and dichloromethane were added to the reaction solution, and then the aqueous layer and the organic layer were separated. The aqueous layer was subjected to extraction with dichloromethane twice, all of the obtained organic layers were dried over anhydrous sodium carbonate and filtered, and then, the filtrate was concentrated under reduced pressure. The obtained residue was subjected to silica gel column chromatography (DNH silica gel, elution solvent: 1,2-dichloroethane:methanol=100:0 to 95:5 (V/V)), and a fraction containing the compound of interest was concentrated under reduced pressure. The obtained residue was subjected again to silica gel column chromatography (elution solvent: 1,2-dichloroethane:methanol=100:0 to 95:5 (V/V)), and a fraction containing the compound of interest was concentrated under reduced pressure to obtain 0.810 g of the title compound (74% [2 steps]) as a pale yellow oil.

$^1$H-NMR spectrum (400 MHz, DMSO-$d_6$) δ: 6.95-6.91 (m, 1H), 6.81-6.76 (m, 2H), 5.97 (d, J=0.9 Hz, 1H), 5.95 (d, J=0.9 Hz, 1H), 3.99 (dd, J=5.5, 7.0 Hz, 1H), 3.64 (dd, J=5.5, 9.7 Hz, 1H), 3.53 (dd, J=7.0, 9.7 Hz, 1H), 1.81 (br s, 2H), 0.82 (s, 9H), −0.04 (s, 3H), −0.05 (s, 3H).

Reference Example 33

4-Amino-4-phenyl-2-butyn-1-ol hydrochloride

[Chemical Formula 168]

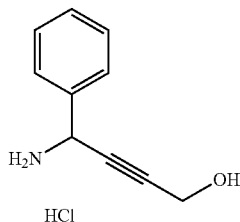

To a solution of 1.01 ml (7.28 mmol) of 2-(2-propynyloxy)tetrahydro-2H-pyran in 20 ml of dehydrated THF, 5.65 ml (7.35 mmol) of 1.3 mol/l lithium bis(trimethylsilyl)amide/THF solution was added with stirring at −78° C. in an argon atmosphere and stirred at the same temperature as above for 15 minutes. Subsequently, 1.02 g (4.87 mmol) of (E)-N-benzylidene-2-methylpropane-2-sulfinamide [synthesized according to the method described in Org. Lett., 2005, 7, 5493-5496] was added at −78° C., stirred at the same temperature as above for 1 hour, and then stirred for 1 hour after the temperature was raised to room temperature.

After the completion of the reaction, a saturated aqueous solution of ammonium chloride was added to the reaction solution, followed by extraction from the mixed solution with ethyl acetate. The obtained organic layer was washed with a saturated aqueous solution of sodium chloride, dried over anhydrous magnesium sulfate, filtered, and concentrated under reduced pressure to obtain a concentration residue.

To a solution of 2.10 g of the obtained concentration residue in 20 ml of methanol, 4.85 ml (19.4 mmol) of 4 N hydrogen chloride/1,4-dioxane solution was added with stirring at 0° C. in an argon atmosphere and stirred for 3 hours after the temperature was raised to room temperature.

After the completion of the reaction, the reaction solution was concentrated under reduced pressure. For the obtained concentration residue, crystallization was performed with diisopropyl ether/methanol, and the deposited solid was collected by filtration, washed by sousing with diisopropyl ether, and then dried under reduced pressure to obtain 0.93 g of the title compound (yield: 97% [2 steps]) as a brown solid.

$^1$H-NMR spectrum (400 MHz, DMSO-$d_6$) δ: 8.97 (br s, 3H), 7.66-7.60 (m, 2H), 7.51-7.40 (m, 3H), 5.78-5.07 (m, 2H), 4.19 (d, J=1.8 Hz, 2H).

Reference Example 34

(S)-2-[(tert-Butoxycarbonyl)amino]-2-phenylethyl acetate

[Chemical Formula 169]

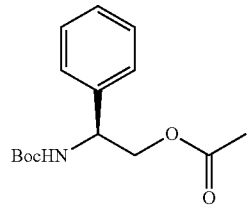

To 10 g (42 mmol) of (S)-tert-butyl(2-hydroxy-1-phenylethyl)carbamate [purchased from Novo Chemy Ltd.] and 7.1 ml (51 mmol) of triethylamine in 100 ml of dehydrated dichloromethane, 4.80 ml (50.8 mmol) of acetic anhydride was added dropwise at 0° C. in an argon atmosphere and stirred for 20 hours after the temperature was raised to room temperature.

After the completion of the reaction, 100 ml of a saturated aqueous solution of sodium bicarbonate was added to the reaction solution and then the aqueous layer and the organic layer were separated. The aqueous layer was subjected to extraction with dichloromethane (100 ml) twice, and all of the obtained organic layers were dried over anhydrous magnesium sulfate, filtered, and concentrated under reduced pressure. The obtained residue was subjected to silica gel column chromatography (elution solvent: n-hexane:ethyl acetate=93:7 to 72:28 (V/V)), and a fraction containing the compound of interest was concentrated under reduced pressure and dried under reduced pressure to obtain 10.5 g of the title compound (yield: 89%) as a white solid.

$^1$H-NMR spectrum (400 MHz, DMSO-d$_6$) δ: 7.53 (d, J=8.9 Hz, 1H), 7.38-7.31 (m, 4H), 7.30-7.22 (m, 1H), 4.87-4.74 (m, 1H), 4.15 (dd, J=4.8, 11.0 Hz, 1H), 4.02 (dd, J=8.8, 11.0 Hz, 1H), 1.98 (s, 3H), 1.43-1.20 (m, 9H).

Reference Example 35

(S)-2-Amino-2-phenylethyl acetate hydrochloride

[Chemical Formula 170]

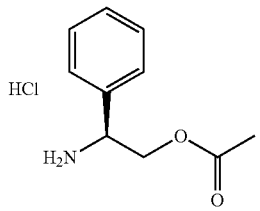

To a solution of 10.5 g (37.6 mmol) of (S)-2-[(tert-butoxycarbonyl)amino]-2-phenylethyl acetate synthesized in the similar manner as in Reference Example 34 in 110 ml of dehydrated dichloromethane, 47 ml (188 mmol) of 4 N hydrogen chloride/1,4-dioxane solution was added at room temperature in an argon atmosphere and stirred for 14 hours.

After the completion of the reaction, the reaction solution was concentrated under reduced pressure. Diethyl ether was added to the obtained concentration residue, ultrasonicated, then filtered, and dried under reduced pressure to obtain 6.78 g of the title compound (yield: 84%) as a white solid.

Mass spectrum (DUIS, m/z): 180 [M (Free form)+1]$^+$.

$^1$H-NMR spectrum (400 MHz, DMSO-d$_6$) δ: 8.80 (br s, 3H), 7.59-7.52 (m, 2H), 7.49-7.38 (m, 3H), 4.58 (dd, J=6.1, 6.1 Hz, 1H), 4.39-4.29 (m, 2H), 2.06 (s, 3H).

Reference Example 36

(S)-tert-Butyl [2-(benzyloxy)-1-phenylethyl]carbamate

[Chemical Formula 171]

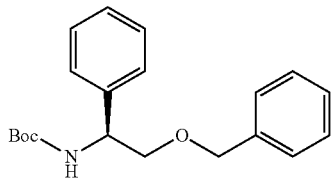

To a solution of 10.01 g (42.2 mmol) of (S)-tert-butyl (2-hydroxy-1-phenylethyl)carbamate [purchased from Novo Chemy Ltd.] in 200 ml of dehydrated DMF, 2.58 g (64.5 mmol) of 60% sodium hydride was added at 0° C. in an argon atmosphere and stirred at the same temperature as above for 20 minutes. Subsequently, 5.50 ml (46.3 mmol) of benzyl bromide was added at 0° C. and stirred at the same temperature as above for 1 hour.

After the completion of the reaction, a saturated aqueous solution of ammonium chloride was added to the reaction solution, followed by extraction from the mixed solution with ethyl acetate. The obtained organic layer was washed with water three times, and a saturated aqueous solution of sodium chloride once, then dried over anhydrous magnesium sulfate, filtered, and concentrated under reduced pressure. The obtained concentration residue was subjected to silica gel chromatography (elution solvent: n-hexane:ethyl acetate=95:5 to 80:20 (V/V)), and a fraction containing the compound of interest was concentrated under reduced pressure and dried under reduced pressure to obtain 9.94 g of the title compound (yield: 72%) as a white solid.

$^1$H-NMR spectrum (400 MHz, DMSO-d$_6$) δ: 7.44 (d, J=8.7 Hz, 1H), 7.37-7.21 (m, 10H), 4.84-4.73 (m, 1H), 4.49 (s, 2H), 3.61-3.46 (m, 2H), 1.46-1.15 (m, 9H).

Reference Example 37

(S)-Ethyl 5-{[2-(benzyloxy)-1-phenylethyl]carbamoyl}-6,6-dimethyl-3-[1-(trimethylsilyl)cyclobutanecarboxamido]-5,6-dihydropyrrolo[3,4-c]pyrazole-2(4H)-carboxylate

[Chemical Formula 172]

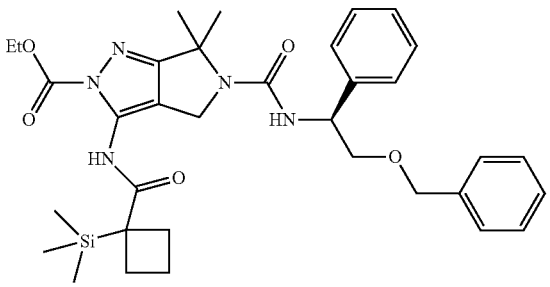

To a solution of 9.94 g (30.4 mmol) of (S)-tert-butyl[2-(benzyloxy)-1-phenylethyl]carbamate synthesized in the similar manner as in Reference Example 36 in 120 ml of dichloromethane, 30 ml of trifluoroacetic acid was added at room temperature in an argon atmosphere and stirred at the same temperature as above for 1 hour.

After the completion of the reaction, the reaction solution was concentrated under reduced pressure and dried under reduced pressure to obtain 10.25 g of a concentration residue.

To a solution of 3.02 g of a portion of the obtained concentration residue and 3.10 ml (17.8 mmol) of DIPEA in 50 ml of dehydrated 1,4-dioxane, 1.95 g (4.42 mmol) of ethyl 5-(chlorocarbonyl)-6,6-dimethyl-3-[1-(trimethylsilyl) cyclobutanecarboxamido]-5,6-dihydropyrrolo[3,4-c]pyrazole-2(4H)-carboxylate synthesized in the similar manner as in Reference Example 3 was added at room temperature in an argon atmosphere and stirred at 60° C. for 8 hours.

After the completion of the reaction, water was added to the reaction solution, followed by extraction from the mixed solution with ethyl acetate. The obtained organic layer was washed with water and a saturated aqueous solution of sodium chloride in this order, then dried over anhydrous magnesium sulfate, filtered, and concentrated under reduced pressure. The obtained concentration residue was subjected to silica gel chromatography (elution solvent: n-hexane:ethyl acetate=90:10 to 50:50 (V/V)), and a fraction containing the compound of interest was concentrated under reduced pressure and dried under reduced pressure to obtain 1.86 g of the title compound (yield: 67%) as a white foam.

Mass spectrum (DUIS, m/z): 632 [M+1]$^+$.

$^1$H-NMR spectrum (400 MHz, DMSO-$d_6$) δ: 9.80 (s, 1H), 7.43-7.18 (m, 10H), 6.56 (d, J=8.2 Hz, 1H), 5.11-5.03 (m, 1H), 4.66 (d, J=13.8 Hz, 1H), 4.60 (d, J=13.8 Hz, 1H), 4.52 (s, 2H), 4.42 (q, J=7.1 Hz, 2H), 3.74 (dd, J=8.0, 10.0 Hz, 1H), 3.63 (dd, J=6.0, 10.0 Hz, 1H), 2.58-2.52 (m, 2H), 2.31-2.22 (m, 2H), 1.95-1.84 (m, 2H), 1.62 (s, 3H), 1.55 (s, 3H), 1.34 (t, J=7.1 Hz, 3H), 0.12 (s, 9H).

Reference Example 38

(S)-Ethyl 5-[(2-hydroxy-1-phenylethyl)carbamoyl]-6,6-dimethyl-3-[1-(trimethylsilyl)cyclobutanecarboxamido]-5,6-dihydropyrrolo[3,4-c]pyrazole-2(4H)-carboxylate

[Chemical Formula 173]

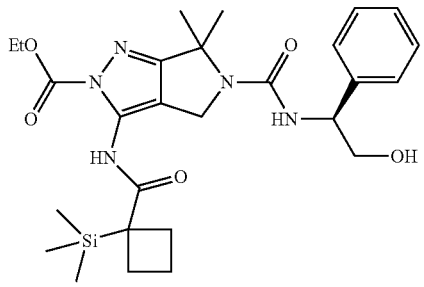

To a solution of 1.86 g (2.94 mmol) of (S)-ethyl 5-{[2-(benzyloxy)-1-phenylethyl]carbamoyl}-6,6-dimethyl-3-[1-(trimethylsilyl)cyclobutanecarboxamido]-5,6-dihydropyrrolo[3,4-c]pyrazole-2 (4H)-carboxylate synthesized in the similar manner as in Reference Example 37 in 30 ml of 2-propanol, 0.19 g of 20% palladium hydroxide/carbon (containing 50 wt % water) was added at room temperature in an argon atmosphere and then, after replacement with a hydrogen atmosphere under reduced pressure, stirred at room temperature for 1.5 hours. After replacement with an argon atmosphere, the reaction solution was filtered through celite. The solid on the celite was washed with ethyl acetate, and then, the filtrate was concentrated under reduced pressure. To a solution of the obtained concentration residue in 30 ml of 2-propanol, 0.19 g of 20% palladium hydroxide/carbon (containing 50 wt % water) was added at room temperature in an argon atmosphere and after replacement with a hydrogen atmosphere under reduced pressure, stirred at room temperature for 3.5 hours.

After the completion of the reaction, replacement with an argon atmosphere was performed, and then, the reaction solution was filtered through celite. The solid on the celite was washed with ethyl acetate, and the filtrate was concentrated under reduced pressure. The obtained concentration residue was subjected to silica gel chromatography (elution solvent: n-hexane:ethyl acetate=80:20 to 60:40 (V/V)), and a fraction containing the compound of interest was concentrated under reduced pressure and dried under reduced pressure to obtain 1.34 g of the title compound (yield: 84%) as a white foam.

Mass spectrum (DUIS, m/z): 542 [M+1]$^+$.

$^1$H-NMR spectrum (400 MHz, DMSO-$d_6$) δ: 9.81 (s, 1H), 7.38-7.26 (m, 4H), 7.23-7.17 (m, 1H), 6.36 (d, J=7.5 Hz, 1H), 4.87 (t, J=6.0 Hz, 1H), 4.82-4.75 (m, 1H), 4.66 (s, 2H), 4.42 (q, J=7.2 Hz, 2H), 3.67-3.55 (m, 2H), 2.60-2.52 (m, 2H), 2.31-2.21 (m, 2H), 1.96-1.85 (m, 2H), 1.62 (s, 3H), 1.54 (s, 3H), 1.34 (t, J=7.2 Hz, 3H), 0.13 (s, 9H).

Reference Example 39

(S)-Benzyl {2-[(tert-butoxycarbonyl)amino]-2-phenylethyl}succinate

[Chemical Formula 174]

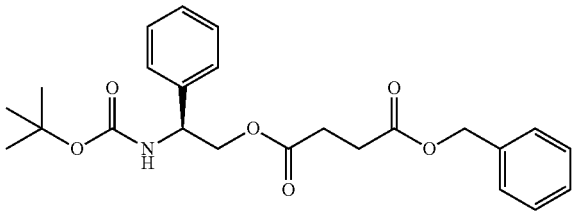

To a solution of 496 mg (2.09 mmol) of (S)-tert-butyl (2-hydroxy-1-phenylethyl)carbamate [purchased from Novo Chemy Ltd.] and 227 mg (2.26 mmmol) of succinic anhydride in 3 ml of dehydrated DMF, 26.2 mg (0.214 mmol) of 4-dimethylaminopyridine was added at room temperature in a nitrogen atmosphere and stirred at room temperature for 3 hours. Subsequently, 0.270 ml (2.27 mmol) of benzyl bromide was added at room temperature and stirred at room temperature for 15 hours.

After the completion of the reaction, toluene was added to the reaction solution, the organic layer obtained after washing with water twice and a saturated aqueous solution of sodium chloride once was dried over anhydrous magnesium sulfate and filtered, and then, the filtrate was concentrated under reduced pressure. The obtained concentration residue was subjected to silica gel column chromatography (elution solvent: n-hexane:ethyl acetate=86:14 to 65:35 (V/V)), and a fraction containing the compound of interest was concentrated under reduced pressure to obtain 872 mg of the title compound (yield: 98%) as a white solid.

Mass spectrum (CI, m/z): 428 [M+1]$^+$.

$^1$H-NMR spectrum (400 MHz, CDCl$_3$) δ: 7.39-7.25 (m, 10H), 5.21-5.08 (m, 3H), 5.04-4.90 (m, 1H), 4.39-4.21 (m, 2H), 2.70-2.59 (m, 4H), 1.42 (br s, 9H).

Reference Example 40

(S)-2-Amino-2-phenylethyl benzyl succinate trifluoroacetate

[Chemical Formula 175]

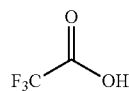

-continued

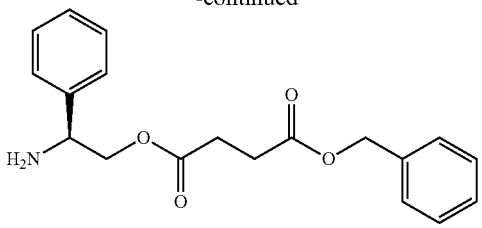

To a solution of 608 mg (1.42 mmol) of (S)-benzyl{2-[(tert-butoxycarbonyl)amino]-2-phenylethyl}succinate synthesized in the similar manner as in Reference Example 39 in 10 ml of dichloromethane, 2.0 ml (26 mmol) of trifluoroacetic acid was added at room temperature in a nitrogen atmosphere and stirred at room temperature for 1 hour.

After the completion of the reaction, the reaction solution was concentrated under reduced pressure, and the operation of adding toluene to the obtained concentration residue and concentrating the resultant under reduced pressure was repeated several times to obtain 813 mg of the title compound (containing impurities).

$^1$H-NMR spectrum (400 MHz, DMSO-$d_6$) δ: 8.57 (br s, 3H), 7.53-7.30 (m, 10H), 5.09 (s, 2H), 4.67-4.55 (m, 1H), 4.38-4.27 (m, 2H), 2.66 (s, 4H).

Reference Example 41

(S)-{2-[(tert-Butoxycarbonyl)amino]-2-phenylethoxy}methyl pivalate

[Chemical Formula 176]

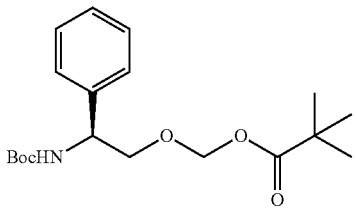

To a solution of 4.09 g (17.2 mmol) of (S)-tert-butyl (2-hydroxy-1-phenylethyl)carbamate [purchased from Novo Chemy Ltd.] in 80 ml of dehydrated THF, 0.762 g (19.1 mmol) of 60 wt % sodium hydride was added at 0° C. in a nitrogen atmosphere and stirred at the same temperature as above for 1 hour. Subsequently, 2.65 ml (18.3 mmol) of chloromethyl pivalate was added at 0° C. and stirred at the same temperature as above for 25 minutes and further for 2.5 hours after the temperature was raised to room temperature.

After the completion of the reaction, a saturated aqueous solution of ammonium chloride was added to the reaction solution and stirred, followed by extraction with a mixed solvent of ethyl acetate and n-hexane twice. All of the obtained organic layers were dried over anhydrous magnesium sulfate, filtered, and concentrated under reduced pressure. The obtained concentration residue was subjected to silica gel column chromatography (elution solvent: n-hexane:ethyl acetate=95:5 to 75:25 (V/V)), and a fraction containing the compound of interest was concentrated under reduced pressure and dried under reduced pressure to obtain 3.32 g of the title compound (yield: 55%) as a white solid.

Mass spectrum (CI, m/z): 352 [M+1]$^+$.

$^1$H-NMR spectrum (400 MHz, CDCl$_3$) δ: 7.36-7.23 (m, 5H), 5.27 (d, J=6.3 Hz, 1H), 5.33-5.21 (m, 1H), 5.19 (d, J=6.3 Hz, 1H), 4.80 (br s, 1H), 3.91 (dd, J=4.4, 9.6 Hz, 1H), 3.87-3.77 (m, 1H), 1.41 (br s, 9H), 1.18 (s, 9H).

Reference Example 42

(S)-(2-Amino-2-phenylethoxy)methyl pivalate

[Chemical Formula 177]

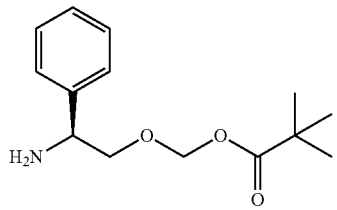

To a solution of 3.32 g (9.45 mmol) of (S)-{2-[(tert-butoxycarbonyl)amino]-2-phenylethoxy}methyl pivalate synthesized in the similar manner as in Reference Example 41 in 50 ml of dehydrated dichloromethane, 6.0 ml (78 mmol) of trifluoroacetic acid was added at 0° C. in a nitrogen atmosphere, stirred at the same temperature as above for 2 hours, and then stirred for 70 minutes after the temperature was raised to room temperature.

After the completion of the reaction, the reaction solution was poured to a saturated aqueous solution of sodium bicarbonate for neutralization, followed by extraction with dichloromethane three times. All of the obtained organic layers were dried over anhydrous magnesium sulfate, filtered, and concentrated under reduced pressure. The obtained concentration residue was subjected to silica gel column chromatography (DNH silica gel, elution solvent: n-hexane:ethyl acetate=95:5 to 80:20 (V/V)), and a fraction containing the compound of interest was concentrated under reduced pressure and dried under reduced pressure to obtain 1.83 g of the title compound (yield: 77%) as a colorless oil.

Mass spectrum (CI, m/z): 252 [M+1]$^+$.

$^1$H-NMR spectrum (400 MHz, CDCl$_3$) δ: 7.40-7.24 (m, 5H), 5.36 (d, J=6.1 Hz, 1H), 5.26 (d, J=6.1 Hz, 1H), 4.21 (dd, J=3.8, 8.8 Hz, 1H), 3.78 (dd, J=3.8, 9.6 Hz, 1H), 3.59 (dd, J=8.8, 9.6 Hz, 1H), 1.21 (s, 9H).

Reference Example 43

(S)-2-({[(2,5-Dioxopyrrolidin-1-yl)oxy]carbonyl}oxy)-2-phenylethyl acetate

[Chemical Formula 178]

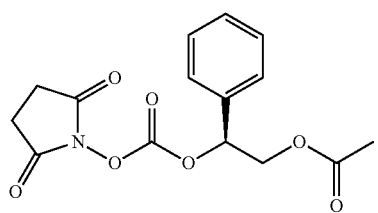

To a solution of 0.84 g (4.7 mmol) of (S)-2-hydroxy-2-phenylethyl acetate [synthesized according to the method described in J. Org. Chem., 2013, 78 (22), 11618-11622] in 30 ml of dehydrated acetonitrile, 0.90 ml (6.4 mmol) of triethylamine and 1.33 g (5.19 mmol) of N,N'-disuccinimidyl carbonate were added in this order at room temperature in a nitrogen atmosphere and stirred at the same temperature as above for 15 hours.

After the completion of the reaction, the reaction solution was concentrated under reduced pressure. The obtained concentration residue was dissolved in ethyl acetate, and it was washed with water. An organic layer and an aqueous layer were separated, and then, the aqueous layer was subjected to extraction with ethyl acetate once. All of the obtained organic layers were dried over anhydrous magnesium sulfate, filtered, and concentrated under reduced pressure. The obtained concentration residue was subjected to silica gel column chromatography (elution solvent: n-hexane:ethyl acetate=85:15 to 60:40 (V/V)), and a fraction containing the compound of interest was concentrated under reduced pressure and dried under reduced pressure to obtain 1.28 g of the title compound (yield: 85%) as a colorless oil.

Mass spectrum (CI, m/z): 322 [M+1]$^+$.

$^1$H-NMR spectrum (400 MHz, CDCl$_3$) δ: 7.45-7.34 (m, 5H), 5.95 (dd, J=5.2, 7.2 Hz, 1H), 4.39 (d, J=5.2 Hz, 1H), 4.38 (d, J=7.2 Hz, 1H), 2.83 (s, 4H), 2.12 (s, 3H).

Reference Example 44

(S)-Benzyl 2-[(tert-butoxycarbonyl)amino]-2-phenylacetate

[Chemical Formula 179]

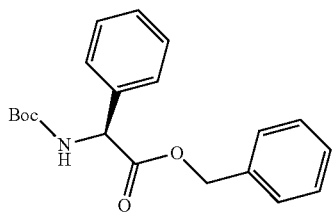

To a solution of 2.50 g (9.95 mmol) of (S)-2-[(tert-butoxycarbonyl)amino]-2-phenylacetic acid in 30 ml of DMF, 1.47 g (10.6 mmol) of potassium carbonate was dividedly added with stirring at room temperature in a nitrogen atmosphere, and subsequently, 1.20 ml (10.1 mmol) of benzyl bromide was added dropwise at room temperature, stirred at the same temperature as above for 7 hours, and then left at room temperature for 3 days.

After the completion of the reaction, toluene was added to the reaction solution and washed with water twice. All of the obtained organic layers were washed with a saturated aqueous solution of sodium chloride, then dried over anhydrous magnesium sulfate, filtered, and then concentrated under reduced pressure. The obtained concentration residue was subjected to silica gel column chromatography (elution solvent: n-hexane:ethyl acetate=100:0 to 79:21 (V/V)), and a fraction containing the compound of interest was concentrated under reduced pressure to obtain 3.24 g of the title compound (yield: 95%) as a white solid.

Mass spectrum (CI, m/z): 342 [M+1]$^+$.

$^1$H-NMR spectrum (400 MHz, CDCl$_3$) δ: 7.37-7.27 (m, 8H), 7.23-7.15 (m, 2H), 5.61-5.50 (m, 1H), 5.40-5.33 (m, 1H), 5.23-5.08 (m, 2H), 1.49-1.29 (m, 9H).

Reference Example 45

(S)-Benzyl 2-amino-2-phenylacetate trifluoroacetate

[Chemical Formula 180]

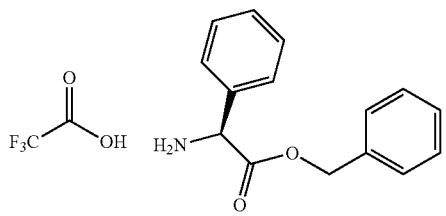

To a solution of 462 mg (1.35 mmol) of (S)-benzyl 2-[(tert-butoxycarbonyl)amino]-2-phenylacetate synthesized in the similar manner as in Reference Example 44 in 10 ml of dichloromethane, 2.0 ml (26 mmol) of trifluoroacetic acid was added at room temperature and stirred at room temperature for 24 hours.

After the completion of the reaction, the reaction solution was concentrated under reduced pressure. The operation of adding dichloromethane to the obtained concentration residue and concentrating the resultant under reduced pressure was repeated several times to obtain 572 mg of the title compound (containing impurities).

$^1$H-NMR spectrum (400 MHz, DMSO-d$_6$) δ: 8.93 (br s, 3H), 7.54-7.44 (m, 5H), 7.38-7.31 (m, 3H), 7.27-7.21 (m, 2H), 5.40 (br s, 1H), 5.27 (d, J=12.5 Hz, 1H), 5.21 (d, J=12.5 Hz, 1H).

Reference Example 46

Ethyl 6,6-dimethyl-3-[1-(trimethylsilyl)cyclopropanecarboxamido]-5,6-dihydropyrrolo[3,4-c]pyrazole-2(4H)-carboxylate

[Chemical Formula 181]

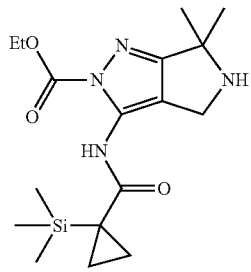

To a solution of 9.70 g (61.3 mmol) of 1-(trimethylsilyl)cyclopropanecarboxylic acid [synthesized according to the method described in J. Org. Chem., 1982 (47) 5, 893-895] in 120 ml of dehydrated dichloromethane, 6.60 ml (76.9 mmol) of oxalyl chloride and 0.25 ml (3.2 mmol) of dehydrated DMF were added in this order at 0° C. in a nitrogen atmosphere and then stirred for 2.5 hours with the temperature unchanged.

After the completion of the reaction, the reaction solution was concentrated under reduced pressure and dried under reduced pressure to obtain a concentration residue.

To a solution of 19.0 ml (109 mmol) of DIPEA and 9.94 g (30.6 mmol) of 5-tert-butyl 2-ethyl 3-amino-6,6-dimethylpyrrolo[3,4-c]pyrazole-2,5(4H,6H)-dicarboxylate [synthesized according to the method described in Journal of Medicinal Chemistry 2012, 55 (10), 4728-4739] in 170 ml of dehydrated dichloromethane, a solution of the obtained concentration residue in 30 ml of dehydrated dichloromethane was added at 0° C. in a nitrogen atmosphere and then stirred for 24 hours with the temperature unchanged.

After the completion of the reaction, a saturated aqueous solution of sodium bicarbonate was added to the reaction solution and stirred, followed by extraction with dichloromethane once and ethyl acetate twice. All of the obtained organic layers were dried over anhydrous magnesium sulfate, then filtered, and concentrated under reduced pressure. The obtained concentration residue was subjected to silica gel column chromatography (elution solvent: n-hexane:ethyl acetate=90:10 to 70:30 (V/V)), and a fraction containing the compound of interest was concentrated under reduced pressure. A concentration residue of a fraction containing impurities was subjected again to silica gel column chromatography (elution solvent: n-hexane:ethyl acetate=90:10 to 75:25 (V/V)), combined with the purified form obtained above, concentrated under reduced pressure, and dried under reduced pressure to obtain 10.63 g of a concentration residue.

To a solution of the obtained concentration residue in 100 ml of ethyl acetate, 60.0 ml (240 mmol) of 4 N hydrogen chloride/ethyl acetate was added at room temperature in a nitrogen atmosphere and then stirred for 5 hours with the temperature unchanged.

After the completion of the reaction, the reaction solution was concentrated under reduced pressure. The obtained concentration residue was suspended in diisopropyl ether, and the suspension was stirred at room temperature. Insoluble matter was collected by filtration, and the obtained solid was washed with diisopropyl ether. The obtained solid was dissolved in water, and then, a saturated aqueous solution of sodium bicarbonate and dichloromethane were added and stirred at room temperature for 5 minutes. After separation into an aqueous layer and an organic layer, the aqueous layer was subjected to extraction with dichloromethane twice. All of the organic layers were washed with a saturated aqueous solution of sodium chloride, then dried over anhydrous magnesium sulfate, filtered, concentrated under reduced pressure, and dried under reduced pressure to obtain 8.27 g of the title compound (yield: 73% [2 steps]) as a light orange solid.

Mass spectrum (DUIS, m/z): 365 [M+1]$^+$.

$^1$H-NMR spectrum (400 MHz, CDCl$_3$) δ: 10.02 (s, 1H), 4.53 (q, J=7.2 Hz, 2H), 4.16 (s, 2H), 1.50-1.43 (m, 9H), 1.14-1.08 (m, 2H), 0.84-0.77 (m, 2H), 0.12 (s, 9H).

Reference Example 47

N-(2,2-Difluoro-3-hydroxy-1-phenylpropyl)-2-methylpropane-2-sulfinamide

[Chemical Formula 182]

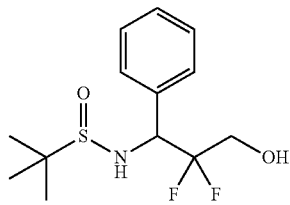

To 32 ml of degassed dehydrated THF, 3.29 g (50.3 mmol) of an active zinc powder was added at room temperature in an argon atmosphere and then heated to 40° C. Subsequently, 8.60 ml (66.1 mmol) of ethyl bromodifluoroacetate was dividedly added to the reaction solution at 40° C. and then stirred at 40° C. for 1 hour. To the reaction solution allowed to cool to room temperature, a solution of 3.47 g (16.6 mmol) of N-benzylidene-2-methylpropane-2-sulfinamide [synthesized according to the method described in Org. Lett., 2005, 7, 5493-5496] in 18 ml of dehydrated THF was added at room temperature and then stirred at room temperature for 23 hours.

After the completion of the reaction, ethyl acetate and a saturated aqueous solution of sodium bicarbonate were added to the reaction solution and then stirred at room temperature for 10 minutes. The obtained suspension was filtered using a celite filter, subsequently the removed solid was washed with ethyl acetate, and then, the filtrate was separated into an aqueous layer and an organic layer. The aqueous layer was subjected to extraction with ethyl acetate twice, and then, all of the obtained organic layers were dried over anhydrous magnesium sulfate, filtered, and concentrated under reduced pressure. The obtained concentration residue was subjected to silica gel column chromatography (elution solvent: n-hexane:ethyl acetate=85:15 to 65:35 (V/V)), and a fraction containing the compound of interest was concentrated under reduced pressure and dried under reduced pressure to obtain 4.08 g of a concentration residue.

To a solution of 1.01 g of a portion of the obtained concentration residue in 20 ml of dehydrated THF, 136 mg (6.23 mmol) of lithium borohydride was added at room temperature in a nitrogen atmosphere and then stirred for 1.5 hours with the temperature unchanged.

After the completion of the reaction, a saturated aqueous solution of ammonium chloride was added dropwise to the reaction solution until foaming settled, and then, an excessive amount of a saturated aqueous solution of ammonium chloride was further added and stirred at room temperature for 10 minutes. Subsequently, extraction was performed with ethyl acetate three times. All of the obtained organic layers were dried over anhydrous magnesium sulfate, then filtered, and concentrated under reduced pressure. The obtained concentration residue was subjected to silica gel column chromatography (elution solvent: n-hexane:ethyl acetate=80:20 to 50:50 (V/V)), subsequently concentrated under reduced pressure, and dried under reduced pressure to obtain 573 mg of the title compound (yield: 48% [2 steps]) as a colorless oil.

Mass spectrum (CI, m/z): 292 [M+1]⁺.
$^1$H-NMR spectrum (400 MHz, CDCl$_3$) δ: 7.42-7.33 (m, 5H), 4.97-4.85 (m, 1H), 4.37 (d, J=6.8 Hz, 1H), 4.03-3.74 (m, 3H), 1.25 (s, 9H).

Reference Example 48

3-Amino-2,2-difluoro-3-phenylpropan-1-ol

[Chemical Formula 183]

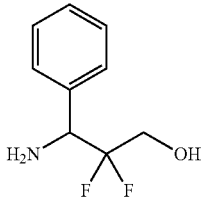

To a solution of 568 mg (1.95 mmol) of N-(2,2-difluoro-3-hydroxy-1-phenylpropyl)-2-methylpropane-2-sulfinamide synthesized in the similar manner as in Reference Example 47 in 5 ml of ethanol, 2.0 ml (8.0 mmol) of 4 N hydrogen chloride/1,4-dioxane was added at room temperature in a nitrogen atmosphere and then stirred for 1.5 hours with the temperature unchanged.

After the completion of the reaction, the reaction solution was neutralized by adding a saturated aqueous solution of sodium bicarbonate, followed by extraction with dichloromethane three times. All of the obtained organic layers were dried over anhydrous magnesium sulfate, then filtered, and concentrated under reduced pressure. The obtained concentration residue was subjected to silica gel column chromatography (elution solvent: n-hexane:ethyl acetate=70:30 to 30:70 (V/V)), and a fraction containing the compound of interest was concentrated under reduced pressure and dried under reduced pressure to obtain 254 mg of the title compound (yield: 70%) as a white solid.

Mass spectrum (CI, m/z): 188 [M+1]⁺.
$^1$H-NMR spectrum (400 MHz, CDCl$_3$) δ: 7.46-7.32 (m, 5H), 4.44 (dd, J=9.8, 13.1 Hz, 1H), 3.88 (ddd, J=8.6, 12.4, 17.8 Hz, 1H), 3.79-3.67 (m, 1H).

Reference Example 49

2-(2-Isopropoxy-1-phenylethyl)isoindolin-1,3-dione

[Chemical Formula 184]

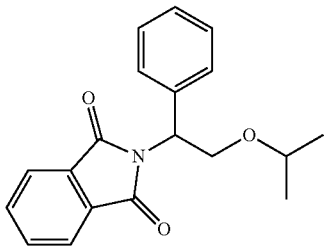

To a solution of 0.500 g (2.78 mmol) of 2-isopropoxy-1-phenylethanol [synthesized according to the method described in J. Fluorine Chem., 2004, 125, 1779-1790], 0.818 g (5.56 mmol) of isoindolin-1,3-dione, and 1.46 g (5.57 mmol) of triphenylphosphine in 20 ml of dehydrated dichloromethane, 1.10 ml (5.66 mmol) of diisopropyl azodicarboxylate was added with stirring at 0° C. in an argon atmosphere, then brought back to room temperature, and stirred at room temperature for 16 hours.

A 5% aqueous potassium bisulfate solution was added to the reaction solution and separated into an aqueous layer and an organic layer. The organic layer was washed with a saturated aqueous solution of sodium bicarbonate, dried over anhydrous magnesium sulfate, and filtered, and then, the filtrate was concentrated under reduced pressure. The obtained residue was subjected to silica gel column chromatography (elution solvent: n-hexane:ethyl acetate=93:7 to 72:28 (V/V)), and a fraction containing the compound of interest was concentrated under reduced pressure to obtain 0.677 g of the title compound (yield: 79%) as a colorless oil.

Mass spectrum (CI, m/z): 310 [M+1]⁺.
$^1$H-NMR spectrum (400 MHz, DMSO-d$_6$) δ: 7.93-7.83 (m, 4H), 7.47-7.41 (m, 2H), 7.39-7.27 (m, 3H), 5.44 (dd, J=6.0, 9.9 Hz, 1H), 4.33 (t, J=9.9 Hz, 1H), 4.01 (dd, J=6.0, 9.9 Hz, 1H), 3.61 (spt, J=6.1 Hz, 1H), 1.02 (d, J=6.1 Hz, 3H), 0.98 (d, J=6.1 Hz, 3H).

Reference Example 50

2-Isopropoxy-1-phenylethanamine

[Chemical Formula 185]

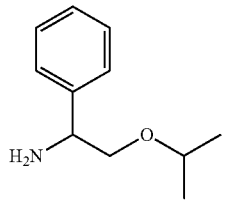

To a solution of 0.670 g (2.17 mmol) of 2-(2-isopropoxy-1-phenylethyl)isoindolin-1,3-dione synthesized in the similar manner as in Reference Example 49 in 10 ml of ethanol, 0.37 ml (6.5 mmol) of acetic acid and 0.32 ml (6.6 mmol) of hydrazine monohydrate were added in an argon atmosphere and heated to reflux for 3 hours.

After standing to cool, ethanol was added and filtered, and the filtrate was concentrated under reduced pressure. Dichloromethane and a 5% aqueous sodium carbonate solution were added to the residue and stirred at room temperature. After separation into an aqueous layer and an organic layer, the organic layer was dried over anhydrous sodium sulfate and filtered, and then, the filtrate was concentrated under reduced pressure. The residue was subjected to silica gel column chromatography (DIOL silica gel, elution solvent: 1,2-dichloroethane:methanol=100:0 to 95:5 (V/V)), and a fraction containing the compound of interest was concentrated under reduced pressure to obtain 0.348 g of the title compound (yield: 90%) as a colorless oil.

Mass spectrum (CI, m/z): 180 [M+1]⁺.
$^1$H-NMR spectrum (400 MHz, CDCl$_3$) δ: 7.43-7.37 (m, 2H), 7.37-7.30 (m, 2H), 7.29-7.23 (m, 1H), 4.17 (dd, J=3.6, 9.2 Hz, 1H), 3.66-3.55 (m, 2H), 3.31 (t, J=9.2 Hz, 1H), 1.20-1.14 (m, 6H).

Reference Example 51

2-(2-Phenoxy-1-phenylethyl)isoindolin-1,3-dione

[Chemical Formula 186]

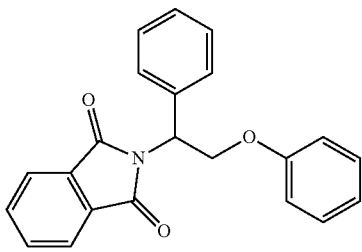

To a solution of 1.04 g (4.85 mmol) of 2-phenoxy-1-phenylethanol [synthesized according to the method described in J. Org. Chem., 2011, 76, 1883-1886], 1.40 g (9.52 mmol) of isoindolin-1,3-dione, and 2.45 g (9.34 mmol) of triphenylphosphine in 40 ml of dehydrated dichloromethane, 1.90 ml (9.77 mmol) of diisopropyl azodicarboxylate was added with stirring at 0° C. in an argon atmosphere, then brought back to room temperature, and stirred at room temperature for 20 hours.

A 5% aqueous potassium bisulfate solution was added to the reaction solution and separated into an aqueous layer and an organic layer. The organic layer was washed with a saturated aqueous solution of sodium bicarbonate, dried over anhydrous magnesium sulfate, and filtered, and then, the filtrate was concentrated under reduced pressure. The residue was subjected to silica gel column chromatography (elution solvent: n-hexane:ethyl acetate=93:7 to 72:28 (V/V)), and a fraction containing the compound of interest was concentrated under reduced pressure to obtain 1.15 g of the title compound (containing impurities) as a colorless viscous liquid.

Mass spectrum (CI, m/z): 344[M+1]$^+$.

Reference Example 52

2-Phenoxy-1-phenylethanamine

[Chemical Formula 187]

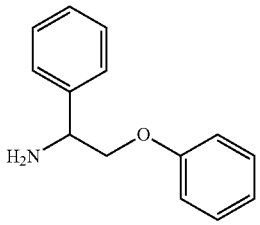

To a solution of 1.14 g of 2-(2-phenoxy-1-phenylethyl)isoindolin-1,3-dione (containing impurities) synthesized in Reference Example 51 in 15 ml of ethanol, 0.60 ml (10 mmol) of acetic acid was added with stirring in a nitrogen atmosphere, and subsequently, 0.50 ml (10 mmol) of hydrazine monohydrate was added at room temperature and then heated to reflux for 2.5 hours.

After standing to cool, ethanol was added and filtered, and the filtrate was concentrated under reduced pressure. 50 ml of dichloromethane and 50 ml of a 5% aqueous sodium carbonate solution were added to the residue and stirred at room temperature. After separation into an aqueous layer and an organic layer, the organic layer was dried over anhydrous sodium sulfate and filtered, and then, the filtrate was concentrated under reduced pressure. The residue was subjected to silica gel column chromatography (DIOL silica gel, elution solvent: 1,2-dichloroethane:methanol=100:0 to 95:5 (V/V)), and a fraction containing the compound of interest was concentrated under reduced pressure to obtain 0.59 g of the title compound (yield: 58% [2 steps]) as a colorless oil.

Mass spectrum (CI, m/z): 214 [M+1]$^+$.

$^1$H-NMR spectrum (400 MHz, CDCl$_3$) δ: 7.49-7.43 (m, 2H), 7.41-7.24 (m, 5H), 6.98-6.88 (m, 3H), 4.43 (dd, J=3.7, 9.0 Hz, 1H), 4.09 (dd, J=3.7, 9.0 Hz, 1H), 3.92 (t, J=9.0 Hz, 1H).

Reference Example 53

3,3,8,8,9,9-Hexamethyl-5-phenyl-2,4,7-trioxa-8-siladecane

[Chemical Formula 188]

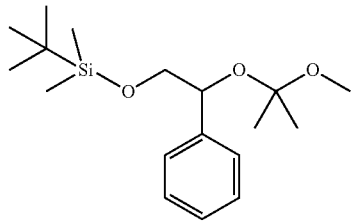

A solution of 1.78 g (7.05 mmol) of 2-[(tert-butyldimethylsilyl)oxy]-1-phenylethanol [synthesized according to the method described in WO 2011/19090, page 43] in 35 ml of dehydrated dichloromethane was cooled in ice, and 0.86 ml (9.1 mmol) of 2-methoxy-1-propene and subsequently 0.180 g (0.716 mmol) of pyridinium p-toluenesulfonate were added thereto in a nitrogen atmosphere and stirred at the same temperature as above for 3 hours.

20 ml of a saturated aqueous solution of sodium bicarbonate was added to the reaction solution, stirred, and then separated into an aqueous layer and an organic layer. The aqueous layer was subjected to extraction with dichloromethane, all of the obtained organic layers were dried over anhydrous magnesium sulfate and filtered, and then, the filtrate was concentrated under reduced pressure. The residue was subjected to silica gel column chromatography (elution solvent: n-hexane:ethyl acetate=99:1 to 94:6 (V/V)), and a fraction containing the compound of interest was concentrated under reduced pressure to obtain 1.38 g of the title compound (yield: 60%) as a colorless oil.

$^1$H-NMR spectrum (400 MHz, CDCl$_3$) δ: 7.39-7.18 (m, 5H), 4.74 (dd, J=5.4, 7.3 Hz, 1H), 3.75 (dd, J=7.3, 10.4 Hz, 1H), 3.54 (dd, J=5.4, 10.4 Hz, 1H), 3.15 (s, 3H), 1.42 (s, 3H), 1.12 (s, 3H), 0.84 (s, 9H), −0.04 (s, 3H), −0.07 (s, 3H).

Reference Example 54

2-[(2-Methoxypropan-2-yl)oxy]-2-phenylethanol

[Chemical Formula 189]

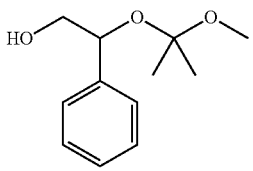

To a solution of 1.36 g (4.19 mmol) of 3,3,8,8,9,9-hexamethyl-5-phenyl-2,4,7-trioxa-8-siladecane synthesized in the similar manner as in Reference Example 53 in 24 ml of dehydrated THF, 6.3 ml (6.3 mmol) of 1 M tetra-n-butylammonium fluoride/THF solution was added dropwise with stirring at 0° C. in a nitrogen atmosphere and stirred at the same temperature as above for 2 hours.

A saturated aqueous solution of sodium bicarbonate was added to the reaction solution, followed by extraction with a n-hexane/ethyl acetate mixed solution (1:1 (V/V)) three times. The extracts were dried over anhydrous magnesium sulfate and filtered, and then, the filtrate was concentrated under reduced pressure. The residue was subjected to silica gel column chromatography (elution solvent: n-hexane:ethyl acetate=84:16 to 63:37 (V/V)), and a fraction containing the compound of interest was concentrated under reduced pressure to obtain 0.697 g of the title compound (yield: 79%) as a colorless oil.

$^1$H-NMR spectrum (400 MHz, CDCl$_3$) δ: 7.37-7.23 (m, 5H), 4.84 (dd, J=4.8, 7.0 Hz, 1H), 3.70-3.58 (m, 2H), 3.18 (s, 3H), 2.34-2.20 (m, 1H), 1.44 (s, 3H), 1.21 (s, 3H).

Reference Example 55

2,5-Dioxopyrrolidin-1-yl{2-[(2-methoxypropan-2-yl)oxy]-2-phenylethyl}carbonate

[Chemical Formula 190]

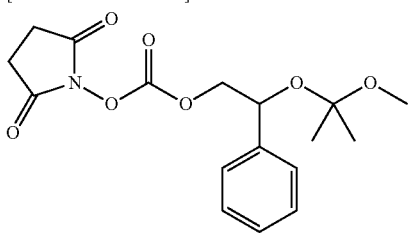

To a solution of 0.685 g (3.26 mmol) of 2-[(2-methoxypropan-2-yl)oxy]-2-phenylethanol synthesized in the similar manner as in Reference Example 54 in 20 ml of dehydrated acetonitrile, 1.00 g (3.90 mmol) of bis(2,5-dioxopyrrolidin-1-yl)carbonate and 0.70 ml (5.0 mmol) of triethylamine were added with stirring at room temperature in a nitrogen atmosphere and stirred at room temperature for 3 hours.

The reaction solution was concentrated under reduced pressure, and water was added to the residue, followed by extraction with ethyl acetate. The organic layer was dried over anhydrous magnesium sulfate and filtered, and then, the filtrate was concentrated under reduced pressure. The residue was subjected to silica gel column chromatography (elution solvent: n-hexane:ethyl acetate=71:29 to 50:50 (V/V)), and a fraction containing the compound of interest was concentrated under reduced pressure to obtain 0.636 g of the title compound (yield: 56%) as a colorless viscous liquid.

$^1$H-NMR spectrum (400 MHz, CDCl$_3$) δ: 7.42-7.27 (m, 5H), 5.04 (dd, J=3.7, 8.8 Hz, 1H), 4.41 (dd, J=8.8, 11.1 Hz, 1H), 4.24 (dd, J=3.7, 11.1 Hz, 1H), 3.17 (s, 3H), 2.83 (s, 4H), 1.45 (s, 3H), 1.13 (s, 3H).

Reference Example 56

2-[(2-Methoxypropan-2-yl)oxy]-2-phenylethyl 6,6-dimethyl-3-[1-(trimethylsilyl)cyclobutanecarboxamido]-4,6-dihydropyrrolo[3,4-c]pyrazole-5-(1H)-carboxylate

[Chemical Formula 191]

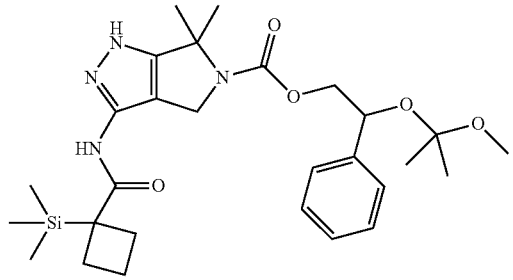

To a solution of 0.102 g (0.269 mmol) of ethyl 6,6-dimethyl-3-[1-(trimethylsilyl)cyclobutanecarboxamido]-5,6-dihydropyrrolo[3,4-c]pyrazole-1(4H)-carboxylate synthesized in the similar manner as in Reference Example 5 and 0.145 g (0.411 mmol) of 2,5-dioxopyrrolidin-1-yl {2-[(2-methoxypropan-2-yl)oxy]-2-phenylethyl}carbonate synthesized in the similar manner as in Reference Example 55 in 3 ml of dehydrated dichloromethane, 0.14 ml (0.80 mmol) of DIPEA was added at room temperature in a nitrogen atmosphere and stirred at room temperature for 1.5 hours. The reaction solution was concentrated under reduced pressure, and 2.5 ml of methanol and 0.080 ml (1.3 mmol) of 2-aminoethanol were added at room temperature and stirred at room temperature for 14 hours.

The reaction solution was concentrated under reduced pressure, water was added, the organic layer after extraction with ethyl acetate was washed with a saturated aqueous solution of sodium chloride, dried over anhydrous magnesium sulfate, and filtered, and then, the filtrate was concentrated under reduced pressure. The residue was subjected to silica gel column chromatography (DIOL silica gel, elution solvent: 1,2-dichloroethane:ethyl acetate=100:0 to 84:16 (V/V)), and a fraction containing the compound of interest was concentrated under reduced pressure to obtain 0.127 g of the title compound (containing impurities) as a white foam.

Mass spectrum (DUIS, m/z): 541 [M−1]$^-$.

Reference Example 57

Ethyl 6,6-dimethyl-5-(2-phenoxyacetyl)-3-[1-(trimethylsilyl)cyclobutanecarboxamido]-5,6-dihydropyrrolo[3,4-c]pyrazole-2(4H)-carboxylate

[Chemical Formula 192]

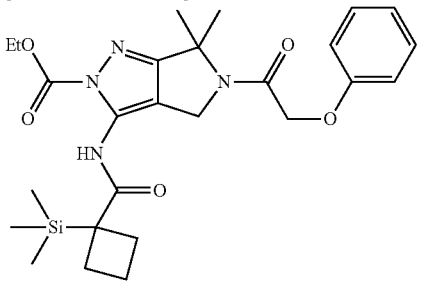

To a solution of 0.180 g (1.19 mmol) of 2-phenoxyacetic acid in 3 ml of dehydrated dichloromethane, 0.005 ml (0.07 mmol) of DMF was added at room temperature in a nitrogen atmosphere and then cooled in ice. Subsequently, 0.102 ml (1.19 mmol) of oxalyl chloride was added dropwise at 0° C. and after the completion of the dropwise addition, stirred at room temperature for 2 hours. Then, the reaction solution was concentrated under reduced pressure at room temperature.

To a solution of 0.171 g (0.388 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 in 3.5 ml of dehydrated dichloromethane, 0.35 ml (2.0 mmol) of DIPEA was added at room temperature in a nitrogen atmosphere, and subsequently, a solution of the concentration residue obtained by the operation described above in 3 ml of dehydrated dichloromethane was added with stirring at 0° C. and then stirred at room temperature for 2 hours. Subsequently, 5 ml of 2-propanol was added and stirred at room temperature for 18 hours.

The reaction solution was concentrated under reduced pressure, the residue was subjected to silica gel column chromatography (elution solvent: 1,2-dichloroethane:ethyl acetate=100:0 to 0:100 (V/V)), and a fraction containing the compound of interest was concentrated under reduced pressure to obtain 0.148 g of the title compound (yield: 74%) as a pale yellow foam.

Mass spectrum (DUIS, m/z): 513 [M+1]$^+$.

$^1$H-NMR spectrum (400 MHz, DMSO-d$_6$) δ: 9.78 (s, 1H), 7.30-7.24 (m, 2H), 6.99-6.90 (m, 3H), 4.89-4.75 (m, 4H), 4.43 (q, J=7.1 Hz, 2H), 2.56-2.44 (m, 2H), 2.32-2.20 (m, 2H), 1.96-1.83 (m, 2H), 1.66 (s, 6H), 1.35 (t, J=7.1 Hz, 3H), 0.12 (s, 9H).

Reference Example 58

Ethyl 3-(benzyloxy)-2-bromopropanoate

[Chemical Formula 193]

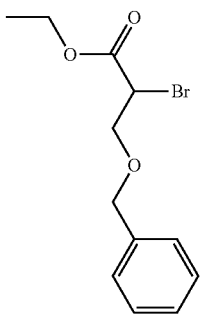

To a solution of 2.00 g (7.72 mmol) of 3-(benzyloxy)-2-bromopropanoic acid [synthesized according to the method described in WO 2008/128942, page 38] in 20 ml of ethanol, 1.00 ml (18.8 mmol) of concentrated sulfuric acid was added with stirring at room temperature in an argon atmosphere and stirred at 80° C. for 5 hours.

After the completion of the reaction, the reaction solution allowed to cool to room temperature was concentrated under reduced pressure. The obtained concentration residue was neutralized by adding a 1 N aqueous sodium hydroxide solution, followed by extraction with ethyl acetate. The obtained organic layer was washed with a saturated aqueous solution of sodium chloride, then dried over anhydrous magnesium sulfate, and filtered, and the filtrate was concentrated under reduced pressure to obtain 2.00 g of the title compound (containing impurities) as a colorless oil.

Mass spectrum (CI, m/z): 287, 289 [M+1]$^+$.

$^1$H-NMR spectrum (400 MHz, CDCl$_3$) δ: 7.38-7.27 (m, 5H), 4.59 (s, 2H), 4.32 (dd, J=5.9, 8.4 Hz, 1H), 4.29-4.21 (m, 2H), 3.97 (dd, J=8.4, 10.2 Hz, 1H), 3.79 (dd, J=5.9, 10.2 Hz, 1H), 1.30 (t, J=7.2 Hz, 3H).

Reference Example 59

Ethyl 3-(benzyloxy)-2-phenoxypropanoate

[Chemical Formula 194]

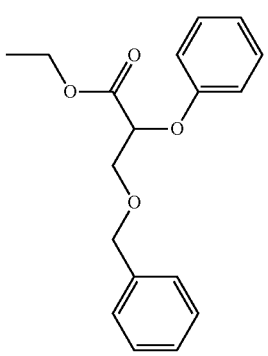

To a solution of 1.31 g (13.9 mmol) of phenol in 20 ml of dehydrated DMF, 608 mg (13.9 mmol) of 55% sodium hydride was dividedly added with stirring at 0° C. in an argon atmosphere and stirred at the same temperature as above for 30 minutes. Subsequently, a solution of 2.00 g of ethyl 3-(benzyloxy)-2-bromopropanoate (containing impurities) synthesized in the similar manner as in Reference Example 58 in 5 ml of dehydrated DMF was added dropwise at 0° C. and then stirred at room temperature for 1 hour.

After the completion of the reaction, ice water was added to the reaction solution and neutralized with 1 N hydrochloric acid, followed by extraction with ethyl acetate. The obtained organic layer was washed with a saturated aqueous solution of sodium chloride, then dried over anhydrous magnesium sulfate, and filtered, and the filtrate was concentrated under reduced pressure. The obtained residue was subjected to silica gel chromatography (elution solvent: n-hexane:ethyl acetate=100:0 to 80:20 (V/V)), and a fraction containing the compound of interest was concentrated under reduced pressure to obtain 1.10 g of the title compound (yield: 53%) as a colorless oil.

Mass spectrum (CI, m/z): 301 [M+1]$^+$.

$^1$H-NMR spectrum (400 MHz, CDCl$_3$) δ: 7.42-7.21 (m, 7H), 7.02-6.89 (m, 3H), 4.91-4.78 (m, 1H), 4.68 (d, J=12.2 Hz, 1H), 4.64 (d, J=12.2 Hz, 1H), 4.23 (q, J=7.1 Hz, 2H), 3.99-3.91 (m, 2H), 1.24 (t, J=7.1 Hz, 3H).

Reference Example 60

3-(Benzyloxy)-2-phenoxypropanoic acid

[Chemical Formula 195]

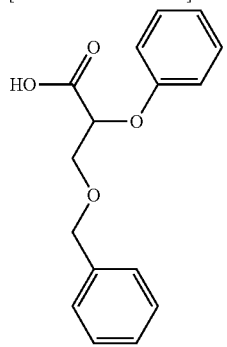

To a solution of 400 mg (1.33 mmol) of ethyl 3-(benzyloxy)-2-phenoxypropanoate synthesized in the similar manner as in Reference Example 59 in 10 ml of THF, 12 ml (12 mmol) of a 1 N aqueous sodium hydroxide solution was added with stirring at room temperature and stirred at 80° C. for 3 hours.

After the completion of the reaction, 1 N hydrochloric acid was added to the reaction solution at 0° C. to adjust the pH to 2, followed by extraction with ethyl acetate. The obtained organic layer was washed with a saturated aqueous solution of sodium chloride, then dried over anhydrous magnesium sulfate, and filtered, and the filtrate was concentrated under reduced pressure to obtain 341 mg of the title compound (containing impurities) as a white solid.

Mass spectrum (CI, m/z): 273 [M+1]$^+$.

$^1$H-NMR spectrum (400 MHz, CDCl$_3$) δ: 7.42-7.21 (m, 7H), 7.08-6.90 (m, 3H), 4.91-4.85 (m, 1H), 4.67 (d, J=12.3 Hz, 1H), 4.63 (d, J=12.3 Hz, 1H), 4.03-3.90 (m, 2H).

Reference Example 61

Methyl 2-bromo-3-methoxypropanoate

[Chemical Formula 196]

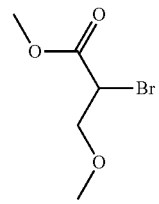

To a solution prepared by adding 20 ml of dehydrated methanol to 2.50 g (13.0 mmol) of a solution of 28% sodium methoxide in methanol, a solution of 3.00 g (11.5 mmol) of ethyl 2,3-dibromopropanoate in 20 ml of dehydrated methanol was added dropwise with stirring at 0° C. in an argon atmosphere and then stirred at room temperature for 2 hours.

After the completion of the reaction, 1 N hydrochloric acid was added thereto for neutralization and then concentrated under reduced pressure. The operation of adding toluene to the obtained concentration residue and concentrating the resultant under reduced pressure was repeated several times. Toluene was added, precipitates were filtered off, and the filtrate was concentrated under reduced pressure and dried under reduced pressure to obtain 580 mg of the title compound (yield: 26%) as an orange oil.

Mass spectrum (CI, m/z): 197 [M+1]$^+$.

$^1$H-NMR spectrum (400 MHz, CDCl$_3$) δ: 4.33 (dd, J=5.8, 8.2 Hz, 1H), 3.90 (dd, J=8.2, 10.2 Hz, 1H), 3.81 (s, 3H), 3.72 (dd, J=5.8, 10.2 Hz, 1H), 3.41 (s, 3H).

Reference Example 62

Methyl 3-methoxy-2-phenoxypropanoate

[Chemical Formula 197]

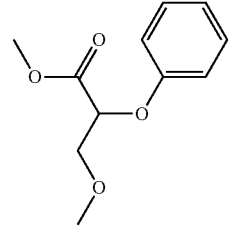

To a solution of 555 mg (5.90 mmol) of phenol in 10 ml of dehydrated DMF, 260 mg (5.96 mmol) of 55% sodium hydride was dividedly added with stirring at 0° C. in an argon atmosphere and stirred at the same temperature as above for 30 minutes. Subsequently, a solution of 580 mg (2.94 mmol) of methyl 2-bromo-3-methoxypropanoate synthesized in the similar manner as in Reference Example 61 in 10 ml of dehydrated DMF was added dropwise at 0° C. and then stirred at room temperature for 16 hours.

After the completion of the reaction, ice water was added to the reaction solution and then neutralized by adding 1 N hydrochloric acid, followed by extraction with ethyl acetate. The obtained organic layer was washed with a saturated aqueous solution of sodium chloride, then dried over anhydrous magnesium sulfate, and filtered, and the filtrate was concentrated under reduced pressure. The obtained residue was subjected to silica gel chromatography (elution solvent: n-hexane:ethyl acetate=100:0 to 80:20 (V/V)), and a fraction containing the compound of interest was concentrated under reduced pressure to obtain 380 mg of the title compound (yield: 61%) as a colorless oil.

Mass spectrum (CI, m/z): 211 [M+1]+.

$^1$H-NMR spectrum (400 MHz, CDCl$_3$) δ: 7.33-7.23 (m, 2H), 7.03-6.96 (m, 1H), 6.95-6.88 (m, 2H), 4.84 (dd, J=3.8, 5.3 Hz, 1H), 3.91 (dd, J=5.3, 10.5 Hz, 1H), 3.86 (dd, J=3.8, 10.5 Hz, 1H), 3.78 (s, 3H), 3.46 (s, 3H).

Reference Example 63

3-Methoxy-2-phenoxypropanoic acid

[Chemical Formula 198]

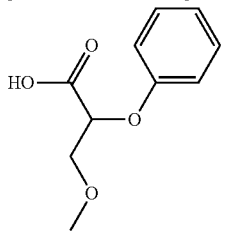

To a solution of 120 mg (0.571 mmol) of methyl 3-methoxy-2-phenoxypropanoate synthesized in the similar manner as in Reference Example 62 in 2 ml of THF, 0.700 ml (0.700 mmol) of a 1 N aqueous sodium hydroxide solution was added with stirring at room temperature and stirred at the same temperature as above for 3 hours.

After the completion of the reaction, the reaction solution was adjusted to pH 2 by adding 1 N hydrochloric acid, followed by extraction with ethyl acetate. The obtained organic layer was washed with a saturated aqueous solution of sodium chloride, then dried over anhydrous magnesium sulfate, and filtered, and the filtrate was concentrated under reduced pressure to obtain 116 mg of the title compound (containing impurities) as a brown solid.

Mass spectrum (CI, m/z): 197 [M+1]+.

$^1$H-NMR spectrum (400 MHz, CDCl$_3$) δ: 7.34-7.25 (m, 2H), 7.06-7.00 (m, 1H), 6.99-6.91 (m, 2H), 4.90-4.81 (m, 1H), 3.98-3.84 (m, 2H), 3.46 (s, 3H).

Reference Example 64

Ethyl 3-hydroxy-2-phenoxypropanoate

[Chemical Formula 199]

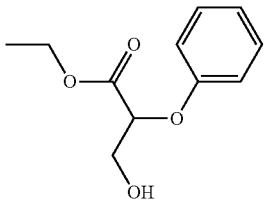

To a solution of 3.00 g (9.99 mmol) of ethyl 3-(benzyloxy)-2-phenoxypropanoate synthesized in the similar manner as in Reference Example 59 in 20 ml of ethanol, 200 mg of 20% palladium hydroxide/carbon (containing 50% water) was added in an argon atmosphere and after replacement with a hydrogen atmosphere, stirred at room temperature for 2 hours.

After the completion of the reaction, replacement with an argon atmosphere was performed, and the reaction solution was filtered through celite. The solid on the celite was washed with ethanol, and all of the filtrates were concentrated under reduced pressure. The obtained concentration residue was subjected to silica gel column chromatography (elution solvent: n-hexane:ethyl acetate=80:20 to 50:50 (V/V)), and a fraction containing the compound of interest was concentrated under reduced pressure to obtain 1.89 g of the title compound (yield: 90%) as a colorless oil.

Mass spectrum (CI, m/z): 211 [M+1]+.

$^1$H-NMR spectrum (400 MHz, CDCl$_3$) δ: 7.35-7. 25 (m, 2H), 7.05-6.97 (m, 1H), 6.95-6.88 (m, 2H), 4.78 (dd, J=3.8, 5.3 Hz, 1H), 4.29-4.22 (m, 2H), 4.15-4.01 (m, 2H), 2.22 (t, J=7.0 Hz, 1H), 1.26 (t, J=7.1 Hz, 3H).

Reference Example 65

Ethyl 3-(dimethylamino)-2-phenoxypropanoate

[Chemical Formula 200]

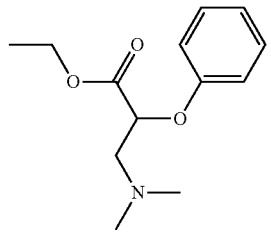

To a solution of 470 mg (2.24 mmol) of ethyl 3-hydroxy-2-phenoxypropanoate synthesized in the similar manner as in Reference Example 64 in 12 ml of dehydrated dichloromethane, 1.10 g (2.59 mmol) of Dess-Martin periodinane was added at 0° C. in an argon atmosphere and stirred at room temperature for 1 hour.

After the completion of the reaction, an aqueous sodium thiosulfate solution and a saturated aqueous solution of sodium bicarbonate were added to the reaction solution and stirred for 30 minutes, followed by extraction with dichloromethane. The organic layer was washed with a saturated aqueous solution of sodium chloride, then dried over anhydrous magnesium sulfate, and filtered, and then, the filtrate was concentrated under reduced pressure.

To a solution of 470 mg of the obtained concentration residue in 6 ml of dehydrated dichloromethane, 0.260 ml (4.54 mmol) of acetic acid and 4.50 ml (9.00 mmol) of a solution of dimethylamine in THF were added in this order with stirring at room temperature in an argon atmosphere and then stirred at room temperature for 30 minutes. Subsequently, 720 mg (3.40 mmol) of sodium triacetoxyborohydride was dividedly added at 0° C. and stirred at room temperature for 16 hours.

After the completion of the reaction, a saturated aqueous solution of sodium bicarbonate was added to the reaction solution, followed by extraction with dichloromethane. The obtained organic layer was washed with a saturated aqueous solution of sodium chloride, then dried over anhydrous sodium sulfate, and filtered, and the filtrate was concentrated under reduced pressure. The obtained concentration residue was subjected to silica gel column chromatography (elution solvent: n-hexane:ethyl acetate=100:0 to 80:20 (V/V)), and a fraction containing the compound of interest was concentrated under reduced pressure.

To a solution of 162 mg of the obtained concentration residue in 4 ml of ethanol, 75 mg of 10% palladium/carbon (containing 54% water, PE-type manufactured by N.E. Chemcat Corp.) was added in an argon atmosphere and after replacement with a hydrogen atmosphere, stirred at room temperature for 3 hours.

After the completion of the reaction, replacement with an argon atmosphere was performed, and the reaction solution was filtered through celite. The solid on the celite was washed with ethanol, and all of the filtrates were concentrated under reduced pressure. The obtained concentration residue was subjected to silica gel column chromatography (elution solvent: n-hexane:ethyl acetate=50:50 to 0:100 (V/V)), and a fraction containing the compound of interest was concentrated under reduced pressure to obtain 94 mg of the title compound (yield: 18% [3 steps]) as a colorless oil.

Mass spectrum (CI, m/z): 238 [M+1]$^+$.

$^1$H-NMR spectrum (400 MHz, CDCl$_3$) δ: 7.32-7.22 (m, 2H), 7.01-6.94 (m, 1H), 6.94-6.85 (m, 2H), 4.79 (dd, J=4.4, 7.2 Hz, 1H), 4.22 (q, J=7.1 Hz, 2H), 2.94 (dd, J=7.2, 13.2 Hz, 1H), 2.85 (dd, J=4.4, 13.2 Hz, 1H), 2.36 (s, 6H), 1.24 (t, J=7.1 Hz, 3H).

Reference Example 66

3-(Dimethylamino)-2-phenoxypropanoic acid

[Chemical Formula 201]

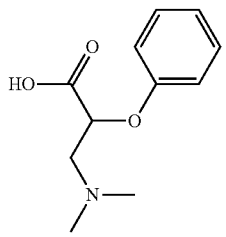

To a solution of 129 mg (0.544 mmol) of ethyl 3-(dimethylamino)-2-phenoxypropanoate synthesized in the similar manner as in Reference Example 65 in 4 ml of THF, 0.700 ml (0.700 mmol) of a 1 N aqueous sodium hydroxide solution was added with stirring at room temperature and stirred at the same temperature as above for 3 hours.

After the completion of the reaction, 1 N hydrochloric acid was added for neutralization and concentrated under reduced pressure. The operation of adding toluene to the obtained concentration residue and concentrating the resultant under reduced pressure was repeated several times. Dichloromethane was added to the obtained concentration residue and ultrasonicated, then the deposited solid was filtered off, and the filtrate was concentrated under reduced pressure to obtain 75 mg of the title compound (yield: 66%) as a white solid.

Mass spectrum (CI, m/z): 210 [M+1]$^+$.

$^1$H-NMR spectrum (400 MHz, DMSO-d$_6$) δ: 7.31-7.22 (m, 2H), 6.96-6.86 (m, 3H), 4.75 (dd, J=5.3, 6.7 Hz, 1H), 3.01 (dd, J=6.7, 13.0 Hz, 1H), 2.95 (dd, J=5.3, 13.0 Hz, 1H), 2.45 (s, 6H).

Reference Example 67

Ethyl 2-bromo-3-(3,3-difluoropyrrolidin-1-yl)propanoate

[Chemical Formula 202]

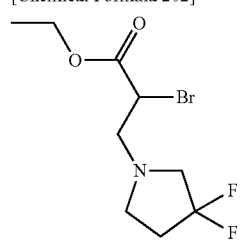

To a solution of 0.900 g (6.27 mmol) of 3,3-difluoropyrrolidine hydrochloride in 20 ml of dehydrated THF, 1.70 ml (12.1 mmol) of triethylamine was added with stirring at room temperature in an argon atmosphere, and subsequently, a solution of 1.50 g (5.77 mmol) of ethyl 2,3-dibromopropanoate in 20 ml of dehydrated THF was added dropwise at 0° C. and stirred at room temperature for 16 hours.

After the completion of the reaction, precipitates were filtered off, the filtrate was washed with water, then dried over anhydrous magnesium sulfate, and filtered, and the filtrate was dried under reduced pressure to obtain 1.30 g of the title compound (yield: 79%) as an orange oil.

Mass spectrum (CI, m/z): 286 [M+1]$^+$.

$^1$H-NMR spectrum (400 MHz, CDCl$_3$) δ: 4.25 (q, J=7.1 Hz, 2H), 4.18 (dd, J=5.8, 9.5 Hz, 1H), 3.27-3.19 (m, 1H), 3.12-2.77 (m, 5H), 2.31-2.16 (m, 2H), 1.30 (t, J=7.1 Hz, 3H).

Reference Example 68

Ethyl 3-(3,3-difluoropyrrolidin-1-yl)-2-phenoxypropanoate

[Chemical Formula 203]

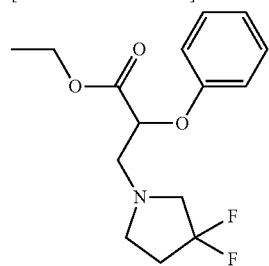

To a solution of 860 mg (9.14 mmol) of phenol in 15 ml of dehydrated DMF, 400 mg (9.17 mmol) of 55% sodium hydride was dividedly added with stirring at 0° C. in an argon atmosphere and stirred at the same temperature as above for 30 minutes. Subsequently, a solution of 1.30 g (4.54 mmol) of ethyl 2-bromo-3-(3,3-difluoropyrrolidin-1-yl)propanoate synthesized in the similar manner as in Reference Example 67 in 10 ml of dehydrated DMF was added dropwise at 0° C. and then stirred at room temperature for 16 hours.

After the completion of the reaction, ice water was added to the reaction solution and then neutralized with 1 N hydrochloric acid, followed by extraction with ethyl acetate. The obtained organic layer was washed with a saturated aqueous solution of sodium chloride, then dried over anhydrous magnesium sulfate, and filtered, and the filtrate was concentrated under reduced pressure. The obtained residue was subjected to silica gel chromatography (DIOL silica gel, elution solvent: n-hexane:ethyl acetate=100:0 to 70:30 (V/V)), and a fraction containing the compound of interest was concentrated under reduced pressure to obtain 476 mg of the title compound (containing impurities) as a pale yellow oil.

Mass spectrum (CI, m/z): 300 [M+1]$^+$.

Reference Example 69

3-(3,3-Difluoropyrrolidin-1-yl)-2-phenoxypropanoic acid

[Chemical Formula 204]

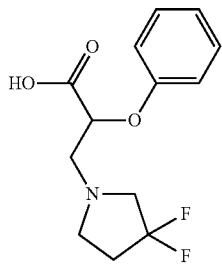

To a solution of 476 mg of ethyl 3-(3,3-difluoropyrrolidin-1-yl)-2-phenoxypropanoate (containing impurities) synthesized in Reference Example 68 in 6 ml of THF, 2.00 ml of a 1 N aqueous sodium hydroxide solution was added with stirring at room temperature and stirred at the same temperature as above for 3 hours.

After the completion of the reaction, 1 N hydrochloric acid was added to the reaction solution to adjust the pH to 2, followed by extraction with ethyl acetate. The obtained organic layer was washed with a saturated aqueous solution of sodium chloride, then dried over anhydrous magnesium sulfate, and filtered, and the filtrate was concentrated under reduced pressure to obtain 393 mg of the title compound (containing impurities) as a white foam.

Mass spectrum (CI, m/z): 272 [M+1]$^+$.

Reference Example 70

(S)—N-{5-[3-(Benzyloxy)-2-phenylpropanoyl]-6,6-dimethyl-1,4,5,6-tetrahydropyrrolo[3,4-c]pyrazol-3-yl}-1-(trimethylsilyl)cyclobutanecarboxamide

[Chemical Formula 205]

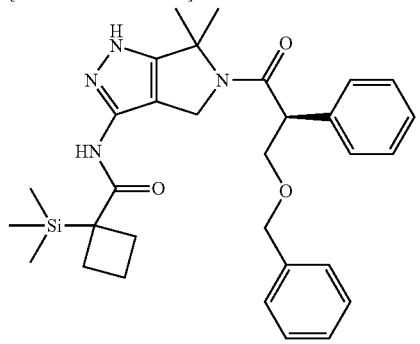

To a solution of 168 mg (0.657 mmol) of (S)-3-(benzyloxy)-2-phenylpropanoic acid [synthesized according to the method described in Tetrahedron Lett., 2002 (43), 9691-9693] in 3 ml of dehydrated dichloromethane, 0.10 ml (1.2 mmol) of oxalyl chloride and 0.010 ml (0.13 mmol) of dehydrated DMF were added in this order at 0° C. in a nitrogen atmosphere and then stirred for 3.5 hours with the temperature unchanged.

After the completion of the reaction, the reaction solution was concentrated under reduced pressure to obtain a concentration residue.

To a solution of 127 mg (0.335 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 and 0.23 ml (1.3 mmol) of DIPEA in 3 ml of dehydrated dichloromethane, a solution of the obtained concentration residue in 1 ml of dehydrated dichloromethane was added at 0° C. in a nitrogen atmosphere and then stirred for 1 hour with the temperature unchanged. Subsequently, 1.0 ml (7.2 mmol) of triethylamine and 1.0 ml (25 mmol) of methanol were added to the reaction solution at room temperature and then stirred for 19 hours with the temperature unchanged.

After the completion of the reaction, a saturated aqueous solution of sodium bicarbonate was added to the reaction solution and stirred, followed by extraction with dichloromethane three times. All of the obtained organic layers were dried over anhydrous magnesium sulfate, then filtered, and concentrated under reduced pressure. The obtained concentration residue was subjected to silica gel column chromatography (DIOL silica gel, elution solvent: n-hexane:ethyl acetate=80:20 to 50:50 (V/V)), and a fraction containing the compound of interest was concentrated under reduced pressure and dried under reduced pressure to obtain 142 mg of the title compound (yield: 78%) as a pale yellow foam.

Mass spectrum (CI, m/z): 545 [M+1]$^+$.

$^1$H-NMR spectrum (400 MHz, CDCl$_3$) δ: 7.43-7.37 (m, 2H), 7.35-7.16 (m, 10H), 4.89 (d, J=12.0 Hz, 1H), 4.59 (d, J=12.0 Hz, 1H), 4.50-4.39 (m, 2H), 4.19-4.12 (m, 1H), 4.05 (dd, J=5.3, 8.6 Hz, 1H), 3.61 (dd, J=5.3, 8.8 Hz, 1H), 2.62-2.49 (m, 2H), 2.33-2.23 (m, 2H), 2.00-1.89 (m, 2H), 1.86 (s, 3H), 1.73 (s, 3H), 0.14 (s, 9H).

Reference Example 71

3-(3-Methoxy-2-phenylpropanoyl)oxazolidin-2-one

[Chemical Formula 206]

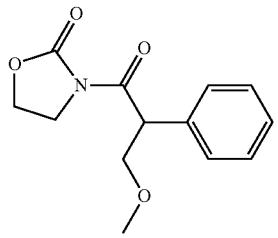

To a solution of 506 mg (2.46 mmol) of 3-(2-phenylacetyl)oxazolidin-2-one [synthesized according to the method described in Tetrahedron, 1998 (54) 2697-2708] in 10 ml of dehydrated dichloromethane, 0.33 ml (3.0 mmol) of titanium tetrachloride was added at 0° C. in a nitrogen atmosphere and then stirred for 5 minutes with the temperature unchanged. Subsequently, 0.52 ml (3.0 mmol) of DIPEA was added thereto at 0° C. and then stirred for 1 hour with the temperature unchanged. Subsequently, 0.37 ml (4.9 mmol) of chloromethyl methyl ether was added thereto dropwise at 0° C. and then stirred for 2 hours with the temperature unchanged.

After the completion of the reaction, water was added to the reaction solution at 0° C. and stirred, followed by extraction with dichloromethane three times. All of the obtained organic layers were washed with a saturated aqueous solution of sodium bicarbonate and a saturated aqueous solution of sodium chloride in this order, then dried over anhydrous magnesium sulfate, filtered, and concentrated under reduced pressure. The obtained concentration residue was subjected to silica gel column chromatography (elution solvent: n-hexane:ethyl acetate=75:25 to 50:50 (V/V)), and a fraction containing the compound of interest was concentrated under reduced pressure and dried under reduced pressure to obtain 522 mg of the title compound (yield: 85%) as an orange oil.

Mass spectrum (CI, m/z): 250 [M+1]$^+$.

$^1$H-NMR spectrum (400 MHz, CDCl$_3$) δ: 7.44-7.38 (m, 2H), 7.35-7.27 (m, 3H), 5.38 (dd, J=4.6, 10.2 Hz, 1H), 4.44-4.27 (m, 2H), 4.18-4.07 (m, 2H), 3.95 (ddd, J=6.8, 9.2, 11.0 Hz, 1H), 3.50 (dd, J=4.6, 9.2 Hz, 1H), 3.37 (s, 3H).

Reference Example 72

3-Methoxy-2-phenylpropanoic acid

[Chemical Formula 207]

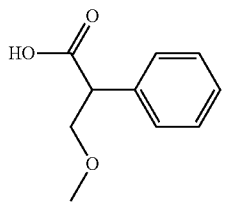

To a solution of 517 mg (2.07 mmol) of 3-(3-methoxy-2-phenylpropanoyl)oxazolidin-2-one synthesized in the similar manner as in Reference Example 71 in 12 ml of THF/4 ml of water, 1.0 ml (9.7 mmol) of an aqueous hydrogen peroxide solution [30%] at room temperature and 111 mg (4.63 mmol) of lithium hydroxide at 0° C. were added in this order in a nitrogen atmosphere and then stirred for 2.5 hours with the temperature unchanged. Subsequently, 10 ml of a 10% aqueous sodium thiosulfate solution and 10 ml of a saturated aqueous solution of sodium bicarbonate were added in small portions at 0° C. and then stirred at room temperature for 1 hour.

After the completion of the reaction, the reaction solution was concentrated under reduced pressure, and THF was distilled off. The concentration residue was washed with dichloromethane twice and then adjusted to pH 2 by adding 6 N hydrochloric acid, and subsequently, this solution was subjected to extraction with ethyl acetate three times. All of the obtained organic layers were washed with a saturated aqueous solution of sodium chloride, then dried over anhydrous magnesium sulfate, filtered, and concentrated under reduced pressure. The obtained concentration residue was subjected to silica gel column chromatography (elution solvent: n-hexane:ethyl acetate=80:20 to 65:35 (V/V)), and a fraction containing the compound of interest was concentrated under reduced pressure and dried under reduced pressure to obtain 331 mg of the title compound (yield: 89%) as a colorless oil.

Mass spectrum (CI, m/z): 181 [M+1]$^+$.

$^1$H-NMR spectrum (400 MHz, CDCl$_3$) δ: 7.38-7.27 (m, 5H), 4.01-3.95 (m, 1H), 3.91 (dd, J=4.8, 9.2 Hz, 1H), 3.63 (dd, J=4.8, 8.7 Hz, 1H), 3.39 (s, 3H).

Reference Example 73

Benzyl 4-methoxy-2-phenylbutanoate

[Chemical Formula 208]

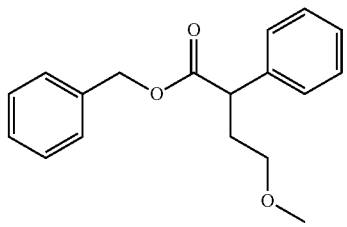

To a solution of 0.45 ml (2.2 mmol) of benzyl phenylacetate in 6 ml of dehydrated DMF, 139 mg (3.19 mmol) of 55% sodium hydride was added at 0° C. in an argon atmosphere and then stirred for 30 minutes with the temperature unchanged. Subsequently, 0.35 ml (3.7 mmol) of 2-bromoethyl methyl ether was added to the reaction solution at 0° C. and then stirred at room temperature for 2 hours.

After the completion of the reaction, a saturated aqueous solution of ammonium chloride was added to the reaction solution, followed by extraction with ethyl acetate. All of the obtained organic layers were washed with a saturated aqueous solution of sodium chloride, dried over anhydrous magnesium sulfate, then filtered, and concentrated under reduced pressure. The obtained concentration residue was subjected to silica gel column chromatography (elution solvent: n-hexane:ethyl acetate=100:0 to 95:5 (V/V)), and a fraction containing the compound of interest was concentrated under reduced pressure to obtain 528 mg of the title compound (yield: 84%) as a colorless oil.

Mass spectrum (ESI, m/z): 285 [M+1]$^+$.

$^1$H-NMR spectrum (400 MHz, CDCl$_3$) δ: 7.34-7.21 (m, 10H), 5.15 (d, J=12.5 Hz, 1H), 5.05 (d, J=12.5 Hz, 1H), 3.83 (t, J=7.7 Hz, 1H), 3.38-3.30 (m, 1H), 3.29-3.20 (m, 4H), 2.45-2.34 (m, 1H), 2.06-1.95 (m, 1H)

Reference Example 74

4-Methoxy-2-phenylbutanoic acid

[Chemical Formula 209]

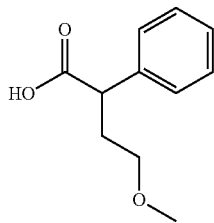

To a solution of 528 mg (1.86 mmol) of benzyl 4-methoxy-2-phenylbutanoate synthesized in the similar manner as in Reference Example 73 in 7 ml of ethanol, 130 mg of 10% Pd—C (containing 54.33% water, PE-type manufactured by N.E. Chemcat Corp.) was added at room temperature in an argon atmosphere. After replacement with a hydrogen atmosphere, the resultant was stirred at room temperature for 2 hours.

After the completion of the reaction, the reaction solution was filtered through celite and concentrated under reduced pressure. The obtained concentration residue was subjected to silica gel column chromatography (DIOL silica gel, elution solvent: n-hexane:ethyl acetate=60:40 to 40:60 (V/V)), and a fraction containing the compound of interest was concentrated under reduced pressure to obtain 304 mg of the title compound (yield: 84%) as a white solid.

Mass spectrum (CI, m/z): 195 [M+1]$^+$.

$^1$H-NMR spectrum (400 MHz, DMSO-d$_6$) δ: 12.37 (br s, 1H), 7.38-7.20 (m, 5H), 3.61 (t, J=7.7 Hz, 1H), 3.29-3.16 (m, 5H), 2.26-2.14 (m, 1H), 1.88-1.77 (m, 1H)

Reference Example 75

(S)—N-{5-[3-(Benzyloxy)-2-phenylpropanoyl]-6,6-dimethyl-1,4,5,6-tetrahydropyrrolo[3,4-c]pyrazol-3-yl}-1-(trimethylsilyl)cyclopropanecarboxamide

[Chemical Formula 210]

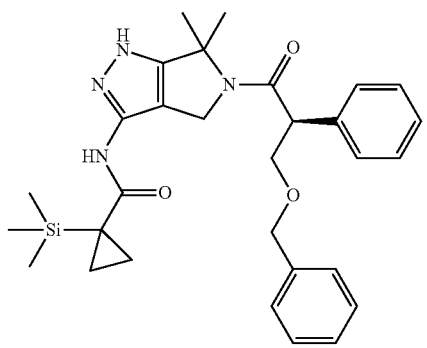

To a solution of 51.9 mg (0.202 mmol) of (S)-3-(benzyloxy)-2-phenylpropanoic acid [synthesized according to the method described in Tetrahedron Lett., 2002 (43), 9691-9693] in 2 ml of dehydrated dichloromethane, 0.040 ml (0.47 mmol) of oxalyl chloride and 0.0050 ml (0.065 mmol) of dehydrated DMF were added in this order at 0° C. in a nitrogen atmosphere and then stirred for 2.5 hours with the temperature unchanged.

After the completion of the reaction, the reaction solution was concentrated under reduced pressure to obtain a concentration residue.

To a solution of 47.0 mg (0.129 mmol) of ethyl 6,6-dimethyl-3-[1-(trimethylsilyl)cyclopropanecarboxamido]-5,6-dihydropyrrolo[3,4-c]pyrazole-2(4H)-carboxylate synthesized in the similar manner as in Reference Example 46 and 0.10 ml (0.57 mmol) of DIPEA in 1 ml of dehydrated dichloromethane, a solution of the obtained concentration residue in 1 ml of dehydrated dichloromethane was added at 0° C. in a nitrogen atmosphere and then stirred for 2 hours with the temperature unchanged. Subsequently, 0.10 ml (0.92 mmol) of N,N-dimethylethane-1,2-diamine was added to the reaction solution at 0° C. and then stirred at room temperature for 3 hours.

After the completion of the reaction, the reaction solution diluted with dichloromethane was washed with a 5% aqueous potassium bisulfate solution and then separated into an aqueous layer and an organic layer. The aqueous layer was subjected to extraction with dichloromethane twice, and then, all of the obtained organic layers were dried over anhydrous magnesium sulfate, filtered, and concentrated under reduced pressure. The obtained concentration residue was subjected to silica gel column chromatography (DIOL silica gel, elution solvent: n-hexane:ethyl acetate=80:20 to 50:50 (V/V)), and a fraction containing the compound of interest was concentrated under reduced pressure and dried under reduced pressure to obtain 48 mg of the title compound (yield: 70%) as a pale yellow foam.

Mass spectrum (DUIS, m/z): 531 [M+1]$^+$.

$^1$-NMR spectrum (400 MHz, CDCl$_3$) δ: 7.55 (s, 1H), 7.41-7.37 (m, 2H), 7.34-7.20 (m, 9H), 4.84 (d, J=12.0 Hz, 1H), 4.60 (d, J=12.0 Hz, 1H), 4.47 (d, J=12.0 Hz, 1H), 4.42 (d, J=12.0 Hz, 1H), 4.16 (t, J=8.8 Hz, 1H), 4.02 (dd, J=5.4, 8.8 Hz, 1H), 3.61 (dd, J=5.4, 8.8 Hz, 1H), 1.85 (s, 3H), 1.72 (s, 3H), 1.09-1.04 (m, 2H), 0.81-0.76 (m, 2H), 0.10 (s, 9H).

Reference Example 76

(R)-Benzyl 2-ethoxy-2-phenylacetate

[Chemical Formula 211]

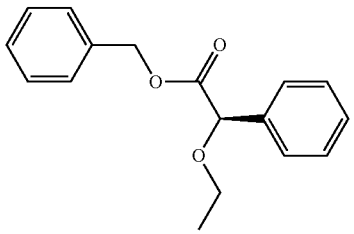

To a solution of 1.01 g (4.17 mol) of (R)-benzyl 2-hydroxy-2-phenylacetate in 20 ml (0.25 mol) of iodoethane, 1.93 g (8.33 mmol) of silver oxide was added at room temperature in an argon atmosphere and stirred at 60° C. for 18 hours.

After the completion of the reaction, the reaction solution was filtered through celite, the solid component was washed with ethyl acetate, and then, the filtrate was concentrated under reduced pressure. The obtained concentration residue was subjected to silica gel column chromatography (elution solvent: n-hexane:ethyl acetate=100:0 to 80:20 (V/V)), and a fraction containing the compound of interest was concentrated under reduced pressure to obtain 1.03 g of the title compound (yield: 91%) as a colorless oil.

$^1$H-NMR spectrum (400 MHz, CDCl$_3$) δ: 7.49-7.43 (m, 2H), 7.38-7.27 (m, 6H), 7.24-7.18 (m, 2H), 5.19 (d, J=12.4 Hz, 1H), 5.11 (d, J=12.4 Hz, 1H), 4.92 (s, 1H), 3.65-3.46 (m, 2H), 1.27 (t, J=7.0 Hz, 3H).

Reference Example 77

(R)-2-Ethoxy-2-phenylacetic acid

[Chemical Formula 212]

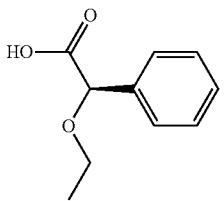

To a solution of 1.03 g (3.81 mmol) of (R)-benzyl 2-ethoxy-2-phenylacetate synthesized in the similar manner as in Reference Example 76 in 20 ml of methanol, 0.11 of palladium/carbon (ASCA2 (trade name), manufactured by N.E. Chemcat Corp., containing 54% water) was added in an argon atmosphere and then, after replacement with a hydrogen atmosphere under reduced pressure, stirred at room temperature for 2 hours.

After the completion of the reaction, the reaction solution was filtered through celite, the solid component was washed with methanol, and then, the filtrate was concentrated under reduced pressure to obtain 0.63 g of the title compound (yield: 92%) as a pale yellow oil.

$^1$H-NMR spectrum (400 MHz, DMSO-d$_6$) δ: 12.80 (br s, 1H), 7.44-7.28 (m, 5H), 4.84 (s, 1H), 3.60-3.50 (m, 1H), 3.47-3.20 (m, 1H), 1.15 (t, J=7.0 Hz, 3H).

Reference Example 78

Methyl 2-{[(benzyloxy)carbonyl](2-cyanoethyl)amino}-2-methylpropanoate

[Chemical Formula 213]

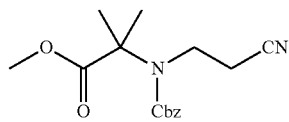

To a solution of 5.00 g (29.4 mmol) of methyl 2-[(2-cyanoethyl)amino]-2-methylpropanoate [synthesized according to the method described in J. Med. Chem., 1968, 11 (3), 616-618] in 23 ml of toluene, 15.5 ml (90.7 mol) of DIPEA and 32.0 ml of a solution of 30 to 35% benzyl chloroformate in toluene [purchased from Tokyo Chemical Industry Co., Ltd.)] were added in this order with stirring at room temperature in an argon atmosphere and stirred for 1.5 hours with the temperature unchanged. Subsequently, the resultant was stirred at 50° C. for 1.5 hours and then allowed to cool to room temperature, and 4.80 ml (44.1 mmol) of N,N-dimethylethane-1,2-diamine was added at room temperature and stirred for 2.5 hours with the temperature unchanged.

After the completion of the reaction, the reaction solution was poured to 2 N hydrochloric acid and stirred. An aqueous layer and an organic layer were separated, the organic layer was washed with a saturated aqueous solution of sodium bicarbonate and a saturated aqueous solution of sodium chloride in this order, dried over anhydrous magnesium sulfate, and filtered, and then, the filtrate was concentrated under reduced pressure. The obtained concentration residue was subjected to silica gel column chromatography (elution solvent: n-hexane:ethyl acetate=84:16 to 50:50 (V/V)), and a fraction containing the compound of interest was concentrated under reduced pressure to obtain 8.32 g of the title compound (yield: 93%) as a colorless oil.

Mass spectrum (CI, m/z): 305 [M+1]$^+$.

$^1$H-NMR spectrum (400 MHz, DMSO-d$_6$) δ: 7.43-7.28 (m, 5H), 5.07 (s, 2H), 3.64 (t, J=6.7 Hz, 2H), 3.50 (br s, 3H), 2.76 (t, J=6.7 Hz, 2H), 1.45 (s, 6H).

Reference Example 79

Benzyl 4-cyano-3-hydroxy-2,2-dimethyl-2,5-dihydro-1H-pyrrole-1-carboxylate

[Chemical Formula 214]

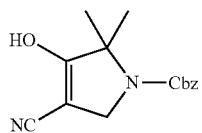

52 ml (52 mmol) of a 1 mol/L solution of potassium tert-butoxide in THF was heated to 60° C., and a solution of 12.1 g (39.7 mmol) of methyl 2-{[(benzyloxy)carbonyl](2-cyanoethyl)amino}-2-methylpropanoate synthesized in the similar manner as in Reference Example 78 in 30 ml of dehydrated THF was added dropwise with stirring under argon stream and stirred for 1 hour while heated to reflux.

After the completion of the reaction, 90 ml of water was added to the reaction solution allowed to cool to room temperature and adjusted to pH <2 by further adding 2 N hydrochloric acid. Extraction was performed from the mixed solution with 100 ml of ethyl acetate twice, and all of the organic layers were combined and washed with 100 ml of water and 100 ml of a saturated aqueous solution of sodium chloride in this order. After drying over magnesium sulfate, filtration and concentration under reduced pressure were performed, and half the amount of the solvent was distilled off. 12 g of active carbon was added to the obtained solution, stirred at room temperature for 30 minutes, filtered, and concentrated under reduced pressure. The obtained concentration residue was diluted with 10 ml of diisopropyl ether, and 50 ml of n-hexane was added thereto and stirred at room temperature for 30 minutes after the deposited solid was disrupted. The solid component was collected by filtration and dried under reduced pressure at 50° C. to obtain 8.27 g of the title compound (yield: 76%) as a pale yellow solid.

Mass spectrum (DUIS, m/z): 273 [M+1]$^+$.

$^1$H-NMR spectrum (400 MHz, DMSO-d$_6$) δ: 12.32 (br s, 1H), 7.46-7.25 (m, 5H), 5.18-5.02 (m, 2H), 4.24-4.02 (m, 2H), 1.51-1.35 (m, 6H).

Reference Example 80

Benzyl 3-amino-6,6-dimethyl-4,6-dihydropyrrolo[3,4-c]pyrazole-5(1H)-carboxylate

[Chemical Formula 215]

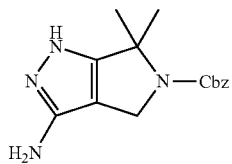

To a solution of 200 mg (0.734 mmol) of benzyl 4-cyano-3-hydroxy-2,2-dimethyl-2,5-dihydro-1H-pyrrole-1-carboxylate synthesized in the similar manner as in Reference Example 79 in 5 ml of ethanol, 0.336 ml (5.87 mmol) of acetic acid was added with stirring at room temperature under argon stream and stirred at room temperature for 5 minutes. Subsequently, 0.178 ml (3.66 mmol) of hydrazine monohydrate was added thereto dropwise with stirring at room temperature and stirred for 12 hours under heating to reflux.

After the completion of the reaction, 15 ml of water was added to the reaction solution allowed to cool to room temperature, and then adjusted to pH 8 by adding an aqueous sodium bicarbonate solution. Extraction was performed from the mixed solution with ethyl acetate three times, and all of the organic layers were washed with a saturated aqueous solution of sodium chloride, dried over anhydrous magnesium sulfate, filtered, and concentrated under reduced pressure. The obtained residue was subjected to silica gel column chromatography (elution solvent: n-hexane:ethyl acetate=50:50 to 0:100 (V/V)→1,2-dichloroethane:methanol=80:20 (V/V)), and a fraction containing the compound of interest was concentrated under reduced pressure to obtain 141 mg of the title compound (yield: 67%) as a pale yellow foam.

Mass spectrum (CI, m/z): 287 [M+1]$^+$.

$^1$H-NMR spectrum (400 MHz, DMSO-d$_6$) δ: 11.20 (br s, 1H), 7.45-7.28 (m, 5H), 5.18-5.05 (m, 2H), 5.05-4.77 (m, 2H), 4.28-4.14 (m, 2H), 1.58-1.46 (m, 6H).

Reference Example 81

5-Benzyl 2-ethyl 3-amino-6,6-dimethylpyrrolo[3,4-c]pyrazole-2,5(4H,6H)-dicarboxylate

[Chemical Formula 216]

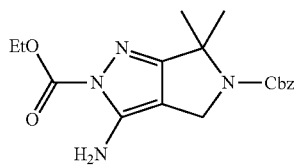

To a solution of 400 mg (1.40 mmol) of benzyl 3-amino-6,6-dimethyl-4,6-dihydropyrrolo[3,4-c]pyrazole-5(1H)-carboxylate synthesized in the similar manner as in Reference Example 80 in 4 ml of dehydrated THF, 0.594 ml (3.49 mmol) of DIPEA was added with stirring at room temperature under argon stream and stirred at room temperature for 3 minutes. Subsequently, 0.133 ml (1.40 mmol) of ethyl chloroformate was added thereto dropwise with stirring at 0° C. and stirred at 0° C. for 30 minutes.

After the completion of the reaction, water was added to the reaction solution, followed by extraction from the mixed solution with ethyl acetate twice. All of the organic layers were washed with a saturated aqueous solution of sodium chloride, dried over anhydrous magnesium sulfate, filtered, and concentrated under reduced pressure. The obtained residue was subjected to silica gel column chromatography (elution solvent: n-hexane:ethyl acetate=71:29 to 30:70 (V/V)), and a fraction containing the compound of interest was concentrated under reduced pressure to respectively obtain 200 mg of the title compound (yield: 40%) as a white foam and 190 mg of an isomer of the title compound (5-benzyl 1-ethyl 3-amino-6,6-dimethylpyrrolo[3,4-c]pyrazole-1,5(4H,6H)-dicarboxylate) (yield: 38%) as a white foam.

Title compound (5-benzyl 2-ethyl 3-amino-6,6-dimethylpyrrolo[3,4-c]pyrazole-2,5(4H,6H)-dicarboxylate)

Mass spectrum (CI, m/z): 359 [M+1]$^+$.

$^1$H-NMR spectrum (400 MHz, DMSO-d$_6$) δ: 7.45-7.29 (m, 5H), 6.63-6.49 (m, 2H), 5.19-5.04 (m, 2H), 4.41-4.30 (m, 2H), 4.28-4.15 (m, 2H), 1.62-1.49 (m, 6H), 1.36-1.28 (m, 3H).

Isomer of the title compound (5-benzyl 1-ethyl 3-amino-6,6-dimethylpyrrolo[3,4-c]pyrazole-1,5(4H,6H)-dicarboxylate)

Mass spectrum (CI, m/z): 359 [M+1]$^+$.

$^1$H-NMR spectrum (400 MHz, DMSO-d$_6$) δ: 7.45-7.29 (m, 5H), 5.78-5.65 (m, 2H), 5.19-5.05 (m, 2H), 4.36-4.17 (m, 4H), 1.79-1.66 (m, 6H), 1.33-1.25 (m, 3H).

Reference Example 82

5-Benzyl 2-ethyl 6,6-dimethyl-3-[1-(trimethylsilyl)cyclobutanecarboxamido]pyrrolo[3,4-c]pyrazole-2,5(4H,6H)-dicarboxylate

[Chemical Formula 217]

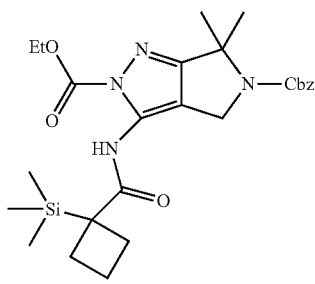

To a solution of 885 mg (5.14 mmol) of 1-(trimethylsilyl)cyclobutanecarboxylic acid synthesized in the similar manner as in Reference Example 1 in 20 ml of dehydrated dichloromethane, 0.530 ml (6.17 mmol) of oxalyl chloride and 0.020 mL (0.26 mmol) of DMF were added in this order at 0° C. in an argon atmosphere and stirred for 1 hour with the temperature unchanged.

After the completion of the reaction, the reaction solution was concentrated under reduced pressure.

To a solution of 2.25 ml (12.9 mmol) of DIPEA and 920 mg (2.57 mmol) of 5-benzyl 2-ethyl 3-amino-6,6-dimethyl-pyrrolo[3,4-c]pyrazole-2,5(4H,6H)-dicarboxylate synthesized in the similar manner as in Reference Example 81 in 10 ml of dehydrated dichloromethane, a solution of the obtained concentration residue in 10 ml of dehydrated dichloromethane was added dropwise at 0° C. in an argon atmosphere and then stirred at room temperature for 24 hours.

After the completion of the reaction, a saturated aqueous solution of sodium bicarbonate was added to the reaction solution, followed by extraction from the solution with dichloromethane twice. All of the organic layers were combined, washed with a 5% aqueous potassium bisulfate solution and a saturated aqueous solution of sodium chloride in this order, dried over anhydrous magnesium sulfate, filtered, and concentrated under reduced pressure. The obtained residue was subjected to silica gel column chromatography (elution solvent: n-hexane:ethyl acetate=100:0 to 70:30 (V/V)), and a fraction containing the compound of interest was concentrated under reduced pressure to obtain 991 mg of the title compound (yield: 75%) as a pale yellow foam.

Mass spectrum (DUIS, m/z): 513 [M+1]$^+$.

$^1$H-NMR spectrum (400 MHz, DMSO-d$_6$) δ: 9.78-9.70 (m, 1H), 7.45-7.29 (m, 5H), 5.20-5.08 (m, 2H), 4.63-4.50 (m, 2H), 4.47-4.37 (m, 2H), 2.58-2.41 (m, 2H), 2.31-2.18 (m, 2H), 1.95-1.80 (m, 2H), 1.67-1.51 (m, 6H), 1.39-1.29 (m, 3H), 0.12-0.06 (m, 9H).

Reference Example 83

Ethyl 6,6-dimethyl-3-[1-(trimethylsilyl)cyclobutanecarboxamido]-5,6-dihydropyrrolo[3,4-c]pyrazole-2(4H)-carboxylate

[Chemical Formula 218]

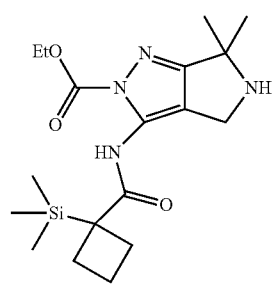

To a solution of 150 mg (0.293 mmol) of 5-benzyl 2-ethyl 6,6-dimethyl-3-[1-(trimethylsilyl)cyclobutanecarboxamido]pyrrolo[3,4-c]pyrazole-2,5(4H,6H)-dicarboxylate synthesized in the similar manner as in Reference Example 82 in 4 ml of 2-propanol, 75 mg of 10% palladium/carbon [manufactured by N.E. Chemcat Corp., PE type, containing 50% water] and 1 ml of acetic acid were added in this order at room temperature. After replacement with a hydrogen atmosphere, the resultant was stirred at room temperature for 1 hour.

After the completion of the reaction, the reaction solution was diluted with ethyl acetate and filtered by adding celite. An aqueous sodium bicarbonate solution was added to the filtrate, stirred, and neutralized. This was subjected to extraction with ethyl acetate twice. All of the organic layers were combined, washed with a saturated aqueous solution of sodium bicarbonate, dried over anhydrous magnesium sulfate, filtered, and concentrated under reduced pressure. The obtained residue was subjected to silica gel column chromatography (elution solvent: 1,2-dichloroethane:methanol=100:0 to 86:14 (V/V)), and a fraction containing the compound of interest was concentrated under reduced pressure to obtain 101 mg of the title compound (yield: 91%) as a white foam.

Mass spectrum (DUIS, m/z): 379 [M+1]$^+$.

$^1$H-NMR spectrum (400 MHz, CDCl$_3$) δ: 9.86 (s, 1H), 4.52 (q, J=7.1 Hz, 2H), 4.22 (s, 2H), 2.65-2.52 (m, 2H), 2.38-2.26 (m, 2H), 2.03-1.88 (m, 2H), 1.50-1.43 (m, 9H), 0.15 (s, 9H).

Reference Example 84

Ethyl 6,6-dimethyl-3-[1-(trimethylsilyl)cyclobutan-
ecarboxamido]-5,6-dihydropyrrolo[3,4-c]pyrazole-2
(4H)-carboxylate

[Chemical Formula 219]

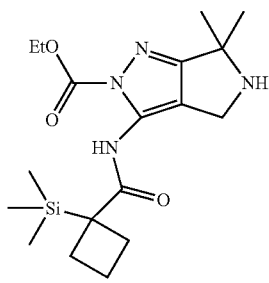

To a solution of 57.1 g (119 mmol) of 5-tert-butyl 2-ethyl 6,6-dimethyl-3-[1-(trimethylsilyl)cyclobutanecarboxamido] pyrrolo[3,4-c]pyrazole-2,5(4H,6H)-dicarboxylate synthesized in the similar manner as in Reference Example 2 in 500 ml of dichloromethane, 28.0 ml (242 mmol) of 2,6-dimethylpyridine and 43.0 ml (238 mmol) of trimethylsilyl trifluoromethanesulfonate were added dropwise in this order at 0° C. in a nitrogen atmosphere and reacted with stirring at 0° C. for 2 hours.

After the completion of the reaction, the reaction solution was poured to 1000 ml of a saturated aqueous solution of sodium bicarbonate, then stirred at room temperature, and subsequently separated into an aqueous layer and an organic layer. The aqueous layer was subjected to extraction with 500 ml of ethyl acetate twice, and then, all of the obtained organic layers were washed with a saturated aqueous solution of sodium chloride, dried over anhydrous magnesium sulfate, filtered, and concentrated under reduced pressure. The operation of adding toluene to the obtained concentration residue and concentrating the resultant under reduced pressure was performed three times, then the obtained brown oil was refrigerated overnight, and subsequently, 50 ml of diethyl ether and 100 ml of n-hexane were added and stirred at room temperature for 0.5 hours. The deposited solid was collected by filtration, washed with n-hexane, and then dried under reduced pressure to obtain 17.0 g of the title compound (yield: 38%) as a white solid.

Mass spectrum (DUIS, m/z): 379 [M+1]$^+$.

$^1$H-NMR spectrum (400 MHz, CDCl$_3$) δ: 9.86 (s, 1H), 4.52 (q, J=7.1 Hz, 2H), 4.23 (s, 2H), 2.64-2.52 (m, 2H), 2.38-2.27 (m, 2H), 2.03-1.89 (m, 2H), 1.53-1.42 (m, 9H), 0.14 (s, 9H).

Reference Example 85

(R)-Benzyl 2-cyclopropoxy-2-phenylacetate

[Chemical Formula 220]

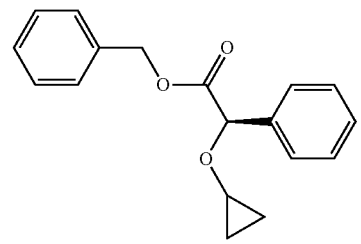

To a solution of 7.50 ml (7.50 mmol) of a 1 M solution of diethylzinc in n-hexane in 4 ml of dehydrated dichloromethane, a solution of 0.750 ml (9.31 mmol) of diiodomethane in 1 ml of dehydrated dichloromethane was added dropwise with stirring at 0° C. in an argon atmosphere and stirred at the same temperature as above for 30 minutes. Subsequently, a solution of 500 mg (1.86 mmol) of (R)-benzyl 2-phenyl-2-(vinyloxy)acetate [synthesized according to the method described in J. Am. Chem. Soc., 2006, 128, 2587-2593] in 1 ml of dehydrated dichloromethane was added dropwise with stirring at 0° C. and stirred at room temperature for 6 hours.

After the completion of the reaction, a saturated aqueous solution of ammonium chloride was added to the reaction solution, followed by extraction with dichloromethane. The obtained organic layer was washed with a saturated aqueous solution of sodium chloride, then dried over anhydrous magnesium sulfate, and filtered, and the filtrate was concentrated under reduced pressure. The obtained concentration residue was subjected to silica gel chromatography (elution solvent: n-hexane:ethyl acetate=100:0 to 80:20 (V/V)), and a fraction containing the compound of interest was concentrated under reduced pressure to obtain 416 mg of the title compound (yield: 79%) as a colorless oil.

$^1$H-NMR spectrum (400 MHz, CDCl$_3$) δ: 7.47-7.41 (m, 2H), 7.38-7.28 (m, 6H), 7.25-7.20 (m, 2H), 5.20 (d, J=12.5 Hz, 1H), 5.12 (d, J=12.5 Hz, 1H), 5.01 (s, 1H), 3.43 (tt, J=3.0, 6.1 Hz, 1H), 0.76-0.65 (m, 2H), 0.53-0.43 (m, 2H).

Reference Example 86

(R)-2-Cyclopropoxy-2-phenylacetic acid

[Chemical Formula 221]

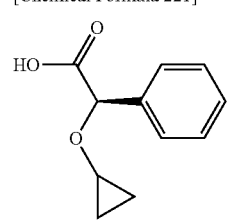

To a solution of 416 mg (1.47 mmol) of (R)-benzyl 2-cyclopropoxy-2-phenylacetate synthesized in the similar manner as in Reference Example 85 in 2 ml of methanol/2 ml of water, 93 mg (2.2 mmol) of lithium hydroxide monohydrate was added at room temperature and then reacted with stirring at room temperature for 2 hours.

After the completion of the reaction, diethyl ether was added to the reaction solution and then the aqueous layer and the organic layer were separated. The aqueous layer was adjusted to pH 2 by adding 2 N hydrochloric acid, followed by extraction with ethyl acetate three times. All of the obtained organic layers were washed with a saturated aqueous solution of sodium chloride, then dried over anhydrous magnesium sulfate, filtered, and concentrated under reduced pressure to obtain 274 mg of the title compound (yield: 97%) as a colorless oil.

Mass spectrum (DUIS, m/z): 191 [M−1]⁻.

¹H-NMR spectrum (400 MHz, CDCl₃) δ: 7.48-7.32 (m, 5H), 4.99 (s, 1H), 3.43 (tt, J=2.9, 6.0 Hz, 1H), 0.76-0.64 (m, 2H), 0.61-0.43 (m, 2H).

Reference Example 87

(R)-2-Isopropoxy-2-phenylacetic acid

[Chemical Formula 222]

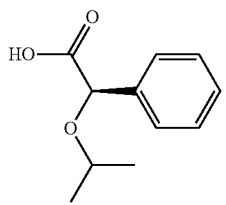

To a suspension of 1.46 g (6.03 mmol) of (R)-benzyl 2-hydroxy-2-phenylacetate in 14.0 ml (140 mmol) of 2-iodopropane, 2.79 g (12.0 mmol) of silver(I) oxide was added at room temperature in an argon atmosphere and then reacted with stirring for 14.5 hours under heating to reflux.

After the completion of the reaction, the reaction solution was allowed to cool to room temperature and then filtered using a celite filter. The filtration cake was washed with ethyl acetate, and then, all of the filtrates were concentrated under reduced pressure. The obtained concentration residue was subjected to silica gel column chromatography (elution solvent: n-hexane:ethyl acetate=95:5 to 90:10 (V/V)), and a fraction containing the compound of interest was concentrated under reduced pressure and dried under reduced pressure to obtain 675 mg of a concentration residue.

To a solution of the obtained concentration residue in 10 ml of methanol/2.0 ml of water, 176 mg (4.19 mmol) of lithium hydroxide monohydrate was added at room temperature in an argon atmosphere and then reacted with stirring at room temperature for 4 hours.

After the completion of the reaction, water and diethyl ether were added to the reaction solution, stirred, and then the aqueous layer and the organic layer were separated. The aqueous layer was adjusted to pH 2 by adding 2 N hydrochloric acid, followed by extraction with ethyl acetate three times. All of the obtained organic layers were washed with a saturated aqueous solution of sodium chloride, then dried over anhydrous magnesium sulfate, filtered, and concentrated under reduced pressure. The obtained concentration residue was subjected to silica gel column chromatography (DIOL silica gel, elution solvent: n-hexane:ethyl acetate=85:15 to 70:30 (V/V)), and a fraction containing the compound of interest was concentrated under reduced pressure to obtain 467 mg of a concentration residue. The obtained concentration residue was subjected to preparative HPLC (column: X-Bridge (trade name) ODS, elution solvent: 1 vol % formic acid/acetonitrile:1 vol % aqueous formic acid solution=20:80 to 70:30 (V/V)), a fraction containing the compound of interest was concentrated under reduced pressure, and acetonitrile was distilled off. The obtained concentration residue was subjected to extraction with ethyl acetate three times, and subsequently, all of the organic layers were washed with a saturated aqueous solution of sodium chloride, then dried over anhydrous magnesium sulfate, filtered, concentrated under reduced pressure, and dried under reduced pressure to obtain 346 mg of the title compound (yield: 30% [2 steps]) as a white solid.

Mass spectrum (CI, m/z): 195 [M+1]⁺.

¹H-NMR spectrum (400 MHz, DMSO-d₆) δ: 12.74 (br s, 1H), 7.43-7.27 (m, 5H), 4.95 (s, 1H), 3.62 (spt, J=6.1 Hz, 1H), 1.15 (d, J=6.1 Hz, 3H), 1.09 (d, J=6.1 Hz, 3H).

Reference Example 88

(R)-Ethyl 2-phenyl-2-(trifluoromethoxy)acetate

[Chemical Formula 223]

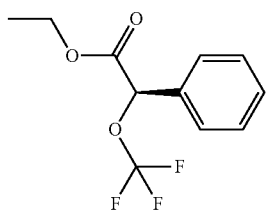

To a solution of 25.0 g (139 mmol) of (R)-ethyl 2-hydroxy-2-phenylacetate in 10 ml of deuterated chloroform, 3.75 g (4.75 mmol) of 40% 1-trifluoromethyl-3,3-dimethyl-1,2-benziodoxole [Togni Reagent II (trade name), diatomaceous earth mixture, purchased from Tokyo Chemical Industry Co., Ltd.] and 0.900 g (1.44 mmol) of bis(trifluoromethylsulfonyl)imide zinc(II) were added with stirring at room temperature in an argon atmosphere and stirred at room temperature for 88 hours.

After the completion of the reaction, a saturated aqueous solution of sodium bicarbonate was added to the reaction solution, followed by extraction with ethyl acetate. The obtained organic layer was washed with a saturated aqueous solution of sodium chloride, then dried over anhydrous magnesium sulfate, and filtered, and the filtrate was concentrated under reduced pressure. The obtained concentration residue was subjected to silica gel chromatography (elution solvent: n-hexane:ethyl acetate=100:0 to 60:40 (V/V)), and a fraction containing the compound of interest was concentrated under reduced pressure to obtain 421 mg of the title compound (containing impurities) as a yellow oil.

Mass spectrum (CI, m/z): 249 [M+1]⁺.

¹H-NMR spectrum (400 MHz, CDCl₃) δ: 7.53-7.36 (m, 5H), 5.52 (s, 1H), 4.32-4.16 (m, 2H), 1.25 (t, J=7.1 Hz, 3H).

Reference Example 89

(R)-2-Phenyl-2-(trifluoromethoxy)acetic acid

[Chemical Formula 224]

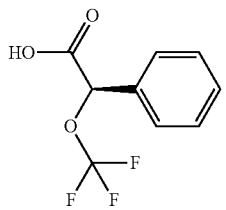

To a solution of 421 mg of (R)-ethyl 2-phenyl-2-(trifluoromethoxy)acetate (containing impurities) synthesized in the similar manner as in Reference Example 88 in 3 ml of methanol/3 ml of water, 93 mg (2.2 mmol) of lithium hydroxide monohydrate was added at room temperature and then reacted with stirring at room temperature for 4 hours.

After the completion of the reaction, diethyl ether was added to the reaction solution and then the aqueous layer and the organic layer were separated. The aqueous layer was adjusted to pH 2 by adding 2 N hydrochloric acid, followed by extraction with ethyl acetate three times. All of the obtained organic layers were washed with a saturated aqueous solution of sodium chloride, then dried over anhydrous magnesium sulfate, filtered, and concentrated under reduced pressure to obtain 390 mg of the title compound (containing impurities) as a pale yellow oil.

Mass spectrum (DUIS, m/z): 219 [M−1]−.

$^1$H-NMR spectrum (400 MHz, CDCl$_3$) δ: 7.52-7.37 (m, 5H), 5.57 (s, 1H).

Reference Example 90

(R)-Benzyl 2-phenyl-2-propoxyacetate

[Chemical Formula 225]

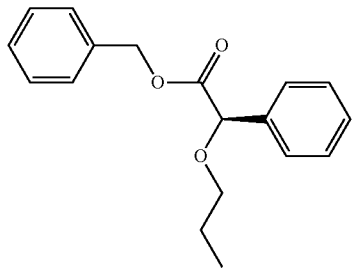

To a suspension of 1.58 g (6.52 mmol) of (R)-benzyl 2-hydroxy-2-phenylacetate in 14.5 ml (149 mmol) of 1-iodopropane, 3.03 g (13.1 mmol) of silver(I) oxide was added at room temperature in an argon atmosphere and then reacted with stirring at 80° C. for 14 hours.

After the completion of the reaction, the reaction solution was allowed to cool to room temperature and then filtered using a celite filter. The filtration cake was washed with ethyl acetate, and then, all of the filtrates were concentrated under reduced pressure. The obtained concentration residue was subjected to silica gel column chromatography (elution solvent: n-hexane:ethyl acetate=97:3 to 90:10 (V/V)), and a fraction containing the compound of interest was concentrated under reduced pressure and dried under reduced pressure to obtain 1.23 g of the title compound (yield: 66%) as a colorless oil.

Mass spectrum (CI, m/z): 285 [M+1]+.

$^1$H-NMR spectrum (400 MHz, DMSO-d$_6$) δ: 7.43-7.27 (m, 8H), 7.26-7.20 (m, 2H), 5.13 (s, 2H), 5.06 (s, 1H), 3.46 (td, J=6.6, 9.0 Hz, 1H), 3.40-3.28 (m, 1H), 1.60-1.49 (m, 2H), 0.85 (t, J=7.4 Hz, 3H).

Reference Example 91

(R)-2-Phenyl-2-propoxyacetic acid

[Chemical Formula 226]

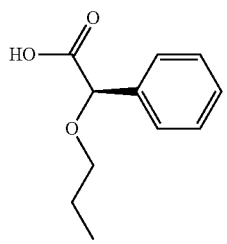

To a solution of 1.23 g (4.33 mmol) of (R)-benzyl 2-phenyl-2-propoxyacetate synthesized in the similar manner as in Reference Example 90 in 15 ml of ethanol, 274 mg of 10% palladium/carbon [PE type (trade name), manufactured by N.E. Chemcat Corp., containing 54% water] was added at room temperature in an argon atmosphere and then, after replacement with a hydrogen atmosphere under reduced pressure, reacted with stirring at room temperature for 1.5 hours.

After the completion of the reaction, the inside of the reaction container was replaced with an argon atmosphere under reduced pressure. The reaction solution was filtered using a celite filter, the removed solid was washed with ethanol, and then, the filtrate was concentrated under reduced pressure and dried under reduced pressure to obtain 892 mg of the title compound (containing impurities) as a colorless oil.

Mass spectrum (CI, m/z): 195 [M+1]+.

$^1$H-NMR spectrum (400 MHz, DMSO-d$_6$) δ: 12.78 (br s, 1H), 7.42-7.29 (m, 5H), 4.83 (s, 1H), 3.47 (td, J=6.6, 9.0 Hz, 1H), 3.40-3.25 (m, 1H), 1.61-1.49 (m, 2H), 0.87 (t, J=7.4 Hz, 3H).

Reference Example 92

Methyl 2-(4-fluorophenyl)-2-methoxyacetate

[Chemical Formula 227]

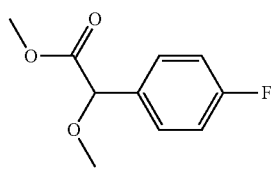

To a solution of 800 mg (4.70 mmol) of 4-fluoromandelic acid in 20 ml of dehydrated DMF, 450 mg (10.3 mmol) of 55% sodium hydride was dividedly added with stirring at 0° C. in an argon atmosphere and stirred at the same temperature as above for 1 hour. Subsequently, 0.732 ml (11.8 mmol) of iodomethane was added dropwise at 0° C. and then stirred at room temperature for 2 hours. 0.732 ml (11.8 mmol) of iodomethane was further added dropwise at 0° C. and then stirred at room temperature for 2 hours.

After the completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, and filtered, and the filtrate was concentrated under reduced pressure. The obtained concentration residue was subjected to silica gel chromatography (elution solvent: n-hexane:ethyl acetate=100:0 to 70:30 (V/V)), and a fraction containing the compound of interest was concentrated under reduced pressure to obtain 247 mg of the title compound (yield: 27%) as a colorless oil.

Mass spectrum (CI, m/z): 199 [M+1]$^+$.

$^1$H-NMR spectrum (400 MHz, CDCl$_3$) δ: 7.46-7.38 (m, 2H), 7.11-7.02 (m, 2H), 4.76 (s, 1H), 3.73 (s, 3H), 3.40 (s, 3H).

Reference Example 93

2-(4-Fluorophenyl)-2-methoxyacetic acid

[Chemical Formula 228]

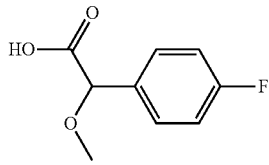

To a solution of 247 mg (1.25 mmol) of methyl 2-(4-fluorophenyl)-2-methoxyacetate synthesized in the similar manner as in Reference Example 92 in 5 ml of THF, 2.0 ml (2.0 mmol) of a 1 N aqueous sodium hydroxide solution was added with stirring at room temperature and stirred at the same temperature as above for 16 hours.

After the completion of the reaction, 1 N hydrochloric acid was added to the reaction solution to adjust the pH to 2, followed by extraction with ethyl acetate. The obtained organic layer was washed with a saturated aqueous solution of sodium chloride, then dried over anhydrous magnesium sulfate, and filtered, and the filtrate was concentrated under reduced pressure and dried under reduced pressure to obtain 260 mg of the title compound (containing impurities) as a brown oil.

Mass spectrum (CI, m/z): 185 [M+1]$^+$.

$^1$H-NMR spectrum (400 MHz, CDCl$_3$) δ: 7.49-7.36 (m, 2H), 7.13-7.03 (m, 2H), 4.77 (s, 1H), 3.43 (s, 3H).

Reference Example 94

Ethyl 2-(3-fluorophenyl)-2-hydroxyacetate

[Chemical Formula 229]

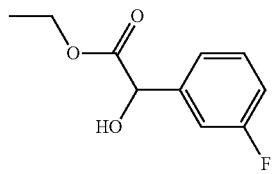

To a suspension of 1.00 g (7.15 mmol) of 3-fluorophenylboronic acid in 30 ml of dehydrated toluene, 2.20 g (10.8 mmol) of a solution of 50% ethyl oxoacetate in toluene [purchased from Apollo scientific limited] and 107 mg (0.359 mmol) of 2-(di-tert-butylphosphino)biphenyl were added with stirring at room temperature in an argon atmosphere, followed by replacement with a nitrogen atmosphere under reduced pressure. Subsequently, 92.0 mg (0.100 mmol) of tris(dibenzylideneacetone)dipalladium(0) was added with stirring at room temperature and reacted at 80° C. for 9 hours.

The reaction solution was filtered using a celite filter, and water was added to the filtrate, followed by extraction with ethyl acetate. The obtained organic layer was washed with a saturated aqueous solution of sodium chloride, then dried over anhydrous magnesium sulfate, and filtered, and the filtrate was concentrated under reduced pressure. The obtained concentration residue was subjected to silica gel chromatography (elution solvent: n-hexane:ethyl acetate=100:0 to 60:40 (V/V)), and a fraction containing the compound of interest was concentrated under reduced pressure to obtain 263 mg of the title compound (yield: 19%) as a pale yellow oil.

Mass spectrum (CI, m/z): 199 [M+1]$^+$.

$^1$H-NMR spectrum (400 MHz, CDCl$_3$) δ: 7.38-7.29 (m, 1H), 7.25-7.20 (m, 1H), 7.19-7.13 (m, 1H), 7.06-6.98 (m, 1H), 5.15 (d, J=5.4 Hz, 1H), 4.34-4.14 (m, 2H), 3.50 (d, J=5.4 Hz, 1H), 1.25 (t, J=7.2 Hz, 3H).

Reference Example 95

Ethyl 2-(3-fluorophenyl)-2-methoxyacetate

[Chemical Formula 230]

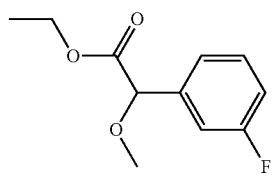

To a solution of 263 mg (1.33 mmol) of ethyl 2-(3-fluorophenyl)-2-hydroxyacetate synthesized in the similar manner as in Reference Example 94 in 8.0 ml (130 mmol) of iodomethane, 615 mg (2.65 mmol) of silver oxide was added at room temperature in an argon atmosphere and reacted with stirring at the same temperature as above for 3 hours.

After the completion of the reaction, the resultant was filtered using a celite filter, and the filtrate was concentrated under reduced pressure. The obtained concentration residue was subjected to silica gel column chromatography (elution solvent: n-hexane:ethyl acetate=100:0 to 60:40 (V/V)), and a fraction containing the compound of interest was concentrated under reduced pressure to obtain 155 mg of the title compound (yield: 55%) as a colorless oil.

Mass spectrum (CI, m/z): 213 [M+1]$^+$.

$^1$H-NMR spectrum (400 MHz, CDCl$_3$) δ: 7.37-7.29 (m, 1H), 7.25-7.15 (m, 2H), 7.07-7.00 (m, 1H), 4.75 (s, 1H), 4.28-4.12 (m, 2H), 3.43 (s, 3H), 1.23 (t, J=7.1 Hz, 3H).

Reference Example 96

2-(3-Fluorophenyl)-2-methoxyacetic acid

[Chemical Formula 231]

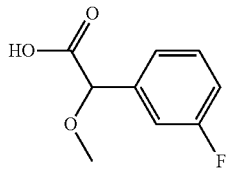

To a solution of 155 mg (0.730 mmol) of ethyl 2-(3-fluorophenyl)-2-methoxyacetate synthesized in the similar manner as in Reference Example 95 in 5 ml of THF, 1.0 ml (1.0 mmol) of a 1 N aqueous sodium hydroxide solution was added with stirring at room temperature and stirred at the same temperature as above for 20 hours.

After the completion of the reaction, 1 N hydrochloric acid was added to the reaction solution to adjust the pH to 2, followed by extraction with ethyl acetate. The obtained organic layer was washed with a saturated aqueous solution of sodium chloride, then dried over anhydrous magnesium sulfate, and filtered, and the filtrate was concentrated under reduced pressure to obtain 144 mg of the title compound (containing impurities) as a colorless oil.

Mass spectrum (CI, m/z): 185 [M+1]$^+$.

$^1$H-NMR spectrum (400 MHz, CDCl$_3$) δ: 7.41-7.32 (m, 1H), 7.25-7.20 (m, 1H), 7.19-7.13 (m, 1H), 7.10-7.03 (m, 1H), 4.79 (s, 1H), 3.46 (s, 3H).

Reference Example 97

(R)-Methyl 2-(2-fluorophenyl)-2-methoxyacetate

[Chemical Formula 232]

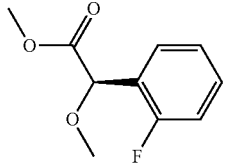

To a solution of 1.00 g (5.88 mmol) of (R)-2-(2-fluorophenyl)-2-hydroxyacetic acid [purchased from Combi-Blocks Inc.] in 20 ml of dehydrated DMF, 310 mg (7.10 mmol) of 55% sodium hydride was dividedly added with stirring at 0° C. in an argon atmosphere and stirred at the same temperature as above for 1 hour. Subsequently, 0.842 ml (13.5 mmol) of iodomethane was added dropwise at 0° C. and then stirred at room temperature for 4 hours.

After the completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, and filtered, and the filtrate was concentrated under reduced pressure. The obtained concentration residue was subjected to silica gel chromatography (elution solvent: n-hexane:ethyl acetate=100:0 to 70:30 (V/V)), and a fraction containing the compound of interest was concentrated under reduced pressure to obtain 858 mg of the title compound (yield: 74%) as a colorless oil.

Mass spectrum (CI, m/z): 199 [M+1]$^+$.

$^1$H-NMR spectrum (400 MHz, CDCl$_3$) δ: 7.50-7.42 (m, 1H), 7.38-7.30 (m, 1H), 7.21-7.14 (m, 1H), 7.13-7.05 (m, 1H), 5.14 (s, 1H), 3.43 (s, 3H).

Reference Example 98

(R)-2-(2-Fluorophenyl)-2-methoxyacetic acid

[Chemical Formula 233]

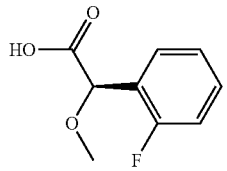

To a solution of 858 mg (4.33 mmol) of (R)-methyl 2-(2-fluorophenyl)-2-methoxyacetate synthesized in the similar manner as in Reference Example 97 in 10 ml of THF, 5.2 ml (5.2 mmol) of a 1 N aqueous sodium hydroxide solution was added with stirring at room temperature and stirred at 50° C. for 3 hours.

After the completion of the reaction, the resultant was allowed to cool to room temperature, and then, 1 N hydrochloric acid was added to the reaction solution to adjust the pH to 2, followed by extraction with ethyl acetate. The obtained organic layer was washed with a saturated aqueous solution of sodium chloride, then dried over anhydrous magnesium sulfate, and filtered, and the filtrate was concentrated under reduced pressure to obtain 390 mg of the title compound (yield: 49%) as a brown oil.

Mass spectrum (CI, m/z): 185 [M+1]$^+$.

$^1$H-NMR spectrum (400 MHz, CDCl$_3$) δ: 7.46-7.32 (m, 2H), 7.22-7.05 (m, 2H), 5.11 (s, 1H), 3.43 (s, 3H).

Reference Example 99

Ethyl 2-hydroxy-2-(thiophen-2-yl)acetate

[Chemical Formula 234]

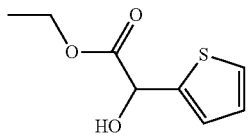

To a suspension of 1.00 g (7.82 mmol) of thiophene-2-boronic acid in 30 ml of dehydrated toluene, 2.40 g (11.8 mmol) of a solution of 50% ethyl oxoacetate in toluene [purchased from Apollo scientific limited] and 117 mg (0.392 mmol) of 2-(di-tert-butylphosphino)biphenyl were added with stirring at room temperature in an argon atmosphere, followed by replacement with a nitrogen atmosphere under reduced pressure. Subsequently, 101 mg (0.110 mmol) of tris(dibenzylideneacetone)dipalladium(0) was added with stirring at room temperature and reacted at 80° C. for 9 hours.

The reaction solution was filtered using a celite filter, and water was added to the filtrate, followed by extraction with ethyl acetate. The obtained organic layer was washed with a saturated aqueous solution of sodium chloride, then dried over anhydrous magnesium sulfate, and filtered, and the filtrate was concentrated under reduced pressure. The obtained concentration residue was subjected to silica gel chromatography (elution solvent: n-hexane:ethyl acetate=100:0 to 60:40 (V/V)), and a fraction containing the compound of interest was concentrated under reduced pressure to obtain 86 mg of the title compound (yield: 6%) as a yellow oil.

$^1$H-NMR spectrum (400 MHz, CDCl$_3$) δ: 7.29 (dd, J=1.2, 5.1 Hz, 1H), 7.13-7.09 (m, 1H), 7.00 (dd, J=3.6, 5.1 Hz, 1H), 5.43-5.37 (m, 1H), 4.37-4.22 (m, 2H), 3.48 (d, J=6.4 Hz, 1H), 1.30 (t, J=7.2 Hz, 3H).

Reference Example 100

Ethyl 2-methoxy-2-(thiophen-2-yl)acetate

[Chemical Formula 235]

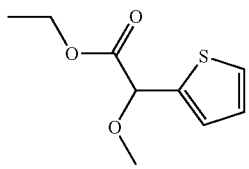

To a solution of 86 mg (0.46 mmol) of ethyl 2-hydroxy-2-(thiophen-2-yl)acetate synthesized in the similar manner as in Reference Example 99 in 4.0 ml (64 mmol) of iodomethane, 214 mg (0.923 mmol) of silver oxide was added at room temperature in an argon atmosphere and reacted with stirring at the same temperature as above for 3 hours.

After the completion of the reaction, the resultant was filtered using a celite filter, and the filtrate was concentrated under reduced pressure. The obtained concentration residue was subjected to silica gel column chromatography (elution solvent: n-hexane:ethyl acetate=100:0 to 60:40 (V/V)), and a fraction containing the compound of interest was concentrated under reduced pressure to obtain 68.5 mg of the title compound (yield: 74%) as a colorless oil.

$^1$H-NMR spectrum (400 MHz, CDCl$_3$) δ: 7.33 (dd, J=1.2, 5.1 Hz, 1H), 7.16-7.10 (m, 1H), 7.00 (dd, J=3.5, 5.1 Hz, 1H), 5.02 (s, 1H), 4.33-4.17 (m, 2H), 3.44 (s, 3H), 1.28 (t, J=7.2 Hz, 3H).

Reference Example 101

2-Methoxy-2-(thiophen-2-yl)acetic acid

[Chemical Formula 236]

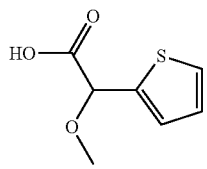

To a solution of 68 mg (0.34 mmol) of ethyl 2-methoxy-2-(thiophen-2-yl)acetate synthesized in the similar manner as in Reference Example 100 in 3 ml of THF, 0.5 ml (0.5 mmol) of a 1 N aqueous sodium hydroxide solution was added with stirring at room temperature and stirred at the same temperature as above for 16 hours.

After the completion of the reaction, 1 N hydrochloric acid was added to the reaction solution to adjust the pH to 2, followed by extraction with ethyl acetate. The obtained organic layer was washed with a saturated aqueous solution of sodium chloride, then dried over anhydrous magnesium sulfate, and filtered, and the filtrate was concentrated under reduced pressure and dried under reduced pressure to obtain 60 mg of the title compound (containing impurities) as a pale yellow oil.

Mass spectrum (DUIS, m/z): 171 [M−1]$^−$.

$^1$H-NMR spectrum (400 MHz, CDCl$_3$) δ: 7.36 (dd, J=1.2, 5.1 Hz, 1H), 7.19-7.14 (m, 1H), 7.02 (dd, J=3.5, 5.1 Hz, 1H), 5.07 (s, 1H), 3.48 (s, 3H).

Reference Example 102

Mixture of 2-ethyl 5-(trichloromethyl) 6,6-dimethyl-3-[1-(trimethylsilyl)cyclobutanecarboxamido]pyrrolo[3,4-c]pyrazole-2,5(4H,6H)-dicarboxylate, and ethyl 5-(chlorocarbonyl)-6,6-dimethyl-3-[1-(trimethylsilyl)cyclobutanecarbox amido]-5,6-dihydropyrrolo[3,4-c]pyrazole-2(4H)-carboxylate

[Chemical Formula 237]

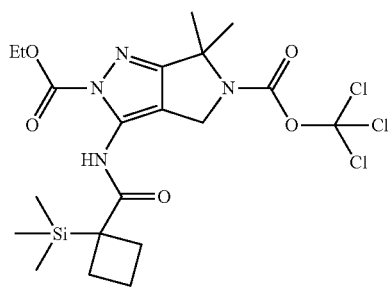

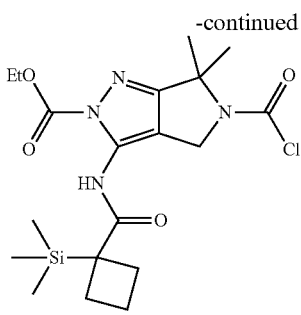

To a solution of 8.03 g (21.2 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 84 in 100 ml of dehydrated dichloromethane, 12.9 ml (74.1 mmol) of DIPEA was added at room temperature in an argon atmosphere. Subsequently, a solution of 4.40 g (14.8 mmol) of bis(trichloromethyl)carbonate in 10 ml of dehydrated dichloromethane was added dropwise at −78° C. and then stirred for 1.5 hours with the temperature unchanged.

After the completion of the reaction, a saturated aqueous solution of sodium bicarbonate and dichloromethane were added to the reaction solution and then stirred for 1 hour while the temperature was raised to room temperature for a while. The reaction solution was separated into an aqueous layer and an organic layer, and then, the aqueous layer was subjected to extraction with ethyl acetate twice. All of the organic layers were washed with a saturated aqueous solution of sodium chloride, then dried over anhydrous magnesium sulfate, filtered, and concentrated under reduced pressure. The obtained concentration residue was subjected to silica gel column chromatography (elution solvent: n-hexane:ethyl acetate=85:15→75:25 (V/V)), and a fraction containing the compound of interest was concentrated under reduced pressure. n-Hexane was added to the obtained concentration residue, stirred at room temperature for 10 minutes, and then left standing for 15 minutes in a freezer. The deposited solid was filtered off, and the filtrate obtained by washing the removed solid with n-hexane was concentrated under reduced pressure and dried under reduced pressure to obtain a mixture of 2.90 g of 2-ethyl 5-(trichloromethyl) 6,6-dimethyl-3-[1-(trimethylsilyl)cyclobutanecarboxamido]pyrrolo[3,4-c]pyrazole-2,5(4H,6H)-dicarboxylate (yield: 25%) and 1.75 g of ethyl 5-(chlorocarbonyl)-6,6-dimethyl-3-[1-(trimethylsilyl)cyclobutanecarbox amido]-5,6-dihydropyrrolo[3,4-c]pyrazole-2(4H)-carboxylate (yield: 19%) as a white foam.

Mass spectrum (ESI, m/z): 539 [M+1]$^+$, 441 [M+1]$^+$.

$^1$H-NMR spectrum (400 MHz, CDCl$_3$) δ: 9.99-9.84 (m, total 1H), 4.97 (s, 0.85H), 4.84-4.79 (m, total 1.15H), 4.59-4.51 (m, total 2H), 2.64-2.53 (m, total 2H), 2.39-2.28 (m, total 2H), 2.03-1.92 (m, total 2H), 1.82-1.75 (m, total 6H), 1.51-1.44 (m, total 3H), 0.19-0.13 (m, total 9H).

Reference Example 103

{1-[Amino(phenyl)methyl]cyclobutyl}methanol

[Chemical Formula 238]

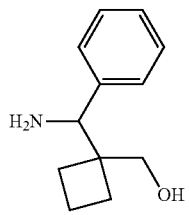

To a solution of 2.07 g (23.2 mmol) of ethyl carbamate in 20 ml of toluene, 2.36 ml (23.2 mmol) of benzaldehyde and 235 mg (1.23 mmol) of p-toluenesulfonic acid monohydrate were added in this order at room temperature in an argon atmosphere and then stirred at room temperature for 5 minutes. Subsequently, 1.80 ml (23.2 mmol) of cyclobutanecarbaldehyde was added at room temperature and then stirred at 60° C. for 4 hours.

After the completion of the reaction, the reaction solution was poured to a saturated aqueous solution of sodium bicarbonate and then stirred at room temperature. After separation into an aqueous layer and an organic layer, the aqueous layer was subjected to extraction with toluene once. All of the obtained organic layers were washed with a saturated aqueous solution of sodium chloride, then dried over anhydrous magnesium sulfate, filtered, and concentrated under reduced pressure. The obtained concentration residue was subjected to silica gel column chromatography (elution solvent: n-hexane:ethyl acetate=90:10 to 60:40 (V/V)), and a fraction containing the compound of interest was concentrated under reduced pressure and dried under reduced pressure to obtain 2.20 g of a concentration residue.

To a solution of the obtained concentration residue in 10 ml of ethanol, 199 mg (5.26 mmol) of sodium borohydride was dividedly added at 0° C. in an argon atmosphere and then stirred at 0° C. for 0.5 hours and further at room temperature for 2.5 hours. Subsequently, 990 mg (17.7 mmol) of potassium hydroxide and 5.0 ml of water were added to the reaction solution at room temperature and then stirred for 2.5 hours under heating to reflux.

After the completion of the reaction, the reaction solution was concentrated under reduced pressure, and ethanol was distilled off. 2 N hydrochloric acid was added to the concentration residue and then washed with diethyl ether. After separation into an aqueous layer and an organic layer, the obtained aqueous layer was adjusted to pH >10 by adding a 2 N aqueous sodium hydroxide solution, followed by extraction with dichloromethane three times. All of the obtained organic layers were washed with a saturated aqueous solution of sodium chloride, then dried over anhydrous magnesium sulfate, filtered, and concentrated under reduced pressure. The obtained concentration residue was dissolved in 1,2-dichloroethane, then n-hexane was added, and the deposited solid was collected by filtration, washed with n-hexane, and then dried under reduced pressure to obtain 859 mg of the title compound (yield: 19% [2 steps]) as a white solid.

Mass spectrum (CI, m/z): 192 [M+1]$^+$.

$^1$H-NMR spectrum (400 MHz, DMSO-d$_6$) δ: 7.36-7.25 (m, 4H), 7.24-7.16 (m, 1H), 3.97 (s, 1H), 3.41 (d, J=10.7 Hz, 1H), 3.25 (d, J=10.7 Hz, 1H), 2.06-1.92 (m, 2H), 1.79-1.63 (m, 2H), 1.61-1.50 (m, 1H), 1.47-1.37 (m, 1H).

Reference Example 104

(R)—N-[2-(1-Hydroxycyclopropyl)-1-phenylethyl]-2,2,2-trifluoroacetamide

[Chemical Formula 239]

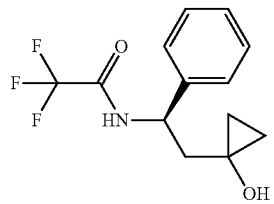

To a solution of 1.01 g (3.67 mmol) of (R)-methyl 3-phenyl-3-(2,2,2-trifluoroacetamido)propanoate synthesized in the similar manner as in Reference Example 22 in 10 ml of dehydrated THF, 0.22 ml (0.75 mmol) of tetraisopropyl orthotitanate was added at 0° C. in an argon atmosphere, and then, 11.0 ml (11.0 mmol) of 1 M ethyl magnesium bromide/THF solution was added dropwise at 0° C. over 1 hour and then stirred for 3 hours with the temperature unchanged and subsequently for 1.5 hours after the temperature was raised to room temperature.

After the completion of the reaction, a saturated aqueous solution of ammonium chloride was added to the reaction solution and stirred, and then, insoluble matter was filtered off using a celite filter. The solid collected by filtration was washed with ethyl acetate, and then, the filtrate was separated into an aqueous layer and an organic layer. The aqueous layer was subjected to extraction with ethyl acetate once, and then, all of the organic layers were dried over anhydrous magnesium sulfate, filtered, and concentrated under reduced pressure. The obtained concentration residue was subjected to silica gel column chromatography (elution solvent: n-hexane:ethyl acetate=95:5 to 75:25 (V/V)), and a fraction containing the compound of interest was concentrated under reduced pressure and dried under reduced pressure to obtain 489 mg of the title compound (yield: 49%) as a pale yellow solid.

Mass spectrum (CI, m/z): 274 [M+1]$^+$.

$^1$H-NMR spectrum (400 MHz, DMSO-d$_6$) δ: 9.67 (br s, 1H), 7.37-7.30 (m, 4H), 7.30-7.21 (m, 1H), 5.33-5.05 (m, 2H), 2.01 (dd, J=5.2, 14.2 Hz, 1H), 1.93 (dd, J=9.2, 14.2 Hz, 1H), 0.57-0.46 (m, 2H), 0.45-0.37 (m, 1H), 0.11-0.04 (m, 1H).

Reference Example 105

(R)-1-(2-Amino-2-phenylethyl)cyclopropanol

[Chemical Formula 240]

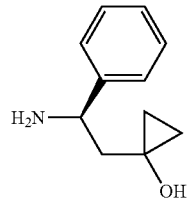

To a solution of 412 mg (1.51 mmol) of (R)—N-[2-(1-hydroxycyclopropyl)-1-phenylethyl]-2,2,2-trifluoroacetamide synthesized in the similar manner as in Reference Example 104 in 7 ml of ethanol, 174 mg (4.60 mmol) of sodium borohydride was added at room temperature in an argon atmosphere and then stirred at room temperature for 14.5 hours.

After the completion of the reaction, a saturated aqueous solution of ammonium chloride was added to the reaction solution at 0° C. and then stirred at room temperature. Insoluble matter was dissolved by adding water, followed by extraction with dichloromethane twice. All of the organic layers were dried over anhydrous magnesium sulfate, filtered, and concentrated under reduced pressure. The obtained concentration residue was subjected to silica gel column chromatography (DIOL silica gel, elution solvent: n-hexane:ethyl acetate=75:25 to 60:40 (V/V)), and a fraction containing the compound of interest was concentrated under reduced pressure and dried under reduced pressure to obtain 259 mg of the title compound (containing impurities) as a pale yellow solid.

Mass spectrum (CI, m/z): 178 [M+1]$^+$.

$^1$H-NMR spectrum (400 MHz, DMSO-d$_6$) δ: 7.38-7.24 (m, 4H), 7.21-7.14 (m, 1H), 4.15 (dd, J=4.0, 9.4 Hz, 1H), 1.82 (ddd, J=1.3, 9.4, 13.9 Hz, 1H), 1.51-1.44 (m, 1H), 0.58-0.51 (m, 1H), 0.49-0.42 (m, 1H), 0.41-0.34 (m, 1H), 0.21-0.14 (m, 1H).

Reference Example 106

(R)—N-(3-Ethyl-3-hydroxy-1-phenylpentyl)-2,2,2-trifluoroacetamide

[Chemical Formula 241]

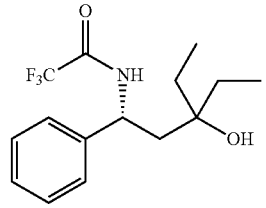

To a solution of 700 mg (2.54 mmol) of (R)-methyl 3-phenyl-3-(2,2,2-trifluoroacetamido)propanoate synthesized in the similar manner as in Reference Example 22 in 10 ml of dehydrated THF, 7.63 ml (7.63 mmol) of 1 M ethyl magnesium bromide-THF solution was added dropwise at 0° C. in an argon atmosphere and then stirred at room temperature for 6 hours.

After the completion of the reaction, a saturated aqueous solution of ammonium chloride was added to the reaction solution, followed by extraction with ethyl acetate. All of the obtained organic layers were washed with a saturated aqueous solution of sodium chloride, dried over anhydrous magnesium sulfate, then filtered, and concentrated under reduced pressure. The obtained concentration residue was subjected to silica gel column chromatography (elution solvent: n-hexane:ethyl acetate=100:0 to 90:10 (V/V)), and a fraction containing the compound of interest was concentrated under reduced pressure and dried under reduced pressure to obtain 714 mg of the title compound (containing impurities) as a colorless oil.

Mass spectrum (CI, m/z): 304 [M+1]$^+$.

Reference Example 107

(R)-1-Amino-3-ethyl-1-phenylpentan-3-ol

[Chemical Formula 242]

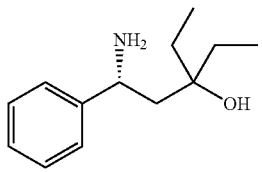

To a solution of 714 mg of (R)—N-(3-ethyl-3-hydroxy-1-phenylpentyl)-2,2,2-trifluoroacetamide (containing impurities) synthesized in Reference Example 106 in 1 ml of water/5 ml of methanol, 651 mg (4.71 mmol) of potassium carbonate was added at room temperature in an argon atmosphere and then stirred for 20 hours with the temperature unchanged.

After the completion of the reaction, a saturated aqueous solution of ammonium chloride was added to the reaction solution, followed by extraction with ethyl acetate. All of the obtained organic layers were washed with a saturated aqueous solution of sodium chloride, dried over anhydrous magnesium sulfate, then filtered, and concentrated under reduced pressure. The obtained concentration residue was subjected to silica gel column chromatography (elution solvent: n-hexane:ethyl acetate=75:25 to 60:40 (V/V)), and a fraction containing the compound of interest was concentrated under reduced pressure and dried under reduced pressure to obtain 120 mg of the title compound (yield: 23% [2 steps]) as a colorless oil.

Mass spectrum (CI, m/z): 208 [M+1]$^+$.

$^1$H-NMR spectrum (400 MHz, DMSO-$d_6$) δ: 7.38-7.25 (m, 4H), 7.22-7.15 (m, 1H), 4.01 (dd, J=2.6, 10.9 Hz, 1H), 1.66-1.41 (m, 4H), 1.38-1.25 (m, 2H), 0.86-0.71 (m, 6H)

Reference Example 108

(E)-Methyl 3-(4-fluorophenyl)acrylate

[Chemical Formula 243]

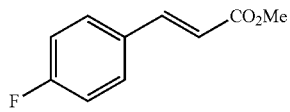

To a solution of 2.0 g (16 mmol) of 4-fluorobenzaldehyde in 20 ml of dehydrated THF, 6.47 g (19.4 mmol) of methyl 2-(triphenylphosphoranylidene)acetate was added at room temperature in an argon atmosphere and then stirred for 20 hours with the temperature unchanged.

After the completion of the reaction, the reaction solution was concentrated under reduced pressure. 20 ml of TBME was added to the obtained concentration residue and filtered, and the filtrate was concentrated under reduced pressure. The obtained concentration residue was subjected to silica gel column chromatography (elution solvent: n-hexane:ethyl acetate=100:0 to 90:10(v/v)), and a fraction containing the compound of interest was concentrated under reduced pressure and dried under reduced pressure to obtain 2.74 g of the title compound (yield: 94%) as a white solid.

Mass spectrum (CI, m/z): 181 [M+1]$^+$.

$^1$H-NMR spectrum (400 MHz, CDCl$_3$) δ: 7.66 (d, J=16.0 Hz, 1H), 7.55-7.47 (m, 2H), 7.13-7.03 (m, 2H), 6.41-6.33 (m, 1H), 3.81 (s, 3H).

Reference Example 109

(R)-Methyl 3-{benzyl [(S)-1-phenylethyl]amino}-3-(4-fluorophenyl)propanoate

[Chemical Formula 244]

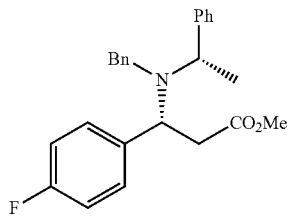

To a solution of 2.79 ml (13.3 mmol) of (S)—N-benzyl-1-phenylethanamine in 30 ml of dehydrated THF, 7.80 ml (12.5 mmol) of a 1.6 M solution of n-butyllithium in n-hexane was added dropwise at −78° C. in an argon atmosphere and then stirred for 30 minutes with the temperature unchanged. Subsequently, a solution of 1.5 g (8.3 mmol) of (E)-methyl 3-(4-fluorophenyl)acrylate synthesized in the similar manner as in Reference Example 108 in 5 ml of THF was added at −78° C. and then stirred for 1 hour with the temperature unchanged.

After the completion of the reaction, a saturated aqueous solution of ammonium chloride was added to the reaction solution, followed by extraction with ethyl acetate. The obtained organic layer was washed with a saturated aqueous solution of sodium chloride, dried over anhydrous magnesium sulfate, then filtered, and concentrated under reduced pressure. The obtained concentration residue was subjected to silica gel column chromatography (elution solvent: n-hexane:ethyl acetate=100:0 to 95:5 (V/V)), and a fraction containing the compound of interest was concentrated under reduced pressure to obtain 1.53 g of the title compound (yield: 47%) as a pale yellow oil.

Mass spectrum (CI, m/z): 392 [M+1]$^+$.

$^1$H-NMR spectrum (400 MHz, CDCl$_3$) δ: 7.43-7.16 (m, 12H), 7.08-6.96 (m, 2H), 4.42 (dd, J=5.4, 9.7 Hz, 1H), 3.97 (q, J=6.9 Hz, 1H), 3.72 (d, J=14.7 Hz, 1H), 3.65 (d, J=14.7 Hz, 1H), 3.47 (s, 3H), 2.65 (dd, J=5.4, 14.9 Hz, 1H), 2.52 (dd, J=9.7, 14.9 Hz, 1H), 1.27-1.21 (m, 3H).

Reference Example 110

(R)-4-{Benzyl[(S)-1-phenylethyl]amino}-4-(4-fluorophenyl)-2-methylbutan-2-ol

[Chemical Formula 245]

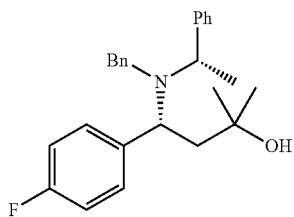

To a solution of 1.35 g (3.45 mmol) of (R)-methyl 3-{benzyl [(S)-1-phenylethyl]amino}-3-(4-fluorophenyl)propanoate synthesized in the similar manner as in Reference Example 109 in 20 ml of dehydrated THF, 10.4 ml (10.4 mmol) of 1 M methyl magnesium bromide-THF solution was added dropwise at 0° C. under argon stream and then stirred at room temperature for 20 hours.

After the completion of the reaction, a saturated aqueous solution of ammonium chloride was added to the reaction solution, followed by extraction with ethyl acetate. The obtained organic layer was washed with a saturated aqueous solution of sodium chloride, dried over anhydrous magnesium sulfate, then filtered, and concentrated under reduced pressure. The obtained concentration residue was subjected to silica gel column chromatography (elution solvent: n-hexane:ethyl acetate=95:5 to 85:15 (V/V)), and a fraction containing the compound of interest was concentrated under reduced pressure and dried under reduced pressure to obtain 850 mg of the title compound (yield: 63%) as a colorless oil.

Mass spectrum (ESI, m/z): 392 [M+1]$^+$.

$^1$H-NMR spectrum (400 MHz, DMSO-d$_6$) δ: 7.48-7.09 (m, 14H), 4.21 (s, 1H), 4.09-3.98 (m, 1H), 3.92-3.85 (m, 1H), 3.74 (d, J=15.1 Hz, 1H), 3.63 (d, J=15.1 Hz, 1H), 2.10 (dd, J=9.2, 13.9 Hz, 1H), 2.02-1.93 (m, 1H), 0.93 (d, J=6.8 Hz, 3H), 0.82 (s, 3H), 0.69 (s, 3H).

Reference Example 111

(R)-4-Amino-4-(4-fluorophenyl)-2-methylbutan-2-ol

[Chemical Formula 246]

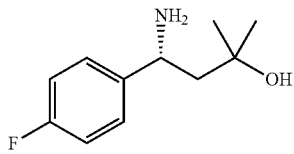

To a solution of 850 mg (2.17 mmol) of (R)-4-{benzyl[(S)-1-phenylethyl]amino}-4-(4-fluorophenyl)-2-methylbutan-2-ol synthesized in the similar manner as in Reference Example 110 in 10 ml of methanol, 425 mg of 20% palladium hydroxide/carbon (containing 50% water) was added at room temperature under argon stream and after replacement with a hydrogen atmosphere, stirred at room temperature for 7 hours.

After the completion of the reaction, the reaction solution was diluted with ethyl acetate and filtered through celite. The filtrate was concentrated under reduced pressure, the obtained concentration residue was subjected to silica gel column chromatography (DIOL, elution solvent: n-hexane: ethyl acetate=75:25 to 50:50 (V/V)), and a fraction containing the compound of interest was concentrated under reduced pressure to obtain 248 mg of the title compound (containing impurities) as a colorless oil.

Mass spectrum (CI, m/z): 198 [M+1]$^+$.

Reference Example 112

(E)-Methyl 3-(3-fluorophenyl)acrylate

[Chemical Formula 247]

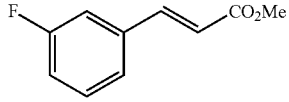

To a solution of 1.27 ml (12.1 mmol) of 3-fluorobenzaldehyde in ml of dehydrated THF, 5.25 g (15.7 mmol) of methyl 2-(triphenylphosphoranylidene)acetate was added at room temperature under argon stream and then stirred for 16 hours with the temperature unchanged.

After the completion of the reaction, the reaction solution was concentrated under reduced pressure. 20 ml of TBME was added to the obtained concentration residue, insoluble matter was filtered off, and the filtrate was concentrated under reduced pressure. The obtained concentration residue was subjected to silica gel column chromatography (elution solvent: n-hexane:ethyl acetate=100:0 to 90:10 (V/V)), and a fraction containing the compound of interest was concentrated under reduced pressure to obtain 1.75 g of the title compound (yield: 80%) as a colorless oil.

Mass spectrum (CI, m/z): 181 [M+1]$^+$.

$^1$H-NMR spectrum (400 MHz, CDCl$_3$) δ: 7.65 (d, J=16.1 Hz, 1H), 7.40-7.33 (m, 1H), 7.32-7.27 (m, 1H), 7.25-7.19 (m, 1H), 7.12-7.05 (m, 1H), 6.44 (d, J=16.1 Hz, 1H), 3.82 (s, 3H).

Reference Example 113

(R)-Methyl 3-{benzyl[(S)-1-phenylethyl] amino}-3-(3-fluorophenyl)propanoate

[Chemical Formula 248]

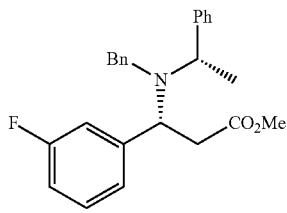

To a solution of 3.25 ml (15.5 mmol) of (S)—N-benzyl-1-phenylethanamine in 30 ml of dehydrated THF, 9.11 ml (14.6 mmol) of a 1.6 M solution of n-butyllithium in n-hexane was added dropwise at −78° C. in an argon atmosphere and then stirred for 1 hour with the temperature unchanged. Subsequently, a solution of 1.75 g (9.71 mmol) of (E)-methyl 3-(3-fluorophenyl)acrylate synthesized in the similar manner as in Reference Example 112 in 5 ml of THF was added at −78° C. and then stirred for 1 hour with the temperature unchanged.

After the completion of the reaction, a saturated aqueous solution of ammonium chloride was added to the reaction solution, followed by extraction with ethyl acetate. The obtained organic layer was washed with a saturated aqueous solution of sodium chloride, dried over anhydrous magnesium sulfate, then filtered, and concentrated under reduced pressure. The obtained concentration residue was subjected to silica gel column chromatography (elution solvent: n-hexane:ethyl acetate=100:0 to 95:5 (V/V)), and a fraction containing the compound of interest was concentrated under reduced pressure to obtain 2.22 g of the title compound (yield: 58%) as a pale yellow oil.

Mass spectrum (CI, m/z): 392 [M+1]$^+$.

$^1$H-NMR spectrum (400 MHz, CDCl$_3$) δ: 7.45-7.09 (m, 13H), 7.00-6.91 (m, 1H), 4.44 (dd, J=5.4, 9.4 Hz, 1H), 3.98 (q, J=6.9 Hz, 1H), 3.73 (d, J=14.6 Hz, 1H), 3.66 (d, J=14.6 Hz, 1H), 3.49 (s, 3H), 2.63 (dd, J=5.4, 15.2 Hz, 1H), 2.54 (dd, J=9.4, 15.2 Hz, 1H), 1.25 (d, J=6.9 Hz, 3H).

Reference Example 114

(R)-4-{Benzyl[(S)-1-phenylethyl]amino}-4-(3-fluorophenyl)-2-methylbutan-2-ol

[Chemical Formula 249]

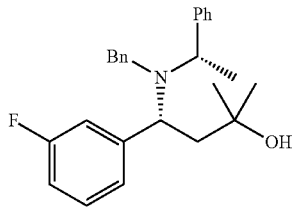

To a solution of 2.22 g (5.67 mmol) of (R)-methyl 3-{benzyl [(S)-1-phenylethyl]amino}-3-(3-fluorophenyl) propanoate synthesized in the similar manner as in Reference Example 113 in 20 ml of dehydrated THF, 17.0 ml (17.0 mmol) of 1 M methyl magnesium bromide-THF solution was added dropwise at 0° C. in an argon atmosphere and then stirred at room temperature for 17 hours.

After the completion of the reaction, a saturated aqueous solution of ammonium chloride was added to the reaction solution, followed by extraction with ethyl acetate. The obtained organic layer was washed with a saturated aqueous solution of sodium chloride, dried over anhydrous magnesium sulfate, then filtered, and concentrated under reduced pressure. The obtained concentration residue was subjected to silica gel column chromatography (elution solvent: n-hexane:ethyl acetate=95:5 to 85:15 (V/V)), and a fraction containing the compound of interest was concentrated under reduced pressure to obtain 1.95 g of the title compound (yield: 88%) as a colorless oil.

Mass spectrum (CI, m/z): 392 [M+1]$^+$.

$^1$H-NMR spectrum (400 MHz, CDCl$_3$) δ: 7.42-7.22 (m, 11H), 7.20-7.15 (m, 1H), 7.13-7.07 (m, 1H), 7.06-6.99 (m, 1H), 5.45 (s, 1H), 4.32-4.20 (m, 2H), 4.17-4.05 (m, 1H), 3.61 (d, J=13.2 Hz, 1H), 2.39 (dd, J=10.6, 14.7 Hz, 1H), 1.40 (dd, J=3.4, 14.7 Hz, 1H), 1.12 (s, 3H), 1.03 (d, J=7.0 Hz, 3H), 0.62 (s, 3H).

Reference Example 115

(R)-4-Amino-4-(3-fluorophenyl)-2-methylbutan-2-ol

[Chemical Formula 250]

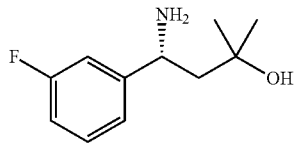

To a solution of 1.1 g (2.8 mmol) of (R)-4-{benzyl [(S)-1-phenylethyl] amino}-4-(3-fluorophenyl)-2-methylbutan-2-ol synthesized in the similar manner as in Reference Example 114 in 10 ml of methanol, 200 mg of 20% palladium hydroxide/carbon (containing 50% water) was added at room temperature under argon stream and after replacement with a hydrogen atmosphere, stirred at room temperature for 6 hours. Subsequently, after replacement with an argon atmosphere, 0.354 g (5.61 mmol) of ammonium formate was added at room temperature and stirred at 60° C. for 2 hours.

After the completion of the reaction, the reaction solution was diluted with ethyl acetate and then filtered through celite, and the filtrate was concentrated under reduced pressure. The obtained concentration residue was subjected to silica gel column chromatography (DIOL, elution solvent: n-hexane:ethyl acetate=75:25 to 50:50 (V/V)), and a fraction containing the compound of interest was concentrated under reduced pressure to obtain 276 mg of the title compound (yield: 50%) as a colorless oil.

Mass spectrum (CI, m/z): 198 [M+1]$^+$.

$^1$H-NMR spectrum (400 MHz, DMSO-d$_6$) δ: 7.37-7.28 (m, 1H), 7.25-7.14 (m, 2H), 7.03-6.95 (m, 1H), 4.08 (dd, J=3.0, 10.5 Hz, 1H), 1.63 (dd, J=10.5, 13.9 Hz, 1H), 1.52 (dd, J=3.0, 13.9 Hz, 1H), 1.22 (s, 3H), 1.09 (s, 3H).

Reference Example 116

(R)-Ethyl 5-{[1-(3-fluorophenyl)-3-hydroxy-3-methylbutyl]carbamoyl}-6,6-dimethyl-3-[1-(trimethylsilyl)cyclobutanecarboxamido]-5,6-dihydropyrrolo[3,4-c]pyrazole-2(4H)-carboxylate

[Chemical Formula 251]

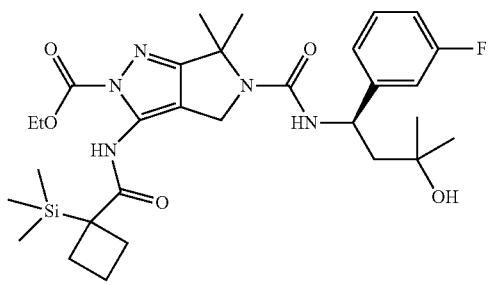

To a solution of 70 mg (0.35 mmol) of (R)-4-amino-4-(3-fluorophenyl)-2-methylbutan-2-ol synthesized in the similar manner as in Reference Example 115 in 5 ml of 1,4-dioxane, 0.31 ml (1.8 mol) of DIPEA and 172 mg (0.390 mmol) of ethyl 5-(chlorocarbonyl)-6,6-dimethyl-3-[1-(trimethylsilyl)cyclobutanecarbox amido]-5,6-dihydropyrrolo[3,4-c]pyrazole-2(4H)-carboxylate synthesized in the similar manner as in Reference Example 3 were added in this order with stirring at room temperature under argon stream and stirred at 90° C. for 2 hours.

After the completion of the reaction, a saturated aqueous solution of ammonium chloride was added to the reaction solution allowed to cool to room temperature, followed by extraction from the mixed solution with ethyl acetate. The organic layer was washed with a saturated aqueous solution of sodium chloride, dried over anhydrous magnesium sulfate, filtered, and concentrated under reduced pressure. The obtained concentration residue was subjected to silica gel column chromatography (elution solvent: n-hexane:ethyl acetate=70:30 to 27:73 (V/V)), and a fraction containing the compound of interest was concentrated under reduced pressure to obtain 149 mg of the title compound (yield: 70%) as a white foam.

Mass spectrum (CI, m/z): 602 [M+1]$^+$.
$^1$H-NMR spectrum (400 MHz, DMSO-d$_6$) δ: 9.78 (s, 1H), 7.36-7.26 (m, 1H), 7.19-7.12 (m, 2H), 7.01-6.93 (m, 1H), 6.71 (d, J=6.2 Hz, 1H), 4.96-4.88 (m, 1H), 4.67-4.60 (m, 2H), 4.54 (d, J=13.6 Hz, 1H), 4.41 (q, J=7.1 Hz, 2H), 2.59-2.42 (m, 2H), 2.29-2.21 (m, 2H), 2.02-1.84 (m, 3H), 1.66 (dd, J=3.2, 14.2 Hz, 1H), 1.59 (s, 3H), 1.54 (s, 3H), 1.33 (t, J=7.1 Hz, 3H), 1.14 (s, 3H), 1.13 (s, 3H), 0.11 (s, 9H).

Reference Example 117

(E)-Methyl 3-(2-fluorophenyl)acrylate

[Chemical Formula 252]

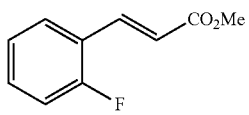

To a solution of 1.26 ml (12.1 mmol) of 2-fluorobenzaldehyde in ml of dehydrated THF, 5.25 g (15.7 mmol) of methyl 2-(triphenylphosphoranylidene)acetate was added at room temperature under argon stream and then stirred for 17 hours with the temperature unchanged.

After the completion of the reaction, the reaction solution was concentrated under reduced pressure. 20 ml of TBME was added to the obtained concentration residue, insoluble matter was filtered off, and the filtrate was concentrated under reduced pressure. The obtained concentration residue was subjected to silica gel column chromatography (elution solvent: n-hexane:ethyl acetate=100:0 to 90:10 (V/V)), and a fraction containing the compound of interest was concentrated under reduced pressure to obtain 1.58 g of the title compound (yield: 73%) as a colorless oil.

Mass spectrum (CI, m/z): 181 [M+1]$^+$.
$^1$H-NMR spectrum (400 MHz, CDCl$_3$) δ: 7.83 (d, J=16.3 Hz, 1H), 7.57-7.50 (m, 1H), 7.40-7.33 (m, 1H), 7.20-7.07 (m, 2H), 6.55 (d, J=16.3 Hz, 1H), 3.82 (s, 3H).

Reference Example 118

(R)-Methyl 3-{benzyl [(S)-1-phenylethyl]amino}-3-(2-fluorophenyl)propanoate

[Chemical Formula 253]

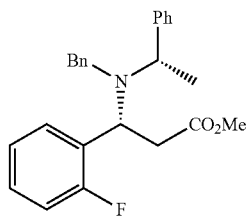

To a solution of 2.94 ml (14.1 mmol) of (S)—N-benzyl-1-phenylethanamine in 30 ml of dehydrated THF, 8.22 ml (13.2 mmol) of a 1.6 M solution of n-butyllithium in n-hexane was added dropwise at −78° C. under argon stream and then stirred for 1 hour with the temperature unchanged. Subsequently, a solution of 1.58 g (8.77 mmol) of (E)-methyl 3-(2-fluorophenyl)acrylate synthesized in the similar manner as in Reference Example 117 in 5 ml of THF was added dropwise at −78° C. and then stirred for 1 hour with the temperature unchanged.

After the completion of the reaction, a saturated aqueous solution of ammonium chloride was added to the reaction solution, followed by extraction with ethyl acetate. The obtained organic layer was washed with a saturated aqueous solution of sodium chloride, dried over anhydrous magnesium sulfate, then filtered, and concentrated under reduced pressure. The obtained concentration residue was subjected to silica gel column chromatography (elution solvent: n-hexane:ethyl acetate=100:0 to 95:5 (V/V)), and a fraction containing the compound of interest was concentrated under reduced pressure to obtain 1.27 g of the title compound (yield: 37%) as a pale yellow oil.

Mass spectrum (CI, m/z): 392 [M+1]$^+$.
$^1$H-NMR spectrum (400 MHz, CDCl$_3$) δ: 7.45-7.03 (m, 14H), 4.75 (dd, J=6.8, 8.9 Hz, 1H), 4.05 (q, J=6.9 Hz, 1H), 3.81 (d, J=14.6 Hz, 1H), 3.65 (d, J=14.6 Hz, 1H), 3.44 (s, 3H), 2.79 (dd, J=6.8, 14.9 Hz, 1H), 2.65 (dd, J=8.9, 14.9 Hz, 1H), 1.20 (d, J=6.9 Hz, 3H).

Reference Example 119

(R)-4-{Benzyl[(S)-1-phenylethyl]amino}-4-(2-fluorophenyl)-2-methylbutan-2-ol

[Chemical Formula 254]

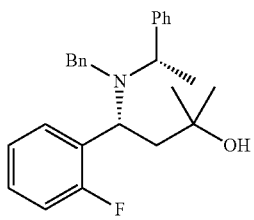

To a solution of 1.27 g (3.24 mmol) of (R)-methyl 3-{benzyl[(S)-1-phenylethyl]amino}-3-(2-fluorophenyl)propanoate synthesized in the similar manner as in Reference Example 118 in 15 ml of dehydrated THF, 9.73 ml (9.73 mmol) of 1 M methyl magnesium bromide-THF solution was added dropwise at 0° C. under argon stream and then stirred at room temperature for 17 hours.

After the completion of the reaction, a saturated aqueous solution of ammonium chloride was added to the reaction solution, followed by extraction with ethyl acetate. The obtained organic layer was washed with a saturated aqueous solution of sodium chloride, dried over anhydrous magnesium sulfate, then filtered, and concentrated under reduced pressure. The obtained concentration residue was subjected to silica gel column chromatography (elution solvent: n-hexane:ethyl acetate=95:5 to 85:15 (V/V)), and a fraction containing the compound of interest was concentrated under reduced pressure to obtain 1.10 g of the title compound (yield: 87%) as a pale yellow oil.

Mass spectrum (CI, m/z): 392 [M+1]$^+$.

$^1$H-NMR spectrum (400 MHz, CDCl$_3$) δ: 7.51-7.08 (m, 14H), 5.58 (s, 1H), 4.72 (dd, J=3.1, 11.3 Hz, 1H), 4.31 (d, J=12.9 Hz, 1H), 4.16-4.05 (m, 1H), 3.55 (d, J=12.9 Hz, 1H), 2.47 (dd, J=11.3, 14.6 Hz, 1H), 1.32 (dd, J=3.1, 14.6 Hz, 1H), 1.11 (s, 3H), 1.06 (d, J=7.0 Hz, 3H), 0.53 (s, 3H).

Reference Example 120

(R)-4-Amino-4-(2-fluorophenyl)-2-methylbutan-2-ol

[Chemical Formula 255]

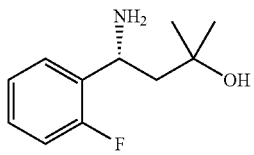

To a solution of 1.1 g (2.8 mmol) of (R)-4-{benzyl[(S)-1-phenylethyl]amino}-4-(2-fluorophenyl)-2-methylbutan-2-ol synthesized in the similar manner as in Reference Example 119 in 10 ml of methanol, 200 mg of 20% palladium hydroxide/carbon (containing 50% water) was added at room temperature under argon stream and after replacement with a hydrogen atmosphere, stirred at room temperature for 6 hours. Subsequently, after replacement with an argon atmosphere, 354 mg (5.61 mmol) of ammonium formate was added at room temperature and stirred at 60° C. for 2 hours.

After the completion of the reaction, the reaction solution was diluted with ethyl acetate and then filtered through celite, and the filtrate was concentrated under reduced pressure. The obtained concentration residue was subjected to silica gel column chromatography (DIOL, elution solvent: n-hexane:ethyl acetate=75:25 to 50:50 (V/V)), and a fraction containing the compound of interest was concentrated under reduced pressure and dried under reduced pressure to obtain 265 mg of the title compound (yield: 48%) as a colorless oil.

Mass spectrum (CI, m/z): 198 [M+1]$^+$.

$^1$H-NMR spectrum (400 MHz, DMSO-d$_6$) δ: 7.61-7.55 (m, 1H), 7.28-7.21 (m, 1H), 7.20-7.14 (m, 1H), 7.13-7.06 (m, 1H), 4.39 (dd, J=2.7, 10.4 Hz, 1H), 1.64 (dd, J=10.4, 13.8 Hz, 1H), 1.52 (dd, J=2.7, 13.8 Hz, 1H), 1.22 (s, 3H), 1.09 (s, 3H).

Reference Example 121

(R)-Ethyl 5-{[1-(2-fluorophenyl)-3-hydroxy-3-methylbutyl]carbamoyl}-6,6-dimethyl-3-[1-(trimethylsilyl)cyclobutanecarboxamido]-5,6-dihydropyrrolo[3,4-c]pyrazole-2(4H)-carboxylate

[Chemical Formula 256]

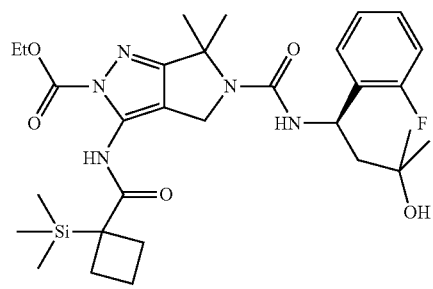

To a solution of 70 mg (0.35 mmol) of (R)-4-amino-4-(2-fluorophenyl)-2-methylbutan-2-ol synthesized in the similar manner as in Reference Example 120 in 5 ml of 1,4-dioxane, 0.309 ml (1.77 mol) of DIPEA and 235 mg (0.533 mmol) of ethyl 5-(chlorocarbonyl)-6,6-dimethyl-3-[1-(trimethylsilyl)cyclobutanecarbox amido]-5,6-dihydropyrrolo[3,4-c]pyrazole-2(4H)-carboxylate synthesized in the similar manner as in Reference Example 3 were added in this order with stirring at room temperature under argon stream and stirred at 90° C. for 2 hours.

After the completion of the reaction, a saturated aqueous solution of ammonium chloride was added to the reaction solution allowed to cool to room temperature, followed by extraction from the mixed solution with ethyl acetate. The organic layer was washed with a saturated aqueous solution of sodium chloride, dried over anhydrous magnesium sulfate, filtered, and concentrated under reduced pressure. The obtained concentration residue was subjected to silica gel column chromatography (elution solvent: n-hexane:ethyl acetate=65:35 to 29:71 (V/V)), and a fraction containing the compound of interest was concentrated under reduced pressure and dried under reduced pressure to obtain 150 mg of the title compound (yield: 70%) as a white solid.

Mass spectrum (CI, m/z): 602 [M+1]$^+$.

$^1$H-NMR spectrum (400 MHz, DMSO-d$_6$) δ: 9.79 (s, 1H), 7.54-7.46 (m, 1H), 7.27-7.07 (m, 3H), 6.70 (d, J=5.8 Hz, 1H), 5.24-5.16 (m, 1H), 4.71-4.54 (m, 3H), 4.42 (q, J=7.2 Hz, 2H), 2.58-2.44 (m, 2H), 2.32-2.22 (m, 2H), 2.02-1.87 (m, 3H), 1.67-1.57 (m, 4H), 1.53 (s, 3H), 1.34 (t, J=7.2 Hz, 3H), 1.19-1.14 (m, 6H), 0.13 (s, 9H).

Reference Example 122

(R)-Methyl 3-[(tert-butoxycarbonyl)amino]-4-methylpentanoate

[Chemical Formula 257]

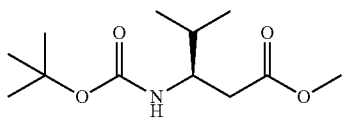

To a solution of 600 mg (2.59 mmol) of (R)-3-[(tert-butoxycarbonyl)amino]-4-methylpentanoic acid in 6 ml of dichloromethane, 63 mg (0.52 mmol) of 4-dimethylaminopyridine and 0.53 ml (13 mmol) of methanol were added in this order with stirring at room temperature under argon stream.

Subsequently, 746 mg (3.89 mmol) of 1-(3-dimethylaminopropyl)-3-ethylcarbodiimide hydrochloride was added in one portion with stirring at 0° C. and stirred at room temperature for 2 hours.

After the completion of the reaction, water was added to the reaction solution, followed by extraction from the mixed solution with ethyl acetate twice. The organic layer was washed with a saturated aqueous solution of sodium chloride, dried over anhydrous magnesium sulfate, filtered, and concentrated under reduced pressure. The obtained concentration residue was subjected to silica gel column chromatography (elution solvent: n-hexane:ethyl acetate=100:0 to 80:20 (V/V)), and a fraction containing the compound of interest was concentrated under reduced pressure to obtain 630 mg of the title compound (yield: 99%) as a colorless oil.

Mass spectrum (CI, m/z): 246 [M+1]$^+$.

$^1$H-NMR spectrum (400 MHz, DMSO-d$_6$) δ: 6.72 & 6.37 (br d, J=9.2 Hz, total 1H), 3.71-3.61 (m, 1H), 3.60-3.52 (m, 3H), 2.44 (dd, J=4.6, 15.0 Hz, 1H), 2.30 (dd, J=9.4, 15.0 Hz, 1H), 1.71-1.58 (m, 1H), 1.36 (s, 9H), 0.86-0.73 (m, 6H).

Reference Example 123

(R)-tert-Butyl (5-hydroxy-2,5-dimethylhexan-3-yl)carbamate

[Chemical Formula 258]

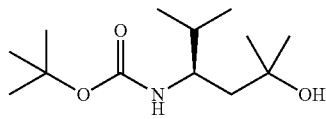

To a solution of 630 mg (2.57 mmol) of (R)-methyl 3-[(tert-butoxycarbonyl)amino]-4-methylpentanoate synthesized in the similar manner as in Reference Example 122 in 6 ml of dehydrated THF, 7.7 ml (7.7 mol) of 1 M methyl magnesium bromide-THF solution was added dropwise with stirring at 0° C. under argon stream and stirred at room temperature for 4 hours.

After the completion of the reaction, a saturated aqueous solution of ammonium chloride was added to the reaction solution, followed by extraction from the mixed solution with ethyl acetate. The organic layer was washed with a saturated aqueous solution of sodium chloride, dried over anhydrous magnesium sulfate, filtered, and concentrated under reduced pressure. The obtained concentration residue was subjected to silica gel column chromatography (elution solvent: n-hexane:ethyl acetate=91:9 to 70:30 (V/V)), and a fraction containing the compound of interest was concentrated under reduced pressure to obtain 133 mg of the title compound (yield: 21%) as a white solid.

Mass spectrum (CI, m/z): 246 [M+1]$^+$.

$^1$H-NMR spectrum (400 MHz, DMSO-d$_6$) δ: 6.53 & 6.14 (br d, J=8.9 Hz, total 1H), 4.09 (s, 1H), 3.47-3.39 (m, 1H), 1.63-1.50 (m, 1H), 1.42-1.33 (m, 11H), 1.06 (s, 3H), 1.05 (s, 3H), 0.80-0.74 (m, 6H).

Reference Example 124

(R)-4-Amino-2,5-dimethylhexan-2-ol hydrochloride

[Chemical Formula 259]

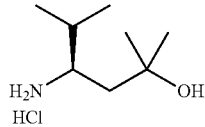

To a solution of 133 mg (0.542 mmol) of (R)-tert-butyl (5-hydroxy-2,5-dimethylhexan-3-yl)carbamate synthesized in the similar manner as in Reference Example 123 in 2 ml of 1,4-dioxane, 0.678 ml (2.71 mol) of 4 N hydrogen chloride/1,4-dioxane was added in one portion with stirring at room temperature under argon stream and stirred at room temperature for 3 hours. Subsequently, 0.678 ml (2.71 mol) of 4 N hydrogen chloride/1,4-dioxane was added in one portion with stirring at room temperature and stirred at room temperature for 15 hours.

After the completion of the reaction, the reaction solution was concentrated. 5 ml of n-hexane was added thereto and stirred at room temperature for 2 hours. The deposited solid was collected by filtration, washed with n-hexane, and dried under reduced pressure to obtain 58 mg of the title compound (yield: 59%) as a white solid.

Mass spectrum (CI, m/z): 146 [M+1]$^+$.

$^1$H-NMR spectrum (400 MHz, DMSO-d$_6$) δ: 8.25-4.63 (m, 3H), 3.16-3.04 (m, 1H), 1.96-1.82 (m, 1H), 1.58 (dd, J=2.0, 15.0 Hz, 1H), 1.49 (dd, J=9.8, 15.0 Hz, 1H), 1.21 (s, 3H), 1.17 (s, 3H), 0.91 (d, J=6.8 Hz, 3H), 0.89 (d, J=6.8 Hz, 3H).

Reference Example 125

(R)-Ethyl 5-[(5-hydroxy-2,5-dimethylhexan-3-yl)carbamoyl]-6,6-dimethyl-3-[1-(trimethylsilyl)cyclobutanecarboxamido]-5,6-dihydropyrrolo[3,4-c]pyrazole-2(4H)-carboxylate

[Chemical Formula 260]

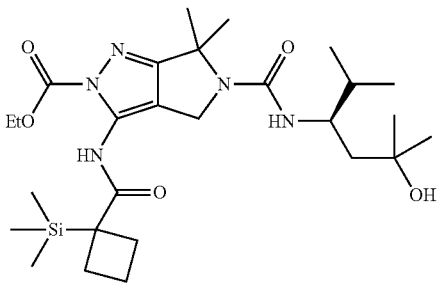

To a solution of 260 mg (0.590 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the similar manner as in Reference Example 3 in 4 ml of 1,4-dioxane, 0.342 ml (1.96 mol) of DIPEA and 57 mg (0.31 mmol) of (R)-4-amino-2,5-dimethylhexan-2-ol hydrochloride synthesized in the similar manner as in Reference Example 124 were added in this order with stirring at room temperature under argon stream and stirred at 90° C. for 1.5 hours.

After the completion of the reaction, a saturated aqueous solution of ammonium chloride was added to the reaction solution allowed to cool to room temperature, followed by extraction from the mixed solution with ethyl acetate. The organic layer was washed with a saturated aqueous solution of sodium chloride, dried over anhydrous magnesium sulfate, filtered, and concentrated under reduced pressure. The obtained concentration residue was subjected to silica gel column chromatography (elution solvent: n-hexane:ethyl acetate=70:30 to 30:70 (V/V)), and a fraction containing the compound of interest was concentrated under reduced pressure and dried under reduced pressure to obtain 99 mg of the title compound (yield: 57%) as a white foam.

Mass spectrum (CI, m/z): 550 [M+1]$^+$.

$^1$H-NMR spectrum (400 MHz, DMSO-d$_6$) δ: 9.78 (s, 1H), 5.83 (d, J=7.7 Hz, 1H), 4.55 (d, J=13.6 Hz, 1H), 4.47 (d, J=13.6 Hz, 1H), 4.42 (q, J=7.1 Hz, 2H), 4.30 (s, 1H), 3.73-3.62 (m, 1H), 2.58-2.43 (m, 2H), 2.31-2.21 (m, 2H), 1.96-1.82 (m, 2H), 1.75-1.57 (m, 8H), 1.50-1.42 (m, 1H), 1.34 (t, J=7.1 Hz, 3H), 1.10 (s, 3H), 1.08 (s, 3H), 0.89-0.78 (m, 6H), 0.15-0.08 (m, 9H).

Reference Example 126

Ethyl [1-(4-fluorophenyl)-2,2-dimethyl-3-oxopropyl] carbamate

[Chemical Formula 261]

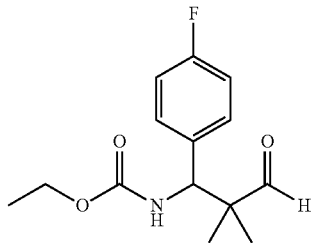

To a solution of 2.63 g (29.5 mmol) of ethyl carbamate in 25 ml of toluene, 3.1 ml (29 mmol) of 4-fluorobenzaldehyde and 0.281 g (1.48 mmol) of p-toluenesulfonic acid monohydrate were added in this order with stirring at room temperature under argon stream and stirred at room temperature for 5 minutes. Subsequently, 2.68 ml (29.5 mmol) of isobutylaldehyde was added thereto dropwise with stirring at room temperature and stirred at 60° C. for 3 hours.

After the completion of the reaction, the reaction solution was poured to a saturated aqueous solution of sodium bicarbonate and subsequently stirred at room temperature for 5 minutes. An organic layer and an aqueous layer were separated, and then, the separated aqueous layer was subjected to extraction with toluene once. All of the obtained organic layers were washed with a saturated aqueous solution of sodium chloride, then dehydrated over anhydrous magnesium sulfate, filtered, and concentrated under reduced pressure. The obtained concentration residue was subjected to silica gel column chromatography (elution solvent: n-hexane:ethyl acetate=90:10 to 69:31 (V/V)), and a fraction containing the compound of interest was concentrated under reduced pressure and dried under reduced pressure to obtain 3.85 g of the title compound (yield: 49%) as a colorless oil.

Mass spectrum (CI, m/z): 268 [M+1]$^+$.

$^1$H-NMR spectrum (400 MHz, DMSO-d$_6$) δ: 9.59 (s, 1H), 7.95 (d, J=10.1 Hz, 1H), 7.43-7.33 (m, 2H), 7.21-7.12 (m, 2H), 5.04 (d, J=10.1 Hz, 1H), 4.01-3.93 (m, 2H), 1.15 (t, J=7.1 Hz, 3H), 0.94 (s, 3H), 0.87 (s, 3H).

Reference Example 127

3-Amino-3-(4-fluorophenyl)-2,2-dimethylpropan-1-ol

[Chemical Formula 262]

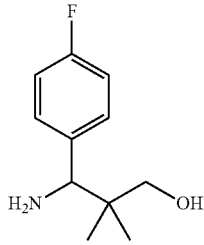

To a solution of 3.84 g (14.4 mmol) of ethyl [1-(4-fluorophenyl)-2,2-dimethyl-3-oxopropyl]carbamate synthesized in the similar manner as in Reference Example 126 in 20 ml of ethanol, 0.326 g (8.62 mmol) of sodium borohydride was dividedly added with stirring at 0° C. under argon stream and stirred at room temperature for 1 hour. Subsequently, 1.61 g (28.7 mmol) of potassium hydroxide and water (10 ml) were added with stirring at room temperature and then stirred for 2 hours under heating to reflux.

After the completion of the reaction, the reaction solution allowed to cool was concentrated under reduced pressure, and ethanol was distilled off. The concentration residue was adjusted to pH 2 by adding 2 N hydrochloric acid and washed with diethyl ether. The aqueous layer was rendered basic (pH 9) by adding 1 N aqueous sodium hydroxide solution, followed by extraction with dichloromethane three times. All of the obtained organic layers were washed with a saturated aqueous solution of sodium chloride, then dehydrated over anhydrous sodium sulfate, filtered, concentrated under reduced pressure, and dried under reduced pressure to obtain 1.93 g of the title compound (yield: 68%) as a white solid.

Mass spectrum (CI, m/z): 198 [M+1]$^+$.

$^1$H-NMR spectrum (400 MHz, DMSO-d$_6$) δ: 7.38-7.29 (m, 2H), 7.15-7.03 (m, 2H), 3.81 (s, 1H), 3.25 (d, J=10.5 Hz, 1H), 3.13 (d, J=10.5 Hz, 1H), 0.74 (s, 3H), 0.65 (s, 3H).

Reference Example 128

Ethyl [1-(3-fluorophenyl)-2,2-dimethyl-3-oxopropyl]carbamate

[Chemical Formula 263]

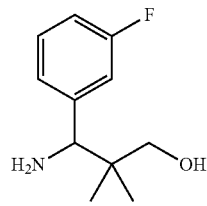

To a solution of 2.63 g (29.5 mmol) of ethyl carbamate in 25 ml of toluene, 3.10 ml (29.5 mmol) of 3-fluorobenzaldehyde and 288 mg (1.51 mmol) of p-toluenesulfonic acid monohydrate were added in this order at room temperature in an argon atmosphere and then stirred at room temperature for 5 minutes. Subsequently, 2.70 ml (29.7 mmol) of isobutylaldehyde was added at room temperature and then stirred for 3 hours under heating to reflux after a Dean-Stark apparatus was loaded. Subsequently, 2.70 ml (29.7 mmol) of isobutylaldehyde was added and then further stirred for 3 hours under heating to reflux.

After the completion of the reaction, the reaction solution was poured to a saturated aqueous solution of sodium bicarbonate and then stirred at room temperature. After separation into an aqueous layer and an organic layer, the aqueous layer was subjected to extraction with toluene once. All of the obtained organic layers were washed with a saturated aqueous solution of sodium chloride, then dried over anhydrous magnesium sulfate, filtered, and concentrated under reduced pressure. The obtained concentration residue was subjected to silica gel column chromatography (elution solvent: n-hexane:ethyl acetate=90:10 to 60:40 (V/V)), and a fraction containing the compound of interest was concentrated under reduced pressure and dried under reduced pressure to obtain 4.61 g of the title compound (yield: 59%) as a pale yellow oil.

Mass spectrum (CI, m/z): 268 [M+1]$^+$.

$^1$H-NMR spectrum (400 MHz, DMSO-d$_6$) δ: 9.59 (s, 1H), 7.95 (br d, J=10.2 Hz, 1H), 7.36 (dt, J=6.2, 7.9 Hz, 1H), 7.27-7.06 (m, 3H), 5.07 (d, J=10.2 Hz, 1H), 4.06-3.89 (m, 2H), 1.18-1.12 (m, 3H), 0.94 (s, 3H), 0.88 (s, 3H).

Reference Example 129

3-Amino-3-(3-fluorophenyl)-2,2-dimethylpropan-1-ol

[Chemical Formula 264]

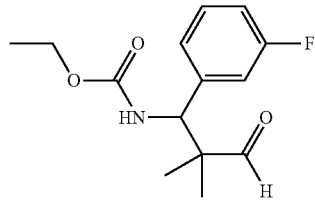

To a solution of 4.75 g (17.8 mmol) of ethyl [1-(3-fluorophenyl)-2,2-dimethyl-3-oxopropyl]carbamate synthesized in the similar manner as in Reference Example 128 in 12 ml of ethanol, 352 mg (9.30 mmol) of sodium borohydride was dividedly added with stirring at 0° C. in an argon atmosphere and then stirred at room temperature for 4 hours.

After the completion of the reaction, the reaction solution was concentrated under reduced pressure, and 75 ml of dichloromethane was added to the residue. This solution was poured to 50 ml of a saturated aqueous solution of ammonium chloride, stirred at room temperature until foaming settled, and then the aqueous layer and the organic layer were separated. The aqueous layer was subjected to extraction with 25 ml of dichloromethane, all of the organic layers were dried over anhydrous magnesium sulfate and filtered, and then, the filtrate was concentrated under reduced pressure. The residue was subjected to silica gel column chromatography (DIOL silica gel, elution solvent: n-hexane:ethyl acetate=78:22 to 57:43 (V/V)), and a fraction containing the compound of interest was concentrated under reduced pressure.

12 ml of ethanol and 2.45 g (37.1 mmol) of 85% potassium hydroxide were added to the obtained residue (3.91 g) and heated to reflux for 4 hours.

After standing to cool, the resultant was concentrated under reduced pressure, and 50 ml of water and 50 ml of dichloromethane were added thereto and stirred at room temperature. After separation into an aqueous layer and an organic layer, the aqueous layer was subjected to extraction with 50 ml of dichloromethane twice. All of the organic layers were dried over anhydrous sodium sulfate and then filtered, and the filtrate was concentrated under reduced pressure to obtain 2.58 g of the title compound (yield: 74%) as a pale yellow viscous liquid.

Mass spectrum (CI, m/z): 198 [M+1]$^+$.

$^1$H-NMR spectrum (400 MHz, DMSO-d$_6$) δ: 7.36-7.25 (m, 1H), 7.19-7.08 (m, 2H), 7.06-6.97 (m, 1H), 5.00 (br s, 1H), 3.81 (s, 1H), 3.25 (d, J=10.5 Hz, 1H), 3.14 (d, J=10.5 Hz, 1H), 1.99 (br s, 2H), 0.77 (s, 3H), 0.66 (s, 3H).

Reference Example 130

3-Amino-3-(2-fluorophenyl)-2,2-dimethylpropan-1-ol

[Chemical Formula 265]

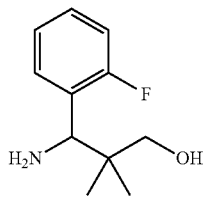

To a solution of 2.62 g (29.4 mmol) of ethyl carbamate in 25 ml of toluene, 3.05 ml (29.2 mmol) of 2-fluorobenzaldehyde and 286 mg (1.51 mmol) of p-toluenesulfonic acid monohydrate were added in this order at room temperature in an argon atmosphere and then reacted at room temperature for 5 minutes. Subsequently, 2.70 ml (29.7 mmol) of isobutylaldehyde was added at 60° C. and then reacted at the same temperature as above for 5.5 hours.

After the completion of the reaction, the reaction solution was poured to a saturated aqueous solution of sodium bicarbonate and stirred at room temperature for 5 minutes. After separation into an aqueous layer and an organic layer, the aqueous layer was subjected to extraction with toluene once. All of the obtained organic layers were washed with a saturated aqueous solution of sodium chloride, then dried over anhydrous magnesium sulfate, filtered, and concentrated under reduced pressure. The obtained concentration residue was subjected to silica gel column chromatography (elution solvent: n-hexane:ethyl acetate=90:10 to 60:40 (V/V)), and a fraction containing the compound of interest was concentrated under reduced pressure and dried under reduced pressure to obtain a concentration residue.

To a solution of 6.23 g of the obtained residue in 15 ml of ethanol, 478 mg (12.6 mmol) of sodium borohydride was dividedly added with stirring at 0° C. in an argon atmosphere and then stirred at room temperature for 4 hours.

After the completion of the reaction, the reaction solution was concentrated under reduced pressure, and 75 ml of dichloromethane was added to the residue. This solution was poured to 50 ml of a saturated aqueous solution of ammonium chloride, stirred at room temperature until foaming settled, and then the aqueous layer and the organic layer were separated. The aqueous layer was subjected to extraction with 25 ml of dichloromethane, all of the organic layers were dehydrated over anhydrous magnesium sulfate and filtered, and then, the filtrate was concentrated under reduced pressure. The residue was subjected to silica gel column chromatography (DIOL silica gel, elution solvent: n-hexane:ethyl acetate=77:23 to 56:44 (V/V)), and a fraction containing the compound of interest was concentrated under reduced pressure.

15 ml of ethanol and 3.08 g (46.7 mmol) of 85% potassium hydroxide were added to 5.03 g of the obtained residue and heated to reflux for 5 hours.

After standing to cool, the resultant was concentrated under reduced pressure, 50 ml of water and 100 ml of dichloromethane were added, stirred at room temperature, and then the aqueous layer and the organic layer were separated. The aqueous layer was subjected to extraction with 50 ml of dichloromethane twice. Diethyl ether was added until the turbidity of all of the obtained organic layers was eliminated, then dried over anhydrous sodium sulfate, and filtered, and the filtrate was concentrated under reduced pressure to obtain 3.60 g of the title compound (yield: 63%) as a pale yellow viscous liquid.

Mass spectrum (CI, m/z): 198 [M+1]$^+$.

$^1$H-NMR spectrum (400 MHz, DMSO-d$_6$) δ: 7.55-7.49 (m, 1H), 7.30-7.21 (m, 1H), 7.20-7.13 (m, 1H), 7.12-7.03 (m, 1H), 5.03 (br s, 1H), 4.15 (s, 1H), 3.35 (d, J=10.5 Hz, 1H), 3.21 (d, J=10.5 Hz, 1H), 2.01 (br s, 2H), 0.73 (s, 3H), 0.71-0.66 (m, 3H).

Reference Example 131

Ethyl (2,2,4-trimethyl-1-oxopentan-3-yl)carbamate

[Chemical Formula 266]

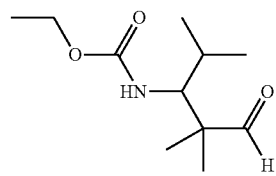

To a solution of 2.06 g (23.1 mmol) of ethyl carbamate in 20 ml of toluene, 6.00 ml (66.1 mmol) of isobutylaldehyde and 224 mg (1.18 mmol) of p-toluenesulfonic acid monohydrate were added in this order at room temperature in an argon atmosphere and then stirred at room temperature for 5 minutes and at 60° C. for 4 hours.

After the completion of the reaction, the reaction solution was poured to a saturated aqueous solution of sodium bicarbonate and then stirred at room temperature. After separation into an aqueous layer and an organic layer, the aqueous layer was subjected to extraction with toluene once. All of the obtained organic layers were washed with a saturated aqueous solution of sodium chloride, then dried over anhydrous magnesium sulfate, filtered, and concentrated under reduced pressure. The obtained concentration residue was subjected to silica gel column chromatography (elution solvent: n-hexane:ethyl acetate=90:10 to 60:40 (V/V)), and a fraction containing the compound of interest was concentrated under reduced pressure and dried under reduced pressure to obtain 1.55 g of the title compound (yield: 31%) as a pale yellow oil.

Mass spectrum (CI, m/z): 216 [M+1]+.

1H-NMR spectrum (400 MHz, DMSO-d6) δ: 9.55 (s, 1H), 7.11 (br d, J=10.4 Hz, 1H), 4.01 (q, J=7.1 Hz, 2H), 3.67 (dd, J=6.2, 10.4 Hz, 1H), 1.80-1.66 (m, 1H), 1.17 (t, J=7.1 Hz, 3H), 0.98 (s, 3H), 0.90 (s, 3H), 0.80 (d, J=6.8 Hz, 3H), 0.75 (d, J=6.8 Hz, 3H).

Reference Example 132

3-Amino-2,2,4-trimethylpentan-1-ol

[Chemical Formula 267]

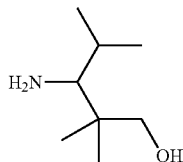

To a solution of 1.55 g (7.20 mmol) of ethyl (2,2,4-trimethyl-1-oxopentan-3-yl)carbamate synthesized in the similar manner as in Reference Example 131 in 10 ml of ethanol, 176 mg (4.66 mmol) of sodium borohydride was dividedly added at 0° C. in an argon atmosphere and then stirred at 0° C. for 1 hour and further at room temperature for 13.5 hours. Subsequently, 853 mg (15.2 mmol) of potassium hydroxide and 5.0 ml of water were added to the reaction solution at room temperature and then stirred for 3 hours under heating to reflux.

After the completion of the reaction, the reaction solution was concentrated under reduced pressure, and ethanol was distilled off. 2 N hydrochloric acid was added to the concentration residue and then washed with diethyl ether. After separation into an aqueous layer and an organic layer, the obtained the aqueous layer was adjusted to pH >10 by adding a 1 N aqueous sodium hydroxide solution, followed by extraction with dichloromethane three times. All of the obtained organic layers were washed with a saturated aqueous solution of sodium chloride, then dried over anhydrous magnesium sulfate, filtered, and concentrated under reduced pressure. The obtained concentration residue was subjected to silica gel column chromatography (DIOL silica gel, elution solvent: 1,2-dichloroethane:n-hexane=30:70 to 100:0→1,2-dichloroethane:methanol=95:5 (V/V)), and a fraction containing the compound of interest was concentrated under reduced pressure and dried under reduced pressure to obtain 577 mg of the title compound (yield: 55%) as a colorless oil.

Mass spectrum (CI, m/z): 146 [M+1]+.

1H-NMR spectrum (400 MHz, DMSO-d6) δ: 3.23 (d, J=10.4 Hz, 1H), 3.15 (d, J=10.4 Hz, 1H), 2.36 (d, J=1.8 Hz, 1H), 1.87 (dspt, J=1.8, 6.8 Hz, 1H), 0.88 (d, J=6.8 Hz, 3H), 0.81-0.76 (m, 9H).

Reference Example 133

(R)-Benzyl 2-butoxy-2-phenylacetate

[Chemical Formula 268]

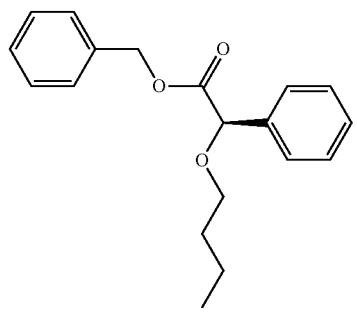

To a suspension of 2.34 g (9.66 mmol) of (R)-benzyl 2-hydroxy-2-phenylacetate in 25.0 ml (219 mmol) of 1-iodobutane, 4.55 g (19.6 mmol) of silver(I) oxide was added at room temperature in an argon atmosphere and then reacted at 80° C. for 10.5 hours with stirring.

After the completion of the reaction, the reaction solution was allowed to cool to room temperature and then filtered using a celite filter. The filtration cake was washed with ethyl acetate, and then, all of the filtrates were concentrated under reduced pressure. The obtained concentration residue was subjected to silica gel column chromatography (elution solvent: n-hexane:ethyl acetate=97:3 to 93:7 (V/V)), and a fraction containing the compound of interest was concentrated under reduced pressure and dried under reduced pressure to obtain 1.65 g of the title compound (yield: 57%) as a colorless oil.

Mass spectrum (CI, m/z): 299 [M+1]+.

1H-NMR spectrum (400 MHz, DMSO-d6) δ: 7.45-7.17 (m, 10H), 5.18-5.09 (m, 2H), 5.05 (s, 1H), 3.50 (td, J=6.4, 9.2 Hz, 1H), 3.40 (td, J=6.4, 9.2 Hz, 1H), 1.58-1.46 (m, 2H), 1.38-1.26 (m, 2H), 0.85 (t, J=7.4 Hz, 3H).

Reference Example 134 tert-Butyl (3-hydroxy-2,2-dimethyl-1-phenylpropyl)carbamate

[Chemical Formula 269]

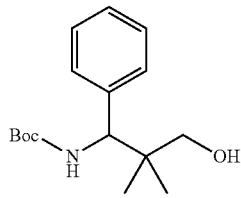

To a solution of 1.00 g (5.58 mmol) of 3-amino-2,2-dimethyl-3-phenylpropan-1-ol [synthesized according to the method described in Synthetic Communications, 1994, 24 (7), 899-906] in 5 ml of dichloromethane, 2.34 ml (16.8 mmol) of triethylamine and 2.56 ml (11.1 mmol) of di-tert-butyl dicarbonate were added in this order at room temperature under argon stream and stirred at room temperature for 2 hours.

After the completion of the reaction, a saturated aqueous solution of ammonium chloride was added to the reaction solution, followed by extraction from the mixed solution with ethyl acetate. The organic layer was washed with saturated saline, dried over anhydrous magnesium sulfate, filtered, and concentrated under reduced pressure. The obtained concentration residue was subjected to silica gel column chromatography (elution solvent: n-hexane:ethyl acetate=91:9 to 70:30 (V/V)), and a fraction containing the compound of interest was concentrated under reduced pressure to obtain 1.45 g of the title compound (yield: 93%) as a white solid.

Mass spectrum (CI, m/z): 280 [M+1]$^+$.

$^1$H-NMR spectrum (400 MHz, DMSO-d$_6$) δ: 7.37-7.18 (m, 6H), 4.97-4.75 (m, 1H), 4.62-4.32 (m, 1H), 3.22-3.08 (m, 1H), 3.05-2.90 (m, 1H), 1.40-1.29 (m, 9H), 0.83-0.73 (m, 6H).

Reference Example 135 tert-Butyl (3-methoxy-2,2-dimethyl-1-phenylpropyl)carbamate

[Chemical Formula 270]

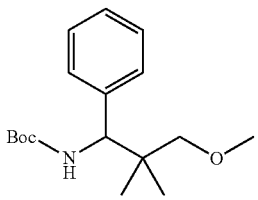

To a solution of 600 mg (2.15 mmol) of tert-butyl (3-hydroxy-2,2-dimethyl-1-phenylpropyl)carbamate synthesized in the similar manner as in Reference Example 134 in 6 ml of dichloromethane, 370 mg (6.59 mmol) of potassium hydroxide was added in one portion with stirring at 0° C. under argon stream and stirred at 0° C. for 15 minutes. Subsequently, 0.407 ml (4.29 mmol) of dimethylsulfuric acid was added dropwise at 0° C. and stirred at room temperature for 8 hours.

After the completion of the reaction, water was added to the reaction solution, followed by extraction from the mixed solution with dichloromethane. The organic layer was washed with saturated saline, dried over anhydrous sodium sulfate, filtered, and concentrated under reduced pressure. The obtained concentration residue was subjected to silica gel column chromatography (elution solvent: n-hexane:ethyl acetate=100:0 to 87:13 (V/V)), and a fraction containing the compound of interest was concentrated under reduced pressure to obtain 114 mg of the title compound (yield: 18%) as a colorless oil.

Mass spectrum (CI, m/z): 294 [M+1]$^+$.

$^1$H-NMR spectrum (400 MHz, DMSO-d$_6$) δ: 7.35-7.16 & 6.95-6.82 (m, total 6H), 4.67-4.37 (m, 1H), 3.28-3.19 (m, 3H), 3.08-2.91 (m, 1H), 2.88-2.76 (m, 1H), 1.43-1.13 (m, 9H), 0.90-0.82 (m, 3H), 0.81-0.70 (m, 3H).

Reference Example 136

3-Methoxy-2,2-dimethyl-1-phenylpropan-1-amine

[Chemical Formula 271]

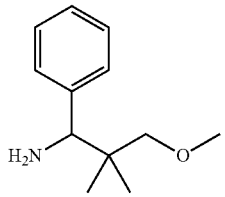

To a solution of 114 mg (0.389 mmol) of tert-butyl (3-methoxy-2,2-dimethyl-1-phenylpropyl)carbamate synthesized in the similar manner as in Reference Example 135 in 2 ml of 1,4-dioxane, 0.486 ml (1.94 mmol) of 4 N hydrogen chloride/1,4-dioxane was added in one portion with stirring at room temperature under argon stream and stirred at room temperature for 20 hours.

After the completion of the reaction, the reaction solution was concentrated. The residue was dissolved by adding water and then adjusted to pH 8 by adding a saturated aqueous solution of sodium bicarbonate, followed by extraction with ethyl acetate twice. The organic layer was dried over anhydrous magnesium sulfate, filtered, and concentrated under reduced pressure to obtain 71 mg of the title compound (yield: 95%) as a colorless oil.

Mass spectrum (CI, m/z): 194 [M+1]$^+$.

$^1$H-NMR spectrum (400 MHz, DMSO-d$_6$) δ: 7.34-7.16 (m, 5H), 3.78 (s, 1H), 3.23 (s, 3H), 3.13 (d, J=8.8 Hz, 1H), 2.92 (d, J=8.8 Hz, 1H), 1.82 (br s, 2H), 0.83 (s, 3H), 0.70 (s, 3H).

Reference Example 137

Ethyl 5-[(3-methoxy-2,2-dimethyl-1-phenylpropyl) carbamoyl]-6,6-dimethyl-3-[1-(trimethylsilyl)cyclobutanecarboxamido]-5,6-dihydropyrrolo[3,4-c] pyrazole-2(4H)-carboxylate

[Chemical Formula 272]

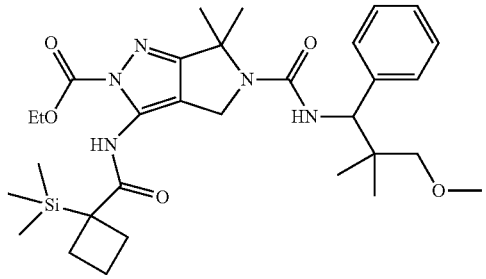

To a solution of 70 mg (0.36 mmol) of 3-methoxy-2,2-dimethyl-1-phenylpropan-1-amine synthesized in the similar manner as in Reference Example 136 in 5 ml of 1,4-dioxane, 0.315 ml (1.81 mol) of DIPEA and 176 mg (0.399 mmol) of ethyl 5-(chlorocarbonyl)-6,6-dimethyl-3-[1-(trimethylsilyl)cyclobutanecarbox amido]-5,6-dihydropyrrolo[3, 4-c]pyrazole-2(4H)-carboxylate synthesized in the similar manner as in Reference Example 3 were added in this order with stirring at room temperature under argon stream and stirred at 90° C. for 2 hours.

After the completion of the reaction, a saturated aqueous solution of ammonium chloride was added to the reaction solution allowed to cool to room temperature, followed by extraction from the mixed solution with ethyl acetate. The organic layer was washed with saturated saline, dried over anhydrous magnesium sulfate, filtered, and concentrated under reduced pressure. The obtained concentration residue was subjected to silica gel column chromatography (elution solvent: n-hexane:ethyl acetate=61:39 to 40:60 (V/V)), and a fraction containing the compound of interest was concentrated under reduced pressure to obtain 131 mg of the title compound (yield: 61%) as a white foam.

Mass spectrum (CI, m/z): 598 [M+1]$^+$.

$^1$H-NMR spectrum (400 MHz, DMSO-d$_6$) δ: 9.75 (s, 1H), 7.38-7.20 (m, 5H), 6.78 (d, J=8.3 Hz, 1H), 4.64-4.50 (m, 3H), 4.42 (q, J=7.1 Hz, 2H), 3.40 (s, 3H), 3.15 (d, J=9.2 Hz, 1H), 2.93 (d, J=9.2 Hz, 1H), 2.57-2.45 (m, 2H), 2.32-2.23 (m, 2H), 1.97-1.82 (m, 2H), 1.61 (s, 3H), 1.52 (s, 3H), 1.35 (t, J=7.0 Hz, 3H), 1.13 (s, 3H), 0.68 (s, 3H), 0.13 (s, 9H).

Test Example 1

CDK7 Enzyme Inhibition Test

The preparation of a buffer solution was performed by mixing a N-2-hydroxyethylpiperazine-N'-2-ethanesulfonic acid buffer solution (HEPES buffer solution) (pH 7.4), dithiothreitol (DTT), Triton X-100, and magnesium chloride (MgCl$_2$). A 500 μM [γ-$^{33}$P]ATP solution was used by diluting a 10 mM ATP solution and a commercially available [γ-$^{33}$P]ATP solution (manufactured by PerkinElmer, Inc., Code No. NEG-302H) with the buffer solution. A CDK7 solution was used by diluting commercially available CDK7 (manufactured by Carna Biosciences, Inc., Catalog No. 04-108) with the buffer solution. A substrate solution was used by diluting myelin basic protein (MBP) with the buffer solution. As for the preparation of a reaction solution, the buffer solution, the 500 μM [γ-$^{33}$P]ATP solution, the CDK7 solution, and the substrate solution were mixed at 4° C. to obtain a reaction solution.

CDK7 enzyme reaction was performed by adding 5 μL of a test compound solution prepared with 10% dimethyl sulfoxide (DMSO)/90% injectable distilled water, and 45 μL of the reaction solution to a 1.5 mL microtube at 4° C. and reacting in the microtube at 30° C. for 20 minutes in a water bath incubator. After the reaction, a 10% aqueous trichloroacetic acid (TCA) solution was added to each microtube while cooled to 4° C., and mixed to terminate the reaction. The resultant was left standing at 4° C. for 10 minutes and then centrifuged in a centrifuge, and the supernatant was discarded. Next, a 2% aqueous TCA solution was added, mixed, and then centrifuged in a centrifuge, and the supernatant was discarded. This washing operation was performed twice. After the washing, precipitates were dissolved in a 1 N aqueous sodium hydroxide (NaOH) solution, and the energy quantity (radioactivity) of the reaction product was measured with a liquid scintillation counter.

The calculation of the inhibitory activity of the test compound against CDK7 was performed as a test compound concentration inhibiting 50% of the amount of $^{33}$P bound to MBP (IC$_{50}$ value) by using EXSUS (version 8.0.0 or version 8.0.1, manufactured by CAC Exicare Corp.).

The calculation of a Ki value was performed according to the following calculation expression. S means the concentration of ATP contained in the reaction solution, and Km means a Michaelis-Menten constant.

$$Ki=IC_{50}/(1+S/Km)$$

In this test, the compounds of the present invention exhibited excellent CDK7 inhibitory activity, and, for example, the Ki values of compound Nos. II-114, II-116, III-114, III-170, III-226, III-298, III-353, III-592, III-1059, III-1140, IV-2, IV-114, IV-117, IV-119, IV-123, IV-139, IV-171, IV-227, IV-283, IV-291, IV-299, IV-362, IV-378, IV-403 (sodium salt), IV-438, IV-442, IV-446, IV-450, IV-455, IV-475, IV-495, IV-510, IV-519, IV-527, IV-534, IV-542, IV-632, IV-633, IV-634, IV-673, IV-743, IV-786, IV-787, IV-815, IV-822, IV-862, IV-911, IV-920, IV-939, IV-959, IV-1067, IV-1175, IV-1176, IV-1178, IV-1180, IV-1188, IV-1196, IV-1204, IV-1208, IV-1215, IV-1241, IV-1255, IV-1258, IV-1274, IV-1330, IV-1348, IV-1372, IV-1383, IV-1404, IV-1427, IV-1546, and IV-1547 were 50 nM or lower.

Test Example 2

CDK2 Enzyme Inhibition Test

The preparation of a buffer solution was performed by mixing a HEPES buffer solution (pH 7.4), DTT, Triton X-100, and MgCl$_2$. A 500 μM [γ-$^{33}$P]ATP solution was used by diluting a 10 mM ATP solution and a commercially available [γ-$^{33}$P]ATP solution (manufactured by PerkinElmer, Inc., Code No. NEG-302H) with the buffer solution. A CDK2 solution was used by diluting commercially available CDK2 (manufactured by Invitrogen Corp., Catalog No. PV3267) with the buffer solution. A substrate solution was used by diluting MBP with the buffer solution. As for the preparation of a reaction solution, the buffer solution, the 500 μM [γ-$^{33}$P]ATP solution, the CDK2 solution, and the substrate solution were mixed at 4° C. to obtain a reaction solution.

CDK2 enzyme reaction was performed by adding 5 μL of a test compound solution prepared with 10% DMSO/90% injectable distilled water, and 45 μL of the reaction solution in a 1.5 mL microtube at 4° C. and reacting in the microtube at 30° C. for 20 minutes in a water bath incubator. After the reaction, a 10% aqueous TCA solution was added to each microtube while cooled to 4° C., and mixed to terminate the reaction. The resultant was left standing at 4° C. for 10 minutes and then centrifuged in a centrifuge, and the supernatant was discarded. Next, a 2% aqueous TCA solution was added, mixed thereto, and then centrifuged in a centrifuge, and the supernatant was discarded. This washing operation was performed twice. After the washing, precipitates were dissolved in a 1 N aqueous NaOH solution, and the radioactivity was measured with a liquid scintillation counter.

The calculation of the inhibitory activity of the test compound against CDK2 was performed as a test compound concentration inhibiting 50% of the amount of $^{33}$P bound to MBP (IC$_{50}$ value) by using EXSUS (version 8.0.0 or version 8.0.1, manufactured by CAC Exicare Corp.).

The calculation of a Ki value was performed according to the following calculation expression. S means the concentration of ATP contained in the reaction solution, and Km means a Michaelis-Menten constant.

$$Ki=IC_{50}/(1+S/Km)$$

In this test, the Ki values of CDK2 inhibitory activity of the compounds of the present invention, for example, compound Nos. II-114, II-116, III-114, III-298, III-353, IV-2, IV-114, IV-115, IV-117, IV-119, IV-123, IV-171, IV-227, IV-283, IV-291, IV-299, IV-403 (sodium salt), IV-438, IV-442, IV-450, IV-455, IV-475, IV-495, IV-534, IV-632, IV-718, IV-743, IV-822, IV-883, IV-890, IV-911, IV-939, IV-946, IV-1184, IV-1196, IV-1204, and IV-1258 were 1000 nM or higher; thus they had high selectivity for CDK7 inhibitory activity with respect to CDK2 inhibitory activity.

Test Example 3

PAK4 Enzyme Inhibition Test

The preparation of a buffer solution was performed by mixing a trishydroxyaminomethane buffer solution (Tris buffer solution) (pH 7.5), DTT, Triton X-100, $MgCl_2$, ethylene glycol bis(β-aminoethyl ether)-N,N,N',N'-tetraacetic acid (EGTA), (3-glycerol phosphate, and sodium orthovanadate(V). A 40 μM [γ-$^{33}$P]ATP solution was used by diluting a 10 mM ATP solution and a commercially available [γ-$^{33}$P]ATP solution (manufactured by PerkinElmer, Inc., Code No. NEG-302H) with the buffer solution. A PAK4 solution was used by diluting commercially available PAK4 (manufactured by Invitrogen Corp., Catalog No. PV4212) with the buffer solution. A substrate solution was used by diluting MBP with the buffer solution. As for the preparation of a reaction solution, the buffer solution, the 40 μM [γ-$^{33}$P]ATP solution, the PAK4 solution, and the substrate solution were mixed at 4° C. to obtain a reaction solution.

PAK4 enzyme reaction was performed by adding 5 μL of a test compound solution prepared with 10% DMSO/90% injectable distilled water, and 45 μL of the reaction solution in a 1.5 mL microtube at 4° C. and reacting in the microtube at 30° C. for 20 minutes in a water bath incubator. After the reaction, a 10% aqueous TCA solution was added to each microtube while cooled to 4° C., and mixed to terminate the reaction. The resultant was left standing at 4° C. for 10 minutes and then centrifuged in a centrifuge, and the supernatant was discarded. Next, a 2% aqueous TCA solution was added, mixed, and then centrifuged in a centrifuge, and the supernatant was discarded. This washing operation was performed twice. After the washing, precipitates were dissolved in a 1 N aqueous NaOH solution, and the radioactivity was measured with a liquid scintillation counter.

The calculation of the inhibitory activity of the test compound against PAK4 was performed as a test compound concentration inhibiting 50% of the amount of $^{33}$P bound to MBP ($IC_{50}$ value) by using EXSUS (version 8.0.0 or version 8.0.1, manufactured by CAC Exicare Corp.).

The calculation of a Ki value was performed according to the following calculation expression. S means the concentration of ATP contained in the reaction solution, and Km means a Michaelis-Menten constant.

$$Ki=IC_{50}/(1+S/Km)$$

In this test, the Ki values of PAK4 inhibitory activity of the compounds of the present invention, for example, compound Nos. II-114, II-116, III-114, III-298, III-353, IV-2, IV-114, IV-115, IV-117, IV-119, IV-123, IV-171, IV-227, IV-283, IV-291, IV-299, IV-403 (sodium salt), IV-438, IV-442, IV-450, IV-455, IV-475, IV-495, IV-534, IV-632, IV-673, IV-718, IV-743, IV-822, IV-883, IV-911, IV-918, IV-946, IV-1184, IV-1196, IV-1204, IV-1208, IV-1258, IV-1383, IV-1404, and IV-1546 were 500 nM or higher; thus they had high selectivity for CDK7 inhibitory activity with respect to PAK4 inhibitory activity.

Test Example 4

Human Large Intestine Cancer (HCT-116) Cell Growth Inhibition Test

The measurement of a human large intestine cancer cell growth inhibitory effect was carried out by modifying the method of Simak et al. (Cancer Research, 69, 6208 (2009)).

A human large intestine cancer cell line (HCT-116) (manufactured by DS Pharma Biomedical Co., Ltd., Cat. No. EC91091005) was cultured in McCoy's 5a (manufactured by GIBCO/Thermo Fisher Scientific, Inc., REF. 16600-082) medium containing 10% FBS (manufactured by GIBCO/Thermo Fisher Scientific, Inc., REF. 10082-147) and 1% penicillin/streptomycin/amphotericin B (manufactured by GIBCO/Thermo Fisher Scientific, Inc., REF. 15240-096) and inoculated at $1.0\times10^3$ cells/well in a 96-well plate (manufactured by Corning Inc., REF. 353072). After overnight culture in a carbon dioxide incubator, it was replaced with a fresh McCoy's 5a medium containing 10% FBS on the next day, and a test compound dissolved in DMSO (manufactured by Wako Pure Chemical Industries, Ltd., Code No. 043-07216) (final DMSO concentration: 0.1%) was added and left standing in a carbon dioxide incubator. After culturing for 3 days, the absorbance of each well was measured by using In Vitro Toxicology Assay Kit Sulforhodamine B based (manufactured by Sigma-Aldrich Co. LLC., Pcode 1001910706).

The rate of inhibition of cell growth at each concentration was calculated from the test compound concentration and the absorbance of sulforhodamine B, and the concentration of the test compound necessary for inhibiting 50% of cell growth ($IC_{50}$ value) was calculated by using EXSUS (version 8.0.0 or version 8.0.1, manufactured by CAC Exicare Corp.).

In this test, the compounds of the present invention exhibited excellent HCT-116 cell growth inhibitory activity, and, for example, the $IC_{50}$ values of compound Nos. II-114, II-116, III-114, III-170, III-226, III-298, III-353, III-592, III-1059, III-1140, IV-2, IV-114, IV-117, IV-119, IV-123, IV-131, IV-139, IV-171, IV-227, IV-235, IV-283, IV-291, IV-299, IV-354, IV-362, IV-378, IV-438, IV-442, IV-446, IV-450, IV-475, IV-495, IV-510, IV-519, IV-527, IV-534, IV-558, IV-562, IV-632, IV-633, IV-634, IV-672, IV-673, IV-718, IV-743, IV-759, IV-786, IV-787, IV-815, IV-822, IV-861, IV-862, IV-883, IV-890, IV-911, IV-918, IV-939, IV-946, IV-959, IV-1067, IV-1175, IV-1176, IV-1178, IV-1180, IV-1184, IV-1188, IV-1196, IV-1204, IV-1208, IV-1211, IV-1215, IV-1224, IV-1241, IV-1255, IV-1258, IV-1266, IV-1268, IV-1274, IV-1330, IV-1348, IV-1383, IV-1404, IV-1427, and IV-1546 were 500 nM or lower.

Test Example 5

Human Breast Cancer (MCF-7) Cell Growth Inhibition Test

The measurement of a human breast cancer cell growth inhibitory effect was carried out by modifying the method of Simak et al. (Cancer Research, 69, 6208 (2009)).

A human breast cancer cell line (MCF-7) manufactured by DS Pharma Biomedical Co., Ltd., Cat. No. EC86012803, was cultured in MEM (manufactured by GIBCO/Thermo Fisher Scientific, Inc., REF. 11095-080) medium containing 10% FBS (manufactured by GIBCO/Thermo Fisher Scientific, Inc., REF. 10082-147), nonessential amino acids (manufactured by GIBCO/Thermo Fisher Scientific, Inc., REF. 11140-050), and 1% penicillin/streptomycin/amphotericin B (manufactured by GIBCO/Thermo Fisher Scientific, Inc., REF. 15240-096) and inoculated at $3.0\times10^3$ cells/ well to a 96-well plate (manufactured by Corning Inc., REF. 353072). After overnight culture in a carbon dioxide incubator, it was replaced with a fresh MEM medium containing 10% FBS, nonessential amino acids, and 1% penicillin/streptomycin/amphotericin B on the next day, and a test compound dissolved in DMSO (manufactured by Wako Pure Chemical Industries, Ltd., Code No. 043-07216) (final DMSO concentration: 0.1%) was added and left standing in a carbon dioxide incubator. After culture for 3 days, the absorbance of each well was measured by using In Vitro Toxicology Assay Kit Sulforhodamine B based (manufactured by Sigma-Aldrich Co. LLC., Pcode 1001910706).

The rate of inhibition of cell growth at each concentration was calculated from the test compound concentration and the absorbance of sulforhodamine B, and the concentration of the test compound necessary for inhibiting 50% of cell growth ($IC_{50}$ value) was calculated by using EXSUS (version 8.0.0 or version 8.0.1, manufactured by CAC Exicare Corp.).

In this test, the compounds of the present invention exhibited excellent MCF-7 cell growth inhibitory activity, and, for example, the $IC_{50}$ values of compound Nos. IV-114, IV-117, IV-123, IV-171, IV-227, IV-291, IV-438, IV-455, IV-475, and IV-495 were 500 nM or lower.

Test Example 6

Human Peripheral Blood Mononuclear Cell (PBMC) CD3/CD28-Induced IL-2 Production Inhibition Test PBMC was separated and collected by using Ficoll-Paque (17-1440-02 manufactured by GE Healthcare Japan Corp.) from blood collected from healthy human adult in the presence of heparin. RPMI1640 medium (manufactured by GIBCO/Thermo Fisher Scientific, Inc., REF. 11875) containing 10% FBS (manufactured by GIBCO/Thermo Fisher Scientific, Inc. REF. 10082) and containing a test compound dissolved in DMSO and 2 µg/mL anti-hCD28 (manufactured by R&D Systems, Inc., Cat. No. MAB342) was added at 100 µL/well to T cell Activation Plate Anti-Human CD3 96-well plate (manufactured by Corning Inc., REF. 354725), and subsequently, a PBMC suspension adjusted such that the number of cells was 2×10⁶ cells/mL was added at 100 µL/well (final DMSO concentration: 0.1%). A RPMI1640 medium containing 10% FBS and containing 0.1% DMSO and 2 µg/mL anti-hCD28 was similarly added to wells not supplemented with the test compound. After incubation for 2 days in a carbon dioxide incubator, the culture supernatant was collected. The collected culture supernatant was stored at −20° C. until IL-2 content measurement.

In the measurement of IL-2 content in the culture supernatant, a sandwich ELISA kit Quantikine Human IL-2 (manufactured by R&D Systems, Inc., Cat. No. S2050) was used. The IL-2 content of each sample was calculated from the calibration curve of Standard IL-2 included in the kit. When the amount of IL-2 produced by CD3/CD28 stimulation in the case of the addition of only DMSO was defined as 100%, the rate of inhibition of IL-2 production at each concentration of the test compound was calculated. A test compound concentration inhibiting 50% of IL-2 production was calculated as an $IC_{50}$ value (nM) from the concentration of the added test compound and the rate of inhibition of IL-2 production by the test compound by using EXSUS (version 8.0.0 or version 8.0.1, manufactured by CAC Exicare Corp.).

In this test, the compounds of the present invention exhibited excellent IL-2 production inhibitory activity, and, for example, the $IC_{50}$ values of compound Nos. II-114, III-114, III-170, III-226, IV-114, IV-123, IV-139, IV-171, IV-227, IV-235, IV-283, IV-299, IV-354, IV-450, IV-510, IV-519, IV-527, IV-1175, IV-1178, IV-1180, IV-1188, and IV-1255 were 50 nM or lower.

Test Example 7

Human PBMC Various-Stimulant Cocktail-Induced IL-17 Production Inhibition Test

PBMC was separated and collected by using Ficoll-Paque (17-1440-02 manufactured by GE Healthcare Japan Corp.) from blood collected from healthy human adult in the presence of heparin. The collected PBMC was further cultured in a flask for a certain time, and then, non-adherent cells in the supernatant were collected and used as a T-cell suspension. RPMI1640 medium (manufactured by GIBCO/Thermo Fisher Scientific, Inc., REF. 11875), which is containing 10% FBS (manufactured by GIBCO/Thermo Fisher Scientific, Inc., REF. 10082), 1% penicillin/streptomycin/amphotericin B (manufactured by GIBCO/Thermo Fisher Scientific, Inc., REF. 15240-096), 1% nonessential amino acids (manufactured by GIBCO/Thermo Fisher Scientific, Inc., REF. 11140-050), and 1% pyruvic acid (manufactured by GIBCO/Thermo Fisher Scientific, Inc., REF. 11140) and containing a test compound dissolved in DMSO, 2 µg/mL (final concentration) CD28 antibody (manufactured by BioLegend, Inc., Cat. No. 302914), 10 µg/mL (final concentration) human IFN-γ antibody (manufactured by BD Biosciences, Cat. No. 554698), 10 µg/mL (final concentration) human IL-4 antibody (manufactured by BD Biosciences, Cat. No. 554481), 20 ng/mL (final concentration) human IL-6 (manufactured by BioLegend, Inc., Cat. No. 570802), 10 ng/mL (final concentration) human IL-23 (manufactured by BioLegend, Inc., Cat. No. 574102), 10 ng/mL (final concentration) human IL-1β (manufactured by PeproTech Inc., Cat. No. 200-01B), and 10 ng/mL (final concentration) human TGF-1β (manufactured by BioLegend, Inc., Cat. No. 580702), was added at 100 µL/well to T cell Activation Plate Anti-Human CD3 96-well plate (manufactured by Corning Inc., REF. 354725). Subsequently, 100 µL of a T-cell suspension adjusted to 2×10⁵ cells/mL was added to each well (final DMSO concentration: 0.1%). Only DMSO was added to wells in the absence of the test compound. After incubation for 5 days in a carbon dioxide incubator, the culture supernatant was collected and stored at −20° C. until IL-17 content measurement.

In the IL-17 content measurement in the culture supernatant, a sandwich ELISA kit (Quantikine Human IL-17, manufactured by R&D Systems, Inc.) was used. The IL-17 content of each sample was calculated from the calibration curve of Standard IL-17 included in the kit. When the amount of IL-17 produced by the cocktail of various stimulants in the case of the addition of only DMSO was defined as 100%, the rate of inhibition of IL-17 production at each concentration of the test compound was calculated. The concentration of the test compound necessary for inhibiting 50% of IL-17 production ($IC_{50}$ value) was calculated from the concentration of the added test compound and the rate of inhibition of IL-17 production by the test compound by using EXSUS (version 8.0.0 or version 8.0.1, manufactured by CAC Exicare Corp.).

In this test, the compounds of the present invention exhibited excellent IL-17 production inhibitory activity, and, for example, the $IC_{50}$ values of compound Nos. IV-299, IV-354, IV-673, IV-718, IV-743, IV-911, IV-918, IV-939, IV-946, IV-1175, IV-1178, IV-1180, IV-1184, IV-1188, IV-1196, IV-1204, IV-1208, IV-1383, IV-1404, and IV-1546 were 50 nM or lower.

Test Example 8

Human Keratinocyte Growth Inhibition Assay

The measurement of a human keratinocyte growth inhibitory effect was carried out by modifying the method of Schafer et al. (British Journal of Pharmacology, 159, 842 (2011)).

Human keratinocytes (NHEK-Neo Pooled, manufactured by Lonza Group AG, Cat. No. 00192906) were cultured in KGM-Gold Bullet Kit (manufactured by Lonza Group AG, Cat. No. 00192060) and inoculated at $2.0 \times 10^3$ cells/well to a 96-well plate. After overnight culture in a carbon dioxide incubator, a test compound dissolved in DMSO (final DMSO concentration: 0.1%) was added and left standing in a carbon dioxide incubator. After culture for 2 days, the absorbance thereof was measured by using Cell Counting Kit-8 (343-07623 manufactured by Dojindo Laboratories)).

The rate of inhibition of cell growth at each concentration was calculated from the test compound concentration and the absorbance of Cell Counting Kit-8, and the concentration of the test compound necessary for inhibiting 50% of cell growth ($IC_{50}$ value) was calculated by using EXSUS (version 8.0.0 or version 8.0.1, manufactured by CAC Exicare Corp.).

In this test, the compounds of the present invention exhibited excellent human keratinocyte growth inhibitory activity, and, for example, the $IC_{50}$ values of compound Nos. III-170, III-226, III-1059, IV-123, IV-131, IV-139, IV-171, IV-227, IV-235, IV-299, IV-354, IV-378, IV-519, IV-527, IV-1175, IV-1178, IV-1180, and IV-1188 were 500 nM or lower.

Test Example 9

IL-6 Production Inhibition Test in Rat Adjuvant Arthritis Model

A single-dose drug efficacy test using rat adjuvant arthritis models was carried out by modifying the method of Magari. K et al. (J. Rheumatol. 30 (10), 2193 (2003)).

LEW rats (female, supplied by Charles River Laboratories Japan, Inc.) were used as laboratory animals. An adjuvant prepared from heat-killed bacteria of *Mycobacterium butyricum* (264010 manufactured by Difco Laboratories Ltd.) and liquid paraffin (manufactured by Wako Pure Chemical Industries, Ltd., Code No. 128-04375) was subcutaneously administered as a phlogogenic material to the right hind leg footpads of the rats under inhalation anesthesia with isoflurane (manufactured by Wako Pure Chemical Industries, Ltd., Code No. 099-06571) to prepare arthritis models. Approximately 2 weeks later, left paw edema was measured with a paw volume meter (model TK-101CMP manufactured by Unicorn Co., Ltd.), and grouping was performed such that the average volume of left paw edema was equal among groups. A test compound or only a solvent was administered, after a certain time, they were sacrificed by exsanguination from the abdomens under isoflurane anesthesia, and the left ankles were collected, chopped, and frozen by using liquid nitrogen. The collected left ankle portions were disrupted in CRYOPress (model CP-100WP manufactured by Microtec Co., Ltd.), then supplemented with a buffer solution, shaken overnight at 4° C., and then centrifuged to collected a supernatant. The preparation of the buffer solution was performed by mixing a Tris buffer solution (pH 7.4), sodium chloride (NaCl), phenyl methyl sulfonyl fluoride (PMSF), Triton X-100, EDTA-free complete tablets (manufactured by F. Hoffmann-La Roche, Ltd., REF. 11 873 580 001), and Otsuka distilled water (manufactured by Otsuka Pharmaceutical Co., Ltd., product No. 1323). IL-6 in the collected supernatant was measured by using a sandwich ELISA kit (manufactured by R&D Systems, Inc., Catalog No. S6050).

The IL-6 content of each sample was calculated from the calibration curve of Standard IL-6 included in the kit. When the amount of IL-6 produced in the solvent administration control group was defined as 100%, the rate of inhibition of IL-6 production (%) at each dose of the test compound was calculated.

In this test, the compounds of the present invention exhibited excellent IL-6 production inhibitory activity, and, for example, compound Nos. II-114, IV-2, IV-119, IV-171, and IV-235 exhibited 50% or more rate of inhibition by the administration of 10 mg/kg, and compound Nos. IV-123, IV-139, IV-227, IV-299, and IV-632 exhibited 50% or more rate of inhibition by the administration of 3 mg/kg.

Test Example 10

Paw Edema Suppression Test in Rat Adjuvant Arthritis Model

LEW rats (female, supplied by Charles River Laboratories Japan, Inc.) were used as laboratory animals. An adjuvant prepared from heat-killed bacteria of *Mycobacterium butyricum* (264010 manufactured by Difco Laboratories Ltd.) and liquid paraffin (manufactured by Wako Pure Chemical Industries, Ltd., Code No. 128-04375) was subcutaneously administered as a phlogogenic material to the right hind leg footpads of the rats under inhalation anesthesia with isoflurane (manufactured by Wako Pure Chemical Industries, Ltd., Code No. 099-06571) to prepare arthritis models. Also, liquid paraffin not containing the killed bacteria was administered by a similar method to obtain an untreated group. The administration of the test compound or only the solvent was performed by oral administration 28 times once a day from the adjuvant injection day (day 0) to day 27. The volumes of the adjuvant-administered right hind legs and the non-administered left hind legs were measured several times on days 7 to 28 after the adjuvant administration with a paw volume meter (model TK-101CMP manufactured by Unicorn Co., Ltd.), and the rate of edema was calculated according to the following expression.

Rate of edema (%)=[{(Footpad volume at the time of measurement)−(Footpad volume before the start of the test)}/(Footpad volume before the start of the test)]×100

The rate of suppression of edema in the solvent-administered control group was further calculated according to the following expression.

Rate of suppression of edema (%)=[1−{(Rate of edema of the test compound-administered group)−(Rate of edema of the untreated group)}/{Rate of edema of the control group)−(Rate of edema of the untreated group)}]×100

In this test, the compounds of the present invention exhibited excellent edema suppressive activity, and, for example, compound Nos. IV-114 and IV-171 exhibited 50% or more rate of suppression by the administration of 10 mg/kg.

Test Example 11

Tumor Growth Inhibition Test in Human Large Intestine Cancer Cell (HCT116)-Subcutaneously Transplanted Nude Mouse A human large intestine cancer cell line (HCT-116) (manufactured by DS Pharma Biomedical Co., Ltd., Cat. No. EC91091005) was cultured in a McCoy's 5a medium containing 10% FBS (manufactured by GIBCO/Thermo Fisher Scientific, Inc., REF. 10082-147) and 1% penicillin/ streptomycin/amphotericin B (manufactured by GIBCO/ Thermo Fisher Scientific, Inc., REF.15240-096) and adjusted to $1.0 \times 10^8$ cells/mL with PBS (manufactured by GIBCO/Thermo Fisher Scientific, Inc., REF. 10010-031) or Hanks solution (HBSS(−)) (manufactured by GIBCO/ Thermo Fisher Scientific, Inc., REF. 14025-076). The adjusted cell suspension was subcutaneously injected at 0.1 mL/mouse to the right abdomens of BALB/c-nu/nu mice (female, supplied by Charles River Laboratories Japan, Inc.). After rearing for a certain period, the long diameter (mm) and short diameter (mm) of tumor were measured with electronic calipers (manufactured by Mitsutoyo Corp., Cat. 500-712-10), and the tumor volume was calculated according to the following expression.

Tumor volume (mm$^3$)=(Long diameter)×(Short diameter)×(Short diameter)×0.5

Individuals whose tumor volume was within the range of 50 to 200 mm$^3$ were selected and grouped such that the tumor volume was almost equivalent, and then, a test compound or only a solvent was orally administered. When the first day of administration was defined as day 0, the oral administration was repeated once a day up to day 3, and the tumor size was measured on day 4. When increase in tumor volume from day 0 of the solvent-administered control group was defined as 100%, the rate of suppression of tumor volume (%) at each dose of the test compound was calculated.

In this test, the compounds of the present invention exhibited excellent tumor growth inhibitory activity, and, for example, compound Nos. III-170, IV-171, IV-299, and IV-632 exhibited 50% or more rate of inhibition by the administration of 100 mg/kg.

Test Example 12

Ear Thickening Suppression Test Using Mouse Imiquimod-Induced Psoriasis Model

An imiquimod-induced psoriasis model test was carried out by modifying the method of Leslie van der Fits et al. (J. Immunol. 182, 5836 (2009)). BALB/c mice were used (female, supplied by Charles River Laboratories Japan, Inc.) as laboratory animals. On the start day of the test, the thicknesses of the right auricles of the mice were measured with a thickness gauge (model SMD-565J manufactured by TECLOCK Corp.). A test compound solution or only a solvent was applied or orally administered, and after 60 minutes, 5 mg of imiquimod (Beselna Cream 5% manufactured by Mochida Pharmaceutical Co., Ltd.) was applied to the insides of the right auricles. The test compound solution or solvent administration and the imiquimod application were carried out for 4 days, and the thicknesses of the right auricles were measured again on day 5. When increase in the thicknesses of the right auricles of the solvent-administered group on day 5 was defined as 100%, the rate of inhibition of increase (%) at each dose of the test compound was calculated.

In this test, the compounds of the present invention exhibited excellent activity, and, for example, compound Nos. IV-114, IV-123, IV-227, V-1442, V-1446, V-1454, V-1462, V-1470, and V-1474 exhibited 50% or more rate of inhibition by the application of a 1% solution in methanol, and compound Nos. III-1059, IV-299, IV-354, IV-673, IV-676, IV-718, IV-743, IV-911, IV-918, IV-939, IV-946, IV-1175, IV-1178, IV-1180, IV-1184, IV-1188, IV-1196, IV-1200, IV-1204, IV-1208, IV-1383, IV-1404, and IV-1546 exhibited 50% or more rate of inhibition by the application of a 0.01% methanol solution.

Test Example 13

Metabolism Test Using Human Liver Microsome Fraction

To a reaction composition solution (50 μL of NADPH production system solution A (manufactured by Corning Inc., REF. 451220), 10 μL of NADPH production system solution B (manufactured by Corning Inc., REF. 451200), 40 μL of 250 mM UDP-glucuronic acid, 200 μL of UGT Reaction Mix solution B (manufactured by Corning Inc., REF. 451320), and 590 μL of distilled water) in which human liver microsome (manufactured by Sekisui Xeno-Tech, LLC., Cat No. H610) corresponding to 2 mg of protein was suspended, 10 μL of a test compound (prodrug represented by formula (V) or (VI)) dissolved in DMSO (manufactured by Wako Pure Chemical Industries, Ltd., Code No. 043-07216) (final DMSO concentration: 1.0%) was added and incubated at 37° C. for 5 minutes.

The peak areas (measurement UV wavelength: 245 nm) of the test compound (prodrug represented by formula (V) or (VI)) and an alcohol form which was a produced pharmacologically active form were calculated by high-performance liquid chromatography (model LC-20A series manufactured by Shimadzu Corp.).

HPLC conditions: column: Phenomenex Kinetex C18 (manufactured by Phenomenex Inc., Part No. 00D-4462-AN), 2.1 mm×100 mm, 2.6 μm, column temperature: 40° C., eluent: solution A: 0.1% formic acid (manufactured by Wako Pure Chemical Industries, Ltd., Code No. 063-04192), solution B: acetonitrile (manufactured by Wako Pure Chemical Industries, Ltd., Code No. 019-08631)/methanol (manufactured by Wako Pure Chemical Industries, Ltd., Code No. 138-06473)/formic acid=500/500/1, gradient conditions: 0→3 min: 90% solution A, 3→11 min: 20% solution A→5%, 11→15 min: 5% solution A, analysis time: 20 min)

In this test, for example, for compound No. V-1442, only the peak of compound No. IV-114 which was a produced alcohol form was detected after incubation for 5 minutes.

In this test, the prodrug of the present invention was immediately converted to the pharmacologically active form.

From the results of Test Examples 1 to 13 described above, it is concluded that the compound of the present invention has excellent CDK7 inhibitory activity and high selectivity in itself or functions as a prodrug of a compound having excellent CDK7 inhibitory activity and high selectivity, and is useful as, for example, a therapeutic drug and/or a prophylactic drug for cancers or inflammatory diseases.

A novel substituted dihydropyrrolopyrazole compound having a particular structure represented by formula (I) of the present invention or a pharmacologically acceptable salt thereof has excellent CDK7 inhibitory activity in itself or is capable of functioning as a prodrug of a compound having excellent CDK7 inhibitory activity, and is useful as a drug (e.g., a therapeutic drug and/or a prophylactic drug for cancers or inflammatory diseases).

The invention claimed is:
1. A compound represented by formula (I) or a pharmacologically acceptable salt thereof:

[Chemical Formula 1]

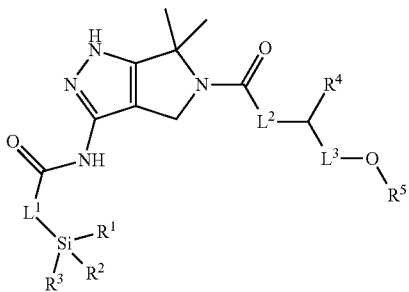

(I)

wherein
L¹ is an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group,
L² is a single bond, an oxygen atom, an optionally substituted nitrogen atom, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group,
L³ is a single bond, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group,
R¹, R², and R³ are each independently an optionally substituted linear or branched $C_{1-4}$ alkyl group, an optionally substituted linear or branched $C_{2-4}$ alkenyl group, an optionally substituted linear or branched $C_{2-4}$ alkynyl group, an optionally substituted $C_{6-10}$ aryl group, or an optionally substituted heterocyclic group,
R⁴ is a hydrogen atom, an optionally substituted linear or branched $C_{1-6}$ alkyl group, an optionally substituted linear or branched $C_{2-6}$ alkenyl group, an optionally substituted linear or branched $C_{2-6}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group, and
R⁵ is a hydrogen atom, an optionally substituted linear or branched $C_{1-16}$ alkyl group, an optionally substituted linear or branched $C_{2-16}$ alkenyl group, an optionally substituted linear or branched $C_{2-16}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group.

2. The compound or a pharmacologically acceptable salt thereof according to claim 1, wherein L¹ is an optionally substituted linear or branched $C_{1-6}$ alkylene group or an optionally substituted $C_{3-6}$ cycloalkylene group.

3. The compound or a pharmaceutically acceptable salt thereof according to claim 1, where the compound or a pharmaceutically acceptable thereof is a compound represented by formula (II) or a pharmacologically acceptable salt thereof:

[Chemical Formula 2]

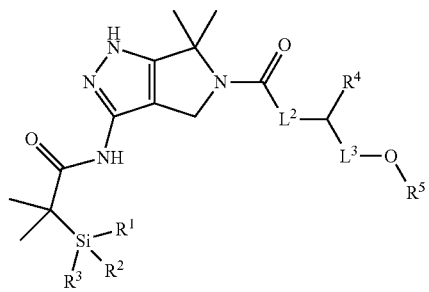

(II)

wherein
L² is a single bond, an oxygen atom, an optionally substituted nitrogen atom, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group,
L³ is a single bond, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group,
R¹, R², and R³ are each independently an optionally substituted linear or branched $C_{1-4}$ alkyl group, an optionally substituted linear or branched $C_{2-4}$ alkenyl group, an optionally substituted linear or branched $C_{2-4}$ alkynyl group, an optionally substituted $C_{6-10}$ aryl group, or an optionally substituted heterocyclic group,
R⁴ is a hydrogen atom, an optionally substituted linear or branched $C_{1-6}$ alkyl group, an optionally substituted linear or branched $C_{2-6}$ alkenyl group, an optionally substituted linear or branched $C_{2-6}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group, and
R⁵ is a hydrogen atom, an optionally substituted linear or branched $C_{1-16}$ alkyl group, an optionally substituted linear or branched $C_{2-16}$ alkenyl group, an optionally substituted linear or branched $C_{2-16}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group.

4. The compound or a pharmacologically acceptable salt thereof according to claim 3, wherein $R^1$, $R^2$, and $R^3$ each independently represent an optionally substituted linear or branched $C_{1-4}$ alkyl group.

5. The compound or a pharmaceutically acceptable salt thereof according to claim 1, wherein the compound or a pharmaceutically acceptable thereof is a compound represented by formula (III) or a pharmacologically acceptable salt thereof:

[Chemical Formula 3]

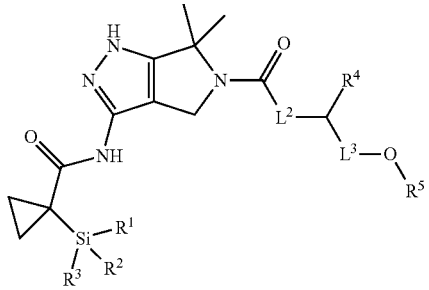

(III)

wherein
- $L^2$ is a single bond, an oxygen atom, an optionally substituted nitrogen atom, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group,
- $L^3$ is a single bond, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group,
- $R^1$, $R^2$, and $R^3$ are each independently an optionally substituted linear or branched $C_{1-4}$ alkyl group, an optionally substituted linear or branched $C_{2-4}$ alkenyl group, an optionally substituted linear or branched $C_{2-4}$ alkynyl group, an optionally substituted $C_{6-10}$ aryl group, or an optionally substituted heterocyclic group,
- $R^4$ is a hydrogen atom, an optionally substituted linear or branched $C_{1-6}$ alkyl group, an optionally substituted linear or branched $C_{2-6}$ alkenyl group, an optionally substituted linear or branched $C_{2-6}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group, and
- $R^5$ is a hydrogen atom, an optionally substituted linear or branched $C_{1-16}$ alkyl group, an optionally substituted linear or branched $C_{2-16}$ alkenyl group, an optionally substituted linear or branched $C_{2-16}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group.

6. The compound or a pharmacologically acceptable salt thereof according to claim 5, wherein $R^1$, $R^2$, and $R^3$ are each independently an optionally substituted linear or branched $C_{1-4}$ alkyl group.

7. The compound or a pharmaceutically acceptable salt thereof according to claim 1, wherein the compound or a pharmaceutically acceptable thereof is a compound represented by formula (IV) or a pharmacologically acceptable salt thereof:

[Chemical Formula 4]

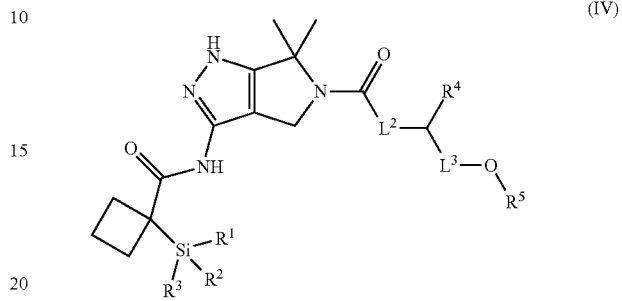

(IV)

wherein
- $L^2$ is a single bond, an oxygen atom, an optionally substituted nitrogen atom, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group,
- $L^3$ is a single bond, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group,
- $R^1$, $R^2$, and $R^3$ are each independently an optionally substituted linear or branched $C_{1-4}$ alkyl group, an optionally substituted linear or branched $C_{2-4}$ alkenyl group, an optionally substituted linear or branched $C_{2-4}$ alkynyl group, an optionally substituted $C_{6-10}$ aryl group, or an optionally substituted heterocyclic group,
- $R^4$ is a hydrogen atom, an optionally substituted linear or branched $C_{1-6}$ alkyl group, an optionally substituted linear or branched $C_{2-6}$ alkenyl group, an optionally substituted linear or branched $C_{2-6}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group, and
- $R^5$ is a hydrogen atom, an optionally substituted linear or branched $C_{1-16}$ alkyl group, an optionally substituted linear or branched $C_{2-16}$ alkenyl group, an optionally substituted linear or branched $C_{2-16}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group.

8. The compound or a pharmacologically acceptable salt thereof according to claim 7, wherein $R^1$, $R^2$, and $R^3$ are each independently an optionally substituted linear or branched $C_{1-4}$ alkyl group.

9. The compound or a pharmaceutically acceptable salt thereof according to claim 1, wherein the compound or a pharmaceutically acceptable thereof is a compound represented by formula (V) or (VI) or a pharmacologically acceptable salt thereof:

[Chemical Formula 5]

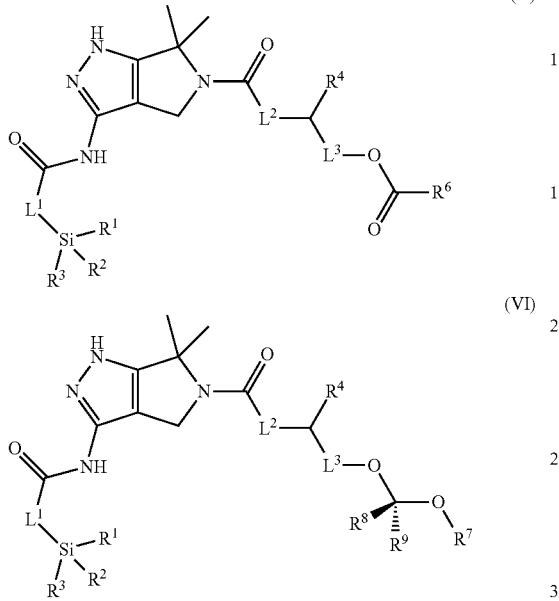

wherein
- $L^1$ is an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group,
- $L^2$ is a single bond, an oxygen atom, an optionally substituted nitrogen atom, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group,
- $L^3$ is a single bond, an optionally substituted linear or branched $C_{1-6}$ alkylene group, an optionally substituted linear or branched $C_{2-6}$ alkenylene group, an optionally substituted linear or branched $C_{2-6}$ alkynylene group, an optionally substituted $C_{3-6}$ cycloalkylene group, or an optionally substituted $C_{3-6}$ cycloalkenylene group,
- $R^1$, $R^2$, and $R^3$ are each independently an optionally substituted linear or branched $C_{1-4}$ alkyl group, an optionally substituted linear or branched $C_{2-4}$ alkenyl group, an optionally substituted linear or branched $C_{2-4}$ alkynyl group, an optionally substituted $C_{6-10}$ aryl group, or an optionally substituted heterocyclic group,
- $R^4$ is a hydrogen atom, an optionally substituted linear or branched $C_{1-6}$ alkyl group, an optionally substituted linear or branched $C_{2-6}$ alkenyl group, an optionally substituted linear or branched $C_{2-6}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group,
- $R^6$ is a hydrogen atom, an optionally substituted linear or branched $C_{1-16}$ alkyl group, an optionally substituted linear or branched $C_{2-16}$ alkenyl group, an optionally substituted linear or branched $C_{2-16}$ alkynyl group, an optionally substituted $C_{3-6}$ cycloalkyl group, an optionally substituted $C_{3-6}$ cycloalkenyl group, an optionally substituted linear or branched $C_{1-6}$ alkoxy group, an optionally substituted $C_{6-10}$ aryl group, or an optionally substituted heterocyclic group,
- $R^7$ is an optionally substituted linear or branched $C_{1-16}$ alkyl group, an optionally substituted linear or branched $C_{2-16}$ alkenyl group, an optionally substituted linear or branched $C_{2-16}$ alkynyl group, an optionally substituted $C_{3-6}$ cycloalkyl group, an optionally substituted $C_{3-6}$ cycloalkenyl group, an optionally substituted $C_{6-10}$ aryl group, or an optionally substituted heterocyclic group, and
- $R^8$ and $R^9$ are each independently a hydrogen atom or a $C_{1-4}$ alkyl group.

10. The compound or a pharmaceutically acceptable salt thereof according to claim 9, wherein $L^1$ is an optionally substituted linear or branched $C_{1-6}$ alkylene group or an optionally substituted $C_{3-6}$ cycloalkylene group, and $R^1$, $R^2$, and $R^3$ are each independently an optionally substituted linear or branched $C_{1-4}$ alkyl group.

11. A compound selected from a compound group consisting of
- (S)—N-(2-hydroxy-1-phenylethyl)-6,6-dimethyl-3-[1-(trimethylsilyl)cyclobutanecarboxamido]-4,6-dihydropyrrolo [3,4-c]pyrazole-5(1H)-carboxamide,
- (S)—N-(2-hydroxy-1-phenylethyl)-6,6-dimethyl-3-[1-(trimethylsilyl)cyclopropanecarboxamido]-4,6-dihydropyrrolo [3,4-c]pyrazole-5(1H)-carboxamide,
- (S)—N-(2-hydroxy-1-phenylethyl)-6,6-dimethyl-3-[2-methyl-2-(trimethylsilyl)propaneamido]-4,6-dihydropyrrolo[3,4-c]pyrazole-5(1H)-carboxamide,
- (S)-3-[1-(ethyldimethylsilyl)cyclobutanecarboxamido]-N-(2-hydroxy-1-phenylethyl)-6,6-dimethyl-4,6-dihydropyrrolo [3,4-c]pyrazole-5(1H)-carboxamide,
- (S)-3-[2-(ethyldimethylsilyl)-2-methylpropaneamido]-N-(2-hydroxy-1-phenylethyl)-6,6-dimethyl-4,6-dihydropyrrolo[3,4-c]pyrazole-5(1H)-carboxamide,
- (S)—N-(2-hydroxy-1-phenylethyl)-N,6,6-trimethyl-3-[1-(trimethylsilyl)cyclobutanecarboxamido]-4,6-dihydropyrrolo [3,4-c]pyrazole-5(1H)-carboxamide,
- (S)-2-[(2-methoxypropan-2-yl)oxy]-1-phenylethyl 6,6-dimethyl-3-[1-(trimethylsilyl)cyclobutanecarboxamido]-4,6-dihydropyrrolo [3,4-c]pyrazole-5(1H)-carboxylate,
- (S)-2-hydroxy-1-phenylethyl 6,6-dimethyl-3-[1-(trimethylsilyl)cyclobutanecarboxamido]-4,6-dihydropyrrolo [3,4-c]pyrazole-5(1H)-carboxylate,
- 2-Methoxy-1-phenylethyl 6,6-dimethyl-3-[1-(trimethylsilyl)cyclopropanecarboxamido]-4,6-dihydropyrrolo [3,4-c]pyrazole-5(1H)-carboxylate,
- N-[5-(4-hydroxy-3-phenylbutanoyl)-6,6-dimethyl-1,4,5,6-tetrahydropyrrolo[3,4-c]pyrazol-3-yl]-1-(trimethylsilyl)cyclobutanecarboxamide,
- N-[5-(3-hydroxy-3-phenylpropanoyl)-6,6-dimethyl-1,4,5,6-tetrahydropyrrolo[3,4-c]pyrazol-3-yl]-1-(trimethylsilyl)cyclobutanecarboxamide, (R)—N-(3-hydroxy-1-phenylpropyl)-6,6-dimethyl-3-[1-(trimethylsilyl)cyclobutanecarboxamido]-4,6-dihydropyrrolo [3,4-c]pyrazole-5(1H)-carboxamide, (R)—N-(3-hydroxy-1-phenylpropyl)-6,6-dimethyl-3-[1-(trimethylsilyl)cyclopropanecarboxamido]-4,6-dihydropyrrolo [3,4-c]pyrazole-5(1H)-carboxamide, (R)—N-(4-hydroxy-1-phenylbutyl)-6,6-dimethyl-3-[1-(trimethylsilyl)cyclobutanecarboxamido]-4,6-dihydropyrrolo [3,4-c]pyrazole-5(1H)-carboxamide, (R)—N-(5-hydroxy-1-phenylpentyl)-6,6-dimethyl-3-[1-(trimethylsilyl)cyclobutanecarboxamido]-4,6-dihydropyrrolo [3,4-c]pyrazole-5(1H)-carboxamide, (S)—N-(2-hydroxy-2-methyl-1-phenylpropyl)-6,6-dimethyl-3-[1-(trimethylsilyl)cyclobutanecarboxamido]-4,6-dihydropyrrolo [3,4-c]pyrazole-5(1H)-carboxamide, (S)—N-(2-hydroxy-2-methyl-1-phenylpropyl)-6,6-dimethyl-3-[1-(trimethylsilyl)cyclopropanecarboxamido]-4,6-dihydropyrrolo [3,4-c]pyrazole-5(1H)-carboxamide, N-(3-hydroxy-2,2-dimethyl-1-phenylpropyl)-6,6-dimethyl-3-[1-(trimethylsilyl)cyclobutanecarboxamido]-4,6-dihydropyrrolo [3,4-c]pyrazole-5(1H)-carboxamide, (R)—N-(3-hydroxy-3-methyl-1-phenylbutyl)-6,6-dimethyl-3-[1-(trimethylsilyl)cyclobutanecarboxamido]-4,6-dihydropyrrolo [3,4-c]pyrazole-5(1H)-carboxamide, (S)—N-(2-methoxy-1-phenylethyl)-6,6-dimethyl-3-[1-(trimethylsilyl)cyclobutanecarboxamido]-4,6-dihydropyrrolo [3,4-c]pyrazole-5(1H)-carboxamide, (S)—N-[2-(difluoromethoxy)-1-phenylethyl]-6,6-dimethyl-3-[1-(trimethylsilyl)cyclobutanecarboxamido]-4,6-dihydropyrrolo [3,4-c]pyrazole-5(1H)-carboxamide, (S)—N-(2-ethoxy-1-phenylethyl)-6,6-dimethyl-3-[1-(trimethylsilyl)cyclobutanecarboxamido]-4,6-dihydropyrrolo [3,4-c]pyrazole-5(1H)-carboxamide, (R)—N-(3-methoxy-1-phenylpropyl)-6,6-dimethyl-3-[1-(trimethylsilyl)cyclobutanecarboxamido]-4,6-dihydropyrrolo [3,4-c]pyrazole-5(1H)-carboxamide, Sodium (S)-2-{6,6-dimethyl-3-[1-(trimethylsilyl)cyclobutanecarboxamido]-1,4,5,6-tetrahydropyrrolo[3,4-c]pyrazole-5-carboxamide}-2-phenylacetate, (R)—N-(2-hydroxy-1-phenylethyl)-6,6-dimethyl-3-[1-(trimethylsilyl)cyclobutanecarboxamido]-4,6-dihydropyrrolo [3,4-c]pyrazole-5(1H)-carboxamide, N-[1-(2-fluorophenyl)-2-hydroxyethyl]-6,6-dimethyl-3-[1-(trimethylsilyl)cyclobutanecarboxamido]-4,6-dihydropyrrolo [3,4-c]pyrazole-5(1H)-carboxamide, (S)—N-[1-(3-fluorophenyl)-2-hydroxyethyl]-6,6-dimethyl-3-[1-(trimethylsilyl)cyclobutanecarboxamido]-4,6-dihydropyrrolo [3,4-c]pyrazole-5(1H)-carboxamide, (S)—N-[1-(4-fluorophenyl)-2-hydroxyethyl]-6,6-dimethyl-3-[1-(trimethylsilyl)cyclobutanecarboxamido]-4,6-dihydropyrrolo [3,4-c]pyrazole-5(1H)-carboxamide, N-[2-hydroxy-1-(pyridin-2-yl)ethyl]-6,6-dimethyl-3-[1-(trimethylsilyl)cyclobutanecarboxamido]-4,6-dihydropyrrolo [3,4-c]pyrazole-5(1H)-carboxamide, N-[2-hydroxy-1-(pyridin-3-yl)ethyl]-6,6-dimethyl-3-[1-(trimethylsilyl)cyclobutanecarboxamido]-4,6-dihydropyrrolo [3,4-c]pyrazole-5(1H)-carboxamide, N-[1-(benzo[d][1,3]dioxol-4-yl)-2-hydroxyethyl]-6,6-dimethyl-3-[1-(trimethylsilyl)cyclobutanecarboxamido]-4,6-dihydropyrrolo [3,4-c]pyrazole-5(1H)-carboxamide, (S)—N-(1-cyclohexyl-2-hydroxyethyl)-6,6-dimethyl-3-[1-(trimethylsilyl)cyclobutanecarboxamido]-4,6-dihydropyrrolo [3,4-c]pyrazole-5(1H)-carboxamide, (S)—N-(1-hydroxy-3-methylbutan-2-yl)-6,6-dimethyl-3-[1-(trimethylsilyl)cyclobutanecarboxamido]-4,6-dihydropyrrolo [3,4-c]pyrazole-5(1H)-carboxamide, (S)—N-(1-hydroxypropan-2-yl)-6,6-dimethyl-3-[1-(trimethylsilyl)cyclobutanecarboxamido]-4,6-dihydropyrrolo [3,4-c]pyrazole-5(1H)-carboxamide, N-(2-hydroxyethyl)-6,6-dimethyl-3-[1-(trimethylsilyl)cyclobutanecarboxamido]-4,6-dihydropyrrolo [3,4-c]pyrazole-5(1H)-carboxamide, N-(2-hydroxy-2-phenylethyl)-6,6-dimethyl-3-[1-(trimethylsilyl)cyclobutanecarboxamido]-4,6-dihydropyrrolo [3,4-c]pyrazole-5(1H)-carboxamide, N-(2-hydroxypropyl)-6,6-dimethyl-3-[1-(trimethylsilyl)cyclobutanecarboxamido]-4,6-dihydropyrrolo [3,4-c]pyrazole-5(1H)-carboxamide, N-[(2S)-1-hydroxy-3-methyl-1-phenylbutan-2-yl]-6,6-dimethyl-3-[1-(trimethylsilyl)cyclobutanecarboxamido]-4,6-dihydropyrrolo [3,4-c]pyrazole-5(1H)-carboxamide, N-(4-hydroxy-1-phenyl-2-butyn-1-yl)-6,6-dimethyl-3-[1-(trimethylsilyl)cyclobutanecarboxamido]-4,6-dihydropyrrolo [3,4-c]pyrazole-5(1H)-carboxamide, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl acetate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl propionate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl butanoate, (S)-2-{6,6-dimethyl-3-[1-(trimethylsilyl)cyclobutanecarboxamido]-1,4,5,6-tetrahydropyrrolo [3,4-c]pyrazole-5-carboxamido}-2-phenylethyl pentanoate, (S)-2-{6,6-dimethyl-3-[1-(trimethylsilyl)cyclobutanecarboxamido]-1,4,5,6-tetrahydropyrrolo [3,4-c]pyrazole-5-carboxamido}-2-phenylethyl octanoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl dodecanoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl palmitate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl isobutanoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl pivalate, (S)-2-{6,6-dimethyl-3-[1-(trimethylsilyl)cyclobutanecarboxamido]-1,4,5,6-tetrahydropyrrolo [3,4-c]pyrazole-5-carboxamido}-2-phenylethyl 3-methylbutanoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl benzoate, (S)-2-{6,6-dimethyl-3-[1-(trimethylsilyl)cyclobutanecarboxamido]-1,4,5,6-tetrahydropyrrolo[3,4-c]pyrazole-5-carboxamido}-2-phenylethyl ethyl carbonate, Sodium (S)-4-(2-{6,6-dimethyl-3-[1-(trimethylsilyl)cyclobutanecarboxamido]-1,4,5,6-tetrahydropyrrolo [3,4-c]pyrazole-5-carboxamido}-2-phenylethoxy)-4-oxobutanoate, (S)-(2-{6,6-dimethyl-3-[1-(trimethylsilyl)cyclobutanecarboxamido]-1,4,5,6-tetrahydropyrrolo[3,4-c]pyrazole-5-carboxamido}-2-phenylethoxy)methyl pivalate, (S)-2-acetoxy-1-phenylethyl 6,6-dimethyl-3-[1-(trimethylsilyl)cyclobutanecarboxamido]-4,6-dihydropyrrolo [3,4-c]pyrazole-5(1H)-carboxylate, (S)-benzyl 2-{6,6-dimethyl-3-[1-(trimethylsilyl)cyclobutanecarboxamido]-1,4,5,6-tetrahydropyrrolo[3,4-c]pyrazole-5-carboxamido}-2-phenylacetate, (S)-methyl 2-{6,6-dimethyl-3-[1-(trimethylsilyl)cyclobutanecarboxamido]-1,4,5,6-tetrahydropyrrolo[3,4-c]pyrazole-5-carboxamido}-2-phenylacetate, N-(2,2-difluoro-3-hydroxy-1-phenylpropyl)-6,6-dimethyl-3-[1-(trimethylsilyl)cyclobutanecarboxamido]-4,6-dihydropyrrolo [3,4-c]pyrazole-5(1H)-carboxamide, N-(2-isopropoxy-1-phenylethyl)-6,6-dimethyl-3-[1-(trimethylsilyl)cyclobutanecarboxamido]-4,6-dihydropyrrolo [3,4-c]pyrazole-5(1H)-carboxamide, 6,6-Dimethyl-N-(2-phenoxy-1-phenylethyl)-3-[1-(trimethylsilyl)cyclobutanecarboxamido]-4,6-dihydropyrrolo [3,4-c]pyrazole-5(1H)-carboxamide, (S)—N-[1-(2-chlorophenyl)-2-hydroxyethyl]-6,6-dimethyl-3-[1-(trimethylsilyl)cyclobutanecarboxamido]-4,6-dihydropyrrolo [3,4-c]pyrazole-5(1H)-carboxamide, (S)—N-[2-hydroxy-1-(o-tolyl)ethyl]-6,6-dimethyl-3-[1-(trimethylsilyl)cyclobutanecarboxamido]-4,6-dihydropyrrolo [3,4-c]pyrazole-5(1H)-carboxamide, (S)—N-(1-hydroxy-3-phenylpropan-2-yl)-6,6-dimethyl-3-[1-(trimethylsilyl)cyclobutanecarboxamido]-4,6-dihydropyrrolo [3,4-c]pyrazole-5(1H)-carboxamide, N-(2-hydroxy-3-methylbutyl)-6,6-dimethyl-3-[1-(trimethylsilyl)cyclobutanecarboxamido]-4,6-dihydropyrrolo [3,4-c]pyrazole-5(1H)-carboxamide, (R)—N-(1-hydroxy-3-phenylpropan-2-yl)-6,6-dimethyl-3-[1-(trimethylsilyl)cyclobutanecarboxamido]-4,6-dihydropyrrolo [3,4-c]pyrazole-5(1H)-carboxamide, (R)—N-(2-hydroxy-2-phenylethyl)-6,6-dimethyl-3-[1-(trimethylsilyl)cyclobutanecarboxamido]-4,6-dihydropyrrolo [3,4-c]pyrazole-5(1H)-carboxamide, (S)—N-(2-hydroxy-2-phenylethyl)-6,6-dimethyl-3-[1-(trimethylsilyl)cyclobutanecarboxamido]-4,6-dihydropyrrolo [3,4-c]pyrazole-5(1H)-carboxamide, 2-Hydroxy-2-phenylethyl 6,6-dimethyl-3-[1-(trimethylsilyl)cyclobutanecarboxamido]-4,6-dihydropyrrolo [3,4-c]pyrazole-5(1H)-carboxylate, (R)—N-[6,6-dimethyl-5-(2-phenoxypropanoyl)-1,4,5,6-tetrahydropyrrolo[3,4-c]pyrazol-3-yl]-1-(trimethylsilyl)cyclobutanecarboxamide, (S)—N-[6,6-dimethyl-5-(2-phenoxypropanoyl)-1,4,5,6-tetrahydropyrrolo[3,4-c]pyrazol-3-yl]-1-(trimethylsilyl)cyclobutanecarboxamide, N-[6,6-dimethyl-5-(2-phenoxyacetyl)-1,4,5,6-tetrahydropyrrolo[3,4-c]pyrazol-3-yl]-1-(trimethylsilyl)cyclobutanecarboxamide, (R)—N-[6,6-dimethyl-5-(2-phenoxypropanoyl)-1,4,5,6-tetrahydropyrrolo[3,4-c]pyrazol-3-yl]-1-(trimethylsilyl)cyclopropanecarboxamide, N-{5-[3-(benzyloxy)-2-phenoxypropanoyl]-6,6-dimethyl-1,4,5,6-tetrahydropyrrolo [3,4-c]pyrazol-3-yl}-1-(trimethylsilyl)cyclobutanecarboxamide, N-[5-(3-hydroxy-2-phenoxypropanoyl)-6,6-dimethyl-1,4,5,6-tetrahydropyrrolo[3,4-c]pyrazol-3-yl]-1-(trimethylsilyl)cyclobutanecarboxamide, N-{5-[2-(4-chlorophenoxy)propanoyl]-6,6-dimethyl-1,4,5,6-tetrahydropyrrolo[3,4-c]pyrazol-3-yl}-1-(trimethylsilyl)cyclobutanecarboxamide, N-{5-[2-(2-chlorophenoxy)propanoyl]-6,6-dimethyl-1,4,5,6-tetrahydropyrrolo[3,4-c]pyrazol-3-yl}-1-(trimethylsilyl)cyclobutanecarboxamide, N-{5-[2-(cyclohexyloxy)propanoyl]-6,6-dimethyl-1,4,5,6-tetrahydropyrrolo [3,4-c]pyrazol-3-yl}-1-(trimethylsilyl)cyclobutanecarboxamide, N-{5-[2-(3-chlorophenoxy)propanoyl]-6,6-dimethyl-1,4,5,6-tetrahydropyrrolo[3,4-c]pyrazol-3-yl}-1-(trimethylsilyl)cyclobutanecarboxamide, N-[5-(2-methoxypropanoyl)-6,6-dimethyl-1,4,5,6-tetrahydropyrrolo[3,4-c]pyrazol-3-yl]-1-(trimethylsilyl)cyclobutanecarboxamide, N-[5-(3-methoxy-2-phenoxypropanoyl)-6,6-dimethyl-1,4,5,6-tetrahydropyrrolo[3,4-c]pyrazol-3-yl]-1-(trimethylsilyl)cyclobutanecarboxamide, N-{6,6-dimethyl-5-[2-(pyridin-3-yloxy)propanoyl]-1,4,5,6-tetrahydropyrrolo[3,4-c]pyrazol-3-yl}-1-(trimethylsilyl)cyclobutanecarboxamide, N-{5-[3-(dimethylamino)-2-phenoxypropanoyl]-6,6-dimethyl-1,4,5,6-tetrahydropyrrolo [3,4-c]pyrazol-3-yl}-1-(trimethylsilyl)cyclobutanecarboxamide, N-[6,6-dimethyl-5-(2-phenoxy-2-phenylacetyl)-1,4,5,6-tetrahydropyrrolo[3,4-c]pyrazol-3-yl]-1-(trimethylsilyl)cyclobutanecarboxamide, N-{5-[3-(3,3-difluoropyrrolidin-1-yl)-2-phenoxypropanoyl]-6,6-dimethyl-1,4,5,6-tetrahydropyrrolo [3,4-c]pyrazol-3-yl}-1-(trimethylsilyl)cyclobutanecarboxamide, N-[5-(3-hydroxy-2-phenylpropanoyl)-6,6-dimethyl-1,4,5,6-tetrahydropyrrolo[3,4-c]pyrazol-3-yl]-1-(trimethylsilyl)cyclobutanecarboxamide, (S)—N-[5-(3-hydroxy-2-phenylpropanoyl)-6,6-dimethyl-1,4,5,6-tetrahydropyrrolo [3,4-c]pyrazol-3-yl]-1-(trimethylsilyl)cyclobutanecarboxamide, (R)—N-{5-[3-(benzyloxy)-2-phenylpropanoyl]-6,6-dimethyl-1,4,5,6-tetrahydropyrrolo [3,4-c]pyrazol-3-yl}-1-(trimethylsilyl)cyclobutanecarboxamide, (R)—N-[5-(3-hydroxy-2-phenylpropanoyl)-6,6-dimethyl-1,4,5,6-tetrahydropyrrolo[3,4-c]pyrazol-3-yl]-1-(trimethylsilyl)cyclobutanecarboxamide, (R)—N-[5-(2-methoxy-2-phenylacetyl)-6,6-dimethyl-1,4,5,6-tetrahydropyrrolo[3,4-c]pyrazol-3-yl]-1-(trimethylsilyl)cyclobutanecarboxamide, (S)—N-[5-(2-methoxy-2-phenylacetyl)-6,6-dimethyl-1,4,5,6-tetrahydropyrrolo [3,4-c]pyrazol-3-yl]-1-(trimethylsilyl)cyclobutanecarboxamide, N-[5-(3-methoxy-2-phenylpropanoyl)-6,6-dimethyl-1,4,5,6-tetrahydropyrrolo[3,4-c]pyrazol-3-yl]-1-(trimethylsilyl)cyclobutanecarboxamide, N-[5-(4-methoxy-2-phenylbutanoyl)-6,6-dimethyl-1,4,5,6-tetrahydropyrrolo[3,4-c]pyrazol-3-yl]-1-(trimethylsilyl)cyclobutanecarboxamide, (S)—N-[5-(3-hydroxy-2-phenylpropanoyl)-6,6-dimethyl-1,4,5,6-tetrahydropyrrolo [3,4-c]pyrazol-3-yl]-1-(trimethylsilyl)cyclopropanecarboxamide, (R)—N-[5-(2-methoxy-2-phenylacetyl)-6,6-dimethyl-1,4,5,6-tetrahydropyrrolo[3,4-c]pyrazol-3-yl]-1-(trimethylsilyl)cyclopropanecarboxamide, (R)—N-{5-[2-(difluoromethoxy)-2-phenylacetyl]-6,6-dimethyl-1,4,5,6-tetrahydropyrrolo[3,4-c]pyrazol-3-yl}-1-(trimethylsilyl)cyclobutanecarboxamide, (R)—N-[5-(2-ethoxy-2-phenylacetyl)-6,6-dimethyl-1,4,5,6-tetrahydropyrrolo[3,4-c]pyrazol-3-yl]-1-(trimethylsilyl)cyclobutanecarboxamide, (R)-1-(ethyldimethylsilyl)-N-[5-(2-methoxy-2-phenylacetyl)-6,6-dimethyl-1,4,5,6-tetrahydropyrrolo[3,4-c]pyrazol-3-yl]cyclobutanecarboxamide, (R)—N-[5-(2-cyclopropoxy-2-phenylacetyl)-6,6-dimethyl-1,4,5,6-tetrahydropyrrolo[3,4-c]pyrazol-3-yl]-1-(trimethylsilyl)cyclobutanecarboxamide, (R)—N-[5-(2-isopropoxy-2-phenylacetyl)-6,6-dimethyl-1,4,5,6-tetrahydropyrrolo [3,4-c]pyrazol-3-yl]-1-(trimethylsilyl)cyclobutanecarboxamide, (R)—N-{6,6-dimethyl-5-[2-phenyl-2-(trifluoromethoxy)acetyl]-1,4,5,6-tetrahydropyrrolo[3,4-c]pyrazol-3-yl}-1-(trimethylsilyl)cyclobutanecarboxamide, (R)—N-[6,6-dimethyl-5-(2-phenyl-2-propoxyacetyl)-1,4,5,6-tetrahydropyrrolo[3,4-c]pyrazol-3-yl]-1-(trimethylsilyl)cyclobutanecarboxamide, N-{5-[2-(4-fluorophenyl)-2-methoxyacetyl]-6,6-dimethyl-1,4,5,6-tetrahydropyrrolo [3,4-c]pyrazol-3-yl}-1-(trimethylsilyl)cyclobutanecarboxamide, N-{5-[2-(3-fluorophenyl)-2-methoxyacetyl]-6,6-dimethyl-1,4,5,6-tetrahydropyrrolo [3,4-c]pyrazol-3-yl}-1-(trimethylsilyl)cyclobutanecarboxamide, (R)—N-{5-[2-(2-fluorophenyl)-2-methoxyacetyl]-6,6-dimethyl-1,4,5,6-tetrahydropyrrolo [3,4-c]pyrazol-3-yl}-1-(trimethylsilyl)cyclobutanecarboxamide, N-{5-[2-methoxy-2-(thiophen-2-yl)acetyl]-6,6-dimethyl-1,4,5,6-tetrahydropyrrolo [3,4-c]pyrazol-3-yl}-1-(trimethylsilyl)cyclobutanecarboxamide, (−)-N-{5-[2-methoxy-2-(thiophen-2-yl)acetyl]-6,6-dimethyl-1,4,5,6-tetrahydropyrrolo [3,4-c]pyrazol-3-yl}-1-(trimethylsilyl)cyclobutanecarboxamide, (+)-N-{5-[2-methoxy-2-(thiophen-2-yl)acetyl]-6,6-dimethyl-1,4,5,6-tetrahydropyrrolo [3,4-c]pyrazol-3-yl}-1-(trimethylsilyl)cyclobutanecarboxamide, N-{[1-(hydroxymethyl)cyclobutyl](phenyl)methyl}-6,6-dimethyl-3-[1-(trimethylsilyl)cyclobutanecarboxamido]-4,6-dihydropyrrolo [3,4-c]pyrazole-5(1H)-carboxamide, (R)—N-[2-(1-hydroxycyclopropyl)-1-phenylethyl]-6,6-dimethyl-3-[1-(trimethylsilyl)cyclobutanecarboxamido]-4,6-dihydropyrrolo [3,4-c]pyrazole-5(1H)-carboxamide, (R)—N-(3-ethyl-3-hydroxy-1-phenylpentyl)-6,6-dimethyl-3-[1-(trimethylsilyl)cyclobutanecarboxamido]-4,6-dihydropyrrolo [3,4-c]pyrazole-5(1H)-carboxamide, (R)—N-[1-(4-fluorophenyl)-3-hydroxy-3-methylbutyl]-6,6-dimethyl-3-[1-(trimethylsilyl)cyclobutanecarboxamido]-4,6-dihydropyrrolo [3,4-c]pyrazole-5(1H)-carboxamide, (R)—N-[1-(3-fluorophenyl)-3-hydroxy-3-methylbutyl]-6,6-dimethyl-3-[1-(trimethylsilyl)cyclobutanecarboxamido]-4,6-dihydropyrrolo [3,4-c]pyrazole-5(1H)-carboxamide, (R)—N-[1-(2-fluorophenyl)-3-hydroxy-3-methylbutyl]-6,6-dimethyl-3-[1-(trimethylsilyl)cyclobutanecarboxamido]-4,6-dihydropyrrolo [3,4-c]pyrazole-5(1H)-carboxamide, (R)—N-(5-hydroxy-2,5-dimethylhexan-3-yl)-6,6-dimethyl-3-[1-(trimethylsilyl)cyclobutanecarboxamido]-4,6-dihydropyrrolo [3,4-c]pyrazole-5(1H)-carboxamide, N-[1-(4-fluorophenyl)-3-hydroxy2,2-dimethylpropyl]-6,6-dimethyl-3-[1-(trimethylsilyl)cyclobutanecarboxamido]-4,6-dihydropyrrolo [3,4-c]pyrazole-5(1H)-carboxamide, N-[1-(3-fluorophenyl)-3-hydroxy-2,2-dimethylpropyl]-6,6-dimethyl-3-[1-(trimethylsilyl)cyclobutanecarboxamido]-4,6-dihydropyrrolo [3,4-c]pyrazole-5(1H)-carboxamide, (−)-N-[1-(3-fluorophenyl)-3-hydroxy-2,2-dimethylpropyl]-6,6-dimethyl-3-[1-(trimethylsilyl)cyclobutanecarboxamido]-4,6-dihydropyrrolo [3,4-c]pyrazole-5(1H)-carboxamide, (+)-N-[1-(3-fluorophenyl)-3-hydroxy-2,2-dimethylpropyl]-6,6-dimethyl-3-[1-(trimethylsilyl)cyclobutanecarboxamido]-4,6-dihydropyrrolo [3,4-c]pyrazole-5(1H)-carboxamide, N-[1-(2-fluorophenyl)-3-hydroxy-2,2-dimethylpropyl]-6,6-dimethyl-3-[1-(trimethylsilyl)cyclobutanecarboxamido]-4,6-dihydropyrrolo [3,4-c]pyrazole-5(1H)-carboxamide, N-(1-hydroxy-2,2,4-trimethylpentan-3-yl)-6,6-dimethyl-3-[1-(trimethylsilyl)cyclobutanecarboxamido]-4,6-dihydropyrrolo [3,4-c]pyrazole-5(1H)-carboxamide, (R)—N-(3-hydroxy-3-methyl-1-phenylbutyl)-6,6-dimethyl-3-[1-(trimethylsilyl)cyclopropanecarboxamido]-4,6-dihydropyrrolo [3,4-c]pyrazole-5(1H)-carboxamide, N-(3-hydroxy-2,2-dimethyl-1-phenylpropyl)-6,6-dimethyl-3-[1-(trimethylsilyl)cyclopropanecarboxamido]-4,6-dihydropyrrolo [3,4-c]pyrazole-5(1H)-carboxamide, (−)-N-(3-hydroxy-2,2-dimethyl-1-phenylpropyl)-6,6-dimethyl-3-[1-(trimethylsilyl)cyclobutanecarboxamido]-4,6-dihydropyrrolo [3,4-c]pyrazole-5(1H)-carboxamide, (+)-N-(3-hydroxy-2,2-dimethyl-1-phenylpropyl)-6,6-dimethyl-3-[1-(trimethylsilyl)cyclobutanecarboxamido]-4,6-dihydropyrrolo [3,4-c]pyrazole-5(1H)-carboxamide, (R)—N-[5-(2-butoxy-2-phenylacetyl)-6,6-dimethyl-1,4,5,6-tetrahydropyrrolo[3,4-c]pyrazol-3-yl]-1-(trimethylsilyl)cyclobutanecarboxamide, and N-(3-methoxy-2,2-dimethyl-1-phenylpropyl)-6,6-dimethyl-3-[1-(trimethylsilyl)cyclobutanecarboxamido]-4,6-dihydropyrrolo [3,4-c]pyrazole-5(1H)-carboxamide or a pharmacologically acceptable salt thereof.

12. The compound or a pharmaceutically acceptable salt thereof according to claim 1, wherein the compound or a pharmaceutically acceptable thereof is (R)—N-[1-(4-fluorophenyl)-3-hydroxy-3-methylbutyl]-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof.

13. The compound or a pharmaceutically acceptable salt thereof according to claim 1, wherein the compound or a pharmaceutically acceptable thereof is (−)-N-(3-hydroxy-2,2-dimethyl-1-phenylpropyl)-6,6-dimethyl-3-[1-(trimethylsilyl)cyclopropane-1-carboxamido]-4,6-dihydropyrrolo[3,4-c]pyrazole-5(1H)-carboxamide or a pharmacologically acceptable salt thereof.

14. The compound or a pharmaceutically acceptable salt thereof according to claim 1, wherein the compound or a pharmaceutically acceptable thereof is (R)—N-[5-(2-methoxy-2-phenylacetyl)-6,6-dimethyl-1,4,5,6-tetrahydropyrrolo[3,4-c]pyrazol-3-yl]-1-(trimethylsilyl)cyclobutanecarboxamide or a pharmacologically acceptable salt thereof.

15. The compound or a pharmaceutically acceptable salt thereof according to claim 1, wherein the compound or a pharmaceutically acceptable thereof is (R)—N-[6,6-dimethyl-5-(2-phenyl-2-propoxyacetyl)-1,4,5,6-tetrahydropyrrolo[3,4-c]pyrazol-3-yl]-1-(trimethylsilyl)cyclobutanecarboxamide or a pharmacologically acceptable salt thereof.

16. The compound or a pharmaceutically acceptable salt thereof according to claim 1, wherein the compound or a pharmaceutically acceptable thereof is (R)—N-{5-[2-(2-fluorophenyl)-2-methoxyacetyl]-6,6-dimethyl-1,4,5,6-tetrahydropyrrolo[3,4-c]pyrazol-3-yl}-1-(trimethylsilyl)cyclobutanecarboxamide or a pharmacologically acceptable salt thereof.

17. The compound or a pharmaceutically acceptable salt thereof according to claim 1, wherein the compound or a pharmaceutically acceptable thereof is (R)—N-[5-(2-ethoxy-2-phenylacetyl)-6,6-dimethyl-1,4,5,6-tetrahydropyrrolo[3,4-c]pyrazol-3-yl]-1-(trimethylsilyl)cyclobutanecarboxamide or a pharmacologically acceptable salt thereof.

18. The compound or a pharmaceutically acceptable salt thereof according to claim 1, wherein the compound or a pharmaceutically acceptable thereof is (R)—N-[5-(2-cyclopropoxy-2-phenylacetyl)-6,6-dimethyl-1,4,5,6-tetrahydropyrrolo[3,4-c]pyrazol-3-yl]-1-(trimethylsilyl)cyclobutanecarboxamide or a pharmacologically acceptable salt thereof.

19. The compound or a pharmaceutically acceptable salt thereof according to claim 1, wherein the compound or a pharmaceutically acceptable thereof is (R)—N-[5-(2-isopropoxy-2-phenylacetyl)-6,6-dimethyl-1,4,5,6-tetrahydropyrrolo[3,4-c]pyrazol-3-yl]-1-(trimethylsilyl)cyclobutanecarboxamide or a pharmacologically acceptable salt thereof.

20. The compound or a pharmaceutically acceptable salt thereof according to claim 1, wherein the compound or a pharmaceutically acceptable thereof is (+)-N-{5-[2-methoxy-2-(thiophen-2-yl)acetyl]-6,6-dimethyl-1,4,5,6-tetrahydropyrrolo[3,4-c]pyrazol-3-yl}-1-(trimethylsilyl)cyclobutanecarboxamide or a pharmacologically acceptable salt thereof.

21. The compound or a pharmaceutically acceptable salt thereof according to claim 1, wherein the compound or a pharmaceutically acceptable thereof is (−)-N-[1-(3-fluorophenyl)-3-hydroxy-2,2-dimethylpropyl]-6,6-dimethyl-3-[1-(trimethylsilyl)cyclobutanecarboxamido]-4,6-dihydropyrrolo [3,4-c]pyrazole-5(1H)-carboxamide or a pharmacologically acceptable salt thereof.

22. The compound or a pharmaceutically acceptable salt thereof according to claim 1, wherein the compound or a pharmaceutically acceptable thereof is N-{5-[2-(3-fluorophenyl)-2-methoxyacetyl]-6,6-dimethyl-1,4,5,6-tetrahydropyrrolo[3,4-c]pyrazol-3-yl}-1-(trimethylsilyl)cyclobutanecarboxamide or a pharmacologically acceptable salt thereof.

23. The compound or a pharmaceutically acceptable salt thereof according to claim 1, wherein the compound or a pharmaceutically acceptable thereof is N-[1-(4-fluorophenyl)-3-hydroxy-2,2-dimethylpropyl]-6,6-dimethyl-3-[1-(trimethylsilyl)cyclobutanecarboxamido]-4,6-dihydropyrrolo [3,4-c]pyrazole-5(1H)-carboxamide or a pharmacologically acceptable salt thereof.

24. The compound or a pharmaceutically acceptable salt thereof according to claim 1, wherein the compound or a pharmaceutically acceptable thereof is (R)—N-[1-(3-fluorophenyl)-3-hydroxy-3-methylbutyl]-6,6-dimethyl-3-[1-(trimethylsilyl)cyclobutanecarboxamido]-4,6-dihydropyrrolo [3,4-c]pyrazole-5(1H)-carboxamide or a pharmacologically acceptable salt thereof.

25. The compound or a pharmaceutically acceptable salt thereof according to claim 1, wherein the compound or a pharmaceutically acceptable thereof is (R)—N-{6,6-dimethyl-5-[2-phenyl-2-(trifluoromethoxy)acetyl]-1,4,5,6-tetrahydropyrrolo[3,4-c]pyrazol-3-yl}-1-(trimethylsilyl)cyclobutanecarboxamide or a pharmacologically acceptable salt thereof.

26. The compound or a pharmaceutically acceptable salt thereof according to claim 1, wherein the compound or a pharmaceutically acceptable thereof is (R)—N-[2-(1-hydroxycyclopropyl)-1-phenylethyl]-6,6-dimethyl-3-[1-(trimethylsilyl)cyclobutanecarboxamido]-4,6-dihydropyrrolo [3,4-c]pyrazole-5(1H)-carboxamide or a pharmacologically acceptable salt thereof.

27. The compound or a pharmaceutically acceptable salt thereof according to claim 1, wherein the compound or a pharmaceutically acceptable thereof is (R)—N-(3-hydroxy-3-methyl-1-phenylbutyl)-6,6-dimethyl-3-[1-(trimethylsilyl) cyclobutanecarboxamido]-4,6-dihydropyrrolo [3,4-c]pyrazole-5(1H)-carboxamide or a pharmacologically acceptable salt thereof.

28. The compound or a pharmaceutically acceptable salt thereof according to claim 1, wherein the compound or a pharmaceutically acceptable thereof is (R)—N-[5-(2-methoxy-2-phenylacetyl)-6,6-dimethyl-1,4,5,6-tetrahydropyrrolo[3,4-c]pyrazol-3-yl]-1-(trimethylsilyl)cyclopropanecarboxamide or a pharmacologically acceptable salt thereof.

29. The compound or a pharmaceutically acceptable salt thereof according to claim 1, wherein the compound or a pharmaceutically acceptable thereof is (R)—N-{5-[2-(difluoromethoxy)-2-phenylacetyl]-6,6-dimethyl-1,4,5,6-tetrahydropyrrolo[3,4-c]pyrazol-3-yl}-1-(trimethylsilyl)cyclobutanecarboxamide or a pharmacologically acceptable salt thereof.

30. The compound or a pharmaceutically acceptable salt thereof according to claim 1, wherein the compound or a pharmaceutically acceptable thereof is (R)-1-(ethyldimethylsilyl)-N-[5-(2-methoxy-2-phenylacetyl)-6,6-dimethyl-1,4,5,6-tetrahydropyrrolo[3,4-c]pyrazol-3-yl]cyclobutanecarboxamide or a pharmacologically acceptable salt thereof.

31. The compound or a pharmaceutically acceptable salt thereof according to claim 1, wherein the compound or a pharmaceutically acceptable thereof is N-{[1-(hydroxymethyl)cyclobutyl](phenyl)methyl}-6,6-dimethyl-3-[1-(trimethylsilyl)cyclobutanecarboxamido]-4,6-dihydropyrrolo [3,4-c]pyrazole-5(1H)-carboxamide or a pharmacologically acceptable salt thereof.

32. A pharmaceutical composition comprising the compound or a pharmacologically acceptable salt thereof according to claim 1.

33. A pharmaceutical composition comprising the compound or a pharmacologically acceptable salt thereof according to claim 3.

34. A pharmaceutical composition comprising the compound or a pharmacologically acceptable salt thereof according to claim 5.

35. A pharmaceutical composition comprising the compound or a pharmacologically acceptable salt thereof according to claim 7.

36. A pharmaceutical composition comprising the compound or a pharmacologically acceptable salt thereof according to claim 9.

37. A pharmaceutical composition comprising the compound or a pharmacologically acceptable salt thereof according to claim 11.

38. A method for treating a cancer, an inflammatory disease, atopic dermatitis, chronic obstructive pulmonary disease (COPD), an infection by HIV, an infection by EBV, an infection by HCV, idiopathic pulmonary fibrosis, cardiomegaly, or Alzheimer's disease; wherein
the cancer is selected from a group consisting of urinary bladder cancer, breast cancer, large intestine cancer, kidney cancer, liver cancer, lung cancer, esophageal cancer, gallbladder cancer, ovary cancer, pancreatic cancer, stomach cancer, cervical cancer, thyroid gland cancer, head and neck cancer, prostate cancer, skin cancer, hematopoietic organ tumors of the lymph system, hematopoietic organ tumors of the myeloid system, mesenchymal tumors, tumors of the central or peripheral nervous system, melanoma, teratoma, osteosarcoma, and Kaposi's sarcoma, and the inflammatory disease is selected from a group consisting of autoimmune hepatitis, autoimmune pancreatitis, aortitis syndrome, Goodpasture's syndrome, autoimmune hemolytic anemia, autoimmune neutropenia, rheumatoid arthritis, and psoriasis; comprising administering the compound or the pharmacologically acceptable salt thereof according to claim 1 to a subject in need thereof.

39. A method for treating a CDK-7-mediated cancer or a CDK-7-mediated autoimmune disease, wherein the cancer or the autoimmune disease is treated by inhibiting CDK-7, comprising administering the compound or the pharmacologically acceptable salt thereof according to claim 1 to a subject in need thereof.

* * * * *